US006156700A

United States Patent [19]
Wepplo et al.

[11] Patent Number: 6,156,700
[45] Date of Patent: Dec. 5, 2000

[54] 3-(1,2-BENZISOTHIAZOL- AND ISOXAZOL-5-YL)-2,4(1H,3H)-PYRIMIDINEDIONE OR THIONE AND 3-(1,2-BENZISOTHIAZOL- AND ISOXAZOL-5-YL)-4(3H)-PYRIMIDINONE OR THIONE HERBICIDAL AGENTS

[75] Inventors: Peter John Wepplo, Princeton; Mark Christopher Manfredi, Hamilton; Richard Anthony Rampulla, Whitehouse Station; Michael Vernie Cossette, Plainsboro; Michael Anthony Guaciaro, East Windsor, all of N.J.; Gregory Jay Haley, Langhorne, Pa.; Billy Gene Bullock, Englishtown; Sergio Ivan Alvarado, Trenton, both of N.J.; Keith Douglas Barnes, Newtown, Pa.; Gary Allen Meier, Lambertville; David Allen Hunt, Newtown, both of N.J.; Marianne Carlsen, Yardley, Pa.; Gavin David Heffernan, Bordentown, N.J.

[73] Assignee: American Cyanmid Company, Madison, N.J.

[21] Appl. No.: 09/152,524

[22] Filed: Sep. 14, 1998

Related U.S. Application Data

[60] Provisional application No. 60/059,318, Sep. 17, 1997, and provisional application No. 60/095,356, Aug. 4, 1998.

[51] Int. Cl.[7] .................. A01N 43/54; A61K 31/505; C07F 9/02; C07D 401/00; C07D 239/02
[52] U.S. Cl. .................. 504/242; 504/243; 514/269; 514/274; 544/243; 544/310; 544/319
[58] Field of Search ............... 514/269, 274; 544/243, 310, 319; 504/242, 243

[56] References Cited

U.S. PATENT DOCUMENTS 5,484,763 1/1996 Wepplo .................. 504/269
5,523,278 6/1996 Wepplo .................. 504/271

FOREIGN PATENT DOCUMENTS

| 0408382 A2 | 7/1990 | European Pat. Off. . |
| 0442655 A2 | 2/1991 | European Pat. Off. . |
| WO 95/32952 | 12/1995 | WIPO . |
| WO 97/08170 | 8/1996 | WIPO . |
| WO 97/12886 | 10/1996 | WIPO . |

*Primary Examiner*—Mukund J. Shah
*Assistant Examiner*—Ben Schroeder
*Attorney, Agent, or Firm*—Joseph M. Mazzaree; Barbara V. Maurer

[57] ABSTRACT

There are provided 3-(1,2-benzisothiazol- and isoxazol-5-yl)-2,4(1H,3H)-pyrimidinedione or thione compounds of formula I and 3-(1,2-benzisothiazol- and isoxazol-5-yl)-4(3H)-pyrimidinone or thione compounds of formula II

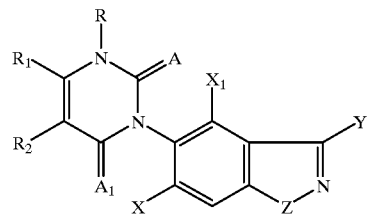

(I)

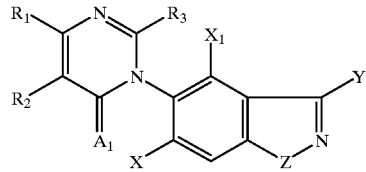

(II)

Further provided are compositions and methods comprising those compounds for the control of undesirable plant species.

32 Claims, No Drawings

3-(1,2-BENZISOTHIAZOL- AND ISOXAZOL-5-YL)-2,4(1H,3H)-PYRIMIDINEDIONE OR THIONE AND 3-(1,2-BENZISOTHIAZOL- AND ISOXAZOL-5-YL)-4(3H)-PYRIMIDINONE OR THIONE HERBICIDAL AGENTS

This application claims priority from copending provisional application(s) serial Nos. 60/059318 filed on Sep. 17, 1997 and 60/095356 filed on Aug. 4, 1998.

BACKGROUND OF THE INVENTION

Weeds cause tremendous global economic losses by reducing crop yields and lowering crop quality. Worldwide, agronomic crops must compete with hundreds of weed species.

In spite of the commercial herbicides available today, damage to crops caused by weeds still occurs. Accordingly, there is ongoing research to create more effective and/or more selective herbicidal agents.

Certain benzisoxazole and benzisothiazole herbicidal agents are described in U.S. Pat. Nos. 5,484,763 and 5,523,278. Those patents generically disclose benzisoxazole and benzisothiazole compounds that are substituted with a Q group which may be one of 22 specified groups. However, only one Q group (Q6) is exemplified in those patents. In addition, those patents do not disclose that their compounds are useful for the selective control of weeds in the presence of corn and wheat.

Surprisingly, it has now been found that certain of the compounds generically disclosed in those patents are more effective and/or more selective herbicidal agents than the corresponding compounds wherein Q is Q6.

It is therefore an object of the present invention to provide compounds which are highly effective for the control of undesirable plant species.

It is also an object of the present invention to provide methods for the control of undesirable plant species.

It is a further object of the present invention to provide methods for the selective control of undesirable plant species in the presence of crops.

Those and other objects and features of the present invention will become more apparent from the detailed description thereof set forth below.

SUMMARY OF THE INVENTION

The present invention describes 3-(1,2-benzisothiazol- and isoxazol-5-yl)-2,4(1H,3H)-pyrimidinedione or thione and 3-(1,2-benzisothiazol- and isoxazol-5-yl)-4(3H)-pyrimidinone or thione compounds which are useful as herbicidal agents.

The compounds of the present invention are represented by structural formulas I and II

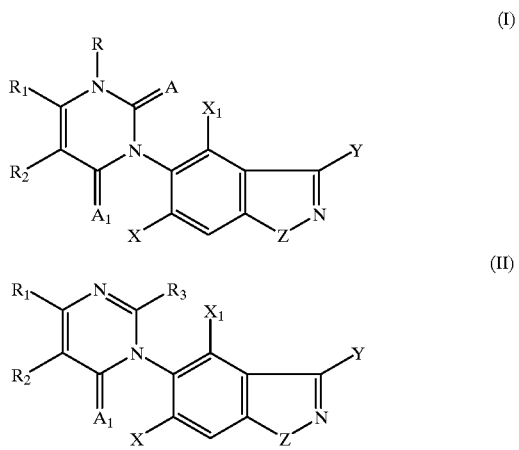

wherein

R is $C_1$–$C_6$alkyl, $C_1$–$C_6$haloalkyl, $C_3$–$C_7$cycloalkyl, $C_3$–$C_6$alkenyl, $C_3$–$C_6$alkynyl, benzyl, $OR_4$ or $NR_5R_6$;

$R_1$ and $R_2$ are each independently hydrogen, halogen, $C_1$–$C_6$alkyl, $C_3$–$C_7$cycloalkyl, $C_1$–$C_6$haloalkyl, $C_3$–$C_6$alkenyl, $C_3$–$C_6$haloalkenyl, $C_3$–$C_6$alkynyl, $OR_7$, $S(O)_nR_8$ or $NR_9R_{10}$, and when $R_1$ and $R_2$ are taken together with the atoms to which they are attached, they represent a four- to seven-membered saturated or unsaturated ring optionally interrupted by oxygen, sulfur or nitrogen, and optionally substituted with one to three methyl groups or one or more halogen atoms;

$R_3$ is halogen or $A_2R_{11}$;

X is hydrogen, halogen or $C_1$–$C_4$alkyl;

$X_1$ is hydrogen, halogen, $C_1$–$C_4$alkyl, $C_1$–$C_4$haloalkyl, $C_1$–$C_4$alkoxy or $C_1$–$C_4$haloalkoxy;

Z is O or $S(O)_m$;

Y is halogen, cyano, $R_{12}$, $X_2R_{12}$, $X_3R_{12}$, $X_2X_3R_{12}$ or $X_3X_2R_{12}$;

$X_2$ is O, $S(O)_p$ or $NR_{13}$;

$X_3$ is —C(=$A_3$)—, —C(=$NOR_{14}$)— or —C(=N—$NR_{13}R_{50}$);

$R_4$, $R_5$, $R_6$, $R_7$, $R_8$, $R_9$, $R_{10}$, $R_{11}$ and $R_{14}$ are each independently hydrogen, $C_1$–$C_6$alkyl, $C_3$–$C_7$cycloalkyl, $C_2$–$C_8$alkoxyalkyl, $C_2$–$C_6$alkenyl, $C_2$–$C_6$alkynyl or benzyl;

$R_{12}$ is hydrogen, a $C_1$–$C_8$alkyl, $C_3$–$C_7$cycloalkyl, $C_2$–$C_6$alkenyl, $C_5$–$C_6$cycloalkenyl or $C_2$–$C_8$alkynyl group, wherein each group is optionally substituted with any combination of one to six halogen atoms, one to three $C_1$–$C_{20}$alkoxy groups optionally substituted with one $C_1$–$C_8$alkoxy, benzyloxy or $C_1$–$C_6$alkylthio group, one or two $C_1$–$C_{10}$haloalkoxy groups, one or two $NR_{15}R_{16}$ groups, one to three $S(O)_qR_{17}$ groups, one or two cyano groups, one or two $C_3$–$C_7$cycloalkyl groups, one thiocyano group, one $O(SO_2)R_{17}$ group, one $O(NO_2)$ group, one or two $C(O)R_{18}$ groups, one or two $CO_2R_{19}$ groups, one or two $C(O)SR_{19}$ groups, one or two $C(O)NR_{20}R_{21}$ groups, one to three $X_4R_{22}$ groups, one or two $P(O)(OR_{23})_2$ groups, one or two $Si(R_{24})_3$ groups, one 4- to 10-membered monocyclic or fused bicyclic heterocyclic ring optionally substituted with any combination of one or two oxo groups, one or two thioxo groups, one to three halogen atoms, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups or one or two $X_4R_{22}$ groups, one quaternary organic ammonium group, or one or two phenyl groups wherein each phenyl group is independently optionally substituted with any combination of one to three halogen atoms, one to three $C_1$–$C_6$alkyl groups, one to three $C_1$–$C_6$alkoxy groups, one $C_3$–$C_7$cycloalkyl group, one $C_1$–$C_4$haloalkyl group, one $C_1$–$C_4$alkylthio group, one cyano group, one nitro group, one $C(O)R_{25}$ group, one $CO_2R_{26}$ group or one $X_5R_{27}$ group, phenyl optionally substituted with any combination of one to three halogen atoms, one to three $C_1$–$C_4$alkyl groups, one to three $C_1$–$C_4$alkoxy groups, one $C_3$–$C_6$cycloalkyl group, one $C_1$–$C_4$haloalkyl group, one $C_1$–$C_4$alkylthio group, one cyano group, one nitro group, one $C(O)R_{25}$ group, one $CO_2R_{26}$ group, one $X_4R_{22}$ group, one $CH{=}CHR_{22}$ group, one $CH_2CH(R_{28})R_{22}$ group or one $N(R_{29})SO_2R_{30}$ group, or indan optionally substituted with any combination of one or two halogen atoms, one or two $C_1$–$C_4$alkyl groups, one $C_1$–$C_4$alkoxy group, one $C_1$–$C_4$haloalkyl group, one $C_1$–$C_4$alkylthio group, one cyano group, one nitro group, one $C(O)R_{25}$ group, one $CO_2R_{26}$ group, one $X_4R_{22}$ group, one $CH{=}CHR_{22}$ group, one $CH_2CH(R_{28})R_{22}$ group or one $N(R_{29})SO_2R_{30}$ group, and when $R_{12}$ and $R_{13}$ are taken together with the nitrogen atom to which they are attached, they form a 5- to 12-membered monocyclic or fused bicyclic, heterocyclic ring optionally substituted with one or more groups independently selected from halogen, cyano, nitro, amino, hydroxyl, $C_1$–$C_4$alkyl, $C_1$–$C_4$haloalkyl, $C_1$–$C_4$alkoxy, $C_1$–$C_4$haloalkoxy, $C_1$–$C_4$haloalkylsulfonyl or $X_4R_{22}$ groups;

$R_{13}$ is hydrogen, $C_1$–$C_8$alkoxyalkyl, $C_1$–$C_6$alkyl, $C_3$–$C_7$cycloalkyl, $C_3$–$C_6$alkenyl, $C_3$–$C_6$alkynyl, benzyl, $OR_{23}$, cyano, $SO_2R_{51}$ or one 5- to 12-membered monocyclic or fused bicyclic heterocyclic ring optionally substituted with one or more groups independently selected from halogen, cyano, nitro, amino, hydroxyl, $C_1$–$C_4$alkyl, $C_1$–$C_4$haloalkyl, $C_1$–$C_4$alkoxy or $C_1$–$C_4$haloalkoxy, and when $R_{13}$ and $R_{12}$ are taken together with the nitrogen atom to which they are attached, they form a 5- to 12-membered monocyclic or fused bicyclic, heterocyclic ring optionally substituted with one or more groups independently selected from halogen, cyano, nitro, amino, hydroxyl, $C_1$–$C_4$alkyl, $C_1$–$C_4$haloalkyl, $C_1$–$C_4$alkoxy, $C_1$–$C_4$haloalkoxy, $C_1$–$C_4$haloalkylsulfonyl or $X_4R_{22}$ groups;

$R_{28}$ is halogen;

$R_{22}$ and $R_{27}$ are each independently hydrogen, $Si(R_{31})_3$, $C(O)NR_{35}R_{36}$, $C(O)R_{33}$, $SO_2R_{47}$, $C_1$–$C_{20}$alkyl substituted with one hydroxyl, benzyloxy, nitro, $OC(O)R_{33}$, $C_1$–$C_6$alkoxy, $CO_2R_{32}$, $C(O)R_{33}$, $C(A_4R_{34})_2$, $C(O)NR_{35}R_{36}$, $C(O)ON{=}CR_{37}R_{38}$, $P(O)(OH)NH_2$, $P(O)(OH)(OR_{23})$, $C(O)NR_{35}OR_{23}$ cyano or 2-dioxolanyl group, one phenyl, dihydrofuranone or furanone ring wherein each ring is optionally substituted with any combination of one to three halogen atoms, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups, or one 5- to 12-membered monocyclic or fused bicyclic, heterocyclic ring optionally substituted with one or more groups independently selected from halogen, cyano, nitro, amino, hydroxyl, $C_1$–$C_4$alkyl, $C_1$–$C_4$haloalkyl, $C_1$–$C_4$alkoxy, $C_1$–$C_4$haloalkoxy or $C_1$–$C_4$haloalkylsulfonyl groups, $C_3$–$C_{20}$alkenyl optionally substituted with one to three halogen atoms, one hydroxyl group, one $C_1$–$C_6$alkoxy, $CO_2R_{32}$, $C(O)R_{33}$, $C(A_4R_{34})_2$, $C(O)NR_{35}R_{36}$, $C(O)ON{=}CR_{37}R_{38}$, $C(O)NR_{35}OR_{23}$, cyano or 2-dioxolanyl group, or one phenyl, dihydrofuranone or furanone ring wherein each ring is optionally substituted with any combination of one to three halogen atoms, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups, $C_5$–$C_8$cycloalkenyl optionally substituted with one hydroxyl, $C_1$–$C_6$alkoxy, $C_1$–$C_4$alkyl, $C_2$–$C_4$alkenyl, $CO_2R_{32}$, $C(O)R_{33}$, $C(A_4R_{34})_2$, $C(O)NR_{35}R_{36}$, $C(O)ON{=}CR_{37}R_{38}$, $C(O)NR_{35}OR_{23}$, cyano or 2-dioxolanyl group, or one phenyl, dihydrofuranone or furanone ring wherein each ring is optionally substituted with any combination of one to three halogen atoms, one to three $C_1$–$C_4$alkyl groups, one to three $C_1$–$C_4$alkoxy groups or one to three $C_1$–$C_4$haloalkoxy groups, $C_3$–$C_{10}$alkynyl optionally substituted with one hydroxyl, $C_1$–$C_6$alkoxy, $CO_2R_{32}$, $C(O)R_{33}$, $C(A_4R_{34})_2$, $C(O)NR_{35}R_{36}$, $C(O)ON{=}CR_{37}R_{38}$, $C(O)NR_{35}OR_{23}$, cyano or 2-dioxolanyl group, or one phenyl, dihydrofuranone or furanone ring wherein each ring is optionally substituted with any combination of one to three halogen atoms, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups, phenyl optionally substituted with any combination of one to three halogen atoms, one to three $C_1$–$C_6$alkyl groups, one to three $C_1$–$C_6$alkoxy groups, one $C_1$–$C_4$haloalkyl group, one $C_1$–$C_4$haloalkoxy group, one cyano group, one nitro group, one $NR_{39}R_{40}$ group or one $C(O)R_{33}$ group, benzyl optionally substituted on the phenyl ring with any combination of one to three halogen atoms, one to three $C_1$–$C_6$alkyl groups, one to three $C_1$–$C_6$alkoxy groups, one $C_1$–$C_4$haloalkyl group, one $C_1$–$C_4$haloalkoxy group, one cyano group, one nitro group, one $NR_{39}R_{40}$ group or one $C(O)R_{33}$ group, or a 4- to 10-membered heterocyclic ring optionally substituted with any combination of one or two oxo groups, one or two thioxo groups, one to three halogen atoms, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups;

$R_{15}$ and $R_{20}$ are each independently hydrogen, a $C_1$–$C_6$alkyl, $C_3$–$C_7$cycloalkyl, $C_2$–$C_6$alkenyl or $C_2$–$C_6$alkynyl group wherein each group is optionally substituted with one $CO_2R_{42}$ group, benzyl optionally substituted with any combination of one to three halogen atoms, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups, phenyl optionally substituted with any combination of one to three halogen atoms, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups, one $CO_2R_{26}$ group, $C(O)R_{43}$, or $CO_2R_{42}$;

$R_{16}$ and $R_{22}$ are each independently hydrogen, $C_1$–$C_6$alkyl, $C_1$–$C_4$alkoxy, $C_3$–$C_7$cycloalkyl, $C_2$–$C_6$alkenyl, $C_3$–$C_7$cycloalkenyl, $C_2$–$C_6$alkynyl, $P(O)(OR_{44})_2$, $SO_2R_{45}$, $C(O)R_{46}$, benzyl optionally substituted with any combination of one to three halogen atoms, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups or one $X_4R_{22}$ group, or phenyl optionally substituted with any combination of one to three halogen atoms, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups or one $X_4R_{22}$ group;

$R_{17}$, $R_{18}$, $R_{25}$, $R_{30}$, $R_{33}$, $R_{45}$ and $R_{51}$ are each independently $NR_{46}R_{48}$, —N=$CR_{46}R_{48}$, $C_1$–$C_8$alkyl optionally substituted with one $C_1$–$C_6$alkoxy, thiophene or furan group, $C_1$–$C_6$haloalkyl, $C_3$–$C_8$cycloalkyl, $CO_2R_{23}$, $C_2$–$C_6$alkenyl optionally substituted with phenyl, benzyl optionally substituted with any combination of one to three halogen atoms, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups, one nitro group, one cyano group or one $X_4R_{22}$ group, phenyl optionally substituted with any combination of one to three halogen atoms, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups, one nitro group, one cyano group or one $X_4R_{22}$ group, or a 5- to 12-membered monocyclic or fused bicyclic, heterocyclic ring optionally substituted with one or more groups independently selected from halogen, cyano, nitro, amino, hydroxyl, $C_1$–$C_4$alkyl, $C_1$–$C_4$haloalkyl, $C_1$–$C_4$alkoxy, $C_1$–$C_4$haloalkoxy, $C_1$–$C_4$haloalkylsulfonyl or $X_4R_{22}$ groups;

$R_{19}$ and $R_{26}$ are each independently hydrogen, $C_1$–$C_{20}$alkyl, $C_1$–$C_8$haloalkyl, $C_3$–$C_7$cycloalkyl, $C_3$–$C_7$halocycloalkyl, $C_3$–$C_{20}$alkenyl, $C_3$–$C_8$haloalkenyl, $C_5$–$C_8$cycloalkenyl, $C_5$–$C_8$halocycloalkenyl, $C_3$–$C_8$alkynyl, $C_3$–$C_8$haloalkynyl, $Si(R_{41})_3$, benzyl, phenyl, furfuryl, pyridyl, thienyl, oximino or an alkali metal, alkaline earth metal, manganese, copper, zinc, cobalt, silver, nickel, ammonium or organic ammonium cation;

$R_{32}$ is hydrogen, $Si(R_{47})_3$, di($C_1$–$C_4$alkyl)imino, $C_1$–$C_{20}$alkyl optionally substituted with one $CO_2R_{48}$, $C_1$–$C_6$alkoxy, $C_1$–$C_6$thioalkyl, $C_2$–$C_{20}$alkoxyalkoxy, phenyl, $OSi(R_{47})_3$, $OC(O)R_{33}$, $C_3$–$C_7$cycloalkyl or di($C_1$–$C_4$alkyl)imino group, $C_1$–$C_{15}$haloalkyl, $C_3$–$C_8$cycloalkyl optionally substituted with one $CO_2R_{48}$ group, $C_3$–$C_8$halocycloalkyl, $C_3$–$C_{20}$ alkenyl optionally substituted with one phenyl group, $C_3$–$C_{15}$haloalkenyl, $C_5$–$C_8$cycloalkenyl, $C_5$–$C_8$halocycloalkenyl, $C_3$–$C_{20}$alkynyl optionally substituted with one phenyl group, $C_3$–$C_{20}$haloalkynyl, benzyl optionally substituted with one or more groups independently selected from halogen, cyano, nitro, $C_1$–$C_4$alkyl, $C_1$–$C_4$haloalkyl, $C_1$–$C_4$alkoxy and $C_1$–$C_4$haloalkoxy groups, phenyl optionally substituted with one or more groups independently selected from halogen, cyano, nitro, $C_1$–$C_4$alkyl, $C_1$–$C_4$haloalkyl, $C_1$–$C_4$alkoxy and $C_1$–$C_4$haloalkoxy groups, 2-, 3- or 4-pyridyl, 2- or 3-furyl, 2- or 3-thienyl, 2-tetrahydrofuranyl, $C_1$–$C_4$alkyl substituted with one pyridyl, furyl, thienyl, tetrahydrofuryl, $C_3$–$C_8$cycloalkyl, dioxane or $NR_{49}R_{50}$ group, or an alkali metal, alkaline earth metal, manganese, copper, zinc, cobalt, silver, nickel, ammonium or organic ammonium cation;

$R_{34}$, $R_{37}$ and $R_{38}$ are each independently $C_1$–$C_6$alkyl;

$R_{35}$ and $R_{49}$ are each independently hydrogen or $C_1$–$C_6$alkyl and $R_{36}$ and $R_{50}$ are each independently hydrogen, cyano, $C_1$–$C_6$alkyl, $SO_2R_{51}$ or phenyl optionally substituted with one or more groups independently selected from halogen, cyano, nitro, $C_1$–$C_4$alkyl, $C_1$–$C_4$haloalkyl, $C_1$–$C_4$alkoxy and $C_1$–$C$ haloalkoxy groups, or when $R_{35}$ and $R_{36}$ or $R_{49}$ and $R_{50}$ are taken together with the nitrogen atom to which they are attached, they form a 5- to 12-membered monocyclic or fused bicyclic, heterocyclic ring optionally substituted with one or more groups independently selected from halogen, cyano, nitro, amino, hydroxyl, $C_1$–$C_4$alkyl, $C_1$–$C_4$haloalkyl, $C_1$–$C_4$alkoxy, $C_1$–$C_4$haloalkoxy or $C_1$–$C_4$haloalkylsulfonyl groups;

m, n, p and q are each independently an integer of 0, 1 or 2;

$R_{29}$ is hydrogen, $C_1$–$C_4$alkyl or $C_1$–$C_4$haloalkyl;

$R_{24}$, $R_{31}$, $R_{41}$ and $R_{47}$ are each independently $C_1$–$C_4$alkyl, benzyl optionally substituted with one or more groups independently selected from halogen, cyano, nitro, $C_1$–$C_4$alkyl, $C_1$–$C_4$haloalkyl, $C_1$–$C_4$alkoxy and $C_1$–$C_4$haloalkoxy groups, or phenyl optionally substituted with one or more groups independently selected from halogen, cyano, nitro, $C_1$–$C_4$alkyl, $C_1$–$C_4$haloalkyl, $C_1$–$C_4$alkoxy and $C_1$–$C_4$haloalkoxy groups;

$R_{23}$, $R_{39}$, $R_{40}$, $R_{42}$, $R_{43}$, $R_{44}$, $R_{46}$ and $R_{48}$ are each independently hydrogen, $C_2$–$C_6$alkenyl, $C_3$–$C_8$cycloalkyl, $C_1$–$C_8$alkyl optionally substituted with one or two $C_1$–$C_4$alkoxy groups, benzyl optionally substituted with one or more groups independently selected from halogen, cyano, nitro, $C_1$–$C_4$alkyl, $C_1$–$C_4$haloalkyl, $C_1$–$C_4$alkoxy and $C_1$–$C_4$haloalkoxy groups, or phenyl optionally substituted with one or more groups independently selected from halogen, cyano, nitro, $C_1$–$C_4$alkyl, $C_1$–$C_4$haloalkyl, $C_1$–$C_4$alkoxy and $C_1$–$C_4$haloalkoxy groups, and when $R_{46}$ and $R_{48}$ are taken together with the atom to which they are attached, they form a 5- to 12-membered monocyclic or fused bicyclic, heterocyclic or cycloalkyl ring optionally substituted with one or more groups independently selected from halogen, cyano, nitro, amino, hydroxyl, $C_1$–$C_4$alkyl, $C_1$–$C_4$haloalkyl, $C_1$–$C_4$alkoxy, $C_1$–$C_4$haloalkoxy or $C_1$–$C_4$haloalkylsulfonyl groups; and A, $A_1$, $A_2$, $A_3$, $A_4$, $X_4$ and $X_5$ are each independently O or S; and the optical isomers, diastereomers and/or tautomers thereof.

This invention also relates to compositions containing those compounds and methods for using those compounds and compositions. Advantageously, it has been found that the compounds of the present invention, and compositions containing them, are useful for the control of undesirable plant species. The compounds of the present invention are especially useful for the selective control of undesirable plant species in the presence of crops.

DETAILED DESCRIPTION OF THE INVENTION

The present invention provides a method for the control of undesirable plant species which comprises applying to the foliage of said plants or to the soil or water containing seeds or other propagating organs thereof, a herbicidally effective amount of a 3-(1,2-benzisothiazol- or isoxazol-5-yl)-2,4(1H,3H)-pyrimidinedione or thione compound of formula I or a 3-(1,2-benzisothiazol- or isoxazol-5-yl)-4(3H)-pyrimidinone or thione compound of formula II.

The herbicidal compounds of the present invention are represented by structural formulas I and II

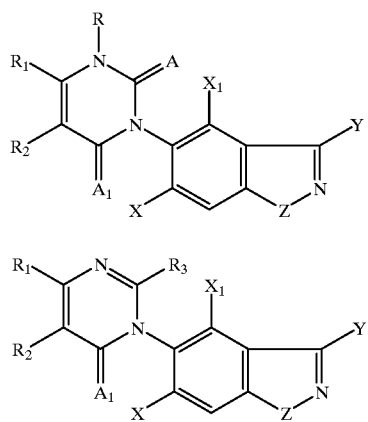

wherein R, $R_1$, $R_2$, $R_3$, A, $A_1$, X, $X_1$, Y and Z are as defined above for formulas I and II.

Surprisingly, it has been discovered that the formula I and II compounds of this invention are more effective and/or more selective herbicidal agents than the corresponding compounds exemplified in U.S. Pat. Nos. 5,484,763 and 5,523,278 wherein Q is Q6. In addition, we have found that the formula I compounds of the present invention are particularly useful for the selective control of undesirable plant species in the presence of crops such as corn, wheat, rice and soybeans.

Preferred compounds of the present invention are those represented by structural formulas I and II

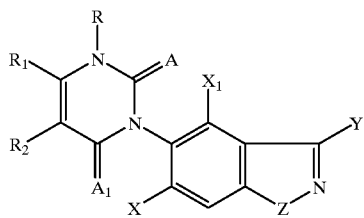

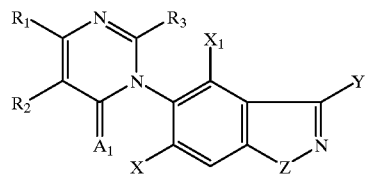

wherein

R is $C_1$–$C_6$alkyl, $C_1$–$C_6$haloalkyl, $C_3$–$C_7$cycloalkyl, $C_3$–$C_6$alkenyl, $C_3$–$C_6$alkynyl, benzyl, $OR_4$ or $NR_5R_6$;

$R_1$ and $R_2$ are each independently hydrogen, halogen, $C_1$–$C_6$alkyl, $C_3$–$C_7$cycloalkyl, $C_1$–$C_6$haloalkyl, $C_3$–$C_6$alkenyl, $C_3$–$C_6$haloalkenyl, $C_3$–$C_6$alkynyl, $OR_2$, $S(O)_nR_6$ or $NR_9R_{10}$, and when $R_1$ and $R_2$ are taken together with the atoms to which they are attached, they represent a four- to seven-membered saturated or unsaturated ring optionally interrupted by oxygen, sulfur or nitrogen, and optionally substituted with one to three methyl groups or one or more halogen atoms;

$R_3$ is halogen or $A_2R_{11}$;

X is hydrogen, halogen or $C_1$–$C_4$alkyl;

$X_1$ is hydrogen, halogen, $C_1$–$C_4$alkyl, $C_1$–$C_4$haloalkyl, $C_1$–$C_4$alkoxy or $C_1$–$C_4$haloalkoxy;

Z is O or $S(O)_m$;

Y is halogen, cyano, $R_{12}$, $X_2R_{12}$, $X_3R_{12}$, $X_2X_3R_{12}$ or $X_3X_2R_{12}$;

$X_2$ is O, $S(O)_p$ or $NR_{13}$;

$X_3$ is —C(=$A_3$)— or —C(=$NOR_{14}$)—;

$R_4$, $R_5$, $R_6$, $R_7$, $R_8$, $R_9$, $R_{10}$, $R_{11}$ and $R_{14}$ are each independently hydrogen, $C_1$–$C_6$alkyl, $C_3$–$C_7$cycloalkyl, $C_2$–$C_6$alkenyl, $C_2$–$C_6$ alkynyl or benzyl;

$R_{12}$ is hydrogen, a $C_1$–$C_6$alkyl, $C_3$–$C_7$cycloalkyl, $C_2$–$C_6$alkenyl, $C_5$–$C_6$cycloalkenyl or $C_2$–$C_6$alkynyl group, wherein each group is optionally substituted with any combination of one to six halogen atoms, one to three $C_1$–$C_{20}$alkoxy groups, one or two $C_1$–$C_{10}$haloalkoxy groups, one or two $NR_{15}R_{16}$ groups, one to three $S(O)_qR_{17}$ groups, one or two cyano groups, one or two $C(O)R_{18}$ groups, one or two $CO_2R_{19}$ groups, one or two $C(O)NR_{20}R_{21}$ groups, one to three $X_4R_{22}$ groups, one or two $P(O)(OR_{23})_2$ groups, one or two $Si(R_{24})_3$ groups, one 4- to 10-membered heterocyclic ring optionally substituted with any combination of one or two oxo groups, one or two thioxo groups, one to three halogen atoms, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups or one or two $X_4R_{22}$ groups, one quaternary organic ammonium group, or one phenyl group optionally substituted with any combination of one to three halogen atoms, one to three $C_1$–$C_6$alkyl groups, one to three $C_1$–$C_6$alkoxy groups, one $C_3$–$C_7$cycloalkyl group, one $C_1$–$C_4$haloalkyl group, one $C_1$–$C_4$alkylthio group, one cyano group, one nitro group, one $C(O)R_{25}$ group, one $CO_2R_{26}$ group or one $X_5R_{27}$ group, or phenyl optionally substituted with any combination of one to three halogen atoms, one to three $C_1$–$C_4$alkyl groups, one to three $C_1$–$C_4$alkoxy groups, one $C_3$–$C_6$cycloalkyl group, one $C_1$–$C_4$haloalkyl group, one $C_1$–$C_4$alkylthio group, one cyano group, one nitro group, one $C(O)R_{25}$ group, one $CO_2R_{26}$ group, one $X_4R_{22}$ group, one $CH=CHR_{22}$ group, one $CH_2CH(R_{28})R_{22}$ group or one $N(R_{29})SO_2R_{30}$ group, and when $R_{12}$ and $R_{13}$ are taken together with the nitrogen atom to which they are attached, they form a 5- to 12-membered monocyclic or fused bicyclic, heterocyclic ring optionally substituted with one or more groups independently selected from halogen, cyano, nitro, amino, hydroxyl, $C_1$–$C_4$alkyl, $C_1$–$C_4$haloalkyl, $C_1$–$C_4$alkoxy, $C_1$–$C_4$haloalkoxy, $C_1$–$C_4$haloalkylsulfonyl or $X_4R_{22}$ groups;

$R_{13}$ is hydrogen, $C_1$–$C_6$alkyl, $C_3$–$C_7$cycloalkyl, $C_3$–$C_6$alkenyl, $C_3$–$C_6$alkynyl, benzyl, $OR_{23}$, cyano or $SO_2R_{51}$, and when $R_{13}$ and $R_{12}$ are taken together with the nitrogen atom to which they are attached, they form a 5- to 12-membered monocyclic or fused bicyclic, heterocyclic ring optionally substituted with one or more groups independently selected from halogen, cyano, nitro, amino, hydroxyl, $C_1$–$C_4$alkyl, $C_1$–$C_4$haloalkyl, $C_1$–$C_4$alkoxy, $C_1$–$C_4$haloalkoxy, $C_1$–$C_4$haloalkylsulfonyl or $X_4R_{22}$ groups;

$R_{28}$ is halogen;

$R_{22}$ and $R_{27}$ are each independently hydrogen, $Si(R_{31})_3$, $C_1$–$C_{20}$alkyl substituted with one $C_1$–$C_6$alkoxy, $CO_2R_{32}$, $C(O)R_{33}$, $C(A_4R_{34})_2$, $C(O)NR_{35}R_{36}$, $C(O)ON=CR_{37}R_{38}$, $P(O)(OH)NH_2$, $P(O)(OH)(OR_{23})$, $C(O)NHOR_{23}$, cyano or 2-dioxolanyl group, one phenyl, dihydrofuranone or furanone ring wherein each ring is optionally substituted with any combination of one to three halogen atoms, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups, or one 5- to 12-membered monocyclic or fused bicyclic, heterocyclic ring optionally substituted with one or more groups independently selected from halogen, cyano, nitro, amino, hydroxyl, $C_1$–$C_4$alkyl, $C_1$–$C_4$haloalkyl, $C_1$–$C_4$alkoxy, $C_1$–$C_4$haloalkoxy or $C_1$–$C_4$haloalkylsulfonyl groups, $C_3$–$C_{20}$alkenyl optionally substituted with one to three halogen atoms, one $C_1$–$C_6$alkoxy, $CO_2R_{32}$, $C(O)R_{33}$, $C(A_4R_{34})_2$, $C(O)NR_{35}R_{36}$, $C(O)ON=CR_{37}R_{38}$, $C(O)NHOR_{23}$, cyano or 2-dioxolanyl group, or one phenyl, dihydrofuranone or furanone ring wherein each ring is optionally substituted with any combination of one to three halogen atoms, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups, $C_5$–$C_8$cycloalkenyl optionally substituted with one $C_1$–$C_6$alkoxy, $C_1$–$C_4$alkyl, $C_2$–$C_4$alkenyl, $CO_2R_{32}$, $C(O)R_{33}$, $C(A_4R_{34})_2$, $C(O)NR_{35}R_{36}$, $C(O)ON=CR_{37}R_{38}$, $C(O)NHOR_{23}$, cyano or 2-dioxolanyl group, or one phenyl, dihydrofuranone or furanone ring wherein each ring is optionally substituted with any combination of one to three halogen atoms, one to three $C_1$–$C_4$alkyl groups, one to three $C_1$–$C_4$alkoxy groups or one to three $C_1$–$C_4$haloalkoxy groups, $C_3$–$C_{10}$alkynyl optionally substituted with one $C_1$–$C_6$alkoxy, $CO_2R_{32}$, $C(O)R_{33}$, $C(A_4R_{34})_2$, $C(O)NR_{35}R_{36}$, $C(O)ON=CR_{37}R_{38}$, $C(O)NHOR_{23}$, cyano or 2-dioxolanyl group, or one phenyl, dihydrofuranone or furanone ring wherein each ring is optionally substituted with any combination of one to three halogen atoms, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups, phenyl optionally substituted with any combination of one to three halogen atoms, one to three $C_1$–$C_6$alkyl groups, one to three $C_1$–$C_6$alkoxy groups, one $C_1$–$C_4$haloalkyl group, one $C_1$–$C_4$haloalkoxy group, one cyano group, one nitro group, one $NR_{39}R_{40}$ group or one $C(O)R_{33}$ group, benzyl optionally substituted on the phenyl ring with any combination of one to three halogen atoms, one to three $C_1$–$C_6$alkyl groups, one to three $C_1$–$C_6$alkoxy groups, one $C_1$–$C_4$haloalkyl group, one $C_1$–$C_4$haloalkoxy group, one cyano group, one nitro group, one $NR_{39}R_{40}$ group or one $C(O)R_{33}$ group, or a 4- to 10-membered heterocyclic ring optionally substituted with any combination of one or two oxo groups, one or two thioxo groups, one to three halogen atoms, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups;

$R_{15}$ and $R_{20}$ are each independently hydrogen, a $C_1$–$C_6$alkyl, $C_3$–$C_7$cycloalkyl, $C_2$–$C_6$alkenyl or $C_2$–$C_6$alkynyl group wherein each group is optionally substituted with one $CO_2R_{42}$ group, benzyl optionally substituted with any combination of one to three halogen atoms, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups, phenyl optionally substituted with any combination of one to three halogen atoms, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups, or $C(O)R_{43}$;

$R_{16}$ and $R_{21}$ are each independently hydrogen, $C_1$–$C_6$alkyl, $C_3$–$C_7$cycloalkyl, $C_2$–$C_6$alkenyl, $C_3$–$C_7$cycloalkenyl, $C_2$–$C_6$alkynyl, $P(O)(OR_{44})_2$, $SO_2R_{45}$, $C(O)R_{46}$, benzyl optionally substituted with any combination of one to three halogen atoms, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups or one $X_4R_{22}$ group, or phenyl optionally substituted with any combination of one to three halogen atoms, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups or one $X_4R_{22}$ group;

$R_{17}$, $R_{18}$, $R_{25}$, $R_{30}$, $R_{33}$, $R_{45}$ and $R_{51}$ are each independently $C_1$–$C_4$alkyl, $C_1$–$C_4$haloalkyl, $CO_2R_{23}$, $C_2$–$C_6$alkenyl optionally substituted with phenyl, benzyl optionally substituted with any combination of one to three halogen atoms, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups, one nitro group, one cyano group or one $X_4R_{22}$ group, phenyl optionally substituted with any combination of one to three halogen atoms, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups, one nitro group, one cyano group or one $X_4R_{22}$ group, or a 5- to 12-membered monocyclic or fused bicyclic, heterocyclic ring optionally substituted with one or more groups independently selected from halogen, cyano, nitro, amino, hydroxyl, $C_1$–$C_4$alkyl, $C_1$–$C_4$haloalkyl, $C_1$–$C_4$alkoxy, $C_1$–$C_4$haloalkoxy, $C_1$–$C_4$haloalkylsulfonyl or $X_4R_{22}$ groups;

$R_{19}$ and $R_{26}$ are each independently hydrogen, $C_1$–$C_{20}$alkyl, $C_1$–$C_8$haloalkyl, $C_3$–$C_7$cycloalkyl, $C_3$–$C_7$halocycloalkyl, $C_3$–$C_{20}$alkenyl, $C_3$–$C_8$haloalkenyl, $C_5$–$C_8$cycloalkenyl, $C_5$–$C_8$halocycloalkenyl, $C_3$–$C_8$alkynyl, $C_3$–$C_8$haloalkynyl, $Si(R_{41})_3$, benzyl, phenyl, furfuryl, pyridyl, thienyl, oximino or an alkali metal, alkaline earth metal, manganese, copper, zinc, cobalt, silver, nickel, ammonium or organic ammonium cation;

$R_{32}$ is hydrogen,
$Si(R_{47})_3$,
$di(C_1$–$C_4$alkyl)imino,
$C_1$–$C_{20}$alkyl optionally substituted with one $CO_2R_{48}$, $C_1$–$C_6$alkoxy or $di(C_1$–$C_4$alkyl)imino group,
$C_1$–$C_{15}$haloalkyl,
$C_3$–$C_8$cycloalkyl,
$C_3$–$C_8$halocycloalkyl,
$C_3$–$C_{20}$alkenyl optionally substituted with one phenyl group,
$C_3$–$C_5$haloalkenyl,
$C_5$–$C_8$cycloalkenyl,
$C_5$–$C_8$halocycloalkenyl,
$C_3$–$C_{20}$alkynyl optionally substituted with one phenyl group,
$C_3$–$C_{20}$haloalkynyl,
benzyl optionally substituted with one or more groups independently selected from halogen, cyano, nitro, $C_1$–$C_4$alkyl, $C_1$–$C_4$haloalkyl, $C_1$–$C_4$alkoxy and $C_1$–$C_4$haloalkoxy groups,
phenyl optionally substituted with one or more groups independently selected from halogen, cyano, nitro, $C_1$–$C_4$alkyl, $C_1$–$C_4$haloalkyl, $C_1$–$C_4$alkoxy and $C_1$–$C_4$haloalkoxy groups,
2-, 3- or 4-pyridyl,
2- or 3-furyl,
2- or 3-thienyl,
2-tetrahydrofuranyl,
$C_1$–$C_4$alkyl substituted with one pyridyl, furyl, thienyl, tetrahydrofuryl or $NR_{49}R_{50}$ group, or
an alkali metal, alkaline earth metal, manganese, copper, cobalt, silver, nickel, ammonium or organic ammonium cation;

$R_{34}$, $R_{37}$ and $R_{38}$ are each independently $C_1$–$C_6$alkyl;

$R_{35}$ and $R_{36}$ are each independently hydrogen or $C_1$–$C_6$alkyl and $R_{36}$ and $R_{50}$ are each independently hydrogen, cyano, $C_1$–$C_6$alkyl, $SO_2R_{51}$ or phenyl optionally substituted with one or more groups independently selected from halogen, cyano, nitro, $C_1$–$C_4$alkyl, $C_1$–$C_4$haloalkyl, $C_1$–$C_4$alkoxy and $C_1$–$C_4$haloalkoxy groups, or when $R_{35}$ and $R_{36}$ or $R_{49}$ and $R_{50}$ are taken together with the nitrogen atom to which they are attached, they form a 5- to 12-membered monocyclic or fused bicyclic, heterocyclic ring optionally substituted with one or more groups independently selected from halogen, cyano, nitro, amino, hydroxyl, $C_1$–$C_4$alkyl, $C_1$–$C_4$haloalkyl, $C_1$–$C_4$alkoxy, $C_1$–$C_4$haloalkoxy or $C_1$–$C_4$haloalkylsulfonyl groups;

m, n, p and q are each independently an integer of 0, 1 or 2;

$R_{29}$ is hydrogen, $C_1$–$C_4$alkyl or $C_1$–$C_4$haloalkyl;

$R_{24}$, $R_{31}$, $R_{41}$ and $R_{47}$ are each independently $C_1$–$C_4$alkyl,
benzyl optionally substituted with one or more groups independently selected from halogen, cyano, nitro, $C_1$–$C_4$alkyl, $C_1$–$C_4$haloalkyl, $C_1$–$C_4$alkoxy and $C_1$–$C_4$haloalkoxy groups, or
phenyl optionally substituted with one or more groups independently selected from halogen, cyano, nitro, $C_1$–$C_4$alkyl, $C_1$–$C_4$haloalkyl, $C_1$–$C_4$alkoxy and $C_1$–$C_4$haloalkoxy groups;

$R_{23}$, $R_{39}$, $R_{40}$, $R_{42}$, $R_{43}$, $R_{44}$, $R_{46}$ and $R_{48}$ are each independently hydrogen, $C_1$–$C_4$alkyl,
benzyl optionally substituted with one or more groups independently selected from halogen, cyano, nitro, $C_1$–$C_4$alkyl, $C_1$–$C_4$haloalkyl, $C_1$–$C_4$alkoxy and $C_1$–$C_4$haloalkoxy groups, or
phenyl optionally substituted with one or more groups independently selected from halogen, cyano, nitro, $C_1$–$C_4$alkyl, $C_1$–$C_4$haloalkyl, $C_1$–$C_4$alkoxy and $C_1$–$C_4$haloalkoxy groups; and A, $A_1$, $A_2$, $A_3$, $A_4$, $X_4$ and $X_5$ are each independently O or S; and the optical isomers, diastereomers and/or tautomers thereof.

Another group of preferred compounds of the present invention are those having the structural formula I

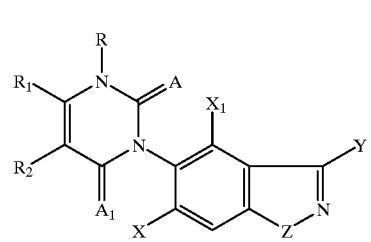

wherein

R is $C_1$–$C_6$alkyl, $C_1$–$C_6$haloalkyl, $C_3$–$C_7$cycloalkyl, $C_3$–$C_6$alkenyl, $C_3$–$C_6$alkynyl, benzyl, $OR_4$ or $NR_5R_6$;

$R_1$ and $R_2$ are each independently hydrogen, halogen, $C_1$–$C_6$alkyl, $C_3$–$C_7$cycloalkyl, $C_1$–$C_6$haloalkyl, $C_3$–$C_6$alkenyl, $C_3$–$C_6$haloalkenyl, $C_3$–$C_6$alkynyl, $OR_7$, $S(O)_nR_8$ or $NR_9R_{10}$, and when $R_1$ and $R_2$ are taken together with the atoms to which they are attached, they represent a four- to seven-membered saturated or unsaturated ring optionally interrupted by oxygen, sulfur or nitrogen, and optionally substituted with one to three methyl groups or one or more halogen atoms;

X is hydrogen, halogen or $C_1$–$C_4$alkyl;

$X_1$ is hydrogen, halogen, $C_1$–$C_4$alkyl, $C_1$–$C_4$haloalkyl, $C_1$–$C_4$alkoxy or $C_1$–$C_4$haloalkoxy;

Z is O or $S(O)_m$;

Y is halogen, cyano, $R_{12}$, $X_2R_{12}$, $X_3R_{12}$, $X_2X_3R_{12}$ or $X_3X_2R_{12}$;

$X_2$ is O, $S(O)_p$ or $NR_{13}$;

$X_3$ is $-C(=A_3)-$, $-C(=NOR_{14})-$ or $-C(=N-NR_{13}R_{50})$;

$R_4$, $R_5$, $R_6$, $R_7$, $R_8$, $R_9$, $R_{10}$ and $R_{14}$ are each independently hydrogen, $C_1-C_6$alkyl, $C_3-C_7$cycloalkyl, $C_2-C_8$alkoxyalkyl, $C_2-C_6$alkenyl, $C_2-C_6$alkynyl or benzyl;

$R_{12}$ is hydrogen,
- a $C_1-C_6$alkyl, $C_3-C_7$cycloalkyl, $C_2-C_6$alkenyl, $C_5-C_6$cycloalkenyl or $C_2-C_8$alkynyl group, wherein each group is optionally substituted with any combination of one to six halogen atoms, one to three $C_1-C_{20}$alkoxy groups optionally substituted with one $C_1-C_6$alkoxy, benzyloxy or $C_1-C_6$alkylthio group, one or two $C_1-C_{10}$haloalkoxy groups, one or two $NR_{15}R_{16}$ groups, one to three $S(O)_qR_{17}$ groups, one or two cyano groups, one or two $C_3-C_7$cycloalkyl groups, one thiocyano group, one $O(SO_2)R_{17}$ group, one $O(NO_2)$ group, one or two $C(O)R_{18}$ groups, one or two $CO_2R_{19}$ groups, one or two $C(O)SR_{19}$ groups, one or two $C(O)NR_{20}R_{21}$ groups, one to three $X_4R_{22}$ groups, one or two $P(O)(OR_{23})_2$ groups, one or two $Si(R_{24})_3$ groups, one 4- to 10-membered monocyclic or fused bicyclic heterocyclic ring optionally substituted with any combination of one or two oxo groups, one or two thioxo groups, one to three halogen atoms, one to three $C_1-C_4$alkyl groups, one to three $C_1-C_4$haloalkyl groups, one to three $C_1-C_4$alkoxy groups, one to three $C_1-C_4$haloalkoxy groups or one or two $X_4R_{22}$ groups,
- one quaternary organic ammonium group, or
- one or two phenyl groups wherein each phenyl group is independently optionally substituted with any combination of one to three halogen atoms, one to three $C_1-C_6$alkyl groups, one to three $C_1-C_6$alkoxy groups, one $C_3-C_7$cycloalkyl group, one $C_1-C_4$haloalkyl group, one $C_1-C_4$alkylthio group, one cyano group, one nitro group, one $C(O)R_{25}$ group, one $CO_2R_{26}$ group or one $X_5R_{27}$ group,
- phenyl optionally substituted with any combination of one to three halogen atoms, one to three $C_1-C_4$alkyl groups, one to three $C_1-C_4$alkoxy groups, one $C_3-C_6$cycloalkyl group, one $C_1-C_4$haloalkyl group, one $C_1-C_4$alkylthio group, one cyano group, one nitro group, one $C(O)R_{25}$ group, one $CO_2R_{26}$ group, one $X_4R_{22}$ group, one $CH=CHR_2$, group, one $CH_2CH(R_{28})R_{22}$ group or one $N(R_{29})SO_2R_{30}$ group, or
- indan optionally substituted with any combination of one or two halogen atoms, one or two $C_1-C_4$alkyl groups, one $C_1-C_4$alkoxy group, one $C_1-C_4$haloalkyl group, one $C_1-C_4$alkylthio group, one cyano group, one nitro group, one $C(O)R_{25}$ group, one $CO_2R_{26}$ group, one $X_4R_{22}$ group, one $CH=CHR_{22}$ group, one $CH_2CH(R_{28})R_{22}$ group or one $N(R_{29})SO_2R_{30}$ group,
- and when $R_{12}$ and $R_{13}$ are taken together with the nitrogen atom to which they are attached, they form a 5- to 12-membered monocyclic or fused bicyclic, heterocyclic ring optionally substituted with one or more groups independently selected from halogen, cyano, nitro, amino, hydroxyl, $C_1-C_4$alkyl, $C_1-C_4$haloalkyl, $C_1-C_4$alkoxy, $C_1-C_4$haloalkoxy, $C_1-C_4$haloalkylsulfonyl or $X_4R_{22}$ groups;

$R_{13}$ is hydrogen, $C_1-C_8$alkoxyalkyl, $C_1-C_6$alkyl, $C_3-C_7$cycloalkyl, $C_3-C_6$alkenyl, $C_3-C_6$alkynyl, benzyl, $OR_{23}$, cyano, $SO_2R_{51}$ or one 5- to 12-membered monocyclic or fused bicyclic heterocyclic ring optionally substituted with one or more groups independently selected from halogen, cyano, nitro, amino, hydroxyl, $C_1-C_4$alkyl, $C_1-C_4$haloalkyl, $C_1-C_4$alkoxy or $C_1-C_4$haloalkoxy, and when $R_{13}$ and $R_{12}$ are taken together with the nitrogen atom to which they are attached, they form a 5- to 12-membered monocyclic or fused bicyclic, heterocyclic ring optionally substituted with one or more groups independently selected from halogen, cyano, nitro, amino, hydroxyl, $C_1-C_4$alkyl, $C_1-C_4$haloalkyl, $C_1-C_4$alkoxy, $C_1-C_4$haloalkoxy, $C_1-C_4$haloalkylsulfonyl or $X_4R_{22}$ groups;

$R_{28}$ is halogen;

$R_{22}$ and $R_{27}$ are each independently hydrogen, $Si(R_{31})_3$, $C(O)NR_{35}R_{36}$, $C(O)R_{33}$, $SO_2R_{47}$,
- $C_1-C_{20}$alkyl substituted with one hydroxyl, benzyloxy, nitro, $OC(O)R_{33}$, $C_1-C_6$alkoxy, $CO_2R_{32}$, $C(O)R_{33}$, $C(A_4R_{34})_2$, $C(O)NR_{35}R_{36}$, $C(O)ON=CR_{37}R_{38}$, $P(O)(OH)NH_2$, $P(O)(OH)(OR_{23})$, $C(O)NR_{35}OR_{23}$, cyano or 2-dioxolanyl group,
  - one phenyl, dihydrofuranone or furanone ring wherein each ring is optionally substituted with any combination of one to three halogen atoms, one to three $C_1-C_4$alkyl groups, one to three $C_1-C_4$haloalkyl groups, one to three $C_1-C_4$alkoxy groups or one to three $C_1-C_4$haloalkoxy groups, or
  - one 5- to 12-membered monocyclic or fused bicyclic, heterocyclic ring optionally substituted with one or more groups independently selected from halogen, cyano, nitro, amino, hydroxyl, $C_1-C_4$alkyl, $C_1-C_4$haloalkyl, $C_1-C_4$alkoxy, $C_1-C_4$haloalkoxy or $C_1-C_4$haloalkylsulfonyl groups,
- $C_3-C_{20}$alkenyl optionally substituted with one to three halogen atoms, one hydroxyl group, one $C_1-C_6$alkoxy, $CO_2R_{32}$, $C(O)R_{33}$, $C(A_4R_{34})_2$, $C(O)NR_{35}R_{36}$, $C(O)ON=CR_{37}R_{38}$, $C(O)NR_{35}OR_{23}$, cyano or 2-dioxolanyl group, or one phenyl, dihydrofuranone or furanone ring wherein each ring is optionally substituted with any combination of one to three halogen atoms, one to three $C_1-C_4$alkyl groups, one to three $C_1-C_4$haloalkyl groups, one to three $C_1-C_4$alkoxy groups or one to three $C_1-C_4$haloalkoxy groups,
- $C_5-C_8$cycloalkenyl optionally substituted with one hydroxyl, $C_1-C_6$alkoxy, $C_1-C_4$alkyl, $C_2-C_4$alkenyl, $CO_2R_{32}$, $C(O)R_{33}$, $C(A_4R_{34})_2$, $C(O)NR_{35}R_{36}$, $C(O)ON=CR_{37}R_{38}$, $C(O)NR_{35}OR_{23}$, cyano or 2-dioxolanyl group, or one phenyl, dihydrofuranone or furanone ring wherein each ring is optionally substituted with any combination of one to three halogen atoms, one to three $C_1-C_4$alkyl groups, one to three $C_1-C_4$alkoxy groups or one to three $C_1-C_4$haloalkoxy groups,
- $C_3-C_{10}$alkynyl optionally substituted with one hydroxyl, $C_1-C_6$alkoxy, $CO_2R_{32}$, $C(O)R_{33}$, $C(A_4R_{34})_2$, $C(O)NR_{35}R_{36}$, $C(O)ON=CR_{37}R_{38}$, $C(O)NR_{35}OR_{23}$, cyano or 2-dioxolanyl group, or one phenyl, dihydrofuranone or furanone ring wherein each ring is optionally substituted with any combination of one to three halogen atoms, one to three $C_1-C_4$alkyl groups, one to three $C_1-C_4$haloalkyl groups, one to three $C_1-C_4$alkoxy groups or one to three $C_1-C_4$haloalkoxy groups, phenyl optionally substituted with any combination of one to three halogen atoms, one to three $C_1-C_6$alkyl groups, one to three $C_1-C_6$alkoxy groups, one $C_1-C_4$haloalkyl group, one $C_1-C_4$haloalkoxy group, one cyano group, one nitro group, one $NR_{39}R_{40}$ group or one $C(O)R_{33}$ group, benzyl optionally substituted on the phenyl ring with any combination of one to three halogen atoms, one to three $C_1-C_6$alkyl groups, one to three $C_1-C_6$alkoxy groups, one $C_1-C_4$haloalkyl group, one $C_1-C_4$haloalkoxy group, one cyano group, one nitro group, one $NR_{39}R_{40}$ group or one $C(O)R_{33}$ group, or a 4- to 10-membered heterocyclic ring optionally substituted with any combination of one or two oxo groups, one or two thioxo groups, one to three halogen atoms, one to three $C_1-C_4$alkyl groups, one to three $C_1-C_4$haloalkyl groups, one to three $C_1-C_4$alkoxy groups or one to three $C_1-C_4$haloalkoxy groups;

$R_{15}$ and $R_{16}$ are each independently hydrogen,
a $C_1-C_4$alkyl, $C_3-C_7$cycloalkyl, $C_2-C_6$alkenyl or $C_2-C_6$alkynyl group wherein each group is optionally substituted with one $CO_2R_{42}$ group, benzyl optionally substituted with any combination of one to three halogen atoms, one to three $C_1-C_4$alkyl groups, one to three $C_1-C_4$haloalkyl groups, one to three $C_1-C_4$alkoxy groups or one to three $C_1-C_4$haloalkoxy groups, phenyl optionally substituted with any combination of one to three halogen atoms, one to three $C_1-C_4$alkyl groups, one to three $C_1-C_4$haloalkyl groups, one to three $C_1-C_4$alkoxy groups, one to three $C_1-C_4$haloalkoxy groups, one $CO_2R_{26}$ group, $C(O)R_{43}$, or
$CO_2R_{42}$;

$R_{16}$ and $R_{21}$ are each independently hydrogen, $C_1-C_6$alkyl, $C_1-C_4$alkoxy, $C_3-C_7$cycloalkyl, $C_2-C_6$alkenyl, $C_3-C_7$cycloalkenyl, $C_2-C_6$alkynyl, $P(O)(OR_{44})_2$, $SO_2R_{45}$, $C(O)R_{46}$, benzyl optionally substituted with any combination of one to three halogen atoms, one to three $C_1-C_4$alkyl groups, one to three $C_1-C_4$haloalkyl groups, one to three $C_1-C_4$alkoxy groups, one to three $C_1-C_4$haloalkoxy groups or one $X_4R_{22}$ group, or phenyl optionally substituted with any combination of one to three halogen atoms, one to three $C_1-C_4$alkyl groups, one to three $C_1-C_4$haloalkyl groups, one to three $C_1-C_4$alkoxy groups, one to three $C_1-C_4$haloalkoxy groups or one $X_4R_{22}$ group;

$R_{17}$, $R_{18}$, $R_{25}$, $R_{30}$, $R_{33}$, $R_{45}$ and $R_{51}$ are each independently $NR_{46}R_{48}$, $-N=CR_{46}R_{48}$, $C_1-C_8$alkyl optionally substituted with one $C_1-C_6$alkoxy, thiophene or furan group, $C_1-C_6$haloalkyl, $C_3-C_8$cycloalkyl, $CO_2R_{23}$, $C_2-C_6$alkenyl optionally substituted with phenyl, benzyl optionally substituted with any combination of one to three halogen atoms, one to three $C_1-C_4$alkyl groups, one to three $C_1-C_4$haloalkyl groups, one to three $C_1-C_4$alkoxy groups, one to three $C_1-C_4$haloalkoxy groups, one nitro group, one cyano group or one $X_4R_{22}$ group, phenyl optionally substituted with any combination of one to three halogen atoms, one to three $C_1-C_4$alkyl groups, one to three $C_1-C_4$haloalkyl groups, one to three $C_1-C_4$alkoxy groups, one to three $C_1-C_4$haloalkoxy groups, one nitro group, one cyano group or one $X_4R_{22}$ group, or a 5- to 12-membered monocyclic or fused bicyclic, heterocyclic ring optionally substituted with one or more groups independently selected from halogen, cyano, nitro, amino, hydroxyl, $C_1-C_4$alkyl, $C_1-C_4$haloalkyl, $C_1-C_4$alkoxy, $C_1-C_4$haloalkoxy, $C_1-C_4$haloalkylsulfonyl or $X_4R_{22}$ groups;

$R_{19}$ and $R_{26}$ are each independently hydrogen, $C_1-C_{20}$alkyl, $C_1-C_8$haloalkyl, $C_3-C_7$cycloalkyl, $C_3-C_7$halocycloalkyl, $C_3-C_{20}$alkenyl, $C_3-C_8$haloalkenyl, $C_5-C_8$cycloalkenyl, $C_5-C_8$halocycloalkenyl, $C_3-C_8$alkynyl, $C_3-C_8$haloalkynyl, $Si(R_{41})_3$, benzyl, phenyl, furfuryl, pyridyl, thienyl, oximino or an alkali metal, alkaline earth metal, manganese, copper, zinc, cobalt, silver, nickel, ammonium or organic ammonium cation;

$R_{32}$ is hydrogen,
$Si(R_{47})_3$,
di($C_1-C_4$alkyl)imino,
$C_1-C_{20}$alkyl optionally substituted with one $CO_2R_{48}$, $C_1-C_6$alkoxy, $C_1-C_6$thioalkyl, $C_2-C_{20}$alkoxyalkoxy, phenyl, $OSi(R_{47})_3$, $OC(O)R_{33}$, $C_3-C_7$cycloalkyl or di($C_1-C_4$alkyl)imino group,
$C_1-C_{15}$haloalkyl,
$C_3-C_8$cycloalkyl optionally substituted with one $CO_2R_{48}$ group,
$C_3-C_8$halocycloalkyl,
$C_3-C_{20}$alkenyl optionally substituted with one phenyl group,
$C_3-C_{15}$haloalkenyl,
$C_5-C_8$cycloalkenyl,
$C_5-C_8$halocycloalkenyl,
$C_3-C_{20}$alkynyl optionally substituted with one phenyl group,
$C_3-C_{20}$haloalkynyl, benzyl optionally substituted with one or more groups independently selected from halogen, cyano, nitro, $C_1-C_4$alkyl, $C_1-C_4$haloalkyl, $C_1-C_4$alkoxy and $C_1-C_4$haloalkoxy groups, phenyl optionally substituted with one or more groups independently selected from halogen, cyano, nitro, $C_1-C_4$alkyl, $C_1-C_4$haloalkyl, $C_1-C_4$alkoxy and $C_1-C_4$haloalkoxy groups, 2-, 3- or 4-pyridyl,
2- or 3-furyl,
2- or 3-thienyl,
2-tetrahydrofuranyl,
$C_1-C_4$alkyl substituted with one pyridyl, furyl, thienyl, tetrahydrofuryl, $C_3-C_8$cycloalkyl, dioxane or $NR_{49}R_{50}$ group, or an alkali metal, alkaline earth metal, manganese, copper, zinc, cobalt, silver, nickel, ammonium or organic ammonium cation;

$R_{34}$, $R_{37}$, and $R_{38}$ are each independently $C_1-C_6$alkyl;

$R_{35}$ and $R_{49}$ are each independently hydrogen or $C_1-C_4$alkyl and $R_{36}$ and $R_{50}$ are each independently hydrogen, cyano, $C_1-C_6$alkyl, $SO_2R_{51}$ or phenyl optionally substituted with one or more groups independently selected from halogen, cyano, nitro, $C_1-C_4$alkyl, $C_1-C_4$haloalkyl, $C_1-C_4$alkoxy and $C_1-C_4$haloalkoxy groups, or when $R_{35}$ and $R_{36}$ or $R_{49}$ and $R_{50}$ are taken together with the nitrogen atom to which they are attached, they form a 5- to 12-membered monocyclic or fused bicyclic, heterocyclic ring optionally substituted with one or more groups independently selected from halogen, cyano, nitro, amino, hydroxyl, $C_1-C_4$alkyl, $C_1-C_4$haloalkyl, $C_1-C_4$alkoxy, $C_1-C_4$haloalkoxy or $c_1-C_4$haloalkylsulfonyl groups;

m, n, p and q are each independently an integer of 0, 1 or 2;

$R_{29}$ is hydrogen, $C_1$–$C_4$alkyl or $C_1$–$C_4$haloalkyl;

$R_{24}$, $R_{31}$, $R_{41}$ and $R_{47}$ are each independently $C_1$–$C_4$alkyl,
  benzyl optionally substituted with one or more groups independently selected from halogen, cyano, nitro, $C_1$–$C_4$alkyl, $C_1$–$C_4$haloalkyl, $C_1$–$C_4$alkoxy and $C_1$–$C_4$haloalkoxy groups, or
  phenyl optionally substituted with one or more groups independently selected from halogen, cyano, nitro, $C_1$–$C_4$alkyl, $C_1$–$C_4$haloalkyl, $C_1$–$C_4$alkoxy and $C_1$–$C_4$haloalkoxy groups;

$R_{23}$, $R_{39}$, $R_{40}$, $R_{42}$, $R_{43}$, $R_{44}$, $R_{46}$ and $R_{48}$ are each independently hydrogen, $C_2$–$C_6$alkenyl, $C_3$–$C_8$cycloalkyl, $C_1$–$C_8$alkyl optionally substituted with one or two $C_1$–$C_4$ alkoxy groups,
  benzyl optionally substituted with one or more groups independently selected from halogen, cyano, nitro, $C_1$–$C_4$alkyl, $C_1$–$C_4$haloalkyl, $C_1$–$C_4$alkoxy and $C_1$–$C_4$haloalkoxy groups, or
  phenyl optionally substituted with one or more groups independently selected from halogen, cyano, nitro, $C_1$–$C_4$alkyl, $C_1$–$C_4$haloalkyl, $C_1$–$C_4$alkoxy and $C_1$–$C_4$haloalkoxy groups, and
  when $R_{46}$ and $R_{48}$ are taken together with the atom to which they are attached, they form a 5- to 12-membered monocyclic or fused bicyclic, heterocyclic or cycloalkyl ring optionally substituted with one or more groups independently selected from halogen, cyano, nitro, amino, hydroxyl, $C_1$–$C_4$alkyl, $C_1$–$C_4$haloalkyl, $C_1$–$C_4$alkoxy, $C_1$–$C_4$haloalkoxy or $C_1$–$C_4$haloalkylsulfonyl groups; and A, $A_1$, $A_3$, $A_4$, $X_4$ and $X_5$ are each independently O or S; and the optical isomers, diastereomers and/or tautomers thereof.

More preferred formula I herbicidal agents of the present invention are those wherein R is $C_1$–$C_4$alkyl, $C_1$–$C_4$haloalkyl, $C_3$–$C_4$alkenyl, $C_3$–$C_4$alkynyl or benzyl;

$R_1$ is halogen or $C_1$–$C_4$haloalkyl;

$R_2$ is hydrogen, halogen or $C_1$–$C_4$haloalkyl;

X and $X_1$ are each independently hydrogen or halogen;

Z is O or S;

Y is cyano, $R_{12}$, $X_2R_{12}$ or $X_3X_2R_{12}$;

$X_2$ is O, S or $NR_{13}$;

$X_3$ is —C(=$A_3$)—, —C(=$NOR_{14}$)— or —C(=N—$NR_{13}R_{50}$);

$R_{12}$ is hydrogen,
  a $C_1$–$C_6$alkyl, $C_3$–$C_7$cycloalkyl, $C_2$–$C_6$alkenyl, $C_5$–$C_6$cycloalkenyl or $C_2$–$C_6$ alkynyl group, wherein each group is optionally substituted with any combination of one to three halogen atoms, one or two $C_1$–$C_{20}$alkoxy groups, one or two $C_1$–$C_{10}$haloalkoxy groups, one $NR_{15}R_{16}$ group, one $S(O)_qR_{17}$ group, one or two cyano groups, one or two $C(O)R_{18}$ groups, one or two $CO_2R_{19}$ groups, one or two $C(O)SR_{15}$ groups, one or two $C(O)NR_{20}R_{21}$ groups, one or two $X_4R_{22}$ groups, one $P(O)(OR_{23})_2$ group, one $Si(R_{24})_3$ group,
    one 4- to 10-membered monocyclic or fused bicyclic heterocyclic ring optionally substituted with any combination of one or two oxo groups, one or two thioxo groups, one to three halogen atoms, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups or one or two $X_4R_{22}$ groups,
    one quaternary organic ammonium group, or
    one phenyl group optionally substituted with any combination of one to three halogen atoms, one $C_1$–$C_6$alkyl group, one $C_1$–$C_6$alkoxy group, one $C_3$–$C_7$cycloalkyl group, one cyano group, one nitro group, one $C(O)R_{25}$ group, one $CO_2R_{26}$ group or one $X_5R_{27}$ group, or
  phenyl optionally substituted with any combination of one or two halogen atoms, one to three $C_1$–$C_4$alkyl groups, one or two $C_1$–$C_4$alkoxy groups, one $C_3$–$C_6$cycloalkyl group, one $C_1$–$C_4$haloalkyl group, one $C_1$–$C_4$alkylthio group, one cyano group, one nitro group, one $C(O)R_{25}$ group, one $CO_2R_{26}$ group, one $X_4R_{22}$ group, one CH=$CHR_{22}$ group, one $CH_2CH(R_{28})R_{22}$ group or one $N(R_{29})SO_2R_{30}$ group;

$R_{13}$ is hydrogen, $C_2$–$C_6$alkoxyalkyl, $C_1$–$C_4$alkyl, $C_3$–$C_7$cycloalkyl, $C_3$–$C_6$alkenyl, $C_3$–$C_6$alkynyl, benzyl, $OR_{23}$, cyano or $SO_2R_{51}$;

$R_{28}$ is halogen;

$R_{22}$ and $R_{27}$ are each independently hydrogen, $Si(R_{31})_3$, $C(O)NR_{35}R_{36}$, $C(O)R_{33}$, $SO_2R_{47}$,
  $C_{1-20}$alkyl substituted with one hydroxyl, benzyloxy, nitro, $OC(O)R_{33}$, $C_1$–$C_6$alkoxy, $CO_2R_{32}$, $C(O)R_{33}$, $C(A_4R_{34})_2$, $C(O)NR_{35}R_{36}$, $C(O)ON=CR_{37}R_{38}$, $P(O)(OH)NH_2$, $P(O)(OH)(OR_{23})$, $C(O)NR_{35}OR_{23}$, cyano or 2-dioxolanyl group,
    one phenyl, dihydrofuranone or furanone ring wherein each ring is optionally substituted with any combination of one to three halogen atoms, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups, or
    one 5- to 12-membered monocyclic or fused bicyclic, heterocyclic ring optionally substituted with one or more groups independently selected from halogen, cyano, nitro, amino, hydroxyl, $C_1$–$C_4$alkyl, $C_1$–$C_4$haloalkyl, $C_1$–$C_4$alkoxy, $C_1$–$C_4$haloalkoxy or $C_1$–$C_4$haloalkylsulfonyl groups,
  $C_3$–$C_{20}$alkenyl optionally substituted with one to three halogen atoms, one hydroxyl group, one $C_1$–$C_6$alkoxy, $CO_2R_{32}$, $C(O)R_{33}$, $C(A_4R_{34})_2$, $C(O)NR_{35}R_{36}$, $C(O)ON=CR_{37}R_{38}$, $C(O)NR_{35}OR_{23}$, cyano or 2-dioxolanyl group, or one phenyl, dihydrofuranone or furanone ring wherein each ring is optionally substituted with any combination of one to three halogen atoms, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups,
  $C_5$–$C_8$cycloalkenyl optionally substituted with one hydroxyl, $C_1$–$C_6$alkoxy, $C_1$–$C_4$alkyl, $C_2$–$C_4$alkenyl, $CO_2R_{32}$, $C(O)R_{33}$, $C(A_4R_{34})_2$, $C(O)NR_{35}R_{36}$, $C(O)ON=CR_{37}R_{38}$, $C(O)NR_{35}OR_{23}$, cyano or 2-dioxolanyl group, or one phenyl, dihydrofuranone or furanone ring wherein each ring is optionally substituted with any combination of one to three halogen atoms, one to three $C_1$–$C_4$alkyl groups, one to three $C_1$–$C_4$alkoxy groups or one to three $C_1$–$C_4$haloalkoxy groups,
  $C_3$–$C_{10}$alkynyl optionally substituted with one hydroxyl, $C_1$–$C_6$alkoxy, $CO_2R_{32}$, $C(O)R_{33}$, $C(A_4R_{34})_2$, $C(O)NR_{35}R_{36}$, $C(O)ON=CR_{37}R_{38}$, $C(O)NR_{35}OR_{23}$, cyano or 2-dioxolanyl group, or one phenyl, dihydrofuranone or furanone ring wherein each ring is optionally substituted with any combination of one to three halogen atoms, one to three $C_1$–$C_4$alkyl groups, one to three $C_1$–$C_5$haloalkyl groups, one to three $C_1$–$C_4$alkoxy groups or one to three $C_1$–$C_4$haloalkoxy groups, phenyl optionally substituted with any combination of one to three halogen atoms, one to three $C_1$–$C_6$alkyl groups, one to three $C_1$–$C_4$alkoxy groups, one $C_1$–$C_4$haloalkyl group, one $C_1$–$C_4$haloalkoxy group, one cyano group, one nitro group, one $NR_{39}R_{40}$ group or one $C(O)R_{33}$ group, benzyl optionally substituted on the phenyl ring with any combination of one to three halogen atoms, one to three $C_1$–$C_6$alkyl groups, one to three $C_1$–$C_6$alkoxy groups, one $C_1$–$C_4$haloalkyl group, one $C_1$–$C_4$haloalkoxy group, one cyano group, one nitro group, one $NR_{39}R_{40}$ group or one $C(O)R_{33}$ group, or a 4- to 10-membered heterocyclic ring optionally substituted with any combination of one or two oxo groups, one or two thioxo groups, one to three halogen atoms, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups;

$R_{15}$ and $R_{20}$ are each independently hydrogen, a $C_1$–$C_6$alkyl, $C_3$–$C_7$cycloalkyl, $C_2$–$C_6$alkenyl or $C_2$–$C_6$alkynyl group wherein each group is optionally substituted with one $CO_2R_{42}$ group, benzyl optionally substituted with any combination of one to three halogen atoms, one to three $C_3$–$C_4$alkyl groups, one to three $C_1$–$C_4$haloalkyl groups, one to three $C_1$–$C_4$alkoxy groups or one to three $C_1$–$C_4$haloalkoxy groups, phenyl optionally substituted with any combination of one to three halogen atoms, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups, one $CO_2R_{26}$ group, $C(O)R_{43}$, or $CO_2R_{42}$;

$R_{14}$ is hydrogen, $C_1$–$C_6$alkyl, $C_3$–$C_7$cycloalkyl, $C_2$–$C_8$alkoxyalkyl, $C_2$–$C_6$alkenyl, $C_2$–$C_6$alkynyl or benzyl;

$R_{16}$ and $R_{21}$ are each independently hydrogen, $C_1$–$C_6$alkyl, $C_1$–$C_4$alkoxy, $C_3$–$C_7$cycloalkyl, $C_2$–$C_6$alkenyl, $C_3$–$C_7$cycloalkenyl, $C_2$–$C_6$alkynyl, $P(O)(OR_{44})_2$, $SO_2R_{45}$, $C(O)R_{46}$, benzyl optionally substituted with any combination of one to three halogen atoms, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups, or phenyl optionally substituted with any combination of one to three halogen atoms, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups;

$R_{17}$, $R_{18}$, $R_{25}$, $R_{30}$, $R_{33}$, $R_{45}$ and $R_{51}$ are each independently $NR_{46}R_{48}$, $-N=CR_{46}R_{48}$, $C_1$–$C_8$alkyl optionally substituted with one $C_1$–$C_6$alkoxy, thiophene or furan group, $C_1$–$C_6$haloalkyl, $C_3$–$C_8$cycloalkyl, $CO_2R_{23}$, $C_2$–$C_6$alkenyl optionally substituted with phenyl, benzyl optionally substituted with any combination of one to three halogen atoms, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups, one nitro group, one cyano group or one $X_4R_{22}$ group, phenyl optionally substituted with any combination of one to three halogen atoms, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups, one nitro group, one cyano group or one $X_4R_{22}$ group, or a 5- to 12-membered monocyclic or fused bicyclic, heterocyclic ring optionally substituted with one or more groups independently selected from halogen, cyano, nitro, amino, hydroxyl, $C_1$–$C_4$alkyl, $C_1$–$C_4$haloalkyl, $C_1$–$C_4$alkoxy, $C_1$–$C_4$haloalkoxy, $C_1$–$C_4$haloalkylsulfonyl or $X_4R_{22}$ groups;

$R_{19}$ and $R_{26}$ are each independently hydrogen, $C_1$–$C_{20}$alkyl, $C_1$–$C_8$haloalkyl, $C_3$–$C_7$cycloalkyl, $C_3$–$C_7$halocycloalkyl, $C_3$–$C_{20}$alkenyl, $C_3$–$C_8$haloalkenyl, $C_3$–$C_8$cycloalkenyl, $C_5$–$C_8$halocycloalkenyl, $C_3$–$C_8$alkynyl, $C_3$–$C_8$haloalkynyl, $Si(R_{41})_3$, benzyl, phenyl, furfuryl, pyridyl, thienyl, oximino or an alkali metal, alkaline earth metal, manganese, copper, zinc, cobalt, silver, nickel, ammonium or organic ammonium cation;

$R_{32}$ is hydrogen, $Si(R_{47})_3$, $C_1$–$C_{20}$ alkyl optionally substituted with one $CO_2R_{48}$, $C_1$–$C_6$alkoxy, $C_1$–$C_6$thioalkyl, $C_2$–$C_{20}$alkoxyalkoxy, phenyl, $OSi(R_{47})_3$, $OC(O)R_{33}$, $C_3$–$C_7$cycloalkyl or $di(C_1$–$C_4$alkyl)imino group, $C_1$–$C_{15}$haloalkyl, $C_3$–$C_8$cycloalkyl optionally substituted with one $CO_2R_{48}$ group, $C_3$–$C_8$halocycloalkyl, $C_3$–$C_{20}$alkenyl optionally substituted with one phenyl group, $C_3$–$C_{15}$haloalkenyl, $C_5$–$C_8$cycloalkenyl, $C_5$–$C_8$halocycloalkenyl, $C_3$–$C_{20}$ alkynyl optionally substituted with one phenyl group, $C_3$–$C_{20}$ haloalkynyl, benzyl optionally substituted with one or more groups independently selected from halogen, cyano, nitro, $C_1$–$C_4$alkyl, $C_1$–$C_4$haloalkyl, $C_1$–$C_4$alkoxy and $C_1$–$C_4$haloalkoxy groups, phenyl optionally substituted with one or more groups independently selected from halogen, cyano, nitro, $C_1$–$C_4$alkyl, $C_1$–$C_4$haloalkyl, $C_1$–$C_4$alkoxy and $C_1$–$C_4$haloalkoxy groups, $C_1$–$C_4$alkyl substituted with one pyridyl, furyl, thienyl, tetrahydrofuryl, $C_3$–$C_8$cycloalkyl, dioxane or $NR_{49}R_{50}$ group, or an alkali metal, alkaline earth metal, manganese, copper, zinc, cobalt, silver, nickel, ammonium or organic ammonium cation;

$R_{34}$, $R_{37}$ and $R_{38}$ are each independently $C_1$–$C_6$alkyl;

$R_{35}$ and $R_{49}$ are each independently hydrogen or $C_1$–$C_6$alkyl and $R_{36}$ and $R_{40}$ are each independently hydrogen, cyano, $C_1$–$C_6$alkyl, $SO_2R_{51}$ or phenyl optionally substituted with one or more groups independently selected from halogen, cyano, nitro, $C_1$–$C_4$alkyl, $C_1$–$C_4$haloalkyl, $C_1$–$C_4$alkoxy and $C_1$–$C_4$haloalkoxy groups, or when $R_{35}$ and $R_{36}$ or $R_{49}$ and $R_{50}$ are taken together with the nitrogen atom to which they are attached, they form a 5- to 12-membered monocyclic or fused bicyclic, heterocyclic ring optionally substituted with one or more groups independently selected from halogen, cyano, nitro, amino, hydroxyl, $C_1$–$C_4$alkyl, $C_1$–$C_4$haloalkyl, $C_1$–$C_4$alkoxy, $C_1$–$C_4$haloalkoxy or $C_1$–$C_4$haloalkylsulfonyl groups;

q is an integer of 0, 1 or 2;

$R_{29}$ is hydrogen, $C_1$–$C_4$alkyl or $C_1$–$C_4$haloalkyl;

$R_{24}$, $R_{31}$, $R_{41}$ and $R_{47}$ are each independently $C_1$–$C_4$alkyl,
  benzyl optionally substituted with one or more groups independently selected from halogen, cyano, nitro, $C_1$–$C_4$alkyl, $C_1$–$C_4$haloalkyl, $C_1$–$C_4$alkoxy and $C_1$–$C_4$haloalkoxy groups, or
  phenyl optionally substituted with one or more groups independently selected from halogen, cyano, nitro, $C_1$–$C_4$alkyl, $C_1$–$C_4$haloalkyl, $C_1$–$C_4$alkoxy and $C_1$–$C_4$haloalkoxy groups;

$R_{23}$, $R_{39}$, $R_{40}$, $R_{42}$, $R_{43}$, $R_{44}$, $R_{46}$ and $R_{48}$ are each independently hydrogen, $C_2$–$C_6$alkenyl, $C_3$–$C_8$cycloalkyl,
  $C_1$–$C_8$alkyl optionally substituted with one or two $C_1$–$C_4$alkoxy groups,
  benzyl optionally substituted with one or more groups independently selected from halogen, cyano, nitro, $C_1$–$C_4$alkyl, $C_1$–$C_4$haloalkyl, $C_1$–$C_4$alkoxy and $C_1$–$C_4$haloalkoxy groups, or
  phenyl optionally substituted with one or more groups independently selected from halogen, cyano, nitro, $C_1$–$C_4$alkyl, $C_1$–$C_4$haloalkyl, $C_1$–$C_4$alkoxy and $C_1$–$C_4$haloalkoxy groups; and A, $A_1$, $A_3$, $A_4$, $X_4$ and $X_5$ are each independently O or S; and the optical isomers, diastereomers and/or tautomers thereof.

Another group of more preferred herbicidal agents of formula I are those wherein R is $C_1$–$C_4$alkyl;

$R_1$ is $C_1$–$C_4$haloalkyl;

$R_2$ is hydrogen,

X and $X_1$ are each independently hydrogen or halogen;

Z is O or S;

Y is $R_{12}$, $OR_{12}$, $C(O)NR_{13}R_{12}$, $C(O)R_{12}$, $CO_2R_{12}$, $C(O)SR_{12}$ or $C(=NOR_{14})$;

$R_{12}$ is hydrogen,
  a $C_1$–$C_6$alkyl or $C_2$–$C_6$alkenyl group, wherein each group is optionally substituted with any combination of one to three halogen atoms, one or two $C_1$–$C_4$alkoxy groups, one $C_1$–$C_{10}$haloalkoxy group, one $NR_{15}R_{16}$ group, one $S(O)_qR_{17}$ group, one or two cyano groups, one or two $C(O)R_{18}$ groups, one or two $CO_2R_{19}$ groups, one or two $C(O)NR_{20}R_{21}$ groups, one $X_4R_{22}$ group, one $P(O)(OR_{23})_2$ group, one $OC(O)R_{33}$ group,
    one imidazole ring optionally substituted with any combination of one to three halogen atoms, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups,
    one phthalimide ring optionally substituted with any combination of one to three halogen atoms, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups,
    one quaternary organic ammonium group, or
    one phenyl group optionally substituted with any combination of one to three halogen atoms, one $C_1$–$C_4$alkyl group, one $C_1$–$C_4$alkoxy group or one $X_5R_{27}$ group, or
  phenyl optionally substituted with any combination of one or two halogen atoms, one to three $C_1$–$C_4$alkyl groups, one $C_1$–$C_4$alkoxy group, one $C(O)R_{25}$ group, one $CO_2R_{26}$ group, one $X_4R_{22}$ group, one $CH=CHR_{22}$ group, one $CH_2CH(R_{28})R_{22}$ group or one $N(R_{29})SO_2R_{30}$ group;

$R_{13}$ is hydrogen, $C_1$–$C_6$alkoxyalkyl, $C_1$–$C_4$alkyl, $OR_{23}$, cyano or $SO_2R_{51}$;

$R_{28}$ is halogen;

$R_{22}$ and $R_{27}$ are each independently hydrogen, $C(O)R_{33}$, $SO_2R_{47}$,
  $C_1$–$C_4$alkyl substituted with one $C_1$–$C_6$alkoxy, $CO_2R_{32}$, $C(O)R_{33}$, $C(O)N_{35}R_{36}$, $C(O)ON=CR_{37}R_{38}$, $C(O)NHOR_{23}$, cyano or 2-dioxolanyl group, or one phenyl, dihydrofuranone or furanone ring wherein each ring is optionally substituted with any combination of one to three halogen atoms, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups,
  $C_3$–$C_6$alkenyl optionally substituted with one $C_1$–$C_6$alkoxy, $CO_2R_{32}$, $C(O)R_{33}$ or $C(OR_{34})_2$ group,
  $C_3$–$C_6$alkynyl,
  phenyl optionally substituted with any combination of one to three halogen atoms, one or two $C_1$–$C_4$alkyl groups, one or two $C_1$–$C_4$alkoxy groups, one $C_1$–$C_4$haloalkyl group, one $C_1$–$C_4$haloalkoxy group, one cyano group, one nitro group, one $NR_{39}R_{40}$ group or one $C(O)R_{33}$ group, or
  benzyl optionally substituted on the phenyl ring with any combination of one to three halogen atoms, one or two $C_1$–$C_4$alkyl groups, one or two $C_1$–$C_4$alkoxy groups, one $C_1$–$C_4$haloalkyl group, one $C_1$–$C_4$haloalkoxy group, one cyano group, one nitro group, one $NR_{39}R_{40}$ group or one $C(O)R_{33}$ group;

$R_{20}$ is hydrogen,
  a $C_1$–$C_6$alkyl, $C_3$–$C_7$cycloalkyl, $C_2$–$C_6$alkenyl or $C_2$–$C_6$alkynyl group wherein each group is optionally substituted with one $CO_2R_{42}$ group,
  benzyl optionally substituted with any combination of one to three halogen atoms, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups,
  phenyl optionally substituted with any combination of one to three halogen atoms, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups, one $CO_2R_{26}$ group,
  $C(O)R_{43}$, or
  $CO_2R_{42}$;

$R_{14}$ is hydrogen, $C_1$–$C_6$alkyl, $C_3$–$C_7$cycloalkyl, $C_2$–$C_8$alkoxyalkyl, $C_2$–$C_6$alkenyl, $C_2$–$C_6$alkynyl or benzyl;

$R_{15}$ is hydrogen,
  $C_1$–$C_4$alkyl optionally substituted with one $CO_2R_{42}$ group,
  benzyl optionally substituted with any combination of one to three halogen atoms, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups, or
  $C(O)R_{43}$;

$R_{16}$ is hydrogen, $C_1$–$C_4$alkyl, $P(O)(OR_{44})_2$, $SO_2R_{45}$, $C(O)R_{46}$, or
  benzyl optionally substituted with any combination of one to three halogen atoms, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups;

$R_{21}$ is hydrogen, $C_1$–$C_6$alkyl, $C_1$–$C_4$alkoxy, $C_3$–$C_7$cycloalkyl, $C_2$–$C_6$alkenyl, $C_3$–$C_7$cycloalkenyl, $C_2$–$C_6$alkynyl, $P(O)(OR_{44})_2$, $SO_2R_{45}$, $C(O)R_{46}$,
  benzyl optionally substituted with any combination of one to three halogen atoms, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups, or
  phenyl optionally substituted with any combination of one to three halogen atoms, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups;

$R_{17}$, $R_{18}$, $R_{25}$, $R_{30}$, $R_{33}$, $R_{45}$ and $R_{51}$ are each independently $NR_{46}R_{48}$, $C_1$–$C_4$alkyl, $C_1$–$C_4$haloalkyl,
  $C_2$–$C_6$alkenyl optionally substituted with phenyl,
  benzyl optionally substituted with any combination of one to three halogen atoms, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups, one nitro group, one cyano group or one $X_4R_{22}$ group, or
  phenyl optionally substituted with any combination of one to three halogen atoms, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups, one nitro group, one cyano group or one $X_4R_{22}$ group;

$R_{19}$ and $R_{25}$ are each independently hydrogen, $C_1$–$C_4$alkyl, $C_3$–$C_6$alkenyl, $C_3$–$C_6$alkynyl, $Si(R_{41})_3$, benzyl, phenyl, furfuryl, pyridyl, thienyl, oximino or an alkali metal, alkaline earth metal, manganese, copper, zinc, cobalt, silver, nickel, ammonium or organic ammonium cation;

$R_{32}$ is hydrogen,
  $Si(R_{47})_3$,
  $C_1$–$C_4$alkyl optionally substituted with one $CO_2R_{48}$, $OC(O)R_{33}$ or $C_1$–$C_4$alkoxy group,
  $C_1$–$C_4$haloalkyl,
  $C_3$–$C_8$cycloalkyl,
  $C_3$–$C_8$halocycloalkyl,
  $C_3$–$C_6$alkenyl optionally substituted with one phenyl group,
  $C_3$–$C_6$haloalkenyl,
  $C_5$–$C_8$cycloalkenyl,
  $C_5$–$C_8$halocycloalkenyl,
  $C_3$–$C_6$alkynyl optionally substituted with one phenyl group,
  $C_3$–$C_6$haloalkynyl,
  benzyl optionally substituted with one or more groups independently selected from halogen, cyano, nitro, $C_1$–$C_4$alkyl, $C_1$–$C_4$haloalkyl, $C_1$–$C_4$alkoxy and $C_1$–$C_4$haloalkoxy groups,
  phenyl optionally substituted with one or more groups independently selected from halogen, cyano, nitro, $C_1$–$C_4$alkyl, $C_1$–$C_4$haloalkyl, $C_1$–$C_4$alkoxy and $C_1$–$C_4$haloalkoxy groups,
  $C_1$–$C_4$alkyl substituted with one pyridyl, furyl, thienyl, tetrahydrofuryl or $NR_{49}R_{50}$ group, or
  an alkali metal, alkaline earth metal, manganese, copper, zinc, cobalt, silver, nickel, ammonium or organic ammonium cation;

$R_{34}$, $R_{37}$ and $R_{38}$ are each independently $C_1$–$C_6$alkyl;

$R_{35}$ and $R_{49}$ are each independently hydrogen or $C_1$–$C_4$alkyl and $R_{36}$ and $_{50}$ are each independently hydrogen, cyano, $C_1$–$C_4$alkyl, $SO_2R_{51}$ or phenyl optionally substituted with one or more groups independently selected from halogen, cyano, nitro, $C_1$–$C_4$alkyl, $C_1$–$C_4$haloalkyl, $C_1$–$C_4$alkoxy and $C_1$–$C_4$haloalkoxy groups, or when $R_{35}$ and $R_{36}$ or $R_{49}$ and $R_{50}$ are taken together with the nitrogen atom to which they are attached, they form a 5- to 12-membered monocyclic or fused bicyclic, heterocyclic ring optionally substituted with one or more groups independently selected from halogen, cyano, nitro, amino, hydroxyl, $C_1$–$C_4$alkyl, $C_1$–$C_4$haloalkyl, $C_1$–$C_4$alkoxy, $C_1$–$C_4$haloalkoxy or $C_1$–$C_4$haloalkylsulfonyl groups;

q is an integer of 0, 1 or 2;

$R_{29}$ is hydrogen, $C_1$–$C_4$alkyl or $C_1$–$C_4$haloalkyl;

$R_{41}$ and $R_{47}$ are each independently $C_1$–$C_4$alkyl,
  benzyl optionally substituted with one or more groups independently selected from halogen, cyano, nitro, $C_1$–$C_4$alkyl, $C_1$–$C_4$haloalkyl, $C_1$–$C_4$alkoxy and $C_1$–$C_4$haloalkoxy groups, or
  phenyl optionally substituted with one or more groups independently selected from halogen, cyano, nitro, $C_1$–$C_4$alkyl, $C_1$–$C_4$haloalkyl, $C_1$–$C_4$alkoxy and $C_1$–$C_4$haloalkoxy groups;

$R_{39}$, $R_{40}$, $R_{42}$, $R_{43}$, $R_{44}$, $R_{46}$ and $R_{48}$ are each independently hydrogen, $C_1$–$C_6$alkenyl, $C_3$–$C_8$cycloalkyl,
  $C_1$–$C_8$alkyl optionally substituted with one or two $C_1$–$C_4$alkoxy groups,
  benzyl optionally substituted with one or more groups independently selected from halogen, cyano, nitro, $C_1$–$C_4$alkyl, $C_1$–$C_4$haloalkyl, $C_1$–$C_4$alkoxy and $C_1$–$C_4$haloalkoxy groups, or
  phenyl optionally substituted with one or more groups independently selected from halogen, cyano, nitro, $C_1$–$C_4$alkyl, $C_1$–$C_4$haloalkyl, $C_1$–$C_4$alkoxy and $C_1$–$C_4$haloalkoxy groups;

$A_1$, $X_4$ and $X_5$ are each independently O or S;

$R_{23}$ is hydrogen or $C_1$–$C_4$ alkyl; and

A is O.

A third group of more preferred herbicidal agents of formula I are those wherein R is methyl;

$R_1$ is trifluoromethyl;

$R_2$ and $X_1$ are hydrogen;

X is hydrogen or fluorine;

Z is O or S;

Y is $R_{12}$, $CO_2R_{12}$, $C(O)R_{12}$ or $C(O)NR_{13}R_{12}$;

$R_{12}$ is hydrogen,
  $C_1$–$C_6$alkyl optionally substituted with any combination of one to three halogen atoms, one hydroxyl group, one or two $C_1$–$C_4$alkoxy groups, one $C_1$–$C_4$haloalkoxy group, one $SO_2R_{17}$ group, one or two cyano groups, one $C(O)R_{18}$ group, one or two $CO_2R_{19}$ groups, one or two $C(O)NR_{20}R_{21}$ groups, one $P(O)(OR_{23})_2$ group or one $OC(O)R_{33}$ group,
  $C_2$–$C_6$alkenyl optionally substituted with any combination of one $C(O)R_{18}$ group or one $CO_2R_{19}$ group,

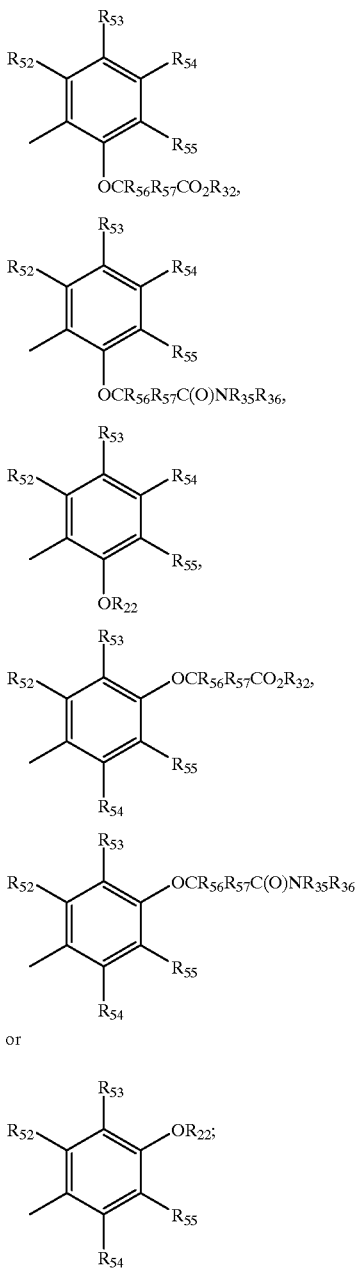

$R_{13}$ is hydrogen, $C_1$–$C_4$alkyl or $SO_2R_{51}$;

$R_{14}$ is hydrogen, $C_1$–$C_4$alkyl or benzyl;

$R_{18}$, $R_{23}$, $R_{56}$ and $R_{57}$ are each independently hydrogen or $C_1$–$C_3$alkyl;

$R_{52}$, $R_{53}$, $R_{54}$ and $R_{55}$ are each independently hydrogen, $C_1$–$C_3$alkyl, $C_2$–$C_3$alkenyl, $C_1$–$C_3$alkoxy or halogen, provided that at least one of $R_{52}$, $R_{53}$, $R_{54}$ and $R_{55}$ is hydrogen;

$R_{19}$ is hydrogen, $C_1$–$C_4$alkyl, $C_3$–$C_6$alkenyl, $C_3$–$C_6$alkynyl, benzyl, pyridyl or an alkali metal, alkaline earth metal, ammonium or organic ammonium cation;

$R_{20}$ is hydrogen,
 a $C_1$–$C_6$alkyl, $C_3$–$C_7$cycloalkyl, $C_2$–$C_6$alkenyl or $C_2$–$C_6$alkynyl group wherein each group is optionally substituted with one $CO_2R_{42}$ group,
 benzyl optionally substituted with any combination of one to three halogen atoms, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups,
 phenyl optionally substituted with any combination of one to three halogen atoms, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups, one $CO_2R_{26}$ group, $C(O)R_{43}$, or
$CO_2R_{42}$;

$R_{21}$ is hydrogen, $C_1$–$C_6$alkyl, $C_1$–$C_4$alkoxy, $C_3$–$C_7$cycloalkyl, $C_2$–$C_6$alkenyl, $C_3$–$C_7$cycloalkenyl, $C_2$–$C_6$alkynyl, $P(O)(OR_{44})_2$, $SO_2R_{45}$, $C(O)R_{46}$,
 benzyl optionally substituted with any combination of one to three halogen atoms, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups, or
 phenyl optionally substituted with any combination of one to three halogen atoms, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups;

$R_{22}$ is hydrogen, $C(O)R_{33}$, $SO_2R_{47}$,
 $C_1$–$C_4$alkyl optionally substituted with one cyano group,
 $C_3$–$C_6$alkenyl, or
 $C_3$–$C_6$alkynyl;

$R_{32}$ is hydrogen,
 $C_1$–$C_4$alkyl optionally substituted with one $CO_2R_{48}$ or $C_1$–$C_4$alkoxy group,
 $C_1$–$C_4$haloalkyl,
 $C_3$–$C_6$alkenyl optionally substituted with one phenyl group,
 $C_3$–$C_6$alkynyl optionally substituted with one phenyl group,
 $C_1$–$C_4$alkyl substituted with one pyridyl, furyl, thienyl, tetrahydrofuryl or $NR_{49}R_{50}$ group, or
 an alkali metal, alkaline earth metal, ammonium or organic ammonium cation;

$R_{35}$ and $R_{49}$ are each independently hydrogen or $C_1$–$C_4$alkyl;

$R_{36}$ is $SO_2R_{51}$ or $C_1$–$C_3$alkoxy;

$R_{17}$, $R_{33}$ and $R_{51}$ are each independently $C_1$–$C_4$alkyl, $C_1$–$C_4$haloalkyl, $NR_{46}R_{48}$, $C_3$–$C_6$cycloalkyl or an isoxazole ring;

$R_{45}$ is $NR_{46}R_{48}$, $C_1$–$C_4$alkyl, $C_1$–$C_4$haloalkyl,
 $C_2$–$C_6$alkenyl optionally substituted with phenyl,
 benzyl optionally substituted with any combination of one to three halogen atoms, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups, one nitro group, one cyano group or one $X_4R_{22}$ group, or
 phenyl optionally substituted with any combination of one to three halogen atoms, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups, one nitro group, one cyano group or one $X_4R_{22}$ group;

$R_{26}$ is hydrogen, $C_1$–$C_4$alkyl, $C_3$–$C_6$alkenyl, $C_3$–$C_6$alkynyl, $Si(R_{41})_3$, benzyl, phenyl, furfuryl, pyridyl, thienyl, oximino or an alkali metal, alkaline earth metal, manganese, copper, zinc, cobalt, silver, nickel, ammonium or organic ammonium cation;

$R_{41}$ is $C_1$–$C_4$alkyl,
benzyl optionally substituted with one or more groups independently selected from halogen, cyano, nitro, $C_1$–$C_4$alkyl, $C_1$–$C_4$haloalkyl, $C_1$–$C_4$alkoxy and $C_1$–$C_4$haloalkoxy groups, or
phenyl optionally substituted with one or more groups independently selected from halogen, cyano, nitro, $C_1$–$C_4$alkyl, $C_1$–$C_4$haloalkyl, $C_1$–$C_4$ alkoxy and $C_1$–$C_4$haloalkoxy groups;

$R_{42}$, $R_{43}$ and $R_{44}$ are each independently hydrogen, $C_2$–$C_6$alkenyl, $C_3$–$C_8$cycloalkyl,
$C_1$–$C_8$alkyl optionally substituted with one or two $C_1$–$C_4$alkoxy groups,
benzyl optionally substituted with one or more groups independently selected from halogen, cyano, nitro, $C_1$–$C_4$alkyl, $C_1$–$C_4$haloalkyl, $C_1$–$C_4$alkoxy and $C_1$–$C_4$haloalkoxy groups, or
phenyl optionally substituted with one or more groups independently selected from halogen, cyano, nitro, $C_1$–$C_4$alkyl, $C_1$–$C_4$haloalkyl, $C_1$–$C_4$alkoxy and $C_1$–$C_4$haloalkoxy groups;

$X_4$ is O or S;
$R_{46}$ and $R_{48}$ are each independently hydrogen, $C_1$–$C_4$alkyl or benzyl;
$R_{47}$ is $C_1$–$C_4$alkyl;
$R_{50}$ is $C_1$–$C_4$alkyl or
phenyl optionally substituted with one or more groups independently selected from halogen, cyano, $C_1$–$C_4$alkyl, $C_1$–$C_4$haloalkyl, $C_1$–$C_4$alkoxy and $C_1$–$C_4$haloalkoxy groups; and
A and $A_1$ are O.

Most preferred formula I compounds of this invention are those wherein
R is methyl;
$R_1$ is trifluoromethyl;
$R_2$ and $X_1$ are hydrogen;
X is hydrogen or fluorine;
Z is O or S;
Y is $C_1$–$C_3$alkyl, $CO_2R_{32}$, halomethyl, cyanomethyl, $C(CH_3)_2CO_2R_{32}$, $C_1$–$C_3$alkoxyethyl, $C_1$–$C_3$alkoxymethyl, hydroxymethyl, CHO, $C(O)CH_3$, $CH(CH_3)(C_1$–$C_4$alkoxy), $C(CH_3)_2CN$, $CH[O(C_1$–$C_3$alkyl)]_2$, $CH_2SO_2R_{17}$, $C(O)NHSO_2R_{51}$,

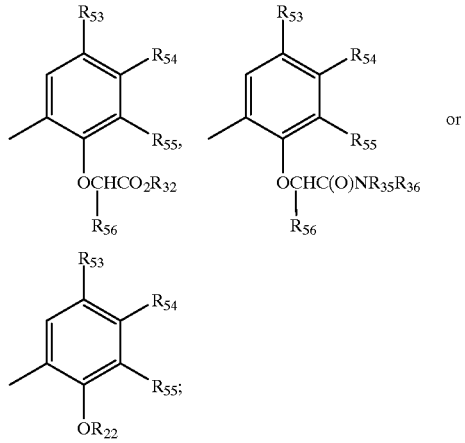

$R_{53}$, $R_{54}$, $R_{55}$ and $R_{56}$ are each independently hydrogen or methyl, provided that at least one of $R_{53}$, $R_{54}$ and $R_{55}$ is hydrogen;

$R_{22}$ is cyanomethyl, methyl, ethyl, allyl or propargyl;
$R_{32}$ is hydrogen,
$C_1$–$C_4$alkyl optionally substituted with one $CO_2R_{48}$ group,
$C_1$–$C_4$haloalkyl,
$C_3$–$C_6$alkenyl, or
$C_3$–$C_6$alkynyl;
$R_{35}$ is hydrogen;
$R_{36}$ is $SO_2R_{51}$ or $C_1$–$C_3$alkoxy;
$R_{17}$ and $R_{51}$ are each independently $C_1$–$C_4$alkyl, $C_1$–$C_4$haloalkyl, $NR_{46}R_{48}$, $C_3$–$C_6$cycloalkyl or an isoxazole ring;
$R_{46}$ and $R_{48}$ are each independently hydrogen, $C_1$–$C_4$alkyl or benzyl; and
A and $A_1$ are O.

3-(1,2-Benzisothiazol- and isoxazol-5-yl)-2,4(1H,3H)-pyrimidinedione or thiodione compounds of the present invention which are particularly effective herbicidal agents include the group consisting of
isopropyl{{2-{5-[3,6-dihydro-3-methyl-2,6-dioxo-4-(trifluoromethyl)-1(2H)-pyrimidinyl]-1,2-benzisothiazol-3-yl}-p-tolyl}oxy}acetate;
methyl{{2-{5-[3,6-dihydro-3-methyl-4-(trifluoromethyl)-2,6-dioxo-1(2H)-pyrimidinyl]-1,2-benzisothiazol-3-yl}-p-tolyl}oxy}acetate;
2-(dimethylamino)ethyl{{2-{5-[3,6-dihydro-3-methyl-2,6-dioxo-4-(trifluoromethyl)-1(2H)-pyrimidinyl]-1,2-benzisothiazol-3-yl}-p-tolyl}oxy}acetate;
methyl 2-{{2-{5-[3,6-dihydro-3-methyl-4-(trifluoromethyl)-2,6-dioxo-1(2H)-pyrimidinyl]-1,2-benzisothiazol-3-yl}-p-tolyl}oxy}propionate;
methyl 2-{{6-{5-[3,6-dihydro-3-methyl-4-(trifluoromethyl)-2,6-dioxo-1(2H)-pyrimidinyl]-1,2-benzisothiazol-3-yl}-3,4-xylyl}oxy}propionate;
2-propynyl{{2-{5-[3,6-dihydro-3-methyl-2,6-dioxo-4-(trifluoromethyl)-1(2H)-pyrimidinyl]-1,2-benzisothiazol-3-yl}-p-tolyl}oxy}acetate;
3-[3-(6-methoxy-m-tolyl)-1,2-benzisothiazol-5-yl]-1-methyl-6-(trifluoromethyl)-2,4(1H,3H)-pyrimidinedione;
3-[3-(p-ethylphenyl)-1,2-benzisothiazol-5-yl]-1-methyl-6-(trifluoromethyl)-2,4(1H,3H)-pyrimidinedione;
1-methyl-3-(3-methyl-1,2-benzisothiazol-5-yl)-6-(trifluoromethyl)-2,4(1H,3H)-pyrimidinedione;
methyl 2-{{6-{5-[3,6-dihydro-3-methyl-4-(trifluoromethyl)-2,6-dioxo-1(2H)-pyrimidinyl]-1,2-benzisothiazol-3-yl}-m-tolyl}oxy}propionate;
methyl{{6-{5-[3,6-dihydro-3-methyl-4-(trifluoromethyl)-2,6-dioxo-1(2H)-pyrimidinyl]-1,2-benzisothiazol-3-yl}-3,4-xylyl}oxy}acetate;
3-[3-(dibromomethyl)-1,2-benzisothiazol-5-yl]-1-methyl-6-(trifluoromethyl)-2,4(1H,3H)-pyrimidinedione;
3-(6-fluoro-3-methyl-1,2-benzisoxazol-5-yl)-1-methyl-6-(trifluoromethyl)-2,4(1H,3H)-pyrimidinedione;
ethyl{{2-{5-[3,6-dihydro-3-methyl-2,6-dioxo-4-(trifluoromethyl)-1(2H)-pyrimidinyl]-1,2-benzisothiazol-3-yl}-p-tolyl}oxy}acetate;
1-methyl-3-[3-[6-(2-propynyloxy)-m-tolyl]-1,2-benzisothiazol-5-yl]-6-(trifluoromethyl)-2,4(1H,3H)-pyrimidinedione;
3-{3-{6-[(1-benzimidazolylcarbonyl)methoxy]-m-tolyl}-1,2-benzisothiazol-5-yl}-1-methyl-6-trifluoromethyl)-2,4(1H,3H)-pyrimidinedione;
3-{3-{6-{[(m-cyanophenyl)carbamoyl]methoxyl-m-tolyl}-1,2-benzisothiazol-5-yl}-1-methyl-6-(trifluoromethyl)-2,4(1H,3H)pyrimidinedione;
allyl{{2-{5-[3,6-dihydro-3-methyl-2,6-dioxo-4-(trifluoromethyl)-1(2H)-pyrimidinyl]-1,2-benzisothiazol-3-yl}-p-tolyl}oxy}acetate;

3-phenyl-2-propynyl{{2-{5-[3,6-dihydro-3-methyl-2,6-dioxo-4-(trifluoromethyl)-1(2H)-pyrimidinyl]-1,2-benzisothiazol-3-yl}-p-tolyl}oxy}acetate;

1-methyl-2-propynyl{{2-{5-[3,6-dihydro-3-methyl-2,6-dioxo-4-(trifluoromethyl)-1(2H)-pyrimidinyl]-1,2-benzisothiazol-3-yl}-p-tolyl}oxy}acetate;

2-chloroethyl 2-{{2-{5-[3,6-dihydro-3-methyl-2,6-dioxo-4-(trifluoromethyl)-1(2H)-pyrimidinyl]-1,2-benzisothiazol-3-yl}-p-tolyl}oxy}propionate;

2,2,2-trifluoroethyl{{2-{5-[3,6-dihydro-3-methyl-2,6-dioxo-4-(trifluoromethyl)-1(2H)-pyrimidinyl]-1,2-benzisothiazol-3-yl}-p-tolyl}oxy}acetate;

3-[3-(2-methoxy-p-tolyl)-1,2-benzisothiazol-5-yl]-1-methyl-6-(trifluoromethyl)-2,4(1H,3H)-pyrimidinedione;

2-[3-(6-methoxy-3,4-xylyl)-1,2-benzisothiazol-5-yl]-1-methyl-6-(trifluoromethyl)-2,4(1H,3H)-pyrimidinedione;

methyl 2-{{6-{5-[3,6-dihydro-3-methyl-4-(trifluoromethyl)-2,6-dioxo-1(2H)-pyrimidinyl]-1,2-benzisothiazol-3-yl}-3,4-xylyl}oxy}propionate;

methyl{{6-{5-[3,6-dihydro-3-methyl-2,6-dioxo-4-(trifluoromethyl)-1(2H)-pyrimidinyl]-1,2-benzisothiazol-3-yl}-2,4-xylyl}oxy}acetate;

3-{3-{6-{[(m-cyanophenyl)carbamoyl]methoxy}-m-tolyl}-1,2-benzisothiazol-5-yl}-1-methyl-6-(trifluoromethyl)-2,4(1H,3H)-pyrimidinedione;

methyl{{2-{5-[3,6-dihydro-3-methyl-2,6-dioxo-4-(trifluoromethyl)-1(2H)-pyrimidinyl]-1,2-benzisoxazol-3-yl}-p-tolyl}oxy}acetate;

1-methyl-3-{3-[(methylsulfonyl)methyl]-1,2-benzisothiazol-5-yl}-6-(trifluoromethyl)-2,4(1H,3H)-pyrimidinedione;

2-propynyl{{2-{5-[3,6-dihydro-3-methyl-2,6-dioxo-4-(trifluoromethyl)-1(2H)-pyrimidinyl]-1,2-benzisoxazol-3-yl}-p-tolyl}oxy}acetate;

3-[3-(o-methoxyphenyl)-1,2-benzisothiazol-5-yl]-1-methyl-6-(trifluoromethyl)-2,4(1H,3H)-pyrimidinedione;

N-{{{2-{5-[3,6-dihydro-3-methyl-2,6-dioxo-4-(trifluoromethyl)-1(2H)-pyrimidinyl]-1,2-benzisothiazol-3-yl}-p-tolyl}oxy}acetyl}methanesulfonamide;

2-propynyl 2-{{2-{5-[3,6-dihydro-3-methyl-2,6-dioxo-4-(trifluoromethyl)-1(2H)-pyrimidinyl]-1,2-benzisoxazol-3-yl}-p-tolyl}oxy}propionate;

2-propynyl{o-{5-[3,6-dihydro-3-methyl-2,6-dioxo-4-(trifluoromethyl)-1(2H)-pyrimidinyl]-1,2-benzisothiazol-3-yl}phenoxy}acetate;

5-[3,6-dihydro-3-methyl-2,6-dioxo-4-(trifluoromethyl)-1(2H)-pyrimidinyl]-1,2-benzisothiazole-3-acetonitrile;

3-{3-[(allyloxy)methyl]-1,2-benzisothiazol-5-yl}-1-methyl-6-(trifluoromethyl)-2,4(1H,3H)-pyrimidinedione;

5-[3,6-dihydro-3-methyl-2,6-dioxo-4-(trifluoromethyl)-1(2H)-pyrimidinyl]-N-(methylsulfonyl)-1,2-benzisothiazole-3-carboxamide;

methyl{{2-{5-[3,6-dihydro-3-methyl-2,6-dioxo-4-(trifluoromethyl)-1(2H)-pyrimidinyl]-6-fluoro-1,2-benzisoxazol-3-yl}-p-tolyl}oxy}acetate;

methyl{{6-{5-[3,6-dihydro-3-methyl-2,6-dioxo-4-(trifluoromethyl)-1(2H)-pyrimidinyl]-6-fluoro-1,2-benzisothiazol-3-yl}-m-tolyl}oxy}acetate;

{o-{5-[3,6-dihydro-3-methyl-2,6-dioxo-4-(trifluoromethyl)-1(2H)-pyrimidinyl]-1,2-benzisothiazol-3-yl}phenoxy}acetic acid;

2-{o-{5-[3,6-dihydro-3-methyl-2,6-dioxo-4-(trifluoromethyl)-1(2H)-pyrimidinyl]-1,2-benzisothiazol-3-yl}phenoxy}propionic acid;

2-{{2-{5-[3,6-dihydro-3-methyl-2,6-dioxo-4-(trifluoromethyl)-1(2H)-pyrimidinyl]-1,2-benzisothiazol-3-yl}-p-tolyl}oxy}-N-methoxyacetamide;

methyl 2-{2-{5-[3,6-dihydro-3-methyl-2,6-dioxo-4-(trifluoromethyl)-1(2H)-pyrimidinyl]-1,2-benzisothiazol-3-yl}-4-methoxyphenoxy}propionate;

2-{o-{5-[3,6-dihydro-3-methyl-2,6-dioxo-4-(trifluoromethyl)-1(2H)-pyrimidinyl]-1,2-benzisothiazol-3-yl}phenoxy}-N-(methylsulfonyl)acetamide;

2-{o-{5-[3,6-dihydro-3-methyl-2,6-dioxo-4-(trifluoromethyl)-1(2H)-pyrimidinyl]-1,2-benzisothiazol-3-yl}phenoxy]-N-(methylsulfonyl)propionamide;

2-{{2-{5-[3,6-dihydro-3-methyl-2,6-dioxo-4-(trifluoromethyl)-1(2H)-pyrimidinyl]-1,2-benzisothiazol-3-yl}-p-tolyl}oxy}-N-methyl-N-(methylsulfonyl)acetamide;

2-{o-{5-[3,6-dihydro-3-methyl-2,6-dioxo-4-(trifluoromethyl)-1(2H)-pyrimidinyl]-1,2-benzisothiazol-3-yl}phenoxy}-N-methyl-N-(methylsulfonyl)acetamide;

2-{o-{5-[3,6-dihydro-3-methyl-2,6-dioxo-4-(trifluoromethyl)-1(2H)-pyrimidinyl]-1,2-benzisothiazol-3-yl}phenoxy}-N-(ethylsulfonyl)acetamide;

3-[3-(hydroxymethyl)-1,2-benzisothiazol-5-yl]-1-methyl-6-(trifluoromethyl)-2,4(1H,3H)-pyrimidinedione, 2-thiophenecarboxylate (ester);

3-[3-(hydroxymethyl)-1,2-benzisothiazol-5-yl]-1-methyl-6-(trifluoromethyl)-2,4(1H,3H)-pyrimidinedione, benzoate (ester);

3-[3-(hydroxymethyl)-1,2-benzisothiazol-5-yl]-1-methyl-6-(trifluoromethyl)-2,4(1H,3H)-pyrimidinedione, methoxyacetate (ester);

5-[3,6-dihydro-3-methyl-2,6-dioxo-4-(trifluoromethyl)-1(2H)-pyrimidinyl]-N-(ethylsulfonyl)-1,2-benzisothiazole-3-carboxamide;

5-[3,6-dihydro-3-methyl-2,6-dioxo-4-(trifluoromethyl)-1(2H)-pyrimidinyl]-α,α-dimethyl-1,2-benzisothiazole-3-acetonitrile;

5-[3,6-dihydro-3-methyl-2,6-dioxo-4-(trifluoromethyl)-1(2H)-pyrimidinyl]-6-fluoro-1,2-benzisothiazole-3-acetonitrile;

5-[3,6-dihydro-3-methyl-2,6-dioxo-4-(trifluoromethyl)-1(2H)-pyrimidinyl]-α-ethyl-1,2-benzisothiazole-3-acetonitrile;

5-[3,6-dihydro-3-methyl-2,6-dioxo-4-(trifluoromethyl)-1(2H)-pyrimidinyl]-α,α-diethyl-1,2-benzisothiazole-3-acetonitrile;

3-[6-fluoro-3-(methoxymethyl)-1,2-benzisothiazol-5-yl]-1-methyl-6-(trifluoromethyl)-2,4(1H,3H)-pyrimidinedione;

3-[3-(hydroxymethyl)-1,2-benzisothiazol-5-yl]-1-methyl-6-(trifluoromethyl)-2,4(1H,3H)-pyrimidinedione, 5-isoxazolecarboxylate (ester);

3-[3-(hydroxymethyl)-1,2-benzisothiazol-5-yl]-1-methyl-6-(trifluoromethyl)-2,4(1H,3H)-pyrimidinedione, cyclopropanecarboxylate (ester);

3-(3-acetyl-1,2-benzisothiazol-5-yl)-1-methyl-6-(trifluoromethyl)-2,4(1H,3H)-pyrimidinedione;

3-[3-(1-methoxyethyl)-1,2-benzisothiazol-5-yl]-1-methyl-6-(trifluoromethyl)-2,4(1H,3H)-pyrimidinedione;

N-(benzylsulfonyl)-5-[3,6-dihydro-3-methyl-2,6-dioxo-4-(trifluoromethyl)-1(2H)-pyrimidinyl]-1,2-benzisothiazole-3-carboxamide;

methyl 5-[3,6-dihydro-3-methyl-2,6-dioxo-4-(trifluoromethyl)-1(2H)-pyrimidinyl]-1,2-benzisothiazole-3-carboxylate;

benzyl 5-[3,6-dihydro-3-methyl-2,6-dioxo-4-(trifluoromethyl)-1(2H)-pyrimidinyl]-α,α-dimethyl-1,2-benzisothiazole-3-acetate;

N-(benzylsulfonyl)-5-[3,6-dihydro-3-methyl-2,6-dioxo-4-(trifluoromethyl)-1(2H)-pyrimidinyl]-6-fluoro-1,2-benzisothiazole-3-carboxamide;

5-[3,6-dihydro-3-methyl-2,6-dioxo-4-(trifluoromethyl)-1 (2H)-pyrimidinyl]-N-(methylsulfonyl)-1,2-benzisothiazole-3-carboxamide;

5-[3,6-dihydro-3-methyl-2,6-dioxo-4-(trifluoromethyl)-1 (2H)-pyrimidinyl]-N-(isopropylsulfonyl)-1,2-benzisothiazole-3-carboxamide;

5-[3,6-dihydro-3-methyl-2,6-dioxo-4-(trifluoromethyl)-1 (2H)-pyrimidinyl]-N-(ethylsulfonyl)-1,2-benzisothiazole-3-carboxamide;

5-[3,6-dihydro-3-methyl-2,6-dioxo-4-(trifluoromethyl)-1 (2H)-pyrimidinyl]-N-[(p-methylbenzyl)sulfonyl]-1,2-benzisothiazole-3-carboxamide;

N-(benzylsulfonyl)-5-[3,6-dihydro-3-methyl-2,6-dioxo-4-(trifluoromethyl)-1(2H)-pyrimidinyl]-6-fluoro-1,2-benzisothiazole-3-carboxamide;

3-[3-(1-hydroxyethyl)-1,2-benzisothiazol-5-yl]-1-methyl-6-(trifluoromethyl)-2,4(1H,3H)-pyrimidinedione;

5-[3,6-dihydro-3-methyl-2,6-dioxo-4-(trifluoromethyl)-1 (2H)-pyrimidinyl]-1,2-benzisothiazole-3-carboxaldehyde, 3-(dimethyl acetal);

3-(6-fluoro-3-methyl-1,2-benzisothiazol-5-yl)-1-methyl-6-(trifluoromethyl)-2,4(1H,3H)-pyrimidinedione;

5-[3,6-dihydro-3-methyl-2,6-dioxo-4-(trifluoromethyl)-1 (2H)-pyrimidinyl]-6-fluoro-1,2-benzisothiazole-3-carboxaldehyde, 3-(dimethyl acetal);

5-[3,6-dihydro-3-methyl-2,6-dioxo-4-(trifluoromethyl)-1 (2H)-pyrimidinyl]-6-fluoro-1,2-benzisothiazole-3-carboxylic acid;

5-[3,6-dihydro-3-methyl-2,6-dioxo-4-(trifluoromethyl)-1 (2H)-pyrimidinyl]-α-methyl-1,2-benzisothiazole-3-acetonitrile;

N-(benzylsulfonyl)-5-[3,6-dihydro-3-methyl-2,6-dioxo-4-(trifluoromethyl)-1(2H)-pyrimidinyl]-N-(ethoxymethyl)-1,2-benzisothiazole-3-carboxamide;

5-[3,6-dihydro-3-methyl-2,6-dioxo-4-(trifluoromethyl)-1 (2H)-pyrimidinyl]-N-(dimethylsulfamoyl)-1,2-benzisothiazole-3-carboxamide;

5-[3,6-dihydro-3-methyl-2,6-dioxo-4-(trifluoromethyl)-1 (2H)-pyrimidinyl]-N-(isopropylsulfamoyl)-1,2-benzisothiazole-3-carboxamide;

methyl 5-[3,6-dihydro-3-methyl-2,6-dioxo-4-(trifluoromethyl)-1(2H)-pyrimidinyl]-α,α-dimethyl-1,2-benzisothiazole-3-acetate;

3-[3-(hydroxymethyl)-1,2-benzisothiazol-5-yl]-1-methyl-6-(trifluoromethyl)-2,4(1H,3H)-pyrimidinedione, 2-furoate (ester);

N-[(m-chlorobenzyl)sulfonyl]-5-[3,6-dihydro-3-methyl-2, 6-dioxo-4-(trifluoromethyl)-1(2H)-pyrimidinyl]-1,2-benzisothiazole-3-carboxamide;

5-[3,6-dihydro-3-methyl-2,6-dioxo-4-(trifluoromethyl)-1 (2H)-pyrimidinyl]-N-(diisopropylsulfamoyl)-1,2-benzisothiazole-3-carboxamide; and 3-[3-(hydroxymethyl)-1,2-benzisothiazol-5-yl]-1-methyl-6-(trifluoromethyl)-2,4(1H,3H)-pyrimidinedione, methylcarbamate (ester), among others.

Exemplary of halogen hereinabove are fluorine, chlorine, bromine and iodine. The terms haloalkyl, halocycloalkyl, haloalkoxy, haloalkenyl, halocycloalkenyl and haloalkynyl as used in the specification and claims designate an alkyl group, a cycloalkyl group, an alkoxy group, an alkenyl group, a cycloalkenyl group and an alkynyl group substituted with one or more halogen atoms, respectively. In formulas I and II above, alkali metals include: sodium, potassium and lithium. Alkaline earth metals of formulas I and II include magnesium and calcium. Further, the term organic ammonium is defined as a group consisting of a positively charged nitrogen atom joined to from one to four aliphatic groups, each containing from one to sixteen carbon atoms.

In formulas I and II above, 5- to 12-membered monocyclic or fused bicyclic, heterocyclic rings include, but are not limited to, benzimidazole, imidazole, imidazoline-2-thione, indole, isatoic anhydride, morpholine, piperazine, piperidine, purine, pyrazole, pyrrole, pyrrolidine and 1,2,4-triazole rings wherein each ring is optionally substituted with one or more groups independently selected from halogen, cyano, nitro, amino, hydroxyl, $C_1$–$C_4$alkyl, $C_1$–$C_4$haloalkyl, $C_1$–$C_4$alkoxy, $C_1$–$C_4$haloalkoxy or $C_1$–$C_4$haloalkylsulfonyl groups.

In formulas I and II above, 4- to 10-membered heterocyclic rings include, but are not limited to, imidazole and phthalimide rings wherein each ring is optionally substituted with any combination of one to three halogen atoms, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups or one or two $X_4R_{22}$ groups.

The formula I and II compounds of the present invention are effective herbicidal agents useful for the control of a wide variety of undesirable plant species. Those compounds are effective for controlling weeds native to both dry land and wet land areas. The compounds are effective in controlling the above-said plants when applied to the foliage thereof or to the soil or water containing seeds or other propagating organs thereof such as stolons, tubers or rhizomes, at rates of from about 0.001 kg/ha to 4 kg/ha and preferably from about 0.001 kg/ha to 1 kg/ha.

Advantageously, it has been found that the formula I and II compounds of this invention are particularly useful for the selective control of undesirable plant species in the presence of crop plants, crop seeds or other crop propagating organs. In particular, some of the compounds of this invention are selective in soybeans and/or cereal crops such as corn, wheat and rice when applied as preemergence and/or postemergence treatments.

In addition, it has been found that the formula I and II compounds of this invention may be used for the selective control of undesirable plant species in transplanted rice culture by applying a herbicidally effective amount of a formula I compound to the soil or water containing seeds or other propagating organs of said undesirable plant species after the rice has been transplanted.

Formula I compounds of this invention which are especially useful for the selective control of undesirable plant species in the presence of corn include isopropyl{{2-{5-[3,6-dihydro-3-methyl-2,6-dioxo-4-(trifluoromethyl)-1(2H)-pyrimidinyl]-1,2-benzisothiazol-3-yl}-p-tolyl}oxy}acetate;

methyl{{2-{5-[3,6-dihydro-3-methyl-4-(trifluoromethyl)-2, 6-dioxo-1(2H)-pyrimidinyl]-1,2-benzisothiazol-3-yl}-p-tolyl}oxy}acetate;

2-(dimethylamino)ethyl{{2-{5-[3,6-dihydro-3-methyl-2,6-dioxo-4-(trifluoromethyl)-1(2H)-pyrimidinyl]-1,2-benzisothiazol-3-yl}-p-tolyl}oxy}acetate;

2-propynyl{{2-{5-[3,6-dihydro-3-methyl-2,6-dioxo-4-(trifluoromethyl)-1(2H)-pyrimidinyl]-1,2-benzisothiazol-3-yl}-p-tolyl}oxy}acetate;

3-[3-(p-ethylphenyl)-1,2-benzisothiazol-5-yl]-1-methyl-6-(trifluoromethyl)-2,4(1H,3H)-pyrimidinedione;

methyl{{6-{5-[3,6-dihydro-3-methyl-4-(trifluoromethyl)-2, 6-dioxo-1(2H)-pyrimidinyl]-1,2-benzisothiazol-3-yl}-3, 4-xylyl}oxy}acetate;

3-[3-(dibromomethyl)-1,2-benzisothiazol-5-yl]-1-methyl-6-(trifluoromethyl)-2,4(1H,3H)-pyrimidinedione;

1-methyl-2-propynyl{{2-{5-[3,6-dihydro-3-methyl-2,6-dioxo-4-(trifluoromethyl)-1(2H)-pyrimidinyl]-1,2-benzisothiazol-3-yl}-p-tolyl}oxy}acetate;

methyl{{2-{5-[3,6-dihydro-3-methyl-2,6-dioxo-4-(trifluoromethyl)-1(2H)-pyrimidinyl]-1,2-benzisoxazol-3-yl}-p-tolyl}oxy}acetate;
1-methyl-3-{3-[(methylsulfonyl)methyl]-1,2-benzisothiazol-5-yl}-6-(trifluoromethyl)-2,4(1H,3H)-pyrimidinedione;
2-propynyl{{2-{5-[3,6-dihydro-3-methyl-2,6-dioxo-4-(trifluoromethyl)-1(2H)-pyrimidinyl]-1,2-benzisoxazol-3-yl}-p-tolyl}oxy}acetate;
3-[3-(o-methoxyphenyl)-1,2-benzisothiazol-5-yl]-1-methyl-6-(trifluoromethyl)-2,4(1H,3H)-pyrimidinedione;
N-{{{2-{5-[3,6-dihydro-3-methyl-2,6-dioxo-4-(trifluoromethyl)-1(2H)-pyrimidinyl]-1,2-benzisothiazol-3-yl}-p-tolyl}oxy}acetyl}methanesulfonamide;
2-propynyl{o-{5-[3,6-dihydro-3-methyl-2,6-dioxo-4-(trifluoromethyl)-1(2H)-pyrimidinyl]-1,2-benzisothiazol-3-yl}phenoxy}acetate;
5-[3,6-dihydro-3-methyl-2,6-dioxo-4-(trifluoromethyl)-1(2H)-pyrimidinyl]-1,2-benzisothiazole-3-acetonitrile;
3-{3-[(allyloxy)methyl]-1,2-benzisothiazol-5-yl}-1-methyl-6-(trifluoromethyl)-2,4(1H,3H)-pyrimidinedione;
5-[3,6-dihydro-3-methyl-2,6-dioxo-4-(trifluoromethyl)-1(2H)-pyrimidinyl]-N-(methylsulfonyl)-1,2-benzisothiazole-3-carboxamide;
2-{{2-{5-[3,6-dihydro-3-methyl-2,6-dioxo-4-(trifluoromethyl)-1(2H)-pyrimidinyl]-1,2-benzisothiazol-3-yl}-p-tolyl}oxy}-N-methyl-N-(methylsulfonyl)acetamide;
3-[3-(hydroxymethyl)-1,2-benzisothiazol-5-yl]-1-methyl-6-(trifluoromethyl)-2,4(1H,3H)-pyrimidinedione, methylcarbamate (ester);
N-(benzylsulfonyl)-5-[3,6-dihydro-3-methyl-2,6-dioxo-4-(trifluoromethyl)-1(2H)-pyrimidinyl]-1,2-benzisothiazole-3-carboxamide;
5-[3,6-dihydro-3-methyl-2,6-dioxo-4-(trifluoromethyl)-1(2H)-pyrimidinyl]-N-(isopropylsulfonyl)-1,2-benzisothiazole-3-carboxamide;
5-[3,6-dihydro-3-methyl-2,6-dioxo-4-(trifluoromethyl)-1(2H)-pyrimidinyl]-N-(ethylsulfonyl)-1,2-benzisothiazole-3-carboxamide;
5-[3,6-dihydro-3-methyl-2,6-dioxo-4-(trifluoromethyl)-1(2H)-pyrimidinyl]-N-(diisopropylsulfamoyl)-1,2-benzisothiazole-3-carboxamide;
5-[3,6-dihydro-3-methyl-2,6-dioxo-4-(trifluoromethyl)-1(2H)-pyrimidinyl]-N-(isopropylsulfamoyl)-1,2-benzisothiazole-3-carboxamide;
5-[3,6-dihydro-3-methyl-2,6-dioxo-4-(trifluoromethyl)-1(2H)-pyrimidinyl]-N-(dimethylsulfamoyl)-1,2-benzisothiazole-3-carboxamide;
5-[3,6-dihydro-3-methyl-2,6-dioxo-4-(trifluoromethyl)-1(2H)-pyrimidinyl]-6-fluoro-1,2-benzisothiazole-3-carboxylic acid; and
N-(benzylsulfonyl)-5-[3,6-dihydro-3-methyl-2,6-dioxo-4-(trifluoromethyl)-1(2H)-pyrimidinyl]-6-fluoro-1,2-benzisothiazole-3-carboxamide, among others.

Formula I compounds of the present invention which are particularly useful for the selective control of undesirable plant species in the presence of wheat include
isopropyl{{2-{5-[3,6-dihydro-3-methyl-2,6-dioxo-4-(trifluoromethyl)-1(2H)-pyrimidinyl]-1,2-benzisothiazol-3-yl}-p-tolyl}oxy}acetate;
methyl{{2-{5-[3,6-dihydro-3-methyl-4-(trifluoromethyl)-2,6-dioxo-1(2H)-pyrimidinyl]-1,2-benzisothiazol-3-yl}-p-tolyl}oxy}acetate;
2-(dimethylamino)ethyl{{2-{5-[3,6-dihydro-3-methyl-2,6-dioxo-4-(trifluoromethyl)-1(2H)-pyrimidinyl]-1,2-benzisothiazol-3-yl}-p-tolyl}oxy}acetate;
2-propynyl{{2-{5-[3,6-dihydro-3-methyl-2,6-dioxo-4-(trifluoromethyl)-1(2H)-pyrimidinyl]-1,2-benzisothiazol-3-yl}-p-tolyl}oxy}acetate;
methyl 2-{{6-{5-[3,6-dihydro-3-methyl-4-(trifluoromethyl)-2,6-dioxo-1(2H)-pyrimidinyl]-1,2-benzisothiazol-3-yl}-m-tolyl}oxy}propionate;
3-(6-fluoro-3-methyl-1,2-benzisoxazol-5-yl)-1-methyl-6-(trifluoromethyl)-2,4(1H,3H)-pyrimidinedione;
3-{3-{6-[(1-benzimidazolylcarbonyl)methoxy]-m-tolyl}-1,2-benzisothiazol-5-yl}-1-methyl-6-trifluoromethyl)-2,4(1H,3H)-pyrimidinedione;
allyl{{2-{5-[3,6-dihydro-3-methyl-2,6-dioxo-4-(trifluoromethyl)-1(2H)-pyrimidinyl]-1,2-benzisothiazol-3-yl}-p-tolyl}oxy}acetate;
3-phenyl-2-propynyl{{2-{5-[3,6-dihydro-3-methyl-2,6-dioxo-4-(trifluoromethyl)-1(2H)-pyrimidinyl]-1,2-benzisothiazol-3-yl}-p-tolyl}oxy}acetate;
2-chloroethyl 2-{{2-{5-[3,6-dihydro-3-methyl-2,6-dioxo-4-(trifluoromethyl)-1(2H)-pyrimidinyl]-1,2-benzisothiazol-3-yl}-p-tolyl}oxy}propionate;
2,2,2-trifluoroethyl{{2-{5-[3,6-dihydro-3-methyl-2,6-dioxo-4-(trifluoromethyl)-1(2H)-pyrimidinyl]-1,2-benzisothiazol-3-yl}-p-tolyl}oxy}acetate;
methyl{{6-{5-[3,6-dihydro-3-methyl-2,6-dioxo-4-(trifluoromethyl)-1(2H)-pyrimidinyl]-1,2-benzisothiazol-3-yl}-2,4-xylyl}oxy}acetate;
{o-{5-[3,6-dihydro-3-methyl-2,6-dioxo-4-(trifluoromethyl)-1(2H)-pyrimidinyl]-1,2-benzisothiazol-3-yl}phenoxy}acetic acid;
2-{{2-{5-[3,6-dihydro-3-methyl-2,6-dioxo-4-(trifluoromethyl)-1(2H)-pyrimidinyl]-1,2-benzisothiazol-3-yl}-p-tolyl}oxy}-N-methoxyacetamide;
2-{{2-{5-[3,6-dihydro-3-methyl-2,6-dioxo-4-(trifluoromethyl)-1(2H)-pyrimidinyl]-1,2-benzisothiazol-3-yl}-p-tolyl}oxy}-N-methyl-N-(methylsulfonyl)acetamide;
methyl{{6-{5-[3,6-dihydro-3-methyl-2,6-dioxo-4-(trifluoromethyl)-1(2H)-pyrimidinyl]-6-fluoro-1,2-benzisothiazol-3-yl}-m-tolyl}oxy}acetate;
3-(3-acetyl-1,2-benzisothiazol-5-yl)-1-methyl-6-(trifluoromethyl)-2,4(1H,3H)-pyrimidinedione;
methyl 5-[3,6-dihydro-3-methyl-2,6-dioxo-4-(trifluoromethyl)-1(2H)-pyrimidinyl]-1,2-benzisothiazole-3-carboxylate;
5-[3,6-dihydro-3-methyl-2,6-dioxo-4-(trifluoromethyl)-1(2H)-pyrimidinyl]-N-(isopropylsulfonyl)-1,2-benzisothiazole-3-carboxamide;
5-[3,6-dihydro-3-methyl-2,6-dioxo-4-(trifluoromethyl)-1(2H)-pyrimidinyl]-N-(ethylsulfonyl)-1,2-benzisothiazole-3-carboxamide;
N-[(m-chlorobenzyl)sulfonyl]-5-[3,6-dihydro-3-methyl-2,6-dioxo-4-(trifluoromethyl)-1(2H)-pyrimidinyl]-1,2-benzisothiazole-3-carboxamide;
5-[3,6-dihydro-3-methyl-2,6-dioxo-4-(trifluoromethyl)-1(2H)-pyrimidinyl]-N-(diisopropylsulfamoyl)-1,2-benzisothiazole-3-carboxamide;
5-[3,6-dihydro-3-methyl-2,6-dioxo-4-(trifluoromethyl)-1(2H)-pyrimidinyl]-N-((isopropylsulfamoyl)-1,2-benzisothiazole-3-carboxamide; and
5-[3,6-dihydro-3-methyl-2,6-dioxo-4-(trifluoromethyl)-1(2H)-pyrimidinyl]-N-(dimethylsulfamoyl)-1,2-benzisothiazole-3-carboxamide, among others.

3-(1,2-Benzisothiazol-5-yl)-2,4(1H,3H)-pyrimidinedione compounds of this invention which are especially useful for the selective control of undesirable plant species in the presence of rice include
isopropyl{{2-{5-[3,6-dihydro-3-methyl-2,6-dioxo-4-(trifluoromethyl)-1(2H)-pyrimidinyl]-1,2-benzisothiazol-3-yl}-p-tolyl}oxy}acetate;

methyl{{2-{5-[3,6-dihydro-3-methyl-4-(trifluoromethyl)-2,
6-dioxo-1(2H)-pyrimidinyl]-1,2-benzisothiazol-3-yl}-p-
tolyl}oxy}acetate;
3-[3-(6-methoxy-m-tolyl)-1,2-benzisothiazol-5-yl]-1-
methyl-6-(trifluoromethyl)-2,4(1H,3H)-pyrimidinedione;
ethyl{{2-{5-[3,6-dihydro-3-methyl-2,6-dioxo-4-
(trifluoromethyl)-1(2H)-pyrimidinyl]-1,2-benzisothiazol-
3-yl}-p-tolyl}oxy}acetate;
1-methyl-3-{3-[6-(2-propynyloxy)-m-tolyl]-1,2-
benzisothiazol-5-yl}-6-(trifluoromethyl)-2,4(1H,3H)-
pyrimidinedione;
3-{3-{6-{[(m-cyanophenyl)carbamoyl]methoxy}-m-tolyl}-
1,2-benzisothiazol-5-yl}-1-methyl-6-(trifluoromethyl)-2,
4(1H,3H)pyrimidinedione;
3-[3-(2-methoxy-p-tolyl)-1,2-benzisothiazol-5-yl]-1-
methyl-6-(trifluoromethyl)-2,4(1H,3H)-pyrimidinedione;
2-[3-(6-methoxy-3,4-xylyl)-1,2-benzisothiazol-5-yl]-1-
methyl-6-(trifluoromethyl)-2,4(1H,3H)-pyrimidinedione;
3-{3-{6-{[(m-cyanophenyl)carbamoyl]methoxy}-m-tolyl}-
1,2-benzisothiazol-5-yl}-1-methyl-6-(trifluoromethyl)-2,
4(1H,3H)-pyrimidinedione;
2-propynyl{o-{5-[3,6-dihydro-3-methyl-2,6-dioxo-4-
(trifluoromethyl)-1(2H)-pyrimidinyl]-1,2-benzisothiazol-
3-yl}phenoxy}acetate;
3-{3-[(allyloxy)methyl]-1,2-benzisothiazol-5-yl}-1-methyl-
6-(trifluoromethyl)-2,4(1H,3H)-pyrimidinedione;
5-[3,6-dihydro-3-methyl-2,6-dioxo-4-(trifluoromethyl)-1
(2H)-pyrimidinyl]-α-ethyl-1,2-benzisothiazole-3-
acetonitrile;
5-[3,6-dihydro-3-methyl-2,6-dioxo-4-(trifluoromethyl)-1
(2H)-pyrimidinyl]-α,α-diethyl-1,2-benzisothiazole-3-
acetonitrile;
3-[3-(hydroxymethyl)-1,2-benzisothiazol-5-yl]-1-methyl-6-
(trifluoromethyl)-2,4(1H,3H)-pyrimidinedione,
5-isoxazolecarboxylate (ester);
3-[3-(hydroxymethyl)-1,2-benzisothiazol-5-yl]-1-methyl-6-
(trifluoromethyl)-2,4(1H,3H)-pyrimidinedione,
cyclopropanecarboxylate (ester);
methyl 5-[3,6-dihydro-3-methyl-2,6-dioxo-4-
(trifluoromethyl)-1(2H)-pyrimidinyl]-1,2-
benzisothiazole-3-carboxylate;
5-[3,6-dihydro-3-methyl-2,6-dioxo-4-(trifluoromethyl)-1
(2H)-pyrimidinyl]-N-(isopropylsulfonyl)-1,2-
benzisothiazole-3-carboxamide;
5-[3,6-dihydro-3-methyl-2,6-dioxo-4-(trifluoromethyl)-1
(2H)-pyrimidinyl]-N-(ethylsulfonyl)-1,2-
benzisothiazole-3-carboxamide;
benzyl 5-[3,6-dihydro-3-methyl-2,6-dioxo-4-
(trifluoromethyl)-1(2H)-pyrimidinyl]-α,α-dimethyl-1,2-
benzisothiazole-3-acetate;
5-[3,6-dihydro-3-methyl-2,6-dioxo-4-(trifluoromethyl)-1
(2H)-pyrimidinyl]-N-(diisopropylsulfamoyl)-1,2-
benzisothiazole-3-carboxamide;
5-[3,6-dihydro-3-methyl-2,6-dioxo-4-(trifluoromethyl)-1
(2H)-pyrimidinyl]-N-(isopropylsulfamoyl)-1,2-
benzisothiazole-3-carboxamide; and
5-[3,6-dihydro-3-methyl-2,6-dioxo-4-(trifluoromethyl)-1
(2H)-pyrimidinyl]-N-(dimethylsulfamoyl)-1,2-
benzisothiazole-3-carboxamide, among others.

Formula I compounds of this invention which are particularly useful for the selective control of undesirable plant species in the presence of soybeans include
methyl 2-{{2-{5-[3,6-dihydro-3-methyl-4-
(trifluoromethyl)-2,6-dioxo-1(2H)-pyrimidinyl]-1,2-
benzisothiazol-3-yl}-p-tolyl}oxy}propionate;
methyl 2-{{6-{5-[3,6-dihydro-3-methyl-4-
(trifluoromethyl)-2,6-dioxo-1(2H)-pyrimidinyl]-1,2-
benzisothiazol-3-yl}-3,4-xylyl}oxy}propionate;
1-methyl-3-(3-methyl-i,2-benzisothiazol-5-yl)-6-
(trifluoromethyl)-2,4(1H,3H)-pyrimidinedione;
methyl 2-{{6-{5-[3,6-dihydro-3-methyl-4-
(trifluoromethyl)-2,6-dioxo-1(2H)-pyrimidinyl]-1,2-
benzisothiazol-3-yl}-3,4-xylyl}oxy}propionate;
2-propynyl{{2-{5-[3,6-dihydro-3-methyl-2,6-dioxo-4-
(trifluoromethyl)-1(2H)-pyrimidinyl]-1,2-benzisoxazol-
3-yl}-p-tolyl}oxy}acetate;
3-[3-(o-methoxyphenyl)-1,2-benzisothiazol-5-yl]-1-methyl-
6-(trifluoromethyl)-2,4(1H,3H)-pyrimidinedione;
2-propynyl 2-{{2-{5-[3,6-dihydro-3-methyl-2,6-dioxo-4-
(trifluoromethyl)-1(2H)-pyrimidinyl]-1,2-benzisoxazol-
3-yl}-p-tolyl}oxy}propionate;
2-propynyl{o-{5-[3,6-dihydro-3-methyl-2,6-dioxo-4-
(trifluoromethyl)-1(2H)-pyrimidinyl]-1,2-benzisothiazol-
3-yl}phenoxy}acetate;
3-{3-[(allyloxy)methyl]-1,2-benzisothiazol-5-yl}-1-methyl-
6-(trifluoromethyl)-2,4(1H,3H)-pyrimidinedione;
5-[3,6-dihydro-3-methyl-2,6-dioxo-4-(trifluoromethyl)-1
(2H)-pyrimidinyl]-N-(methylsulfonyl)-1,2-
benzisothiazole-3-carboxamide;
methyl{{2-{5-[3,6-dihydro-3-methyl-2,6-dioxo-4-
(trifluoromethyl)-1(2H)-pyrimidinyl]-6-fluoro-1,2-
benzisoxazol-3-yl}-p-tolyl}oxy}acetate;
methyl{{6-{5-[3,6-dihydro-3-methyl-2,6-dioxo-4-
(trifluoromethyl)-1(2H)-pyrimidinyl]-6-fluoro-1,2-
benzisothiazol-3-yl}-m-tolyl}oxy}acetate;
3-(3-(hydroxymethyl)-1,2-benzisothiazol-5-yl]-1-methyl-6-
(trifluoromethyl)-2,4(1H,3H)-pyrimidinedione, benzoate
(ester);
3-[3-(hydroxymethyl)-1,2-benzisothiazol-5-yl]-1-methyl-6-
(trifluoromethyl)-2,4(1H,3H)-pyrimidinedione,
2-thiophenecarboxylate (ester);
3-[3-(hydroxymethyl)-1,2-benzisothiazol-5-yl]-1-methyl-6-
(trifluoromethyl)-2,4(1H,3H)-pyrimidinedione, methoxy-
acetate (ester);
3-[3-(hydroxymethyl)-1,2-benzisothiazol-5-yl]-1-methyl-6-
(trifluoromethyl)-2,4(1H,3H)-pyrimidinedione,
cyclopropanecarboxylate (ester);
3-[3-(hydroxymethyl)-1,2-benzisothiazol-5-yl]-1-methyl-6-
(trifluoromethyl)-2,4(1H,3H)-pyrimidinedione, 2-furoate
(ester);
5-[3,6-dihydro-3-methyl-2,6-dioxo-4-(trifluoromethyl)-1
(2H)-pyrimidinyl]-N-(methylsulfonyl)-1,2-
benzisothiazole-3-carboxamide;
5-[3,6-dihydro-3-methyl-2,6-dioxo-4-(trifluoromethyl)-1
(2H) -pyrimidinyl]-N-(isopropylsulfonyl)-1,2-
benzisothiazole-3-carboxamide;
5-[3,6-dihydro-3-methyl-2,6-dioxo-4-(trifluoromethyl)-1
(2H)-pyrimidinyl 3-N-(ethylsulfonyl)-1,2-
benzisothiazole-3-carboxamide;
5-[3,6-dihydro-3-methyl-2,6-dioxo-4-(trifluoromethyl)-1
(2H)-pyrimidinyl]-N-(isopropylsulfamoyl)-1,2-
benzisothiazole-3-carboxamide; and
5-[3,6-dihydro-3-methyl-2,6-dioxo-4-(trifluoromethyl)-1
(2H)-pyrimidinyl]-N-(dimethylsulfamoyl)-1,2-
benzisothiazole-3-carboxamide, among others.

While the compounds of this invention are effective for controlling undesirable plant species when employed alone, they may also be used in combination with other biological chemicals, including herbicides.

The compounds of this invention may be applied to the foliage of undesirable plant species or to the soil or water containing seeds or other propagating organs thereof in the form of a solid or liquid herbicidal composition, comprising a herbicidally effective amount of the desired compound dispersed or dissolved in an agronomically acceptable, inert solid or liquid carrier. The compositions may be applied as preemergence or postemergence treatments.

The formula I and II compounds of the present invention may be formulated as emulsifiable concentrates, wettable powders, granular formulations, suspension concentrates, flowable concentrates and the like.

Formula I compounds wherein Z is S may be prepared, as illustrated in Flow Diagram I, by cyclizing a ketone of formula III with sulfur and ammonium hydroxide or ammonia to form a nitrobenzisothiazole of formula IV, reducing the formula IV compounds using conventional reducing agents such as an iron in acetic acid to form an aminobenzisothiazole of formula V, reacting the formula V compound with phosgene or a phosgene equivalent to form an isocyanate of formula VI, reacting the isocyanate with a 3-aminoacrylate of formula VII in the presence of a base such as sodium hydride to form an intermediate compound of formula VIII, and reacting the formula VIII compound with an electrophile of formula IX in the presence of a base such as potassium carbonate.

FLOW DIAGRAM I

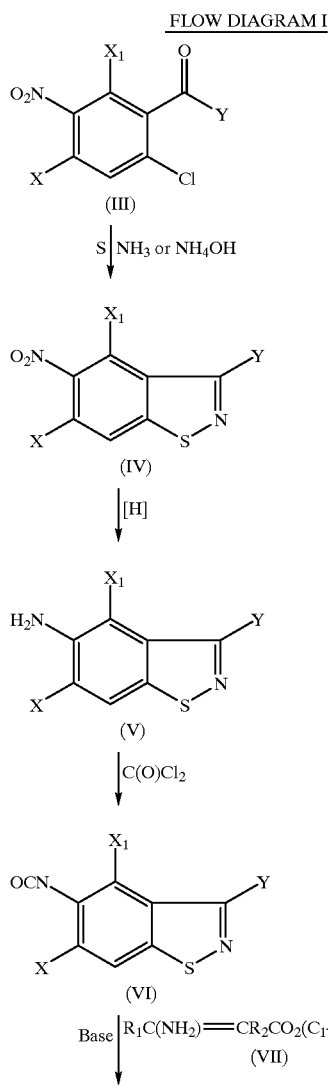

Formula I compounds wherein Z is S may also be prepared, as shown in Flow Diagram II, by reacting an aminobenzisothiazole of formula V with a 1,3-propanedione of formula X in the presence of a base such as triethylamine to form an intermediate compound of formula XI, and reacting the formula XI compound with phosgene or thiophosgene or an equivalent thereof followed by an amine of formula XII in the presence of a base such as triethylamine or pyridine.

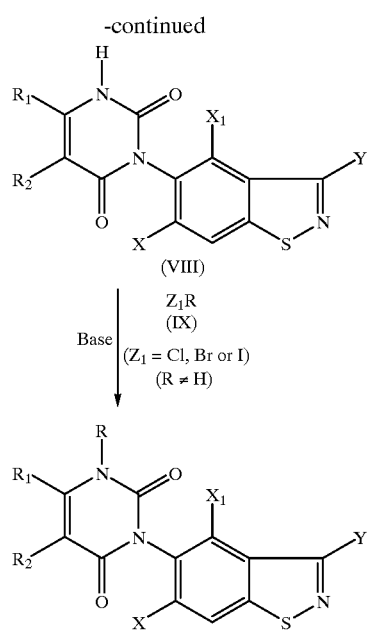

FLOW DIAGRAM II

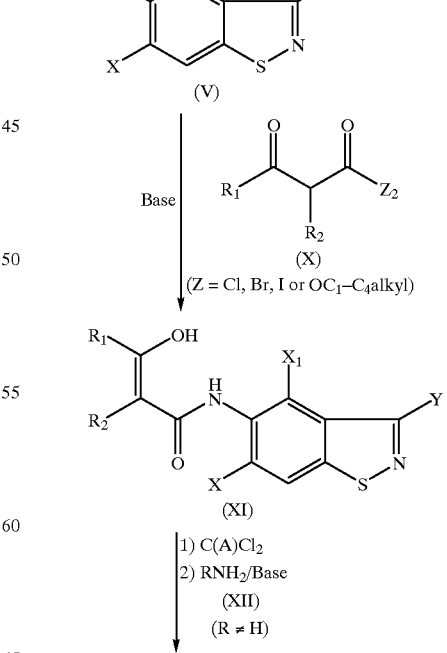

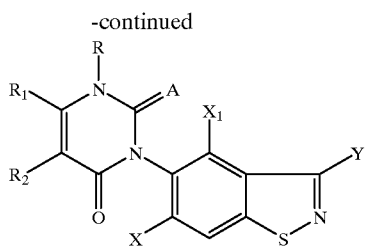

Alternatively, formula I compounds wherein Z is S may be prepared, as shown in Flow Diagram III, by reacting an aminobenzisothiazole of formula V with a 2-dialkylamino-6H-1,3-oxazin-6-one of formula XIII in the presence of an organic acid such as acetic acid to form an intermediate compound of formula VIII, and reacting the formula VIII compound with an electrophile of formula IX in the presence of a base such as potassium carbonate.

reacting the thus formed compound with an electrophile of formula $Z_1R_{22}$ ($Z_1$=Cl, Br or I) in the presence of base such as potassium hydroxide.

Formula I compounds wherein Z is O may be prepared, as shown in Flow Diagram IV, by reacting a ketone of formula III with hydroxylamine hydrochloride optionally in the presence of sodium acetate to form an oxime of formula XIV, cyclizing the formula XIV compound with a base such as potassium hydroxide to form a nitrobenzisoxazole of formula XV, reducing the formula XV compound using conventional reducing agents such as tin(II) chloride in acetic acid to form an aminobenzisoxazole of formula XVI, reacting the formula XVI compound with a 2-dialkylamino-6H-1,3-oxazin-6-one of formula XIII in the presence of an organic acid such as acetic acid to form an intermediate compound of formula XVII, and reacting the formula XVII compound with an electrophile of formula IX in the presence of a base such as potassium carbonate.

FLOW DIAGRAM III

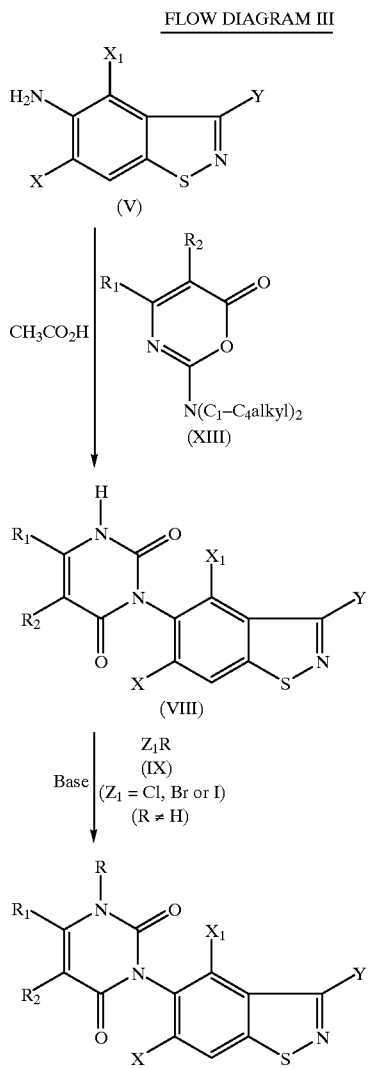

FLOW DIAGRAM IV

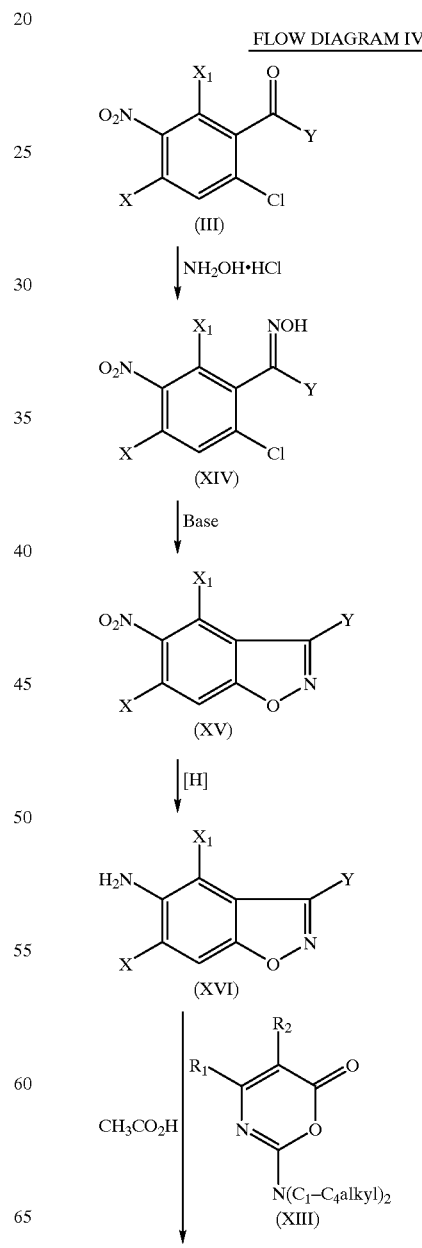

Formula I compounds wherein Y is phenyl substituted with one $X_4R_{22}$ group may be prepared by reacting a formula I compound wherein Y is phenyl substituted with one $C_1$–$C_4$alkoxy or $C_1$–$C_4$alkylthio group with boron tribromide to form the corresponding compound wherein Y is phenyl substituted with one hydroxy or thio group, and

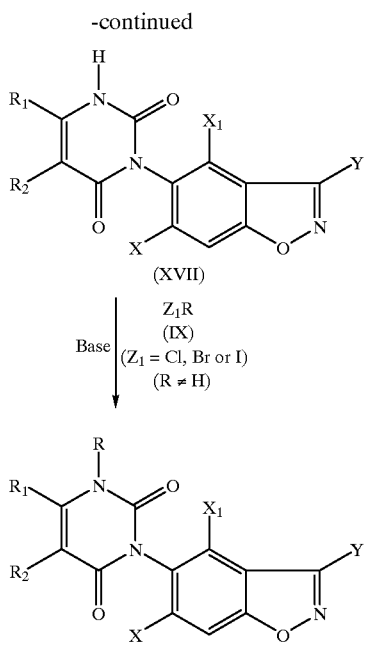

(XVII)

Base | $Z_1R$ (IX) ($Z_1$ = Cl, Br or I) (R ≠ H)

Alternatively, nitrobenzisoxazole compounds of formula XV may be prepared, as shown in Flow Diagram V, by reacting a ketone of formula XVIII with hydroxylamine hydrochloride optionally in the presence of a base such as sodium acetate to form an oxime of formula XIX, cyclizing the formula XIX compound with 1,1'-carbonyldiimidazole in the presence of a base such as triethylamine to form a benzisoxazole of formula XX, and nitrating the formula XX compound using conventional methods such as a nitric acid/sulfuric acid mixture.

FLOW DIAGRAM V

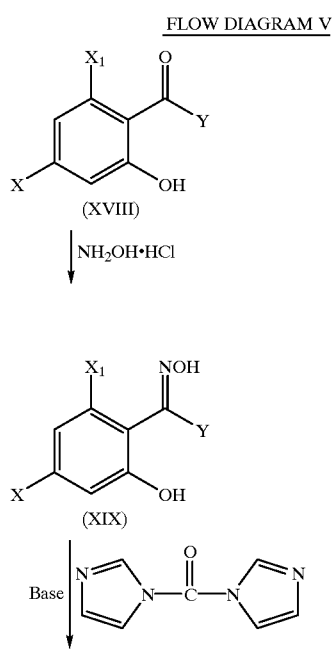

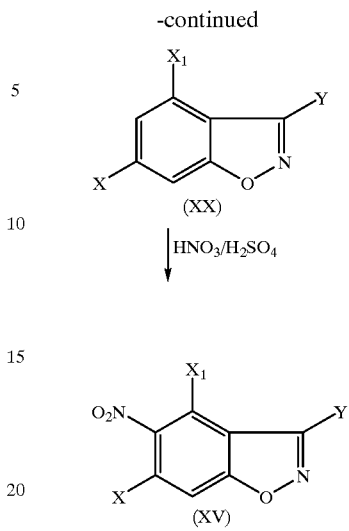

Formula I compounds wherein Y is halomethyl may be prepared, as shown in Flow Diagram VI, by halogenating a formula I compound wherein Y is methyl with a halogenating agent such as N-bromosuccinimide, N-chlorosuccinimide, N-iodosuccinimide, bromine, chlorine, sulfuryl chloride, sulfuryl bromide and the like.

FLOW DIAGRAM VI

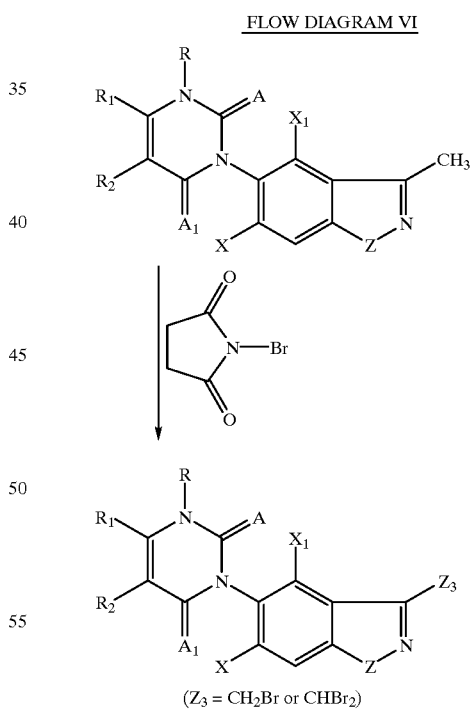

($Z_3$ = $CH_2Br$ or $CHBr_2$)

Formula I compounds wherein Y is a $C_1$–$C_{20}$alkoxymethyl group may be prepared, as shown in Flow Diagram VII, by reacting a formula I compound wherein Y is bromomethyl with a $C_1$–$C_{20}$alcohol in the presence of silver trifluoromethanesulfonate.

FLOW DIAGRAM VII

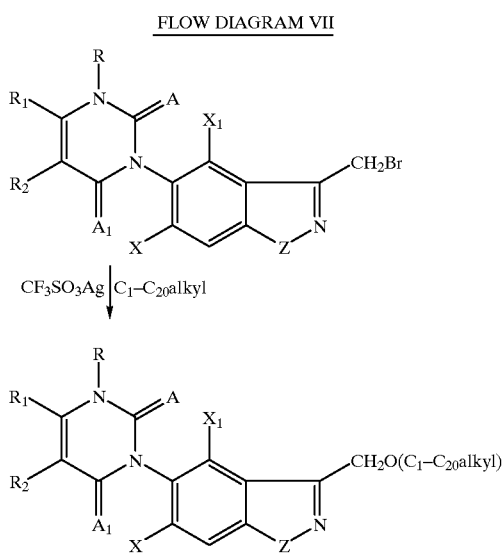

Formula I compounds wherein Y is methyl substituted with one $X_4R_{22}$ group may be prepared, as shown in Flow Diagram VIII, by reacting a formula I compound wherein Y is bromomethyl with an alcohol or thiol of formula XXI in the presence of a base such as sodium hydride.

FLOW DIAGRAM VIII

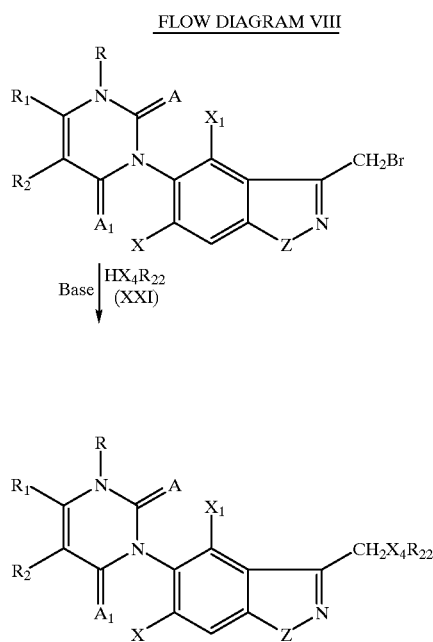

Formula I compounds wherein Y is $C_1$–$C_4$alkylthiomethyl may be prepared, as shown in Flow Diagram IX, by reacting a formula I compound wherein Y is bromomethyl with an alkali metal thioalkoxide.

FLOW DIAGRAM IX

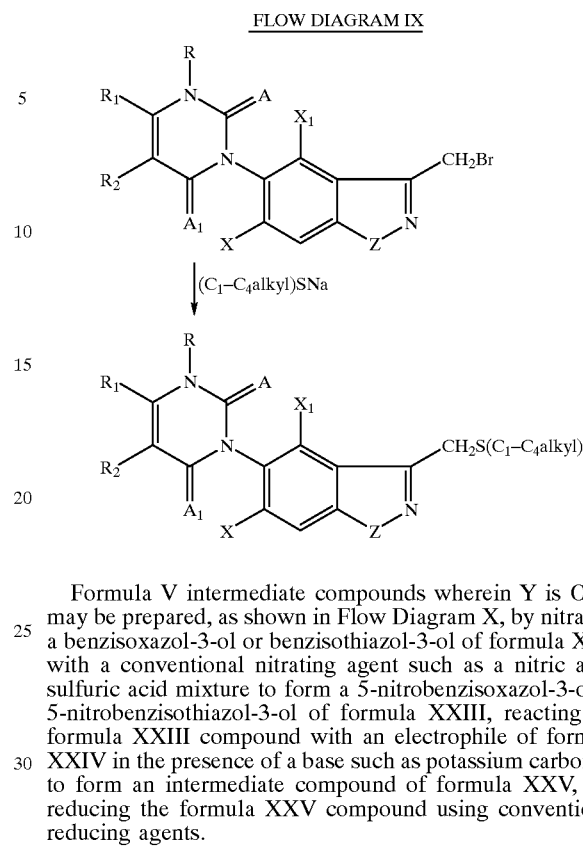

Formula V intermediate compounds wherein Y is $OR_{12}$ may be prepared, as shown in Flow Diagram X, by nitrating a benzisoxazol-3-ol or benzisothiazol-3-ol of formula XXII with a conventional nitrating agent such as a nitric acid/sulfuric acid mixture to form a 5-nitrobenzisoxazol-3-ol or 5-nitrobenzisothiazol-3-ol of formula XXIII, reacting the formula XXIII compound with an electrophile of formula XXIV in the presence of a base such as potassium carbonate to form an intermediate compound of formula XXV, and reducing the formula XXV compound using conventional reducing agents.

FLOW DIAGRAM X

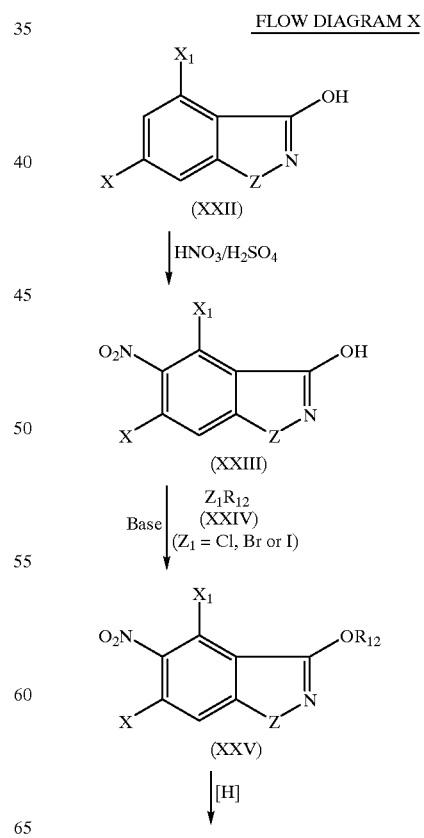

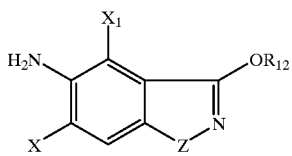

Formula V intermediate compounds wherein Y is Cl or Br may be prepared, as shown in Flow Diagram XI, by reacting a 5-nitrobenzisoxazol-3-ol or 5-nitrobenzisothiazol-3-ol of formula XXIII with phosphorous oxychloride, phosphorous oxybromide or phosphorous pentabromide to form a 3-halo-5-nitrobenzisoxazol or 3-halo-5-nitrobenzisothiazol of formula XXVI, and reducing the formula XXVI compound using conventional reducing agents.

FLOW DIAGRAM XI

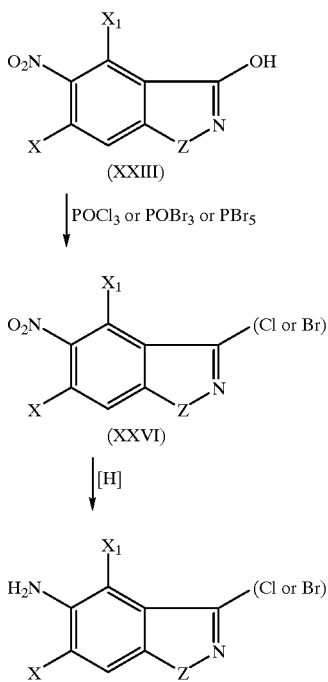

Formula I compounds wherein A is O and $A_1$ is S may be prepared, as shown in Flow Diagram XII, by reacting a formula I compound wherein A and $A_1$ are O with Lawesson's Reagent (2,4-bis(4-methoxyphenyl)-1,3-dithia-2,4-diphosphetane-2,4-disulfide) in the presence of a base such as sodium hydrogen carbonate.

FLOW DIAGRAM XII

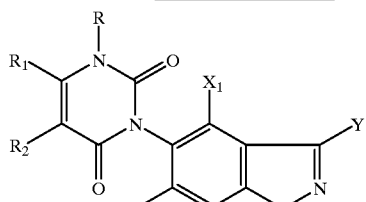

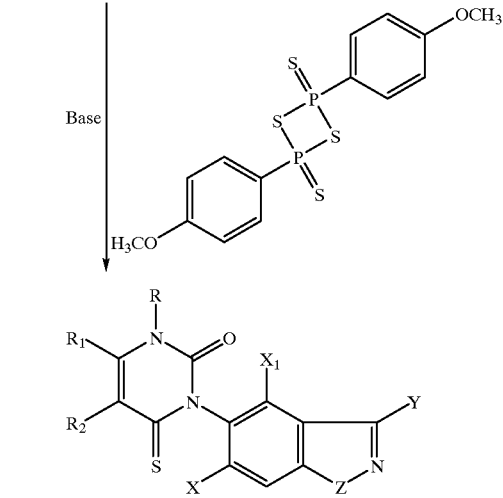

Formula I compounds wherein A and $A_1$ are S may be prepared, as shown in Flow Diagram XIII, by reacting a formula I compound wherein A is S and $A_1$ is O with Lawesson's Reagent in the presence of a base.

FLOW DIAGRAM XIII

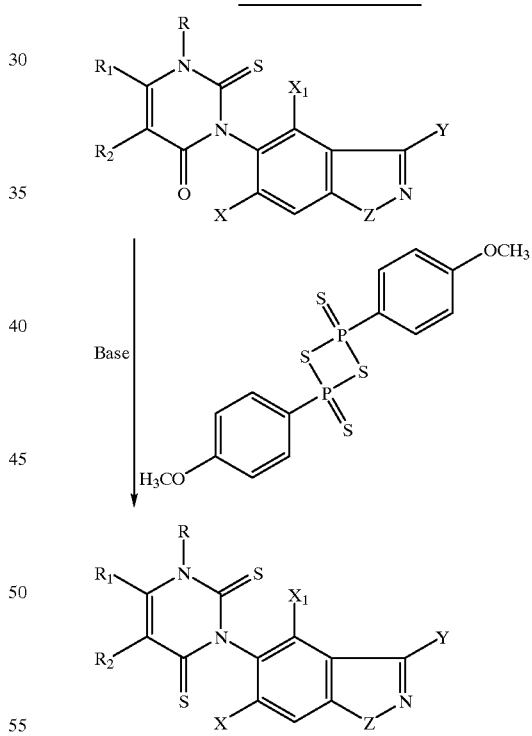

Formula I compounds wherein $R_{19}$, $R_{26}$ and $R_{32}$ are hydrogen may be prepared by hydrolyzing a corresponding formula I ester with an acid such as trifluoroacetic acid. The resultant formula I acid may then be reacted with thionyl chloride or oxalyl chloride to form an acid chloride which is then reacted with an $R_{19}OH$, $R_{26}OH$ or $R_{32}OH$ alcohol or an $HNR_{20}R_{21}$, $HNR_{35}R_{36}$ or $HNR_{49}R_{50}$ amine to form additional compounds of formula I.

Formula I compounds wherein $R_{19}$, $R_{26}$ and $R_{32}$ are an alkali metal, alkaline earth metal, manganese, copper, zinc, cobalt, silver, nickel, ammonium or organic ammonium cation may be prepared from formula I compounds wherein $R_{19}$, $R_{26}$ and $R_{32}$ are hydrogen using conventional methods.

Intermediate compounds of formula IV wherein Y is alkyl substituted with one $CO_2R_{19}$ group may be prepared, as shown in Flow Diagram XIV, by reacting an intermediate compound of formula XXVI with an oxylate of formula XXVII in the presence of a base to form an intermediate compound, reacting the intermediate compound with urea to form a compound of formula XXVIII wherein Y is methyl substituted with one $CO_2R_{19}$ group, and optionally reacting the formula XXVIII compound with a $C_1$–$C_5$alkyl halide in the presence of a base such as sodium hydride to form a compound of formula XXIX. In addition, the formula XXVIII and XXIX compounds may be saponified to form compounds wherein $R_{19}$ is hydrogen.

FLOW DIAGRAM XIV

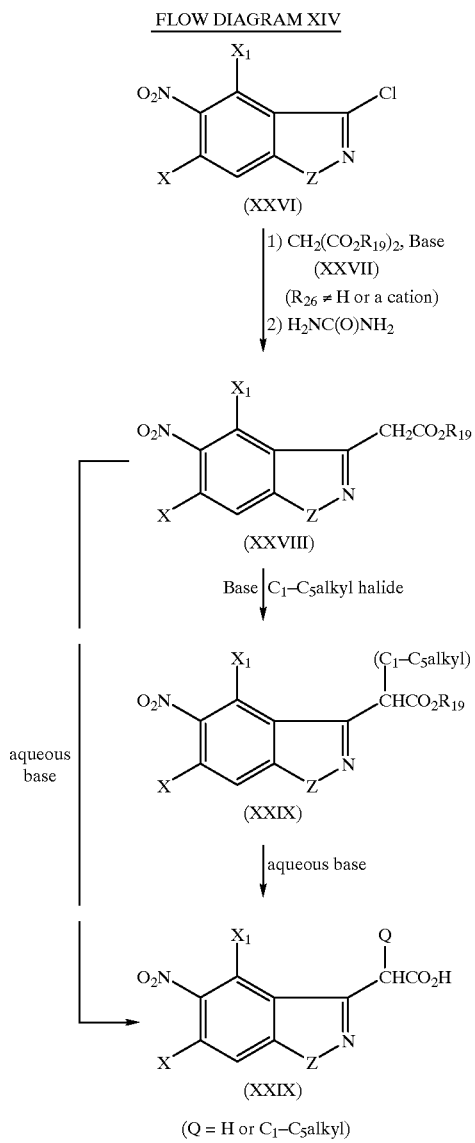

Alternatively, formula III compounds wherein Y is an α-methylacetate group may be prepared as shown in Flow Diagram XV.

FLOW DIAGRAM XV

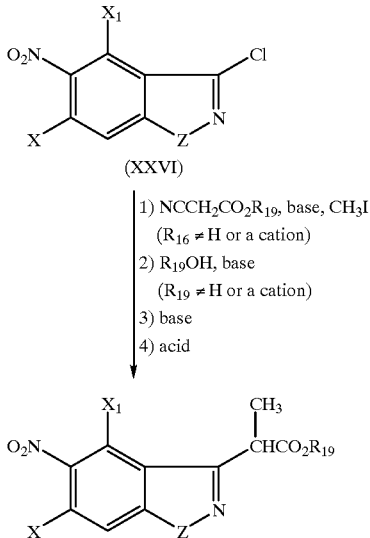

Intermediate compounds of formula III wherein Y is methyl substituted with one $CO_2R_{19}$ group may be prepared by reacting an acid chloride of formula XXX with an acetate of formula XXXI in the presence of a base such as sodium hydride, and optionally reacting the formula III compound wherein Y is methyl substituted with one $CO_2R_{19}$ group with a $C_1$–$C_5$alkyl halide in the presence of a base such as sodium hydride to form a formula III compound wherein Y is an α-alkylacetate group. The reactions are shown below in Flow Diagram XVI.

FLOW DIAGRAM XVI

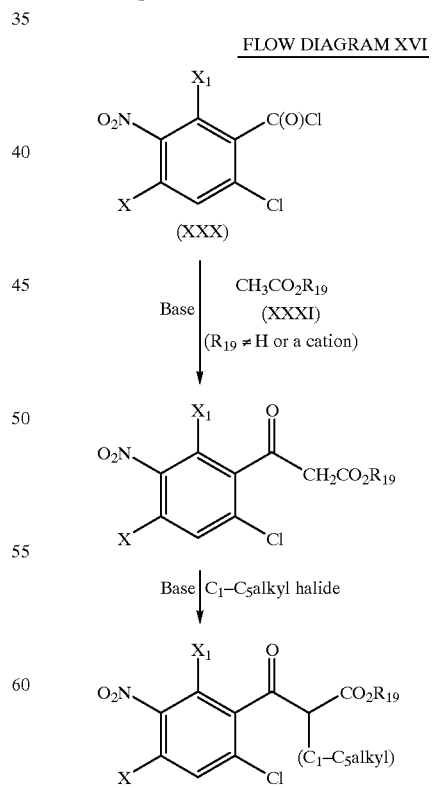

Formula IV and XV compounds wherein Y is an alkyl or phenyl group substituted with one $C(O)R_{18}$ or $C(O)R_{25}$ group may be prepared by reacting the corresponding acid chloride with an appropriately substituted magnesium bromide compound, copper bromide compound or lithium compound. The reaction scheme is exemplified below for the case where Y is phenyl substituted with one $C(O)R_{25}$ group.

FLOW DIAGRAM XVII

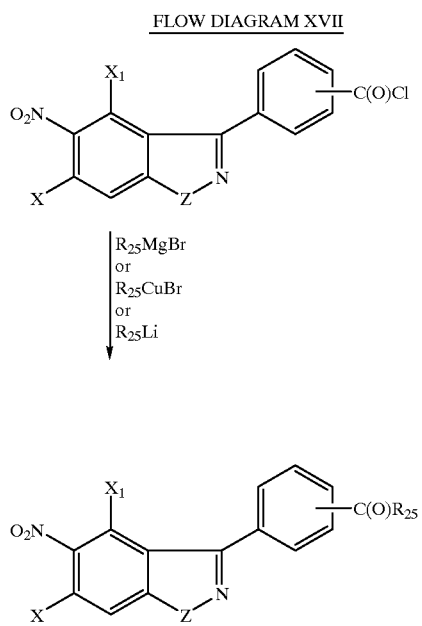

Formula I, IV and XV compounds wherein Y is alkyl, cycloalkyl, alkenyl, cycloalkenyl, alkynyl or phenyl substituted with a CHO group may be prepared by reducing a formula I, IV or XV compound wherein Y is alkyl, cycloalkyl, alkenyl, cycloalkenyl, alkynyl or phenyl substituted with a $CO_2H$ group with a conventional reducing agent such as a borane-tetrahydrofuran complex to form a formula I, IV or XV compound wherein Y is alkyl, cycloalkyl, alkenyl, cycloalkenyl, alkynyl or phenyl substituted with a $CH_2OH$ group, and oxidizing the resultant alcohol with a conventional oxidizing agent such as chromium(VI) oxide. The reaction scheme is exemplified in Flow Diagram XVIII for the case where Y is phenyl substituted with one CHO group.

FLOW DIAGRAM XVIII

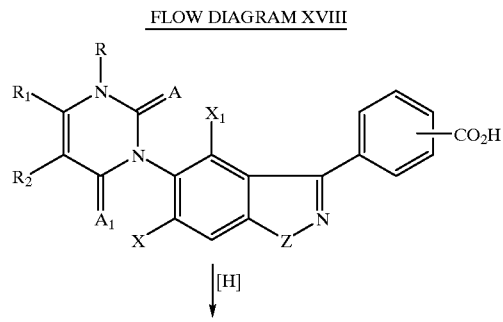

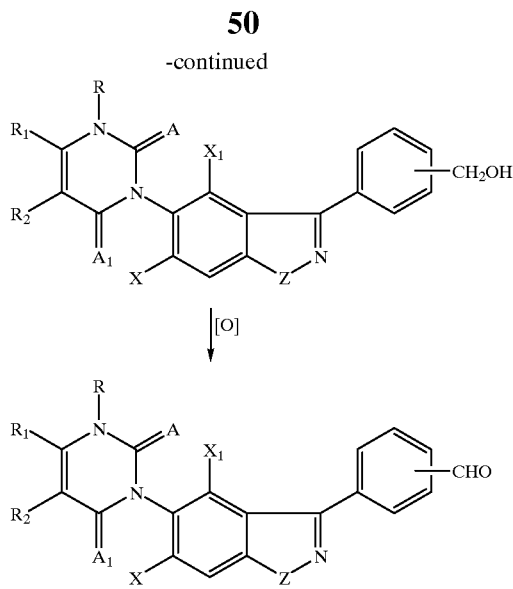

Formula IV an XV compounds wherein Y is alkyl or cycloalkyl substituted with a $C(O)R_{18}$ group may be prepared by reacting a formula IV or XV compound wherein Y is haloalkyl or halocycloalkyl with a lithium reagent of formula XXXII to form an intermediate compound, and reacting the intermediate compound with a Lewis Acid such as borontrifluoride in the presence of water. The reaction scheme is exemplified in Flow Diagram XIX for the case where Y is methyl substituted with one $C(O)R_{18}$ group.

FLOW DIAGRAM XIX

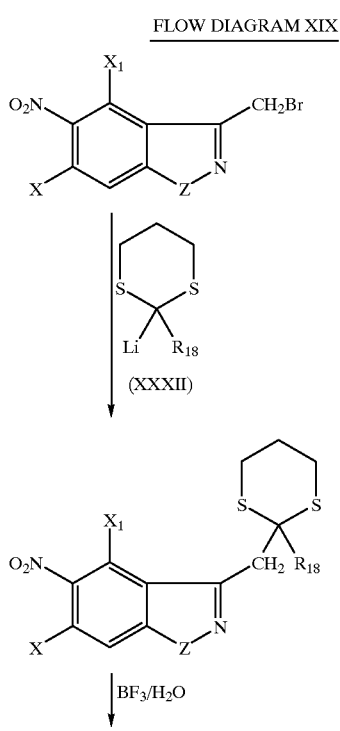

-continued

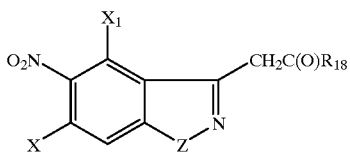

Formula I compounds wherein Y is formyl may also be prepared as shown in Flow Diagram XX.

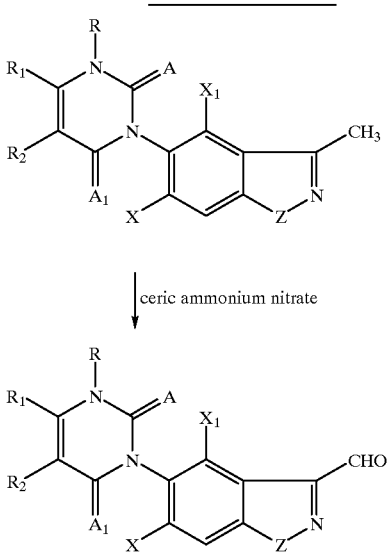

Formula IV an XV compounds wherein Y is $X_2R_{12}$ and $R_{12}$ is optionally substituted phenyl may be prepared, as shown in Flow Diagram XXI, by reacting a formula IV or XV compound wherein Y is Br with an $R_{12}X_2H$ compound in the presence of a base such as potassium carbonate.

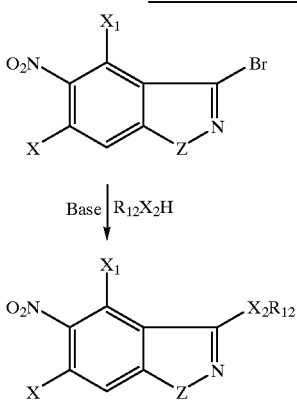

Formula IV and XV compounds wherein Y is trifluoromethyl may be prepared, as shown in Flow Diagram XXII, by reacting a formula IV or XV compound wherein Y is Br with a silyl compound of formula XXXIII in the presence of copper(I) iodide and potassium iodide.

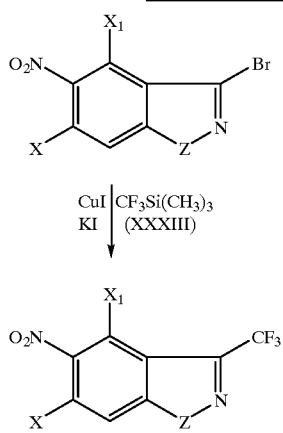

Alternatively, formula III and XIV compounds wherein Y is trifluoromethyl may be prepared by reacting a formula IV or XV compound wherein Y is Br with sodium trifluoroacetate in the presence of a catalyst such as a tetrasubstituted palladium catalyst. The reaction scheme is shown in Flow Diagram XXIII.

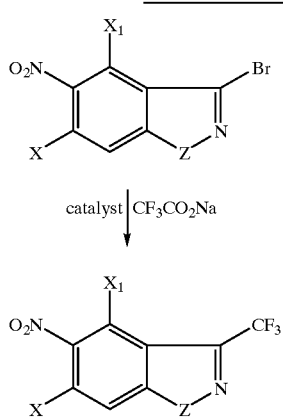

Formula I compounds wherein Y is $CH_2CN$ may be prepared, as shown in Flow Diagram XXIV, by reacting a formula I compound wherein Y is $CH_2Br$ with potassium cyanide.

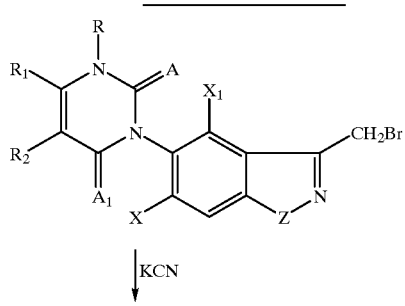

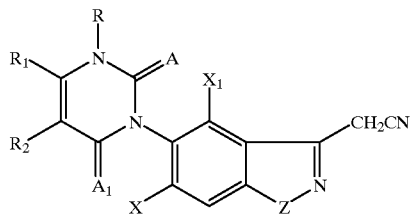

FLOW DIAGRAM XXVI

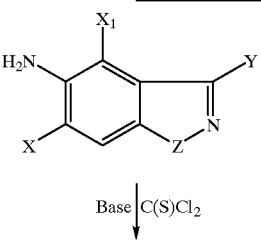

Formula I compounds wherein Y is $R_{12}$ or $X_2R_{12}$ and $R_{12}$ is chloroalkyl, fluoroalkyl or iodoalkyl may be prepared by reacting the corresponding formula I compound wherein $R_{12}$ is bromoalkyl with lithium chloride, sodium iodide, potassium fluoride or silver(I) fluoride. The reaction scheme is exemplified below in Flow Diagram XXV for the case where Y is fluoromethyl, iodomethyl and chloromethyl.

FLOW DIAGRAM XXV

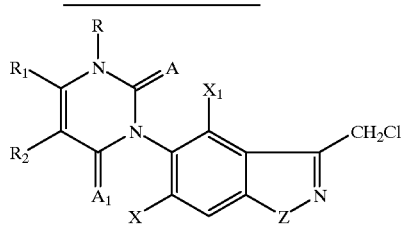

↑ LiCl

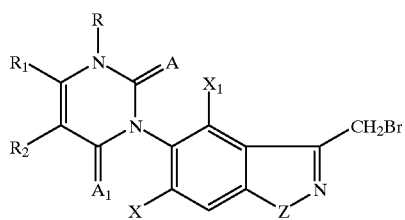

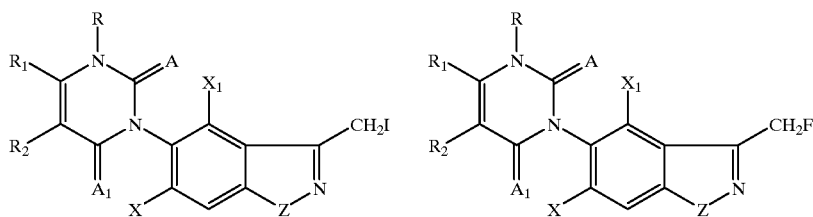

Formula I compounds wherein A is S and $A_1$ is O may be prepared, as shown in Flow Diagram XXVI, by reacting an amine of formula V or XVI with thiophosgene or a thiophosgene equivalent in the presence of a base such as triethylamine to form an isothiocyanate of formula XXXIV, and reacting the formula XXXIV compound with an alkene of formula XXXV in the presence of a base such as sodium hydride.

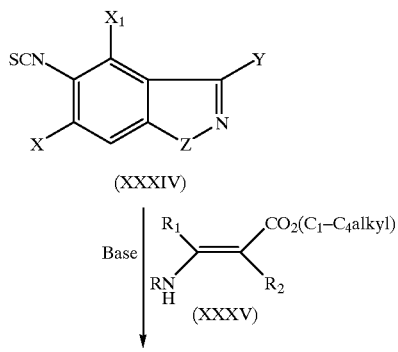

(XXXIV)

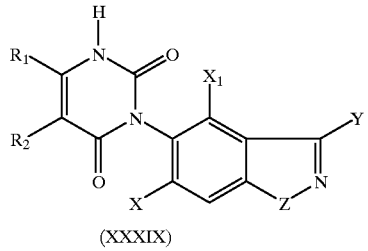

(XXXIX)

Base | (XXXV)

Base | $Z_1R$ (XL) ($Z_1$ = Cl, Br or I) (R ≠ H)

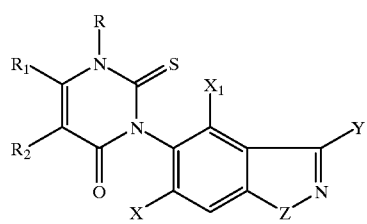

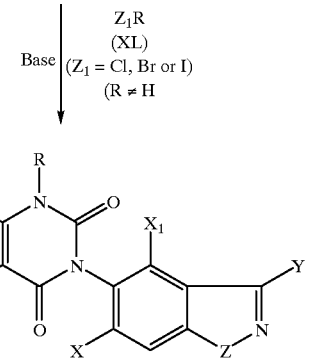

Formula I compounds wherein A and $A_1$ are O may be prepared, as shown in Flow Diagram XXVII, by reacting an isocyanate of formula XXXVI with an alkene of formula XXXVII in the presence of a base such as sodium hydride to form a urea of formula XXXVIII, cyclizing the formula XXXVIII compound with acid to form an intermediate compound of formula XXXIX, and reacting the formula XXXIX compound with an electrophile of formula XL in the presence of a base such as potassium carbonate.

Intermediate compounds of formula III wherein Y is acetate substituted with α-($C_1$–$C_6$alkyl) or α,α-bis ($C_1$–$C_6$alkyl) may be prepared by treated an acid chloride of formula XLI with zinc and an a-halo ester of formula XLII to form an intermediate keto-ester of formula XLIII, which is nitrated to form an intermediate of formula III. The reaction scheme is shown in Flow Diagram XXVIII.

FLOW DIAGRAM XXVII

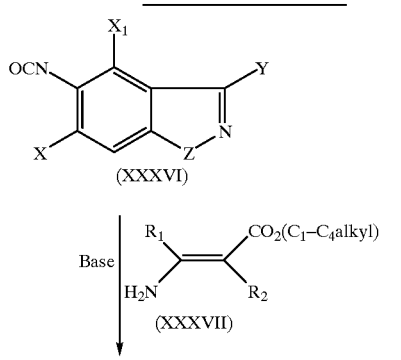

(XXXVI)

Base | (XXXVII)

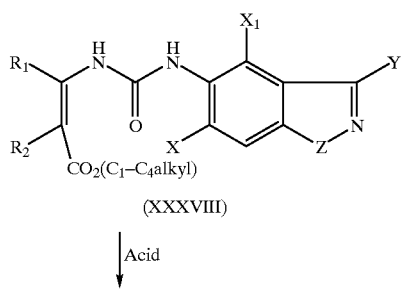

(XXXVIII)

| Acid

FLOW DIAGRAM XXVIII

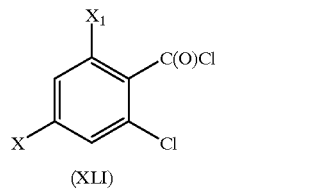

(XLI)

zinc, 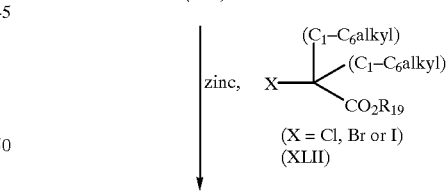

(X = Cl, Br or I)
(XLII)

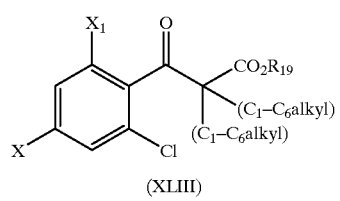

(XLIII)

| $HNO_3$
| $H_2SO_4$

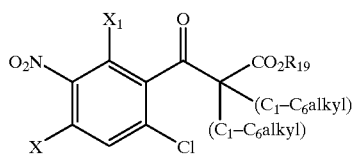

Formula V intermediate compounds wherein Y is Cl or Br may also be prepared, as shown in Flow Diagram XXIX, by reacting a 5-nitrobenzisothiazole or 5-nitrobenzisoxazole of formula XLIV with chlorine or bromine in an acid such as acetic acid. The reaction scheme is shown below in Flow Diagram XXIX.

FLOW DIAGRAM XXIX

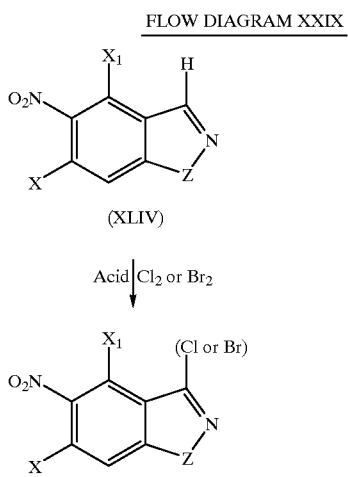

Formula I compounds wherein Y is $C(O)X_2R_{12}$ and $X_2$ is O or S may be prepared as shown in Flow Diagram XXX.

FLOW DIAGRAM XXX

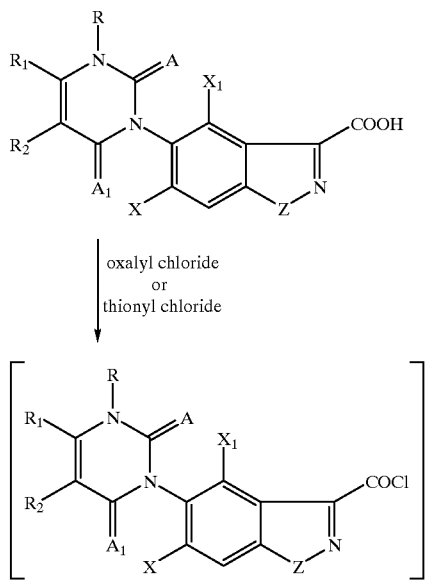

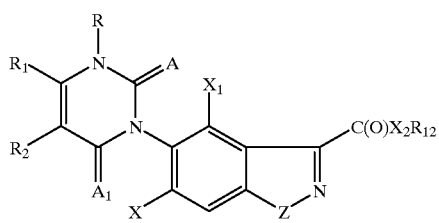

Formula I compounds wherein Y is $C(O)NR_{12}R_{13}$ may be prepared as shown below in Flow Diagram XXXI.

FLOW DIAGRAM XXXI

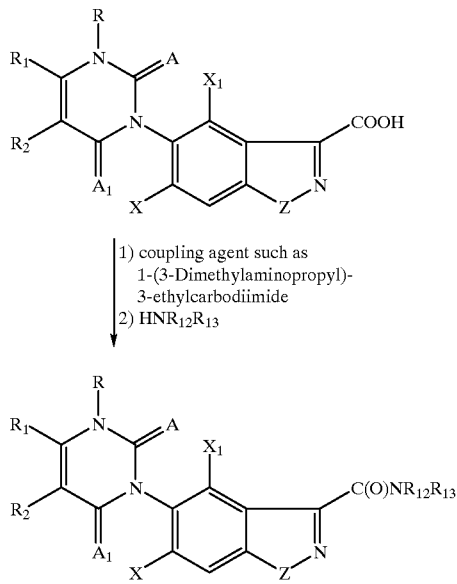

Formula I compounds wherein Y is $C(O)NR_{13}SO_2NR_{46}R_{48}$ may be prepared as shown below in Flow Diagram XXXII.

FLOW DIAGRAM XXXII

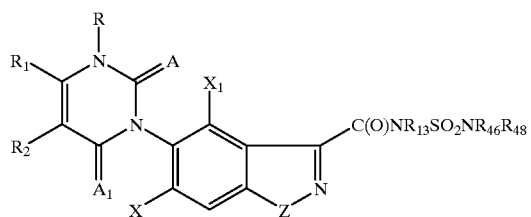
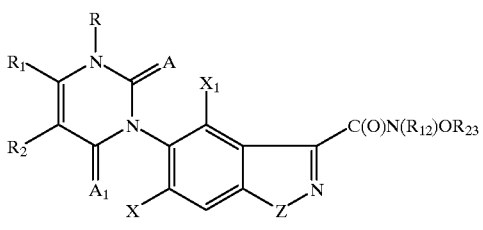
Formula I compounds wherein Y is $C(O)N(R_{12})OR_{23}$ may be prepared as shown in Flow Diagram XXXIV.
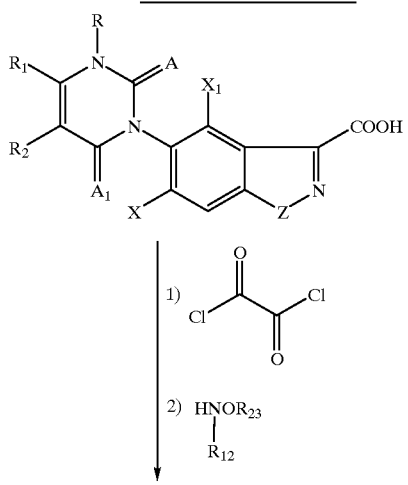
Formula I compounds wherein Y is $CH(OH)R_{23}$, $C(O)R_{23}$, $CH(OR_{22})R_{23}$ and $CH(R_{23})OC(O)R_{23}$ may be prepared as shown below in Flow Diagram XXXV.
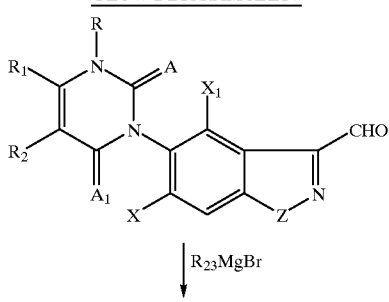

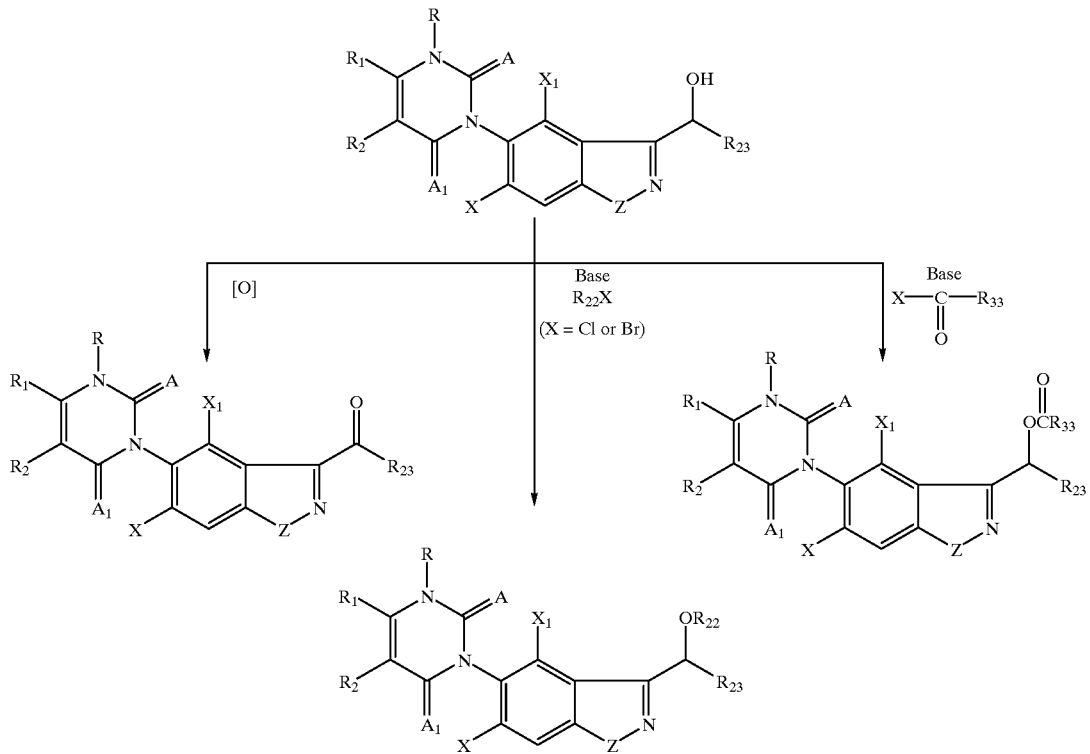

Other methods for the preparation of formula I compounds and methods for the preparation of formula II compounds will become apparent from the examples set forth below. In addition, certain compounds of formulas I and II may be converted into other compounds of formulas I and II by using conventional procedures known to those skilled in the art.

The present invention also relates to intermediate compounds having the structural formula XLV

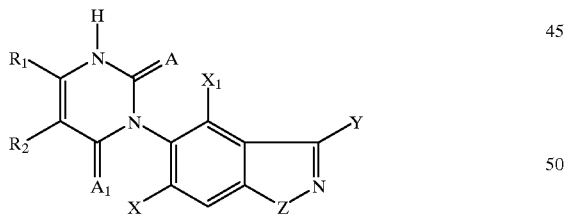

(XLI)

wherein $R_1$, $R_2$, A, $A_1$, X, $X_1$, Y and Z are as described hereinabove for formula I.

Preferred intermediate compounds of formula XLV are those wherein $R_1$ and $R_2$ are each independently hydrogen, halogen, $C_1$–$C_6$alkyl, $C_3$–$C_7$cycloalkyl, $C_3$–$C_6$haloalkyl, $C_3$–$C_6$alkenyl, $C_3$–$C_6$haloalkenyl, $C_3$–$C_6$alkynyl, $OR_7$, $S(O)_nR_8$ or $NR_9R_{10}$, and when $R_1$ and $R_2$ are taken together with the atoms to which they are attached, they represent a four- to seven-membered saturated or unsaturated ring optionally interrupted by oxygen, sulfur or nitrogen, and optionally substituted with one to three methyl groups or one or more halogen atoms;

X is hydrogen, halogen or $C_1$–$C_4$alkyl;
$X_1$ is hydrogen, halogen, $C_1$–$C_4$alkyl, $C_1$–$C_4$haloalkyl, $C_1$–$C_4$alkoxy or $C_1$–$C_4$haloalkoxy;
Z is O or $S(O)_m$;
Y is halogen, cyano, $R_{12}$, $X_2R_{12}$, $X_3R_{12}$, $X_2X_3R_{12}$ or $X_3X_2R_{12}$;
$X_2$ is O, $S(O)_p$ or $NR_{13}$;
$X_3$ is —C(=$A_3$)— or —C(=$NOR_{14}$)—;
$R_4$, $R_5$, $R_6$, $R_7$, $R_8$, $R_9$, $R_{10}$ and $R_{14}$ are each independently hydrogen, $C_1$–$C_4$alkyl, $C_3$–$C_7$cycloalkyl, $C_2$–$C_6$alkenyl, $C_2$–$C_6$alkynyl or benzyl;
$R_{12}$ is hydrogen,
a $C_1$–$C_6$alkyl, $C_3$–$C_7$cycloalkyl, $C_2$–$C_6$alkenyl, $C_5$–$C_6$cycloalkenyl or $C_2$–$C_6$alkynyl group, wherein each group is optionally substituted with any combination of one to six halogen atoms, one to three $C_1$–$C_{20}$alkoxy groups, one or two $C_1$–$C_{10}$haloalkoxy groups, one or two $NR_{15}R_{16}$ groups, one to three $S(O)_qR_{17}$ groups, one or two cyano groups, one or two $C(O)R_{18}$ groups, one or two $CO_2R_{19}$ groups, one or two $C(O)NR_{20}R_{21}$ groups, one to three $X_4R_{22}$ groups, one or two $P(O)(OR_{23})_2$ groups, one or two $Si(R_{24})_3$ groups,
one 4- to 10-membered heterocyclic ring optionally substituted with any combination of one or two oxo groups, one or two thioxo groups, one to three halogen atoms, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups or one or two $X_4R_{22}$ groups,
one quaternary organic ammonium group, or
one phenyl group optionally substituted with any combination of one to three halogen atoms, one to three $C_1$–$C_6$alkyl groups, one to three $C_1$–$C_6$alkoxy groups, one $C_3$–$C_7$cycloalkyl group, one $C_1$–$C_4$haloalkyl group, one $C_1$–$C_4$alkylthio group, one cyano group, one nitro group, one $C(O)R_{25}$ group, one $CO_2R_{26}$ group or one $X_5R_{27}$ group, or phenyl optionally substituted with any combination of one to three halogen atoms, one to three $C_1$–$C_4$alkyl groups, one to three $C_1$–$C_4$alkoxy groups, one $C_3$–$C_6$cycloalkyl group, one $C_1$–$C_4$haloalkyl group, one $C_1$–$C_4$alkylthio group, one cyano group, one nitro group, one $C(O)R_{25}$ group, one $CO_2R_{26}$ group, one $X_4R_{22}$ group, one $CH=CHR_{22}$ group, one $CH_2CH(R_{28})R_{22}$ group or one $N(R_{29})SO_2R_{30}$ group, and when $R_{12}$ and $R_{13}$ are taken together with the nitrogen atom to which they are attached, they form a 5- to 12-membered monocyclic or fused bicyclic, heterocyclic ring optionally substituted with one or more groups independently selected from halogen, cyano, nitro, amino, hydroxyl, $C_1$–$C_4$alkyl, $C_1$–$C_4$haloalkyl, $C_1$–$C_4$alkoxy, $C_1$–$C_4$haloalkoxy, $C_1$–$C_4$haloalkylsulfonyl or $X_4R_{22}$ groups;

$R_{13}$ is hydrogen, $C_1$–$C_6$alkyl, $C_3$–$C_7$cycloalkyl, $C_3$–$C_6$alkenyl, $C_3$–$C_6$alkynyl, benzyl, $OR_{23}$, cyano or $SO_2R_{51}$, and when $R_{13}$ and $R_{12}$ are taken together with the nitrogen atom to which they are attached, they form a 5- to 12-membered monocyclic or fused bicyclic, heterocyclic ring optionally substituted with one or more groups independently selected from halogen, cyano, nitro, amino, hydroxyl, $C_1$–$C_4$alkyl, $C_1$–$C_4$haloalkyl, $C_1$–$C_4$alkoxy, $C_1$–$C_4$haloalkoxy, $C_1$–$C_4$haloalkylsulfonyl or $X_4R_{22}$ groups;

$R_{28}$ is halogen;

$R_{22}$ and $R_{27}$ are each independently hydrogen, $Si(R_{31})_3$, $C_1$–$C_{20}$alkyl substituted with one $C_1$–$C_6$alkoxy, $CO_2R_{32}$, $C(O)R_{33}$, $C(A_4R_{34})_2$, $C(O)NR_{35}R_{36}$, $C(O)ON=CR_{37}R_{38}$, $P(O)(OH)NH_2$, $P(O)(OH)(OR_{23})$, $C(O)NHOR_{23}$, cyano or 2-dioxolanyl group, one phenyl, dihydrofuranone or furanone ring wherein each ring is optionally substituted with any combination of one to three halogen atoms, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups, or one 5- to 12-membered monocyclic or fused bicyclic, heterocyclic ring optionally substituted with one or more groups independently selected from halogen, cyano, nitro, amino, hydroxyl, $C_1$–$C_4$alkyl, $C_1$–$C_4$haloalkyl, $C_1$–$C_4$alkoxy, $C_1$–$C_4$haloalkoxy or $C_1$–$C_4$haloalkylsulfonyl groups, $C_3$–$C_{20}$alkenyl optionally substituted with one to three halogen atoms, one $C_1$–$C_6$alkoxy, $CO_2R_{32}$, $C(O)R_{33}$, $C(A_4R_{34})_2$, $C(O)NR_{35}R_{36}$, $C(O)ON=CR_{37}R_{38}$, $C(O)NHOR_{23}$, cyano or 2-dioxolanyl group, or one phenyl, dihydrofuranone or furanone ring wherein each ring is optionally substituted with any combination of one to three halogen atoms, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups, $C_5$–$C_8$cycloalkenyl optionally substituted with one $C_1$–$C_6$alkoxy, $C_1$–$C_4$alkyl, $C_2$–$C_4$alkenyl, $CO_2R_{32}$, $C(O)R_{33}$, $C(A_4R_{34})_2$, $C(O)NR_{35}R_{36}$, $C(O)ON=CR_{37}R_{38}$, $C(O)NHOR_{23}$, cyano or 2-dioxolanyl group, or one phenyl, dihydrofuranone or furanone ring wherein each ring is optionally substituted with any combination of one to three halogen atoms, one to three $C_1$–$C_4$alkyl groups, one to three $C_1$–$C_4$alkoxy groups or one to three $C_1$–$C_4$haloalkoxy groups, $C_3$–$C_{10}$alkynyl optionally substituted with one $C_1$–$C_6$alkoxy, $CO_2R_{32}$, $C(O)R_{33}$, $C(A_4R_{34})_2$, $C(O)NR_{35}R_{36}$, $C(O)ON=CR_{37}R_{38}$, $C(O)NHOR_{23}$, cyano or 2-dioxolanyl group, or one phenyl, dihydrofuranone or furanone ring wherein each ring is optionally substituted with any combination of one to three halogen atoms, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups, phenyl optionally substituted with any combination of one to three halogen atoms, one to three $C_1$–$C_6$alkyl groups, one to three $C_1$–$C_6$alkoxy groups, one $C_1$–$C_4$haloalkyl group, one $C_1$–$C_4$haloalkoxy group, one cyano group, one nitro group, one $NR_{39}R_{40}$ group or one $C(O)R_{33}$ group, benzyl optionally substituted on the phenyl ring with any combination of one to three halogen atoms, one to three $C_1$–$C_6$alkyl groups, one to three $C_1$–$C_6$alkoxy groups, one $C_1$–$C_4$haloalkyl group, one $C_1$–$C_4$haloalkoxy group, one cyano group, one nitro group, one $NR_{39}R_{40}$ group or one $C(O)R_{33}$ group, or a 4- to 10-membered heterocyclic ring optionally substituted with any combination of one or two oxo groups, one or two thioxo groups, one to three halogen atoms, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups;

$R_{15}$ and $R_{20}$ are each independently hydrogen, a $C_1$–$C_6$alkyl, $C_3$–$C_7$cycloalkyl, $C_2$–$C_6$alkenyl or $C_2$–$C_6$alkynyl group wherein each group is optionally substituted with one $CO_2R_{42}$ group, benzyl optionally substituted with any combination of one to three halogen atoms, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups, phenyl optionally substituted with any combination of one to three halogen atoms, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups, or $C(O)R_{43}$;

$R_{16}$ and $R_{21}$ are each independently hydrogen, $C_1$–$C_6$alkyl, $C_3$–$C_7$cycloalkyl, $C_2$–$C_6$alkenyl, $C_3$–$C_7$cycloalkenyl, $C_2$–$C_6$alkynyl, $P(O)(OR_{44})_2$, $SO_2R_{45}$, $C(O)R_{46}$, benzyl optionally substituted with any combination of one to three halogen atoms, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups or one $X_4R_{22}$ group, or phenyl optionally substituted with any combination of one to three halogen atoms, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups or one $X_4R_{22}$ group;

$R_{17}$, $R_{18}$, $R_{25}$, $R_{33}$, $R_{45}$ and $R_{51}$ are each independently $C_1$–$C_4$alkyl, $C_1$–$C_4$haloalkyl, $CO_2R_{23}$, $C_2$–$C_6$alkenyl optionally substituted with phenyl, benzyl optionally substituted with any combination of one to three halogen atoms, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups, one nitro group, one cyano group or one $X_4R_{22}$ group, phenyl optionally substituted with any combination of one to three halogen atoms, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups, one nitro group, one cyano group or one $X_4R_{22}$ group, or a 5- to 12-membered monocyclic or fused bicyclic, heterocyclic ring optionally substituted with one or more groups independently selected from halogen, cyano, nitro, amino, hydroxyl, $C_1$–$C_4$alkyl, $C_1$–$C_4$haloalkyl, $C_1$–$C_4$alkoxy, $C_1$–$C_4$haloalkoxy, $C_1$–$C_4$haloalkylsulfonyl or $X_4R_{22}$ groups;

$R_{19}$ and $R_{26}$ are each independently hydrogen, $C_1$–$C_{20}$alkyl, $C_1$–$C_8$haloalkyl, $C_3$–$C_7$cycloalkyl, $C_3$–$C_7$halocycloalkyl, $C_3$–$C_{20}$alkenyl, $C_3$–$C_8$haloalkenyl, $C_5$–$C_8$cycloalkenyl, $C_5$–$C_8$halocycloalkenyl, $C_3$–$C_8$alkynyl, $C_3$–$C_8$haloalkynyl, Si($R_{41}$)$_3$, benzyl, phenyl, furfuryl, pyridyl, thienyl, oximino or an alkali metal, alkaline earth metal, manganese, copper, zinc, cobalt, silver, nickel, ammonium or organic ammonium cation;

$R_{32}$ is hydrogen,
Si($R_{47}$)$_3$,
di($C_1$–$C_4$alkyl)imino,
$C_1$–$C_{20}$alkyl optionally substituted with one $CO_2R_{48}$, $C_1$–$C_6$alkoxy or di($C_1$–$C_4$alkyl)imino group,
$C_1$–$C_{15}$haloalkyl,
$C_3$–$C_8$cycloalkyl,
$C_3$–$C_8$halocycloalkyl,
$C_3$–$C_{20}$alkenyl optionally substituted with one phenyl group,
$C_3$–$C_{15}$haloalkenyl,
$C_5$–$C_8$cycloalkenyl,
$C_5$–$C_8$halocycloalkenyl,
$C_3$–$C_{20}$alkynyl optionally substituted with one phenyl group,
$C_3$–$C_{20}$haloalkynyl,
benzyl optionally substituted with one or more groups independently selected from halogen, cyano, nitro, $C_1$–$C_4$alkyl, $C_1$–$C_4$haloalkyl, $C_1$–$C_4$alkoxy and $C_1$–$C_4$haloalkoxy groups,
phenyl optionally substituted with one or more groups independently selected from halogen, cyano, nitro, $C_1$–$C_4$alkyl, $C_1$–$C_4$haloalkyl, $C_1$–$C_4$alkoxy and $C_1$–$C_4$haloalkoxy groups,
2-, 3- or 4-pyridyl,
2- or 3-furyl,
2- or 3-thienyl,
2-tetrahydrofuranyl,
$C_1$–$C_4$alkyl substituted with one pyridyl, furyl, thienyl, tetrahydrofuryl or $NR_{49}R_{50}$ group, or
an alkali metal, alkaline earth metal, manganese, copper, zinc, cobalt, silver, nickel, ammonium or organic ammonium cation;

$R_{34}$, $R_{37}$ and $R_{38}$ are each independently $C_1$–$C_6$alkyl;

$R_{39}$ and $R_{49}$ are each independently hydrogen or $C_1$–$C_6$alkyl and $R_{36}$ and $R_{50}$ are each independently hydrogen, cyano, $C_1$–$C_6$alkyl, $SO_2R_{51}$ or phenyl optionally substituted with one or more groups independently selected from halogen, cyano, nitro, $C_1$–$C_4$alkyl, $C_1$–$C_4$haloalkyl, $C_1$–$C_4$alkoxy and $C_1$–$C_4$haloalkoxy groups, or when $R_{35}$ and $R_{36}$ or $R_{49}$ and $R_{50}$ are taken together with the nitrogen atom to which they are attached, they form a 5- to 12-membered monocyclic or fused bicyclic, heterocyclic ring optionally substituted with one or more groups independently selected from halogen, cyano, nitro, amino, hydroxyl, $C_1$–$C_4$alkyl, $C_1$–$C_4$haloalkyl, $C_1$–$C_4$alkoxy, $C_1$–$C_4$haloalkoxy or $C_1$–$C_4$haloalkylsulfonyl groups;

m, n, p and q are each independently an integer of 0, 1 or 2;

$R_{29}$ is hydrogen, $C_1$–$C_4$alkyl or $C_1$–$C_4$haloalkyl;

$R_{24}$, $R_{31}$, $R_{41}$ and $R_{47}$ are each independently $C_1$–$C_4$alkyl, benzyl optionally substituted with one or more groups independently selected from halogen, cyano, nitro, $C_1$–$C_4$alkyl, $C_1$–$C_4$haloalkyl, $C_1$–$C_4$alkoxy and $C_1$–$C_4$haloalkoxy groups, or
phenyl optionally substituted with one or more groups independently selected from halogen, cyano, nitro, $C_1$–$C_4$alkyl, $C_1$–$C_4$haloalkyl, $C_1$–$C_4$alkoxy and $C_1$–$C_4$haloalkoxy groups;

$R_{23}$, $R_{39}$, $R_{40}$, $R_{42}$, $R_{43}$, $R_{44}$, $R_{46}$ and $R_{48}$ are each independently hydrogen, $C_1$–$C_4$alkyl,
benzyl optionally substituted with one or more groups independently selected from halogen, cyano, nitro, $C_1$–$C_4$alkyl, $C_1$–$C_4$haloalkyl, $C_1$–$C_4$alkoxy and $C_1$–$C_4$haloalkoxy groups, or
phenyl optionally substituted with one or more groups independently selected from halogen, cyano, nitro, $C_1$–$C_4$alkyl, $C_1$–$C_4$haloalkyl, $C_1$–$C_4$alkoxy and $C_1$–$C_4$haloalkoxy groups; and A, $A_1$, $A_3$, $A_4$, $X_4$ and $X_5$ are each independently O or S; and
the optical isomers, diastereomers and/or tautomers thereof.

Another group of preferred intermediate compounds of formula XLV are those wherein $R_1$ and $R_2$ are each independently hydrogen, halogen, $C_1$–$C_6$alkyl, $C_3$–$C_7$cycloalkyl, $C_1$–$C_6$haloalkyl, $C_3$–$C_6$alkenyl, $C_3$–$C_6$haloalkenyl, $C_3$–$C_6$alkynyl, $OR_7$, $S(O)_nR_8$ or $NR_9R_{10}$, and when $R_1$ and $R_2$ are taken together with the atoms to which they are attached, they represent a four- to seven-membered saturated or unsaturated ring optionally interrupted by oxygen, sulfur or nitrogen, and optionally substituted with one to three methyl groups or one or more halogen atoms;

X is hydrogen, halogen or $C_1$–$C_4$alkyl;

$X_1$ is hydrogen, halogen, $C_1$–$C_4$alkyl, $C_1$–$C_4$haloalkyl, $C_1$–$C_4$alkoxy or $C_1$–$C_4$haloalkoxy;

Z is O or $S(O)_m$;

Y is halogen, cyano, $R_{12}$, $X_2R_{12}$, $X_3R_{12}$, $X_2X_3R_{12}$ or $X_3X_2R_{12}$;

$X_2$ is O, $S(O)_p$ or $NR_{13}$;

$X_3$ is —C(=$A_3$)—, —C(=$NOR_{14}$)— or —C(=$NR_{13}R_{50}$);

$R_4$, $R_5$, $R_6$, $R_7$, $R_8$, $R_9$, $R_{10}$ and $R_{14}$ are each independently hydrogen, $C_1$–$C_6$alkyl, $C_3$–$C_7$cycloalkyl, $C_2$–$C_8$-alkoxyalkyl, $C_2$–$C_6$alkenyl, $C_2$–$C_6$alkynyl or benzyl;

$R_{12}$ is hydrogen,
a $C_1$–$C_8$alkyl, $C_3$–$C_7$cycloalkyl, $C_2$–$C_8$alkenyl, $C_5$–$C_6$cycloalkenyl or $C_2$–$C_8$alkynyl group, wherein each group is optionally substituted with any combination of one to six halogen atoms, one to three $C_1$–$C_{20}$alkoxy groups optionally substituted with one $C_1$–$C_6$alkoxy, benzyloxy or $C_1$–$C_6$alkylthio group, one or two $C_1$–$C_{10}$haloalkoxy groups, one or two $NR_{15}R_{16}$ groups, one to three $S(O)_qR_{17}$ groups, one or two cyano groups, one or two $C_3$–$C_7$cycloalkyl groups, one thiocyano group, one $O(SO_2)R_{17}$ group, one $O(NO_2)$ group, one or two $C(O)R_{18}$ groups, one or two $CO_2R_{19}$ groups, one or two $C(O)SR_{19}$ groups, one or two $C(O)NR_{20}R_{21}$ groups, one to three $X_4R_{22}$ groups, one or two $P(O)(OR_{23})_2$ groups, one or two $Si(R_{24})_3$ groups, one 4- to 10-membered monocyclic or fused bicyclic heterocyclic ring optionally substituted with any combination of one or two oxo groups, one or two thioxo groups, one to three halogen atoms, one to three $C_1$–$C_4$ alkyl groups, one to three $C_1$–$C_4$haloalkyl groups, one to three $C_1$–$C_4$alkoxy groups, one to three $C_1$–$C_4$haloalkoxy groups or one or two $X_4R_{22}$ groups, one quaternary organic ammonium group, or one or two phenyl groups wherein each phenyl group is independently optionally substituted with any combination of one to three halogen atoms, one to three $C_1$–$C_6$alkyl groups, one to three $C_1$–$C_6$alkoxy groups, one $C_3$–$C_7$cycloalkyl group, one $C_1$–$C_4$haloalkyl group, one $C_1$–$C_4$alkylthio group, one cyano group, one nitro group, one $C(O)R_{25}$ group, one $CO_2R_{26}$ group or one $X_9R_{27}$ group, phenyl optionally substituted with any combination of one to three halogen atoms, one to three $C_1$–$C_4$alkyl groups, one to three $C_1$–$C_4$alkoxy groups, one $C_3$–$C_6$cycloalkyl group, one $C_1$–$C_4$haloalkyl group, one $C_1$–$C_4$alkylthio group, one cyano group, one nitro group, one $C(O)R_{25}$ group, one $CO_2R_{26}$ group, one $X_4R_{22}$ group, one $CH{=}CHR_{22}$ group, one $CH_2CH(R_{28})R_{22}$ group or one $N(R_{29})SO_2R_{30}$ group, or indan optionally substituted with any combination of one or two halogen atoms, one or two $C_1$–$C_4$alkyl groups, one $C_1$–$C_4$alkoxy group, one $C_1$–$C_4$haloalkyl group, one $C_1$–$C_4$alkylthio group, one cyano group, one nitro group, one $C(O)R_{25}$ group, one $CO_2R_{26}$ group, one $X_4R_{22}$ group, one $CH{=}CHR_{22}$ group, one $CH_2CH(R_{28})R_{22}$ group or one $N(R_{29})SO_2R_{30}$ group, and when $R_{12}$ and $R_{13}$ are taken together with the nitrogen atom to which they are attached, they form a 5- to 12-membered monocyclic or fused bicyclic, heterocyclic ring optionally substituted with one or more groups independently selected from halogen, cyano, nitro, amino, hydroxyl, $C_1$–$C_4$alkyl, $C_1$–$C_4$haloalkyl, $C_1$–$C_4$alkoxy, $C_1$–$C_4$haloalkoxy, $C_1$–$C_4$haloalkylsulfonyl or $X_4R_{22}$ groups;

$R_{13}$ is hydrogen, $C_1$–$C_8$alkoxyalkyl, $C_1$–$C_6$alkyl, $C_3$–$C_7$cycloalkyl, $C_3$–$C_6$alkenyl, $C_3$–$C_6$alkynyl, benzyl, $OR_{23}$, cyano, $SO_2R_{51}$ or one 5- to 12-membered monocyclic or fused bicyclic heterocyclic ring optionally substituted with one or more groups independently selected from halogen, cyano, nitro, amino, hydroxyl, $C_1$–$C_4$alkyl, $C_1$–$C_4$haloalkyl, $C_1$–$C_4$alkoxy or $C_1$–$C_4$haloalkoxy, and when $R_{13}$ and $R_{12}$ are taken together with the nitrogen atom to which they are attached, they form a 5- to 12-membered monocyclic or fused bicyclic, heterocyclic ring optionally substituted with one or more groups independently selected from halogen, cyano, nitro, amino, hydroxyl, $C_1$–$C_4$alkyl, $C_1$–$C_4$haloalkyl, $C_1$–$C_4$alkoxy, $C_1$–$C_4$haloalkoxy, $C_1$–$C_4$haloalkylsulfonyl or $X_4R_{22}$ groups;

$R_{28}$ is halogen;

$R_{22}$ and $R_{27}$ are each independently hydrogen, $Si(R_{31})_3$, $C(O)NR_{35}R_{36}$, $C(O)R_{33}$, $SO_2R_{47}$, $C_1$–$C_{20}$alkyl substituted with one hydroxyl, benzyloxy, nitro, $OC(O)R_{33}$, $C_1$–$C_6$alkoxy, $CO_2R_{32}$, $C(O)R_{33}$, $C(A_4R_{34})_2$, $C(O)NR_{35}R_{36}$, $C(O)ON{=}CR_{37}R_{38}$, $P(O)(OH)NH_2$, $P(O)(OH)(OR_{23})$, $C(O)NR_{35}OR_{23}$, cyano or 2-dioxolanyl group, one phenyl, dihydrofuranone or furanone ring wherein each ring is optionally substituted with any combination of one to three halogen atoms, one to three $C_1$–$C_4$alkyl groups, one to three $C_1$–$C_4$haloalkyl groups, one to three $C_1$–$C_4$alkoxy groups ox one to three $C_1$–$C_4$haloalkoxy groups, or one 5- to 12-membered monocyclic or fused bicyclic, heterocyclic ring optionally substituted with one or more groups independently selected from halogen, cyano, nitro, amino, hydroxyl, $C_1$–$C_4$alkyl, $C_1$–$C_4$haloalkyl, $C_1$–$C_4$alkoxy, $C_1$–$C_4$haloalkoxy or $C_1$–$C_4$haloalkylsulfonyl groups, $C_3$–$C_{20}$alkenyl optionally substituted with one to three halogen atoms, one hydroxyl group, one $C_1$–$C_6$alkoxy, $CO_2R_{32}$, $C(O)R_{33}$, $C(A_4R_{34})_2$, $C(O)NR_{35}R_{36}$, $C(O)ON{=}CR_{37}R_{38}$, $C(O)NR_{35}R_{23}$, cyano or 2-dioxolanyl group, or one phenyl, dihydrofuranone or furanone ring wherein each ring is optionally substituted with any combination of one to three halogen atoms, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups, $C_5$–$C_8$cycloalkenyl optionally. substituted with one hydroxyl, $C_1$–$C_6$alkoxy, $C_1$–$C_4$alkyl, $C_2$–$C_4$alkenyl, $CO_2R_{32}$, $C(O)R_{33}$, $C(A_4R_{34})_2$, $C(O))NR_{35}R_{36}$, $C(O)ON{=}CR_{37}R_{38}$, $C(O)NR_{35}OR_{23}$, cyano or 2-dioxolanyl group, or one phenyl, dihydrofuranone or furanone ring wherein each ring is optionally substituted with any combination of one to three halogen atoms, one to three $C_1$–$C_4$alkyl groups, one to three $C_1$–$C_4$alkoxy groups or one to three $C_1$–$C_4$haloalkoxy groups, $C_3$–$C_{10}$alkynyl optionally substituted with one hydroxyl, $C_1$–$C_6$alkoxy, $CO_2R_{32}$, $C(O)R_{33}$, $C(A_4R_{344})_2$, $C(O)NR_{35}R_{36}$, $C(O)ON{=}CR_{37}R_{38}$, $C(O)NR_{35}OR_{23}$, cyano or 2-dioxolanyl group, or one phenyl, dihydrofuranone or furanone ring wherein each ring is optionally substituted with any combination of one to three halogen atoms, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups, phenyl optionally substituted with any combination of one to three halogen atoms, one to three $C_1$–$C_6$alkyl groups, one to three $C_1$–$C_6$alkoxy groups, one $C_1$–$C_4$haloalkyl group, one $C_1$–$C_4$haloalkoxy group, one cyano group, one nitro group, one $NR_{39}R_{40}$ group or one $C(O)R_{23}$ group, benzyl optionally substituted on the phenyl ring with any combination of one to three halogen atoms, one to three $C_1$–$C_6$alkyl groups, one to three $C_1$–$C_6$alkoxy groups, one $C_1$–$C_4$haloalkyl group, one $C_1$–$C_4$haloalkoxy group, one cyano group, one nitro group, one $NR_{39}R_{40}$ group or one $C(O)R_{33}$ group, or a 4- to 10-membered heterocyclic ring optionally substituted with any combination of one or two oxo groups, one or two thioxo groups, one to three halogen atoms, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups;

$R_{15}$ and $R_{20}$ are each independently hydrogen,
- a $C_1$–$C_6$alkyl, $C_3$–$C_7$cycloalkyl, $C_2$–$C_6$alkenyl or $C_2$–$C_6$alkynyl group wherein each group is optionally substituted with one $CO_2R_{42}$ group,
- benzyl optionally substituted with any combination of one to three halogen atoms, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups,
- phenyl optionally substituted with any combination of one to three halogen atoms, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups, one $CO_2R_{26}$ group,
- $C(O)R_{43}$, or
- $CO_2R_{42}$;

$R_{16}$ and $R_{21}$ are each independently hydrogen, $C_1$–$C_6$alkyl, $C_1$–$C_4$alkoxy, $C_3$–$C_7$cycloalkyl, $C_2$–$C_6$alkenyl, $C_3$–$C_7$cycloalkenyl, $C_2$–$C_6$alkynyl, $P(O)(OR_{44})_2$, $SO_2R_{45}$, $C(O)R_{46}$,
- benzyl optionally substituted with any combination of one to three halogen atoms, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups or one $X_4R_{22}$ group, or
- phenyl optionally substituted with any combination of one to three halogen atoms, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups or one $X_4R_{22}$ group;

$R_{17}$, $R_{18}$, $R_{25}$, $R_{30}$, $R_{33}$, $R_{45}$ and $R_{51}$ are each independently $NR_{46}R_{48}$, —N=$CR_{46}R_{48}$, $C_1$–$C_8$alkyl optionally substituted with one $C_1$–$C_6$alkoxy, thiophene or furan group, $C_1$–$C_6$haloalkyl, $C_3$–$C_8$cycloalkyl, $CO_2R_{23}$, $C_2$–$C_6$alkenyl optionally substituted with phenyl,
- benzyl optionally substituted with any combination of one to three halogen atoms, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups, one nitro group, one cyano group or one $X_4R_{22}$ group,
- phenyl optionally substituted with any combination of one to three halogen atoms, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups, one nitro group, one cyano group or one $X_4R_{22}$ group, or
- a 5- to 12-membered monocyclic or fused bicyclic, heterocyclic ring optionally substituted with one or more groups independently selected from halogen, cyano, nitro, amino, hydroxyl, $C_1$–$C_4$alkyl, $C_1$–$C_4$haloalkyl, $C_1$–$C_4$alkoxy, $C_1$–$C_4$haloalkoxy, $C_1$–$C_4$haloalkylsulfonyl or $X_4R_{22}$ groups;

$R_{19}$ and $R_{26}$ are each independently hydrogen, $C_1$–$C_{20}$alkyl, $C_1$–$C_8$haloalkyl, $C_3$–$C_7$cycloalkyl, $C_3$–$C_7$halocycloalkyl, $C_3$–$C_{20}$alkenyl, $C_3$–$C_8$haloalkenyl, $C_5$–$C_8$cycloalkenyl, $C_5$–$C_8$halocycloalkenyl, $C_3$–$C_8$alkynyl, $C_3$–$C_8$haloalkynyl, $Si(R_{41})_3$, benzyl, phenyl, furfuryl, pyridyl, thienyl, oximino or an alkali metal, alkaline earth metal, manganese, copper, zinc, cobalt, silver, nickel, ammonium or organic ammonium cation;

$R_{32}$ is hydrogen,
- $Si(R_{47})_3$,
- $di(C_1$–$C_4$alkyl)imino,
- $C_1$–$C_{20}$alkyl optionally substituted with one $CO_2R_{48}$, $C_1$–$C_6$alkoxy, $C_1$–$C_6$thioalkyl, $C_2$–$C_{20}$alkoxyalkoxy, phenyl, $OSi(R_{47})_3$, $OC(O)R_{33}$, $C_3$–$C_7$cycloalkyl or di($C_1$–$C_4$alkyl)imino group,
- $C_1$–$C_{15}$haloalkyl,
- $C_3$–$C_8$cycloalkyl optionally substituted with one $CO_2R_{48}$ group,
- $C_3$–$C_8$halocycloalkyl,
- $C_3$–$C_{20}$alkenyl optionally substituted with one phenyl group,
- $C_3$–$C_{15}$haloalkenyl,
- $C_5$–$C_8$cycloalkenyl,
- $C_5$–$C_8$halocycloalkenyl,
- $C_3$–$C_{20}$alkynyl optionally substituted with one phenyl group,
- $C_3$–$C_{20}$haloalkynyl,
- benzyl optionally substituted with one or more groups independently selected from halogen, cyano, nitro, $C_1$–$C_4$alkyl, $C_1$–$C_4$haloalkyl, $C_1$–$C_4$alkoxy and $C_1$–$C_4$haloalkoxy groups,
- phenyl optionally substituted with one or more groups independently selected from halogen, cyano, nitro, $C_1$–$C_4$alkyl, $C_1$–$C_4$haloalkyl, $C_1$–$C_4$alkoxy and $C_1$–$C_4$haloalkoxy groups,
- 2-, 3- or 4-pyridyl,
- 2- or 3-furyl,
- 2- or 3-thienyl,
- 2-tetrahydrofuranyl,
- $C_1$–$C_4$alkyl substituted with one pyridyl, furyl, thienyl, tetrahydrofuryl, $C_3$–$C_8$cycloalkyl, dioxane or $NR_{49}R_{50}$ group, or
- an alkali metal, alkaline earth metal, manganese, copper, zinc, cobalt, silver, nickel, ammonium or organic ammonium cation;

$R_{34}$, $R_{37}$ and $R_{38}$ are each independently $C_1$–$C_6$alkyl;

$R_{35}$ and $R_{49}$ are each independently hydrogen or $C_1$–$C_6$alkyl and $R_{36}$ and $R_{50}$ are each independently hydrogen, cyano, $C_1$–$C_6$alkyl, $SO_2R_{51}$ or phenyl optionally substituted with one or more groups independently selected from halogen, cyano, nitro, $C_1$–$C_4$alkyl, $C_1$–$C_4$haloalkyl, $C_1$–$C_4$alkoxy and $C_1$–$C_4$haloalkoxy groups, or when $R_{35}$ and $R_{36}$ or $R_{49}$ and $R_{50}$ are taken together with the nitrogen atom to which they are attached, they form a 5- to 12-membered monocyclic or fused bicyclic, heterocyclic ring optionally substituted with one or more groups independently selected from halogen, cyano, nitro, amino, hydroxyl, $C_1$–$C_4$alkyl, $C_1$–$C_4$haloalkyl, $C_1$–$C_4$alkoxy, $C_1$–$C_4$haloalkoxy or $C_1$–$C_4$haloalkylsulfonyl groups;

m, n, p and q are each independently an integer of 0, 1 or 2;

$R_{29}$ is hydrogen, $C_1$–$C_4$alkyl or $C_1$–$C_4$haloalkyl;

$R_{24}$, $R_{31}$, $R_{41}$ and $R_{47}$ are each independently $C_1$–$C_4$alkyl,
- benzyl optionally substituted with one or more groups independently selected from halogen, cyano, nitro, $C_1$–$C_4$alkyl, $C_1$–$C_4$haloalkyl, $C_1$–$C_4$alkoxy and $C_1$–$C_4$haloalkoxy groups, or
- phenyl optionally substituted with one or more groups independently selected from halogen, cyano, nitro, $C_1$–$C_4$alkyl, $C_1$–$C_4$haloalkyl, $C_1$–$C_4$alkoxy and $C_1$–$C_4$haloalkoxy groups;

$R_{23}$, $R_{39}$, $R_{40}$, $R_{42}$, $R_{43}$, $R_{44}$, $R_{46}$ and $R_{48}$ are each independently hydrogen, $C_2$–$C_6$alkenyl, $C_3$–$C_8$cycloalkyl, $C_1$–$C_8$alkyl optionally substituted with one or two $C_1$–$C_4$alkoxy groups, benzyl optionally substituted with one or more groups independently selected from halogen, cyano, nitro, $C_1$–$C_4$alkyl, $C_1$–$C_4$haloalkyl, $C_1$–$C_4$alkoxy and $C_1$–$C_4$haloalkoxy groups, or phenyl optionally substituted with one or more groups independently selected from halogen, cyano, nitro, $C_1$–$C_4$alkyl, $C_1$–$C_4$haloalkyl, $C_1$–$C_4$alkoxy and $C_1$–$C_4$haloalkoxy groups, and when $R_{46}$ and $R_{48}$ are taken together with the atom to which they are attached, they form a 5- to 12-membered monocyclic or fused bicyclic, heterocyclic or cycloalkyl ring optionally substituted with one or more groups independently selected from halogen, cyano, nitro, amino, hydroxyl, $C_1$–$C_4$alkyl, $C_1$–$C_4$haloalkyl, $C_1$–$C_4$alkoxy, $C_1$–$C_4$haloalkoxy or $C_1$–$C_4$haloalkylsulfonyl groups; and A, $A_1$, $A_3$, $A_4$, $X_4$ and $X_5$ are each independently O or S; and the optical isomers, diastereomers and/or tautomers thereof.

More preferred formula XLV intermediate compounds of this invention are those wherein $R_1$ is halogen or $C_1$–$C_4$haloalkyl;

$R_2$ is hydrogen, halogen or $C_1$–$C_4$haloalkyl;

X and $X_1$ are each independently hydrogen or halogen;

Z is O or S;

Y is cyano, $R_{12}$, $X_2R_{12}$ or $X_3X_2R_{12}$;

$X_2$ is O, S or $NR_{13}$;

$X_3$ is —C(=$A_3$)—, —C(=$NOR_{14}$)— or —C(=N—$NR_{13}R_{50}$);

$R_{12}$ is hydrogen, a $C_1$–$C_6$alkyl, $C_3$–$C_7$cycloalkyl, $C_2$–$C_6$alkenyl, $C_5$–$C_6$cycloalkenyl or $C_2$–$C_6$alkynyl group, wherein each group is optionally substituted with any combination of one to three halogen atoms, one or two $C_1$–$C_{20}$alkoxy groups, one or two $C_1$–$C_{10}$haloalkoxy groups, one $NR_{15}R_{16}$ group, one S(O)$_q$R$_{17}$ group, one or two cyano groups, one or two $C(O)R_{18}$ groups, one or two $CO_2R_{19}$ groups, one or two $C(O)SR_{19}$ groups, one or two $C(O)NR_{20}R_{21}$ groups, one or two $X_4R_{22}$ groups, one P(O)(OR$_{23}$)$_2$ group, one Si(R$_{24}$)$_3$ group, one 4- to 10-membered monocyclic or fused bicyclic heterocyclic ring optionally substituted with any combination of one or two oxo groups, one or two thioxo groups, one to three halogen atoms, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups or one or two $X_4R_{22}$ groups, one quaternary organic ammonium group, or one phenyl group optionally substituted with any combination of one to three halogen atoms, one $C_1$–$C_6$alkyl group, one $C_1$–$C_6$alkoxy group, one $C_3$–$C_7$cycloalkyl group, one cyano group, one nitro group, one $C(O)R_{25}$ group, one $CO_2R_{26}$ group or one $X_5R_{27}$ group, or phenyl optionally substituted with any combination of one or two halogen atoms, one to three $C_1$–$C_4$alkyl groups, one or two $C_1$–$C_4$alkoxy groups, one $C_3$–$C_6$cycloalkyl group, one $C_1$–$C_4$haloalkyl group, one $C_1$–$C_4$alkylthio group, one cyano group, one nitro group, one $C(O)R_{25}$ group, one $CO_2R_{26}$ group, one $X_4R_{22}$ group, one CH=CHR$_{22}$ group, one CH$_2$CH(R$_{28}$)R$_{22}$ group or one N(R$_{29}$)SO$_2$R$_{30}$ group;

$R_{13}$ is hydrogen, $C_2$–$C_6$alkoxyalkyl, $C_1$–$C_4$alkyl, $C_3$–$C_7$cycloalkyl, $C_5$–$C_6$alkenyl, $C_3$–$C_6$alkynyl, benzyl, $OR_{23}$, cyano or SO$_2$R$_{51}$;

$R_{28}$ is halogen;

$R_{22}$ and $R_{27}$ are each independently hydrogen, Si(R$_{31}$)$_3$, C(O)NR$_{35}$R$_{36}$, C(O)R$_{33}$, SO$_2$R$_{47}$, $C_1$–$C_{20}$ alkyl substituted with one hydroxyl, benzyloxy, nitro, OC(O)R$_{33}$, $C_1$–$C_6$alkoxy, CO$_2$R$_{32}$, C(O)R$_{33}$, C(A$_4$R$_{34}$)$_2$, C(O)NR$_{35}$R$_{36}$, C(O)ON=CR$_{37}$R$_{38}$, P(O)(OH)NR$_2$, P(O)(OH)(OR$_{23}$), C(O)NR$_{35}$OR$_{23}$, cyano or 2-dioxolanyl group, one phenyl, dihydrofuranone or furanone ring wherein each ring is optionally substituted with any combination of one to three halogen atoms, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups, or one 5- to 12-membered monocyclic or fused bicyclic, heterocyclic ring optionally substituted with one or more groups independently selected from halogen, cyano, nitro, amino, hydroxyl, $C_1$–$C_4$alkyl, $C_1$–$C_4$haloalkyl, $C_1$–$C_4$alkoxy, $C_1$–$C_4$haloalkoxy or $C_1$–$C_4$haloalkylsulfonyl groups, $C_3$–$C_{20}$alkenyl optionally substituted with one to three halogen atoms, one hydroxyl group, one $C_1$–$C_6$alkoxy, CO$_2$R$_{32}$, C(O)R$_{33}$, C(A$_4$R$_{34}$)$_2$, C(O)NR$_{35}$R$_{36}$, C(O)ON=CR$_{37}$R$_{38}$, C(O)NR$_{35}$OR$_{23}$, cyano or 2-dioxolanyl group, or one phenyl, dihydrofuranone or furanone ring wherein each ring is optionally substituted with any combination of one to three halogen atoms, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups, $C_5$–$C_8$cycloalkenyl optionally substituted with one hydroxyl, $C_1$–$C_6$alkoxy, $C_1$–$C_4$alkyl, $C_2$–$C_4$alkenyl, CO$_2$R$_{32}$, C(O)R$_{33}$, C(A$_4$R$_{34}$)$_2$, C(O)NR$_{35}$R$_{36}$, C(O)ON=CR$_{37}$R$_{38}$, C(O)NR$_{35}$OR$_{23}$, cyano or 2-dioxolanyl group, or one phenyl, dihydrofuranone or furanone ring wherein each ring is optionally substituted with any combination of one to three halogen atoms, one to three $C_1$–$C_4$alkyl groups, one to three $C_1$–$C_4$alkoxy groups or one to three $C_1$–$C_4$haloalkoxy groups, $C_3$–$C_{10}$alkynyl optionally substituted with one hydroxyl, $C_1$–$C_6$alkoxy, CO$_2$R$_{32}$, C(O)R$_{33}$, C(A$_4$R$_{34}$)$_2$, C(O)NR$_{35}$R$_{36}$, C(O)ON=CR$_{37}$R$_{38}$, C(O)NR$_{35}$OR$_{23}$, cyano or 2-dioxolanyl group, or one phenyl, dihydrofuranone or furanone ring wherein each ring is optionally substituted with any combination of one to three halogen atoms, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups, phenyl optionally substituted with any combination of one to three halogen atoms, one to three $C_1$–$C_6$alkyl groups, one to three $C_1$–$C_6$alkoxy groups, one $C_1$–$C_4$haloalkyl group, one $C_1$–$C_4$haloalkoxy group, one cyano group, one nitro group, one NR$_{39}$R$_{40}$ group or one C(O)R$_{33}$ group, benzyl optionally substituted on the phenyl ring with any combination of one to three halogen atoms, one to three $C_1$–$C_6$alkyl groups, one to three $C_1$–$C_6$alkoxy groups, one $C_1$–$C_4$haloalkyl group, one $C_1$–$C_4$haloalkoxy group, one cyano group, one nitro group, one NR$_{39}$R$_{40}$ group or one C(O)R$_{33}$ group, or a 4- to 10-membered heterocyclic ring optionally substituted with any combination of one or two oxo groups, one or two thioxo groups, one to three halogen atoms, one to three $C_1$–$C_4$alkyl groups, one to three $C_1$–$C_4$haloalkyl groups, one to three $C_1$–$C_4$ alkoxy groups or one to three $C_1$–$C_4$haloalkoxy groups;

$R_{15}$ and $R_{20}$ are each independently hydrogen,
- a $C_1$–$C_6$alkyl, $C_3$–$C_7$cycloalkyl, $C_2$–$C_6$alkenyl or $C_2$–$C_6$alkynyl group wherein each group is optionally substituted with one $CO_2R_{42}$ group,
- benzyl optionally substituted with any combination of one to three halogen atoms, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups,
- phenyl optionally substituted with any combination of one to three halogen atoms, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups, one $CO_2R_{26}$ group,
- $C(O)R_{43}$, or
- $CO_2R_{42}$;

$R_{14}$ is hydrogen, $C_1$–$C_6$alkyl, $C_3$–$C_7$cycloalkyl, $C_2$–$C_6$alkoxyalkyl, $C_2$–$C_6$alkenyl, $C_2$–$C_6$alkynyl or benzyl;

$R_{16}$ and $R_{21}$ are each independently hydrogen, $C_1$–$C_4$alkyl, $C_1$–$C_4$alkoxy, $C_3$–$C_7$cycloalkyl, $C_2$–$C_6$alkenyl, $C_3$–$C_7$cycloalkenyl, $C_2$–$C_6$alkynyl, $P(O)(OR_{44})_2$, $SO_2R_{45}$, $C(O)R_{46}$,
- benzyl optionally substituted with any combination of one to three halogen atoms, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups, or
- phenyl optionally substituted with any combination of one to three halogen atoms, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups;

$R_{17}$, $R_{18}$, $R_{25}$, $R_{30}$, $R_{33}$, $R_{45}$ and $R_{51}$ are each independently $NR_{46}R_{48}$, —N=$CR_{46}R_{48}$, $C_1$–$C_8$alkyl optionally substituted with one $C_1$–$C_6$alkoxy, thiophene or furan group, $C_1$–$C_6$haloalkyl, $C_3$–$C_6$cycloalkyl, $CO_2R_{23}$, $C_2$–$C_6$alkenyl optionally substituted with phenyl,
- benzyl optionally substituted with any combination of one to three halogen atoms, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups, one nitro group, one cyano group or one $X_4R_{22}$ group,
- phenyl optionally substituted with any combination of one to three halogen atoms, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups, one nitro group, one cyano group or one $X_4R_{22}$ group, or
- a 5- to 12-membered monocyclic or fused bicyclic, heterocyclic ring optionally substituted with one or more groups independently selected from halogen, cyano, nitro, amino, hydroxyl, $C_1$–$C_4$alkyl, $C_1$–$C_4$haloalkyl, $C_1$–$C_4$alkoxy, $C_1$–$C_4$haloalkoxy, $C_1$–$C_4$haloalkylsulfonyl or $X_4R_{22}$ groups;

$R_{19}$ and $R_{26}$ are each independently hydrogen, $C_1$–$C_{20}$alkyl, $C_1$–$C_8$haloalkyl, $C_3$–$C_7$cycloalkyl, $C_3$–$C_7$halocycloalkyl, $C_3$–$C_{20}$alkenyl, $C_3$–$C_8$haloalkenyl, $C_5$–$C_8$cycloalkenyl, $C_5$–$C_8$halocycloalkenyl, $C_3$–$C_8$alkynyl, $C_3$–$C_8$haloalkynyl, $Si(R_{41})_3$, benzyl, phenyl, furfuryl, pyridyl, thienyl, oximino or an alkali metal, alkaline earth metal, manganese, copper, zinc, cobalt, silver, nickel, ammonium or organic ammonium cation;

$R_{32}$ is hydrogen,
- $Si(R_{47})_3$,
- $C_1$–$C_{20}$alkyl optionally substituted with one $CO_2R_{48}$, $C_1$–$C_6$alkoxy, $C_1$–$C_6$thioalkyl, $C_2$–$C_{20}$alkoxyalkoxy, phenyl, $OSi(R_{47})_3$, $OC(O)R_{33}$, $C_3$–$C_7$cycloalkyl or di($C_1$–$C_4$alkyl)imino group,
- $C_1$–$C_{15}$haloalkyl,
- $C_3$–$C_8$cycloalkyl optionally substituted with one $CO_2R_{48}$ group,
- $C_3$–$C_8$halocycloalkyl,
- $C_3$–$C_{20}$alkenyl optionally substituted with one phenyl group,
- $C_3$–$C_{15}$haloalkenyl,
- $C_5$–$C_8$cycloalkenyl,
- $C_5$–$C_8$halocycloalkenyl,
- $C_3$–$C_{20}$alkynyl optionally substituted with one phenyl group,
- $C_3$–$C_{20}$haloalkynyl,
- benzyl optionally substituted with one or more groups independently selected from halogen, cyano, nitro, $C_1$–$C_4$alkyl, $C_1$–$C_4$haloalkyl, $C_1$–$C_4$alkoxy and $C_1$–$C_4$haloalkoxy groups,
- phenyl optionally substituted with one or more groups independently selected from halogen, cyano, nitro, $C_1$–$C_4$alkyl, $C_1$–$C_4$haloalkyl, $C_1$–$C_4$alkoxy and $C_1$–$C_4$haloalkoxy groups,
- $C_1$–$C_4$alkyl substituted with one pyridyl, furyl, thienyl, tetrahydrofuryl, $C_3$–$C_8$cycloalkyl, dioxane or $NR_{49}R_{50}$ group, or
- an alkali metal, alkaline earth metal, manganese, copper, zinc, cobalt, silver, nickel, ammonium or organic ammonium cation;

$R_{34}$, $R_{37}$ and $R_{38}$ are each independently $C_1$–$C_6$alkyl;

$R_{35}$ and $R_{49}$ are each independently hydrogen or $C_1$–$C_6$alkyl and $R_{36}$ and $R_{50}$ are each independently hydrogen, cyano, $C_1$–$C_6$alkyl, $SO_2R_{51}$ or phenyl optionally substituted with one or more groups independently selected from halogen, cyano, nitro, $C_1$–$C_4$alkyl, $C_1$–$C_4$haloalkyl, $C_1$–$C_4$alkoxy and $C_1$–$C_4$haloalkoxy groups, or when $R_{35}$ and $R_{36}$ or $R_{49}$ and $R_{50}$ are taken together with the nitrogen atom to which they are attached, they form a 5- to 12-membered monocyclic or fused bicyclic, heterocyclic ring optionally substituted with one or more groups independently selected from halogen, cyano, nitro, amino, hydroxyl, $C_1$–$C_4$alkyl, $C_1$–$C_4$haloalkyl, $C_1$–$C_4$alkoxy, $C_1$–$C_4$haloalkoxy or $C_1$–$C_4$haloalkylsulfonyl groups;

q is an integer of 0, 1 or 2;

$R_{29}$ is hydrogen, $C_1$–$C_4$alkyl or $C_1$–$C_4$haloalkyl;

$R_{24}$, $R_{31}$, $R_{41}$ and $R_{47}$ are each independently $C_1$–$C_4$alkyl,
- benzyl optionally substituted with one or more groups independently selected from halogen, cyano, nitro, $C_1$–$C_4$alkyl, $C_1$–$C_4$haloalkyl, $C_1$–$C_4$alkoxy and $C_1$–$C_4$haloalkoxy groups, or
- phenyl optionally substituted with one or more groups independently selected from halogen, cyano, nitro, $C_1$–$C_4$alkyl, $C_1$–$C_4$haloalkyl, $C_1$–$C_4$alkoxy and $C_1$–$C_4$haloalkoxy groups;

$R_{23}$, $R_{39}$, $R_{40}$, $R_{42}$, $R_{43}$, $R_{44}$, $R_{46}$ and $R_{48}$ are each independently hydrogen, $C_2-C_6$alkenyl, $C_3-C_8$cycloalkyl, $C_1-C_8$alkyl optionally substituted with one or two $C_1-C_4$alkoxy groups, benzyl optionally substituted with one or more groups independently selected from halogen, cyano, nitro, $C_1-C_4$alkyl, $C_1-C_4$haloalkyl, $C_1-C_4$alkoxy and $C_1-C_4$haloalkoxy groups, or phenyl optionally substituted with one or more groups independently selected from halogen, cyano, nitro, $C_1-C_4$alkyl, $C_1-C_4$haloalkyl, $C_1-C_4$alkoxy and $C_1-C_4$haloalkoxy groups; and A, $A_1$, $A_3$, $A_4$, $X_4$ and $X_5$ are each independently O or S; and the optical isomers, diastereomers and/or tautomers thereof.

In order to facilitate a further understanding of the invention, the following examples are presented to illustrate more specific details thereof. The invention is not to be limited thereby except as defined in the claims.

EXAMPLE 1

Preparation of 2'-Chloro-2-methoxy-5-methyl-5'-nitrobenzophenone

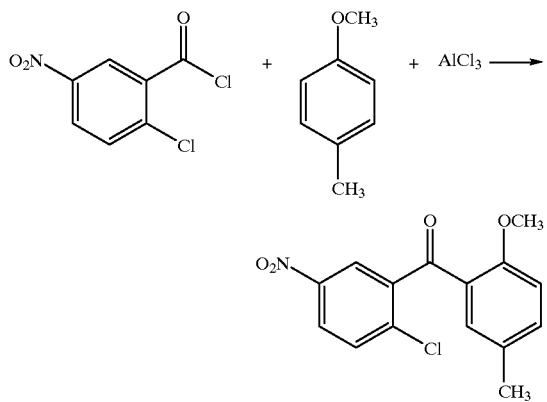

A mixture of aluminum chloride (33.3 g, 25.0 mmol) in methylene chloride is cooled to about 5° C., treated over one hour with p-methylanisole (31.6 g, 25.0 mmol) while maintaining the reaction mixture temperature below 10° C., treated over 20 minutes with a solution of 2-chloro-5-nitrobenzoyl chloride (50.0 g, 22.7 mmol) in methylene chloride while maintaining the reaction mixture temperature below 10° C., warmed to and stirred at room temperature for 60 minutes, and poured onto ice. The resultant aqueous mixture is treated with concentrated hydrochloric acid (50 mL) and extracted with methylene chloride. The organic extract is dried over anhydrous magnesium sulfate and concentrated in vacuo to give a yellow solid. After placing the solid in a Kugelrohr apparatus at 40° C. to remove residual p-methylanisole, the title product is obtained as a beige solid (68.8 g, 99.1%) which is identified by NMR spectral analyses.

Using essentially the same procedure, the following compounds are obtained:

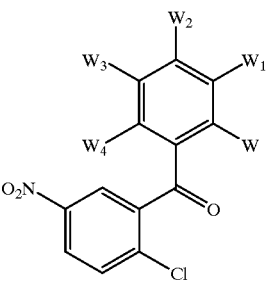

| W | $W_1$ | $W_2$ | $W_3$ | $W_4$ | mp ° C. |
|---|---|---|---|---|---|
| H | I | H | H | $OCH_3$ | 115–116.5 |
| H | H | $CH_3$ | H | $OCH_3$ | |
| H | H | $C_2H_5$ | H | H | |
| H | $CH_3$ | $CH_3$ | H | $OCH_3$ | |
| H | H | $OCH_3$ | H | H | 108–112 |
| H | $C_2H_5$ | H | H | $OCH_3$ | 98–99.5 |
| H | H | $OCH_3$ | H | $CH_3$ | 91–92 |
| H | H | $CH_3$ | H | H | 95.5–96.5 |
| H | H | $SCH_3$ | H | H | 127–128 |
| H | H | $CH_3$ | H | $OCH_3$ | 91–92.5 |
| H | H | $C_2H_5$ | H | H | |
| H | H | Cl | H | H | 88.5–90.5 |
| H | H | F | H | H | 68–69.5 |
| H | Cl | H | H | $OCH_3$ | 124–126 |
| H | $OCH_3$ | H | H | $OCH_3$ | 71–73 |
| H | H | $OCH_3$ | H | $OCH_3$ | 98–100 |
| H | $CH_3$ | $CH_3$ | H | $OCH_3$ | 127–129 |
| H | H | Cl | H | $OCH_3$ | 96–99 |
| $CH_3$ | H | $CH_3$ | H | $OCH_3$ | 108.5–110 |
| H | H | H | $CH_3$ | $OCH_3$ | 71–74 |
| H | H | $N(CH_3)SO_2CH_3$ | H | H | |
| H | $CH_3$ | Cl | H | $OCH_3$ | 126–128 |
| H | $CH_3$ | H | $CH_3$ | $OCH_3$ | 110–112 |
| $CH_3$ | $CH_3$ | $CH_3$ | H | $OCH_3$ | 104–106 |
| H | $CH(CH_3)_2$ | H | H | $OCH_3$ | 69–71 |
| H | $CH_3$ | H | H | H | |
| H | H | H | H | CN | |
| H | H | H | H | $OCH_3$ | |
| H | $OCH_3$ | H | H | H | |
| H | F | H | H | $OCH_3$ | |
| H | H | F | H | $OCH_3$ | |
| H | H | H | H | $SCH_3$ | |
| H | H | H | H | $CH_3$ | |
| H | H | H | H | F | |
| H | $SCH_3$ | H | H | H | |
| H | H | $OCH_3$ | H | H | |
| H | —$(CH_2)_3$— | | H | $OCH_3$ | |

EXAMPLE 2

Preparation of 3-(6-Methoxy-m-tolyl)-5-nitro-1,2-benzisothiazole

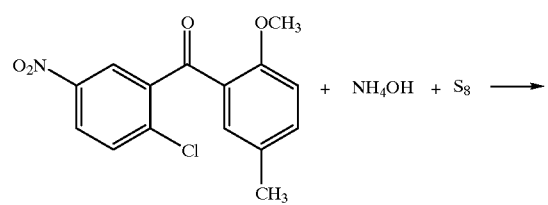

77

-continued

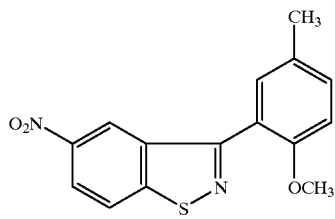

Ammonium hydroxide (350 mL of a 30% solution, 270 mmol) is added to a mixture of 2'-chloro-2-methoxy-5-methyl-5'-nitrobenzophenone (68.7 g, 22.5 mmol) and sulfur (7.57 g, 23.6 mmol) in N,N-dimethylformamide. The resultant reaction mixture is stirred at 80° C. for 19.5 hours, cooled to 40° C., treated with additional ammonium hydroxide (50 mL of a 30% solution), stirred at 80° C. for 25 hours, cooled, and poured onto ice. The resultant aqueous mixture is filtered to obtain the title product as a yellow solid (63.5 g, 93.9%) which is identified by NMR spectral analyses.

Using essentially the same procedure, the following compounds are obtained:

| W | $W_1$ | $W_2$ | $W_3$ | $W_4$ | mp ° C. |
|---|---|---|---|---|---|
| H | H | $CH_3$ | H | $OCH_3$ | 201–203 |
| H | $CH_3$ | $CH_3$ | H | $OCH_3$ | 199–200 |
| H | $CH_3$ | H | H | H | 116.5–117.5 |
| H | H | Cl | H | $OCH_3$ | 229–231 |
| H | H | H | $CH_3$ | $OCH_3$ | 134–136 |
| H | H | H | H | CN | 187.5–189 |
| H | H | H | H | $OCH_3$ | 193–198 |
| H | H | $OCH_3$ | H | H | 201–203 |
| H | $OCH_3$ | H | H | H | 174–175 |
| H | F | H | H | $OCH_3$ | 224–226 |
| H | $C_2H_5$ | H | H | $OCH_3$ | 153–154.5 |
| H | H | $CH_3$ | H | H | 188–189 |
| H | H | $N(CH_3)SO_2CH_3$ | H | H | |
| H | $CH_3$ | Cl | H | $OCH_3$ | 230–234 |
| H | I | H | H | $OCH_3$ | |
| H | H | $SCH_3$ | H | H | 177.5–178.5 |
| H | H | $OCH_3$ | H | $CH_3$ | 131–135 |
| H | H | F | H | H | 226–228 |
| H | H | Cl | H | H | 217.5–219 |
| H | H | F | H | $OCH_3$ | 224–225 |
| H | H | H | H | $SCH_3$ | 114.5–115.5 |
| H | H | $CH_3$ | H | $OCH_3$ | 201–203 |
| H | $OCH_3$ | H | H | $OCH_3$ | 195–196 |
| H | H | H | H | $CH_3$ | 145–146 |
| H | H | H | H | F | 181–182 |
| H | H | $OCH_3$ | H | $OCH_3$ | 171–172.5 |
| H | $SCH_3$ | H | H | H | 139–140.5 |
| H | $CH_3$ | H | $CH_3$ | $OCH_3$ | |
| $CH_3$ | $CH_3$ | $CH_3$ | H | $OCH_3$ | |
| H | $CH(CH_3)_2$ | H | H | $OCH_3$ | |
| H | H | $CH_3$ | $CH_3$ | $OCH_3$ | |
| H | —$(CH_2)_3$— | | H | $OCH_3$ | |

78

EXAMPLE 3

Preparation of 3-Methyl-5-nitro-1,2-benzisothiazole

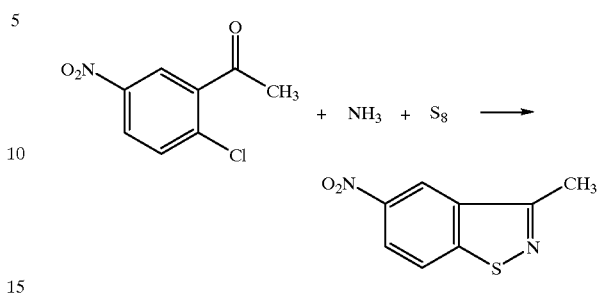

Ammonia (45 g, 2,642 mmol) is bubbled into methanol at −40° C. in a steel bomb. Sulfur (30.5 g, 95.0 mmol) and 2'-chloro-5'-nitroacetophenone (19 g, 95.0 mmol) are then added. The bomb is sealed and heated at about 90° C. overnight. After cooling, the reaction mixture is removed from the bomb and concentrated in vacuo to obtain a residue. The residue is diluted with methylene chloride, passed through a plug of silica gel and concentrated in vacuo to give the title product as an orange solid (12.0 g) which is identified by NMR spectral analyses.

Using essentially the same procedure, the following compounds are obtained:

| Y |
|---|
| H |
| $C_2H_5$ |
| ![4-ethyl-methylphenyl] |
| ![methylphenyl] |

EXAMPLE 4

Preparation of 5-Amino-3-(6-methoxy-m-tolyl)-1,2-benzisothiazole

-continued

CH₃CO₂H ⟶

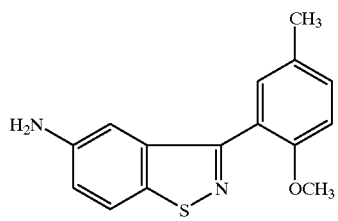

A mixture of 3-(6-methoxy-m-tolyl)-5-nitro-1,2-benzisothiazole (63.0 g, 0.210 mol), 5% acetic acid (1.52 L, 1.21 mol) and ethyl acetate (975 mL) is heated to 65° C., treated portionwise with iron powder (58.6 g, 1.05 mol), stirred at 65° C., and filtered through quartz filter paper. The filtrate phases are separated and the aqueous phase is extracted with ethyl acetate. The organic phase and extracts are combined, washed sequentially with water and brine, dried over anhydrous magnesium sulfate, and concentrated in vacuo to obtain the title product as an orange oil (55.7 g, 98.1%) which is identified by NMR spectral analyses.

Using essentially the same procedure, the following compounds are obtained:

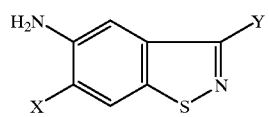

| X | Y | mp ° C. |
|---|---|---------|
| H | H |  |
| H | CN | 118.5–120 |
| H | CH₃ | 112–113.5 |
| H | C₂H₅ |  |
| H | 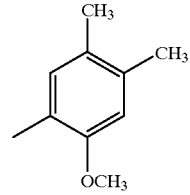 | 179–181 |
| H | 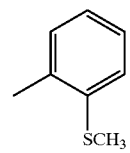 | 90–91 |
| F | 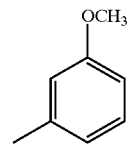 |  |
| H | 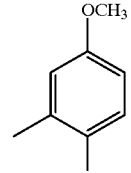 | 130–130.5 |

-continued

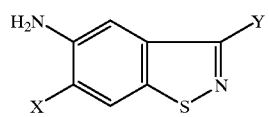

| X | Y | mp ° C. |
|---|---|---------|
| H | CH₃ | 152–153 |
| H | 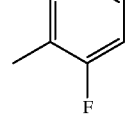 | 121.5–123 |
| H | 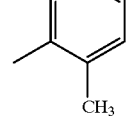 | 108.5–109.5 |
| H | 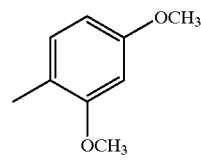 | 158.5–161 |
| H | 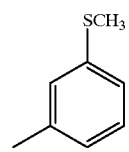 | 101.5–102.5 |
| H |  | 104–105 |
| H |  | 191–192.5 |
| H |  |  |

-continued
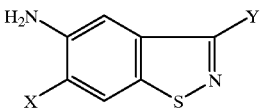
| X | Y | mp °C. |
|---|---|---|
| H | 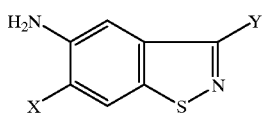 4-OCH₃-phenyl | |
| H | 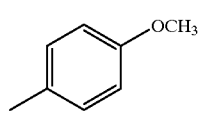 4-CH₃-phenyl | 128–129 |
| H | 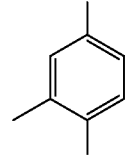 6-methoxyindan-5-yl | |
| H | 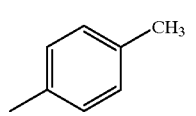 4-I, 3-CH₃, 2-OCH₃-phenyl (I / OCH₃) | 64 |
| H | 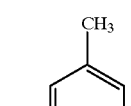 4-SCH₃-phenyl | 108.5–109.5 |
| H | 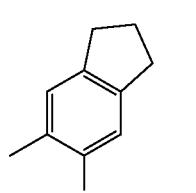 4-Cl-phenyl | 133–134 |
| H | 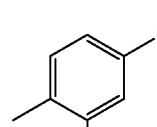 4-F-phenyl | 114.5–115 |
| H | 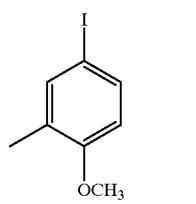 4-OCH₃, 3-CH₃-phenyl | 152–153.5 |
-continued
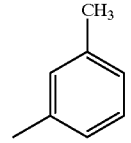
| X | Y | mp °C. |
|---|---|---|
| H | 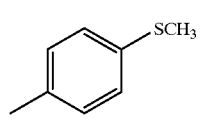 | 146–147 |
| H | 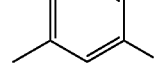 | 60–65 |
| H | 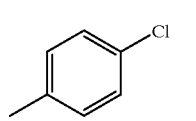 | 143–145 |
| H | 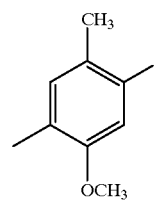 | 100–101 |
| H | 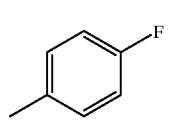 | |
| H | 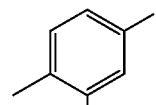 | 125–127 |
| H | 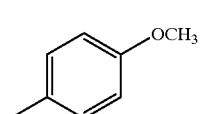 | 172–174 |
| H | 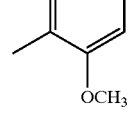 | 146–147 |

-continued

![structure: H2N-benzisothiazole with X, Y substituents]

| X | Y | mp °C. |
|---|---|---|
| H | 3,5-dimethyl-4-methoxyphenyl | 161–162 |
| H | 2,3,5-trimethyl-4-methoxyphenyl (H3C, CH3, CH3, OCH3) | 173–175 |
| H | 3-methyl-4-ethylphenyl (C2H5, CH3) | |
| H | 3-methyl-4-isopropylphenyl (CH(CH3)2, CH3) | |
| H | 2,3-dimethyl-4-methoxyphenyl (CH3, CH3, OCH3) | |
| H | 3-methyl-4-[N(CH3)SO2CH3]phenyl | |

EXAMPLE 5

Preparation of 3-[3-(6-Methoxy-3,4-xylyl)-1,2-benzisothiazol-5-yl]-6-(trifluoromethyl)-2,4(1H,3H)-pyrimidinedione

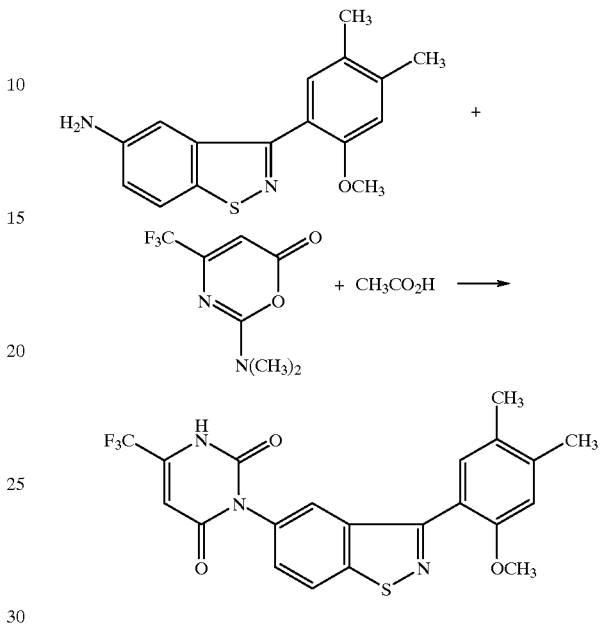

A mixture of 5-amino-3-(6-methoxy-3,4-xylyl)-1,2-benzisothiazole (8.53 g, 30.0 mmol), 2-dimethylamino-4-(trifluoromethyl)-6H-1,3-oxazin-6-one (6.87 g, 33.0 mmol) and acetic acid is refluxed for 2 hours, cooled, and poured into water. The resultant aqueous mixture is filtered to obtain a solid. A solution of the solid in methylene chloride is washed sequentially with water and brine, dried over anhydrous magnesium sulfate, and concentrated in vacuo to obtain an oil. Column chromatography of the oil using silica gel and a 5% diethyl ether in methylene chloride solution gives the title product as a yellow foam (8.37 g, 62.0%) which is identified by NMR spectral analyses.

Using essentially the same procedure, the following compounds are obtained:

![general structure with R1, X, X1, Y substituents]

| X | $X_1$ | $R_1$ | Y | mp °C. |
|---|---|---|---|---|
| H | H | $CF_3$ | CN | 255–258 |
| H | H | $CF_3$ | H | >260 |
| H | H | $CF_3$ | $CH_3$ | 273–274 |
| H | H | $CF_3$ | $C_2H_5$ | |

-continued

Structure: R₁-substituted pyrimidinedione N-linked to benzisothiazole with X, X₁ substituents and Y at 3-position.

| X | X₁ | R₁ | Y | mp °C. |
|---|----|----|---|--------|
| H | H | CF₃ | 2-methoxy-5-methylphenyl (with CH₃ at 4-position, OCH₃) — 2,5-dimethyl-4-methoxyphenyl | 230–231 |
| H | H | CF₃ | 2,3-dimethyl-4-methoxyphenyl | |
| H | H | CF₃ | 2-methyl-4-methoxyphenyl | 125–130 |
| H | H | CF₃ | phenyl | >280 |
| H | H | CF₃ | 4-ethylphenyl | 253–254 |
| H | H | CF₃ | 2,4-dimethyl-5-methoxyphenyl | 149–152 |
| H | H | CF₃ | 3-methoxyphenyl | |
| H | H | CH₃ | 3-methyl-4-methoxyphenyl | >250 |

-continued

| X | X₁ | R₁ | Y | mp °C. |
|---|----|----|---|--------|
| H | H | CF₃ | 2,3,5-trimethyl-4-methoxyphenyl | |
| H | H | CF₃ | 5-methyl-6-methoxy-indanyl | |
| H | H | CF₃ | 4-ethyl-2-methyl-anisyl | |
| H | H | CF₃ | 4-isopropyl-2-methyl-anisyl | |
| H | H | CF₃ | 4-methoxy-2-methylphenyl | |
| H | H | CF₃ | 2-methyl-6-(methylthio)phenyl | |
| H | H | CF₃ | 4-chloro-2-methylphenyl | |

-continued

| X | X₁ | R₁ | Y | mp °C |
|---|----|----|---|-------|
| H | H | CF₃ | *m-methoxyphenyl* | |
| H | H | CF₃ | *2-chloro-4-methoxy-5-methylphenyl* | 208–210 |
| H | H | CF₃ | *4-iodo-2-methyl-phenyl (OCH₃)* | |
| H | H | CF₃ | *2-methoxy-phenyl* | |
| H | H | CF₃ | *4-[N(CH₃)SO₂CH₃]-phenyl* | |
| F | Br | CF₃ | CH₃ | |
| F | H | CF₃ | *5-fluoro-2-methoxyphenyl* | |
| F | H | CF₃ | CH₃ | |

EXAMPLE 6

Preparation of 3-(6-Methoxy-m-tolyl)-1,2-benzisothiazol-5-yl isocyanate

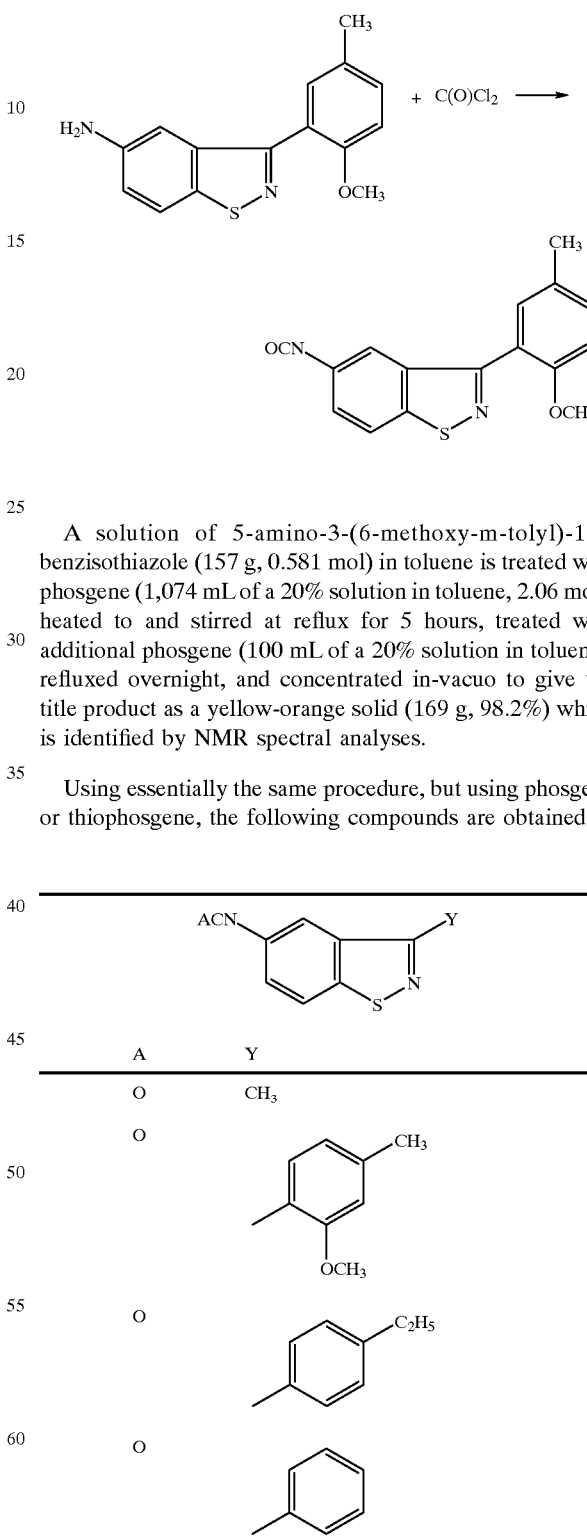

A solution of 5-amino-3-(6-methoxy-m-tolyl)-1,2-benzisothiazole (157 g, 0.581 mol) in toluene is treated with phosgene (1,074 mL of a 20% solution in toluene, 2.06 mol), heated to and stirred at reflux for 5 hours, treated with additional phosgene (100 mL of a 20% solution in toluene), refluxed overnight, and concentrated in-vacuo to give the title product as a yellow-orange solid (169 g, 98.2%) which is identified by NMR spectral analyses.

Using essentially the same procedure, but using phosgene or thiophosgene, the following compounds are obtained:

| A | Y |
|---|---|
| O | CH₃ |
| O | *2-methoxy-4,5-dimethylphenyl* |
| O | *4-ethylphenyl* |
| O | *phenyl* |

-continued

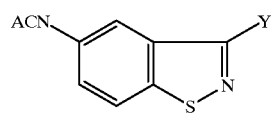

| A | Y |
|---|---|
| O | 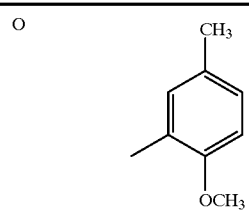 |
| S | 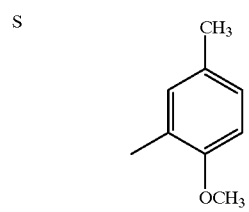 |

EXAMPLE 7

Preparation of 3-[3-(6-Methoxy-m-tolyl-1,2-benzisothiazol-5-yl]-6-(trifluoromethyl)-2,4(1H,3H)-pyrimidinedione

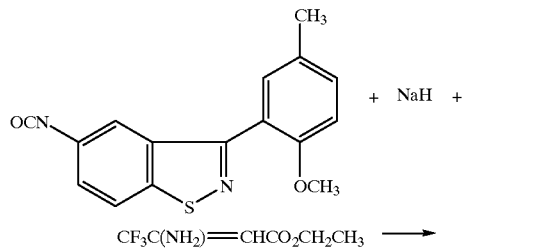

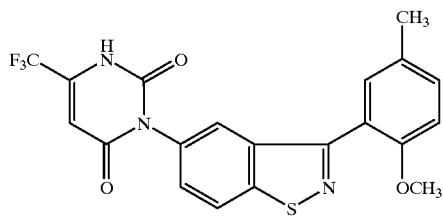

A mixture of 60% sodium hydride in mineral oil (15.9 g, 0.397 mol) and N,N-dimethylformamide is cooled to −10° C., treated over one hour with a solution of ethyl 3-amino-4,4,4-trifluorocrotonate (72.7 g, 0.397 mol) in ether, warmed to and stirred at room temperature for 90 minutes, cooled to −70° C., treated over 80 minutes with a solution of 3-(6-methoxy-m-tolyl)-1,2-benzisothiazol-5-yl isocyanate (107 g, 0.361 mol) in N,N-dimethylformamide while maintaining the temperature below about −65° C., slowly warmed to and stirred at room temperature overnight, and poured onto ice.

The resultant aqueous mixture is washed with ethyl acetate, acidified to pH 2 with concentrated hydrochloric acid, and extracted with diethyl ether. The organic extract is dried over anhydrous magnesium sulfate and concentrated in vacuo to give the title product as an orange oil (110 g, 70.5%) which is identified by NMR spectral analyses.

Using essentially the same procedure, the following compounds are obtained:

| $R_1$ | A | Y | mp ° C. |
|---|---|---|---|
| $CF_3$ | O | $CH_3$ | 273–274 |
| $CF_3$ | O | (3-methyl-4-methoxyphenyl) | |
| $CF_3$ | O | (4-methyl-3-ethylphenyl) | 253–254 |
| $CF_3$ | O | (4-methylphenyl) | >280 |
| $CH_3$ | O | (3-methyl-4-methoxy-phenyl) | >250 |
| $CF_3$ | S | (3-methyl-4-methoxyphenyl) | 213–216 |

EXAMPLE 8

Preparation of 3-[3-(6-Methoxy-m-tolyl)-1,2-benzisothiazol-5-yl]-1-methyl-6-(trifluoromethyl)-2,4(1H,3H)-pyrimidinedione

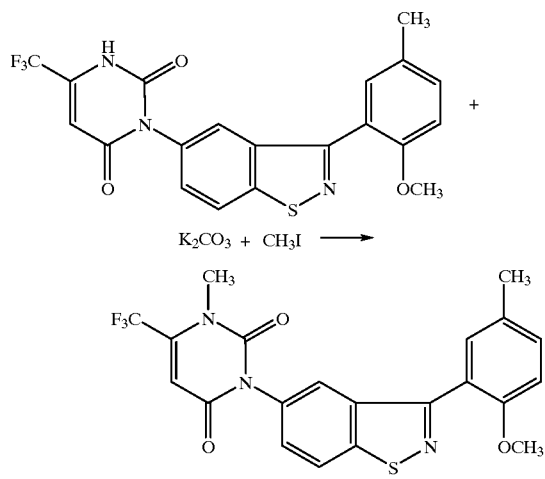

A mixture of 3-[3-(6-methoxy-m-tolyl)-1,2-benzisothiazol-5-yl]-6-(trifluoromethyl)-2,4(1H,3H)-pyrimidinedione (160 g, 0.369 mol), potassium carbonate (76.6 g, 0.554 mol) and iodomethane (34.5 mL, 0.554 mol) in N,N-dimethylformamide is stirred at room temperature for 4 hours, and poured onto ice. The resultant aqueous mixture is extracted with methylene chloride. The organic extract is diluted with hexanes, washed with water, dried over anhydrous magnesium sulfate, and concentrated in vacua to obtain the title product as an orange foam (163 g, 98.8%) which is identified by NMR spectral analyses.

Using essentially the same procedure, the following compounds are obtained:

| X | $X_1$ | R | $R_1$ | Y | mp ° C. |
|---|---|---|---|---|---|
| H | H | $CH_3$ | $CF_3$ | H | 223–225 |
| H | H | $CH_3$ | $CF_3$ | CN | 239–240 |
| H | H | $CH_3$ | $CF_3$ | $CH_3$ | 244–245 |
| H | H | $CH_2C\equiv CH$ | $CF_3$ | $CH_3$ | |
| H | H | $CH_3$ | $CF_3$ | $CH_2OCH_2CO_2CH_3$ | 143–144 |
| H | H | $CH_2C_6H_5$ | $CF_3$ | $CH_3$ | |
| H | H | $CH_2CN$ | $CF_3$ | $CH_3$ | |
| H | H | $CH_2CH_2F$ | $CF_3$ | $CH_3$ | |
| H | H | $CH_3$ | $CF_3$ | $C_2H_5$ | 171–172 |
| H | H | $CH_3$ | $CF_3$ | 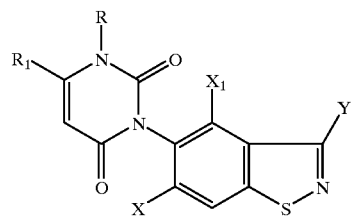 | 198–200 |
| H | H | $CH_3$ | $CF_3$ | (4-ethylphenyl) | 170.5–172 |
| H | H | $CH_3$ | $CF_3$ | (phenyl) | 175.5–180 |

-continued
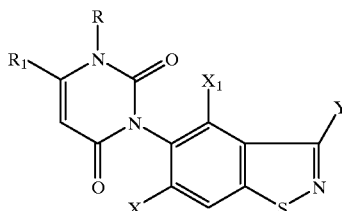
| X | X₁ | R | R₁ | Y | mp ° C. |
|---|----|----|----|----|---------|
| H | H | CH₃ | CF₃ | 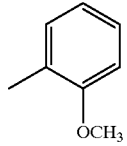 | 173–175 |
| H | H | CH₃ | CF₃ | 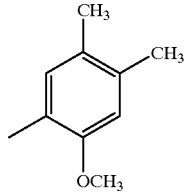 | 225–227 |
| H | H | CH₃ | CF₃ | 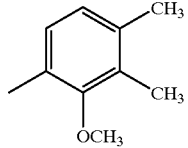 | 185–187 |
| H | H | CH(CH₃)₂ | CF₃ | 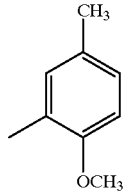 | |
| H | H | CH₃ | CF₃ | 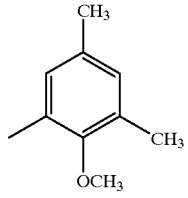 | |
| H | H | CH₃ | CF₃ | 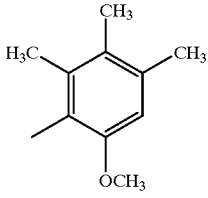 | 187–190 |

-continued

| X | X₁ | R | R₁ | Y | mp °C. |
|---|----|----|----|---|--------|
| H | H | CH₃ | CF₃ | (phenyl with C₂H₅, CH₃, OCH₃) | 83–86 |
| H | H | CH₃ | CF₃ | (6-methylindane) | 299 |
| H | H | CH₃ | CF₃ | (phenyl-CH₃ with N(CH₃)SO₂CH₃) | 220–225 |
| H | H | CH₃ | CF₃ | (phenyl with I, CH₃, OCH₃) | 216–217 |
| H | H | CH₃ | CF₃ | (phenyl with CH(CH₃)₂, CH₃, OCH₃) | 103–105 |
| H | H | CH₂CH=CH₂ | CF₃ | (phenyl with CH₃, CH₃, OCH₃) | |

-continued
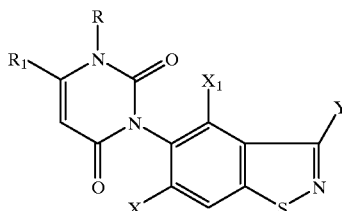
| X | X₁ | R | R₁ | Y | mp ° C. |
|---|----|---|----|---|---------|
| H | H | CH₂CH₃ | CF₃ | 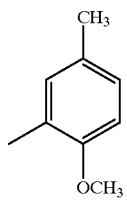 | |
| H | H | CH₃ | CH₃ | 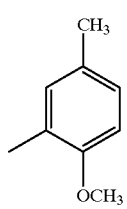 | 210–213 |
| H | H | C₂H₅ | CF₃ | 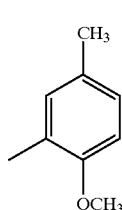 | 105–107 |
| H | H | CH₃ | CF₃ | 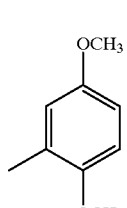 | 170–172 |
| H | H | CH(CH₃)₂ | CF₃ | 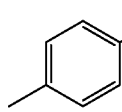 | 151–154 |
| H | H | CH₃ | CF₃ |  | |

-continued
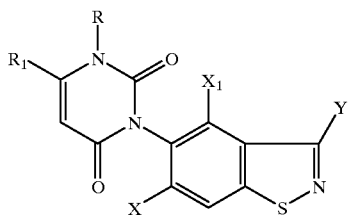
| X | X₁ | R | R₁ | Y | mp ° C. |
|---|----|---|----|----|---------|
| H | H | CH₃ | CF₃ | 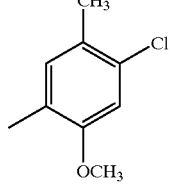 | 227–228 |
| F | H | CH₃ | CF₃ | CH₃ | |
| Cl | H | CH₃ | CF₃ | 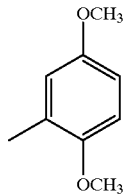 | |
| F | Br | CH₃ | CF₃ | CH₃ | 211–213 |
| H | H | C₂H₅ | CH₃ | 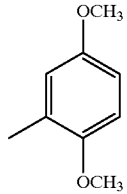 | |
| H | H | CH₂CH=CH₂ | CF₃ | 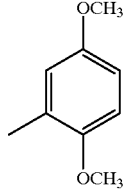 | 122–127 |
| H | H | CH₃ | CF₃ | 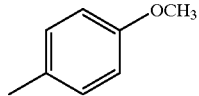 | |
| H | H | CH₃ | CF₃ | 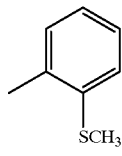 | |

-continued

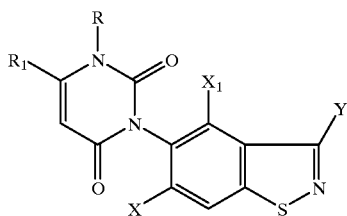

| X | X₁ | R | R₁ | Y | mp ° C. |
|---|----|----|----|---|---------|
| H | H | CH₃ | CF₃ | (3-methoxyphenyl) | 147–149 |
| F | H | CH₃ | CF₃ | (2,5-dimethoxyphenyl) | |

Additionally, in certain instances where R is $CF_3$ and Y is methyl, the alkylation occurs on both nitrogen and oxygen to afford the following mixtures:

[Structure A: N-alkylated pyrimidinedione-benzisothiazole]

+

[Structure B: O-alkylated pyrimidine-benzisothiazole]

| R | % A | % B |
|---|-----|-----|
| CH₂CH₃ | 50 | 50 |
| CH₂CH(CH₃)₂ | 55 | 45 |
| CH₂CH=CH₂ | 85 | 15 |

Similarly, the following O-alkylated and N-alkylated compounds are isolated as mixtures and subsequently separated by column chromatography:

| R | mp ° C. |
|---|---------|
| [structure with 2,5-dimethylphenyl N-alkylated isomer] | |
| CH₂CH₃ | 105–107 |
| CH₂CH=CH₂ | 122–127 |
| [structure with 2,5-dimethylphenyl other isomer] | |
| CH₂CH₃ | 143–146 |
| CH₂CH=CH₂ | 129–133 |

In addition, the following S-alkylated product is obtained when A is sulfur:

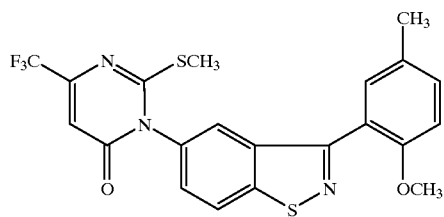

EXAMPLE 9

Preparation of 3-[3-(6-Hydroxy-m-tolyl)-1,2-benzisothiazol-5-yl]-1-methyl-6-(trifluoromethyl)-2,4(1H,3H)-pyrimidinedione

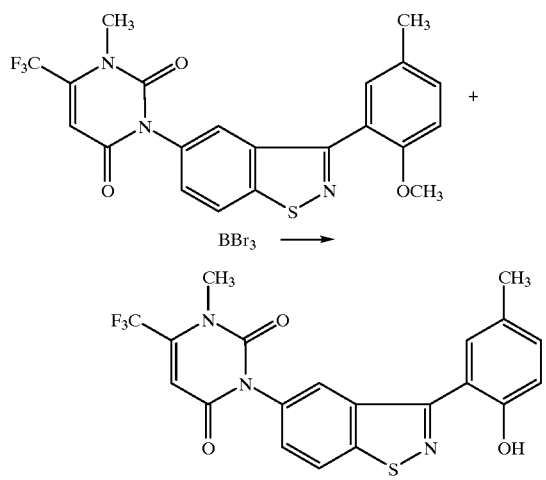

A solution of 3-[3-(6-methoxy-m-tolyl)-1,2-benzisothiazol-5-yl]-1-methyl-6-(trifluoromethyl)-2,4(1H,3H)-pyrimidinedione (111 g, 0.248 mol) in methylene chloride is cooled to −5° C., treated over one hour with a 1 M solution of boron tribromide in methylene chloride (322 mL, 0.322 mol), stirred for one hour, washed sequentially with water and brine, dried over anhydrous magnesium sulfate, and concentrated in vacuo to give the title product as a yellow solid (105 g, 98.1%) which is identified by NMR spectral analyses.

Using essentially the same procedure, the following compounds are obtained:

| X | R | $R_1$ | $W_1$ | $W_2$ | $W_3$ | $W_4$ | mp ° C. |
|---|---|---|---|---|---|---|---|
| H | $CH_3$ | $CF_3$ | I | H | H | OH | |
| H | $CH_3$ | $CF_3$ | H | $CH_3$ | H | OH | |
| H | $CH_3$ | $CF_3$ | $CH_3$ | $CH_3$ | H | OH | 265–266 |

-continued

| X | R | $R_1$ | $W_1$ | $W_2$ | $W_3$ | $W_4$ | mp ° C. |
|---|---|---|---|---|---|---|---|
| H | $CH_3$ | $CH_3$ | $CH_3$ | H | H | OH | >250 |
| H | $C_2H_5$ | $CF_3$ | $CH_3$ | H | H | OH | |
| H | $CH_2CH=CH_2$ | $CF_3$ | $CH_3$ | H | H | OH | |
| H | $CH_3$ | $CF_3$ | $CH_3$ | H | $CH_3$ | OH | |
| H | $CH_3$ | $CF_3$ | $C_2H_5$ | H | H | OH | |
| H | $CH_3$ | $CF_3$ | $CH(CH_3)_2$ | H | H | OH | |
| H | $C_2H_5$ | $CH_3$ | $CH_3$ | H | H | OH | |
| H | $CH_3$ | $CF_3$ | H | H | H | OH | |
| H | $CH_3$ | $CF_3$ | H | OH | H | H | |
| H | $CH_3$ | $CF_3$ | CHO | H | H | OH | |
| H | $CH_3$ | $CF_3$ | H | $CH_3$ | $CH_3$ | OH | >260 |
| H | $CH_3$ | $CF_3$ | H | H | OH | H | 200–202 |
| H | $CH_3$ | $CF_3$ | I | $CH_3$ | H | OH | >250 |
| H | $CH_3$ | $CF_3$ | —(CH$_2$)$_3$— | | H | OH | 244–247 |
| H | $CH_3$ | $CF_3$ | OH | H | H | OH | 239–242 |
| H | $CH_3$ | $CF_3$ | $OCH_3$ | H | H | OH | 180–182 |
| H | $CH_3$ | $CF_3$ | $CH_3$ | H | Cl | OH | 232–235 |
| F | $CH_3$ | $CF_3$ | $CH_3$ | H | H | OH | |

EXAMPLE 10

Preparation of Methyl{{2-{5-[3,6-dihydro-3-methyl-4-(trifluoromethyl)-2,6-dioxo-1(2H)-pyrimidinyl]-1,2-benzisothiazol-3-yl}-p-tolyl}oxy}acetate

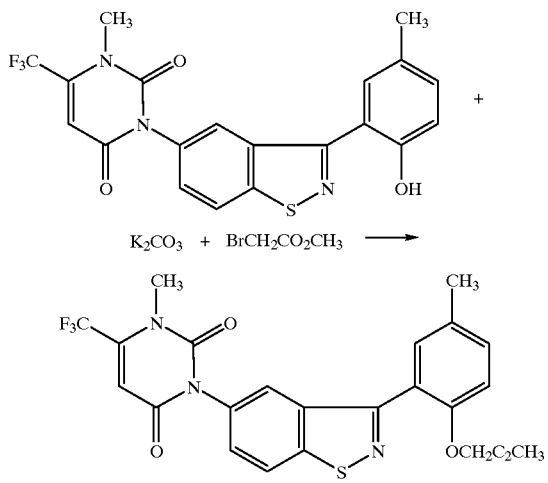

A mixture of 3-[3-(6-hydroxy-m-tolyl)-1,2-benzisothiazol-5-yl]-1-methyl-6-(trifluoromethyl)-2,4(1H,3H)-pyrimidinedione (70.6 g, 0.163 mol), potassium carbonate (27.1 g, 0.196 mol) and methyl bromoacetate in N,N-dimethylformamide is stirred at room temperature for 39 hours, diluted with ethyl acetate, washed sequentially with water and brine, dried over anhydrous magnesium sulfate, and concentrated in vacuo to obtain a yellow foam. Flash column chromatography of the yellow foam using silica gel and 39:1 to 9:1 methylene chloride in diethyl ether solutions gives the title product as a white foam (67.9 g, 82.4%) which is identified by NMR spectral analyses.

Using essentially the same procedure, the following compounds are obtained:

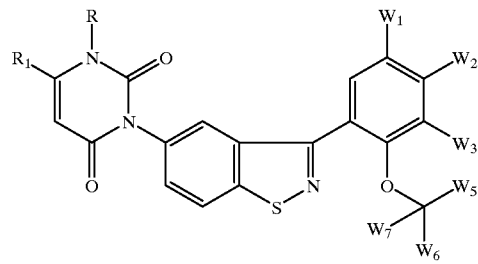

| R | R₁ | W₁ | W₂ | W₃ | W₅ | W₆ | W₇ | mp °C. |
|---|---|---|---|---|---|---|---|---|
| CH₃ | CF₃ | CH₃ | H | H |  | —CH₂CH(CH₃)OC(=O)— | H |  |
| CH₃ | CF₃ | CH₃ | H | H | CH₃ | CO₂CH₃ | H | 100–110 |
| CH₃ | CF₃ | H | CH₃ | H | H | CO₂CH₃ | H | 160–162 |
| CH₃ | CF₃ | H | CH₃ | H | CH₃ | CO₂CH₃ | H | 162–163.5 |
| CH₃ | CF₃ | CH₃ | CH₃ | H | H | CO₂CH₃ | H | 128–130 |
| CH₃ | CF₃ | CH₃ | H | I | H | CO₂CH₃ | H |  |
| CH₃ | CF₃ | CH₃ | CH₃ | H | CH₃ | CO₂CH₃ | H |  |
| CH₃ | CF₃ | CH₃ | Cl | H | H | CO₂CH₃ | H | 165–167 |
| CH₃ | CF₃ | I | H | H | CH₃ | CO₂CH₃ | H | 178–180 |
| CH₃ | CF₃ | I | H | H | H | CO₂CH₃ | H | 183–184 |
| CH₃ | CF₃ | I | CH₃ | H | H | CO₂CH₃ | H | 203–206 |
| CH₃ | CF₃ | I | CH₃ | H | CH₃ | CO₂CH₃ | H | 179–181 |
| CH₃ | CF₃ | CH₃ | H | H | CH₃ | CO₂CH₃ | H | 100–106[1] |
| CH₃ | CF₃ | CH₃ | H | H | CH₃ | CO₂CH₃ | H | 99–104[2] |
| CH₃ | CF₃ | CH₃ | H | CH₃ | H | CO₂CH₃ | H | 139–141 |
| CH₃ | CF₃ | CH₃ | H | CH₃ | CH₃ | CO₂CH₃ | H | 88 |
| CH₃ | CF₃ | C₂H₅ | H | H | CH₃ | CO₂CH₃ | H | 75–77 |
| CH₃ | CF₃ | CH₃ | H | H | C₂H₅ | CO₂CH₃ | H |  |
| CH₃ | CF₃ | CH(CH₃)₂ | H | H | CH₃ | CO₂CH₃ | H | 90–92.5 |
| CH₃ | CH₃ | CH₃ | H | H | H | CO₂CH₃ | H | 117–125 |
| CH₃ | CH₃ | CH₃ | H | H | CH₃ | CO₂CH₃ | H | 112–115 |
| C₂H₅ | CH₃ | CH₃ | H | H | H | CO₂CH₃ | H | 77–85 |
| CH₃ | CF₃ | CH₃ | H | H | C₂H₅ | CO₂CH₃ | H |  |
| CH₃ | CF₃ | CH₃ | H | H | H | C≡CH | H |  |
| CH₃ | CF₃ | CH₃ | H | H | H | CN | H |  |
| CH₃ | CF₃ | CH₃ | H | H | CH₃ | CN | H |  |
| CH₃ | CF₃ | CH₃ | H | H | CH₃ | CH₃ | H |  |
| CH₃ | CF₃ | CH₃ | H | H | H | CH₃ | H |  |
| CH₃ | CF₃ | CH₃ | H | H | H | (1,3-dioxolan-2-yl)methyl | H |  |
| CH₃ | CF₃ | CH₃ | H | H | H | CH=CHCO₂CH₃ | H |  |
| CH₃ | CF₃ | CH₃ | H | H | H | (CH₂)₂CO₂C₂H₅ | H |  |
| CH₃ | CF₃ | CH₃ | H | H | H | CH₂CO₂CH₃ | H |  |
| CH₃ | CF₃ | CH₃ | H | H | H | CO₂C(CH₃)₃ | H |  |
| CH₃ | CF₃ | CH₃ | H | H | H | CH(CH₃)₂ | H |  |
| CH₃ | CF₃ | CH₃ | H | H | H | CH=CH₂ | H |  |
| CH₃ | CF₃ | CH₃ | H | H | CH₃ | CO₂C(CH₃)₃ | H |  |
| CH₃ | CF₃ | CH₃ | H | H | C₂H₅ | CO₂CH₃ | H |  |
| CH₃ | CF₃ | CH₃ | H | H | CH₃ | CO₂CH₃ | CH₃ |  |
| CH₃ | CF₃ | CH₃ | H | H | n-C₃H₇ | CO₂CH₃ | H |  |
| CH₃ | CF₃ | CH₃ | H | H | CH₃ | CO₂C(CH₃)₃ | CH₃ |  |
| CH₃ | CF₃ | H | CH₃ | H | H | CO₂CH₂C≡CH | H | 192–195 |
| CH₂CH=CH₂ | CF₃ | CH₃ | H | H | H | CO₂CH₂C≡CH | H | 138–145 |
| CH₃ | CF₃ | CH₃ | CH₃ | H | H | CO₂CH₂C≡CH | H | 188.5–190 |
| C₂H₅ | CF₃ | CH₃ | H | H | H | CO₂CH₃ | H |  |
| CH₃ | CF₃ | CH₃ | H | H | H | CH=CHCO₂CH₃ | H |  |
| CH₃ | CF₃ | CH₃ | H | H | n-C₃H₇ | CO₂C₂H₅ | H |  |
| CH₃ | CF₃ | H | H | H | H | CO₂CH₃ | H | 154–156 |
| CH₃ | CF₃ | H | H | H | CH₃ | CO₂CH₃ | H | 174–175 |
| CH₃ | CF₃ | H | H | H | H | CO₂CH₂C≡CH | H | 148–150 |
| CH₃ | CF₃ | CH₃ | Cl | H | CH₃ | CO₂CH₃ | H | 93–104 |
| CH₃ | CF₃ | CHO | H | H | H | CO₂CH₃ | H | 78–81 |

-continued

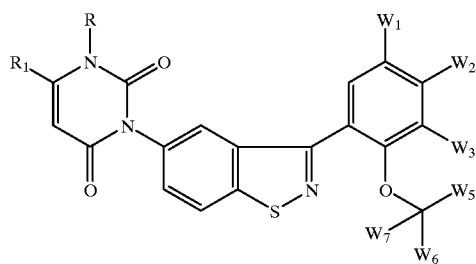

| R | R$_1$ | W$_1$ | W$_2$ | W$_3$ | W$_5$ | W$_6$ | W$_7$ | mp ° C. |
|---|---|---|---|---|---|---|---|---|
| CH$_3$ | CF$_3$ | CH$_3$ | H | H | H | C(O)C$_6$H$_5$ | H | |
| CH$_3$ | CF$_3$ | CH$_3$ | H | H | H | C(O)—⟨4-Cl-C$_6$H$_4$⟩ | H | |
| CH$_3$ | CF$_3$ | CH$_3$ | H | H | H | C(O)C(CH$_3$)$_3$ | H | |
| CH$_3$ | CF$_3$ | H | H | H | H | C(O)C(CH$_3$)$_3$ | H | |
| CH$_3$ | CF$_3$ | H | H | H | CH$_3$ | C(O)—⟨3,4-diMe-C$_6$H$_3$⟩ | H | |
| CH$_3$ | CF$_3$ | CH$_3$ | H | H | H | CH$_2$CH(OCH$_3$)$_2$ | H | 70–75 |
| CH$_3$ | CF$_3$ | H | CH$_3$ | CH$_3$ | H | CO$_2$CH$_3$ | H | 96–98 |
| CH$_3$ | CF$_3$ | H | CH$_3$ | CH$_3$ | CH$_3$ | CO$_2$CH$_3$ | H | |
| CH$_3$ | CF$_3$ | H | CH$_3$ | CH$_3$ | H | CO$_2$CH$_2$C≡CH | H | 155–156 |
| CH$_3$ | CF$_3$ | OCH$_3$ | H | H | H | CO$_2$CH$_3$ | H | 148–151 |
| CH$_3$ | CF$_3$ | OCH$_3$ | H | H | CH$_3$ | CO$_2$CH$_3$ | H | 142–144 |
| CH$_3$ | CF$_3$ | OCH$_3$ | H | H | H | CO$_2$CH$_2$C≡CH | H | 149–151 |
| CH$_3$ | CF$_3$ | —(CH$_2$)$_3$— | | H | H | CO$_2$CH$_3$ | H | 166–167 |
| CH$_3$ | CF$_3$ | —(CH$_2$)$_3$— | | H | CH$_3$ | CO$_2$CH$_3$ | H | 108–113 |
| CH$_3$ | CF$_3$ | —(CH$_2$)$_3$— | | H | H | CO$_2$CH$_2$C≡CH | H | 188–190 |
| CH$_3$ | CF$_3$ | CH$_3$ | H | H | F | CO$_2$CH$_3$ | F | |
| CH$_3$ | CF$_3$ | CH$_3$ | H | H | CH$_3$ | CH$_2$C(O)—⟨3,4-diMe-C$_6$H$_3$⟩ | H | |
| CH$_3$ | CF$_3$ | CH$_3$ | H | H | H | CH$_2$C(O)—⟨4-OCHF$_2$-C$_6$H$_4$⟩ | H | |

$^1$R-isomer
$^2$S-isomer

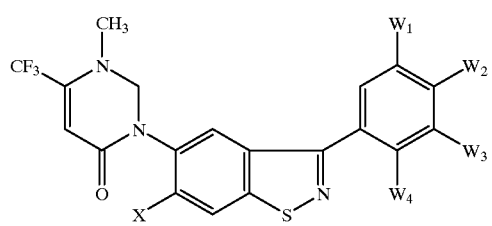

| X | W$_1$ | W$_2$ | W$_3$ | W$_4$ | mp ° C. |
|---|---|---|---|---|---|
| Cl | CH$_3$ | H | H | OCH$_2$CO$_2$CH$_3$ | |

-continued

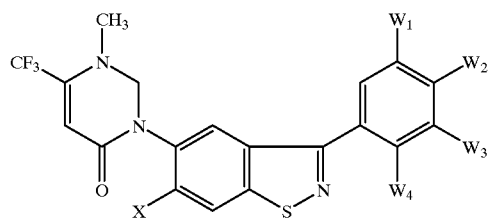

| X | W₁ | W₂ | W₃ | W₄ | mp °C. |
|---|----|----|----|----|--------|
| F | CH₃ | H | H | OCH₂CO₂CH₃ | |
| F | H | H | H | OCH₂CO₂CH₃ | |
| F | H | H | H | OCH(CH₃)CO₂CH₃ | |
| F | CH₃ | H | H | OCH(CH₃)CO₂CH₃ | |
| H | H | H | OCH₂CH₃ | H | 173–174 |
| H | H | H | OCH(CH₃)₂ | H | 189–190 |
| H | H | OCH₂CO₂CH₃ | H | H | 164–166 |
| H | H | OCH(CH₃)CO₂CH₃ | H | H | 149–153 |
| H | H | OCH₂CO₂CH₂C≡CH | H | H | 144–146 |
| H | H | OCH₂CO₂C(CH₃)₃ | H | H | 150–152 |
| H | H | H | OCH(CH₃)CO₂CH₃ | H | 119–121 |
| H | H | H | OCH₂CO₂CH₂C≡CH | H | 178.5–180 |
| H | H | H | OCH₂CO₂CH₃ | H | 201.5–202 |

EXAMPLE 11

Preparation of 2-Chloro-2'-methoxy-5'-methyl-5-nitrobenzophenone, oxime

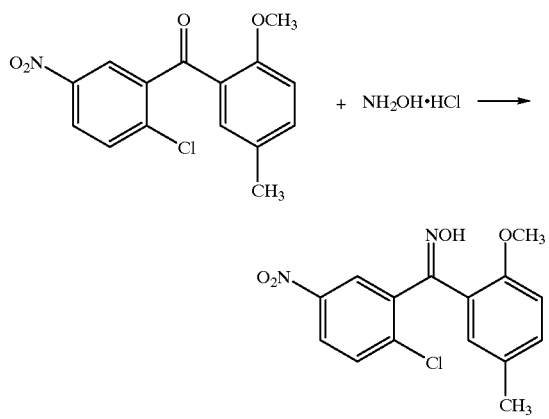

A mixture of 2-chloro-2'-methoxy-5'-methyl-5-nitrobenzophenone (90.0 g, 0.294 mol) in ethanol is treated with a solution of hydroxylamine hydrochloride (102.3 g, 1.47 mol) in water, refluxed overnight, and poured onto ice. The resultant aqueous mixture is filtered to obtain a solid. The solid is washed with water and dried in a hot vacuum oven overnight to give the title product as a white solid (84.2 g) which is identified by $^1$H NMR spectral analysis.

Using essentially the same procedure, the following compounds are obtained:

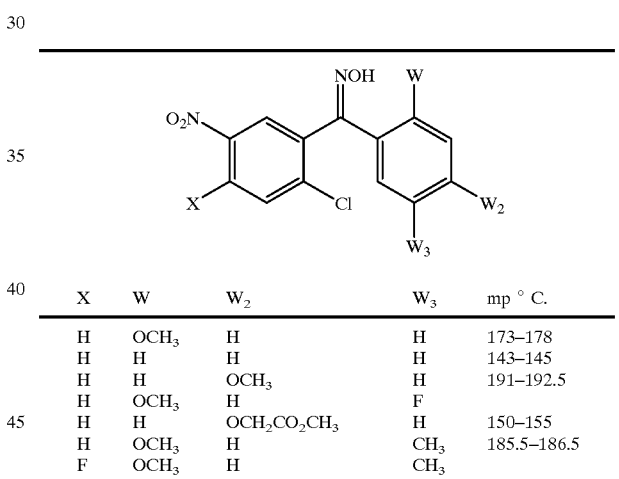

| X | W | W₂ | W₃ | mp °C. |
|---|---|----|----|--------|
| H | OCH₃ | H | H | 173–178 |
| H | H | H | H | 143–145 |
| H | H | OCH₃ | H | 191–192.5 |
| H | OCH₃ | H | F | |
| H | H | OCH₂CO₂CH₃ | H | 150–155 |
| H | OCH₃ | H | CH₃ | 185.5–186.5 |
| F | OCH₃ | H | CH₃ | |

EXAMPLE 12

Preparation of 3-(6-Methoxy-m-tolyl)-5-nitro-1,2-benzisoxazole

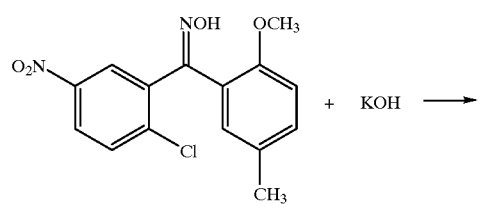

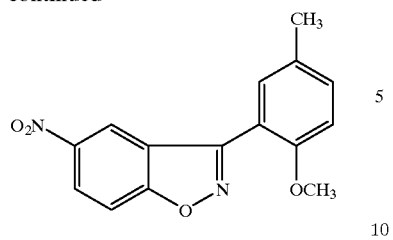

A mixture of 2-chloro-2'-methoxy-5'-methyl-5-nitrobenzophenone, oxime (84.0 g, 0.262 mol) in ethanol is warmed to 65° C., treated with 150 mL of 10% potassium hydroxide solution over 25 minutes, heated to 78° C. over one hour, cooled, and poured onto ice. The resultant aqueous mixture is filtered to obtain a solid. The solid is washed with water, dried, recrystallized from N,N-dimethylformamide, washed sequentially with N,N-dimethylformamide and ethanol, and dried in a vacuum oven at 80° C. to give the title product as a solid (mp 225–226° C.) which is identified by $^1$H NMR spectral analysis.

Using essentially the same procedure, the following compounds are obtained:

| X | W | $W_1$ | $W_2$ | mp ° C. |
|---|---|---|---|---|
| H | OCH$_3$ | H | H | 170–171 |
| H | H | H | H | 138–139 |
| H | H | H | OCH$_3$ | 205–207 |
| F | OCH$_3$ | CH$_3$ | H | |

EXAMPLE 13

Preparation of 5-Amino-3-(6-methoxy-m-tolyl)-1,2-benzisoxazole and 5-Amino-4-chloro-3-(6-methoxy-m-tolyl)-1,2-benzisoxazole

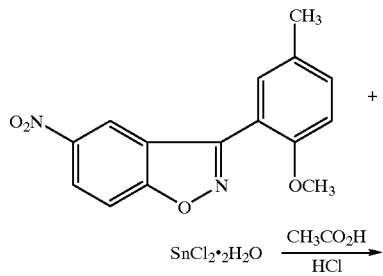

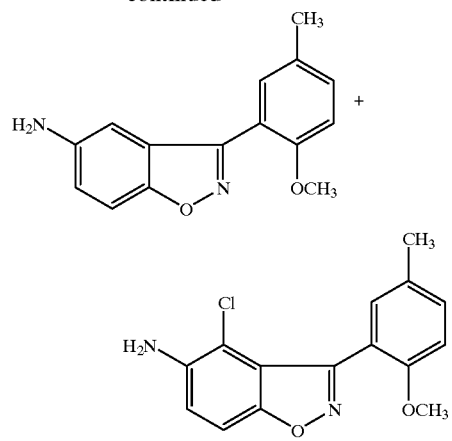

A mixture of 3-(6-methoxy-m-tolyl)-5-nitro-1,2-benzisoxazole (20.0 g, 0.0703 mol) in acetic acid (380 mL) is warmed, treated with a warm solution of tin(II) chloride dihydrate (47.4 g, 0.210 mol) in concentrated hydrochloric acid (110 mL), refluxed for one hour, cooled to 10° C., and concentrated in vacua to obtain a gum. The gum is added to water with stirring to obtain a slurry. The slurry is treated with 80 g of 50% sodium hydroxide solution, stirred at 60° C. to 80° C. over one hour, cooled, and decanted to obtain a residue. A mixture of the residue in ethanol is treated with potassium hydroxide (10 g), heated overnight, cooled to room temperature, neutralized with hydrochloric acid, and concentrated in vacuo to obtain a residue. The residue is diluted with ethyl acetate and filtered. The filtrate is concentrated in vacuo and chromatographed using silica gel and a 2% ethyl acetate in methylene chloride solution to give the title products as semi-solids which are identified by elemental and mass spectral analyses.

Using essentially the same procedure, but substituting 5-nitro-3-phenyl-1,2-benzisoxazole for 3-(6-methoxy-m-tolyl)-5-nitro-1,2-benzisoxazole, 5-amino-3-phenyl-1,2-benzisoxazole is obtained.

EXAMPLE 14

Preparation of 3-[3-(6-Methoxy-m-tolyl)-1,2-benzisoxazol-5-yl]-6-trifluoromethyl)-2,4(1H,3H)-pyrimidinedione

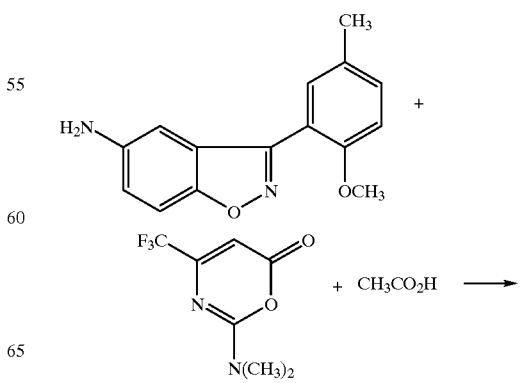

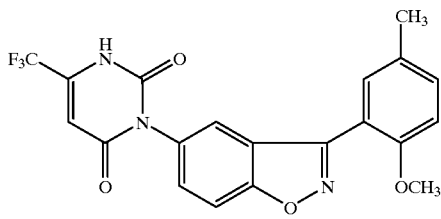

A mixture of 5-amino-3-(6-methoxy-m-tolyl)-1,2-benzisoxazole (8.40 g, 0.033 mol), 2-dimethylamino-4-(trifluoromethyl)-6H-1,3-oxazin-6-one (7.60 g, 0.036 mol), and acetic acid is refluxed for three hours, cooled, poured onto ice, and diluted with water. The resultant aqueous mixture is filtered to obtain a solid. The solid is washed with water and dried to give the title product as a pink solid which is identified by NMR spectral analyses.

Using essentially the same procedure, the following compounds are obtained:

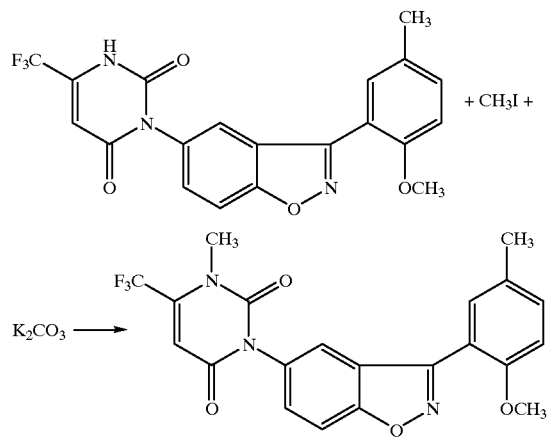

| X | $X_1$ | W | $W_3$ | mp ° C. |
|---|---|---|---|---|
| H | H | $OCH_3$ | H | 214–216 |
| H | H | H | H | |
| H | Cl | $OCH_3$ | $CH_3$ | |
| F | H | $OCH_3$ | $CH_3$ | |

EXAMPLE 15

Preparation of 3-[3-(6-Methoxy-m-tolyl)-1,2-benzisoxazol-5-yl]-1-methyl-6-(trifluoromethyl)-2,4 (1H,3H)-pyrimidinedione

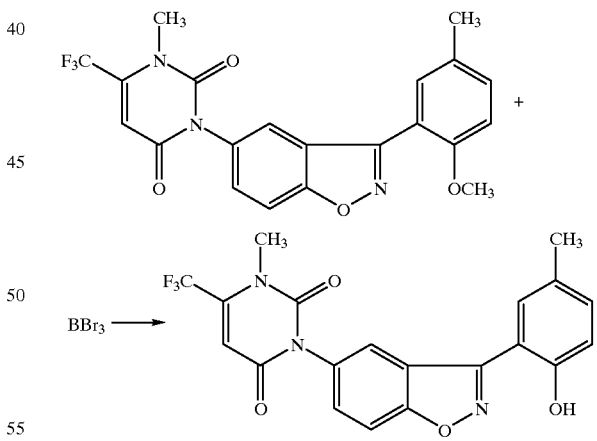

A mixture of 3-[3-(6-methoxy-m-tolyl)-1,2-benzisoxazol-5-yl]-6-(trifluoromethyl)-2,4(1H,3H)-pyrimidinedione (10.5 g, 0.0255 mol) and potassium carbonate (7.04 g, 0.051 mol) in N,N-dimethylformamide is stirred for 15 minutes, treated with methyl iodide (7.24 g, 0.051 mol), stirred overnight, and poured onto ice. The resultant aqueous mixture is extracted with methylene chloride. The organic extracts are combined, washed with water, dried over anhydrous sodium sulfate, and concentrated in vacua to obtain a brown glass. Dry column chromatography of the glass using silica gel and a hexanes/ethyl acetate solution (3:1) gives the title product as an off-white solid which is identified by NMR spectral analyses.

Using essentially the same procedure, the following compounds are obtained:

| X | $X_1$ | W | $W_3$ | mp ° C. |
|---|---|---|---|---|
| H | H | $OCH_3$ | H | |
| H | H | H | H | 225–226.5 |
| H | Cl | $OCH_3$ | $CH_3$ | |
| F | H | $OCH_3$ | $CH_3$ | |
| F | H | $OCH_3$ | H | |

EXAMPLE 16

Preparation of 3-[3-(6-Hydroxy-m-tolyl)-1,2-benzisoxazol-5-yl]-1-methyl-6-(trifluoromethyl)-2,4 (1H,3H)-pyrimidinedione A mixture of 3-[3-(6-methoxy-m-tolyl)-1,2-benzisoxazol-5-yl]-1-methyl-6-(trifluoromethyl)- 2,4(1H,3H)-pyrimidinedione (5.00 g, 0.0116 mol) in methylene chloride is cooled to −10° C., treated dropwise with 15.1 mL of 1 M boron tribromide in methylene chloride while maintaining the reaction mixture temperature at −15° C. to 0° C., warmed to room temperature, treated dropwise with 5 mL of the boron tribromide solution, stirred at room temperature for one hour, and poured into dilute hydrochloric acid. The resultant aqueous mixture is diluted with acetone, concentrated In vacuo, diluted with water, and filtered to obtain a solid. The solid is washed with water and dried in a vacuum oven at 60° C. to give the title product as a yellow solid which is identified by mass spectral analysis.

Using essentially the same procedure, the following compounds are obtained:

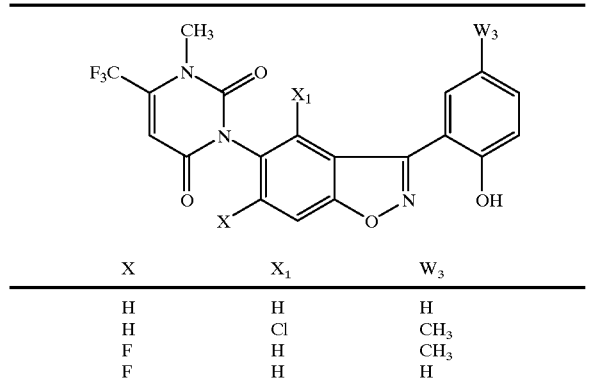

| X | $X_1$ | $W_3$ |
|---|---|---|
| H | H | H |
| H | Cl | $CH_3$ |
| F | H | $CH_3$ |
| F | H | H |

EXAMPLE 17

Preparation of Methyl{{2-{5-[3,6-dihydro-3-methyl-2,6-dioxo-4-(trifluoromethyl)-1(2H)-pyrimidinyl]-1,2-benzisoxazol-3-yl}-p-tolyl}oxy}acetate

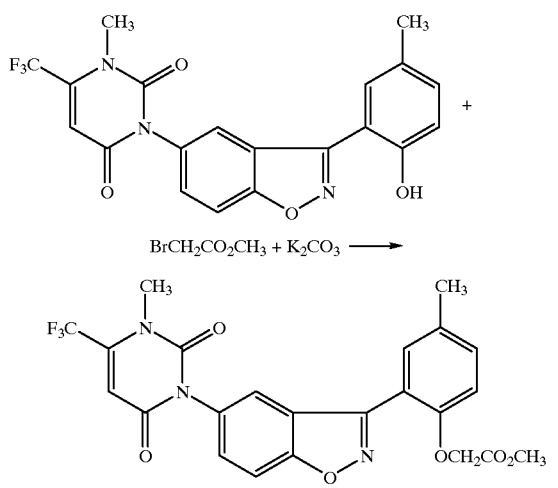

A mixture of 3-[3-(6-hydroxy-m-tolyl)-1,2-benzisoxazol-5-yl]-1-methyl-6-(trifluoromethyl)-2,4(1H,3H)-pyrimidinedione (2.25 g, 0.00540 mol), and potassium carbonate (1.50 g, 0.0108 mol) in N,N-dimethylformamide is stirred for several minutes, treated with methyl bromoacetate (0.903 g, 0.00590 mol), stirred at room temperature, and poured into an ice-water mixture. The resultant aqueous mixture is filtered to obtain a solid. Dry column chromatography of the solid using silica gel and a 4% ether in methylene chloride solution gives the title product as a glass which is identified by NMR spectral analyses.

Using essentially the same procedure, the following compounds are obtained:

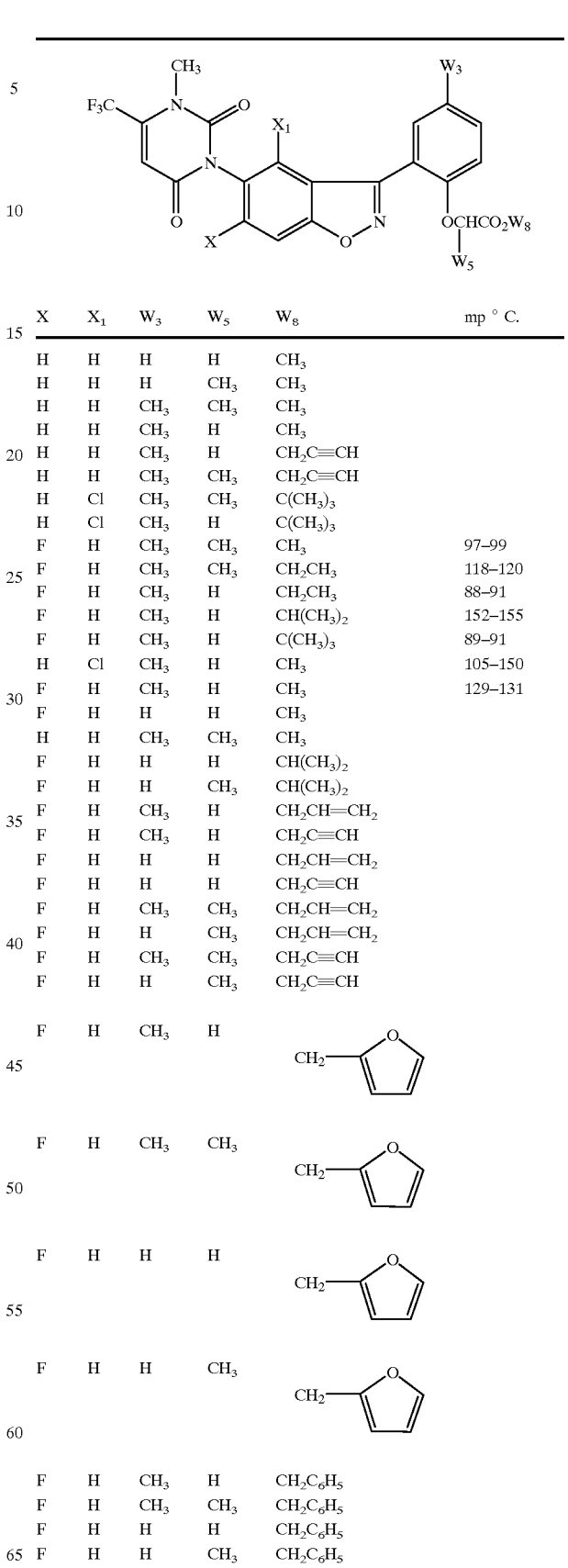

| X | $X_1$ | $W_3$ | $W_5$ | $W_8$ | mp ° C. |
|---|---|---|---|---|---|
| H | H | H | H | $CH_3$ | |
| H | H | H | $CH_3$ | $CH_3$ | |
| H | H | $CH_3$ | $CH_3$ | $CH_3$ | |
| H | H | $CH_3$ | H | $CH_3$ | |
| H | H | $CH_3$ | H | $CH_2C\equiv CH$ | |
| H | H | $CH_3$ | $CH_3$ | $CH_2C\equiv CH$ | |
| H | Cl | $CH_3$ | $CH_3$ | $C(CH_3)_3$ | |
| H | Cl | $CH_3$ | H | $C(CH_3)_3$ | |
| F | H | $CH_3$ | $CH_3$ | $CH_3$ | 97–99 |
| F | H | $CH_3$ | $CH_3$ | $CH_2CH_3$ | 118–120 |
| F | H | $CH_3$ | H | $CH_2CH_3$ | 88–91 |
| F | H | $CH_3$ | H | $CH(CH_3)_2$ | 152–155 |
| F | H | $CH_3$ | H | $C(CH_3)_3$ | 89–91 |
| H | Cl | $CH_3$ | H | $CH_3$ | 105–150 |
| F | H | $CH_3$ | H | $CH_3$ | 129–131 |
| F | H | H | H | $CH_3$ | |
| H | H | $CH_3$ | $CH_3$ | $CH_3$ | |
| F | H | H | H | $CH(CH_3)_2$ | |
| F | H | H | $CH_3$ | $CH(CH_3)_2$ | |
| F | H | $CH_3$ | H | $CH_2CH=CH_2$ | |
| F | H | $CH_3$ | H | $CH_2C\equiv CH$ | |
| F | H | H | H | $CH_2CH=CH_2$ | |
| F | H | H | H | $CH_2C\equiv CH$ | |
| F | H | $CH_3$ | $CH_3$ | $CH_2CH=CH_2$ | |
| F | H | H | $CH_3$ | $CH_2CH=CH_2$ | |
| F | H | $CH_3$ | $CH_3$ | $CH_2C\equiv CH$ | |
| F | H | H | H | $CH_2C\equiv CH$ | |
| F | H | $CH_3$ | H | $CH_2$-furan | |
| F | H | $CH_3$ | $CH_3$ | $CH_2$-furan | |
| F | H | H | H | $CH_2$-furan | |
| F | H | H | $CH_3$ | $CH_2$-furan | |
| F | H | $CH_3$ | H | $CH_2C_6H_5$ | |
| F | H | $CH_3$ | $CH_3$ | $CH_2C_6H_5$ | |
| F | H | H | H | $CH_2C_6H_5$ | |
| F | H | H | $CH_3$ | $CH_2C_6H_5$ | |

EXAMPLE 18

Preparation of 3-[3-(Bromomethyl)-1,2-benzisothiazol-5-yl]-1-methyl-6-(trifluoromethyl)-2,4(1H,3H)-pyrimidinedione and 3-[3-(Dibromomethyl)-1,2-benzisothiazol-5-yl]-1-methyl-6-(trifluoromethyl)-2,4(1H,3H)-pyrimidinedione

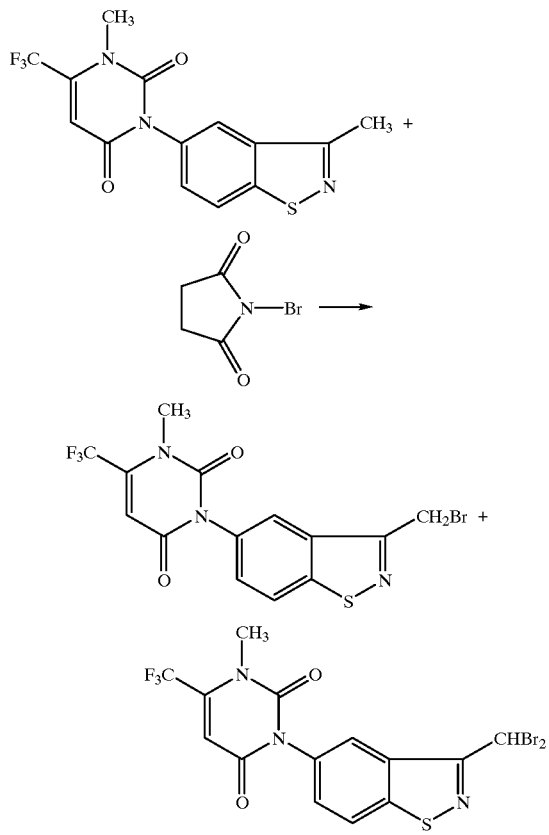

A mixture of 1-methyl-3-(3-methyl-1,2-benzisothiazol-5-yl)-6-(trifluoromethyl)-2,4(1H,3H)-pyrimidinedione (16.6 g, 48.8 mmol), N-bromosuccinimide (34.8 g, 195 mmol) and benzoyl peroxide (0.295 g, 1.22 mmol) in 1,2-dichloroethane is refluxed for one hour, treated with additional benzoyl peroxide (0.30 g), refluxed for 3.5 hours, and cooled to room temperature. Column chromatography of the cooled reaction mixture using silica gel and a methylene chloride/hexanes solution (1:1) gives a mixture of the title products which is dissolved in methylene chloride. The resultant organic solution is washed sequentially with 15% sodium hydrogen sulfite solution and water, dried over anhydrous magnesium sulfate, and concentrated in vacuo to obtain a yellow solid. Column chromatography of the yellow solid using silica gel and a 1% tert-butyl methyl ether in methylene chloride solution gives 3-[3-(bromomethyl)-1,2-benzisothiazol-5-yl]-1-methyl-6-(trifluoromethyl)-2,4(1H,3H)-pyrimidinedione as an off-white solid, mp 203–204° C., and 3-[3-(dibromomethyl)-1,2-benzisothiazol-5-yl]-1-methyl-6-(trifluoromethyl)-2,4(1H,3H)-pyrimidinedione as an off-white solid, mp 107–110° C.

Using essentially the same procedure on 1-methyl-3-(3-methyl-6-fluoro-1,2-benzisothiazol-5-yl)-6-(trifluoromethyl)-2,4(1H,3H)-pyrimidinedione, the following compounds are obtained:

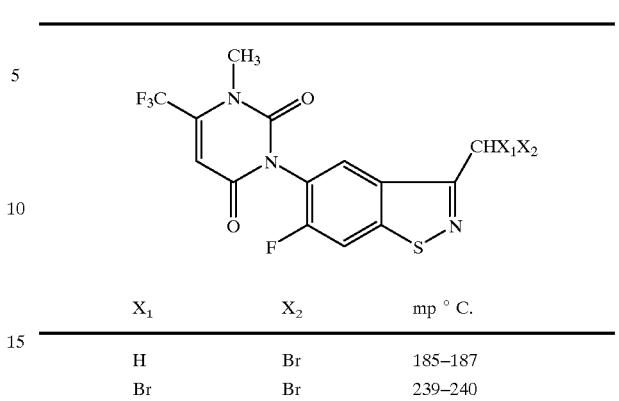

| $X_1$ | $X_2$ | mp ° C. |
|---|---|---|
| H | Br | 185–187 |
| Br | Br | 239–240 |

EXAMPLE 19

Preparation of 3-[3-(Methoxymethyl)-1,2-benzisothiazol-5-yl]-1-methyl-6-(trifluoromethyl)-2,4(1H,3H)-pyrimidinedione

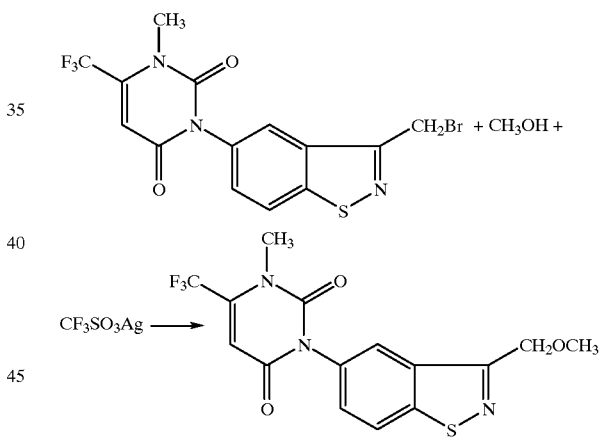

A solution of 3-[3-(bromomethyl)-1,2-benzisothiazol-5-yl]-1-methyl-6-(trifluoromethyl)-2,4(1H,3H)-pyrimidinedione (0.750 g, 1.79 mmol) in 1,2-dichloroethane is diluted with methanol, treated with silver trifluoromethanesulfonate (0.610 g, 2.37 mmol), stirred overnight at room temperature, and filtered through diatomaceous earth. The resultant filtrate is washed with saturated sodium hydrogen carbonate solution, dried over anhydrous magnesium sulfate, and concentrated in vacuo to obtain a solid. Column chromatography of the solid using silica gel, and 2% and 5% diethyl ether in methylene chloride solutions gives the title product as a white solid (0.600 g, mp 161–163° C.) which is identified by $^1$H NMR spectral analysis.

Using essentially the same procedure, the following compounds are obtained:

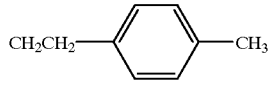

| X | W₄ | mp ° C. |
|---|---|---|
| H | H | |
| R | CH₃ | |
| H | CH(CH₃)₂ | |
| H | CH₂C₆H₅ | |
| H | CH₂CH=CH₂ | |
| H | CH(CH₂Cl)₂ | |
| H | CH₂CF₃ | |
| H | (CH₂)₃CH₃ | |
| H | CH(CH₃)CH=CH₂ | |
| H | CH(CH₃)CF₃ | |
| H | CH₂CH=C(CH₃)₂ | |
| H | CH(CH₃)C(CO₂CH₃)=CH₂ | |
| H | (CH₂)₃CH=CH₂ | |
| H | CH₂CH₂CH=CH₂ | |
| H | C(O)CH₃ | |
| H | CH₂CH₂F | |
| H | C₂H₅ | |
| H | CH₂CH₂Cl | |
| H | CH₂CH₂OCH₂CH₃ | |
| H | CH₂CHF₂ | |
| H | CH₂CH=CHCH₃ | |
| H | CH(CH₂F)₂ | |
| H | CH₂CH₂CH=CHCH₂CH₃ | |
| H | CH₂CH₂CH₂Cl | |
| H | 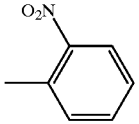 | |
| H | 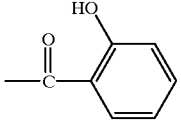 | |
| H | 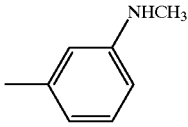 | |
| H | 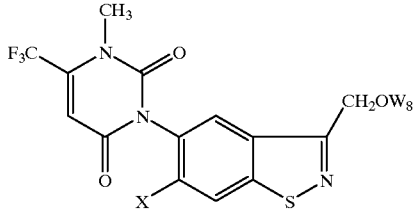 | |

-continued

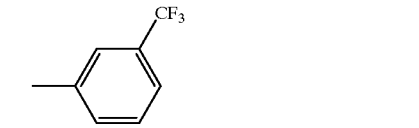

| X | W₄ | mp ° C. |
|---|---|---|
| H | 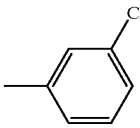 | |
| H | 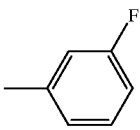 | |
| H | 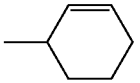 | |
| H | 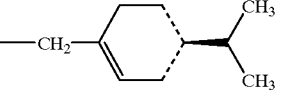 | |
| H | 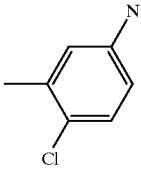 | |
| H | 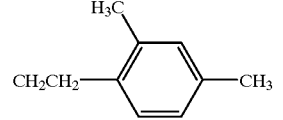 | |
| H | 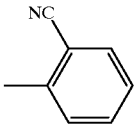 | |
| H | 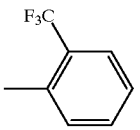 | |
| H | 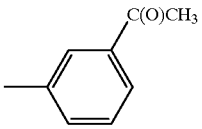 | |

-continued

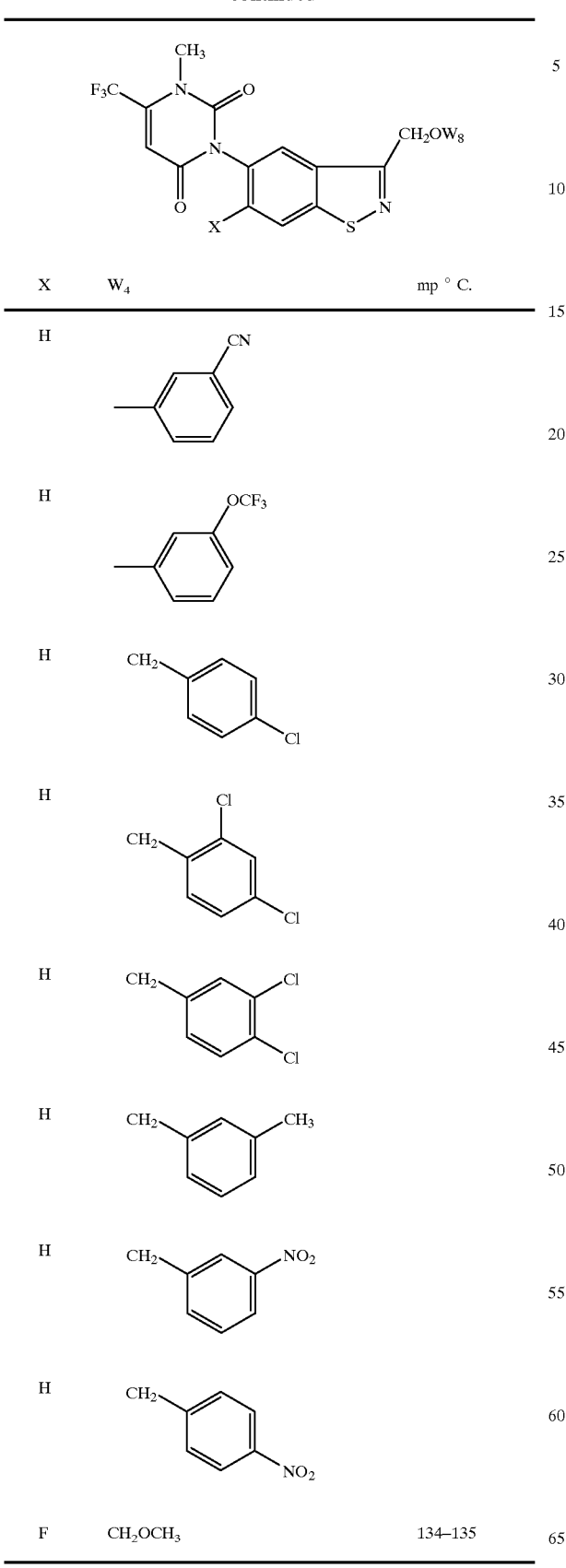

| X | W₄ | mp °C. |
|---|---|---|
| H | 3-cyanophenyl | |
| H | 3-(trifluoromethoxy)phenyl | |
| H | CH₂-(4-chlorophenyl) | |
| H | CH₂-(2,4-dichlorophenyl) | |
| H | CH₂-(3,4-dichlorophenyl) | |
| H | CH₂-(3-methylphenyl) | |
| H | CH₂-(3-nitrophenyl) | |
| H | CH₂-(4-nitrophenyl) | |
| F | CH₂OCH₃ | 134–135 |

EXAMPLE 20

Preparation of Methyl{{{5-[3,6-dihydro-3-methyl-2, 6-dioxo-4-(trifluoromethyl)-1(2H)-pyrimidinyl]-1,2-benzisothiazol-3-yl}methyl}thio}acetate

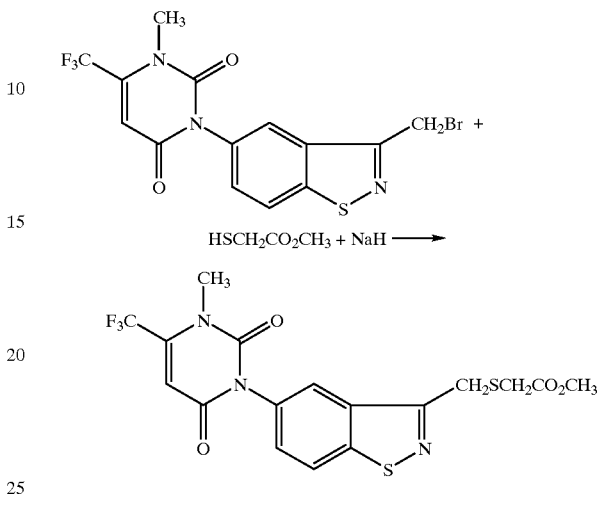

A mixture of hexanes washed sodium hydride (0.0360 g of a 60% dispersion in oil, 0.900 mmol) in tetrahydrofuran is treated with methyl thioglycolate (90.0 mL, 1.00 mmol), stirred until gas evolution stops, treated dropwise with a solution of 3-[3-(bromomethyl)-1,2-benzisothiazol-5-yl]-1-methyl-6-(trifluoromethyl)-2,4(1H,3H)-pyrimidinedione (0.300 g, 0.710 mmol) in tetrahydrofuran, stirred for 10 minutes, and concentrated in vacuo to obtain a residue. The residue is diluted with methylene chloride and water. The organic phase is separated, dried over anhydrous magnesium sulfate, and concentrated in vacuo to obtain an oil. Column chromatography of the oil using silica gel and a 5% diethyl ether in methylene chloride solution gives the title product as a clear oil which is identified by $^1$H NMR spectral analysis.

Using essentially the same procedure, the following compounds are obtained:

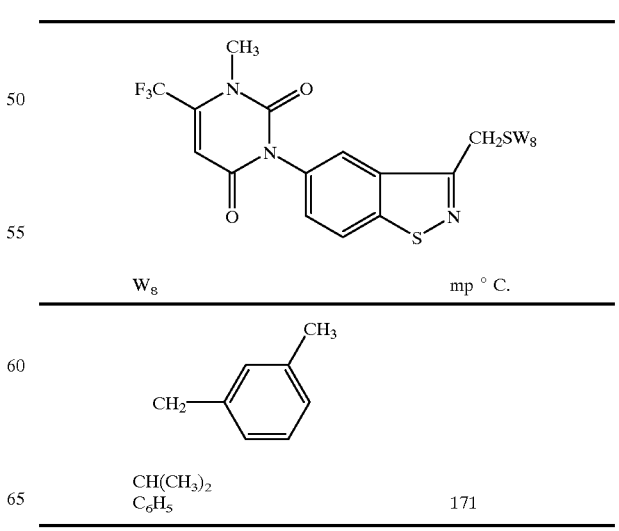

| W₈ | mp °C. |
|---|---|
| CH₂-(3-methylphenyl) | |
| CH(CH₃)₂ C₆H₅ | 171 |

EXAMPLE 21

Preparation of 1-Methyl-3-{3-[(methylthio)methyl]-1,2-benzisothiazol-5-yl}-6-(trifluoromethyl)-2,4(1H,3H)-pyrimidinedione

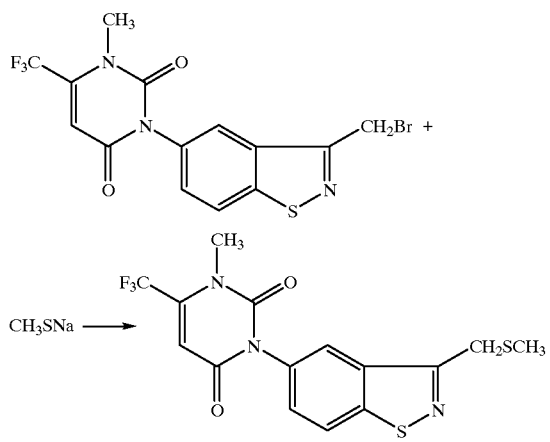

A solution of 3-[3-(bromomethyl)-1,2-benzisothiazol-5-yl]-1-methyl-6-(trifluoromethyl)-2,4(1H,3H)-pyrimidinedione (1.66 g, 3.95 mmol) in acetonitrile is treated with sodium thiomethoxide (0.332 g, 4.74 mmol), stirred overnight at room temperature, treated with additional sodium thiomethoxide (about 15 mg), stirred for one hour, and concentrated in vacuo to obtain a residue. The residue is diluted with methylene chloride and water. The organic phase is separated, washed with brine, dried over anhydrous magnesium sulfate, and concentrated in vacuo to obtain a solid. Column chromatography of the solid using silica gel and a 2% diethyl ether in methylene chloride solution gives the title product as a white solid which is identified by $^1$H NMR spectral analysis.

EXAMPLE 22

Preparation of m-Fluorophenyl acetate

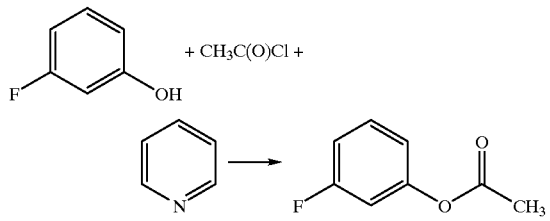

A solution of 3-fluorophenol (100 g, 0.890 mol) in methylene chloride is cooled to 0° C. to 5° C., treated with pyridine (75.0 mL, 0.930 mol), stirred for several minutes, treated dropwise with acetyl chloride (66.0 mL, 0.930 mol) while maintaining the reaction mixture temperature below 17° C., stirred at ice-bath temperature for two hours, warmed to room temperature, and poured into an ice-water mixture. The organic phase is separated, washed with brine, dried over anhydrous magnesium sulfate, and concentrated in vacuo to obtain the title product as a yellow oil which is identified by $^1$H NMR spectral analysis.

EXAMPLE 23

Preparation of 4'-Fluoro-2'-hydroxyacetophenone

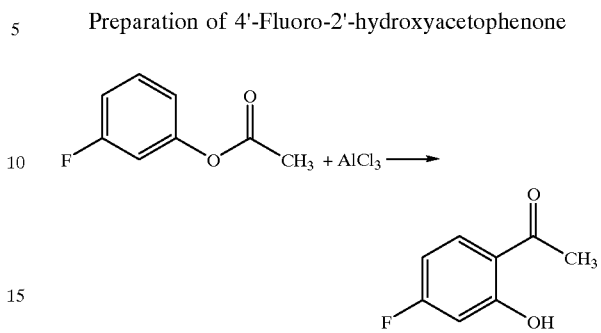

m-Fluorophenyl acetate (123 g, 0.798 mol) is cooled with an ice-bath, treated portionwise with aluminum chloride (150 g, 1.12 mol), stirred at 190° C. for one hour, and cooled to obtain a solid. A mixture of ice, water and hydrochloric acid, and methylene chloride are added to the solid. The resultant mixture is stirred for several minutes, and the phases are separated. The organic phase is washed sequentially with water, saturated sodium hydrogen carbonate solution and brine, dried over anhydrous magnesium sulfate, and concentrated in vacuo to obtain the title product (99.0 g) which is identified by $^1$H NMR spectral analysis.

EXAMPLE 24

Preparation of 4'-Fluoro-2'-hydroxyacetophenone, oxime

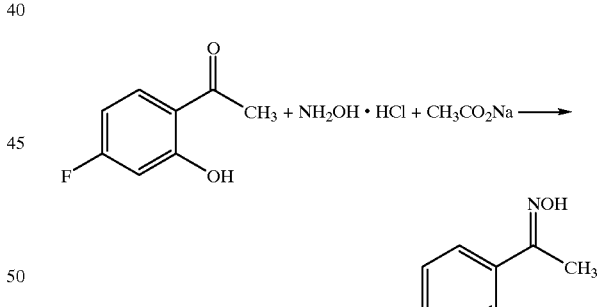

A mixture of 4'-fluoro-2'-hydroxyacetophenone (99.0 g, 0.640 mol), hydroxylamine hydrochloride (89.0 g, 1.28 mol), and sodium acetate (79.0 g, 0.960 mol) in methanol is refluxed for one hour and poured into an ice-water mixture. The resultant aqueous mixture is filtered to obtain a solid. The solid is dissolved in methylene chloride, and the resultant organic solution is dried over anhydrous magnesium sulfate, concentrated in vacuo, diluted with hexanes, and filtered to give the title product as a solid (55.0 g, mp 112–114° C.) which is identified by $^1$H NMR spectral analysis.

EXAMPLE 25

Preparation of 6-Fluoro-3-methyl-1,2-benzisoxazole

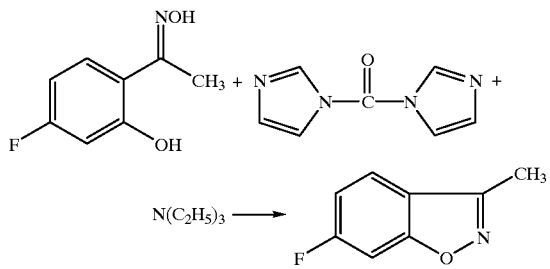

A mixture of 4'-fluoro-2'-hydroxyacetophenone, oxime (47.0 g, 0.278 mol) in tetrahydrofuran is heated to just under reflux, treated with a solution of 1,1'-carbonyldiimidazole (55.0 g, 0.340 mol) and triethylamine (39.0 g, 0.390 mol) in tetrahydrofuran, refluxed for one hour, cooled, concentrated in vacuo, and poured into an ice-water mixture. The resultant aqueous mixture is extracted with ether. The organic extracts are combined, washed sequentially with saturated ammonium chloride solution and brine, dried over anhydrous magnesium sulfate, and concentrated in vacuo to obtain an oil. Column chromatography of the oil using silica gel and a methylene chloride/hexanes solution (1:1) gives the title product as a yellow oil which is identified by $^1$H NMR spectral analysis.

EXAMPLE 26

Preparation of 6-Fluoro-3-methyl-5-nitro-1,2-benzisoxazole

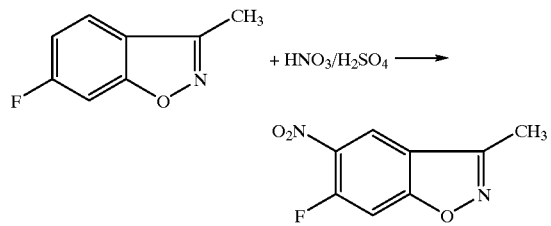

A mixture of 6-fluoro-3-methyl-1,2-benzisoxazole (23.5 g, 0.156 mol) in concentrated sulfuric acid is cooled with an ice-bath, treated dropwise with 90% nitric acid (8.50 mL) while maintaining the reaction mixture temperature below 15° C., stirred for one hour at ice-bath temperature, treated with additional 90% nitric acid (5.80 mL), warmed to and stirred at room temperature overnight, and poured onto ice. The resultant aqueous mixture is filtered to obtain a solid. The solid is air-dried and dissolved in methylene chloride. The resultant organic solution is dried over anhydrous magnesium sulfate, diluted with hexanes, and filtered to give the title product as a purple solid which is identified by $^2$H NMR spectral analysis.

EXAMPLE 27

Preparation of 5-Amino-6-fluoro-3-methyl-1,2-benzisoxazole and 5-Amino-4-chloro-6-fluoro-3-methyl-1,2-benzisoxazole

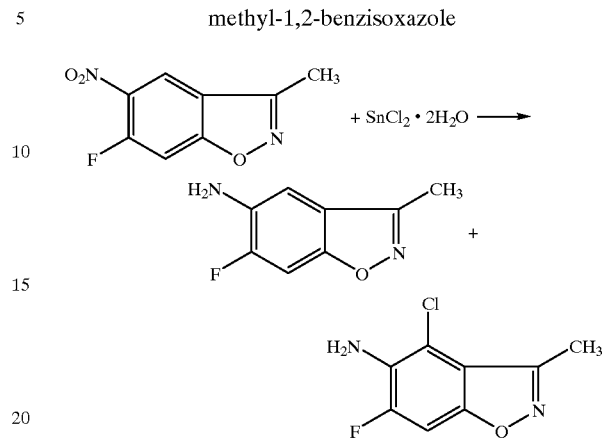

A mixture of 6-fluoro-3-methyl-5-nitro-1,2-benzisoxazole (3.00 g, 0.0153 mol) and acetic acid (85.0 mL) is heated to 40° C., treated with a solution of tin(II) chloride dihydrate (9.70 g, 0.0430 mol) and concentrated hydrochloric acid (45.0 mL), refluxed for 90 minutes, concentrated in vacuo, neutralized with 2N sodium hydroxide solution and filtered to obtain a solid. Column chromatography of the solid using silica gel and methylene chloride gives the title products as solids which are identified by NMR spectral analyses.

Using essentially the same procedure, but using an ethyl acetate/ethanol mixture instead of acetic acid, the following compounds are obtained:

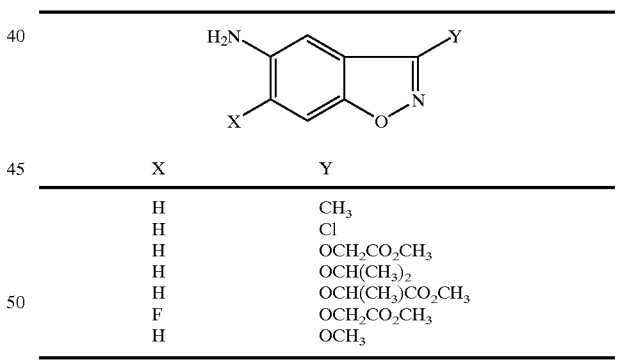

| X | Y |
|---|---|
| H | CH$_3$ |
| H | Cl |
| H | OCH$_2$CO$_2$CH$_3$ |
| H | OCH(CH$_3$)$_2$ |
| H | OCH(CH$_3$)CO$_2$CH$_3$ |
| F | OCH$_2$CO$_2$CH$_3$ |
| H | OCH$_3$ |

EXAMPLE 28

Preparation of 3-(6-Fluoro-3-methyl-1,2-benzisoxazol-5-yl)-6-(trifluoromethyl)-2,4(1H,3H)-pyrimidinedione

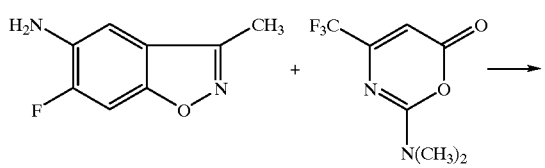

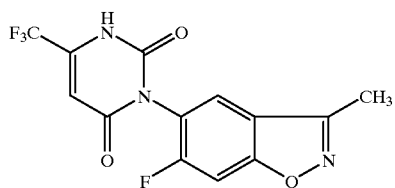

A mixture of 5-amino-6-fluoro-3-methyl-1,2-benzisoxazole (4.85 g, 0.029 mol) and 2-dimethylamino-4-(trifluoromethyl)-6H-1,3-oxazin-6-one (6.70 g, 0.0320 mol) in acetic acid is refluxed for 90 minutes, cooled to room temperature, and poured into an ice-water mixture. The resultant aqueous mixture is filtered to obtain a solid. The solid is air-dried and dissolved in ethyl acetate. The resultant organic solution is washed with brine, dried over anhydrous magnesium sulfate, and concentrated in vacuo to give the title product as a yellow solid (7.00 g, mp 235–237° C.) which is identified by NMR spectral analyses.

Using essentially the same procedure, the following compounds are obtained:

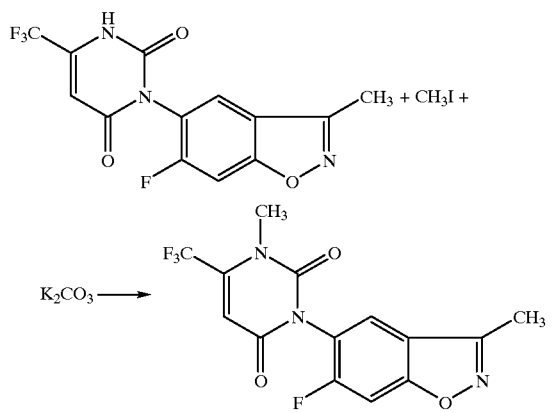

| X | $X_1$ | Y | mp ° C. |
|---|---|---|---|
| H | H | $CH_3$ | 283–285 |
| H | H | Cl | |
| H | H | $OCH_2CO_2CH_3$ | 180–182 |
| H | H | $OCH(CH_3)_2$ | 213–215 |
| H | H | $OCH_3$ | 230–235 |
| F | Cl | $CH_3$ | 125–130 |

EXAMPLE 29

Preparation of 3-(6-Fluoro-3-methyl-1,2-benzisoxazol-5-yl)-1-methyl-6-(trifluoromethyl)-2,4(1H,3H)-pyrimidinedione A mixture of 3-(6-fluoro-3-methyl-1,2-benzisoxazol-5-yl)-6-(trifluoromethyl)-2,4(1H,3H)-pyrimidinedione (3.00 g, 9.12 mmol) and potassium carbonate (2.52 g, 18.2 mmol) in N,N-dimethylformamide is stirred for 15 minutes, treated with methyl iodide (2.58 g, 18.2 mmol), stirred at room temperature overnight, and poured into an ice-water mixture. The resultant aqueous mixture is filtered to obtain a solid which is recrystallized from a methylene chloride/hexanes solution to give the title product as a white solid (mp 158–159° C.) which is identified by NMR spectral analyses.

Using essentially the same procedure, the following compounds are obtained:

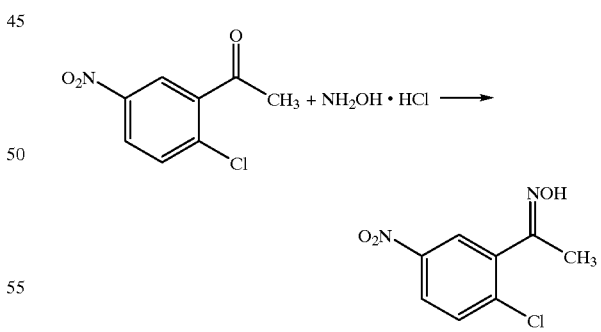

| X | $X_1$ | Y | mp ° C. |
|---|---|---|---|
| H | H | $CH_3$ | 196–198 |
| H | H | Cl | 168.5–170 |
| H | H | $OCH_2CO_2CH_3$ | 156–157 |
| H | H | $OCH(CH_3)_2$ | |
| H | H | $OCH_3$ | 160–161 |
| F | Cl | $CH_3$ | 154–155 |

EXAMPLE 30

Preparation of 2'-Chloro-5'-nitroacetophenone, oxime

A mixture of 2'-chloro-5'-nitroacetophenone (50.0 g, 0.250 mol) in ethanol is treated with a solution of hydroxylamine hydrochloride (83.0 g, 1.19 mol) in water, refluxed overnight, cooled to room temperature, and filtered to give the title product as a solid (mp 165–167° C.) which is identified by NMR spectral analyses.

EXAMPLE 31

Preparation of 3-Methyl-5-nitro-1,2-benzisoxazole

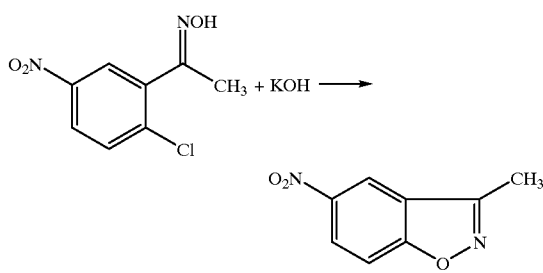

A mixture of 2'-chloro-5'-nitroacetophenone, oxime (30.0 g, 0.140 mol) in ethanol is treated dropwise with 10% potassium hydroxide solution (7.86 g KOH), stirred at room temperature for one hour, refluxed overnight, cooled, and poured into water. The resultant aqueous mixture is filtered to obtain a solid. Column chromatography of the solid using silica gel and methylene chloride gives the title product as a yellow solid (mp 84.5–86.5° C.) which is identified by NMR spectral analyses.

EXAMPLE 32

Preparation of 5-Nitro-1,2-benzisoxazol-3-ol

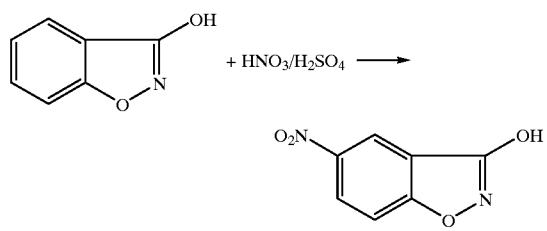

1,2-Benzisoxazol-3-ol (19.7 g, 0.146 mol) is added portionwise to concentrated sulfuric acid. The resultant reaction mixture is treated dropwise with 70% nitric acid (11.3 mL), stirred for 90 minutes, and poured onto ice. The resultant aqueous mixture is filtered to obtain a waxy paste. The paste is recrystallized from a methanol/water mixture to give the title product as a solid which is identified by $^1$H NMR spectral analysis.

Using essentially the same procedure, the following compounds are obtained:

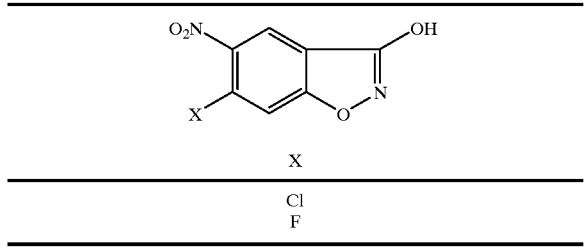

| X |
|---|
| Cl |
| F |

EXAMPLE 33

Preparation of Methyl[(5-nitro-1,2-benzisoxazol-3-yl)oxy]acetate

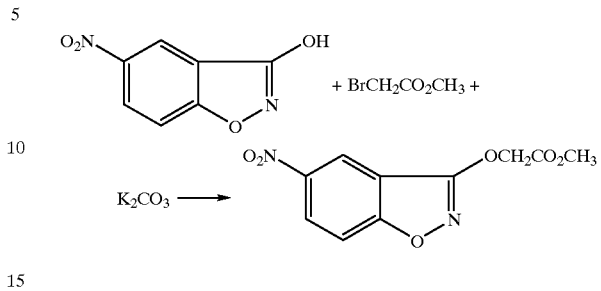

A mixture of 5-nitro-1,2-benzisoxazol-3-ol (3.90 g, 0.0220 mol) and potassium carbonate (4.17 g, 0.0300 mol) in N,N-dimethylformamide is stirred for 30 minutes, treated with methyl bromoacetate (3.96 g, 0.0260 mol), stirred overnight at room temperature, and poured into an acidic ice-water mixture. The resultant aqueous mixture is extracted with ethyl acetate. The organic extracts are combined, washed sequentially with water and brine, dried over anhydrous magnesium sulfate, and concentrated in vacuo to obtain a yellow oil. Column chromatography of the oil using silica gel and a (1:1) to (4:1) methylene chloride/hexanes gradient gives the title product as a white solid (2.80 g, mp 72–73.5° C.) which is identified by NMR spectral analyses.

Using essentially the same procedure, the following compounds are obtained:

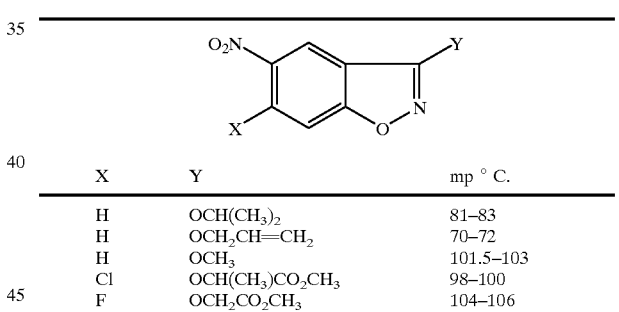

| X | Y | mp ° C. |
|---|---|---------|
| H | OCH(CH$_3$)$_2$ | 81–83 |
| H | OCH$_2$CH=CH$_2$ | 70–72 |
| H | OCH$_3$ | 101.5–103 |
| Cl | OCH(CH$_3$)CO$_2$CH$_3$ | 98–100 |
| F | OCH$_2$CO$_2$CH$_3$ | 104–106 |

EXAMPLE 34

Preparation of 3-Chloro-5-nitro-1,2-benzisoxazole

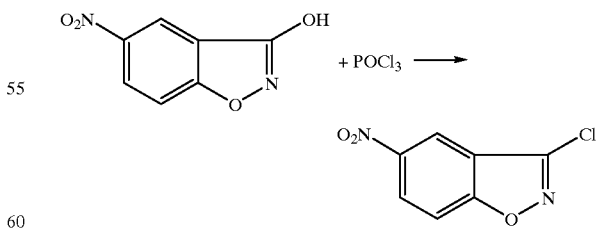

A mixture of 5-nitro-1,2-benzisoxazol-3-ol (4.00 g, 0.0220 mol) and phosphorus oxychloride (40.0 mL, 65.8 g, 0.429 mol) is placed in a glass bomb, heated at 150–155° C. for two hours, cooled overnight, concentrated in vacuo, diluted with methylene chloride, and brought to about pH 8 with sodium hydrogen carbonate solution. The phases are separated. The organic phase is washed sequentially with water and brine, dried over anhydrous magnesium sulfate, and concentrated in vacuo to obtain a residue. Column chromatography of the residue using silica gel and a methylene chloride/hexanes solution (1:1) gives the title product as an amber oil which is identified by NMR spectral analysis.

EXAMPLE 35

Preparation of Methyl 2-{{2-{5-[3,6-dihydro-3-methyl-2-oxo-6-thioxo-4-(trifluoromethyl)-1(2H)-pyrimidinyl]-1,2-benzisothiazol-3-yl}-p-tolyl}oxy}-propionate

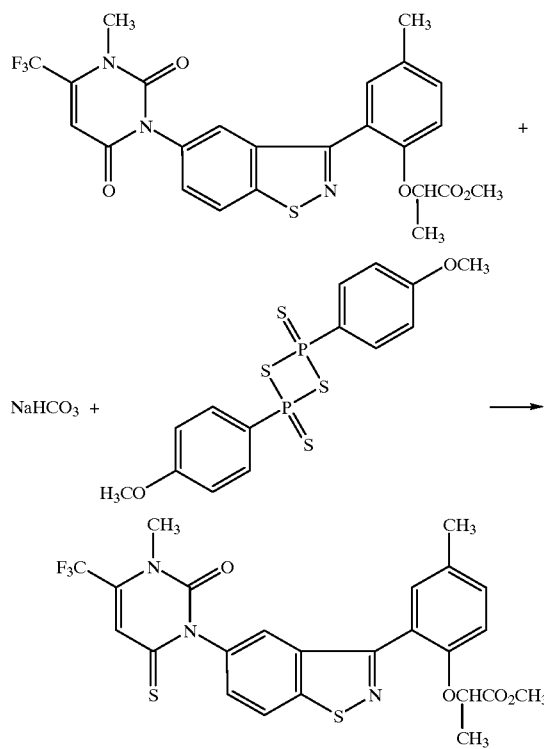

A mixture of methyl 2-{{2-{5-[3,6-dihydro-3-methyl-4-(trifluoromethyl)-2,6-dioxo-1(2H)-pyrimidinyl]-1,2-benzisothiazol-3-yl}-p-tolyl}oxy}propionate (2.00 g, 3.80 mmol), sodium hydrogen carbonate (1.24 g, 14.8 mmol) and Lawesson's Reagent (2,4-bis(4-methoxyphenyl)-1,3-dithia-2,4-diphosphetane-2,4-disulfide, 1.70 g, 4.20 mmol) in toluene is refluxed for two hours, filtered to remove solids, and concentrated in vacuo to obtain an orange foam. Column chromatography of the foam using silica gel, and 0% and 1% diethyl ether in methylene chloride solutions gives the title product as an orange foam (1.45 g, mp 110–112° C.) which is identified by NMR spectral analyses.

EXAMPLE 36

Preparation of 2-Chloro-2'-methoxy-5-nitrobenzophenone

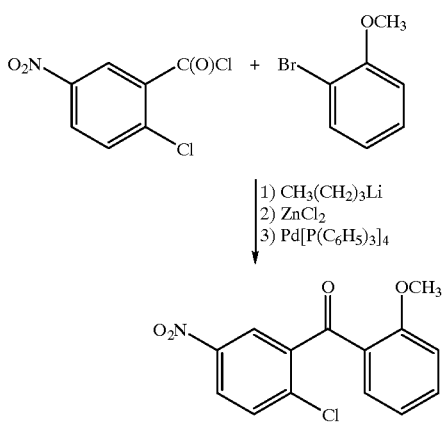

A solution of 2-bromoanisole (27.9 g, 145 mmol) in diethyl ether is cooled to −70° C., treated with butyllithium (64.0 mL, 160 mmol), stirred at −70° C. for one hour, treated with 0.5 M zinc chloride in tetrahydrofuran solution (320 mL, 160 mmol), stirred for one hour at −70° C., warmed to about 0° C., and concentrated in vacuo to obtain a yellow-green oil. A solution of the oil in tetrahydrofuran is treated sequentially with tetrakis(triphenylphosphine)palladium(0) (5.00 g, 4.35 mmol) and a solution of 2-chloro-5-nitrobenzoyl chloride (35.0 g, 159 mmol) in tetrahydrofuran, stirred for three days, and poured into 10% hydrochloric acid. The resultant aqueous mixture is extracted with methylene chloride. The organic extracts are combined, washed sequentially with water and brine, dried over anhydrous magnesium sulfate, and concentrated in vacuo to obtain a semi-solid. The solid is triturated with diethyl ether to give the title product as a yellow solid which is identified by NMR spectral analyses.

Using essentially the same procedure, the following compounds are obtained:

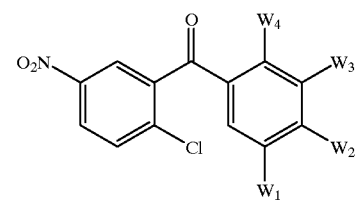

| $W_1$ | $W_2$ | $W_3$ | $W_4$ | mp ° C. |
|---|---|---|---|---|
| H | Cl | H | $OCH_3$ | 96–99 |
| H | H | $CH_3$ | $OCH_3$ | 71–74 |
| F | H | H | $OCH_3$ | |
| Cl | H | H | $OCH_3$ | 124–126 |
| $OCH_3$ | H | H | $OCH_3$ | 71–73 |
| H | $OCH_3$ | H | $OCH_3$ | 98–100 |
| H | F | H | $OCH_3$ | |
| H | H | $CH_3$ | H | 65–66.5 |
| H | H | $SCH_3$ | H | 87–88 |
| H | H | H | F | 118–120 |
| H | H | H | $CH_3$ | 78–79.5 |
| H | H | H | $SCH_3$ | 123–124.5 |

-continued

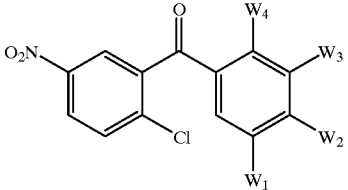

| $W_1$ | $W_2$ | $W_3$ | $W_4$ | mp °C. |
|---|---|---|---|---|
| H | F | H | H | |
| H | H | $OCH_3$ | H | |
| H | H | H | $OCH_3$ | |
| H | $CH_3$ | $CH_3$ | $OCH_3$ | |

EXAMPLE 37

Preparation of 2-Chloro-2'-methoxy-5-nitrobenzhydrol

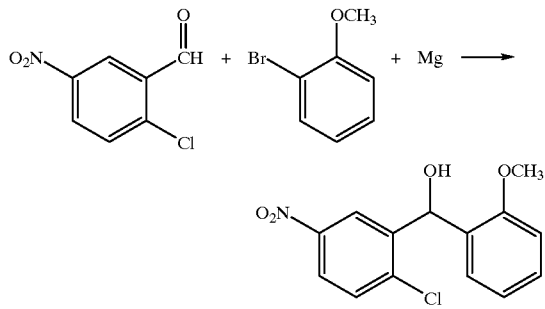

A solution of 2-bromoanisole (50.0 g, 0.267 mol) in ether is added portionwise to a mixture of magnesium (7.10 g, 0.293 mol) in ether. After the addition is complete, the reaction mixture is heated at reflux for one hour, diluted with ether, cooled to 0° C., treated with a solution of 2-chloro-5-nitrobenzaldehyde (39.0 g, 0.210 mol) in tetrahydrofuran, warmed to room temperature, and diluted with an ice-water mixture. After acidifying the aqueous mixture with hydrochloric acid (pH 2–pH 3), the organic phase is separated and the aqueous phase is extracted with ether. The organic extracts are combined, washed sequentially with 10% sodium hydrogen carbonate solution and brine, dried over anhydrous sodium sulfate, and concentrated in vacuo to give the title product as a brown gum.

Using essentially the same procedure, the following compounds are obtained:

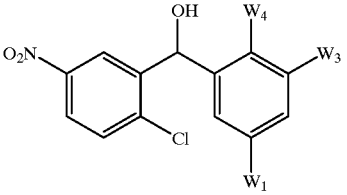

| W | $W_3$ | $W_4$ |
|---|---|---|
| $OCH_3$ | H | $OCH_3$ |
| $CH_3$ | H | $OCH_3$ |
| F | H | $OCH_3$ |
| H | $OCH_3$ | H |

EXAMPLE 38

Preparation of 2-Chloro-2'-methoxy-5-nitrobenzophenone

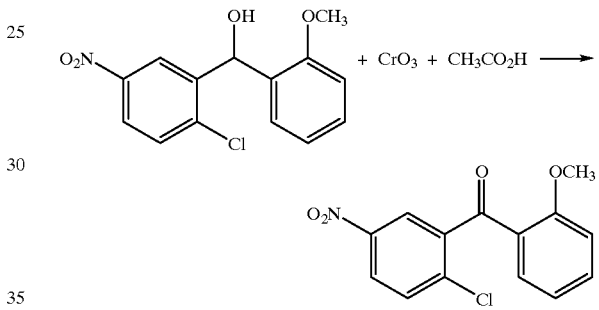

A solution of chromium(VI) oxide (91.0 g, 0.919 mol) in a water/acetic acid solution (1:4) is added portionwise to 2-chloro-2'-methoxy-5-nitrobenzhydrol (64.2 g, 0.219 mol) while maintaining the reaction mixture temperature at 25° C. to 35° C. The reaction mixture is then stirred at 25° C. to 35° C. for one hour, cooled, diluted with water, and concentrated in vacuo to obtain a residue. The residue is diluted with water, and extracted with methylene chloride. The organic extracts are combined, dried over anhydrous sodium sulfate, mixed with silica gel (10 g), and filtered. The filtrate is concentrated in vacuo to obtain an oil. A solution of the oil in a methanol/water solution is decolorized with charcoal and concentrated in vacuo to yield a residue. Column chromatography of the residue using silica gel and methylene chloride/hexanes solutions gives the title product as a white solid.

Using essentially the same procedure, the following compounds are obtained:

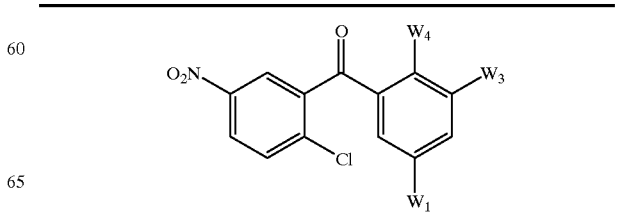

| $W_1$ | $W_3$ | $W_4$ | mp ° C. |
|---|---|---|---|
| OCH$_3$ | H | OCH$_3$ | |
| CH$_3$ | H | OCH$_3$ | 109–111 |
| F | H | OCH$_3$ | 94–95 |
| H | OCH$_3$ | H | 79–81 |

EXAMPLE 39

Preparation of 2-{{2-{5-[3,6-dihydro-3-methyl-2,6-dioxo-4-(trifluoromethyl)-1(2H)-pyrimidinyl]-1,2-benzisothiazol-3-yl}-p-tolyl}oxy}propionic acid

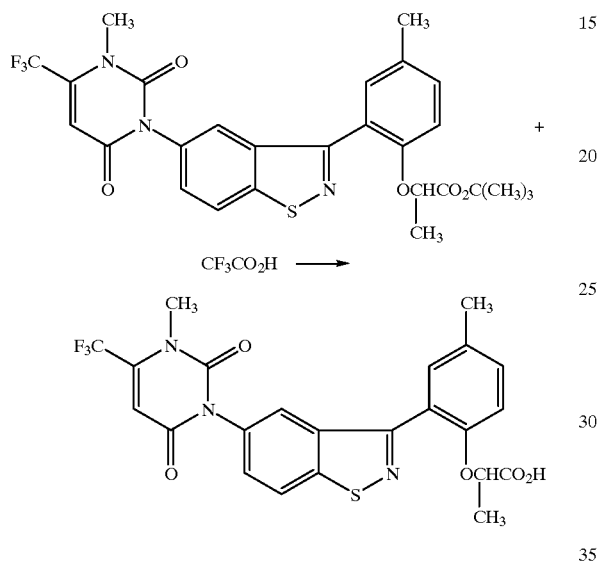

Trifluoroacetic acid (75 mL) is added to a solution of tert-butyl 2-{{2-{5-[3,6-dihydro-3-methyl-2,6-dioxo-4-(trifluoromethyl)-1(2H)-pyrimidinyl]-1,2-benzisothiazol-3-yl}-p-tolyl}oxy}propionate (12.0 g, 21.4 mmol) in methylene chloride. The reaction mixture is stirred at room temperature for 24 hours and concentrated in vacuo to give the title product as a yellow foam which is identified by NMR spectral analyses.

Using essentially the same procedure, the following compounds are obtained:

| $W_3$ | $W_5$ | $W_6$ | mp ° C. |
|---|---|---|---|
| CH$_3$ | CH$_3$ | CH$_3$ | |
| H | H | H | 152–158 |
| H | CH$_3$ | H | 215–216 |
| CH$_3$ | H | H | |

Using essentially the same procedure, the following compound is also obtained:

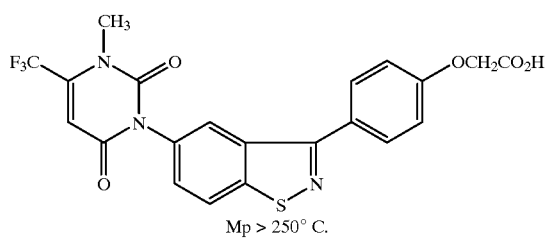

Mp > 250° C.

EXAMPLE 40

Preparation of 2-Propynyl 2-{{2-{5-[3.6-dihydro-3-methyl-2,6-dioxo-4-(trifluoromethyl)-1(2H)-pyrimidinyl]-1,2-benzisothiazol-3-yl}-p-tolyl}oxy}propionate

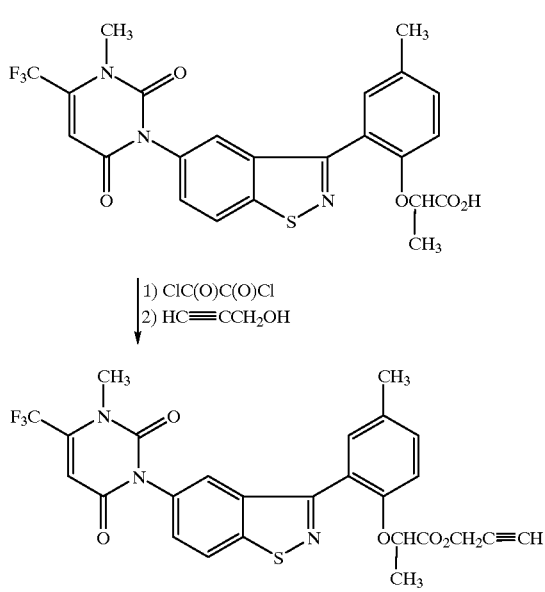

A mixture of 2-{{2-{5-[3,6-dihydro-3-methyl-2,6-dioxo-4-(trifluoromethyl)-1(2H)-pyrimidinyl]-1,2-benzisothiazol-3-yl}-p-tolyl}oxy}propionic acid (0.510 g, 1.00 mmol) and oxalyl chloride (0.380 g, 3.00 mmol) in methylene chloride is stirred at room temperature for 30 minutes and concentrated in vacuo to obtain a yellow foam. The foam is diluted with methylene chloride and the resultant solution is treated with a solution of propargyl alcohol (0.110 g, 2.00 mmol) in methylene chloride, stirred at room temperature for 24 hours, and concentrated in vacuo to obtain an oil. Flash column chromatography of the oil using silica gel, a hexanes/methylene chloride solution (1:1) and a 5% diethyl ether in methylene chloride solution gives the title product (0.400 g) which is identified by NMR spectral analyses.

Using essentially the same procedure, the following compounds are obtained:

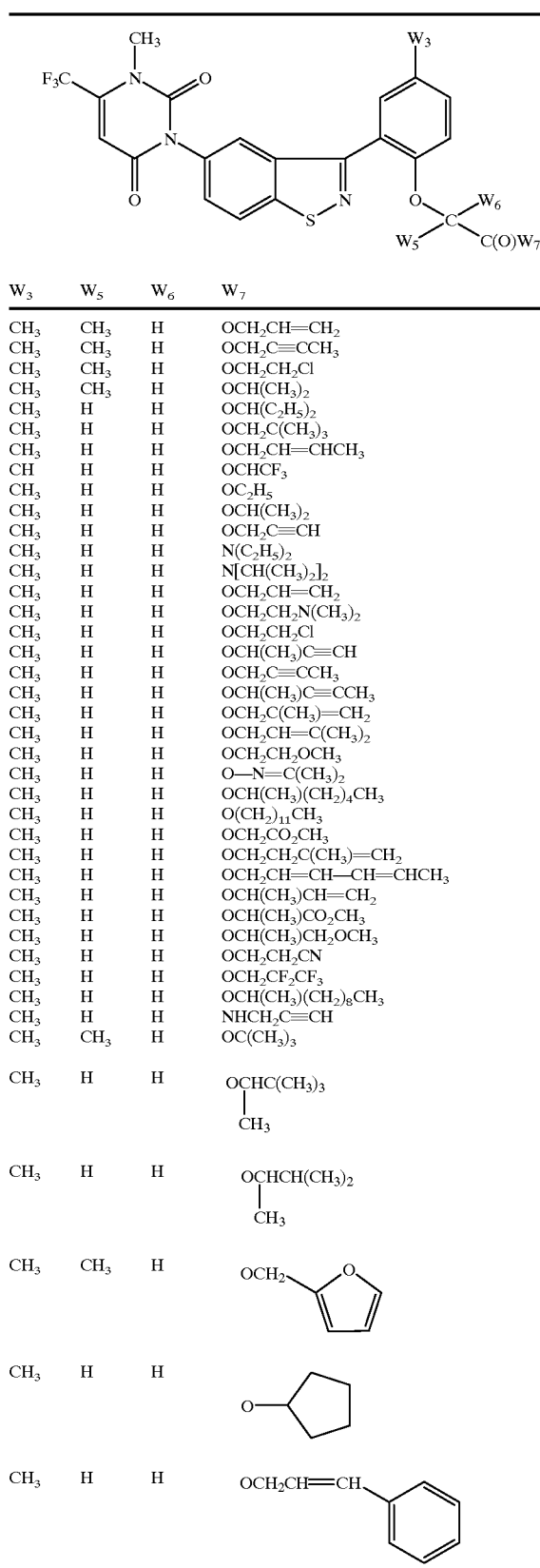

| $W_3$ | $W_5$ | $W_6$ | $W_7$ |
|---|---|---|---|
| $CH_3$ | $CH_3$ | H | $OCH_2CH=CH_2$ |
| $CH_3$ | $CH_3$ | H | $OCH_2C\equiv CCH_3$ |
| $CH_3$ | $CH_3$ | H | $OCH_2CH_2Cl$ |
| $CH_3$ | $CH_3$ | H | $OCH(CH_3)_2$ |
| $CH_3$ | H | H | $OCH(C_2H_5)_2$ |
| $CH_3$ | H | H | $OCH_2C(CH_3)_3$ |
| $CH_3$ | H | H | $OCH_2CH=CHCH_3$ |
| CH | H | H | $OCHCF_3$ |
| $CH_3$ | H | H | $OC_2H_5$ |
| $CH_3$ | H | H | $OCH(CH_3)_2$ |
| $CH_3$ | H | H | $OCH_2C\equiv CH$ |
| $CH_3$ | H | H | $N(C_2H_5)_2$ |
| $CH_3$ | H | H | $N[CH(CH_3)_2]_2$ |
| $CH_3$ | H | H | $OCH_2CH=CH_2$ |
| $CH_3$ | H | H | $OCH_2CH_2N(CH_3)_2$ |
| $CH_3$ | H | H | $OCH_2CH_2Cl$ |
| $CH_3$ | H | H | $OCH(CH_3)C\equiv CH$ |
| $CH_3$ | H | H | $OCH_2C\equiv CCH_3$ |
| $CH_3$ | H | H | $OCH(CH_3)C\equiv CCH_3$ |
| $CH_3$ | H | H | $OCH_2C(CH_3)=CH_2$ |
| $CH_3$ | H | H | $OCH_2CH=C(CH_3)_2$ |
| $CH_3$ | H | H | $OCH_2CH_2OCH_3$ |
| $CH_3$ | H | H | $O-N=C(CH_3)_2$ |
| $CH_3$ | H | H | $OCH(CH_3)(CH_2)_4CH_3$ |
| $CH_3$ | H | H | $O(CH_2)_{11}CH_3$ |
| $CH_3$ | H | H | $OCH_2CO_2CH_3$ |
| $CH_3$ | H | H | $OCH_2CH_2C(CH_3)=CH_2$ |
| $CH_3$ | H | H | $OCH_2CH=CH-CH=CHCH_3$ |
| $CH_3$ | H | H | $OCH(CH_3)CH=CH_2$ |
| $CH_3$ | H | H | $OCH(CH_3)CO_2CH_3$ |
| $CH_3$ | H | H | $OCH(CH_3)CH_2OCH_3$ |
| $CH_3$ | H | H | $OCH_2CH_2CN$ |
| $CH_3$ | H | H | $OCH_2CF_2CF_3$ |
| $CH_3$ | H | H | $OCH(CH_3)(CH_2)_8CH_3$ |
| $CH_3$ | H | H | $NHCH_2C\equiv CH$ |
| $CH_3$ | $CH_3$ | H | $OC(CH_3)_3$ |
| $CH_3$ | H | H | $OCHC(CH_3)_3$ <br> $\quad\quad\quad CH_3$ |
| $CH_3$ | H | H | $OCHCH(CH_3)_2$ <br> $\quad\quad\quad CH_3$ |
| $CH_3$ | $CH_3$ | H | $OCH_2$-（2-furyl） |
| $CH_3$ | H | H | $O$-cyclopentyl |
| $CH_3$ | H | H | $OCH_2CH=CH$-Ph |

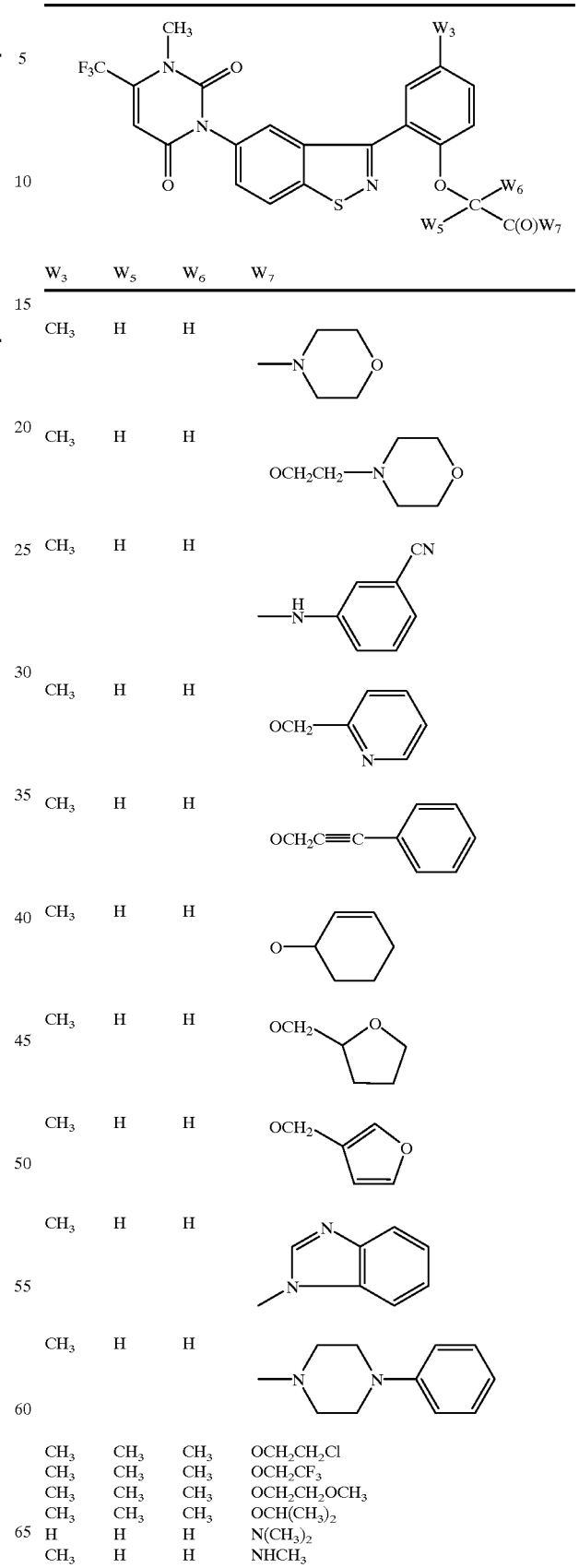

| $W_3$ | $W_5$ | $W_6$ | $W_7$ |
|---|---|---|---|
| $CH_3$ | H | H | N-methylmorpholine |
| $CH_3$ | H | H | $OCH_2CH_2$-morpholine |
| $CH_3$ | H | H | NH-（3-cyanophenyl） |
| $CH_3$ | H | H | $OCH_2$-（2-pyridyl） |
| $CH_3$ | H | H | $OCH_2C\equiv C$-Ph |
| $CH_3$ | H | H | O-cyclohexenyl |
| $CH_3$ | H | H | $OCH_2$-（tetrahydrofuryl） |
| $CH_3$ | H | H | $OCH_2$-（3-furyl） |
| $CH_3$ | H | H | N-methylbenzimidazole |
| $CH_3$ | H | H | N-methyl-N'-phenylpiperazine |
| $CH_3$ | $CH_3$ | $CH_3$ | $OCH_2CH_2Cl$ |
| $CH_3$ | $CH_3$ | $CH_3$ | $OCH_2CF_3$ |
| $CH_3$ | $CH_3$ | $CH_3$ | $OCH_2CH_2OCH_3$ |
| $CH_3$ | $CH_3$ | $CH_3$ | $OCH(CH_3)_2$ |
| H | H | H | $N(CH_3)_2$ |
| $CH_3$ | H | H | $NHCH_3$ |

-continued

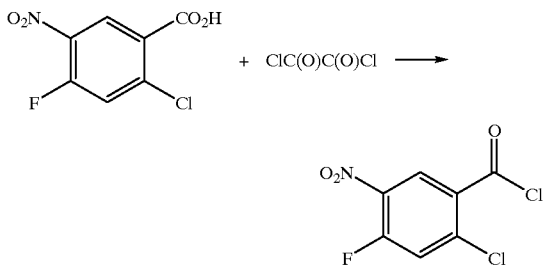

| $W_3$ | $W_5$ | $W_6$ | $W_7$ |
|---|---|---|---|
| H | H | H | $NHCH_3$ |
| H | H | H | $NH_2$ |
| H | H | H | $N(CH_3)OH$ |
| $CH_3$ | H | H | $N(CH_3)OH$ |
| H | H | H | $N(CH_3)OCH_3$ |
| $CH_3$ | H | H | $NH_2$ |
| $CH_3$ | H | H | $NHOH$ |
| $CH_3$ | H | H | $NHOCH_3$ |
| $CH_3$ | H | H | ![OCH2 C6H5 cyclopropyl] |
| $CH_3$ | H | H | $O(CH_2)_4SCH_3$ |
| $CH_3$ | H | H | $O(CH_2)_8CH_3$ |
| $CH_3$ | H | H | $OCH(CH=CH_2)(CH_2)_3CH_3$ |
| $CH_3$ | H | H | $OCH_2C(C_2H_5)(CH_2OCH_2CH=CH_2)_2$ |
| $CH_3$ | H | H | $OCH_2CH_2C\equiv C(CH_2)_5CH_3$ |
| $CH_3$ | H | H | (cyclohexyl)-$CO_2CH_2CH_3$ single diastereomer |
| $CH_3$ | H | H | (cyclohexyl)-$CO_2CH_2CH_3$ single diastereomer |
| $CH_3$ | H | H | $O(CH_2)_{10}CH=CHCH_2CH_3$ |
| $CH_3$ | H | H | $OCH_2C(CH_3)(CH_3)CH_2C_6H_5$ |
| $CH_3$ | H | H | $OCH_2C(O)CH_3$ |
| $CH_3$ | H | H | $OCH_2CH_2C(O)CH_3$ |

EXAMPLE 41

Preparation of 2-Chloro-4-fluoro-5-nitrobenzoyl chloride

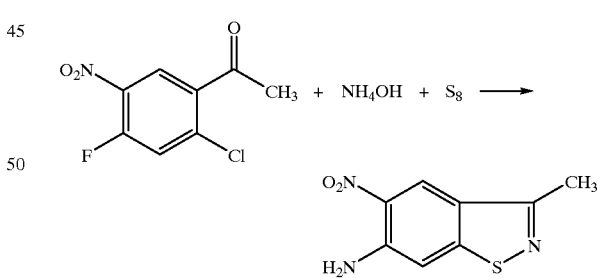

A mixture of 2-chloro-4-fluoro-5-nitrobenzoic acid (50.0 g, 0.228 mol) and N,N-dimethylformamide (5 drops) in 1,2-dichloroethane is treated dropwise with oxalyl chloride (30.8 mL, 0.353 mol), refluxed for 3 hours, cooled, and concentrated in vacuo to obtain the title product as an orange solid which is identified by NMR spectral analyses.

EXAMPLE 42

Preparation of 2'-Chloro-4'-fluoro-5'-nitroacetophenone

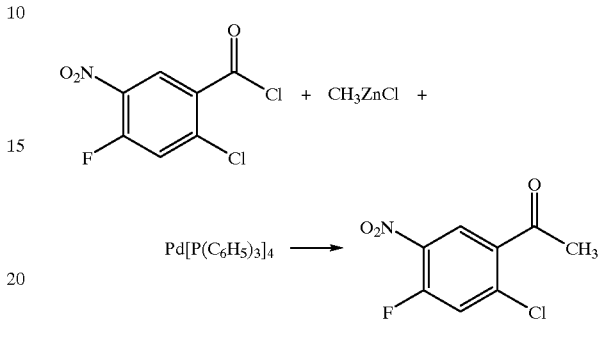

A 2 M solution of methylzinc chloride in tetrahydrofuran (5.00 mL, 10.1 mmol) is treated dropwise with a solution of 2-chloro-4-fluoro-5-nitrobenzoyl chloride (2.00 g, 8.40 mmol) in tetrahydrofuran, treated with tetrakis(triphenylphosphine)palladium(0) (0.400 g, 0.350 mmol), stirred at room temperature for one hour, and poured into 3 N hydrochloric acid. The resultant aqueous mixture is extracted with ethyl acetate. The organic extracts are combined, washed sequentially with water and saturated sodium hydrogen carbonate solution, dried over anhydrous magnesium sulfate, and concentrated in vacuo to obtain a dark liquid. Flash column chromatography of the liquid using silica gel and a methylene chloride in hexanes solution (6:4) gives the title product as an off-white solid (mp 66–68° C.) which is identified by NMR spectral analyses.

EXAMPLE 43

Preparation of 6-Amino-3-methyl-5-nitro-1,2-benzisothiazole $O_2N$-(aryl)-$C(O)CH_3$ + $NH_4OH$ + $S_8$ →

(3-methyl-5-nitro-6-amino-benzisothiazole structure)

A mixture of 2'-chloro-4'-fluoro-5'-nitroacetophenone (12.0 g, 0.0552 mol), sulfur (1.77 g, 0.0552 mol), 30% ammonium hydroxide solution (100 mL, 0.856 mol), and methanol is placed in a steel bomb, heated at 85° C. overnight, cooled, treated with additional sulfur (0.270 g) and 30% ammonium hydroxide solution (50 mL), heated at 85° C. overnight, cooled, filtered to remove solids, and extracted with ethyl acetate. The organic extracts are combined, washed sequentially with water and brine, dried over anhydrous magnesium sulfate, and concentrated in vacuo to obtain a solid. Flash column chromatography of the solid using silica gel, and 0%, 1% and 2% diethyl ether in methylene chloride solutions gives the title product as an orange solid (4.19 g, mp 189–191° C.) which is identified by NMR spectral analyses.

Using essentially the same procedure, the following compound is obtained:

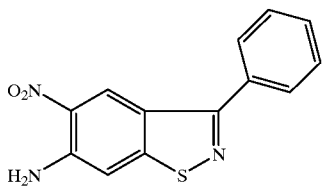

EXAMPLE 44

Preparation of 6-Chloro-3-methyl-5-nitro-1,2-benzisothiazole

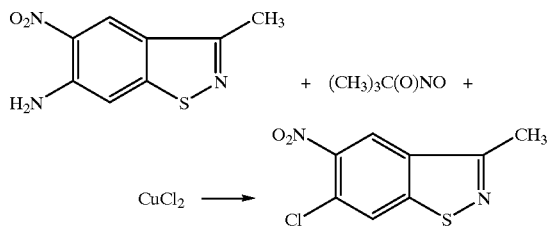

A mixture of tert-butyl nitrite (3.30 mL, 0.0278 mol) and copper(II) chloride (2.98 g, 0.0222 mol) in acetonitrile is heated to 65° C., treated portionwise with 6-amino-3-methyl-5-nitro-1,2-benzisothiazole (3.88 g, 0.0185 mol), stirred at 65° C., cooled to room temperature, and poured into 20% hydrochloric acid. The resultant aqueous mixture is extracted with ethyl acetate. The organic extracts are combined, washed with 20% hydrochloric acid, dried over anhydrous magnesium sulfate, and concentrated in vacuo to obtain a solid. Flash column chromatography of the solid using silica gel and methylene chloride/hexanes solutions (1:1 and 3:1) gives the title product as a pale, yellow solid (2.54 g, mp 156–158° C.) which is identified by NMR spectral analyses.

Using essentially the same procedure, the following compound is obtained:

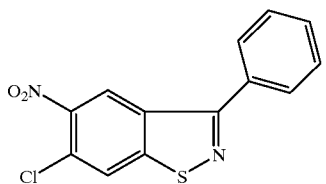

EXAMPLE 45

Preparation of 6-Fluoro-3-methyl-5-nitro-1,2-benzisothiazole

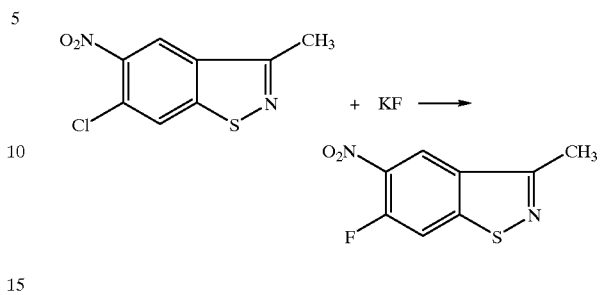

A mixture of 6-chloro-3-methyl-5-nitro-1,2-benzisothiazole (2.25 g, 9.80 mmol), potassium fluoride (2.85 g, 49.0 mmol), and 18-crown-6 (1.50 g, 5.70 mmol) in acetonitrile is heated in a sealed tube for 29 days, filtered to remove solids, and partially concentrated in vacuo to obtain a liquid. The liquid is diluted with ethyl acetate, washed sequentially with water and brine, dried over anhydrous magnesium sulfate, and concentrated in vacuo to obtain a dark, brown solid. Flash column chromatography of the solid using silica gel and a 10% to 50% ethyl acetate in hexanes gradient gives a yellow solid containing two components. Flash column chromatography of the yellow solid using silica gel and a 50% to 70% methylene chloride in hexanes gradient gives the title product as a pale, yellow solid (0.870 g, mp 118–119° C.) which is identified by NMR spectral analyses.

Using essentially the same procedure, the following compound is obtained:

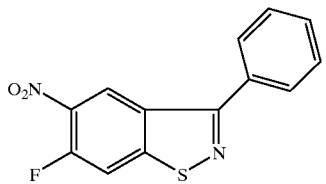

EXAMPLE 46

Preparation of 5-Amino-6-fluoro-3-methyl-1,2-benzisothiazole

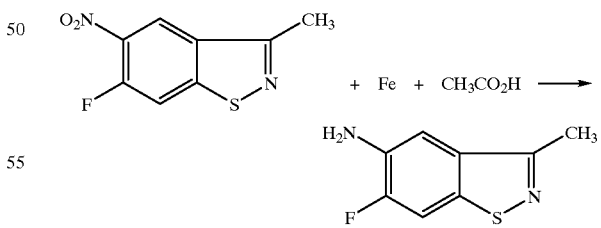

A solution of 6-fluoro-3-methyl-5-nitro-1,2-benzisothiazole (0.740 g, 3.50 mmol), 5% acetic acid (25.0 mL) and ethyl acetate is heated to 65° C., treated with iron powder (0.980 g, 17.5 mmol), stirred at 65° C. for one hour, cooled to room temperature, and filtered to remove solids. The organic phase is separated, washed sequentially with water, saturated sodium hydrogen carbonate solution and brine, dried over anhydrous magnesium sulfate, and concentrated in vacuo to give the title product as an orange solid (0.610 g) which is identified by NMR spectral analyses.

Using essentially the same procedure, the following compound is obtained:

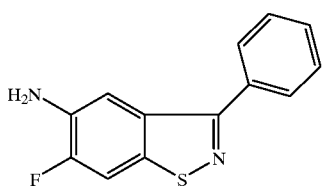

EXAMPLE 47

Preparation of 2-Chloro-4-fluoro-5-nitrobenzophenone

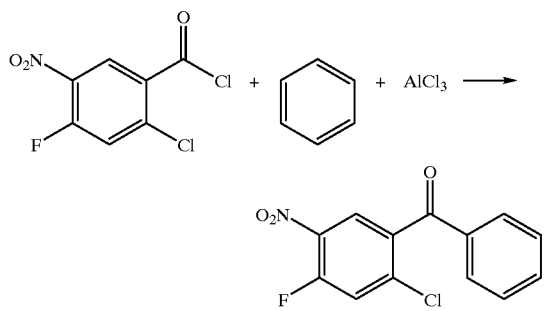

A solution of 2-chloro-4-fluoro-5-nitrobenzoyl chloride (26.7 g, 0.112 mol) and benzene (12.0 mL, 0.134 mol) in 1,1,2,2-tetrachloroethane is cooled to 0° C. to 5° C., treated with aluminum chloride (18.1 g, 0.136 mol), stirred for 15 minutes at about 8° C., heated to and stirred at 50° C. for one hour, cooled to room temperature, and diluted sequentially with an ice-water mixture and concentrated hydrochloric acid. The organic phase is separated, washed sequentially with water and saturated sodium hydrogen carbonate solution, dried over anhydrous magnesium sulfate, and concentrated in vacuo to obtain a solid. Flash column chromatography of the solid using silica gel and methylene chloride gives the title product as an orange solid (30.8 g) which is identified by NMR spectral analyses.

EXAMPLE 48

Preparation of Methyl 2-{{2-{5-[3,6-dihydro-3-methyl-2,6-dioxo-4-(trifluoromethyl)-1(2H)-pyrimidinyl]-1,2-benzisothiazol-3-yl}-p-tolyl}oxy}propionate,S,S-dioxide

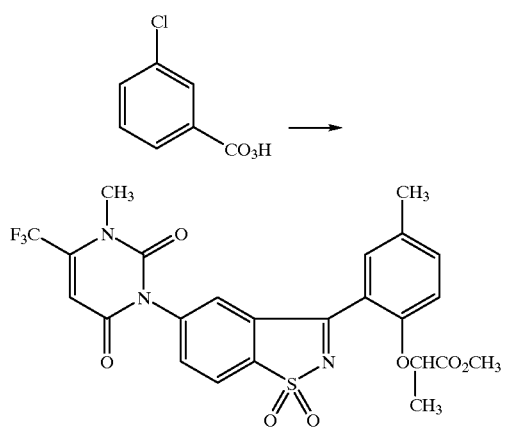

A mixture of methyl 2-{{2-{5-[3,6-dihydro-3-methyl-4-(trifluoromethyl)-2,6-dioxo-1(2H)-pyrimidinyl]-1,2-benzisothiazol-3-yl]-p-tolyl}oxy}propionate (2.00 g) and 3-chloroperoxybenzoic acid (2.00 g) in chloroform (50.0 mL) is stirred at room temperature overnight and diluted with saturated sodium hydrogen carbonate solution (100 mL). The organic phase is separated, dried over anhydrous sodium sulfate, concentrated in vacuo, diluted with methanol (15.0 mL), heated, cooled to room temperature and filtered to obtain a solid. The solid is washed with methanol and air-dried to give the title product as a yellow powder (1.50 g, mp 225–226° C.).

EXAMPLE 49

Preparation of 3-}3-[5-(Bromomethyl)-2-methoxyphenyl]-1,2-benzisothiazol-5-yl}-1-methyl-6-(trifluoromethyl)-2,4(1H,3H)pyrimidinedione and 3-{5-[3,6-Dihydro-3-methyl-2,6-dioxo-4-(trifluoromethyl)-1(2H)-pyrimidinyl]-1,2-benzisothiazol-3-yl}-4-methoxybenzaldehyde

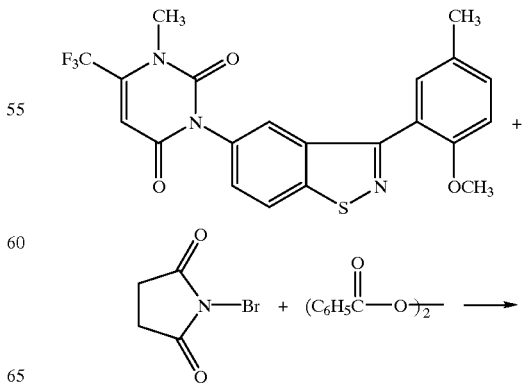

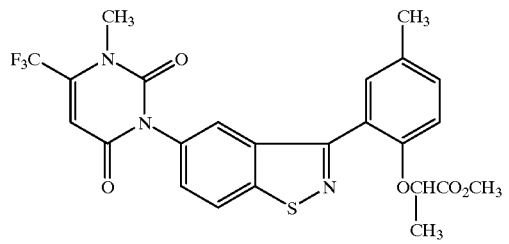

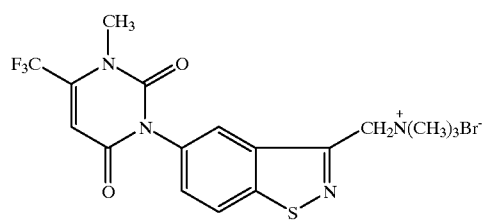

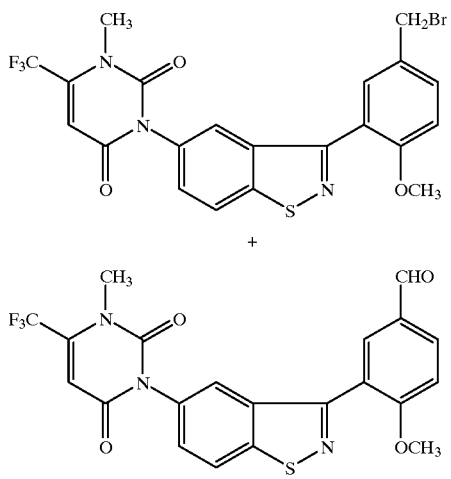

A mixture of 3-[3-(6-methoxy-m-tolyl)-1,2-benzisothiazol-5-yl]-1-methyl-6-(trifluoromethyl)-2,4(1H,3H)-pyrimidinedione (5.00 g, 11.2 mmol), N-bromosuccinimide (3.00 g, 16.9 mmol), and benzoyl peroxide (0.460 g, 1.90 mmol) in carbon tetrachloride is refluxed overnight, cooled to room temperature, diluted with methylene chloride, and filtered to remove solids. The filtrate is washed sequentially with 5% sodium m-bisulfate solution and 5% sodium bicarbonate solution, dried over anhydrous magnesium sulfate, and concentrated in vacuo to obtain an amber oil. Column chromatography of the oil using silica gel and a hexanes/ethyl acetate solution (9:1) gives 3-{3-[5-(bromomethyl)-2-methoxyphenyl]-1,2-benzisothiazol-5-yl}-1-methyl-6-(trifluoromethyl)-2,4(1H,3H)-pyrimidinedione as a light yellow solid (0.700 g, mp 158–160° C.) and 3-{5-[3,6-dihydro-3-methyl-2,6-dioxo-4-(trifluoromethyl)-1(2H)-pyrimidinyl]-1,2-benzisothiazol-3-yl}-4-methoxybenzaldehyde as a light yellow solid (1.50 g, mp 118–120° C.).

EXAMPLE 50

Preparation of {{5-[3,6-Dihydro-3-methyl-2,6-dioxo-4-(trifluoromethyl)-1(2H)-pyrimidinyl]-1,2-benzisothiazol-3-yl}methyl}trimethylammonium bromide

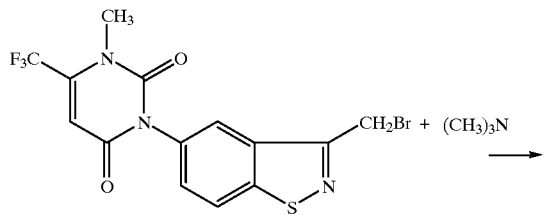

A mixture of 3-[3-(bromomethyl)-1,2-benzisothiazol-5-yl]-1-methyl-6-(trifluoromethyl)-2,4(1H,3H)-pyrimidinedione (20.0 g, 0.0480 mol) and toluene is heated to 90° C., cooled to room temperature, treated with liquid trimethylamine (8.60 g, 0.145 mol), stirred at room temperature for 90 minutes, and filtered to obtain a solid. The solid is washed with toluene and dried in a vacuum oven at 45–50° C. to give the title product as a white solid which is identified by NMR spectral analysis.

Using essentially the same procedure, but using the appropriate secondary amine, the following compounds are obtained:

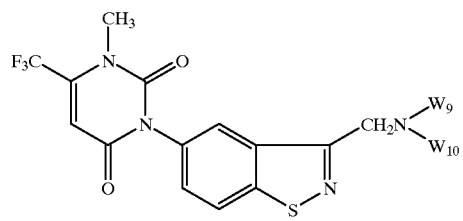

| $W_9$ | $W_{10}$ | mp °C. |
|---|---|---|
| $CH_3$ | $CH_2CO_2C_2H_5$ | 119–121 |
| $CH_3$ | $CH_3$ | 200–201 |
| —CH=CH—N=CH— | | 206–207 |
| H | $SOCH_3$ | 119–121 |

EXAMPLE 51

Preparation of N-{{{2-{5-[3,6-Dihydro-3-methyl-2,6-dioxo-4-(trifluoromethyl)-1(2H)-pyrimidinyl]-1,2-benzisothiazol-3-yl}-p-tolyl}oxy}acetyl}-p-toluenesulfonamide

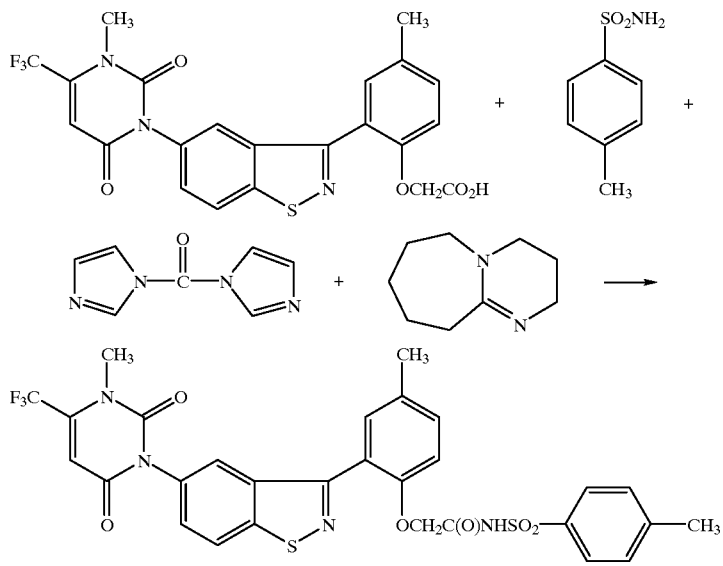

A mixture of 1,1'-carbonyldiimidazole (0.198 g, 1.22 mmol) and {{2-{5-[3,6-dihydro-3-methyl-2,6-dioxo-4-(trifluoromethyl)-1(2H)-pyrimidinyl]-1,2-benzisothiazol-3-yl}-p-tolyl}oxy}acetic acid (0.300 g, 0.610 mmol) in tetrahydrofuran is stirred overnight at room temperature, refluxed for 30 minutes, cooled to room temperature, treated sequentially with a solution of p-toluenesulfonamide (0.209 g, 1.22 mmol) in tetrahydrofuran and a solution of 1,8-diazabicyclo[5.4.0]undec-7-ene (0.204 g, 1.34 mmol) in tetrahydrofuran, stirred at room temperature for three hours, and poured into 10% hydrochloric acid. The resulting aqueous mixture is filtered to obtain a solid. The solid is recrystallized from an acetonitrile/water solution to give the title product as an off-white solid (0.200 g, mp 140–144° C.).

Using essentially the same procedure, the following compounds are obtained:

| $W_3$ | $W_5$ | $W_6$ | $W_8$ | $W_9$ | mp ° C. |
|---|---|---|---|---|---|
| $CH_3$ | H | H | $CH_3$ | H | |
| $CH_3$ | H | H | $CH_2$–phenyl | H | |
| $CH_3$ | H | H | 4-Cl-phenyl | H | |
| $CH_3$ | H | H | 5-Cl-2-thienyl | H | |

-continued
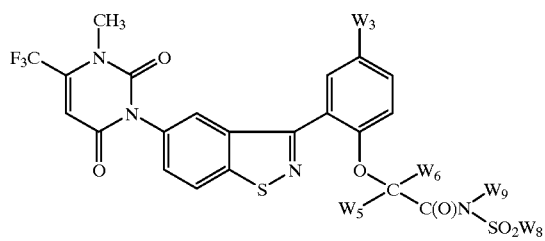
| W$_3$ | W$_5$ | W$_6$ | W$_8$ | W$_9$ | mp °C. |
|---|---|---|---|---|---|
| CH$_3$ | H | H | 3-chlorophenyl | H | |
| CH$_3$ | H | H | 2-chlorophenyl | H | |
| CH$_3$ | H | H | 3-(trifluoromethyl)phenyl | H | |
| CH$_3$ | H | H | phenyl | H | |
| CH$_3$ | H | H | 4-methoxyphenyl | H | |
| CH$_3$ | H | H | 4-fluorophenyl | H | |
| CH$_3$ | H | H | 4-nitrophenyl | H | |
| CH$_3$ | H | H | 3-nitrophenyl | H | |
| CH$_3$ | H | H | 2-methylphenyl | H | |
| CH | H | H | CH=CH(C$_6$H$_5$) | H | |
| CH$_3$ | CH$_3$ | CH$_3$ | H | CH$_3$ | |

-continued

[Structure: trifluoromethyl-N-methyl-pyrimidinedione attached to benzisothiazole with W3-substituted phenyl bearing O-C(W5)(W6)-C(O)N(W9)SO2W8 group]

| W3 | W5 | W6 | W8 | W9 | mp °C |
|---|---|---|---|---|---|
| CH3 | H | H | [5-chloro-2-thienyl] | H | 120 (dec) |
| H | H | H | CH3 | H | 151 |
| CH3 | H | H | [5-(NHC(O)CH3)-1,3,4-thiadiazol-2-yl] | H | 235–239 |
| CH3 | H | H | [3,4,5-trimethylisoxazol-?-yl] | H | 204–207 |
| CH3 | H | H | [2,4,5-trimethylthiazol-?-yl] | H | 114–117 |
| CH3 | H | H | [2-methyl-5-ethoxybenzothiazol-?-yl] | H | 156–158 |
| CH3 | H | H | [2-methyl-5-chlorobenzothiazol-?-yl] | H | 236 |
| H | CH3 | H | CH3 | H | 175–177 |
| CH3 | H | H | CH2Cl | H | 174–184 |
| H | H | H | CH2Cl | H | 220–230 |
| CH3 | H | H | CH3 | CH3 | 135–145 |
| H | H | H | CH3 | CH3 | 195–199 |
| CH3 | H | H | CH2CH2CH3 | H | |
| CH3 | H | H | CH=CH2 | H | |
| CH3 | H | H | CH2CH3 | H | |
| H | H | H | CH(CH3)2 | H | |
| H | H | H | CH2CH2CH3 | H | |
| H | H | H | CH=CH2 | H | |
| H | H | H | CH2CH3 | H | |
| CH3 | H | H | CH(CH3)2 | H | |
| CH3 | CH3 | H | CH(CH3)2 | H | |
| CH3 | CH3 | H | CH2CH2CH3 | H | |
| CH3 | CH3 | H | CH=CH2 | H | |
| CH3 | CH3 | H | CH2CH3 | H | |
| CH3 | CH3 | H | CH3 | H | |
| CH3 | H | H | (CH2)3CH3 | H | |
| H | H | H | (CH2)3CH3 | H | |
| CH3 | CH3 | H | (CH2)3CH3 | H | |

-continued

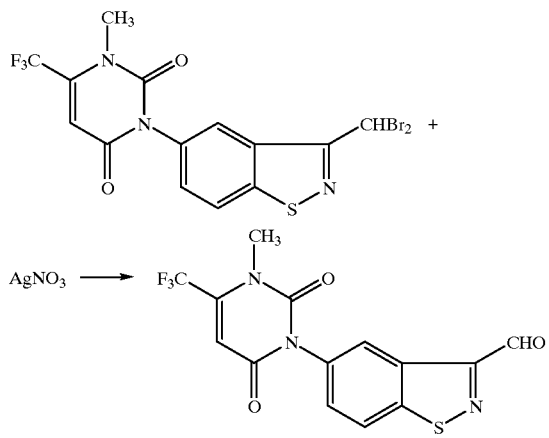

| $W_3$ | $W_5$ | $W_6$ | $W_8$ | $W_9$ | mp ° C. |
|---|---|---|---|---|---|
| H | H | H | $N[CH(CH_3)_2]_2$ | H | |

EXAMPLE 52

Preparation of 5-[3,6-Dihydro-3-methyl-2,6-dioxo-4-(trifluoromethyl)-1(2H)-pyrimidinyl]-1,2-benzisothiazole-3-carboxaldehyde

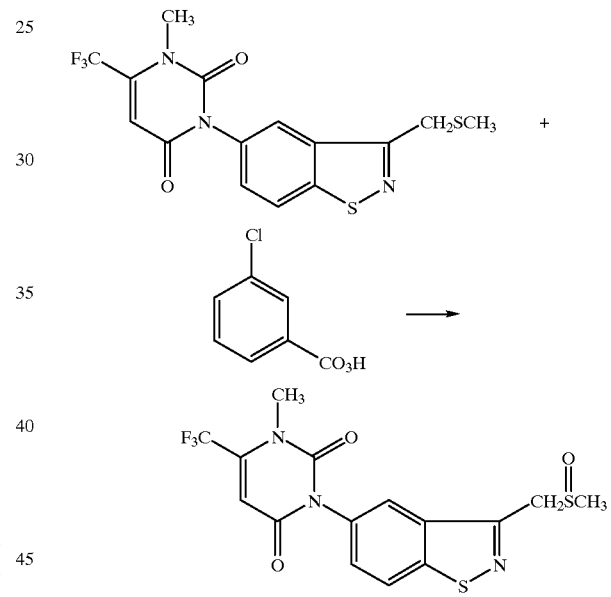

A solution of 3-[3-(dibromomethyl)-1,2-benzisothiazol-5-yl]-1-methyl-6-(trifluoromethyl)-2,4(1H,3H)-pyrimidinedione (0.500 g, 0.00100 mol) in a dioxane/water mixture (5:2) is treated with silver nitrate (0.340 g, 0.00200 mol), refluxed for 90 minutes, cooled to and stirred at room temperature overnight, refluxed for three hours, cooled, and filtered through a pad of diatomaceous earth. The resultant filtrate is concentrated in vacuo to obtain an aqueous mixture. The aqueous mixture is extracted with methylene chloride. The organic extract is washed sequentially with water and brine, dried over anhydrous magnesium sulfate, and concentrated in vacuo to obtain a solid. Column chromatography of the solid using silica gel and methylene chloride gives the title product as a solid (0.240 g, mp 193–194.5° C.).

Using essentially the same procedure on 3-[6-fluoro-3-(dibromomethyl)-1,2-benzisothiazol-5-yl]-1-methyl-6-(trifluoromethyl)-2,4(1H,3H)-pyrimidinedione, 5-[3,6-dihydro-3-methyl-2,6-dioxo-4-(trifluoromethyl)-1(2H)-pyrimidnyl-6-fluoro-1,2-benzisothiazole-3-carboxaldehyde is obtained.

EXAMPLE 53

Preparation of 1-Methyl-3-{3-[(methylsulfinyl)methyl]-1,2-benzisothiazol-5-yl}-6-(trifluoromethyl)-2,4(1H,3H)-pyrimidinedione A solution of 1-methyl-3-{3-[(methylthio)methyl]-1,2-benzisothiazol-5-yl}-6-(trifluoromethyl)-2,4(1H,3H)-pyrimidinedione (0.740 g, 1.90 mmol) in methylene chloride is treated with 3-chloroperoxybenzoic acid (0.580 g, 60%, 2.00 mmol), stirred at room temperature for five minutes, diluted with additional methylene chloride, washed with 5% sodium carbonate solution, dried over anhydrous magnesium sulfate, and concentrated in vacuo to obtain a solid. Flash column chromatography of the solid using silica gel and a 10% ethyl acetate in methylene chloride solution gives the title product as a white solid which is identified by NMR spectral analysis.

Using essentially the same procedure, 1-methyl-3-{3-[(phenylsulfinyl)methyl]-1,2-benzisothiazol-5-yl}-6-(trifluoromethyl)-2,4(1H,3H)-pyrimidinedione is obtained from 1-methyl-3-{3-[(phenylthio)methyl]-1,2-benzisothiazol-5-yl]-6-(trifluoromethyl)-2,4(1H,3H)-pyrimidinedione.

EXAMPLE 54

Preparation of 1-Methyl-3-{3-[(methylsulfonyl)methyl]-1,2-benzisothiazol-5-yl}-6-(trifluoromethyl)-2,4(1H,3H)-pyrimidinedione

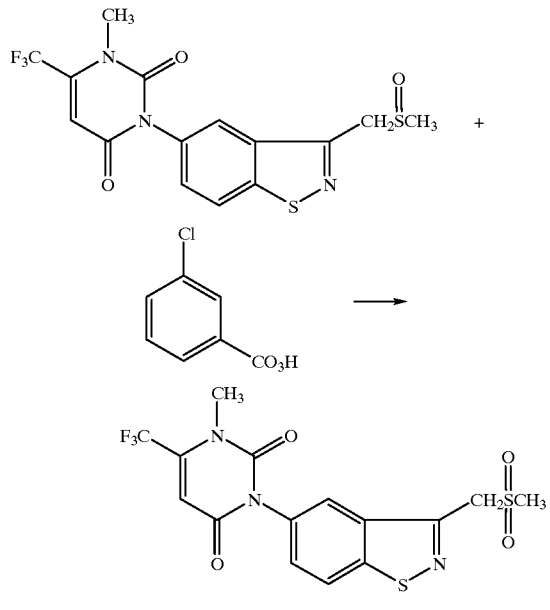

A mixture of 1-methyl-3-{3-[(methylsulfinyl)methyl]-1,2-benzisothiazol-5-yl}-6-(trifluoromethyl)-2,4(1H,3H)-pyrimidinedione (0.480 g, 1.24 mmol) and 3-chloroperoxybenzoic acid (0.600 g, 60%, 2.10 mmol) in methylene chloride is stirred at room temperature for four hours, washed with 5% sodium carbonate solution, dried over anhydrous magnesium sulfate, and concentrated in vacuo to obtain a solid. Flash column chromatography of the solid using silica gel and a 10% diethyl ether in methylene chloride solution gives the title product as a white solid which is identified by NMR spectral analyses.

Using essentially the same procedure, 1-methyl-3-{3-[(phenylsulfonyl)methyl]-1,2-benzisothiazol-5-yl}-6-(trifluoromethyl)-2,4(1H,3H)-pyrimidinedione is obtained from 1-methyl-3-{3-[(phenylsulfinyl)methyl]-1,2-benzisothiazol-5-yl}-6-(trifluoromethyl)-2,4(1H,3H)-pyrimidinedione.

EXAMPLE 55

Preparation of 2-Ethoxy-3-[3-(6-hydroxy-m-tolyl)-1,2-benzisothiazol-5-yl]-6-(trifluoromethyl)-4(3H)-pyrimidinone

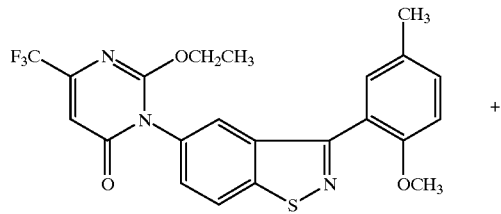

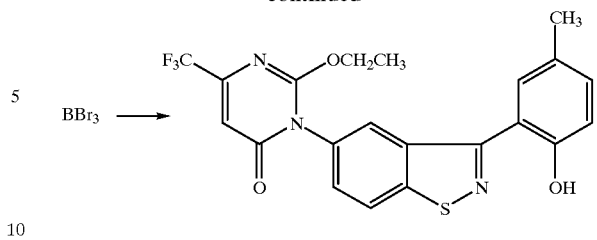

A solution of 2-ethoxy-[3-(6-methoxy-m-tolyl)-1,2-benzisothiazol-5-yl]-6-(trifluoromethyl)-4(3H)-pyrimidinone (0.490 g, 1.06 mmol) in methylene chloride is cooled to −5° C., treated with a 1 M solution of boron tribromide in methylene chloride (1.38 mL, 1.38 mmol), stirred for six hours, washed sequentially with water and brine, dried over anhydrous magnesium sulfate, and concentrated in vacuo to give the title product as an off-white solid which is identified by NMR spectral analysis.

Using essentially the same procedure, the following compound is obtained:

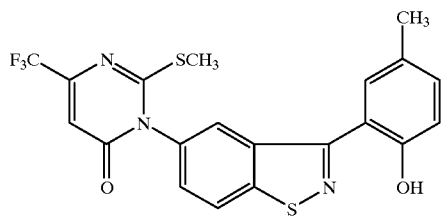

EXAMPLE 56

Preparation of Methyl{{2-[5-[2-ethoxy-6-oxo-4-(trifluoromethyl)-1(6H)-pyrimidinyl]-1,2-benzisothiazol-3-yl}-p-tolyl}oxy}acetate

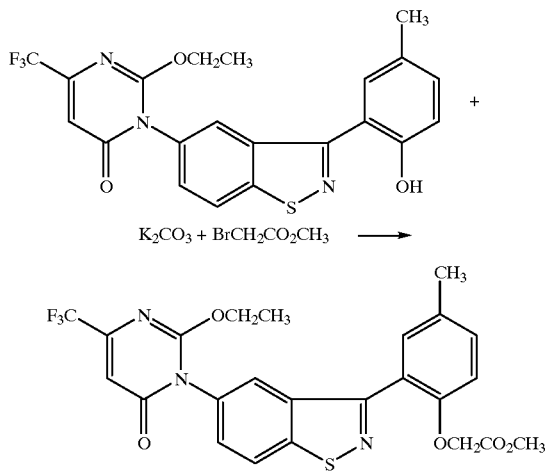

A mixture of 2-ethoxy-3-[3-(6-hydroxy-m-tolyl)-1,2-benzisothiazol-5-yl]-6-(trifluoromethyl)-4(3H)-pyrimidinone (0.470 g, 1.05 mmol), potassium carbonate (0.190 g, 1.37 mmol) and methyl bromoacetate (0.210 g, 1.37 mmol) in N,N-dimethylformamide is stirred overnight at room temperature, diluted with ethyl acetate, washed sequentially with water and brine, dried over anhydrous magnesium sulfate, and concentrated in vacuo to obtain a solid. Flash column chromatography of the solid using silica gel and a 10% diethyl ether in methylene chloride solution gives the title product as an off-white solid (0.450 g, mp 171–174° C.).

Using essentially the same procedure, the following compounds are obtained:

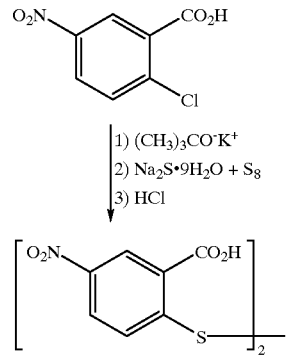

| $W_5$ | $W_6$ | mp ° C. |
|---|---|---|
| H | $CH_3$ | 95–99 |
| $CH_3$ | $CH_3$ | 93–100 |
| H | $CH_2\!\!=\!\!CH$ | 187–188 |

EXAMPLE 57

Preparation of 2,2'-Dithiobis[5-nitrobenzoic acid]

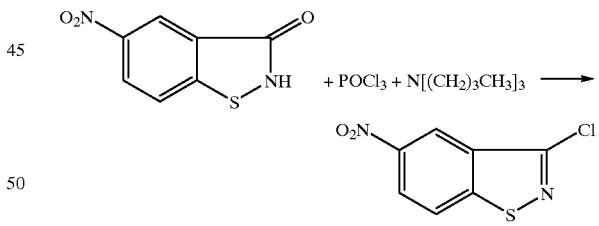

A mixture of 2-chloro-5-nitrobenzoic acid (100 g, 0.496 mol) in ethanol is treated portionwise with potassium tert-butoxide (55.5 g, 0.495 mol), diluted with additional ethanol, heated to reflux, treated portionwise with a solution prepared from sodium sulfide nonahydrate (60.0 g, 0.249 mol), sulfur (8.80 g, 0.274 mol) and water, refluxed for two hours, cooled to room temperature, and treated with concentrated hydrochloric acid. The resultant acidic mixture is stirred for one hour and filtered to obtain a solid. The solid is washed with water and air-dried to give the title product as a yellow powder which is identified by NMR spectral analysis.

EXAMPLE 58

Preparation of 5-Nitro-1,2-benzisothiazol-3(2H)-one

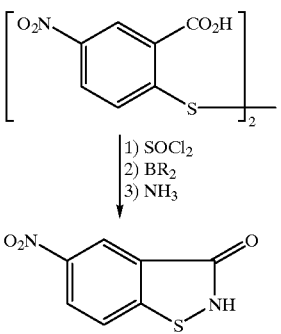

A mixture of 2,2'-dithiobis[5-nitrobenzoic acid] (44.6 g, 0.113 mol) and thionyl chloride (49.0 mL, 0.670 mol) in methylene chloride is treated with N,N-dimethylformamide (0.800 mL), refluxed overnight, concentrated in vacuo, and diluted with 1,2-dichloroethane. The resultant organic solution is treated with bromine (22.5 mL, 0.436 mol), stirred at room temperature for 20 minutes, refluxed for 3.5 hours, and concentrated in vacuo to obtain a residue. A solution of the residue in 1,2-dichloroethane is cooled with an ice-water bath, treated with concentrated ammonia (112 mL) over 15 minutes, stirred at room temperature for 16 hours, cooled with an ice-water bath, and treated with concentrated hydrochloric acid. The resultant aqueous mixture is stirred at room temperature for one hour and filtered to obtain a solid. The solid is washed with water and air-dried to give the title product as a yellow solid which is identified by NMR spectral analysis.

EXAMPLE 59

Preparation of 3-Chloro-5-nitro-1,2-benzisothiazole

A mixture of 5-nitro-1,2-benzisothiazol-3(2H)-one (10.0 g, 0.0510 mol), phosphorus oxychloride (40.0 mL, 0.429 mol) and tributylamine (12.0 mL, 0.050 mol) is heated at 103–115° C. for six hours, stirred at room temperature overnight, and poured into an ice-water mixture. The resultant aqueous mixture is extracted with methylene chloride. The combined organic extracts are washed sequentially with water and saturated sodium hydrogen carbonate solution, dried over anhydrous sodium sulfate, and concentrated in vacuo to obtain a gum. Column chromatography of the gum using silica gel and methylene chloride gives the title product as an orange-yellow solid which is identified by NMR spectral analysis.

EXAMPLE 60

Preparation of Ethyl α-cyano-5-nitro-1,2-benzisothiazole-3-acetate

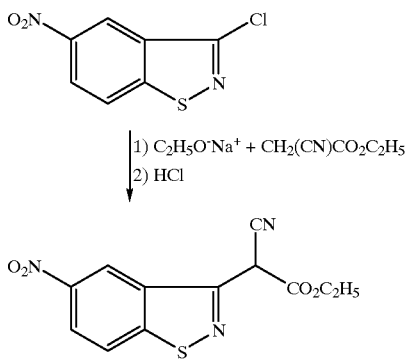

A sodium ethoxide solution (previously prepared from ethanol and sodium (1.00 g, 0.0430 mol)) is cooled with an ice-acetone bath, treated portionwise with ethyl cyanoacetate (4.51 g, 0.0398 mol), stirred at room temperature for 30 minutes, treated with 3-chloro-5-nitro-1,2-benzisothiazole (4.27 g, 0.0199 mol), stirred at room temperature overnight, cooled to 0° C., and treated dropwise with 10% hydrochloric acid (15.0 mL). The resultant aqueous mixture is stirred at room temperature for one hour and filtered to obtain a solid. The solid is washed with ethanol and air-dried to give the title product as a yellow solid which is identified by NMR spectral analysis.

EXAMPLE 61

Preparation of Ethyl 5-nitro-1,2-benzisothiazole-3-acetate

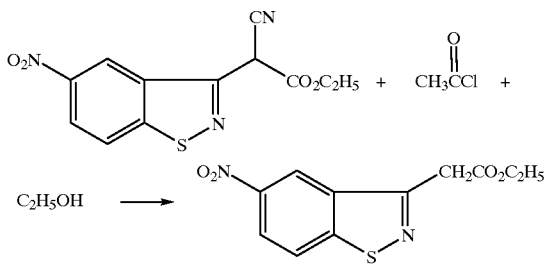

Ethyl α-cyano-5-nitro-1,2-benzisothiazole-3-acetate (6.67 g, 0.0229 mol) is added to a solution of acetyl chloride (67.0 mL) in ethanol. The reaction mixture is refluxed overnight, cooled, and filtered to remove solids. The resultant filtrate is concentrated in vacuo to obtain a brown semi-solid. A mixture of the semi-solid in diethyl ether is stirred for two hours and filtered to obtain a solid. The solid is washed with diethyl ether and air-dried to give the title product as yellow crystals (1.04 g, mp 91–92° C.).

EXAMPLE 62

Preparation of Ethyl 5-amino-1,2-benzisothiazole-3-acetate

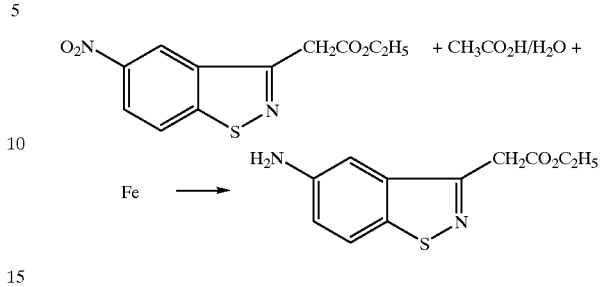

A 10% acetic acid solution (31.0 mL) is stirred at 50° C., treated with iron powder (0.656 g), treated dropwise with a solution of ethyl 5-nitro-1,2-benzisothiazole-3-acetate (1.03 g, 3.88 mmol) in ethyl acetate, stirred at 50° C. for two hours, treated with additional iron powder (0.305 g), stirred at 50° C. for 15 minutes, and poured into saturated sodium hydrogen carbonate solution. The resultant aqueous mixture is extracted with ethyl acetate. The combined organic extracts are washed sequentially with water and brine, dried over anhydrous sodium sulfate, and concentrated in vacuo to obtain an oil. Column chromatography of the oil using silica gel and methylene chloride gives the title product as a yellow oil.

EXAMPLE 63

Preparation of Ethyl 5-[3,6-dihydro-2,6-dioxo-4-(trifluoromethyl)-1(2H)-pyrimidinyl]-1,2-benzisothiazole-3-acetate

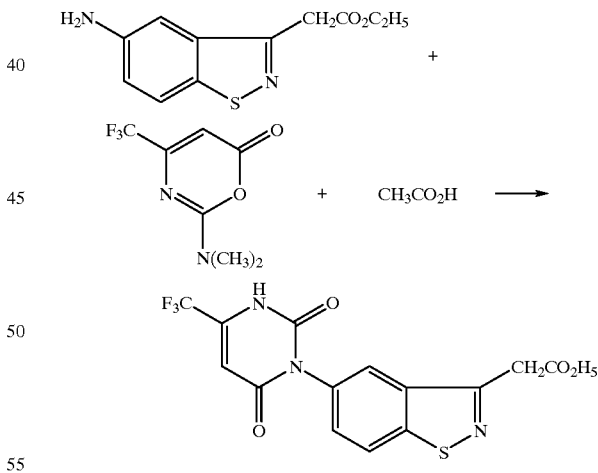

A mixture of ethyl 5-amino-1,2-benzisothiazole-3-acetate (0.748 g, 3.16 mmol) and 2-dimethylamino-4-(trifluoromethyl)-6H-1,3-oxazin-6-one (0.660 g, 3.17 mmol) in acetic acid is refluxed for three hours, concentrated in vacuo, and diluted with saturated sodium hydrogen carbonate solution. The resultant mixture is extracted with methylene chloride. The combined organic extracts are washed with water, dried over anhydrous sodium sulfate, and concentrated in vacuo to give the title product as a tan solid which is identified by NMR spectral analysis.

EXAMPLE 64

Preparation of Ethyl 5-[3,6-dihydro-3-methyl-2,6-dioxo-4-(trifluoromethyl)-1(2H)-pyrimidinyl]-1,2-benzisothiazole-3-acetate

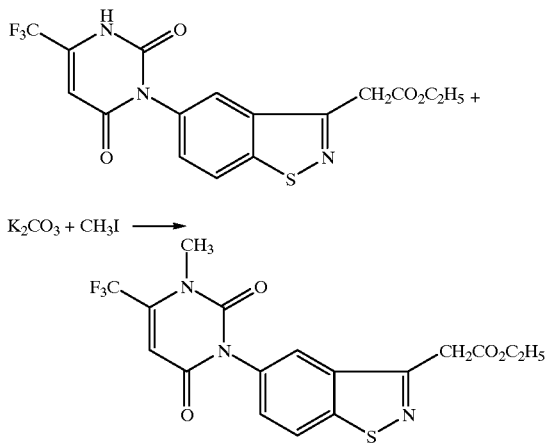

A mixture of ethyl 5-[3,6-dihydro-2,6-dioxo-4-(trifluoromethyl)-1(2H)-pyrimidinyl]-1,2-benzisothiazole-3-acetate (0.643 g, 0.00160 mol) and potassium carbonate (0.243 g, 0.00170 mol) in N,N-dimethylformamide is stirred at room temperature for 90 minutes, treated with iodomethane (0.320 mL, 0.00500 mol), stirred at room temperature overnight, and diluted with water. The resultant aqueous mixture is extracted with methylene chloride. The organic extract is washed with water, dried over anhydrous magnesium sulfate, and concentrated in vacuo to obtain a brown oil. Column chromatography of the oil using silica gel and a 10% ethyl acetate in hexanes solution gives the title product as a tan solid (0.362 g, mp 150–152° C.).

EXAMPLE 65

Preparation of 5-Amino-1,2-benzisothiazole-3-ethanol

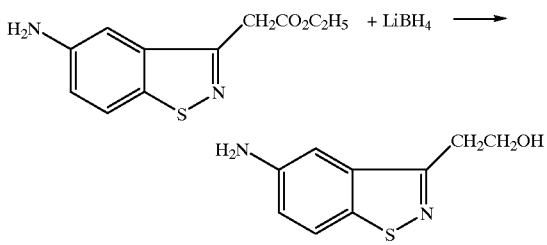

A mixture of ethyl 5-amino-1,2-benzisothiazole-3-acetate (3.14 g, 0.0133 mol) in tetrahydrofuran is cooled to −8° C., treated dropwise with a 2 M solution of lithium borohydride in tetrahydrofuran (5.00 mL, 0.0100 mol), stirred at room temperature for 3.5 hours, cooled to −5° C., treated with additional lithium borohydride solution (4.20 mL, 0.0084 mol), stirred at room temperature overnight, cooled to 0° C., quenched sequentially with water (5.00 mL) and 10% hydrochloric acid (10.0 mL), stirred at room temperature for one hour, neutralized with saturated sodium hydrogen carbonate solution (10.0 mL), and concentrated in vacuo to obtain a residue. The residue is diluted with a 5% methanol in methylene chloride solution. The resultant mixture is diluted with water, brine and methylene chloride. The phases are separated and the organic phase is concentrated in vacuo to obtain an orange gum. The gum is crystallized from methanol to give the title product as a tan solid which is identified by NMR spectral analysis.

EXAMPLE 66

Preparation of 3-[3-(2-Hydroxyethyl)-1,2-benzisothiazol-5-yl-1-methyl-6-(trifluoromethyl)-2,4 (1H,3H)-pyrimidinedione acetate

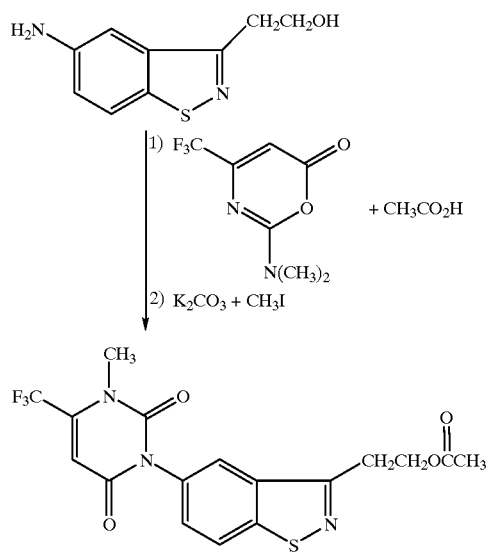

A mixture of 5-amino-1,2-benzisothiazole-3-ethanol (0.794 g, 4.09 mmol) and 2-dimethylamino-4-(trifluoromethyl)-6H-1,1,3-oxazin-6-one (0.850 g, 4.08 mmol) in acetic acid is refluxed for five hours and concentrated in vacuo to obtain a tan solid. A solution of the solid in N,N-dimethylformamide is treated with potassium carbonate (0.615 g, 4.45 mmol), stirred for one hour, treated with iodomethane (0.800 mL, 12.8 mmol), stirred overnight, and poured into an ice-water mixture. The resultant aqueous mixture is extracted with methylene chloride. The combined organic extracts are washed sequentially with water, 3% hydrochloric acid, water, saturated sodium hydrogen carbonate solution and water, dried over anhydrous sodium sulfate, and concentrated in vacuo to obtain a solid. Column chromatography of the solid using silica gel and methylene chloride gives the title product as a white solid which is identified by NMR spectral analysis.

EXAMPLE 67

Preparation of 3-[3-(2-Hydroxyethyl)-1,2-benzisothiazol-5-yl]-1-methyl-6-(trifluoromethyl)-2,4(1H,3H)-pyrimidinedione

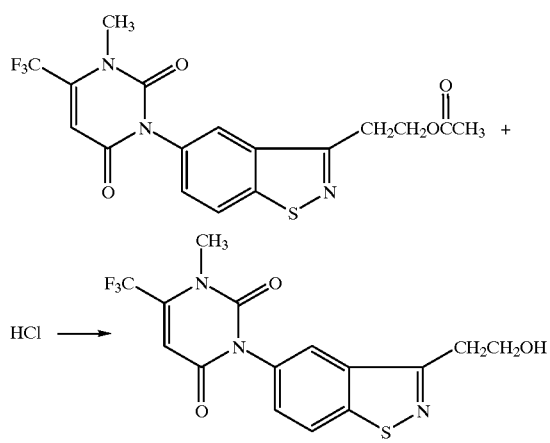

A mixture of 3-[3-(2-hydroxyethyl)-1,2-benzisothiazol-5-yl-1-methyl-6-(trifluoromethyl)-2,4(1H,3H)-pyrimidinedione acetate (1.00 g, 2.42 mmol) in 10% hydrochloric acid (250 mL) is refluxed for 35 minutes and filtered through glass wool to remove solids. The resultant filtrate is cooled and extracted with methylene chloride. The combined organic extracts are washed with water, dried over anhydrous sodium sulfate, and concentrated in vacuo to give the title product as a yellow solid which is identified by NMR spectral analysis.

EXAMPLE 68

Preparation of 5-Nitro-1,2-benzisothiazole-3-acetonitrile

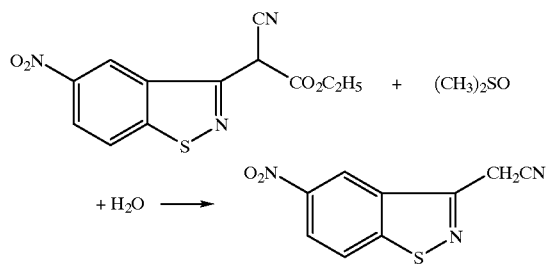

A mixture of ethyl 5-nitro-1,2-benzisothiazole-3-acetate (5.00 g, 17.2 mmol), water (1.00 mL), and methyl sulfoxide (35.0 mL) is stirred at 107° C. for 24 hours, stirred at room temperature for two days, and poured into an ice-water mixture. The resultant aqueous mixture is stirred for two hours and filtered to obtain a solid. The solid is washed with water and air-dried to give the title product as a tan solid.

EXAMPLE 69

Preparation of α,α-Dimethyl-5-nitro-1,2-benzisothiazole-3-acetonitrile

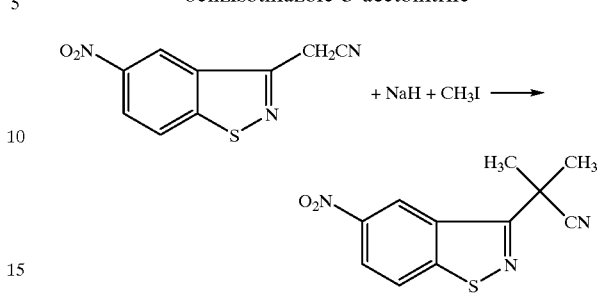

A mixture of 5-nitro-1,2-benzisothiazole-3-acetonitrile (1.29 g, 5.89 mmol) in N,N-dimethylformamide is cooled to −9° C., treated with sodium hydride (1.00 g of a 60% dispersion in oil), stirred at −3° C. for 20 minutes, treated with iodomethane (5.00 mL), stirred at room temperature for four hours, and poured onto ice. The resultant aqueous mixture is treated with 10% hydrochloric acid and extracted with methylene chloride. The combined organic extracts are washed sequentially with water, saturated sodium hydrogen carbonate solution and water, dried over anhydrous sodium sulfate, and concentrated in vacuo to obtain a solid. Column chromatography of the solid using silica gel and methylene chloride gives the title product as a yellow solid which is identified by NMR spectral analysis.

EXAMPLE 70

Preparation of Ethyl α,α-dimethyl-5-nitro-1,2-benzisothiazole-3-acetate

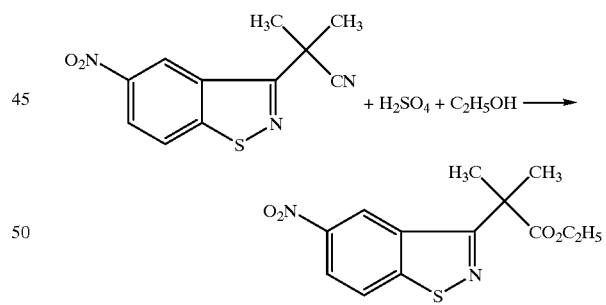

A mixture of α,α-dimethyl-5-nitro-1,2-benzisothiazole-3-acetonitrile (0.913 g, 3.69 mmol), water (0.450 mL), concentrated sulfuric acid (4.55 mL) and ethanol (9.10 mL) is refluxed for one hour, cooled, and poured onto ice. The resultant aqueous mixture is neutralized with saturated sodium bicarbonate solution and extracted with methylene chloride. The organic extract is washed with water, dried over anhydrous sodium sulfate, and concentrated in vacuo to obtain a solid. Column chromatography of the solid using silica gel and methylene chloride gives the title product as pale yellow crystals.

EXAMPLE 71

Preparation of Ethyl 5-amino-α,α-dimethyl-1,2-benzisothiazole-3-acetate

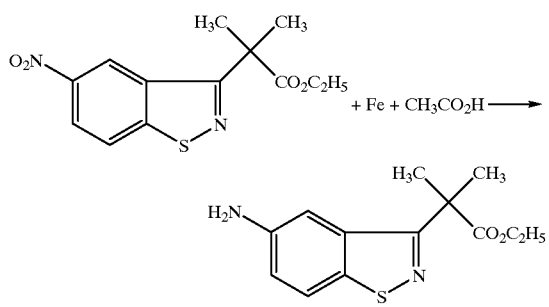

A mixture of ethyl α,α-dimethyl-5-nitro-1,2-benzisothiazole-3-acetate (0.714 g, 2.42 mmol), iron powder (0.500 g), 10% acetic acid (23.0 mL) and ethyl acetate (23.0 mL) is stirred at 54–58° C. for one hour, cooled, and poured into saturated sodium hydrogen carbonate solution. The resultant aqueous mixture is extracted with ethyl acetate. The combined organic extracts are washed sequentially with water and brine, dried over anhydrous sodium sulfate, and concentrated in vacuo to obtain a yellow oil. Column chromatography of the oil using silica gel and a 10% ethyl acetate in methylene chloride solution gives the title product as a light brown oil which is identified by NMR spectral analysis.

EXAMPLE 72

Preparation of Ethyl 5-[3,6-dihydro-3-methyl-2,6-dioxo-4-(trifluoromethyl)-1(2H)-pyrimidinyl]-α,α-dimethyl-1,2-benzisothiazole-3-acetate

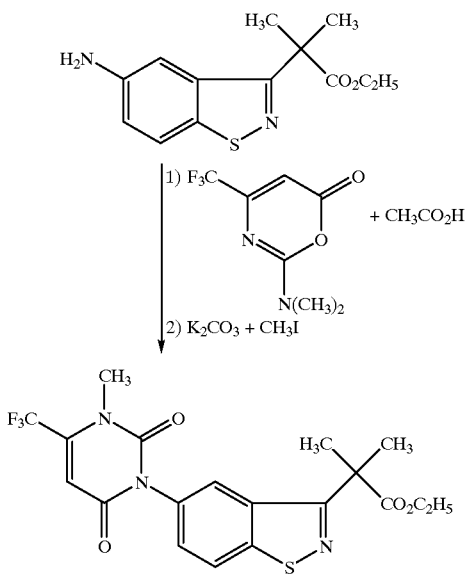

A mixture of ethyl 5-amino-α,α-dimethyl-1,2-benzisothiazole-3-acetate (0.546 g, 2.06 mmol) and 2-dimethylamino-4-(trifluoromethyl)-6H-1,3-oxazin-6-one (0.430 g, 2.06 mmol) in acetic acid is refluxed for 4.5 hours, concentrated in vacuo, and diluted with saturated sodium hydrogen carbonate solution. The resultant aqueous mixture is extracted with methylene chloride. The combined organic extracts are washed with water, dried over anhydrous sodium sulfate, and concentrated in vacuo to obtain a brown foam. A solution of the foam in N,N-dimethylformamide is treated with potassium carbonate (0.312 g, 2.25 mmol), stirred for one hour, treated with iodomethane (0.420 mL, 6.70 mmol), stirred overnight at room temperature, and poured into an ice-water mixture containing 20 mL of concentrated hydrochloric acid. The resultant aqueous-mixture is extracted with methylene chloride. The combined organic extracts are washed sequentially with 10% hydrochloric acid, water, saturated sodium hydrogen carbonate solution and water, dried over anhydrous sodium sulfate and concentrated in vacuo to obtain a brown oil. Column chromatography of the oil using silica gel and a 33% ethyl acetate in methylene chloride solution affords a pink foam which is recrystallized from ethanol to give the title product as pink crystals, mp 164–167° C.

EXAMPLE 73

Preparation of 5-Amino-3-chloro-1,2-benzisothiazole

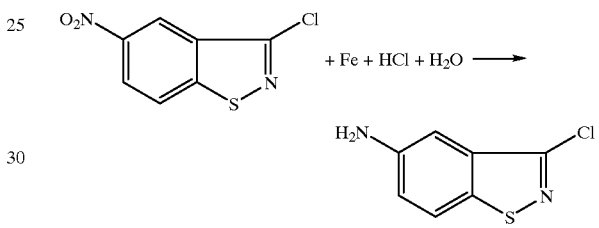

A solution of 3-chloro-5-nitro-1,2-benzisothiazole (2.00 g) in toluene is treated with iron powder (8.40 g, 325 mesh) and concentrated hydrochloric acid (8 drops), heated to reflux, treated dropwise with water (8.00 mL), refluxed for 35 minutes, cooled to room temperature, and filtered through diatomaceous earth. The resultant filtrate is concentrated in vacuo to obtain a residue. Flash column chromatography of the residue using silica gel and an ethyl acetate/hexanes solution (1:1) gives the title product.

EXAMPLE 74

Preparation of 3-(3-Chloro-1,2-benzisothiazol-5-yl)-6-(trifluoromethyl)-2,4(1H,3H)-pyrimidinedione

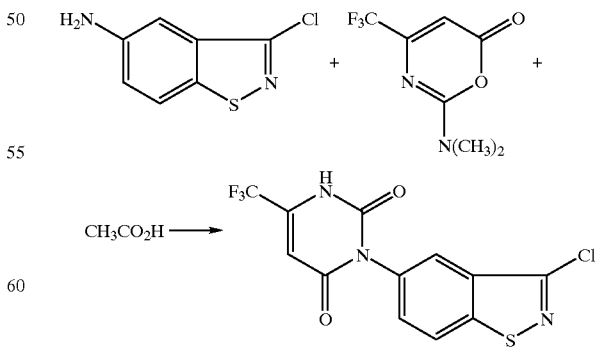

A mixture of 5-amino-3-chloro-1,2-benzisothiazole (1.10 g) and 2-dimethylamino-4-(trifluoromethyl)-6H-1,3-oxazin-6-one (1.38 g) in acetic acid (15.1 mL) is stirred at 90–105°

C. for two hours, cooled to room temperature, and filtered to obtain 0.500 g of the title product as a solid. The resultant filtrate is diluted with water and filtered to obtain an additional 1.11 g of the title product.

EXAMPLE 75

Preparation of 3-(3-Chloro-1,2-benzisothiazol-5-yl)-1-methyl-6-(trifluoromethyl)-2,4(1H,3H)-pyrimidinedione

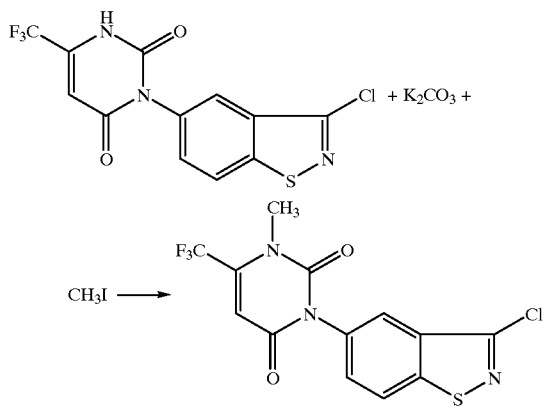

A mixture of 3-(3-chloro-1,2-benzisothiazol-5-yl)-6-(trifluoromethyl)-2,4(1H,3H)-pyrimidinedione (1.06 g), potassium carbonate (0.470 g) and iodomethane (0.500 mL) in N,N-dimethylformamide is stirred at room temperature for 90 minutes, treated with additional iodomethane (0.500 mL), stirred at room temperature for 15 minutes, and diluted with water. The resultant aqueous mixture is filtered to obtain a solid. The solid is washed with water and dried in a vacuum oven at room temperature to give the title product as a solid which is identified by NMR spectral analysis.

EXAMPLE 76

Preparation of 5-[3,6-Dihydro-3-methyl-2,6-dioxo-4-(trifluoromethyl)-1(2H)-pyrimidinyl]-1,2-benzisothiazole-3-malononitrile

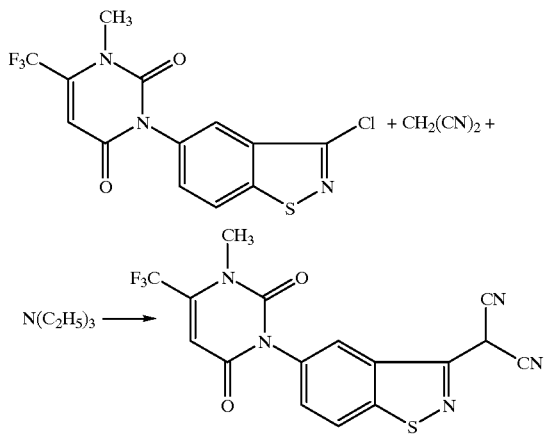

A mixture of 3-(3-chloro-1,2-benzisothiazol-5-yl)-1-methyl-6-(trifluoromethyl)-2,4(1H,3H)-pyrimidinedione (0.500 g), malononitrile (0.270 g) and triethylamine (1.50 g) in methyl sulfoxide is stirred at 60° C. for 15 minutes, cooled to room temperature, and diluted with water. The resultant aqueous mixture is extracted with ethyl acetate. The organic extract is washed with water, dried over anhydrous magnesium sulfate, and concentrated in vacuo to obtain a brown oil. The extracted aqueous phase is diluted with brine, acidified with concentrated hydrochloric acid, and extracted with ethyl acetate. The organic extract is dried over anhydrous magnesium sulfate and concentrated in vacuo to obtain a brown oil. Flash column chromatography of the combined oils using silica gel and an ethyl acetate/hexanes/methanol/acetic acid solution (10:10:4:1) gives the title product as an oil which is identified by NMR spectral analyses.

EXAMPLE 77

Preparation of 5-[3,6-Dihydro-3-methyl-2,6-dioxo-4-(trifluoromethyl)-1(2H)-pyrimidinyl]-1-2-benzisothiazole-3-acetonitrile

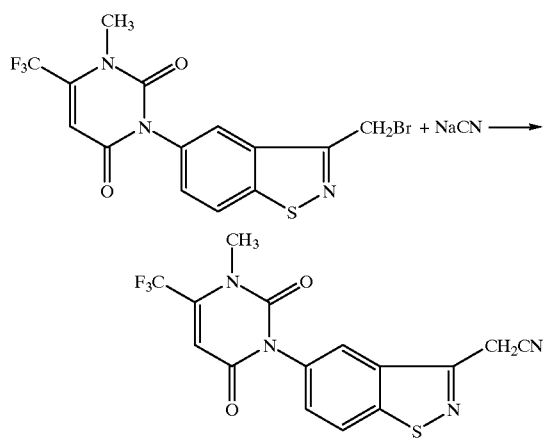

A mixture of 3-[3-(bromomethyl)-1,2-benzisothiazol-5-yl]-1-methyl-6-(trifluoromethyl)-2,4(1H,3H)-pyrimidinedione (0.420 g, 0.00100 mol) and sodium cyanide (0.0750 g, 0.00150 mol) in acetonitrile is stirred at room temperature overnight, and filtered to obtain a solid. The solid is dissolved in methylene-chloride and the resultant solution is dried over anhydrous sodium sulfate, and concentrated in vacuo to obtain an off-white solid. Column chromatography of the solid using silica gel and a 10% ethyl acetate in methylene chloride solution gives the title product as a white solid which is identified by NMR spectral analysis.

Using essentially the same procedure 5-[3,6-dihydro-3-methyl-2,6-dioxo-4-(trifluoromethyl)-1(2H)-pyrimidinyl]-1,2-benzisothiazole-6-fluoro-3-acetonitrile is obtained from 3-[3-(bromomethyl)-6-fluoro-1,2-benzisothiazol-5-yl]-1-methyl-6-(trifluoromethyl)-2,4(1H,3H)-pyrimidinedione.

EXAMPLE 78

Preparation of Ethyl 5-[3,6-dihydro-3-methyl-2,6-dioxo-4-(trifluoromethyl)-1(2H)-pyrimidinyl]-1,2-benzisothiazole-3-acetate

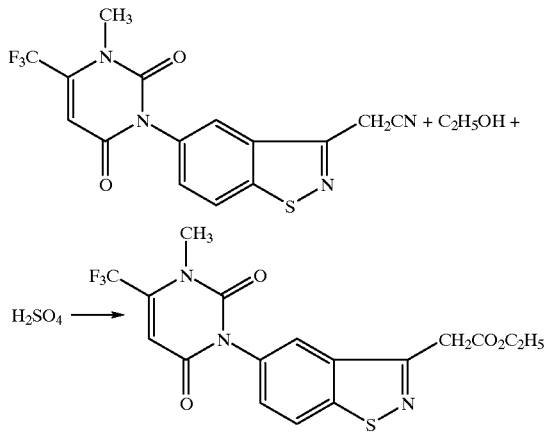

A mixture of 5-[3,6-dihydro-3-methyl-2,6-dioxo-4-(trifluoromethyl)-1(2H)-pyrimidinyl]-1,2-benzisothiazole-3-acetonitrile (1.00 g), ethanol (20.0 mL) and water (1.00 mL) is treated with concentrated sulfuric acid (10.0 mL), refluxed for 15 minutes, and poured into an ice-water mixture. The resultant aqueous mixture is extracted with methylene chloride. The combined organic extracts are washed sequentially with water, saturated sodium hydrogen carbonate solution and water, dried over anhydrous sodium sulfate, and concentrated in vacuo to obtain an orange foam. Column chromatography of the foam using silica gel and a 10% ethyl acetate in methylene chloride solution gives the title product as a solid which is identified by NMR spectral analysis.

EXAMPLE 79

Preparation of 5-[3,6-Dihydro-3-methyl-2,6-dioxo-4-(trifluoromethyl)-1(2H)-pyrimidinyl]-1,2-benzisothiazole-3-acetic acid

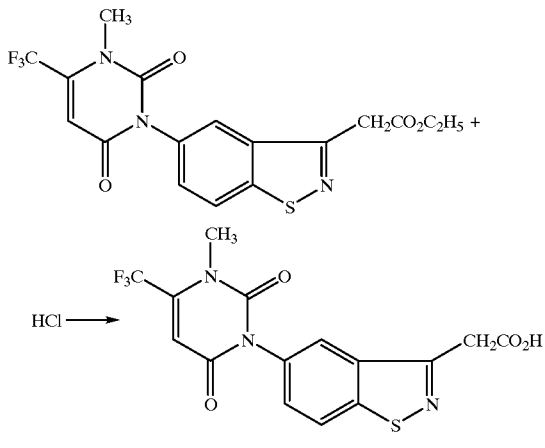

A mixture of ethyl 5-[3,6-dihydro-3-methyl-2,6-dioxo-4-(trifluoromethyl)-1(2H)-pyrimidinyl]-1,2-benzisothiazole-3-acetate (0.600 g), 10% hydrochloric acid (20.0 mL), and 1,2-dichloroethane (2.00 mL) is boiled for 30 minutes while allowing the 1,2-dichloroethane to evaporate, cooled, and poured onto ice. The resultant aqueous mixture is filtered to obtain a solid. The solid is washed with water and air-dried to give the title product as a white solid (0.550 g, mp 240–242° C.).

EXAMPLE 80

Preparation of Methyl 5-[3,6-dihydro-3-methyl-2,6-dioxo-4-(trifluoromethyl)-1(2H)-pyrimidinyl]-2-benzisothiazole-3-acetate

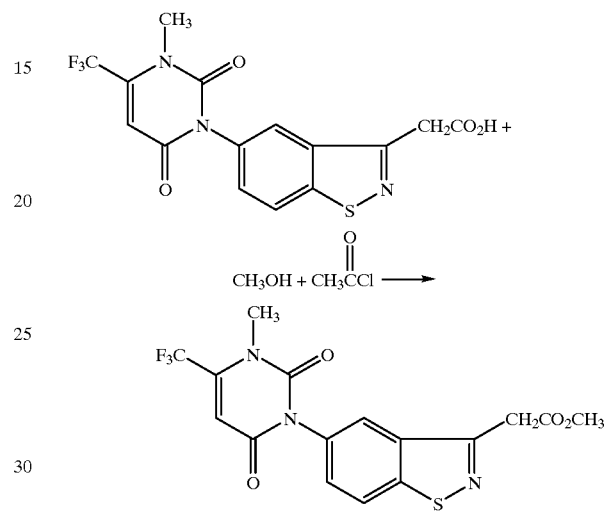

Acetyl chloride (11.0 mL) is added to methanol (110 mL) previously cooled with an ice-acetone bath. The resultant mixture is stirred at room temperature for 30 minutes, treated with 5-[3,6-dihydro-3-methyl-2,6-dioxo-4-(trifluoromethyl)-1(2H)-pyrimidinyl]-1,2-benzisothiazole-3-acetic acid (0.617 g, 1.60 mmol), refluxed for four hours, and poured into saturated sodium hydrogen carbonate solution. The resultant aqueous mixture is extracted with methylene chloride. The combined organic extracts are washed with water and concentrated in vacuo to obtain a residue. The residue is recrystallized from an acetone/hexanes solution to give the title product as a white solid (0.540 g, mp 175–176° C.).

EXAMPLE 81

Preparation of 5-[3,6-Dihydro-3-methyl-2,6-dioxo-4-(trifluoromethyl)-1(2H)-pyrimidinyl]-1,2-benzisothiazole-3-acetamide

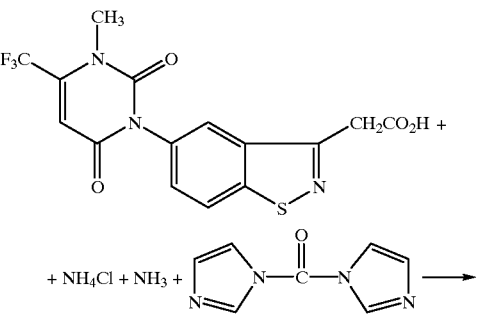

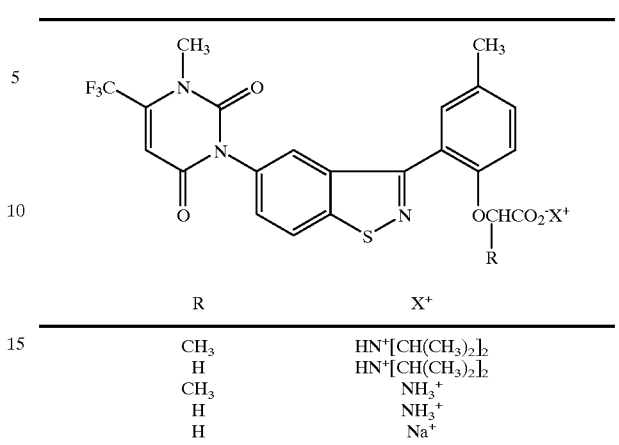

A mixture of 5-[3,6-dihydro-3-methyl-2,6-dioxo-4-(trifluoromethyl)-1(2H)-pyrimidinyl]-1,2-benzisothiazole-3-acetic acid (0.960 g, 0.00250 mol) and 1,1'-carbonyldiimidazole (0.420 g, 0.00259 mol) in tetrahydrofuran is stirred at room temperature for 4.5 hours, treated with ammonium chloride (0.230 g, 0.00430 mol), stirred overnight at room temperature, treated with concentrated ammonia (1.00 mL), stirred for 5 minutes, acidified with 10% hydrochloric acid, and concentrated in vacuo to obtain a residue. The residue is diluted with a 5% methanol in methylene chloride solution and the resultant mixture is stirred for three hours and filtered to obtain a solid. The solid is washed with a 5% methanol in methylene chloride solution, slurried in water, filtered, and dried to give the title product as a white solid which is identified by NMR spectral analysis.

EXAMPLE 82

Preparation of Sodium 2-{{2-{5-[3,6-dihydro-3-methyl-2,6-dioxo-4-(trifluoromethyl)-1(2H)-pyrimidinyl]-1,2-benzisothiazol-3-yl}-p-tolyl}oxy}propionate, DL-

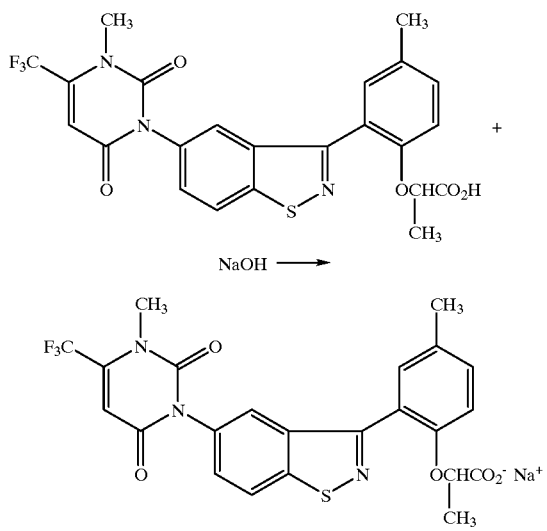

A mixture of 2-{{2-{5-[3,6-dihydro-3-methyl-2,6-dioxo-4-(trifluoromethyl)-1(2H)-pyrimidinyl]-1,2-benzisothiazol-3-yl}-p-tolyl}oxy}propionic acid (0.500 g) and sodium hydroxide (0.0360 g) in water is stirred at room temperature overnight, concentrated in vacuo to one-half volume, and filtered to give the title product as a solid which is identified by NMR spectral analysis.

Using essentially the same procedure, the following compounds are obtained:

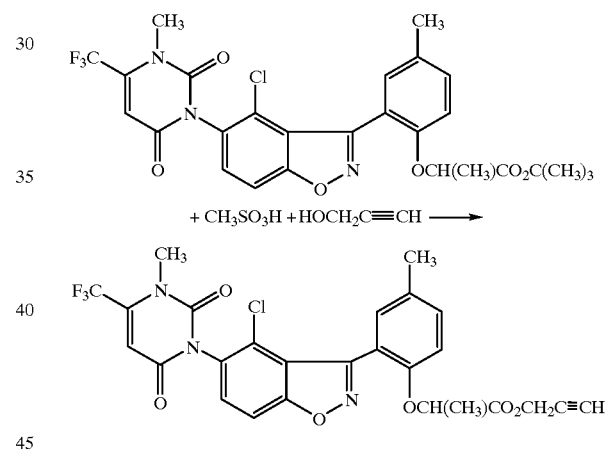

| R | $X^+$ |
|---|---|
| $CH_3$ | $HN^+[CH(CH_3)_2]_2$ |
| H | $HN^+[CH(CH_3)_2]_2$ |
| $CH_3$ | $NH_3^+$ |
| H | $NH_3^+$ |
| H | $Na^+$ |

EXAMPLE 83

Preparation of 2-Propynyl 2-{{2-{4-chloro-5-[3,6-dihydro-3-methyl-2,6-dioxo-4-(trifluoromethyl)-1(2H)-pyrimidinyl]-1,2-benzisoxazol-3-yl}-p-tolyl}oxy}propionate A mixture of tert-butyl 2-{{2-{4-chloro-5-[3,6-dihydro-3-methyl-2,6-dioxo-4-(trifluoromethyl)-1(2H)-pyrimidinyl]-1,2-benzisoxazol-3-yl}-p-tolyl}oxy}propionate (1.00 g, 0.00172 mol), propargyl alcohol (20.0 mL) and methanesulfonic acid (52.0 mg, 0.542 mmol) is stirred at 75–93° C. for 12 hours, stirred at room temperature for seven hours, and concentrated in vacuo to obtain a residue. The residue is diluted with methylene chloride and the resultant solution is passed through a silica gel slug and concentrated in vacuo to obtain a yellow gum. The gum is dissolved in diethyl ether and the resultant solution is washed with water, dried over anhydrous magnesium sulfate, and concentrated in vacuo to obtain a yellow gum. Column chromatography of the gum using silica gel and an ether/methylene chloride/hexanes solution (4:3:7) gives a foam. The foam is recrystallized from a methylene chloride/hexanes solution to provide the title product as a white solid, mp 137–147° C.

Using essentially the same procedure, the following compounds are obtained:

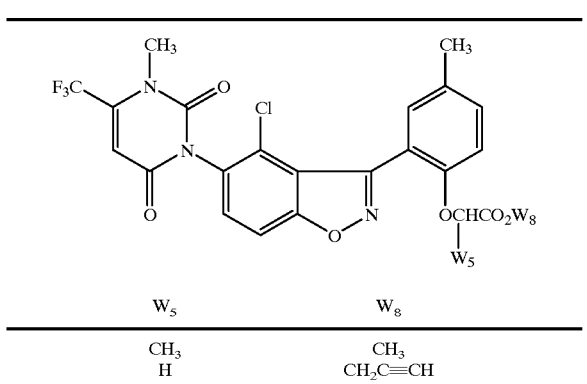

| $W_5$ | $W_8$ |
|---|---|
| $CH_3$ | $CH_3$ |
| H | $CH_2C{\equiv}CH$ |

EXAMPLE 84

Preparation of [(5-Nitro-1,2-benzisothiazol-3-yl)-oxy]acetonitrile

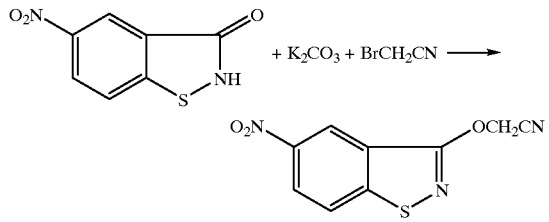

A mixture of 5-nitro-1,2-benzisothiazol-3(2H)-one (17.5 g, 89.2 mmol) in N,N-dimethylformamide is treated with potassium carbonate (18.5 g, 134 mmol), stirred at room temperature for 30 minutes, treated with bromoacetonitrile (16.0 g, 133 mmol), stirred at room temperature overnight, and poured onto ice. The resultant aqueous mixture is acidified to pH 3 with hydrochloric acid and extracted with ethyl acetate. The combined organic extracts are washed sequentially with water and brine, dried over anhydrous magnesium sulfate, and concentrated in vacuo to obtain a solid. Column chromatography of the solid using silica gel and methylene chloride gives the title product as a yellow solid (15.0 g, mp 123–124.5° C.).

Using essentially the same procedure, the following compounds are obtained:

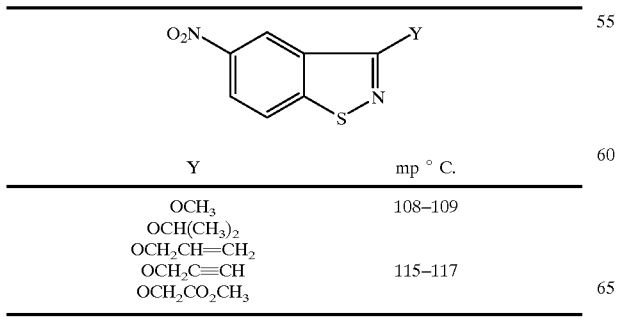

| Y | mp ° C. |
|---|---|
| $OCH_3$ | 108–109 |
| $OCH(CH_3)_2$ | |
| $OCH_2CH{=}CH_2$ | |
| $OCH_2C{\equiv}CH$ | 115–117 |
| $OCH_2CO_2CH_3$ | |

EXAMPLE 85

Preparation of [(5-Amino-1,2-benzisothiazol-3-yl)-oxy]acetonitrile

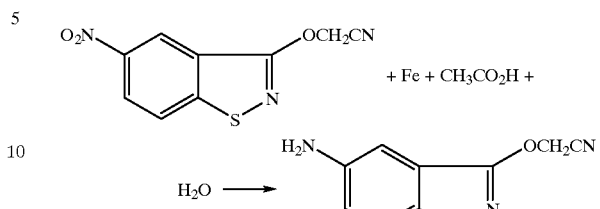

A mixture of iron powder (13.0 g, 0.233 mol) in a 5% acetic acid solution (65.0 mL) is heated to 50° C., treated portionwise with a mixture of [(5-nitro-1,2-benzisothiazol-3-yl)oxy]acetonitrile (11.0 g, 0.047 mol), acetic acid (100 mL) and ethyl acetate (65.0 mL), refluxed for two hours, cooled to 40° C., and filtered to remove solids. The phases are separated and the aqueous phase is extracted with ethyl acetate. The organic phase and the organic extracts are combined, washed sequentially with water and brine, dried over anhydrous magnesium sulfate, and concentrated in vacuo to give the title product as an oil which is identified by NMR spectral analysis.

Using essentially the same procedure, the following compounds are obtained:

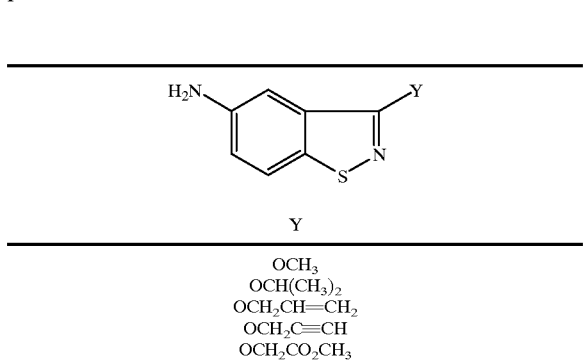

| Y |
|---|
| $OCH_3$ |
| $OCH(CH_3)_2$ |
| $OCH_2CH{=}CH_2$ |
| $OCH_2C{\equiv}CH$ |
| $OCH_2CO_2CH_3$ |

EXAMPLE 86

Preparation of {{5-[3,6-Dihydro-2,6-dioxo-4-(trifluoromethyl)-1(2H)-pyrimidinyl]-1,2-benzisothiazol-3-yl}oxy}acetonitrile

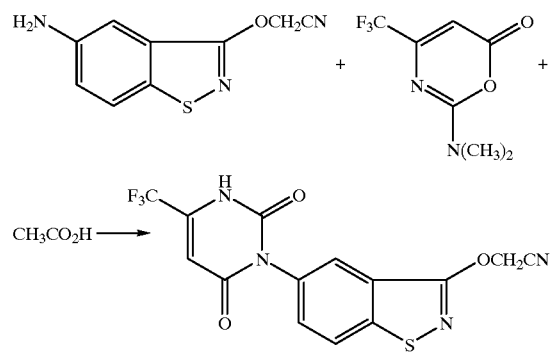

A mixture of [(5-amino-1,2-benzisothiazol-3-yl)oxy]acetonitrile (4.30 g, 21.0 mmol) and 2-dimethylamino-4-

(trifluoromethyl)-6H-1,3-oxazin-6-one (4.37 g, 21.0 mmol) in acetic acid is refluxed for three hours, stirred overnight at room temperature, and poured into an ice-water mixture. The resultant aqueous mixture is filtered to obtain a solid. The solid is washed with water and dried overnight in a vacuum oven at 55° C. to give the title product as a brown solid (2.63 g, mp 254–258° C.).

Using essentially the same procedure, the following compounds are obtained:

| Y | mp ° C. |
|---|---|
| $OCH_3$ | |
| $OCH(CH_3)_2$ | 180–185 |
| $OCH_2CH=CH_2$ | 210–212 |
| $OCH_2C\equiv CH$ | 212–215 |
| $OCH_2CO_2CH_3$ | |

EXAMPLE 87

Preparation of {{5-[3,6-Dihydro-3-methyl-2,6-dioxo-4-(trifluoromethyl)-1(2H)-pyrimidinyl]-1,2-benzisothiazol-3-yl}oxy}acetonitrile

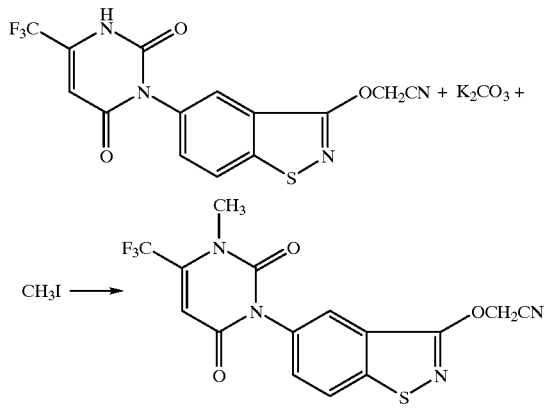

A mixture of {{5-[3,6-dihydro-2,6-dioxo-4-(trifluoromethyl)-1(2H)-pyrimidinyl]-1,2-benzisothiazol-3-yl}oxy}acetonitrile (2.63 g, 7.15 mmol) and potassium carbonate (1.97 g, 14.3 mmol) in N,N-dimethylformamide is stirred for 30 minutes, treated with iodomethane (2.03 g, 14.3 mmol), stirred overnight at room temperature, and poured into an ice-water mixture. The resultant aqueous mixture is filtered to obtain a solid. The solid is dissolved in ethyl acetate and the resultant solution is washed sequentially with water and brine, dried over anhydrous magnesium sulfate, and concentrated in vacuo to obtain a brown solid. Column chromatography of the solid using silica gel and methylene chloride affords a yellow solid. The yellow solid is recrystallized from a methylene chloride/hexanes solution to give the title product as an off-white solid, mp 265–266° C.

Using essentially the same procedure, the following compounds are obtained:

| Y | mp ° C. |
|---|---|
| $OCH_3$ | 198–199 |
| $OCH(CH_3)_2$ | 125–127 |
| $OCH_2CH=CH_2$ | 184–185 |
| $OCH_2C\equiv CH$ | 201–202.5 |
| $OCH_2CO_2CH_3$ | 181–183 |

EXAMPLE 88

Preparation of 3-[3-(Dichloromethyl)-1,2-benzisothiazol-5-yl]-1-methyl-6-(trifluoromethyl)-2,4(1H,3H)-pyrimidinedione

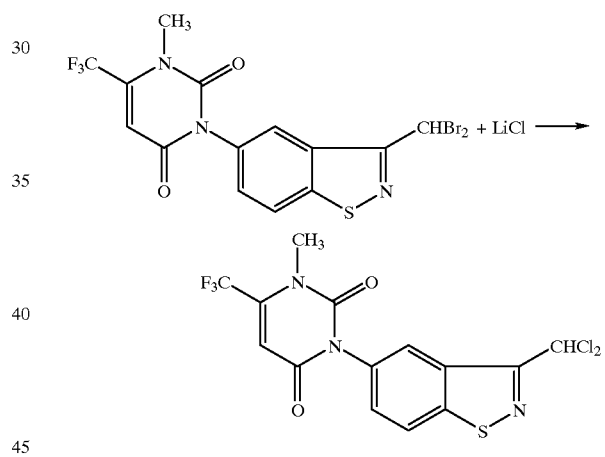

A solution of 3-[3-(dibromomethyl)-1,2-benzisothiazol-5-yl]-1-methyl-6-(trifluoromethyl)-2,4(1H,3H)-pyrimidinedione (0.750 g, 0.00150 mol) and lithium chloride (0.950 g, 0.0225 mol) in N,N-dimethylformamide is stirred at room temperature for 48 hours and diluted with ethyl acetate. The resultant mixture is washed sequentially with water and brine, dried over anhydrous magnesium sulfate, and concentrated in vacuo to obtain a foam. Column chromatography of the foam using silica gel, methylene chloride, and a 1% diethyl ether in methylene chloride solution gives the title product as a white foam (0.530 g, mp 148–149° C.).

Using essentially the same procedure, but substituting 3-[3-(bromomethyl)-1,2-benzisothiazol-5-yl]-1-methyl-6-(trifluoromethyl)-2,4(1H,3H)-pyrimidinedione for 3-[3-(dibromomethyl)-1,2-benzisothiazol-5-yl]-1-methyl-6-(trifluoromethyl)-2,4(1H,3H)-pyrimidinedione, 3-[3-(chloromethyl)-1,2-benzisothiazol-5-yl]-1-methyl-6-(trifluoromethyl)-2,4(1H,3H)-pyrimidinedione is obtained as a white solid, mp 201–203° C.

EXAMPLE 89

Preparation of 3-[3-(Fluoromethyl)-1,2-benzisothiazol-5-yl]-1-methyl-6-(trifluoromethyl)-2,4(1H,3H)-pyrimidinedione

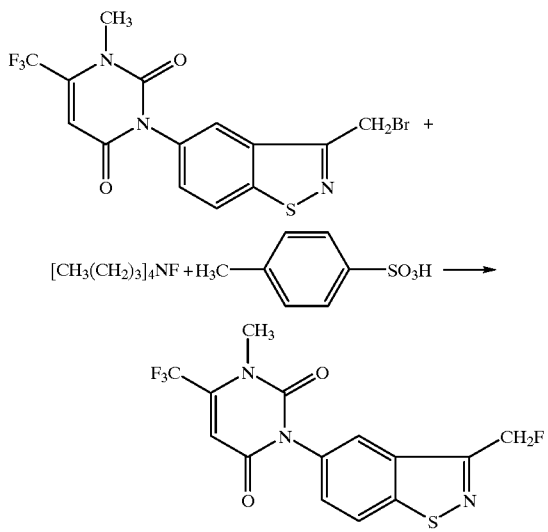

A solution of 3-[3-(bromomethyl)-1,2-benzisothiazol-5-yl]-1-methyl-6-(trifluoromethyl)-2,4(1H,3H)-pyrimidinedione (1.00 g, 0.00240 mol), 14.4 mL of a 1 M tetrabutylammonium fluoride in tetrahydrofuran solution (0.0144 mol) and anhydrous p-toluenesulfonic acid (1.36 g, 0.00790 mol) in tetrahydrofuran is stirred at room temperature for 30 minutes, refluxed for three hours, stirred at room temperature for three days, refluxed for 22 hours, partially concentrated in vacuo, and diluted with ethyl acetate. The resultant mixture is washed sequentially with water and brine, dried over anhydrous magnesium sulfate, and concentrated in vacuo to obtain an orange solid. Column chromatography of the solid using silica gel and a 2.5% diethyl ether in methylene chloride solution gives the title product as a white solid (0.42 g, mp 201–202° C.).

EXAMPLE 90

Preparation of 3-[3-(Difluoromethyl)-1,2-benzisothiazol-5-yl]-1-methyl-6-(trifluoromethyl)-2,4(1H3H)-pyrimidinedione

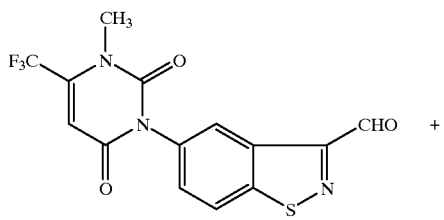

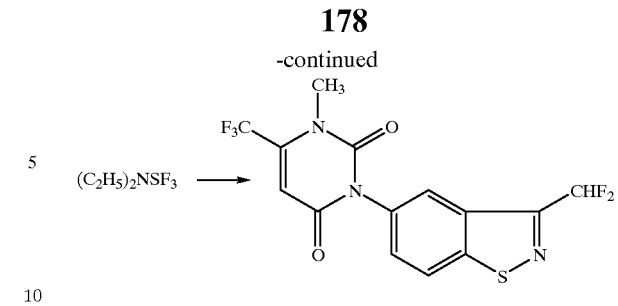

A solution of 5-[3,6-dihydro-3-methyl-2,6-dioxo-4-(trifluoromethyl)-1(2H)-pyrimidinyl]-1,2-benzisothiazole-3-carboxaldehyde (0.750 g, 0.00200 mol) and diethylaminosulfur trifluoride (0.260 mL, 0.00200 mol) in methylene chloride is stirred at room temperature for one hour, treated with additional diethylaminosulfur trifluoride (several drops), stirred at room temperature for 90 minutes, washed sequentially with water and brine, dried over anhydrous magnesium sulfate, and concentrated in vacuo to obtain a yellow solid. Flash column chromatography of the solid using silica gel and a 1% diethyl ether in methylene chloride solution gives the title product as a white solid (0.680 g, mp 183–184° C.).

EXAMPLE 91

Preparation of Diethyl{{5-[3,6-dihydro-3-methyl-2,6-dioxo-4-(trifluoromethyl)-1(2H)-pyrimidinyl]-1,2-benzisothiazol-3-yl}methyl}phosphonate

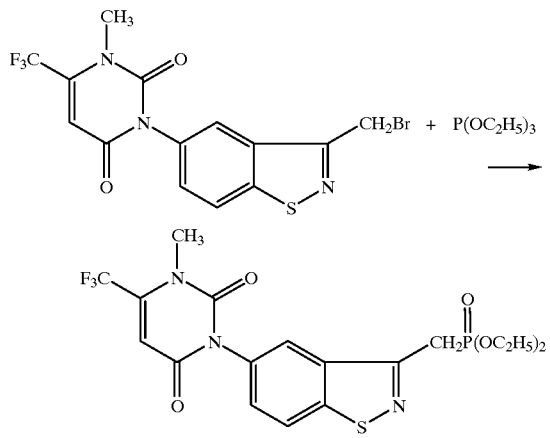

A mixture of 3-[3-(bromomethyl)-1,2-benzisothiazol-5-yl]-1-methyl-6-(trifluoromethyl)-2,4(1H,3H)-pyrimidinedione (1.00 g, 0.00240 mol) in diethyl ether is cooled to 10° C., treated dropwise with triethyl phosphite (0.580 mL, 0.00340 mol), stirred at 10° C. for 90 minutes, diluted with 10 mL of tetrahydrofuran, stirred at room temperature overnight, refluxed for 1 day, cooled, partially concentrated in vacuo and diluted with methylene chloride. The resultant organic solution is washed with water, dried over anhydrous magnesium sulfate, and concentrated in vacuo to obtain a yellow solid. Flash column chromatography of the solid using silica gel and a diethyl ether/methylene chloride solution (1:1) gives the title product as a white solid (0.930 g, mp 142–144° C.).

Using essentially the same procedure, with the appropriate trialkyl phosphite, the following compounds are obtained:

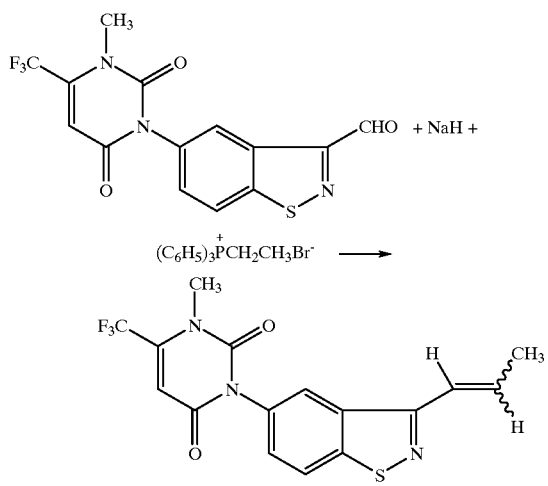

| X | R₂₃ | mp ° C. |
|---|-----|---------|
| H | CH₃ | 124–127 |
| H | CH(CH₃)₂ | 55–65 |
| F | CH₂CH₃ | 65–75 |

EXAMPLE 92

Preparation of {{5-[3,6-Dihydro-3-methyl-2,6-dioxo-4-(trifluoromethyl)-1(2H)-pyrimidinyl]-1,2-benzisothiazol-3-yl}methyl}phosphonic acid

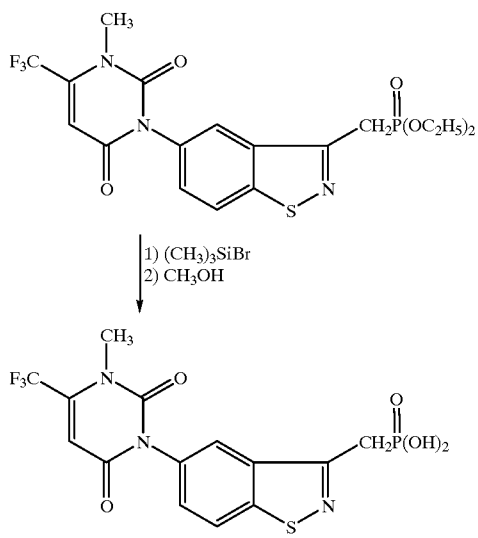

A solution of diethyl{{5-[3,6-dihydro-3-methyl-2,6-dioxo-4-(trifluoromethyl)-1(2H)-pyrimidinyl]-1,2-benzisothiazol-3-yl}methyl}phosphonate (1.00 g, 0.00210 mol) and bromotrimethylsilane (2.20 mL, 0.0168 mol) in methylene chloride (5.0 mL) is stirred at room temperature overnight and concentrated in vacuo to obtain a residue. The residue is diluted with methanol (10.0 mL), stirred at room temperature for 3.5 hours and concentrated in vacuo to obtain a tan solid. The solid is triturated in boiling methylene chloride, filtered and dried to give the title product as a beige solid (0.650 g, mp >230° C.).

EXAMPLE 93

Preparation of 1-Methyl-3-(3-propenyl-1,2-benzisothiazol-5-yl)-6-(trifluoromethyl)-2,4(1H,3H)-pyrimidinedione, (Z)- and 1-Methyl-3-propenyl-1,2-benzisothiazol-5-yl)-6-(trifluoromethyl)-2,4(1H,3H)-pyrimidinedione, (E)- and (Z)-, (3:1)

A mixture of (ethyl)triphenylphosphonium bromide (1.15 g, 0.00310 mol) in tetrahydrofuran is treated with sodium hydride (0.120 g, 0.00310 mol), stirred at room temperature for one hour, treated with a mixture of 5-[3,6-dihydro-3-methyl-2,6-dioxo-4-(trifluoromethyl)-1(2H)-pyrimidinyl]-1,2-benzisothiazole-3-carboxaldehyde (1.00 g, 0.00280 mol) in tetrahydrofuran, stirred at room temperature for one hour, and filtered. The resultant filtrate is partially concentrated in vacuo, diluted with methylene chloride, washed sequentially with water and brine, dried over anhydrous magnesium sulfate, and concentrated in vacuo to obtain an orange solid. Flash column chromatography of the solid using silica gel and a 1% diethyl ether in methylene chloride solution gives 1-methyl-3-(3-propenyl-1,2-benzisothiazol-5-yl)-6 -(trifluoromethyl)-2,4(1H,3H)-pyrimidinedione,(Z)- as a white solid (0.350 g, mp 200–201° C.) and 1-methyl-3-(3-propenyl-1,2-benzisothiazol-5-yl)-6-(trifluoromethyl)-2,4(1H,3H)-pyrimidinedione,(E)- and (Z)-, (3:1) as a white solid (0.450 g, mp 228–230° C.).

Following essentially the same procedure and using the appropriately substituted phosphonium bromide, the following compounds are obtained:

| W₁₀ | W₁₁ | mp ° C. |
|-----|-----|---------|
| CO₂CH₃ | H | >230 |
| C(O)CH₃ | H | >230 |

-continued

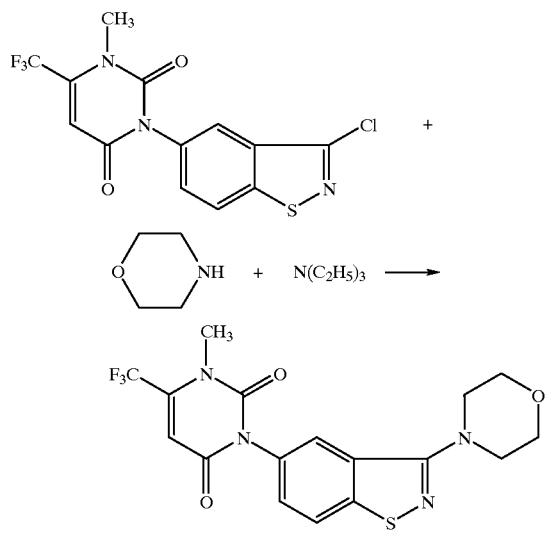

| $W_{10}$ | $W_{11}$ | mp °C. |
|---|---|---|
| CHO | H | >230 |
| CH$_2$Br | H | 235 (dec) |
| C(O)C$_6$H$_5$ | H | |
| C(O)N(CH$_3$)OCH$_3$ | H | |
| CO$_2$CH$_2$=CH$_2$ | H | |
| CHO | CH$_2$CH$_3$ | |

EXAMPLE 94

Preparation of 1-Methyl-3-(3-morpholino-1,2-benzisothiazol-5-yl)-6-(trifluoromethyl)-2,4(1H,3H)-pyrimidinedione A mixture of 3-(3-chloro-1,2-benzisothiazol-5-yl)-1-methyl-6-(trifluoromethyl)-2,4(1H,3H)-pyrimidinedione (0.300 g), morpholine (2.00 g) and triethylamine (5.00 g) in tetrahydrofuran is refluxed for 18 hours and concentrated in vacuo to obtain a residue. Column chromatography of the residue using silica gel and 25% and 50% ethyl acetate in heptane solutions gives the title product as a yellow solid (0.210 g, mp 200–205° C.).

Using essentially the same procedure, but using the appropriate amine, the following compounds are obtained:

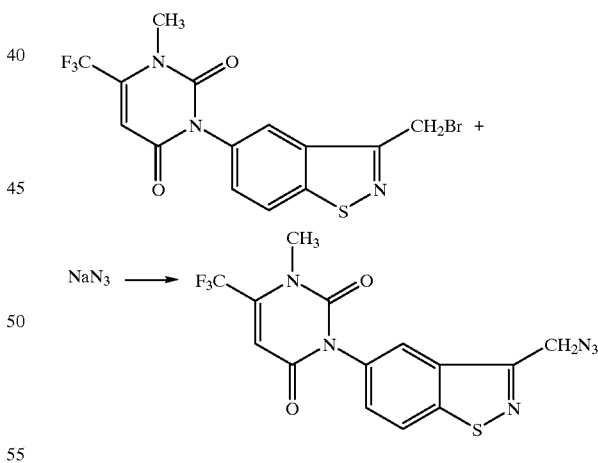

| Y | mp °C. |
|---|---|
| NHSO$_2$CH$_3$ | 135–145 |
| (piperazine) | 198–203 |
| N(C$_2$H$_5$)$_2$ | |
| (2-amino-4-trifluoromethyl-5-chlorothiazole) | >280 |

EXAMPLE 95

Preparation of 3-[3-(Azidomethyl)-1,2-benzisothiazol-5-yl]-1-methyl-6-(trifluoromethyl)-2,4(1H,3H)-pyrimidinedione A solution of 3-[3-(bromomethyl)-1,2-benzisothiazol-5-yl]-1-methyl-6-(trifluoromethyl)-2,4(1H,3H)-pyrimidinedione (2.00 g, 4.76 mmol) in N,N-dimethylformamide is treated with sodium azide (0.325 g, 5.00 mmol), stirred overnight at room temperature, treated with 18-crown-6, stirred at room temperature for two hours, and poured into an ice-water mixture. The resultant aqueous mixture is filtered to obtain a solid. The solid is washed with water and air-dried to give the title product as a white solid which is identified by NMR spectral analysis.

EXAMPLE 96

Preparation of Diethyl{{5-[3,6-dihydro-3-methyl-2,6-dioxo-4-(trifluoromethyl)-1(2H)-pyrimidinyl]-1,2-benzisothiazol-3-yl}methyl}phosphoramidate

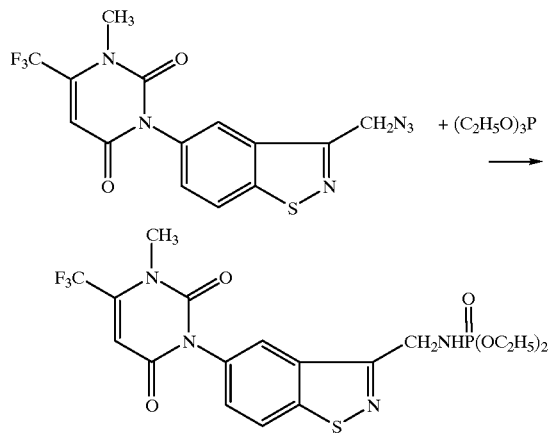

A mixture of 3-[3-(azidomethyl)-1,2-benzisothiazol-5-yl]-1-methyl-6-(trifluoromethyl)-2,4(1H,3H)-pyrimidinedione (1.61 g, 4.20 mmol) and triethyl phosphite (0.860 mL, 5.00 mmol) in dioxane is refluxed for 30 minutes, concentrated in vacuo, diluted with water and extracted with methylene chloride. The organic extracts are combined, dried over anhydrous magnesium sulfate, and concentrated in vacuo to obtain a yellow oil. Column chromatography of the oil using silica gel and 10% to 40% acetonitrile in methylene chloride solutions gives the title product as a yellow foam (1.00 g, mp 133–134° C.).

EXAMPLE 97

Preparation of tert-Butyl α-acetyl-5-[3,6-dihydro-3-methyl-2,6-dioxo-4-(trifluoromethyl)-1(2H)-pyrimidinyl]-1,2-benzisothiazole-3-propionate

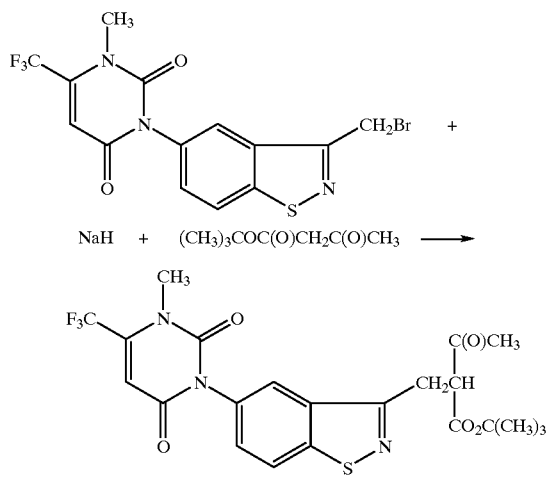

A mixture of sodium hydride (60% in oil, 0.293 g, 7.33 mmol) in tetrahydrofuran is cooled to 0° C., treated dropwise with a solution of tert-butyl acetoacetate (1.00 mL, 6.03 mmol) in tetrahydrofuran, and stirred for several minutes. The resultant mixture is added dropwise to a solution of 3-[3-(bromomethyl)-1,2-benzisothiazol-5-yl]-1-methyl-6-(trifluoromethyl)-2,4(1H,3H)-pyrimidinedione (1.40 g, 3.33 mmol) in methyl sulfoxide. After the addition is complete, the reaction mixture is poured into an ice-water mixture containing a trace of 10% hydrochloric acid. The resultant aqueous mixture is extracted with methylene chloride. the organic extracts are combined, dried over anhydrous magnesium sulfate, and concentrated in vacuo to obtain an oil. Column chromatography of the oil using silica gel and 0%, 2%, 3%, and 15% diethyl ether in methylene chloride solutions gives the title product as a solid, mp 76–78° C.

Using essentially the same procedure, the following compounds are obtained:

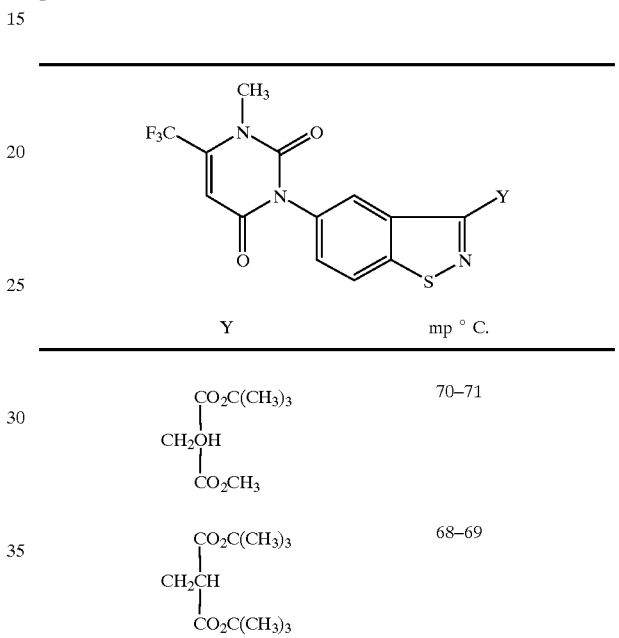

| Y | mp ° C. |
|---|---|
| CO$_2$C(CH$_3$)$_3$<br>\|<br>CH$_2$OH<br>\|<br>CO$_2$CH$_3$ | 70–71 |
| CO$_2$C(CH$_3$)$_3$<br>\|<br>CH$_2$CH<br>\|<br>CO$_2$C(CH$_3$)$_3$ | 68–69 |

EXAMPLE 98

Preparation of 1-Methyl-3-[3-(3-oxobutyl)-1,2-benzisothiazol-5-yl]-6-(trifluoromethyl)-2,4(1H,3H)-pyrimidinedione and α-Acetyl-5-[3,6-dihydro-3-methyl-2,6-dioxo-4-(trifluoromethyl)-1(2H)-pyrimidinyl]-1,2-benzisothiazole-3-propionic acid

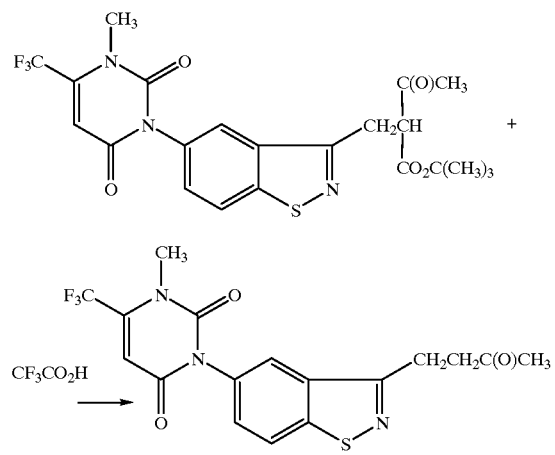

185

-continued

+

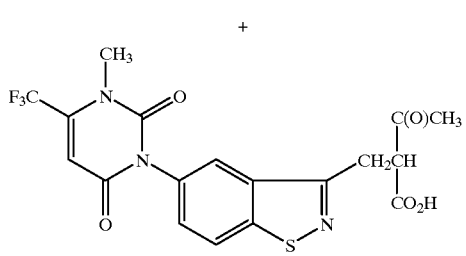

A mixture of tert-butyl α-acetyl-5-[3,6-dihydro-3-methyl-2,6-dioxo-4-(trifluoromethyl)-1(2H)-pyrimidinyl]-1,2-benzisothiazole-3-propionate (0.700 g) and trifluoroacetic acid (10.0 mL) in methylene chloride is stirred overnight at room temperature, concentrated in vacuo, and diluted with methylene chloride and saturated sodium hydrogen carbonate solution. The phases are separated. The organic phase is dried over anhydrous magnesium sulfate and concentrated in vacuo to give 1-methyl-3-[3-(3-oxobutyl)-1,2-benzisothiazol-5-yl]-6-(trifluoromethyl)-2,4(1H,3H)-pyrimidinedione as a white solid (0.310 g, mp 198–199° C.). The aqueous phase is acidified with concentrated hydrochloric acid, stirred for several minutes, and filtered to obtain a solid. The solid is washed with water and air-dried to give α-acetyl-5-[3,6-dihydro-3-methyl-2,6-dioxo-4-(trifluoromethyl)-1(2H)-pyrimidinyl]-1,2-benzisothiazole-3-propionic acid as a white solid, mp 191–193° C.

Using essentially the same procedure, the following compound is obtained:

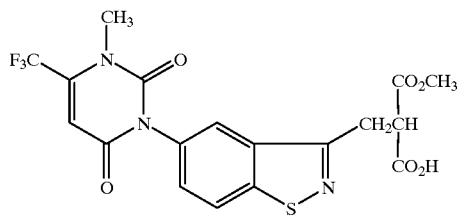

EXAMPLE 99

Preparation of Methyl 5-[3,6-dihydro-3-methyl-2,6-dioxo-4-(trifluoromethyl)-1(2H)-pyrimidinyl]-1,2-benzisothiazole-3-propionate

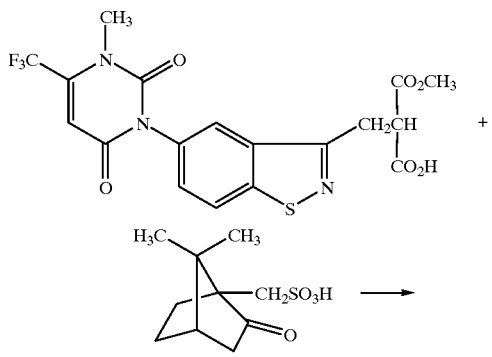

186

-continued

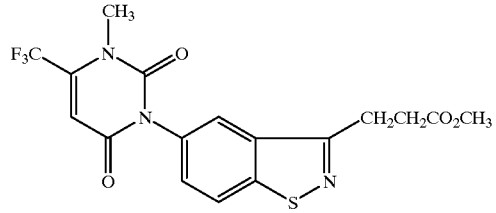

A mixture of monomethyl{5-[3,6-dihydro-3-methyl-2,6-dioxo-4-(trifluoromethyl)-1(2H)-pyrimidinyl)-1,2-benzisothiazol-3-yl}methyl}malonate (0.610 g) and camphor sulfonic acid (0.100 g) in toluene is refluxed for two hours, treated with additional camphor sulfonic acid (0.400 g), refluxed for three hours, concentrated in vacuo, diluted with 1,1,2,2-tetrachloroethane, refluxed for four hours, cooled to room temperature, concentrated in vacuo, and diluted with methylene chloride and saturated sodium hydrogen carbonate solution. The organic phase is separated, dried over anhydrous magnesium sulfate, and concentrated in vacuo to obtain a solid. The solid is stirred in hexanes for one hour, filtered, and dried to give the title product as a white solid (0.400 g, mp 176–178° C.).

EXAMPLE 100

Preparation of N-{{5-[3,6-Dihydro-3-methyl-2,6-dioxo-4-(trifluoromethyl)-1(2H)-pyrimidinyl[-1,2-benzisothiazole-3-yl}methyl}phthalimide

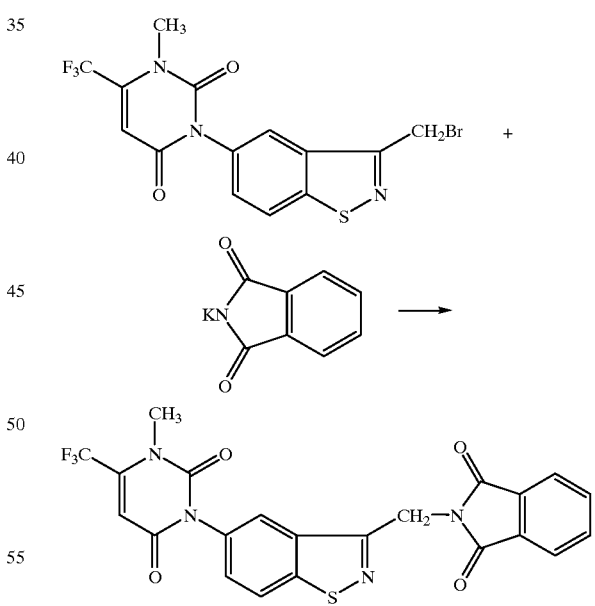

A mixture of 3-[3-(bromomethyl)-1,2-benzisothiazol-5-yl]-1-methyl-6-(trifluoromethyl)-2,4(1H,3H)-pyrimidinedione (0.750 g) and potassium phthalimide (0.350 g) in acetonitrile is refluxed for one hour, cooled to room temperature, and poured into an ice-water mixture. The resultant aqueous mixture is filtered to obtain a solid. The solid is washed with water and air-dried to give the title product (0.720 g, mp 204–208° C.).

EXAMPLE 101

Preparation of 3-[3-(o-Hydroxyphenyl)-1,2-benzisothiazol-5-yl]-1-methyl-6-(trifluoromethyl)-2,4(1H,3H)-pyrimidinedione trifluoromethylsulfonate (ester)

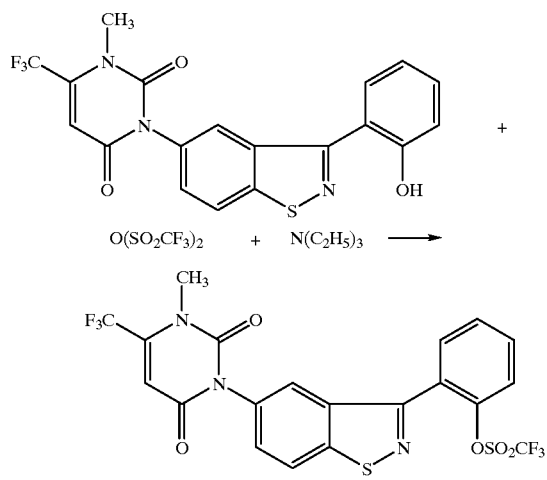

A mixture of 3-[3-(o-hydroxyphenyl)-1,2-benzisothiazol-5-yl]-1-methyl-6-(trifluoromethyl)-2,4(1H,3H)-pyrimidinedione (3.67 g, 8.75 mmol) and triethylamine (0.970 g, 9.63 mmol) in methylene chloride is cooled with an ice-water bath, treated with triflic anhydride (2.72 g, 9.63 mmol), stirred at room temperature overnight, and poured into water. The resultant aqueous mixture is extracted with methylene chloride. The organic extracts are combined, washed with brine, dried over anhydrous magnesium sulfate, and concentrated in vacuo to obtain an oil. Column chromatography of the oil using silica gel and a 3% diethyl ether in methylene chloride solution gives the title product as a white foam which is identified by NMR spectral analyses.

EXAMPLE 102

Preparation of Methyl o-{{5-[3,6-dihydro-3-methyl-2,6-dioxo-4-(trifluoromethyl)-1(2H)-pyrimidinyl]-1,2-benzisothiazol-3-yl}cinnamate

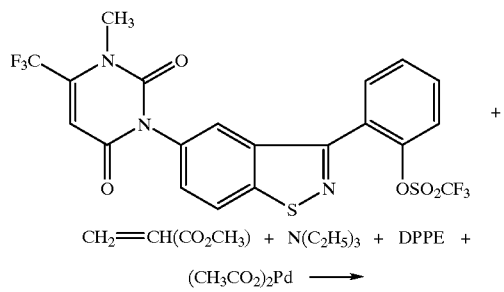

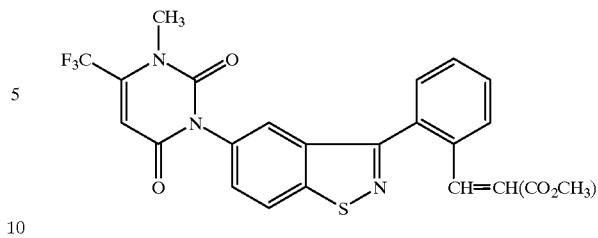

A solution of 3-[3-(o-hydroxyphenyl)-1,2-benzisothiazol-5-yl]-1-methyl-6-(trifluoromethyl)-2,4(1H,3H)-pyrimidinedione trifluoromethylsulfonate (ester) (1.00 g, 1.81 mmol) in N,N-dimethylformamide is treated sequentially with triethylamine (0.200 g, 1.99 mmol), methyl acrylate (0.310 g, 3.62 mmol), diphenylphosphinoethane (DPPE, 0.0220 g, 0.0500 mmol) and palladium(II) acetate (0.0100 g, 0.0450 mmol), stirred overnight at 100° C., cooled to room temperature, and poured into water. The resultant aqueous mixture is filtered to obtain a solid. The solid is washed with water and dissolved in methylene chloride. The resultant organic solution is washed sequentially with water and brine, dried over anhydrous magnesium sulfate, and concentrated in vacuo to obtain an oil. Column chromatography of the oil using silica gel and a 5% diethyl ether in methylene chloride solution affords an oil which is triturated with diethyl ether to give the title product as an off-white solid (0.460 g, mp 150–152° C.).

EXAMPLE 103

Preparation of a mixture of 3-[3-(Hydroxymethyl)-1,2-benzisothiazol-5-yl]-1-methyl-6-(trifluoromethyl)-2,4(1H,3H)-pyrimidinedione and 5-[3,6-Dihydro-3-methyl-2,6-dioxo-4-(trifluoromethyl)-1(2H)-pyrimidinyl]-1,2-benzisothiazole-3-carboxaldehyde, (2:3)

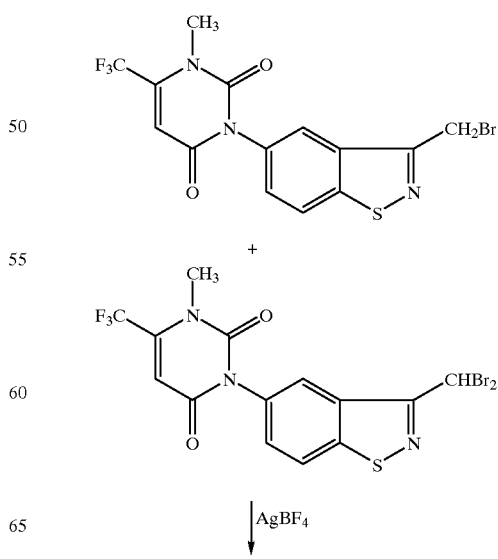

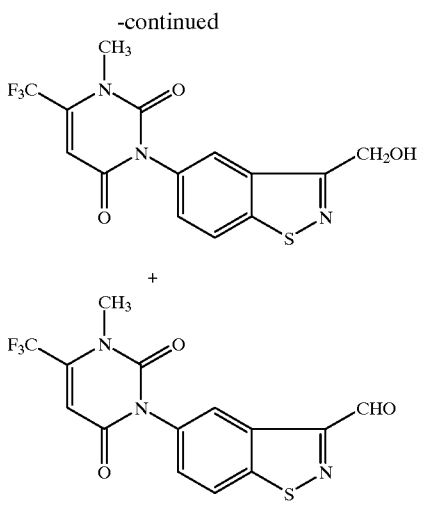

+

A solution of a 2:3 mixture of 3-[3-(bromomethyl)-1,2-benzisothiazol-5-yl]-1-methyl-6-(trifluoromethyl)-2,4(1H,3H)-pyrimidinedione and 3-[3-(dibromomethyl)-1,2-benzisothiazol-5-yl]-1-methyl-6-(trifluoromethyl)-2,4(1H,3H)-pyrimidinedione (5.00 g), silver tetrafluoroborate (3.50 g), 1,4-dioxane (30.0 mL) and water (10.0 mL) is refluxed for 2 hours, cooled, and filtered to remove solids. The resultant filtrate is poured into a methylene chloride and water mixture. The organic phase is separated, washed sequentially with water and brine, dried over anhydrous sodium sulfate, and concentrated in vacuo to give a 2:3 mixture of the title products.

EXAMPLE 104

Preparation of 5-[3,6-Dihydro-3-methyl-2,6-dioxo-4-(trifluoromethyl)-1(2H)-pyrimidinyl]-1,2-benzisothiazole-3-carboxylic acid

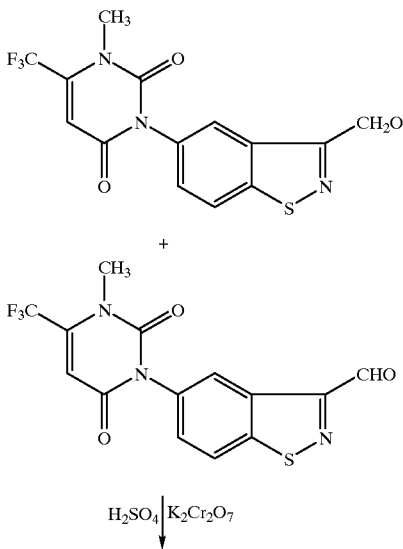

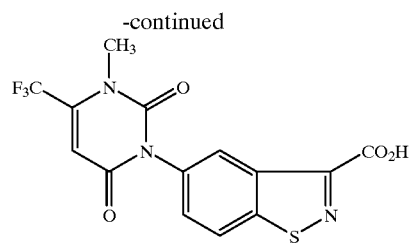

A solution of potassium dichromate (10.0 g) in 1.5 M sulfuric acid (200 mL) is cooled to 0° C., treated dropwise with a solution of a 2:3 mixture of 3-[3-(hydromethyl)-1,2-benzisothiazol-5-yl]-1-methyl-6-(trifluoromethyl)-2,4(1H,3H)-pyrimidinedione and 5-[3,6-dihydro-3-methyl-2,6-dioxo-4-(trifluoromethyl)-1(2H)-pyrimidinyl]-1,2-benzisothiazole-3-carboxaldehyde (12.0 g) in acetic acid, stirred at room temperature for 2 hours, and diluted with water. The resultant aqueous mixture is extracted with methylene chloride. The organic extracts are combined, washed sequentially with water and brine, dried over anhydrous sodium sulfate, and concentrated in vacuo to give the title product as a white solid (8.50 g, mp 149–152° C.).

EXAMPLE 105

Preparation of 5-[3,6-Dihydro-3-methyl-2,6-dioxo-4-(trifluoromethyl)-1(2H)-pyrimidinyl]-N-(methylsulfonyl)-1,2-benzisothiazole-3-carboxamide

A solution of 5-[3,6-dihydro-3-methyl-2,6-dioxo-4-(trifluoromethyl)-1(2H)-pyrimidinyl]-1,2-benzisothiazole-3-carboxylic acid (0.400 g, 1.08 mmol) in tetrahydrofuran is treated with 1,1'-carbonyldiimidazole (0.260 g, 1.58 mmol), stirred at room temperature for 30 minutes, refluxed for 2 hours, cooled to room temperature, treated dropwise with a solution of methanesulfonamide (0.130 g, 1.37 mmol) and 1,8-diazabicyclo[5.4.0]undec-7-ene (0.230 g, 1.50 mmol), stirred at room temperature for 3 hours, and poured into 0.5

N hydrochloric acid. The resultant aqueous mixture is extracted with methylene chloride. The organic extracts are combined, washed with brine, dried over anhydrous sodium sulfate, and concentrated in vacuo to obtain a residue. Column chromatography of the residue using silica gel and a methylene chloride/acetic acid solution (10:1) gives the title product as a white solid (0.350 g, 72%, mp 241–243° C.).

Using essentially the same procedure, but using the appropriately substituted sulfonamide, the following compounds are obtained:

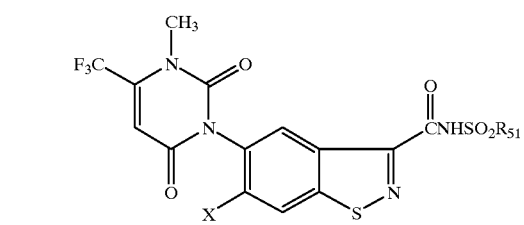

| X | $R_{51}$ | mp ° C. |
|---|---|---|
| H | $CH_2Cl$ | 190–192 |
| H | $CH_2$-C$_6$H$_5$ (benzyl) | 147–149 |
| H | 4-CH$_3$-C$_6$H$_4$- (p-tolyl) | 147–149 |
| H | 4-CH$_3$-C$_6$H$_4$- | 235–237 |
| H | 2-thienyl | 177–180 |
| H | $CH(CH_3)CH_2CH_3$ | >225 |
| H | 4-Cl-C$_6$H$_4$- | 217–219 |
| H | 2-naphthyl | 172–174 |
| H | $(CH_2)_{11}CH_3$ | |
| H | $CH(CH_3)_2$ | 156–158 |
| H | $CH_2CH_3$ | 197–200 |
| H | 2-$O_2N$-C$_6$H$_4$-CH$_2$- | >225 |

-continued

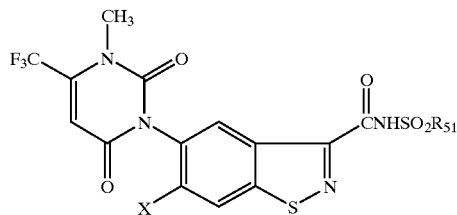

| X | $R_{51}$ | mp ° C. |
|---|---|---|
| H | 4-$C(CH_3)_3$-C$_6$H$_4$-CH$_2$- | >230 |
| H | 4-$OCF_3$-C$_6$H$_4$-CH$_2$- | >230 |
| H | $CH(CH_3)$-C$_6$H$_5$ | 215–220 |
| H | 4-CH$_3$-C$_6$H$_4$-CH$_2$- | 226–228 |
| H | 2-CH$_3$-C$_6$H$_4$-CH$_2$- | 155–159 |
| H | 4-Cl-C$_6$H$_4$-CH$_2$- | >220 |
| F | $CH_2C_6H_5$ | 120–125 |
| H | 3,5-(CH$_3$)$_2$-C$_6$H$_3$-CH$_2$- | 220–225 |
| H | $CH_2CH_2C_6H_5$ | >220 |
| H | 3-Cl-C$_6$H$_4$-CH$_2$- | 143–148 |
| H | $CH=CHC_6H_5$ | 198–203 |

EXAMPLE 106

Preparation of 2-{{2-[5-[3,6-Dihydro-3-methyl-2,6-dioxo-4-(trifluoromethyl)-1(2H)-pyrimidinyl]-6-fluoro-1,2-benzisoxazol-3-yl}-p-tolyl}oxy-N-(methylsulfonyl)acetamide

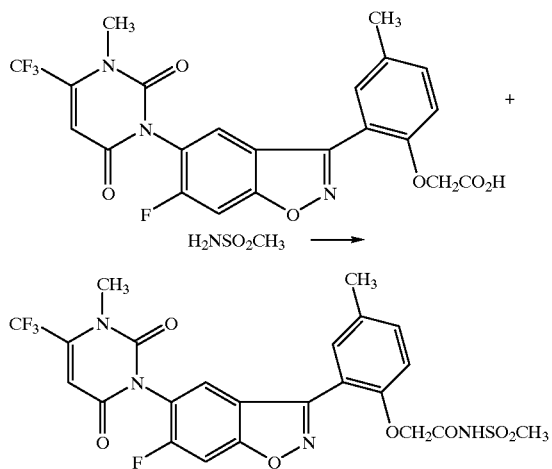

A solution of {{2-{5-[3,6-dihydro-3-methyl-2,6-dioxo-4-(trifluoromethyl)-1(2H)-pyrimidinyl]-6-fluoro-1,2-benzisoxazol-3-yl}-p-tolyl}oxy}acetic acid (1.54 g, 0.00312 mol) in tetrahydrofuran is added dropwise to a suspension of 1,1'-carbonyldiimidazole (1.06 g, 0.00655 mol) in tetrahydrofuran. The resultant mixture is stirred 1.5 hours and cooled to room temperature. A mixture of methanesulfonamide (0.594 g, 0.00624 mol), diazabicycloundecane (1.09 g, 0.00702 mol) and tetrahydrofuran is added dropwise. The resultant mixture is stirred overnight at room temperature and poured into 10% hydrochloric acid. The resultant white solid is filtered and dried to give the title compound (1.65 g, 91.6%, mp 123–125° C.) which is identified by NMR spectral analysis.

EXAMPLE 107

Preparation of N-{{2-{{5-[3,6-Dihydro-3-methyl-2,6-dioxo-4-(trifluoromethyl)-1(2H)-pyrimidinyl]-1,2-benzisoxazol-3-yl}-p-tolyl}oxy}acetyl}glycine, methyl ester

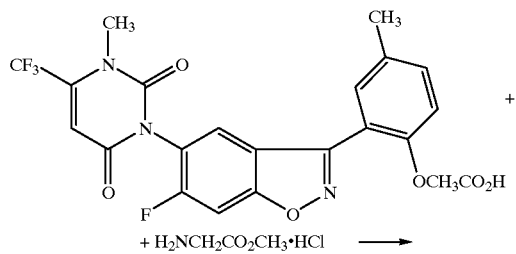

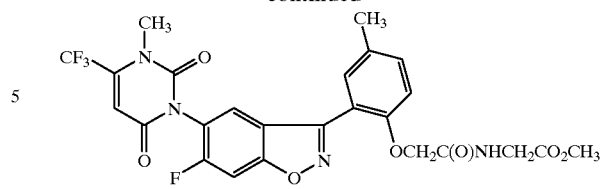

1,1'-Carbonyldiimidazole (0.340 g, 0.00203 mol) is added to a solution of {{2-{5-[3,6-dihydro-3-methyl-2,6-dioxo-4-(trifluoromethyl)-1(2H)-pyrimidinyl]-6-fluoro-1,2-benzisoxazol-3-yl}-p-tolyl}oxy}acetic acid (1.00 g, 0.00203 mol) in dimethylformamide at 0° C. The mixture is stirred 30 minutes at 0° C. and warmed to room temperature. Glycine methyl ester hydrochloride (0.260 g, 0.00207 mol) is added and the resultant mixture is stirred three days at room temperature. The mixture is diluted with water and filtered to afford a white solid, which is chromatographed on silica gel with ether:methylene chloride to afford the title compound as a white foam (0.830 g, 74.8%) which is identified by NMR spectral analysis.

EXAMPLE 108

Preparation of {{2-{5-[3,6-Dihydro-3-methyl-2,6-dioxo-4-(trifluoromethyl)-1(2H)-pyrimidinyl]-6-fluoro-1,2-benzisoxazol-3-yl}-p-tolyl}oxy}acetic acid

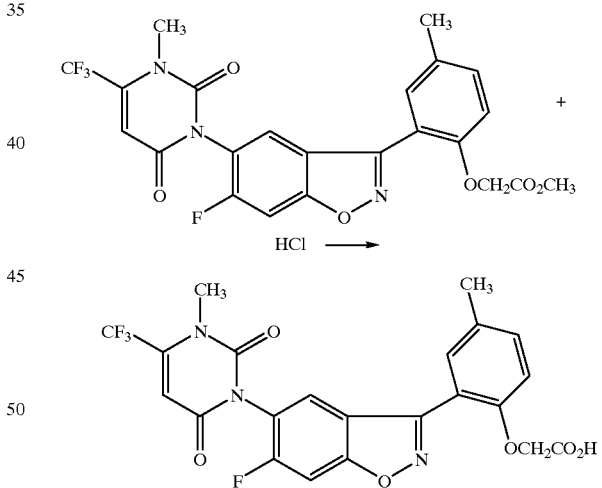

A mixture of {{2-{5-[3,6-dihydro-3-methyl-2,6-dioxo-4-(trifluoromethyl)-1(2H)-pyrimidinyl]-6-fluoro-1,2-benzisoxazol-3-yl}-p-tolyl}oxy}acetic acid, methyl ester (10.9 g, 0.0190 mol), 10% hydrochloric acid and acetic acid is stirred two hours at 90° C., cooled, poured into water and extracted with ethyl acetate. The organic layers are combined, washed with water and brine, dried over anhydrous sodium sulfate, filtered and concentrated in vacuo to a foam. The foam is recrystallized from ethyl acetate to afford the title compound as a white solid (6.20 g, 66.2%, mp 123–126° C.).

EXAMPLE 109

Preparation of 2-{{2-{5-[3,6-Dihydro-3-methyl-2,6-dioxo-4-(trifluoromethyl)-1(2H)-pyrimidinyl]-1,2-benzisothiazol-3-yl}-p-tolyl}oxy}-2-methylpropionic acid, 2-propynyl ester

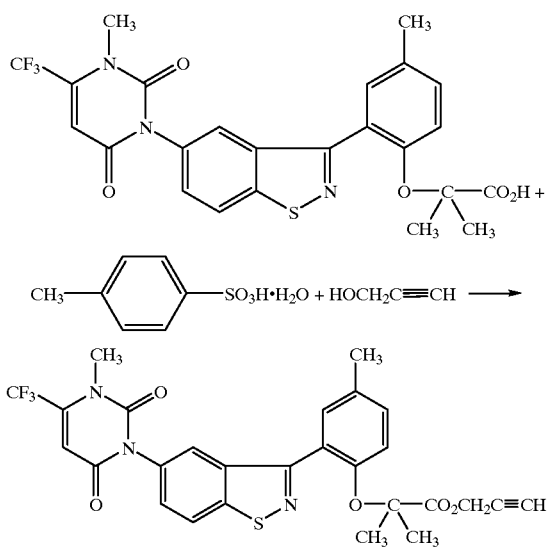

A mixture of 2-{{2-{5-[3,6-dihydro-3-methyl-2,6-dioxo-4-(trifluoromethyl)-1(2H)-pyrimidinyl]-1,2-benzisothiazol-3-yl}-p-tolyl}oxy}-2-methylpropionic acid (0.500 g, 0.000960 mol), p-toluenesulfonic acid (0.0100 g), propargyl alcohol (0.0538 g, 0.000960 mol) and toluene is stirred one day at 50° C., cooled to room temperature and concentrated in vacuo to obtain a residue. Chromatography of the residue on silica gel with ether:methylene chloride affords the title compound (0.360 g, 67.2%) which is identified by NMR spectral analysis.

Following essentially the same procedure, but using the appropriate carboxylic acids and alcohols, the following compounds are obtained:

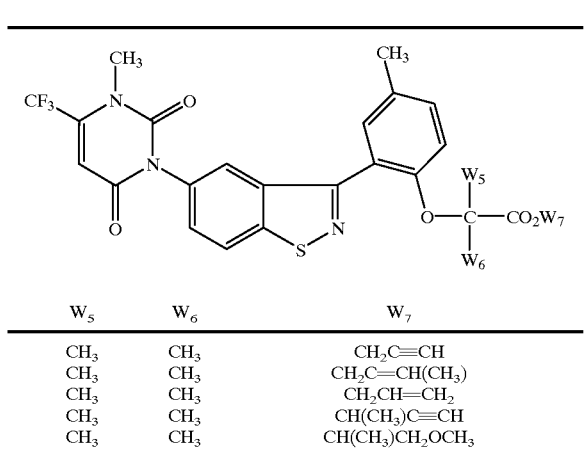

| $W_5$ | $W_6$ | $W_7$ |
|---|---|---|
| $CH_3$ | $CH_3$ | $CH_2C≡CH$ |
| $CH_3$ | $CH_3$ | $CH_2C=CH(CH_3)$ |
| $CH_3$ | $CH_3$ | $CH_2CH=CH_2$ |
| $CH_3$ | $CH_3$ | $CH(CH_3)C≡CH$ |
| $CH_3$ | $CH_3$ | $CH(CH_3)CH_2OCH_3$ |
| H | H | $(CH_2)_3O(CH_2)_3OCH_3$ |

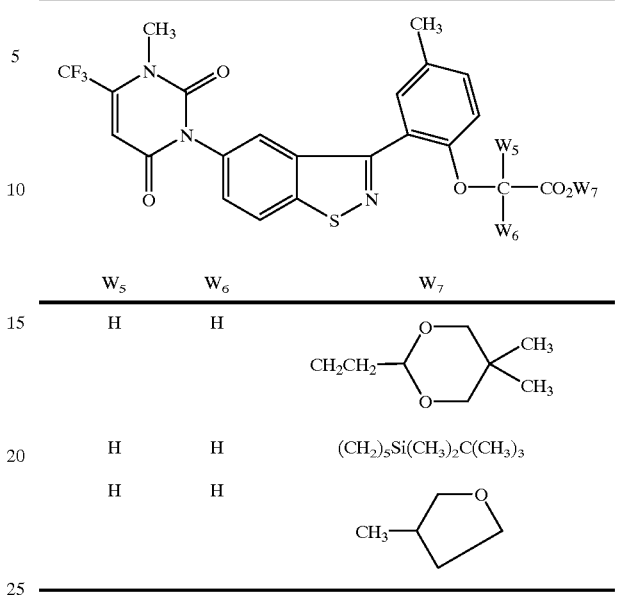

| $W_5$ | $W_6$ | $W_7$ |
|---|---|---|
| H | H | $CH_2CH_2$-[1,3-dioxane-5,5-(CH_3)_2] |
| H | H | $(CH_2)_5Si(CH_3)_2C(CH_3)_3$ |
| H | H | $CH_3$-tetrahydrofuran-3-yl |

EXAMPLE 110

Preparation of 3-[3-(2-Hydroxy-3-iodo-m-tolyl)-1,2-benzisothiazol-5-yl]-1-methyl-6-(trifluoromethyl)-2,4(1H,3H)-pyrimidinedione

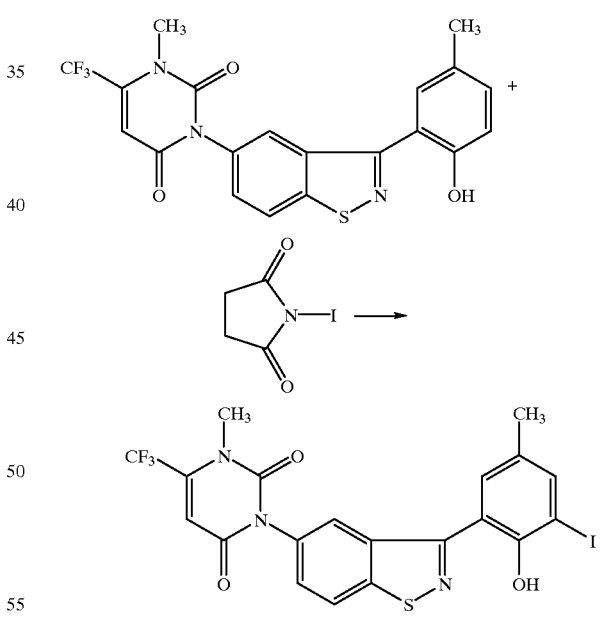

A solution of N-iodosuccinimide (0.240 g, 0.00107 mol) in acetone is added dropwise to a solution of 3-[3-(2-hydroxy-m-tolyl)-1,2-benzisothiazol-5-yl]-1-methyl-6-(trifluoromethyl)-2,4(1H,3H)-pyrimidinedione (0.430 g, 0.000992 mol) in acetone and the resultant mixture is stirred overnight at room temperature. Additional N-iodosuccinimide (0.120 g, 0.000635 mol) is added and the mixture is stirred three hours at room temperature. The mixture is concentrated in vacuo to afford a red gum which is chromatographed on silica gel with ether:methylene chloride. The fractions containing the title compound are washed with 1M sodium thiosulfate and brine, dried over anyhdrous magnesium sulfate and concentrated in vacuo to afford the title compound as a yellow solid (0.280 g, 46.8%, mp 241–242° C.).

EXAMPLE 111

Preparation of 3-[3-(5-Iodo-2-methoxy-p-tolyl)-1,2-benzisothiazol-5-yl]-1-methyl-6-(trifluoromethyl)-2,4(1H,3H)-pyrimidinedione

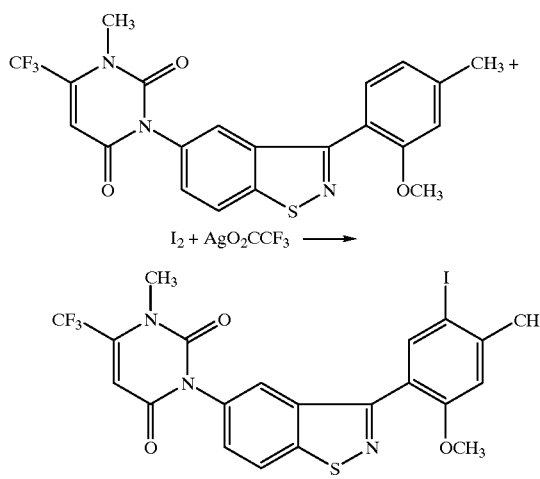

A mixture of 3-[3-(6-methoxy-p-tolyl)-1,2-benzisothiazol-5-yl]-1-methyl-6-(trifluoromethyl)-2,4(1H,3H)-pyrimidinedione (1.34 g, 0.00300 mol), silver trifluoroacetate and methylene chloride is treated with iodine (1.14 g, 0.00450 mol) in portions, stirred overnight at room temperature, diluted with methylene chloride, washed with 1M sodium thiosulfate and brine, dried over anhydrous magnesium sulfate, and concentrated in vacuo to a brown oil which solidifies on standing. Recrystallization from ether affords the title compound as a light yellow crystalline solid (1.50 g, 87.2%, mp 210–212° C.).

EXAMPLE 112

Preparation of 3-[3-(α,α-Dibromo-2-methoxy-p-tolyl)-1,2-benzisothiazol-5-yl]-1-methyl-6-(trifluoromethyl)-2,4(1H,3H)-pyrimidinedione

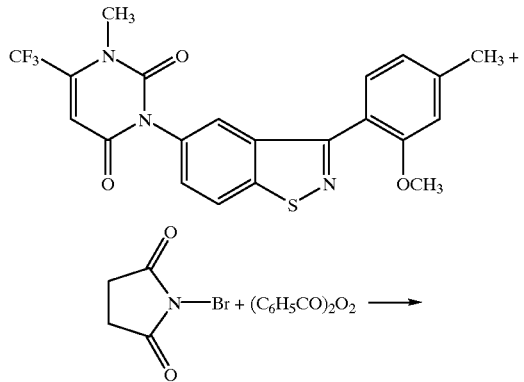

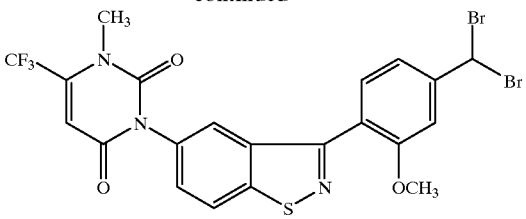

A mixture of 3-[3-(2-methoxy-p-tolyl)-1,2-benzisothiazol-5-yl]-1-methyl-6-(trifluoromethyl)-2,4-(1H,3H)-pyrimidinedione (1.34 g, 0.00300 mol), N-bromosuccinimide (1.39 g, 0.00780 mol), benzoyl peroxide (0.200 g) and carbon tetrachloride is stirred three hours at reflux and filtered hot. The filtrate is cooled to room temperature and concentrated in vacuo. The residue is chromatographed on silica gel with ether:methylene chloride to afford the title compound as a white foam (0.640 g, 35.3%) which is identified by NMR spectral analysis.

EXAMPLE 113

Preparation of 5-Nitro-1,2-benzisothiazole

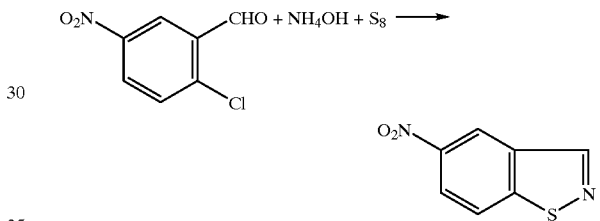

To a mixture of ammonium hydroxide (1000 ml) and N,N-dimethylformamide is added 2-chloro-5-nitrobenzaldehyde (300 g, 1.62 mol) and sulfur (54.4 g, 1.70 mol). The mixture is heated slowly to and stirred at 90° C. for one hour, cooled to room temperature, poured onto ice, and diluted with water. Filtration affords the title compound as a yellow solid (277.1 g, 94.9%).

EXAMPLE 114

Preparation of 3-Chloro-5-nitro-1,2-benzisothiazole

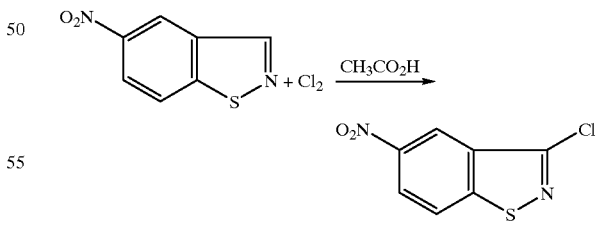

A suspension of 5-nitro-1,2-benzisothiazole (271 g, 1.50 mol) in acetic acid is heated to 80° C. to form a solution. The heating source is removed and chlorine gas is added continuously over six hours at 70–80° C. until saturation of the mixture occurs. The mixture is cooled to room temperature and stirred overnight. Filtration affords the title compound as a yellow crystalline solid (237 g, 73.6%) which is identified by NMR spectral analysis.

EXAMPLE 115

Preparation of 2'-Chloro-2-methyl-2-carboethoxy propiophenone

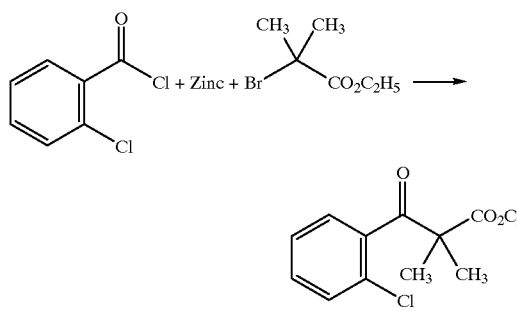

A mixture of 2-chlorobenzoyl chloride (52.2 g, 0.298 mol), ethyl 2-bromoisobutyrate (58.2 g, 0.298 mol) and ether is added in portions to zinc foil (19.5 g, 0.298 mol) and the resultant mixture stirred at reflux for three hours and overnight at room temperature. The mixture is poured into cold, dilute sulfuric acid and the organic layer is washed with saturated sodium bicarbonate and brine, dried over anhydrous magnesium sulfate and concentrated in vacuo to a yellow oil. The oil is chromatographed on silica gel with hexanes:ethyl acetate to afford the title compound as a colorless oil (41.8 g, 55.1%).

EXAMPLE 116

Preparation of 2'-Chloro-5'-nitro-2-methyl-2-carboethoxypropiophenone

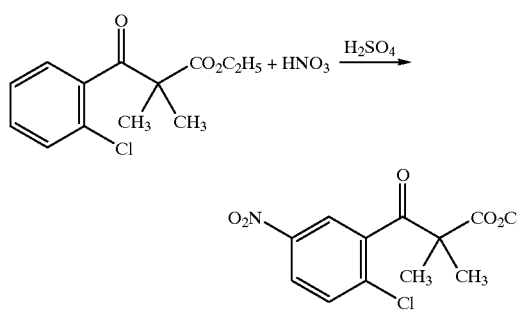

To concentrated sulfuric acid (15.0 ml) at 5° C. is added 2'-chloro-2-methyl-2-carboethoxypropiophenone (4.00 g, 0.01570 mol) followed by dropwise addition of concentrated nitric acid (90%, 0.740 ml, 0.0204 mol). After stirring 5 minutes, the mixture is poured onto ice and extracted with ethyl acetate. The organic layers are washed with saturated sodium bicarbonate and brine, dried over anhydrous magnesium sulfate, filtered and concentrated in vacuo to afford the title compound as a yellow oil (3.90 g, 83.0%) which is identified by NMR spectral analysis.

EXAMPLE 117

Preparation of Ethyl α,α-dimethyl-5-nitro-1,2-benzisothiazole-3-acetate

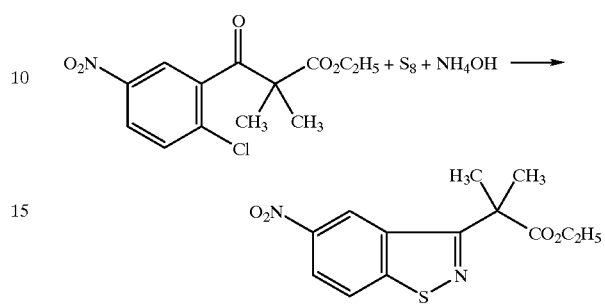

A mixture of 2'-chloro-5'-nitro-2-methyl-2-carboethoxypropiophenone (3.24 g, 0.00108 mol), N,N-dimethylformamide and sulfur (0.350 g, 0.00109 mol) is treated dropwise with ammonium hydroxide (9 ml), heated to and stirred at 70–80° C. for two hours, cooled to room temperature, and diluted with water. Filtration affords the title compound as a solid (2.49 g, 78.3%, mp 75–77° C.) which is identified by NMR spectral analysis.

EXAMPLE 118

Preparation of 1-Benzothiophen-2,3-dione

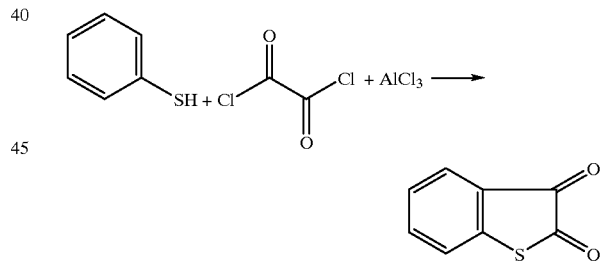

To a solution of thiophenol (100 g, 0.907 mol) in ether is added dropwise a solution of oxalyl chloride (175 g, 1.38 mol) in ether. The mixture is stirred two hours at reflux and concentrated in vacuo. The residue is taken up in methylene chloride and cooled to 0° C. Aluminum chloride (145 g, 1.09 mol) is added in portions such that the temperature does not exceed 25° C. The resultant mixture is stirred 30 minutes at reflux, cooled to room temperature and poured into ice water with stirring. The organic layer is washed with saturated sodium bicarbonate, water and brine, dried over anhydrous magnesium sulfate, filtered and concentrated in vacuo to an orange solid which is recrystallized from methylene chloride:hexanes to afford the title compound (102 g, 69.0%) which is identified by NMR spectral analysis.

EXAMPLE 119

Preparation of 1,2-Benzisothiazole-3-carboxamide

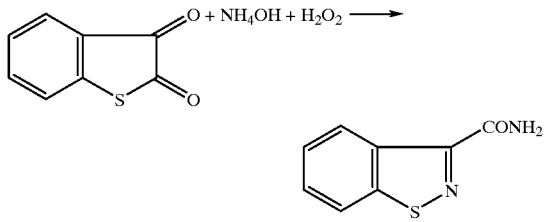

To ammonium hydroxide (1.78 l) is added 1-benzothiophen-2,3-dione (87.0 g, 0.530 mol) at 5–10° C., followed by hydrogen peroxide (30% aqueous, 178 ml). The resultant mixture is filtered to obtain a yellow solid which is dried (77.0 g, 81.7%) and identified as the title compound by NMR and IR spectral analysis.

EXAMPLE 120

Preparation of 3-Cyano-5-nitro-1,2-benzisothiazole

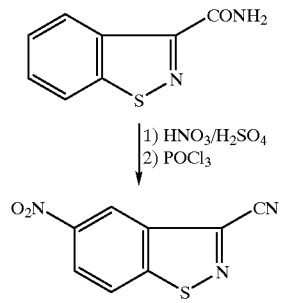

A solution of 1,2-benzisothiazole-3-carboxamide (12.0 g, 0.0674 mol) in concentrated sulfuric acid at 0–5° C. is treated dropwise with nitric acid (90%, 4.12 ml) such that the temperature does not exceed 10° C., stirred one hour at 5° C., and poured into ice water with vigorous stirring. The resultant suspension is filtered to obtain a solid. The solid is dried and recrystallized from acetonitrile to afford a white solid (10.0 g) which is treated with phosphorus oxychloride (60.0 ml). The resultant mixture is stirred at 90–100° C. for 90 minutes, cooled to room temperature, slowly poured into ice water with stirring, and filtered to obtain a solid. Recrystallization of the solid from methylene chloride:hexanes gives the title compound as an orange solid (8.00 g, 87.9%, mp 168–170° C.) which is identified by NMR and IR spectral analyses.

EXAMPLE 121

Preparation of 2,4-Difluoro-5-nitrobenzoyl chloride

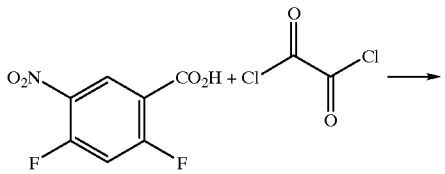

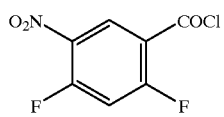

Oxalyl chloride (94.0 g, 0.739 mol) is added dropwise to a mixture of 2,4-difluoro-5-nitrobenzoic acid (100.0 g, 0.492 mol), methylene chloride and N,N-dimethylformamide (0.600 ml). The resultant mixture is stirred 3.25 hours at reflux, cooled to room temperature, and concentrated in vacuo to afford the title compound as a brown oil (111 g, 95.2%).

EXAMPLE 122

Preparation of 2,4-Difluoro-2-methoxy-5-methyl-5'-nitrobenzophenone

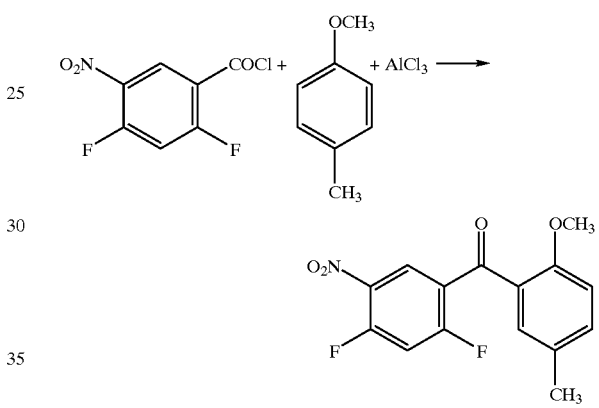

A mixture of aluminum chloride (62.3 g, 0.467 mol) and methylene chloride is cooled to −20° C. to −10° C., treated with 4-methylanisole (60.1 g, 0.492 mol), treated dropwise with a mixture of 2,4-difluoro-5-nitrobenzoyl chloride (111 g, 0.468 mol) and methylene chloride over a 10 minute period, warmed to 0° C., stirred overnight at ambient temperature, slowly poured onto ice with stirring, and diluted with methylene chloride. The organic layer is washed with water and brine, dried over anhydrous magnesium sulfate and concentrated in vacuo to a solid. The solid is recrystallized from acetonitrile to afford the title compound as a yellow solid (82.1 g, 54.0%) which is identified by NMR spectral analysis.

EXAMPLE 123

Preparation of 3-(6-Methoxy-m-tolyl)-6-amino-5-nitro-1,2-benzisothiazole

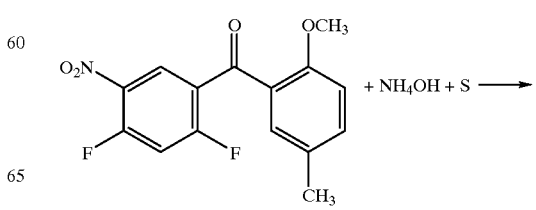

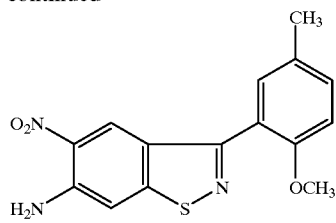

Ammonium hydroxide (330 ml) is added to a suspension of 2',4'-difluoro-2-methoxy-5-methyl-5'-nitrobenzophenone (60.0 g, 0.186 mol), sulfur (6.25 g, 0.195 mol) and N,N-dimethylformamide on an ice bath. The resultant mixture is allowed to warm to 35° C., heated gradually to 81° C. over a two hour period, cooled to room temperature, and poured into water. The resultant solid is taken up in ethyl acetate and N,N-dimethylformamide, and washed with water. The organic layer is concentrated in vacuo to afford the title compound which is identified by NMR spectral analysis.

EXAMPLE 124

Preparation of 3-(6-Methoxy-m-tolyl)-6-chloro-5-nitro-1,2-benzisothiazole

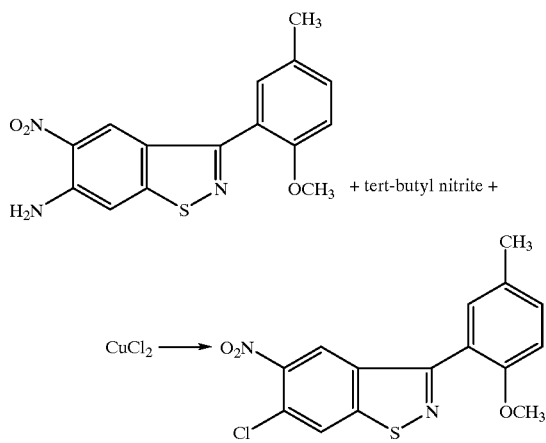

A mixture of tert-butyl nitrite (5.90 g, 0.0571 mol), copper chloride (6.20 g, 0.0457 mol) and acetonitrile is heated to 65–75° C., treated with 3-(6-methoxy-m-tolyl)-6-amino-5-nitro-1,2-benzisothiazole (12.0 g, 0.0381 mol) over 10 minutes, stirred for two hours at 67–75° C., treated with tert-butyl nitrite (1.50 ml) and copper chloride (1.00 g), stirred 40 minutes at 67–75° C., cooled to room temperature, and diluted with ethyl acetate. The organic layer is washed with 10% hydrochloric acid and filtered. The filtrate is washed with water and concentrated in vacua to afford the title compound as a solid (10.6 g, 83.1%) which is identified by NMR and IR spectral analyses.

EXAMPLE 125

Preparation of 3-(6-Methoxy-m-tolyl)-6-fluoro-5-nitro-1,2-benzisothiazole

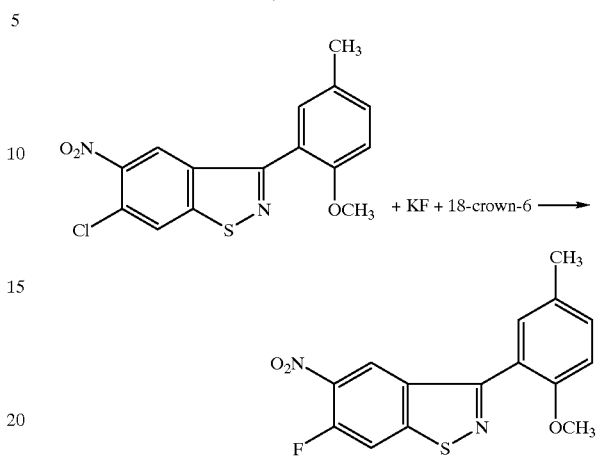

A mixture of 3-(6-methoxy-m-tolyl)-6-chloro-5-nitro-1,2-benzisothiazole (7.30 g, 0.0218 mol), potassium fluoride (6.33 g, 0.109 mol) 18-crown-6 (2.31 g, 0.0872 mol) and sulfolane is stirred 19 hours at 154° C., cooled to room temperature, and poured into ice water. The resultant solid is filtered and chromatographed on silica gel with methylene chloride to afford a solid which is recrystallized from acetonitrile to afford a tan powder. The powder is recrystallized from ethyl acetate to give the title compound as a tan solid (2.09 g, 29.9%) which is identified by NMR spectral analysis.

EXAMPLE 126

Preparation of 5-Amino-4-bromo-6-fluoro-3-methyl-1,2-benzisothiazole

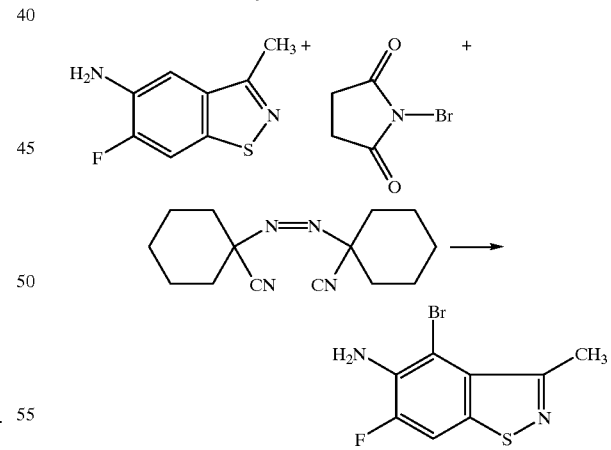

To a solution of 5-amino-6-fluoro-3-methyl-1,2-benzisothiazole (0.600 g, 0.00329 mol) in 1,2-dichloroethane is added N-bromosuccinimide (0.586 g, 0.00329 mol) followed by 1,1'-azobis (cyclohexanecarbonitrile) (0.0200 g). The mixture is stirred two hours at 70° C., additional N-bromosuccinimide (0.240 g, 0.00135 mol) is added, and the mixture is stirred 40 minutes at 70° C. The mixture is then cooled to room temperature, filtered and concentrated in vacuo to obtain a residue. The residue is chromatographed on silica gel to give the title compound (0.870 g, 100%) which is identified by NMR spectral analysis.

EXAMPLE 127

Preparation of 5-Chloro-1-methyl-3-(3-methyl-1,2-benzisothiazol-5-yl)-6-(trifluoromethyl)-2,4(1H,3H)-pyrimidinedione

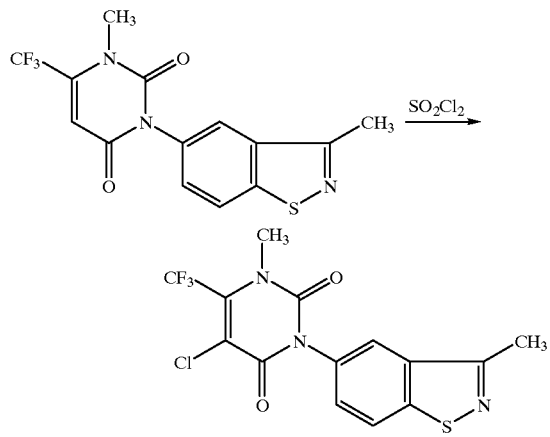

A mixture of 1-methyl-3-(3-methyl-1,2-benzisothiazol-5-yl)-6-(trifluoromethyl)-2,4(1H,3H)-pyrimidinedione (1.00 g, 0.00293 mol), sulfuryl chloride (2.00 g 0.0148 mol) and 1,2-dichloroethane is stirred for five hours at reflux, cooled to room temperature, and diluted with methylene chloride. The resultant mixture is washed with saturated sodium bicarbonate and brine, dried over anhydrous sodium sulfate, filtered and concentrated in vacuo to obtain a residue. The residue is chromatographed on silica gel with ethyl acetate/hexanes to afford the title product as a white solid (0.350 g, 31.8%, mp 252–254° C.) which is identified by NMR spectral analysis.

EXAMPLE 128

Preparation of 3-[3-(1-Bromoethyl)-1,2-benzisothiazol-5-yl]-1-methyl-6-(trifluoromethyl)-2,4(1H,3H)-pyrimidinedione and 3-[3-(1,1-dibromoethyl)-1,2-benzisothiazol-5-yl]-1-methyl-6-(trifluoromethyl)-2,4(1H,3H)-pyrimidinedione

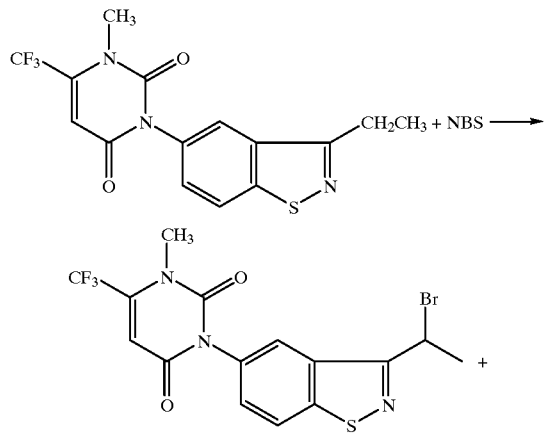

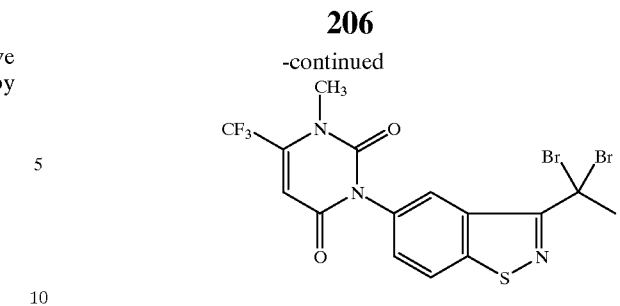

A mixture of 1-methyl-3-(3-methyl-1,2-benzisothiazol-5-yl)-6-(trifluoromethyl)-2,4(1H,3H)-pyrimidinedione (1.44 g, 0.00405 mol), N-bromosuccinimide (0.790 g, 0.00446 mol) and 1,2-dichloroethane is stirred under a 150 watt lamp for one hour at 60° C., cooled to room temperature, and concentrated in vacuo to a yellow solid. The yellow solid is flash chromatographed on silica gel with 80% to 70% hexanes:ethyl acetate to afford the 1,1-dibromoethyl benzisothiazole as a white foam (0.0600 g, 2.88%) and the 1-bromoethyl benzisothiazole as white crystals (1.73 g, 98.9%, mp 163° C.). Both products are identified by NMR spectral analyses.

In a similar manner, treatment of the above substrate with N-chlorosuccinimide affords 3-[3-(1-chloroethyl)-1,2-benzisothiazol-5-yl]-1-methyl-6-(trifluoromethyl)-2,4(1H,3H)-pyrimidinedione as a white solid, mp 169–171° C.

EXAMPLE 129

Preparation of 3-[3-(Bromochloromethyl)-1,2-benzisothiazol-5-yl]-1-methyl-6-(trifluoromethyl)-2,4(1H,3H)-pyrimidinedione

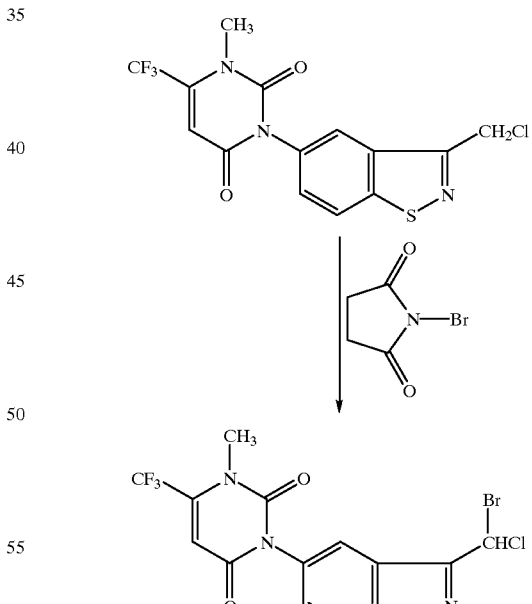

A mixture of 3-[3-(chloromethyl)-1,2-benzisothiazol-5-yl]-1-methyl-6-(trifluoromethyl)-2,4(1H,3H)-pyrimidinedione (1.00 g, 0.00266 mol), azo-bis-isobutyronitrile (0.100 g), N-bromosuccinimide (0.712 g, 0.00400 mol) and 1,2-dichloroethane is stirred one hour at reflux. Additional azo-bis-isobutyronitrile (0.0500 g) and N-bromosuccinimide (0.100 g) are added and the mixture is stirred two hours at reflux, cooled to room temperature, diluted with methylene chloride, washed with water, dried over anhydrous magnesium sulfate, and concentrated in vacuo to an orange gum. Chromatography of the gum on silica gel with methylene chloride:ether gives the title compound as a white foam (0.950 g, 80.2%, mp 93–96° C.) which is identified by NMR spectral analysis.

EXAMPLE 130

Preparation of Methyl 5-[3,6-dihydro-3-methyl-2,6-dioxo-4-(trifluoromethyl)-1(2H)-pyrimidinyl]-α-bromo-1,2-benzisothiazole-3-acetate

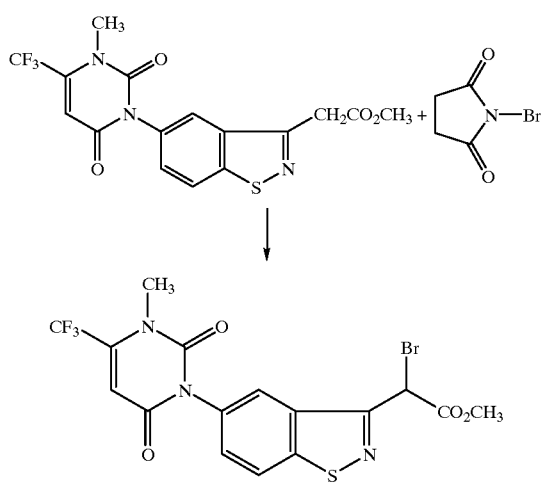

A mixture of methyl 5-[3,6-dihydro-3-methyl-2,6-dioxo-4-(trifluoromethyl)-1(2H)-pyrimidinyl]-1,2-benzisothiazole-3-acetate (0.400 g, 0.00100 mol), N-bromosuccinimide (0.370 g, 0.00210 mol), benzoyl peroxide (0.0100 g) and tetrachloroethane is stirred 2.5 hours at reflux, cooled to room temperature, and chromatographed on silica gel with methylene chloride to afford the title compound as an off-white solid (0.430 g, 90.0%, mp 84–87° C.) which is identified by NMR spectral analysis.

EXAMPLE 131

Preparation of 3-[3-(2-Bromoethyl)-1,2-benzisothiazol-5-yl]-1-methyl-6-(trifluoromethyl)-2,4(1H,3H)-pyrimidinedione

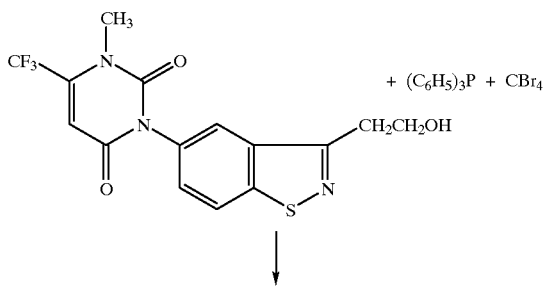

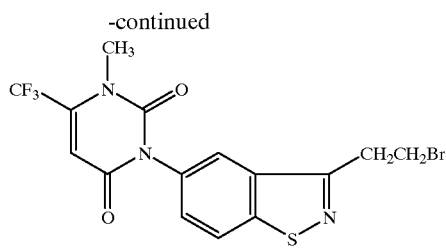

To a solution of 3-[3-(2-hydroxyethyl)-1,2-benzisothiazol-5-yl]-1-methyl-6-(trifluoromethyl)-2,4(1H,3H)-pyrimidinedione (0.690 g, 0.00185 mol) in methylene chloride is added carbon tetrabromide (0.655 g, 0.00197 mol) followed by triphenylphosphine (0.517 g, 0.00197 mol). The mixture is stirred three hours at ambient temperature and treated with additional carbon tetrabromide (0.328 g, 0.000988 mol) and triphenyl phosphine (0.259 g, 0.000987 mol). The resultant mixture is stirred 85 minutes, diluted with methanol, and concentrated in vacuo. The resultant solid is taken up in methylene chloride, washed with saturated sodium bicarbonate and water, dried over anhydrous sodium sulfate, filtered, and concentrated in vacuo to a yellow solid. The yellow solid is chromatographed on silica gel with methylene chloride to give the title product as an off-white solid (0.530 g, 66.0%) which is identified by NMR and elemental analyses.

EXAMPLE 132

Preparation of 3-[3-(2,2-Dibromovinyl)-1,2-benzisothiazol-5-yl]-1-methyl-6-(trifluoromethyl)-2,4(1H,3H)-pyrimidinedione

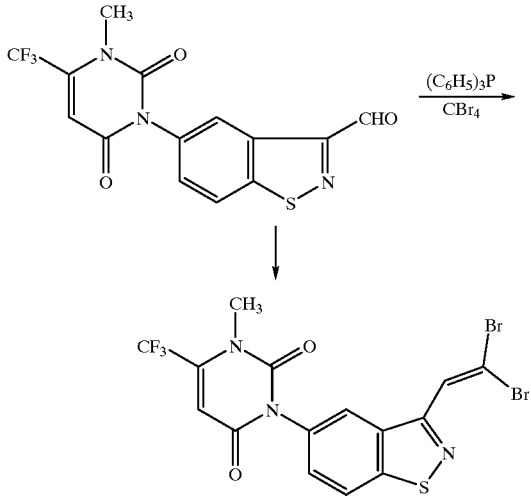

Triphenylphosphine (0.354 g, 0.00138 mol) is added to a solution of carbon tetrabromide (0.223 g, 0.000676 mol) in methylene chloride. The resultant mixture is stirred at room temperature for 10 minutes and treated dropwise with a solution of 5-[3,6-dihydro-3-methyl-2,6-dioxo-4-(trifluoromethyl)-1(2H)-pyrimidinyl]-1,2-benzisothiazole-3-carboxaldehyde (0.200 g, 0.000563 mol) in methylene chloride. The resultant mixture is stirred 20 minutes and concentrated in vacuo. The resultant residue is purified by flash column chromatography using silica gel and 10:1 methylene chloride/ethyl acetate to give the title product as a white solid (0.240 g, 83.6%, mp 260–262° C.) which is identified by NMR and IR spectral analyses.

Using essentially the same procedure, the following compounds are obtained:

| $W_{10}$ | $W_{11}$ | mp ° C. |
|---|---|---|
| Br | F | |
| Cl | Cl | 254–256 |

EXAMPLE 133

Preparation of (1R,2S)-3-[3-(1,2-Dibromopropyl)-1,2-benzisothiazol-5-yl]-1-methyl-6-(trifluoromethyl)-2,4-(1H,3H)-pyrimidinedione and (1R,2R)-3-[3-(1,2-Dibromopropyl)-1,2-benzisothiazol-5-yl]-1-methyl-6-(trifluoromethyl)-2,4(1H,3H)-pyrimidinedione

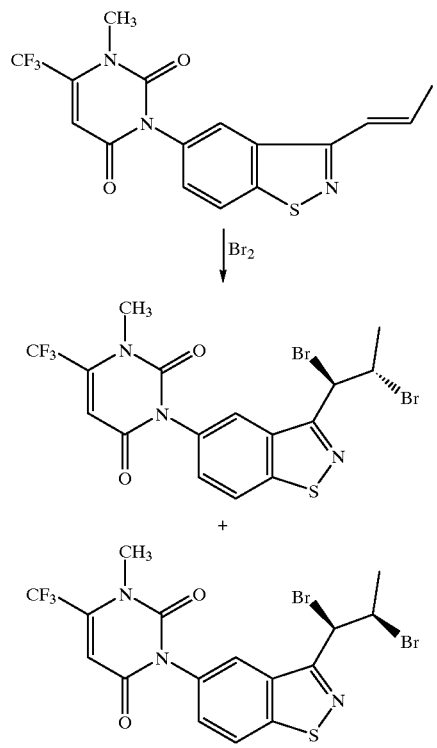

To a mixture of 1-methyl-(3-propenyl-1,2-benzisothiazol-5-yl)-6-(trifluoromethyl)-2,4(1H,3H)-pyrimidinedione (0.500 g, 0.00136 mol) and carbon tetrachloride is added bromine (0.220 g, 0.00138 mol). The resultant mixture is stirred 2.5 hours at room temperature and concentrated in vacuo to a yellow foam, which is chromatographed on silica gel with methylene chloride:ether. The (1R,2S)-isomer elutes first and is isolated as an off-white solid (0.310 g 41.9%, mp 214° C.) which is identified by NMR spectral analysis. The (1R,2R)-isomer elutes second and is isolated as an off-white foam (0.290 g 39.2%, mp 188–189° C.) which is identified by NMR spectral analysis.

EXAMPLE 134

Preparation of 3-[3-(2(and 1)-Bromo-1(and 2)-hydroxypropyl)-1,2-benzisothiazol-5-yl]-1-methyl-6-(trifluoromethyl)-2,4(1H,3H)-pyrimidinedione, (4:1) mixture of diastereomers

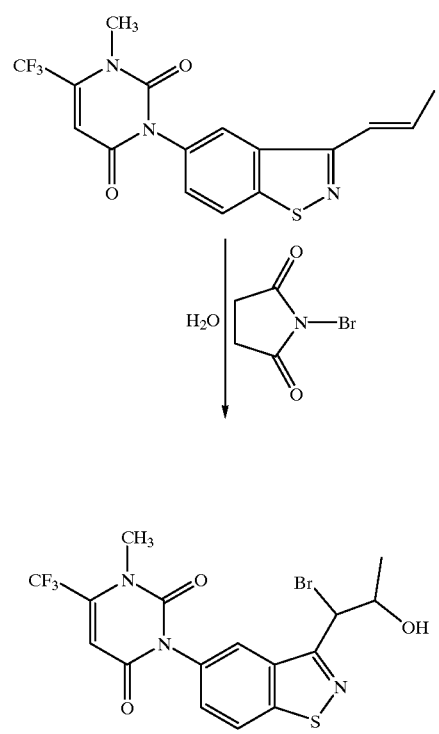

To a mixture of 1-methyl-(3-propenyl-1,2-benzisothiazol-5-yl)-6-(trifluoromethyl)-2,4(1H,3H)-pyrimidinedione (1.00 g, 0.00272 mol), dioxane and water is added N-bromosuccinimide (0.570 g, 0.00321 mol). The resultant mixture is stirred 23 hours at room temperature, poured into water and extracted with ether. The organic layers are washed with water, dried over anhydrous magnesium sulfate, filtered, and concentrated in vacuo to a yellow foam. The foam is chromatographed on silica gel with methylene chloride:ether to afford the title mixture of isomers as a white foam (1.03 g, 82.4%, mp 100–103° C.) which is identified by NMR spectral analysis.

EXAMPLE 135

Preparation of Methyl 5-[3,6-dihydro-5-bromo-3-methyl-2,6-dioxo-4-(trifluoromethyl)-1(2H)-pyrimidinyl]-α,α-dibromo-1,2-benzisothiazole-3-acetate and Methyl-5-[3,6-dihydro-3-methyl-2,6-dioxo-4-(trifluoromethyl)-1(2H)-pyrimidinyl]-α,α-dibromo-1,2-benzisothiazole-3-acetate

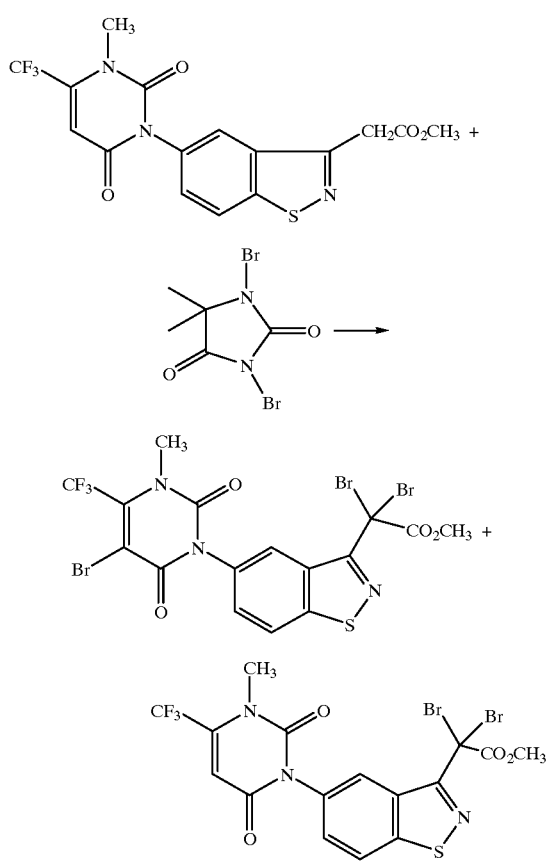

A mixture of methyl 5-[3,6-dihydro-5-bromo-3-methyl-2,6-dioxo-4-(trifluoromethyl)-1(2H)-pyrimidinyl]-1,2-benzisothiazole-3-acetate (1.20 g, 0.00300 mol), dimethyl-N,N-dibromohydantoin (4.20 g, 0.0150 mol), and 1,2-dichloroethane is stirred 3 days at reflux, cooled to room temperature, diluted with methylene chloride, washed with 10% sodium thiosulfate, water and brine, dried over anhydrous magnesium sulfate, filtered, and concentrated in vacuo. The resultant residue is chromatographed on silica gel with methylene chloride. The bromouracil substituted α,α-dibromo-1,2-benzisothiazole-3-acetate elutes first and is isolated as a white solid (0.400 g, 30.0%, mp 241° C.) which is identified by NMR spectral analysis. The α,α-dibromo-1,2-benzisothiazole-3-acetate elutes second and is isolated as a white solid (0.520 g, 31.1%, mp 194–196° C.) which is identified by NMR spectral analysis.

EXAMPLE 136

Preparation of α-Bromo-5-[3,6-dihydro-3-methyl-2,6-dioxo-4-(trifluoromethyl)-1(2H)-pyrimidyl]-1,2-benzisothiazole-3-acetonitrile

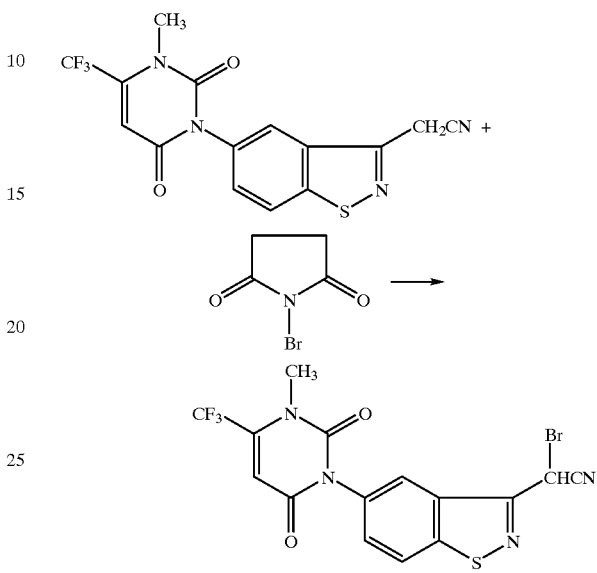

To a solution of 5-[3,6-dihydro-3-methyl-2,6-dioxo-4-(trifluoromethyl)-1(2H)-pyrimidinyl]-1,2-benzisothiazole-3-acetonitrile (0.500 g, 0.00140 mol) in 1,2-dichloroethane is added N-bromosuccinimide (0.250 g, 0.00140 mol). The resultant mixture is irradiated with a UV lamp and stirred at reflux six hours. Additional N-bromosuccinimide (0.250 g, 0.00140 mol) is added and the resultant mixture is stirred 1.5 hours at reflux under a UV lamp. The mixture is cooled to room temperature and concentrated in vacuo. The resultant residue is taken up in methylene chloride, washed with water, treated with charcoal, dried over anhydrous magnesium sulfate, filtered, and concentrated in vacuo to give the title product as a red glass (0.350 g, 56.2%, mp 185–187° C.) which is identified by IR and NMR spectral analyses.

EXAMPLE 137

Preparation of {5-[3,6-Dihydro-3-methyl-2,6-dioxo-4-(trifluoromethyl)-1(2H)-pyrimidinyl]-1,2-benzisothiazol-3-yl}-iso-thiocyanic acid, methyl ester

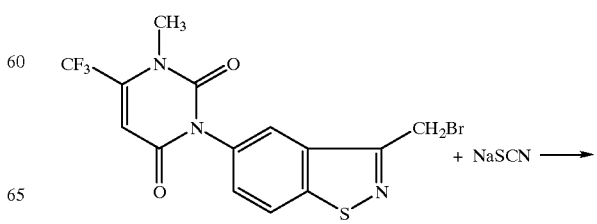

-continued

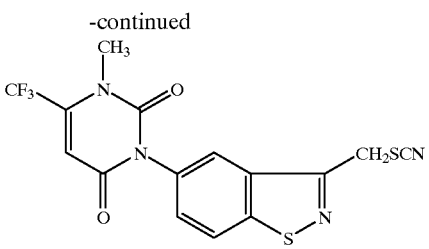

To a solution of potassium thiocyanate (0.300 g, 0.00309 mol) in dimethyl sulfoxide is added 3-[3-(bromomethyl)-1,2-benzisothiazol-5-yl]-1-methyl-6-(trifluoromethyl)-2,4(1H,3H)-pyrimidinedione (0.500 g, 0.00119 mol). The resultant mixture is stirred two hours at room temperature, diluted with ethyl acetate, washed with water, dried over anhydrous magnesium sulfate, filtered, and concentrated in vacuo to give the title compound as a white solid (0.475 g, 100%, mp 239–241° C.) which is identified by NMR and IR spectral analyses.

EXAMPLE 138

Preparation of 3-[3-Hydroxymethyl-1,2-benzisothiazol-5-yl]-1-methyl-6-(trifluoromethyl)-2,4(1H,3H)-pyrimidinedione, nitrate (ester)

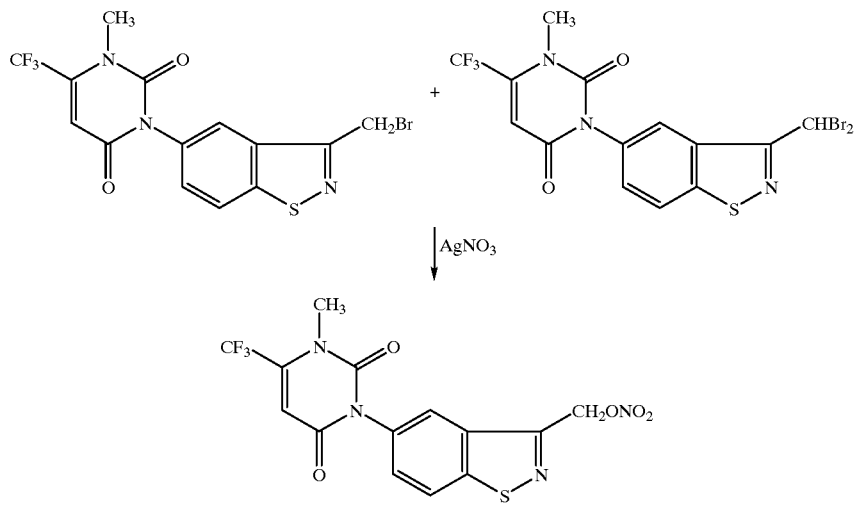

A mixture of 3-[3-(dibromo-(33%) and -bromomethyl (67%))-1,2-benzisothiazol-5-yl]-1-methyl-6-(trifluoromethyl)-2,4(1H,3H)-pyrimidinedione (2.00 g, 0.00434 mol), silver nitrate (1.50 g, 0.00887 mol), dioxane and water is stirred one hour at reflux, cooled to room temperature, and filtered. The filtrate is concentrated in vacuo. The residue is partitioned between methylene chloride and water. The organic layer is washed with brine, dried over anhydrous magnesium sulfate, filtered, and concentrated in vacuo. The residue is chromatographed on silica gel with methylene chloride:methanol to give the title compound as a white solid (0.450 g, 25.9%, mp 188–190° C.) which is identified by NMR spectral analysis.

EXAMPLE 139

Preparation of 3-[3-(1-Methoxyethyl)-1,2-benzisothiazol-5-yl]-1-methyl-6-(trifluoromethyl)-2,4(1H,3H)pyrimidinedione

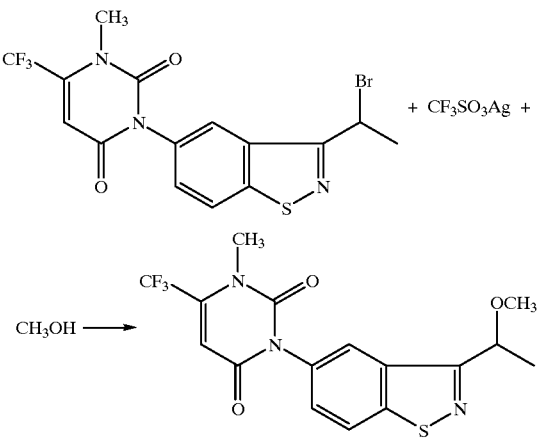

To a mixture of 3-[3-(1-bromoethyl)-1,2-benzisothiazol-5-yl]-1-methyl-6-(trifluoromethyl)-2,4(1H,3H)-pyrimidinedione (0.720 g, 0.00166 mol), methanol and 1,2-dichloroethane is added silver trifluoromethane sulfonate (0.510 g, 0.00199 mol). The resultant mixture is stirred 23 hours at room temperature and filtered through diatomaceous earth with ethyl acetate. Saturated sodium bicarbonate is added to the filtrate and the resultant mixture is stirred vigorously for one hour. The organic layer is saved while the aqueous layer is extracted with ethyl acetate. The combined organic layers are dried over magnesium sulfate, filtered and concentrated in vacuo to a syrup, which is chromatographed on silica gel with hexanes:ethyl acetate to give the title compound as a white solid (0.660 g, 100%, mp 133–135° C.) which is identified by NMR spectral analysis.

Using essentially the same procedure, but substituting the appropriate alcohol for methanol, the following compound is prepared:

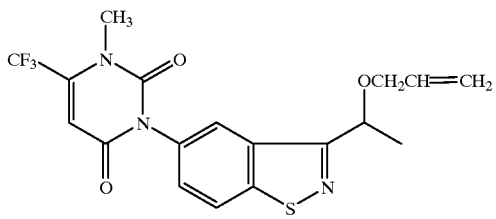

EXAMPLE 140

Preparation of Methyl 5-[3,6-dihydro-3-methyl-2,6-dioxo-4-(trifluoromethyl)-1(2H)-pyrimidinyl]-α-methoxy-1,2-benzisothiazole-3-acetate

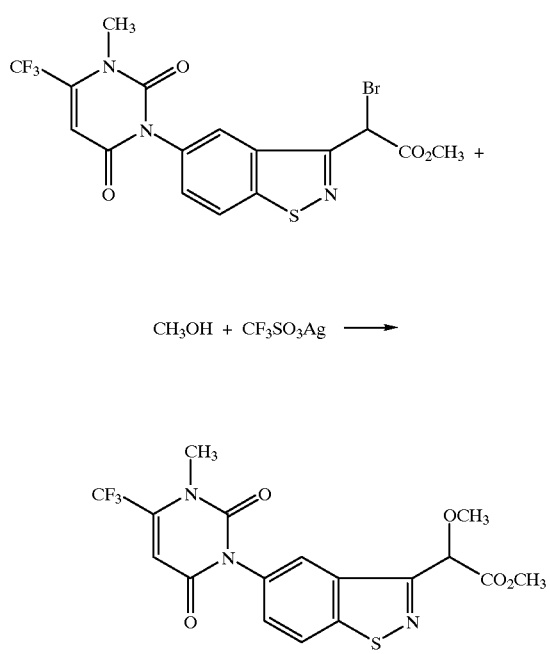

A mixture of methyl 5-[3,6-dioxo-3-methyl-2,6-dioxo-4-(trifluoromethyl)-1(2H)-pyrimidinyl]-α-bromo-1,2-benzisothiazole-3-acetate (0.600 g, 0.00125 mol), silver trifluoromethane sulfonate (0.400 g, 0.00156 mol) and methanol is stirred 36 hours at reflux, cooled and concentrated in vacuo. The residue is partitioned between methylene chloride and saturated sodium bicarbonate. The organic layer is saved and the aqueous layer extracted with methylene chloride. The combined organic layers are washed with brine, dried over anhydrous magnesium sulfate, filtered, and concentrated in vacuo. The residue is chromatographed on silica gel with methylene chloride to give the title compound as a white solid (0.220 g, 41.0%, mp 166–168° C.) which is identified by NMR spectral analysis.

Using essentially the same procedure, methyl 5-[3,6-dihydro-3-methyl-2,6-dioxo-4-(trifluoromethyl)-1(2H)-pyrimidinyl]-α,α-dimethoxy-1,2-benzisothiazole-3-acetate is obtained from methyl 5-[3,6-dihydro-3-methyl-2,6-dioxo-4-(trifluoromethyl)-1(2H)-pyrimidinyl]-α,α-dibromo-1,2-benzisothiazole-3-acetate.

EXAMPLE 141

Preparation of 5-[3,6-Dihydro-3-methyl-2,6-dioxo-4-(trifluoromethyl)-1(2H)-pyrimidinyl]-6-fluoro-1,2-benzisothiazole-3-carboxaldehyde, 3-(dimethylacetal)

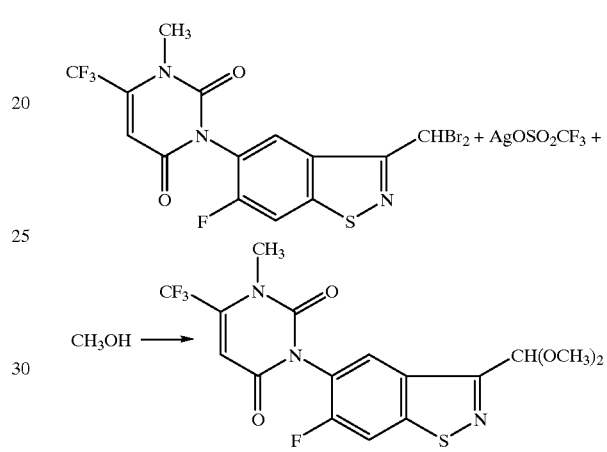

To a mixture of 3-[6-fluoro-3-(dibromomethyl)-1,2-benzisothiazol-5-yl]-1-methyl-6-(trifluoromethyl)-2,4(1H, 3H)-pyrimidinedione (0.500 g, 0.000967 mol), 1,2-dichloroethane and methanol (1.00 ml) is added silver trifluoromethyl sulfonate (0.620 g, 0.00241 mol). The resultant mixture is stirred overnight at room temperature with the exclusion of light. The mixture is filtered with methylene chloride wash. The filtrate is washed with saturated sodium bicarbonate, water and brine, dried over anhydrous magnesium sulfate, filtered, and concentrated in vacuo to an oil. The oil is chromatographed on silica gel with ethyl acetate-:hexanes to give the title compound as a white solid (0.330 g, 81.4%, mp 63–65° C.) which is identified by NMR spectral analysis.

Using essentially the same procedure, the following compound is obtained:

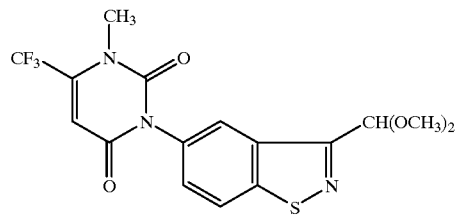

EXAMPLE 142

Preparation of {{5-[3,6-Dihydro-3-methyl-2,6-dioxo-4-(trifluoromethyl)-1(2H)-pyrimidinyl]-1,2-benzisothiazol-3-yl}methyl}(methylsulfonyl)carbamic acid, tert-butyl ester

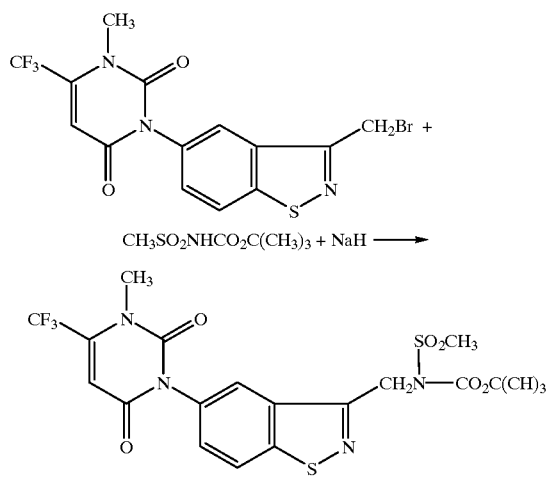

tert-Butyl(methylsulfonyl)carbamate (1.52 g, 0.00780 mol) is added to a mixture of sodium hydride (60%, 0.312 g, 0.00780 mol) and tetrahydrofuran at 0° C. The mixture is allowed to come to room temperature. A solution of 3-[3-(bromomethyl)-1,2-benzisothiazol-5-yl]-1-methyl-6-(trifluoromethyl)-2,4(1H,3H)-pyrimidinedione (3.00 g, 0.00714 mol) in dimethyl sulfoxide is added dropwise. The resultant mixture is stirred overnight at room temperature, poured into dilute hydrochloric acid, and extracted with methylene chloride. The combined organic layers are washed with water, dried over anhydrous magnesium sulfate, filtered, and concentrated in vacuo. The resultant residue is chromatographed on silica gel with ether:methylene chloride to give the title compound as a white solid (3.00 g, 78.7%, mp 109–111° C.) which is identified by NMR spectral analysis.

EXAMPLE 143

Preparation of 3-[3-(Hydroxymethyl)-1,2-benzisothiazol-5-yl]-1-methyl-6-(trifluoromethyl)-2,4(1H,3H)-pyrimidinedione, benzoate (ester)

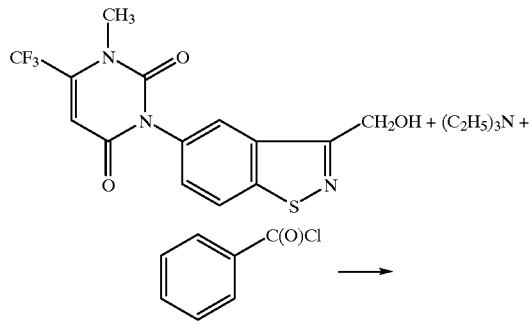

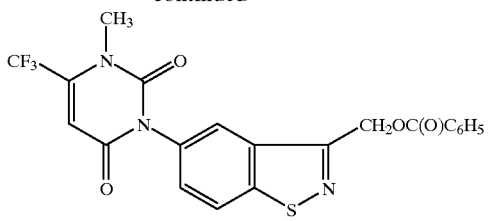

To a mixture of 3-[3-(hydroxymethyl)-1,2-benzisothiazol-5-yl]-1-methyl-6-(trifluoromethyl)-2,4(1H,3H)-pyrimidinedione (0.650 g, 0.00182 mol) and methylene chloride at 0° C. is added triethylamine (0.330 ml, 0.00236 mol) followed by benzoyl chloride (0.210 ml, 0.00182 mol). The mixture is stirred one hour at 0° C. and quenched with saturated sodium bicarbonate with stirring over a 15 minute period. The resultant mixture is diluted with ether and the organic layer is washed with saturated sodium bicarbonate and brine, dried over anhydrous magnesium sulfate, filtered, and concentrated in vacuo to an orange syrup. The syrup is chromatographed on silica gel with hexanes:ethyl acetate to afford a solid. The solid is recrystallized from ethyl acetate and hexanes to give the title compound as a white solid (0.340 g, 40.5%, mp 140–142° C.).

Following essentially the same procedure, but using the appropriate acid chloride and hydroxyalkylbenzisothiazole, the following compounds are obtained:

| $W_{12}$ | $R_{33}$ | mp ° C. |
|---|---|---|
| H | $CH_2Cl$ | 166–168 |
| H | $CH_2C_6H_5$ | 125–127 |
| H | $CH_2$—⟨C₆H₄⟩—$OCH_3$ (para) | 144–146 |
| H | $CH_2$—⟨thienyl⟩ | 139–142 |
| H | $CH_2$—⟨C₆H₄⟩—Cl (para) | 164–167 |
| H | $CH_2$—⟨C₆H₄⟩—$OCH_3$ (meta) | 124–126 |

-continued

[Structure: benzisothiazole with N-methyl-5-trifluoromethyl-uracil substituent, CH(W₁₂)-O-C(=O)-R₃₃ group]

| W₁₂ | R₃₃ | mp °C |
|---|---|---|
| H | 4-methylpyridin-yl | 81–83 |
| H | CH(CH₂CH₃)C₆H₅ | |
| H | 4-methyl-2,6-dichloropyridinyl | 245–247 |
| H | 5-methylisoxazol-yl | 148–150 |
| H | 5-methyl-2-nitrofuranyl | 195–198 |
| H | 2-methylthienyl | 178–180 |
| H | 2-chloro-3-methylpyridinyl | 201–204 |
| H | CH₂OCH₃ | 165–166 |
| H | cyclopropyl | 134–136 |
| H | 2-methylfuranyl | 178–180 |
| H | C(CH₃)₃ | 50–52 |
| H | CH₂-(3,4-dimethoxyphenyl) | 160–162 |

-continued

[Structure: same benzisothiazole/uracil framework]

| W₁₂ | R₃₃ | mp °C |
|---|---|---|
| H | CH₂-(2,4-dimethoxyphenyl) | 148–150 |
| H | CH(Cl)C₆H₅ | 159–161 |
| H | CH₂-(2,4-dichlorophenyl) | 195–197 |
| H | CH₂-(2-chlorophenyl) | 160–162 |
| CH₃ | CH₂Cl | 145–147 |
| CH₃ | CH₂OCH₃ | 111–114 |
| CH₃ | cyclopropyl | |
| CH₃ | 5-methylisoxazol-yl | 102–104 |
| CH₃ | CH(Cl)C₆H₅ | 66–68 |
| CH₃ | 2-methylfuranyl | 79–81 |
| CH₃ | CH₃ | 76 |

EXAMPLE 144

Preparation of 3-[3-(1-Hydroxyethyl)-1,2-benzisothiazol-5-yl]-1-methyl-6-(trifluoromethyl)-2,4(1H,3H)-pyrimidinedione

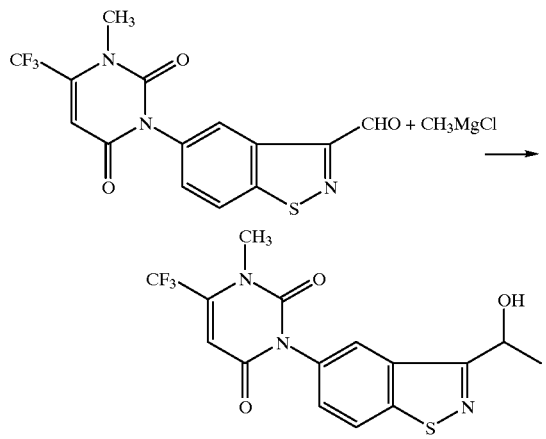

Methyl magnesium chloride (14.1 ml, 0.0422 mol) is added dropwise to a solution of 5-[3,6-dihydro-3-methyl-2,6-dioxo-4-(trifluoromethyl)-1(2H)-pyrimidinyl]-1,2-benzisothiazole-3-carboxaldehyde (6.00 g, 0.00170 mol) in tetrahydrofuran at −78° C. over 15 minutes. The resultant mixture is stirred at −78° C. for 30 minutes, quenched with saturated ammonium chloride and allowed to warm to room temperature. After dilution with ethyl acetate, the mixture is washed with saturated ammonium chloride, water and brine, dried over anhydrous magnesium sulfate, filtered, and concentrated in vacuo to a solid. The solid is chromatographed on silica gel with hexanes/ethyl acetate to give the title compound as a white crystalline solid (4.49 g, 71.1%) which is identified by NMR spectral analysis.

EXAMPLE 145

Preparation of 3-(3-Acetyl-1,2-benzisothiazol-5-yl)-1-methyl-6-(trifluoromethyl)-2,4(1H,3H)-pyrimidinedione

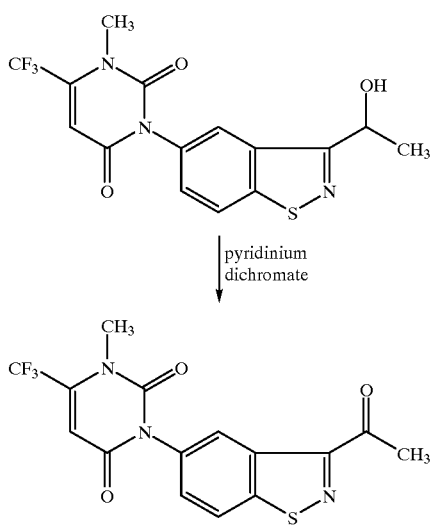

To a solution of 3-[3-(1-hydroxyethyl)-1,2-benzisothiazol-5-yl]-1-methyl-6-(trifluoromethyl)-2,4(1H,3H)-pyrimidinedione (3.99 g, 0.0107 mol) in dry methylene chloride under a nitrogen atmosphere is added powdered 4 Å molecular sieves followed by pyridinium dichromate (4.85 g, 0.0129 mol). The resultant mixture is stirred 22 hours at room temperature, diluted with ether, filtered through silica gel and diatomaceous earth, and concentrated in vacuo to a solid. The solid is recrystallized from ethyl acetate:hexanes to afford he title compound as a white crystalline solid (2.34 g, 59.2%, mp 149° C.) which is identified by NMR spectral analysis.

EXAMPLE 146

Preparation of 3-[3-(Hydroxymethyl)-1,2-benzisothiazol-5-yl)-1-methyl-6-(trifluoromethyl)-2,4(1H,3H)-pyrimidinedione, methylcarbamate (ester)

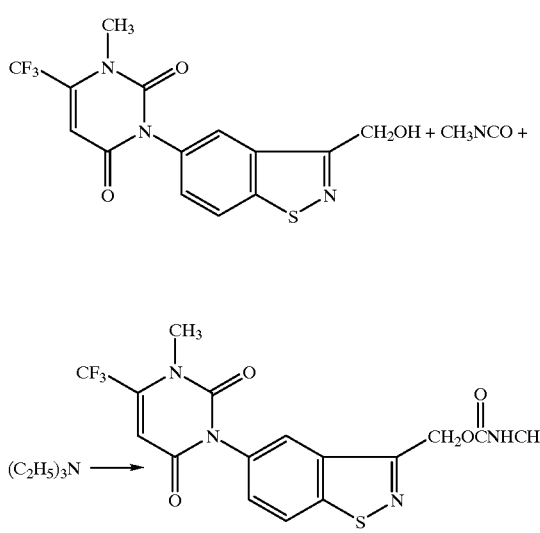

To a mixture of 3-(3-(hydroxymethyl)-1,2-benzisothiazol-5-yl]-6-(trifluoromethyl)-2,4(1H,3H)-pyrimidinedione (1.00 g, 0.00280 mol) and methylene chloride at 0° C., is added triethylamine (0.590 ml, 0.00420 mol) followed by methyl isocyanate (0.190 ml, 0.00320 mol). The resultant mixture is stirred 27 hours at ambient temperature, diluted with ethyl acetate and saturated sodium bicarbonate, and stirred 15 minutes. The organic layer is washed with saturated sodium bicarbonate and brine, dried over anhydrous magnesium sulfate, filtered and concentrated in vacuo to a yellow solid. The solid is recrystallized from ethyl acetate to give the title compound as tan crystals (0.440 g, 37.9%, mp >230° C.).

Following essentially the same procedure, but using the appropriate isocyanate, the following compounds are obtained:

| R$_{36}$ | mp ° C. |
|---|---|
| C$_6$H$_5$ | 209 |
| CH$_2$C$_6$H$_5$ | 174–177 |

EXAMPLE 147

Preparation of 3-[3-(1-Hydroxyethyl)-1,2-benzisothiazol-5-yl)-1-methyl-6-(trifluoromethyl)-2,4(1H,3H)-pyrimidinedione, methane sulfonate (ester)

To a solution of 3-[3-(1-hydroxyethyl)-1,2-benzisothiazol-5-yl]-1-methyl-6-(trifluoromethyl)-2,4(1H,3H)-pyrimidinedione (0.650 g, 0.00175 mol) in methylene chloride at 0° C. is added methane sulfonyl chloride (0.150 ml, 0.00193 mol) followed by triethylamine (0.320 ml, 0.00228 mol). The resultant mixture is stirred 80 minutes at 0° C. and quenched with pH:7 buffer. The organic layer, after dilution with ethyl acetate and ether, is washed with pH:7 buffer and brine, dried over anhydrous magnesium sulfate, filtered, and concentrated in vacuo to a colorless syrup. The syrup is dissolved in ethyl acetate and crystallized by the addition of hexanes to give the title compound as a white, crystalline solid (0.640 g, 81.4%, mp 157° C.) which is identified by NMR spectral analysis.

Following essentially the same procedure, but using the appropriate sulfonyl chloride, the following compounds are prepared:

| R$_{47}$ | mp ° C. |
|---|---|
| CH(CH$_3$)$_2$ | 113–115 |
| (CH$_2$)$_3$CH$_3$ | 124–125 |
| C$_6$H$_5$ | 92–94 |

Following essentially the same procedure, but using the appropriate sulfonyl chloride on 3-[3-(hydroxymethyl)-1,2-benzisothiazol-5-yl]-1-methyl-6-(trifluoromethyl)-2,4(1H, 3H)-pyrimidinedione, the following compounds are obtained:

| R$_{47}$ | mp ° C. |
|---|---|
| CH$_3$ | 178–180 |
| CH(CH$_3$)$_2$ | 141–143 |
| (CH$_2$)$_3$CH$_3$ | 142–145 |
| C$_6$H$_5$ | 150–152 |

EXAMPLE 148

Preparation of 5-[3,6-Dihydro-3-methyl-2,6-dioxo-4-(trifluoromethyl)-1(2H)-pyrimidinyl]-1,2-benzisothiazole-3-carboxaldehyde, 3-(diethylacetal)

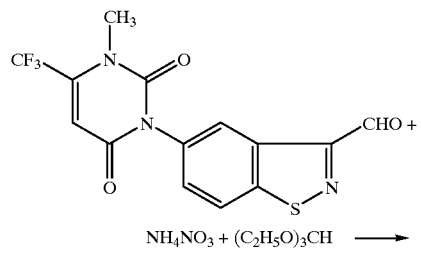

-continued

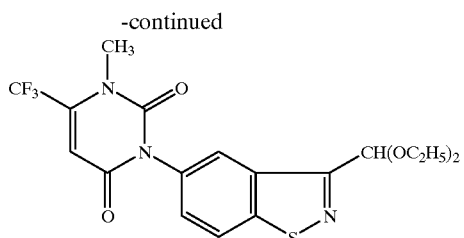

To a suspension of 5-[3,6-dihydro-3-methyl-2,6-dioxo-4-(trifluoromethyl)-1(2H)-pyrimidinyl]-1,2-benzisothiazole-3-carboxaldehyde (0.800 g, 0.00225 mol) in ethanol is added triethyl orthoformate (0.560 ml, 0.00338 mol), followed by ammonium nitrate (0.0100 g). The resultant mixture is stirred 19 hours at room temperature and three hours at reflux. After cooling to room temperature, the mixture is concentrated in vacuo to a yellow oil. The oil is chromatographed on silica gel with hexanes:ethyl acetate to give the title compound as a yellow foam (0.690 g, 71.4%, mp 49° C.) which is identified by NMR spectral analysis.

EXAMPLE 149

Preparation of 5-[3,6-Dihydro-3-methyl-2,6-dioxo-4-trifluoromethyl)-1(2H)-pyrimidinyl]-1,2-benzisothiazole-3-carboxaldehyde, 3-[bis(3-hydroxypropyl)dithioacetal]

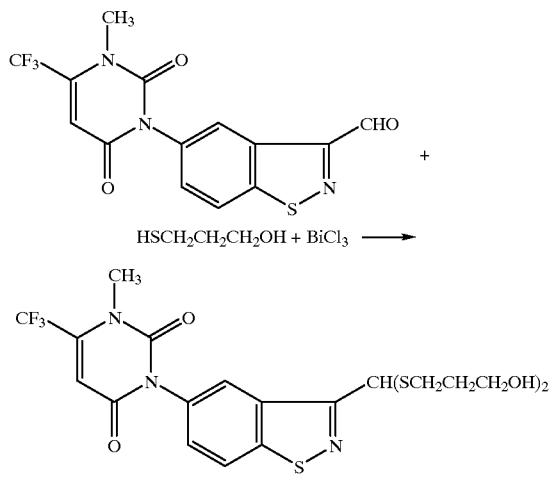

To a mixture of 5-[3,6-dihydro-3-methyl-2,6-dioxo-4-(trifluoromethyl)-1(2H)-pyrimidinyl]-1,2-benzisothiazole-3-carboxaldehyde (2.86 g, 0.00805 mol) and acetonitrile is added 3-mercapto-1-propanol (0.600 ml, 0.00684 mol) followed by bismuth(III) chloride (0.0900 g). The resultant mixture is stirred overnight at room temperature. Additional 3-mercapto-1-propanol (0.200 ml, 0.00228 mol) is added and the mixture is concentrated in vacuo. The residue is chromatographed on silica gel with acetone:ethyl acetate; the second component, isolated as a yellow oil, is taken up in ether, washed with water and brine, dried over anhydrous magnesium sulfate, filtered, and concentrated in vacuo to give the title compound as a yellow solid (1.00 g, 23.8%) which is identified by NMR spectral analysis.

EXAMPLE 150

Preparation of 5-[3,6-Dihydro-3-methyl-2,6-dioxo-4-(trifluoromethyl)-1(2H)-pyrimidinyl]-1,2-benzisothiazole-3-carboxaldehyde, 3-[bis(2-hydroxyethyl dithioacetal], diacetate (diester)

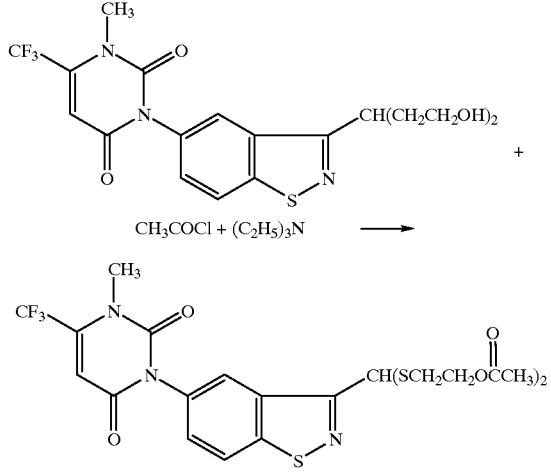

To a solution of 5-[3,6-dihydro-3-methyl-2,6-dioxo-4-(trifluoromethyl)-1(2H)-pyrimidinyl]-1,2-benzisothiazole-3-carboxaldehyde, 3-[bis(2-hydroxyethyl)dithioacetal (0.500 g, 0.00101 mol) in methylene chloride is added triethylamine (0.400 ml, 0.00300 mol) followed by acetyl chloride (0.160 ml, 0.00220 mol). The resultant mixture is stirred one hour at room temperature, poured into water and diluted with methylene chloride. The organic layer is saved and the aqueous layer is extracted with methylene chloride. The combined organic layers are washed with water and brine, dried over anhydrous magnesium sulfate, filtered, and concentrated in vacuo to a yellow oil. The oil is chromatographed on silica gel with hexanes:ethyl acetate to give the title compound as a yellow oil (0.340 g, 58.3%) which is identified by NMR spectral analysis.

Using essentially the same procedure 5-[3,6-dihydro-3-methyl-2,6-dioxo-4-(trifluoromethyl)-1(2H)-pyrimidinyl]-1,2-benzisothiazole-3-carboxaldehyde, 3-[bis(3-hydroxypropyl)dithioacetal], diacetate (diester) is obtained from 5-[3,6-dihydro-3-methyl-2,6-dioxo-4-(trifluoromethyl)-1(2H)-pyrimidinyl]-1,2-benzisothiazole-3-carboxaldehyde, 3-[bis(3-hydroxypropyl)dithioacetal.

EXAMPLE 151

Preparation of 5-[3,6-Dihydro-3-methyl-2,6-dioxo-4-(trifluoromethyl)-1(2H)-pyrimidinyl]-1,2-benzisothiazole-3-carboxaldehyde, 3-[bis(2-hydroxyethyl)dithioacetal]

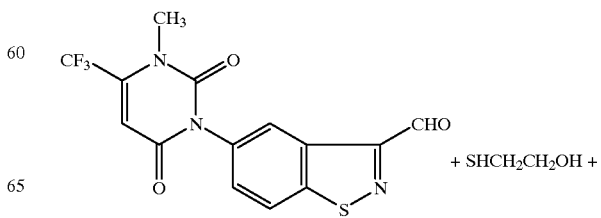

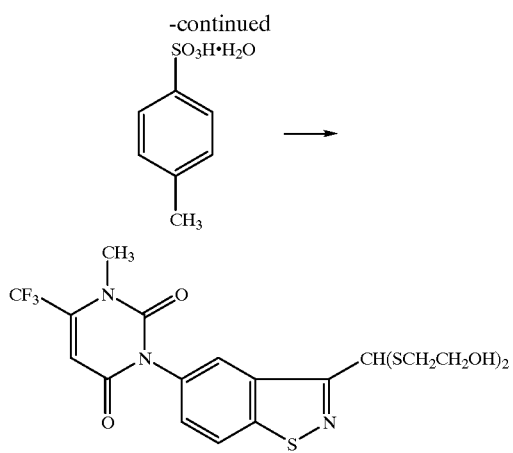

A mixture of 5-[3,6-dihydro-3-methyl-2,6-dioxo-4-(trifluoromethyl)-1(2H)-pyrimidinyl]-1,2-benzisothiazole-3-carboxaldehyde (3.00 g, 0.00844 mol), 2-mercaptoethanol (1.80 ml, 0.0252 mol), p-toluenesulfonic acid (0.0800 g, 0.000420 mol) and toluene is stirred two hours at reflux with azeotropic removal of water. After cooling to room temperature, the mixture is stirred overnight, diluted with ethyl acetate, washed with water and brine, dried over anhydrous magnesium sulfate, filtered, and concentrated in vacuo to obtain a brown oil. The oil is chromatographed on silica gel to give the title compound as a white solid (1.10 g, 31.3%) which is identified by NMR spectral analysis.

EXAMPLE 152

Preparation of 5-[3,6-Dihydro-3-methyl-2,6-dioxo-4-(trifluoromethyl)-1(2H)-pyrimidinyl]-1,2-benzisothiazole-3-carboxaldehyde, 3-oxime, (E)-isomer

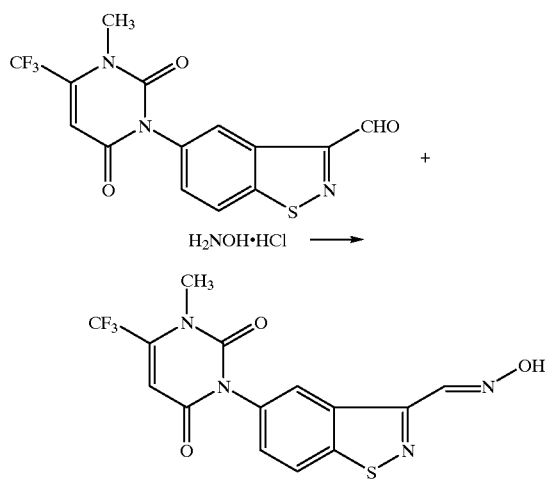

A mixture of 5-[3,6-dihydro-3-methyl-2,6-dioxo-4-(trifluoromethyl)-1(2H)-pyrimidinyl]-1,2-benzisothiazole-3-carboxaldehyde (0.200 g, 0.000563 mol), hydroxylamine hydrochloride (0.0700 g, 0.00100 mol), sodium acetate (0.150 g, 0.0018.3 mol) and ethanol is stirred one hour at 50–60° C., and concentrated in vacuo. The residue is partitioned between methylene chloride and water. The organic layer is separated, washed with brine, dried over anhydrous magnesium sulfate, filtered, and concentrated in vacuo. The residue is chromatographed on silica gel with methylene chloride:ethyl acetate to give the title compound as a white solid (0.140 g, 67.3%, mp 234–236° C.) which is identified by NMR spectral analysis.

Following essentially the same procedure, but using the appropriate aldehyde with various hydroxylamines or hydrazines, the following oximes and hydrazones are obtained:

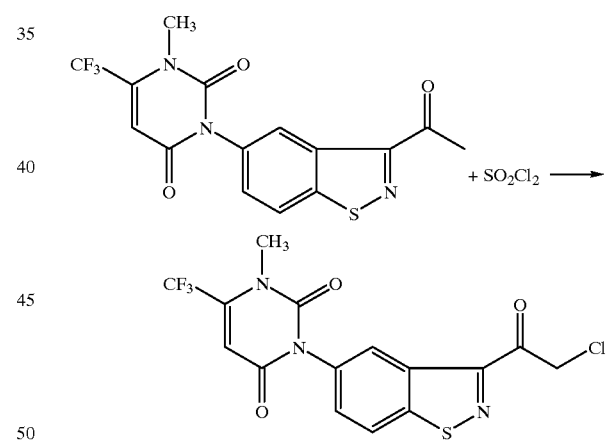

| n | $W_{13}$ | mp ° C. |
|---|---|---|
| 1 | OH | 186–188 |
| 0 | $OCH_3$ | 235–237 |
| 0 | $NHC_6H_5$ | >220 |
| 0 | $N(CH_3)_2$ | 192–192.5 |
| 0 | $N(CH_3)C_6H_5$ | 198.5 |

EXAMPLE 153

Preparation of 3-[3-(Chloroacetyl)-1,2-benzisothiazol-5-yl]-1-methyl-6-(trifluoromethyl)-2,4(1H,3H)-pyrimidinedione To a solution of 3-(3-acetyl-1,2-benzisothiazol-5-yl)-1-methyl-6-(trifluoromethyl)-2,4(1H,3H)-pyrimidinedione (0.570 g, 0.00154 mol) in chloroform is added sulfuryl chloride (0.350 ml, 0.00433 mol). The resultant mixture is stirred one hour at reflux. Concentrated hydrochloric acid (one drop) is added followed by sulfuryl chloride (1.05 ml, 0.0130 mol) and the resultant mixture is stirred three days at reflux. The mixture is cooled to room temperature, diluted with ethyl acetate and ether, washed with saturated sodium bicarbonate and brine, dried over anhydrous magnesium sulfate, and concentrated in vacuo to a solid. The resultant solid is chromatographed on silica gel with hexanes:ethyl acetate to afford a white solid. The solid is chromatographed on silica gel with chloroform to afford a white solid, which is recrystallized from ethyl acetate and hexanes to give the title compound as a white crystalline solid (mp 215–215° C.) which is identified by NMR spectral analysis.

EXAMPLE 154

Preparation of 3-[3-(Bromoacetyl)-1,2-benzisothiazol-5-yl]-1-methyl-6-(trifluoromethyl)-2,4(1H,3H)-pyrimidinedione

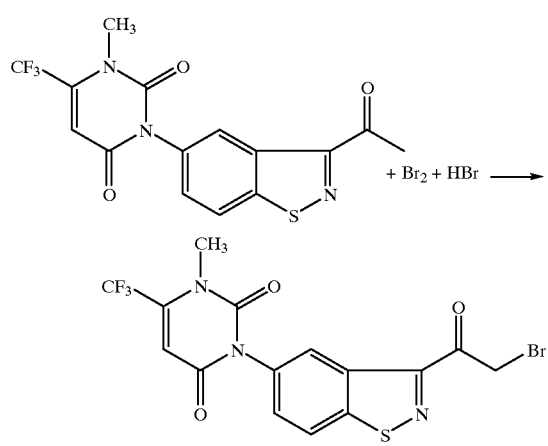

To a solution of 3-(3-acetyl-1,2-benzisothiazol-5-yl)-1-methyl-6-(trifluoromethyl)-2,4(1H,3H)-pyrimidinedione (0.800 g, 0.00217 mol) in ethyl acetate at room temperature is added hydrobromic acid (48%, 3 drops) followed by bromine in ethyl acetate (0.522 M, 4.35 ml, 0.00277 mol). The resultant mixture is stirred two hours at reflux, cooled to room temperature, diluted with ethyl acetate, washed sequentially with sodium thiosulfate, saturated sodium bicarbonate and brine, dried over anhydrous magnesium sulfate, filtered, and concentrated in vacuo to a white solid. The solid is recrystallized from hexanes:ethyl acetate to give the title compound as a white, crystalline solid (mp 191–193° C.) which is identified by NMR spectral analysis.

EXAMPLE 155

Preparation of (E)- and (Z)-α-(Cyclopropylmethylene)-5-[3,6-dihydro-3-methyl-2,6-dioxo-4-(trifluoromethyl)-1(2H)-pyrimidinyl]-1,2-benzisothiazole-3-acetonitrile

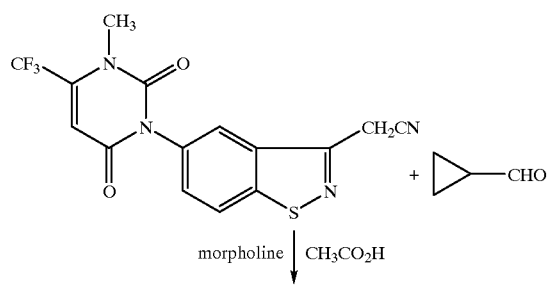

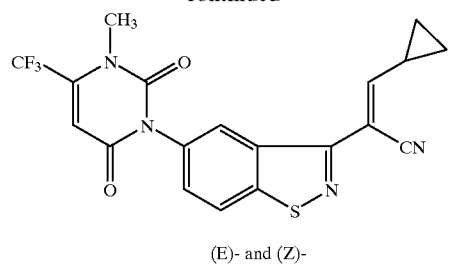

(E)- and (Z)-

A mixture of 5-[3,6-dihydro-3-methyl-2,6-dioxo-4-(trifluoromethyl)-1(2H)-pyrimidinyl]-1,2-benzisothiazole-3-acetonitrile (0.730 g, 0.00199 mol), cyclopropane aldehyde (0.300 g, 0.00428 mol), morpholine (0.100 ml), acetic acid (0.0500 ml) and ethanol is stirred 45 minutes at reflux, cooled and poured into 10% aqueous hydrochloric acid. The resultant precipitate is filtered, washed with water, and dried in vacuo to give the title compound (0.780 g, 93.8%, mp 201–205° C.) which is identified by IR and NMR spectral analysis.

Using essentially the same procedure, the following compounds are obtained:

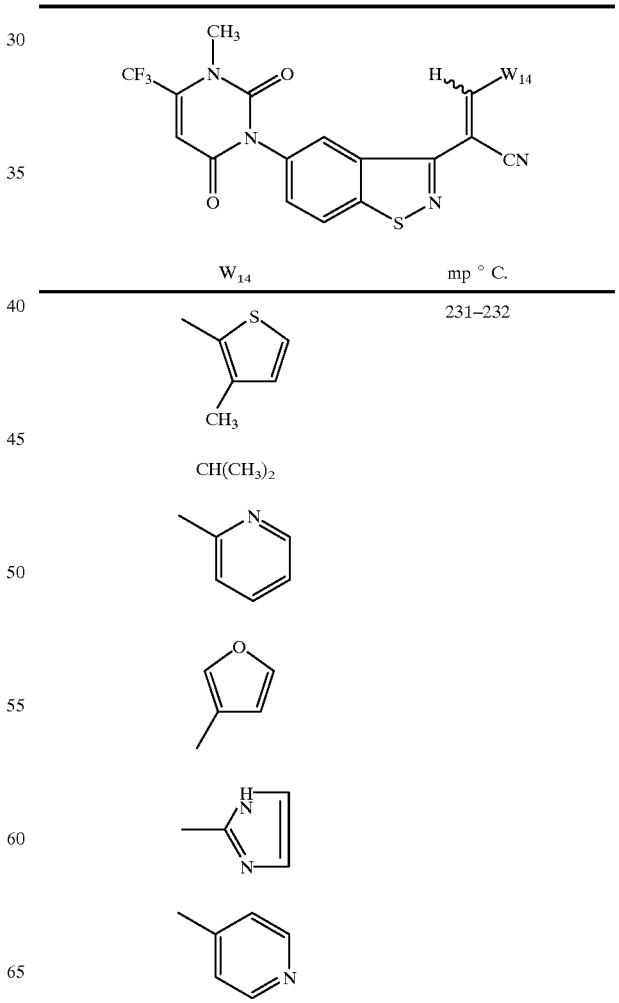

-continued

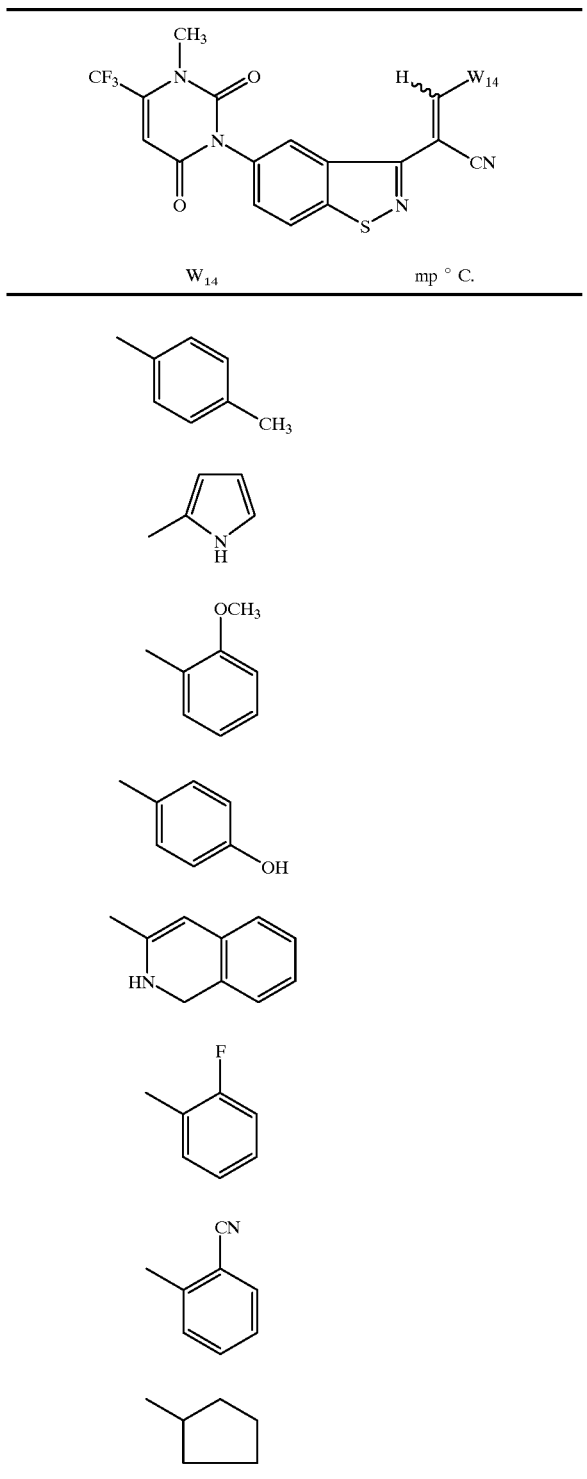

| $W_{14}$ | mp ° C. |
|---|---|

Using essentially the same procedure with methyl 5-[3,6-dihydro-3-methyl-2,6-dioxo-4-(trifluoromethyl)-1(2H)-pyrimidinyl]-1,2-benzisothiazole-3-acetate as substrate and the appropriate aldehyde, the following compounds are obtained:

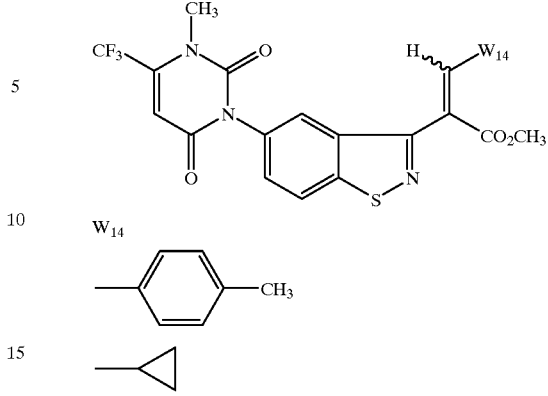

EXAMPLE 156

Preparation of 5-[3,6-Dihydro-3-methyl-2,6-dioxo-4-(trifluoromethyl)-1(2H)-pyrimidinyl]-α-ethyl-1,2-benzisothiazole-3-acetonitrile

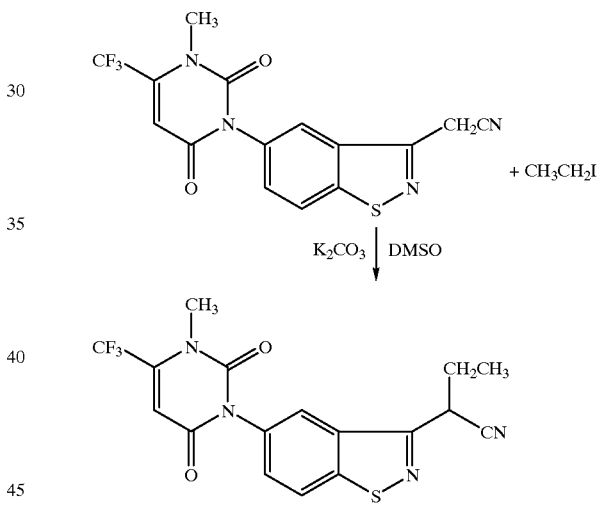

To a solution of 5-[3,6-dihydro-3-methyl-2,6-dioxo-4-(trifluoromethyl)-1(2H)-pyrimidinyl]-1,2-benzisothiazole-3-acetonitrile (0.730 g, 0.00199 mol) in dimethyl sulfoxide is added iodoethane (0.170 ml, 0.00210 mol) followed by potassium carbonate (0.750 g, 0.00543 mol). The resultant mixture is stirred overnight at room temperature and poured onto a mixture of ice and 5% aqueous hydrochloric acid. The resultant solid is filtered, dried and taken up in a minimal amount of methylene chloride. Flash column chromatography using silica gel and 100% to 99:1 methylene chloride/diethyl ether gives the title compound as a white solid (0.220 g, 28.0%, mp 107–109° C.) which is identified by NMR spectral analysis.

Using essentially the same procedure and iodomethane as alkylating agent 5-[3,6-dihydro-3-methyl-2,6-dioxo-4-(trifluoromethyl)-1(2H)-pyrimidinyl]-α-methyl-1,2-benzisothiazole-3-acetonitrile is obtained.

Using essentially the same procedure with the appropriate alkylating agent and methyl 5-[3,6-dihydro-3-methyl-2,6-dioxo-4-(trifluoromethyl)-1(2H)-pyrimidinyl]-1,2-benzisothiazole-3-acetate as substrate, the following compounds are obtained:

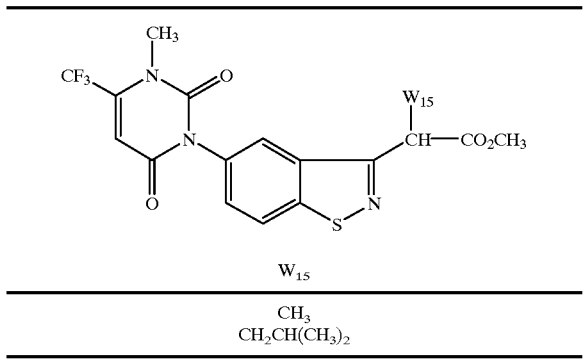

| $W_{15}$ |
|---|
| $CH_3$ |
| $CH_2CH(CH_3)_2$ |

EXAMPLE 157

Preparation of 5-[3,6-Dihydro-3-methyl-2,6-dioxo-4-(trifluoromethyl)-1(2H)-pyrimidinyl]-α,α-diethyl-1,2-benzisothiazole-3-acetonitrile

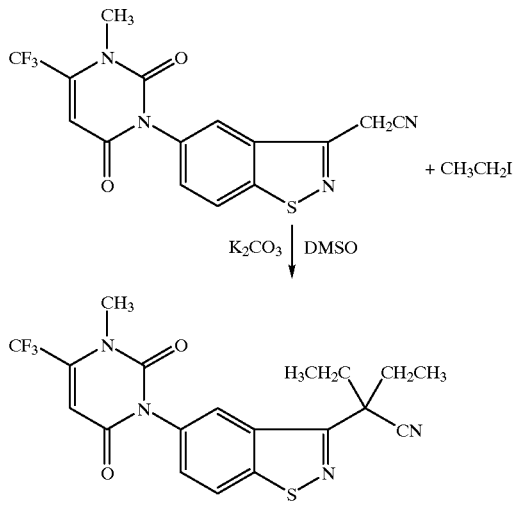

To a solution of 5-[3,6-dihydro-3-methyl-2,6-dioxo-4-(trifluoromethyl)-1(2H)-pyrimidinyl]-1,2-benzisothiazole-3-acetonitrile (0.730 g, 0.00199 mol) in dimethyl sulfoxide is added iodoethane (0.326 ml, 0.00408 mol) followed by potassium carbonate (0.750 g, 0.00543 mol). The resultant mixture is stirred overnight at room temperature, poured into water, and extracted with methylene chloride. The combined organic layers are dried over anhydrous magnesium sulfate, and concentrated in vacuo to a yellow oil. The oil is flash chromatographed on silica gel with 100% to 99:1 methylene chloride/ethyl ether to afford the title compound as a white solid (0.430 g, 51.2%, mp 76–78° C.) which is identified by NMR spectral analysis.

Using the same starting material, different alkylating agents and essentially the same procedure, the following compounds are obtained:

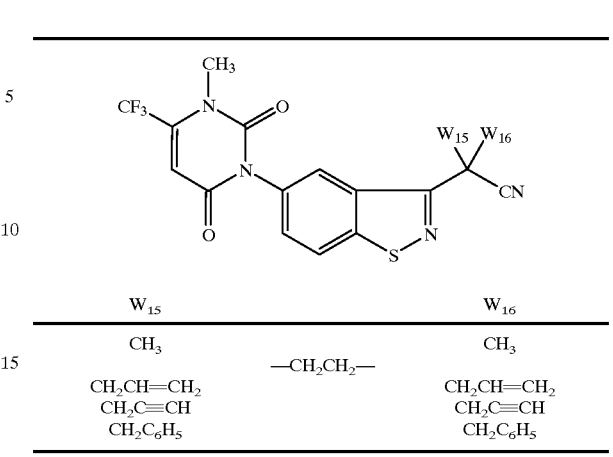

| $W_{15}$ | $W_{16}$ |
|---|---|
| $CH_3$ | $CH_3$ |
| $CH_2CH=CH_2$ | —$CH_2CH_2$— | $CH_2CH=CH_2$ |
| $CH_2C\equiv CH$ | | $CH_2C\equiv CH$ |
| $CH_2C_6H_5$ | | $CH_2C_6H_5$ |

EXAMPLE 158

Preparation of 5-[3,6-Dihydro-3-methyl-2,6-dioxo-4-trifluoromethyl)-1(2H)-pyrimidinyl]-1,2-benzisothiazole-3-carboxylic acid, 2-butynyl ester

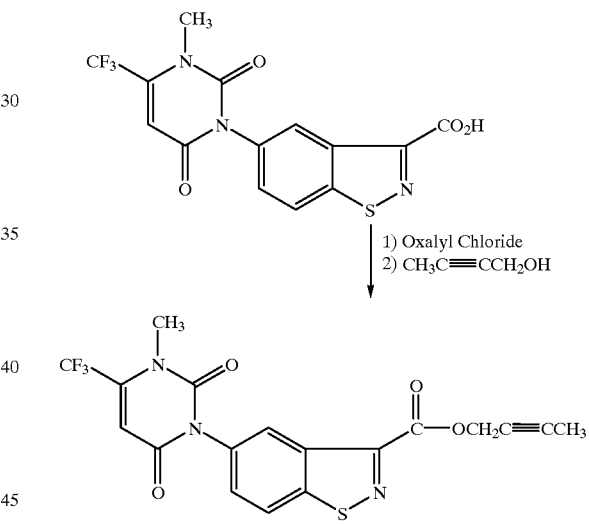

To a mixture of 5-[3,6-dihydro-3-methyl-2,6-dioxo-4-(trifluoromethyl-1(2H)-pyrimidinyl)-1,2-benzisothiazole-3-carboxylic acid (2.00 g, 0.00538 mol), methylene chloride and tetrahdrofuran is added N,N-dimethylformamide (8 drops). The resultant mixture is cooled on an ice bath, treated with oxalyl chloride (6.70 ml, 0.0135 mol), stirred one hour on an ice bath, and concentrated in vacuo. 12.5% of the residue as a solution in tetrahydrofuran is added to a mixture of 2-butyn-1-ol (0.200 ml), triethylamine and tetrahydrofuran. The resultant mixture is stirred overnight at ambient temperature and poured into cold 10% hydrochloric acid. The mixture is extracted with methylene chloride and the combined organic layers are dried over anhydrous magnesium sulfate, filtered, and concentrated in vacuo to give the title compound as an off-white solid (0.140 g, 49.1%, mp 138–139° C.) which is identified by NMR spectral analysis.

Using essentially the same procedure, with the appropriate alcohols or thioalcohols, the following compounds are obtained:

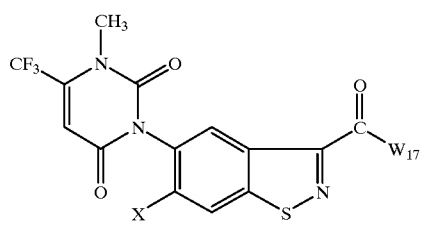

| X | W₁₇ | mp ° C. |
|---|---|---|
| H | OCH₂CH₂SCH₂CH₃ | 118–119 |
| H | OCH₂C(Cl)=CH₂ | 147 |
| H | OCH₂CH₂NHCOCH₃ | 188 |
| H | O(CH₂)₆CH₃ | 79 |
| H | OCH₂CH₂OCH₂CH₂OCH₃ | 68 |
| H | OCH₂CH₂CH₂OH | 72–75 |
| H | OCH₂CH₂OCH₃ | 148–149 |
| H | SCH₂C₆H₅ | 185–187 |
| H | SCH₂CH₃ | 165–167 |
| F | OCH₂CH₃ | 145–148.5 |
| F | OCH₃ | 186.5–189.5 |
| H | SCH₃ | 184 |
| H | SCH(CH₃)₂ | 94 |
| H | S(CH₂)₃CH₃ | 174.5 |
| F | SCH₂CH₃ | |
| H | SC(CH₃)₃ | 114 |
| F | OCH₂—[tetrahydrofuran] | |

EXAMPLE 159

Preparation of 5-[3,6-Dihydro-3-methyl-2,6-dioxo-4-(trifluoromethyl)-1(2H)-pyrimidinyl]-1,2-benzisothiazole-3-carboxylic acid, methyl ester

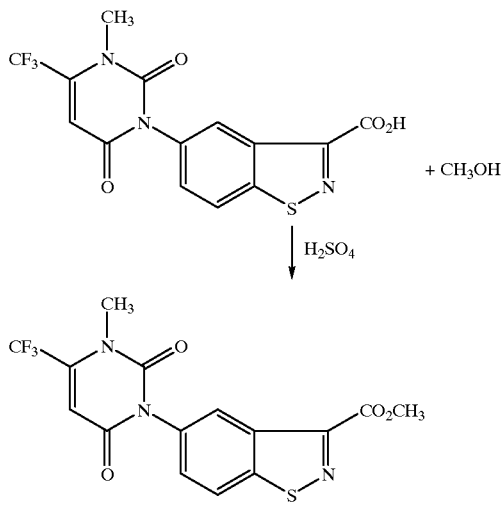

To a solution of 5-[3,6-dihydro-3-methyl-2,6-dioxo-4-(trifluoromethyl)-1(2H)-pyrimidinyl]-1,2-benzisothiazole-3-carboxylic acid (0.300 g, 0.000809 mol) in methanol is added sulfuric acid (98%, 5 drops) at room temperature. The resultant mixture is stirred overnight at room temperature and concentrated in vacuo. The residue is taken up in methylene chloride, washed with saturated sodium bicarbonate and brine, dried over anhydrous sodium sulfate, filtered, and concentrated in vacuo. Column chromatography of the residue on silica gel with methylene chloride:ethyl acetate gives the title compound as a white solid (0.235 g, 75.3%, mp 153–156° C.).

EXAMPLE 160

Preparation of 5-[3,6-Dihydro-3-methyl-2,6-dioxo-4-(trifluoromethyl)-1(2H)-pyrimidinyl]-1,2-benzisothiazole-3-carboxylic acid, isopropyl ester

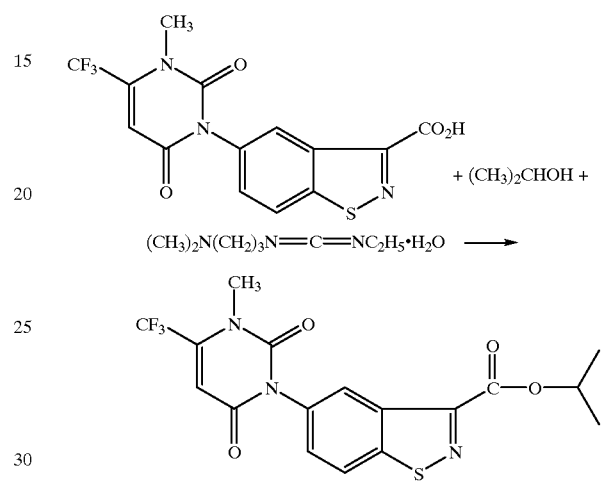

1-(3-Dimethylaminopropyl)-3-ethyl carbodiimide hydrochloride (0.200 g, 0.00105 mol) is added to a mixture of 5-[3,6-dihydro-3-methyl-2,6-dioxo-4-(trifluoromethyl)-1(2H)-pyrimidinyl-1,2-benzisothiazole-3-carboxylic acid (0.200 g, 0.000539 mol), dimethylaminopyridine (0.0100 mg), isopropanol (0.200 g, 0.00330 mol) and methylene chloride at room temperature. The resultant mixture is stirred overnight at room temperature and partitioned between water and methylene chloride. The organic layer is separated, washed with water and brine, dried over anhydrous sodium sulfate, filtered, and concentrated in vacuo. The resultant residue is chromatographed on silica gel with methylene chloride:ethyl acetate to give the title compound as a white solid (0.180 g, 80.7%, mp 94–97° C.).

Following essentially the same procedure, but using the appropriate alcohol, the following compounds are obtained:

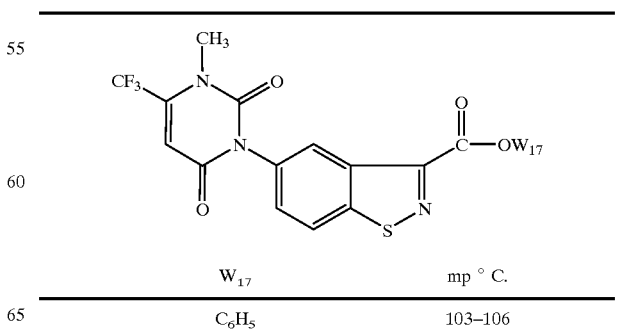

| W₁₇ | mp ° C. |
|---|---|
| C₆H₅ | 103–106 |

-continued

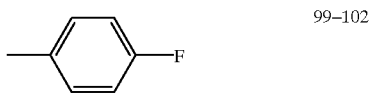

99–102

EXAMPLE 161

Preparation of 5-[3,6-Dihydro-3-methyl-2,6-dioxo-4-(trifluoromethyl)-1(2H)-pyrimidinyl]-N-(diisopropylsulfamoyl)-1,2-benzisothiazole-3-carboxamide

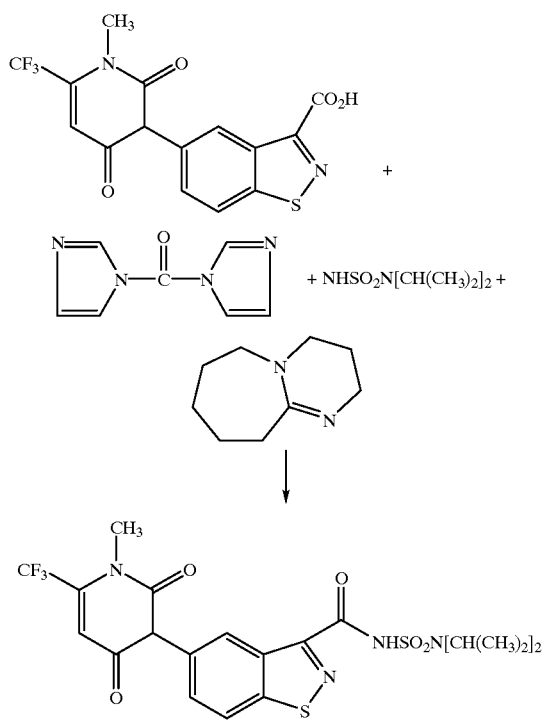

A solution of 5-[3,6-dihydro-3-methyl-2,6-dioxo-4-(trifluoromethyl)-1(2H)-pyrimidinyl-1,2-benzisothiazole-3-carboxylic acid (1.00 g, 0.00270 mol) and carbonyldiimidazole (0.480 g, 0.00296 mol) in tetrahydrofuran is stirred at reflux. After 30 minutes, the reaction mixture is cooled to room temperature, treated with N,N-diisopropylsulfamide, stirred for 15 minutes, and treated with 1,8-diazabicyclo[5.4.0]undec-7-ene (0.400 ml, 0.00270 mol). After stirring overnight at room temperature, the reaction mixture is concentrated in vacuo, and partitioned between water and ethyl acetate. The aqueous layer is extracted with ethyl acetate and the combined organic layers are washed with brine, dried over anhydrous magnesium sulfate, and concentrated in vacuo. Flash chromatography of the resultant residue on silica gel using 1:2 ethyl acetate/hexanes gives the title compound as a white solid (0.200 g, mp 214° C.).

Using essentially the same procedure, the following compounds are obtained:

| X | $R_{46}$ | $R_{48}$ | mp ° C. |
|---|---|---|---|
| H | $CH_3$ | $CH_3$ | 213 |
| H | H | $CH(CH_3)_2$ | 236 |
| H | $CH_3$ | $CH_2$-C$_6$H$_4$-Cl | 174–175 |
| F | $CH(CH_3)_2$ | $CH(CH_3)_2$ | 206–207 |

Using essentially the same procedure but starting with the appropriate C-3 phenyl acid, the following compounds are prepared:

| X | $W_3$ | mp ° C. |
|---|---|---|
| H | H | 121–123 |
| H | $CH_3$ | 193–195 |
| F | $CH_3$ | 192 |

EXAMPLE 162

Preparation of 5-[3,6-Dihydro-3-methyl-2,6-dioxo-4-(trifluoromethyl)-1(2H)-pyrimidinyl]-N-sulfamoyl-1,2-benzisothiazole-3-carboxamide

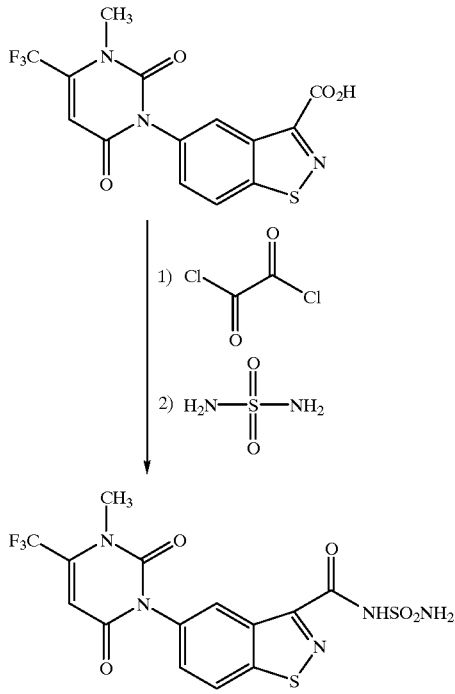

A solution of 5-[3,6-dihydro-3-methyl-2,6-dioxo-4-(trifluoromethyl)-1(2H)-pyrimidinyl-1,2-bnezisothiazole-3-carboxylic acid (0.500 g, 0.00135 mol) in 9:1 methylene chloride/tetrahydrofuran at 10° C. is treated with oxalyl chloride (1.68 ml, 0.00337 mol) and N,N-dimethylformamide (1 drop). After 1 hour, the reaction mixture is concentrated in vacuo, taken up into 1,4-dioxane, and added dropwise to a solution of sulfamide (1.29 g, 0.0135 mol) in 1,4-dioxane at 0° C. After stirring overnight at room temperature, the reaction mixture is concentrated in vacuo, taken up into ethyl acetate, washed sequentially with brine and 10% aqueous HCl, dried over anhydrous magnesium sulfate, and concentrated in vacuo to give a crude product. The crude product is filtered through silica gel, using 6:4 ethyl acetate/hexanes to give the title product as an off-white solid, mp 221° C.

EXAMPLE 163

Preparation of 5-[3,6-Dihydro-3-methyl-2,6-dioxo-4-(trifluoromethyl)-1(2H)-pyrimidinyl]-N-isopropyl-1,2-benzisothiazole-3-carboxamide

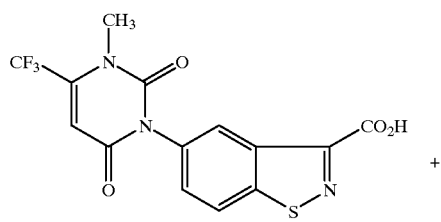

+

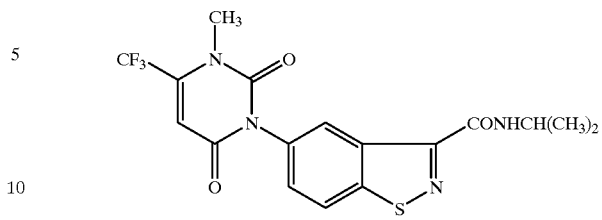

To a mixture of 5-[3,6-dihydro-3-methyl-2,6-dioxo-4-(trifluoromethyl)-1(2H)-pyrimidinyl-1,2-benzisothiazole-3-carboxylic acid (0.400 g, 0.00108 mol), isopropylamine (0.140 g, 0.00237 mol), dimethylaminopyridine (0.000100 g) and methylene chloride is added 1-(3-dimethylaminopropyl)-3-ethylcarbodiimide hydrochloride (0.300 g, 0.00157 mol) at room temperature. The resultant mixture is stirred overnight at room temperature and partitioned between methylene chloride and water. The organic layers are washed with 0.5 M hydrochloric acid and brine, dried over anhydrous sodium sulfate, filtered, and concentrated in vacuo. The resultant residue is chromatographed on silica gel with methylene chloride:ethyl acetate to give the title compound as a white solid (0.250 g, 56.2%, mp 110–113° C.).

Following essentially the same procedure, but using the appropriately substituted amine, the following compounds are obtained:

| $R_{13}$ | $R_{12}$ | mp ° C. |
|---|---|---|
| H | —C(CH₃)₃ attached to 3-methylisoxazol-5-yl | 93–96 |
| CH₃ | 4-chlorophenyl | 117–119 |
| H | H | 227–229 |
| CH₃ | CH₃ | 95–98 |
| H | 2-methyl-4-trifluoromethyl-5-chlorothiazolyl | 275 |
| H | CH₂CO₂H | |

EXAMPLE 164

Preparation of 5-[3,6-Dihydro-3-methyl-2,6-dioxo-4-(trifluoromethyl)-1(2H)-pyrimidinyl]-N-methoxy-1,2-benzisothiazole-3-carboxamide

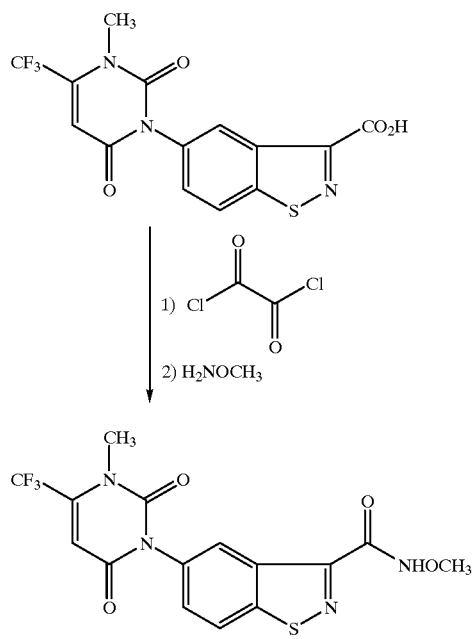

To a mixture of 5-[3,6-dihydro-3-methyl-2,6-dioxo-4-(trifluoromethyl)-1(2H)-pyrimidinyl]-1,2-benzisothiazole-3-carboxylic acid (4.00 g, 0.0108 mol), methylene chloride and tetrahydrofuran on an ice bath is added N,N-dimethylformamide (5 drops) followed by oxalyl chloride (13.5 ml, 0.0269 mol). The resultant mixture is stirred 90 minutes at ambient temperature and concentrated in vacuo. The residue is taken up in tetrahydrofuran and 25% of the solution is added to a mixture of O-methyl hydroxylamine hydrochloride (0.900 g, 0.0108 mol), tetrahydrofuran and triethylamine (2.25 ml, 0.0162 mol). The resultant mixture is stirred overnight at room temperature, poured into ice water, and extracted with methylene chloride. The organic layers are dried over anhydrous magnesium sulfate, filtered, and concentrated in vacuo. The residue is chromatographed on silica gel with methylene chloride to give the title compound as a light yellow solid (0.240 g, 22.3%, mp 125–127° C.).

Using essentially the same procedure, with the appropriate hydroxylamines, the following compounds are obtained:

| $R_{12}$ | $R_{23}$ | mp ° C. |
|---|---|---|
| H | $CH_2CH=CH_2$ | 91–92 |
| $CH_3$ | H | 118–120 |
| H | $CH_2C_6H_5$ | 96–97 |
| H | $SO_2OH$ | 221 |
| H | H | 234 |

EXAMPLE 165

Preparation of 1-Methyl-6-(trifluoromethyl)-3-(3-valeryl-1,2-benzisothiazol-5-yl)-2,4(1H,3H)-pyrimidinedione

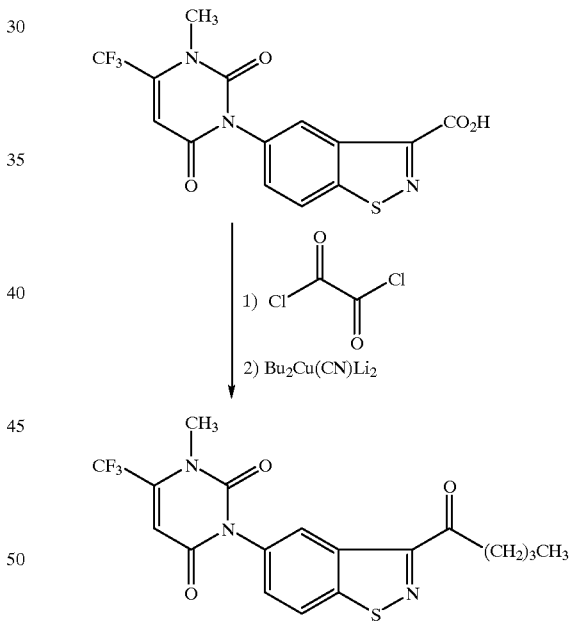

To a solution of 5-[3,6-dihydro-3-methyl-2,6-dioxo-4-(trifluoromethyl)-1(2H)-pyrimidinyl]-1,2-benzisothiazole-3-carboxylic acid (0.200 g, 0.000540 mol) in methylene chloride is added N,N-dimethylformamide (one drop) followed by oxalyl chloride in methylene chloride (2.0 M, 0.540 ml, 0.00108 mol). The resultant mixture is stirred at room temperature for 90 minutes and concentrated in vacuo to a white solid, which is saved. To a suspension of copper cyanide (0.061 g, 0.000675 mol) in tetrahydrofuran, is added dropwise n-butyllithium (2.5 M in hexanes, 0.540 ml, 0.00135 mol) at −78° C. The reaction mixture is allowed to warm for 5 minutes and then cooled back to −78° C. The mixture is then treated with a solution of the white solid from the first step in tetrahydrofuran, and the resultant mixture stirred one hour at −78° C. The reaction mixture is quenched with saturated ammonium chloride and diluted with ethyl acetate. The organic layer is washed sequentially with saturated ammonium chloride, water and brine, dried over anhydrous magnesium sulfate, filtered, and concentrated in vacuo to a yellow syrup. Chromatography of the syrup on silica gel using hexanes:ethyl acetate gives the title compound as a colorless syrup (0.142 g, 64.0%) which is identified by NMR spectral analysis.

Using essentially the same procedure, the following compounds are obtained:

| $R_{12}$ | mp ° C. |
|---|---|
| $C(CH_3)_3$ | 83–85 |
| $C_6H_5$ | 93–95 |
| $CH(CH_3)CH_2CH_3$ | 75–77 |

EXAMPLE 166

Preparation of 5-[3,6-Dihydro-3-methyl-2,6-dioxo-4-(trifluoromethyl)-1(2H)-pyrimidinyl]-N-methyl-N-(methylsulfonyl)-1,2-benzisothiazole-3-carboxamide

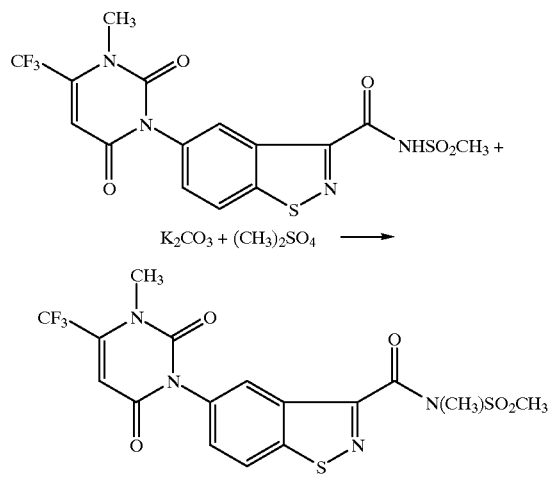

To a solution of 5-[3,6-dihydro-3-methyl-2,6-dioxo-4-(trifluoromethyl)-1(2H)-pyrimidinyl]-N-(methylsulfonyl)-1,2-benzisothiazole-3-carboxamide (0.300 g, 0.000670 mol) in acetone is added dimethyl sulfate (0.180 g, 0.00140 mol) followed by potassium carbonate (0.250 g, 0.00180 mol). The resultant mixture is stirred one hour at reflux and concentrated in vacuo. The residue is partitioned between methylene chloride and water. The organic layer is saved and the aqueous layer is extracted with methylene chloride. The combined organic layers are washed with water, dried over anhydrous sodium sulfate, filtered, and concentrated in vacuo. The residue is chromatographed on silica gel with ethyl acetate:hexanes to give the title compound as a white solid (0.232 g, 74.9%, mp 120–122° C.).

Using essentially the same procedure, the following compounds are obtained:

| $R_{12}$ | $R_{51}$ | mp ° C. |
|---|---|---|
| $CH_2OCH_2CH_3$ | $CH_3$ | 91–93 |
| $CH_2OCH_2CH_3$ | $CH_2C_6H_5$ | 185–186 |
| $CH_2CO_2CH_3$ | $CH_2C_6H_5$ | 158–160 |
| $CH_3$ | $CH_2C_6H_5$ | >225 |

EXAMPLE 167

Preparation of 3-(3-Isopropyl-1,2-benzisothiazol-5-yl)-1-methyl-6-(trifluoromethyl)-2,4(1H,3H)-pyrimidinedione

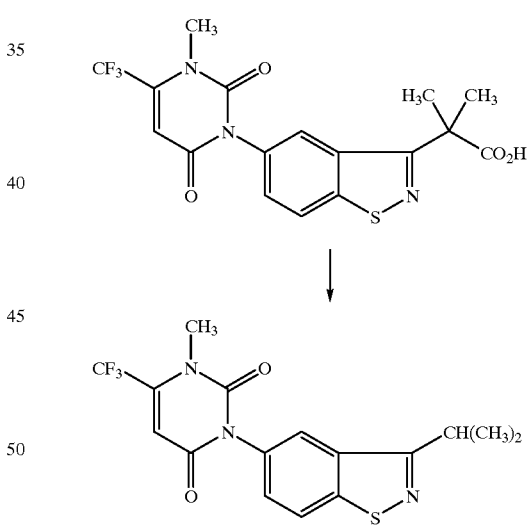

A mixture of 5-[3,6-dihydro-3-methyl-2,6-dioxo-4-(trifluoromethyl)-1(2H)-pyrimidinyl]-α,α-dimethyl-1,2-benzisothiazole-3-acetic acid (2.00 g, 0.00484 mol) and quinoline (20.0 ml) is heated to 140° C. with stirring. After 15 minutes, the mixture is cooled to room temperature, diluted with ethyl acetate, washed sequentially with 2 N hydrochloric acid, saturated sodium bicarbonate and brine, dried over anhydrous magnesium sulfate, and concentrated in vacuo to a yellow solid. The solid is recrystallized from hexanes:methylene chloride to give the title compound as an off-white solid (0.640 g, 35.8%, mp 139–140° C.) which is identified by NMR and IR spectral analyses.

EXAMPLE 168

Preparation of 5-[3,6-Dihydro-3-methyl-2,6-dioxo-4-(trifluoromethyl-1(2H)-pyrimidinyl]-α,α-dimethyl-1,2-benzisothiazole-3-acetic acid, allyl ester

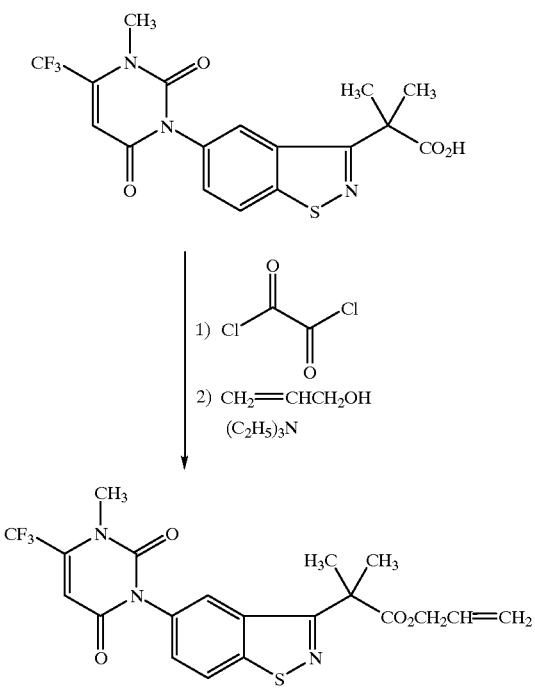

N,N-dimethylformamide (8 drops) is added to a mixture of 5-[3,6-dihydro-3-methyl-2,6-dioxo-4-(trifluoromethyl)-1(2H)-pyrimidinyl]-α,α-dimethyl-1,2-benzisothiazole-3-acetic acid (2.00 g, 0.00484 mol) and methylene chloride. The mixture is cooled on an ice bath and oxalyl chloride (2.0 M in methylene chloride, 6.05 ml, 0.0121 mol) is added. The resultant mixture is stirred one hour on an ice bath and concentrated in vacuo. The residue is taken up in tetrahydrofuran. To this solution are added allyl alcohol (0.420 g, 0.0185 mol) and triethylamine (1.50 ml 0.0108 mol). The mixture is stirred three days at room temperature. Dimethylaminopyridine (0.0100 g) is added and the mixture is stirred 24 hours at room temperature and filtered. The filtrate is concentrated in vacuo. The residue is taken up in ether, washed with saturated sodium bicarbonate and brine, dried over anhydrous magnesium sulfate, filtered, and concentrated in vacuo. The residue is chromatographed on silica gel with hexanes:ethyl acetate to afford the title compound as a white solid (mp 115–116° C.) which is identified by NMR spectral analysis.

Following essentially the same procedure, but using the appropriate alcohol or thioalcohol, the following compounds are obtained:

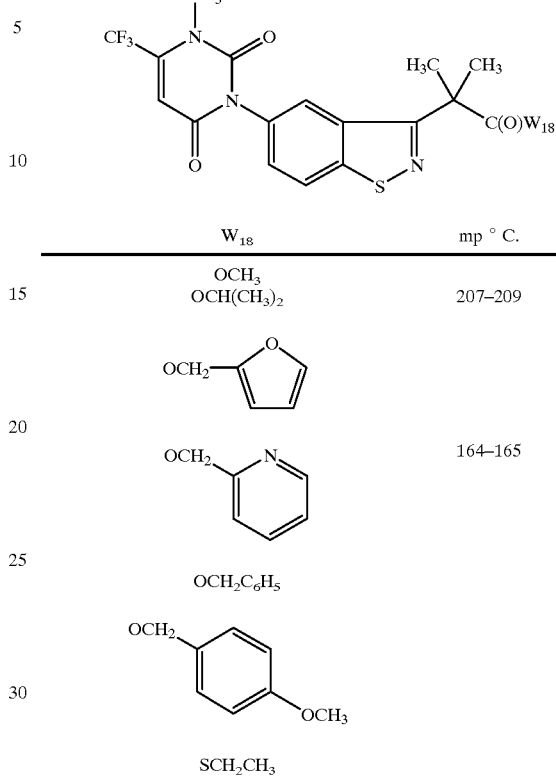

| $W_{18}$ | mp ° C. |
|---|---|
| OCH$_3$ | |
| OCH(CH$_3$)$_2$ | 207–209 |
| OCH$_2$-(2-furyl) | |
| OCH$_2$-(2-pyridyl) | 164–165 |
| OCH$_2$C$_6$H$_5$ | |
| OCH$_2$-C$_6$H$_4$-OCH$_3$ | |
| SCH$_2$CH$_3$ | |

EXAMPLE 169

Preparation of 5-[3,6-Dihydro-3-methyl-2,6-dioxo-4-(trifluoromethyl)-1(2H)-pyrimidinyl]-α,α-dimethyl-1,2-benzisothiazole-3-acetic acid

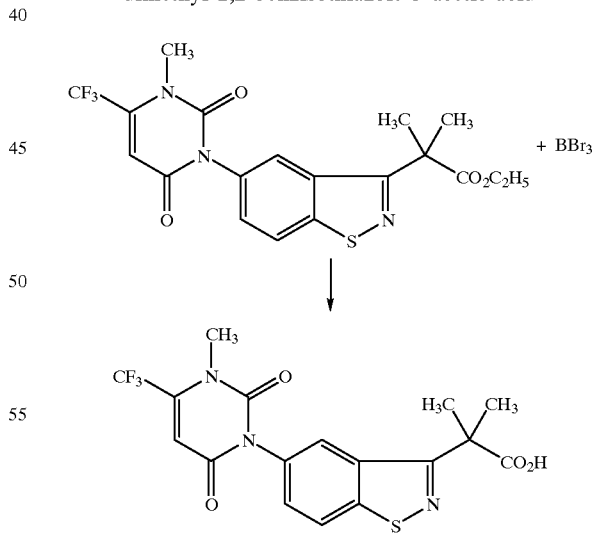

To a solution of ethyl 5-[3,6-dihydro-3-methyl-2,6-dioxo-4-(trifluoromethyl)-1(2H)-pyrimidinyl]-α,α-dimethyl-1,2-benzisothiazole-3-acetate (6.30 g, 0.0143 mol) in methylene chloride at 0° C. is added boron tribromide in methylene chloride (1.0 M, 100 ml, 0.100 mol) such that the temperature does not exceed 15° C. The resultant mixture is stirred one hour at ambient temperature, quenched with 3 N hydrochloric acid, and diluted with methylene chloride. The organic layer is separated, washed sequentially with water and brine, dried over anhydrous magnesium sulfate, and concentrated in vacuo to give the title compound as an off-white solid (mp 155–156° C.) which is identified by NMR and IR spectral analyses.

Using essentially the same procedure, 5-[3,6-dihydro-3-methyl-2,6-dioxo-4-(trifluoromethyl)-1(2H)-pyrimidinyl]-6-fluoro-1,2-benzisothiazole-3-carboxylic acid is prepared from its ethyl ester.

EXAMPLE 170

Preparation of 5-[3,6-Dihydro-3-methyl-2,6-dioxo-4-(trifluoromethyl)-1(2H)-pyrimidinyl]-N-(diisopropylsulfamoyl)-α,α-dimethyl-1,2-benzisothiazole-3-acetamide

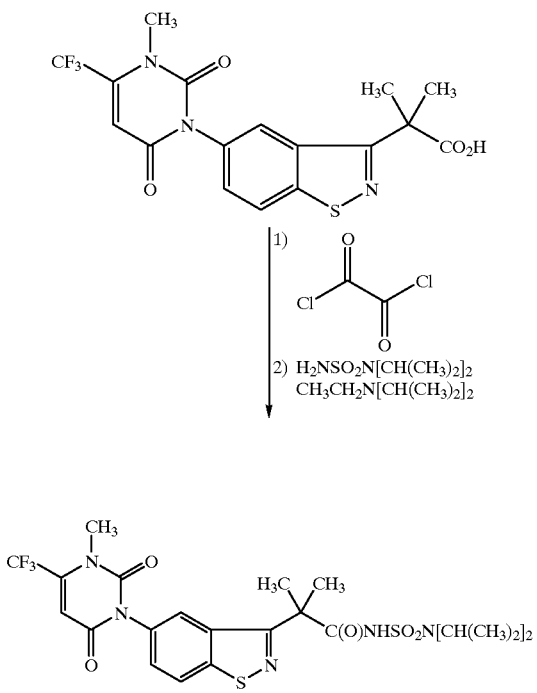

N,N-dimethylformamide (8 drops) is added to a mixture of 5-[3,6-dihydro-3-methyl-2,6-dioxo-4-(trifluoromethyl)-1(2H)-pyrimidinyl]-α,α-dimethyl-1,2-benzisothiazole-3-acetic acid (0.800 g, 0.00194 mol) and methylene chloride. The mixture is cooled on an ice bath and oxalyl chloride (2.0 M in methylene chloride, 2.42 ml, 0.00485 mol) is added. The resultant mixture is stirred one hour on an ice bath and concentrated in vacuo. The residue is taken up in tetrahydrofuran. N,N-Diisopropylaminosulfonamide (0.410 g, 0.00278 mol), ethyldiisopropylamine (0.310 g, 0.00240 mol) and dimethylaminopyridine (0.0100 g) are added and the resultant mixture is stirred overnight at room temperature. The mixture is then filtered and the filtrate is concentrated in vacuo to afford a yellow resin. The resin is filtered through silica gel to afford the title compound as a tan resin (0.500 g, 44.8%).

EXAMPLE 171

Preparation of 3-[3-(1,1-Dimethyl-2-oxopropyl)-1,2-benzisothiazol-5-yl]-1-methyl-6-(trifluoromethyl)-2,4(1H,3H)-pyrimidinedione

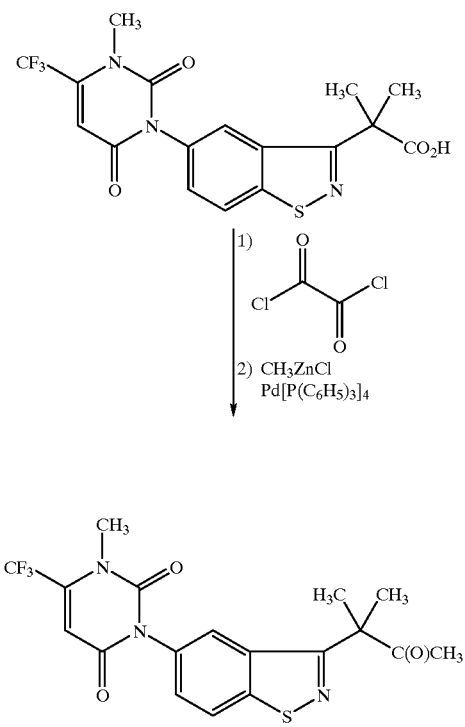

N,N-Dimethylformamide (8 drops) is added to a mixture of 5-[3,6-dihydro-3-methyl-2,6-dioxo-4-(trifluoromethyl)-1(2H)-pyrimidinyl]-α,α-dimethyl-1,2-benzisothiazole-3-acetic acid (0.800 g, 0.00194 mol) and methylene chloride. The mixture is cooled on an ice bath and oxalyl chloride (2.0 M in methylene chloride, 2.42 ml, 0.00484 mol) is added. The resultant mixture is stirred one hour on an ice bath and concentrated in vacuo. The residue is taken up in tetrahydrofuran. The resultant solution is added dropwise to a mixture of methyl zinc chloride (2.0 M, 0.970 ml, 0.00194 mol) in tetrahydrofuran, followed by addition of palladium tetrakistriphenylphosphine (0.220 g, 0.000190 mol). The resultant mixture is stirred overnight at room temperature, quenched with 10% hydrochloric acid, and extracted with ethyl acetate. The organic layer is washed with saturated sodium bicarbonate and brine, dried over anhydrous magnesium sulfate, filtered, and concentrated in vacuo to an orange solid. The solid is chromatographed on silica gel to afford the title compound as an off-white solid (0.270 g, 65.7%, mp 195–196° C.).

EXAMPLE 172

Preparation of 5-[3,6-Dihydro-3-methyl-2,6-dioxo-4-(trifluoromethyl)-1(2H)-pyrimidinyl]-α,α-dimethyl-1,2-benzisothiazole-3-acetamide

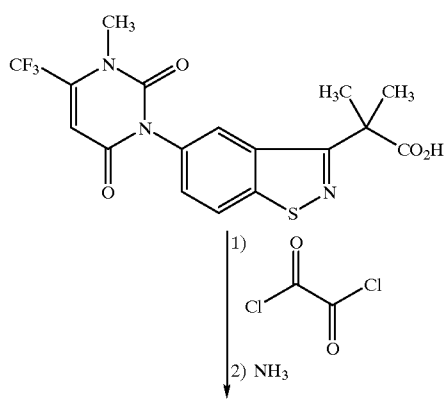

N,N-Dimethylformamide (8 drops) is added to a mixture of 5-[3,6-dihydro-3-methyl-2,6-dioxo-4-(trifluoromethyl)-1 (2H)-pyrimidinyl]-α,α-dimethyl-1,2-benzisothiazole-3-acetic acid (2.00 g, 0.00484 mol) and methylene chloride. The mixture is cooled on an ice bath and oxalyl chloride (2.0 M in methylene chloride, 6.05 ml, 0.0121 mol) is added. The resultant mixture is stirred one hour on an ice bath and concentrated in vacuo. The residue is taken up in tetrahydrofuran. The resultant solution is saturated with ammonia gas followed by the addition of triethylamine. The mixture is filtered and the filtrate is concentrated in vacuo to a solid. The solid is recrystallized from methylene chloride:hexanes to afford the title compound as a tan solid (1.65 g, 82.7%, mp 192–196° C.) which is identified by NMR and IR spectral analyses.

EXAMPLE 173

Preparation of 5-[3,6-Dihydro-3-methyl-2,6-dioxo-4-(trifluoromethyl)-1(2H)-pyrimidinyl]-α,α-dimethyl-N-(methylsulfonyl)-1,2-benzisothiazole-3-acetamide

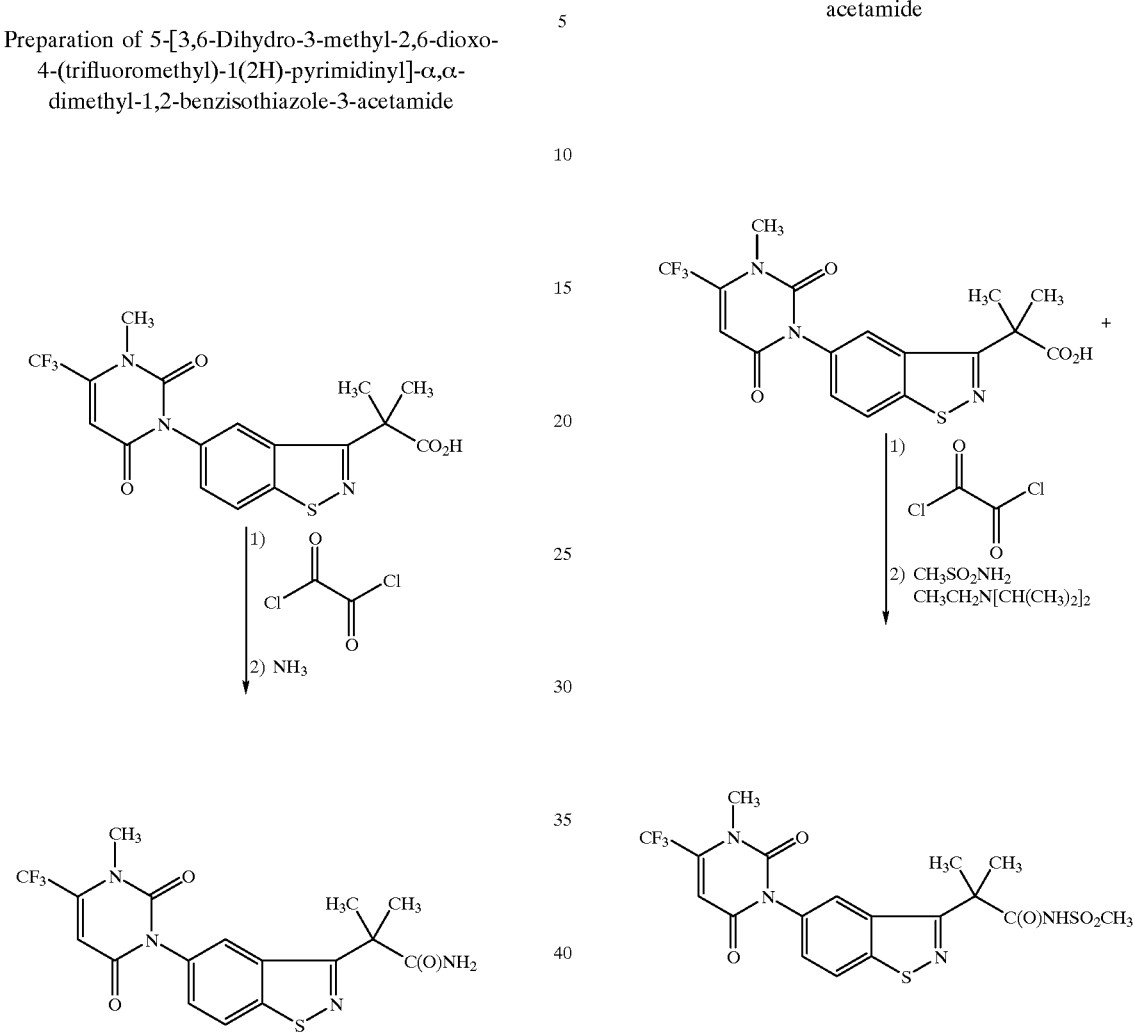

N,N-Dimethylformamide (8 drops) is added to a mixture of 5-[3,6-dihydro-3-methyl-2,6-dioxo-4-(trifluoromethyl)-1 (2H)-pyrimidinyl]-α,α-dimethyl-1,2-benzisothiazole-3-acetic acid (2.00 g, 0.00484 mol) and methylene chloride. The mixture is cooled on an ice bath and oxalyl chloride (2.0 M in methylene chloride, 6.05 ml, 0.0121 mol) is added. The resultant mixture is stirred one hour on an ice bath and concentrated in vacuo. The residue is taken up in tetrahydrofuran. Methylsulfonamide (0.690 g, 0.00726 mol) is added, followed by ethyldiisopropylamine (0.940 g, 0.00727 mol) and dimethylaminopyridine (0.100 g). The resultant mixture is stirred at room temperature and filtered. The filtrate is concentrated in vacuo and the residue is filtered through silica gel with hexanes:ethyl acetate. The filtrate is concentrated in vacuo to a tan solid. The solid is suspended in methylene chloride, stirred, and refiltered to give the title compound as a white solid (0.320 g, 13.5%, mp 264–265° C.).

Using essentially the same procedure, the following compounds are obtained:

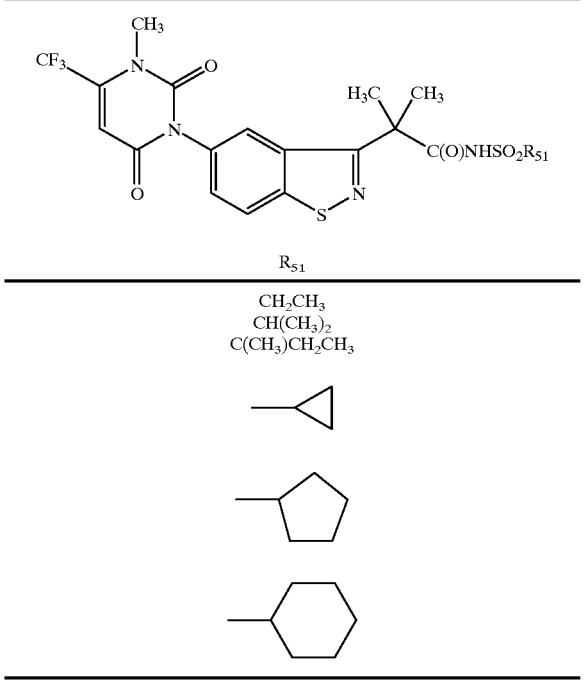

EXAMPLE 174

Preparation of {{{5-[3,6-Dihydro-3-methyl-2,6-dioxo-4-(trifluoromethyl)-1(2H)pyrimidinyl]-1,2-benzisothiazol-3-yl}methyl}sulfonyl}acetic acid

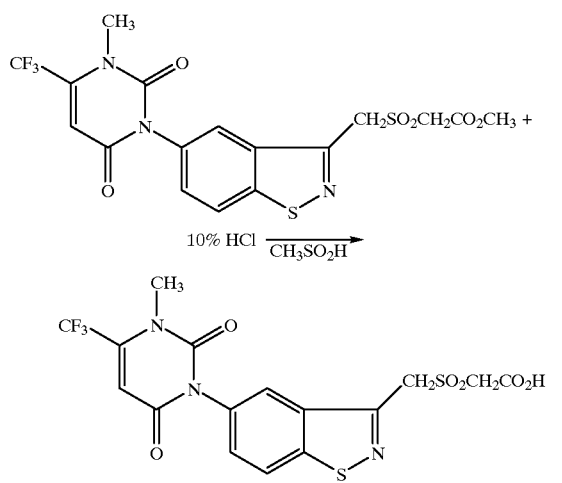

A mixture of methyl{{{5-[3,6-dihydro-3-methyl-2,6-dioxo-4-(trifluoromethyl)-1(2H)-pyrimidinyl]-1,2-benzisothiazol-3-yl}methyl}sulfonyl}acetate (1.00 g, 0.00210 mol), acetic acid and 10% hydrochloric acid (2.00 ml) is stirred overnight at 60° C. Additional hydrochloric acid (37%, 1.20 ml) is added and the mixture is stirred 5 hours at 80° C. The mixture is cooled to room temperature, poured into ice water with stirring, and filtered to give the title compound as a white solid (0.760 g, 78.4%, mp 215° C.) which is identified by NMR spectral analysis.

Using essentially the same procedure {{{5-[3,6-dihydro-3-methyl-2,6-dioxo-4-(trifluoromethyl)-1(2H)-pyrimidinyl]-1,2-benzisothiazol-3-yl}methyl}thio}acetic acid is obtained from its methyl ester.

EXAMPLE 175

Preparation of Methyl{{{5-[3,6-dihydro-3-methyl-2,6-dioxo-4-(trifluoromethyl)-1(2H)-pyrimidinyl]-1,2-benzisothiazol-3-yl}methyl}sulfonyl}acetate

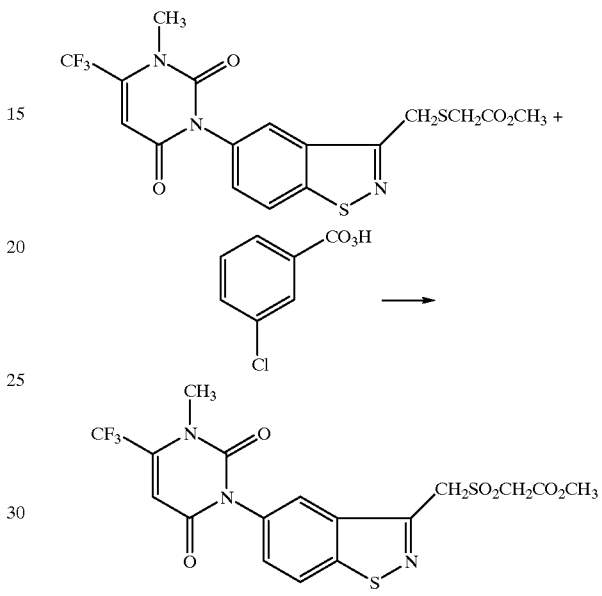

A solution of meta-chloroperbenzoic acid (70% purity, 1.91 g, 0.00774 mol) in methylene chloride is added to a solution of methyl{{{5-[3,6-dihydro-3-methyl-2,6-dioxo-4-(trifluoromethyl)-1(2H)-pyrimidinyl]-1,2-benzisothiazol-3-yl}methyl}thio}acetate (1.00 g, 0.00225 mol) in methylene chloride at 0° C. When the reaction is complete by thin layer chromatography analysis, the mixture is washed sequentially with 5% sodium carbonate and brine, and concentrated in vacuo to a white foam. The foam is triturated in ether to give the title compound as a white solid (0.500 g, 46.7%, mp 209–210° C.) which is identified by NMR spectral analysis.

EXAMPLE 176

Preparation of N-{{5-[3,6-Dihydro-3-methyl-2,6-dioxo-4-(trifluoromethyl)-1(2H)-pyrimidinyl]-1,2-benzisothiazol-3-yl}methyl}-N-(methylsulfonyl)-glycine, methyl ester

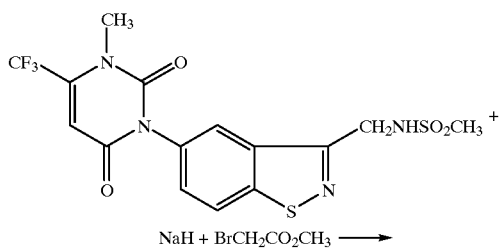

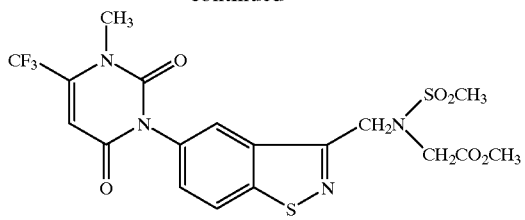

To a mixture of 2-{{5-[3,6-dihydro-3-methyl-2,6-dioxo-4-(trifluoromethyl)-1(2H)-pyrimidinyl]-1,2-benzisothiazol-3-yl}methoxy}-N-(methylsulfonyl)-acetamide (0.500 g, 0.00115 mol) and tetrahydrofuran is added methyl bromoacetate (0.130 ml, 0.00138 mol) followed by sodium hydride (60%, 0.0690 g, 0.00173 mol). The resultant mixture is poured into water and extracted with methylene chloride. The combined organic layers are dried over anhydrous magnesium sulfate, filtered, and concentrated in vacuo to an oil. The oil is triturated in ether to give the title compound as a white solid (0.270 g, 46.4%, mp 135–136° C.) which is identified by NMR spectral analysis.

EXAMPLE 177

Preparation of 3-[3-[(Ethoxymethoxy)methyl]-1,2-benzisothiazol-5-yl]-1-methyl-6-(trifluoromethyl)-2,4(1H,3H)-pyrimidinedione

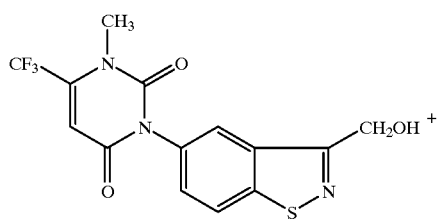

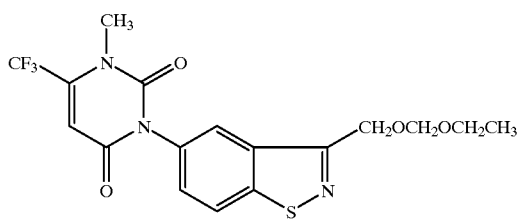

To a mixture of 3-[3-(hydroxymethyl)-1,2-benzisothiazol-5-yl]-1-methyl-6-(trifluoromethyl)-2,4(1H,3H)-pyrimidinedione (0.800 g, 0.00224 mol) and methylene chloride is added ethyldiisopropylamine (0.780 ml, 0.00448 mol) followed by chloromethyl ethyl ether (0.310 ml, 0.00336 mol). The resultant mixture is stirred 42.5 hours at room temperature, diluted with ether, washed sequentially with 1 M aqueous hydrochloric acid, saturated sodium bicarbonate and brine, dried over anhydrous magnesium sulfate, filtered, and concentrated in vacuo to a yellow syrup. The syrup is chromatographed on silica gel with hexanes-:ethyl acetate to give the product as a white solid which is identified by NMR spectral analysis.

Following essentially the same procedure, but using the appropriate alkylating agent, the following compounds are obtained:

structure

| $R_{22}$ | mp ° C. |
|---|---|
| ![tetrahydropyranyl] | |
| $CH_2OCH_2C_6H_5$ | 114 |
| $CH_2OCH_3$ | 138–141 |
| ![CH2-4-chlorophenyl] | |
| ![CH2-2,4-dichlorophenyl] | |
| $CH_2SCH_3$ | 145–147 |
| ![CH2-3,4-dichlorophenyl] | |
| ![CH2-3-methylphenyl] | |
| ![CH2-3-nitrophenyl] | |
| ![CH2-4-nitrophenyl] | |

EXAMPLE 178

Preparation of {{5-[3,6-Dihydro-3-methyl-2,6-dioxo-4-(trifluoromethyl)-1(2H)-pyrimidinyl]-1,2-benzisothiazol-3-yl}methoxy}acetic acid

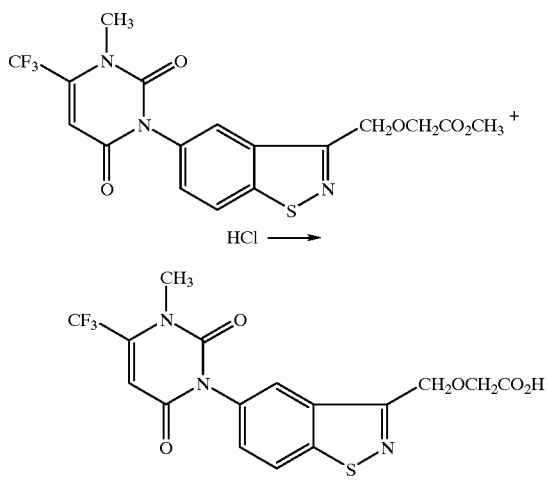

To a mixture of {{5-[3,6-dihydro-3-methyl-2,6-dioxo-4-(trifluoromethyl)-1(2H)-pyrimidinyl]-1,2-benzisothiazol-3-yl}methoxy}acetic acid, methyl ester (4.19 g, 0.00977 mol) and acetic acid is added 37% hydrochloric acid (5.00 ml). The resultant mixture is stirred overnight at 65° C. and cooled to room temperature. The mixture is concentrated in vacuo. The residue is suspended in water and quenched slowly by the addition of solid sodium bicarbonate to neutral pH. The resultant mixture is partitioned between ether and saturated sodium bicarbonate, and filtered. The filtrate is washed with methylene chloride, acidified with hydrochloric acid, and filtered to give the title product as a white solid (2.87 g, 70.7%, mp 191–192° C.) which is identified by NMR spectral analysis.

EXAMPLE 179

Preparation of 2-{{5-[3,6-Dihydro-3-methyl-2,6-dioxo-4-(trifluoromethyl)-1(2H)-pyrimidinyl]-1,2-benzisothiazol-3-yl}methoxy}-N-(methylsulfonyl)acetamide, dimethylamine salt

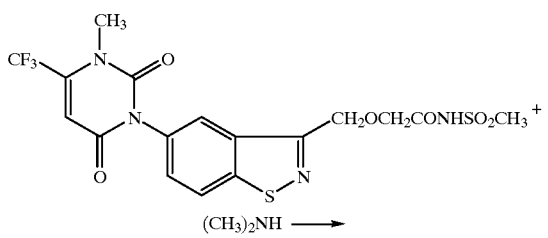

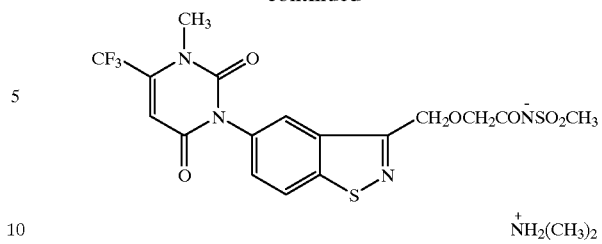

Dimethylamine (2.0 M in tetrahydrofuran, 1.04 ml, 0.00208 mol) is added to a solution of 2-{{5-[3,6-dihydro-3-methyl-2,6-dioxo-4-(trifluoromethyl)-1(2H)-pyrimidinyl]-1,2-benzisothiazol-3-yl}methoxy}-N-(methylsulfonyl)acetamide (0.510 g, 0.00104 mol) in tetrahydrofuran. The resultant mixture is stirred 5 minutes and concentrated in vacuo. The residue is taken up in tetrahydrofuran and crystallized by the addition of ether. The resultant off-white solid (0.420 g, 75.1%, mp 102–107° C.) is identified as the title compound by NMR spectral analysis.

Using essentially the same procedure on 2-{{{5-[3,6-dihydro-3-methyl-2,6-dioxo-4-(trifluoromethyl)-1(2H)-pyrimidinyl]-1,2-benzisothiazol-3-yl}methyl}thio}-N-(methylsulfonyl)acetamide; 2-{{{5-[3,6-dihydro-3-methyl-2,6-dioxo-4-(trifluoromethyl)-1(2H)-pyrimidinyl]-1,2-benzisothiazol-3-yl}methyl}thio}-N-(methylsulfonyl)acetamide, dimethylamine salt is obtained.

EXAMPLE 180

Preparation of {{5-[3,6-Dihydro-3-methyl-2,6-dioxo-4-(trifluoromethyl)-1(2H)-pyrimidinyl]-1,2-benzisothiazol-3-yl}methoxy}acetic acid, dimethylamine salt

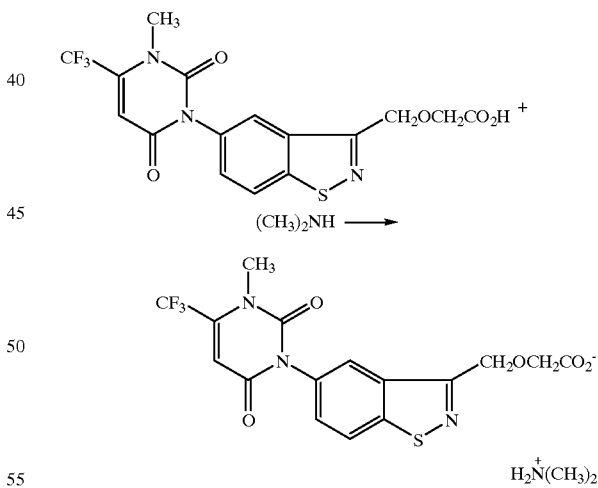

Dimethylamine in tetrahydrofuran (2.0 M, 1.23 ml, 0.00246 mol) is added to a solution of {{5-[3,6-dihydro-3-methyl-2,6-dioxo-4-(trifluoromethyl)-1(2H)-pyrimidinyl]-1,2-benzisothiazol-3-yl}methoxy}acetic acid (0.510 g, 0.00123 mol) in tetrahydrofuran. The mixture is stirred 15 minutes, diluted with ether and the resultant off-white solid is isolated (0.420 g, 74.2%, mp 175–176° C.) and identified as the title compound by NMR spectral analysis.

Using essentially the same procedure on {{{5-[3,6-dihydro-3-methyl-2,6-dioxo-4-(trifluoromethyl)-1(2H)- pyrimidinyl]-1,2-benzisothiazol-3-yl}methyl}thio}acetic acid; {{{5-[3,6-dihydro-3-methyl-2,6-dioxo-4-(trifluoromethyl)-1(2H)-pyrimidinyl]-1,2-benzisothiazol-3-yl}methyl}thio}acetic acid, dimethylamine salt is obtained.

EXAMPLE 181

Preparation of 2-{{5-[3,6-Dihydro-3-methyl-2,6-dioxo-4-(trifluoromethyl)-1(2H)-pyrimidinyl]-1,2-benzisothiazol-3-yl}methoxy-N-(methylsulfonyl)acetamide

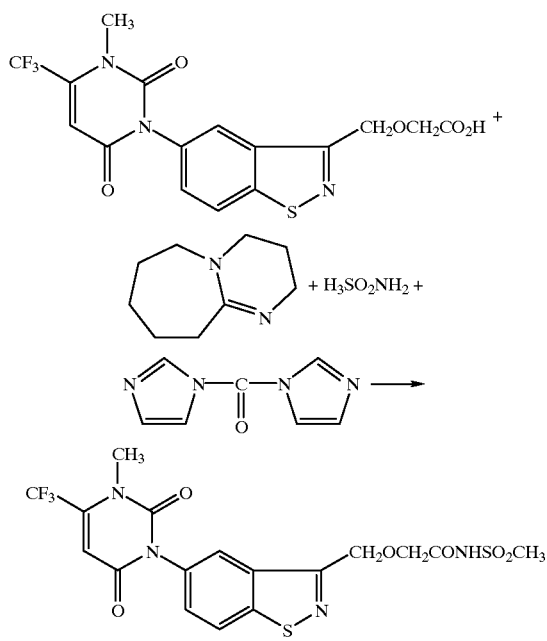

1,1'-Carbonyldiimidazole (1.17 g, 0.00722 mol) is added to a solution of {{5-[3,6-dihydro-3-methyl-2,6-dioxo-4-(trifluoromethyl)-1(2H)-pyrimidinyl]-1,2-benzisothiazol-3-yl}methoxy}acetic acid (1.50 g, 0.00361 mol) in tetrahydrofuran. The mixture is stirred one hour at reflux and cooled to room temperature. Methylsulfonamide (0.755 g, 0.00794 mol) is added, followed by 1,8-diazabicyclo[5.4.0]undec-7-ene (1.19 ml, 0.00794 mol). The resultant mixture is stirred overnight at room temperature, poured into 10% hydrochloric acid, and filtered. The resultant white solid is triturated in tetrahydrofuran, and filtered to give the title compound as an off-white solid (1.00 g, 56.2%, mp >240° C.) which is identified by NMR spectral analysis.

Using essentially the same procedure, 2-{{{5-[3,6-dihydro-3-methyl-2,6-dioxo-4-(trifluoromethyl)-1(2H)-pyrimidinyl]-1,2-benzisothiazol-3-yl}methyl}thio}-N-(methylsulfonyl)acetamide is obtained from {{{5-[3,6-dihydro-3-methyl-2,6-dioxo-4-(trifluoromethyl)-1(2H)-pyrimidinyl]-1,2-benzisothiazol-3-yl}methyl}sulfonyl}acetic acid.

EXAMPLE 182

Preparation of 3-{3-[Bromo(phenylsulfonyl)methyl]-1,2-benzisothiazol-5-yl}-1-methyl-6-(trifluoromethyl)-2,4(1H,3H)-pyrimidinedione

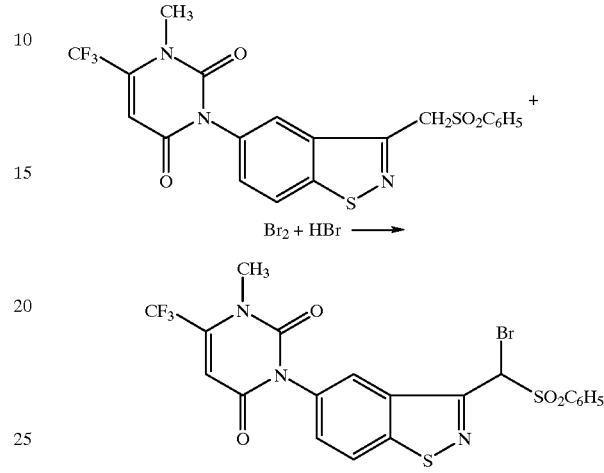

To a solution of 3-[3-(phenylsulfonyl)methyl-1,2-benzisothiazol-5-yl]-1-methyl-6-(trifluoromethyl)-2,4(1H,3H)-pyrimidinedione (0.400 g, 0.000831 mol) in ethyl acetate is added 48% hydrobromic acid (4 drops) followed by bromine in ethyl acetate (0.522 M, 1.67 ml, 0.000872 mol). The resultant mixture is stirred 1.5 hours at reflux. Additional bromine in ethyl acetate (1.67 ml) is added and the resultant mixture is stirred one hour at reflux. The mixture is cooled to room temperature, diluted with ethyl acetate, washed sequentially with 0.1 M sodium sulfite, saturated sodium bicarbonate and brine, dried over anhydrous magnesium sulfate, filtered, and concentrated in vacuo. The residue is chromatographed on silica gel with hexanes:ethyl acetate to give the title compound as a white crystalline solid (0.420 g, 90.1%, mp 182–183° C.) which is identified by NMR spectral analysis.

EXAMPLE 183

Preparation of Methyl 5-[3,6-dihydro-3-methyl-2,6-dioxo-4-(trifluoromethyl)-1(2H)-pyrimidinyl]-α-ethyl-1,2-benzisothiazole-3-acetate

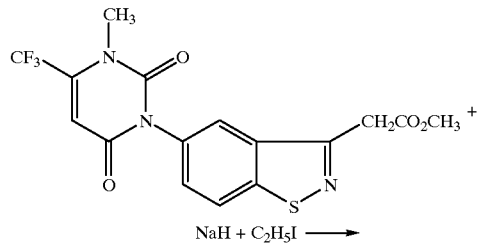

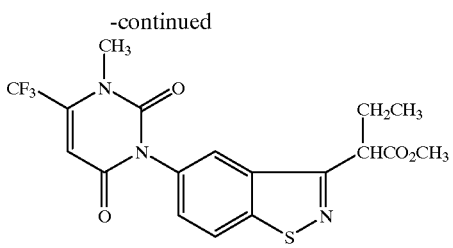

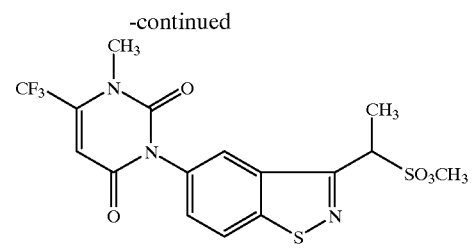

To a mixture of methyl 5-[3,6-dihydro-3-methyl-2,6-dioxo-4-(trifluoromethyl)-1(2H)-pyrimidinyl]-1,2-benzisothiazole-3-acetate (0.400 g, 0.00100 mol), N,N-dimethylformamide and ethyl iodide (0.980 g, 0.00628 mol) is added sodium hydride (60%, 0.0900 g, 0.00225 mol) in portions. The mixture is stirred 5 days at room temperature, diluted with methylene chloride, washed sequentially with 8% hydrochloric acid, water and brine, dried over anhydrous magnesium sulfate, filtered, and concentrated in vacuo. The residue is chromatographed on silica gel with ether:hexanes::methylene chloride to give the title compound (0.260 g, 60.9%) which is identified by NMR spectral analysis.

Following essentially the same procedure, but using the appropriate alkylating agent, the following compounds are obtained:

To a suspension of 1-methyl-3-{3-[(methylsulfonyl)methyl]-1,2-benzisothiazol-5-yl}-6-(trifluoromethyl)-2,4(1H,3H)-pyrimidinedione (1.00 g, 0.00238 mol) in tetrahydrofuran is added sodium hydride (60%, 0.120 g, 0.00300 mol). The resultant mixture is stirred one hour at room temperature and treated with iodomethane (0.220 ml, 0.00360 mol). The mixture is stirred two hours at room temperature, partially concentrated in vacuo, diluted with water, and extracted with ethyl acetate. The organic layer is washed with water, filtered through anhydrous magnesium sulfate and concentrated in vacuo to a brown foam. The foam is chromatographed on silica gel with methylene chloride/ether to give the title compound as an off-white solid (0.420 g, 40.4%) which is identified by NMR spectral analysis.

Following essentially the same procedure, but using the appropriate alkylating agent, the following compounds are obtained:

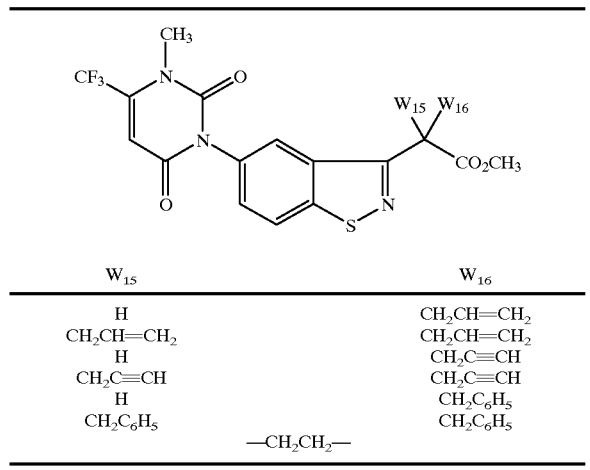

| $W_{15}$ | $W_{16}$ |
|---|---|
| H | $CH_2CH=CH_2$ |
| $CH_2CH=CH_2$ | $CH_2CH=CH_2$ |
| H | $CH_2C≡CH$ |
| $CH_2C≡CH$ | $CH_2C≡CH$ |
| H | $CH_2C_6H_5$ |
| $CH_2C_6H_5$ | $CH_2C_6H_5$ |
| —$CH_2CH_2$— | |

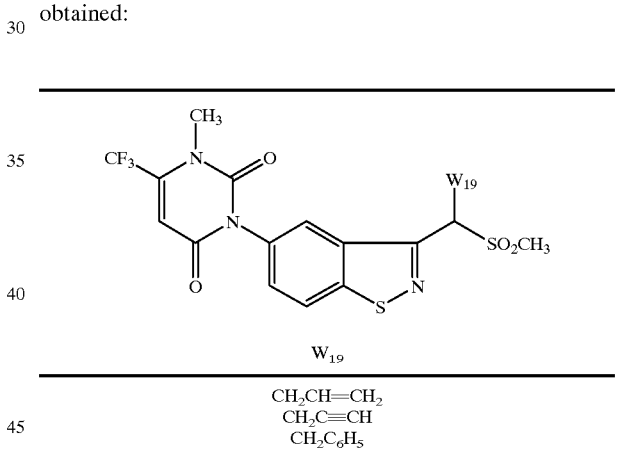

| $W_{19}$ |
|---|
| $CH_2CH=CH_2$ |
| $CH_2C≡CH$ |
| $CH_2C_6H_5$ |

EXAMPLE 184

Preparation of 1-Methyl-3-{3-[1-(methylsulfonyl)ethyl]-1,2-benzisothiazol-5-yl}-6-(trifluoromethyl)-2,4(1H,3H)-pyrimidinedione

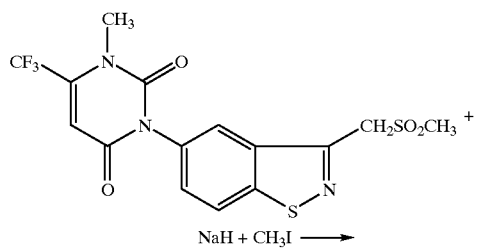

EXAMPLE 185

Postemergence Herbicidal Evaluation of Test Compounds

The postemergence herbicidal activity of the compounds of the present invention is demonstrated by the following tests wherein a variety of dicotyledonous and monocotyledonous plants are treated with test compounds. In the tests, seedling plants are grown in jiffy flats for about two weeks. The test compounds are dispersed in 50/50 acetone/water mixtures containing 0.5% TWEEN®20, a polyoxyethylene sorbitan monolaurate surfactant of Atlas Chemical Industries, in sufficient quantities to provide the equivalent of about 0.0157 kg to 0.500 kg per hectare of active compound when applied to the plants through a spray nozzle operating at 40 psi for a predetermined time. After spraying, the plants are placed on greenhouse benches and are cared for in accordance with conventional greenhouse procedures. From four to five weeks after treatment, the seedling plants are examined and rated according to the rating system set forth below. Data obtained are reported in Table I below. Where more than one test is involved for a given compound, the data are averaged.

Plant species employed in these evaluations are reported by header abbreviation, common name and scientific name.

Compounds employed in this postemergence herbicidal evaluation are given a compound number and identified by name. Data in Table I are reported by compound number.

Herbicide Rating Scale

Results of herbicide evaluation are expressed on a rating scale (0–9). The scale is based upon a visual observation of plant stand, vigor, malformation, size, chlorosis and overall plant appearance as compared with a control.

| Rating | Meaning | % Control Compared to Check |
|---|---|---|
| 9 | Complete kill | 100 |
| 8 | Approaching Complete Kill | 91–99 |
| 7 | Good Herbicidal Effect | 80–90 |
| 6 | Herbicidal Effect | 65–79 |
| 5 | Definite Injury | 45–64 |
| 4 | Injury | 30–44 |
| 3 | Moderate Effect | 16–29 |
| 2 | Slight Effect | 6–15 |
| 1 | Trace Effect | 1–5 |
| 0 | No Effect | 0 |

A "blank space" indicates that no evaluation was conducted.

PLANT SPECIES EMPLOYED IN HERBICIDAL EVALUATIONS

| Header Abbr. | Common Name | Scientific Name |
|---|---|---|
| ABUTH | Velvetleaf | *Abutilon theophrasti*, Medic. |
| AMBEL | Ragweed, Common | *Ambrosia artemisifolia*, L. |
| CASOB | Sicklepod | *Cassia obtusifolia*, L. |
| CHEAL | Lambsquarters, Common | *Chenopodium album*, L. |
| GALAP | Galium | *Galium aparine* |
| IPOHE | Morningglory, Ivyleaf | *Ipomoea hederacea*, (L.) Jacq. |
| IPOSS | Morningglory Spp. | Ipomoea Spp. |
| ECHCG | Barnyardgrass | *Echinochloa crus-galli*, (L.) Beau |
| SETVI | Foxtail, Green | *Setaria viridis*, (L.) Beau |
| GLXMAW | Soybean, Williams | Glycine max, (L.) Merr. cv Williams |
| GLXMA | Soybean | Glycine max, (L.) Merr. |
| ORYSAT | Rice, Tebonnet | *Oryza sativa*, (L.) Tebonnet |
| TRZAWR | Wheat, Winter, cv Riband | *Triticum aestivum*, cv Riband |
| ZEAMX | Corn, Field | *Zea mays*, L. |

COMPOUNDS EVALUATED AS HERBICIDAL AGENTS

| Compound Number | |
|---|---|
| 1 | 3-[3-(6-Methoxy-m-tolyl)-1,2-benzisothiazol-5-yl]-1-methyl-6-(trifluoromethyl)-2,4(1H,3H)-pyrimidinedione |
| 2 | Methyl {{2-{5-[3,6-dihydro-3-methyl-4-(trifluoromethyl) -2,6-dioxo-1(2H)-pyrimidinyl]-1,2-benzisothiazol-3-yl]-p-tolyl}oxy}acetate |
| 3 | Methyl {{2-{2-{5-[3,6-dihydro-3-methyl-4-(trifluoromethyl) -2,6-dioxo-1(2H)-pyrimidinyl]-1,2-benzisothiazol-3-yl]-p-tolyl}oxy}propionate |
| 4 | 1-Methyl-3-(3-phenyl-1,2-benzisothiazol-5-yl)-6-(trifluoromethyl)-2,4(1H,3H)-pyrimidinedione |

-continued

COMPOUNDS EVALUATED AS HERBICIDAL AGENTS

| Compound Number | |
|---|---|
| 5 | 3-[3-(p-Ethylphenyl)-1,2-benzisothiazol-5-yl]-1-methyl-6-(trifluoromethyl)-2,4 (1H,3H)-pyrimidinedione |
| 6 | 1-Methyl-3-(3-methyl-1,2-benzisothiazol-5-yl)-6-(trifluoromethyl)-2,4(1H,3H)-pyrimidinedione |
| 7 | 3-[3-(2-Methoxy-p-tolyl)-1,2-benzisothiazol-5-yl]-1-methyl-6-(trifluoromethyl)-2,4(1H,3H)-pyrimidinedione |
| 8 | Methyl {{6-{5-[3,6-dihydro-3-methyl-4-(trifluoromethyl)-2,6-dioxo-1(2H)-pyrimidinyl]-1,2-benzisothiazol-3-yl}-m-tolyl}oxy}acetate |
| 9 | Methyl 2-{{6-{5-[3,6-dihydro-3-methyl-4-(trifluoromethyl)-2,6-dioxo-1(2H)-pyrimidinyl]-1,2-benzisothiazol-3-yl}-m-tolyl}oxy}propionate |
| 10 | 2-[3-(6-Methoxy-3,4-xylyl)-1,2-benzisothiazol-5-yl]-1-methyl-6-(trifluoromethyl)-2,4(1H,3H)-pyrimidinedione |
| 11 | 3-[3-(6-Hydroxy-3,4-xylyl)-1,2-benzisothiazol-5-yl]-1-methyl-6-(trifluoromethyl)-2,4(1H,3H)-pyrimidinedione |
| 12 | Methyl {{6-{5-[3,6-dihydro-3-methyl-4-(trifluoromethyl)-2,6-dioxo-1(2H)-pyrimidinyl]-1,2-benzisothiazol-3-yl}-3,4-xylyl}oxy}acetate |
| 13 | Methyl 2-{{6-{5-[3,6-dihydro-3-methyl-4-(trifluoromethyl)-2,6-dioxo-1(2H)-pyrimidinyl]-1,2-benzisothiazol-3-yl}-3,4-xylyl}oxy}propionate |
| 14 | Methyl 2-{{2-{5-[3,6-dihydro-3-methyl-2,6-dioxo-4-(trifluoromethyl)-1(2H)-pyrimidinyl]-1,2-benzisothiazol-3-yl}-p-tolyl}oxy}propionate,(R)- |
| 15 | Methyl 2-{{2-{5-[3,6-dihydro-3-methyl-2,6-dioxo-4-(trifluoromethyl)-1(2H)-pyrimidinyl]-1,2-benzisothiazol-3-yl}-p-tolyl}oxy}propionate, (S)- |
| 16 | 3-[3-(Bromomethyl)-1,2-benzisothiazol-5-yl]-1-methyl-6-(trifluoromethyl)-2,4(1H,3H)-pyrimidinedione |
| 17 | 3-[3-(Dibromomethyl)-1,2-benzisothiazol-5-yl]-1-methyl-6-(trifluoromethyl)-2,4 (1H,3H)-pyrimidinedione |
| 18 | 3-[3-(2-Methoxy-3,5-xylyl)-1,2-benzisothiazol-5-yl]-1-methyl-6-(trifluoromethyl)-2,4(1H,3H)-pyrimidinedione |
| 19 | 3-(3-Isopropoxy-1,2-benzisoxazol-5-yl)-1-methyl-6-(trifluoromethyl)-2,4(1H,3H)-pyrimidinedione |
| 20 | 3-(3-Chloro-1,2-benzisoxazol-5-yl)-1-methyl-6-(trifluoromethyl)-2,4(1H,3H)-pyrimidinedione |
| 21 | 1-Methyl-3-(3-methyl-1,2-benzisoxazol-5-yl)-6-(trifluoromethyl)-2,4(1H,3H)-pyrimidinedione |
| 22 | Methyl {{5-[3,6-dihydro-3-methyl-2,6-dioxo-4-(trifluoromethyl)-1(2H)-pyrimidinyl]-1,2-benzisoxazol- 3-yl}oxy}acetate |
| 23 | 3-(6-Fluoro-3-methyl-1,2-benzisoxazol-5-yl)-1-methyl-6-(trifluoromethyl)-2,4(1H,3H)-pyrimidinedione |
| 24 | 3-[3-(6-Methoxy-m-tolyl)-1,2-benzisothiazol-5-yl]-1,6-dimethyl-2,4(1H,3H)-pyrimidinedione |
| 25 | 1-Methyl-3-(3-phenyl-1,2-benzisoxazol-5-yl)-6-(trifluoromethyl)-2,4 (1H,3H)-pyrimidinedione |
| 26 | Methyl {{6-{5-[3,6-dihydro-3-methyl-2,6-dioxo-4-(trifluoromethyl)-1(2H)-pyrimidinyl]-1,2-benzisothiazol-3-yl}-2,4-xylyl}oxy}acetate |
| 27 | Methyl 2-{{6-{5-[3,6-dihydro-3-methyl-2,6-dioxo-4-(trifluoromethyl)-1(2H)-pyrimidinyl]-1,2-benzisothiazol-3-yl}-2,4-xylyl}oxy}propionate |
| 28 | Methyl 2-{2-{5-[3,6-dihydro-3-methyl-2,6-dioxo-4-(trifluoromethyl)-1(2H)-pyrimidinyl]-1,2-benzisothiazol-3-yl}-4-ethylphenoxy}propionate |
| 29 | 1-Ethyl-3-[3-(6-methoxy-m-tolyl)-1,2-benzisothiazol-5-yl]-6-(trifluoromethyl)-2,4(1H,3H)-pyrimidinedione |
| 30 | Methyl 2-{2-{5-[3,6-dihydro-3-methyl-4-(trifluoromethyl)-2,6-dioxo-1(2H)-pyrimidinyl]-1,2-benzisothiazol-3-yl}-4-isopropylphenoxy}propionate |

COMPOUNDS EVALUATED AS HERBICIDAL AGENTS

| Compound Number | |
|---|---|
| 31 | 3-[3-(Methoxymethyl)-1,2-benzisothiazol-5-yl]-1-methyl-6-(trifluoromethyl)-2,4 (1H,3H)-pyrimidinedione |
| 32 | 3-[3-(Hydroxymethyl)-1,2-benzisothiazol-5-yl]-1-methyl-6-(trifluoromethyl)-2,4(1H,3H)-pyrimidinedione,acetate ester |
| 33 | Methyl 2-{{2-{5-[3,6-dihydro-3-methyl-2-oxo-6-thioxo-4-(trifluoromethyl)-1(2H)-pyrimidinyl]-1,2-benzisothiazol-3-yl}-p-tolyl}oxy}propionate |
| 34 | 3-[3-(6-Methoxy-2,3,4-trimethylphenyl)-1,2-benzisothiazol-5-yl]-1-methyl-6-(trifluoromethyl)-2,4(1H,3H)-pyrimidinedione |
| 35 | 3-(1,2-Benzisothiazol-5-yl)-1-methyl-6-(trifluoromethyl)-2,4(1H,3H)-pyrimidinedione |
| 36 | 3-(3-Bromo-1,2-benzisothiazol-5-yl)-1-methyl-6-(trifluoromethyl)-2,4(1H,3H)-pyrimidinedione |
| 37 | 3-(3-chloro-1,2-benzisothiazol-5-yl)-1-methyl-6-(trifluoromethyl)-2,4(1H,3H)-pyrimidinedione |
| 38 | Methyl {{2-[5-(3,6-dihydro-3,4-dimethyl-2,6-dioxo-1(2H)-pyrimidinyl)-1,2-benzisothiazol-3-yl]-p-tolyl}oxyacetate |
| 39 | Methyl 2-{{2-[5-(3,6-dihydro-3,4-dimethyl-2,6-dioxo-1(2H)-pyrimidinyl)-1,2-benzisothiazol-3-yl]p-tolyl}oxy}propionate |
| 40 | 3-[3-(6-Methoxy-m-tolyl)-1,2-benzisoxazol-5-yl]-1-methyl-6-(trifluoromethyl)-2,4(1H,3H)-pyrimidinedione |
| 41 | 3-[4-Chloro-3-(6-hydroxy-m-tolyl)-1,2-benzisoxazol-5-yl]-1-methyl-6-(trifluoromethyl)-2,4(1H,3H)-pyrimidinedione |
| 42 | 3-(3-Methoxy-1,2-benzisoxazol-5-yl)-1-methyl-6-(trifluoromethyl)-2,4(1H,3H)-pyrimidinedione |
| 43 | 3-[3-(o-Methoxyphenoxy)-1,2-benzisoxazol-5-yl]-1-methyl-6-(trifluoromethyl)-2,4(1H,3H)-pyrimidinedione |
| 44 | 1-Methyl-3-(2-methyl-3-oxo-1,2-benzisoxazolin-5-yl)-6-(trifluoromethyl)-2,4(1H,3H)-pyrimidinedione |
| 45 | 3-[3-(5-Ethyl-2-methoxyphenyl)-1,2-benzisothiazol-5-yl]-1-methyl-6-(trifluoromethyl)-2,4(1H,3H)-pyrimidinedione |
| 46 | 3-[3-(5-Isopropyl-2-methoxyphenyl)-1,2-benzisothiazol-5-yl]-1-methyl-6-(trifluoromethyl)-2,4 (1H,3H)-pyrimidinedione |
| 47 | Methyl 2-{o-{{5-(3,6-dihydro-3-methyl-2,6-dioxo-4-(trifluoromethyl)-1(2H)-pyrimidinyl]-1,2-benzisoxazol-3-yl}oxy}phenoxy}propionate |
| 48 | Methyl {o-{{5-[3,6-dihydro-3-methyl-2,6-dioxo-4-(trifluoromethyl)-1(2H)-pyrimidinyl]-i,2-benzisoxazol-3-yl}oxy}phenoxy}acetate |
| 49 | Ethyl {{2-{5-[3,6-dihydro-3-methyl-2,6-dioxo-4-(trifluoromethyl)-1(2H)-pyrimidinyl]-1,2-benzisothiazol-3-yl}-p-tolyl}oxy}acetate |
| 50 | Isopropyl {{2-{5-[3,6-dihydro-3-methyl-2,6-dioxo-4-(trifluoromethyl)-1(2H)-pyrimidinyl]-1,2-benzisothiazol-3-yl}-p-tolyl}oxy}acetate |
| 51 | 2-Propynyl {{2-{5-[3,6-dihydro-3-methyl-2,6-dioxo-4-(trifluoromethyl)-1(2R)-pyrimidinyl]-1,2-benzisothiazol-3-yl}-p-tolyl}oxy}acetate |
| 52 | 1-Methyl-3-{3-{6-[(morpholinocarbanyl)methoxy)-m-tolyl}-1,2-benzisothiazol-5-yl}-6-(trifluoromethyl)-2,4(1H,3H)-pyrimidinedione |
| 53 | 2-Morpholinoethyl {{2-{5-[3,6-dihydro-3-methyl-2,6-dioxo-4-(trifluoromethyl)-1(2H)-pyrimidinyl]-1,2-benzisothiazol-3-yl}-p-tolyl}oxy}acetate |
| 54 | 1-Methyl-3-{3-{6-{[(4-phenyl-1-piperazinyl)-carbonyl]methoxy}-m-tolyl}1,2-benzisothiazol-5-yl)-6-(trifluoromethyl)-2,4(1H,3H)-pyrimidinedione |
| 55 | Methyl 2-{{2-{5-[3,6-dihydro-3-methyl-2,6-dioxo-4-(trifluoromethyl)-1(2H)-pyrimidinyl]-1,2-benzisothiazol-3-yl}-p-tolyl}oxy}butyrate |
| 56 | 1-Methyl-3-{3-[6-(2-propynyloxy)-m-tolyl]-1,2-benzisothiazol-5-yl}-6-(trifluoromethyl)-2,4(1H,3H)-pyrimidinedione |
| 57 | 3-{3-[6-(Cyanomethoxy)-m-tolyl]-1,2-benzisothiazol-5-yl}-1-methyl-6-(trifluoromethyl)-2,4(1H,3H)-pyrimidinedione |
| 58 | 3-{3-[6-(1-Cyanoethoxy)-m-tolyl]-1,2-benzisothiazol-5-yl}-1-methyl-6-(trifluoromethyl)-2,4(1H,3H)-pyrimidinedione |
| 59 | 3-[3-(6-Isopropoxy-m-tolyl)-1,2-benzisothiazol-5-yl]-1-methyl-6-(trifluoromethyl)-2,4(1H,3H)-pyrimidinedione |
| 60 | 3-{3-{6-[(Diethylcarbamoyl)methoxy]-m-tolyl}-1,2-benzisothiazol-5-yl}-1-methyl-6-(trifluoromethyl)-2,4(1H,3H)-pyrimidinedione |
| 61 | 3-{3-{6-[(Diisopropylcarbamoyl)methoxy]-m-tolyl}-1,2-benzisothiazol-5-yl}-1-methyl-6-(trifluoromethyl)-2,4(1H,3H)-pyrimidinedione |
| 62 | 3-{3-{6-[(1-Benzimidazolylcarbonyl)methoxy]-m-tolyl}-1,2-benzisothiazol-5-yl}-1-methyl-6-trifluoromethyl)-2,4(1H,3H)-pyrimidinedione |
| 63 | 3-{3-{6-{[(m-Cyanophenyl)carbamoyl]methoxy}-m-tolyl}-1,2-benzisothiazol-5-yl}-1-methyl-6-(trifluoromethyl)-2,4(1H,3H)-pyrimidinedione |
| 64 | {{2-{5-[3,6-Dihydro-3-methyl-2,6-dioxo-4-(trifluoromethyl)-1(2H)-pyrimidinyl]-1,2-benzisothiazol-3-yl}-p-tolyl}oxy}acetic acid |
| 65 | 3-{3-[6-(Allyloxy)-m-tolyl]-1,2-benzisothiazol-5-yl}-1-methyl-6-(trifluoromethyl)-2,4(1H,3H)-pyrimidinedione |
| 66 | 3-[3-(6-Ethoxy-m-tolyl)-1,2-benzisothiazol-5-yl]-1-methyl-6-(trifluoromethyl)-2,4(1H,3H)-pyrimidinedione |
| 67 | Ethyl 2-{{[2-{5-[3,6-dihydro-3-methyl-2,6-dioxo-4-(trifluoromethyl)-1(2H)-pyrimidinyl]-1,2-benzisothiazol-3-yl}-p-tolyl}oxy}butyrate |
| 68 | tert-Butyl {{2-{5-[3,6-dihydro-3-methyl-2,6-dioxo-4-(trifluoromethyl)-1(2H)-pyrimidinyl]-1,2-benz isothiazol-3-yl}-p-tolyl}oxy}acetate |
| 69 | Allyl {{2-{5-[3,6-dihydro-3-methyl-2,6-dioxo-4-(trifluoromethyl)-1(2H)-pyrimidinyl]-1,2-benzisothiazol-3-yl}-p-tolyl}oxy}acetate |
| 70 | 2-(Dimethylamino)ethyl {{2-{5-[3,6-dihydro-3-methyl-2,6-dioxo-4-(trifluoromethyl)-1(2H)-pyrimidinyl]-1,2-benzisothiazol-3-yl}-p-tolyl}-oxy}acetate |
| 71 | 2-Chloroethyl {{2-{5-[3,6-dihydro-3-methyl-2,6-dioxo-4-(trifluoromethyl)-1(2H)-pyrimidinyl]-1,2-benzisothiazol-3-yl}-p-tolyl}oxy}acetate |
| 72 | 2-Pyridylmethyl {{2-{5-[3,6-dihydro-3-methyl-2,6-dioxo-4-(trifluoromethyl)-1(2H)-pyrimidinyl]-1,2-benzisothiazol-3-yl}-p-tolyl}oxy}acetate |
| 73 | 3-Phenyl-2-propynyl [{{2-{5-[3,6-dihydro-3-methyl-2,6-dioxo-4-(trifluoromethyl)-1(2H)-pyrimidinyl]-1,2-benzisothiazol-3-yl}-p-tolyl}oxy}acetate |
| 74 | 1-Methyl-2-propynyl {{2-{5-[3,6-dihydro-3-methyl-2,6-dioxo-4-(trifluoromethyl)-1(2H)-pyrimidinyl]-1,2-benzisothiazol-3-yl}-p-tolyl}oxy}acetate |
| 75 | 2-Butynyl {{(2-{5-[3,6-dihydro-3-methyl-2,6-dioxo-4-(trifluoromethyl)-1(2H)-pyrimidinyl]-1,2-benzisothiazol-3-yl}-p-tolyl}oxy}acetate |
| 76 | 1-Methyl-2-butynyl {{2-{5-[3,6-dihydro-3-methyl-2,6-dioxo-4-(trifluoromethyl)-1(2H)-pyrimidinyl]-1,2-benzisothiazol-3-yl}-p-tolyl}oxy}acetate |
| 77 | 2-Propynyl 2-{{2-{5-[3,6-dihydro-3-methyl-2,6-dioxo-4-(trifluoromethyl)-1(2H)-pyrimidinyl]-1,2-benzisothiazol-3-yl}-p-tolyl}oxy}propionate |
| 78 | Allyl 2-{{2-{5-[3,6-dihydro-3-methyl-2,6-dioxo-4-(trifluoromethyl)-1(2H)-pyrimidinyl]-1,2-benzisothiazol-3-yl}-p-tolyl}oxy}propionate |
| 79 | Furfuryl 2-{{2-{5-[3,6-dihydro-3-methyl-2,6-dioxo-4-(trifluoromethyl)-1(2H)-pyrimidinyl]-1,2-benzisothiazol-3-yl}-p-tolyl}oxy}propionate |

COMPOUNDS EVALUATED AS HERBICIDAL AGENTS

| Compound Number | |
|---|---|
| 80 | 2-Butynyl 2-{{2-{5-[3,6-dihydro-3-methyl-2,6-dioxo-4-(trifluoromethyl)-1(2H)-pyrimidinyl]-1,2-benzisothiazol-3-yl}-p-tolyl}oxy}propionate |
| 81 | 2-Chloroethyl 2-{{2-{5-[3,6-dihydro-3-methyl-2,6-dioxo-4-(trifluoromethyl)-1(2H)-pyrimidinyl]-1,2-benzisothiazol-3-yl}-p-tolyl}oxy}propionate |
| 82 | Isopropyl 2-{{2-{5-[3,6-dihydro-3-methyl-2,6-dioxo-4-(trifluoromethyl)-1(2H)-pyrimidinyl)-1,2-benz isothiazol-3-yl}-p-tolyl}oxy}propionate |
| 83 | 1-Ethylpropyl {{2-{5-[3,6-dihydro-3-methyl-2,6-dioxo-4-(trifluoromethyl)-1(2H)-pyrimidinyl)-1,2-benzisothiazol-3-yl}-p-tolyl}oxy}acetate |
| 84 | Cyclopentyl {{2-{5-[3,6-dihydro-3-methyl-2,6-dioxo-4-(trifluoromethyl)-1(2H)-pyrimidinyl)-1,2-benzisothiazol-3-yl}-p-tolyl}acetate |
| 85 | 1,2,2-Trimethylpropyl {{2-{5-[3,6-dihydro-3-methyl-2,6-dioxo-4-(trifluoromethyl)-1(2H)-pyrimidinyl]-1,2-benzisothiazol-3-yl}-p-tolyl}-oxy}acetate |
| 86 | 1,2-Dimethylpropyl {{2-{5-[3,6-dihydro-3-methyl-2,6-dioxo-4-(trifluoromethyl)-1(2H)-pyrimidinyl)-1,2-benzisothiazol-3-yl}-p-tolyl}oxy}acetate |
| 87 | 2,2-Dimethylpropyl {{2-{5-[3,6-dihydro-3-methyl-2,6-dioxo-4-(trifluoromethyl)-1(2H)-pyrimidinyl)-1,2-benzisothiazol-3-yl}-p-tolyl}oxy}acetate |
| 88 | 2-Butenyl {{2-[5-[3,6-dihydro-3-methyl-2,6-dioxo-4-(trifluoromethyl)-1(2H)-pyrimidinyl]-1,2-benzisothiazol-3-yl}-p-tolyl}oxy}acetate,(E)- or (Z)- |
| 89 | Cinnamyl {{2-{5-[3,6-dihydro-3-methyl-2,6-dioxo-4-(trifluoromethyl)-1(2H)-pyrimidinyl]-1,2-benzisothiazol-3-yl}-p-tolyl}oxy}acetate,(E)- or (Z)- |
| 90 | 2,2,2-Trifluoroethyl {{2-{5-[3,6-dihydro-3-methyl-2,6-dioxo-4-(trifluoromethyl)-1(2H)-pyrimidinyl]-1,2-benzisothiazol-3-yl}-p-tolyl}oxy}acetate |
| 91 | tert-Butyl 2-{{2-{5-[3,6-dihydro-3-methyl-2,6-dioxo-4-(trifluoromethyl)-1(2H)-pyrimidinyl]-1,2-benzisothiazol-3-yl}-p-tolyl}oxy}propionate |
| 92 | 2-{{2-{5-[3,6-Dihydro-3-methyl-2,6-dioxo-4-(trifluoromethyl)-1(2H)-pyrimidinyl]-1,2-benzisothiazol-3-yl}-p-tolyl}oxy}propionic acid |
| 93 | Methyl {{2-{5-[3,6-dihydro-3-methyl-2,6-dioxo-4-(trifluoromethyl)-1(2H)-pyrimidinyl)-1,2-benzisoxazol-3-yl}-p-tolyl}oxy}acetate |
| 94 | 1-Allyl-3-[3-(6-methoxy-m-tolyl)-1,2-benzisothiazol-5-yl]-6-(trifluoromethyl)-2,4(1H,3H)-pyrimidinedione |
| 95 | 1-Isopropyl-3-[3-(6-methoxy-m-tolyl)-1,2-benzisothiazol-5-yl]-6- (trifluoromethyl)-2,4 (1H,3H)-pyrimidinedione |
| 96 | Methyl {{2-{5-[3-ethyl-3,6-dihydro-2,6-dioxo-4-(trifluoromethyl)-1(2H)-pyrimidinyl]-1,2-benzisothiazol-3-yl}-p-tolyl}oxy}acetate |
| 97 | Methyl 2-{{2-{5-[3,6-dihydro-3-methyl-2,6-dioxo-4-(trifluoromethyl)-1(2H)-pyrimidinyl]-1,2-benzisoxazol-3-yl}-p-tolyl}oxy}propionate |
| 98 | 1-Methyl-3-{3-[(methylthio)methyl]-1,2-benzisothiazol-5-yl}-6-(trifluoromethyl)-2,4(1H,3H)-pyrimidinedione |
| 99 | Methyl {{{5-[3,6-dihydro-3-methyl-2,6-dioxo-4-(trifluoromethyl)-1(2H)-pyrimidinyl]-1,2-benzisothiazol-3-yl}methyl}thio}acetate |
| 100 | 1-Methyl-3-{3-[(methylsulfonyl)methyl]-1,2-benzisothiazol-5-yl}-6-(trifluoromethyl)-2,4(1H,3H)-pyrimidinedione |
| 101 | 3-{3-[(Dimethylamino)methyl]-1,2-benzisothiazol-5-yl}-1-methyl-6-(trifluoromethyl)-2,4(1H,3H)-pyrimidinedione |
| 102 | Ethyl N-{{5-[3,6-dihydro-3-methyl-2,6-dioxo-4-(trifluoromethyl)-1(2H)-pyrimidinyl]-1,2-benzisothiazol-3-yl}methyl}-N-methylglycinate |
| 103 | 2-Propynyl {{2-{5-[3,6-dihydro-3-methyl-2,6-dioxo-4-(trifluoromethyl)-1(2H)-pyrimidinyl]-1,2-benzisoxazol-3-yl}-p-tolyl}oxy}acetate |
| 104 | Ethyl 5-[3,6-dihydro-3-methyl-2,6-dioxo-4-(trifluoromethyl)-1(2H)-pyrimidinyl]-1,2-benzisothiazole-3-acetate |
| 105 | 3-[3-(o-Methoxyphenyl)-1,2-benzisothiazol-5-yl]-1-methyl-6-(trifluoromethyl)-2,4(1H,3H)-pyrimidinedione |
| 106 | 3-[3-(Imidazol-1-ylmethyl)-1,2-benzisothiazol-5-yl]-1-methyl-6-(trifluoromethyl)-2,4 (1H,3H)-pyrimidinedione |
| 107 | 1-Methyl-3-[3-(2-propynyloxy)-1,2-benzisothiazol-5-yl]-6-(trifluoromethyl)-2,4(1H,3H)-pyrimidinedione |
| 108 | {{5-[3,6-Dihydro-3-methyl-2,6-dioxo-4-(trifluoromethyl)-1(2H)-pyrimidinyl]-1,2-benzisothiazol-3-yl}oxy}acetonitrile |
| 109 | 3-[3-(Allyloxy)-1,2-benzisothiazol-5-yl]-1-methyl-6-(trifluoromethyl)-2,4(1H,3H)-pyrimidinedione |
| 110 | 3-(3-Isopropoxy-1,2-benzisothiazol-5-yl)-1-methyl-6-(trifluoromethyl)-2,4(1H,3H)-pyrimidinedione |
| 111 | 3-(3-Methoxy-1,2-benzisothiazol-5-yl)-1-methyl-6-(trifluoromethyl)-2,4(1H,3H)-pyrimidinedione |
| 112 | Methyl {{5-[3,6-dihydro-3-methyl-2,6-dioxo-4-(trifluoromethyl)-1(2H)-pyrimidinyl]-1,2-benzisothiazol-3-yl}oxy}acetate |
| 113 | 5-[3,6-Dihydro-3-methyl-2,6-dioxo-4-(trifluoromethyl)-1(2H)-pyrimidinyl]-1,2-benzisothiazole-3-carboxaldehyde |
| 114 | 3-[3-(Dichloromethyl)-1,2-benzisothiazol-5-yl]-1-methyl-6-(trifluoromethyl)-2,4(1H,3H)-pyrimidinedione |
| 115 | 2-Propynyl {{2-{5-[3-allyl-3,6-dihydro-2,6-dioxo-4-(trifluoromethyl)-1(2H)-pyrimidinyl]-1,2-benzisothiazol-3-yl}-p-tolyl}oxy}acetate |
| 116 | 1-Methyl-3-(3-morpholino-1,2-benzisothiazol-5-yl)-6-(trifluoromethyl)-2,4(1H,3H)-pyrimidinedione |
| 117 | N-{5-[3,6-Dihydro-3-methyl-2,6-dioxo-4-(trifluoromethyl)-1(2H)-pyrimidinyl]-1,2-benzisothiazol-3-yl}methanesulfonamide |
| 118 | 3-[3-(Diethylamino)-1,2-benzisothiazol-5-yl]-1-methyl-6-(trifluoromethyl)-2,4(1H,3H)-pyrimidinedione |
| 119 | 3-(3-Ethyl-1,2-benzisothiazol-5-yl)-1-methyl-6-(trifluoromethyl)-2,4(1H,3H)-pyrimidinedione |
| 120 | 3-[3-(o-Hydroxyphenyl)-1,2-benzisothiazol-5-yl]-1-methyl-6-(trifluoromethyl)-2,4(1H,3H)-pyrimidinedione |
| 121 | N-{{{2-{5-[3,6-Dihydro-3-methyl-2,6-dioxo-4-(trifluoromethyl)-1(2H)-pyrimidinyl]-1,2-benzisothiazol-3-yl}-p-tolyl}oxy}acetyl}methanesulfonamide |
| 122 | N-{{{2-{5-[3,6-Dihydro-3-methyl-2,6-dioxo-4-(trifluoromethyl)-1(2H)-pyrimidinyl)-1,2-benzisothiazol-3-yl}-p-tolyl}oxy}acetyl}-p-toluenesulfonamide |
| 123 | p-Chloro-N-{{{2-{5-[3,6-dihydro-3-methyl-2,6-dioxo-4- (trifluoromethyl)-1(2H)-pyrimidinyl]-1,2-benzisothiazol-3-yl}-p-tolyl}oxy}acetyl}-benzenesulfonamide |
| 124 | N-{{{2-{5-[3,6-Dihydro-3-methyl-2,6-dioxo-4-(trifluoromethyl)-1(2H)-pyrimidinyl]-1,2-benzisothiazol-3-yl}-p-tolyl}oxy}acetyl}-α-toluenesulfonamide |
| 125 | 2-Propynyl 2-{{2-{5-[3,6-dihydro-3-methyl-2,6-dioxo-4-(trifluoromethyl)-1(2H)-pyrimidinyl]-1,2-benzisoxazol-3-yl}-p-tolyl}oxy}propionate |
| 126 | 3-{3-[5-(Bromomethyl)-2-methoxyphenyl]-1,2-benzisothiazol-5-yl}-1-methyl-6-(trifluoromethyl)-2,4(1H,3H)-pyrimidinedione |

COMPOUNDS EVALUATED AS HERBICIDAL AGENTS

| Compound Number | |
|---|---|
| 127 | 3-}5-[3,6-Dihydro-3-methyl-2,6-dioxo-4-(trifluoromethyl)-1(2H)-pyrimidinyl]-1,2-benzisothiazol-3-yl]-4-methoxybenzaldehyde |
| 128 | 3-[3-(Chloromethyl)-1,2-benzisothiazol-5-yl]-1-methyl-6-(trifluoromethyl)-2,4(1H,3H)-pyrimidinedione |
| 129 | tert-Butyl α-acetyl-5-[3,6-dihydro-3-methyl-2,6-dioxo-4-(trifluoromethyl)-1(2H)-pyrimidinyl]-1,2-benzisothiazole-3-propionate |
| 130 | α-Acetyl-5-[3,6-dihydro-3-methyl-2,6-dioxo-4-(trifluoromethyl)-1(2H)-pyrimidinyl]-1,2-benzisothiazole-3-propionic acid |
| 131 | 1-Methyl-3-[3-(3-oxobutyl)-1,2-benzisothiazol-5-yl]-6-(trifluoromethyl)-2,4(1H,3H)-pyrimidinedione |
| 132 | Methyl {o-{5-[3,6-dihydro-3-methyl-2,6-dioxo-4-(trifluoromethyl)-1(2H)-pyrimidinyl]-1,2-benzisothiazol-3-yl}phenoxy}acetate |
| 133 | Methyl 2-{o-{5-[3,6-dihydro-3-methyl-2,6-dioxo-4-(trifluoromethyl)-1(2H)-pyrimidinyl]-1,2-benzisothiazol-3-yl}phenoxy}propionate |
| 134 | 2-Propynyl {o-{5-[3,6-dihydro-3-methyl-2,6-dioxo-4-(trifluoromethyl)-1(2H)-pyrimidinyl]-1,2-benzisothiazol- 3-yl}phenoxy}acetate |
| 135 | 2-Propynyl {{6-{5-[3,6-dihydro-3-methyl-2,6-dioxo-4-(trifluoromethyl)-1(2H)-pyrimidinyl]-1,2-benzisothiazol-3-yl}-3,4-xylyl}oxy}acetate |
| 136 | Methyl {2-{5-[3,6-dihydro-3-methyl-2,6-dioxo-4-(trifluoromethyl)-1(2H)-pyrimidinyl]-1,2-benzisothiazol-3-yl}-4-formylphenoxy}acetate |
| 137 | 3-[3-(Fluoromethyl)-1,2-benzisothiazol-5-yl]-1-methyl-6-(trifluoromethyl)-2,4(1H,3H)-pyrimidinedione |
| 138 | 2-Propynyl {{2-{4-chloro-5-[3,6-dihydro-3-methyl-2,6-dioxo-4-(trifluoromethyl)-1(2H)-pyrimidinyl]-1,2-benzisoxazol-3-yl}-p-tolyl}oxy}acetate |
| 139 | 3-[3-(p-Chlorophenyl)-1,2-benzisothiazol-5-yl]-1-methyl-6-(trifluoromethyl)-2,4(1H,3H)-pyrimidinedione |
| 140 | 3-[3-(Difluoromethyl)-1,2-benzisothiazol-5-yl]-1-methyl-6-(trifluoromethyl)-2,4(1H,3H)-pyrimidinedione |
| 141 | 5-[3,6-Dihydro-3-methyl-2,6-dioxo-4-(trifluoromethyl)-1(2H)-pyrimidinyl]-1,2-benzisothiazole-3-acetonitrile |
| 142 | 2-Propynyl {{6-{5-[3,6-dihydro-3-methyl-2,6-dioxo-4-(trifluoromethyl)-1(2H)-pyrimidinyl]-1,2-benzisoxazol-3-yl}-m-tolyl}oxy}acetate |
| 143 | 3-[3-(2-Hydroxyethyl)-1,2-benzisothiazol-5-yl]-1-methyl-6-(trifluoromethyl)-2,4(1H,3H)-pyrimidinedione, acetate (ester) |
| 144 | 2-Propynyl 2-{{2-{4-chloro-5-[3,6-dihydro-3-methyl-2,6-dioxo-4-(trifluoromethyl)-1(2H)-pyrimidinyl]-1,2-benzisoxazol-3-yl}-p-tolyl}-oxy}propionate |
| 145 | Di-tert-butyl {{5-[3,6-dihydro-3-methyl-2,6-dioxo-4-(trifluoromethyl)-1(2H)-pyrimidinyl]-1,2-benzisothiazol-3-yl}methyl}malonate |
| 146 | tert-Butyl methyl {{5-[3,6-dihydro-3-methyl-2,6-dioxo-4-(trifluoromethyl)-1(2H)-pyrimidinyl]-1,2-benz isothiazol-3-yl}methyl}malonate |
| 147 | Monomethyl {{5-[3,6-dihydro-3-methyl-2,6-dioxo-4-(trifluoromethyl)-1(2H)-pyrimidinyl]-1,2-benzisothiazol-3-yl}methyl}malonate |
| 148 | Methyl 5-[3,6-dihydro-3-methyl-2,6-dioxo-4-(trifluoromethyl)-1(2H)-pyrimidinyl]-1,2-benzisothiazole-3-propionate |
| 149 | 3-{3-[(2-Chloro-5-nitrophenoxy)methyl]-1,2-benzisothiazol-5-yl}-1-methyl-6-(trifluoromethyl)-2,4(1H,3H)-pyrimidinedione |
| 150 | 5-[3,6-Dihydro-3-methyl-2,6-dioxo-4-(trifluoromethyl)-1(2H)-pyrimidinyl]-1,2-benzisothiazole-3-acetic acid |
| 151 | 1-Methyl-3-[3-(1-piperazinyl)-1,2-benzisothiazol-5-yl]-6-(trifluoromethyl)-2,4(1H,3H)-pyrimidinedione |
| 152 | 3-{3-{[5-Chloro-4-(trifluoromethyl)-2-thiazolyl]amino}-1,2-benzisothiazol-5-yl]-1-methyl-6-(trifluoromethyl)-2,4(1H,3H)-pyrimidinedione |
| 153 | Methyl 2-{{2-{4-chloro-5-[3,6-dihydro-3-methyl-2,6-dioxo-4-(trifluoromethyl)-1(2H)-pyrimidinyl]-1,2-benzisoxazol-3-yl}-p-tolyl}oxy}propionate |
| 154 | 3-[3-(2-Hydroxyethyl)-1,2-benzisothiazol-5-yl)-1-methyl-6-(trifluoromethyl)-2,4(1H,3H)-pyrimidinedione |
| 155 | Diethyl {{5-[3,6-dihydro-3-methyl-2,6-dioxo-4-(trifluoromethyl)-1(2H)-pyrimidinyl]-1,2-benzisothiazol- 3-yl]methyl}phosphonate |
| 156 | {{5-[3,6-Dihydro-3-methyl-2,6-dioxo-4-(trifluoromethyl)-1(2H)-pyrimidinyl]-1,2-benzisothiazol-3-yl}methyl}trimethylammonium bromide |
| 157 | Methyl 5-[3,6-dihydro-3-methyl-2,6-dioxo-4-(trifluoromethyl)-1(2H)-pyrimidinyl]-1,2-benzisothiazole-3-acetate |
| 158 | N-{{5-[3,6-Dihydro-3-methyl-2,6-dioxo-4-(trifluoromethyl)-1(2H)-pyrimidinyl]-1,2-benzisothiazol- 3-yl}methyl}phthalimide |
| 159 | Diethyl {{5-[3,6-dihydro-3-methyl-2,6-dioxo-4-(trifluoromethyl)-1(2H)-pyrimidinyl]-1,2-benzisothiazol-3-yl]methyl}phosphoramidate |
| 160 | {{5-[3,6-Dihydro-3-methyl-2,6-dioxo-4-(trifluoromethyl)-1(2H)-pyrimidinyl]-1,2-benzisothiazol-3-yl}methyl}phosphonic acid |
| 161 | 3-(4-chloro-6-fluoro-3-methyl-1,2-benzisoxazol-5-yl)-1-methyl-6-(trifluoromethyl)-2,4(1H,3H)-pyrimidinedione |
| 162 | Methyl {{2-[5-[2-(methylthio)-6-oxo-4-(trifluoromethyl)-1(6H)-pyrimidinyl]-1,2-benzisothiazol-3-yl}-p-tolyl}oxy}acetate |
| 163 | 2-Propynyl {{2-{5-[2-(methylthio)-6-oxo-4-(trifluoromethyl)-1(6H)-pyrimidinyl]-1,2-benzisothiazol-3-yl}-p-tolyl}oxy}acetate |
| 164 | Methyl o-{{5-[3,6-dihydro-3-methyl-2,6-dioxo-4-(trifluoromethyl)-1(2H)-pyrimidinyl]-1,2-benzisothiazol-3-yl}cinnamate |
| 165 | 5-[3,6-Dihydro-3-methyl-2,6-dioxo-4-(trifluoromethyl)-1(2H)-pyrimidinyl]-1,2-benzisothiazole-3-malononitrile |
| 166 | Methyl 2-{{2-{5-[3,6-dihydro-3-methyl-2,6-dioxo-4-(trifluoromethyl)-1(2H)-pyrimidinyl]-1,2-benzisothiazol-3-yl}-p-tolyl}oxy}propionate,s,s-dioxide |
| 167 | 5-[3,6-Dihydro-3-methyl-2,6-dioxo-4-(trifluoromethyl)-1(2H)-pyrimidinyl]-1,2-benzisothiazole-3-acetamide |
| 168 | 1-Methyl-3-{3-[(methylsulfinyl)methyl]-1,2-benzisothiazol-5-yl}-6-(trifluoromethyl)-2,4(1H,3H)-pyrimidinedione |
| 169 | 3-[3-(p-Methoxyphenyl)-1,2-benzisothiazol-5-yl]-1-methyl-6-(trifluoromethyl)-2,4(1H,3H)-pyrimidinedione |
| 170 | Methyl 2-{{2-{5-[3,6-dihydro-3-methyl-2,6-dioxo-4-(trifluoromethyl)-1(2H)-pyrimidinyl]-1,2-benzisothiazol-3-yl}-p-tolyl}oxy}-2-methylpropionate |
| 171 | Ethyl 2-{{2-{5-[3,6-dihydro-3-methyl-2,6-dioxo-4-(trifluoromethyl)-1(2H)-pyrimidinyl]-1,2-benzisothiazol-3-yl}-p-tolyl}oxy}valerate, DL- |
| 172 | Methyl {{{2-{5-[3,6-dihydro-3-methyl-2,6-dioxo-4-(trifluoromethyl)-1(2H)-pyrimidinyl]-1,2-benzisothiazol-3-yl}-p-tolyl}oxy}acetoxy}acetate |
| 173 | Sodium 2-{{2-{5-[3,6-dihydro-3-methyl-2,6-dioxo-4-(trifluoromethyl)-1(2H)-pyrimidinyl]-1,2-benzisothiazol-3-yl}-p-tolyl}oxy}propionate, DL- |

-continued

COMPOUNDS EVALUATED AS HERBICIDAL AGENTS

| Compound Number | |
|---|---|
| 174 | 2-{{2-{5-[316-Dihydro-3-methyl-2,6-dioxo-4-(trifluoromethyl)-1(2H)-pyrimidinyl]-1,2-benzisothiazol-3-yl}-p-tolyl}oxy}propionic acid, DL-, compound with diisopropylamine |
| 175 | {{2-{5-[3,6-Dihydro-3-methyl-2,6-dioxo-4-(trifluoromethyl)-1(2H)-pyrimidinyl]-1,2-benzisothiazol-3-yl}-p-tolyl}oxy}acetic acid, compound with diisopropylamine |
| 176 | 2-{{2-{5-[3,6-Dihydro-3-methyl-2,6-dioxo-4-(trifluoromethyl)-1(2H)-pyrimidinyl]-1,2-benzisothiazol-3-yl}-p-tolyl}oxy}propionic acid, ammonium salt, DL- |
| 177 | {{2-{5-[3,6-Dihydro-3-methyl-2,6-dioxo-4-(trifluoromethyl)-1(2H)-pyrimidinyl]-1,2-benzisothiazol-3-yl}-p-tolyl}oxy}acetic acid, ammonium salt |
| 178 | Sodium {{2-[5-(3,6-dihydro-3-methyl-2,6-dioxo-4-(trifluoromethyl)-1(2H)-pyrimidinyl]-1,2-benzisothiazol-3-yl}-p-tolyl}oxy}acetate |
| 179 | 3-{3-[(Isopropoxy)methyl]-1,2-benzisothiazol-5-yl}-1-methyl-6-(trifluoromethyl)-2,4(1H,3H)-pyrimidinedione |
| 180 | 3-{3-[(2-Fluoroethoxy)methyl]-1,2-benzisothiazol-5-yl}-1-methyl-6-(trifluoromethyl)-2,4(1H,3H)-pyrimidinedione |
| 181 | 3-{3-[(Benzyloxy)methyl]-1,2-benzisothiazol-5-yl}-1-methyl-6-(trifluoromethyl)-2,4(1H,3H)-pyrimidinedione |
| 182 | 3-Methyl-3-butenyl {{2-{5-[3,6-dihydro-3-methyl-2,6-dioxo-4-(trifluoromethyl)-1(2H)-pyrimidinyl]-1,2-benzisothiazol-3-yl}-p-tolyl}oxy}acetate |
| 183 | 2-Methylallyl {{2-{5-[3,6-dihydro-3-methyl-2,6-dioxo-4-(trifluoromethyl)-1(2H)-pyrimidinyl]-1,2-benzisothiazol-3-yl}-p-tolyl}oxy}acetate |
| 184 | 2,4-Hexadienyl {{2-{5-[3,6-dihydro-3-methyl-2,6-dioxo-4-(trifluoromethyl)-1(2H)-pyrimidinyl]-1,2-benzisothiazol-3-yl}-p-tolyl}oxy}acetate |
| 185 | 2-Cyclohexen-1-yl {{2-{5-[3,6-dihydro-3-methyl-2,6-dioxo-4-(trifluoromethyl)-1(2H)-pyrimidinyl]-1,2-benzisothiazol-3-yl}-p-tolyl}oxy}acetate |
| 186 | 1-Methylallyl {{2-{5-[3,6-dihydro-3-methyl-2,6-dioxo-4-(trifluoromethyl)-1(2H)-pyrimidinyl]-1,2-benzisothiazol-3-yl}-p-tolyl}oxy}acetate |
| 187 | 3-Methyl-2-butenyl {{2-{5-[3,6-dihydro-3-methyl-2,6-dioxo-4-(trifluoromethyl)-1(2H)-pyrimidinyl]-1,2-benzisothiazol-3-yl}-p-tolyl}oxy}acetate |
| 188 | Methyl 4-{{2-{5-[3,6-dihydro-3-methyl-2,6-dioxo-4-(trifluoromethyl)-1(2H)-pyrimidinyl]-1,2-benzisothiazol-3-yl}-p-tolyl}oxy}-2-butenoate, (E)- and (Z)- |
| 189 | 1-Methyl-3-{3-}6-(tetrahydro-5-methyl-2-oxo-3-furyl)oxy]-m-tolyl}-1,2-benzisothiazol-5-yl}-6-(trifluoromethyl)-2,4 (1H,3H)-pyrimidinedione, DL- |
| 190 | 2-{{2-{5-[3,6-Dihydro-3-methyl-2,6-dioxo-4-(trifluoromethyl)-1(2H)-pyrimidinyl]-1,2-benzisothiazol-3-yl}-p-tolyl}oxy}acetoxy}-propionic acid, DL- |
| 191 | 2-Methoxyethyl {{2-{5-[3,6-dihydro-3-methyl-2,6-dioxo-4-(trifluoromethyl)-1(2H)-pyrimidinyl]-1,2-benzisothiazol-3-yl}p-tolyl}oxy}acetate |
| 192 | 1-Methyl-2-methoxyethyl {{2-{5-[3,6-dihydro-3-methyl-2,6-dioxo-4-(trifluoromethyl)-1(2H)-pyrimidinyl]-1,2-benzisothiazol-3-yl}-p-tolyl}-oxy}acetate, DL- |
| 193 | 2-{{2-{5-[3,6-Dihydro-3-methyl-2,6-dioxo-4-(trifluoromethyl)-1(2H)-pyrimidinyl]-1,2-benzisoxazol-3-yl}-p-tolyl}oxy}-N-(2-propynyl)-acetamide |
| 194 | O-{{2-{5-[3,6-Dihydro-3-methyl-2,6-dioxo-4-(trifluoromethyl)-1(2H)-pyrimidinyl]-1,2-benzisothiazol-3-yl}-p-tolyl}oxy}acetoxy}oxime acetone |

-continued

COMPOUNDS EVALUATED AS HERBICIDAL AGENTS

| Compound Number | |
|---|---|
| 195 | 3-[3-(Ethoxymethyl)-1,2-benzisothiazol-5-yl]-1-methyl-6-(trifluoromethyl)-2,4(1H,3H)-pyrimidinedione |
| 196 | 3-{3-[(Allyloxy)methyl]-1,2-benzisothiazol-5-yl}-1-methyl-6-(trifluoromethyl)-2,4(1H,3H) pyrimidinedione |
| 197 | 1-Methyl-3-{3-{[(m-methylbenzyl)thio]methyl}-1-2 benzisothiazol-5-yl}-6-(trifluoromethyl)-2,4(1H,3H)-pyrimidinedione |
| 198 | 3-{3-[(2-Chloroethoxy)methyl]-1,2-benzisothiazol-5-yl}-1-methyl-6-(trifluoromethyl)-2,4(1H,3H)-pyrimidinedione |
| 199 | 3-{3-[2-Chloro-1-(chloromethyl)ethyl]-1,2-benzisothiazol-5-yl}-1-methyl-6-(trifluoromethyl)-2,4(1H,3H)-pyrimidinedione |
| 200 | 3-{3-[(2-Ethoxyethoxy)methyl]-1,2-benzisothiazol-5-yl}-1-methyl-6-(trifluoromethyl)-2,4(1H,3H)-pyrimidinedione |
| 201 | 1-Methyl-3-{3-[(2,2,2-trifluoroethoxy)methyl]-1,2-benzisothiazol-5-yl}-6-(trifluoromethyl)-2,4(1H,3H)-pyrimidinedione |
| 202 | 3-{3-[(Isopropylthio)methyl]-1,2-benzisothiazol-5-yl}-1-methyl-6-(trifluoromethyl)-2,4(1H,3H)-pyrimidinedione |
| 203 | 3-{3-[(2,2-Difluoroethoxy)methyl]-1,2-benzisothiazol-5-yl}-1-methyl-6-(trifluoromethyl)-2,4(1H,3H)-pyrimidinedione |
| 204 | 3-[3-(Butoxymethyl)-1,2-benzisothiazol-5-yl]-1-methyl-6-(trifluoromethyl)-2,4(1H,3H)-pyrimidinedione |
| 205 | 3-{3-[(2-Butenyloxy)methyl]-1,2-benzisothiazol-5-yl}-1-methyl-6-(trifluoromethyl)-2,4(1H,3H)-pyrimidinedione |
| 206 | 1-Methyl-3-{3-[(1-methylallyloxy)methyl]-1-2 benzisothiazol-5-yl}-6-(trifluoromethyl)-2,4(1H,3H)-pyrimidinedione |
| 207 | 3-{3-{[2-Fluoro-1-(fluoromethyl)ethoxy]methyl}-1,2-benzisothiazol-5-yl}-1-methyl-6-(trifluoromethyl)-2,4(1H,3H)-pyrimidinedione |
| 208 | 1-Methyl-6-(trifluoromethyl)-3-[(2,2,2-trifluoro-1-methylethoxy)methyl]-1,2-benzisothiazol-5-yl]-2,4(1H,3H)-pyrimidinedione |
| 209 | 3-{3-[(2-cyclohexen-1-yloxy)methyl]-1,2-benzisothiazol-5-yl}-1-methyl-6-(trifluoromethyl)-2,4(1H,3H)-pyrimidinedione |
| 210 | 1-Methyl-3-{3-[(3-methyl-2-butenyloxy)methyl]-1,2-benzisothiazol-5-yl}-6-(trifluoromethyl)-2,4(1H,3H)-pyrimidinedione |
| 211 | 1-Methyl-3-{3-{[(4-(1-methylvinyl)-1-cyclohexen-1-yl]methoxy}methyl]-1,2-benzisothiazol-5-yl}-2,4(1H,3H)-pyrimidinedione |
| 212 | Methyl 3-{{5-[3,6-dihydro-3-methyl-2,6-dioxo-4-(trifluoromethyl)-1(2H)-pyrimidinyl]-1,2-benzisothiazol-3-yl}methoxy}-2-methylenebutyrate |
| 213 | 3,4-Dihydro-3-(3-methyl-1,2-benzisothiazol-5-yl)-2,4-dioxo-6-(trifluoromethyl)-1(2H)-pyrimidineacetonitrile |
| 214 | 1-Ethyl-3-(3-methyl-1,2-benzisothiazol-5-yl)-6-(trifluoromethyl)-2,4(1H,3H)-pyrimidinedione and 2-Ethoxy-3-(3-methyl-1,2-benzisothiazol-5-yl)-6-(trifluoromethyl)-4(3H)-pyrimidinone (1:1) |
| 215 | 1-Isobutyl-3-(3-methyl-1,2-benzisothiazol-5-yl)-6-(trifluoromethyl)-2,4(1H,3H)-pyrimidinedione and 2-Isobutoxy-3-(3-methyl-1,2-benzisothiazol-5-yl)-6-(trifluoromethyl)-4(3H)-pyrimidinone (55:45) |
| 216 | 1-Allyl-3-(3-methyl-1,2-benzisothiazol-5-yl)-6-(trifluoromethyl)-2,4(1H,3H)-pyrimidinedione and 2-(Allyloxy)-3-(3-methyl-1,2-benzisothiazol-5-yl)-6-(trifluoromethyl)-4(3H)-pyrimidinone (85:15) |
| 217 | 3-(3-Methyl-1,2-benzisothiazol-5-yl)-1-(2-propynyl)-6-(trifluoromethyl)-2,4(1H,3H) pyrimidinedione |

COMPOUNDS EVALUATED AS HERBICIDAL AGENTS

| Compound Number | |
|---|---|
| 218 | 1-Benzyl-3-(3-methyl-1,2-benzisothiazol-5-yl)-6-(trifluoromethyl)-2,4 (1H,3H)-pyrimidinedione |
| 219 | 1-Methyl-3-{3-[(4-pentenyloxy)methyl]-1,2-benzisothiazol-5-yl}-6-(trifluoromethyl)-2,4(1H,3H)-pyrimidinedione |
| 220 | 3-{3-[(3-Hexenyloxy)methyl]-1,2-benzisothiazol-5-yl}-1-methyl-6-(trifluoromethyl)-2,4(1H,3H) pyrimidinedione, (E)- |
| 221 | 1-Methyl-3-{3-{[(p-methylphenethyl)oxy]methyl}-1,2-benzisothiazol-5-yl}-6-(trifluoromethyl)-2,4(1H,3H)-pyrimidinedione |
| 222 | 3-{[(2,4-Dimethylphenethyl)oxy]methyl}-1,2-benzisothiazol-5-yl}-1-methyl-6-(trifluoromethyl)-2,4(1H,3H)-pyrimidinedione |
| 223 | 3-{3-[(3-Butenyloxy)methyl]-1,2-benzisothiazol-5-yl}-1-methyl-6-(trifluoromethyl)-2,4(1H,3H)-pyrimidinedione |
| 224 | 3-{3-[(3-Chloropropoxy)methyl]-1,2-benzisothiazol-5-yl}-1-methyl-6-(trifluoromethyl)-2,4(1H,3H)-pyrimidinedione |
| 225 | 3-[3-(Hydroxymethyl)-1,2-benzisothiazol-5-yl]-1-methyl-6-(trifluoromethyl)-2,4(1H,3H)-pyrimidinedione |
| 226 | 2-{{2-{5-[3,6-Dihydro-3methyl-2,6-dioxo-4-(trifluoromethyl)-1(2H)-pyrimidinyl]-1,2-benzisothiazol-3-yl}-p-tolyl}oxy}-N-(o-tolylsulfonyl)acetamide |
| 227 | 2-{{2-{5-[3,6-Dihydro-3-methyl-2,6-dioxo-4-(trifluoromethyl)-1(2H)-pyrimidinyl]-1,2-benzisothiazol-3-yl}-p-tolyl}oxy}-N-(styrylsulfonyl)acetamide |
| 228 | 2-{{2-{5-[3,6-Dihydro-3-methyl-2,6-dioxo-4-(trifluoromethyl)-1(2H)-pyrimidinyl]-1,2-benzisothiazol-3-yl}-p-tolyl}oxy}-N-[(m-nitrophenyl)sulfonyl]acetamide |
| 229 | 2-{{2-{5-[3,6-Dihydro-3-methyl-2,6-dioxo-4-(trifluoromethyl)-1(2H)-pyrimidinyl]-1,2-benzisothiazol-3-yl}-p-tolyl}oxy}-N-[(p-nitrophenyl)sulfonyl]acetamide |
| 230 | 2-{{2-{5-[3,6-Dihydro-3-methyl-2,6-dioxo-4-(trifluoromethyl)-1(2H)-pyrimidinyl]-i,2-benzisothiazol-3-yl}-p-tolyl}oxy}-N-[(p-fluorophenyl)sulfonyl]acetamide |
| 231 | 2-{{2-{5-[3,6-Dihydro-3-Methyl-2,6-dioxo-4-(trifluoromethyl)-1(2H)-pyrimidinyl]-1,2-benzisothiazol-3-yl}-p-tolyl}oxy}-N-[(p-methoxyphenyl)sulfonyl]acetamide |
| 232 | 2-{{2-{5-[3,6-Dihydro-3-methyl-2,6-dioxo-4-(trifluoromethyl)-1(2H)-pyrimidinyl]-1,2-benzisothiazol-3-yl}-p-tolyl}oxy}-N-(phenylsulfonyl)acetamide |
| 233 | 2-{{2-{5-[3,6-Dihydro-3-methyl-2,6-dioxo-4-(trifluoromethyl)-1(2H)-pyrimidinyl]-1,2-benzisothiazol-3-yl}-p-tolyl}oxy}-N-[(α, α, α-trifluoro-m-tolyl)sulfonyl]acetamide |
| 234 | 2-{{2-{5-[3,6-Dihydro-3-methyl-2,6-dioxo-4-(trifluoromethyl)-1(2H)-pyrimidinyl]-1,2-benzisothiazol-3-yl}-p-tolyl}oxy}-N-[(o-chlorophenyl)sulfonyl]acetamide |
| 235 | 2-{{2-{5-[3,6-Dihydro-3-methyl-2,6-dioxo-4-(trifluoromethyl)-1(2H)-pyrimidinyl]-1,2-benzisothiazol-3-yl}-p-tolyl}oxy}-N-[(m-chlorophenyl)sulfonyl]acetamide |
| 236 | o-{{5-[3,6-Dihydro-3-methyl-2,6-dioxo-4-(trifluoromethyl)-1(2H)-pyrimidinyl]-1,2-benzisothiazol-3-yl}methoxy}benzonitrile |
| 237 | 1-Methyl-3-{3-[(o-nitrophenoxy)methyl]-1,2-benzisothiazol-5-yl}-6-(trifluoromethyl)-2,4(1H,3H)-pyrimidinedione |
| 238 | 1-Methyl-6-(trifluoromethyl)-3-{3-{[(α, α,α-trifluoro-o-tolyl)oxy]methyl}-1,2-benzisothiazol-5-yl}-2,4(1H,3H)-pyrimidinedione |
| 239 | {2-{5-[3,6-Dihydro-3-methyl-2,6-dioxo-4-(trifluoromethyl)-1(2H)-pyrimidinyl]-i,2-benzisothiazol-3-yl}methyl salicylate |
| 240 | 1-Methyl-3-{3-{[m-(methylamino)phenoxy]-ethyl)-1,2-benzisothiazol-5-yl}-6-(trifluoromethyl)-2,4(1H,3H)-pyrimidinedione |
| 241 | 3-{3-{(m-Acetylphenoxy)methyl]-1,2-benzisothiazol-5-yl)-1-methyl-6-(trifluoromethyl)-2,4(1H,3H)-pyrimidinedione |
| 242 | m-{{5-[3,6-Dihydro-3-methyl-2,6-dioxo-4-(trifluoromethyl)-1(2H)-pyrimidinyl]-1,2-benzisothiazol-3-yl}methoxy}benzonitrile |
| 243 | 1-Methyl-6-(trifluoromethyl)-3-{3-{[(α, α, α-trifluoro-m-tolyl)oxy]methyl}-1,2-benzisothiazol-5-yl}-2,4(1H,3H)-pyrimidinedione |
| 244 | 1-Methyl-3-{3-{[m-(trifluoromethoxy)phenoxy]methyl]-1,2-benzisothiazol-5-yl}-6-(trifluoromethyl)-2,4(1H,3H)-pyrimidinedione |
| 245 | 2-(Allyloxy)-3-[3-(6-methoxy-m-tolyl)-1,2-benzisothiazol-5-yl]-6-(trifluoromethyl)-4(3H)-pyrimidinone |
| 246 | Methyl {{2-{5-[2-ethoxy-6-oxo-4-(trifluoromethyl)-1(6H)-pyrimidinyl]-1,2-benzisothiazol-3-yl}-p-tolyl}oxy}acetate |
| 247 | Ethyl 5-[3,6-dihydro-3-methyl-2,6-dioxo-4-(trifluoromethyl)-1(2H)-pyrimidinyl]-α,α-dimethyl-1,2-benzisothiazole-3-acetate |
| 248 | 3-{3- [(m-Fluorophenoxy)methyl]-1,2-benzisothiazol-5-yl}-1-methyl-6-(trifluoromethyl)-2,4(1H,3H)-pyrimidinedione |
| 249 | 2-Cyanoethyl {{2-{5-[3,6-dihydro-3-methyl-2,6-dioxo-4-(trifluoromethyl)-1(2H)-pyrimidinyl]-1,2-benzisothiazol-3-yl}-p-tolyl}oxy}acetate |
| 250 | 1-Methylhexyl {{2-{5-[3,6-dihydro-3-methyl-2,6-dioxo-4-(trifluoromethyl)-1(2H)-pyrimidinyl]-1,2-benzisothiazol-3-yl}-p-tolyl}oxy}acetate, DL- |
| 251 | 2,2,3,3,3-pentafluoropropyl {{2-{5-[3,6-dihydro-3-methyl-2,6-dioxo-4-(trifluoromethyl)-1(2H)-pyrimidinyl]-1,2-benzisothiazol-3-yl}-p-tolyl}oxy}acetate |
| 252 | Dodecyl {{2-{5-[3,6-dihydro-3-methyl-2,6-dioxo-4-(trifluoromethyl)-1(2H)-pyrimidinyl]-1,2-benzisothiazol-3-yl}-p-tolyl}oxy}acetate |
| 253 | 3-Furylmethyl {{2-{5-[3,6-dihydro-3-methyl-2,6-dioxo-4-(trifluoromethyl)-1(2H)-pyrimidinyl]-1,2-benzisothiazol-3-yl}-p-tolyl}oxy}acetate |
| 254 | Tetrahydrofurfuryl {{2- {5- [3,6-dihydro-3-methyl-2,6-dioxo-4-(trifluoromethyl)-1(2H)-pyrimidinyl]-1,2-benzisothiazol-3-yl}-p-tolyl}oxy}acetate, DL- |
| 255 | 1-Methyldecyl {[2-{5-[3,6-dihydro-3-methyl-2,6-dioxo-4-(trifluoromethyl)-1(2H)-pyrimidinyll-1,2-benzisothiazol-3-yl}-p-tolyl}oxy}acetate, DL- |
| 256 | 1,2-Benzisothiazole-3-acetonitrile,5-[3,6-dihydro-3-methyl-2,6-dioxo-4-(trifluoromethyl)-1(2H)-pyrimidinyl]-alpha,alpha-dimethyl- |
| 257 | Acetic acid,{p-{5- [3,6-dihydro-3-methyl-2,6-dioxo-4-(trifluoromethyl)-1(2H)-pyrimidinyl]-1,2-benzisothiazol-3-yl}phenoxy}-, methyl ester |
| 258 | Propionic acid, 2-{p-{5-[3,6-dihydro-3-methyl-2 ,6-dioxo-4-(trifluoromethyl)-1(2H)-pyrimidinyl]-1,2-benzisothiazol-3-yl}phenoxy}-, methyl ester |
| 259 | Acetic acid,{p-{5-{3,6-dihydro-3-methyl-2,6-dioxo-4-(trifluoromethyl)-1(2H)-pyrimidinyl]-1,2-benzisothiazol-3-yl}phenoxy}-, 2-propynyl ester |
| 260 | 2,4(1H,3H)-Pyrimidinedione-1,3-[3-(2-bromoethyl)-1,2-benzisothiazol-5-yl]-1-methyl-6-(trifluoromethyl)- |
| 261 | Acetic acid,{{2-{4-chloro-5-[3,6-dihydro-3-methyl-2,6-dioxo-4-(trifluoromethyl)-1(2H)-pyrimidinyl]-1,2-benzisoxazol-3-yl}-p-tolyl}oxy}-, methyl ester |
| 262 | 1,2-Benzisothiazole-3-methanephosphonic acid, 5-[3,6-dihydro-3-methyl-2,6-dioxo-4-(trifluoromethyl)-1(2H)-pyrimidinyl]-, dimethyl ester |

COMPOUNDS EVALUATED AS HERBICIDAL AGENTS

| Compound Number | |
|---|---|
| 263 | 1,2-Benzisothiazole-3-methanephosphonic acid, 5-[3,6-dihydro-3-methyl-2,6-dioxo-4-(trifluoromethyl)-1(2H)-pyrimidinyl]-, diisopropyl ester |
| 264 | 1,2-Benzisothiazole-3-acetonitrile, alpha-bromo-5-[3,6-dihydro-3-methyl-2,6-dioxo-4-(trifluoromethyl)-1(2H)-pyrimidinyl]- |
| 265 | Acetic acid,{{2-{4-chloro-5-[3,6-dihydro-3-methyl-2,6-dioxo-4-(trifluoromethyl)-1(2H)-pyrimidinyl]-1,2-benzisoxazol-3-yl}-p-tolyl}oxy}-, tert-butyl ester |
| 266 | 1,2-Benzisothiazole-3-acetaldehyde, 5-[3,6-dihydro-3-methyl-2,6-dioxo-4-(trifluoromethyl)-1(2H)-pyrimidinyl]-,3-oxime, (E)- and (Z)- |
| 267 | 2,4(1H,3H)-Pyrimidinedione,3-[3-(2-methoxy-3,4-xylyl)-1,2-benzisothiazol-5-yl]-1-methyl-6-(trifluoromethyl)- |
| 268 | Acetamide, 2-{o-{5-[3,6-dihydro-3-methyl-2,6-dioxo-4-(trifluoromethyl)-1(2H)-pyrimidinyl]-1,2-benzisothiazol-3-yl}phenoxy}-N-(methylsulfonyl)- |
| 269 | Acetamide, N-[(5-acetamido-1,3,4-thiadiazol-2-yl)sulfonyl]-2-{{2-{5-[3,6-dihydro-3-methyl-2,6-dioxo-4-(trifluoromethyl)-1(2H)-pyrimidinyl]-1,2-benzisothiazol-3-yl}-p-tolyl}oxy}- |
| 270 | Acetamide, 2-{{2-{5-[3,6-dihydro-3-methyl-2,6-dioxo-4-(trifluoromethyl)-1(2H)-pyrimidinyl]-1,2-benzisothiazol-3-yl}-p-tolyl}oxy}-N-[(3,5-dimethylisoxazol-4-yl)sulfonyl]- |
| 271 | 2,4(1H,3H)-Pyrimidinedione, 5-chloro-1-methyl-3-(3-methyl-1,2-benzisothiazol-5-yl)-6-(trifluoromethyl)- |
| 272 | Acetic acid, {{{5-[3,6-dihydro-3-methyl-2,6-dioxo-4-(trifluoromethyl)-1(2H)-pyrimidinyl]-1,2-benzisothiazol-3-yl}methyl}sulfonyl}-,methyl ester |
| 273 | Acetic acid, {p-{5-[3,6-dihydro-3-methyl-2,6-dioxo-4-(trifluoromethyl)-1(2H)-pyrimidinyl]-1,2-benzisothiazol-3-yl}phenoxy}-, tert-butyl ester |
| 274 | Acetic acid, {{6-{5-[3,6-dihydro-3-methyl-2,6-dioxo-4-(trifluoromethyl)-1(2H)-pyrimidinyll-1,2-benzisothiazol-3-yl}-2,3-xylyl}oxy}-, methyl ester |
| 275 | Propionic acid, 2-{{6-{5-[3,6-dihydro-3-methyl-2,6-dioxo-4-(trifluoromethyl)-1(2H)-pyrimidinyl]-1,2-benzisothiazol-3-yl}-2,3-xylyl}oxy}-, methyl ester |
| 276 | 2,4(1H,3H) pyrimidinedione, 1-methyl-6-(trifluoromethyl)-3-(3-vinyl-1,2-benzisothiazol-5-yl)- |
| 277 | 1,2-Benzisothiazole-3-carboxaldehyde, 5-[3,6-dihydro-3-methyl-2,6-dioxo-4-(trifluoromethyl)-1(2H)-pyrimidinyl]-, 3-(O-methyloxime), (E)- |
| 278 | 1,2-Benzisothiazole-3-carboxaldehyde, 5-[3,6-dihydro-3-methyl-2,6-dioxo-4-(trifluoromethyl)-1(2H)-pyrimidinyl]-, 3-oxime, (E)- |
| 279 | 1,2-Benzisothiazole-3-acrylic acid, 5-[3,6-dihydro-3-methyl-2,6-dioxo-4-(trifluoromethyl)-1(2H)-pyrimidinyl]-, methyl ester, (E)- |
| 280 | Acetic acid, {{6-{5-[3,6-dihydro-3-methyl-2,6-dioxo-4-(trifluoromethyl)-1(2H) pyrimidinyl]-1,2-benzisothiazol-3-yl}-2,3-xyly}oxy}-, 2-propynyl ester |
| 281 | Acetic acid, {p-{5-[3,6-dihydro-3-methyl-2,6-dioxo-4-(trifluoromethyl)-1(2H)pyrimidinyl]-1,2-benzisothiazol-3-yl}phenoxy}- |
| 282 | Acetic acid, {{{5-[3,6-dihydro-3-methyl-2,6-dioxo-4-(trifluoromethyl)-1(2H)-pyrimidinyl]-1,2-benzisothiazol-3-yl}methyl}sulfonyl}- |
| 283 | Acetic acid, {{{5-[3,6-dihydro-3-methyl-2,6-dioxo-4-(trifluoromethyl)-1(2H)-pyrimidinyl]-1,2-benzisothiazol-3-yl}methyl}thio}- |
| 284 | 2,4(1H,3H)-Pyrimidinedione, 3-[3-(2,2-dibromovinyl)-1,2-benzisothiazol-5-yl]-1-methyl-6-(trifluoromethyl)- |
| 285 | 2,4(1H,3H)-Pyrimidinedione, 1-methyl-3-[3-(3-oxo-1-butenyl)-1,2-benzisothiazol-5-yl]-6-(trifluoromethyl)-, (E)- |
| 286 | 2,4(1H,3H)-Pyrimidinedione, 3-[3-(2-bromo-2-fluorovinyl)-1,2-benzisothiazol-5-yl]-1-methyl-6-(trifluoromethyl)- |
| 287 | 2,4(1H,3H)-Pyrimidinedione, 3-[3-(2,2-dichlorovinyl)-1,2-benzisothiazol-5-yl]-1-methyl-6-(trifluoromethyl)- |
| 288 | Acetamide, 2-{{2-{5-[3,6-dihydro-3-methyl-2,6-dioxo-4-(trifluoromethyl)-1(2H)-pyrimidinyl]-1,2-benzisothiazol-3-yl}-p-tolyl}oxy}-N-[(2,4-dimethylthiazol-5-yl)sulfonyl]- |
| 289 | Acetamide,2-{{2-{5-[3,6-dihydro-3-methyl-2,6 dioxo-4-(trifluoromethyl)-1(2H)-pyrimidinyl]-1,2-benzisothiazol-3-yl}-p-tolyl}oxy}-N-[(5-ethoxybenzothiazol-2-yl)sulfonyl]- |
| 290 | Acetamide, N-[(5-chloro-3-methylbenzo[b]thien-2-yl)sulfonyl]-2-{{2-{5-[3,6-dihydro-3-methyl-2,6-dioxo-4-(trifluoromethyl)-1(2H)-pyrimidinyl]-1,2-benzisothiazol-3-yl}-p-tolyl}oxy}- |
| 291 | 1,2-Benzisothiazole-3-acrylaldehyde, 5-[3,6-dihydro-3-methyl-2,6-dioxo-4-(trifluoromethyl)-1(2H)-pyrimidinyl]-, (E)- |
| 292 | Acetic acid, {{5-[3,6-dihydro-3-methyl-2,6-dioxo-4-(trifluoromethyl)-1(2H)-pyrimidinyl]-1,2-benzisothiazol-3-yl}methoxy}-, methyl ester |
| 293 | Acetic acid, {{5-[3,6-dihydro-3-methyl-2,6-dioxo-4-(trifluoromethyl)-1(2H)-pyrimidinyl]-1,2-benzisothiazol-3-yl}methoxy}- |
| 294 | Acetamide, 2-{{5-[3,5-dihydro-3-methyl-2,6-dioxo-4-(trifluoromethyl)-1(2H)-pyrimidinyl]-1,2-benzisothiazol-3-yl}methoxy}-N-(methylsulfonyl)- |
| 295 | Acetamide, 2-{{5-[3,5-dihydro-3-methyl-2,6-dioxo-4-(trifluoromethyl)-1(2H)-pyrimidinyl]-1,2-benzisothiazol-3-yl}methoxy}-N-(methylsulfonyl)-dimethylamine salt |
| 296 | Acetic acid, {{5-[3,6-dihydro-3-methyl-2,6-dioxo 4-(trifluoromethyl)-1(2H)-pyrimidinyl]-1,2-benzisothiazol-3-yl}methoxy}-, dimethylamine salt |
| 297 | Acetamide,2-{{{5-[3,6-dihydro-3-methyl-2,6 dioxo-4-(trifluoromethyl)-1(2H)-pyrimidinyl]-1,2-benzisothiazol-3-yl}methyl}thio}-N-(methylsulfonyl)- |
| 298 | Acetamide, 2-{{{5-[3,6-dihydro-3-methyl-2,6 dioxo-4-(trifluoromethyl)-1(2H)-pyrimidinyl]-1,2-benzisothiazol-3-yl}methyl}thio}-N-(methylsulfonyl)-, dimethylamine salt |
| 299 | Acetic acid, {{{5-[3,6-dihydro-3-methyl-2,6 dioxo-4-(trifluoromethyl)-1(2H)-pyrimidinyl]-1,2-benzisothiazol-3-yl}methyl}thio}-, dimethylamine salt |
| 300 | 2,4(1H,3H)-Pyrimidinedione, 3-[3-(bromochloromethyl)-1,2-benzisothiazol-5-yl]-1-methyl-6-(trifluoromethyl)- |
| 301 | 2,4(1H,3H)-Pyrimidinedione, 3-[3-(m-methoxyphenyl)-1,2-benzisothiazol-5-yl]-1-methyl-6-(trifluoromethyl)- |
| 302 | 2,4(1H,3H)-Pyrimidinedione, 3-[3-(1,2-dibromopropyl)-1,2-benzisothiazol-5-yl]-1-methyl-6-(trifluoromethyl)-, (1R,2S)- |
| 303 | 2,4(1H,3H)-Pyrimidinedione, 3-[3-(1,2-dibromopropyl)-1,2-benzisothiazol-5-yl]-1-methyl-6-(trifluoromethyl)-, (1R,2R)- |
| 304 | Carbamic acid, {{5-[3,6-dihydro-3-methyl-2,6-dioxo-4-(trifluoromethyl)-1(2H)-pyrimidinyl]-1,2-benzisothiazol-3-yl}methyl}(methylsulfonyl)-tert-butyl ester |
| 305 | Methanesulfonamide,N-{{5-[3,6-dihydro-3-methyl 2,6-dioxo-4-(trifluoromethyl)-1(2H)-pyrimidinyl]-1,2-benzisothiazol-3-yl}methyl}- |

-continued

COMPOUNDS EVALUATED AS HERBICIDAL AGENTS

| Compound Number | |
|---|---|
| 306 | Glycine, N-{{5-[3,6-dihydro-3-methyl-2,6-dioxo-4-(trifluoromethyl)-1(2H)-pyrimidinyl]-1,2-benzisothiazol-3-yl}methyl}-N-(methylsulfonyl)-methyl ester |
| 307 | 2,4(1H,3H)-Pyrimidinedione, 3-(3-acetyl-1-2-benzisothiazol-5-yl)-1-methyl-6-(trifluoromethyl)- |
| 308 | 2,4(1H,3H)-Pyrimidinedione, 3-[3-(1-hydroxyethyl)-1,2-benzisothiazol-5-yl]-1-methyl-6-(trifluoromethyl)- |
| 309 | 2,4(1H,3H)-Pyrimidinedione, 3-[3-(1-hydroxyethyl)-1,2-benzisothiazol-5-yl]-1-methyl-6-(trifluoromethyl)-, methanesulfonate (ester) |
| 310 | 2,4(1H,3H)-Pyrimidinedione, 3-[3-(hydroxymethyl)1,2-benzisothiazol-5-yl]-1-methyl-6-(trifluoromethyl)-, nitrate (ester) |
| 311 | Isothiocyanic acid, {5-[3,6-dihydro-3-methyl-2,6-dioxo-4-(trifluoromethyl)-1(2H) pyrimidinyl]-1,2-benzisothiazol-3 yl}methyl ester |
| 312 | Acetic acid,{o-{5-[3,6-dihydro-3-methyl-2,6-dioxo-4-(trifluoromethyl)-1(2H)-pyrimidinyl]-1,2-benzisothiazol-3-yl}phenoxy}- |
| 313 | Acetohydroxamic acid, 2-{{2-[5-[3,6-dihydro-3-methyl-2,6-dioxo-4-(trifluoromethyl)-1(2H)-pyrimidinyl]-1,2-benzisothiazol-3-yl]-p tolyl}oxy}- |
| 314 | Propionic acid, 2-{o-{5-[3,6-dihydro-3-methyl-2,6-dioxo-4-(trifluoromethyl)-1(2H)-pyrimidinyl]-1,2-benzisothiazol-3-yl}phenoxy}- |
| 315 | 1,2-Benzisothiazole-3-carboxylic acid, 5-[3 ,6-dihydro-3-methyl-2,6-dioxo-4-(trifluoromethyl)-1(2H)-pyrimidinyl]- |
| 316 | Acetamide, 2-{{2-{5-[3,6-dihydro-3-methyl-2,6-dioxo-4-(trifluoromethyl)-1(2H) pyrimidinyl]-1,2-benzisothiazol-3-yl}-p-tolyl}oxy}-N-methoxy- |
| 317 | 1,2-Benzisothiazole-3-carboxylic acid, 5-[3,6-dihydro-3-methyl-2,6-dioxo-4-(trifluoromethyl)-1(2H)-pyrimidinyl]-1 methyl ester |
| 318 | 1,2-Benzisothizole-3-carboxylic acid, 5-[3,6-dihydro-3-methyl-2,6-dioxo-4-(trifluoromethyl)-1(2H)-pyrimidinyl]-, methyl ester |
| 319 | 1,2-Benzisothiazole-3-carboxylic acid, 5-[3,6-dihydro-3-methyl-2,6-dioxo-4-(trifluoromethyl)-1(2H)-pyrimidinyl]-, phenyl ester |
| 320 | 1,2-Benzisothiazole-3-carboxylic acid, 5-[3,6-dihydro-3-methyl-2,6-dioxo-4-(trifluoromethyl)-1(2H)-pyrimidinyl]-, p-fluorophenyl ester |
| 321 | 2,4(1H,3H)-Pyrimidinedione, 3-[3-(2(and 1)-bromo-1(and 2)-hydroxypropyl)-1,2-benzisothiazol-5-yl]-1-methyl-6-(trifluoromethyl)-, (4:1), mixture of diastereomers |
| 322 | 1,2-Benzisothiazole-3-carboxamide,5-[3,6-dihydro-3-methyl-2,6-dioxo-4-(trifluoromethyl)-1(2H)-pyrimidinyl]- |
| 323 | 1,2-Benzisothiazole-3-carboxamide,5-[3,6-dihydro-3-methyl-2,6-dioxo-4-(trifluoromethyl)-1(2H)-pyrimidinyl]-N-(methylsulfonyl)- |
| 324 | 1,2-Benzisothiazole-3-carboxamide, N-[(chloromethyl)sulfonyl]-5-[3,6-dihydro-3-methyl-2,6-dioxo-4-(trifluoromethyl)-1(2H)-pyrimidinyl]- |
| 325 | Propionic acid,2-{m-[5-{3,6-dihydro-3-methyl-2,6-dioxo-4-(trifluoromethyl)-1(2H)-pyrimidinyl]-1,2-benzisothiazol-3-yl}phenoxy}-, methyl ester |
| 326 | Acetic acid, {m-{5-[3,6-dihydro-3-methyl-2,6-dioxo-4-(trifluoromethyl)-1(2H)-pyrimidinylI-1,2-benzisothiazol-3-yl}phenoxy}-, 2-propynyl ester |
| 327 | 2,4(1H,3H)-Pyrimidinedione, 3-[3-(m-ethoxyphenyl)-1,2-benzisothiazol-5-yl]-1-methyl-6-(trifluoromethyl)- |
| 328 | 2,4(1H,3H)-Pyrimidinedione, 3-[3-(m-isopropoxyphenyl)-1,2-benzisothiazol-5-yl]-1-methyl-6-(trifluoromethyl)- |

-continued

COMPOUNDS EVALUATED AS HERBICIDAL AGENTS

| Compound Number | |
|---|---|
| 329 | 1,2-Benzisothiazole-3-carboxamide,5-[3,6-dihydro-3-methyl-2,6-dioxo-4-(trifluoromethyl)-1(2H)-pyrimidinyl]-N,N-dimethyl- |
| 330 | 1,2-Benzisothiazole-3-carboxamide, 5-[3,6-dihydro-3-methyl-2,6-dioxo-4-(trifluoromethyl)-1(2H)-pyrimidinyl]-N-isopropyl- |
| 331 | 1,2-Benzisothiazole-3-carboxamide,N-(5-tert-butylisoxazol-3-yl)-5-[3,6-dihydro-3-methyl-2,6-dioxo-4-(trifluoromethyl)-1(2H)-pyrimidinyl]- |
| 332 | Acetic acid, {m-{5-[3,6-dihydro-3-methyl-2,6 dioxo-4-(trifluoromethyl)-1(2H)-pyrimidinyl)-1,2-benzisothiazol-3-yl}phenoxy}-, methyl ester |
| 333 | 2,4(1H,3H)-Pyrimidinedione, 3-[3-(2,5-dimethoxyphenyl)-1,2-benzisothiazol-5-yl]-1-methyl-6-(trifluoromethyl)- |
| 334 | 1,2-Benzisothiazole-3-carboxamide,N-[(chloromethyl)sulfonyl]-5-[3 ,6-dihydro-3-methyl-2,6-dioxo-4-(trifluoromethyl)-1(2H)-pyrimidinyl]- |
| 335 | Propionamide, 2-{0-{5-[3,6-dihydro-3-methyl-2,6-dioxo-4-(trifluoromethyl)-1(2H)-pyrimidinylI-1,2-benzisothiazol-3-yl}phenoxy}-N-(methylsulfonyl)- |
| 336 | Acetohydroxamic acid, 2-{o-{5-[3,6-dihydro-3-methyl-2,6-dioxo-4-(trifluoromethyl)-1(2H)-pyrimidinyl]-1,2-benzisothiazol-3-yl}phenoxy}-N-methyl- |
| 337 | 2,4(1H,3H)-Pyrimidinedione,3-[3-(bromoacetyl)-1,2-benzisothiazol-5-yl]-1-methyl-6-(trifluoromethyl)- |
| 338 | 2,4(1H,3H)-Pyrimidinedione, 3-[3-(chloroacetyl)-1,2-benzisothiazol-5-yl]-1-methyl-6-(trifluoromethyl)- |
| 339 | 2,4(1H,3H)-Pyrimidinedione, 3-[3-(1-bromoethyl)-1,2-benzisothiazol-5-yl]-1-methyl-6-(trifluoromethyl)- |
| 340 | 2,4(1H,3H)-Pyrimidinedione, 3-[3-(1,1-dibromoethyl)-1,2-benzisothiazol-5-yl]-1-methyl-6-(trifluoromethyl)- |
| 341 | 1,2-Benzisothiazole-3-carboxamide,N-(benzylsulfonyl)-5-[3,6-dihydro-3-methyl-2,6-dioxo-4-(trifluoromethyl)-1(2H)-pyrimidinyl]- |
| 342 | 2,4(1H,3H)-Pyrimidinedione, 1-methyl-3-{3-[6 (methylthio)-m-tolyl]-1,2-benzisothiazol-5-yl}-6-(trifluoromethyl)- |
| 343 | Acetamide, N-[(chloromethyl)sulfonyl]-2-{{2-{5-[3,6-dihydro-3-methyl-2,6-dioxo-4-(trifluoromethyl)-1(2H)-pyrimidinyl)-1,2-benzisothiazol-3-yl}-p-toly}oxy}- |
| 344 | Acetamide, N-[(chloromethyl)sulfonyl]-2-{o-{5-[3,6-dihydro-3-methyl-2,6-dioxo-4-(trifluoromethyl)-1(2H)-pyrimidinyl]-1,2-benzisothiazol-3-yl}phenoxy}- |
| 345 | 2,4(1H,3H)-Pyrimidinedione, 3-[6-fluoro-3-(6-methoxy-m-tolyl)-1,2-benzisoxazol-5-yl)-1-methyl-6-(trifluoromethyl)- |
| 346 | 2,4(1H,3H)-Pyrimidinedione, 3-[6-fluoro-3-(6-hydroxy-m-tolyl)-1,2-benzisoxazol-5-yl]-1-methyl-6-(trifluoromethyl)- |
| 347 | Acetic acid, {2-{5-[3,6-dihydro-3-methyl-2,6-dioxo-4-(trifluoromethyl)-1(2H)-pyrimidinyl]-1,2-benzisothiazol-3-yl}-4-methoxyphenoxy}-, methyl ester |
| 348 | Propionic acid, 2-{2-{5-[3,6-dihydro-3-methyl-2,6-dioxo-4-(trifluoromethyl)-1(2H)-pyrimidinyl]-1,2-benzisothiazol-3-yl}-4-methoxyphenoxy}-, methyl ester |
| 349 | Acetic acid, {2-{5-[3,6-dihydro-3-methyl-2,6-dioxo-4-(trifluoromethyl)-1(2H)-pyrimidinyl]-1,2-benzisothiazol-3-yl}-4-methoxyphenoxy}-, 2-propynyl ester |
| 350 | 2,4(1H,3H)-Pyrimidinedione,3-[3-(1-methoxyethyl)-1,2-benzisothiazol-5-yl]-1-methyl-6-(trifluoromethyl)- |

-continued

COMPOUNDS EVALUATED AS HERBICIDAL AGENTS

| Compound Number | |
|---|---|
| 351 | 2,4(1H,3H)-Pyrimidinedione,3-{3-[1-(allyloxy)ethyl]-1,2-benzisothiazol-5-yl}-1-methyl-6-(trifluoromethyl)- |
| 352 | 1,2-Benzisothiazole-3-carboxamide,5-[3,6-dihydro-3-methyl-2,6-dioxo-4-(trifluoromethyl)-1(2H)-pyrimidinyl]-N-(phenylsulfonyl)- |
| 353 | 1,2-Benzisothiazole-3-carboxamide,5-[3,6-dihydro-3-methyl-2,6-dioxo-4-(trifluoromethyl)-1(2H)-pyrimidinyl]-N-(p-tolylsulfonyl)- |
| 354 | Acetamide,2-{o-{5-[3,6-dihydro-3-methyl-2,6-dioxo-4-(trifluoromethyl)-1(2H)-pyrimidinyl]-1,2-benzisothiazol-3-yl}phenoxy}-N-methoxy-N-methyl- |
| 355 | Acetohydroxamic acid,2-{{2-{5-[3,6-dihydro-3-methyl-2,6-dioxo-4-(trifluoromethyl)-1(2H)-pyrimidinyl]-1,2-benzisothiazol-3-yl}-p-tolyl}oxy}-N-methyl- |
| 356 | 1,2-Benzisothiazole-3-carboxamide, N-[(p-chlorophenyl)sulfonyl]-5-[3,6-dihydro-3-methyl-2,6-dioxo-4-(trifluoromethyl)-1(2H)-pyrimidinyl]- |
| 357 | 1,2-Benzisothiazole-3-carboxamide, 5-[3,6-dihydro-3-methyl-2,6-dioxo-4-(trifluoromethyl)-1(2H)-pyrimidinyl]-N-(2-naphthylsulfonyl)- |
| 358 | 1,2-Benzisothiazole-3-carboxamide, 5-[3,6-dihydro-3-methyl-2,6-dioxo-4-(trifluoromethyl)-1(2H)-pyrimidinyl]-N-(dodecylsulfonyl)- |
| 359 | Acetic acid, {{2-{5-[3,6-dihydro-3-methyl-2,6-dioxo-4-(trifluoromethyl)-1(2H)-pyrimidinyl]-6-fluoro-1,2-benzisoxazol-3-yl}-p-tolyl}oxy}-, methyl ester |
| 360 | 2,4(1H,3H)-Pyrimidinedione, 3-[3-(3-bromopropenyl)-1,2-benzisothiazol-5-yl]-1-methyl-6-(trifluoromethyl)-1 (E)- |
| 361 | 2,4(1H,3H)-Pyrimidinedione, 3-[3-(2-hydroxy-5-methoxyphenyl)-1,2-benzisothiazol-5-yl]-1-methyl-6-(trifluoromethyl)- |
| 362 | 1,2-Benzisothiazole-3-carboxamide,5-[3,6-dihydro-3-methyl-2,6-dioxo-4-(trifluoromethyl)-1(2H)-pyrimidinyl]-N-(isopropylsulfonyl)- |
| 363 | 2,4(1H,3H)-Pyrimidinedione, 3-[3-(hydroxymethyl)-1,2-benzisothiazol-5-yl)-1-methyl-6-(trifluoromethyl)-, methanesulfonate (ester) |
| 364 | 2,4(1H,3H)-Pyrimidinedione, 3-[3-(hydroxymethyl)-1,2-benzisothiazol-5-yl]-1-methyl-6-(trifluoromethyl)-, benzoate (ester) |
| 365 | 1,2-Benzisothiazole-3-carboxanilide,4'-chloro-5-[3,6-dihydro-3-methyl-2,6-dioxo-4-(trifluoromethyl)-1(2H)-pyrimidinyl]-N-methyl- |
| 366 | 2,4(1H,3H)-Pyrimidinedione, 3-(6-fluoro-3-methyl-1,2-benzisothiazol-5-yl)-1-methyl-6-(trifluoromethyl)- |
| 367 | 1,2-Benzisothiazole-3-carboxamide, 5-[3,6-dihydro-3-methyl-2,6-dioxo-4-(trifluoromethyl)-1(2H)-pyrimidinyl]-N-methyl-N-(methylsulfonyl)- |
| 368 | 2,4(1H,3H)-Pyrimidinedione, 3-[3-(hydroxymethyl)-1,2-benzisothiazol-5-yl]-1-methyl-6 (trifluoromethyl)-, chloroacetate (ester) |
| 369 | 2,4(1H,3H)-Pyrimidinedione, 3-[3-(hydroxymethyl)-1,2-benzisothiazol-5-yl]-1-methyl-6-(trifluoromethyl)-, phenylacetate (ester) |
| 370 | 1,2-Benzisothiazole-3-carboxamide, 5-[3,6-dihydro-3-methyl-2,6-dioxo-4-(trifluoromethyl)-1(2H)-pyrimidinyl]-N-(ethoxymethyl)-N-(methylsulfonyl)- |
| 371 | 2,4(1H,3H)-Pyrimidinedione, 3-[3-(hydroxymethyl)-1,2-benzisothiazol-5-yl]-1-methyl-6-(trifluoromethyl)-, 1-methylethanesulfonate (ester) |
| 372 | 2,4(1H,3H)-Pyrimidinedione, 3-[3-(dibromoluethyl)-6-fluoro-1,2-benzisothiazol-5-yl]-1-methyl-6-(trifluoromethyl)- |
| 373 | 1,2-Benzisothiazole-3-carbonitrile, 5-[3,6-dihydro-3-methyl-2,6-dioxo-4-(trifluoromethyl)-1(2H)-pyrimidinyl]- |
| 374 | 2,4(1H,3H)-Pyrimidinedione, 3-[3-(hydroxymethyl)-1,2-benzisothiazol-5-yl]-1-methyl-6-(trifluoromethyl)-, methylcarbamate (ester) |
| 375 | 2,4(1H,3H)-Pyrimidinedione, 3-[3-(hydroxymethyl)-1,2-benzisothiazol-5-yl]-1-methyl-6-(trifluoromethyl)-, phenylcarbamate (ester) |
| 376 | 2,4(1H,3H)-Pyrimidinedione, 3-[3-(bromomethyl)-6-fluoro-1,2-benzisothiazol-5-yl]-1-methyl-6-(trifluoromethyl)- |
| 377 | 1,2-Benzisothiazole-3-methanephosphonic acid, 5-[3,6-dihydro-3-methyl-2,6-dioxo-4-(trifluoromethyl)-1(2H)-pyrimidinyl]-6-fluoro-, diethyl ester |
| 378 | 2,4(1H,3H)-Pyrimidinedione, 3-[6-fluoro-3-(methoxymethyl)-1,2-benzisothiazol-5-yl]-1-methyl-6-(trifluoromethyl)- |
| 379 | 1,2-Benzisothiazole-3-acetonitrile, 5-[3,6-dihydro-3-methyl-2,6-dioxo-4-(trifluoromethyl)-1(2H)-pyrimidinyl]-6-fluoro- |
| 380 | 2,4(1H,3H)-Pyrimidinedione, 3-[3-(6-methoxy-5-indanyl)-1,2-benzisothiazol-5-yl]-1-methyl-6-(trifluoromethyl)- |
| 381 | 2,4(1H,3H)-Pyrimidinedione, 3-[3-(hydroxymethyl)-1,2-benzisothiazol-5-yl]-1-methyl-6-(trifluoromethyl)-, butanesulfonate (ester) |
| 382 | 2,4(1H,3H)-Pyrimidinedione, 3-[3-(hydroxymethyl)-1,2-benzisothiazol-5-yl]-1-methyl-6 (trifluoromethyl)-, benzenesulfonate (ester) |
| 383 | 1,2-Benzisothiazole-3-carboxamide, 5-[3,6-dihydro-3-methyl-2,6-dioxo-4-(trifluoromethyl)-1(2H)-pyrimidinyl]-N-(ethylsulfonyl)- |
| 384 | 1,2-Benzisothiazole-3-carboxylic acid, 5-[3,6-dihydro-3-methyl-2,6-dioxo-4-(trifluoromethyl)-1(2H)-pyrimidinyl]-, 2-butynyl ester |
| 385 | 1,2-Benzisothiazole-3-carboxylic acid, 5-[3,6-dihydro-3-methyl-2,6-dioxo-4-(trifluoromethyl)-1(2H)-pyrimidinyl]-, 2-(ethylthio)ethyl ester |
| 386 | 1,2-Benzisothiazole-3-carboxylic acid, 5-[3,6-dihydro-3-methyl-2,6-dioxo-4-(trifluoromethyl)-1(2H)-pyrimidinyl]-, 2-chloroallyl ester |
| 387 | 1,2-Benzisothiazole-3-carboxylic acid, 5-[3,6-dihydro-3-methyl-2,6-dioxo-4-(trifluoromethyl)-1(2H)-pyrimidinyl]-, 2-acetamidoethyl ester |
| 388 | 1,2-Benzisothiazole-3-carboxylic acid, 5-[3,6-dihydro-3-methyl-2,6-dioxo-4-(trifluoromethyl)-1(2H)-pyrimidinyl]-, heptyl ester |
| 389 | 1,2-Benzisothiazole-3-carboxylic acid, 5-[3,6-dihydro-3-methyl-2,6-dioxo-4-(trifluoromethyl)-1(2H)-pyrimidinyl]-, 2-(2-methoxyethoxy) ethyl ester |
| 390 | 2,4(1H,3H)-Pyrimidinedione, 3-[3-(hydroxymethyl)-1,2-benzisothiazol-5-yl]-1-methyl-6-(trifluoromethyl)-, benzylcarbamate (ester) |
| 391 | 1,2-Benzisothiazole-3-carboxamide,5-[3,6-dihydro-3-methyl-2,6-dioxo-4-(trifluoromethyl)-1( 2H)-pyrimidinyl]-N-(2-thienylsulfonyl)- |
| 392 | 2,4(1H,3H)-Pyrimidinedione, 1-methyl-3-[3-[(phenylthio)methyl]-1,2-benzisothiazol-5-yl)-6-(trifluoromethyl)- |
| 393 | 2,4(1H,3H)-Pyrimidinedione, 1-methyl-3-[3-[(phenylsulfonyl)methyl]-1,2-benzisothiazol-5-yl)-6-(trifluoromethyl)- |
| 394 | 2,4(1H,3H)-Pyrimidinedione, 1-methyl-3-(3-[(phenylsulfinyl)methyl]-1,2-benzisothiazol-5-yl)-6-(trifluoromethyl)- |
| 395 | 1,2-Benzisothiazole-3-carboxamide, 5-[3,6-dihydro-3-methyl-2,6-dioxo-4-(trifluoromethyl)-1(2H)-pyrimidinyl]-N-[(1-methylpropyl)sulfonyl]- |
| 396 | 1,2-Benzisothiazole-3-acetic acid, 5-[3,6-dihydro-3-methyl-2,6-dioxo-4-(trifluoromethyl)-1(2H)-pyrimidinyl]-alpha,alpha-dimethyl-, benzyl ester |

COMPOUNDS EVALUATED AS HERBICIDAL AGENTS

| Compound Number | |
|---|---|
| 397 | 1,2-Benzisothiazole-3-acetic acid, 5-[3,6-dihydro-2,6-dioxo-4-(trifluoromethyl)-1(2H)-pyrimidinyl]-alpha,alpha-dimethyl-, p-methoxybenzyl ester |
| 398 | 1,2-Benzisothiazole-3-carbohydroxamic acid, 5-[3,6-dihydro-3-methyl-2,6-dioxo-4-(trifluoromethyl)-1(2H)-pyrimidinyl]-N-methyl- |
| 399 | 1,2-Benzisothiazole-3-carboxamide, N-(allyloxy)-5-[3,6-dihydro-3-methyl-2,6-dioxo-4-(trifluoromethyl)-1(2H)-pyrimidinyl]- |
| 400 | 1,2-Benzisothiazole-3-carboxamide, N-(benzyloxy)-5-[3,6-dihydro-3-methyl-2,6-dioxo-4-(trifluoromethyl)-1(2H)-pyrimidinyl]- |
| 401 | 2,4(1H,3H)-Pyrimidinedione, 3-[3-(hydroxymethyl)-1,2-benzisothiazol-5-yl]-1-methyl-6-(trifluoromethyl)-, (2,4-dichlorophenyl)acetate (ester) |
| 402 | 2,4(1H,3H)-Pyrimidinedione, 3-[3-(hydroxymethyl)-1,2-benzisothiazol-S-yl]-1-methyl-6-(trifluoromethyl)-, (o-chlorophenyl)acetate (ester) |
| 403 | 1,2-Benzisothiazole-3-carboxamide, 5-[3,6-dihydro-3-methyl-2,6-dioxo-4-(trifluoromethyl)-1(2H)-pyrimidinyl]-N-methoxy- |
| 404 | 1,2-Benzisothiazole-3-carboxamide, 5-[3,6-dihydro-3-methyl-2,6-dioxo-4-(trifluoromethyl)-1(2H)-pyrimidinyl]-N-[(o-nitrobenzyl)sulfonyl]- |
| 405 | 1,2-Benzisothiazole-3-carboxamide, N-[(p-tert-butylbenzyl)sulfonyl]-5-[3,6-dihydro-3-methyl-2,6-dioxo-4-(trifluoromethyl)-1(2H)-pyrimidinyl]- |
| 406 | 1,2-Benzisothiazole-3-carboxamide, 5-[3,6-dihydro-3-methyl-2,6-dioxo-4-(trifluoromethyl)-1(2H)-pyrimidinyl]-N-{[p-(trifluoromethoxy)benzyl]sulfonyl}- |
| 407 | 2,4(1H,3H)-Pyrimidinedione, 3-{3-[bromo(phenylsulfonyl)methyl]-1,2-benzisothiazol-5-yl}-1-methyl-6-(trifluoromethyl)- |
| 408 | 1,2-Benzisothiazole-3-carboxaldehyde, 5-[3,6-dihydro-3-methyl-2,6-dioxo-4-(trifluoromethyl)-1(2H)-pyrimidinyl]-, 3-(phenylhydrazine), (E)- |
| 409 | 1,2-Benzisothiazole-3-carboxaldehyde, 5-[3,6-dihydro-3-methyl-2,6-dioxo-4-(trifluoromethyl)-1(2H)-pyrimidinyl]-, 3-(dimethylhydrazone), (E) |
| 410 | 1,2-Benzisothiazole-3-carboxylic acid, 5-[3,6-dihydro-3-methyl-2,6-dioxo-4-(trifluoromethyl)-1(2H)-pyrimidinyl]-, 3-hydroxypropyl ester |
| 411 | 1,2-Benzisothiazole-3-carboxylic acid, 5-[3,6-dihydro-3-methyl-2,6-dioxo-4-(trifluoromethyl)-1(2H)-pyrimidinyl]-, 2-methoxyethyl ester |
| 412 | 1,2-Benzisothiazole-3-carboxaldehyde, 5-[3,6-dihydro-3-methyl-2,6-dioxo-4-(trifluoromethyl)-1(2H)-pyrimidinyl]-, 3-(methylphenylhydrazone) (E)- |
| 413 | 2,4(1H,3H)-Pyrimidinedione, 3-[3-(1-hydroxyethyl)-1,2-benzisothiazol-5-yl]-1-methyl-6-(trifluoromethyl)-, 1-methylethanesulfonate (ester) |
| 414 | 2,4(1H,3H)-Pyrimidinedione, 3-[3-(1-hydroxyethyl)-1,2-benzisothiazol-5-yl]-1-methyl-6-(trifluoromethyl)-, butanesulfonate (ester) |
| 415 | 2,4(1H,3H)-Pyrimidinedione, 3-[3-(1-hydroxyethyl)-1,2-benzisothiazol-5-yl]-1-methyl-6-(trifluoromethyl)-, benzenesulfonate (ester) |
| 416 | 2,4(1H,3H)-Pyrimidinedione, 3-[3-(1-chloroethyl)-1,2-benzisothiazol-5-yl]-1-methyl-6-(trifluoromethyl)- |
| 417 | 1,2-Benzisothiazole-3-carbohydroxamic acid, 5-[3,6-dihydro-3-methyl-2,6-dioxo-4-(trifluoromethyl)-1(2H)-pyrimidinyl]-, hydrogen sulfate (ester) |
| 418 | 1,2-Benzisothiazole-3-carboxaldehyde, 5-[3,6-dihydro-3-methyl-2,6-dioxo-4-(trifluoromethyl)-1 (2H)-pyrimidinyl]-, 3-[bis(2-hydroxyethyl) dithioacetal), diacetate (diester) |
| 419 | 1,2-Benzisothiazole-3-carboxaldehyde, 5-[3,6-dihydro-3-methyl-2,6-dioxo-4-(trifluoromethyl)-1(2H)-pyrimidinyl]-, 3-[bis(2-hydroxyethyl) dithioacetal] |
| 420 | 1,2-Benzisothiazole-3-carboxamide, N-[(p-chlorobenzyl)methylsulfamoyl]-5-[3,6-dihydro-3-methyl-2,6-dioxo-4-(trifluoromethyl)-1(2H)-pyrimidinyl]- |
| 421 | 1,2-Benzisothiazole-3-thiocarboxylic acid, 5-[3,6-dihydro-3-methyl-2,6-dioxo-4-(trifluoromethyl)-1(2H)-pyrimidinyl]-, S-benzyl ester |
| 422 | 1,2-Benzisothiazole-3-thiocarboxylic acid, 5-[3,6-dihydro-3-methyl-2,6-dioxo-4-(trifluoromethyl)-1(2H)-pyrimidinyl]-, S-ethyl ester |
| 423 | 1,2-Benzisothiazole-3-carboxylic acid, 5-[3,6-dihydro-3-methyl-2,6-dioxo-4-(trifluoromethyl)-1(2H)-pyrimidinyl]-6-fluoro-, ethyl ester |
| 424 | 1,2-Benzisothiazole-3-carboxaldehyde, 5-[3,6-dihydro-3-methyl-2,6-dioxo-4-(trifluoromethyl)-1(2H)-pyrimidinyl]-, 3-[bis(3-hydroxypropyl) dithioacetal] |
| 425 | Acetic acid, {{2-{5-[3,6-dihydro-3-methyl-2,6-dioxo-4-(trifluoromethyl)-1(2H)-pyrimidinyl]-6-fluoro-1,2-benzisoxazol-3-yl}-p-tolyl}oxy}- |
| 426 | 1,2-Benzisothiazole-3-carboxaldehyde, 5-[3,6-dihydro-3-methyl-2,6-dioxo-4-(trifluoromethyl)-1(2H)-pyrimidinyl]-, 3-[bis(3-hydroxypropyl) dithioacetal], diacetate (diester) |
| 427 | 1,2-Benzisothiazole-3-carboxamide, 5-[3,6-dihydro-3-methyl-2,6-dioxo-4-(trifluoromethyl)-1(2H)-pyrimidinyl]-N-[(alpha-methylbenzyl)sulfonyl]- |
| 428 | Acetamide,2-{{2-{5-[3,6-dihydro-3-methyl-2,6-dioxo-4-(trifluoromethyl)-1(2H)-pyrimidinyl]-6-fluoro-1,2-benzisoxazol-3-yl}-p-tolyl}oxy}-N-(methylsulfonyl)- |
| 429 | 2,4(1H,3H)-Pyrimidinedione,3-[3-(5-iodo-2-methoxy-p-tolyl)-1,2-benzisothiazol-5-yl]-1-methyl-6-(trifluoromethyl)- |
| 430 | Methanesulfonanilide, 4'-{5-[3,6-dihydro-3-methyl-2,6-dioxo-4-(trifluoromethyl)-1(2H)-pyrimidinyl]-1,2-benzisothiazol-3-yl}-N-methyl- |
| 431 | 2,4(1H,3H)-Pyrimidinedione, 1-methyl-6-(trifluoromethyl)-3-(3-valeryl-1,2-benzisothiazol-5-yl)- |
| 432 | 2,4(1H,3H)-Pyrimidinedione, 1-methyl-3-(3-pivaloyl-1,2-benzisothiazol-5-yl)-6-(trifluoromethyl)- |
| 433 | 2,4(1H,3H)-Pyrimidinedione, 1-methyl-3-[(2-methylbutyryl)-1,2-benzisothiazol-5-yl)-6-(trifluoromethyl)- |
| 434 | Acetic acid, {{6-{5-[3,6-dihydro-3-methyl-2,6-dioxo-4-(trifluoromethyl)-1(2H)-pyrimidinyl]-1,2-benzisothiazol-3-yl}-5-indanyl}oxy}-, methyl ester |
| 435 | Propionic acid, 2-{{6-{5-[3,6-dihydro-3-methyl-2,6-dioxo-4-(trifluoromethyl)-1(2H)-pyrimidinyl]-1,2-benzisothiazol-3-yl}-5-indanyl}oxy}-, methyl ester |
| 436 | Acetic acid, {[6-{5-[3,6-dihydro-3-methyl-2,6-dioxo-4-(trifluoromethyl)-1(2H)-pyrimidinyl]-1,2-benzisothiazol-3-yl}-5-indanyl}oxy}-, 2-propynyl ester |
| 437 | Acetamide, 2-{{2-{5-[3,6-dihydro-3-methyl-2,6-dioxo-4-(trifluoromethyl)-1(2H)-pyrimidinyl]-1,2-benzisothiazol-3-yl}-p-tolyl}oxy}-N-methyl-N-(methylsulfonyl)- |
| 438 | Acetamide, 2-{o-{5-[3,6-dihydro-3-methyl-2,6-dioxo-4-(trifluoromethyl)-1(2H)-pyrimidinyl]-1,2-benzisothiazol-3-yl}phenoxy}-N-methyl-N-(methylsulfonyl)- |

COMPOUNDS EVALUATED AS HERBICIDAL AGENTS

| Compound Number | |
|---|---|
| 439 | 1,2-Benzisothiazole-3-carboxamide, N-[5-chloro-4-(trifluoromethyl)thiazol-2-yl]-5-[3,6-dihydro-3-methyl-2,6-dioxo-4-(trifluoromethyl)-1(2H)-pyrimidinyl]- |
| 440 | 1,2-Benzisothiazole-3-carboxamide,N-(benzylsulfonyl)-5-[3,6-dihydro-3-methyl-2,6-dioxo-4-(trifluoromethyl)-1(2H)-pyrimidinyl]-N-(ethoxymethyl)- |
| 441 | Glycine,N-(benzylsulfonyl)-N-{{5-[3,6-dihydro-3-methyl-2,6-dioxo-4-(trifluoromethyl)-1(2H)-pyrimidinyl]-1,2-benzisothiazol-3-yl]carbonyl]-, methyl ester |
| 442 | 2,4(1H,3H)-Pyrimidinedione, 3-[6-chloro-3-(6-methoxy-m-tolyl)-1,2-benzisothiazol-5-yl]-1-methyl-6-(trifluoromethyl)- |
| 443 | Acetic acid, {{2-{6-chloro-5-[3,6-dihydro-3-methyl-2,6-dioxo-4-(trifluoromethyl)-1(2H)-pyrimidinyl]-1,2-benzisothiazol-3-yl}-p-tolyl}oxy}-, methyl ester |
| 444 | 1,2-Benzisothiazole-3-acetonitrile, 5-[3,6-dihydro-3-methyl-2,6-dioxo-4-(trifluoromethyl)-1(2H)-pyrimidinyl]-alpha-ethyl- |
| 445 | 1,2-Benzisothiazole-3-acetonitrile, 5-[3,6-dihydro-3-methyl-2,6-dioxo-4-(trifluoromethyl)-1(2H)-pyrimidinyl]-alpha,alpha-diethyl- |
| 446 | Cyclopropanecarbonitrile, 1-{5-[3,6-dihydro-3-methyl-2,6-dioxo-4-(trifluoromethyl)-1(2H)-pyrimidinyl]-1,2-benzisothiazol-3-yl}- |
| 447 | 2,4(1H,3H)-Pyrimidinedione, 3-[3-(alpha,alpha-dibromo-2-methoxy-p-tolyl)-1,2-benzisothiazol-5-yl]-1-methyl-6-(trifluoromethyl)- |
| 448 | 2,4(1H,3H)-Pyrimidinedione, 3-[3-(5-iodo-2-methoxyphenyl)-1,2-benzisothiazol-5-yl]-1-methyl-6-(trifluoromethyl)- |
| 449 | 2,4(1H,3H)-Pyrimidinedione, 3-(3-benzoyl-1,2-benzisothiazol-5-yl)-1-methyl-6-(trifluoromethyl)- |
| 450 | 2,4(1H,3H)-Pyrimidinedione, 3-[3-(hydroxymethyl)-1,2-benzisothiazol-5-yl]-1-methyl-6-(trifluoromethyl)-, (p-methoxyphenyl)acetate (ester) |
| 451 | 2,4(1H,3H)-Pyrimidinedione, 3-[3-(hydroxymethyl)-1,2-benzisothiazol-5-yl]-1-methyl-6-(trifluoromethyl)-, 2-thienylacetate (ester) |
| 452 | 2,4(1H,3H)-Pyrimidinedione, 3-[3-(hydroxymethyl)-1,2-benzisothiazol-5-yl]-1-methyl-6-(trifluoromethyl)-, (p-chlorophenyl)acetate (ester) |
| 453 | 1,2-Benzisothiazole-3-carboxaldehyde, 5-(3,6-dihydro-3-methyl-2,6-dioxo-4-(trifluoromethyl))-1(2H)-pyrimidinyl]-, 3-(dimethyl acetal) |
| 454 | 2,4(1H,3H)-Pyrimidinedione, 3-[3-(hydroxymethyl)-1,2-benzisothiazol-5-yl]-1-methyl-6-(trifluoromethyl)-, (m-methoxyphenyl)acetate (ester) |
| 455 | 2,4(1H,3H)-Pyrimidinedione, 3-{3-[(ethoxymethoxy)methyl]-1,2-benzisothiazol-5-yl}-1-methyl-6-(trifluoromethyl)- |
| 456 | 2,4(1H,3H)-Pyrimidinedione, 1-methyl-3-[3-[[(tetrahydro-2H-pyran-2-yl)oxy]methyl]-1,2-benzisothiazol-5-yl]-6-(trifluoromethyl)- |
| 457 | 1,2-Benzisothiazole-3-acetonitrile, 5-[3,6-dihydro-3-methyl-2,6-dioxo-4-(trifluoromethyl)-1(2H)-pyrimidinyl]-alpha-(3-methyl-2-thenylidene)- |
| 458 | 1,2-Benzisothiazole-3-acetonitrile, alpha-(cyclopropylmethylene)-5-[3,6-dihydro-3-methyl-2,6-dioxo-4-(trifluoromethyl)-1(2H)-pyrimidinyl]-, (E)- and (Z)- |
| 459 | Acetic acid, {2-{5-[3,6-dihydro-3-methyl-2,6-dioxo-4-(trifluoromethyl)-1(2H)-pyrimidinyl]-1,2-benzisothiazol-3-yl}-4-iodophenoxy}-, methyl ester |
| 460 | Propionic acid, 2-{2-{5-[3,6-dihydro-3-methyl-2,6-dioxo-4-(trifluoromethyl)-1(2H)-pyrimidinyl]-1,2-benzisothiazol-3-yl}-4-iodophenoxy}-, methyl ester |
| 461 | 2,4(1H,3H)-Pyrimidinedione, 3-{3-{[(benzyloxy)methoxy]methyl}-1,2-benzisothiazol-5-yl}-1-methyl-6-(trifluoromethyl)- |
| 462 | 2,4(1H,3H)-Pyrimidinedione, 3-[6-fluoro-3-(6-methoxy-m-tolyl)-1,2-benzisothiazol-5-yl]-1-methyl-6-(trifluoromethyl)- |
| 463 | 2,4(1H,3H)-Pyrimidinedione, 3-[3-(hydroxymethyl)-1,2-benzisothiazol-5-yl]-1-methyl-6-(trifluoromethyl)-, isonicotinate (ester) |
| 464 | 1,2-Benzisothiazole-3-carboxamide,5-[3,6-dihydro-3-methyl-21 6-dioxo-4-(trifluoromethyl)-1(2H)-pyrimidinyl]-N-[(p-methylbenzyl)sulfonyl]- |
| 465 | 1,2-Benzisothiazole-3-carboxamide, 5-[3,6-dihydro-3-methyl-21 6-dioxo-4-(trifluoromethyl)-1(2H)-pyrimidinyl]-N-[(o-methylbenzyl)sulfonyl]- |
| 466 | 1,2-Benzisothiazole-3-acetic acid, 5-[3,6-dihydro-3-methyl-2,6-dioxo-4-(trifluoromethyl)-1(2H)-pyrimidinyl]-alpha,alpha-dimethyl- |
| 467 | Propionaldehyde, 3-{{2-{5-[3,6-dihydro-3-methyl-2,6-dioxo-4-(trifluoromethyl)-1(2H)-pyrimidinyl]-1,2-benzisothiazol-3-yl}-p-tolyl}oxy}-,1-(dimethyl acetal) |
| 468 | 1,2-Benzisothiazole-3-carboxamide, N-[(p-chlorobenzyl)sulfonyl]-5-[3,6-dihydro-3-methyl-2,6-dioxo-4-(trifluoromethyl)-1(2H)-pyrimidinyl]- |
| 469 | Acetic acid, {{6-{5-(3,6-dihydro-3-methyl-2,6-dioxo-4-(trifluoromethyl)-i(2H)-pyrimidinyl]-1,2-benzisothiazol-3-yl}-4-iodo-m-tolyl}oxy}-, methyl ester |
| 470 | Propionic acid, 2-{{6-{5-[3,6-dihydro-3-methyl-2,6-dioxo-4-(trifluoromethyl)-1(2H)-pyrimidinyl]-1,2-benzisothiazol-3-yl}-4-iodo-m-tolyl}oxy}-, methyl ester |
| 471 | 1,2-Benzisothiazole-3-carbohydroxamic acid, 5-[3,6-dihydro-3-methyl-2,6-dioxo-4-(trifluoromethyl)-1(2H)-pyrimidinyl]- |
| 472 | 1,2-Benzisothiazole-3-carboxamide, 5-[3,6-dihydro-3-methyl-2,6-dioxo-4-(trifluoromethyl)-1(2H)-pyrimidinyl]-N-sulfamoyl- |
| 473 | 2,4(1H,3H)-Pyrimidinedione, 3-[3-(hydroxymethyl)-1,2-benzisothiazol-5-yl]-1-methyl-6-(trifluoromethyl)-, 2-phenylbutyrate (ester) |
| 474 | 2,4(1H,3H)-Pyrimidinedione, 3-[3-(hydroxymethyl)-1,2-benzisothiazol-5-yl]-1-methyl-6-(trifluoromethyl)-, 2,6-dichloroisonicotinate (ester) |
| 475 | 2,4(1H,3H)-Pyrimidinedione, 3-[3-(hydroxymethyl)-1,2-benzisothiazol-5-yl]-1-methyl-6-(trifluoromethyl)-,5-isoxazolecarboxylate (ester) |
| 476 | 2,4(1H,3H)-Pyrimidinedione, 3-[3-(hydroxymethyl)-1,2-benzisothiazol-5-yl]-1-methyl-6-(trifluoromethyl)-, 5-nitro-2-furoate (ester) |
| 477 | 2,4(1H,3H)-Pyrimidinedione, 3-[3-(hydroxymethyl)-1,2-benzisothiazol-5-yl]-1-methyl-6-(trifluoromethyl)-, 2-thiophenecarboxylate (ester) |
| 478 | 2,4(1H,3H)-Pyrimidinedione, 3-{3-[(methoxymethoxy)methyl]-1,2-benzisothiazol-5-yl}-1-methyl-6-(trifluoromethyl)- |
| 479 | Acetic acid, {{6-{5-[3,6-dihydro-3-methyl-2,6-dioxo-4-(trifluoromethyl)-1(2H)-pyrimidinyl]-6-fluoro-1,2-benzisothiazol-3-yl}-m-tolyl}oxy}-, methyl ester |
| 480 | 2,4(1H,3H)-Pyrimidinedione, 3-[3-(hydroxymethyl)-1,2-benzisothiazol-5-yl]-1-methyl-6-(trifluoromethyl)-, 2-chloronicotinate (ester) |
| 481 | 2,4(1H,3H)-Pyrimidinedione, 3-[3-(hydroxymethyl)-1,2-benzisothiazol-5-yl]-1-methyl-6-(trifluoromethyl)-, 6-chloronicotinate (ester) |
| 482 | 1,2-Benzisothiazole-3-carboxamide, N-(benzylsulfonyl)-5-[3,6-dihydro-3-methyl-2,6-dioxo-4-(trifluoromethyl)-1(2H)-pyrimidinyl]-6-fluoro- |
| 483 | 1,2-Benzisothiazole-3-carboxamide, 5-[3,6-dihydro-3-methyl-2,6-dioxo-4-(trifluoromethyl)-1(2H)-pyrimidinyl]-N-[(m-methylbenzyl)sulfonyl]- |

COMPOUNDS EVALUATED AS HERBICIDAL AGENTS

| Compound Number | |
|---|---|
| 484 | 2,4(1H,3H)-Pyrimidinedione, 1-methyl-3-{3-{[(methylthio)methoxy]methyl}-1,2-benzisothiazol-5-yl}-6-(trifluoromethyl)- |
| 485 | 1,2-Benzisothiazole-3-carboxamide, 5-[3,6-dihydro-3-methyl-2,6-dioxo-4-(trifluoromethyl)-1(2H)-pyrimidinyl]-N-(phenethylsulfonyl)- |
| 486 | 1,2-Benzisothiazole-3-carboxamide, N-[(m-chlorobenzyl) sulfonyl]-5-[3,6-dihydro-3-methyl-2,6-dioxo-4-(trifluoromethyl)-1(2H)-pyrimidinyl]- |
| 487 | 1,2-Benzisothiazole-3-acetic acid, 5-[3,6-dihydro-3-methyl-2,6-dioxo-4-(trifluoromethyl)-1(2H)-pyrimidinyl]-alpha,alpha-dimethyl-furfuryl ester |
| 488 | 1,2-Benzisothiazole-3-acetamide, 5-[3,6-dihydro-3-methyl-2,6-dioxo-4-(trifluoromethyl)-1(2H)-pyrimidinyl]-alpha,alpha-dimethyl-N-(methylsulfonyl)- |
| 489 | 1,2-Benzisothiazole-3-acetic acid, 5-[3,6-dihydro-3-methyl-2,6-dioxo-4-(trifluoromethyl)-1(2H)-pyrimidinyl]-alpha,alpha-dimethyl-, isopropyl ester |
| 490 | 1,2-Benzisothiazole-3-acetic acid,5-[3,6-dihydro-3-methyl-2,6-dioxo-4-(trifluoromethyl)-1 (2H)-pyrimidinyl]-alpha,alpha-dimethyl-,methyl ester |
| 491 | 1,2-Benzisothiazole-3-acetic acid, 5-[3,6-dihydro-3-methyl-2,6-dioxo-4-(trifluoromethyl)-1(2H)-pyrimidinyl]-alpha,alpha-dimethyl-, allyl ester |
| 492 | Propionic acid, 2-{{5-chloro-2-{5-[3,6-dihydro-3-methyl-2,6-dioxo-4-(trifluoromethyl)-1(2H)-pyrimidinyl]-1,2-benzisothiazol-3-yl}-p-tolyl}oxy}-, methyl ester |
| 493 | Acetic acid, {{5-chloro-2-(5-[3,6-dihydro-3-methyl-2,6-dioxo-4-(trifluoromethyl)-1(2H)-pyrimidinyl]-1,2-benzisothiazol-3-yl}-p-tolyl}oxy}-, methyl ester |
| 494 | 1,2-Benzisothiazole-3-carboxamide, N-(benzyl-sulfonyl)-5-[3,6-dihydro-3-methyl-2,6-dioxo-4-(trifluoromethyl)-1(2H)-pyrimidinyl]-N-methyl- |
| 495 | 2,4(1H,3H)-Pyrimidinedione, 3-[3-(hydroxymethyl)-1,2-benzisothiazol-5-yl]-1-methyl-6-(trifluoromethyl)-, methoxyacetate (ester) |
| 496 | 2,4(1H,3H)-Pyrimidinedione, 3-[3-(hydroxymethyl)-1,2-benzisothiazol-5-yl]-1-methyl-6-(trifluoromethyl)-, cyclopropanecarboxylate (ester) |
| 497 | 2,4(1H,3H)-Pyrimidinedione, 3-[3-(hydroxymethyl)-1,2-benzisothiazol-5-yl]-1-methyl-6-(trifluoromethyl)-, 2-furoate (ester) |
| 498 | 2,4(1H,3H)-Pyrimidinedione, 3-[3-(hydroxymethyl)-1,2-benzisothiazol-5-yl]-1-methyl-6-(trifluoromethyl)-, pivalate (ester) |
| 499 | 2,4(1H,3H)-Pyrimidinedione,3-(3-isopropyl-1,2-benzisothiazol-5-yl)-1-methyl-6-(trifluoromethyl)- |
| 500 | 1,2-Benzisothiazole-3-carboxamide, 5-[3,6-dihydro-3-methyl-2,6-dioxo-4-(trifluoromethyl)-1(2H)-pyrimidinyl]-N-(diisopropylsulfamoyl)- |
| 501 | 1,2-Benzisothiazole-3-carboxamide, 5-[3,6-dihydro-3-methyl-2,6-dioxo-4-(trifluoromethyl)-1(2H)-pyrimidinyl]-N-(styrylsulfonyl)-, (E)- |
| 502 | 2,4(1H,3H)-Pyrimidinedione, 3-[3-(hydroxymethyl)-1,2-benzisothiazol-5-yl]-1-methyl-6-(trifluoromethyl)-, (3,4-dimethoxyphenyl)acetate (ester) |
| 503 | 2,4(1H,3H)-Pyrimidinedione, 3-[3-(hydroxymethyl)-1,2-benzisothiazol-5-yl]-1-methyl-6-(trifluoromethyl)-,(2,5-dimethoxyphenyl)acetate (ester) |
| 504 | 2,4(1H,3H)-Pyrimidinedione, 3-[3-(hydroxymethyl)-1,2-benzisothiazol-5-yl]-1-methyl-6-(trifluoromethyl)-, chlorophenylacetate (ester) |
| 505 | 2,4(1H,3H)-Pyrimidinedione,3-{3-[6-(allyloxy)-5-iodo-m-tolyl]-1,2-benzisothiazol-5-yl}-1-methyl-6-(trifluoromethyl)- |
| 506 | 2,4(1H,3H)-Pyrimidinedione, 3-[3-(4-chloro-6-methoxy-m-tolyl)-1,2-benzisothiazol-5-yl]-1-methyl-6-(trifluoromethyl)- |
| 507 | 1,2-Benzisothiazole-3-carboxamide, 5-[3,6-dihydro-3-methyl-2,6-dioxo-4-(trifluoromethyl)-1(2H)-pyrimidinyl]-N-(dimethylsulfamoyl)- |
| 508 | 1,2-Benzisothiazole-3-carboxamide, 5-[3,6-dihydro-3-methyl-2,6-dioxo-4-(trifluoromethyl)-1(2H)-pyrimidinyl]-N-(isopropylsulfamoyl)- |
| 509 | 1,2-Benzisothiazole-3-acetamide, 5-[3,6-dihydro-3-methyl-2,6-dioxo-4-(trifluoromethyl)-1(2H)-pyrimidinyl]-alpha,alpha-dimethyl- |
| 510 | 1,2-Benzisothiazole-3-acetic acid,5- [3,6-dihydro-3-methyl-2,6-dioxo-4-(trifluoromethyl)-1( 2H)-pyrimidinyl]-alpha,alpha-dimethyl-, 2-pyridylmethyl ester |
| 511 | 1,2-Benzisothiazole-3-acetamide,5-(3,6-dihydro-3-methyl-2,6-dioxo-4-(trifluoromethyl)-1(2H)-pyrimidinyl]-N-(diisopropylsulfamoyl)-alpha,alpha-dimethyl- |
| 512 | Acetamide,2-{o-{5-[3,6-dihydro-3-methyl-2,6 dioxo-4-(trifluoromethyl)-1(2H)-pyrimdinyl]-1,2-benzisothiazol-3-yl}phenoxy}-N-(diisopropyl-sulfamoyl)- |
| 513 | 1,2-Benzisothiazole-3-carboxylic acid, 5-[3,6-dihydro-3-methyl-2,6-dioxo-4-(trifluoromethyl)-1 (2H)-pyrimidinyl]-6-fluoro-, methyl ester |
| 514 | Propionic acid, 2-{{2-{5-[3,6-dihydro-3-methyl-2,6-dioxo-4-(trifluoromethyl)-1(2H)-pyrimidinyl]-1,2-benzisothiazol-3-yl}-p-tolyl}oxy}-2-methyl-, tert-butyl ester |
| 515 | Propionic acid, 2-{{2-{5-[3,6-dihydro-3-methyl-2,6-dioxo-4-(trifluoromethyl)-1(2H)-pyrimidinyl]-1,2-benzisothiazol-3-yl}-p-tolyl}oxy}-2-methyl- |
| 516 | 2,4(1H,3H)-Pyrimidinedione, 1-(2-fluoroethyl)-3-(3-methyl-1,2-benzisothiazol-5-yl)-6-(trifluoro-methyl)- |
| 517 | Acetic acid, {{2-{5-[3,6-dihydro-3-methyl-2,6-dioxo-4-(trifluoromethyl)-1(2H)-pyrimidinyl]-1,2-benzisothiazol-3-yl}-p-tolyl}oxy}-, (1-phenyl-cyclopropyl)methyl ester |
| 518 | Acetic acid, {{2-{5-[3,6-dihydro-3-methyl-2,6-dioxo-4-(trifluoromethyl)-1(2H)-pyrimidinyl]-1,2-benzisothiazol-3-yl}-p-tolyl}oxy}-, 4-(methyl-thio)butyl ester |
| 519 | Acetic acid, {{2-{5-[3,6-dihydro-3-methyl-2,6-dioxo-4-(trifluoromethyl)-1(2H)-pyrimidinyl]-1,2-benzisothiazol-3-yl}-p-tolyl}oxy}-, nonyl ester |
| 520 | Acetic acid, {{2-{5-[3,6-dihydro-3-methyl-2,6-dioxo-4-(trifluoromethyl)-1(2H)-pyrimidinyl]-1,2-benzisothiazol-3-yl}-p-tolyl}oxy}-, 1-vinylpentyl ester |
| 521 | Acetic acid, {{2-{5-[3,6-dihydro-3-methyl-2,6-dioxo-4-(trifluoromethyl)-1(2H)-pyrimidinyl]-1,2-benzisothiazol-3-yl}-p-tolyl}oxy}-, 2,2-bis-[(allyloxy)methyl]butyl ester |
| 522 | Acetic acid, {{2-{5-[3,6-dihydro-3-methyl-2,6-dioxo-4-(trifluoromethyl)-1(2H)-pyrimidinyll-1,2-benzisothiazol-3-yl}-p-tolyl}oxy}-, 3-decynyl ester |
| 523 | Acetic acid, {{2-{5-[3,6-dihydro-3-methyl-2,6-dioxo-4-(trifluoromethyl)-1(2H)-pyrimidinyl]-1,2-benzisothiazol-3-yl}-p-tolyl}oxy}-, 3-(3-methoxy-propoxy)propyl ester |
| 524 | Acetic acid, {{2-{5-[3,6-dihydro-3-methyl-2,6-dioxo-4-(trifluoromethyl)-1(2H)-pyrimidinyl]-1,2-benzisothiazol-3-yl}-p-tolyl}oxy}-, ester with ethyl 4-hydroxycyclohexanecarboxylate, isomer A |
| 525 | Acetic acid, {{2-{5-[3,6-dihydro-3-methyl-2,6-dioxo-4-(trifluoromethyl)-1(2H)-pyrimidinyl]-1,2-benzisothiazol-3-yl}-p-tolyl}oxy}-, ester with ethyl 4-hydroxycyclohexanecarboxylate, isomer B |

COMPOUNDS EVALUATED AS HERBICIDAL AGENTS

| Compound Number | |
|---|---|
| 526 | Acetic acid, {{2-{5-[3,6-dihydro-3-methyl-2,6-dioxo-4-(trifluoromethyl)-1(2H)-pyrimidinyl]-1,2-benzisothiazol-3-yl}-p-tolyl}oxy}-, 11-tetradecenyl ester, (E)- |
| 527 | Acetic acid, {{2-{5-[3,6-dihydro-3-methyl-2,6-dioxo-4-(trifluoromethyl)-1(2H)-pyrimidinyl]-1,2-benzisothiazol-3-yl}-p-tolyl}oxy}-, 2,2-dimethyl-3-phenylpropyl ester |
| 528 | Propionic acid, 2-{{2-{5-[3,6-dihydro-3-methyl-2,6-dioxo-4-(trifluoromethyl)-i(2H)-pyrimidinyl]-1,2-benzisothiazol-3-yl}-p-tolyl}oxy}-2-methyl-, 2-propynyl ester |
| 529 | Propionic acid, 2-{{2-{5-[3,6-dihydro-3-methyl-2,6-dioxo-4-(trifluoromethyl)-1(2H)-pyrimidinyl]-1,2-benzisothiazol-3-yl}-p-tolyl}oxy}-2-methyl-, 2-butenyl ester |
| 530 | Propionic acid, 2-{{2-{5-[3,6-dihydro-3-methyl-2,6-dioxo-4-(trifluoromethyl)-1(2H)-pyrimidinyl]-1,2-benzisothiazol-3-yl}-p-tolyl}oxy}-2-methyl-, allyl ester |
| 531 | Propionic acid, 2-{{2-{5-[3,6-dihydro-3-methyl-2,6-dioxo-4-(trifluoromethyl)-1(2H)-pyrimidinyl]-1,2-benzisothiazol-3-yl}-p-tolyl}oxy}-2-methyl-, 1-methyl-2-propynyl ester |
| 532 | Propionic acid, 2-{{2-{5-[3,6-dihydro-3-methyl-2,6-dioxo-4-(trifluoromethyl)-1(2H)-pyrimidinyl]-1,2-benzisothiazol-3-yl}-p-tolyl}oxy}-2-methyl-, 2-methoxy-1-methylethyl ester |
| 533 | Acetic acid, {{2-{5-[3,6-dihydro-3-methyl-2,6-dioxo-4-(trifluoromethyl)-1(2H)-pyrimidinyl]-1,2-benzisothiazol-3-yl}-p-tolyl}oxy}-, 2-(5,5-dimethyl-m-dioxan-2-yl)ethyl ester |
| 534 | Acetic acid, {{2-{5-[3,6-dihydro-3-methyl-2,6-dioxo-4-(trifluoromethyl)-1(2H)-pyrimidinyl]-1,2-benzisothiazol-3-yl}-p-tolyl}oxy}-, 5-(tert-butyldimethylsiloxy)pentyl ester |
| 535 | Acetic acid, {{2-{5-[3,6-dihydro-3-methyl-2,6-dioxo-4-(trifluoromethyl)-1(2H)-pyrimidinyl]-1,2-benzisothiazol-3-yl}-p-tolyl}oxy}-, (tetrahydro-3-furyl)methyl ester, DL- |
| 536 | Acetic acid, {{2-{5-[3,6-dihydro-3-methyl-2,6-dioxo-4-(trifluoromethyl)-1(2H)-pyrimidinyl]-1,2-benzisothiazol-3-yl}-p-tolyl}oxy}-, 3-(3-methoxypropoxy)propyl ester |
| 537 | 2,4(1H,3H)-Pyrimidinedione, 1-methyl-3-{3-[6-(phenacyloxy)-m-tolyl]-1,2-benzisothiazol-5-yl]-6-(trifluoromethyl)- |
| 538 | 2,4(1H,3H)-Pyrimidinedione, 3-{3-{6-[(p-chlorophenacyl)oxy}-m-tolyl}-1,2-benzisothiazol-5-yl}-1-methyl-6-(trifluoromethyl)- |
| 539 | Acetamide, 2-{{2-{5-[3,6-dihydro-3-methyl-2,6-dioxo-4-(trifluoromethyl)-1(2H)-pyrimidinyl]-1,2-benzisothiazol-3-yl}-p-tolyl}oxy}- |
| 540 | 2,4(1H,3H)-Pyrimidinedione, 3-{3-[6-(3,3-dimethyl-2-oxobutoxy)-m-tolyl]-1,2-benzisothiazol-5-yl}-1-methyl-6-(trifluoromethyl)- |
| 541 | Benzoic acid, p-{2-{{2-{5-[3,6-dihydro-3-methyl-2,6-dioxo-4-(trifluoromethyl)-1(2H)-pyrimidinyl]-1,2-benzisothiazol-3-yl}-p-tolyl}oxy}-propionamido}-, ethyl ester |
| 542 | 2,4(1H,3H)-Pyrimidinedione, 3-{3-{6-[1-(3,4-dimethylbenzoyl)ethoxy]-m-tolyl}-1,2-benzisothiazol-5-yl}-1-methyl-6-(trifluoromethyl)- |
| 543 | 2,4(1H,3H)-Pyrimidinedione, 3-{3-{6-{[p-(difluoromethoxy)phenacyl]oxy}-m-tolyl}-1,2-benzisothiazol-5-yl}-1-methyl-6-(trifluoromethyl)- |
| 544 | Propionic acid, 2-{{2-{5-[3,6-dihydro-3-methyl-2,6-dioxo-4-(trifluoromethyl)-1(2H)-pyrimidinyl]-1,2-benzisothiazol-3-yl}-p-tolyl}oxy}-2-methyl-, 2-chloroethyl ester |
| 545 | Propionic acid, 2-{{2-{5-[3,6-dihydro-3-methyl-2,6-dioxo-4-(trifluoromethyl)-1(2H)-pyrimidinyl]-1,2-benzisothiazol-3-yl}-p-tolyl}oxy}-2-methyl-, 2,2,2-trifluoroethyl ester |
| 546 | Propionic acid, 2-{{2-{5-[3,6-dihydro-3-methyl-2,6-dioxo-4-(trifluoromethyl)-1(2H)-pyrimidinyl]-1,2-benzisothiazol-3-yl}-p-tolyl}oxy}-2-methyl-, 2-methoxyethyl ester |
| 547 | Propionic acid, 2-{{2-{5-[3,6-dihydro-3-methyl-2,6-dioxo-4-(trifluoromethyl)-1(2H)-pyrimidinyl]-1,2-benzisothiazol-3-yl}-p-tolyl}oxy}-2-methyl-1 isopropyl ester |
| 548 | Acetamide,2-{o-{5-[3,6-dihydro-3-methyl-2,6-dioxo-4-(trifluoromethyl)-1(2H)-pyrimidinyl]-1,2-benzisothiazol-3-yl}phenoxy}- |
| 549 | 2,4(1H,3H)-Pyrimidinedione, 3-{3-[o-(3,3-dimethyl-2-oxobutoxy)phenyl]-1,2-benzisothiazol-5-yl}-1-methyl-6-(trifluoromethyl)- |
| 550 | 2,4(1H,3H)-Pyrimidinedione, 3-{3-{o-[1-(3,4-dimethylbenzoyl)ethoxy]phenyl]-1,2-benzisothiazol-5-yl}-1-methyl-6-(trifluoromethyl)- |
| 551 | Propionamide, 2-{o-{5-[3,6-dihydro-3-methyl-2,6-dioxo-4-(trifluoromethyl)-1(2H)-pyrimidinyl]-1,2-benzisothiazol-3-yl}phenoxy}-N,N-dimethyl- |
| 552 | Acetamide, 2-{{2-{5-[3,6-dihydro-3-methyl-2,6-dioxo-4-(trifluoromethyl)-1(2H)-pyrimidinyl]-1,2-benzisothiazol-3-yl}-p-tolyl}oxy}-N-(propylsulfonyl)- |
| 553 | Acetamide, 2-{{2-{5-[3,6-dihydro-3-methyl-2,6-dioxo-4-(trifluoromethyl)-1(2H)-pyrimidinyl]-1,2-benzisothiazol-3-yl}-p-tolyl}oxy}-N-(vinylsulfonyl)- |
| 554 | Acetamide, 2-{{2-{5-[3,6-dihydro-3-methyl-2,6-dioxo-4-(trifluoromethyl)-1(2H)-pyrimidinyl]-1,2-benzisothiazol-3-yl}-p-tolyl}oxy}-N-(ethylsulfonyl)- |
| 555 | Acetamide, 2-{o-{5-[3,6-dihydro-3-methyl-2,6-dioxo-4-(trifluoromethyl)-1(2H)-pyrimidinyl]-1,2-benzisothiazol-3-yl}phenoxy}-N-(isopropylsulfonyl)- |
| 556 | Acetamide, 2-{o-{5-[3,6-dihydro-3-methyl-2,6-dioxo-4-(trifluoromethyl)-1(2H)-pyrimidinyl]-1,2-benzisothiazol-3-yl}phenoxy}-N-(propylsulfonyl)- |
| 557 | Acetamide, 2-{o-{5-[3,6-dihydro-3-methyl-2,6-dioxo-4-(trifluoromethyl)-1(2H)-pyrimidinyl]-1,2-benzisothiazol-3-yl}phenoxy}-N-(vinylsulfonyl)- |
| 558 | Acetamide, 2-{o-{5-[3,6-dihydro-3-methyl-2,6-dioxo-4-(trifluoromethyl)-1(2H)-pyrimidinyl]-1,2-benzisothiazol-3-yl}phenoxy}-N-(ethylsulfonyl)- |
| 559 | Acetic acid, {{2-{5-[3,6-dihydro-3-methyl-2,6-dioxo-4-(trifluoromethyl)-1(2H)-pyrimidinyl]-1,2-benzisothiazol-3-yl}-p-tolyl}oxy}difluoro-, ethyl ester |
| 560 | Acetamide, 2-{{2-{5-[3,6-dihydro-3-methyl-2,6-dioxo-4-(trifluoromethyl)-1(2H)-pyrimidinyl]-1,2-benzisothiazol-3-yl}-p-toly}oxy}-N-(isopropylsulfonyl)- |
| 561 | Acetamide, 2-{{2-{5-[3,6-dihydro-3-methyl-2,6-dioxo-4-(trifluoromethyl)-1(2H)-pyrimidinyl]-1,2-benzisothiazol-3-yl}-p-tolyl}oxy}-N-methyl- |
| 562 | Acetamide, 2-{o-{5-[3,6-dihydro-3-methyl-2,6-dioxo-4-(trifluoromethyl)-1(2H)-pyrimidinyl]-1,2-benzisothiazol-3-yl}phenoxy}-N-methyl- |
| 563 | Acetamide, 2-{o-{5-[3,6-dihydro-3-methyl-2,6-dioxo-4-(trifluoromethyl)-1(2H)-pyrimidinyl]-i,2-benzisothiazol-3-yl}phenoxy}- |
| 564 | 2,4(1H,3H)-Pyrimidinedione, 1-methyl-3-[3-(3-oxo-3-phenylpropenyl)-1,2-benzisothiazol-5-yl]-6-(trifluoromethyl)-, (E)- |
| 565 | 1,2-Benzisothiazole-3-acrylamide, 5-[3,6-dihydro-3-methyl-2,6-dioxo-4-(trifluoromethyl)-1(2H)-pyrimidinyl]-N-methoxy-N-methyl-, (E)- |

COMPOUNDS EVALUATED AS HERBICIDAL AGENTS

| Compound Number | |
|---|---|
| 566 | 1,2-Benzisothiazole-3-acrylic acid, 5-[3,6-dihydro-3-methyl-2,6-dioxo-4-(trifluoromethyl)-1(2H)-pyrimidinyl]-, allyl ester, (E)- |
| 567 | 1,2-Benzisothiazole-3-acrylaldehyde, 5-[3,6-dihydro-3-methyl-2,6-dioxo-4-(trifluoromethyl)-1(2H)-pyrimidinyl]-alpha-ethyl-, (E)- |
| 568 | Propionamide, 2-{{2-{5-[3,6-dihydro-3-methyl-2,6-dioxo-4-(trifluoromethyl)-1(2H)-pyrimidinyl]-1,2-benzisothiazol-3-yl}-p-tolyl}oxy}-N-(isopropylsulfonyl)- |
| 569 | Propionamide, 2-{{2-{5-[3,6-dihydro-3-methyl-2,6-dioxo-4-(trifluoromethyl)-1(2H)-pyrimidinyl]-1,2-benzisothiazol-3-yl}-p-tolyl}oxy}-N-(propyl-sulfonyl)- |
| 570 | Propionamide, 2-{{2-{5-[3,6-dihydro-3-methyl-2,6-dioxo-4-(trifluoromethyl)-1(2H)-pyrimidinyl]-1,2-benzisothiazol-3-yl}-p-tolyl}oxy}-N-(vinyl-sulfonyl)- |
| 571 | Propionamide, 2-{{2-{5-[3,6-dihydro-3-methyl-2,6-dioxo-4-(trifluoromethyl)-1(2H)-pyrimidinyl]-1,2-benzisothiazol-3-yl}-p-tolyl}oxy}-N-(ethyl-sulfonyl) |
| 572 | Propionamide, 2-{{2-{5-[3,6-dihydro-3-methyl-2,6-dioxo-4-(trifluoromethyl)-1(2H)-pyrimidinyl]-1,2-benzisothiazol-3-yl}-p-tolyl}oxy}-N-(methyl-sulfonyl)- |
| 573 | Acetamide, N-(butylsulfonyl)-2-{{2-{5-[3,6-dihydro-3-methyl-2,6-dioxo-4-(trifluoromethyl)-1(2H)-pyrimidinyl]-1,2-benzisothiazol-3-yl}-p-tolyl}oxy}- |
| 574 | Acetamide, N-(butylsulfonyl)-2-{o-{5-[3,6-dihydro-3-methyl-2,6-dioxo-4-(trifluoromethyl)-1(2H)-pyrimidinyl]-1,2-benzisothiazol-3-yl}-phenoxy}- |
| 575 | Propionamide, N-(butylsulfonyl)-2-{{2-{5-[3,6-dihydro-3-methyl-2,6-dioxo-4-(trifluoromethyl)-1(2H)-pyrimidinyl]-1,2-benzisothiazol-3-yl}-p-tolyl}oxy}- |
| 576 | Propionamide, 2-{{2-{5-[3,6-dihydro-3-methyl-2,6-dioxo-4-(trifluoromethyl)-1(2H)-pyrimidinyl]-1,2-benzisothiazol-3-yl}-p-tolyl}oxy}-2-methyl-N-(methylsulfonyl)- |
| 577 | Acetic acid, {{2-{5-[3,6-dihydro-3-methyl-2,6-dioxo-4-(trifluoromethyl)-1(2H)-pyrimidinyl]-1,2-benzisothiazol-3-yl}-p-tolyl}oxy}-, 2-oxobutyl ester |
| 578 | Acetic acid, {{2-{5-[3,6-dihydro-3-methyl-2,6-dioxo-4-(trifluoromethyl)-1(2H)-pyrimidinyl]-1,2-benzisothiazol-3-yl}-p-tolyl}oxy}-, 2-hydroxyethyl ester, acetate (ester) |
| 579 | Glycine, N-{{5-[3,6-dihydro-3-methyl-2,6-dioxo-4-(trifluoromethyl)-1(2H)-pyrimidinyl]-1,2-benzisothiazol-3-yl}carbonyl}- |
| 580 | 1,2-Benzisothiazole-3-acetonitrile,alpha,alpha-diallyl-5-[3,6-dihydro-3-methyl-2,6-dioxo-4-(trifluoromethyl)-1(2H)-pyrimidinyl]- |
| 581 | 1,2-Benzisothiazole-3-acetonitrile, 5-[3,6-dihydro-3-methyl-2,6-dioxo-4-(trifluoromethyl)-1(2H)-pyrimidinyl]-alpha,alpha-di-2-propynyl- |
| 582 | 1,2-Benzisothiazole-3-acetonitrile,alpha,alpha-dibenzyl-5-[3,6-dihydro-3-methyl-2,6-dioxo-4-(trifluoromethyl)-1(2H)-pyrimidinyl]- |
| 583 | 1,2-Benzisothiazole-3-acetonitrile, 5-[3,6-dihydro-3-methyl-2,6-dioxo-4-(trifluoromethyl)-1(2H)-pyrimidinyl]-alpha-methyl- |
| 584 | 2,4(1H,3H)-Pyrimidinedione, 3-{3-{[(p-chlorobenzyl)oxy]methyl}-1,2-benzisothiazol-5-yl}-1-methyl-6-(trifluoromethyl)- |
| 585 | 2,4(1H,3H)-Pyrimidinedione, 3-{3-{[(2,4-dichlorobenzyl)oxy]methyl}-1,2-benzisothiazol-5-yl}-1-methyl-6-(trifluoromethyl)- |
| 586 | 2,4(1H,3H)-Pyrimidinedione, 3-{3-{[(3,4-dichlorobenzyl)oxy]methyl}-1,2-benzisothiazol-5-yl}-1-methyl-6-(trifluoromethyl)- |
| 587 | 2,4(1H,3H)-Pyrimidinedione, 1-methyl-3-{3-{[(m-methylbenzyl)oxy]methyl}-1,2-benzisothiazol-5-yl}-6-(trifluoromethyl)- |
| 588 | 2,4(1H,3H)-Pyrimidinedione, 1-methyl-3-{3-{[(m-nitrobenzyl)oxy]methyl}-1,2-benzisothiazol-5-yl}-6-(trifluoromethyl)- |
| 589 | 2,4(1H,3H)-Pyrimidinedione, 1-methyl-3-{3-{[(p-nitrobenzyl)oxy]methyl}-1,2-benzisothiazol-5-yl}-6-(trifluoromethyl)- |
| 590 | 2,4(1H,3H)-Pyrimidinedione, 1-methyl-3-{3-[1-(methylsulfonyl)ethyl]-1,2-benzisothiazol-5-yl}-6-(trifluoromethyl)- |
| 591 | 1,2-Benzisothiazole-3-acetonitrile, 5-[3,6-dihydro-3-methyl-2,6-dioxo-4-(trifluoromethyl)-1(2H)-pyrimidinyl]-alpha-(2-methylpropylidene)- |
| 592 | 1,2-Benzisothiazole-3-acetonitrile, 5-[3,6-dihydro-3-methyl-2,6-dioxo-4-(trifluoromethyl)-1(2H)-pyrimidinyl]-alpha-(2-pyridylmethylene)- |
| 593 | 1,2-Benzisothiazole-3-acetonitrile, 5-[3,6-dihydro-3-methyl-2,6-dioxo-4-(trifluoromethyl)-1(2H)-pyrimidinyl]-alpha-(3-furylmethylene)- |
| 594 | 1,2-Benzisothiazole-3-acetonitrile, 5-[3,6-dihydro-3-methyl-2,6-dioxo-4-(trifluoromethyl)-1(2H)-pyrimidinyl]-alpha-furfurylidene- |
| 595 | 1,2-Benzisothiazole-3-acetonitrile, 5-[3,6-dihydro-3-methyl-2,6-dioxo-4-(trifluoromethyl)-1(2H)-pyrimidinyl]-alpha-imidazol-5-ylmethylene)- |
| 596 | 1,2-Benzisothiazole-3-acetonitrile, 5-[3,6-dihydro-3-methyl-2,6-dioxo-4-(trifluoromethyl)-1(2H)-pyrimidinyl]-alpha-(4-pyridylmethylene)- |
| 597 | 1,2-Benzisothiazole-3-acetonitrile, 5-[3,6-dihydro-3-methyl-2,6-dioxo-4-(trifluoromethyl)-1(2H)-pyrimidinyl]-alpha-(p-methylbenzylidene)- |
| 598 | 1,2-Benzisothiazole-3-acetonitrile, 5-[3,6-dihydro-3-methyl-2,6-dioxo-4-(trifluoromethyl)-1(2H)-pyrimidinyl]-alpha-(pyrrol-2-ylmethylene)- |
| 599 | 1,2-Benzisothiazole-3-acetonitrile, 5-[3,6-dihydro-3-methyl-2,6-dioxo-4-(trifluoromethyl)-1(2H)-pyrimidinyl]-alpha-(o-methoxybenzylidene)- |
| 600 | 1,2-Benzisothiazole-3-acetonitrile, 5-[3,6-dihydro-3-methyl-2,6-dioxo-4-(trifluoromethyl)-1(2H)-pyrimidinyl]-alpha-(p-hydroxybenzylidene)- |
| 601 | 1,2-Benzisothiazole-3-acetonitrile, 5-[3,6-dihydro-3-methyl-2,6-dioxo-4-(trifluoromethyl)-1(2H)-pyrimidinyl]-alpha-(indol-2-ylmethylene)- |
| 602 | 2,4(1H,3H)-Pyrimidinedione, 1-methyl-3-{3-[1-(methylsulfonyl)-3-butenyl]-1,2-benzisothiazol-5-yl}-6-(trifluoromethyl)- |
| 603 | 2,4(1H,3H)-Pyrimidinedione, 1-methyl-3-{3-[1-(methylsulfonyl)-3-butynyl]-1,2-benzisothiazol-5-yl}-6-(trifluoromethyl)- |
| 604 | 2,4(1H,3H)-Pyrimidinedione, 1-methyl-3-{3-[alpha-(methylsulfonyl)phenethyl]-1,2-benzisothiazol-5-yl}-6-(trifluoromethyl)- |
| 605 | 1,2-Benzisothiazole-3-acetonitrile, 5-[3,6-dihydro-3-methyl-2,6-dioxo-4-(trifluoromethyl)-1(2H)-pyrimidinyl]-alpha-(o-fluorobenzylidene)- |
| 606 | 1,2-Benzisothiazole-3-acetonitrile, alpha-(o-cyanobenzylidene)-5-[3,6-dihydro-3-methyl-2,6-dioxo-4-(trifluoromethyl)-1(2H)-pyrimidinyl]-, (E)- and (Z)- |
| 607 | 1,2-Benzisothiazole-3-acetonitrile, alpha-(cyclopentylmethylene)-5-[3,6-dihydro-3-methyl-2,6-dioxo-4-(trifluoromethyl)-1(2H)-pyrimidinyl]-(E)- and (Z)- |

TABLE I

Postemergence Herbicidal Evaluations of Test Compounds

| Compound Number | Rate (kg/ha) | ABUTH | AMBEL | CASOB | CHEAL | GALAP | IPOHE | IPOSS | ECHCG | SETVI | GLXMAW | GLXMA | ORYSAT | TRZAWR | ZEAMX |
|---|---|---|---|---|---|---|---|---|---|---|---|---|---|---|---|
| 1 | 0.5000 | 9.0 | 9.0 | 9.0 | 9.0 | 9.0 |  | 9.0 | 9.0 | 9.0 | 9.0 | 8.0 | 7.0 | 7.0 | 8.0 |
|  | 0.2500 | 9.0 | 9.0 | 8.0 | 9.0 | 9.0 |  | 9.0 | 9.0 | 9.0 | 7.0 | 9.0 | 5.0 | 5.5 | 7.0 |
|  | 0.1250 | 9.0 | 9.0 | 9.0 | 9.0 | 9.0 |  | 9.0 | 9.0 | 9.0 | 7.0 | 9.0 | 5.0 | 5.0 | 5.0 |
|  | 0.0630 | 9.0 | 9.0 | 9.0 | 9.0 | 9.0 | 9.0 |  | 7.0 | 9.0 | 6.0 |  | 4.3 | 5.3 | 6.0 |
|  | 0.0625 | 9.0 | 9.0 | 9.0 | 9.0 | 9.0 |  | 9.0 | 7.0 | 9.0 | 4.0 | 8.0 | 4.5 | 3.5 | 5.0 |
|  | 0.0315 | 9.0 | 9.0 | 9.0 | 9.0 | 9.0 | 9.0 |  | 5.0 | 9.0 | 6.3 |  | 5.0 | 7.0 | 5.7 |
|  | 0.0313 | 9.0 | 9.0 | 9.0 | 9.0 | 9.0 |  | 9.0 | 6.0 | 9.0 | 3.0 | 8.0 | 3.0 | 3.5 | 4.0 |
|  | 0.0158 | 9.0 | 9.0 | 9.0 | 9.0 | 5.0 | 9.0 |  | 4.0 | 9.0 | 5.3 |  | 3.0 | 4.0 | 5.7 |
|  | 0.0157 | 7.0 | 9.0 | 9.0 | 9.0 | 9.0 |  | 9.0 | 4.0 | 9.0 | 3.0 | 6.0 | 3.0 | 3.0 | 3.5 |
| 2 | 0.5000 | 9.0 | 9.0 | 9.0 | 9.0 | 9.0 |  | 9.0 | 9.0 | 9.0 |  | 9.0 | 9.0 | 7.0 | 8.0 |
|  | 0.2500 | 9.0 | 9.0 | 9.0 | 9.0 | 9.0 |  | 9.0 | 9.0 | 9.0 |  | 9.0 | 9.0 | 9.0 | 7.5 |
|  | 0.1250 | 9.0 | 9.0 | 6.5 | 9.0 | 9.0 |  | 9.0 | 9.0 | 9.0 |  | 9.0 | 8.5 | 6.5 | 7.5 |
|  | 0.0630 | 9.0 | 9.0 | 9.0 | 9.0 | 9.0 | 9.0 |  | 9.0 | 9.0 | 8.8 |  | 7.8 | 7.2 | 8.0 |
|  | 0.0625 | 9.0 | 9.0 | 5.0 | 9.0 | 9.0 |  | 9.0 | 9.0 | 9.0 |  | 8.5 | 8.5 | 6.5 | 6.5 |
|  | 0.0320 | 9.0 | 9.0 | 6.5 | 9.0 | 9.0 | 9.0 |  | 9.0 | 9.0 | 8.3 |  | 6.3 | 5.3 | 6.3 |
|  | 0.0315 | 9.0 | 9.0 | 9.0 | 9.0 | 9.0 |  | 9.0 | 9.0 | 9.0 | 8.0 |  | 7.6 | 6.6 | 7.8 |
|  | 0.0313 | 7.0 | 9.0 | 9.0 | 9.0 | 9.0 |  | 9.0 | 9.0 | 9.0 |  | 7.5 | 8.0 | 5.5 | 6.0 |
|  | 0.0160 | 9.0 | 9.0 | 7.2 | 9.0 | 5.8 | 9.0 |  | 9.0 | 9.0 | 7.4 |  | 6.0 | 5.5 | 6.8 |
|  | 0.0158 | 9.0 | 9.0 | 6.5 | 8.0 | 7.0 | 9.0 |  | 9.0 | 9.0 | 7.8 |  | 7.2 | 6.4 | 7.4 |
|  | 0.0157 | 9.0 | 9.0 | 4.0 | 9.0 | 9.0 |  | 9.0 | 9.0 | 8.0 |  | 6.5 | 7.0 | 5.5 | 6.0 |
| 3 | 0.5000 | 9.0 | 9.0 | 9.0 | 9.0 | 9.0 |  | 9.0 | 9.0 | 9.0 |  | 8.0 | 9.0 | 9.0 | 9.0 |
|  | 0.2500 | 9.0 | 9.0 | 9.0 | 9.0 | 9.0 |  | 9.0 | 9.0 | 9.0 |  | 7.5 | 9.0 | 8.0 | 9.0 |
|  | 0.1250 | 9.0 | 9.0 | 9.0 | 9.0 | 9.0 | 9.0 |  | 9.0 | 9.0 | 7.0 | 7.5 | 8.5 | 8.0 | 8.5 |
|  | 0.0630 | 9.0 | 9.0 | 9.0 | 9.0 | 9.0 |  | 9.0 | 9.0 | 9.0 |  |  | 7.2 | 8.8 | 8.3 |
|  | 0.0625 | 9.0 | 9.0 | 6.7 | 9.0 | 9.0 |  | 9.0 | 9.0 | 9.0 |  | 6.5 | 9.0 | 8.5 | 8.0 |
|  | 0.0315 | 9.0 | 9.0 | 4.0 | 9.0 | 7.5 | 9.0 |  | 9.0 | 9.0 | 6.8 |  | 6.8 | 8.7 | 8.2 |
|  | 0.0313 | 9.0 | 9.0 | 9.0 | 9.0 | 9.0 |  | 9.0 | 9.0 | 9.0 |  | 4.5 | 8.5 | 5.5 | 6.5 |
|  | 0.0160 | 9.0 | 9.0 | 3.0 | 9.0 | 7.5 | 9.0 |  | 9.0 | 9.0 | 5.5 |  | 6.3 | 7.5 | 7.3 |
|  | 0.0158 | 9.0 | 9.0 | 5.3 | 8.3 | 9.0 | 9.0 |  | 9.0 | 9.0 | 5.8 |  | 6.0 | 8.3 | 7.7 |
|  | 0.0157 | 9.0 | 9.0 | 2.0 | 9.0 | 9.0 |  | 9.0 | 7.0 | 9.0 |  | 4.0 | 7.0 | 5.5 | 6.5 |
| 4 | 0.5000 | 9.0 | 9.0 | 9.0 | 9.0 | 9.0 |  | 9.0 | 9.0 | 9.0 |  | 9.0 | 4.0 | 4.0 | 3.0 |
|  | 0.2500 | 9.0 | 9.0 | 9.0 | 9.0 | 9.0 |  | 9.0 | 8.0 | 9.0 |  | 7.0 | 3.0 | 3.0 | 3.0 |
|  | 0.1250 | 9.0 | 9.0 | 9.0 | 9.0 | 9.0 |  | 9.0 | 8.0 | 9.0 |  | 7.0 | 3.0 | 3.0 | 3.0 |
|  | 0.0625 | 9.0 | 9.0 | 9.0 | 9.0 | 9.0 |  | 9.0 | 7.0 | 9.0 |  | 4.0 | 2.0 | 2.0 | 3.0 |
|  | 0.0313 | 9.0 | 7.0 | 7.0 | 9.0 | 4.0 |  | 9.0 | 5.0 | 8.0 |  | 5.0 | 2.0 | 2.0 | 2.0 |
|  | 0.0157 | 9.0 | 9.0 | 7.0 | 9.0 | 8.0 |  | 9.0 | 2.0 | 9.0 |  | 6.0 | 2.0 | 2.0 | 2.0 |
| 5 | 0.5000 | 9.0 | 9.0 | 9.0 | 9.0 | 9.0 |  | 9.0 | 9.0 | 9.0 |  | 7.0 | 3.0 | 3.0 | 3.0 |
|  | 0.2500 | 9.0 | 9.0 | 9.0 | 9.0 | 9.0 |  | 9.0 | 7.0 | 9.0 |  | 7.0 | 3.0 | 2.0 | 3.0 |
|  | 0.1250 | 9.0 | 9.0 | 9.0 | 9.0 | 9.0 |  | 9.0 | 7.0 | 9.0 |  | 7.0 | 3.0 | 2.0 | 3.0 |
|  | 0.0625 | 9.0 | 9.0 | 7.0 | 9.0 | 9.0 |  | 9.0 | 6.0 | 9.0 |  | 6.0 | 2.0 | 2.0 | 2.0 |
|  | 0.0313 | 9.0 | 9.0 | 7.0 | 9.0 | 7.0 |  | 9.0 | 6.0 | 8.0 |  | 4.0 | 1.0 | 2.0 | 1.0 |
|  | 0.0157 | 7.0 | 9.0 | 9.0 | 9.0 | 9.0 |  | 4.0 | 7.0 | 9.0 |  | 7.0 | 5.0 | 6.0 | 3.0 |
| 6 | 0.5000 | 9.0 | 9.0 | 8.0 | 9.0 | 9.0 |  | 9.0 | 6.0 | 9.0 | 7.0 | 6.0 | 5.0 | 5.0 | 3.0 |
|  | 0.2500 | 9.0 | 9.0 | 7.0 | 9.0 | 9.0 |  | 9.0 | 7.0 | 9.0 | 7.0 | 6.0 | 4.5 | 2.5 | 3.5 |
|  | 0.1250 | 9.0 | 9.0 |  | 9.0 | 9.0 | 9.0 | 9.0 | 3.0 | 7.0 | 6.0 | 6.0 | 1.0 | 3.0 | 5.0 |
|  | 0.0640 | | | | | | | | | | | | | | |

TABLE I-continued

Postemergence Herbicidal Evaluations of Test Compounds

| Compound Number | Rate (kg/ha) | ABUTH | AMBEL | CASOB | CHEAL | GALAP | IPOHE | IPOSS | ECHCG | SETVI | GLXMAW | GLXMA | ORYSAT | TRZAWR | ZEAMX |
|---|---|---|---|---|---|---|---|---|---|---|---|---|---|---|---|
|   | 0.0630 | 9.0 | 6.5 | 2.5 | 7.0 | 5.0 | 5.0 | 9.0 | 1.5 | 2.0 | 4.8 |     | 1.8 | 1.5 | 4.5 |
|   | 0.0625 | 9.0 | 9.0 | 4.0 | 9.0 | 9.0 |     | 9.0 | 2.0 | 9.0 | 7.0 | 4.0 | 1.5 | 2.0 | 3.5 |
|   | 0.0320 | 9.0 | 9.0 | 2.3 | 6.5 | 3.0 |     |     | 1.0 | 6.0 | 5.5 | 5.0 | 1.5 | 2.5 | 3.8 |
|   | 0.0315 | 9.0 | 6.0 | 1.5 | 5.0 | 3.0 | 9.0 |     | 1.0 | 2.5 | 3.8 |     | 1.0 | 0.8 | 4.3 |
|   | 0.0313 | 9.0 | 8.0 | 0.0 | 9.0 | 9.0 | 4.0 | 8.0 | 2.0 | 7.0 | 7.0 | 4.0 | 1.5 | 1.5 | 3.5 |
|   | 0.0160 | 5.7 | 7.7 | 0.0 | 3.0 | 2.7 |     | 7.5 | 0.7 | 3.7 | 5.5 | 2.5 | 1.5 | 2.0 | 3.5 |
|   | 0.0158 | 5.0 | 3.0 | 0.0 | 0.0 | 0.0 | 6.0 |     | 0.0 | 0.0 | 3.0 |     | 0.5 | 0.0 | 4.0 |
|   | 0.0157 | 8.0 | 7.0 | 0.0 | 0.0 | 4.0 | 2.5 | 7.0 | 2.0 | 7.0 |     | 4.0 | 2.0 | 2.0 | 2.0 |
| 7 | 0.2500 | 9.0 | 9.0 | 9.0 | 9.0 | 8.0 |     | 9.0 | 8.0 | 9.0 | 9.0 |     | 6.5 | 7.0 | 7.0 |
|   | 0.1250 | 9.0 | 9.0 | 9.0 | 9.0 | 7.0 |     | 9.0 | 7.0 | 9.0 | 7.5 |     | 5.5 | 5.5 | 6.0 |
|   | 0.0625 | 9.0 | 9.0 | 9.0 | 9.0 | 5.0 |     | 8.0 | 3.0 | 9.0 | 9.0 |     | 4.5 | 5.0 | 5.5 |
|   | 0.0313 | 9.0 | 9.0 | 9.0 | 9.0 | 5.0 |     | 9.0 | 3.0 | 9.0 | 8.5 |     | 3.5 | 5.0 | 6.0 |
|   | 0.0157 | 9.0 | 9.0 | 8.0 | 9.0 | 3.0 |     | 9.0 | 3.0 | 9.0 | 8.0 |     | 4.0 | 5.0 | 6.0 |
| 8 | 0.2500 | 9.0 | 9.0 | 9.0 | 9.0 | 9.0 | 9.0 | 9.0 | 9.0 | 9.0 | 9.0 |     | 8.5 | 9.0 | 9.0 |
|   | 0.1250 | 9.0 | 9.0 | 9.0 |     | 9.0 |     | 9.0 | 9.0 | 9.0 | 9.0 |     | 8.5 | 9.0 | 9.0 |
|   | 0.0625 | 9.0 | 9.0 | 9.0 |     | 7.0 |     | 9.0 | 9.0 | 9.0 | 9.0 |     | 5.0 | 9.0 | 7.0 |
|   | 0.0320 | 9.0 | 9.0 | 9.0 |     | 7.0 | 9.0 |     | 5.0 | 5.0 | 8.5 |     | 8.5 | 8.5 | 8.0 |
|   | 0.0313 | 9.0 | 9.0 | 9.0 |     | 5.0 |     | 9.0 | 9.0 | 9.0 | 8.5 |     | 4.5 | 7.5 | 7.0 |
|   | 0.0160 | 9.0 | 9.0 | 9.0 |     | 7.0 |     | 9.0 | 9.0 | 9.0 | 9.0 |     | 7.5 | 8.5 | 8.0 |
|   | 0.0157 | 9.0 | 9.0 | 9.0 |     | 8.0 |     | 9.0 | 9.0 | 9.0 | 9.0 |     | 8.5 | 9.0 | 9.0 |
| 9 | 0.2500 | 9.0 | 9.0 | 9.0 |     | 9.0 |     | 9.0 | 9.0 | 9.0 | 9.0 |     | 8.5 | 9.0 | 9.0 |
|   | 0.1250 | 9.0 | 9.0 | 9.0 |     | 7.0 |     | 9.0 | 9.0 | 9.0 | 9.0 |     | 8.5 | 9.0 | 9.0 |
|   | 0.0625 | 9.0 | 9.0 | 9.0 | 9.0 | 4.0 |     | 7.0 | 9.0 | 9.0 | 9.0 |     | 7.0 | 8.0 | 8.5 |
|   | 0.0320 | 9.0 |     | 9.0 |     | 6.0 |     |     | 9.0 | 9.0 | 8.0 |     | 7.0 | 8.0 | 8.5 |
|   | 0.0313 | 9.0 | 6.0 | 9.0 | 9.0 | 2.0 | 9.0 | 9.0 | 9.0 | 9.0 | 7.0 |     | 6.5 | 9.0 | 7.0 |
|   | 0.0160 | 9.0 |     | 9.0 | 9.0 | 5.0 |     | 9.0 | 9.0 | 9.0 | 7.5 |     | 6.5 | 7.5 | 9.0 |
|   | 0.0157 | 9.0 | 9.0 | 9.0 | 9.0 | 7.0 |     | 9.0 | 5.0 | 9.0 | 7.5 |     | 3.5 | 5.5 | 6.0 |
| 10 | 0.2500 | 9.0 | 9.0 | 9.0 | 9.0 | 8.0 |     | 8.0 | 3.0 | 9.0 | 8.0 |     | 2.5 | 5.0 | 6.0 |
|   | 0.1250 | 9.0 | 9.0 | 9.0 | 9.0 | 4.0 |     | 9.0 | 5.0 | 9.0 | 7.5 |     | 2.5 | 5.0 | 5.5 |
|   | 0.0625 | 8.0 | 9.0 | 9.0 | 8.0 | 4.0 |     | 9.0 | 2.0 | 7.0 | 5.5 |     | 2.5 | 3.5 | 6.0 |
|   | 0.0313 | 9.0 | 9.0 | 8.0 | 5.0 | 3.0 |     | 2.0 | 2.0 | 6.0 | 5.5 |     | 2.0 | 3.5 | 5.5 |
|   | 0.0157 | 7.0 | 8.0 | 5.0 | 9.0 | 2.0 |     | 1.0 | 2.0 | 8.0 | 4.0 |     | 2.0 | 5.0 | 5.5 |
| 11 | 0.2500 | 9.0 | 9.0 | 7.0 | 9.0 | 6.0 |     | 9.0 | 9.0 | 8.0 | 6.0 |     | 2.0 | 4.0 | 9.0 |
|   | 0.1250 | 9.0 | 9.0 | 6.0 | 6.0 | 4.0 |     | 8.0 | 7.0 | 9.0 | 6.0 |     | 2.0 | 3.0 | 6.0 |
|   | 0.0625 | 8.0 | 9.0 | 4.0 | 8.0 | 2.0 |     | 5.0 | 4.0 | 9.0 | 5.5 |     | 1.5 | 4.0 | 5.5 |
|   | 0.0313 | 9.0 | 9.0 | 4.0 | 8.0 | 2.0 |     | 2.0 | 4.0 | 7.0 | 5.5 |     | 1.5 | 3.0 | 5.5 |
|   | 0.0157 | 7.0 | 6.0 | 3.0 | 5.0 | 5.0 |     | 1.0 | 2.0 | 6.0 | 4.0 |     | 1.5 | 3.0 | 5.5 |
| 12 | 0.2500 | 9.0 | 9.0 | 9.0 | 9.0 | 9.0 |     | 9.0 | 9.0 | 9.0 | 9.0 |     | 9.0 | 9.0 | 9.0 |
|   | 0.1250 | 9.0 | 9.0 | 9.0 | 9.0 | 7.0 |     | 9.0 | 9.0 | 9.0 | 9.0 |     | 8.0 | 7.5 | 9.0 |
|   | 0.0625 | 9.0 | 9.0 | 5.0 | 9.0 | 5.0 |     | 9.0 | 9.0 | 8.5 | 8.5 |     | 7.5 | 9.0 | 8.0 |
|   | 0.0313 | 9.0 | 9.0 | 7.0 | 9.0 | 3.0 | 9.0 |     | 4.0 | 8.0 | 7.5 |     | 4.5 | 6.5 | 7.5 |
|   | 0.0160 | 9.0 | 9.0 | 9.0 |     | 4.0 |     | 9.0 | 8.0 | 9.0 | 8.5 |     | 7.5 | 8.0 | 9.0 |
|   | 0.0157 | 9.0 | 9.0 | 5.0 | 9.0 | 8.0 |     | 9.0 | 9.0 | 9.0 | 8.5 |     | 8.0 | 8.5 | 9.0 |
| 13 | 0.2500 | 9.0 | 9.0 | 7.0 | 9.0 | 7.0 |     | 9.0 | 9.0 | 9.0 | 8.0 |     | 8.0 | 7.5 | 9.0 |
|   | 0.1250 | 9.0 | 9.0 | 9.0 | 9.0 | 5.0 |     | 9.0 | 9.0 | 7.0 | 7.5 |     | 7.5 | 8.0 | 8.0 |
|   | 0.0625 | 9.0 | 9.0 | 7.0 | 9.0 | 5.0 |     | 8.0 | 9.0 | 7.0 | 7.5 |     | 7.5 | 8.0 | 9.0 |
|   | 0.0320 | 9.0 | 9.0 | 8.0 | 9.0 | 3.0 | 9.0 |     | 7.0 | 7.0 | 4.0 |     | 3.0 | 3.5 | 7.0 |

TABLE I-continued

Postemergence Herbicidal Evaluations of Test Compounds

| Compound Number | Rate (kg/ha) | ABUTH | AMBEL | CASOB | CHEAL | GALAP | IPOHE | IPOSS | ECHCG | SETVI | GLXMAW | GLXMA | ORYSAT | TRZAWR | ZEAMX |
|---|---|---|---|---|---|---|---|---|---|---|---|---|---|---|---|
|  | 0.0313 | 9.0 | 9.0 | 9.0 | 9.0 | 4.0 |  | 9.0 | 9.0 | 9.0 | 8.0 |  | 6.0 | 6.0 | 8.5 |
|  | 0.0160 | 9.0 | 9.0 | 5.0 | 9.0 | 2.0 | 9.0 |  | 5.0 | 6.0 | 4.0 |  | 3.0 | 3.0 | 5.0 |
|  | 0.0157 | 9.0 | 9.0 | 7.0 | 9.0 | 3.0 |  |  | 9.0 | 9.0 | 6.5 |  | 5.5 | 6.0 | 8.5 |
| 14 | 0.1250 | 9.0 | 9.0 | 7.0 | 9.0 | 6.0 | 9.0 |  | 9.0 | 9.0 | 7.0 |  | 7.0 | 7.5 | 8.5 |
|  | 0.0640 | 9.0 | 9.0 | 3.0 | 9.0 | 6.0 | 5.0 |  | 9.0 | 9.0 | 5.0 |  | 5.5 | 5.5 | 7.5 |
|  | 0.0625 | 9.0 | 9.0 | 9.0 | 9.0 | 6.0 | 9.0 |  | 9.0 | 9.0 | 6.5 |  | 3.0 | 7.5 | 8.0 |
|  | 0.0320 | 9.0 | 7.0 | 3.0 | 6.0 | 4.0 | 6.0 |  | 8.0 | 9.0 | 4.5 |  | 3.5 | 7.0 | 7.5 |
|  | 0.0313 | 9.0 | 9.0 | 6.0 | 9.0 | 5.0 | 8.0 |  | 9.0 | 9.0 | 5.5 |  | 3.0 | 7.5 | 8.0 |
|  | 0.0160 | 9.0 |  | 2.0 | 5.0 | 3.0 | 5.0 |  | 5.0 | 5.0 | 4.0 |  | 3.0 | 5.0 | 6.0 |
|  | 0.0156 | 9.0 |  | 4.0 | 9.0 | 4.0 | 9.0 |  | 7.0 | 9.0 | 4.5 |  | 1.5 | 4.5 | 7.0 |
| 15 | 0.0640 | 9.0 | 9.0 | 4.0 | 9.0 | 6.0 | 9.0 |  | 8.0 | 9.0 | 7.5 |  | 9.0 | 8.5 | 7.5 |
|  | 0.0630 | 9.0 | 9.0 | 9.0 | 9.0 | 9.0 | 9.0 |  | 9.0 | 9.0 | 8.5 |  | 7.5 | 8.5 | 8.5 |
|  | 0.0320 | 9.0 | 9.0 | 9.0 | 9.0 | 5.0 | 9.0 |  | 9.0 | 9.0 | 6.5 |  | 6.0 | 8.5 | 7.5 |
|  | 0.0315 | 9.0 | 9.0 | 9.0 | 9.0 | 9.0 | 9.0 |  | 9.0 | 9.0 | 7.0 |  | 7.0 | 9.0 | 8.5 |
|  | 0.0160 | 9.0 | 9.0 | 6.0 | 9.0 | 4.0 | 4.0 |  | 9.0 | 9.0 | 5.5 |  | 4.5 | 8.0 | 6.5 |
|  | 0.0158 | 8.0 | 3.0 | 7.0 | 9.0 | 3.0 | 9.0 |  | 9.0 | 9.0 | 6.5 |  | 5.0 | 8.5 | 8.5 |
| 16 | 0.0640 | 0.0 | 0.0 | 0.0 | 0.0 | 0.0 | 2.0 |  | 2.0 | 4.0 | 4.0 |  | 0.0 | 0.0 | 1.5 |
|  | 0.0320 | 0.0 | 0.0 | 0.0 | 0.0 | 0.0 | 0.0 |  | 0.0 | 0.0 | 2.5 |  | 0.0 | 0.0 | 0.0 |
|  | 0.0160 | 0.0 | 0.0 | 0.0 | 0.0 | 0.0 | 0.0 |  | 0.0 | 0.0 | 1.5 |  | 0.0 | 0.0 | 0.0 |
| 17 | 0.0640 | 9.0 | 9.0 | 7.0 | 9.0 | 5.0 | 5.0 |  | 3.0 | 7.0 | 6.0 |  | 4.0 | 3.5 | 6.0 |
|  | 0.0320 | 9.0 | 5.0 | 5.0 | 5.0 | 4.0 | 5.0 |  | 2.0 | 5.0 | 4.5 |  | 2.5 | 2.5 | 5.5 |
|  | 0.0160 | 9.0 | 6.0 | 4.0 | 7.0 | 3.0 | 3.0 |  | 2.0 | 3.0 | 4.5 |  | 2.0 | 2.5 | 5.5 |
| 18 | 0.0630 | 9.0 | 6.0 |  | 9.0 | 5.0 | 9.0 |  | 4.0 | 5.0 | 4.0 |  | 2.0 | 2.0 | 5.0 |
|  | 0.0315 | 6.0 | 9.0 | 9.0 | 9.0 | 4.0 | 4.0 |  | 3.0 | 7.0 | 3.5 |  | 1.5 | 1.5 | 5.5 |
|  | 0.0158 | 5.0 | 9.0 | 2.0 | 9.0 | 0.0 | 2.0 |  | 0.0 | 0.0 | 3.5 |  | 1.0 | 1.5 | 5.5 |
| 19 | 0.0640 | 5.0 | 4.0 | 2.0 | 0.0 | 3.0 | 2.0 |  | 0.0 | 1.0 | 5.5 |  | 1.0 | 1.0 | 5.0 |
|  | 0.0320 | 4.0 | 3.0 | 0.0 | 0.0 | 3.0 | 2.0 |  | 0.0 | 0.0 | 5.0 |  | 1.0 | 1.0 | 5.0 |
|  | 0.0160 | 1.0 | 2.0 | 0.0 | 0.0 | 0.0 | 0.0 |  | 0.0 | 0.0 | 4.5 |  | 0.0 | 0.0 | 4.5 |
| 20 | 0.0640 | 5.0 | 0.0 | 0.0 | 0.0 | 3.0 | 3.0 |  | 2.0 | 0.0 | 3.5 |  | 0.5 | 0.5 | 5.0 |
|  | 0.0320 | 4.0 | 0.0 | 0.0 | 0.0 | 0.0 | 0.0 |  | 0.0 | 3.0 | 3.5 |  | 0.0 | 0.0 | 4.5 |
|  | 0.0160 | 1.0 | 0.0 | 0.0 | 0.0 | 0.0 | 0.0 |  | 0.0 | 0.0 | 3.5 |  | 0.0 | 0.0 | 4.0 |
| 21 | 0.2500 |  |  |  |  |  |  |  |  |  | 7.0 |  | 2.0 | 2.0 | 5.0 |
|  | 0.1250 |  |  |  |  |  |  |  |  |  | 7.0 |  | 2.0 | 1.0 | 5.0 |
|  | 0.0640 | 9.0 | 7.0 | 6.0 | 9.0 | 6.0 | 5.0 |  | 0.0 | 6.0 | 5.5 |  | 1.0 | 1.0 | 4.5 |
|  | 0.0625 |  |  |  |  |  |  |  |  |  | 7.0 |  | 2.0 | 1.0 | 5.0 |
|  | 0.0320 | 9.0 | 5.0 | 4.0 | 8.0 | 4.0 | 3.0 |  | 0.0 | 1.0 | 5.5 |  | 1.0 | 1.0 | 5.0 |
|  | 0.0313 |  |  |  |  |  |  |  |  |  | 6.0 |  | 1.0 | 1.0 | 5.0 |
| 22 | 0.0640 | 6.0 | 0.0 | 0.0 | 0.0 | 0.0 | 2.0 |  | 0.0 | 1.0 | 4.5 |  | 0.5 | 0.0 | 3.5 |
|  | 0.0320 | 0.0 | 0.0 | 0.0 | 0.0 | 0.0 | 1.0 |  | 3.0 | 0.0 | 5.0 |  | 2.0 | 2.0 | 5.0 |
|  | 0.0160 | 0.0 | 0.0 | 0.0 | 0.0 | 0.0 | 0.0 |  | 0.0 | 0.0 | 4.5 |  | 2.0 | 2.0 | 4.5 |
| 23 | 0.0640 | 9.0 | 9.0 | 7.0 | 9.0 | 9.0 | 9.0 |  | 2.0 | 8.0 | 7.5 |  | 1.0 | 3.0 | 3.0 |
|  | 0.0320 | 9.0 | 9.0 | 5.0 | 9.0 | 9.0 | 9.0 |  | 0.0 | 4.0 | 6.5 |  | 2.0 | 2.0 | 6.0 |
|  | 0.0160 | 9.0 | 6.0 | 5.0 | 6.0 | 4.0 | 7.0 |  | 0.0 | 6.0 | 6.5 |  | 1.0 | 1.0 | 5.5 |
| 24 | 0.0630 | 7.0 | 3.0 |  | 0.0 | 0.0 | 4.0 |  | 0.0 | 0.0 | 3.0 |  | 0.5 | 3.0 | 5.0 |
|  | 0.0315 | 4.0 | 3.0 |  | 0.0 | 0.0 | 3.0 |  | 0.0 | 0.0 | 3.0 |  | 3.5 | 2.0 | 5.0 |
|  | 0.0158 | 0.0 | 0.0 | 0.0 | 0.0 | 0.0 | 3.0 |  | 0.0 | 0.0 | 2.0 |  | 0.0 | 0.0 | 4.0 |

TABLE I-continued

Postemergence Herbicidal Evaluations of Test Compounds

| Compound Number | Rate (kg/ha) | ABUTH | AMBEL | CASOB | CHEAL | GALAP | IPOHE | IPOSS | ECHCG | SETVI | GLXMAW | GLXMA | ORYSAT | TRZAWR | ZEAMX |
|---|---|---|---|---|---|---|---|---|---|---|---|---|---|---|---|
| 25 | 0.0630 | 9.0 | 5.0 |  | 9.0 | 5.0 | 8.0 |  | 2.0 | 7.0 | 7.0 |  | 3.5 | 3.5 | 4.5 |
|  | 0.0315 | 9.0 | 5.0 |  | 9.0 | 2.0 | 5.0 |  | 2.0 | 6.0 | 4.0 |  | 2.0 | 3.5 | 4.5 |
|  | 0.0158 | 7.0 | 5.0 | 9.0 | 9.0 | 2.0 | 5.0 |  | 2.0 | 9.0 | 4.0 |  | 0.0 | 3.0 | 5.0 |
| 26 | 0.0630 | 9.0 | 9.0 | 6.0 | 9.0 | 9.0 | 9.0 |  | 9.0 | 9.0 | 7.5 |  | 2.0 | 8.0 | 7.0 |
|  | 0.0315 | 9.0 | 9.0 | 5.0 | 9.0 | 6.0 | 9.0 |  | 7.0 | 7.0 | 7.0 |  | 2.5 | 8.0 | 7.0 |
|  | 0.0158 | 9.0 | 9.0 | 5.0 | 9.0 | 4.0 | 9.0 |  | 5.0 | 5.0 | 7.5 |  | 1.0 | 6.5 | 7.0 |
| 27 | 0.0630 | 9.0 | 9.0 | 4.0 | 9.0 | 9.0 | 9.0 |  | 7.0 | 7.0 | 7.0 |  | 4.5 | 8.5 | 7.0 |
|  | 0.0315 | 9.0 | 9.0 | 3.0 | 9.0 | 6.0 | 9.0 |  | 7.0 | 9.0 | 7.0 |  | 3.0 | 6.5 | 7.0 |
|  | 0.0158 | 9.0 | 6.0 | 2.0 | 9.0 | 3.0 | 6.0 |  | 7.0 | 9.0 | 6.0 |  | 1.5 | 4.5 | 7.0 |
| 28 | 0.0630 | 9.0 | 9.0 | 6.0 | 9.0 | 9.0 | 9.0 |  | 9.0 | 9.0 | 4.0 |  | 9.0 | 9.0 | 8.0 |
|  | 0.0315 | 9.0 | 9.0 | 9.0 | 9.0 | 8.0 | 9.0 |  | 9.0 | 9.0 | 3.5 |  | 4.0 | 8.0 | 8.0 |
|  | 0.0158 | 9.0 | 9.0 | 4.0 | 5.0 | 4.0 | 5.0 |  | 8.0 | 5.0 | 4.0 |  | 1.0 | 4.5 | 7.0 |
| 29 | 0.0630 | 5.0 | 4.0 | 3.0 | 9.0 | 2.0 | 6.0 |  | 3.0 | 6.0 | 4.5 |  | 3.5 | 3.5 | 5.5 |
|  | 0.0315 | 4.0 | 3.0 | 2.0 | 5.0 | 2.0 | 5.0 |  | 0.0 | 9.0 | 2.5 |  | 1.0 | 1.0 | 5.0 |
|  | 0.0158 | 0.0 | 0.0 | 0.0 | 4.0 | 0.0 | 4.0 |  | 0.0 | 9.0 | 2.5 |  | 2.0 | 1.0 | 5.0 |
| 30 | 0.0630 | 9.0 | 9.0 | 9.0 | 9.0 | 5.0 | 9.0 |  | 9.0 | 9.0 | 7.0 |  | 1.0 | 7.5 | 9.0 |
|  | 0.0315 | 9.0 | 9.0 | 8.0 | 9.0 | 4.0 | 9.0 |  | 7.0 | 7.0 | 6.0 |  | 7.5 | 8.5 | 9.0 |
|  | 0.0158 | 9.0 | 8.0 | 9.0 | 9.0 | 3.0 | 9.0 |  | 4.0 | 7.0 | 5.5 |  | 5.5 | 5.5 | 9.0 |
| 31 | 0.0630 | 9.0 | 9.0 | 9.0 | 9.0 | 8.0 | 9.0 |  | 4.0 | 9.0 | 9.0 |  | 2.5 | 3.0 | 6.0 |
|  | 0.0315 | 9.0 | 9.0 | 7.0 | 9.0 | 5.0 | 9.0 |  | 1.0 | 9.0 | 7.5 |  | 2.5 | 2.5 | 6.0 |
|  | 0.0158 | 9.0 | 9.0 | 5.0 | 9.0 | 3.0 | 9.0 |  | 1.0 | 4.0 | 6.5 |  | 1.5 | 1.5 | 5.5 |
| 32 | 0.0630 | 9.0 | 9.0 | 4.0 | 9.0 | 7.0 | 9.0 |  | 2.0 | 5.0 | 5.5 |  | 2.0 | 2.0 | 5.5 |
|  | 0.0315 | 9.0 | 7.0 | 4.0 | 9.0 | 3.0 | 9.0 |  | 2.0 | 5.0 | 4.5 |  | 1.0 | 1.0 | 5.0 |
|  | 0.0158 | 9.0 | 5.0 | 2.0 | 9.0 | 2.0 | 7.0 |  | 0.0 | 1.0 | 4.0 |  | 0.0 | 0.0 | 4.0 |
| 33 | 0.0630 | 9.0 | 9.0 | 8.0 | 9.0 | 9.0 | 9.0 |  | 9.0 | 9.0 | 6.0 |  | 7.5 | 8.5 | 8.5 |
|  | 0.0315 | 9.0 | 9.0 | 4.0 | 9.0 | 5.0 | 9.0 |  | 9.0 | 9.0 | 5.5 |  | 4.5 | 8.5 | 9.0 |
|  | 0.0158 | 9.0 | 9.0 | 6.0 | 9.0 | 4.0 | 9.0 |  | 5.0 |  | 5.0 |  | 3.0 | 7.5 | 7.0 |
| 34 | 0.0630 | 0.0 | 1.0 | 0.0 | 4.0 | 0.0 | 0.0 |  | 1.0 | 7.0 | 3.0 |  | 0.0 | 0.0 | 4.0 |
|  | 0.0315 | 0.0 | 0.0 | 0.0 | 0.0 | 0.0 | 0.0 |  | 0.0 | 6.0 | 3.0 |  | 0.0 | 0.5 | 3.0 |
|  | 0.0158 | 0.0 | 0.0 | 0.0 | 0.0 |  | 0.0 |  | 0.0 | 0.0 | 2.0 |  | 0.0 | 0.0 | 2.5 |
| 35 | 0.0315 | 9.0 | 9.0 | 5.0 | 9.0 | 2.0 | 4.0 |  | 2.0 | 2.0 | 4.0 |  | 1.0 | 1.5 | 5.0 |
|  | 0.0158 | 9.0 | 5.0 | 2.0 | 9.0 | 0.0 | 3.0 |  | 1.0 | 2.0 | 3.5 |  | 0.5 | 1.0 | 4.5 |
| 36 | 0.0630 | 0.0 | 0.0 | 0.0 | 0.0 | 0.0 | 1.0 |  | 0.0 | 9.0 | 0.0 |  | 0.5 | 0.5 | 1.5 |
|  | 0.0315 | 0.0 | 0.0 | 0.0 | 0.0 | 0.0 | 0.0 |  | 0.0 | 9.0 | 0.0 |  | 0.5 | 0.5 | 1.0 |
|  | 0.0158 | 0.0 | 0.0 | 0.0 | 0.0 | 0.0 | 0.0 |  | 0.0 | 0.0 | 1.5 |  | 0.5 | 0.5 | 0.5 |
| 37 | 0.0630 | 1.0 | 0.0 | 1.0 | 1.0 | 1.0 | 0.0 |  | 5.0 | 0.0 | 0.5 |  | 0.5 | 0.5 | 2.0 |
|  | 0.0315 | 1.0 | 0.0 | 1.0 | 1.0 | 0.0 | 0.0 |  | 5.0 | 6.0 | 2.5 |  | 0.5 | 0.5 | 2.0 |
|  | 0.0158 | 1.0 | 1.0 | 1.0 | 0.0 | 1.0 | 2.0 |  | 1.0 | 6.0 | 2.0 |  | 0.5 | 0.5 | 0.0 |
| 38 | 0.1250 | 1.0 | 1.0 | 0.0 | 1.0 | 0.0 | 1.0 |  | 3.0 | 5.0 | 2.0 |  | 3.0 | 3.5 | 5.5 |
|  | 0.0625 | 1.0 | 1.0 | 1.0 | 0.0 | 0.0 | 1.0 |  | 2.0 | 1.0 | 2.0 |  | 2.5 | 3.5 | 4.5 |
|  | 0.0313 | 1.0 | 0.0 | 1.0 | 0.0 | 0.0 | 1.0 |  | 1.0 | 5.0 | 2.5 |  | 1.5 | 3.0 | 4.5 |
|  | 0.0156 | 0.0 | 0.0 | 0.0 | 0.0 | 0.0 | 2.0 |  | 3.0 | 1.0 | 2.5 |  | 1.5 | 4.0 | 5.0 |
| 39 | 0.1250 | 8.0 | 3.0 | 0.0 | 1.0 | 1.0 | 2.0 |  | 2.0 | 5.0 | 2.5 |  | 1.0 | 3.5 | 4.5 |
|  | 0.0625 | 4.0 | 1.0 | 0.0 | 1.0 | 0.0 | 1.0 |  | 1.0 | 1.0 | 1.0 |  | 1.0 | 2.5 | 4.5 |
|  | 0.0313 | 1.0 | 0.0 | 0.0 | 0.0 | 0.0 | 1.0 |  | 1.0 | 1.0 | 1.0 |  | 1.0 | 2.0 | 4.5 |
|  | 0.0156 | 1.0 | 0.0 | 0.0 | 0.0 | 0.0 | 1.0 |  | 1.0 | 1.0 | 1.0 |  | 1.0 | 2.0 | 4.5 |
| 40 | 0.1250 | 9.0 | 9.0 | 6.0 | 6.0 | 5.0 | 9.0 |  | 2.0 | 8.0 | 6.0 |  | 3.5 | 5.5 | 5.0 |

TABLE I-continued

Postemergence Herbicidal Evaluations of Test Compounds

| Compound Number | Rate (kg/ha) | ABUTH | AMBEL | CASOB | CHEAL | GALAP | IPOHE | IPOSS | ECHCG | SETVI | GLXMAW | GLXMA | ORYSAT | TRZAWR | ZEAMX |
|---|---|---|---|---|---|---|---|---|---|---|---|---|---|---|---|
| | 0.0625 | 9.0 | 9.0 | 6.0 | 6.0 | 1.0 | 9.0 | | 2.0 | 7.0 | 6.0 | | 3.5 | 5.0 | 4.5 |
| | 0.0313 | 9.0 | 4.0 | 4.0 | 5.0 | 1.0 | 9.0 | | 2.0 | 7.0 | 5.0 | | 2.0 | 4.0 | 4.5 |
| | 0.0156 | 9.0 | 3.0 | 3.0 | 4.0 | 0.0 | 9.0 | | 2.0 | | 5.0 | | 2.0 | 4.5 | 4.5 |
| 41 | 0.1250 | 9.0 | 1.0 | 2.0 | 1.0 | 1.0 | 4.0 | | 0.0 | 0.0 | 5.5 | | 2.0 | 4.0 | 4.5 |
| | 0.0625 | 9.0 | 1.0 | 0.0 | 1.0 | 1.0 | 4.0 | | 0.0 | 0.0 | 4.5 | | 2.0 | 3.0 | 4.0 |
| | 0.0313 | 5.0 | 1.0 | 0.0 | 1.0 | 1.0 | 2.0 | | 0.0 | 0.0 | 3.0 | | 1.5 | 2.0 | 4.0 |
| | 0.0156 | 2.0 | 0.0 | 0.0 | 0.0 | 0.0 | 1.0 | | 0.0 | 0.0 | 2.5 | | 1.5 | 2.0 | 4.0 |
| 42 | 0.1250 | 8.0 | 3.0 | 3.0 | 2.0 | 2.0 | 6.0 | | 2.0 | 3.0 | 4.5 | | 3.0 | 3.0 | 4.5 |
| | 0.0625 | 8.0 | 2.0 | 3.0 | 1.0 | 1.0 | 4.0 | | 1.0 | 3.0 | 4.5 | | 2.5 | 2.0 | 4.5 |
| | 0.0313 | 8.0 | 2.0 | 0.0 | 1.0 | 0.0 | 4.0 | | 1.0 | 3.0 | 4.5 | | 0.5 | 1.5 | 4.0 |
| | 0.0156 | 1.0 | 1.0 | 0.0 | 0.0 | 0.0 | 3.0 | | 0.0 | 3.0 | 3.5 | | 0.5 | 1.5 | 3.5 |
| 43 | 0.1250 | 9.0 | 9.0 | 3.0 | 5.0 | 4.0 | 9.0 | | 3.0 | 9.0 | 7.0 | | 3.5 | 4.0 | 5.5 |
| | 0.0625 | 9.0 | 7.0 | 2.0 | 4.0 | 2.0 | 9.0 | | 3.0 | 1.0 | 6.0 | | 2.5 | 3.5 | 5.5 |
| | 0.0313 | 9.0 | 6.0 | 1.0 | 3.0 | 2.0 | 3.0 | | 3.0 | | 5.5 | | 2.5 | 3.5 | 5.0 |
| | 0.0156 | 7.0 | 4.0 | 1.0 | 1.0 | 1.0 | 3.0 | | 0.0 | | 5.0 | | 1.0 | 1.5,4.5 | |
| 44 | 0.1250 | 6.0 | 3.0 | 2.0 | 2.0 | 1.0 | 4.0 | | 0.0 | 1.0 | 5.0 | | 0.5 | 2.0 | 4.5 |
| | 0.0625 | 5.0 | 2.0 | 1.0 | 1.0 | 1.0 | 4.0 | | 0.0 | 3.0 | 5.0 | | 0.5 | 1.5 | 4.5 |
| | 0.0313 | 5.0 | 2.0 | 0.0 | 1.0 | 1.0 | 4.0 | | 0.0 | 0.0 | 4.0 | | 1.0 | 1.0 | 4.0 |
| | 0.0156 | 3.0 | 2.0 | 0.0 | 0.0 | 0.0 | 1.0 | | 0.0 | 0.0 | 3.0 | | 0.5 | 1.0 | 4.5 |
| 45 | 0.1250 | 9.0 | 9.0 | 9.0 | 7.0 | 5.0 | 9.0 | | 7.0 | 8.0 | 6.5 | | 4.0 | 6.0 | 5.5 |
| | 0.0625 | 9.0 | 9.0 | 7.0 | 7.0 | 9.0 | 9.0 | | 7.0 | 9.0 | 6.5 | | 4.0 | 5.5 | 5.5 |
| | 0.0313 | 9.0 | 9.0 | 6.0 | 7.0 | 3.0 | 9.0 | | 5.0 | 8.0 | 5.5 | | 4.0 | 4.5 | 5.5 |
| | 0.0156 | 9.0 | 5.0 | 0.0 | 7.0 | 2.0 | 9.0 | | 5.0 | 7.0 | 7.0 | | 3.5 | 4.5 | 5.5 |
| 46 | 0.1250 | 9.0 | 9.0 | 7.0 | 9.0 | 4.0 | 9.0 | | 7.0 | 7.0 | 7.0 | | 4.0 | 5.0 | 6.0 |
| | 0.0625 | 9.0 | 9.0 | 7.0 | 7.0 | 4.0 | 9.0 | | 7.0 | 7.0 | 7.0 | | 3.5 | 5.0 | 6.0 |
| | 0.0313 | 9.0 | 9.0 | 6.0 | 7.0 | 3.0 | 8.0 | | 4.0 | 6.0 | 6.0 | | 3.5 | 5.0 | 5.5 |
| | 0.0156 | 9.0 | 8.0 | 3.0 | 5.0 | 1.0 | 9.0 | | 4.0 | 5.0 | 6.0 | | 3.0 | 3.5 | 5.0 |
| 47 | 0.1250 | 9.0 | 9.0 | 6.0 | 6.0 | 4.0 | 9.0 | | 5.0 | 9.0 | 8.0 | | 8.0 | 8.5 | 9.0 |
| | 0.0625 | 9.0 | 7.0 | 6.0 | 4.0 | 4.0 | 9.0 | | 7.0 | 7.0 | 7.5 | | 9.0 | 8.0 | 7.5 |
| | 0.0313 | 9.0 | 9.0 | 5.0 | 4.0 | 2.0 | 9.0 | | 7.0 | 7.0 | 6.5 | | 7.5 | 8.0 | 7.0 |
| 48 | 0.1250 | 9.0 | 9.0 | 7.0 | 6.0 | 6.0 | 9.0 | | 7.0 | 9.0 | 8.0 | | 7.0 | 8.5 | 8.5 |
| | 0.0625 | 9.0 | 9.0 | 3.0 | 5.0 | 6.0 | 9.0 | | 7.0 | 9.0 | 7.5 | | 8.5 | 8.5 | 8.5 |
| | 0.0313 | 9.0 | 9.0 | 0.0 | 2.0 | 2.0 | 9.0 | | 6.0 | 9.0 | 7.5 | | 6.5 | 7.0 | 8.0 |
| | 0.0156 | 9.0 | 6.0 | 0.0 | 1.0 | 1.0 | 9.0 | | 5.0 | 6.0 | 6.0 | | 5.0 | 8.5 | 7.0 |
| 49 | 0.0320 | 9.0 | 9.0 | 5.0 | 9.0 | 4.0 | 9.0 | | 9.0 | 9.0 | 7.5 | | 5.5 | 4.0 | 6.5 |
| | 0.0160 | 9.0 | 7.0 | 3.0 | 4.0 | 5.0 | 9.0 | | 7.0 | 9.0 | 6.0 | | 5.0 | 4.0 | 6.0 |
| 50 | 0.0320 | 9.0 | 9.0 | 4.0 | 4.0 | 4.0 | 9.0 | | 9.0 | 9.0 | 7.0 | | 4.5 | 4.5 | 6.5 |
| | 0.0160 | 9.0 | 9.0 | 4.0 | 9.0 | 3.0 | 9.0 | | 9.0 | 9.0 | 6.0 | | 2.0 | 2.0 | 6.0 |
| 51 | 0.0640 | 9.0 | 9.0 | 4.0 | 9.0 | 9.0 | 9.0 | | 6.0 | 9.0 | 7.5 | | 6.0 | 6.0 | 7.5 |
| | 0.0320 | 9.0 | 9.0 | 0.0 | 9.0 | 6.0 | 9.0 | | 5.0 | 9.0 | 7.5 | | 6.0 | 6.0 | 7.0 |
| | 0.0160 | 8.0 | 9.0 | 5.0 | 9.0 | 1.0 | 9.0 | | 7.0 | 9.0 | 6.5 | | 5.0 | 8.5 | 6.0 |
| 52 | 0.0640 | 9.0 | 7.0 | 6.0 | 8.0 | 4.0 | 2.0 | | 2.0 | 4.0 | 4.0 | | 2.0 | 4.0 | 5.0 |
| | 0.0320 | 9.0 | 5.0 | 5.0 | 5.0 | 0.0 | 2.0 | | 0.0 | 2.0 | 4.0 | | 1.5 | 1.5 | 4.5 |
| 53 | 0.0640 | 9.0 | 9.0 | 4.0 | 9.0 | 9.0 | 9.0 | | 9.0 | 9.0 | 7.5 | | 6.5 | 6.5 | 7.5 |
| | 0.0320 | 9.0 | 9.0 | 4.0 | 4.0 | 5.0 | 9.0 | | 9.0 | 4.0 | 6.0 | | 5.5 | 5.0 | 6.5 |
| | 0.0160 | 9.0 | 9.0 | 9.0 | 9.0 | 3.0 | 9.0 | | 9.0 | 4.0 | 6.0 | | 3.0 | 3.5 | 5.5 |
| 54 | 0.0630 | 9.0 | 9.0 | 2.0 | 9.0 | 1.0 | 9.0 | | 9.0 | 7.0 | 6.5 | | 1.0 | 2.0 | 5.5 |

TABLE I-continued

Postemergence Herbicidal Evaluations of Test Compounds

| Compound Number | Rate (kg/ha) | ABUTH | AMBEL | CASOB | CHEAL | GALAP | IPOHE | IPOSS | ECHCG | SETVI | GLXMAW | GLXMA | ORYSAT | TRZAWR | ZEAMX |
|---|---|---|---|---|---|---|---|---|---|---|---|---|---|---|---|
|  | 0.0315 | 9.0 |  | 2.0 | 9.0 | 0.0 | 7.0 |  | 5.0 | 9.0 | 4.0 |  | 0.5 | 3.0 | 5.0 |
|  | 0.0158 | 9.0 | 3.0 | 1.0 | 9.0 | 0.0 | 7.0 |  | 5.0 | 6.0 | 3.5 |  | 0.0 | 1.0 | 4.5 |
| 55 | 0.0640 | 9.0 | 9.0 | 7.0 | 9.0 | 4.0 | 7.0 |  | 8.0 | 8.0 | 5.5 |  | 1.5 | 7.0 | 7.5 |
|  | 0.0320 | 9.0 | 9.0 | 9.0 | 9.0 | 4.0 | 5.0 |  | 7.0 | 7.0 | 5.0 |  | 1.5 | 7.5 | 7.0 |
|  | 0.0160 | 9.0 | 7.0 | 5.0 | 7.0 | 1.0 | 4.0 |  | 5.0 | 3.0 | 4.0 |  | 1.5 | 4.5 | 5.5 |
| 56 | 0.1600 | 9.0 | 8.0 | 8.0 | 7.0 | 0.0 | 1.0 |  | 0.0 | 0.0 | 4.0 |  | 1.5 | 1.5 | 4.5 |
|  | 0.0640 | 9.0 | 9.0 |  | 9.0 | 6.0 | 6.0 |  | 2.0 | 4.0 | 4.5 |  | 1.5 | 2.0 | 5.5 |
|  | 0.0320 | 9.0 | 9.0 |  | 9.0 | 4.0 | 1.0 |  | 0.0 | 2.0 | 3.5 |  | 1.5 | 2.0 | 4.5 |
| 57 | 0.0640 | 9.0 | 9.0 | 9.0 |  | 9.0 | 9.0 |  | 4.0 | 7.0 | 7.5 |  | 4.5 | 5.0 | 6.5 |
|  | 0.0320 | 9.0 | 9.0 | 9.0 |  | 6.0 | 9.0 |  | 2.0 | 6.0 | 5.0 |  | 2.5 | 3.5 | 5.5 |
|  | 0.0160 | 9.0 | 9.0 | 4.0 | 9.0 | 6.0 | 5.0 |  | 2.0 | 2.0 | 4.5 |  | 2.5 | 3.0 | 5.0 |
| 58 | 0.0640 |  | 9.0 | 9.0 | 9.0 | 3.0 | 9.0 |  | 4.0 | 5.0 | 5.0 |  | 3.5 | 4.0 | 6.5 |
|  | 0.0320 | 9.0 | 8.0 |  | 9.0 | 2.0 | 8.0 |  | 2.0 | 5.0 | 5.0 |  | 3.0 | 3.5 | 5.5 |
|  | 0.0160 |  | 7.0 | 9.0 | 9.0 | 3.0 | 6.0 |  | 2.0 | 7.0 | 4.5 |  | 2.0 | 3.0 | 5.0 |
| 59 | 0.0640 | 9.0 | 6.0 |  | 8.0 | 3.0 | 4.0 |  | 3.0 | 5.0 | 5.0 |  | 2.5 | 3.5 | 5.5 |
|  | 0.0320 | 9.0 | 5.0 | 0.0 | 7.0 | 1.0 | 4.0 |  | 2.0 | 5.0 | 4.5 |  | 2.5 | 2.5 | 5.5 |
|  | 0.0160 | 9.0 | 7.0 |  | 5.0 | 2.0 | 4.0 |  | 2.0 | 2.0 | 3.0 |  | 1.5 | 1.5 | 4.5 |
| 60 | 0.0640 | 9.0 | 4.0 | 5.0 | 9.0 | 0.0 | 3.0 |  | 2.0 | 4.0 | 6.0 |  | 2.0 | 2.5 | 6.5 |
|  | 0.0320 | 4.0 | 0.0 | 0.0 | 5.0 | 0.0 | 0.0 |  | 0.0 | 2.0 | 5.0 |  | 1.5 | 1.5 | 6.0 |
|  | 0.0160 | 5.0 | 9.0 |  | 9.0 | 4.0 | 4.0 |  | 5.0 | 5.0 | 4.5 |  | 1.0 | 1.0 | 5.0 |
| 61 | 0.0640 | 6.0 | 4.0 |  | 4.0 | 0.0 | 3.0 |  | 3.0 | 4.0 | 4.0 |  | 0.5 | 2.5 | 5.0 |
|  | 0.0320 | 6.0 | 4.0 | 0.0 | 4.0 | 0.0 | 0.0 |  | 2.0 | 2.0 | 1.0 |  | 0.5 | 0.0 | 1.0 |
|  | 0.0160 | 9.0 | 4.0 | 7.0 | 9.0 | 6.0 | 9.0 |  | 9.0 | 9.0 | 9.0 |  | 0.0 | 0.0 | 7.0 |
| 62 | 0.0630 | 9.0 | 9.0 | 4.0 | 9.0 | 7.0 | 9.0 |  | 9.0 | 9.0 | 7.0 |  | 5.5 | 5.5 | 4.0 |
|  | 0.0315 | 9.0 | 9.0 | 5.0 | 9.0 | 6.0 | 9.0 |  | 7.0 | 7.0 | 7.0 |  | 2.0 | 4.0 | 4.0 |
|  | 0.0158 | 9.0 | 9.0 | 3.0 | 9.0 | 2.0 | 5.0 |  | 7.0 | 7.0 | 7.0 |  | 3.0 | 3.0 | 5.5 |
| 63 | 0.0630 | 9.0 | 9.0 | 3.0 | 9.0 | 0.0 | 3.0 |  | 9.0 | 9.0 | 5.0 |  | 2.0 | 3.5 | 4.5 |
|  | 0.0315 | 9.0 | 5.0 | 2.0 | 9.0 | 0.0 | 5.0 |  | 9.0 | 7.0 | 5.0 |  | 2.0 | 3.0 | 4.5 |
|  | 0.0158 | 9.0 | 4.0 | 2.0 | 9.0 | 0.0 | 3.0 |  | 6.0 | 6.0 | 4.0 |  | 1.0 | 1.0 | 4.0 |
| 64 | 0.0640 | 9.0 | 9.0 | 9.0 | 9.0 | 9.0 | 9.0 |  | 9.0 | 9.0 | 8.0 |  | 5.5 | 5.5 | 7.0 |
|  | 0.0320 | 9.0 | 9.0 | 9.0 | 9.0 | 9.0 | 9.0 |  | 9.0 | 8.0 | 5.5 |  | 5.0 | 5.0 | 5.5 |
|  | 0.0160 | 9.0 | 9.0 | 9.0 | 9.0 | 9.0 | 9.0 |  | 8.0 | 7.0 | 5.5 |  | 4.5 | 4.5 | 5.5 |
| 65 | 0.0630 | 9.0 | 9.0 | 9.0 | 9.0 | 4.0 | 4.0 |  | 1.0 | 3.0 | 5.5 |  | 1.5 | 3.5 | 5.5 |
|  | 0.0315 | 9.0 | 9.0 | 2.0 | 9.0 | 2.0 | 4.0 |  | 3.0 | 3.0 | 5.5 |  | 0.0 | 3.0 | 5.5 |
|  | 0.0158 | 9.0 | 5.0 | 2.0 | 9.0 | 1.0 | 9.0 |  | 3.0 | 9.0 | 5.0 |  | 0.0 | 2.0 | 5.5 |
| 66 | 0.0630 | 9.0 | 9.0 | 9.0 | 9.0 | 4.0 | 9.0 |  | 3.0 | 9.0 | 6.0 |  | 1.0 | 3.0 | 6.0 |
|  | 0.0315 | 9.0 | 9.0 | 7.0 | 9.0 | 3.0 | 9.0 |  | 3.0 | 9.0 | 6.0 |  | 0.5 | 2.0 | 5.5 |
|  | 0.0158 | 9.0 | 9.0 | 5.0 | 9.0 | 2.0 | 4.0 |  | 2.0 | 9.0 | 5.0 |  | 0.5 | 2.0 | 5.0 |
| 67 | 0.0630 | 9.0 | 5.0 | 2.0 | 5.0 | 1.0 | 5.0 |  | 6.0 | 9.0 | 4.5 |  | 1.5 | 6.5 | 4.5 |
|  | 0.0315 | 9.0 | 5.0 | 2.0 | 5.0 | 1.0 | 3.0 |  | 5.0 | 6.0 | 4.5 |  | 1.0 | 3.5 | 4.5 |
|  | 0.0158 | 9.0 | 2.0 | 0.0 | 0.0 | 1.0 | 4.0 |  | 2.0 | 3.0 | 4.0 |  | 0.0 | 2.5 | 4.0 |
| 68 | 0.0630 | 6.0 | 5.0 | 9.0 | 9.0 | 2.0 | 9.0 |  | 5.0 | 9.0 | 5.5 |  | 0.0 | 3.5 | 5.0 |
|  | 0.0315 | 9.0 | 5.0 | 5.0 | 5.0 | 1.0 | 9.0 |  | 2.0 | 8.0 | 5.0 |  | 2.0 | 3.0 | 5.5 |
|  | 0.0158 | 9.0 | 4.0 | 5.0 | 5.0 | 0.0 | 7.0 |  | 4.0 | 4.0 | 4.5 |  | 0.5 | 2.0 | 5.0 |
| 69 | 0.0630 | 9.0 | 9.0 | 9.0 | 9.0 | 9.0 | 9.0 |  | 9.0 | 9.0 | 9.0 |  | 8.0 | 8.0 | 8.5 |
|  | 0.0315 | 9.0 | 9.0 | 7.0 | 9.0 | 9.0 | 9.0 |  | 9.0 | 9.0 | 9.0 |  | 7.0 | 7.5 | 8.0 |
|  | 0.0158 | 9.0 | 9.0 | 7.0 | 9.0 | 9.0 | 9.0 |  | 9.0 | 9.0 | 7.5 |  | 4.5 | 4.5 | 7.0 |

TABLE I-continued

Postemergence Herbicidal Evaluations of Test Compounds

| Compound Number | Rate (kg/ha) | ABUTH | AMBEL | CASOB | CHEAL | GALAP | IPOHE | IPOSS | ECHCG | SETVI | GLXMAW | GLXMA | ORYSAT | TRZAWR | ZEAMX |
|---|---|---|---|---|---|---|---|---|---|---|---|---|---|---|---|
| 70 | 0.0630 | 9.0 | 9.0 | 9.0 | 9.0 | 5.0 | 9.0 | 8.0 | 9.0 | 9.0 | 8.0 | | 3.0 | 5.0 | 6.0 |
| | 0.0315 | 9.0 | 9.0 | 5.0 | 9.0 | 4.0 | 9.0 | | 9.0 | 9.0 | 8.0 | | 2.0 | 4.0 | 6.0 |
| | 0.0158 | 9.0 | 9.0 | 2.0 | 9.0 | 2.0 | 9.0 | | 9.0 | 8.0 | 7.0 | | 2.0 | 3.0 | 6.0 |
| 71 | 0.0630 | 9.0 | 9.0 | 9.0 | 9.0 | 9.0 | 9.0 | | 9.0 | 9.0 | 9.0 | | 8.0 | 9.0 | 8.5 |
| | 0.0315 | 9.0 | 9.0 | 7.0 | 9.0 | 5.0 | 9.0 | | 9.0 | 9.0 | 9.0 | | 6.5 | 6.5 | 7.5 |
| | 0.0158 | 9.0 | 9.0 | 8.0 | 9.0 | 8.0 | 9.0 | | 9.0 | 8.0 | 7.0 | | 5.0 | 7.0 | 5.5 |
| 72 | 0.0630 | 9.0 | 9.0 | 7.0 | 9.0 | 9.0 | 9.0 | | 9.0 | 9.0 | 9.0 | | 7.5 | 7.5 | 8.0 |
| | 0.0315 | 9.0 | 9.0 | 7.0 | 9.0 | 9.0 | 9.0 | | 9.0 | 9.0 | 9.0 | | 5.0 | 5.0 | 7.0 |
| | 0.0158 | 9.0 | 9.0 | 7.0 | 9.0 | 5.0 | 9.0 | | 9.0 | 9.0 | 7.0 | | 3.0 | 4.0 | 6.0 |
| 73 | 0.0630 | 9.0 | 9.0 | 9.0 | 9.0 | 9.0 | 9.0 | | 9.0 | 9.0 | 9.0 | | 5.5 | 4.5 | 6.0 |
| | 0.0315 | 9.0 | 9.0 | 7.0 | 9.0 | 8.0 | 9.0 | | 9.0 | 9.0 | 7.5 | | 3.0 | 4.5 | 5.5 |
| | 0.0158 | 9.0 | 9.0 | 9.0 | 9.0 | 9.0 | 9.0 | | 9.0 | 9.0 | 8.5 | | 7.0 | 3.0 | 5.5 |
| 74 | 0.0630 | 9.0 | 9.0 | 5.0 | 9.0 | 9.0 | 9.0 | | 9.0 | 9.0 | 9.0 | | 2.5 | 7.5 | 8.5 |
| | 0.0315 | 9.0 | 9.0 | 7.0 | 9.0 | 7.0 | 9.0 | | 9.0 | 9.0 | 7.5 | | 6.5 | 7.5 | 7.5 |
| | 0.0158 | 9.0 | 9.0 | 7.0 | 9.0 | 7.0 | 9.0 | | 9.0 | 9.0 | 9.0 | | 2.5 | 4.5 | 6.5 |
| 75 | 0.0630 | 9.0 | 9.0 | 8.0 | 9.0 | 8.0 | 9.0 | | 9.0 | 9.0 | 9.0 | | 6.5 | 9.0 | 7.5 |
| | 0.0315 | 9.0 | 9.0 | 9.0 | 9.0 | 7.0 | 9.0 | | 9.0 | 9.0 | 9.0 | | 6.5 | 6.0 | 8.0 |
| | 0.0158 | 9.0 | 9.0 | 9.0 | 9.0 | 9.0 | 9.0 | | 9.0 | 9.0 | 9.0 | | 5.5 | 6.0 | 6.0 |
| 76 | 0.0630 | 9.0 | 9.0 | 9.0 | 9.0 | 7.0 | 9.0 | | 9.0 | 9.0 | 9.0 | | 6.0 | 9.0 | 8.0 |
| | 0.0315 | 9.0 | 9.0 | 4.0 | 9.0 | 5.0 | 9.0 | | 9.0 | 9.0 | 8.5 | | 5.0 | 5.5 | 5.5 |
| | 0.0158 | 9.0 | 9.0 | 4.0 | 7.0 | 9.0 | 9.0 | | 9.0 | 9.0 | 7.0 | | 2.0 | 4.0 | 5.5 |
| 77 | 0.0630 | 9.0 | 9.0 | 3.0 | 9.0 | 7.0 | 9.0 | | 9.0 | 9.0 | 7.0 | | 9.0 | 9.0 | 8.0 |
| | 0.0315 | 9.0 | 9.0 | 1.0 | 9.0 | 7.0 | 9.0 | | 9.0 | 9.0 | 6.5 | | 7.0 | 8.5 | 7.0 |
| | 0.0158 | 9.0 | 9.0 | 3.0 | 9.0 | 7.0 | 9.0 | | 9.0 | 9.0 | 6.5 | | 7.0 | 7.5 | 7.0 |
| 78 | 0.0630 | 9.0 | 9.0 | 2.0 | 9.0 | 3.0 | 9.0 | | 9.0 | 9.0 | 6.5 | | 6.5 | 9.0 | 7.5 |
| | 0.0315 | 9.0 | 9.0 | 2.0 | 6.0 | 9.0 | 9.0 | | 9.0 | 9.0 | 6.0 | | 6.5 | 8.5 | 7.5 |
| | 0.0158 | 9.0 | 9.0 | 7.0 | 9.0 | 6.0 | 9.0 | | 9.0 | 9.0 | 7.5 | | 7.5 | 8.0 | 7.5 |
| 79 | 0.0630 | 9.0 | 9.0 | 2.0 | 9.0 | 9.0 | 9.0 | | 9.0 | 9.0 | 6.5 | | 6.5 | 8.5 | 7.5 |
| | 0.0315 | 9.0 | 9.0 | 2.0 | 4.0 | 3.0 | 9.0 | | 9.0 | 9.0 | 7.5 | | 5.5 | 8.0 | 7.0 |
| | 0.0158 | 9.0 | 9.0 | 2.0 | 9.0 | 9.0 | 9.0 | | 9.0 | 9.0 | 6.5 | | 7.5 | 8.0 | 7.0 |
| 80 | 0.0630 | 9.0 | 9.0 | 7.0 | 7.0 | 7.0 | 9.0 | | 9.0 | 9.0 | 7.5 | | 7.5 | 8.5 | 7.5 |
| | 0.0315 | 9.0 | 9.0 | 1.0 | 6.0 | 9.0 | 9.0 | | 9.0 | 9.0 | 6.5 | | 6.0 | 7.5 | 7.0 |
| | 0.0158 | 9.0 | 9.0 | 1.0 | 9.0 | 7.0 | 9.0 | | 9.0 | 8.0 | 7.0 | | 8.0 | 8.5 | 8.0 |
| 81 | 0.0630 | 9.0 | 9.0 | 3.0 | 9.0 | 9.0 | 9.0 | | 9.0 | 9.0 | 6.5 | | 7.5 | 8.5 | 7.5 |
| | 0.0315 | 9.0 | 9.0 | 2.0 | 6.0 | 6.0 | 9.0 | | 9.0 | 9.0 | 6.0 | | 6.0 | 8.5 | 6.5 |
| | 0.0158 | 9.0 | 6.0 | 1.0 | 9.0 | 4.0 | 9.0 | | 7.0 | 8.0 | 5.5 | | 5.5 | 5.0 | 5.5 |
| 82 | 0.0630 | 9.0 | 9.0 | 1.0 | 7.0 | 2.0 | 9.0 | | 5.0 | 9.0 | 5.0 | | 3.5 | 3.5 | 5.5 |
| | 0.0315 | 9.0 | 9.0 | 0.0 | 4.0 | 1.0 | 9.0 | | 9.0 | 9.0 | 4.0 | | 2.0 | 6.5 | 4.0 |
| 83 | 0.0630 | 9.0 | 9.0 | 3.0 | 9.0 | 7.0 | 9.0 | | 9.0 | 9.0 | 8.0 | | 7.5 | 6.5 | 6.0 |
| | 0.0315 | 9.0 | 9.0 | 1.0 | 9.0 | 7.0 | 9.0 | | 9.0 | 9.0 | 7.0 | | 6.5 | 6.0 | 6.0 |
| | 0.0158 | 9.0 | 9.0 | 1.0 | 8.0 | 7.0 | 9.0 | | 9.0 | 9.0 | 7.0 | | 5.0 | 5.0 | 6.0 |
| 84 | 0.0630 | 9.0 | 9.0 | 4.0 | 9.0 | 9.0 | 9.0 | | 9.0 | 9.0 | 8.0 | | 8.0 | 8.0 | 7.5 |
| | 0.0315 | 9.0 | 9.0 | 3.0 | 9.0 | 7.0 | 9.0 | | 9.0 | 9.0 | 7.5 | | 7.0 | 7.0 | 6.5 |
| 85 | 0.0630 | 5.0 | 2.0 | 2.0 | 5.0 | 5.0 | 9.0 | | 7.0 | 8.0 | 7.0 | | 6.5 | 6.5 | 6.0 |
| | 0.0315 | 3.0 | 1.0 | 1.0 | 4.0 | 4.0 | 5.0 | | 3.0 | 7.0 | 5.0 | | 4.0 | 5.5 | 6.0 |

TABLE I-continued

Postemergence Herbicidal Evaluations of Test Compounds

| Compound Number | Rate (kg/ha) | ABUTH | AMBEL | CASOB | CHEAL | GALAP | IPOHE | IPOSS | ECHCG | SETVI | GLXMAW | GLXMA | ORYSAT | TRZAWR | ZEAMX |
|---|---|---|---|---|---|---|---|---|---|---|---|---|---|---|---|
| 86 | 0.0158 | 1.0 | 1.0 | 1.0 | 1.0 | 1.0 | 5.0 | | 1.0 | 3.0 | 5.0 | | 3.5 | 4.0 | 5.5 |
|  | 0.0630 | 9.0 | 9.0 | 7.0 | 9.0 | 7.0 | 9.0 | | 9.0 | 9.0 | 7.5 | | 7.0 | 6.5 | 6.0 |
|  | 0.0315 | 9.0 | 9.0 | 1.0 | 8.0 | 8.0 | 9.0 | | 7.0 | 7.0 | 7.0 | | 6.5 | 6.5 | 6.0 |
|  | 0.0158 | 9.0 | 9.0 | 1.0 | 5.0 | 6.0 | 9.0 | | 7.0 | 7.0 | 6.5 | | 4.5 | 5.0 | 5.5 |
| 87 | 0.0630 | 9.0 | 9.0 | 6.0 | 9.0 | 9.0 | 9.0 | | 9.0 | 9.0 | 7.5 | | 7.5 | 7.0 | 7.0 |
|  | 0.0315 | 9.0 | 9.0 | 2.0 | 7.0 | 9.0 | 9.0 | | 6.0 | 7.0 | 6.5 | | 5.5 | 6.0 | 6.0 |
|  | 0.0158 | 9.0 | 9.0 | 1.0 | 6.0 | 5.0 | 9.0 | | 9.0 | 3.0 | 6.5 | | 5.5 | 5.5 | 5.5 |
| 88 | 0.0630 | 9.0 | 9.0 | 4.0 | 9.0 | 7.0 | 9.0 | | 6.0 | 9.0 | 8.5 | | 6.5 | 6.5 | 7.5 |
|  | 0.0315 | 9.0 | 9.0 | 4.0 | 9.0 | 7.0 | 9.0 | | 9.0 | 9.0 | 8.0 | | 6.5 | 5.5 | 7.5 |
|  | 0.0158 | 9.0 | 9.0 | 2.0 | 8.0 | 7.0 | 9.0 | | 9.0 | 9.0 | 7.5 | | 6.0 | 5.5 | 7.5 |
| 89 | 0.0630 | 9.0 | 9.0 | 3.0 | 8.0 | 7.0 | 9.0 | | 9.0 | 9.0 | 7.5 | | 7.5 | 7.5 | 6.0 |
|  | 0.0315 | 9.0 | 9.0 | 3.0 | 7.0 | 7.0 | 9.0 | | 9.0 | 9.0 | 7.0 | | 6.5 | 6.5 | 6.5 |
|  | 0.0158 | 9.0 | 9.0 | 2.0 | 6.0 | 5.0 | 9.0 | | 9.0 | 9.0 | 6.5 | | 4.0 | 5.0 | 6.5 |
| 90 | 0.0630 | 9.0 | 9.0 | 9.0 | 9.0 | 9.0 | 9.0 | | 9.0 | 9.0 | 7.5 | | 8.0 | 7.5 | 5.5 |
|  | 0.0315 | 9.0 | 9.0 | 3.0 | 7.0 | 7.0 | 9.0 | | 9.0 | 9.0 | 7.5 | | 7.0 | 7.0 | 7.5 |
|  | 0.0158 | 9.0 | 9.0 | 1.0 | 7.0 | 5.0 | 9.0 | | 9.0 | 9.0 | 7.0 | | 5.5 | 6.0 | 7.5 |
| 91 | 0.0630 | 9.0 | 4.0 | 2.0 | 5.0 | 0.0 | 5.0 | | 6.0 | 9.0 | 3.5 | | 3.5 | 4.5 | 6.5 |
|  | 0.0315 | | 3.0 | 1.0 | 4.0 | 0.0 | 4.0 | | 2.0 | 6.0 | 3.5 | | 2.0 | 4.0 | 5.0 |
|  | 0.0158 | 7.0 | 1.0 | 1.0 | 3.0 | 0.0 | 2.0 | | 1.0 | 3.0 | 2.0 | | 2.0 | 3.5 | 4.5 |
| 92 | 0.0630 | 9.0 | 9.0 | 3.0 | 8.0 | 7.0 | 9.0 | | 9.0 | 9.0 | 7.5 | | 8.0 | 9.0 | 8.0 |
|  | 0.0315 | 9.0 | 9.0 | 3.0 | 7.0 | 3.0 | 9.0 | | 9.0 | 9.0 | 7.5 | | 7.5 | 8.5 | 7.5 |
|  | 0.0158 | 9.0 | 9.0 | 1.0 | 5.0 | 1.0 | 9.0 | | 9.0 | 9.0 | 7.0 | | 6.5 | 8.0 | 7.0 |
| 93 | 0.0630 | 9.0 | 9.0 | 3.0 | 7.0 | 5.0 | 9.0 | | 9.0 | 9.0 | 7.5 | | 6.5 | 8.0 | 7.5 |
|  | 0.0315 | 9.0 | 9.0 | 1.0 | 7.0 | 3.0 | 9.0 | | 9.0 | 9.0 | 6.5 | | 5.5 | 8.0 | 7.5 |
|  | 0.0158 | 9.0 | 9.0 | 3.0 | 6.0 | 1.0 | 9.0 | | 9.0 | 9.0 | 6.0 | | 5.5 | 8.0 | 7.5 |
| 94 | 0.0630 | 0.0 | 0.0 | 0.0 | 0.0 | 0.0 | 1.0 | | 1.0 | 1.0 | 3.0 | | 2.5 | 3.0 | 4.5 |
|  | 0.0315 | 0.0 | 0.0 | 0.0 | 0.0 | 0.0 | 0.0 | | 0.0 | 1.0 | 3.0 | | 1.5 | 1.5 | 4.0 |
|  | 0.0158 | 0.0 | 0.0 | 0.0 | 0.0 | 0.0 | 0.0 | | 0.0 | 1.0 | 1.5 | | 1.5 | 1.5 | 3.0 |
| 95 | 0.0630 | 0.0 | 0.0 | 0.0 | 0.0 | 0.0 | 0.0 | | 0.0 | 0.0 | 0.0 | | 0.0 | 0.0 | 1.5 |
|  | 0.0315 | 0.0 | 0.0 | 0.0 | 0.0 | 0.0 | 0.0 | | 0.0 | 0.0 | 0.0 | | 0.0 | 0.0 | 0.0 |
|  | 0.0158 | 0.0 | 0.0 | 0.0 | 0.0 | 0.0 | 0.0 | | 0.0 | 0.0 | 0.0 | | 0.0 | 0.0 | 0.0 |
| 96 | 0.0630 | 9.0 | 9.0 | 0.0 | 6.0 | 1.0 | 9.0 | | 8.0 | 9.0 | 6.5 | | 5.5 | 7.0 | 7.5 |
|  | 0.0315 | 5.0 | 5.0 | 0.0 | 4.0 | 0.0 | 0.0 | | 7.0 | 6.0 | 6.5 | | 4.0 | 6.0 | 7.5 |
| 97 | 0.0630 | 9.0 | 4.0 | 0.0 | 2.0 | 0.0 | 9.0 | | 9.0 | 2.0 | 4.5 | | 2.0 | 4.5 | 6.0 |
|  | 0.0315 | 9.0 | 9.0 | 0.0 | 9.0 | 6.0 | 9.0 | | 8.0 | 9.0 | 7.5 | | 7.5 | 9.0 | 8.0 |
|  | 0.0158 | 9.0 | 3.0 | 0.0 | 4.0 | 2.0 | 9.0 | | 6.0 | 9.0 | 7.5 | | 7.5 | 8.0 | 8.0 |
| 98 | 0.1250 | 9.0 | 9.0 | 4.0 | 6.0 | 2.0 | 9.0 | | 0.0 | 2.0 | 6.0 | | 6.0 | 5.0 | 7.5 |
|  | 0.0630 | 9.0 | 3.0 | 3.0 | 7.0 | 7.0 | 9.0 | | 0.0 | 8.0 | 8.5 | | 4.5 | 5.5 | 5.5 |
|  | 0.0625 | 9.0 | 9.0 | 4.0 | 4.0 | 4.0 | 9.0 | | 0.0 | 0.0 | 8.5 | | 2.0 | 3.5 | 6.0 |
|  | 0.0315 | 9.0 | 7.0 | 0.0 | 4.0 | 7.0 | 9.0 | | 0.0 | 3.0 | 8.0 | | 4.5 | 5.0 | 5.0 |
|  | 0.0313 | 9.0 | 9.0 | 4.0 | 4.0 | 4.0 | 9.0 | | 0.0 | 0.0 | 7.5 | | 3.5 | 2.5 | 6.0 |
|  | 0.0158 | 9.0 | 4.0 | 0.0 | 5.0 | 4.0 | 6.0 | | 0.0 | 0.0 | 6.0 | | 1.5 | 4.5 | 4.5 |
|  | 0.0156 | 9.0 | 4.0 | 3.0 | 2.0 | 3.0 | 9.0 | | 0.0 | 3.0 | 5.5 | | 2.5 | 2.5 | 5.0 |
| 99 | 0.0630 | 9.0 | 2.0 | 1.0 | 7.0 | 1.0 | 9.0 | | 7.0 | 7.0 | 7.5 | | 1.0 | 6.0 | 4.5 |
|  | 0.0315 | 9.0 | 2.0 | 0.0 | 5.0 | 1.0 | 7.0 | | 4.0 | 4.0 | 5.5 | | 6.0 | 4.5 | 7.5 |
|  | 0.0158 | 9.0 | 2.0 | 0.0 | 3.0 | 0.0 | 6.0 | | 2.0 | 8.0 | 5.5 | | 4.0 | 4.0 | 6.5 |

TABLE I-continued

Postemergence Herbicidal Evaluations of Test Compounds

| Compound Number | Rate (kg/ha) | ABUTH | AMBEL | CASOB | CHEAL | GALAP | IPOHE | IPOSS | ECHCG | SETVI | GLXMAW | GLXMA | ORYSAT | TRZAWR | ZEAMX |
|---|---|---|---|---|---|---|---|---|---|---|---|---|---|---|---|
| 100 | 0.1250 | 9.0 | 9.0 | 0.0 | 8.0 | 8.0 | 9.0 | | 3.0 | 2.0 | 9.0 | | 4.0 | 4.0 | 6.0 |
| | 0.0630 | | | | | | | | | | 7.5 | | 2.5 | 2.0 | 6.5 |
| | 0.0625 | 9.0 | 9.0 | 0.0 | 6.0 | 5.0 | 9.0 | | 0.0 | 0.0 | 8.0 | | 3.0 | 3.0 | 6.0 |
| | 0.0315 | | | | | | | | | | 7.0 | | 2.5 | 2.0 | 6.0 |
| | 0.0313 | 9.0 | 9.0 | 0.0 | 5.0 | 4.0 | 9.0 | | 0.0 | 0.0 | 7.0 | | 2.0 | 3.0 | 5.0 |
| | 0.0158 | | | | | | | | | | 6.0 | | 1.0 | 1.5 | 5.5 |
| | 0.0156 | | | | | | | | | | 7.0 | | 2.0 | 3.0 | 5.0 |
| 101 | 0.0630 | 9.0 | 3.0 | 0.0 | 2.0 | 1.0 | 5.0 | | 0.0 | 0.0 | 4.0 | | 2.0 | 3.0 | 4.5 |
| | 0.0315 | 4.0 | 1.0 | 0.0 | 2.0 | 0.0 | 4.0 | | 0.0 | 0.0 | 3.0 | | 1.0 | 1.5 | 3.5 |
| | 0.0158 | 3.0 | 1.0 | 0.0 | 0.0 | 0.0 | 4.0 | | 0.0 | 0.0 | 1.5 | | 0.5 | 1.0 | 3.5 |
| 102 | 0.0630 | 9.0 | 7.0 | 0.0 | 4.0 | 2.0 | 9.0 | | 1.0 | 3.0 | 8.0 | | 3.5 | 4.0 | 6.0 |
| | 0.0315 | 7.0 | 7.0 | 0.0 | 3.0 | 2.0 | 9.0 | | 0.0 | 0.0 | 8.0 | | 2.5 | 3.0 | 6.0 |
| | 0.0158 | 7.0 | 5.0 | 0.0 | 3.0 | 2.0 | 9.0 | | 0.0 | 0.0 | 7.0 | | 2.0 | 2.5 | 5.5 |
| 103 | 0.0630 | 9.0 | 9.0 | 5.0 | 9.0 | 6.5 | 9.0 | | 0.0 | 9.0 | 7.3 | | 8.0 | 8.8 | 7.8 |
| | 0.0315 | 9.0 | 9.0 | 2.0 | 7.5 | 4.5 | 9.0 | | 9.0 | 9.0 | 7.3 | | 6.8 | 7.0 | 7.8 |
| | 0.0158 | 9.0 | 9.0 | 0.5 | 8.0 | 2.0 | 9.0 | | 9.0 | 9.0 | 7.0 | | 5.8 | 6.8 | 7.5 |
| 104 | 0.0630 | 9.0 | 9.0 | 1.5 | 5.0 | 7.5 | 9.0 | | 6.0 | 8.5 | 7.3 | | 6.5 | 5.8 | 7.3 |
| | 0.0315 | 9.0 | 9.0 | 1.0 | 3.5 | 5.5 | 9.0 | | 3.5 | 9.0 | 6.0 | | 6.0 | 5.5 | 7.3 |
| | 0.0158 | 9.0 | 6.0 | 0.0 | 3.5 | 5.0 | 9.0 | | 1.0 | 5.5 | 5.8 | | 4.3 | 5.5 | 7.0 |
| 105 | 0.1250 | 9.0 | 9.0 | 8.5 | 7.5 | 7.0 | 9.0 | | 6.5 | 9.0 | 8.0 | | 6.0 | 6.0 | 7.0 |
| | 0.0630 | | | | | | | | | | 8.5 | | 5.0 | 5.0 | 6.5 |
| | 0.0315 | 9.0 | 9.0 | 8.0 | 7.0 | 5.5 | 9.0 | | 4.5 | 6.5 | 8.0 | | 3.8 | 4.0 | 7.0 |
| | 0.0313 | | | | | | | | | | 7.8 | | 5.0 | 5.0 | 5.8 |
| | 0.0158 | 9.0 | 9.0 | 6.0 | 6.0 | 5.0 | 9.0 | | 2.0 | 6.0 | 7.0 | | 6.0 | 3.3 | 6.0 |
| | 0.0156 | | | | | | | | | | 7.5 | | 3.3 | 3.3 | 5.8 |
| 106 | 0.0630 | 4.0 | 2.0 | 0.0 | 0.0 | 1.0 | 4.0 | | 0.0 | 0.0 | 7.0 | | 4.0 | 4.0 | 6.0 |
| | 0.0315 | 4.0 | 0.0 | 0.0 | 0.0 | 1.0 | 2.0 | | 0.0 | 0.0 | 3.5 | | 1.5 | 2.5 | 5.0 |
| | 0.0158 | 1.0 | 0.0 | 0.0 | 4.0 | 0.0 | 1.0 | | 0.0 | 0.0 | 3.0 | | 1.0 | 1.5 | 5.0 |
| 107 | 0.0630 | 9.0 | 6.0 | 2.0 | 4.0 | 9.0 | 9.0 | | 0.0 | 5.0 | 2.5 | | 0.5 | 1.0 | 4.5 |
| | 0.0315 | 9.0 | 4.0 | 1.0 | 4.0 | 1.0 | 9.0 | | 0.0 | 3.0 | 5.5 | | 3.0 | 3.5 | 4.0 |
| | 0.0158 | 5.0 | 1.0 | 0.0 | 2.0 | 1.0 | 9.0 | | 0.0 | 0.0 | 5.5 | | 2.5 | 2.0 | 4.0 |
| 108 | 0.0630 | 5.0 | 5.0 | 1.0 | 5.0 | 2.0 | 6.0 | | 0.0 | 0.0 | 4.0 | | 2.5 | 3.5 | 3.5 |
| | 0.0315 | 5.0 | 4.0 | 1.0 | 4.0 | 1.0 | 3.0 | | 0.0 | 0.0 | 4.5 | | 2.0 | 2.0 | 4.0 |
| | 0.0158 | 3.0 | 0.0 | 0.0 | 0.0 | 2.0 | 4.0 | | 0.0 | 0.0 | 3.5 | | 2.0 | 2.0 | 3.0 |
| 109 | 0.0630 | 9.0 | 5.0 | 4.0 | 4.0 | 5.0 | 9.0 | | 1.0 | 0.0 | 4.0 | | 2.0 | 4.5 | 4.0 |
| | 0.0315 | 9.0 | 6.0 | 3.0 | 4.0 | 2.0 | 2.0 | | 2.0 | 4.0 | 5.0 | | 2.5 | 3.5 | 4.0 |
| | 0.0158 | 9.0 | 4.0 | 0.0 | 1.0 | 1.0 | 9.0 | | 0.0 | 2.0 | 6.0 | | 2.5 | 3.0 | 4.0 |
| 110 | 0.1250 | 9.0 | 9.0 | 5.0 | 5.0 | 6.0 | 9.0 | | 2.0 | 9.0 | 4.0 | | 4.0 | 4.0 | 4.5 |
| | 0.0630 | 9.0 | 9.0 | 2.0 | 5.0 | 2.0 | 9.0 | | 1.0 | 5.0 | 8.5 | | 3.0 | 3.0 | 6.0 |
| | 0.0625 | | | | | | | | | | 7.0 | | 2.0 | 2.5 | 5.0 |
| | 0.0315 | 9.0 | 7.0 | 2.0 | 4.0 | 1.0 | 9.0 | | 0.0 | 3.0 | 6.0 | | 2.0 | 2.5 | 5.0 |
| | 0.0313 | | | | | | | | | | 5.5 | | 2.5 | 2.5 | 5.0 |
| | 0.0158 | 9.0 | 2.0 | 0.0 | 2.0 | 0.0 | 4.0 | | 0.0 | 0.0 | 5.0 | | 1.5 | 2.5 | 4.0 |
| | 0.0156 | | | | | | | | | | 5.5 | | 2.5 | 1.5 | 4.5 |
| 111 | 0.0630 | 9.0 | 6.0 | 1.0 | 2.0 | 0.0 | 9.0 | | 0.0 | 0.0 | 5.0 | | 3.0 | 3.0 | 5.0 |
| | 0.0315 | 9.0 | 4.0 | 1.0 | 1.0 | 0.0 | 9.0 | | 0.0 | 0.0 | 4.5 | | 2.0 | 2.0 | 4.0 |

TABLE I-continued

Postemergence Herbicidal Evaluations of Test Compounds

| Compound Number | Rate (kg/ha) | ABUTH | AMBEL | CASOB | CHEAL | GALAP | IPOHE | IPOSS | ECHCG | SETVI | GLXMAW | GLXMA | ORYSAT | TRZAWR | ZEAMX |
|---|---|---|---|---|---|---|---|---|---|---|---|---|---|---|---|
| 112 | 0.0158 | 4.0 | 2.0 | 0.0 | 1.0 | 0.0 | 2.0 | | 0.0 | 0.0 | 3.5 | | 2.0 | 2.0 | 3.5 |
| | 0.0630 | 9.0 | 3.0 | 1.0 | 3.0 | 2.0 | 9.0 | | 2.0 | 5.0 | 7.0 | | 3.0 | 2.5 | 7.0 |
| | 0.0315 | 8.0 | 3.0 | 1.0 | 1.0 | 2.0 | 8.0 | | 2.0 | 2.0 | 5.5 | | 2.5 | 2.5 | 7.0 |
| | 0.0158 | 6.0 | 0.0 | 0.0 | 1.0 | 1.0 | 4.0 | | 0.0 | 2.0 | 4.0 | | 2.5 | 2.5 | 6.0 |
| 113 | 0.0630 | 9.0 | 9.0 | 4.0 | 5.0 | 6.0 | 9.0 | | 4.0 | 6.0 | 6.0 | | 5.0 | 5.0 | 7.0 |
| | 0.0315 | 9.0 | 7.0 | 2.0 | 5.0 | 2.0 | 9.0 | | 1.0 | 4.0 | 4.5 | | 3.5 | 3.5 | 6.0 |
| | 0.0158 | 9.0 | 9.0 | 0.0 | 2.0 | 1.0 | 9.0 | | 0.0 | 0.0 | 4.0 | | 3.5 | 3.5 | 5.0 |
| 114 | 0.0630 | 9.0 | 9.0 | 4.5 | 5.0 | 6.5 | 9.0 | | 2.0 | 5.0 | 6.8 | | 3.8 | 4.5 | 5.8 |
| | 0.0315 | 9.0 | 8.0 | 1.5 | 2.5 | 3.5 | 9.0 | | 0.5 | 6.5 | 5.5 | | 2.8 | 3.3 | 5.5 |
| | 0.0158 | 8.0 | 7.5 | 1.0 | 3.0 | 1.5 | 9.0 | | 0.0 | 0.5 | 5.8 | | 2.5 | 3.0 | 5.0 |
| 115 | 0.1250 | 7.0 | 3.0 | 0.0 | 2.0 | 1.0 | 9.0 | | 5.0 | 8.0 | 5.5 | | 3.0 | 4.5 | 7.5 |
| | 0.0625 | 7.0 | 3.0 | 0.0 | 2.0 | 1.0 | 9.0 | | 5.0 | 8.0 | 5.5 | | 2.5 | 3.5 | 7.5 |
| | 0.0313 | 7.0 | 2.0 | 0.0 | 1.0 | 0.0 | 7.0 | | 4.0 | 3.0 | 5.0 | | 2.5 | 3.0 | 7.0 |
| | 0.0156 | 7.0 | 1.0 | 0.0 | 0.0 | 0.0 | 9.0 | | 4.0 | 0.0 | 4.0 | | 1.5 | 2.5 | 6.5 |
| 116 | 0.1250 | 0.0 | 0.0 | 0.0 | 0.0 | 0.0 | 1.0 | | 0.0 | 0.0 | 1.5 | | 1.5 | 0.0 | 1.5 |
| | 0.0625 | 0.0 | 0.0 | 0.0 | 0.0 | 0.0 | 0.0 | | 0.0 | 0.0 | 0.5 | | 0.0 | 0.0 | 0.5 |
| | 0.0313 | 0.0 | 0.0 | 0.0 | 0.0 | 0.0 | 0.0 | | 0.0 | 0.0 | 0.0 | | 0.0 | 0.0 | 0.0 |
| | 0.0156 | 0.0 | 0.0 | 0.0 | 0.0 | 0.0 | 0.0 | | 0.0 | 0.0 | 0.0 | | 0.0 | 0.0 | 0.0 |
| 117 | 0.1250 | 0.0 | 0.0 | 0.0 | 0.0 | 0.0 | 0.0 | | 0.0 | 0.0 | 1.0 | | 0.0 | 0.0 | 1.0 |
| | 0.0625 | 0.0 | 0.0 | 0.0 | 0.0 | 0.0 | 0.0 | | 0.0 | 0.0 | 0.0 | | 0.0 | 0.0 | 0.0 |
| | 0.0313 | 0.0 | 0.0 | 0.0 | 0.0 | 0.0 | 0.0 | | 0.0 | 0.0 | 0.0 | | 0.0 | 0.0 | 0.0 |
| | 0.0156 | 0.0 | 0.0 | 0.0 | 0.0 | 0.0 | 0.0 | | 0.0 | 0.0 | 0.0 | | 0.0 | 0.0 | 0.0 |
| 118 | 0.1250 | 1.0 | 0.0 | 0.0 | 0.0 | 0.0 | 1.0 | | 0.0 | 0.0 | 1.0 | | 0.0 | 0.5 | 2.0 |
| | 0.0625 | 0.0 | 0.0 | 0.0 | 0.0 | 0.0 | 0.0 | | 0.0 | 0.0 | 1.0 | | 0.5 | 0.0 | 1.0 |
| | 0.0313 | 0.0 | 0.0 | 0.0 | 0.0 | 0.0 | 0.0 | | 0.0 | 0.0 | 0.5 | | 0.0 | 0.0, | 0.0 |
| | 0.0156 | 0.0 | 0.0 | 0.0 | 0.0 | 0.0 | 0.0 | | 0.0 | 0.0 | 0.0 | | 0.0 | 0.0 | 0.0 |
| 119 | 0.1250 | 9.0 | 9.0 | 5.0 | 8.0 | 9.0 | 9.0 | | 5.0 | 8.0 | 8.0 | | 4.5 | 4.0 | 6.0 |
| | 0.0630 | 9.0 | 9.0 | 2.0 | 9.0 | 9.0 | 9.0 | | 1.0 | 9.0 | 6.5 | | 2.5 | 3.0 | 6.0 |
| | 0.0625 | 9.0 | 9.0 | 2.0 | 6.0 | 8.0 | 9.0 | | 2.0 | 7.0 | 7.5 | | 3.0 | 4.0 | 6.0 |
| | 0.0313 | 9.0 | 9.0 | 2.0 | 9.0 | 7.0 | 9.0 | | 0.0 | 0.0 | 6.0 | | 1.5 | 2.5 | 4.5 |
| | 0.0158 | 9.0 | 8.0 | 1.0 | 3.0 | 5.0 | 9.0 | | 0.0 | 2.0 | 7.5 | | 2.0 | 3.5 | 6.0 |
| | 0.0156 | 9.0 | 7.0 | 1.0 | 9.0 | 4.0 | 9.0 | | 0.0 | 0.0 | 4.0 | | 0.5 | 1.5 | 4.5 |
| 120 | 0.0630 | 9.0 | 9.0 | 0.0 | 3.0 | 2.0 | 9.0 | | 0.0 | 0.0 | 6.5 | | 1.5 | 3.0 | 5.0 |
| | 0.0315 | 9.0 | 9.0 | 9.0 | 6.0 | 5.0 | 9.0 | | 9.0 | 8.0 | 7.5 | | 5.0 | 5.0 | 6.5 |
| | 0.0158 | 9.0 | 9.0 | 2.0 | 5.0 | 4.0 | 9.0 | | 6.0 | 4.0 | 7.5 | | 3.5 | 4.5 | 6.5 |
| 121 | 0.0630 | 9.0 | 9.0 | 2.0 | 5.0 | 4.0 | 9.0 | | 6.0 | 3.0 | 6.0 | | 2.5 | 4.5 | 5.0 |
| | 0.0315 | 9.0 | 9.0 | 7.0 | 6.0 | 6.0 | 9.0 | | 7.0 | 9.0 | 9.0 | | 6.5 | 6.5 | 8.0 |
| | 0.0158 | 9.0 | 9.0 | 6.0 | 5.0 | 6.0 | 9.0 | | 7.0 | 9.0 | 8.5 | | 6.0 | 5.0 | 7.5 |
| 122 | 0.0630 | 9.0 | 9.0 | 5.0 | 6.0 | 4.0 | 9.0 | | 7.0 | 9.0 | 6.5 | | 4.0 | 4.8 | 8.0 |
| | 0.0315 | 9.0 | 9.0 | 6.0 | 8.0 | 6.0 | 9.0 | | 6.5 | 9.0 | 6.5 | | 3.5 | 4.5 | 7.0 |
| | 0.0158 | 9.0 | 9.0 | 5.0 | 7.0 | 5.0 | 9.0 | | 6.5 | 8.0 | 6.5 | | 3.3 | 4.5 | 6.3 |
| 123 | 0.0630 | 9.0 | 9.0 | 4.5 | 6.0 | 2.0 | 9.0 | | 5.5 | 8.5 | 5.3 | | 3.3 | 4.3 | 5.5 |
| | 0.0315 | 9.0 | 9.0 | 5.0 | 8.0 | 2.0 | 9.0 | | 4.0 | 7.5 | 6.3 | | 3.0 | 3.8 | 5.5 |
| | 0.0158 | 9.0 | 8.0 | 4.5 | 6.5 | 0.5 | 9.0 | | 2.0 | 2.0 | 5.8 | | 2.3 | 3.8 | 5.3 |
| 124 | 0.0630 | 9.0 | 9.0 | 3.5 | 7.0 | 0.5 | 9.0 | | 0.0 | 0.5 | 5.5 | | 1.5 | 4.8 | 5.0 |
| | 0.0315 | 9.0 | 9.0 | 5.5 | 7.0 | 5.0 | 9.0 | | 6.5 | 7.5 | 7.0 | | 2.8 | 4.8 | 6.5 |
| | 0.0158 | 9.0 | 9.0 | 4.5 | 6.5 | 2.5 | 9.0 | | 3.5 | 6.5 | 5.8 | | 2.0 | 4.3 | 5.8 |

TABLE I-continued

Postemergence Herbicidal Evaluations of Test Compounds

| Compound Number | Rate (kg/ha) | ABUTH | AMBEL | CASOB | CHEAL | GALAP | IPOHE | IPOSS | ECHCG | SETVI | GLXMAW | GLXMA | ORYSAT | TRZAWR | ZEAMX |
|---|---|---|---|---|---|---|---|---|---|---|---|---|---|---|---|
| 125 | 0.0158 | 9.0 | 6.5 | 2.0 | 5.5 | 0.5 | 7.0 | | 1.5 | 5.0 | 5.3 | | 2.0 | 3.5 | 5.8 |
| | 0.1250 | 9.0 | 9.0 | 7.0 | 7.0 | 3.0 | 9.0 | | 9.0 | 9.0 | 7.5 | | 7.5 | 9.0 | 9.0 |
| | 0.0625 | 9.0 | 9.0 | 2.0 | 4.0 | 1.0 | 9.0 | | 9.0 | 9.0 | 7.5 | | 7.5 | 8.5 | 7.5 |
| | 0.0313 | 9.0 | 8.0 | 2.0 | 2.0 | 0.0 | 9.0 | | 9.0 | 9.0 | 7.0 | | 3.0 | 7.5 | 8.0 |
| | 0.0156 | 9.0 | 3.0 | 2.0 | 1.0 | 0.0 | 8.0 | | 9.0 | 9.0 | 7.0 | | 3.0 | 7.5 | 7.5 |
| 126 | 0.0630 | 9.0 | 6.0 | 5.0 | 4.0 | 6.0 | 9.0 | | 1.0 | 4.0 | 6.5 | | 2.5 | 4.0 | 7.0 |
| | 0.0315 | 7.0 | 4.0 | 5.0 | 4.0 | 4.0 | 9.0 | | 0.0 | 1.0 | 5.5 | | 2.5 | 3.5 | 6.0 |
| | 0.0158 | 7.0 | 1.0 | 3.0 | 0.0 | 0.0 | 9.0 | | 0.0 | 1.0 | 5.5 | | 2.5 | 3.0 | 5.5 |
| 127 | 0.0630 | 9.0 | 5.0 | 6.0 | 3.0 | 6.0 | 9.0 | | 1.0 | 9.0 | 7.0 | | 4.5 | 7.0 | 7.5 |
| | 0.0315 | 9.0 | 4.0 | 5.0 | 1.0 | 6.0 | 9.0 | | 1.0 | 1.0 | 7.0 | | 2.5 | 5.5 | 7.0 |
| | 0.0158 | 9.0 | 1.0 | 4.0 | 1.0 | 6.0 | 9.0 | | 1.0 | 1.0 | 5.5 | | 2.5 | 4.5 | 5.5 |
| 128 | 0.0630 | 9.0 | 6.0 | 3.0 | 5.0 | 4.0 | 8.0 | | 1.5 | 2.0 | 5.3 | | 2.5 | 3.8 | 4.0 |
| | 0.0315 | 8.0 | 4.5 | 1.0 | 1.0 | 2.5 | 5.5 | | 0.5 | 3.0 | 4.5 | | 1.5 | 1.8 | 2.8 |
| | 0.0158 | 8.5 | 4.0 | 1.0 | 1.5 | 1.5 | 3.0 | | 0.5 | 1.5 | 4.3 | | 1.3 | 1.3 | 1.8 |
| 129 | 0.0630 | 9.0 | 6.0 | 2.0 | 7.0 | 4.0 | 9.0 | | 2.0 | 3.0 | 7.0 | | 3.0 | 5.5 | 6.0 |
| | 0.0315 | 9.0 | 4.0 | 2.0 | 4.0 | 2.0 | 9.0 | | 1.0 | 1.0 | 6.5 | | 3.5 | 4.5 | 5.5 |
| | 0.0158 | 9.0 | 2.0 | 3.0 | 4.0 | 2.0 | 9.0 | | 1.0 | 1.0 | 6.0 | | 2.5 | 2.5 | 5.0 |
| 130 | 0.0630 | 9.0 | 6.0 | 2.0 | 7.0 | 5.0 | 9.0 | | 2.0 | 4.0 | 7.5 | | 3.0 | 4.5 | 6.0 |
| | 0.0315 | 9.0 | 5.0 | 2.0 | 6.0 | 3.0 | 9.0 | | 4.0 | 6.0 | 8.0 | | 3.0 | 4.5 | 5.5 |
| | 0.0158 | 9.0 | 2.0 | 2.0 | 3.0 | 1.0 | 8.0 | | 1.0 | 1.0 | 7.0 | | 2.5 | 4.5 | 5.5 |
| 131 | 0.0630 | 9.0 | 6.0 | 3.0 | 6.0 | 6.0 | 9.0 | | 2.0 | 4.0 | 7.0 | | 2.5 | 4.5 | 6.0 |
| | 0.0315 | 9.0 | 4.0 | 2.0 | 3.0 | 4.0 | 8.0 | | 1.0 | 1.0 | 5.0 | | 2.5 | 3.0 | 4.0 |
| | 0.0158 | 9.0 | 4.0 | 1.0 | 2.0 | 3.0 | 9.0 | | 2.0 | 1.0 | 4.5 | | 2.5 | 3.0 | 3.5 |
| 132 | 0.0630 | 9.0 | 9.0 | 9.0 | 9.0 | 9.0 | 9.0 | | 9.0 | 9.0 | 9.0 | | 8.5 | 7.0 | 8.0 |
| | 0.0315 | 9.0 | 9.0 | 9.0 | 9.0 | 9.0 | 9.0 | | 9.0 | 9.0 | 9.0 | | 8.5 | 6.0 | 8.0 |
| | 0.0158 | 9.0 | 9.0 | 9.0 | 9.0 | 9.0 | 9.0 | | 9.0 | 9.0 | 9.0 | | 6.5 | 6.5 | 8.0 |
| 133 | 0.0630 | 9.0 | 9.0 | 9.0 | 9.0 | 9.0 | 9.0 | | 9.0 | 9.0 | 9.0 | | 8.0 | 9.0 | 8.0 |
| | 0.0315 | 9.0 | 9.0 | 9.0 | 9.0 | 9.0 | 9.0 | | 9.0 | 9.0 | 9.0 | | 8.0 | 8.5 | 7.5 |
| | 0.0158 | 9.0 | 9.0 | 8.0 | 9.0 | 8.0 | 9.0 | | 9.0 | 9.0 | 7.5 | | 7.5 | 8.5 | 7.5 |
| 134 | 0.0630 | 9.0 | 9.0 | 9.0 | 9.0 | 9.0 | 9.0 | | 9.0 | 9.0 | 9.0 | | 8.5 | 7.0 | 8.0 |
| | 0.0315 | 9.0 | 9.0 | 9.0 | 9.0 | 9.0 | 9.0 | | 9.0 | 9.0 | 9.0 | | 8.5 | 7.0 | 7.0 |
| | 0.0158 | 9.0 | 9.0 | 9.0 | 9.0 | 9.0 | 9.0 | | 9.0 | 9.0 | 7.5 | | 7.5 | 7.0 | 8.5 |
| 135 | 0.0630 | 9.0 | 9.0 | 9.0 | 9.0 | 9.0 | 9.0 | | 9.0 | 9.0 | 9.0 | | 7.5 | 9.0 | 8.5 |
| | 0.0315 | 9.0 | 9.0 | 7.0 | 9.0 | 8.0 | 9.0 | | 9.0 | 9.0 | 8.5 | | 7.5 | 8.5 | 8.5 |
| | 0.0158 | 9.0 | 9.0 | 6.0 | 9.0 | 6.0 | 9.0 | | 9.0 | 6.0 | 7.5 | | 7.0 | 2.0 | 4.5 |
| 136 | 0.0630 | 9.0 | 6.0 | 0.0 | 3.0 | 1.0 | 9.0 | | 0.0 | 6.0 | 8.0 | | 2.5 | 3.5 | 5.0 |
| | 0.0315 | 9.0 | 2.0 | 1.0 | 3.0 | 1.0 | 4.0 | | 0.0 | 4.0 | 3.0 | | 2.0 | 2.5 | 5.5 |
| | 0.0158 | 7.0 | 1.0 | 0.0 | 0.0 | 1.0 | 4.0 | | 0.0 | 0.0 | 3.5 | | 1.5 | 2.5 | 5.5 |
| 137 | 0.0630 | 9.0 | 9.0 | 5.0 | 7.0 | 7.0 | 9.0 | | 3.0 | 7.0 | 6.5 | | 4.5 | 4.5 | 6.0 |
| | 0.0315 | 9.0 | 9.0 | 2.0 | 5.0 | 6.0 | 9.0 | | 2.0 | 4.0 | 6.0 | | 4.0 | 4.5 | 6.0 |
| | 0.0158 | 9.0 | 8.0 | 1.0 | 3.0 | 3.0 | 9.0 | | 0.0 | 0.0 | 6.0 | | 2.5 | 4.0 | 5.5 |
| 138 | 0.0630 | 9.0 | 9.0 | 8.0 | 7.0 | 7.0 | 9.0 | | 7.5 | 9.0 | 9.0 | | 6.3 | 5.8 | 8.3 |
| | 0.0315 | 9.0 | 9.0 | 5.0 | 5.0 | 7.0 | 9.0 | | 45 | 9.0 | 8.0 | | 5.5 | 5.3 | 8.0 |
| | 0.0158 | 9.0 | 6.5 | 1.5 | 1.0 | 2.5 | 9.0 | | 4.5 | 9.0 | 6.8 | | 4.8 | 4.8 | 7.5 |
| 139 | 0.2500 | | | | | | | | | | 7.0 | | 3.0 | 4.0 | 6.0 |
| | 0.1250 | | | | | | | | | | 7.0 | | 3.0 | 3.0 | 6.0 |
| | 0.0630 | 9.0 | 7.0 | 1.0 | 5.0 | 3.0 | 9.0 | | 0.0 | 2.0 | 5.5 | | 3.5 | 4.0 | 6.5 |

TABLE I-continued

Postemergence Herbicidal Evaluations of Test Compounds

| Compound Number | Rate (kg/ha) | ABUTH | AMBEL | CASOB | CHEAL | GALAP | IPOHE | IPOSS | ECHCG | SETVI | GLXMAW | GLXMA | ORYSAT | TRZAWR | ZEAMX |
|---|---|---|---|---|---|---|---|---|---|---|---|---|---|---|---|
| | 0.0625 | 9.0 | 9.0 | 1.0 | 4.0 | 5.0 | 7.0 | | 0.0 | 0.0 | 7.0 | | 3.0 | 3.0 | 6.0 |
| | 0.0315 | | | | | | | | | | 6.0 | | 2.5 | 3.0 | 5.5 |
| | 0.0313 | | | | | | | | | | 7.0 | | 3.0 | 3.0 | 6.0 |
| | 0.0158 | | | | | | | | | | 5.5 | | 2.5 | 3.0 | 5.5 |
| 140 | 0.0630 | 9.0 | 6.0 | 0.0 | 1.0 | 2.0 | 6.0 | | 0.0 | 0.0 | 7.5 | | 4.0 | 5.0 | 6.5 |
| | 0.0315 | 9.0 | 9.0 | 2.0 | 8.0 | 7.0 | 9.0 | | 2.0 | 4.0 | 6.0 | | 3.0 | 3.0 | 5.5 |
| | 0.0158 | 8.0 | 8.0 | 2.0 | 6.0 | 7.0 | 9.0 | | 1.0 | 4.0 | 5.5 | | 2.5 | 2.5 | 5.5 |
| | 0.0158 | 9.0 | 7.0 | 0.0 | 4.0 | 3.0 | 9.0 | | 0.0 | 2.0 | 8.0 | | 3.0 | 3.0 | 7.0 |
| 141 | 0.1250 | | | | | | | | | | 7.0 | | 3.0 | 3.0 | 6.0 |
| | 0.0630 | 9.0 | 7.0 | 1.0 | 7.5 | 8.0 | 9.0 | | 0.5 | 0.5 | 7.0 | | 2.5 | 3.0 | 7.0 |
| | 0.0315 | | | | | | | | | | 5.5 | | 1.0 | 3.0 | 5.5 |
| | 0.0313 | 9.0 | 7.0 | 1.0 | 8.5 | 5.0 | 9.0 | | 0.0 | 0.0 | 7.0 | | 2.0 | 3.0 | 6.0 |
| | 0.0158 | 9.0 | 6.5 | 0.5 | 7.0 | 3.0 | 8.0 | | 0.0 | 0.0 | 5.5 | | 1.8 | 2.3 | 5.3 |
| | 0.0156 | | | | | | | | | | 6.0 | | 1.0 | 2.0 | 5.0 |
| 142 | 0.0630 | 9.0 | 9.0 | 9.0 | 9.0 | 7.0 | 9.0 | | 9.0 | 9.0 | 9.0 | | 7.5 | 8.5 | 8.5 |
| | 0.0315 | 9.0 | 9.0 | 9.0 | 9.0 | 9.0 | 9.0 | | 8.0 | 9.0 | 9.0 | | 7.0 | 9.0 | 8.0 |
| | 0.0158 | 9.0 | 9.0 | 9.0 | 9.0 | 7.0 | 9.0 | | 8.0 | 9.0 | 9.0 | | 6.5 | 8.0 | 7.0 |
| 143 | 0.2500 | | | | | | | | | | 8.0 | | 5.0 | 5.0 | 5.0 |
| | 0.1250 | | | | | | | | | | 8.0 | | 4.0 | 5.0 | 6.0 |
| | 0.0630 | 9.0 | 6.0 | 0.0 | 7.0 | 7.0 | 9.0 | | 0.0 | 0.0 | 6.0 | | 1.5 | 3.0 | 4.0 |
| | 0.0625 | | | | | | | | | | 7.0 | | 4.0 | 5.0 | 5.0 |
| | 0.0315 | 9.0 | 6.0 | 0.0 | 6.0 | 4.0 | 9.0 | | 0.0 | 0.0 | 6.0 | | 1.5 | 3.0 | 4.0 |
| | 0.0313 | | | | | | | | | | 7.0 | | 1.5 | 4.0 | 5.0 |
| | 0.0158 | 8.0 | 2.0 | 0.0 | 2.0 | 2.0 | 2.0 | | 0.0 | 0.0 | 5.0 | | 4.0 | 2.5 | 3.5 |
| | 0.0156 | | | | | | | | | | 7.0 | | 4.0 | 3.0 | 5.0 |
| 144 | 0.0630 | 9.0 | 9.0 | 1.0 | 5.0 | 9.0 | 9.0 | | 7.0 | 8.0 | 7.5 | | 8.0 | 8.5 | 8.5 |
| | 0.0315 | 9.0 | 9.0 | 1.0 | 7.0 | 9.0 | 5.0 | | 7.0 | 7.0 | 6.5 | | 5.5 | 7.0 | 7.5 |
| | 0.0158 | 9.0 | 9.0 | 1.0 | 2.0 | 5.0 | 3.0 | | 4.0 | 7.0 | 6.5 | | 2.0 | 6.5 | 7.5 |
| 145 | 0.1250 | | | | | | | | | | 7.0 | | 6.0 | 6.0 | 7.0 |
| | 0.0625 | 9.0 | 6.0 | 4.0 | 6.0 | 3.0 | 7.0 | | 2.0 | 3.0 | 6.0 | | 4.3 | 4.7 | 6.0 |
| | 0.0315 | 9.0 | 3.0 | 3.0 | 3.0 | 2.0 | 9.0 | | 2.0 | 2.0 | 5.3 | | 3.7 | 4.0 | 5.7 |
| | 0.0313 | 4.0 | 3.0 | 1.0 | 3.0 | 1.0 | 9.0 | | 0.0 | 1.0 | 5.0 | | 3.3 | 3.3 | 5.3 |
| | 0.0158 | 3.0 | 1.0 | 1.0 | 4.0 | 1.0 | 1.0 | | 1.0 | 2.0 | 5.0 | | 2.7 | 3.0 | 5.3 |
| 146 | 0.1250 | 9.0 | 9.0 | 1.0 | 9.0 | 6.0 | 9.0 | | 9.0 | 9.0 | 8.0 | | 7.0 | 7.0 | 8.0 |
| | 0.0625 | 9.0 | 9.0 | 2.0 | 9.0 | 4.0 | 9.0 | | 9.0 | 9.0 | 6.0 | | 6.3 | 6.3 | 7.7 |
| | 0.0313 | 9.0 | 7.0 | 2.0 | 9.0 | 2.0 | 3.0 | | 4.0 | 2.0 | 6.3 | | 5.7 | 5.3 | 7.3 |
| | 0.0156 | 9.0 | 4.0 | 1.0 | 6.0 | 2.0 | 1.0 | | 2.0 | 7.0 | 5.3 | | 5.0 | 5.3 | 7.3 |
| 147 | 0.250.0 | | | | | | | | | | 8.0 | | 3.7 | 4.0 | 6.7 |
| | 0.1250 | 9.0 | 4.0 | 2.0 | 4.0 | 4.0 | 9.0 | | 3.0 | 7.0 | 6.0 | | 6.0 | 6.0 | 7.0 |
| | 0.0625 | 9.0 | 2.0 | 1.0 | 4.0 | 1.0 | 9.0 | | 2.0 | 9.0 | 5.3 | | 3.7 | 4.3 | 6.3 |
| | 0.0313 | 5.0 | 2.0 | 1.0 | 4.0 | 1.0 | 3.0 | | 0.0 | 2.0 | 5.3 | | 3.0 | 3.7 | 4.7 |
| | 0.0156 | 3.0 | 1.0 | 1.0 | 4.0 | 1.0 | 1.0 | | 0.0 | 1.0 | 4.7 | | 2.7 | 3.0 | 3.7 |
| 148 | 0.1250 | 9.0 | 9.0 | 4.0 | 9.0 | 7.0 | 9.0 | | 2.0 | 9.0 | 6.5 | | 6.0 | 6.0 | 7.5 |
| | 0.0625 | 9.0 | 9.0 | 3.0 | 9.0 | 6.0 | 9.0 | | 1.0 | 2.0 | 6.5 | | 5.5 | 5.0 | 7.0 |
| | 0.0313 | 9.0 | 7.0 | 1.0 | 3.0 | 4.0 | 9.0 | | 1.0 | 2.0 | 6.0 | | 4.0 | 4.5 | 6.5 |
| | 0.0156 | 9.0 | 4.0 | 1.0 | 5.0 | 2.0 | 9.0 | | 1.0 | 5.0 | 5.5 | | 3.5 | 4.0 | 6.5 |

TABLE I-continued

Postemergence Herbicidal Evaluations of Test Compounds

| Compound Number | Rate (kg/ha) | ABUTH | AMBEL | CASOB | CHEAL | GALAP | IPOHE | IPOSS | ECHCG | SETVI | GLXMAW | GLXMA | ORYSAT | TRZAWR | ZEAMX |
|---|---|---|---|---|---|---|---|---|---|---|---|---|---|---|---|
| 149 | 0.1250 | 9.0 | 1.0 | 1.0 | 2.0 | 2.0 | 9.0 | | 1.0 | 1.0 | 5.0 | | 4.5 | 4.5 | 5.5 |
| | 0.0630 | | | | | | | | | | 7.0 | | 4.0 | 5.0 | 6.0 |
| | 0.0625 | 9.0 | 1.0 | 1.0 | 1.0 | 2.0 | 9.0 | | 0.0 | 0.0 | 4.0 | | 3.5 | 4.0 | 4.5 |
| | 0.0315 | | | | | | | | | | 6.0 | | 4.0 | 4.0 | 6.0 |
| | 0.0313 | 9.0 | 2.0 | 1.0 | 1.0 | 2.0 | 9.0 | | 0.0 | 0.0 | 4.0 | | 3.0 | 3.5 | 5.0 |
| | 0.0158 | | | | | | | | | | 6.0 | | 4.0 | 4.0 | 5.0 |
| | 0.0156 | 7.0 | 1.0 | 0.0 | 0.0 | 1.0 | 4.0 | | 0.0 | 0.0 | 3.5 | | 2.0 | 3.0 | 5.0 |
| 150 | 0.1250 | 9.0 | 9.0 | 3.0 | 9.0 | 9.0 | 9.0 | | 9.0 | 9.0 | 8.0 | | 7.3 | 6.7 | 7.7 |
| | 0.0625 | 9.0 | 9.0 | 2.0 | 7.0 | 7.0 | 9.0 | | 4.0 | 5.0 | 7.0 | | 6.3 | 6.3 | 7.3 |
| | 0.0313 | 9.0 | 6.0 | 2.0 | 7.0 | 4.0 | 9.0 | | 2.0 | 6.0 | 6.3 | | 4.3 | 5.0 | 7.0 |
| | 0.0156 | 9.0 | 7.0 | 1.0 | 3.0 | 2.0 | 5.0 | | 0.0 | 0.0 | 6.3 | | 4.7 | 4.7 | 6.7 |
| 151 | 0.5000 | 1.0 | 0.0 | 0.0 | 1.0 | 1.0 | 0.0 | | 0.0 | 0.0 | 1.5 | | 1.0 | 1.0 | 2.0 |
| | 0.2500 | 1.0 | 0.0 | 0.0 | 1.0 | 1.0 | 0.0 | | 0.0 | 0.0 | 1.5 | | 0.0 | 1.0 | 1.0 |
| | 0.1250 | 1.0 | 0.0 | 0.0 | 1.0 | 1.0 | 0.0 | | 0.0 | 0.0 | 1.5 | | 0.0 | 0.0 | 1.0 |
| | 0.0625 | 0.0 | 0.0 | 0.0 | 0.0 | 0.0 | 0.0 | | 0.0 | 0.0 | 0.5 | | 0.0 | 0.0 | 0.0 |
| 152 | 0.0313 | 0.0 | 0.0 | 0.0 | 0.0 | 0.0 | 0.0 | | 0.0 | 0.0 | 0.5 | | 1.5 | 2.0 | 2.5 |
| | 0.0630 | 0.0 | 0.0 | 0.0 | 0.0 | 0.0 | 0.0 | | 0.0 | 0.0 | 1.5 | | 0.5 | 1.0 | 2.0 |
| | 0.0315 | 0.0 | 0.0 | 0.0 | 0.0 | 0.0 | 0.0 | | 0.0 | 0.0 | 1.5 | | 0.0 | 1.0 | 1.0 |
| | 0.0158 | 0.0 | 0.0 | 0.0 | 0.0 | 0.0 | 0.0 | | 0.0 | 0.0 | 1.5 | | 0.0 | 0.0 | 0.0 |
| 153 | 0.0630 | 9.0 | 9.0 | 3.0 | 7.0 | 9.0 | 9.0 | | 8.0 | 7.0 | 8.5 | | 6.0 | 6.0 | 8.0 |
| | 0.0315 | 9.0 | 4.0 | 0.0 | 2.0 | 3.0 | 9.0 | | 3.0 | 9.0 | 7.5 | | 6.0 | 6.0 | 8.0 |
| | 0.0630 | 9.0 | 3.0 | 0.0 | 1.0 | 3.0 | 4.0 | | 2.0 | 9.0 | 6.5 | | 5.5 | 6.0 | 7.5 |
| 154 | 0.0315 | 9.0 | 7.0 | 3.0 | 7.0 | 9.0 | 9.0 | | 0.0 | 0.0 | 6.0 | | 1.5 | 2.5 | 5.5 |
| | 0.0158 | 9.0 | 7.0 | 0.0 | 4.0 | 5.0 | 9.0 | | 0.0 | 0.0 | 5.5 | | 1.0 | 1.5 | 4.5 |
| | 0.1250 | 9.0 | 2.0 | 0.0 | 2.0 | 3.0 | 9.0 | | 0.0 | 0.0 | 5.5 | | 1.0 | 1.5 | 4.0 |
| 155 | 0.2500 | 9.0 | 9.0 | 9.0 | 9.0 | 9.0 | 9.0 | | 0.0 | 8.0 | 9.0 | | 2.0 | 5.5 | 6.5 |
| | 0.1250 | 9.0 | 9.0 | 3.0 | 9.0 | 7.0 | 9.0 | | 0.0 | 4.0 | 8.0 | | 2.0 | 4.5 | 5.0 |
| | 0.0625 | 9.0 | 9.0 | 0.0 | 9.0 | 5.0 | 9.0 | | 0.0 | 4.0 | 7.0 | | 2.0 | 4.0 | 5.0 |
| | 0.0313 | 9.0 | 9.0 | 0.0 | 9.0 | 0.0 | 9.0 | | 0.0 | 3.0 | 6.5 | | 1.5 | 4.0 | 4.5 |
| | 0.0156 | 9.0 | 4.0 | 0.0 | 3.0 | 0.0 | 4.0 | | 0.0 | 3.0 | 5.5 | | 1.0 | 4.0 | 4.5 |
| 156 | 0.1250 | 9.0 | 5.0 | 2.0 | 9.0 | 3.0 | 9.0 | | 1.0 | 1.0 | 4.5 | | 2.5 | 3.0 | 3.5 |
| | 0.0625 | 4.0 | 3.0 | 1.0 | 1.0 | 2.0 | 4.0 | | 1.0 | 0.0 | 4.0 | | 2.5 | 2.0 | 3.5 |
| | 0.0313 | 3.0 | 1.0 | 1.0 | 2.0 | 1.0 | 1.0 | | 0.0 | 0.0 | 3.0 | | 1.5 | 1.5 | 1.5 |
| | 0.0156 | 1.0 | 1.0 | 0.0 | 0.0 | 1.0 | 0.0 | | 0.0 | 0.0 | 3.0 | | 0.5 | 0.5 | 1.0 |
| 157 | 0.1250 | 9.0 | 9.0 | 5.0 | 9.0 | 9.0 | 9.0 | | 0.0 | 9.0 | 7.5 | | 6.5 | 6.0 | 7.5 |
| | 0.0625 | 9.0 | 9.0 | 4.0 | 7.0 | 7.0 | 9.0 | | 7.0 | 7.0 | 7.0 | | 6.5 | 5.5 | 7.0 |
| | 0.0313 | 9.0 | 7.0 | 3.0 | 6.0 | 7.0 | 9.0 | | 6.0 | 4.0 | 7.0 | | 5.5 | 5.0 | 7.0 |
| | 0.0156 | 9.0 | 5.0 | 2.0 | 6.0 | 5.0 | 6.0 | | 4.0 | 1.0 | 6.0 | | 4.0 | 3.5 | 5.5 |
| 158 | 0.1250 | 9.0 | 9.0 | 5.0 | 9.0 | 9.0 | 9.0 | | 2.0 | 7.0 | 6.0 | | 4.5 | 4.5 | 7.0 |
| | 0.0625 | 9.0 | 6.0 | 3.0 | 7.0 | 7.0 | 9.0 | | 2.0 | 5.0 | 6.0 | | 5.0 | 5.0 | 7.0 |
| | 0.0313 | 9.0 | 6.0 | 3.0 | 4.0 | 4.0 | 9.0 | | 1.0 | 2.0 | 5.0 | | 3.5 | 4.0 | 5.5 |
| | 0.0156 | 9.0 | 3.0 | 3.0 | 9.0 | 3.0 | 6.0 | | 3.0 | 4.0 | 5.0 | | 3.0 | 3.0 | 5.0 |
| 159 | 0.1250 | 9.0 | 9.0 | 6.0 | 9.0 | 5.0 | 9.0 | | 3.0 | 2.0 | 7.5 | | 5.0 | 5.0 | 6.5 |
| | 0.0625 | 9.0 | 6.0 | 6.0 | 9.0 | 6.0 | 9.0 | | 3.0 | 4.0 | 6.5 | | 4.0 | 4.5 | 6.0 |
| | 0.0313 | 9.0 | 6.0 | 2.0 | 7.0 | 3.0 | 9.0 | | 1.0 | 1.0 | 5.0 | | 3.5 | 4.0 | 5.0 |
| | 0.0156 | 7.0 | 6.0 | 2.0 | 6.0 | 1.0 | 3.0 | | 0.0 | 1.0 | 5.0 | | 2.5 | 4.0 | 5.0 |
| 160 | 0.1250 | 1.0 | 2.0 | 1.0 | 1.0 | 2.0 | 1.0 | | 0.0 | 0.0 | 3.0 | | 0.5 | 1.0 | 1.0 |

TABLE I-continued

Postemergence Herbicidal Evaluations of Test Compounds

| Compound Number | Rate (kg/ha) | ABUTH | AMBEL | CASOB | CHEAL | GALAP | IPOHE | IPOSS | ECHCG | SETVI | GLXMAW | GLXMA | ORYSAT | TRZAWR | ZEAMX |
|---|---|---|---|---|---|---|---|---|---|---|---|---|---|---|---|
|  | 0.0625 | 0.0 | 0.0 | 1.0 | 1.0 | 0.0 | 1.0 |  | 0.0 | 0.0 | 3.0 |  | 0.5 | 0.5 | 0.5 |
|  | 0.0313 | 0.0 | 0.0 | 1.0 | 0.0 | 0.0 | 1.0 |  | 0.0 | 0.0 | 2.5 |  | 0.0 | 0.5 | 0.5 |
|  | 0.0156 | 0.0 | 0.0 | 0.0 | 0.0 | 0.0 | 0.0 |  | 0.0 | 0.0 | 2.0 |  | 0.0 | 0.5 | 0.0 |
| 161 | 0.1250 | 9.0 | 7.0 | 5.0 | 9.0 | 9.0 | 9.0 |  | 5.0 | 6.0 | 8.0 |  | 3.5 | 4.0 | 6.0 |
|  | 0.0625 | 9.0 | 6.0 | 4.0 | 6.0 | 4.0 | 9.0 |  | 4.0 | 5.0 | 5.5 |  | 2.5 | 3.0 | 5.0 |
|  | 0.0313 | 6.0 | 4.0 | 1.0 | 6.0 | 1.0 | 6.0 |  | 2.0 | 5.0 | 6.5 |  | 3.0 | 2.0 | 5.0 |
|  | 0.0156 | 3.0 | 1.0 | 1.0 | 3.0 | 1.0 | 3.0 |  | 1.0 | 1.0 | 4.5 |  | 1.5 | 2.0 | 4.0 |
| 162 | 0.1250 |  |  |  |  |  |  |  |  |  | 5.0 |  | 3.0 | 4.0 | 7.0 |
|  | 0.0625 |  |  |  |  |  |  |  |  |  | 4.0 |  | 3.0 | 3.0 | 6.0 |
|  | 0.0313 |  |  |  |  |  |  |  |  |  | 4.0 |  | 3.0 | 3.0 | 6.0 |
|  | 0.0156 |  |  |  |  |  |  |  |  |  | 4.0 |  | 2.0 | 3.0 | 5.0 |
| 163 | 0.1250 |  |  |  |  |  |  |  |  |  | 5.0 |  | 4.0 | 5.0 | 7.0 |
|  | 0.0625 |  |  |  |  |  |  |  |  |  | 4.0 |  | 3.0 | 4.0 | 6.0 |
|  | 0.0313 |  |  |  |  |  |  |  |  |  | 4.0 |  | 2.0 | 4.0 | 6.0 |
|  | 0.0156 |  |  |  |  |  |  |  |  |  | 3.0 |  | 2.0 | 3.0 | 5.0 |
| 164 | 0.0630 |  |  |  |  |  |  |  |  |  | 7.0 |  | 5.0 | 8.0 | 8.0 |
|  | 0.0315 |  |  |  |  |  |  |  |  |  | 7.0 |  | 5.0 | 7.0 | 7.0 |
|  | 0.0158 |  |  |  |  |  |  |  |  |  | 7.0 |  | 4.0 | 5.0 | 7.0 |
| 165 | 0.1250 |  |  |  |  |  |  |  |  |  | 7.0 |  | 3.0 | 4.0 | 6.0 |
|  | 0.0625 |  |  |  |  |  |  |  |  |  | 7.0 |  | 2.0 | 3.0 | 6.0 |
|  | 0.0313 |  |  |  |  |  |  |  |  |  | 7.0 |  | 1.0 | 3.0 | 5.0 |
|  | 0.0156 |  |  |  |  |  |  |  |  |  | 4.0 |  | 1.0 | 3.0 | 5.0 |
| 166 | 0.0630 |  |  |  |  |  |  |  |  |  | 4.0 |  | 2.0 | 4.0 | 6.0 |
|  | 0.0315 |  |  |  |  |  |  |  |  |  | 4.0 |  | 2.0 | 4.0 | 6.0 |
|  | 0.0158 |  |  |  |  |  |  |  |  |  | 2.0 |  | 2.0 | 3.0 | 5.0 |
| 167 | 0.1250 |  |  |  |  |  |  |  |  |  | 6.0 |  | 2.0 | 3.0 | 5.0 |
|  | 0.0625 |  |  |  |  |  |  |  |  |  | 6.0 |  | 2.0 | 3.0 | 5.0 |
|  | 0.0313 |  |  |  |  |  |  |  |  |  | 5.0 |  | 2.0 | 2.0 | 4.0 |
|  | 0.0156 |  |  |  |  |  |  |  |  |  | 5.0 |  | 1.0 | 2.0 | 4.0 |
| 168 | 0.1250 |  |  |  |  |  |  |  |  |  | 8.0 |  | 4.0 | 4.0 | 6.0 |
|  | 0.0625 |  |  |  |  |  |  |  |  |  | 7.0 |  | 3.0 | 3.0 | 6.0 |
|  | 0.0313 |  |  |  |  |  |  |  |  |  | 7.0 |  | 2.0 | 3.0 | 5.0 |
|  | 0.0156 |  |  |  |  |  |  |  |  |  | 7.0 |  | 2.0 | 3.0 | 5.0 |
| 169 | 0.1250 |  |  |  |  |  |  |  |  |  | 3.0 |  | 4.0 | 4.0 | 3.0 |
|  | 0.0625 |  |  |  |  |  |  |  |  |  | 2.0 |  | 2.0 | 2.0 | 2.0 |
|  | 0.0313 |  |  |  |  |  |  |  |  |  | 1.0 |  | 1.0 | 1.0 | 1.0 |
|  | 0.0156 |  |  |  |  |  |  |  |  |  | 1.0 |  | 1.0 | 1.0 | 1.0 |
| 170 | 0.1250 | 9.0 | 7.0 | 9.0 | 8.0 | 9.0 | 9.0 |  | 9.0 | 9.0 | 7.5 |  | 8.0 | 8.0 | 9.0 |
|  | 0.0630 | 9.0 | 9.0 | 6.0 | 9.0 | 6.0 | 9.0 |  | 9.0 | 9.0 | 7.0 |  | 7.0 | 7.0 | 9.0 |
|  | 0.0625 | 9.0 | 9.0 | 7.0 | 7.0 | 9.0 | 9.0 |  | 8.0 | 9.0 | 7.5 |  | 8.0 | 8.5 | 9.0 |
|  | 0.0315 | 9.0 | 9.0 | 9.0 | 9.0 | 7.0 | 9.0 |  | 9.0 | 9.0 | 6.0 |  | 7.0 | 7.0 | 9.0 |
|  | 0.0313 | 9.0 | 9.0 | 5.0 | 5.0 | 9.0 | 9.0 |  | 8.0 | 7.0 | 6.5 |  | 7.5 | 9.0 | 8.5 |
|  | 0.0158 | 9.0 | 5.0 | 6.0 | 7.0 | 6.0 | 9.0 |  | 7.0 | 8.0 | 5.0 |  | 7.0 | 7.0 | 8.0 |
|  | 0.0156 | 9.0 | 0.0 | 0.0 | 4.0 | 3.0 | 5.0 |  | 3.0 | 1.0 | 6.0 |  | 6.5 | 7.5 | 8.5 |
| 171 | 0.0630 | 9.0 | 1.0 | 1.0 | 7.0 | 1.0 | 7.0 |  | 2.0 | 1.0 | 4.0 |  | 4.0 | 4.0 | 5.0 |
|  | 0.0315 | 3.0 | 1.0 | 1.0 | 1.0 | 1.0 | 5.0 |  | 2.0 | 0.0 | 3.0 |  | 4.0 | 4.0 | 5.0 |
|  | 0.0158 | 4.0 | 1.0 | 0.0 | 0.0 | 0.0 | 5.0 |  | 0.0 | 0.0 | 3.0 |  | 3.0 | 3.0 | 5.0 |

TABLE I-continued

Postemergence Herbicidal Evaluations of Test Compounds

| Compound Number | Rate (kg/ha) | ABUTH | AMBEL | CASOB | CHEAL | GALAP | IPOHE | IPOSS | ECHCG | SETVI | GLXMAW | GLXMA | ORYSAT | TRZAWR | ZEAMX |
|---|---|---|---|---|---|---|---|---|---|---|---|---|---|---|---|
| 172 | 0.0630 | 9.0 | 9.0 | 7.0 | 9.0 | 7.0 | 9.0 | | 9.0 | 9.0 | 9.0 | | 8.0 | 6.0 | 7.0 |
| | 0.0315 | 9.0 | 9.0 | 5.0 | 9.0 | 6.0 | 9.0 | | 9.0 | 9.0 | 7.0 | | 6.0 | 5.0 | 7.0 |
| | 0.0158 | 9.0 | 9.0 | 5.0 | 5.0 | 5.0 | 9.0 | | 9.0 | 9.0 | 7.0 | | 6.0 | 8.0 | 4.0 |
| 173 | 0.1250 | 9.0 | 9.0 | 9.0 | 6.0 | 5.0 | 9.0 | | 9.0 | 9.0 | 7.0 | | 7.5 | 8.5 | 8.0 |
| | 0.0630 | 9.0 | 9.0 | 6.0 | 8.0 | 4.0 | 9.0 | | 9.0 | 9.0 | 7.0 | | 5.0 | 9.0 | 7.0 |
| | 0.0625 | 9.0 | 9.0 | 3.0 | 8.0 | 5.0 | 9.0 | | 3.0 | 7.0 | 7.0 | | 4.5 | 8.5 | 8.0 |
| | 0.0315 | 9.0 | 8.0 | 4.0 | 5.0 | 2.0 | 9.0 | | 9.0 | 9.0 | 6.0 | | 4.0 | 7.0 | 7.0 |
| | 0.0313 | 9.0 | 9.0 | 3.0 | 2.0 | 1.0 | 9.0 | | 9.0 | 9.0 | 6.5 | | 4.0 | 6.0 | 8.0 |
| | 0.0158 | 9.0 | 9.0 | 3.0 | 2.0 | 1.0 | 9.0 | | 9.0 | 7.0 | 3.0 | | 4.0 | 5.0 | 4.0 |
| | 0.0156 | 9.0 | 7.0 | 0.0 | 2.0 | 0.0 | 7.0 | | 2.0 | 7.0 | 6.5 | | 3.0 | 5.5 | 6.0 |
| 174 | 0.0630 | 9.0 | 9.0 | 6.0 | 8.0 | 6.0 | 9.0 | | 9.0 | 9.0 | 9.0 | | 5.0 | 8.0 | 7.0 |
| | 0.0625 | 9.0 | 9.0 | 3.0 | 6.0 | 4.0 | 9.0 | | 9.0 | 9.0 | 7.5 | | 6.0 | 7.0 | 8.0 |
| | 0.0315 | 9.0 | 9.0 | 3.0 | 8.0 | 2.0 | 9.0 | | 9.0 | 9.0 | 7.0 | | 3.0 | 5.0 | 7.0 |
| | 0.0313 | 9.0 | 9.0 | 1.0 | 4.0 | 1.0 | 9.0 | | 2.0 | 9.0 | 7.0 | | 5.0 | 7.0 | 8.0 |
| | 0.0158 | 9.0 | 9.0 | 2.0 | 7.0 | 2.0 | 9.0 | | 8.0 | 7.0 | 6.0 | | 3.0 | 4.0 | 5.0 |
| | 0.0156 | 9.0 | 9.0 | 0.0 | 3.0 | 0.0 | 9.0 | | 5.0 | 4.0 | 7.0 | | 4.5 | 5.0 | 6.5 |
| 175 | 0.0630 | 9.0 | 9.0 | 6.0 | 9.0 | 5.0 | 9.0 | | 9.0 | 9.0 | 9.0 | | 5.0 | 5.0 | 6.0 |
| | 0.0315 | 9.0 | 9.0 | 2.0 | 5.0 | 4.0 | 9.0 | | 8.0 | 9.0 | 7.0 | | 4.0 | 4.0 | 5.0 |
| | 0.0158 | 9.0 | 9.0 | 2.0 | 5.0 | 1.0 | 9.0 | | 9.0 | 7.0 | 7.0 | | 4.0 | 4.0 | 5.0 |
| 176 | 0.1250 | 9.0 | 8.0 | 9.0 | 7.0 | 7.0 | 9.0 | | 9.0 | 9.0 | 8.0 | | 7.5 | 9.0 | 8.5 |
| | 0.0630 | 9.0 | 9.0 | 5.0 | 8.0 | 5.0 | 9.0 | | 5.0 | 9.0 | 7.0 | | 5.0 | 9.0 | 7.0 |
| | 0.0315 | 9.0 | 9.0 | 8.0 | 7.0 | 7.0 | 9.0 | | 8.0 | 9.0 | 8.0 | | 7.5 | 9.0 | 8.0 |
| | 0.0313 | 9.0 | 9.0 | 4.0 | 7.0 | 4.0 | 9.0 | | 8.0 | 9.0 | 6.0 | | 6.0 | 9.0 | 7.0 |
| | 0.0158 | 9.0 | 9.0 | 7.0 | 7.0 | 2.0 | 9.0 | | 7.0 | 8.0 | 7.5 | | 6.5 | 9.0 | 8.5 |
| | 0.0156 | 9.0 | 6.0 | 4.0 | 6.0 | 2.0 | 9.0 | | 8.0 | 3.0 | 5.0 | | 5.0 | 8.0 | 6.0 |
| 177 | 0.0630 | 9.0 | 9.0 | 2.0 | 5.0 | 0.0 | 9.0 | | 3.0 | 7.0 | 7.0 | | 4.0 | 7.5 | 7.0 |
| | 0.0315 | 9.0 | 9.0 | 9.0 | 9.0 | 6.0 | 9.0 | | 9.0 | 9.0 | 9.0 | | 6.0 | 5.0 | 7.0 |
| | 0.0158 | 9.0 | 9.0 | 5.0 | 8.0 | 5.0 | 9.0 | | 8.0 | 7.0 | 7.0 | | 6.0 | 7.0 | 5.0 |
| 178 | 0.0630 | 9.0 | 9.0 | 3.0 | 8.0 | 6.0 | 9.0 | | 9.0 | 7.0 | 7.0 | | 4.0 | 4.0 | 5.0 |
| | 0.0315 | 9.0 | 9.0 | 5.0 | 8.0 | 8.0 | 9.0 | | 9.0 | 9.0 | 9.0 | | 4.0 | 3.0 | 7.0 |
| | 0.0158 | 9.0 | 9.0 | 2.0 | 7.0 | 7.0 | 9.0 | | 9.0 | 9.0 | 7.0 | | 4.0 | 3.0 | 5.0 |
| 179 | 0.1250 | 9.0 | 9.0 | 2.0 | 4.0 | 5.0 | 9.0 | | 7.0 | 9.0 | 5.0 | | 4.0 | 3.0 | 5.0 |
| | 0.0630 | 9.0 | 9.0 | 3.0 | 8.0 | 7.0 | 9.0 | | 8.0 | 8.0 | 8.0 | | 7.5 | 6.5 | 7.0 |
| | 0.0625 | 9.0 | 9.0 | 3.0 | 8.0 | 5.0 | 9.0 | | 2.0 | 7.0 | 7.0 | | 4.0 | 4.0 | 5.0 |
| | 0.0315 | 9.0 | 9.0 | 2.0 | 4.0 | 6.0 | 9.0 | | 5.0 | 5.0 | 7.5 | | 3.0 | 4.0 | 5.5 |
| | 0.0313 | 9.0 | 5.0 | 1.0 | 6.0 | 4.0 | 9.0 | | 2.0 | 9.0 | 5.0 | | 3.0 | 3.0 | 4.0 |
| | 0.0158 | 9.0 | 8.0 | 2.0 | 3.0 | 1.0 | 9.0 | | 1.0 | 2.0 | 7.5 | | 2.0 | 3.5 | 5.0 |
| | 0.0156 | 9.0 | 3.0 | 0.0 | 1.0 | 3.0 | 9.0 | | 3.0 | 7.0 | 5.0 | | 2.0 | 2.0 | 4.0 |
| 180 | 0.0630 | 9.0 | 9.0 | 7.0 | 8.0 | 7.0 | 9.0 | | 1.0 | 6.0 | 5.5 | | 1.5 | 2.0 | 4.5 |
| | 0.0315 | 9.0 | 8.0 | 2.0 | 7.0 | 6.0 | 9.0 | | 0.0 | 1.0 | 7.0 | | 2.0 | 2.0 | 5.0 |
| | 0.0158 | 9.0 | 8.0 | 2.0 | 4.0 | 3.0 | 9.0 | | 0.0 | 0.0 | 7.0 | | 2.0 | 2.0 | 5.0 |
| 181 | 0.0630 | 9.0 | 8.0 | 7.0 | 8.0 | 6.0 | 9.0 | | 4.0 | 9.0 | 6.0 | | 4.0 | 6.0 | 4.0 |
| | 0.0315 | 9.0 | 7.0 | 4.0 | 7.0 | 6.0 | 9.0 | | 4.0 | 9.0 | 5.0 | | 4.0 | 4.0 | 4.0 |
| | 0.0158 | 9.0 | 6.0 | 4.0 | 5.0 | 4.0 | 9.0 | | 4.0 | 8.0 | 5.0 | | 3.0 | 4.0 | 4.0 |
| 182 | 0.0780 | 9.0 | 9.0 | 5.0 | 9.0 | 9.0 | 9.0 | | 9.0 | 9.0 | 7.5 | | 4.5 | 4.5 | 7.0 |
| | 0.0390 | 9.0 | 9.0 | 5.0 | 9.0 | 9.0 | 9.0 | | 9.0 | 9.0 | 8.5 | | 4.5 | 4.5 | 6.5 |

TABLE I-continued

Postemergence Herbicidal Evaluations of Test Compounds

| Compound Number | Rate (kg/ha) | ABUTH | AMBEL | CASOB | CHEAL | GALAP | IPOHE | IPOSS | ECHCG | SETVI | GLXMAW | GLXMA | ORYSAT | TRZAWR | ZEAMX |
|---|---|---|---|---|---|---|---|---|---|---|---|---|---|---|---|
| 183 | 0.0195 | 9.0 | 9.0 | 3.0 | 7.0 | 5.0 | 9.0 | | 9.0 | 9.0 | 7.5 | | 4.5 | 4.5 | 5.5 |
| | 0.0780 | 9.0 | 9.0 | 9.0 | 9.0 | 9.0 | 9.0 | | 9.0 | 9.0 | 8.5 | | 9.0 | 7.5 | 8.0 |
| | 0.0390 | 9.0 | 9.0 | 7.0 | 9.0 | 9.0 | 9.0 | | 9.0 | 9.0 | 8.0 | | 6.5 | 7.5 | 7.5 |
| | 0.0195 | 9.0 | 9.0 | 4.0 | 8.0 | 5.0 | 9.0 | | 9.0 | 9.0 | 7.5 | | 4.0 | 6.0 | 6.5 |
| 184 | 0.0780 | 9.0 | 9.0 | 3.0 | 9.0 | 9.0 | 9.0 | | 9.0 | 9.0 | 7.0 | | 8.0 | 9.0 | 7.5 |
| | 0.0390 | 9.0 | 9.0 | 3.0 | 7.0 | 7.0 | 9.0 | | 9.0 | 9.0 | 7.0 | | 5.5 | 7.5 | 7.5 |
| | 0.0195 | 9.0 | 9.0 | 0.0 | 5.0 | 3.0 | 9.0 | | 9.0 | 9.0 | 6.5 | | 3.5 | 5.5 | 6.5 |
| 185 | 0.0640 | 9.0 | 9.0 | 3.0 | 9.0 | 9.0 | 9.0 | | 9.0 | 9.0 | 8.5 | | 7.0 | 7.0 | 6.0 |
| | 0.0320 | 9.0 | 9.0 | 3.0 | 9.0 | 9.0 | 9.0 | | 9.0 | 9.0 | 8.0 | | 5.5 | 5.5 | 7.5 |
| | 0.0160 | 9.0 | 9.0 | 1.0 | 3.0 | 5.0 | 9.0 | | 7.0 | 8.0 | 8.5 | | 4.5 | 5.5 | 6.0 |
| 186 | 0.0630 | 9.0 | 9.0 | 7.0 | 9.0 | 9.0 | 9.0 | | 9.0 | 9.0 | 8.0 | | 7.0 | 6.5 | 5.0 |
| | 0.0315 | 9.0 | 9.0 | 5.0 | 9.0 | 6.0 | 9.0 | | 9.0 | 9.0 | 7.5 | | 7.0 | 6.0 | 8.0 |
| | 0.0158 | 9.0 | 9.0 | 0.0 | 5.0 | 5.0 | 9.0 | | 9.0 | 9.0 | 7.5 | | 4.5 | 5.0 | 7.0 |
| 187 | 0.0630 | 9.0 | 9.0 | 3.0 | 9.0 | 7.0 | 9.0 | | 9.0 | 9.0 | 7.5 | | 5.0 | 6.5 | 6.0 |
| | 0.0315 | 9.0 | 8.0 | 3.0 | 8.0 | 6.0 | 9.0 | | 9.0 | 7.0 | 7.0 | | 5.0 | 5.5 | 7.5 |
| | 0.0158 | 9.0 | 9.0 | 0.0 | 1.0 | 4.0 | 9.0 | | 7.0 | 3.0 | 6.5 | | 3.0 | 5.0 | 5.5 |
| 188 | 0.0630 | 9.0 | 7.0 | 2.0 | 0.0 | 1.0 | 9.0 | | 2.0 | 5.0 | 5.5 | | 4.0 | 4.0 | 5.5 |
| | 0.0315 | 9.0 | 9.0 | 2.0 | 0.0 | 0.0 | 9.0 | | 5.0 | 9.0 | 5.5 | | 4.0 | 4.5 | 7.0 |
| | 0.0158 | 9.0 | 9.0 | 1.0 | 1.0 | 1.0 | 6.0 | | 1.0 | 8.0 | 5.5 | | 3.0 | 3.5 | 6.0 |
| 189 | 0.0630 | 9.0 | 6.0 | 4.0 | 6.0 | 1.0 | 7.0 | | 4.0 | 9.0 | 4.5 | | 3.0 | 3.5 | 5.0 |
| | 0.0315 | 9.0 | 5.0 | 4.0 | 5.0 | 1.0 | 9.0 | | 1.0 | 3.0 | 4.0 | | 2.5 | 3.5 | 4.5 |
| | 0.0158 | 9.0 | 2.0 | 1.0 | 4.0 | 1.0 | 7.0 | | 1.0 | 1.0 | 4.0 | | 1.5 | 3.5 | 3.5 |
| 190 | 0.0630 | 9.0 | 9.0 | 6.0 | 6.0 | 9.0 | 9.0 | | 9.0 | 9.0 | 8.5 | | 7.0 | 6.3 | 7.5 |
| | 0.0315 | 9.0 | 9.0 | 6.0 | 5.0 | 7.0 | 9.0 | | 8.0 | 7.0 | 8.0 | | 6.3 | 6.0 | 7.3 |
| | 0.0158 | 9.0 | 9.0 | 5.5 | 4.5 | 5.5 | 7.0 | | 8.0 | 9.0 | 7.0 | | 5.3 | 5.3 | 6.0 |
| 191 | 0.0630 | 9.0 | 9.0 | 8.0 | 8.0 | 8.5 | 9.0 | | 9.0 | 9.0 | 8.0 | | 7.5 | 6.8 | 8.0 |
| | 0.0315 | 9.0 | 9.0 | 7.0 | 9.0 | 7.0 | 9.0 | | 9.0 | 9.0 | 7.3 | | 6.5 | 6.5 | 8.0 |
| | 0.0158 | 8.0 | 9.0 | 4.0 | 7.5 | 7.0 | 9.0 | | 9.0 | 9.0 | 7.3 | | 5.3 | 5.8 | 6.8 |
| 192 | 0.0630 | 9.0 | 9.0 | 9.0 | 9.0 | 9.0 | 9.0 | | 9.0 | 9.0 | 8.5 | | 7.0 | 7.0 | 7.5 |
| | 0.0315 | 9.0 | 9.0 | 8.0 | 9.0 | 9.0 | 9.0 | | 9.0 | 9.0 | 8.5 | | 6.5 | 6.5 | 7.0 |
| | 0.0158 | 9.0 | 9.0 | 6.0 | 6.0 | 6.0 | 9.0 | | 9.0 | 9.0 | 7.0 | | 5.5 | 6.0 | 5.5 |
| 193 | 0.0630 | 9.0 | 9.0 | 3.0 | 6.5 | 1.5 | 9.0 | | 0.5 | 2.0 | 5.0 | | 3.5 | 4.0 | 5.5 |
| | 0.0315 | 9.0 | 7.0 | 3.5 | 4.5 | 1.5 | 9.0 | | 0.5 | 1.0 | 5.5 | | 3.3 | 3.3 | 5.3 |
| | 0.0158 | 9.0 | 6.5 | 1.5 | 4.5 | 1.5 | 7.0 | | 0.5 | 0.5 | 5.3 | | 3.3 | 3.5 | 5.0 |
| 194 | 0.0630 | 9.0 | 9.0 | 8.0 | 9.0 | 7.0 | 9.0 | | 9.0 | 9.0 | 8.5 | | 7.5 | 6.0 | 8.0 |
| | 0.0315 | 9.0 | 9.0 | 3.0 | 9.0 | 4.0 | 9.0 | | 5.0 | 9.0 | 8.0 | | 7.0 | 5.5 | 7.5 |
| | 0.0158 | 9.0 | 9.0 | 5.0 | 9.0 | 4.0 | 9.0 | | 5.0 | 9.0 | 8.5 | | 5.5 | 5.0 | 5.5 |
| 195 | 0.0630 | 9.0 | 9.0 | 5.0 | 9.0 | 9.0 | 9.0 | | 2.0 | 9.0 | 8.5 | | 5.0 | 5.0 | 5.5 |
| | 0.0315 | 9.0 | 9.0 | 4.0 | 7.0 | 5.0 | 9.0 | | 1.0 | 9.0 | 7.5 | | 3.0 | 4.0 | 5.0 |
| | 0.0158 | 9.0 | 7.0 | 5.0 | 9.0 | 2.0 | 9.0 | | 6.0 | 4.0 | 7.5 | | 4.3 | 3.5 | 5.7 |
| 196 | 0.0630 | 9.0 | 9.0 | 5.0 | 9.0 | 7.0 | 9.0 | | 4.0 | 8.0 | 7.3 | | 3.3 | 3.3 | 5.3 |
| | 0.0315 | 9.0 | 9.0 | 2.0 | 9.0 | 4.0 | 9.0 | | 2.0 | 4.0 | 6.7 | | 3.0 | 3.0 | 5.3 |
| | 0.0158 | 9.0 | 7.0 | 2.0 | 7.0 | 1.0 | 7.0 | | 0.0 | 2.0 | 6.3 | | 3.0 | 3.0 | 5.5 |
| 197 | 0.2500 | 9.0 | 9.0 | 4.0 | 9.0 | 9.0 | 9.0 | | 0.0 | 3.0 | 5.5 | | 1.5 | 4.5 | 5.5 |
| | 0.1250 | 9.0 | 6.5 | 4.0 | 8.0 | 4.5 | 9.0 | | 0.0 | 4.5 | 6.0 | | 2.3 | 4.0 | 5.5 |
| | 0.0625 | 9.0 | 4.0 | 2.5 | 5.5 | 3.5 | 7.0 | | 0.0 | 3.0 | 5.5 | | 1.5 | 3.8 | 5.5 |
| | 0.0313 | 9.0 | 2.5 | 1.5 | 3.5 | 1.0 | 9.0 | | 0.0 | 1.5 | 5.0 | | 1.5 | 3.3 | 5.0 |

TABLE I-continued

Postemergence Herbicidal Evaluations of Test Compounds

| Compound Number | Rate (kg/ha) | ABUTH | AMBEL | CASOB | CHEAL | GALAP | IPOHE | IPOSS | ECHCG | SETVI | GLXMAW | GLXMA | ORYSAT | TRZAWR | ZEAMX |
|---|---|---|---|---|---|---|---|---|---|---|---|---|---|---|---|
| 198 | 0.0156 | 8.5 | 1.0 | 0.0 | 2.0 | 0.5 | 6.0 | | 0.0 | 0.0 | 4.5 | | 0.8 | 2.8 | 5.0 |
| | 0.1250 | 9.0 | 9.0 | 2.0 | 5.0 | 7.0 | 9.0 | | 2.0 | 5.0 | 7.0 | | 4.5 | 4.5 | 6.5 |
| | 0.0625 | 9.0 | 9.0 | 2.0 | 3.0 | 5.0 | 9.0 | | 0.0 | 3.0 | 6.0 | | 2.5 | 3.0 | 5.0 |
| | 0.0313 | 9.0 | 5.0 | 0.0 | 1.0 | 1.0 | 9.0 | | 0.0 | 0.0 | 6.0 | | 1.5 | 3.0 | 4.5 |
| 199 | 0.0156 | 9.0 | 5.0 | 0.0 | 1.0 | 1.0 | 9.0 | | 0.0 | 0.0 | 4.5 | | 1.5 | 2.5 | 4.5 |
| | 0.1250 | 9.0 | 4.0 | 2.0 | 1.0 | 4.0 | 9.0 | | 0.0 | 1.0 | 5.5 | | 2.0 | 3.0 | 6.0 |
| | 0.0625 | 9.0 | 2.0 | 2.0 | 1.0 | 2.0 | 9.0 | | 0.0 | 1.0 | 5.5 | | 1.5 | 2.5 | 5.0 |
| | 0.0313 | 9.0 | 1.0 | 2.0 | 1.0 | 1.0 | 9.0 | | 0.0 | 1.0 | 4.5 | | 1.0 | 2.0 | 5.0 |
| | 0.0156 | 7.0 | 1.0 | 0.0 | 1.0 | 1.0 | 6.0 | | 0.0 | 0.0 | 4.5 | | 1.0 | 2.0 | 5.0 |
| 200 | 0.1250 | 9.0 | 9.0 | 4.0 | 7.0 | 7.0 | 9.0 | | 7.0 | 7.0 | 8.5 | | 4.5 | 4.5 | 6.5 |
| | 0.0625 | 9.0 | 7.0 | 3.0 | 6.0 | 7.0 | 9.0 | | 0.0 | 2.0 | 7.0 | | 4.5 | 4.0 | 6.0 |
| | 0.0313 | 9.0 | 7.0 | 0.0 | 2.0 | 2.0 | 9.0 | | 0.0 | 0.0 | 6.5 | | 2.5 | 3.0 | 5.0 |
| | 0.0156 | 9.0 | 2.0 | 0.0 | 1.0 | 2.0 | 9.0 | | 0.0 | 0.0 | 5.5 | | 2.0 | 2.5 | 5.0 |
| 201 | 0.1250 | 9.0 | 6.0 | 4.0 | 6.0 | 6.0 | 9.0 | | 0.0 | 3.0 | 7.5 | | 3.5 | 4.0 | 5.0 |
| | 0.0625 | 9.0 | 6.0 | 2.0 | 3.0 | 2.0 | 9.0 | | 0.0 | 2.0 | 6.0 | | 3.0 | 3.5 | 5.5 |
| | 0.0313 | 9.0 | 3.0 | 0.0 | 1.0 | 1.0 | 9.0 | | 0.0 | 2.0 | 5.0 | | 2.5 | 3.0 | 5.5 |
| | 0.0156 | 7.0 | 2.0 | 0.0 | 1.0 | 0.0 | 6.0 | | 0.0 | 0.0 | 5.0 | | 2.0 | 2.5 | 5.0 |
| 202 | 0.2500 | 9.0 | 9.0 | 9.0 | 9.0 | 9.0 | 9.0 | | 0.0 | 9.0 | 8.0 | | 2.5 | 5.5 | 6.0 |
| | 0.1250 | 9.0 | 9.0 | 1.0 | 9.0 | 2.0 | 9.0 | | 0.0 | 2.0 | 8.0 | | 2.0 | 4.0 | 5.5 |
| | 0.0630 | 9.0 | 7.0 | 6.0 | 7.0 | 6.0 | 9.0 | | 3.0 | 4.0 | 7.5 | | 4.0 | 4.5 | 5.0 |
| | 0.0625 | 9.0 | 6.0 | 1.0 | 9.0 | 1.0 | 9.0 | | 0.0 | 0.0 | 6.5 | | 1.5 | 2.5 | 5.5 |
| | 0.0315 | 9.0 | 6.0 | 6.0 | 6.0 | 4.0 | 9.0 | | 2.0 | 1.0 | 5.5 | | 4.0 | 4.5 | 5.5 |
| | 0.0313 | 9.0 | 4.0 | 0.0 | 6.0 | 0.0 | 9.0 | | 0.0 | 0.0 | 6.0 | | 0.5 | 2.0 | 4.5 |
| | 0.0158 | 9.0 | 6.0 | 4.0 | 6.0 | 4.0 | 9.0 | | 2.0 | 1.0 | 5.5 | | 3.0 | 3.5 | 5.0 |
| | 0.0156 | 9.0 | 3.0 | 0.0 | 9.0 | 2.0 | 3.0 | | 0.0 | 0.0 | 5.5 | | 0.5 | 2.0 | 4.5 |
| 203 | 0.0630 | 9.0 | 8.0 | 6.0 | 9.0 | 6.0 | 9.0 | | 5.0 | 5.0 | 7.5 | | 5.0 | 5.0 | 6.0 |
| | 0.0315 | 9.0 | 9.0 | 5.0 | 6.0 | 6.0 | 9.0 | | 2.0 | 5.0 | 7.0 | | 4.0 | 4.0 | 5.5 |
| | 0.0158 | 9.0 | 7.0 | 4.0 | 8.0 | 4.0 | 9.0 | | 2.0 | 3.0 | 7.0 | | 3.0 | 3.5 | 5.5 |
| 204 | 0.0630 | 9.0 | 9.0 | 6.0 | 4.0 | 6.0 | 9.0 | | 4.0 | 5.0 | 7.5 | | 5.5 | 5.5 | 6.0 |
| | 0.0315 | 9.0 | 7.0 | 6.0 | 7.0 | 5.0 | 9.0 | | 3.0 | 2.0 | 6.0 | | 3.5 | 4.5 | 5.5 |
| | 0.0158 | 9.0 | 4.0 | 6.0 | 6.0 | 3.0 | 9.0 | | 2.0 | 5.0 | 7.5 | | 4.0 | 4.5 | 5.5 |
| 205 | 0.0630 | 9.0 | 9.0 | 3.0 | 3.0 | 3.0 | 9.0 | | 4.0 | 2.0 | 6.0 | | 4.5 | 5.5 | 6.0 |
| | 0.0315 | 9.0 | 7.0 | 5.0 | 9.0 | 6.0 | 9.0 | | 3.0 | 4.0 | 8.5 | | 4.5 | 4.5 | 5.5 |
| | 0.0158 | 9.0 | 6.0 | 3.0 | 8.0 | 5.0 | 9.0 | | 2.0 | 4.0 | 7.0 | | 3.0 | 3.5 | 4.5 |
| 206 | 0.0630 | 9.0 | 6.0 | 4.0 | 6.0 | 3.0 | 9.0 | | 5.0 | 2.0 | 7.5 | | 4.0 | 5.0 | 6.5 |
| | 0.0315 | 9.0 | 8.0 | 7.0 | 8.0 | 6.0 | 9.0 | | 3.0 | 6.0 | 7.5 | | 3.0 | 4.0 | 5.5 |
| | 0.0158 | 9.0 | 8.0 | 5.0 | 8.0 | 3.0 | 7.0 | | 3.0 | 4.0 | 7.0 | | 3.5 | 4.0 | 5.5 |
| 207 | 0.0630 | 9.0 | 4.0 | 4.0 | 4.0 | 1.0 | 9.0 | | 4.0 | 2.0 | 6.5 | | 4.0 | 4.0 | 5.5 |
| | 0.0315 | 9.0 | 9.0 | 6.0 | 9.0 | 8.0 | 9.0 | | 3.0 | 5.0 | 7.5 | | 4.0 | 4.5 | 6.0 |
| | 0.0158 | 9.0 | 7.0 | 5.0 | 8.0 | 6.0 | 9.0 | | 2.0 | 4.0 | 7.5 | | 4.5 | 5.5 | 6.0 |
| 208 | 0.0630 | 9.0 | 6.0 | 3.0 | 5.0 | 5.0 | 9.0 | | 4.0 | 2.0 | 6.5 | | 4.5 | 4.5 | 5.5 |
| | 0.0315 | 9.0 | 6.0 | 4.0 | 6.0 | 4.0 | 9.0 | | 3.0 | 3.0 | 6.5 | | 3.0 | 3.5 | 4.5 |
| | 0.0158 | 8.0 | 7.0 | 7.0 | 5.0 | 4.0 | 9.0 | | 2.0 | 2.0 | 6.0 | | 3.5 | 5.0 | 6.0 |
| 209 | 0.0630 | 9.0 | 9.0 | 3.0 | 5.0 | 3.0 | 6.0 | | 2.0 | 2.0 | 6.5 | | 3.0 | 4.0 | 5.5 |
| | 0.0315 | 9.0 | 6.0 | 0.0 | 3.0 | 3.0 | 9.0 | | 1.0 | 9.0 | 7.5 | | 2.5 | 3.0 | 5.0 |
| | 0.0158 | 9.0 | 4.0 | 1.0 | 4.0 | 2.0 | 9.0 | | 0.0 | 7.0 | 6.5 | | 4.5 | 4.5 | 6.0 |
| 210 | 0.0630 | 9.0 | 9.0 | 1.0 | 8.0 | 9.0 | 9.0 | | 1.0 | 2.0 | 5.5 | | 3.5 | 4.0 | 5.0 |
| | | | | | | | | | | 4.0 | 6.0 | | 3.0 | 5.0 | 5.5 |

TABLE I-continued

Postemergence Herbicidal Evaluations of Test Compounds

| Compound Number | Rate (kg/ha) | ABUTH | AMBEL | CASOB | CHEAL | GALAP | IPOHE | IPOSS | ECHCG | SETVI | GLXMAW | GLXMA | ORYSAT | TRZAWR | ZEAMX |
|---|---|---|---|---|---|---|---|---|---|---|---|---|---|---|---|
|  | 0.0315 | 9.0 | 6.0 | 0.0 | 6.0 | 7.0 | 9.0 |  | 0.0 | 4.0 | 6.0 |  | 1.5 | 3.5 | 5.0 |
|  | 0.0158 | 9.0 | 4.0 | 0.0 | 3.0 | 7.0 | 3.0 |  | 0.0 | 4.0 | 6.0 |  | 1.5 | 3.5 | 5.0 |
| 211 | 0.0630 | 9.0 | 9.0 | 2.0 | 7.0 | 9.0 | 9.0 |  | 0.0 | 2.0 | 6.0 |  | 1.5 | 4.0 | 5.5 |
|  | 0.0315 | 9.0 | 4.0 | 1.0 | 4.0 | 5.0 | 9.0 |  | 0.0 | 0.0 | 5.0 |  | 1.5 | 3.5 | 5.0 |
|  | 0.0158 | 9.0 | 0.0 | 0.0 | 0.0 | 0.0 | 2.0 |  | 0.0 | 0.0 | 4.5 |  | 1.0 | 3.5 | 5.0 |
| 212 | 0.0630 | 9.0 | 6.0 | 0.0 | 6.0 | 6.0 | 9.0 |  | 0.0 | 0.0 | 5.5 |  | 1.5 | 3.5 | 5.5 |
|  | 0.0315 | 9.0 | 3.0 | 0.0 | 0.0 | 5.0 | 3.0 |  | 0.0 | 0.0 | 5.0 |  | 1.5 | 3.0 | 5.0 |
|  | 0.0158 | 9.0 | 0.0 | 0.0 | 0.0 | 0.0 | 0.0 |  | 0.0 | 0.0 | 4.0 |  | 1.5 | 2.0 | 4.5 |
| 213 | 0.2500 | 9.0 | 3.0 | 2.0 | 5.0 | 3.0 | 6.0 |  | 2.0 | 7.0 | 4.5 |  | 4.5 | 4.5 | 5.5 |
|  | 0.1250 | 9.0 | 2.0 | 1.0 | 4.0 | 1.0 | 9.0 |  | 0.0 | 0.0 | 4.0 |  | 3.5 | 3.5 | 5.5 |
|  | 0.0630 |  |  |  |  |  |  |  |  |  | 8.0 |  | 6.0 | 6.0 | 7.0 |
|  | 0.0625 | 9.0 | 2.0 | 1.0 | 4.0 | 1.0 | 7.0 |  | 0.0 | 0.0 | 4.5 |  | 3.5 | 3.5 | 5.0 |
|  | 0.0315 |  |  |  |  |  |  |  |  |  | 8.0 |  | 5.0 | 5.0 | 7.0 |
|  | 0.0313 | 7.0 | 1.0 | 1.0 | 1.0 | 1.0 | 4.0 |  | 1.0 | 1.0 | 4.5 |  | 3.5 | 4.0 | 5.0 |
|  | 0.0158 |  |  |  |  |  |  |  |  |  | 8.0 |  | 5.0 | 5.0 | 6.0 |
|  | 0.0156 | 2.0 | 0.0 | 0.0 | 0.0 | 1.0 | 2.0 |  | 0.0 | 0.0 | 4.0 |  | 3.0 | 3.5 | 3.5 |
| 214 | 0.2500 | 6.0 | 2.0 | 2.0 | 7.0 | 2.0 | 4.0 |  | 1.0 | 3.0 | 5.5 |  | 3.0 | 4.0 | 5.0 |
|  | 0.1250 | 4.0 | 0.0 | 1.0 | 2.0 | 2.0 | 2.0 |  | 1.0 | 3.0 | 3.5 |  | 2.0 | 2.5 | 5.0 |
|  | 0.0625 | 4.0 | 1.0 | 1.0 | 2.0 | 1.0 | 1.0 |  | 0.0 | 0.0 | 3.5 |  | 2.5 | 2.0 | 4.5 |
|  | 0.0313 | 3.0 | 0.0 | 0.0 | 1.0 | 0.0 | 0.0 |  | 0.0 | 0.0 | 3.5 |  | 2.0 | 2.5 | 3.5 |
|  | 0.0156 | 1.0 | 0.0 | 0.0 | 0.0 | 0.0 | 0.0 |  | 0.0 | 0.0 | 3.5 |  | 2.5 | 2.0 | 3.5 |
| 215 | 0.2500 | 1.0 | 1.0 | 0.0 | 4.0 | 1.0 | 1.0 |  | 1.0 | 5.0 | 3.5 |  | 1.0 | 1.0 | 2.5 |
|  | 0.1250 | 0.0 | 1.0 | 0.0 | 2.0 | 0.0 | 1.0 |  | 0.0 | 6.0 | 4.0 |  | 0.5 | 0.5 | 2.0 |
|  | 0.0625 | 0.0 | 0.0 | 0.0 | 3.0 | 0.0 | 1.0 |  | 0.0 | 1.0 | 3.0 |  | 1.0 | 1.0 | 0.5 |
|  | 0.0313 | 0.0 | 0.0 | 0.0 | 0.0 | 0.0 | 0.0 |  | 0.0 | 0.0 | 2.5 |  | 0.5 | 0.5 | 0.5 |
|  | 0.0156 | 0.0 | 0.0 | 0.0 | 0.0 | 0.0 | 0.0 |  | 0.0 | 0.0 | 2.0 |  | 0.5 | 0.5 | 0.5 |
| 216 | 0.2500 | 5.0 | 3.0 | 1.0 | 4.0 | 0.0 | 1.0 |  | 0.0 | 0.0 | 3.5 |  | 1.0 | 1.0 | 1.5 |
|  | 0.1250 | 4.0 | 3.0 | 0.0 | 4.0 | 0.0 | 0.0 |  | 0.0 | 0.0 | 4.0 |  | 1.0 | 0.5 | 1.0 |
|  | 0.0625 | 2.0 | 1.0 | 0.0 | 1.0 | 0.0 | 1.0 |  | 0.0 | 0.0 | 4.0 |  | 0.5 | 0.5 | 1.0 |
|  | 0.0313 | 1.0 | 0.0 | 0.0 | 0.0 | 0.0 | 0.0 |  | 0.0 | 0.0 | 4.0 |  | 0.0 | 0.0 | 1.0 |
|  | 0.0156 | 0.0 | 0.0 | 0.0 | 0.0 | 0.0 | 1.0 |  | 0.0 | 0.0 | 3.5 |  | 0.0 | 0.0 | 2.0 |
| 217 | 0.2500 | 9.0 | 1.0 | 1.0 | 4.0 | 3.0 | 3.0 |  | 0.0 | 0.0 | 3.5 |  | 2.5 | 3.5 | 4.0 |
|  | 0.1250 | 9.0 | 1.0 | 0.0 | 2.0 | 1.0 | 2.0 |  | 0.0 | 9.0 | 4.0 |  | 1.0 | 2.0 | 3.5 |
|  | 0.0625 | 9.0 | 0.0 | 0.0 | 0.0 | 0.0 | 3.0 |  | 0.0 | 0.0 | 4.5 |  | 2.5 | 3.0 | 4.5 |
|  | 0.0313 | 4.0 | 1.0 | 1.0 | 1.0 | 0.0 | 3.0 |  | 0.0 | 0.0 | 3.5 |  | 2.0 | 3.0 | 3.0 |
|  | 0.0156 | 0.0 | 0.0 | 0.0 | 0.0 | 0.0 | 3.0 |  | 0.0 | 3.0 | 4.5 |  | 2.0 | 2.0 | 4.0 |
| 218 | 0.2500 | 5.0 | 1.0 | 1.0 | 2.0 | 2.0 | 0.0 |  | 0.0 | 0.0 | 4.0 |  | 1.0 | 1.0 | 2.0 |
|  | 0.1250 | 2.0 | 0.0 | 0.0 | 3.0 | 1.0 | 0.0 |  | 0.0 | 0.0 | 3.5 |  | 0.5 | 0.5 | 1.0 |
|  | 0.0625 | 0.0 | 0.0 | 0.0 | 0.0 | 0.0 | 0.0 |  | 0.0 | 0.0 | 3.5 |  | 0.5 | 0.5 | 1.0 |
|  | 0.0313 | 0.0 | 0.0 | 0.0 | 0.0 | 0.0 | 0.0 |  | 0.0 | 0.0 | 3.5 |  | 0.5 | 1.0 | 1.5 |
|  | 0.0156 | 0.0 | 0.0 | 0.0 | 0.0 | 0.0 | 0.0 |  | 0.0 | 0.0 | 3.5 |  | 0.5 | 1.0 | 1.5 |
| 219 | 0.2500 | 9.0 | 9.0 | 4.0 | 9.0 | 9.0 | 9.0 |  | 2.0 | 9.0 | 9.0 |  | 6.0 | 6.5 | 7.0 |
|  | 0.1250 | 9.0 | 9.0 | 2.0 | 9.0 | 9.0 | 9.0 |  | 0.0 | 9.0 | 9.0 |  | 4.5 | 6.0 | 6.0 |
|  | 0.0625 | 9.0 | 7.0 | 0.0 | 9.0 | 7.0 | 9.0 |  | 0.0 | 3.0 | 8.5 |  | 3.5 | 5.0 | 5.0 |
|  | 0.0313 | 9.0 | 4.0 | 0.0 | 3.0 | 5.0 | 4.0 |  | 0.0 | 0.0 | 7.0 |  | 2.0 | 4.5 | 4.5 |
|  | 0.0156 | 9.0 | 1.0 | 0.0 | 3.0 | 0.0 | 4.0 |  | 0.0 | 0.0 | 5.5 |  | 2.0 | 3.0 | 4.5 |
| 220 | 0.2500 | 9.0 | 9.0 | 9.0 | 9.0 | 9.0 | 9.0 |  | 5.0 | 9.0 | 8.5 |  | 6.0 | 7.0 | 8.0 |

TABLE I-continued

Postemergence Herbicidal Evaluations of Test Compounds

| Compound Number | Rate (kg/ha) | ABUTH | AMBEL | CASOB | CHEAL | GALAP | IPOHE | IPOSS | ECHCG | SETVI | GLXMAW | GLXMA | ORYSAT | TRZAWR | ZEAMX |
|---|---|---|---|---|---|---|---|---|---|---|---|---|---|---|---|
|  | 0.1250 | 9.0 | 9.0 | 3.0 | 9.0 | 7.0 | 9.0 |  | 3.0 | 9.0 | 7.5 |  | 6.0 | 6.0 | 8.0 |
|  | 0.0625 | 9.0 | 7.0 | 1.0 | 9.0 | 4.0 | 9.0 |  | 0.0 | 9.0 | 7.5 |  | 6.0 | 6.0 | 7.0 |
|  | 0.0313 | 9.0 | 5.0 | 1.0 | 9.0 | 4.0 | 9.0 |  | 0.0 | 5.0 | 5.5 |  | 3.0 | 5.5 | 6.0 |
|  | 0.0156 | 9.0 | 1.0 | 0.0 | 4.0 | 4.0 | 9.0 |  | 0.0 |  | 5.0 |  | 2.0 | 4.5 | 4.5 |
| 221 | 0.2500 | 9.0 | 9.0 | 9.0 | 9.0 | 9.0 | 9.0 |  | 2.0 | 9.0 | 8.5 |  | 4.0 | 5.0 | 6.5 |
|  | 0.1250 | 9.0 | 9.0 | 7.0 | 9.0 | 8.0 | 9.0 |  | 2.0 | 9.0 | 7.5 |  | 3.5 | 5.0 | 6.5 |
|  | 0.0625 | 9.0 | 4.0 | 9.0 | 9.0 | 9.0 | 9.0 |  | 2.0 | 7.0 | 7.0 |  | 3.0 | 4.5 | 6.0 |
|  | 0.0313 | 9.0 | 3.0 | 3.0 | 9.0 | 6.0 | 9.0 |  | 0.0 |  | 6.0 |  | 2.0 | 3.5 | 5.0 |
|  | 0.0156 | 9.0 | 3.0 | 0.0 | 8.0 | 3.0 | 9.0 |  | 0.0 |  | 5.5 |  | 2.0 | 4.0 | 5.0 |
| 222 | 0.2500 | 9.0 | 9.0 | 9.0 | 9.0 | 7.0 | 9.0 |  | 1.0 | 9.0 | 6.5 |  | 2.0 | 4.0 | 6.0 |
|  | 0.1250 | 9.0 | 7.0 | 7.0 | 9.0 | 7.0 | 9.0 |  | 0.0 | 9.0 | 6.5 |  | 2.0 | 4.0 | 6.0 |
|  | 0.0625 | 9.0 | 9.0 | 3.0 | 9.0 | 7.0 | 9.0 |  | 0.0 | 9.0 | 6.0 |  | 1.0 | 4.0 | 5.0 |
|  | 0.0313 | 9.0 | 4.0 | 2.0 | 7.0 | 5.0 | 7.0 |  | 0.0 | 6.0 | 5.5 |  | 0.5 | 3.5 | 5.0 |
|  | 0.0156 | 9.0 | 3.0 | 0.0 | 4.0 | 5.0 | 3.0 |  | 0.0 |  | 4.5 |  | 0.5 | 3.0 | 5.0 |
| 223 | 0.2500 | 9.0 | 9.0 | 9.0 | 9.0 | 9.0 | 9.0 |  | 9.0 | 9.0 | 9.0 |  | 7.0 | 7.0 | 7.0 |
|  | 0.1250 | 9.0 | 9.0 | 7.0 | 9.0 | 7.0 | 9.0 |  | 4.0 | 9.0 | 9.0 |  | 5.0 | 6.0 | 7.0 |
|  | 0.0625 | 9.0 | 5.0 | 6.0 | 8.0 | 7.0 | 9.0 |  | 3.0 | 9.0 | 7.5 |  | 5.0 | 5.5 | 6.5 |
|  | 0.0313 | 9.0 | 5.0 | 4.0 | 7.0 | 3.0 | 7.0 |  | 3.0 | 4.0 | 6.0 |  | 4.5 | 5.0 | 5.5 |
|  | 0.0156 | 9.0 | 5.0 | 0.0 | 9.0 | 5.0 | 9.0 |  | 2.0 | 4.0 | 6.0 |  | 3.0 | 4.5 | 5.5 |
| 224 | 0.1250 | 9.0 | 9.0 | 4.0 | 9.0 | 9.0 | 9.0 |  | 2.0 | 3.0 | 6.5 |  | 5.0 | 5.5 | 6.5 |
|  | 0.0625 | 9.0 | 6.0 | 4.0 | 6.0 | 7.0 | 9.0 |  | 2.0 | 3.0 | 7.5 |  | 5.0 | 5.0 | 6.5 |
|  | 0.0313 | 9.0 | 6.0 | 1.0 | 6.0 | 4.0 | 9.0 |  | 2.0 | 1.0 | 5.5 |  | 4.5 | 5.0 | 6.0 |
|  | 0.0156 | 9.0 | 3.0 | 1.0 | 5.0 | 3.0 | 7.0 |  | 0.0 | 1.0 | 5.0 |  | 3.0 | 4.0 | 6.0 |
| 225 | 0.2500 | 9.0 | 9.0 | 7.0 | 9.0 | 9.0 | 9.0 |  | 4.0 | 7.0 | 9.0 |  | 5.0 | 6.0 | 6.5 |
|  | 0.1250 | 9.0 | 9.0 | 6.0 | 9.0 | 7.0 | 9.0 |  | 3.0 | 4.0 | 6.0 |  | 3.5 | 4.0 | 6.0 |
|  | 0.0625 | 9.0 | 9.0 | 3.0 | 7.0 | 6.0 | 9.0 |  | 3.0 | 5.0 | 6.0 |  | 3.0 | 4.0 | 6.0 |
|  | 0.0313 | 9.0 | 6.0 | 1.0 | 4.0 | 3.0 | 9.0 |  | 1.0 | 2.0 | 5.5 |  | 3.0 | 3.0 | 5.0 |
|  | 0.0156 | 9.0 | 4.0 | 1.0 | 4.0 | 2.0 | 9.0 |  | 1.0 | 2.0 | 4.5 |  | 3.0 | 2.5 | 5.0 |
| 226 | 0.0630 | 9.0 | 9.0 | 3.0 | 9.0 | 2.0 | 9.0 |  | 3.0 | 9.0 | 5.0 |  | 3.0 | 5.0 | 6.5 |
|  | 0.0315 | 9.0 | 9.0 | 6.0 | 9.0 | 2.0 | 8.0 |  | 2.0 | 8.0 | 5.0 |  | 2.5 | 4.0 | 6.0 |
|  | 0.0158 | 9.0 | 4.0 | 0.0 | 4.0 | 0.0 | 9.0 |  | 2.0 | 7.0 | 4.5 |  | 2.0 | 3.5 | 5.5 |
| 227 | 0.0630 | 9.0 | 9.0 | 0.0 | 9.0 | 6.0 | 9.0 |  | 7.0 | 9.0 | 8.0 |  | 1.5 | 4.5 | 8.5 |
|  | 0.0315 | 9.0 | 9.0 | 0.0 | 9.0 | 2.0 | 9.0 |  | 3.0 | 8.0 | 5.5 |  | 1.5 | 4.0 | 6.0 |
|  | 0.0158 | 9.0 | 9.0 | 0.0 | 9.0 | 0.0 | 9.0 |  | 0.0 | 3.0 | 5.0 |  | 1.5 | 4.0 | 5.5 |
| 228 | 0.0630 | 9.0 | 9.0 | 4.0 | 5.0 | 0.0 | 9.0 |  | 2.0 | 9.0 | 6.0 |  | 2.0 | 5.5 | 6.0 |
|  | 0.0315 | 9.0 | 6.0 | 3.0 | 5.0 | 3.0 | 9.0 |  | 2.0 | 7.0 | 4.5 |  | 2.0 | 4.0 | 5.5 |
|  | 0.0158 | 3.0 | 0.0 | 0.0 | 4.0 | 0.0 | 6.0 |  | 2.0 | 6.0 | 5.5 |  | 1.5 | 3.5 | 4.5 |
| 229 | 0.0630 | 3.0 | 0.0 | 0.0 | 4.0 | 1.0 | 2.0 |  | 0.0 | 4.0 | 4.0 |  | 1.0 | 3.5 | 4.5 |
|  | 0.0315 | 2.0 | 0.0 | 0.0 | 0.0 | 0.0 | 1.0 |  | 0.0 | 0.0 | 3.5 |  | 1.0 | 3.5 | 4.5 |
|  | 0.0158 | 9.0 | 9.0 | 0.0 | 9.0 | 3.0 | 9.0 |  | 2.0 | 0.0 | 6.0 |  | 2.5 | 6.5 | 6.5 |
| 230 | 0.0630 | 9.0 | 9.0 | 2.0 | 9.0 | 0.0 | 9.0 |  | 0.0 | 0.0 | 6.0 |  | 2.5 | 5.0 | 5.5 |
|  | 0.0315 | 9.0 | 9.0 | 0.0 | 6.0 | 0.0 | 9.0 |  | 0.0 |  | 5.5 |  | 1.5 | 3.0 | 5.5 |
|  | 0.0158 | 9.0 | 9.0 | 4.0 | 9.0 | 4.0 | 9.0 |  | 9.0 | 9.0 | 6.5 |  | 2.5 | 5.0 | 7.0 |
| 231 | 0.0630 | 9.0 | 9.0 | 2.0 | 5.0 | 2.0 | 9.0 |  | 4.0 | 9.0 | 6.0 |  | 2.0 | 4.5 | 5.5 |
|  | 0.0315 | 9.0 | 4.0 | 2.0 | 5.0 | 2.0 | 9.0 |  | 4.0 | 7.0 | 6.0 |  | 2.0 | 4.5 | 5.5 |
|  | 0.0158 | 9.0 | 9.0 | 6.0 | 9.0 | 2.0 | 9.0 |  | 6.0 | 9.0 | 7.5 |  | 3.0 | 7.5 | 8.5 |
| 232 | 0.0630 | 9.0 | 9.0 | 6.0 | 9.0 | 2.0 | 9.0 |  | 6.0 | 9.0 | 7.5 |  | 3.0 | 7.5 | 8.5 |

TABLE I-continued

Postemergence Herbicidal Evaluations of Test Compounds

| Compound Number | Rate (kg/ha) | ABUTH | AMBEL | CASOB | CHEAL | GALAP | IPOHE | IPOSS | ECHCG | SETVI | GLXMAW | GLXMA | ORYSAT | TRZAWR | ZEAMX |
|---|---|---|---|---|---|---|---|---|---|---|---|---|---|---|---|
| 233 | 0.0315 | 9.0 | 9.0 | 6.0 | 9.0 | 0.0 | 9.0 | | 6.0 | 8.0 | 7.0 | | 2.5 | 6.5 | 7.0 |
| | 0.0158 | 9.0 | 7.0 | 3.0 | 9.0 | 0.0 | 9.0 | | 5.0 | 5.0 | 6.5 | | 2.5 | 7.0 | 6.0 |
| | 0.0630 | 9.0 | 9.0 | 3.0 | 9.0 | 0.0 | 9.0 | | 0.0 | 7.0 | 5.5 | | 1.5 | 4.0 | 5.5 |
| | 0.0315 | 9.0 | 8.0 | 0.0 | 7.0 | 0.0 | 9.0 | | 0.0 | 7.0 | 5.5 | | 1.5 | 4.0 | 5.5 |
| | 0.0158 | 4.0 | 3.0 | 0.0 | 4.0 | 0.0 | 9.0 | | 0.0 | 4.0 | 5.0 | | 1.0 | 4.0 | 5.5 |
| 234 | 0.0630 | 9.0 | 9.0 | 7.0 | 9.0 | 4.0 | 9.0 | | 5.0 | 9.0 | 5.5 | | 2.5 | 4.5 | 7.0 |
| | 0.0315 | 9.0 | 9.0 | 0.0 | 9.0 | 0.0 | 9.0 | | 0.0 | 6.0 | 5.0 | | 2.0 | 3.5 | 5.5 |
| | 0.0158 | 9.0 | 9.0 | 0.0 | 4.0 | 0.0 | 7.0 | | 0.0 | 7.0 | 5.0 | | 1.0 | 2.5 | 4.5 |
| 235 | 0.0630 | 9.0 | 9.0 | 4.0 | 9.0 | 3.0 | 9.0 | | 4.0 | 9.0 | 6.0 | | 2.5 | 5.5 | 6.5 |
| | 0.0315 | 7.0 | 7.0 | 4.0 | 5.0 | 0.0 | 9.0 | | 0.0 | 9.0 | 6.0 | | 2.5 | 4.0 | 6.5 |
| | 0.0158 | 9.0 | 9.0 | 4.0 | 5.0 | 0.0 | 9.0 | | 0.0 | 3.0 | 5.5 | | 1.5 | 3.5 | 5.0 |
| 236 | 0.1250 | 9.0 | 4.0 | 1.0 | 6.0 | 2.0 | 2.0 | | 1.0 | 1.0 | 4.5 | | 2.5 | 3.0 | 5.0 |
| | 0.0625 | 8.0 | 3.0 | 1.0 | 5.0 | 2.0 | 2.0 | | 1.0 | 1.0 | 4.0 | | 2.0 | 2.0 | 5.0 |
| | 0.0313 | 6.0 | 1.0 | 1.0 | 4.0 | 7.0 | 3.0 | | 1.0 | 1.0 | 4.0 | | 2.0 | 2.0 | 4.5 |
| | 0.0156 | 4.0 | 2.0 | 1.0 | 3.0 | 1.0 | 1.0 | | 0.0 | 0.0 | 2.5 | | 1.5 | 1.5 | 3.5 |
| 237 | 0.1250 | 9.0 | 6.0 | 4.0 | 7.0 | 7.0 | 9.0 | | 2.0 | 7.0 | 6.0 | | 3.0 | 3.5 | 5.0 |
| | 0.0625 | 9.0 | 6.0 | 3.0 | 9.0 | 5.0 | 9.0 | | 3.0 | 9.0 | 5.5 | | 3.0 | 3.0 | 5.0 |
| | 0.0313 | 9.0 | 5.0 | 2.0 | 6.0 | 3.0 | 4.0 | | 2.0 | 4.0 | 4.0 | | 1.5 | 2.0 | 5.0 |
| | 0.0156 | 2.0 | 3.0 | 0.0 | 2.0 | 1.0 | 1.0 | | 0.0 | 0.0 | 2.5 | | 1.0 | 2.0 | 4.0 |
| 238 | 0.1250 | 9.0 | 9.0 | 4.0 | 9.0 | 6.0 | 9.0 | | 2.0 | 4.0 | 5.5 | | 2.5 | 3.0 | 5.0 |
| | 0.0625 | 9.0 | 9.0 | 3.0 | 7.0 | 5.0 | 9.0 | | 1.0 | 2.0 | 5.0 | | 2.5 | 3.0 | 4.5 |
| | 0.0313 | 9.0 | 7.0 | 2.0 | 6.0 | 3.0 | 9.0 | | 1.0 | 2.0 | 4.5 | | 2.0 | 2.0 | 4.5 |
| | 0.0156 | 5.0 | 4.0 | 1.0 | 3.0 | 2.0 | 3.0 | | 1.0 | 1.0 | 3.5 | | 0.5 | 1.0 | 3.5 |
| 239 | 0.1250 | 9.0 | 9.0 | 6.0 | 9.0 | 7.0 | 9.0 | | 5.0 | 9.0 | 7.0 | | 4.0 | 5.0 | 5.5 |
| | 0.0625 | 9.0 | 9.0 | 4.0 | 7.0 | 5.0 | 9.0 | | 3.0 | 3.0 | 6.0 | | 3.0 | 3.5 | 5.5 |
| | 0.0313 | 9.0 | 9.0 | 3.0 | 6.0 | 4.0 | 9.0 | | 2.0 | 2.0 | 5.5 | | 2.0 | 2.5 | 5.0 |
| | 0.0156 | 9.0 | 5.0 | 2.0 | 4.0 | 2.0 | 9.0 | | 1.0 | 2.0 | 4.0 | | 2.0 | 2.5 | 4.0 |
| 240 | 0.1250 | | | | | | | | | | 7.0 | | 5.0 | 6.0 | 6.0 |
| | 0.0625 | | | | | | | | | | 7.0 | | 4.0 | 5.0 | 6.0 |
| | 0.0313 | | | | | | | | | | 7.0 | | 3.0 | 4.0 | 6.0 |
| | 0.0156 | | | | | | | | | | 6.0 | | 3.0 | 3.0 | 5.0 |
| 241 | 0.1250 | | | | | | | | | | 6.0 | | 4.0 | 5.0 | 5.0 |
| | 0.0625 | | | | | | | | | | 6.0 | | 3.0 | 4.0 | 5.0 |
| | 0.0313 | | | | | | | | | | 6.0 | | 3.0 | 5.0 | 4.0 |
| | 0.0156 | | | | | | | | | | 5.0 | | 3.0 | 4.0 | 4.0 |
| 242 | 0.1250 | | | | | | | | | | 7.0 | | 5.0 | 5.0 | 6.0 |
| | 0.0625 | | | | | | | | | | 7.0 | | 4.0 | 5.0 | 6.0 |
| | 0.0313 | | | | | | | | | | 7.0 | | 4.0 | 4.0 | 6.0 |
| | 0.0156 | | | | | | | | | | 6.0 | | 4.0 | 5.0 | 6.0 |
| 243 | 0.1250 | | | | | | | | | | 7.0 | | 4.0 | 4.0 | 6.0 |
| | 0.0625 | | | | | | | | | | 7.0 | | 4.0 | 5.0 | 6.0 |
| | 0.0313 | | | | | | | | | | 7.0 | | 4.0 | 4.0 | 5.0 |
| | 0.0156 | | | | | | | | | | 6.0 | | 4.0 | 4.0 | 6.0 |
| 244 | 0.1250 | | | | | | | | | | 7.0 | | 4.0 | 4.0 | 6.0 |
| | 0.0625 | | | | | | | | | | 7.0 | | 4.0 | 4.0 | 6.0 |
| | 0.0313 | | | | | | | | | | 6.0 | | 4.0 | 4.0 | 6.0 |
| | 0.0156 | | | | | | | | | | 6.0 | | 3.0 | 4.0 | 5.0 |

TABLE I-continued

Postemergence Herbicidal Evaluations of Test Compounds

| Compound Number | Rate (kg/ha) | ABUTH | AMBEL | CASOB | CHEAL | GALAP | IPOHE | IPOSS | ECHCG | SETVI | GLXMAW | GLXMA | ORYSAT | TRZAWR | ZEAMX |
|---|---|---|---|---|---|---|---|---|---|---|---|---|---|---|---|
| 245 | 0.0630 | 0.0 | 0.0 | 0.0 | 0.0 | 0.0 | 0.0 | | 0.0 | 0.0 | 1.0 | | 0.5 | 0.0 | 0.5 |
| | 0.0315 | 0.0 | 0.0 | 0.0 | 0.0 | 0.0 | 0.0 | | 0.0 | 0.0 | 0.0 | | 0.0 | 0.0 | 0.0 |
| | 0.0158 | 0.0 | 0.0 | 0.0 | 0.0 | 0.0 | 0.0 | | 0.0 | 0.0 | 0.0 | | 0.0 | 0.0 | 0.0 |
| 246 | 0.0630 | 9.0 | 2.0 | 0.0 | 2.0 | 1.0 | 6.0 | | 5.0 | 8.0 | 4.5 | | 3.0 | 4.5 | 7.5 |
| | 0.0315 | 9.0 | 0.0 | 0.0 | 2.0 | 0.0 | 9.0 | | 6.0 | 3.0 | 4.0 | | 2.5 | 3.0 | 6.0 |
| | 0.0158 | 0.0 | 0.0 | 0.0 | 0.0 | 0.0 | 1.0 | | 1.0 | 1.0 | 4.0 | | 2.0 | 2.5 | 5.0 |
| 247 | 0.1250 | | | | | | | | | | 8.0 | | 6.0 | 6.0 | 7.0 |
| | 0.0625 | | | | | | | | | | 8.0 | | 5.0 | 5.0 | 6.0 |
| | 0.0313 | | | | | | | | | | 8.0 | | 3.0 | 5.0 | 6.0 |
| | 0.0156 | | | | | | | | | | 7.0 | | 3.0 | 6.0 | 6.0 |
| 248 | 0.5000 | | | | | | | | | | 7.0 | | 5.0 | 6.0 | 7.0 |
| | 0.2500 | | | | | | | | | | 7.0 | | 4.0 | 4.0 | 7.0 |
| | 0.1250 | | | | | | | | | | 6.0 | | 2.0 | 4.0 | 6.0 |
| | 0.0625 | | | | | | | | | | 6.0 | | 1.0 | 4.0 | 5.0 |
| | 0.0313 | | | | | | | | | | 5.0 | | 1.0 | 4.0 | 5.0 |
| | 0.0156 | | | | | | | | | | 5.0 | | 1.0 | 3.0 | 4.0 |
| 249 | 0.1250 | | | | | | | | | | 9.0 | | 9.0 | 9.0 | 8.0 |
| | 0.0625 | | | | | | | | | | 8.0 | | 9.0 | 8.0 | 8.0 |
| | 0.0313 | | | | | | | | | | 8.0 | | 8.0 | 7.0 | 8.0 |
| | 0.0156 | | | | | | | | | | 8.0 | | 5.0 | 6.0 | 8.0 |
| 250 | 0.1250 | | | | | | | | | | 8.0 | | 7.0 | 5.0 | 5.0 |
| | 0.0625 | | | | | | | | | | 8.0 | | 7.0 | 4.0 | 5.0 |
| | 0.0313 | | | | | | | | | | 8.0 | | 3.0 | 4.0 | 5.0 |
| | 0.0156 | | | | | | | | | | 7.0 | | 2.0 | 4.0 | 5.0 |
| 251 | 0.1250 | | | | | | | | | | 6.0 | | 9.0 | 8.0 | 8.0 |
| | 0.0625 | | | | | | | | | | 9.0 | | 8.0 | 8.0 | 8.0 |
| | 0.0313 | | | | | | | | | | 8.0 | | 8.0 | 8.0 | 8.0 |
| | 0.0156 | | | | | | | | | | 8.0 | | 5.0 | 7.0 | 6.0 |
| 252 | 0.1250 | | | | | | | | | | 8.0 | | 4.0 | 4.0 | 6.0 |
| | 0.0625 | | | | | | | | | | 7.0 | | 3.0 | 4.0 | 6.0 |
| | 0.0313 | | | | | | | | | | 7.0 | | 2.0 | 2.0 | 4.0 |
| | 0.0156 | | | | | | | | | | 5.0 | | 0.0 | 2.0 | 4.0 |
| 253 | 0.1250 | | | | | | | | | | 5.0 | | 0.0 | 8.0 | 8.0 |
| | 0.0625 | | | | | | | | | | 9.0 | | 9.0 | 8.0 | 8.0 |
| | 0.0313 | | | | | | | | | | 9.0 | | 8.0 | 8.0 | 8.0 |
| | 0.0156 | | | | | | | | | | 8.0 | | 8.0 | 8.0 | 8.0 |
| 254 | 0.1250 | | | | | | | | | | 8.0 | | 7.0 | 6.0 | 7.0 |
| | 0.0625 | | | | | | | | | | 9.0 | | 9.0 | 9.0 | 8.0 |
| | 0.0313 | | | | | | | | | | 9.0 | | 9.0 | 9.0 | 8.0 |
| | 0.0156 | | | | | | | | | | 8.0 | | 8.0 | 8.0 | 8.0 |
| 255 | 0.1250 | | | | | | | | | | 8.0 | | 6.0 | 7.0 | 7.0 |
| | 0.0625 | | | | | | | | | | 6.0 | | 2.0 | 4.0 | 6.0 |
| | 0.0313 | | | | | | | | | | 5.0 | | 3.0 | 3.0 | 6.0 |
| | 0.0156 | | | | | | | | | | 4.0 | | 1.0 | 2.0 | 4.0 |
| 256 | 0.0620 | 9.0 | 9.0 | 4.0 | 9.0 | 9.0 | 9.0 | | 2.0 | 9.0 | 1.0 | | 0.0 | 1.0 | 1.0 |
| | 0.0320 | 9.0 | 9.0 | 2.0 | 9.0 | 9.0 | 9.0 | | 0.0 | 7.0 | 9.0 | | 7.0 | 6.5 | 7.0 |
| | 0.0160 | 9.0 | 9.0 | 0.0 | 9.0 | 7.0 | 9.0 | | 0.0 | 0.0 | 9.0 | | 5.5 | 5.0 | 6.5 |
| | | | | | | | | | | | 9.0 | | 4.0 | 3.5 | 5.0 |

TABLE I-continued

Postemergence Herbicidal Evaluations of Test Compounds

| Compound Number | Rate (kg/ha) | ABUTH | AMBEL | CASOB | CHEAL | GALAP | IPOHE | IPOSS | ECHCG | SETVI | GLXMAW | GLXMA | ORYSAT | TRZAWR | ZEAMX |
|---|---|---|---|---|---|---|---|---|---|---|---|---|---|---|---|
| 257 | 0.0620 | 9.0 | 9.0 | 9.0 | 9.0 | 9.0 | 9.0 | | 9.0 | 9.0 | 9.0 | | 6.0 | 9.0 | 8.0 |
| | 0.0320 | 9.0 | 9.0 | 9.0 | 9.0 | 7.0 | 9.0 | | 9.0 | 9.0 | 9.0 | | 5.5 | 8.5 | 8.0 |
| | 0.0160 | 9.0 | 9.0 | 2.0 | 9.0 | 9.0 | 9.0 | | 7.0 | 7.0 | 9.0 | | 2.0 | 6.5 | 7.0 |
| 258 | 0.2500 | 9.0 | 9.0 | 9.0 | 9.0 | 9.0 | 9.0 | | 9.0 | 9.0 | 9.0 | | 9.0 | 9.0 | 9.0 |
| | 0.1250 | 9.0 | 9.0 | 9.0 | 9.0 | 9.0 | 9.0 | | 9.0 | 9.0 | 9.0 | | 9.0 | 8.0 | 9.0 |
| | 0.0620 | 9.0 | 9.0 | 9.0 | 9.0 | 9.0 | 9.0 | | 9.0 | 9.0 | 9.0 | | 9.0 | 9.0 | 9.0 |
| | 0.0320 | 8.9 | 9.0 | 4.0 | 9.0 | 9.0 | 9.0 | | 9.0 | 9.0 | 9.0 | | 9.0 | 9.0 | 9.0 |
| | 0.0160 | 8.6 | 9.0 | 9.0 | 9.0 | 7.0 | 9.0 | | 8.0 | 9.0 | 8.5 | | 7.0 | 8.0 | 8.5 |
| 259 | 0.0620 | 9.0 | 9.0 | 9.0 | 9.0 | 7.0 | 9.0 | | 9.0 | 9.0 | 9.0 | | 5.0 | 8.0 | 8.0 |
| | 0.0320 | 9.0 | 9.0 | 3.0 | 9.0 | 8.0 | 9.0 | | 9.0 | 9.0 | 9.0 | | 3.5 | 6.5 | 8.0 |
| | 0.0160 | 9.0 | 9.0 | 0.0 | 9.0 | 9.0 | 9.0 | | 6.0 | 7.0 | 8.0 | | 2.5 | 5.5 | 8.0 |
| 260 | 0.1250 | 3.0 | 0.0 | 0.0 | 0.0 | 0.0 | 1.0 | | 0.0 | 0.0 | 2.5 | | 3.0 | 2.0 | 1.0 |
| | 0.0620 | 0.0 | 0.0 | 0.0 | 0.0 | 0.0 | 0.0 | | 0.0 | 0.0 | 2.5 | | 2.0 | 2.0 | 1.0 |
| 261 | 0.0620 | 9.0 | 9.0 | 0.0 | 9.0 | 4.0 | 9.0 | | 9.0 | 9.0 | 9.0 | | 8.0 | 7.0 | 8.0 |
| | 0.0320 | 9.0 | 8.0 | 0.0 | 5.0 | 3.0 | 9.0 | | 7.0 | 9.0 | 7.5 | | 8.0 | 6.0 | 7.5 |
| | 0.0160 | 9.0 | 3.0 | 0.0 | 3.0 | 2.0 | 9.0 | | 2.0 | 3.0 | 6.5 | | 6.5 | 5.0 | 7.0 |
| 262 | 0.1250 | 9.0 | 3.0 | 0.0 | 9.0 | 8.0 | 9.0 | | 0.0 | 0.0 | 6.5 | | 3.5 | 4.5 | 5.0 |
| | 0.0620 | 9.0 | 3.0 | 0.0 | 0.0 | 5.0 | 1.0 | | 0.0 | 0.0 | 6.0 | | 3.0 | 4.0 | 4.5 |
| | 0.0320 | 9.0 | 3.0 | 0.0 | 0.0 | 0.0 | 0.0 | | 0.0 | 0.0 | 4.0 | | 1.5 | 3.5 | 4.0 |
| | 0.0160 | 9.0 | 1.0 | 0.0 | 3.0 | 4.0 | 9.0 | | 0.0 | 0.0 | 4.0 | | 1.0 | 3.0 | 4.0 |
| 263 | 0.1250 | 9.0 | 0.0 | 0.0 | 3.0 | 3.0 | 4.0 | | 0.0 | 0.0 | 7.0 | | 2.5 | 4.0 | 5.0 |
| | 0.0620 | 9.0 | 9.0 | 0.0 | 3.0 | 3.0 | 4.0 | | 0.0 | 0.0 | 4.5 | | 1.5 | 4.0 | 4.5 |
| | 0.0320 | 9.0 | 0.0 | 0.0 | 0.0 | 0.0 | 4.0 | | 0.0 | 0.0 | 4.0 | | 1.0 | 4.0 | 3.0 |
| | 0.0160 | 9.0 | 9.0 | 0.0 | 5.0 | 9.0 | 9.0 | | 0.0 | 0.0 | 3.0 | | 0.5 | 3.0 | 3.0 |
| 264 | 0.1250 | 9.0 | 5.0 | 0.0 | 3.0 | 8.0 | 9.0 | | 0.0 | 0.0 | 6.5 | | 1.5 | 2.5 | 5.0 |
| | 0.0620 | 9.0 | 5.0 | 0.0 | 0.0 | 5.0 | 9.0 | | 0.0 | 0.0 | 5.0 | | 0.5 | 2.0 | 4.0 |
| | 0.0320 | 9.0 | 2.0 | 0.0 | 0.0 | 7.0 | 4.0 | | 0.0 | 0.0 | 5.0 | | 0.5 | 1.5 | 3.5 |
| | 0.0160 | 9.0 | 0.0 | 0.0 | 9.0 | 7.0 | 0.0 | | 0.0 | 0.0 | 3.0 | | 0.5 | 1.5 | 3.0 |
| 265 | 0.1250 | 2.0 | 0.0 | 0.0 | 5.0 | 5.0 | 0.0 | | 0.0 | 0.0 | 4.5 | | 0.5 | 3.0 | 7.0 |
| | 0.0620 | 2.0 | 0.0 | 0.0 | 5.0 | 5.0 | 0.0 | | 0.0 | 0.0 | 3.5 | | 5.5 | 3.0 | 4.5 |
| | 0.0320 | 0.0 | 0.0 | 0.0 | 3.0 | 0.0 | 0.0 | | 0.0 | 0.0 | 3.0 | | 3.5 | 1.0 | 3.5 |
| | 0.0160 | 0.0 | 0.0 | 0.0 | 0.0 | 4.0 | 0.0 | | 0.0 | 0.0 | 2.0 | | 1.5 | 0.5 | 2.5 |
| 266 | 0.1250 | 9.0 | 5.0 | 9.0 | 9.0 | 9.0 | 9.0 | | 0.0 | 0.0 | 5.0 | | 0.5 | 5.5 | 5.5 |
| | 0.0620 | 9.0 | 3.0 | 6.0 | 7.0 | 4.0 | 9.0 | | 0.0 | 0.0 | 4.5 | | 3.0 | 4.0 | 3.5 |
| | 0.0320 | 9.0 | 0.0 | 0.0 | 0.0 | 2.0 | 0.0 | | 0.0 | 0.0 | 3.0 | | 2.0 | 2.5 | 3.5 |
| | 0.0160 | 0.0 | 0.0 | 0.0 | 0.0 | 0.0 | 0.0 | | 0.0 | 0.0 | 2.5 | | 1.0 | 1.5 | 1.5 |
| 267 | 0.1250 | 0.0 | 5.0 | 9.0 | 9.0 | 9.0 | 5.0 | | 0.0 | 0.0 | 5.0 | | 0.5 | 5.0 | 1.0 |
| | 0.0620 | 9.0 | 3.0 | 0.0 | 8.0 | 7.0 | 9.0 | | 0.0 | 0.0 | 4.5 | | 3.5 | 4.5 | 5.0 |
| | 0.0320 | 9.0 | 4.0 | 0.0 | 0.0 | 7.0 | 5.0 | | 0.0 | 0.0 | 3.5 | | 2.5 | 3.0 | 5.0 |
| | 0.0160 | 9.0 | 2.0 | 0.0 | 4.0 | 3.0 | 1.0 | | 0.0 | 0.0 | 3.0 | | 2.0 | 3.0 | 4.5 |
| 268 | 0.0620 | 9.0 | 9.0 | 9.0 | 9.0 | 9.0 | 9.0 | | 9.0 | 8.0 | 9.0 | | 7.3 | 6.3 | 8.5 |
| | 0.0320 | 9.0 | 9.0 | 6.0 | 9.0 | 7.0 | 9.0 | | 9.0 | 9.0 | 9.0 | | 8.0 | 7.0 | 9.0 |
| | 0.0160 | 9.0 | 9.0 | 0.0 | 9.0 | 3.0 | 5.0 | | 0.0 | 0.0 | 3.5 | | 3.0 | 2.5 | 4.5 |
| 269 | 0.0620 | 1.0 | 0.0 | 0.0 | 0.0 | 0.0 | 1.0 | | 0.0 | 0.0 | 3.0 | | 2.5 | 2.5 | 5.0 |
| | 0.0320 | 0.0 | 2.0 | 0.0 | 5.0 | 0.0 | 0.0 | | 0.0 | 0.0 | 3.0 | | 2.0 | 3.0 | 4.0 |
| 270 | 0.0620 | 9.0 | 9.0 | 9.0 | 9.0 | 4.0 | 9.0 | | 4.0 | 4.0 | 7.5 | | 7.0 | 7.0 | 7.5 |
| | 0.0320 | 9.0 | 5.0 | 2.0 | 6.0 | 2.0 | 9.0 | | 4.0 | 6.0 | 6.0 | | 5.0 | 4.5 | 6.5 |
| | 0.0160 | 9.0 | 5.0 | 0.0 | 5.0 | 1.0 | 9.0 | | 0.0 | 4.0 | 5.0 | | 4.0 | 4.5 | 4.5 |
| 271 | 0.0620 | 9.0 | 6.0 | 2.0 | 9.0 | 6.0 | 9.0 | | 1.0 | 3.0 | 5.5 | | 2.5 | 3.0 | 4.5 |

TABLE I-continued

Postemergence Herbicidal Evaluations of Test Compounds

| Compound Number | Rate (kg/ha) | ABUTH | AMBEL | CASOB | CHEAL | GALAP | IPOHE | IPOSS | ECHCG | SETVI | GLXMAW | GLXMA | ORYSAT | TRZAWR | ZEAMX |
|---|---|---|---|---|---|---|---|---|---|---|---|---|---|---|---|
| 272 | 0.0320 | 9.0 | 4.0 | 0.0 | 7.0 | 7.0 | 9.0 | | 1.0 | 1.0 | 4.5 | | 2.5 | 3.0 | 3.5 |
| | 0.0160 | 2.0 | 2.0 | 0.0 | 5.0 | 9.0 | 0.0 | | 0.0 | 0.0 | 4.0 | | 2.5 | 2.0 | 3.5 |
| | 0.1250 | 9.0 | 8.0 | 0.0 | 2.0 | 3.0 | 9.0 | | 0.0 | 0.0 | 6.0 | | 1.0 | 2.0 | 4.5 |
| | 0.0620 | 9.0 | 4.0 | 0.0 | 0.0 | 1.0 | 9.0 | | 0.0 | 0.0 | 5.5 | | 0.0 | 1.0 | 4.0 |
| | 0.0320 | 3.0 | 0.0 | 0.0 | 0.0 | 0.0 | 0.0 | | 0.0 | 0.0 | 4.5 | | 0.0 | 1.0 | 3.5 |
| | 0.0160 | 0.0 | 0.0 | 0.0 | 0.0 | 0.0 | 0.0 | | 0.0 | 0.0 | 2.5 | | 0.0 | 1.0 | 2.0 |
| 273 | 0.0620 | 9.0 | 9.0 | 9.0 | 9.0 | 5.0 | 9.0 | | 3.0 | 6.0 | 9.0 | | 3.5 | 4.5 | 5.5 |
| | 0.0320 | 9.0 | 7.0 | 9.0 | 9.0 | 5.0 | 9.0 | | 2.0 | 2.0 | 7.5 | | 3.5 | 4.5 | 6.0 |
| | 0.0160 | 9.0 | 6.0 | 2.0 | 7.0 | | 9.0 | | 1.0 | 1.0 | 5.0 | | 3.0 | 3.0 | 5.5 |
| 274 | 0.0620 | 9.0 | 9.0 | 6.0 | 6.0 | 5.0 | 9.0 | | 9.0 | 9.0 | 9.0 | | 9.0 | 7.5 | 9.0 |
| | 0.0320 | 9.0 | 7.0 | 2.0 | 7.0 | 3.0 | 7.0 | | 9.0 | 9.0 | 9.0 | | 7.5 | 7.5 | 7.5 |
| | 0.0160 | 9.0 | 6.0 | 2.0 | 4.0 | 2.0 | 9.0 | | 9.0 | 9.0 | 8.5 | | 7.5 | 5.5 | 7.5 |
| 275 | 0.0620 | 9.0 | 9.0 | 6.0 | 9.0 | 5.0 | 9.0 | | 9.0 | 9.0 | 6.5 | | 8.5 | 8.5 | 9.0 |
| | 0.0320 | 9.0 | 6.0 | 2.0 | 4.0 | 9.0 | 9.0 | | 7.0 | 5.0 | 6.0 | | 7.5 | 7.5 | 9.0 |
| | 0.0160 | 9.0 | 9.0 | 4.0 | 4.0 | 6.0 | 9.0 | | 6.0 | 7.0 | 4.5 | | 5.5 | 8.5 | 8.5 |
| 276 | 0.0620 | 9.0 | 7.0 | 4.0 | 6.0 | 6.0 | 9.0 | | 2.0 | 4.0 | 5.5 | | 3.5 | 4.5 | 5.0 |
| | 0.0320 | 9.0 | 9.0 | 2.0 | 3.0 | 3.0 | 9.0 | | 1.0 | 3.0 | 4.5 | | 2.5 | 2.5 | 3.5 |
| | 0.0160 | 9.0 | 3.0 | 1.0 | 1.0 | 4.0 | 4.0 | | 2.0 | 1.0 | 3.0 | | 1.5 | 1.5 | 3.0 |
| 277 | 0.0620 | 9.0 | 9.0 | 2.0 | 7.0 | 7.0 | 9.0 | | 2.0 | 5.0 | 8.0 | | 6.0 | 5.0 | 6.0 |
| | 0.0320 | 9.0 | 6.0 | 2.0 | 5.0 | 9.0 | 7.0 | | 1.0 | 4.0 | 8.0 | | 5.5 | 4.0 | 5.5 |
| | 0.0160 | 9.0 | 6.0 | 1.0 | 4.0 | 7.0 | 6.0 | | 2.0 | 2.0 | 5.0 | | 3.5 | 3.5 | 3.5 |
| 278 | 0.0620 | 9.0 | 7.0 | 1.0 | 6.0 | 9.0 | 9.0 | | 2.0 | 7.0 | 5.5 | | 4.5 | 4.5 | 5.0 |
| | 0.0320 | 9.0 | 4.0 | 1.0 | 3.0 | 9.0 | 6.0 | | 1.0 | 5.0 | 5.5 | | 4.5 | 2.5 | 4.5 |
| | 0.0160 | 6.0 | 2.0 | 0.0 | 1.0 | 1.0 | 5.0 | | 1.0 | 1.0 | 4.5 | | 2.0 | 1.5 | 2.0 |
| 279 | 0.0620 | 9.0 | 7.0 | 2.0 | 3.0 | 7.0 | 2.0 | | 3.0 | 3.0 | 6.5 | | 2.5 | 3.5 | 5.5 |
| | 0.0320 | 9.0 | 6.0 | 2.0 | 3.0 | 1.0 | 9.0 | | 2.0 | 3.0 | 6.0 | | 2.0 | 2.5 | 5.0 |
| | 0.0160 | 4.0 | 4.0 | 0.0 | 1.0 | 7.0 | 7.0 | | 2.0 | 1.0 | 4.0 | | 1.5 | 1.5 | 3.5 |
| 280 | 0.0620 | 9.0 | 9.0 | 9.0 | 8.0 | 9.0 | 0.0 | | 9.0 | 9.0 | 9.0 | | 9.0 | 7.5 | 9.0 |
| | 0.0320 | 9.0 | 9.0 | 4.0 | 9.0 | 6.0 | 9.0 | | 9.0 | 9.0 | 9.0 | | 7.0 | 7.0 | 8.0 |
| | 0.0160 | 9.0 | 9.0 | 4.0 | 9.0 | 6.0 | 9.0 | | 6.0 | 9.0 | 9.0 | | 8.0 | 6.0 | 8.0 |
| 281 | 0.0620 | 9.0 | 9.0 | 9.0 | 9.0 | 9.0 | 9.0 | | 7.0 | 9.0 | 9.0 | | 7.0 | 6.5 | 8.0 |
| | 0.0320 | 9.0 | 7.0 | 6.0 | 9.0 | 7.0 | 9.0 | | 6.0 | 7.0 | 9.0 | | 5.5 | 6.5 | 7.5 |
| | 0.0160 | 5.0 | 4.0 | 1.0 | 3.0 | 9.0 | 9.0 | | 1.0 | 9.0 | 7.5 | | 5.5 | 6.5 | 7.5 |
| 282 | 0.0620 | 1.0 | 3.0 | 1.0 | 2.0 | 2.0 | 1.0 | | 1.0 | 2.0 | 5.0 | | 1.5 | 3.0 | 2.0 |
| | 0.0320 | 0.0 | 1.0 | 1.0 | 0.0 | 2.0 | 1.0 | | 3.0 | 0.0 | 3.5 | | 1.0 | 1.5 | 2.0 |
| | 0.0160 | 0.0 | 1.0 | 1.0 | 0.0 | 1.0 | 1.0 | | 1.0 | 0.0 | 2.0 | | 1.0 | 1.5 | 1.5 |
| 283 | 0.0620 | 9.0 | 5.0 | 1.0 | 9.0 | 6.0 | 5.0 | | 3.0 | 6.0 | 7.5 | | 5.5 | 6.0 | 7.0 |
| | 0.0320 | 9.0 | 4.0 | 1.0 | 7.0 | 5.0 | 9.0 | | 3.0 | 4.0 | 7.0 | | 5.0 | 6.0 | 7.0 |
| | 0.0160 | 9.0 | 2.0 | 0.0 | 3.0 | 5.0 | 9.0 | | 0.0 | 5.0 | 6.5 | | 4.0 | 3.5 | 7.0 |
| 284 | 0.0620 | 9.0 | 4.0 | 1.0 | 2.0 | 4.0 | 9.0 | | 2.0 | 2.0 | 5.5 | | 4.0 | 3.5 | 7.0 |
| | 0.0320 | 6.0 | 4.0 | 1.0 | 1.0 | 7.0 | 9.0 | | 1.0 | 2.0 | 4.0 | | 2.5 | 2.5 | 6.0 |
| | 0.0160 | 3.0 | 2.0 | 1.0 | 0.0 | 2.0 | 4.0 | | 0.0 | 2.0 | 3.5 | | 2.5 | 3.0 | 3.0 |
| 285 | 0.0620 | 9.0 | 9.0 | 6.0 | 6.0 | 1.0 | 9.0 | | 2.0 | 4.0 | 7.0 | | 5.0 | 5.0 | 5.0 |
| | 0.0320 | 9.0 | 9.0 | 1.0 | 0.0 | 9.0 | 9.0 | | 1.0 | 2.0 | 6.5 | | 3.5 | 4.0 | 4.5 |
| | 0.0160 | 9.0 | 7.0 | 0.0 | 1.0 | 7.0 | 7.0 | | 1.0 | 4.0 | 5.5 | | 3.5 | 3.0 | 3.5 |
| 286 | 0.0620 | 9.0 | 7.0 | 0.0 | 0.0 | 6.0 | 5.0 | | 1.0 | 2.0 | 5.5 | | 3.5 | 4.0 | 7.0 |
| | 0.0320 | 2.0 | 3.0 | 0.0 | 2.0 | 3.0 | 9.0 | | 1.0 | 4.0 | 5.0 | | 3.0 | 3.5 | 4.5 |

TABLE I-continued

Postemergence Herbicidal Evaluations of Test Compounds

| Compound Number | Rate (kg/ha) | ABUTH | AMBEL | CASOB | CHEAL | GALAP | IPOHE | IPOSS | ECHCG | SETVI | GLXMAW | GLXMA | ORYSAT | TRZAWR | ZEAMX |
|---|---|---|---|---|---|---|---|---|---|---|---|---|---|---|---|
| 287 | 0.0160 | 4.0 | 2.0 | 0.0 | 1.0 | 2.0 | 1.0 | | 0.0 | 1.0 | 3.5 | | 1.5 | 2.0 | 1.5 |
| | 0.0620 | 9.0 | 7.0 | 1.0 | 6.0 | 3.0 | 9.0 | | 2.0 | 2.0 | 5.5 | | 3.5 | 3.5 | 5.0 |
| | 0.0320 | 9.0 | 5.0 | 0.0 | 2.0 | 1.0 | 9.0 | | 2.0 | 2.0 | 6.5 | | 3.0 | 3.0 | 5.0 |
| | 0.0160 | 6.0 | 2.0 | 0.0 | 0.0 | 0.0 | 7.0 | | 0.0 | 1.0 | 4.5 | | 2.0 | 2.5 | 4.5 |
| 288 | 0.0620 | 9.0 | 9.0 | 6.0 | 9.0 | 6.0 | 9.0 | | 9.0 | 7.0 | 9.0 | | 3.0 | 6.5 | 9.0 |
| | 0.0320 | 7.0 | 9.0 | 5.0 | 9.0 | 6.0 | 9.0 | | 9.0 | 9.0 | 9.0 | | 3.5 | 7.0 | 9.0 |
| | 0.0160 | 9.0 | 7.0 | 2.0 | 9.0 | 3.0 | 9.0 | | 5.0 | 3.0 | 6.0 | | 2.0 | 4.0 | 7.0 |
| 289 | 0.0620 | 9.0 | 9.0 | 1.0 | 9.0 | 2.0 | 9.0 | | 3.0 | 4.0 | 5.5 | | 2.5 | 3.5 | 5.0 |
| | 0.0320 | 9.0 | 7.0 | 2.0 | 5.0 | 1.0 | 9.0 | | 2.0 | 6.0 | 5.5 | | 1.5 | 3.0 | 4.5 |
| | 0.0160 | 9.0 | 7.0 | 0.0 | 2.0 | 1.0 | 9.0 | | 0.0 | 1.0 | 5.5 | | 0.5 | 2.0 | 3.5 |
| 290 | 0.0620 | 9.0 | 9.0 | 1.0 | 9.0 | 1.0 | 9.0 | | 1.0 | 2.0 | 4.5 | | 1.5 | 3.0 | 5.0 |
| | 0.0320 | 6.0 | 9.0 | 1.0 | 9.0 | 1.0 | 6.0 | | 1.0 | 1.0 | 4.5 | | 1.0 | 2.5 | 4.5 |
| | 0.0160 | 9.0 | 9.0 | 0.0 | 2.0 | 1.0 | 9.0 | | 0.0 | 0.0 | 4.0 | | 0.5 | 2.0 | 4.5 |
| 291 | 0.0620 | 9.0 | 4.0 | 0.0 | 2.0 | 4.0 | 7.0 | | 0.0 | 0.0 | 7.0 | | 2.5 | 3.0 | 5.5 |
| | 0.0320 | 6.0 | 1.0 | 0.0 | 1.0 | 2.0 | 2.0 | | 0.0 | 0.0 | 6.5 | | 2.0 | 2.0 | 5.0 |
| | 0.0160 | 3.0 | 0.0 | 0.0 | 0.0 | 1.0 | 2.0 | | 5.0 | 0.0 | 6.5 | | 2.0 | 2.0 | 4.5 |
| 292 | 0.0620 | 9.0 | 9.0 | 0.0 | 7.0 | 9.0 | 9.0 | | 0.0 | 7.0 | 8.0 | | 5.0 | 6.5 | 7.5 |
| | 0.0320 | 9.0 | 4.0 | 0.0 | 4.0 | 9.0 | 9.0 | | 0.0 | 0.0 | 6.5 | | 4.0 | 5.5 | 7.5 |
| | 0.0160 | 9.0 | 4.0 | 0.0 | 4.0 | 6.0 | 2.0 | | 6.0 | 0.0 | 5.5 | | 3.0 | 5.5 | 7.0 |
| 293 | 0.1250 | 9.0 | 9.0 | 0.0 | 5.0 | 8.0 | 7.0 | | 6.0 | 8.0 | 5.0 | | 4.5 | 4.5 | 8.5 |
| | 0.0620 | 9.0 | 9.0 | 0.0 | 3.0 | 4.0 | 5.0 | | 2.0 | 5.0 | 6.0 | | 5.0 | 6.5 | 8.0 |
| | 0.0320 | 9.0 | 1.0 | 0.0 | 2.0 | 4.0 | 5.0 | | 0.0 | 0.0 | 6.0 | | 3.5 | 6.0 | 7.5 |
| | 0.0160 | 9.0 | 0.0 | 0.0 | 0.0 | 2.0 | 1.0 | | 0.0 | 0.0 | 4.5 | | 3.0 | 5.0 | 7.5 |
| 294 | 0.1250 | 9.0 | 9.0 | 0.0 | 3.0 | 9.0 | 8.0 | | 0.0 | 0.0 | 7.0 | | 5.0 | 4.5 | 6.5 |
| | 0.0620 | 9.0 | 4.0 | 0.0 | 3.0 | 3.0 | 8.0 | | 0.0 | 0.0 | 7.0 | | 3.5 | 5.5 | 7.0 |
| | 0.0320 | 4.0 | 4.0 | 0.0 | 1.0 | 3.0 | 8.0 | | 0.0 | 0.0 | 6.0 | | 3.5 | 5.0 | 6.5 |
| | 0.0160 | 0.0 | 0.0 | 0.0 | 0.0 | 0.0 | 2.0 | | 0.0 | 0.0 | 5.0 | | 3.0 | 4.0 | 6.0 |
| 295 | 0.1250 | 9.0 | 9.0 | 0.0 | 4.0 | 9.0 | 7.0 | | 0.0 | 3.0 | 7.0 | | 3.5 | 4.5 | 5.5 |
| | 0.0620 | 7.0 | 9.0 | 0.0 | 0.0 | 6.0 | 4.0 | | 0.0 | 0.0 | 5.5 | | 3.0 | 4.0 | 5.5 |
| | 0.0320 | 4.0 | 5.0 | 0.0 | 0.0 | 2.0 | 2.0 | | 0.0 | 0.0 | 5.5 | | 2.5 | 4.5 | 6.0 |
| | 0.0160 | 2.0 | 3.0 | 0.0 | 4.0 | 2.0 | 2.0 | | 2.0 | 0.0 | 4.5 | | 2.5 | 3.0 | 5.0 |
| 296 | 0.1250 | 9.0 | 9.0 | 0.0 | 4.0 | 7.0 | 9.0 | | 1.0 | 7.0 | 7.5 | | 5.5 | 6.0 | 7.5 |
| | 0.0620 | 9.0 | 4.0 | 0.0 | 0.0 | 4.0 | 7.0 | | 0.0 | 0.0 | 6.0 | | 4.0 | 5.5 | 7.0 |
| | 0.0320 | 9.0 | 1.0 | 0.0 | 0.0 | 3.0 | 4.0 | | 0.0 | 0.0 | 5.0 | | 3.0 | 5.0 | 6.5 |
| | 0.0160 | 7.0 | 0.0 | 0.0 | 4.0 | 3.0 | 1.0 | | 0.0 | 2.0 | 5.0 | | 3.0 | 5.0 | 6.5 |
| 297 | 0.1250 | 9.0 | 4.0 | 0.0 | 4.0 | 4.0 | 3.0 | | 0.0 | 0.0 | 7.5 | | 4.0 | 5.0 | 7.5 |
| | 0.0620 | 9.0 | 4.0 | 0.0 | 3.0 | 4.0 | 2.0 | | 0.0 | 0.0 | 7.0 | | 3.0 | 4.5 | 7.0 |
| | 0.0320 | 9.0 | 3.0 | 0.0 | 2.0 | 0.0 | 1.0 | | 0.0 | 0.0 | 5.0 | | 3.0 | 4.0 | 7.0 |
| | 0.0160 | 3.0 | 0.0 | 0.0 | 0.0 | 0.0 | 0.0 | | 0.0 | 0.0 | 6.5 | | 3.0 | 4.5 | 6.0 |
| 298 | 0.1250 | 9.0 | 9.0 | 0.0 | 7.0 | 9.0 | 8.0 | | 0.0 | 0.0 | 6.5 | | 3.0 | 4.5 | 6.5 |
| | 0.0620 | 9.0 | 9.0 | 0.0 | 4.0 | 5.0 | 3.0 | | 1.0 | 3.0 | 6.5 | | 3.0 | 4.0 | 6.0 |
| | 0.0320 | 9.0 | 0.0 | 0.0 | 0.0 | 1.0 | 1.0 | | 0.0 | 0.0 | 6.5 | | 3.0 | 4.0 | 6.0 |
| | 0.0160 | 3.0 | 2.0 | 0.0 | 0.0 | 0.0 | 0.0 | | 0.0 | 0.0 | 6.0 | | 3.0 | 4.0 | 6.0 |
| 299 | 0.1250 | 9.0 | 6.0 | 0.0 | 7.0 | 3.0 | 9.0 | | 0.0 | 0.0 | 7.5 | | 4.5 | 5.5 | 7.0 |
| | 0.0620 | 9.0 | 3.0 | 0.0 | 3.0 | 1.0 | 7.0 | | 0.0 | 0.0 | 7.0 | | 3.0 | 5.0 | 7.0 |
| | 0.0320 | 9.0 | 1.0 | 0.0 | 0.0 | 0.0 | 3.0 | | 0.0 | 0.0 | 6.5 | | 3.0 | 4.5 | 6.5 |

TABLE I-continued

Postemergence Herbicidal Evaluations of Test Compounds

| Compound Number | Rate (kg/ha) | ABUTH | AMBEL | CASOB | CHEAL | GALAP | IPOHE | IPOSS | ECHCG | SETVI | GLXMAW | GLXMA | ORYSAT | TRZAWR | ZEAMX |
|---|---|---|---|---|---|---|---|---|---|---|---|---|---|---|---|
| 300 | 0.0160 | 9.0 | 0.0 | 0.0 | 0.0 | 0.0 | 0.0 | | 0.0 | 0.0 | 4.5 | | 2.5 | 4.0 | 6.5 |
| | 0.2500 | 9.0 | 9.0 | 7.0 | 9.0 | 7.0 | 9.0 | | 6.0 | 9.0 | 7.5 | | 7.5 | 6.5 | 7.0 |
| | 0.1250 | 9.0 | 8.5 | 5.0 | 9.0 | 8.5 | 9.0 | | 2.0 | 9.0 | 7.0 | | 5.0 | 4.8 | 7.0 |
| | 0.0620 | 9.0 | 7.0 | 3.0 | 5.5 | 7.0 | 9.0 | | 1.0 | 8.5 | 6.3 | | 4.3 | 4.3 | 6.5 |
| | 0.0320 | 9.0 | 6.0 | 1.5 | 4.0 | 4.5 | 7.0 | | 1.0 | 2.0 | 6.0 | | 2.8 | 3.5 | 5.5 |
| | 0.0160 | 9.0 | 6.0 | 1.5 | 4.0 | 3.0 | 6.0 | | 0.5 | 2.0 | 5.0 | | 1.8 | 2.8 | 6.0 |
| 301 | 0.0620 | 9.0 | 4.0 | 9.0 | 9.0 | 9.0 | 9.0 | | 0.0 | 1.0 | 5.5 | | 1.0 | 3.5 | 5.0 |
| | 0.0320 | 9.0 | 3.0 | 4.0 | 9.0 | 4.0 | 9.0 | | 0.0 | 1.0 | 5.5 | | 0.5 | 3.5 | 4.5 |
| | 0.0160 | 9.0 | 2.0 | 0.0 | 4.0 | 2.0 | 9.0 | | 0.0 | 0.0 | 5.0 | | 0.5 | 3.5 | 3.5 |
| 302 | 0.0620 | 9.0 | 9.0 | 1.0 | 9.0 | 3.0 | 9.0 | | 0.0 | 9.0 | 7.5 | | 2.0 | 4.5 | 4.5 |
| | 0.0320 | 9.0 | 5.0 | 0.0 | 6.0 | 4.0 | 9.0 | | 0.0 | 3.0 | 7.0 | | 1.5 | 4.0 | 4.5 |
| | 0.0160 | 9.0 | 9.0 | 3.0 | 9.0 | 1.0 | 9.0 | | 0.0 | 0.0 | 5.0 | | 1.0 | 3.0 | 4.0 |
| 303 | 0.0620 | 9.0 | 3.0 | 1.0 | 9.0 | 7.0 | 9.0 | | 0.0 | 8.0 | 7.5 | | 2.0 | 3.5 | 5.0 |
| | 0.0320 | 9.0 | 3.0 | 0.0 | 4.0 | 3.0 | 9.0 | | 0.0 | 4.0 | 7.5 | | 1.5 | 3.0 | 5.0 |
| | 0.0160 | 9.0 | 3.0 | 0.0 | 4.0 | 0.0 | 9.0 | | 0.0 | 0.0 | 7.0 | | 1.0 | 3.0 | 4.5 |
| 304 | 0.0620 | 9.0 | 7.0 | 2.0 | 9.0 | 2.0 | 9.0 | | 0.0 | 4.0 | 6.0 | | 2.5 | 4.5 | 4.5 |
| | 0.0320 | 9.0 | 7.0 | 1.0 | 6.0 | 2.0 | 6.0 | | 0.0 | 1.0 | 5.5 | | 1.5 | 2.5 | 5.0 |
| | 0.0160 | 9.0 | 6.0 | 0.0 | 4.0 | 1.0 | 3.0 | | 0.0 | 0.0 | 5.0 | | 1.0 | 2.0 | 5.0 |
| 305 | 0.0620 | 9.0 | 7.0 | 2.0 | 7.0 | 7.0 | 9.0 | | 1.0 | 5.0 | 6.5 | | 2.0 | 4.5 | 5.0 |
| | 0.0320 | 9.0 | 6.0 | 1.0 | 9.0 | 4.0 | 6.0 | | 1.0 | 1.0 | 6.0 | | 1.5 | 2.5 | 5.0 |
| | 0.0160 | 9.0 | 5.0 | 0.0 | 4.0 | 2.0 | 1.0 | | 0.0 | 0.0 | 4.0 | | 0.0 | 2.0 | 3.5 |
| 306 | 0.0620 | 9.0 | 2.0 | 1.0 | 5.0 | 3.0 | 9.0 | | 2.0 | 3.0 | 6.5 | | 2.5 | 5.0 | 6.5 |
| | 0.0320 | 9.0 | 1.0 | 0.0 | 2.0 | 1.0 | 4.0 | | 1.0 | 1.0 | 5.5 | | 2.5 | 4.0 | 5.5 |
| | 0.0160 | 9.0 | 1.0 | 0.0 | 1.0 | 1.0 | 3.0 | | 1.0 | 0.0 | 5.0 | | 1.5 | 2.5 | 5.0 |
| 307 | 0.0620 | 6.2 | 9.0 | 7.0 | 9.0 | 9.0 | 9.0 | | 3.0 | 6.0 | 9.0 | | 3.0 | 4.0 | 6.0 |
| | 0.0320 | 6.4 | 9.0 | 6.0 | 5.0 | 9.0 | 9.0 | | 3.0 | 4.0 | 9.0 | | 3.0 | 4.0 | 5.5 |
| | 0.0160 | 9.0 | 9.0 | 3.0 | 3.0 | 5.0 | 9.0 | | 3.0 | 3.0 | 6.5 | | 1.5 | 3.0 | 5.5 |
| 308 | 0.0620 | 6.4 | 9.0 | 9.0 | 9.0 | 9.0 | 9.0 | | 7.0 | 7.0 | 9.0 | | 4.5 | 4.5 | 6.5 |
| | 0.0320 | 9.0 | 9.0 | 6.0 | 9.0 | 5.0 | 9.0 | | 3.0 | 5.0 | 8.0 | | 3.5 | 3.5 | 6.0 |
| | 0.0160 | 5.6 | 9.0 | 2.0 | 4.0 | 7.0 | 9.0 | | 1.0 | 1.0 | 6.0 | | 2.5 | 3.0 | 5.0 |
| 309 | 0.0620 | 9.0 | 9.0 | 7.0 | 9.0 | 9.0 | 9.0 | | 2.0 | 9.0 | 9.0 | | 4.0 | 4.0 | 6.0 |
| | 0.0320 | 9.0 | 9.0 | 5.0 | 3.0 | 9.0 | 9.0 | | 3.0 | 3.0 | 8.0 | | 2.5 | 3.5 | 5.0 |
| | 0.0160 | 9.0 | 9.0 | 1.0 | 3.0 | 6.0 | 9.0 | | 1.0 | 3.0 | 8.5 | | 2.0 | 3.0 | 6.0 |
| 310 | 0.0620 | 9.0 | 9.0 | 0.0 | 7.0 | 4.0 | 9.0 | | 4.0 | 5.0 | 4.0 | | 2.5 | 5.0 | 5.0 |
| | 0.0320 | 9.0 | 2.0 | 0.0 | 3.0 | 2.0 | 9.0 | | 1.0 | 3.0 | 3.0 | | 2.0 | 3.0 | 5.0 |
| | 0.0160 | 9.0 | 4.0 | 0.0 | 3.0 | 0.0 | 9.0 | | 0.0 | 3.0 | 4.5 | | 1.0 | 2.5 | 4.5 |
| 311 | 0.0620 | 9.0 | 4.0 | 1.0 | 2.0 | 3.0 | 3.0 | | 1.0 | 1.0 | 3.5 | | 0.5 | 1.5 | 4.0 |
| | 0.0320 | 9.0 | 3.0 | 0.0 | 3.0 | 0.0 | 3.0 | | 0.0 | 3.0 | 3.5 | | 0.5 | 1.0 | 3.5 |
| | 0.0160 | 0.0 | 1.0 | 0.0 | 2.0 | 0.0 | 0.0 | | 1.0 | 0.0 | 4.0 | | 0.0 | 1.0 | 1.5 |
| 312 | 0.0620 | 9.0 | 9.0 | 9.0 | 9.0 | 9.0 | 9.0 | | 9.0 | 9.0 | 9.0 | | 7.5 | 7.0 | 7.5 |
| | 0.0320 | 9.0 | 9.0 | 9.0 | 7.0 | 7.0 | 9.0 | | 9.0 | 9.0 | 9.0 | | 5.5 | 5.5 | 7.5 |
| 313 | 0.0620 | 9.0 | 9.0 | 4.0 | 9.0 | 7.0 | 9.0 | | 6.0 | 9.0 | 7.0 | | 4.5 | 5.0 | 6.5 |
| | 0.0320 | 9.0 | 9.0 | 1.0 | 7.0 | 7.0 | 9.0 | | 6.0 | 9.0 | 6.0 | | 4.5 | 4.0 | 7.5 |
| | 0.0160 | 9.0 | 4.0 | 1.0 | 9.0 | 1.0 | 6.0 | | 3.0 | 5.0 | 6.0 | | 4.0 | 3.5 | 5.5 |
| 314 | 0.0620 | 9.0 | 9.0 | 9.0 | 9.0 | 9.0 | 9.0 | | 9.0 | 9.0 | 9.0 | | 2.0 | 2.5 | 5.5 |
| | 0.0320 | 9.0 | 7.0 | 9.0 | 9.0 | 9.0 | 9.0 | | 9.0 | 9.0 | 9.0 | | 7.5 | 9.0 | 9.0 |
| | | | | | | | | | | | | | 5.5 | 9.0 | 9.0 |

TABLE I-continued

Postemergence Herbicidal Evaluations of Test Compounds

| Compound Number | Rate (kg/ha) | ABUTH | AMBEL | CASOB | CHEAL | GALAP | IPOHE | IPOSS | ECHCG | SETVI | GLXMAW | GLXMA | ORYSAT | TRZAWR | ZEAMX |
|---|---|---|---|---|---|---|---|---|---|---|---|---|---|---|---|
| 315 | 0.0160 | 9.0 | 9.0 | 9.0 | 9.0 | 9.0 | 9.0 | | 9.0 | 9.0 | 9.0 | | 4.0 | 5.5 | 7.5 |
| | 0.0620 | 9.0 | 9.0 | 1.0 | 9.0 | 8.0 | 9.0 | | 7.0 | 9.0 | 9.0 | | 6.0 | 5.5 | 7.5 |
| | 0.0320 | 9.0 | 7.0 | 0.0 | 5.0 | 5.0 | 7.0 | | 3.0 | 6.0 | 7.0 | | 4.5 | 5.0 | 7.0 |
| | 0.0160 | 4.0 | 5.0 | 0.0 | 5.0 | 5.0 | 4.0 | | 0.0 | 4.0 | 6.0 | | 1.54.0 | 6.5 | |
| 316 | 0.0620 | 9.0 | 9.0 | 3.0 | 9.0 | 9.0 | 9.0 | | 9.0 | 9.0 | 8.5 | | 6.0 | 5.5 | 5.5 |
| | 0.0320 | 9.0 | 9.0 | 1.0 | 9.0 | 5.0 | 9.0 | | 9.0 | 9.0 | 8.5 | | 6.0 | 5.0 | 5.5 |
| | 0.0160 | 9.0 | 9.0 | 0.0 | 9.0 | 9.0 | 9.0 | | 9.0 | 9.0 | 8.0 | | 6.5 | 4.5 | 6.0 |
| 317 | 0.0620 | 9.0 | 9.0 | 2.0 | 9.0 | 5.0 | 9.0 | | 2.0 | 9.0 | 9.0 | | 5.0 | 5.0 | 7.0 |
| | 0.0320 | 9.0 | 9.0 | 0.0 | 4.0 | 9.0 | 9.0 | | 0.0 | 9.0 | 8.5 | | 4.0 | 4.5 | 7.0 |
| | 0.0160 | 9.0 | 9.0 | 0.0 | 3.0 | 9.0 | 9.0 | | 0.0 | 9.0 | 7.5 | | 3.0 | 3.5 | 6.0 |
| 318 | 0.0620 | 9.0 | 9.0 | 3.0 | 8.0 | 4.0 | 9.0 | | 0.0 | 9.0 | 8.5 | | 5.0 | 5.0 | 6.0 |
| | 0.0320 | 9.0 | 9.0 | 2.0 | 9.0 | 4.0 | 9.0 | | 0.0 | 6.0 | 8.5 | | 4.0 | 3.5 | 5.0 |
| | 0.0160 | 9.0 | 5.0 | 0.0 | 3.0 | 4.0 | 9.0 | | 0.0 | 5.0 | 8.0 | | 2.5 | 3.0 | 4.0 |
| 319 | 0.0620 | 9.0 | 9.0 | 5.0 | 6.0 | 8.0 | 9.0 | | 7.0 | 9.0 | 8.5 | | 6.5 | 6.5 | 7.0 |
| | 0.0320 | 9.0 | 9.0 | 1.0 | 5.0 | 6.0 | 9.0 | | 6.0 | 9.0 | 8.5 | | 5.5 | 5.5 | 7.0 |
| | 0.0160 | 9.0 | 2.0 | 1.0 | 6.0 | 9.0 | 9.0 | | 4.0 | 7.0 | 7.5 | | 6.0 | 5.0 | 6.5 |
| 320 | 0.0620 | 9.0 | 7.0 | 1.0 | 6.0 | 9.0 | 9.0 | | 7.0 | 9.0 | 7.5 | | 7.0 | 6.5 | 7.0 |
| | 0.0320 | 9.0 | 4.0 | 1.0 | 7.0 | 7.0 | 9.0 | | 4.0 | 9.0 | 8.5 | | 5.5 | 5.5 | 7.0 |
| | 0.0160 | 9.0 | 9.0 | 1.0 | 9.0 | 6.0 | 9.0 | | 3.0 | 4.0 | 7.5 | | 5.5 | 5.0 | 6.5 |
| 321 | 0.0620 | 9.0 | 9.0 | 6.0 | 9.0 | 8.0 | 9.0 | | 0.0 | 6.0 | 7.5 | | 4.0 | 4.5 | 4.5 |
| | 0.0320 | 9.0 | 3.0 | 4.0 | 9.0 | 7.0 | 9.0 | | 0.0 | 5.0 | 7.0 | | 4.0 | 4.5 | 4.5 |
| | 0.0160 | 9.0 | 0.0 | 2.0 | 9.0 | 5.0 | 9.0 | | 0.0 | 3.0 | 7.0 | | 3.5 | 4.5 | 4.5 |
| 322 | 0.0620 | 7.0 | 1.0 | 0.0 | 1.0 | 1.0 | 8.0 | | 0.0 | 0.0 | 6.5 | | 2.0 | 3.0 | 3.5 |
| | 0.0320 | 0.0 | 0.0 | 0.0 | 0.0 | 0.0 | 0.0 | | 0.0 | 0.0 | 5.0 | | 1.5 | 1.5 | 3.5 |
| | 0.0160 | 9.0 | 9.0 | 5.0 | 9.0 | 9.0 | 9.0 | | 0.0 | 0.0 | 4.0 | | 1.0 | 1.0 | 8.0 |
| 323 | 0.2500 | 9.0 | 9.0 | 4.0 | 9.0 | 8.0 | 9.0 | | 9.0 | 9.0 | 8.5 | | 8.5 | 5.5 | 7.5 |
| | 0.1250 | 9.0 | 9.0 | 5.0 | 9.0 | 9.0 | 9.0 | | 9.0 | 9.0 | 7.3 | | 8.5 | 5.5 | 8.0 |
| | 0.1250 | 9.0 | 9.0 | 4.0 | 9.0 | 9.0 | 9.0 | | 9.0 | 9.0 | 8.5 | | 6.8 | 5.5 | 7.5 |
| | 0.0620 | 9.0 | 9.0 | 1.0 | 8.0 | 8.0 | 9.0 | | 9.0 | 9.0 | 7.3 | | 6.5 | 6.5 | 7.5 |
| | 0.0320 | 7.3 | 9.0 | 1.0 | 5.0 | 7.0 | 9.0 | | 7.0 | 9.0 | 7.0 | | 6.0 | 5.0 | 7.0 |
| 324 | 0.0160 | 6.6 | 9.0 | 1.0 | 3.0 | 5.0 | 9.0 | | 6.0 | 5.0 | 6.5 | | 5.0 | 5.0 | 7.0 |
| | 0.0620 | 9.0 | 9.0 | 7.0 | 9.0 | 7.0 | 9.0 | | 3.0 | 9.0 | 9.0 | | 7.0 | 6.0 | 8.0 |
| | 0.0320 | 9.0 | 9.0 | 6.0 | 9.0 | 6.0 | 9.0 | | 0.0 | 8.0 | 8.5 | | 5.5 | 5.0 | 7.5 |
| | 0.0160 | 9.0 | 9.0 | 6.0 | 9.0 | 3.0 | 9.0 | | 0.0 | 4.0 | 7.0 | | 2.5 | 4.0 | 5.0 |
| 325 | 0.0620 | 9.0 | 5.0 | 9.0 | 9.0 | 9.0 | 9.0 | | 9.0 | 9.0 | 9.0 | | 9.0 | 9.0 | 9.0 |
| | 0.0320 | 9.0 | 4.0 | 2.0 | 9.0 | 6.0 | 9.0 | | 9.0 | 9.0 | 8.0 | | 8.0 | 8.0 | 9.0 |
| 326 | 0.0620 | 9.0 | 9.0 | 4.0 | 9.0 | 6.0 | 9.0 | | 9.0 | 9.0 | 9.0 | | 8.0 | 7.5 | 8.0 |
| | 0.0320 | 9.0 | 4.0 | 3.0 | 9.0 | 6.0 | 9.0 | | 9.0 | 9.0 | 9.0 | | 6.5 | 7.5 | 8.0 |
| | 0.0160 | 9.0 | 9.0 | 0.0 | 9.0 | 6.0 | 9.0 | | 8.0 | 8.0 | 8.0 | | 6.0 | 6.0 | 8.0 |
| 327 | 0.0620 | 9.0 | 4.0 | 3.0 | 9.0 | 5.0 | 9.0 | | 0.0 | 6.0 | 8.0 | | 3.5 | 4.0 | 5.0 |
| | 0.0320 | 9.0 | 9.0 | 0.0 | 9.0 | 4.0 | 9.0 | | 0.0 | 3.0 | 8.0 | | 3.0 | 4.0 | 4.5 |
| | 0.0160 | 9.0 | 6.0 | 1.0 | 5.0 | 2.0 | 7.0 | | 0.0 | 0.0 | 6.5 | | 1.5 | 3.0 | 4.5 |
| 328 | 0.0620 | 9.0 | 7.0 | 1.0 | 9.0 | 7.0 | 9.0 | | 0.0 | 3.0 | 7.0 | | 3.5 | 4.0 | 5.0 |
| | 0.0320 | 9.0 | 3.0 | 0.0 | 9.0 | 4.0 | 9.0 | | 0.0 | 3.0 | 7.0 | | 3.5 | 4.0 | 5.0 |
| | 0.0160 | 9.0 | 3.0 | 0.0 | 9.0 | 2.0 | 4.0 | | 0.0 | 0.0 | 4.5 | | 3.5 | 3.5 | 4.5 |

TABLE I-continued

Postemergence Herbicidal Evaluations of Test Compounds

| Compound Number | Rate (kg/ha) | ABUTH | AMBEL | CASOB | CHEAL | GALAP | IPOHE | IPOSS | ECHCG | SETVI | GLXMAW | GLXMA | ORYSAT | TRZAWR | ZEAMX |
|---|---|---|---|---|---|---|---|---|---|---|---|---|---|---|---|
| 329 | 0.0620 | 9.0 | 7.0 | 4.0 | 6.0 | 6.0 | 9.0 |  | 2.0 | 5.0 | 7.0 |  | 5.0 | 5.0 | 5.0 |
|  | 0.0320 | 9.0 | 6.0 | 1.0 | 6.0 | 5.0 | 9.0 |  | 1.0 | 1.0 | 6.5 |  | 3.0 | 3.0 | 4.5 |
|  | 0.0160 | 9.0 | 6.0 | 1.0 | 3.0 | 1.0 | 3.0 |  | 1.0 | 1.0 | 6.0 |  | 2.0 | 2.0 | 4.5 |
| 330 | 0.0620 | 9.0 | 6.0 | 1.0 | 4.0 | 2.0 | 9.0 |  | 1.0 | 1.0 | 6.5 |  | 3.0 | 3.0 | 4.5 |
|  | 0.0320 | 9.0 | 4.0 | 1.0 | 2.0 | 1.0 | 9.0 |  | 2.0 | 1.0 | 5.5 |  | 2.0 | 2.5 | 2.5 |
|  | 0.0160 | 1.0 | 2.0 | 0.0 | 1.0 | 1.0 | 1.0 |  | 1.0 | 0.0 | 4.5 |  | 2.0 | 2.0 | 2.5 |
| 331 | 0.0620 | 8.0 | 2.0 | 0.0 | 4.0 | 2.0 | 9.0 |  | 0.0 | 0.0 | 5.0 |  | 1.53.0 | 4.5 |  |
|  | 0.0320 | 4.0 | 0.0 | 0.0 | 2.0 | 1.0 | 6.0 |  | 0.0 | 0.0 | 4.0 |  | 0.5 | 3.0 | 4.0 |
|  | 0.0160 | 3.0 | 0.0 | 0.0 | 0.0 | 0.0 | 1.0 |  | 0.0 | 0.0 | 3.5 |  | 0.0 | 2.0 | 3.5 |
| 332 | 0.0620 | 9.0 | 9.0 | 4.0 | 9.0 | 9.0 | 9.0 |  | 9.0 | 9.0 | 9.0 |  | 7.0 | 8.0 | 8.5 |
|  | 0.0320 | 9.0 | 9.0 | 3.0 | 9.0 | 9.0 | 9.0 |  | 9.0 | 9.0 | 9.0 |  | 6.5 | 7.5 | 8.5 |
|  | 0.0160 | 9.0 | 9.0 | 9.0 | 9.0 | 5.0 | 9.0 |  | 0.0 | 7.0 | 7.0 |  | 3.5 | 6.0 | 7.5 |
| 333 | 0.0620 | 9.0 | 9.0 | 2.0 | 5.0 | 4.0 | 9.0 |  | 0.0 | 7.0 | 7.0 |  | 2.5 | 4.5 | 5.0 |
|  | 0.0320 | 9.0 | 9.0 | 2.0 | 3.0 | 2.0 | 9.0 |  | 0.0 | 3.0 | 6.5 |  | 2.5 | 4.0 | 4.5 |
|  | 0.0160 | 9.0 | 9.0 | 2.0 |  | 2.0 | 9.0 |  | 3.0 | 7.0 | 6.5 |  | 2.0 | 3.5 | 4.5 |
| 334 | 0.0620 | 9.0 | 7.0 | 2.0 | 4.0 | 1.0 | 9.0 |  | 1.0 | 2.0 | 6.5 |  | 3.5 | 4.0 | 5.5 |
|  | 0.0320 | 9.0 | 6.0 | 1.0 | 4.0 | 1.0 | 9.0 |  | 0.0 | 1.0 | 5.0 |  | 2.5 | 3.5 | 4.5 |
|  | 0.0160 | 9.0 | 2.0 | 1.0 | 9.0 | 1.0 | 7.0 |  | 0.0 | 1.0 | 4.0 |  | 2.5 | 3.5 | 3.5 |
| 335 | 0.2500 | 9.0 | 9.0 | 9.0 | 9.0 | 9.0 | 9.0 |  | 9.0 | 9.0 | 9.0 |  | 9.0 | 9.0 | 9.0 |
|  | 0.1250 | 9.0 | 9.0 | 9.0 | 9.0 | 9.0 | 9.0 |  | 9.0 | 9.0 | 9.0 |  | 9.0 | 8.5 | 9.0 |
|  | 0.0620 | 9.0 | 9.0 | 9.0 |  | 7.0 | 9.0 |  | 9.0 | 9.0 | 9.0 |  | 7.5 | 8.0 | 9.0 |
|  | 0.0320 | 8.7 | 9.0 | 9.0 | 9.0 | 6.0 | 9.0 |  | 9.0 | 9.0 | 9.0 |  | 7.5 | 8.0 | 9.0 |
|  | 0.0160 | 8.4 | 9.0 | 9.0 | 9.0 | 6.0 | 9.0 |  | 9.0 | 9.0 | 9.0 |  | 6.5 | 6.5 | 7.5 |
| 336 | 0.0620 | 9.0 | 9.0 | 6.0 |  | 7.0 | 9.0 |  | 5.0 | 7.0 | 7.5 |  | 6.0 | 5.5 | 5.5 |
|  | 0.0320 | 9.0 | 7.0 | 1.0 | 9.0 | 6.0 | 9.0 |  | 5.0 | 7.0 | 7.0 |  | 5.5 | 5.5 | 5.5 |
|  | 0.0160 | 9.0 | 9.0 | 1.0 |  | 1.0 | 9.0 |  | 2.0 | 9.0 | 9.0 |  | 3.5 | 3.5 | 4.5 |
| 337 | 0.0620 | 9.0 | 9.0 | 4.0 | 7.0 | 9.0 | 9.0 |  | 2.0 | 9.0 | 6.5 |  | 3.5 | 3.5 | 5.0 |
|  | 0.0320 | 9.0 | 9.0 | 3.0 | 7.0 | 3.0 | 9.0 |  | 2.0 | 9.0 | 6.5 |  | 2.0 | 2.5 | 4.5 |
|  | 0.0160 | 9.0 | 7.0 | 7.0 | 9.0 | 2.0 | 9.0 |  | 6.0 | 4.0 | 8.0 |  | 4.0 | 5.0 | 6.0 |
| 338 | 0.0620 | 9.0 | 9.0 | 7.0 | 9.0 | 7.0 | 9.0 |  | 2.0 | 6.0 | 7.0 |  | 3.5 | 4.0 | 5.5 |
|  | 0.0320 | 9.0 | 9.0 | 7.0 | 9.0 | 9.0 | 9.0 |  | 2.0 | 4.0 | 7.5 |  | 2.5 | 4.0 | 5.5 |
|  | 0.0160 | 9.0 | 7.0 | 3.0 | 7.0 | 6.0 | 9.0 |  | 1.0 | 1.0 | 6.5 |  | 4.0 | 4.5 | 5.5 |
| 339 | 0.0620 | 9.0 | 9.0 | 1.0 |  | 9.0 | 9.0 |  | 2.0 | 7.0 | 5.5 |  | 3.5 | 5.0 | 4.5 |
|  | 0.0320 | 9.0 | 7.0 | 1.0 | 7.0 | 4.0 | 9.0 |  | 2.0 | 4.0 | 5.5 |  | 3.0 | 3.0 | 5.0 |
|  | 0.0160 | 9.0 | 9.0 | 1.0 | 9.0 | 2.0 | 9.0 |  | 1.0 | 2.0 | 8.0 |  | 5.0 | 5.0 | 4.0 |
| 340 | 0.0620 | 9.0 | 9.0 | 9.0 | 9.0 | 9.0 | 9.0 |  | 3.0 | 9.0 | 7.0 |  | 5.0 | 5.0 | 6.5 |
|  | 0.0320 | 9.0 | 9.0 | 4.0 | 9.0 | 8.0 | 9.0 |  | 2.0 | 6.0 | 6.5 |  | 3.5 | 4.0 | 5.0 |
|  | 0.0160 | 9.0 | 9.0 | 1.0 | 9.0 | 7.0 | 9.0 |  | 2.0 | 3.0 | 9.0 |  | 6.0 | 6.5 | 8.0 |
| 341 | 0.0620 | 9.0 | 9.0 | 9.0 | 9.0 | 9.0 | 9.0 |  | 9.0 | 9.0 | 9.0 |  | 6.0 | 6.5 | 8.0 |
|  | 0.0320 | 7.9 | 9.0 | 2.0 | 9.0 | 8.0 | 9.0 |  | 9.0 | 3.0 | 8.5 |  | 6.0 | 5.0 | 7.5 |
|  | 0.0160 | 7.4 | 7.0 | 1.0 | 7.0 | 7.0 | 9.0 |  | 1.0 | 1.0 | 5.5 |  | 5.0 | 5.0 | 5.5 |
| 342 | 0.0620 | 9.0 | 9.0 | 2.0 | 7.0 | 2.0 | 6.0 |  | 1.0 | 1.0 | 5.0 |  | 4.5 | 3.5 | 5.0 |
|  | 0.0320 | 9.0 | 5.0 | 1.0 | 4.0 | 2.0 | 9.0 |  | 1.0 | 1.0 | 4.5 |  | 3.5 | 3.5 | 4.5 |
|  | 0.0160 | 9.0 | 4.0 | 1.0 |  | 1.0 | 9.0 |  | 1.0 | 1.0 | 7.5 |  | 3.0 | 5.5 | 7.0 |
| 343 | 0.0620 | 9.0 | 9.0 | 4.0 | 9.0 | 1.0 | 9.0 |  | 9.0 | 9.0 | 7.5 |  | 5.5 | 5.5 | 5.0 |
|  | 0.0320 | 9.0 | 9.0 | 1.0 | 9.0 | 1.0 | 9.0 |  | 9.0 | 9.0 | 5.5 |  | 4.5 | 4.5 | 5.0 |
|  | 0.0160 | 9.0 | 9.0 | 1.0 | 9.0 | 1.0 | 9.0 |  | 9.0 | 1.0 | 5.5 |  | 3.5 | 4.5 | 5.0 |

TABLE I-continued

Postemergence Herbicidal Evaluations of Test Compounds

| Compound Number | Rate (kg/ha) | ABUTH | AMBEL | CASOB | CHEAL | GALAP | IPOHE | IPOSS | ECHCG | SETVI | GLXMAW | GLXMA | ORYSAT | TRZAWR | ZEAMX |
|---|---|---|---|---|---|---|---|---|---|---|---|---|---|---|---|
| 344 | 0.0620 | 9.0 | 9.0 | 9.0 | 9.0 | 9.0 | 9.0 | | 9.0 | 9.0 | 9.0 | | 6.5 | 6.0 | 7.5 |
| | 0.0320 | 9.0 | 9.0 | 7.0 | 9.0 | 7.0 | 9.0 | | 9.0 | 9.0 | 7.0 | | 6.0 | 6.0 | 5.0 |
| | 0.0160 | 9.0 | 9.0 | 2.0 | 9.0 | 3.0 | 9.0 | | 7.0 | 9.0 | 6.5 | | 4.5 | 5.0 | 5.5 |
| 345 | 0.0620 | 9.0 | 9.0 | 9.0 | 9.0 | 4.0 | 9.0 | | 3.0 | 9.0 | 8.5 | | 5.0 | 6.0 | 6.0 |
| | 0.0320 | 9.0 | 7.0 | 9.0 | 9.0 | 4.0 | 9.0 | | 0.0 | 9.0 | 7.5 | | 3.0 | 4.0 | 4.5 |
| | 0.0160 | 7.0 | 4.0 | 4.0 | 9.0 | 0.0 | 9.0 | | 0.0 | 4.0 | 6.0 | | 3.5 | 3.5 | 2.0 |
| 346 | 0.0620 | 9.0 | 7.0 | | | 7.0 | | | 0.0 | 9.0 | 6.0 | | 3.0 | 4.0 | 2.0 |
| 347 | 0.0620 | 9.0 | 9.0 | 9.0 | 9.0 | 9.0 | 9.0 | 7.0 | 9.0 | 9.0 | 6.0 | | 3.0 | 9.0 | 9.0 |
| | 0.0320 | 9.0 | 9.0 | 9.0 | 9.0 | 9.0 | 9.0 | | 9.0 | 9.0 | 9.0 | | 8.5 | 9.0 | 9.0 |
| | 0.0160 | 9.0 | 9.0 | 9.0 | 9.0 | 5.0 | 9.0 | | 9.0 | 9.0 | 9.0 | | 8.0 | 9.0 | 9.0 |
| 348 | 0.0620 | 9.0 | 9.0 | 9.0 | 9.0 | 9.0 | 9.0 | | 9.0 | 9.0 | 8.0 | | 5.0 | 9.0 | 9.0 |
| | 0.0320 | 9.0 | 9.0 | 9.0 | 9.0 | 5.0 | 9.0 | | 9.0 | 9.0 | 8.0 | | 4.0 | 8.0 | 9.0 |
| | 0.0160 | 9.0 | 9.0 | 9.0 | 7.0 | 4.0 | 9.0 | | 9.0 | 9.0 | 8.0 | | 9.0 | 8.5 | 9.0 |
| 349 | 0.0620 | 9.0 | 9.0 | 9.0 | 9.0 | 9.0 | 9.0 | | 9.0 | 9.0 | 9.0 | | 8.5 | 8.5 | 8.5 |
| | 0.0320 | 9.0 | 9.0 | 0.0 | 9.0 | 9.0 | 9.0 | | 9.0 | 9.0 | 7.5 | | 8.5 | 8.5 | 8.0 |
| | 0.0160 | 9.0 | 9.0 | 9.0 | 9.0 | 4.0 | 9.0 | | 3.0 | 9.0 | 9.0 | | 4.5 | 4.0 | 6.0 |
| 350 | 0.0620 | 9.0 | 9.0 | 4.0 | 9.0 | 9.0 | 9.0 | | 0.0 | 9.0 | 9.0 | | 3.0 | 3.5 | 5.0 |
| | 0.0320 | 9.0 | 9.0 | 3.0 | 8.0 | 9.0 | 9.0 | | 0.0 | 6.0 | 7.0 | | 1.5 | 2.5 | 3.0 |
| | 0.0160 | 9.0 | 9.0 | 9.0 | 9.0 | 7.0 | 9.0 | | 2.0 | 9.0 | 9.0 | | 4.0 | 4.0 | 5.0 |
| 351 | 0.0620 | 9.0 | 9.0 | 4.0 | 7.0 | 6.0 | 9.0 | | 0.0 | 4.0 | 8.0 | | 3.5 | 3.5 | 4.5 |
| | 0.0320 | 9.0 | 9.0 | 2.0 | 4.0 | 6.0 | 9.0 | | 0.0 | 0.0 | 9.0 | | 0.5 | 1.5 | 3.5 |
| 352 | 0.0620 | 9.0 | 9.0 | 2.0 | 9.0 | 2.0 | 9.0 | | 2.0 | 2.0 | 7.0 | | 6.0 | 3.5 | 7.5 |
| | 0.0320 | 9.0 | 9.0 | 0.0 | 9.0 | 2.0 | 9.0 | | 0.0 | 0.0 | 9.0 | | 2.0 | 2.5 | 7.5 |
| | 0.0160 | 9.0 | 9.0 | 0.0 | 9.0 | 0.0 | 9.0 | | 0.0 | 0.0 | 8.0 | | 1.5 | 2.5 | 7.5 |
| 353 | 0.1250 | 9.0 | 9.0 | 5.0 | 7.0 | 7.0 | 9.0 | | 3.0 | 7.0 | 8.0 | | 4.5 | 4.5 | 7.5 |
| | 0.0620 | 9.0 | 7.0 | 3.0 | 7.0 | 2.0 | 9.0 | | 2.0 | 6.0 | 7.0 | | 4.0 | 4.0 | 7.0 |
| | 0.0320 | 9.0 | 9.0 | 1.0 | 7.0 | 2.0 | 9.0 | | 2.0 | 1.0 | 6.5 | | 3.5 | 3.5 | 6.0 |
| | 0.0160 | 6.0 | 4.0 | 1.0 | 3.0 | 1.0 | 7.0 | | 1.0 | 1.0 | 5.5 | | 3.5 | 3.5 | 5.0 |
| 354 | 0.1250 | 9.0 | 9.0 | 9.0 | 9.0 | 9.0 | 9.0 | | 9.0 | 9.0 | 9.0 | | 8.5 | 9.0 | 8.0 |
| | 0.0620 | 9.0 | 9.0 | 9.0 | 9.0 | 8.0 | 9.0 | | 9.0 | 9.0 | 9.0 | | 8.0 | 8.0 | 8.0 |
| | 0.0320 | 9.0 | 9.0 | 9.0 | 9.0 | 7.0 | 9.0 | | 9.0 | 9.0 | 9.0 | | 7.0 | 7.0 | 6.5 |
| | 0.0160 | 9.0 | 9.0 | 9.0 | 9.0 | 6.0 | 9.0 | | 7.0 | 9.0 | 9.0 | | 6.0 | 6.0 | 6.0 |
| 355 | 0.1250 | 9.0 | 7.0 | 4.0 | 9.0 | 6.0 | 9.0 | | 9.0 | 9.0 | 6.0 | | 6.5 | 5.5 | 5.5 |
| | 0.0620 | 9.0 | 9.0 | 2.0 | 9.0 | 3.0 | 9.0 | | 7.0 | 7.0 | 6.5 | | 6.0 | 5.5 | 5.0 |
| | 0.0320 | 9.0 | 9.0 | 3.0 | 2.0 | 1.0 | 9.0 | | 7.0 | 7.0 | 5.5 | | 4.5 | 5.5 | 4.5 |
| | 0.0160 | 9.0 | 9.0 | 1.0 | 4.0 | 1.0 | 7.0 | | 4.0 | 1.0 | 4.0 | | 4.5 | 5.0 | 5.0 |
| 356 | 0.1250 | 9.0 | 9.0 | 7.0 | 9.0 | 1.0 | 9.0 | | 4.0 | 3.0 | 9.0 | | 4.0 | 4.5 | 8.0 |
| | 0.0620 | 9.0 | 9.0 | 9.0 | 9.0 | 1.0 | 9.0 | | 3.0 | 3.0 | 8.0 | | 4.0 | 4.0 | 7.5 |
| | 0.0320 | 9.0 | 9.0 | 1.0 | 7.0 | 2.0 | 9.0 | | 2.0 | 3.0 | 9.0 | | 3.0 | 3.5 | 7.5 |
| | 0.0160 | 9.0 | 9.0 | 1.0 | 9.0 | 1.0 | 9.0 | | 1.0 | 1.0 | 7.5 | | 2.5 | 3.0 | 7.5 |
| 357 | 0.1250 | 9.0 | 9.0 | 4.0 | 9.0 | 4.0 | 9.0 | | 5.0 | 7.0 | 9.0 | | 5.0 | 5.0 | 7.5 |
| | 0.0620 | 9.0 | 9.0 | 1.0 | 9.0 | 1.0 | 9.0 | | 1.0 | 2.0 | 9.0 | | 3.0 | 4.5 | 7.5 |
| | 0.0320 | 9.0 | 9.0 | 1.0 | 9.0 | 1.0 | 9.0 | | 2.0 | 3.0 | 7.5 | | 3.0 | 4.0 | 7.5 |
| | 0.0160 | 9.0 | 9.0 | 1.0 | 9.0 | 0.0 | 9.0 | | 1.0 | 1.0 | 6.0 | | 2.5 | 2.5 | 6.5 |
| 358 | 0.1250 | 9.0 | 9.0 | 3.0 | 4.0 | 3.0 | 9.0 | | 0.0 | 0.0 | 5.5 | | 1.5 | 3.5 | 5.0 |
| | 0.0620 | 9.0 | 9.0 | 0.0 | 3.0 | 0.0 | 9.0 | | 0.0 | 0.0 | 4.0 | | 1.0 | 3.5 | 4.5 |

TABLE I-continued

Postemergence Herbicidal Evaluations of Test Compounds

| Compound Number | Rate (kg/ha) | ABUTH | AMBEL | CASOB | CHEAL | GALAP | IPOHE | IPOSS | ECHCG | SETVI | GLXMAW | GLXMA | ORYSAT | TRZAWR | ZEAMX |
|---|---|---|---|---|---|---|---|---|---|---|---|---|---|---|---|
|  | 0.0320 | 9.0 | 4.0 | 0.0 | 1.0 | 0.0 | 9.0 |  | 0.0 | 0.0 | 3.5 |  | 1.0 | 3.0 | 3.5 |
|  | 0.0160 | 9.0 | 4.0 | 0.0 | 0.0 | 0.0 | 5.0 |  | 0.0 | 0.0 | 3.5 |  | 0.5 | 2.5 | 3.5 |
| 359 | 0.1250 | 9.0 | 9.0 | 9.0 | 9.0 | 6.0 | 9.0 |  | 9.0 | 9.0 | 9.0 |  | 8.5 | 9.0 | 9.0 |
|  | 0.0620 | 9.0 | 9.0 | 9.0 | 9.0 | 7.7 | 9.0 |  | 9.0 | 9.0 | 8.1 |  | 8.7 | 8.9 | 9.0 |
|  | 0.0320 | 9.0 | 9.0 | 8.3 | 9.0 | 6.3 | 9.0 |  | 8.3 | 9.0 | 8.0 |  | 8.0 | 7.9 | 9.0 |
|  | 0.0160 | 9.0 | 9.0 | 6.7 | 9.0 | 6.0 | 9.0 |  | 9.0 | 9.0 | 7.0 |  | 6.9 | 4.5 | 8.1 |
| 360 | 0.1250 | 9.0 | 9.0 | 3.0 | 3.0 | 3.0 | 9.0 |  | 0.0 | 3.0 | 9.0 |  | 3.5 | 4.5 | 6.5 |
|  | 0.0620 | 9.0 | 9.0 | 0.0 | 3.0 | 3.0 | 9.0 |  | 0.0 | 0.0 | 6.5 |  | 2.5 | 4.0 | 5.5 |
|  | 0.0320 | 9.0 | 4.0 | 0.0 | 2.0 | 1.0 | 9.0 |  | 0.0 | 0.0 | 5.0 |  | 2.0 | 4.0 | 4.5 |
|  | 0.0160 | 9.0 | 0.0 | 0.0 | 0.0 | 0.0 | 3.0 |  | 0.0 | 0.0 | 4.0 |  | 1.5 | 3.5 | 4.0 |
| 361 | 0.1250 | 9.0 | 3.0 | 3.0 | 9.0 | 4.0 | 9.0 |  | 0.0 | 0.0 | 6.5 |  | 3.0 | 4.0 | 5.0 |
|  | 0.0620 | 9.0 | 2.0 | 3.0 | 7.0 | 3.0 | 9.0 |  | 0.0 | 0.0 | 5.0 |  | 1.5 | 3.0 | 4.0 |
|  | 0.0320 | 9.0 | 2.0 | 0.0 | 3.0 | 0.0 | 7.0 |  | 0.0 | 0.0 | 3.5 |  | 2.0 | 3.0 | 4.0 |
|  | 0.0160 | 9.0 | 2.0 | 0.0 | 2.0 | 0.0 | 1.0 |  | 0.0 | 0.0 | 3.5 |  | 1.5 | 3.0 | 4.0 |
| 362 | 0.2500 | 9.0 | 9.0 | 3.0 | 9.0 | 9.0 | 9.0 |  | 9.0 | 9.0 | 9.0 |  | 7.5 | 6.5 | 8.0 |
|  | 0.1250 | 9.0 | 9.0 | 1.0 | 2.0 | 5.0 | 9.0 |  | 9.0 | 9.0 | 8.0 |  | 7.5 | 5.5 | 8.0 |
|  | 0.0620 | 9.0 | 9.0 | 1.0 | 0.0 | 3.0 | 9.0 |  | 9.0 | 8.0 | 8.0 |  | 7.0 | 5.0 | 7.5 |
|  | 0.0320 | 9.0 | 9.0 | 0.0 | 0.0 | 3.0 | 7.0 |  | 8.0 | 8.0 | 8.0 |  | 5.5 | 4.0 | 7.5 |
|  | 0.0160 | 9.0 | 9.0 | 3.0 | 9.0 | 9.0 | 9.0 |  | 5.0 | 4.0 | 7.5 |  | 5.0 | 4.0 | 7.5 |
| 363 | 0.1250 | 9.0 | 9.0 | 0.0 | 2.0 | 5.0 | 3.0 |  | 0.0 | 0.0 | 4.5 |  | 1.0 | 3.5 | 3.0 |
|  | 0.0620 | 5.0 | 7.0 | 1.0 | 0.0 | 5.0 | 3.0 |  | 0.0 | 0.0 | 4.5 |  | 0.0 | 2.0 | 3.0 |
|  | 0.0320 | 4.0 | 3.0 | 0.0 | 0.0 | 0.0 | 2.0 |  | 0.0 | 0.0 | 4.0 |  | 0.0 | 1.0 | 2.0 |
|  | 0.0160 | 9.0 | 0.0 | 0.0 | 0.0 | 0.0 | 1.0 |  | 0.0 | 0.0 | 3.0 |  | 0.0 | 0.5 | 2.0 |
| 364 | 0.2500 | 9.0 | 9.0 | 2.0 | 9.0 | 9.0 | 9.0 |  | 2.0 | 3.0 | 7.0 |  | 4.0 | 4.5 | 5.0 |
|  | 0.1250 | 9.0 | 9.0 | 2.0 | 8.0 | 8.0 | 9.0 |  | 0.0 | 1.0 | 7.0 |  | 3.0 | 4.5 | 5.0 |
|  | 0.0620 | 9.0 | 9.0 | 0.0 | 8.0 | 7.0 | 9.0 |  | 0.0 | 0.0 | 6.0 |  | 2.0 | 3.5 | 5.0 |
|  | 0.0320 | 9.0 | 4.0 | 0.0 | 6.0 | 4.0 | 9.0 |  | 0.0 | 0.0 | 5.5 |  | 2.0 | 3.0 | 4.5 |
|  | 0.0160 | 9.0 | 9.0 | 0.0 | 4.0 | 2.0 | 9.0 |  | 0.0 | 0.0 | 5.5 |  | 2.0 | 2.5 | 4.5 |
| 365 | 0.2500 | 9.0 | 9.0 | 6.0 | 9.0 | 9.0 | 9.0 |  | 5.0 | 9.0 | 8.5 |  | 5.5 | 6.0 | 7.0 |
|  | 0.1250 | 9.0 | 9.0 | 2.0 | 7.0 | 6.0 | 9.0 |  | 0.0 | 5.0 | 8.0 |  | 5.0 | 5.0 | 5.5 |
|  | 0.0620 | 9.0 | 9.0 | 1.0 | 7.0 | 4.0 | 9.0 |  | 5.0 | 0.0 | 8.0 |  | 3.0 | 4.0 | 5.0 |
|  | 0.0320 | 9.0 | 2.0 | 0.0 | 7.0 | 2.0 | 9.0 |  | 0.0 | 0.0 | 6.0 |  | 2.0 | 3.0 | 5.0 |
|  | 0.0160 | 9.0 | 1.0 | 0.0 | 4.0 | 1.0 | 9.0 |  | 0.0 | 0.0 | 5.5 |  | 1.5 | 3.0 | 5.0 |
| 366 | 0.2500 | 9.0 | 9.0 | 9.0 | 9.0 | 9.0 | 9.0 |  | 8.0 | 9.0 | 9.0 |  | 7.5 | 7.0 | 7.5 |
|  | 0.1250 | 9.0 | 9.0 | 8.5 | 9.0 | 9.0 | 9.0 |  | 8.0 | 9.0 | 9.0 |  | 7.0 | 6.8 | 7.3 |
|  | 0.0620 | 9.0 | 9.0 | 5.5 | 9.0 | 8.5 | 9.0 |  | 7.0 | 9.0 | 9.0 |  | 5.8 | 5.3 | 6.5 |
|  | 0.0320 | 9.0 | 9.0 | 5.0 | 9.0 | 6.0 | 9.0 |  | 3.5 | 6.0 | 8.5 |  | 4.5 | 4.0 | 5.3 |
|  | 0.0160 | 9.0 | 9.0 | 3.5 | 9.0 | 7.5 | 9.0 |  | 2.5 | 9.0 | 7.8 |  | 3.0 | 3.0 | 4.8 |
| 367 | 0.0620 | 9.0 | 9.0 | 1.0 | 5.0 | 2.0 | 9.0 |  | 4.0 | 9.0 | 8.5 |  | 5.0 | 5.0 | 7.0 |
|  | 0.0320 | 9.0 | 7.0 | 1.0 | 5.0 | 2.0 | 9.0 |  | 3.0 | 4.0 | 7.5 |  | 5.0 | 4.5 | 7.0 |
|  | 0.0160 | 9.0 | 4.0 | 1.0 | 7.0 | 4.0 | 9.0 |  | 2.0 | 2.0 | 7.0 |  | 5.0 | 4.5 | 6.5 |
| 368 | 0.0620 | 9.0 | 9.0 | 2.0 | 5.0 | 2.0 | 9.0 |  | 2.0 | 2.0 | 5.5 |  | 4.0 | 4.0 | 5.5 |
|  | 0.0320 | 7.0 | 7.0 | 2.0 | 7.0 | 4.0 | 9.0 |  | 2.0 | 1.0 | 4.5 |  | 3.0 | 4.0 | 5.0 |
|  | 0.0160 | 7.0 | 4.0 | 1.0 | 4.0 | 4.0 | 9.0 |  | 1.0 | 0.0 | 8.0 |  | 2.5 | 3.0 | 4.0 |
| 369 | 0.1250 | 9.0 | 9.0 | 4.0 | 9.0 | 5.0 | 9.0 |  | 2.0 | 3.0 | 6.5 |  | 4.0 | 4.0 | 6.0 |
|  | 0.0620 | 9.0 | 7.0 | 1.0 | 9.0 | 3.0 | 9.0 |  | 2.0 | 1.0 | 6.0 |  | 3.0 | 4.0 | 5.0 |
|  | 0.0320 | 6.2 |  |  |  |  |  |  |  |  |  |  |  |  | 4.5 |

TABLE I-continued

Postemergence Herbicidal Evaluations of Test Compounds

| Compound Number | Rate (kg/ha) | ABUTH | AMBEL | CASOB | CHEAL | GALAP | IPOHE | IPOSS | ECHCG | SETVI | GLXMAW | GLXMA | ORYSAT | TRZAWR | ZEAMX |
|---|---|---|---|---|---|---|---|---|---|---|---|---|---|---|---|
| 370 | 0.0160 | 5.2 | 6.0 | 0.0 | 1.0 | 2.0 | 9.0 | | 2.0 | 0.0 | 5.5 | | 3.0 | 3.5 | 4.0 |
| | 0.0620 | 9.0 | 9.0 | 1.0 | 9.0 | 2.0 | 9.0 | | 9.0 | 9.0 | 9.0 | | 5.0 | 4.5 | 7.5 |
| | 0.0320 | 9.0 | 9.0 | 1.0 | 2.0 | 1.0 | 9.0 | | 4.0 | 7.0 | 9.0 | | 4.5 | 4.0 | 7.5 |
| | 0.0160 | 7.0 | 1.0 | 0.0 | 0.0 | 1.0 | 9.0 | | 1.0 | 1.0 | 8.0 | | 4.0 | 4.0 | 7.0 |
| 371 | 0.0620 | 9.0 | 7.0 | 1.0 | 2.0 | 2.0 | 9.0 | | 1.0 | 1.0 | 4.5 | | 2.5 | 3.5 | 4.0 |
| | 0.0320 | 4.0 | 4.0 | 1.0 | 2.0 | 1.0 | 9.0 | | 0.0 | 0.0 | 3.0 | | 1.5 | 2.5 | 4.0 |
| | 0.0160 | 1.0 | 0.0 | 0.0 | 0.0 | 0.0 | 3.0 | | 0.0 | 0.0 | 2.5 | | 1.0 | 1.5 | 2.5 |
| 372 | 0.1250 | 9.0 | 9.0 | 9.0 | 9.0 | 6.0 | 9.0 | | 3.0 | 9.0 | 8.5 | | 1.0 | 6.0 | 1.0 |
| | 0.0620 | 9.0 | 9.0 | 5.0 | 9.0 | 3.0 | 9.0 | | 3.0 | 7.0 | 8.5 | | 6.5 | 5.0 | 7.0 |
| | 0.0320 | 9.0 | 9.0 | 3.0 | 9.0 | 3.0 | 9.0 | | 2.0 | 7.0 | 8.5 | | 5.5 | 4.5 | 5.5 |
| | 0.0160 | 9.0 | 6.0 | 2.0 | 9.0 | 1.0 | 9.0 | | 1.0 | 4.0 | 7.0 | | 4.5 | 4.0 | 4.5 |
| 373 | 0.0620 | 9.0 | 9.0 | 0.0 | 4.0 | 8.0 | 9.0 | | 3.0 | 6.0 | 7.0 | | 0.5 | 3.0 | 4.5 |
| | 0.0320 | 9.0 | 7.0 | 0.0 | 3.0 | 3.0 | 9.0 | | 3.0 | 6.0 | 7.0 | | 0.5 | 3.0 | 7.0 |
| | 0.0160 | 7.0 | 4.0 | 0.0 | 3.0 | 1.0 | 9.0 | | 0.0 | 2.0 | 7.0 | | 0.5 | 2.0 | 7.0 |
| 374 | 0.0620 | 9.0 | 9.0 | 3.0 | 5.0 | 7.0 | 9.0 | | 0.0 | 3.0 | 9.0 | | 2.0 | 3.0 | 5.0 |
| | 0.0320 | 9.0 | 9.0 | 0.0 | 3.0 | 4.0 | 9.0 | | 0.0 | 0.0 | 7.0 | | 1.0 | 3.0 | 5.0 |
| | 0.0160 | 9.0 | 3.0 | 0.0 | 2.0 | 4.0 | 9.0 | | 0.0 | 0.0 | 5.5 | | 0.5 | 3.0 | 5.0 |
| 375 | 0.0620 | 9.0 | 9.0 | 5.0 | 9.0 | 3.0 | 9.0 | | 2.0 | 3.0 | 8.5 | | 2.5 | 4.5 | 5.0 |
| | 0.0320 | 9.0 | 7.0 | 5.0 | 5.0 | 3.0 | 9.0 | | 0.0 | 7.0 | 8.5 | | 1.5 4.5 | 5.0 | 5.0 |
| | 0.0160 | 9.0 | 3.0 | 0.0 | 4.0 | 3.0 | 9.0 | | 0.0 | 2.0 | 5.0 | | 1.0 | 3.0 | 3.0 |
| 376 | 0.0620 | 9.0 | 9.0 | 0.0 | 1.0 | 4.0 | 9.0 | | 0.0 | 0.0 | 7.5 | | 1.0 | 3.5 | 3.0 |
| | 0.0320 | 9.0 | 3.0 | 0.0 | 0.0 | 2.0 | 9.0 | | 0.0 | 0.0 | 5.0 | | 0.5 | 3.0 | 2.0 |
| | 0.0160 | 4.0 | 0.0 | 0.0 | 0.0 | 0.0 | 3.0 | | 0.0 | 0.0 | 3.5 | | 0.0 | 2.0 | 1.5 |
| 377 | 0.0620 | 9.0 | 9.0 | 7.0 | 9.0 | 5.0 | 9.0 | | 2.0 | 6.0 | 8.5 | | 1.5 | 4.0 | 5.0 |
| | 0.0320 | 9.0 | 9.0 | 3.0 | 9.0 | 5.0 | 9.0 | | 0.0 | 3.0 | 7.5 | | 1.0 | 4.0 | 5.0 |
| | 0.0160 | 9.0 | 9.0 | 1.0 | 9.0 | 2.0 | 9.0 | | 0.0 | 2.0 | 7.5 | | 1.0 | 3.5 | 5.0 |
| 378 | 0.0620 | 9.0 | 9.0 | 7.0 | 9.0 | 9.0 | 9.0 | | 8.0 | 8.0 | 9.0 | | 6.0 | 6.0 | 7.5 |
| | 0.0320 | 9.0 | 9.0 | 6.5 | 9.0 | 9.0 | 9.0 | | 7.5 | 9.0 | 9.0 | | 7.5 | 6.0 | 6.5 |
| | 0.0160 | 9.0 | 9.0 | 9.0 | 9.0 | 9.0 | 9.0 | | 5.0 | 9.0 | 9.0 | | 7.5 | 6.0 | 6.0 |
| 379 | 0.0320 | 9.0 | 9.0 | 4.0 | 4.0 | 7.0 | 9.0 | | 0.0 | 4.0 | 9.0 | | 2.0 | 3.5 | 5.0 |
| | 0.0160 | 9.0 | 9.0 | 1.0 | 9.0 | 4.0 | 9.0 | | 0.0 | 2.0 | 7.5 | | 0.5 | 3.0 | 4.5 |
| 380 | 0.1250 | 9.0 | 9.0 | 9.0 | 9.0 | 7.0 | 9.0 | | 6.0 | 9.0 | 8.5 | | 4.5 | 4.5 | 5.0 |
| | 0.0620 | 9.0 | 9.0 | 7.0 | 9.0 | 4.0 | 9.0 | | 1.0 | 6.0 | 6.0 | | 4.0 | 4.5 | 5.0 |
| | 0.0320 | 9.0 | 9.0 | 6.0 | 9.0 | 4.0 | 9.0 | | 3.0 | 3.0 | 5.5 | | 3.5 | 4.5 | 4.5 |
| | 0.0160 | 9.0 | 9.0 | 4.0 | 7.0 | 1.0 | 9.0 | | 1.0 | 9.0 | 5.5 | | .5 | 4.0 | 4.5 |
| 381 | 0.0620 | 9.0 | 9.0 | 3.0 | 5.0 | 3.0 | 9.0 | | 0.0 | 1.0 | 5.0 | | 2.0 | 2.5 | 5.0 |
| | 0.0320 | 9.0 | 8.0 | 0.0 | 0.0 | 3.0 | 9.0 | | 0.0 | 0.0 | 5.0 | | 1.0 | 2.0 | 4.0 |
| | 0.0160 | 4.0 | 3.0 | 0.0 | 0.0 | 0.0 | 3.0 | | 0.0 | 0.0 | 4.0 | | 0.0 | 1.5 | 4.0 |
| 382 | 0.0620 | 9.0 | 9.0 | 2.0 | 2.0 | 3.0 | 9.0 | | 6.0 | 9.0 | 7.0 | | 1.5 | 2.5 | 4.5 |
| | 0.0320 | 9.0 | 4.0 | 0.0 | 1.0 | 1.0 | 9.0 | | 1.0 | 6.0 | 5.0 | | 0.5 | 2.5 | 3.5 |
| | 0.0160 | 4.0 | 0.0 | 0.0 | 0.0 | 0.0 | 3.0 | | 3.0 | 9.0 | 4.0 | | 0.0 | 1.5 | 2.5 |
| 383 | 0.0620 | 9.0 | 9.0 | 2.0 | 9.0 | 9.0 | 9.0 | | 1.0 | 0.0 | 8.0 | | 6.5 | 5.5 | 8.5 |
| | 0.0320 | 9.0 | 9.0 | 2.0 | 9.0 | 4.0 | 9.0 | | 0.0 | 0.0 | 7.5 | | 5.0 | 5.0 | 8.0 |
| | 0.0160 | 9.0 | 9.0 | 0.0 | 9.0 | 3.0 | 9.0 | | 0.0 | 9.0 | 7.5 | | 3.5 | 4.0 | 7.5 |
| 384 | 0.0620 | 9.0 | 9.0 | 3.0 | 9.0 | 9.0 | 9.0 | | 9.0 | 9.0 | 8.5 | | 6.5 | 5.5 | 8.0 |
| | 0.320 | 9.0 | 9.0 | 3.0 | 5.0 | 7.0 | 9.0 | | 5.0 | 7.0 | 8.5 | | 5.5 | 5.0 | 8.0 |
| | 0.0160 | 9.0 | 9.0 | 1.0 | 4.0 | 4.0 | 9.0 | | 5.0 | 4.0 | 8.0 | | 4.5 | 4.5 | 7.5 |

TABLE I-continued

Postemergence Herbicidal Evaluations of Test Compounds

| Compound Number | Rate (kg/ha) | ABUTH | AMBEL | CASOB | CHEAL | GALAP | IPOHE | IPOSS | ECHCG | SETVI | GLXMAW | GLXMA | ORYSAT | TRZAWR | ZEAMX |
|---|---|---|---|---|---|---|---|---|---|---|---|---|---|---|---|
| 385 | 0.0620 | 9.0 | 9.0 | 3.0 | 7.0 | 7.0 | 9.0 | | 9.0 | 9.0 | 9.0 | | 4.0 | 5.5 | 8.0 |
| | 0.0320 | 9.0 | 9.0 | 0.0 | 7.0 | 5.0 | 9.0 | | 5.0 | 9.0 | 9.0 | | 3.5 | 5.5 | 8.0 |
| | 0.0160 | 9.0 | 4.0 | 0.0 | 3.0 | 3.0 | 9.0 | | 2.0 | 3.0 | 8.0 | | 2.0 | 4.0 | 8.0 |
| 386 | 0.0620 | 9.0 | 9.0 | 3.0 | 7.0 | 7.0 | 9.0 | | 7.0 | 9.0 | 9.0 | | 5.0 | 6.0 | 8.0 |
| | 0.320 | 9.0 | 9.0 | 0.0 | 5.0 | 9.0 | 9.0 | | 7.0 | 9.0 | 9.0 | | 4.0 | 5.5 | 8.0 |
| | 0.0160 | 9.0 | 6.0 | 0.0 | 1.0 | 9.0 | 9.0 | | 3.0 | 9.0 | 7.5 | | 2.5 | 4.0 | 7.5 |
| 387 | 0.0620 | 9.0 | 9.0 | 2.0 | 5.0 | 9.0 | 9.0 | | 5.0 | 9.0 | 9.0 | | 4.5 | 5.5 | 8.0 |
| | 0.0320 | 9.0 | 9.0 | 1.0 | 4.0 | 3.0 | 9.0 | | 4.0 | 5.0 | 8.5 | | 3.5 | 5.0 | 7.5 |
| | 0.0160 | 9.0 | 7.0 | 0.0 | 2.0 | 3.0 | 9.0 | | 4.0 | 5.0 | 7.5 | | 2.0 | 4.5 | 7.5 |
| 388 | 0.0620 | 9.0 | 9.0 | 5.0 | 9.0 | 6.0 | 9.0 | | 9.0 | 9.0 | 9.0 | | 4.5 | 6.5 | 6.0 |
| | 0.0320 | 8.0 | 7.0 | 2.0 | 3.0 | 4.0 | 9.0 | | 5.0 | 5.0 | 7.5 | | 3.0 | 5.5 | 5.5 |
| | 0.0160 | 9.0 | 3.0 | 1.0 | 9.0 | 3.0 | 9.0 | | 1.0 | 5.0 | 7.5 | | 1.5 | 4.0 | 5.0 |
| 389 | 0.0620 | 9.0 | 9.0 | 3.0 | 9.0 | 9.0 | 9.0 | | 5.0 | 9.0 | 8.5 | | 5.0 | 5.5 | 8.0 |
| | 0.0320 | 9.0 | 9.0 | 2.0 | 9.0 | 6.0 | 9.0 | | 2.0 | 8.0 | 8.5 | | 4.5 | 5.0 | 8.5 |
| | 0.0160 | 9.0 | 9.0 | 0.0 | 4.0 | 4.0 | 9.0 | | 0.0 | 2.0 | 8.0 | | 3.0 | 4.5 | 6.0 |
| 390 | 0.1250 | 9.0 | 9.0 | 9.0 | 9.0 | 8.0 | 9.0 | | 4.0 | 9.0 | 9.0 | | 4.5 | 5.0 | 5.5 |
| | 0.0620 | 9.0 | 9.0 | 6.0 | 9.0 | 7.0 | 9.0 | | 3.0 | 7.0 | 9.0 | | 4.5 | 4.5 | 5.5 |
| | 0.0320 | 9.0 | 9.0 | 5.0 | 9.0 | 4.0 | 9.0 | | 2.0 | 6.0 | 8.5 | | 3.5 | 4.0 | 5.5 |
| | 0.0160 | 9.0 | 9.0 | 6.0 | 9.0 | 7.0 | 9.0 | | 2.0 | 4.0 | 8.0 | | 3.0 | 3.5 | 4.5 |
| 391 | 0.1250 | 9.0 | 9.0 | 3.0 | 9.0 | 1.0 | 9.0 | | 7.0 | 9.0 | 6.5 | | 3.5 | 4.5 | 7.0 |
| | 0.0620 | 9.0 | 9.0 | 1.0 | 9.0 | 1.0 | 9.0 | | 7.0 | 7.0 | 6.5 | | 3.5 | 3.5 | 7.0 |
| | 0.0320 | 9.0 | 9.0 | 1.0 | 9.0 | 1.0 | 9.0 | | 4.0 | 6.0 | 6.5 | | 3.0 | 3.0 | 7.0 |
| | 0.0160 | 9.0 | 9.0 | 3.0 | 9.0 | 4.0 | 9.0 | | 4.0 | 2.0 | 6.0 | | 2.5 | 2.5 | 6.0 |
| 392 | 0.0620 | 9.0 | 9.0 | 1.0 | 9.0 | 3.0 | 9.0 | | 1.0 | 3.0 | 7.5 | | 2.5 | 4.5 | 6.0 |
| | 0.0320 | 9.0 | 9.0 | 2.0 | 7.0 | 3.0 | 9.0 | | 0.0 | 0.0 | 6.5 | | 2.5 | 3.5 | 5.0 |
| | 0.0160 | 9.0 | 3.0 | 0.0 | 9.0 | 4.0 | 9.0 | | 0.0 | 0.0 | 5.5 | | 2.0 | 3.5 | 5.0 |
| 393 | 0.0620 | 9.0 | 9.0 | 3.0 | 9.0 | 3.0 | 9.0 | | 2.0 | 3.0 | 8.0 | | 2.0 | 5.0 | 6.0 |
| | 0.0320 | 9.0 | 9.0 | 1.0 | 9.0 | 1.0 | 9.0 | | 1.0 | 1.0 | 7.0 | | 2.5 | 4.5 | 5.5 |
| | 0.0160 | 9.0 | 9.0 | 0.0 | 9.0 | 5.0 | 5.0 | | 0.0 | 0.0 | 7.0 | | 1.5 | 4.0 | 4.5 |
| 394 | 0.0620 | 9.0 | 9.0 | 1.0 | 9.0 | 3.0 | 9.0 | | 0.0 | 1.0 | 8.0 | | 2.5 | 5.0 | 6.0 |
| | 0.0320 | 9.0 | 8.0 | 0.0 | 5.0 | 0.0 | 9.0 | | 0.0 | 0.0 | 7.5 | | 2.0 | 4.5 | 5.0 |
| | 0.0160 | 9.0 | 4.0 | 3.0 | 9.0 | 5.0 | 7.0 | | 7.0 | 0.0 | 7.0 | | 1.5 | 4.0 | 5.0 |
| 395 | 0.0620 | 9.0 | 9.0 | 3.0 | 9.0 | 2.0 | 9.0 | | 4.0 | 5.0 | 6.5 | | 6.0 | 5.0 | 8.0 |
| | 0.0320 | 9.0 | 9.0 | 3.0 | 9.0 | 0.0 | 9.0 | | 2.0 | 3.0 | 7.0 | | 5.5 | 3.5 | 8.0 |
| | 0.0160 | 9.0 | 9.0 | 2.0 | 9.0 | 4.0 | 9.0 | | 3.0 | 5.0 | 6.0 | | 2.0 | 7.0 | 7.5 |
| 396 | 0.0620 | 9.0 | 9.0 | 2.0 | 9.0 | 3.0 | 9.0 | | 0.0 | 0.0 | 8.5 | | 8.5 | 7.0 | 6.0 |
| | 0.0320 | 9.0 | 9.0 | 0.0 | 9.0 | 4.0 | 9.0 | | 2.0 | 5.0 | 7.5 | | 6.5 | 6.5 | 5.5 |
| | 0.0160 | 9.0 | 9.0 | 2.0 | 9.0 | 5.0 | 9.0 | | 0.0 | 3.0 | 6.5 | | 3.5 | 7.5 | 6.0 |
| 397 | 0.0620 | 9.0 | 9.0 | 9.0 | 9.0 | 4.0 | 9.0 | | 1.0 | 2.0 | 9.0 | | 8.0 | 6.5 | 6.0 |
| | 0.0320 | 9.0 | 9.0 | 9.0 | 9.0 | 1.0 | 9.0 | | 1.0 | 0.0 | 9.0 | | 6.0 | 5.5 | 6.0 |
| | 0.0160 | 9.0 | 9.0 | 1.0 | 9.0 | 6.0 | 5.0 | | 1.0 | 3.0 | 7.5 | | 4.5 | 4.0 | 5.5 |
| 398 | 0.0620 | 9.0 | 4.0 | 0.0 | 9.0 | 0.0 | 9.0 | | 1.0 | 2.0 | 7.5 | | 1.5 | 4.0 | 5.5 |
| | 0.0320 | 9.0 | 4.0 | 0.0 | 9.0 | 3.0 | 9.0 | | 1.0 | 2.0 | 5.5 | | 1.5 | 3.5 | 5.0 |
| | 0.0160 | 9.0 | 8.0 | 1.0 | 9.0 | 0.0 | 7.0 | | 0.0 | 2.0 | 7.0 | | 2.0 | 4.0 | 4.5 |
| 399 | 0.0620 | 9.0 | 4.0 | 0.0 | 8.0 | 0.0 | 9.0 | | 0.0 | 2.0 | 7.0 | | 1.0 | 3.5 | 5.5 |
| | 0.0320 | 9.0 | 4.0 | 0.0 | 5.0 | 0.0 | 9.0 | | 0.0 | 2.0 | 5.0 | | 1.0 | 3.5 | 5.0 |
| | 0.0160 | 8.0 | 2.0 | 0.0 | 5.0 | 0.0 | 7.0 | | 0.0 | 0.0 | 5.0 | | 1.0 | 4.5 | 4.5 |

TABLE I-continued

Postemergence Herbicidal Evaluations of Test Compounds

| Compound Number | Rate (kg/ha) | ABUTH | AMBEL | CASOB | CHEAL | GALAP | IPOHE | IPOSS | ECHCG | SETVI | GLXMAW | GLXMA | ORYSAT | TRZAWR | ZEAMX |
|---|---|---|---|---|---|---|---|---|---|---|---|---|---|---|---|
| 400 | 0.0620 | 9.0 | 9.0 | 1.0 | 9.0 | 4.0 | 9.0 | | 1.0 | 3.0 | 7.0 | | 2.5 | 4.0 | 5.5 |
| | 0.0320 | 9.0 | 4.0 | 0.0 | 4.0 | 2.0 | 9.0 | | 0.0 | 0.0 | 6.5 | | 1.0 | 3.5 | 5.0 |
| | 0.0160 | 8.0 | 3.0 | 0.0 | 0.0 | 0.0 | 5.0 | | 0.0 | 0.0 | 5.5 | | 1.0 | 3.5 | 5.0 |
| 401 | 0.0620 | 9.0 | 7.0 | 1.0 | 9.0 | 3.0 | 9.0 | | 2.0 | 2.0 | 5.0 | | 3.0 | 4.0 | 5.0 |
| | 0.0320 | 9.0 | 7.0 | 1.0 | 6.0 | 3.0 | 9.0 | | 3.0 | 2.0 | 5.0 | | 2.5 | 3.0 | 5.0 |
| | 0.0160 | 7.0 | 7.0 | 0.0 | 3.0 | 1.0 | 7.0 | | 2.0 | 0.0 | 5.0 | | 3.0 | 3.0 | 4.5 |
| 402 | 0.0620 | 9.0 | 9.0 | 1.0 | 7.0 | 6.0 | 9.0 | | 3.0 | 0.0 | 5.0 | | 3.5 | 3.5 | 5.0 |
| | 0.0320 | 9.0 | 7.0 | 0.0 | 3.0 | 1.0 | 6.0 | | 2.0 | 1.0 | 5.0 | | 3.0 | 3.0 | 4.5 |
| | 0.0160 | 9.0 | 2.0 | 0.0 | 2.0 | 0.0 | 9.0 | | 0.0 | 0.0 | 4.0 | | 2.5 | 3.0 | 4.0 |
| 403 | 0.0620 | 9.0 | 5.0 | 0.0 | 9.0 | 3.0 | 9.0 | | 2.0 | 0.0 | 8.0 | | 2.0 | 4.5 | 4.0 |
| | 0.0320 | 9.0 | 2.0 | 0.0 | 4.0 | 2.0 | 9.0 | | 0.0 | 0.0 | 7.0 | | 1.0 | 3.5 | 4.0 |
| | 0.0160 | 5.0 | 0.0 | 0.0 | 3.0 | 0.0 | 4.0 | | 0.0 | 0.0 | 5.0 | | 0.0 | 3.0 | 2.5 |
| 404 | 0.0620 | 9.0 | 9.0 | 2.0 | 9.0 | 3.0 | 9.0 | | 7.0 | 6.0 | 7.0 | | 4.0 | 4.5 | 5.0 |
| | 0.0320 | 9.0 | 7.0 | 2.0 | 9.0 | 2.0 | 9.0 | | 5.0 | 2.0 | 7.0 | | 3.0 | 3.5 | 4.5 |
| | 0.0160 | 9.0 | 6.0 | 1.0 | 3.0 | 1.0 | 9.0 | | 3.0 | 2.0 | 7.0 | | 2.5 | 3.0 | 4.0 |
| 405 | 0.0620 | 9.0 | 9.0 | 4.0 | 6.0 | 2.0 | 9.0 | | 5.0 | 6.0 | 8.0 | | 5.0 | 5.5 | 8.0 |
| | 0.0320 | 9.0 | 9.0 | 1.0 | 6.0 | 1.0 | 9.0 | | 5.0 | 3.0 | 7.5 | | 5.0 | 5.5 | 7.5 |
| | 0.0160 | 9.0 | 9.0 | 1.0 | 3.0 | 1.0 | 7.0 | | 4.0 | 2.0 | 6.5 | | 3.5 | 4.5 | 7.0 |
| 406 | 0.0620 | 9.0 | 9.0 | 6.0 | 9.0 | 3.0 | 9.0 | | 7.0 | 7.0 | 9.0 | | 5.0 | 5.5 | 8.0 |
| | 0.0320 | 9.0 | 9.0 | 6.0 | 4.0 | 2.0 | 9.0 | | 9.0 | 9.0 | 7.0 | | 3.0 | 5.0 | 8.0 |
| | 0.0160 | 9.0 | 7.0 | 4.0 | 3.0 | 1.0 | 9.0 | | 7.0 | 9.0 | 7.0 | | 3.5 | 3.5 | 7.0 |
| 407 | 0.0620 | 9.0 | 9.0 | 0.0 | 4.0 | 4.0 | 9.0 | | 1.0 | 2.0 | 6.0 | | 3.0 | 5.5 | 5.0 |
| | 0.0320 | 9.0 | 9.0 | 0.0 | 3.0 | 2.0 | 9.0 | | 0.0 | 0.0 | 5.5 | | 3.0 | 5.0 | 4.5 |
| | 0.0160 | 7.0 | 3.0 | 0.0 | 2.0 | 2.0 | 5.0 | | 0.0 | 0.0 | 5.5 | | 2.5 | 4.5 | 4.5 |
| 408 | 0.0620 | 9.0 | 7.0 | 2.0 | 7.0 | 3.0 | 9.0 | | 3.0 | 9.0 | 8.0 | | 5.5 | 5.5 | 7.5 |
| | 0.0320 | 7.0 | | 0.0 | 4.0 | 1.0 | 9.0 | | 2.0 | 5.0 | 7.5 | | 3.0 | 5.0 | 5.5 |
| | 0.0160 | 7.0 | 1.0 | 0.0 | 3.0 | 0.0 | 7.0 | | 2.0 | 2.0 | 6.5 | | 2.5 | 4.5 | 3.5 |
| 409 | 0.0620 | 9.0 | 9.0 | 2.0 | 9.0 | 7.0 | 9.0 | | 3.0 | 7.0 | 8.0 | | 6.0 | 6.0 | 7.5 |
| | 0.0320 | 9.0 | 9.0 | 0.0 | 4.0 | 3.0 | 9.0 | | 1.0 | 4.0 | 7.5 | | 3.5 | 5.0 | 7.0 |
| | 0.0160 | 9.0 | 4.0 | 0.0 | 4.0 | 0.0 | 9.0 | | 0.0 | 0.0 | 5.5 | | 3.5 | 4.0 | 4.5 |
| 410 | 0.0620 | 9.0 | 4.0 | 0.0 | 9.0 | 4.0 | 9.0 | | 3.0 | 6.0 | 7.5 | | 5.5 | 5.5 | 7.5 |
| | 0.0320 | 9.0 | 3.0 | 0.0 | 4.0 | 3.0 | 9.0 | | 2.0 | 4.0 | 7.5 | | 4.5 | 5.0 | 5.5 |
| | 0.0160 | 9.0 | 2.0 | 0.0 | 3.0 | 3.0 | 9.0 | | 1.0 | 3.0 | 7.0 | | 4.0 | 4.5 | 4.5 |
| 411 | 0.0620 | 9.0 | 9.0 | 0.0 | 9.0 | 6.0 | 9.0 | | 7.0 | 9.0 | 8.5 | | 5.5 | 5.5 | 7.5 |
| | 0.0320 | 9.0 | 9.0 | 2.0 | 7.0 | 4.0 | 9.0 | | 6.0 | 9.0 | 8.5 | | 5.0 | 5.0 | 7.0 |
| | 0.0160 | 9.0 | 4.0 | 4.0 | 4.0 | 3.0 | 9.0 | | 2.0 | 3.0 | 8.5 | | 4.0 | 3.5 | 6.5 |
| 412 | 0.0620 | 9.0 | 9.0 | 3.0 | 4.0 | 4.0 | 9.0 | | 6.0 | 7.0 | 7.0 | | 6.0 | 5.5 | 7.0 |
| | 0.0320 | 9.0 | 9.0 | 3.0 | 7.0 | 6.0 | 9.0 | | 5.0 | 5.0 | 6.5 | | 4.0 | 4.0 | 7.0 |
| | 0.0160 | 4.0 | 9.0 | 1.0 | 2.0 | 1.0 | 9.0 | | 4.0 | 2.0 | 5.0 | | 3.0 | 3.0 | 5.0 |
| 413 | 0.0620 | 9.0 | 9.0 | 5.0 | 9.0 | 5.0 | 9.0 | | 4.0 | 4.0 | 7.5 | | 4.0 | 4.0 | 5.5 |
| | 0.0320 | 9.0 | 9.0 | 3.0 | 4.0 | 4.0 | 9.0 | | 3.0 | 4.0 | 7.0 | | 3.5 | 3.5 | 5.0 |
| | 0.0160 | 9.0 | 9.0 | 1.0 | 7.0 | 4.0 | 9.0 | | 2.0 | 2.0 | 5.5 | | 3.5 | 3.5 | 5.0 |
| 414 | 0.0620 | 9.0 | 7.0 | 7.0 | 7.0 | 7.0 | 9.0 | | 2.0 | 2.0 | 7.0 | | 3.0 | 3.5 | 5.5 |
| | 0.0320 | 9.0 | 9.0 | 2.0 | 7.0 | 6.0 | 9.0 | | 2.0 | 1.0 | 6.0 | | 3.0 | 3.5 | 5.5 |
| | 0.0160 | 9.0 | 7.0 | 6.0 | 4.0 | 2.0 | 7.0 | | 4.0 | 5.0 | 6.5 | | 3.5 | 4.0 | 5.5 |
| 415 | 0.0620 | 9.0 | 9.0 | 6.0 | 9.0 | 6.0 | 9.0 | | 4.0 | 5.0 | 6.5 | | 3.5 | 3.5 | 5.5 |
| | 0.0320 | 9.0 | 9.0 | 2.0 | 4.0 | 4.0 | 9.0 | | 3.0 | 4.0 | 7.0 | | 3.5 | 3.5 | 5.5 |

TABLE I-continued

Postemergence Herbicidal Evaluations of Test Compounds

| Compound Number | Rate (kg/ha) | ABUTH | AMBEL | CASOB | CHEAL | GALAP | IPOHE | IPOSS | ECHCG | SETVI | GLXMAW | GLXMA | ORYSAT | TRZAWR | ZEAMX |
|---|---|---|---|---|---|---|---|---|---|---|---|---|---|---|---|
| 416 | 0.0160 | 9.0 | 9.0 | 1.0 | 7.0 | 3.0 | 9.0 | | 2.0 | 1.0 | 6.0 | | 2.5 | 2.5 | 5.5 |
| | 0.0620 | 9.0 | 9.0 | 4.0 | 9.0 | 5.0 | 9.0 | | 3.0 | 9.0 | 7.5 | | 4.5 | 5.0 | 5.5 |
| 417 | 0.0320 | 9.0 | 9.0 | 3.0 | 9.0 | 4.0 | 9.0 | | 3.0 | 7.0 | 7.0 | | 4.0 | 4.0 | 5.0 |
| | 0.0160 | 9.0 | 9.0 | 2.0 | 7.0 | 3.0 | 9.0 | | 2.0 | 2.0 | 7.0 | | 3.5 | 3.5 | 5.0 |
| | 0.0620 | 9.0 | 7.0 | 4.0 | 7.0 | 4.0 | 9.0 | | 7.0 | 7.0 | 7.5 | | 4.5 | 4.5 | 6.0 |
| | 0.0320 | 6.0 | 5.0 | 1.0 | 4.0 | 3.0 | 9.0 | | 4.0 | 4.0 | 7.0 | | 3.5 | 3.5 | 6.0 |
| 418 | 0.0160 | 4.0 | 4.0 | 1.0 | 2.0 | 1.0 | 3.0 | | 1.0 | 1.0 | 7.0 | | 2.5 | 2.0 | 5.0 |
| | 0.0620 | 9.0 | 9.0 | 1.0 | 7.0 | 1.0 | 9.0 | | 9.0 | 9.0 | 7.5 | | 4.5 | 4.5 | 6.0 |
| | 0.0320 | 9.0 | 3.0 | 0.0 | 4.0 | 0.0 | 9.0 | | 3.0 | 3.0 | 7.5 | | 3.5 | 3.5 | 5.0 |
| 419 | 0.0160 | 9.0 | 9.0 | 0.0 | 2.0 | 0.0 | 9.0 | | 2.0 | 1.0 | 6.0 | | 3.5 | 3.0 | 6.0 |
| | 0.0620 | 9.0 | 4.0 | 1.0 | 7.0 | 3.0 | 9.0 | | 1.0 | 4.0 | 4.5 | | 5.0 | 5.0 | 5.5 |
| | 0.0320 | 9.0 | 4.0 | 0.0 | 3.0 | 0.0 | 7.0 | | 3.0 | 1.0 | 5.5 | | 4.0 | 4.0 | 5.0 |
| | 0.0160 | 2.0 | 1.0 | 0.0 | 1.0 | 0.0 | 9.0 | | 1.0 | 0.0 | 5.0 | | 3.0 | 3.5 | 5.0 |
| 420 | 0.0620 | 9.0 | 9.0 | 9.0 | 9.0 | 4.0 | 9.0 | | 9.0 | 8.0 | 4.5 | | 5.0 | 4.5 | 7.5 |
| | 0.0320 | 9.0 | 9.0 | 3.0 | 9.0 | 3.0 | 9.0 | | 3.0 | 2.0 | 7.5 | | 4.0 | 4.0 | 7.5 |
| | 0.0160 | 9.0 | 9.0 | 3.0 | 9.0 | 2.0 | 9.0 | | 1.0 | 1.0 | 6.5 | | 3.5 | 3.5 | 6.5 |
| 421 | 0.0620 | 9.0 | 9.0 | 1.0 | 4.0 | 0.0 | 9.0 | | 5.0 | 4.0 | 5.0 | | 3.5 | 3.5 | 6.5 |
| | 0.0320 | 9.0 | 9.0 | 0.0 | 4.0 | 1.0 | 9.0 | | 4.0 | 2.0 | 9.0 | | 4.0 | 3.5 | 6.0 |
| | 0.0160 | 2.0 | 1.0 | 0.0 | 1.0 | 0.0 | 9.0 | | 1.0 | 2.0 | 8.5 | | 3.0 | 3.0 | 5.5 |
| 422 | 0.0620 | 9.0 | 9.0 | 3.0 | 9.0 | 9.0 | 9.0 | | 5.0 | 9.0 | 4.5 | | 5.5 | 5.5 | 7.0 |
| | 0.0320 | 9.0 | 9.0 | 3.0 | 8.0 | 6.0 | 9.0 | | 4.0 | 9.0 | 9.0 | | 5.5 | 5.5 | 6.0 |
| | 0.0160 | 9.0 | 9.0 | 1.0 | 4.0 | 5.0 | 9.0 | | 1.0 | 6.0 | 8.0 | | 4.5 | 4.5 | 6.0 |
| 423 | 0.0620 | 9.0 | 9.0 | 8.0 | 9.0 | 9.0 | 9.0 | | 9.0 | 9.0 | 7.5 | | 7.5 | 9.0 | 7.5 |
| | 0.0320 | 9.0 | 9.0 | 6.0 | 9.0 | 8.0 | 9.0 | | 3.0 | 7.0 | 9.0 | | 7.5 | 8.5 | 6.5 |
| | 0.0160 | 9.0 | 9.0 | 9.0 | 9.0 | 4.0 | 9.0 | | 2.0 | 6.0 | 8.0 | | 5.0 | 6.0 | 5.5 |
| 424 | 0.0620 | 9.0 | 6.0 | 1.0 | 5.0 | 2.0 | 9.0 | | 4.0 | 5.0 | 5.5 | | 2.5 | 3.0 | 4.5 |
| | 0.0320 | 9.0 | 6.0 | 1.0 | 4.0 | 2.0 | 9.0 | | 2.0 | 1.0 | 4.0 | | 2.5 | 3.0 | 3.5 |
| | 0.0160 | 0.0 | 0.0 | 0.0 | 0.0 | 0.0 | 0.0 | | 0.0 | 0.0 | 4.0 | | 1.5 | 1.5 | 3.5 |
| 425 | 0.0620 | 9.0 | 9.0 | 9.0 | 9.0 | 6.0 | 9.0 | | 9.0 | 9.0 | 7.0 | | 8.0 | 8.5 | 9.0 |
| | 0.0320 | 9.0 | 9.0 | 9.0 | 9.0 | 9.0 | 9.0 | | 9.0 | 9.0 | 6.5 | | 7.0 | 7.5 | 7.5 |
| | 0.0160 | 9.0 | 9.0 | 2.0 | 3.0 | 4.0 | 9.0 | | 0.0 | 2.0 | 6.0 | | 7.0 | 7.5 | 7.0 |
| 426 | 0.0620 | 9.0 | 7.0 | 1.0 | 2.0 | 0.0 | 8.0 | | 1.0 | 0.0 | 4.0 | | 3.5 | 4.0 | 5.0 |
| | 0.0320 | 9.0 | 3.0 | 0.0 | 0.0 | 0.0 | 9.0 | | 0.0 | 0.0 | 2.5 | | 2.5 | 3.5 | 4.5 |
| | 0.0160 | 7.0 | 0.0 | 0.0 | 0.0 | 0.0 | 5.0 | | 0.0 | 0.0 | 2.5 | | 2.5 | 3.0 | 3.5 |
| 427 | 0.0620 | 9.0 | 9.0 | 9.0 | 9.0 | 3.0 | 9.0 | | 9.0 | 9.0 | 9.0 | | 7.0 | 7.0 | 8.5 |
| | 0.0320 | 9.0 | 9.0 | 9.0 | 5.0 | 0.0 | 9.0 | | 9.0 | 9.0 | 9.0 | | 5.5 | 6.0 | 8.5 |
| | 0.0160 | 9.0 | 9.0 | 7.0 | 3.0 | 0.0 | 9.0 | | 7.0 | 9.0 | 8.5 | | 5.0 | 6.0 | 7.5 |
| 428 | 0.0620 | 9.0 | 9.0 | 3.0 | 9.0 | 3.0 | 9.0 | | 9.0 | 9.0 | 9.0 | | 7.0 | 9.0 | 9.0 |
| | 0.0320 | 9.0 | 9.0 | 1.0 | 9.0 | 0.0 | 9.0 | | 7.0 | 7.0 | 9.0 | | 7.0 | 9.0 | 8.0 |
| | 0.0160 | 9.0 | 9.0 | 9.0 | 7.0 | 2.0 | 9.0 | | 1.0 | 1.0 | 9.0 | | 5.5 | 7.0 | 9.0 |
| 429 | 0.0620 | 9.0 | 9.0 | 3.0 | 4.0 | 0.0 | 9.0 | | 0.0 | 7.0 | 5.5 | | 2.5 | 3.0 | 5.0 |
| | 0.0320 | 9.0 | 9.0 | 1.0 | 5.0 | 0.0 | 9.0 | | 1.0 | 2.0 | 5.5 | | 2.5 | 2.5 | 4.5 |
| | 0.0160 | 9.0 | 7.0 | 2.0 | 9.0 | 0.0 | 9.0 | | 0.0 | 3.0 | 4.5 | | 2.0 | 2.5 | 4.0 |
| 430 | 0.0620 | 9.0 | 9.0 | 6.0 | 9.0 | 2.0 | 9.0 | | 1.0 | 7.0 | 8.0 | | 2.0 | 3.5 | 5.0 |
| | 0.0320 | 9.0 | 9.0 | 2.0 | 9.0 | 0.0 | 9.0 | | 0.0 | 3.0 | 8.0 | | 2.5 | 4.0 | 5.0 |
| | 0.0160 | 9.0 | 7.0 | 1.0 | 9.0 | 1.0 | 9.0 | | 1.0 | 3.0 | 5.5 | | 2.5 | 2.5 | 5.0 |
| 431 | 0.0620 | | | | | | | | | | | | | | |

TABLE I-continued

Postemergence Herbicidal Evaluations of Test Compounds

| Compound Number | Rate (kg/ha) | ABUTH | AMBEL | CASOB | CHEAL | GALAP | IPOHE | IPOSS | ECHCG | SETVI | GLXMAW | GLXMA | ORYSAT | TRZAWR | ZEAMX |
|---|---|---|---|---|---|---|---|---|---|---|---|---|---|---|---|
| 432 | 0.0320 | 9.0 | 7.0 | 1.0 | 9.0 | 0.0 | 9.0 | | 1.0 | 9.0 | 8.0 | | 2.0 | 2.0 | 5.0 |
| | 0.0160 | 9.0 | 7.0 | 1.0 | 7.0 | 0.0 | 9.0 | | 1.0 | 9.0 | 5.0 | | 2.0 | 1.5 | 5.0 |
| 433 | 0.0620 | 9.0 | 9.0 | 3.0 | 9.0 | 1.0 | 9.0 | | 2.0 | 9.0 | 8.0 | | 2.5 | 2.5 | 5.5 |
| | 0.0320 | 9.0 | 7.0 | 1.0 | 9.0 | 1.0 | 9.0 | | 1.0 | 9.0 | 5.5 | | 1.5 | 2.5 | 5.0 |
| | 0.0160 | 9.0 | 7.0 | 0.0 | 4.0 | 0.0 | 9.0 | | 0.0 | 9.0 | 5.0 | | 2.0 | 2.5 | 4.0 |
| | 0.0620 | 9.0 | 9.0 | 1.0 | 4.0 | 2.0 | 9.0 | | 1.0 | 9.0 | 9.0 | | 2.0 | 3.5 | 5.0 |
| | 0.0320 | 9.0 | 9.0 | 0.0 | 4.0 | 2.0 | 9.0 | | 0.0 | 5.0 | 6.0 | | 1.5 | 3.5 | 4.5 |
| | 0.0160 | 9.0 | 9.0 | 0.0 | 4.0 | 0.0 | 9.0 | | 0.0 | 5.0 | 5.5 | | 1.0 | 2.5 | 4.0 |
| 434 | 0.0620 | 9.0 | 9.0 | 9.0 | 9.0 | 3.0 | | | 9.0 | 9.0 | 9.0 | | 5.5 | 7.5 | 9.0 |
| | 0.0320 | 9.0 | 9.0 | 9.0 | 9.0 | 3.0 | 9.0 | | 9.0 | 9.0 | 9.0 | | 5.5 | 7.5 | 9.0 |
| | 0.0160 | 9.0 | 9.0 | 4.0 | 9.0 | 1.0 | 9.0 | | 9.0 | 9.0 | 9.0 | | 5.0 | 7.5 | 9.0 |
| 435 | 0.0620 | 9.0 | 9.0 | 4.0 | 9.0 | 3.0 | 9.0 | | 8.0 | 9.0 | 8.5 | | 5.0 | 6.5 | 9.0 |
| | 0.0320 | 9.0 | 9.0 | 3.0 | 9.0 | 1.0 | 9.0 | | 9.0 | 9.0 | 7.0 | | 5.0 | 6.0 | 9.0 |
| | 0.0160 | 9.0 | 9.0 | 0.0 | 9.0 | 0.0 | 9.0 | | 5.0 | 9.0 | 6.5 | | 3.5 | 5.0 | 9.0 |
| 436 | 0.0620 | 9.0 | 9.0 | 9.0 | 9.0 | 3.0 | 9.0 | | 9.0 | 9.0 | 9.0 | | 3.5 | 7.5 | 9.0 |
| | 0.0320 | 9.0 | 9.0 | 9.0 | 9.0 | 2.0 | 9.0 | | 9.0 | 9.0 | 9.0 | | 3.5 | 7.5 | 9.0 |
| | 0.0160 | 9.0 | 9.0 | 7.0 | 9.0 | 2.0 | 9.0 | | 9.0 | 9.0 | 9.0 | | 3.5 | 8.5 | 9.0 |
| 437 | 0.0620 | 9.0 | 9.0 | 4.0 | 9.0 | 4.0 | 9.0 | | 9.0 | 9.0 | 9.0 | | 8.5 | 8.0 | 7.5 |
| | 0.0320 | 9.0 | 9.0 | 9.0 | 9.0 | 0.0 | 9.0 | | 9.0 | 9.0 | 9.0 | | 7.5 | 5.5 | 6.0 |
| | 0.0160 | 9.0 | 9.0 | 9.0 | 9.0 | 5.0 | 9.0 | | 9.0 | 9.0 | 9.0 | | 7.5 | 8.0 | 9.0 |
| 438 | 0.0620 | 9.0 | 9.0 | 9.0 | 9.0 | 2.0 | 9.0 | | 9.0 | 9.0 | 9.0 | | 9.0 | 8.0 | 9.0 |
| | 0.0320 | 9.0 | 9.0 | 9.0 | 9.0 | 0.0 | 9.0 | | 9.0 | 9.0 | 9.0 | | 9.0 | 7.0 | 5.5 |
| 439 | 0.0160 | 9.0 | 9.0 | 5.0 | 9.0 | 5.0 | 9.0 | | 4.0 | 6.0 | 6.5 | | 3.5 | 3.5 | 5.0 |
| | 0.0620 | 9.0 | 9.0 | 4.0 | 9.0 | 4.0 | 9.0 | | 3.0 | 6.0 | 6.5 | | 3.0 | 2.5 | 4.5 |
| | 0.0320 | 9.0 | 9.0 | 1.0 | 9.0 | 3.0 | 9.0 | | 3.0 | 3.0 | 6.0 | | 1.5 | 1.5 | 4.5 |
| | 0.0160 | 9.0 | 9.0 | 1.0 | 9.0 | 2.0 | 9.0 | | 2.0 | 3.0 | 5.5 | | 2.0 | 2.0 | 4.5 |
| 440 | 0.1250 | 9.0 | 9.0 | 9.0 | 9.0 | 7.0 | 9.0 | | 9.0 | 9.0 | 9.0 | | 6.0 | 6.5 | 8.0 |
| | 0.0620 | 9.0 | 9.0 | 9.0 | 9.0 | 5.0 | 9.0 | | 9.0 | 9.0 | 9.0 | | 6.5 | 5.5 | 8.0 |
| | 0.0320 | 9.0 | 9.0 | 8.0 | 9.0 | 5.0 | 9.0 | | 9.0 | 9.0 | 9.0 | | 5.5 | 5.5 | 8.0 |
| | 0.0160 | 9.0 | 9.0 | 8.0 | 9.0 | 4.0 | 9.0 | | 9.0 | 9.0 | 7.5 | | 4.5 | 4.0 | 7.5 |
| 441 | 0.1250 | 9.0 | 4.0 | 1.0 | 6.0 | 1.0 | 7.0 | | 4.0 | 5.0 | 4.5 | | 2.0 | 3.0 | 5.0 |
| | 0.0620 | 4.0 | 2.0 | 1.0 | 5.0 | 1.0 | 4.0 | | 2.0 | 2.0 | 4.5 | | 1.5 | 2.5 | 4.5 |
| | 0.0320 | 4.0 | 0.0 | 0.0 | 0.0 | 0.0 | 9.0 | | 1.0 | 0.0 | 4.5 | | 1.5 | 2.0 | 4.5 |
| | 0.0160 | 0.0 | 0.0 | 0.0 | 0.0 | 0.0 | 9.0 | | 1.0 | 1.0 | 4.0 | | 1.5 | 2.0 | 4.5 |
| 442 | 0.1250 | 9.0 | 9.0 | 2.0 | 9.0 | 3.0 | 9.0 | | 1.0 | 9.0 | 8.0 | | 2.5 | 4.0 | 5.5 |
| | 0.0620 | 9.0 | 5.0 | 2.0 | 9.0 | 0.0 | 9.0 | | 1.0 | 6.0 | 5.5 | | 1.5 | 4.0 | 5.0 |
| | 0.0320 | 9.0 | 4.0 | 0.0 | 9.0 | 0.0 | 9.0 | | 0.0 | 3.0 | 5.5 | | 1.0 | 4.0 | 5.0 |
| | 0.0160 | 9.0 | 9.0 | 0.0 | 9.0 | 3.0 | 9.0 | | 0.0 | 3.0 | 5.0 | | 0.5 | 3.5 | 5.0 |
| 443 | 0.1250 | 9.0 | 9.0 | 9.0 | 9.0 | 3.0 | 9.0 | | 9.0 | 9.0 | 8.5 | | 5.0 | 8.0 | 8.5 |
| | 0.0620 | 9.0 | 9.0 | 5.0 | 9.0 | 3.0 | 9.0 | | 9.0 | 9.0 | 8.5 | | 3.5 | 8.0 | 8.5 |
| | 0.0320 | 9.0 | 9.0 | 4.0 | 9.0 | 3.0 | 9.0 | | 9.0 | 9.0 | 6.5 | | 3.0 | 6.5 | 8.0 |
| | 0.0160 | 9.0 | 9.0 | 4.0 | 9.0 | 1.0 | 9.0 | | 7.0 | 9.0 | 5.5 | | 2.5 | 5.0 | 8.0 |
| 444 | 0.0620 | 9.0 | 9.0 | 5.0 | 9.0 | 5.0 | 9.0 | | 0.0 | 9.0 | 9.0 | | 1.0 | 3.5 | 4.5 |
| | 0.0320 | 9.0 | 9.0 | 2.0 | 9.0 | 4.0 | 9.0 | | 0.0 | 4.0 | 9.0 | | 1.0 | 3.5 | 4.5 |
| | 0.0160 | 9.0 | 9.0 | 0.0 | 9.0 | 2.0 | 9.0 | | 0.0 | 4.0 | 9.0 | | 0.5 | 3.5 | 4.0 |
| 445 | 0.0620 | 9.0 | 9.0 | 7.0 | 9.0 | 5.0 | 9.0 | | 0.0 | 9.0 | 9.0 | | 2.0 | 4.0 | 6.0 |

TABLE I-continued

Postemergence Herbicidal Evaluations of Test Compounds

| Compound Number | Rate (kg/ha) | ABUTH | AMBEL | CASOB | CHEAL | GALAP | IPOHE | IPOSS | ECHCG | SETVI | GLXMAW | GLXMA | ORYSAT | TRZAWR | ZEAMX |
|---|---|---|---|---|---|---|---|---|---|---|---|---|---|---|---|
| 446 | 0.0320 | 9.0 | 9.0 | 1.0 | 9.0 | 4.0 | 9.0 | | 0.0 | 9.0 | 8.5 | | 1.5 | 3.5 | 5.5 |
| | 0.0160 | 9.0 | 9.0 | 0.0 | 9.0 | 3.0 | 9.0 | | 0.0 | 9.0 | 8.0 | | 1.5 | 3.5 | 5.0 |
| | 0.0620 | 9.0 | 9.0 | 2.0 | 9.0 | 5.0 | 9.0 | | 1.0 | 9.0 | 9.0 | | 2.0 | 4.0 | 5.0 |
| | 0.0320 | 9.0 | 9.0 | 1.0 | 9.0 | 4.0 | 9.0 | | 0.0 | 4.0 | 8.0 | | 1.5 | 3.5 | 4.5 |
| 447 | 0.0160 | 9.0 | 9.0 | 0.0 | 9.0 | 4.0 | 9.0 | | 0.0 | | 7.5 | | 0.5 | 3.5 | 4.0 |
| | 0.1250 | 9.0 | 9.0 | 4.0 | 9.0 | 4.0 | 9.0 | | 9.0 | 9.0 | 8.5 | | 7.5 | 6.5 | 8.0 |
| | 0.0620 | 9.0 | 9.0 | 2.0 | 9.0 | 2.0 | 9.0 | | 2.0 | 9.0 | 8.0 | | 5.5 | 6.0 | 8.0 |
| | 0.0320 | 9.0 | 9.0 | 0.0 | 9.0 | 2.0 | 9.0 | | 2.0 | 9.0 | 7.0 | | 4.0 | 5.0 | 7.5 |
| | 0.0160 | 9.0 | 9.0 | 0.0 | 7.0 | 2.0 | 9.0 | | 1.0 | 4.0 | 6.5 | | 2.0 | 3.5 | 5.0 |
| 448 | 0.1250 | 9.0 | 9.0 | 5.0 | 9.0 | 3.0 | 9.0 | | 3.0 | 9.0 | 7.5 | | 2.0 | 4.5 | 5.5 |
| | 0.0620 | 9.0 | 9.0 | 5.0 | 9.0 | 2.0 | 9.0 | | 1.0 | 7.0 | 5.5 | | 2.0 | 4.0 | 5.5 |
| | 0.0320 | 9.0 | 9.0 | 4.0 | 9.0 | 1.0 | 9.0 | | 0.0 | 4.0 | 5.5 | | 1.5 | 4.0 | 5.5 |
| | 0.0160 | 9.0 | 9.0 | 4.0 | 9.0 | 1.0 | 9.0 | | 0.0 | | 5.0 | | 1.0 | 3.0 | 5.5 |
| 449 | 0.2500 | | | | | | | | | | 5.0 | | 5.0 | 6.0 | 8.0 |
| | 0.1250 | | | | | | | | | | 8.0 | | 4.0 | 5.0 | 7.0 |
| | 0.0620 | | | | | | | | | | 8.0 | | 4.0 | 5.0 | 6.0 |
| | 0.0320 | | | | | | | | | | 8.0 | | 4.0 | 5.0 | 6.0 |
| | 0.0160 | | | | | | | | | | 9.0 | | 4.0 | 4.0 | 6.0 |
| 450 | 0.1250 | 9.0 | 8.0 | 5.0 | 9.0 | 9.0 | 9.0 | | 1.0 | 9.0 | 9.0 | | 2.0 | 5.0 | 4.3 |
| | 0.0620 | 9.0 | 7.0 | 5.0 | 9.0 | 5.0 | 9.0 | | 1.0 | 9.0 | 8.0 | | 2.3 | 4.0 | 4.3 |
| | 0.0320 | 9.0 | 3.0 | 1.0 | 9.0 | 5.0 | 9.0 | | 1.0 | 9.0 | 7.3 | | 1.7 | 3.7 | 3.7 |
| 451 | 0.1250 | 9.0 | 9.0 | 3.0 | 8.0 | 7.0 | 9.0 | | 1.0 | 1.0 | 6.7 | | 4.0 | 4.0 | 6.0 |
| | 0.0620 | 9.0 | 9.0 | 1.0 | 7.0 | 2.0 | 9.0 | | 0.0 | 1.0 | 8.0 | | 2.0 | 4.0 | 4.3 |
| | 0.0320 | 9.0 | 5.0 | 1.0 | 7.0 | 1.0 | 9.0 | | 0.0 | | 7.7 | | 2.0 | 3.7 | 3.7 |
| 452 | 0.1250 | 9.0 | 9.0 | 1.0 | 9.0 | 8.0 | 9.0 | | 1.0 | 9.0 | 7.3 | | 2.7 | 3.0 | 3.7 |
| | 0.0620 | 9.0 | 5.0 | 1.0 | 9.0 | 3.0 | 9.0 | | 0.0 | 2.0 | 8.0 | | 3.0 | 4.0 | 6.0 |
| | 0.0320 | 9.0 | 3.0 | 0.0 | 5.0 | 2.0 | 8.0 | | 0.0 | 1.0 | 7.0 | | 3.3 | 3.0 | 4.3 |
| 453 | 0.2500 | | | | | | | | | | 6.7 | | 2.3 | 2.7 | 4.0 |
| | 0.1250 | 9.0 | 9.0 | 9.0 | 9.0 | 9.0 | 9.0 | | 7.0 | 9.0 | 6.7 | | 1.7 | 2.0 | 3.7 |
| | 0.0620 | 9.0 | 9.0 | 3.0 | 9.0 | 9.0 | 9.0 | | 3.0 | 9.0 | 9.0 | | 7.0 | 7.0 | 8.0 |
| | 0.0320 | 9.0 | 9.0 | 2.0 | 8.0 | 4.0 | 9.0 | | 1.0 | 9.0 | 8.0 | | 5.0 | 5.0 | 7.0 |
| | 0.0160 | 9.0 | 9.0 | 6.0 | 9.0 | 7.0 | 9.0 | | 4.0 | 4.0 | 8.7 | | 6.0 | 6.3 | 6.3 |
| 454 | 0.1250 | 9.0 | 9.0 | 3.0 | 9.0 | 7.0 | 9.0 | | 0.0 | 9.0 | 8.3 | | 5.7 | 5.7 | 6.0 |
| | 0.0620 | 9.0 | 9.0 | 1.0 | 9.0 | 3.0 | 9.0 | | 0.0 | 7.0 | 7.2 | | 4.6 | 5.0 | 4.8 |
| | 0.0320 | 9.0 | 9.0 | 1.0 | 9.0 | 3.0 | 9.0 | | 0.0 | 4.0 | 9.0 | | 2.5 | 4.0 | 8.0 |
| | 0.0160 | 9.0 | 9.0 | 1.0 | 9.0 | 3.0 | 9.0 | | 0.0 | 3.0 | 8.5 | | 0.5 | 3.0 | 7.5 |
| 455 | 0.2500 | 9.0 | 9.0 | 5.0 | 9.0 | 3.0 | 9.0 | | 9.0 | 9.0 | 7.5 | | 0.5 | 2.5 | 5.0 |
| | 0.1250 | 9.0 | 9.0 | 9.0 | 9.0 | 3.0 | 9.0 | | 9.0 | 9.0 | 6.5 | | 0.5 | 8.0 | 4.5 |
| | 0.0620 | 9.0 | 9.0 | 5.0 | 9.0 | 5.0 | 9.0 | | 3.0 | 9.0 | 9.0 | | 6.0 | 8.0 | 8.0 |
| | 0.0320 | 9.0 | 9.0 | 5.0 | 9.0 | 5.0 | 9.0 | | 3.0 | 9.0 | 9.0 | | 4.5 | 7.0 | 7.5 |
| | 0.0160 | 9.0 | 9.0 | 1.0 | 6.0 | 3.0 | 9.0 | | 1.0 | 4.0 | 8.5 | | 3.5 | 5.0 | 6.0 |
| 456 | 0.2500 | 9.0 | 9.0 | 7.0 | 9.0 | 9.0 | 9.0 | | 6.0 | 9.0 | 7.5 | | 1.5 | 4.0 | 5.0 |
| | 0.1250 | 9.0 | 9.0 | 3.0 | 9.0 | 8.0 | 9.0 | | 2.0 | 9.0 | 9.0 | | 1.0 | 4.0 | 5.0 |
| | 0.0620 | 9.0 | 9.0 | 3.0 | 9.0 | 7.0 | 9.0 | | 0.0 | 9.0 | 8.0 | | 5.5 | 7.0 | 8.0 |
| | | | | | | | | | | | 8.5 | | 3.5 | 6.0 | 7.5 |
| | | | | | | | | | | | | | 2.5 | 4.5 | 6.0 |

TABLE I-continued

Postemergence Herbicidal Evaluations of Test Compounds

| Compound Number | Rate (kg/ha) | ABUTH | AMBEL | CASOB | CHEAL | GALAP | IPOHE | IPOSS | ECHCG | SETVI | GLXMAW | GLXMA | ORYSAT | TRZAWR | ZEAMX |
|---|---|---|---|---|---|---|---|---|---|---|---|---|---|---|---|
| | 0.0320 | 9.0 | 9.0 | 2.0 | 4.0 | 5.0 | 9.0 | | 0.0 | 7.0 | 8.5 | | 1.5 | 4.0 | 5.5 |
| | 0.0160 | 9.0 | 9.0 | 1.0 | | 3.0 | 9.0 | | 0.0 | 7.0 | 6.0 | | 1.0 | 3.5 | 4.5 |
| 457 | 0.2500 | 9.0 | 9.0 | 0.0 | 9.0 | 3.0 | 9.0 | | 0.0 | 9.0 | 7.5 | | 1.5 | 3.5 | 4.5 |
| | 0.1250 | 9.0 | 9.0 | 2.0 | 9.0 | 3.0 | 9.0 | | 0.0 | 7.0 | 7.5 | | 1.5 | 3.5 | 4.5 |
| | 0.0620 | 9.0 | 9.0 | 2.0 | 9.0 | 2.0 | 9.0 | | 0.0 | 4.0 | 7.5 | | 1.0 | 3.0 | 4.0 |
| | 0.0320 | 9.0 | 9.0 | 0.0 | 4.0 | 0.0 | 9.0 | | 0.0 | 0.0 | 6.0 | | 0.5 | 2.5 | 3.0 |
| | 0.0160 | 9.0 | 9.0 | 0.0 | 0.0 | 0.0 | 9.0 | | 0.0 | 0.0 | 4.5 | | 0.5 | 2.5 | 3.0 |
| 458 | 0.2500 | 9.0 | 9.0 | 9.0 | 9.0 | 9.0 | 9.0 | | 3.0 | 8.0 | 7.5 | | 2.0 | 3.5 | 5.0 |
| | 0.1250 | 9.0 | 9.0 | 7.0 | 9.0 | 5.0 | 9.0 | | 2.0 | 8.0 | 7.5 | | 1.5 | 2.5 | 5.0 |
| | 0.0620 | 9.0 | 9.0 | 3.0 | 9.0 | 4.0 | 9.0 | | 1.0 | 7.0 | 8.5 | | 1.0 | 2.5 | 5.0 |
| | 0.0320 | 9.0 | 9.0 | 2.0 | 3.0 | 3.0 | 9.0 | | 0.0 | 4.0 | 6.0 | | 1.0 | 2.5 | 4.5 |
| | 0.0160 | 9.0 | 9.0 | 1.0 | 3.0 | 1.0 | 9.0 | | 0.0 | 3.0 | 6.0 | | 0.5 | 2.0 | 4.5 |
| 459 | 0.1250 | 9.0 | 9.0 | 9.0 | 9.0 | 4.0 | 9.0 | | 9.0 | 9.0 | 9.0 | | 3.5 | 9.0 | 9.0 |
| | 0.0620 | 9.0 | 9.0 | 9.0 | 9.0 | 4.0 | 9.0 | | 9.0 | 9.0 | 8.5 | | 3.5 | 8.5 | 8.5 |
| | 0.0320 | 9.0 | 9.0 | 3.0 | 9.0 | 3.0 | 9.0 | | 9.0 | 9.0 | 8.0 | | 2.5 | 8.5 | 7.5 |
| | 0.0160 | 9.0 | 9.0 | 5.0 | 9.0 | 4.0 | 9.0 | | 9.0 | 9.0 | 9.0 | | 3.5 | 9.0 | 9.0 |
| 460 | 0.1250 | 9.0 | 9.0 | 2.0 | 9.0 | 3.0 | 9.0 | | 9.0 | 9.0 | 8.0 | | 2.5 | 8.0 | 9.0 |
| | 0.0620 | 9.0 | 9.0 | 2.0 | 9.0 | 1.0 | 9.0 | | 9.0 | 9.0 | 6.5 | | 2.5 | 7.5 | 8.5 |
| | 0.0320 | 9.0 | 9.0 | 1.0 | 9.0 | 0.0 | 9.0 | | 7.0 | 9.0 | 5.5 | | 2.0 | 6.0 | 7.5 |
| | 0.0160 | 9.0 | 9.0 | 2.0 | 9.0 | 3.0 | 9.0 | | 1.0 | 4.0 | 9.0 | | 1.5 | 5.0 | 6.5 |
| 461 | 0.0620 | 9.0 | 9.0 | 2.0 | 9.0 | 1.0 | 9.0 | | 0.0 | | 8.5 | | 1.0 | 4.5 | 5.0 |
| | 0.0320 | 9.0 | 9.0 | 0.0 | 7.0 | 1.0 | 9.0 | | 0.0 | 3.0 | 6.5 | | 3.0 | 4.0 | 4.0 |
| 462 | 0.0620 | 9.0 | 9.0 | 9.0 | 9.0 | 3.0 | 9.0 | | 4.0 | 9.0 | 8.5 | | 3.0 | 5.5 | 5.5 |
| | 0.0320 | 9.0 | 9.0 | 7.0 | 9.0 | 3.0 | 9.0 | | 2.0 | 4.0 | 9.0 | | 2.0 | 5.5 | 5.0 |
| | 0.0160 | 9.0 | 9.0 | 0.0 | 9.0 | 2.0 | 9.0 | | 1.0 | 4.0 | 7.5 | | 2.0 | 5.5 | 5.0 |
| 463 | 0.0620 | 9.0 | 9.0 | 0.0 | 9.0 | 5.0 | 9.0 | | 0.0 | 3.0 | 7.5 | | 1.0 | 3.5 | 5.0 |
| | 0.0320 | 9.0 | 9.0 | 0.0 | 3.0 | 2.0 | 9.0 | | 0.0 | 0.0 | 7.5 | | 1.0 | 3.0 | 5.0 |
| | 0.0160 | 9.0 | 4.0 | 0.0 | 0.0 | 0.0 | 9.0 | | 0.0 | 0.0 | 5.0 | | 0.5 | 2.5 | 3.5 |
| 464 | 0.0620 | 9.0 | 9.0 | 9.0 | 9.0 | 6.0 | 9.0 | | 9.0 | 9.0 | 9.0 | | 5.5 | 5.0 | 8.0 |
| | 0.0320 | 9.0 | 9.0 | 7.0 | 9.0 | 4.0 | 9.0 | | 9.0 | 9.0 | 9.0 | | 5.5 | 5.0 | 8.0 |
| 465 | 0.0620 | 9.0 | 9.0 | 9.0 | 9.0 | 4.0 | 9.0 | | 9.0 | 9.0 | 8.5 | | 5.0 | 5.0 | 7.5 |
| | 0.0320 | 9.0 | 9.0 | 9.0 | 9.0 | 5.0 | 9.0 | | 9.0 | 9.0 | 8.5 | | 3.5 | 4.0 | 8.0 |
| | 0.0160 | 9.0 | 9.0 | 8.0 | 9.0 | 4.0 | 9.0 | | 5.0 | 9.0 | 8.5 | | 3.5 | 3.5 | 8.0 |
| 466 | 0.0620 | 9.0 | 9.0 | 3.0 | 9.0 | 7.0 | 9.0 | | 4.0 | 9.0 | 8.0 | | 6.5 | 6.5 | 8.0 |
| | 0.0320 | 9.0 | 9.0 | 2.0 | 9.0 | 5.0 | 9.0 | | 5.0 | 6.0 | 7.5 | | 5.5 | 5.5 | 7.0 |
| 467 | 0.0620 | 9.0 | 9.0 | 4.0 | 9.0 | 4.0 | 9.0 | | 4.0 | 9.0 | 6.5 | | 5.0 | 4.5 | 6.0 |
| | 0.0320 | 9.0 | 9.0 | 3.0 | 4.0 | 3.0 | 9.0 | | 4.0 | 6.0 | 6.0 | | 2.5 | 3.0 | 4.5 |
| | 0.0160 | 9.0 | 3.0 | 1.0 | 9.0 | 7.0 | 9.0 | | 2.0 | 4.0 | 5.5 | | 2.0 | 4.0 | 4.5 |
| 468 | 0.0620 | 9.0 | 9.0 | 5.0 | 9.0 | 2.0 | 9.0 | | 9.0 | 9.0 | 9.0 | | 3.5 | 7.0 | 8.0 |
| | 0.0320 | 9.0 | 9.0 | 5.0 | 9.0 | 7.0 | 9.0 | | 9.0 | 8.0 | 8.5 | | 2.0 | 6.5 | 8.0 |
| | 0.0160 | 9.0 | 9.0 | 5.0 | 9.0 | 2.0 | 9.0 | | 8.0 | 7.0 | 8.5 | | 1.0 | 6.5 | 8.0 |
| | 0.0320 | 9.0 | 7.0 | 4.0 | 9.0 | 3.0 | 9.0 | | 9.0 | 4.0 | 6.5 | | 3.5 | 5.0 | 7.5 |
| | 0.0160 | 9.0 | 9.0 | 3.0 | 9.0 | 2.0 | 9.0 | | 4.0 | 4.0 | 5.5 | | 3.5 | 4.0 | 7.5 |
| 470 | 0.0620 | 9.0 | 9.0 | 5.0 | 9.0 | 4.0 | 9.0 | | 5.0 | 9.0 | 5.5 | | 4.0 | 4.0 | 8.0 |

TABLE I-continued

Postemergence Herbicidal Evaluations of Test Compounds

| Compound Number | Rate (kg/ha) | ABUTH | AMBEL | CASOB | CHEAL | GALAP | IPOHE | IPOSS | ECHCG | SETVI | GLXMAW | GLXMA | ORYSAT | TRZAWR | ZEAMX |
|---|---|---|---|---|---|---|---|---|---|---|---|---|---|---|---|
|  | 0.0320 | 9.0 | 9.0 | 2.0 | 9.0 | 4.0 | 9.0 |  | 2.0 | 4.0 | 5.0 |  | 4.0 | 4.0 | 7.5 |
|  | 0.0160 | 5.0 | 7.0 | 2.0 | 7.0 | 3.0 | 9.0 |  | 2.0 | 2.0 | 5.0 |  | 3.0 | 3.0 | 5.0 |
| 471 | 0.0620 | 9.0 | 4.0 | 0.0 | 4.0 | 4.0 | 9.0 |  | 2.0 | 3.0 | 8.5 |  | 1.5 | 4.0 | 4.5 |
|  | 0.0320 | 3.0 | 2.0 | 0.0 | 0.0 | 0.0 | 4.0 |  | 0.0 | 2.0 | 7.5 |  | 1.5 | 3.5 | 4.5 |
|  | 0.0160 | 3.0 | 0.0 | 0.0 | 0.0 | 0.0 | 3.0 |  | 0.0 | 0.0 | 6.0 |  | 0.5 | 3.5 | 3.5 |
| 472 | 0.0620 | 7.0 | 9.0 | 0.0 | 2.0 | 2.0 | 9.0 |  | 6.0 | 9.0 | 8.5 |  | 3.5 | 5.5 | 8.0 |
|  | 0.0320 | 4.0 | 3.0 | 0.0 | 2.0 | 0.0 | 9.0 |  | 3.0 | 5.0 | 8.0 |  | 3.0 | 5.0 | 7.5 |
|  | 0.0160 | 4.0 | 7.0 | 0.0 | 2.0 | 0.0 | 9.0 |  | 3.0 | 0.0 | 8.0 |  | 0.5 | 4.5 | 7.5 |
| 473 | 0.0620 | 9.0 | 7.0 | 2.0 | 9.0 | 4.0 | 9.0 |  | 0.0 | 2.0 | 6.5 |  | 2.0 | 7.0 | 5.0 |
|  | 0.0320 | 9.0 | 7.0 | 0.0 | 3.0 | 2.0 | 9.0 |  | 0.0 | 0.0 | 6.0 |  | 1.0 | 4.5 | 4.0 |
|  | 0.0160 | 9.0 | 3.0 | 0.0 | 3.0 | 1.0 | 9.0 |  | 0.0 | 0.0 | 5.5 |  | 0.5 | 4.0 | 4.0 |
| 474 | 0.0620 | 9.0 | 5.0 | 0.0 | 1.0 | 1.0 | 4.0 |  | 0.0 | 0.0 | 5.0 |  | 1.5 | 3.5 | 4.0 |
|  | 0.0320 | 9.0 |  | 0.0 | 1.0 | 1.0 | 9.0 |  | 0.0 | 0.0 | 5.0 |  | 0.5 | 3.5 | 4.0 |
|  | 0.0160 | 9.0 | 3.0 | 0.0 | 0.0 | 0.0 | 9.0 |  | 0.0 | 0.0 | 5.0 |  | 0.0 | 3.0 | 3.5 |
| 475 | 0.0620 | 9.0 | 9.0 | 0.0 | 0.0 | 5.0 | 9.0 |  | 1.0 | 3.0 | 7.5 |  | 1.5 | 4.0 | 4.5 |
|  | 0.0320 | 9.0 | 9.0 | 0.0 | 9.0 | 3.0 | 9.0 |  | 0.0 | 2.0 | 6.0 |  | 0.5 | 3.5 | 4.0 |
|  | 0.0160 | 9.0 | 5.0 | 0.0 | 3.0 | 3.0 | 9.0 |  | 0.0 | 0.0 | 5.0 |  | 0.5 | 3.0 | 4.0 |
| 476 | 0.0620 | 9.0 | 9.0 | 0.0 | 9.0 | 7.0 | 9.0 |  | 0.0 | 3.0 | 4.5 |  | 0.0 | 4.0 | 4.0 |
|  | 0.0320 | 9.0 | 9.0 | 0.0 | 8.0 | 3.0 | 9.0 |  | 0.0 | 0.0 | 6.0 |  | 0.0 | 3.0 | 3.5 |
|  | 0.0160 | 9.0 | 5.0 | 0.0 | 3.0 | 2.0 | 9.0 |  | 0.0 | 4.0 | 5.0 |  | 1.5 | 3.0 | 3.0 |
| 477 | 0.0620 | 9.0 | 9.0 | 2.0 | 9.0 | 6.0 | 9.0 |  | 0.0 | 0.0 | 4.5 |  | 1.0 | 4.0 | 5.0 |
|  | 0.0320 | 9.0 | 7.0 | 0.0 | 9.0 | 5.0 | 9.0 |  | 0.0 | 0.0 | 7.0 |  | 0.0 | 3.5 | 4.5 |
|  | 0.0160 | 9.0 | 4.0 | 0.0 | 4.0 | 3.0 | 9.0 |  | 0.0 | 0.0 | 5.5 |  | 0.0 | 2.5 | 4.5 |
| 478 | 0.0620 | 9.0 | 9.0 | 3.0 | 9.0 | 8.0 | 9.0 |  | 2.0 | 7.0 | 5.0 |  | 3.0 | 5.0 | 5.5 |
|  | 0.0320 | 9.0 | 9.0 | 1.0 | 9.0 | 5.0 | 9.0 |  | 1.0 | 3.0 | 8.0 |  | 2.5 | 4.0 | 4.5 |
|  | 0.0160 | 9.0 | 9.0 | 0.0 | 3.0 | 2.0 | 9.0 |  | 0.0 | 2.0 | 8.0 |  | 1.0 | 3.5 | 4.0 |
| 479 | 0.0320 | 9.0 | 9.0 | 8.0 | 9.0 | 7.0 | 9.0 |  | 9.0 | 9.0 | 7.0 |  | 6.0 | 6.5 | 9.0 |
|  | 0.0160 | 9.0 | 9.0 | 9.0 | 9.0 | 6.0 | 9.0 |  | 9.0 | 9.0 | 8.5 |  | 6.0 | 6.5 | 8.0 |
| 480 | 0.0620 | 9.0 | 9.0 | 4.0 | 9.0 | 5.0 | 9.0 |  | 5.0 | 5.0 | 7.0 |  | 3.5 | 4.0 | 4.5 |
|  | 0.0320 | 9.0 | 7.0 | 3.0 | 9.0 | 3.0 | 9.0 |  | 3.0 | 4.0 | 6.0 |  | 2.5 | 3.5 | 4.5 |
|  | 0.0160 | 9.0 | 7.0 | 1.0 | 7.0 | 1.0 | 9.0 |  | 1.0 | 1.0 | 5.5 |  | 2.0 | 2.0 | 4.5 |
| 481 | 0.0620 | 9.0 | 9.0 | 2.0 | 6.0 | 5.0 | 9.0 |  | 4.0 | 3.0 | 4.5 |  | 3.5 | 3.5 | 5.0 |
|  | 0.0320 | 9.0 | 9.0 | 2.0 | 9.0 | 2.0 | 9.0 |  | 2.0 | 2.0 | 5.0 |  | 2.5 | 3.5 | 4.5 |
|  | 0.0160 | 6.0 | 4.0 | 0.0 | 3.0 | 1.0 | 9.0 |  | 1.0 | 1.0 | 4.5 |  | 2.0 | 2.0 | 4.0 |
| 482 | 0.0620 | 9.0 | 9.0 | 9.0 | 9.0 | 4.0 | 9.0 |  | 9.0 | 9.0 | 5.0 |  | 5.0 | 5.5 | 8.5 |
|  | 0.0320 | 9.0 | 9.0 | 9.0 | 9.0 | 3.0 | 9.0 |  | 9.0 | 9.0 | 9.0 |  | 4.5 | 5.0 | 8.0 |
|  | 0.0160 | 9.0 | 9.0 | 9.0 | 7.0 | 6.0 | 9.0 |  | 9.0 | 9.0 | 9.0 |  | 7.0 | 6.5 | 8.0 |
| 483 | 0.0620 | 9.0 | 9.0 | 9.0 | 9.0 | 5.0 | 9.0 |  | 9.0 | 9.0 | 9.0 |  | 5.0 | 5.0 | 8.0 |
|  | 0.0320 | 9.0 | 9.0 | 9.0 | 9.0 | 5.0 | 9.0 |  | 9.0 | 9.0 | 9.0 |  | 5.0 | 5.0 | 8.0 |

TABLE I-continued

Postemergence Herbicidal Evaluations of Test Compounds

| Compound Number | Rate (kg/ha) | ABUTH | AMBEL | CASOB | CHEAL | GALAP | IPOHE | IPOSS | ECHCG | SETVI | GLXMAW | GLXMA | ORYSAT | TRZAWR | ZEAMX |
|---|---|---|---|---|---|---|---|---|---|---|---|---|---|---|---|
| 484 | 0.0160 | 9.0 | 9.0 | 9.0 | 9.0 | 4.0 | 9.0 | | 9.0 | 9.0 | 9.0 | | 4.0 | 4.5 | 8.0 |
| | 0.0620 | 9.0 | 9.0 | 6.0 | 9.0 | 4.0 | 9.0 | | 1.0 | 4.0 | 7.0 | | 3.5 | 4.0 | 5.0 |
| | 0.0320 | 9.0 | 7.0 | 5.0 | 9.0 | 3.0 | 9.0 | | 1.0 | 4.0 | 6.5 | | 2.5 | 3.0 | 4.5 |
| | 0.0160 | 9.0 | 7.0 | 4.0 | 9.0 | 1.0 | 9.0 | | 1.0 | 6.0 | 6.0 | | 2.5 | 3.0 | 4.0 |
| 485 | 0.0620 | 9.0 | 9.0 | 9.0 | 9.0 | 7.0 | 9.0 | | 9.0 | 9.0 | 9.0 | | 6.5 | 5.5 | 8.5 |
| | 0.0320 | 9.0 | 9.0 | 7.0 | 9.0 | 6.0 | 9.0 | | 9.0 | 9.0 | 9.0 | | 6.0 | 5.5 | 8.0 |
| | 0.0160 | 9.0 | 9.0 | 9.0 | 7.0 | 1.0 | 9.0 | | 9.0 | 7.0 | 9.0 | | 5.0 | 5.0 | 8.0 |
| 486 | 0.0620 | 9.0 | 9.0 | 9.0 | 9.0 | 7.0 | 9.0 | | 9.0 | 5.0 | 9.0 | | 3.0 | 5.5 | 8.0 |
| | 0.0320 | 9.0 | 9.0 | 6.0 | 9.0 | 4.0 | 9.0 | | 9.0 | 9.0 | 9.0 | | 4.5 | 6.0 | 8.0 |
| | 0.0160 | 9.0 | 9.0 | 6.0 | 9.0 | 3.0 | 9.0 | | 9.0 | 4.0 | 8.5 | | 3.0 | 4.0 | 8.0 |
| 487 | 0.0620 | 9.0 | 8.0 | 5.0 | 9.0 | 6.0 | 9.0 | | 6.0 | 7.0 | 8.0 | | 7.0 | 6.5 | 7.0 |
| | 0.0320 | 9.0 | 9.0 | 3.0 | 9.0 | 4.0 | 9.0 | | 3.0 | 4.0 | 7.5 | | 6.5 | 6.0 | 6.0 |
| | 0.0160 | 9.0 | 9.0 | 3.0 | 9.0 | 2.0 | 9.0 | | 3.0 | 3.0 | 7.0 | | 6.0 | 5.0 | 5.5 |
| 488 | 0.0620 | 9.0 | 9.0 | 3.0 | 9.0 | 5.0 | 9.0 | | 6.0 | 6.0 | 7.0 | | 6.0 | 5.5 | 7.0 |
| | 0.0320 | 9.0 | 7.0 | 2.0 | 7.0 | 4.0 | 9.0 | | 3.0 | 4.0 | 6.5 | | 5.0 | 4.5 | 7.0 |
| | 0.0160 | 9.0 | 7.0 | 1.0 | 4.0 | 2.0 | 9.0 | | 3.0 | 2.0 | 5.5 | | 3.5 | 4.0 | 6.0 |
| 489 | 0.0620 | 9.0 | 7.0 | 7.0 | 9.0 | 5.0 | 9.0 | | 4.0 | 7.0 | 8.5 | | 5.0 | 5.0 | 5.5 |
| | 0.0320 | 9.0 | 9.0 | 4.0 | 9.0 | 1.0 | 9.0 | | 4.0 | 6.0 | 7.0 | | 4.5 | 4.5 | 4.5 |
| | 0.0160 | 9.0 | 7.0 | 3.0 | 9.0 | 3.0 | 9.0 | | 3.0 | 4.0 | 5.5 | | 3.5 | 4.0 | 4.5 |
| 490 | 0.0620 | 9.0 | 9.0 | 5.0 | 9.0 | 7.0 | 9.0 | | 3.0 | 9.0 | 8.5 | | 6.5 | 6.5 | 6.5 |
| | 0.0320 | 9.0 | 9.0 | 5.0 | 9.0 | 6.0 | 9.0 | | 4.0 | 7.0 | 7.0 | | 6.0 | 5.5 | 6.5 |
| | 0.0160 | 9.0 | 9.0 | 3.0 | 7.0 | 4.0 | 9.0 | | 3.0 | 4.0 | 6.5 | | 5.0 | 4.5 | 5.5 |
| 491 | 0.0620 | 9.0 | 9.0 | 7.0 | 9.0 | 6.0 | 9.0 | | 4.0 | 7.0 | 7.0 | | 7.0 | 6.5 | 5.0 |
| | 0.0320 | 9.0 | 9.0 | 4.0 | 9.0 | 5.0 | 9.0 | | 4.0 | 6.0 | 7.0 | | 5.0 | 6.0 | 5.0 |
| | 0.0160 | 9.0 | 9.0 | 2.0 | 9.0 | 2.0 | 9.0 | | 2.0 | 4.0 | 8.5 | | 3.5 | 5.0 | 4.5 |
| 492 | 0.0620 | 9.0 | 9.0 | 2.0 | 9.0 | 6.0 | 9.0 | | 6.0 | 7.0 | 7.0 | | 7.0 | 7.0 | 9.0 |
| | 0.0320 | 9.0 | 9.0 | 1.0 | 9.0 | 4.0 | 9.0 | | 6.0 | 7.0 | 7.0 | | 4.0 | 6.0 | 8.5 |
| | 0.0160 | 9.0 | 9.0 | 1.0 | 9.0 | 1.0 | 9.0 | | 4.0 | 6.0 | 5.5 | | 3.5 | 5.0 | 7.5 |
| 493 | 0.0620 | 9.0 | 9.0 | 9.0 | 9.0 | 5.0 | 9.0 | | 9.0 | 9.0 | 9.0 | | 6.0 | 8.5 | 9.0 |
| | 0.0320 | 9.0 | 9.0 | 2.0 | 9.0 | 2.0 | 9.0 | | 9.0 | 9.0 | 9.0 | | 4.5 | 8.5 | 9.0 |
| | 0.0160 | 9.0 | 9.0 | 2.0 | 9.0 | 0.0 | 9.0 | | 9.0 | 7.0 | 9.0 | | 4.0 | 8.0 | 8.5 |
| 494 | 0.0620 | 9.0 | 9.0 | 1.0 | 9.0 | 3.0 | 9.0 | | 9.0 | 5.0 | 9.0 | | 3.0 | 4.5 | 7.5 |
| | 0.0320 | 9.0 | 9.0 | 0.0 | 9.0 | 1.0 | 9.0 | | 9.0 | 5.0 | 8.5 | | 2.0 | 4.5 | 7.5 |
| | 0.0160 | 8.0 | 4.0 | 0.0 | 9.0 | 0.0 | 9.0 | | 2.0 | 3.0 | 6.0 | | 0.5 | 3.5 | 5.0 |
| 495 | 0.0620 | 9.0 | 9.0 | 2.0 | 9.0 | 7.0 | 9.0 | | 1.0 | 0.0 | 7.5 | | 2.5 | 4.0 | 5.0 |
| | 0.0320 | 9.0 | 7.0 | 0.0 | 9.0 | 5.0 | 9.0 | | 0.0 | 0.0 | 6.5 | | 1.5 | 3.0 | 4.5 |
| | 0.0160 | 9.0 | 4.0 | 0.0 | 9.0 | 0.0 | 9.0 | | 0.0 | 0.0 | 6.0 | | 1.0 | 3.0 | 4.0 |
| 496 | 0.0620 | 9.0 | 9.0 | 3.0 | 9.0 | 7.0 | 9.0 | | 1.0 | 2.0 | 9.0 | | 2.5 | 4.0 | 5.0 |

TABLE I-continued

Postemergence Herbicidal Evaluations of Test Compounds

| Compound Number | Rate (kg/ha) | ABUTH | AMBEL | CASOB | CHEAL | GALAP | IPOHE | IPOSS | ECHCG | SETVI | GLXMAW | GLXMA | ORYSAT | TRZAWR | ZEAMX |
|---|---|---|---|---|---|---|---|---|---|---|---|---|---|---|---|
| | 0.0320 | 9.0 | 9.0 | 2.0 | 9.0 | 5.0 | 9.0 | | 0.0 | 1.0 | 7.5 | | 1.5 | 4.0 | 5.0 |
| | 0.0160 | 9.0 | 5.0 | 0.0 | 9.0 | 2.0 | 9.0 | | 0.0 | 0.0 | 6.5 | | 0.5 | 3.0 | 5.0 |
| 497 | 0.0620 | 9.0 | 9.0 | 2.0 | 9.0 | 5.0 | 9.0 | | 1.0 | 2.0 | 7.5 | | 1.5 | 3.5 | 5.0 |
| | 0.0320 | 9.0 | 9.0 | 2.0 | 9.0 | 4.0 | 9.0 | | 0.0 | 1.0 | 7.0 | | 1.5 | 3.5 | 4.5 |
| | 0.0160 | 9.0 | 4.0 | 0.0 | 4.0 | 3.0 | 9.0 | | 0.0 | | 6.5 | | 0.5 | 3.5 | 4.0 |
| 498 | 0.0620 | 9.0 | 9.0 | 1.0 | 9.0 | 5.0 | 9.0 | | 0.0 | 3.0 | 7.0 | | 2.0 | 4.0 | 5.5 |
| | 0.0320 | 9.0 | 7.0 | 0.0 | 5.0 | 5.0 | 9.0 | | 1.0 | | 7.0 | | 1.0 | 4.0 | 5.0 |
| | 0.0160 | 9.0 | 4.0 | 0.0 | 9.0 | 3.0 | 9.0 | | 1.0 | 0.0 | 6.0 | | 0.5 | 4.0 | 4.5 |
| 499 | 0.0620 | 9.0 | 9.0 | 3.0 | 9.0 | 9.0 | 9.0 | | 2.0 | 8.0 | 9.0 | | 2.0 | 4.5 | 6.5 |
| | 0.0320 | 9.0 | 9.0 | 1.0 | 9.0 | 9.0 | 9.0 | | 1.0 | 7.0 | 9.0 | | 1.0 | 4.0 | 5.0 |
| | 0.0160 | 9.0 | 8.0 | 1.0 | 9.0 | 6.0 | 9.0 | | 0.0 | 3.0 | 7.5 | | 0.5 | 4.0 | 5.0 |
| 500 | 0.1250 | 9.0 | 9.0 | 9.0 | 9.0 | 7.0 | 9.0 | | 9.0 | 9.0 | 9.0 | | 6.5 | 6.5 | 8.0 |
| | 0.0620 | 9.0 | 9.0 | 5.0 | 9.0 | 5.5 | 9.0 | | 9.0 | 9.0 | 8.8 | | 5.8 | 5.2 | 7.6 |
| | 0.0320 | 9.0 | 9.0 | 2.0 | 9.0 | 3.5 | 9.0 | | 7.0 | 7.0 | 8.6 | | 5.2 | 4.8 | 7.2 |
| | 0.0160 | 9.0 | 9.0 | 0.5 | 9.0 | 1.5 | 9.0 | | 9.0 | 2.0 | 8.6 | | 4.6 | 4.6 | 7.2 |
| 501 | 0.1250 | 9.0 | 9.0 | 9.0 | 9.0 | 5.0 | 9.0 | | 9.0 | 9.0 | 9.0 | | 5.0 | 5.0 | 8.0 |
| | 0.0620 | 9.0 | 9.0 | 9.0 | 9.0 | 5.0 | 9.0 | | 9.0 | 7.0 | 9.0 | | 3.5 | 4.0 | 8.0 |
| | 0.0320 | 9.0 | 9.0 | 7.0 | 9.0 | 3.0 | 9.0 | | 7.0 | 6.0 | 9.0 | | 3.0 | 3.5 | 8.0 |
| | 0.0160 | 9.0 | 9.0 | 3.0 | 9.0 | 2.0 | 9.0 | | 2.0 | 1.0 | 9.0 | | 3.5 | 4.0 | 7.5 |

EXAMPLE 186

Preemergence Herbicidal Evaluation of Test Compounds

The preemergence herbicidal activity of the test compounds of the present invention is exemplified by the following tests in which the seeds of a variety of monocotyledonous and dicotyledonous plants are separately mixed with potting soil and planted on top of approximately one inch of soil in separate pint cups. After planting, the cups are sprayed with the selected aqueous acetone solution containing test compound in sufficient quantity to provide the equivalent of about 0.0156 to 0.500 kg per hectare of test compound per cup. The treated cups are then placed on greenhouse benches, watered and cared for in accordance with conventional greenhouse procedures. From four to five weeks after treatment, the tests are terminated and each cup is examined and rated according to the rating system provided in Example 185.

The data obtained are reported in Table II below. The compounds evaluated are reported by compound number given in Example 185.

TABLE II

Preemergence Herbicidal Evaluations of Test Compounds

| Compound Number | Rate (kg/ha) | ABUTH | AMBEL | CASOB | CHEAL | GALAP | IPOHE | IPOSS | ECHCG | SETVI | GLXMAW | GLXMA | ORYSAT | TRZAWR | ZEAMX |
|---|---|---|---|---|---|---|---|---|---|---|---|---|---|---|---|
| 1 | 0.5000 | 9.0 | 9.0 | 9.0 | 9.0 | 9.0 | 8.0 | 9.0 | 9.0 | 9.0 | 7.0 | | 8.0 | 7.0 | 7.0 |
| | 0.2500 | 9.0 | 9.0 | 9.0 | 9.0 | 5.0 | 9.0 | 4.0 | 9.0 | 9.0 | 7.5 | | 7.5 | 6.0 | 6.5 |
| | 0.1250 | 9.0 | 9.0 | 8.0 | 9.0 | | 9.0 | 4.0 | 9.0 | 9.0 | 6.0 | | 6.5 | 5.0 | 6.5 |
| | 0.0625 | 9.0 | 7.5 | 7.5 | 9.0 | | 4.0 | 4.0 | 7.5 | 9.0 | 4.0 | | 5.5 | 4.0 | 4.5 |
| | 0.0313 | 5.5 | 3.5 | 1.0 | 9.0 | 0.0 | | 2.0 | 7.5 | 9.0 | 2.0 | | 4.0 | 3.0 | 3.5 |
| | 0.0156 | 9.0 | 5.0 | | 9.0 | 0.0 | 2.0 | | 6.0 | 9.0 | 1.0 | | 4.0 | 2.0 | 4.0 |
| 2 | 0.5000 | 9.0 | 9.0 | 2.0 | 9.0 | 9.0 | 9.0 | 9.0 | 9.0 | 9.0 | | 9.0 | 9.0 | 4.0 | 6.0 |
| | 0.2500 | 9.0 | 9.0 | 9.0 | 9.0 | 9.0 | 9.0 | 9.0 | 8.3 | 9.0 | 8.5 | 7.0 | 7.7 | 4.0 | 5.6 |
| | 0.1250 | 9.0 | 9.0 | 8.0 | 9.0 | 9.0 | 9.0 | 9.0 | 8.8 | 9.0 | 5.7 | 9.0 | 6.7 | 3.7 | 4.8 |
| | 0.0625 | 8.8 | 8.6 | 5.6 | 9.0 | 5.8 | 7.5 | 9.0 | 7.0 | 8.0 | 3.5 | 3.0 | 6.5 | 2.7 | 3.6 |
| | 0.0313 | 7.8 | 8.2 | 7.5 | 9.0 | 6.0 | 4.3 | 4.0 | 2.6 | 6.2 | 1.5 | 3.0 | 1.3 | 1.3 | 2.1 |
| | 0.0157 | 9.0 | 3.0 | 2.0 | 9.0 | | 0.0 | | 2.0 | 3.0 | 0.0 | | | 1.7 | 2.0 |
| | 0.0156 | 9.0 | 6.0 | 4.3 | 9.0 | 2.3 | 3.3 | | 0.7 | 7.0 | 1.7 | | 0.7 | 0.0 | 1.0 |
| 3 | 0.5000 | 9.0 | 9.0 | 9.0 | 9.0 | 9.0 | 9.0 | 9.0 | 9.0 | 9.0 | | 7.0 | 7.0 | 9.0 | 9.0 |
| | 0.2500 | 9.0 | 9.0 | 9.0 | 9.0 | 7.6 | 8.3 | 9.0 | 8.3 | 9.0 | 5.0 | 4.0 | 6.8 | 6.3 | 7.3 |
| | 0.1250 | 9.0 | 9.0 | 7.0 | 9.0 | 7.3 | 9.0 | 4.0 | 5.5 | 8.5 | 4.3 | 3.0 | 6.3 | 4.0 | 5.7 |
| | 0.0630 | 9.0 | 9.0 | 4.0 | 9.0 | 4.0 | 9.0 | | 7.0 | 9.0 | 2.0 | | 5.0 | 7.0 | 3.0 |
| | 0.0625 | 9.0 | 8.0 | 5.5 | 9.0 | 6.0 | 7.3 | 8.0 | 4.8 | 8.3 | 3.3 | | 4.3 | 3.0 | 5.0 |
| | 0.0315 | 9.0 | 7.0 | 9.0 | 9.0 | 4.0 | 9.0 | | 6.0 | 9.0 | | | 0.0 | 0.0 | 2.0 |
| | 0.0313 | 8.5 | 4.7 | 4.3 | 9.0 | 0.0 | 6.7 | 9.0 | 1.3 | 5.8 | 1.7 | 0.0 | 1.8 | 1.3 | 3.5 |
| | 0.0158 | 9.0 | 9.0 | 0.0 | 9.0 | 2.0 | 0.0 | | 0.0 | 7.0 | 2.0 | | 0.0 | 0.0 | 1.0 |
| | 0.0157 | | | | | 0.0 | | | | | | | | 1.3 | 3.0 |
| | 0.0156 | | | | | | 2.7 | | 0.3 | 6.7 | 2.3 | | 0.3 | 0.3 | 1.7 |
| 4 | 0.5000 | 9.0 | 5.7 | 4.7 | 9.0 | 9.0 | | 9.0 | 9.0 | 9.0 | | 9.0 | 7.0 | 7.0 | 7.0 |
| | 0.2500 | 9.0 | 9.0 | 9.0 | 9.0 | 9.0 | | 9.0 | 9.0 | 9.0 | | 7.0 | 7.0 | 7.0 | 7.0 |
| | 0.1250 | 9.0 | 9.0 | 6.0 | 9.0 | 6.0 | | 7.0 | 9.0 | 9.0 | | 9.0 | 7.0 | 7.0 | 7.0 |
| | 0.0625 | 9.0 | 9.0 | 7.0 | 9.0 | 9.0 | | 4.0 | 9.0 | 9.0 | | 9.0 | 7.0 | 5.0 | 3.0 |
| | 0.0313 | 9.0 | 7.0 | 7.0 | 9.0 | 9.0 | | 2.0 | 9.0 | 9.0 | | 3.0 | 7.0 | 2.0 | 4.0 |
| 5 | 0.5000 | 9.0 | 9.0 | 9.0 | 9.0 | 6.0 | | 9.0 | 9.0 | 9.0 | | 6.0 | 7.0 | 6.0 | 3.0 |
| | 0.2500 | 9.0 | 9.0 | 9.0 | 9.0 | 9.0 | | 9.0 | 9.0 | 9.0 | | 4.0 | 7.0 | 4.0 | 3.0 |
| | 0.1250 | 9.0 | 8.0 | 6.0 | 9.0 | 6.0 | | 4.0 | 9.0 | 9.0 | | 3.0 | 7.0 | 8.0 | 2.0 |
| | 0.0625 | 9.0 | 4.0 | 4.0 | 9.0 | 2.0 | | 2.0 | 7.0 | 9.0 | | 2.0 | 3.0 | 3.0 | 1.0 |
| | 0.0313 | 6.0 | 2.0 | 0.0 | 9.0 | 2.0 | | 0.0 | 6.0 | 9.0 | 0.0 | 2.0 | 3.0 | 1.0 | 0.0 |
| 6 | 0.5000 | 9.0 | 9.0 | 9.0 | 9.0 | 9.0 | | 9.0 | 9.0 | 9.0 | | 9.0 | 8.0 | 8.0 | 9.0 |
| | 0.2500 | 9.0 | 9.0 | 9.0 | 9.0 | 9.0 | 3.0 | 9.0 | 6.0 | 9.0 | 0.0 | 7.0 | 8.0 | 8.7 | 6.5 |
| | 0.1250 | 9.0 | 7.0 | 6.5 | 9.0 | 9.0 | 9.0 | | 9.0 | 9.0 | 7.0 | | 8.0 | 7.0 | 8.0 |
| | 0.0630 | 9.0 | 6.0 | 7.0 | 9.0 | 9.0 | 3.0 | 7.0 | 5.5 | 6.0 | 0.0 | 4.0 | 7.0 | 8.3 | 6.0 |
| | 0.0625 | 9.0 | 6.0 | 5.5 | 9.0 | 5.3 | 4.0 | 7.5 | 5.6 | 8.4 | 2.3 | 2.0 | 7.0 | 5.6 | 4.2 |
| | 0.0320 | 9.0 | 7.4 | 6.0 | 9.0 | 8.5 | 7.5 | | 8.0 | 9.0 | 7.0 | | 4.4 | 6.5 | 7.5 |
| | 0.0315 | 9.0 | 4.5 | 4.5 | 8.0 | 9.0 | 0.0 | 7.0 | 4.5 | 5.5 | 0.0 | 4.0 | 7.0 | 6.3 | 5.3 |
| | 0.0313 | 4.5 | 6.4 | 4.4 | 8.8 | 5.3 | 1.0 | 7.5 | 2.2 | 7.0 | 1.3 | 2.0 | 7.0 | 3.0 | 3.6 |
| | 0.0160 | 8.0 | 8.0 | 6.5 | 9.0 | 4.8 | 5.5 | | 6.0 | 9.0 | 1.5 | | 2.8 | 3.5 | 6.0 |
| | 0.0158 | 9.0 | 0.0 | 0.0 | 5.0 | 8.5 | 0.0 | | 0.0 | 0.0 | 0.0 | | 4.0 | 3.5 | 2.3 |
| | 0.0157 | 3.0 | 0.0 | 0.0 | | | | | | | | | | | |
| 7 | 0.5000 | 9.0 | 9.0 | 9.0 | | | | 9.0 | 9.0 | 9.0 | | | 7.0 | 7.0 | 8.0 |
| | 0.2500 | 9.0 | 9.0 | 9.0 | | | | 9.0 | 9.0 | 9.0 | | | 8.0 | 6.0 | 7.0 |

TABLE II-continued

Preemergence Herbicidal Evaluations of Test Compounds

| Compound Number | Rate (kg/ha) | ABUTH | AMBEL | CASOB | CHEAL | GALAP | IPOHE | IPOSS | ECHCG | SETVI | GLXMAW | GLXMA | ORYSAT | TRZAWR | ZEAMX |
|---|---|---|---|---|---|---|---|---|---|---|---|---|---|---|---|
| | 0.1250 | 9.0 | 9.0 | 9.0 | 9.0 | 7.0 | | 9.0 | 9.0 | 9.0 | | | 8.0 | 6.0 | 7.0 |
| | 0.0630 | 9.0 | 9.0 | 9.0 | | | | 9.0 | 9.0 | 9.0 | | | 6.0 | 5.0 | 6.0 |
| | 0.0625 | 9.0 | 7.0 | 5.0 | | | | 9.0 | 9.0 | 9.0 | 5.0 | | 6.0 | 5.0 | 7.0 |
| | 0.0315 | 9.0 | 9.0 | 9.0 | 9.0 | 0.0 | | 7.0 | 7.0 | 9.0 | | | 5.0 | 2.0 | 4.0 |
| | 0.0313 | 9.0 | 7.0 | 5.0 | | | | 3.0 | 9.0 | 9.0 | | | 4.0 | 5.0 | 5.0 |
| | 0.0158 | 9.0 | 2.0 | 9.0 | 9.0 | 0.0 | | 9.0 | 7.0 | 9.0 | 3.0 | | 5.0 | 2.0 | 2.0 |
| | 0.0157 | 9.0 | 9.0 | 9.0 | | | | 3.0 | 7.0 | 9.0 | | | 5.0 | 2.0 | 5.0 |
| 8 | 0.5000 | 9.0 | 9.0 | 9.0 | | | | 9.0 | 9.0 | 9.0 | | | 9.0 | 9.0 | 9.0 |
| | 0.2500 | 9.0 | 9.0 | 9.0 | | 5.0 | | 9.0 | 9.0 | 9.0 | | | 9.0 | 9.0 | 9.0 |
| | 0.1250 | 9.0 | 9.0 | 9.0 | 9.0 | | | 9.0 | 7.0 | 9.0 | 9.0 | | 5.0 | 7.0 | 7.0 |
| | 0.0630 | 9.0 | 9.0 | 9.0 | | 4.0 | | 9.0 | 5.0 | 9.0 | | | 5.0 | 2.0 | 4.0 |
| | 0.0625 | 9.0 | 9.0 | 9.0 | 9.0 | | | 9.0 | 9.0 | 9.0 | 9.0 | | 7.0 | 5.0 | 5.0 |
| | 0.0315 | 9.0 | 9.0 | 5.0 | | 0.0 | | 9.0 | 4.0 | 9.0 | | | 2.0 | 2.0 | 3.0 |
| | 0.0313 | 9.0 | 9.0 | 2.0 | 9.0 | | | 9.0 | 5.0 | 9.0 | 5.0 | | 5.0 | 4.0 | 4.0 |
| | 0.0158 | 9.0 | 7.0 | 5.0 | | | | 9.0 | 0.0 | 7.0 | | | 2.0 | 0.0 | 2.0 |
| | 0.0157 | 9.0 | 9.0 | 9.0 | | | | 9.0 | 4.0 | 9.0 | | | 0.0 | 5.0 | 9.0 |
| 9 | 0.5000 | 9.0 | 9.0 | 9.0 | | | | 9.0 | 9.0 | 9.0 | | | 9.0 | 9.0 | 9.0 |
| | 0.2500 | 9.0 | 9.0 | 9.0 | | 4.0 | | 9.0 | 9.0 | 9.0 | | | 9.0 | 9.0 | 6.0 |
| | 0.1250 | 9.0 | 9.0 | 9.0 | 9.0 | | | 9.0 | 9.0 | 9.0 | 7.0 | | 6.0 | 4.0 | 6.0 |
| | 0.0630 | 9.0 | 9.0 | 9.0 | | 0.0 | | 9.0 | 7.0 | 9.0 | | | 4.0 | 5.0 | 7.0 |
| | 0.0625 | 9.0 | 9.0 | 5.0 | 9.0 | | | 9.0 | 5.0 | 9.0 | 5.0 | | 5.0 | 2.0 | 2.0 |
| | 0.0315 | 9.0 | 9.0 | 9.0 | | 0.0 | | 9.0 | 0.0 | 6.0 | | | 0.0 | 0.0 | 4.0 |
| | 0.0313 | 9.0 | 9.0 | 9.0 | 9.0 | | | 5.0 | 4.0 | 9.0 | 2.0 | | 5.0 | 4.0 | 3.0 |
| | 0.0158 | 9.0 | 9.0 | 0.0 | | | | 5.0 | 0.0 | 6.0 | | | 0.0 | 0.0 | 0.0 |
| | 0.0157 | 9.0 | 9.0 | 3.0 | | | | 9.0 | 2.0 | 9.0 | | | 4.0 | 4.0 | 5.0 |
| 10 | 0.5000 | 9.0 | 9.0 | 7.0 | | | | 9.0 | 9.0 | 9.0 | | | 7.0 | 6.0 | 7.0 |
| | 0.2500 | 9.0 | 9.0 | 9.0 | | 0.0 | | 9.0 | 9.0 | 9.0 | | | 6.0 | 5.0 | 5.0 |
| | 0.1250 | 9.0 | 9.0 | 9.0 | 9.0 | | | 9.0 | 8.0 | 9.0 | 0.0 | | 5.0 | 5.0 | 7.0 |
| | 0.0630 | 9.0 | 7.0 | 0.0 | | 0.0 | | 5.0 | 3.0 | 6.0 | | | 0.0 | 0.0 | 0.0 |
| | 0.0625 | 9.0 | 6.0 | 0.0 | 9.0 | | | 0.0 | 4.0 | 9.0 | 0.0 | | 0.0 | 0.0 | 4.0 |
| | 0.0315 | 9.0 | 2.0 | 5.0 | | 0.0 | | 0.0 | 0.0 | 6.0 | | | 4.0 | 0.0 | 0.0 |
| | 0.0313 | 9.0 | 0.0 | 9.0 | 9.0 | | | 4.0 | 3.0 | 9.0 | 0.0 | | 2.0 | 2.0 | 2.0 |
| | 0.0158 | 0.0 | 0.0 | | | | | 0.0 | 0.0 | 5.0 | | | 0.0 | 0.0 | 0.0 |
| 11 | 0.5000 | 9.0 | 0.0 | 6.0 | | | | 5.0 | 3.0 | 9.0 | | | 0.0 | 0.0 | 0.0 |
| | 0.2500 | 9.0 | 9.0 | 8.0 | | | | 9.0 | 4.0 | 9.0 | | | 5.0 | 4.0 | 3.0 |
| | 0.1250 | 9.0 | 9.0 | 3.0 | | | | 5.0 | 0.0 | 7.0 | | | 0.0 | 4.0 | 5.0 |
| | 0.0625 | 6.0 | 6.0 | 3.0 | | | | 4.0 | 0.0 | 5.0 | | | 0.0 | 3.0 | 1.0 |
| | 0.0313 | 3.0 | 0.0 | 0.0 | | | | 2.0 | 0.0 | 2.0 | | | 0.0 | 0.0 | 1.0 |
| | 0.0157 | 1.0 | 0.0 | 0.0 | | | | 0.0 | 0.0 | 0.0 | | | 0.0 | 0.0 | 0.0 |
| 12 | 0.5000 | 9.0 | 9.0 | 9.0 | | | | 9.0 | 9.0 | 9.0 | | | 5.0 | 7.0 | 7.0 |
| | 0.2500 | 9.0 | 9.0 | 9.0 | | 5.0 | | 9.0 | 6.0 | 9.0 | | | 7.0 | 5.0 | 7.0 |
| | 0.1250 | 9.0 | 7.0 | 5.0 | 9.0 | | | 9.0 | 5.0 | 9.0 | 5.0 | | 4.0 | 4.0 | 3.0 |
| | 0.0630 | 9.0 | 0.0 | 9.0 | | 0.0 | | 9.0 | 0.0 | 9.0 | | | 0.0 | 4.0 | 1.0 |
| | 0.0625 | 9.0 | 0.0 | 0.0 | 9.0 | | | 9.0 | 0.0 | 7.0 | 3.0 | | 0.0 | 5.0 | 5.0 |
| | 0.0315 | 9.0 | 9.0 | 5.0 | | | | 9.0 | 0.0 | 7.0 | | | 0.0 | 0.0 | 1.0 |

TABLE II-continued

Preemergence Herbicidal Evaluations of Test Compounds

| Compound Number | Rate (kg/ha) | ABUTH | AMBEL | CASOB | CHEAL | GALAP | IPOHE | IPOSS | ECHCG | SETVI | GLXMAW | GLXMA | ORYSAT | TRZAWR | ZEAMX |
|---|---|---|---|---|---|---|---|---|---|---|---|---|---|---|---|
| | 0.0158 | 9.0 | 0.0 | 0.0 | | 0.0 | | 9.0 | 0.0 | 6.0 | 4.0 | | 0.0 | 0.0 | 1.0 |
| | 0.0157 | 9.0 | 9.0 | 9.0 | 9.0 | | | 9.0 | 0.0 | 9.0 | | | 0.0 | 0.0 | 1.0 |
| 13 | 0.5000 | 9.0 | 9.0 | 9.0 | | | | 9.0 | 9.0 | 9.0 | | | 7.0 | 6.0 | 7.0 |
| | 0.2500 | 9.0 | 9.0 | 9.0 | | | | 9.0 | 9.0 | 9.0 | | | 6.0 | 4.0 | 4.0 |
| | 0.1250 | 9.0 | 9.0 | 9.0 | | | | 9.0 | 5.0 | 9.0 | | | 5.0 | 3.0 | 4.0 |
| | 0.0630 | 9.0 | 9.0 | 9.0 | 9.0 | 4.0 | | 9.0 | 0.0 | 7.0 | 3.0 | | 0.0 | 0.0 | 4.0 |
| | 0.0625 | 9.0 | 7.0 | 4.0 | | | | 5.0 | 0.0 | 9.0 | | | 0.0 | 0.0 | 0.0 |
| | 0.0315 | 9.0 | 9.0 | 9.0 | | | | 4.0 | 0.0 | 4.0 | | | 0.0 | 0.0 | 5.0 |
| | 0.0313 | 9.0 | 9.0 | 8.0 | 9.0 | 0.0 | | 5.0 | 0.0 | 7.0 | 0.0 | | 0.0 | 2.0 | 4.0 |
| | 0.0158 | 9.0 | 7.0 | 6.0 | | | | 7.0 | 0.0 | 5.0 | | | 0.0 | 0.0 | 4.0 |
| | 0.0157 | 9.0 | 6.0 | 7.0 | 9.0 | 0.0 | | 0.0 | 0.0 | 5.0 | 0.0 | | 0.0 | 0.0 | 0.0 |
| 14 | 0.2500 | 9.0 | 4.5 | 9.0 | 9.0 | 4.5 | 9.0 | 4.0 | 2.5 | 5.0 | 4.0 | | 6.5 | 3.0 | 2.0 |
| | 0.1250 | 9.0 | 7.0 | 8.0 | 9.0 | 0.5 | 6.5 | | 2.0 | 8.5 | 1.5 | | 3.0 | 1.0 | 2.0 |
| | 0.0625 | 9.0 | 4.5 | 9.0 | 9.0 | 0.0 | 4.5 | | 1.5 | 8.0 | 1.5 | | 1.0 | 0.5 | 1.5 |
| | 0.0313 | 6.5 | 2.5 | 4.5 | 9.0 | 0.0 | 2.5 | | 0.0 | 5.0 | 0.5 | | 0.5 | 0.5 | 0.5 |
| | 0.0156 | 6.0 | 2.0 | 0.0 | 9.0 | 0.0 | 0.0 | | 0.0 | 3.5 | 0.5 | | 0.0 | 0.0 | 0.5 |
| 15 | 0.1250 | 9.0 | 9.0 | 9.0 | 9.0 | 8.0 | 9.0 | | 9.0 | 9.0 | 4.0 | | 7.0 | 6.0 | 9.0 |
| | 0.0625 | 9.0 | 9.0 | 8.0 | 9.0 | 5.5 | 6.5 | | 7.5 | 7.5 | 6.0 | | 6.5 | 4.0 | 4.0 |
| | 0.0313 | 9.0 | 4.5 | 7.5 | 9.0 | 2.0 | 2.5 | | 3.0 | 6.5 | 3.5 | | 4.0 | 2.0 | 3.5 |
| | 0.0156 | 6.5 | 2.5 | 3.5 | 9.0 | 2.0 | 0.5 | | 2.0 | 5.0 | 2.5 | | 1.0 | 1.0 | 1.0 |
| 16 | 0.2500 | 9.0 | 9.0 | 5.5 | 9.0 | 0.0 | 9.0 | | 0.5 | 7.0 | 0.0 | | 7.0 | 0.0 | 0.0 |
| | 0.1250 | 9.0 | 5.0 | 9.0 | 9.0 | 9.0 | 9.0 | | 0.0 | 0.0 | 4.0 | | 0.0 | 1.0 | 2.0 |
| | 0.0625 | 9.0 | 4.0 | 3.0 | 9.0 | 5.0 | 3.0 | | 0.0 | 0.0 | 0.0 | | 0.0 | 0.0 | 1.0 |
| | 0.0313 | 9.0 | 0.0 | 1.0 | 9.0 | 0.0 | 0.0 | | 0.0 | 2.0 | 0.0 | | 0.0 | 0.0 | 1.0 |
| | 0.0156 | 0.0 | 0.0 | 9.0 | 4.0 | 0.0 | 0.0 | | 0.0 | 7.0 | 0.0 | | 0.0 | 0.0 | 1.0 |
| 17 | 0.2500 | 9.0 | 9.0 | 9.0 | 9.0 | 9.0 | 9.0 | | 9.0 | 9.0 | 6.0 | | 7.0 | 5.0 | 4.0 |
| | 0.1250 | 9.0 | 8.0 | 9.0 | 9.0 | 9.0 | 9.0 | | 4.0 | 9.0 | 6.0 | | 2.0 | 2.0 | 2.0 |
| | 0.0625 | 9.0 | 8.0 | 7.0 | 9.0 | 4.0 | 0.0 | | 5.0 | 5.0 | 2.0 | | 0.0 | 0.0 | 3.0 |
| | 0.0313 | 9.0 | 5.0 | 2.0 | 9.0 | 0.0 | 0.0 | | 0.0 | 7.0 | 0.0 | | 0.0 | 0.0 | 0.0 |
| | 0.0156 | 9.0 | 4.0 | 0.0 | 9.0 | 0.0 | 0.0 | | 0.0 | 0.0 | 0.0 | | 0.0 | 0.0 | 0.0 |
| 18 | 0.2500 | 9.0 | 9.0 | 4.0 | 9.0 | 1.0 | 4.0 | | 5.0 | 9.0 | 2.0 | | 0.0 | 0.0 | 3.0 |
| | 0.1250 | 9.0 | 4.0 | 0.0 | 9.0 | 0.0 | 2.0 | | 3.0 | 9.0 | 1.0 | | 2.0 | 1.0 | 2.0 |
| | 0.0625 | 9.0 | 2.0 | 0.0 | 9.0 | 0.0 | 2.0 | | 3.0 | 9.0 | 1.0 | | 4.0 | 2.0 | 1.0 |
| | 0.0313 | 9.0 | 2.0 | 1.0 | 6.0 | 5.0 | 0.0 | | 1.0 | 8.0 | 2.0 | | 0.0 | 0.0 | 0.0 |
| | 0.0156 | 2.0 | 0.0 | | 9.0 | 0.0 | 2.0 | | 4.0 | 0.0 | 1.0 | | 3.0 | 7.0 | 0.0 |
| 19 | 0.2500 | 9.0 | 9.0 | 8.0 | 9.0 | 0.0 | 9.0 | | 9.0 | 9.0 | 7.0 | | 7.0 | 6.0 | 8.0 |
| | 0.1250 | 9.0 | 7.0 | 9.0 | 9.0 | 9.0 | 5.0 | | 6.0 | 9.0 | 5.0 | | 5.0 | 5.0 | 7.0 |
| | 0.0625 | 9.0 | 6.0 | 9.0 | 9.0 | 5.0 | 5.0 | | 0.0 | 6.0 | 2.0 | | 0.0 | 0.0 | 2.0 |
| | 0.0313 | 9.0 | 0.0 | 2.0 | 9.0 | 4.0 | 3.0 | | 0.0 | 4.0 | 1.0 | | 0.0 | 0.0 | 0.0 |
| | 0.0156 | 3.0 | 0.0 | | 9.0 | 3.0 | 0.0 | | 0.0 | 0.0 | 0.0 | | 0.0 | 0.0 | 0.0 |
| 20 | 0.2500 | 9.0 | 5.0 | 7.0 | 9.0 | 5.0 | 3.0 | | 5.0 | 8.0 | 1.0 | | 0.0 | 5.0 | 4.0 |
| | 0.1250 | 9.0 | 7.0 | 0.0 | 9.0 | 0.0 | 2.0 | | 0.0 | 6.0 | 0.0 | | 7.0 | 1.0 | 1.0 |
| | 0.0625 | 9.0 | 4.0 | | 7.0 | 0.0 | 0.0 | | 0.0 | 4.0 | 0.0 | | 0.0 | 0.0 | 0.0 |
| | 0.0313 | 4.0 | 5.0 | 2.0 | 4.0 | 0.0 | 0.0 | | 0.0 | 3.0 | 0.0 | | 0.0 | 0.0 | 0.0 |
| | 0.0156 | 0.0 | 0.0 | 0.0 | | 0.0 | 0.0 | | 0.0 | 1.0 | 0.0 | | 0.0 | 0.0 | 0.0 |
| 21 | 0.2500 | 9.0 | 9.0 | 9.0 | 9.0 | 9.0 | 9.0 | | 7.0 | 9.0 | 9.0 | | 7.0 | 7.0 | 8.0 |

TABLE II-continued

Preemergence Herbicidal Evaluations of Test Compounds

| Compound Number | Rate (kg/ha) | ABUTH | AMBEL | CASOB | CHEAL | GALAP | IPOHE | IPOSS | ECHCG | SETVI | GLXMAW | GLXMA | ORYSAT | TRZAWR | ZEAMX |
|---|---|---|---|---|---|---|---|---|---|---|---|---|---|---|---|
| | 0.1250 | 9.0 | 9.0 | 9.0 | 9.0 | 9.0 | 9.0 | | 6.0 | 9.0 | 8.0 | | 5.0 | 5.0 | 7.0 |
| | 0.0625 | 9.0 | 7.0 | 9.0 | 9.0 | 6.0 | 7.0 | | 4.0 | 7.0 | 7.0 | | 2.0 | 2.0 | 6.0 |
| | 0.0313 | 9.0 | 5.0 | 7.0 | 9.0 | 3.0 | 5.0 | | 0.0 | 3.0 | 2.0 | | 0.0 | 0.0 | 0.0 |
| | 0.0156 | 9.0 | 3.0 | 3.0 | 9.0 | 0.0 | 1.0 | | 0.0 | 2.0 | 1.0 | | 0.0 | 0.0 | 0.0 |
| 22 | 0.2500 | 0.0 | 0.0 | 9.0 | 0.0 | 0.0 | 0.0 | | 0.0 | 0.0 | 2.0 | | 0.0 | 0.0 | 1.0 |
| | 0.1250 | 0.0 | 0.0 | 9.0 | | 4.0 | 0.0 | | 0.0 | 0.0 | 1.0 | | 0.0 | 0.0 | 0.0 |
| | 0.0625 | 0.0 | 0.0 | 0.0 | | 0.0 | 0.0 | | 0.0 | 0.0 | 0.0 | | 0.0 | 0.0 | 0.0 |
| | 0.0313 | 0.0 | 0.0 | 0.0 | 0.0 | 0.0 | 0.0 | | 0.0 | 0.0 | 0.0 | | 0.0 | 0.0 | 0.0 |
| | 0.0156 | 0.0 | 0.0 | 0.0 | | 0.0 | 0.0 | | 0.0 | 0.0 | 0.0 | | 0.0 | 0.0 | 0.0 |
| 23 | 0.2500 | 9.0 | 9.0 | 9.0 | 9.0 | 9.0 | 9.0 | | 9.0 | 9.0 | 9.0 | | 9.0 | 9.0 | 9.0 |
| | 0.1250 | 9.0 | 9.0 | 9.0 | 9.0 | 9.0 | 9.0 | | 9.0 | 9.0 | 9.0 | | 9.0 | 9.0 | 9.0 |
| | 0.0625 | 9.0 | 8.5 | 6.0 | 9.0 | 9.0 | 8.0 | | 9.0 | 9.0 | 7.5 | | 8.0 | 8.0 | 7.0 |
| | 0.0313 | 9.0 | 8.5 | 6.0 | 9.0 | 7.0 | 6.5 | | 7.0 | 9.0 | 6.5 | | 8.0 | 7.0 | 6.0 |
| | 0.0157 | 9.0 | 8.0 | 2.0 | 9.0 | 0.0 | 0.0 | | 2.0 | 9.0 | 2.0 | | 0.0 | 0.0 | 1.0 |
| 24 | 0.0156 | 9.0 | 7.0 | 9.0 | 9.0 | 5.0 | 9.0 | | 6.0 | 9.0 | 7.0 | | 4.0 | 4.0 | 6.0 |
| | 0.2500 | 9.0 | 5.0 | 4.0 | 5.0 | 3.0 | 9.0 | | 3.0 | 5.0 | 1.0 | | 0.0 | 0.0 | 2.0 |
| | 0.1250 | 3.0 | 4.0 | 4.0 | 9.0 | 0.0 | 0.0 | | 0.0 | 4.0 | 0.0 | | 0.0 | 0.0 | 1.0 |
| | 0.0625 | 4.0 | 5.0 | 2.0 | 5.0 | 0.0 | 0.0 | | 0.0 | 3.0 | 1.0 | | 0.0 | 1.0 | 2.0 |
| | 0.0313 | 3.0 | 2.0 | 0.0 | 6.0 | 0.0 | 0.0 | | 0.0 | 5.0 | 2.0 | | 0.0 | 0.0 | 0.0 |
| | 0.0156 | 0.0 | 0.0 | 1.0 | 5.0 | 0.0 | 0.0 | | 0.0 | 3.0 | 1.0 | | 0.0 | 0.0 | 0.0 |
| 25 | 0.2500 | 9.0 | 9.0 | 9.0 | 9.0 | 8.0 | 9.0 | | 9.0 | 9.0 | 9.0 | | 7.0 | 7.0 | 7.0 |
| | 0.1250 | 9.0 | 9.0 | 9.0 | 9.0 | 7.0 | 6.0 | | 9.0 | 9.0 | 5.0 | | 5.0 | 7.0 | 7.0 |
| | 0.0625 | 9.0 | 4.0 | 9.0 | 9.0 | 0.0 | 5.0 | | 7.0 | 9.0 | 1.0 | | 2.0 | 7.0 | 1.0 |
| | 0.0313 | 8.0 | 0.0 | 9.0 | 9.0 | | 0.0 | | 2.0 | 5.0 | 0.0 | | 0.0 | 2.0 | 0.0 |
| | 0.0156 | 9.0 | 3.0 | 9.0 | 9.0 | 0.0 | 0.0 | | 2.0 | 9.0 | 0.0 | | 0.0 | 0.0 | 0.0 |
| 26 | 0.2500 | 9.0 | 9.0 | 9.0 | 9.0 | 4.0 | 7.0 | | 7.0 | 9.0 | 6.0 | | 5.0 | 5.0 | 7.0 |
| | 0.1250 | 9.0 | 9.0 | 7.0 | 9.0 | 7.0 | 7.0 | | 5.0 | 9.0 | 7.0 | | 2.0 | 2.0 | 4.0 |
| | 0.0625 | 9.0 | 4.0 | 2.0 | 9.0 | 8.0 | 0.0 | | 0.0 | 5.0 | 1.0 | | 4.0 | 2.0 | 2.0 |
| | 0.0313 | 9.0 | 0.0 | 0.0 | 9.0 | 5.0 | 0.0 | | 1.0 | 9.0 | 0.0 | | 0.0 | 0.0 | 1.0 |
| | 0.0156 | 9.0 | 3.0 | | 9.0 | 0.0 | 0.0 | | 0.0 | 5.0 | 1.0 | | 0.0 | 0.0 | 0.0 |
| 27 | 0.2500 | 9.0 | 9.0 | 9.0 | 9.0 | 2.0 | 6.0 | | 7.0 | 9.0 | 9.0 | | 2.0 | 0.0 | 4.0 |
| | 0.1250 | 9.0 | 9.0 | 9.0 | 9.0 | 5.0 | 9.0 | | 6.0 | 9.0 | 4.0 | | 2.0 | 5.0 | 3.0 |
| | 0.0625 | 9.0 | 2.0 | 0.0 | 9.0 | 0.0 | 2.0 | | 3.0 | 9.0 | 0.0 | | 0.0 | 4.0 | 4.0 |
| | 0.0313 | 9.0 | 4.0 | 0.0 | 9.0 | 0.0 | 2.0 | | 3.0 | 9.0 | 0.0 | | 0.0 | | 1.0 |
| | 0.0156 | 9.0 | 0.0 | 0.0 | 9.0 | 0.0 | 0.0 | | 8.0 | 7.0 | 0.0 | | 0.0 | 0.0 | 0.0 |
| 28 | 0.2500 | 9.0 | 9.0 | 9.0 | 9.0 | 7.0 | 9.0 | | 4.0 | 9.0 | 6.0 | | 5.0 | 5.0 | 6.0 |
| | 0.1250 | 9.0 | 9.0 | 9.0 | 9.0 | 5.0 | 7.0 | | 4.0 | 9.0 | 4.0 | | 5.0 | 5.0 | 5.0 |
| | 0.0625 | 9.0 | 4.0 | 9.0 | 9.0 | | 5.0 | | 0.0 | 9.0 | 4.0 | | 5.0 | 2.0 | 3.0 |
| | 0.0313 | 9.0 | 0.0 | 0.0 | 9.0 | 0.0 | 0.0 | | 0.0 | 4.0 | 4.0 | | 2.0 | 0.0 | 3.0 |
| | 0.0156 | 2.0 | 0.0 | 0.0 | 7.0 | 0.0 | 0.0 | | 0.0 | 0.0 | 2.0 | | 0.0 | 0.0 | 2.0 |
| 29 | 0.2500 | 0.0 | 0.0 | 0.0 | 0.0 | 0.0 | 0.0 | | 0.0 | 9.0 | 1.0 | | 0.0 | 0.0 | 0.0 |
| | 0.1250 | 0.0 | 0.0 | 0.0 | 0.0 | 0.0 | 0.0 | | 0.0 | 0.0 | 0.0 | | 0.0 | 0.0 | 0.0 |
| | 0.0625 | 0.0 | 0.0 | 0.0 | 0.0 | 0.0 | 0.0 | | 0.0 | 0.0 | 0.0 | | 0.0 | 0.0 | 1.0 |
| | 0.0313 | 0.0 | 0.0 | 0.0 | 9.0 | 7.0 | 9.0 | | 7.0 | 9.0 | 1.0 | | 0.0 | 0.0 | 0.0 |
| | 0.0156 | 0.0 | 9.0 | 9.0 | 9.0 | 7.0 | 9.0 | | 7.0 | 9.0 | 6.0 | | 6.0 | 7.0 | 7.0 |
| 30 | 0.2500 | 9.0 | 9.0 | 9.0 | 9.0 | 1.0 | 9.0 | | 6.0 | 9.0 | 3.0 | | 5.0 | 6.0 | 6.0 |
| | 0.1250 | 9.0 | 9.0 | 9.0 | 9.0 | 1.0 | 9.0 | | 6.0 | 9.0 | 3.0 | | 5.0 | 6.0 | 6.0 |

TABLE II-continued

Preemergence Herbicidal Evaluations of Test Compounds

| Compound Number | Rate (kg/ha) | ABUTH | AMBEL | CASOB | CHEAL | GALAP | IPOHE | IPOSS | ECHCG | SETVI | GLXMAW | GLXMA | ORYSAT | TRZAWR | ZEAMX |
|---|---|---|---|---|---|---|---|---|---|---|---|---|---|---|---|
| | 0.0625 | 7.0 | 3.0 | 0.0 | 9.0 | 0.0 | 2.0 | | 1.0 | 9.0 | 2.0 | | 4.0 | 2.0 | 2.0 |
| | 0.0313 | 9.0 | 2.0 | 0.0 | 9.0 | 3.0 | 2.0 | | 0.0 | 9.0 | 1.0 | | 2.0 | 1.0 | 2.0 |
| | 0.0156 | 9.0 | 2.0 | | 9.0 | 0.0 | 3.0 | | 0.0 | 7.0 | 0.0 | | 1.0 | 0.0 | 1.0 |
| 31 | 0.2500 | 9.0 | 9.0 | 9.0 | 9.0 | 9.0 | 9.0 | | 9.0 | 9.0 | 9.0 | | 9.0 | 8.0 | 9.0 |
| | 0.1250 | 9.0 | 9.0 | 9.0 | 9.0 | 9.0 | 9.0 | | 9.0 | 9.0 | 9.0 | | 9.0 | 9.0 | 8.0 |
| | 0.0625 | 9.0 | 9.0 | 6.0 | 9.0 | 9.0 | 7.5 | | 6.5 | 8.5 | 8.5 | | 8.0 | 8.0 | 8.0 |
| | 0.0313 | 9.0 | 9.0 | 0.0 | 9.0 | 9.0 | 7.0 | | 7.0 | 6.0 | 8.0 | | 8.0 | 8.0 | 7.0 |
| | 0.0157 | 9.0 | 9.0 | 9.0 | 9.0 | | 9.0 | | 9.0 | 9.0 | 6.0 | | | | 5.0 |
| | 0.0156 | 9.0 | 9.0 | 9.0 | 9.0 | 8.0 | 9.0 | | 9.0 | 9.0 | 8.0 | | 8.0 | 7.0 | 8.0 |
| 32 | 0.2500 | 9.0 | 9.0 | 9.0 | 9.0 | 9.0 | 9.0 | | 9.0 | 9.0 | 8.0 | | 9.0 | 8.0 | 8.0 |
| | 0.1250 | 9.0 | 9.0 | 9.0 | 9.0 | 9.0 | 9.0 | | 8.0 | 9.0 | 6.0 | | 8.0 | 7.0 | 8.0 |
| | 0.0625 | 9.0 | 9.0 | 9.0 | 9.0 | 9.0 | 6.0 | | 5.0 | 9.0 | 6.0 | | 7.0 | 7.0 | 7.0 |
| | 0.0313 | 9.0 | 5.0 | 2.0 | 9.0 | 8.0 | 4.0 | | 2.0 | 7.0 | 5.0 | | 6.0 | 2.0 | 5.0 |
| | 0.0156 | 9.0 | 9.0 | 9.0 | 9.0 | 7.0 | 9.0 | | 0.0 | 5.0 | | | 4.0 | 2.0 | 4.0 |
| 33 | 0.2500 | 9.0 | 9.0 | 7.0 | 9.0 | 0.0 | 9.0 | | 9.0 | 9.0 | 4.0 | | 7.0 | 7.0 | 7.0 |
| | 0.1250 | 9.0 | 4.0 | 9.0 | 9.0 | 1.0 | 5.0 | | 7.0 | 9.0 | 7.0 | | 6.0 | 2.0 | 9.0 |
| | 0.0625 | 9.0 | 0.0 | 5.0 | 9.0 | | 5.0 | | 1.0 | 9.0 | 2.0 | | 7.0 | 4.0 | 5.0 |
| | 0.0313 | 9.0 | 4.0 | 9.0 | 9.0 | 0.0 | 4.0 | | 0.0 | 7.0 | | | 2.0 | 1.0 | 2.0 |
| | 0.0156 | 5.0 | 1.0 | 9.0 | 9.0 | 0.0 | 3.0 | | 0.0 | 2.0 | 4.0 | | 3.0 | 2.0 | 3.0 |
| 34 | 0.2500 | 1.0 | 1.0 | 5.0 | 1.0 | 5.0 | 0.0 | | 9.0 | 1.0 | 1.0 | | 1.0 | 1.0 | 2.0 |
| | 0.1250 | 1.0 | 1.0 | 4.0 | 2.0 | 9.0 | 0.0 | | 7.0 | 1.0 | | | 1.0 | 2.0 | 1.0 |
| | 0.0625 | 0.0 | 0.0 | 2.0 | 7.0 | 4.0 | 0.0 | | 0.0 | 2.0 | 1.0 | | 1.0 | 1.0 | 1.0 |
| | 0.0313 | 0.0 | 0.0 | 0.0 | 0.0 | 2.0 | 0.0 | | 0.0 | 0.0 | 0.0 | | 0.0 | 0.0 | 0.0 |
| | 0.0156 | 0.0 | 1.0 | 0.0 | | 2.0 | 0.0 | | 0.0 | 0.0 | 0.0 | | 1.0 | 0.0 | 0.0 |
| 35 | 0.2500 | 9.0 | 9.0 | 9.0 | 9.0 | 9.0 | 9.0 | | 9.0 | 9.0 | 9.0 | | 1.0 | 8.0 | 8.0 |
| | 0.1250 | 9.0 | 9.0 | 9.0 | 9.0 | 9.0 | 9.0 | | 9.0 | 9.0 | 9.0 | | 8.0 | 9.0 | 8.0 |
| | 0.0625 | 9.0 | 9.0 | 9.0 | 9.0 | 8.0 | 9.0 | | 9.0 | 9.0 | 7.0 | | 8.0 | 7.0 | 8.0 |
| | 0.0313 | 9.0 | 8.0 | 7.0 | 9.0 | 7.0 | 7.0 | | 7.0 | 9.0 | 5.0 | | 7.0 | 6.0 | 7.0 |
| | 0.0156 | 9.0 | 0.0 | 6.0 | 9.0 | 7.0 | 6.0 | | 6.0 | 7.0 | 1.0 | | 6.0 | 3.0 | 5.0 |
| 36 | 0.2500 | 0.0 | 0.0 | 0.0 | 0.0 | 0.0 | 0.0 | | 0.0 | 3.0 | 0.0 | | 3.0 | 0.0 | 0.0 |
| | 0.1250 | 0.0 | 0.0 | 0.0 | 0.0 | 0.0 | 0.0 | | 0.0 | 0.0 | 0.0 | | 0.0 | 0.0 | 0.0 |
| | 0.0625 | 0.0 | 0.0 | 0.0 | 0.0 | 0.0 | 0.0 | | 0.0 | 0.0 | 0.0 | | 0.0 | 0.0 | 0.0 |
| | 0.0313 | 0.0 | 0.0 | 0.0 | 0.0 | 0.0 | 0.0 | | 0.0 | 0.0 | 2.0 | | 0.0 | 0.0 | 0.0 |
| | 0.0156 | 0.0 | 0.0 | 0.0 | 0.0 | 0.0 | 0.0 | | 0.0 | 0.0 | 0.0 | | 0.0 | 0.0 | 0.0 |
| 37 | 0.2500 | 1.0 | 0.0 | 0.0 | 3.0 | 0.0 | 0.0 | | 0.0 | 0.0 | 0.0 | | 0.0 | 0.0 | 0.0 |
| | 0.1250 | 0.0 | 0.0 | 0.0 | 0.0 | 0.0 | 0.0 | | 0.0 | 0.0 | 0.0 | | 0.0 | 0.0 | 0.0 |
| | 0.0625 | 0.0 | 0.0 | 0.0 | 0.0 | 0.0 | 0.0 | | 0.0 | 0.0 | 0.0 | | 0.0 | 0.0 | 0.0 |
| | 0.0313 | 0.0 | 0.0 | 0.0 | 0.0 | 0.0 | 0.0 | | 0.0 | 0.0 | 0.0 | | 0.0 | 0.0 | 0.0 |
| | 0.0156 | 0.0 | 0.0 | 0.0 | 0.0 | 0.0 | 0.0 | | 0.0 | 0.0 | 0.0 | | 0.0 | 0.0 | 0.0 |
| 38 | 0.2500 | 0.0 | 0.0 | 0.0 | 3.0 | 9.0 | 1.0 | | 0.0 | 0.0 | 4.0 | | 1.0 | 2.0 | 3.0 |
| | 0.1250 | 0.0 | 0.0 | 4.0 | 5.0 | 5.0 | 0.0 | | 0.0 | 0.0 | 1.0 | | 1.0 | 1.0 | 1.0 |
| | 0.0625 | 0.0 | 0.0 | 0.0 | 0.0 | 5.0 | 0.0 | | 0.0 | 0.0 | 2.0 | | 2.0 | 1.0 | 1.0 |
| | 0.0313 | 0.0 | 0.0 | 0.0 | 0.0 | 0.0 | 0.0 | | 0.0 | 0.0 | 1.0 | | 2.0 | 0.0 | 1.0 |
| | 0.0156 | 0.0 | 0.0 | 0.0 | 0.0 | 0.0 | 1.0 | | 0.0 | 0.0 | 4.0 | | 0.0 | 0.0 | 0.0 |
| 39 | 0.2500 | 2.0 | 1.0 | 0.0 | 7.0 | 7.0 | 1.0 | | 1.0 | 0.0 | 3.0 | | 5.0 | 3.0 | 5.0 |
| | 0.1250 | 0.0 | 1.0 | | 5.0 | 2.0 | 0.0 | | 0.0 | 0.0 | 1.0 | | 5.0 | 3.0 | 2.0 |
| | 0.0625 | 0.0 | 1.0 | 0.0 | 0.0 | 0.0 | 3.0 | | 1.0 | 1.0 | 0.0 | | 6.0 | 7.0 | 0.0 |

TABLE II-continued

Preemergence Herbicidal Evaluations of Test Compounds

| Compound Number | Rate (kg/ha) | ABUTH | AMBEL | CASOB | CHEAL | GALAP | IPOHE | IPOSS | ECHCG | SETVI | GLXMAW | GLXMA | ORYSAT | TRZAWR | ZEAMX |
|---|---|---|---|---|---|---|---|---|---|---|---|---|---|---|---|
|  | 0.0313 | 1.0 | 2.0 | 1.0 | 5.0 | 0.0 | 3.0 |  | 0.0 | 0.0 | 1.0 |  | 5.0 | 1.0 | 2.0 |
|  | 0.0156 | 1.0 | 1.0 | 0.0 | 0.0 | 0.0 | 1.0 |  | 0.0 | 0.0 |  |  | 6.0 | 0.0 | 0.0 |
| 40 | 0.2500 | 9.0 | 9.0 | 6.0 | 9.0 | 9.0 | 7.0 |  | 9.0 | 9.0 | 9.0 |  | 8.0 | 7.0 | 8.0 |
|  | 0.1250 | 9.0 | 7.0 | 2.0 | 9.0 | 9.0 | 9.0 |  | 9.0 | 9.0 | 6.0 |  | 7.0 | 7.0 | 6.0 |
|  | 0.0625 | 9.0 | 7.0 | 1.0 | 9.0 | 7.0 | 6.0 |  | 7.0 | 9.0 | 5.0 |  | 5.0 | 6.0 | 6.0 |
|  | 0.0313 | 9.0 | 6.0 | 2.0 | 9.0 | 7.0 | 6.0 |  | 4.0 | 9.0 | 5.0 |  | 6.0 | 1.0 | 6.0 |
|  | 0.0156 | 9.0 | 0.0 | 0.0 | 5.0 | 0.0 | 0.0 |  | 4.0 | 9.0 | 2.0 |  | 1.0 | 3.0 | 4.0 |
| 41 | 0.2500 | 9.0 | 4.0 | 1.0 | 9.0 | 0.0 | 5.0 |  | 7.0 | 8.0 | 2.0 |  | 2.0 | 4.0 | 3.0 |
|  | 0.1250 | 7.0 | 2.0 | 5.0 | 9.0 | 3.0 | 2.0 |  | 6.0 | 7.0 | 1.0 |  | 1.0 | 1.0 | 5.0 |
|  | 0.0625 | 3.0 | 3.0 | 2.0 | 5.0 |  | 0.0 |  | 2.0 | 5.0 | 1.0 |  | 1.0 | 1.0 | 3.0 |
|  | 0.0313 | 1.0 | 1.0 | 2.0 | 2.0 | 3.0 | 0.0 |  | 0.0 | 0.0 | 1.0 |  | 2.0 | 1.0 | 3.0 |
|  | 0.0156 | 0.0 | 0.0 | 2.0 | 0.0 | 3.0 | 1.0 |  | 0.0 | 0.0 | 1.0 |  | 1.0 | 1.0 | 5.0 |
| 42 | 0.2500 | 9.0 | 9.0 | 9.0 | 9.0 | 9.0 | 8.0 |  | 8.0 | 9.0 | 8.0 |  | 8.0 | 6.0 | 7.0 |
|  | 0.1250 | 9.0 | 7.0 | 5.0 | 7.0 | 7.0 | 7.0 |  | 7.0 | 7.0 | 5.0 |  | 5.0 | 4.0 | 5.0 |
|  | 0.0625 | 9.0 | 6.0 | 5.0 | 2.0 | 2.0 | 2.0 |  | 4.0 | 7.0 | 9.0 |  | 4.0 | 3.0 | 5.0 |
|  | 0.0313 | 7.0 | 1.0 | 2.0 | 0.0 | 1.0 | 1.0 |  | 2.0 | 4.0 | 5.0 |  | 1.0 | 1.0 | 2.0 |
|  | 0.0156 | 5.0 | 1.0 | 0.0 | 6.0 | 1.0 | 0.0 |  | 1.0 | 1.0 | 3.0 |  | 3.0 | 1.0 | 0.0 |
| 43 | 0.2500 | 9.0 | 9.0 | 4.0 | 0.0 | 9.0 | 9.0 |  | 9.0 | 9.0 | 1.0 |  | 7.0 | 7.0 | 8.0 |
|  | 0.1250 | 9.0 | 9.0 |  | 9.0 | 6.0 | 9.0 |  | 8.0 | 9.0 | 9.0 |  | 7.0 | 7.0 | 8.0 |
|  | 0.0625 | 8.0 | 6.0 | 0.0 | 9.0 | 8.0 | 6.0 |  | 9.0 | 9.0 | 7.0 |  | 4.0 | 4.0 | 7.0 |
|  | 0.0313 | 9.0 | 1.0 | 4.0 | 9.0 | 1.0 | 1.0 |  | 7.0 | 9.0 | 3.0 |  | 2.0 | 1.0 | 7.0 |
|  | 0.0156 | 2.0 | 0.0 | 0.0 | 8.0 | 0.0 | 0.0 |  | 0.0 | 5.0 | 5.0 |  | 2.0 | 0.0 | 0.0 |
| 44 | 0.2500 | 9.0 | 7.0 | 0.0 | 9.0 | 1.0 | 9.0 |  | 4.0 | 7.0 | 9.0 |  | 5.0 | 4.0 | 5.0 |
|  | 0.1250 | 9.0 | 6.0 | 9.0 | 9.0 | 7.0 | 6.0 |  | 0.0 | 4.0 | 5.0 |  | 2.0 | 2.0 | 3.0 |
|  | 0.0625 | 7.0 | 4.0 | 5.0 | 9.0 | 7.0 | 1.0 |  | 0.0 | 0.0 | 3.0 |  | 2.0 | 1.0 | 1.0 |
|  | 0.0313 | 0.0 | 0.0 | 0.0 | 1.0 | 2.0 | 0.0 |  | 0.0 | 0.0 | 5.0 |  | 1.0 | 0.0 | 0.0 |
|  | 0.0156 | 0.0 | 0.0 | 0.0 | 0.0 | 0.0 | 0.0 |  | 0.0 | 5.0 | 1.0 |  | 0.0 | 0.0 | 0.0 |
| 45 | 0.2500 | 9.0 | 9.0 | 7.0 | 9.0 | 8.5 | 7.5 |  | 8.0 | 9.0 | 9.0 |  | 6.0 | 5.5 | 6.0 |
|  | 0.1250 | 9.0 | 8.0 | 4.0 | 9.0 | 8.5 | 9.0 |  | 7.0 | 9.0 | 7.0 |  | 5.0 | 4.5 | 5.0 |
|  | 0.0625 | 9.0 | 7.5 | 4.5 | 8.5 | 7.0 | 3.5 |  | 7.5 | 9.0 | 5.5 |  | 5.5 | 4.0 | 4.0 |
|  | 0.0313 | 9.0 | 4.5 | 3.0 | 9.0 | 6.5 | 3.5 |  | 5.5 | 8.0 | 3.0 |  | 4.0 | 1.5 | 2.5 |
|  | 0.0156 | 5.0 | 1.5 | 1.0 | 9.0 | 0.5 | 0.5 |  | 0.5 | 9.0 | 2.5 |  | 1.5 | 1.5 | 1.0 |
| 46 | 0.2500 | 9.0 | 8.5 | 8.0 | 9.0 | 9.0 | 9.0 |  | 7.0 | 9.0 | 9.0 |  | 5.5 | 4.0 | 6.5 |
|  | 0.1250 | 9.0 | 8.5 | 6.0 | 9.0 | 5.0 | 9.0 |  | 5.5 | 9.0 | 7.0 |  | 6.0 | 4.0 | 3.5 |
|  | 0.0625 | 8.5 | 8.0 | 2.5 | 9.0 | 2.0 | 5.5 |  | 4.5 | 8.0 | 5.5 |  | 7.0 | 4.5 | 4.0 |
|  | 0.0313 | 9.0 | 4.0 | 1.5 | 9.0 | 6.0 | 4.5 |  | 2.0 | 8.0 | 4.5 |  | 4.5 | 5.5 | 4.0 |
|  | 0.0156 | 4.5 | 2.0 | 2.0 | 9.0 | 1.0 | 1.0 |  | 0.5 | 7.5 | 4.0 |  | 4.5 | 3.0 | 2.5 |
| 47 | 0.2500 | 9.0 | 9.0 | 6.0 | 9.0 | 8.0 | 9.0 |  | 8.0 | 9.0 | 9.0 |  | 9.0 | 8.0 | 9.0 |
|  | 0.1250 | 9.0 | 7.0 | 7.0 | 9.0 | 0.0 | 6.0 |  | 7.0 | 9.0 | 7.0 |  | 7.0 | 7.0 | 7.0 |
|  | 0.0625 | 6.0 | 7.0 | 4.0 | 9.0 | 7.0 | 5.0 |  | 4.0 | 9.0 | 6.0 |  | 6.0 | 6.0 | 6.0 |
|  | 0.0313 | 9.0 | 0.0 | 0.0 | 0.0 |  | 0.0 |  | 1.0 | 3.0 | 4.0 |  | 4.0 | 2.0 | 4.0 |
|  | 0.0156 | 0.0 | 0.0 | 0.0 | 5.0 | 0.0 | 5.0 |  | 0.0 | 0.0 | 1.0 |  | 2.0 | 0.0 | 1.0 |
| 48 | 0.2500 | 9.0 | 9.0 | 5.0 | 9.0 | 9.0 | 9.0 |  | 8.0 | 9.0 | 9.0 |  | 8.0 | 9.0 | 8.0 |
|  | 0.1250 | 9.0 | 9.0 |  | 9.0 | 7.0 | 7.0 |  | 4.0 | 9.0 | 9.0 |  | 8.0 | 7.0 | 7.0 |
|  | 0.0625 | 7.0 | 1.0 | 3.0 | 9.0 | 8.0 | 3.0 |  | 2.0 | 9.0 | 6.0 |  | 5.0 | 3.0 | 6.0 |
|  | 0.0313 | 9.0 | 7.0 | 3.0 | 2.0 | 6.0 | 1.0 |  | 0.0 | 8.0 | 9.0 |  | 5.0 | 3.0 | 5.0 |
|  | 0.0156 | 0.0 | 0.0 | 2.0 | 0.0 | 6.0 | 1.0 |  | 0.0 | 9.0 | 2.0 |  | 3.0 | 0.0 | 3.0 |

TABLE II-continued

Preemergence Herbicidal Evaluations of Test Compounds

| Compound Number | Rate (kg/ha) | ABUTH | AMBEL | CASOB | CHEAL | GALAP | IPOHE | IPOSS | ECHCG | SETVI | GLXMAW | GLXMA | ORYSAT | TRZAWR | ZEAMX |
|---|---|---|---|---|---|---|---|---|---|---|---|---|---|---|---|
| 49 | 0.0630 | 9.0 | 9.0 | 4.0 | 9.0 | 4.0 | | 9.0 | 4.0 | 7.0 | 6.0 | | 0.0 | 0.0 | 0.0 |
| | 0.0315 | 9.0 | 9.0 | | 9.0 | 4.0 | | 0.0 | 0.0 | 6.0 | 0.0 | | 0.0 | 0.0 | 0.0 |
| | 0.0158 | 3.0 | 5.0 | 0.0 | 9.0 | | | 0.0 | 0.0 | 0.0 | 0.0 | | 0.0 | 0.0 | 0.0 |
| 50 | 0.1250 | 9.0 | 9.0 | 2.0 | 9.0 | | 9.0 | | 9.0 | 9.0 | 4.0 | | 0.0 | 2.0 | 0.0 |
| | 0.0630 | 9.0 | 9.0 | 9.0 | 9.0 | 6.0 | | 9.0 | 5.0 | 9.0 | 8.0 | | 0.0 | 0.0 | 0.0 |
| | 0.0315 | 9.0 | 5.0 | 2.0 | 9.0 | | 4.0 | | 5.0 | 5.0 | 0.0 | | 0.0 | | 0.0 |
| | 0.0158 | 9.0 | 0.0 | 0.0 | 9.0 | 0.0 | 0.0 | 7.0 | 0.0 | 7.0 | 6.0 | | 0.0 | | 0.0 |
| | 0.0157 | 9.0 | 0.0 | 0.0 | 9.0 | | | | 4.0 | 5.0 | 0.0 | | 0.0 | 0.0 | 0.0 |
| 51 | 0.2500 | 9.0 | 9.0 | 9.0 | 9.0 | 9.0 | 0.0 | | 0.0 | 9.0 | 9.0 | | 7.0 | 4.0 | 2.0 |
| | 0.1250 | 9.0 | 9.0 | 4.0 | 9.0 | 7.0 | 9.0 | | 8.0 | 9.0 | 4.0 | | 0.0 | 6.0 | 2.0 |
| | 0.0625 | 9.0 | 7.0 | 1.0 | 9.0 | 5.0 | 8.5 | | 8.0 | 9.0 | 2.0 | | 0.0 | 0.0 | 0.0 |
| | 0.0313 | 9.0 | 7.0 | 4.5 | 9.0 | 0.0 | 7.5 | | 5.5 | 6.5 | 0.0 | | 0.0 | 0.0 | 0.0 |
| | 0.0157 | 9.0 | 9.0 | 0.0 | 9.0 | | 4.5 | | 2.5 | 5.0 | 0.5 | | 0.0 | 0.0 | 0.0 |
| | 0.0156 | 4.0 | 3.0 | 0.0 | | | 0.0 | | 3.0 | 7.0 | 0.0 | | 0.0 | 0.0 | 0.0 |
| 52 | 0.2500 | 9.0 | 5.0 | 4.0 | 9.0 | 5.0 | 4.0 | | 0.0 | 7.0 | 2.0 | | 0.0 | 0.0 | 4.0 |
| | 0.1250 | 4.0 | 4.0 | 0.0 | 9.0 | 0.0 | 0.0 | | 0.0 | 7.0 | 0.0 | | 0.0 | 0.0 | 4.0 |
| | 0.0625 | 1.0 | 0.0 | 0.0 | 9.0 | 0.0 | 0.0 | | 0.0 | 6.0 | 0.0 | | 0.0 | 0.0 | 2.0 |
| | 0.0313 | 0.0 | 0.0 | 3.0 | 9.0 | 0.0 | 0.0 | | 0.0 | 3.0 | 0.0 | | 0.0 | 0.0 | 0.0 |
| | 0.0156 | 0.0 | 0.0 | 0.0 | | 0.0 | 0.0 | | 0.0 | 5.0 | 0.0 | | 0.0 | 0.0 | 0.0 |
| 53 | 0.2500 | 9.0 | 9.0 | 8.0 | 9.0 | 7.0 | 9.0 | | 9.0 | 4.0 | 0.0 | | 0.0 | 0.0 | 0.0 |
| | 0.1250 | 9.0 | 9.0 | 9.0 | 9.0 | 5.0 | 9.0 | | 9.0 | 9.0 | 9.0 | | 7.0 | 5.0 | 4.0 |
| | 0.0625 | 9.0 | 5.0 | 4.0 | 9.0 | 0.0 | 5.0 | | 5.0 | 9.0 | 6.0 | | 5.0 | 2.0 | 2.0 |
| | 0.0313 | 9.0 | 0.0 | 0.0 | 9.0 | 0.0 | 0.0 | | 0.0 | 7.0 | 4.0 | | 8.0 | 0.0 | 0.0 |
| | 0.0156 | 9.0 | 8.0 | 3.0 | 9.0 | 3.0 | 3.0 | | 0.0 | 4.0 | 0.0 | | 7.0 | 0.0 | 2.0 |
| 54 | 0.2500 | 9.0 | 1.0 | 9.0 | 9.0 | 1.0 | 9.0 | | 3.0 | 9.0 | 0.0 | | 2.0 | 1.0 | 1.0 |
| | 0.1250 | 9.0 | 2.0 | 9.0 | 9.0 | 0.0 | 5.0 | | 1.0 | 6.0 | 0.0 | | 0.0 | 0.0 | 0.0 |
| | 0.0625 | 4.0 | 0.0 | 9.0 | 9.0 | 0.0 | 0.0 | | 0.0 | 5.0 | 2.0 | | 0.0 | 0.0 | 0.0 |
| | 0.0313 | 0.0 | 0.0 | 9.0 | 9.0 | 0.0 | 0.0 | | 0.0 | 0.0 | 1.0 | | 0.0 | 0.0 | 0.0 |
| | 0.0156 | 0.0 | 0.0 | 9.0 | 9.0 | 0.0 | 0.0 | | 0.0 | 0.0 | 5.0 | | 0.0 | 0.0 | 2.0 |
| 55 | 0.2500 | 9.0 | 7.0 | 9.0 | 9.0 | 0.0 | 7.0 | | 9.0 | 9.0 | 4.0 | | 5.0 | 0.0 | 3.0 |
| | 0.1250 | 5.0 | 5.0 | 9.0 | 9.0 | 0.0 | 2.0 | | 2.0 | 7.0 | 2.0 | | 4.0 | 0.0 | 0.0 |
| | 0.0625 | 9.0 | 0.0 | 9.0 | 9.0 | 0.0 | 3.0 | | 0.0 | 9.0 | 3.0 | | 0.0 | 0.0 | 0.0 |
| | 0.0313 | 0.0 | 0.0 | 0.0 | 9.0 | 0.0 | 0.0 | | 0.0 | 5.0 | 0.0 | | 0.0 | 0.0 | 0.0 |
| | 0.0156 | 0.0 | 0.0 | 0.0 | 9.0 | 0.0 | 2.0 | | 4.0 | 0.0 | 2.0 | | 0.0 | 0.0 | 1.0 |
| 56 | 0.2500 | 9.0 | 9.0 | 9.0 | 9.0 | 0.0 | 0.0 | | 5.0 | 9.0 | 0.0 | | 0.0 | 0.0 | 1.0 |
| | 0.1250 | 9.0 | 8.0 | 7.0 | 9.0 | 5.0 | 2.0 | | 0.0 | 9.0 | 0.0 | | 0.0 | 0.0 | 0.0 |
| | 0.0625 | 9.0 | 0.0 | 3.0 | 9.0 | 5.0 | 0.0 | | 0.0 | 7.0 | 0.0 | | 0.0 | 0.0 | 0.0 |
| | 0.0313 | 4.0 | 0.0 | 0.0 | 9.0 | 2.0 | 7.0 | | 0.0 | 0.0 | 7.0 | | 0.0 | 0.0 | 0.0 |
| | 0.0156 | 0.0 | 0.0 | 0.0 | 9.0 | 0.0 | 0.0 | | 0.0 | 5.0 | 0.0 | | 0.0 | 0.0 | 0.0 |
| 57 | 0.2500 | 9.0 | 9.0 | 9.0 | 9.0 | 5.0 | 7.0 | | 7.0 | 9.0 | 7.0 | | 7.0 | 5.0 | 7.0 |
| | 0.1250 | 9.0 | 7.0 | 9.0 | 9.0 | 5.0 | 6.0 | | 8.0 | 7.0 | 5.0 | | 2.0 | 1.0 | 3.0 |
| | 0.0625 | 9.0 | 4.0 | 9.0 | 9.0 | 2.0 | 9.0 | | 7.0 | 9.0 | 0.0 | | 0.0 | 0.0 | 0.0 |
| | 0.0313 | 9.0 | 3.0 | 5.0 | 9.0 | 0.0 | 5.0 | | 5.0 | 8.0 | 0.0 | | 0.0 | 0.0 | 0.0 |
| | 0.0156 | 7.0 | 0.0 | 0.0 | 9.0 | 0.0 | 0.0 | | 0.0 | 5.0 | 0.0 | | 0.0 | 5.0 | 0.0 |
| 58 | 0.2500 | 9.0 | 9.0 | 9.0 | 9.0 | 4.0 | 6.0 | | 8.0 | 9.0 | 9.0 | | 6.0 | 6.0 | 7.0 |

TABLE II-continued

Preemergence Herbicidal Evaluations of Test Compounds

| Compound Number | Rate (kg/ha) | ABUTH | AMBEL | CASOB | CHEAL | GALAP | IPOHE | IPOSS | ECHCG | SETVI | GLXMAW | GLXMA | ORYSAT | TRZAWR | ZEAMX |
|---|---|---|---|---|---|---|---|---|---|---|---|---|---|---|---|
|  | 0.1250 | 9.0 | 5.0 | 9.0 | 9.0 | 5.0 | 4.0 |  | 5.0 | 9.0 | 5.0 | 2.0 | 2.0 | 2.0 | 6.0 |
|  | 0.0625 | 6.0 | 7.0 | 9.0 | 9.0 | 3.0 | 0.0 |  | 0.0 | 5.0 | 2.0 |  | 0.0 | 0.0 | 1.0 |
|  | 0.0313 | 9.0 | 1.0 | 9.0 | 9.0 | 0.0 | 0.0 |  | 0.0 | 6.0 | 2.0 |  | 0.0 | 0.0 | 0.0 |
|  | 0.0156 | 5.0 | 0.0 | 9.0 | 9.0 | 9.0 | 9.0 |  | 7.0 | 9.0 | 0.0 |  | 0.0 | 0.0 | 3.0 |
| 59 | 0.2500 | 9.0 | 7.0 | 9.0 | 9.0 | 9.0 | 9.0 |  | 4.0 | 9.0 | 5.0 |  | 0.0 | 0.0 | 2.0 |
|  | 0.1250 | 9.0 | 0.0 | 9.0 | 9.0 | 7.0 | 0.0 |  | 2.0 | 9.0 | 0.0 |  | 0.0 | 0.0 | 1.0 |
|  | 0.0625 | 0.0 | 0.0 | 2.0 | 9.0 | 9.0 | 0.0 |  | 0.0 | 7.0 | 0.0 |  | 0.0 | 0.0 | 0.0 |
|  | 0.0313 | 0.0 | 0.0 | 9.0 | 9.0 | 5.0 | 0.0 |  | 0.0 | 0.0 | 1.0 |  | 0.0 | 0.0 | 0.0 |
|  | 0.0156 | 0.0 | 0.0 | 0.0 | 9.0 | 5.0 | 0.0 |  | 0.0 | 0.0 | 0.0 |  | 0.0 | 0.0 | 1.0 |
| 60 | 0.2500 | 9.0 | 8.0 | 9.0 | 9.0 | 0.0 | 0.0 |  | 0.0 | 7.0 | 1.0 |  | 0.0 | 0.0 | 0.0 |
|  | 0.1250 | 1.0 | 2.0 | 2.0 | 9.0 | 0.0 | 0.0 |  | 0.0 | 3.0 | 1.0 |  | 0.0 | 0.0 | 0.0 |
|  | 0.0625 | 2.0 | 0.0 | 0.0 | 9.0 | 6.0 | 0.0 |  | 0.0 | 3.0 | 0.0 |  | 0.0 | 0.0 | 0.0 |
|  | 0.0313 | 0.0 | 0.0 | 0.0 | 9.0 | 6.0 | 0.0 |  | 0.0 | 0.0 | 0.0 |  | 0.0 | 0.0 | 0.0 |
|  | 0.0156 | 0.0 | 0.0 | 0.0 | 9.0 | 2.0 | 0.0 |  | 0.0 | 0.0 | 0.0 |  | 0.0 | 0.0 | 0.0 |
| 61 | 0.2500 | 2.0 | 0.0 | 9.0 | 9.0 | 4.0 | 0.0 |  | 0.0 | 7.0 | 0.0 |  | 0.0 | 0.0 | 5.0 |
|  | 0.1250 | 0.0 | 0.0 | 3.0 | 9.0 | 0.0 | 0.0 |  | 0.0 | 7.0 | 0.0 |  | 0.0 | 0.0 | 0.0 |
|  | 0.0625 | 3.0 | 0.0 | 4.0 | 9.0 | 0.0 | 0.0 |  | 0.0 | 0.0 | 0.0 |  | 0.0 | 0.0 | 0.0 |
|  | 0.0313 | 0.0 | 0.0 | 0.0 | 9.0 | 0.0 | 0.0 |  | 0.0 | 0.0 | 0.0 |  | 0.0 | 0.0 | 0.0 |
|  | 0.0156 | 0.0 | 0.0 | 0.0 | 9.0 | 0.0 | 0.0 |  | 0.0 | 0.0 | 0.0 |  | 0.0 | 0.0 | 0.0 |
| 62 | 0.2500 | 9.0 | 9.0 | 9.0 | 9.0 | 6.0 | 9.0 |  | 8.0 | 9.0 | 5.0 |  | 5.0 | 2.0 | 6.0 |
|  | 0.1250 | 9.0 | 9.0 | 9.0 | 9.0 | 0.0 | 9.0 |  | 7.0 | 9.0 | 5.0 |  | 1.0 | 0.0 | 4.0 |
|  | 0.0625 | 9.0 | 9.0 | 9.0 | 9.0 |  | 9.0 |  | 3.0 | 9.0 | 5.0 |  | 1.0 | 1.0 | 4.0 |
|  | 0.0313 | 9.0 | 0.0 | 9.0 | 9.0 |  | 9.0 |  | 1.0 | 7.0 | 0.0 |  | 0.0 | 0.0 | 1.0 |
|  | 0.0156 | 9.0 | 0.0 | 0.0 | 9.0 | 0.0 | 9.0 |  | 0.0 | 7.0 | 0.0 |  | 0.0 | 0.0 | 0.0 |
| 63 | 0.2500 | 9.0 | 0.0 | 0.0 | 9.0 | 0.0 | 0.0 |  | 1.0 | 5.0 | 1.0 |  | 0.0 | 0.0 | 0.0 |
|  | 0.1250 | 9.0 | 7.0 | 0.0 | 9.0 | 0.0 | 1.0 |  | 0.0 | 4.0 | 0.0 |  | 0.0 | 0.0 | 2.0 |
|  | 0.0625 | 5.0 | 0.0 |  | 9.0 | 0.0 | 0.0 |  | 0.0 | 0.0 | 1.0 |  | 0.0 | 0.0 | 0.0 |
|  | 0.0313 | 0.0 | 0.0 |  | 9.0 | 0.0 | 0.0 |  | 0.0 | 0.0 | 1.0 |  | 0.0 | 0.0 | 0.0 |
|  | 0.0156 | 0.0 | 0.0 |  | 9.0 | 0.0 | 0.0 |  | 0.0 | 0.0 | 1.0 |  | 0.0 | 0.0 | 0.0 |
| 64 | 0.2500 | 9.0 | 9.0 | 9.0 | 9.0 | 9.0 | 9.0 |  | 9.0 | 9.0 | 9.0 |  | 8.0 | 2.0 | 4.0 |
|  | 0.1250 | 9.0 | 9.0 | 4.0 | 9.0 | 6.0 | 9.0 |  | 8.0 | 8.0 | 7.0 |  | 7.0 | 1.0 | 4.0 |
|  | 0.0625 | 9.0 | 7.0 | 4.0 | 9.0 | 4.0 | 3.0 |  | 4.0 | 9.0 | 2.0 |  | 5.0 | 0.0 | 0.0 |
|  | 0.0313 | 9.0 | 5.0 | 2.0 | 9.0 | 2.0 | 9.0 |  | 0.0 | 4.0 | 0.0 |  | 0.0 | 0.0 | 0.0 |
|  | 0.0156 | 9.0 | 9.0 | 5.0 | 9.0 | 0.0 | 0.0 |  | 3.0 | 3.0 | 0.0 |  | 0.0 | 0.0 | 0.0 |
| 65 | 0.2500 | 9.0 | 9.0 | 9.0 | 9.0 | 8.0 | 9.0 |  | 8.0 | 9.0 | 5.0 |  | 8.0 | 3.0 | 5.0 |
|  | 0.1250 | 9.0 | 9.0 | 9.0 | 9.0 | 4.0 | 2.0 |  | 7.0 | 9.0 | 2.0 |  | 2.0 | 0.0 | 3.0 |
|  | 0.0625 | 9.0 | 0.0 | 6.0 | 9.0 | 2.0 | 0.0 |  | 5.0 | 9.0 | 1.0 |  | 3.0 | 1.0 | 3.0 |
|  | 0.0313 | 4.0 | 2.0 | 5.0 | 9.0 | 0.0 | 0.0 |  | 2.0 | 7.0 | 0.0 |  | 3.0 | 0.0 | 3.0 |
|  | 0.0156 | 9.0 | 2.0 | 1.0 | 9.0 | 0.0 | 1.0 |  | 1.0 | 5.0 | 0.0 |  | 2.0 | 0.0 | 0.0 |
| 66 | 0.2500 | 9.0 | 9.0 | 9.0 | 9.0 | 9.0 | 0.0 |  | 9.0 | 9.0 | 5.0 |  | 5.0 | 4.0 | 5.0 |
|  | 0.1250 | 9.0 | 0.0 | 9.0 | 9.0 | 4.0 | 0.0 |  | 9.0 | 9.0 | 5.0 |  | 4.0 | 3.0 | 5.0 |
|  | 0.0625 | 9.0 | 2.0 | 9.0 | 9.0 | 5.0 | 0.0 |  | 5.0 | 9.0 | 2.0 |  | 4.0 | 3.0 | 2.0 |
|  | 0.0313 | 9.0 | 5.0 | 9.0 | 9.0 | 2.0 | 0.0 |  | 3.0 | 9.0 | 9.0 |  | 1.0 | 1.0 | 1.0 |
|  | 0.0156 | 9.0 | 2.0 | 1.0 | 9.0 | 0.0 | 1.0 |  | 2.0 | 8.0 | 0.0 |  | 3.0 | 0.0 | 2.0 |
| 67 | 0.2500 | 9.0 | 8.0 | 6.0 | 9.0 | 5.0 | 3.0 |  | 5.0 | 9.0 | 3.3 |  | 5.0 | 2.0 | 6.0 |
|  | 0.1250 | 9.0 | 5.0 | 1.0 | 9.0 | 5.0 | 1.0 |  | 0.0 | 9.0 | 4.0 |  | 5.0 | 3.0 | 3.0 |
|  | 0.0625 | 9.0 | 2.0 | 9.0 | 9.0 | 7.0 | 0.0 |  | 0.0 | 9.0 | 1.0 |  | 1.0 | 2.0 | 2.0 |

TABLE II-continued

Preemergence Herbicidal Evaluations of Test Compounds

| Compound Number | Rate (kg/ha) | ABUTH | AMBEL | CASOB | CHEAL | GALAP | IPOHE | IPOSS | ECHCG | SETVI | GLXMAW | GLXMA | ORYSAT | TRZAWR | ZEAMX |
|---|---|---|---|---|---|---|---|---|---|---|---|---|---|---|---|
|  | 0.0313 | 9.0 | 3.0 | 9.0 | 9.0 | 0.0 | 0.0 |  | 0.0 | 8.0 | 0.0 |  | 0.0 | 0.0 | 1.0 |
|  | 0.0156 | 9.0 | 1.0 | 9.0 | 9.0 | 0.0 | 0.0 |  | 0.0 | 7.0 | 0.0 |  | 1.0 | 0.0 | 0.0 |
| 68 | 0.2500 | 9.0 | 7.0 | 9.0 | 9.0 | 0.0 | 5.0 |  | 3.0 | 9.0 | 1.0 |  | 1.0 | 0.0 | 2.0 |
|  | 0.1250 | 7.0 | 4.0 | 2.0 | 9.0 | 0.0 | 0.0 |  | 0.0 | 7.0 | 0.0 |  | 0.0 | 0.0 | 0.0 |
|  | 0.0625 | 3.0 | 0.0 | 3.0 | 9.0 |  | 0.0 |  | 0.0 | 3.0 | 0.0 |  | 0.0 | 0.0 | 0.0 |
|  | 0.0313 | 1.0 | 0.0 | 0.0 | 9.0 |  | 1.0 |  | 0.0 | 2.0 | 1.0 |  | 0.0 | 0.0 | 0.0 |
|  | 0.0156 | 0.0 | 0.0 |  | 9.0 | 0.0 | 0.0 |  | 0.0 | 0.0 | 0.0 |  | 0.0 | 0.0 | 0.0 |
| 69 | 0.2500 | 9.0 | 9.0 | 8.0 | 9.0 | 0.0 | 0.0 |  | 0.0 | 0.0 | 9.0 |  | 8.0 | 2.0 | 5.0 |
|  | 0.1250 | 9.0 | 9.0 | 9.0 | 9.0 | 9.0 | 9.0 |  | 9.0 | 9.0 | 9.0 |  | 9.0 | 1.0 | 6.0 |
|  | 0.0625 | 9.0 | 9.0 | 9.0 | 9.0 | 9.0 | 9.0 |  | 9.0 | 9.0 | 7.0 |  | 7.0 | 1.0 | 6.0 |
|  | 0.0313 | 9.0 | 9.0 | 0.0 | 9.0 | 6.0 | 9.0 |  | 7.0 | 9.0 | 5.0 |  | 6.0 | 1.0 | 1.0 |
|  | 0.0156 | 9.0 | 7.0 | 0.0 | 9.0 | 0.0 | 6.0 |  | 6.0 | 7.0 | 1.0 |  | 2.0 | 3.0 | 0.0 |
| 70 | 0.2500 | 9.0 | 9.0 | 9.0 | 9.0 | 9.0 | 9.0 |  | 9.0 | 9.0 | 5.0 |  | 8.0 | 2.0 | 7.0 |
|  | 0.1250 | 9.0 | 9.0 | 9.0 | 9.0 | 9.0 | 9.0 |  | 9.0 | 7.0 |  |  | 7.0 | 1.0 | 4.0 |
|  | 0.0625 | 9.0 | 9.0 | 9.0 | 9.0 | 7.0 | 4.0 |  | 4.0 | 9.0 | 4.0 |  | 7.0 | 1.0 | 3.0 |
|  | 0.0313 | 9.0 | 9.0 | 9.0 | 9.0 | 0.0 | 5.0 |  | 2.0 | 7.0 | 4.0 |  | 3.0 | 1.0 | 1.0 |
|  | 0.0156 | 9.0 | 7.0 | 0.0 | 9.0 | 9.0 | 9.0 |  | 9.0 | 4.0 | 6.0 |  | 5.0 | 4.0 | 0.0 |
| 71 | 0.2500 | 9.0 | 9.0 | 9.0 | 9.0 | 9.0 | 9.0 |  | 9.0 | 9.0 | 9.0 |  | 8.0 | 2.0 | 6.0 |
|  | 0.1250 | 9.0 | 9.0 | 9.0 | 9.0 | 9.0 | 9.0 |  | 7.0 | 9.0 | 9.0 |  | 7.0 | 2.0 | 4.0 |
|  | 0.0625 | 9.0 | 9.0 | 9.0 | 9.0 | 9.0 | 9.0 |  | 9.0 | 9.0 | 5.0 |  | 6.0 | 2.0 | 4.0 |
|  | 0.0313 | 9.0 | 7.0 | 0.0 | 9.0 | 3.0 | 0.0 |  | 1.0 | 5.0 | 1.0 |  | 1.0 | 1.0 | 2.0 |
|  | 0.0156 | 7.0 | 5.0 | 0.0 | 9.0 | 3.0 | 0.0 |  | 0.0 | 9.0 | 0.0 |  | 1.0 | 0.0 | 0.0 |
| 72 | 0.2500 | 9.0 | 9.0 | 9.0 | 9.0 | 7.0 | 9.0 |  | 9.0 | 9.0 | 7.0 |  | 8.0 | 4.0 | 6.0 |
|  | 0.1250 | 9.0 | 9.0 | 9.0 | 9.0 | 6.0 | 4.0 |  | 5.0 | 9.0 | 6.0 |  | 2.0 | 1.0 | 1.0 |
|  | 0.0625 | 9.0 | 9.0 | 0.0 | 9.0 | 0.0 | 2.0 |  | 1.0 | 5.0 | 1.0 |  | 1.0 | 1.0 | 2.0 |
|  | 0.0313 | 1.0 | 1.0 | 9.0 | 9.0 | 0.0 | 0.0 |  | 0.0 | 4.0 | 0.0 |  | 1.0 | 0.0 | 0.0 |
| 73 | 0.2500 | 9.0 | 9.0 | 9.0 | 9.0 | 9.0 | 9.0 |  | 9.0 | 9.0 | 7.0 |  | 8.0 | 0.0 | 6.0 |
|  | 0.1250 | 9.0 | 9.0 | 8.0 | 9.0 | 4.0 | 4.0 |  | 9.0 | 4.0 | 9.0 |  | 7.0 | 5.0 | 5.0 |
|  | 0.0625 | 9.0 | 9.0 | 2.0 | 9.0 | 0.0 | 4.0 |  | 3.0 | 4.0 | 9.0 |  | 6.0 | 5.0 | 5.0 |
|  | 0.0313 | 9.0 | 5.0 | 9.0 | 9.0 | 0.0 | 5.0 |  | 0.0 | 5.0 | 5.0 |  | 4.0 | 6.0 | 4.0 |
|  | 0.0156 | 9.0 | 0.0 | 3.0 | 9.0 | 0.0 | 0.0 |  | 0.0 |  | 0.0 |  | 1.0 | 1.0 | 0.0 |
| 74 | 0.2500 | 9.0 | 9.0 | 9.0 | 9.0 | 9.0 | 9.0 |  | 9.0 | 9.0 | 9.0 |  | 7.0 | 4.0 | 5.0 |
|  | 0.1250 | 9.0 | 9.0 | 9.0 | 9.0 | 7.0 | 6.0 |  | 9.0 | 9.0 | 3.0 |  | 6.0 | 3.0 | 4.0 |
|  | 0.0625 | 9.0 | 9.0 | 9.0 | 9.0 | 5.0 | 9.0 |  | 9.0 | 9.0 |  |  | 5.0 | 5.0 | 2.0 |
|  | 0.0313 | 9.0 | 3.0 | 0.0 | 9.0 | 5.0 | 9.0 |  | 7.0 | 6.0 | 3.0 |  | 4.0 | 1.0 | 0.0 |
|  | 0.0156 | 9.0 | 0.0 | 0.0 | 9.0 | 0.0 | 0.0 |  | 4.0 | 0.0 | 3.0 |  | 1.0 | 3.0 | 1.0 |
| 75 | 0.2500 | 9.0 | 9.0 | 9.0 | 9.0 | 9.0 | 9.0 |  | 9.0 | 9.0 | 4.0 |  | 9.0 | 3.0 | 5.0 |
|  | 0.1250 | 9.0 | 9.0 | 7.0 | 9.0 | 9.0 | 9.0 |  | 8.0 | 7.0 | 3.0 |  | 7.0 | 3.0 | 4.0 |
|  | 0.0625 | 9.0 | 9.0 | 4.0 | 9.0 | 7.0 | 9.0 |  | 7.0 | 9.0 | 4.0 |  | 7.0 | 3.0 | 3.0 |
|  | 0.0313 | 9.0 | 9.0 | 3.0 | 9.0 | 6.0 | 4.0 |  | 5.0 | 9.0 | 3.0 |  | 4.0 | 2.0 | 3.0 |
|  | 0.0156 | 9.0 | 5.0 | 0.0 | 9.0 | 0.0 | 9.0 |  | 2.0 | 7.0 |  |  | 2.0 | 6.0 | 3.0 |
| 76 | 0.2500 | 9.0 | 9.0 | 9.0 | 9.0 | 8.0 | 9.0 |  | 9.0 | 9.0 | 4.0 |  | 9.0 | 4.0 | 4.0 |
|  | 0.1250 | 9.0 | 9.0 | 2.0 | 9.0 | 5.0 | 9.0 |  | 7.0 | 9.0 | 9.0 |  | 8.0 | 3.0 | 5.0 |
|  | 0.0625 | 9.0 | 9.0 | 9.0 | 9.0 | 3.0 | 5.0 |  | 9.0 | 9.0 | 5.0 |  | 7.0 | 2.0 | 4.0 |
|  | 0.0313 | 9.0 | 7.0 | 4.0 | 9.0 | 3.0 | 9.0 |  | 3.0 | 7.0 | 4.0 |  | 5.0 | 1.0 | 4.0 |
|  | 0.0156 | 9.0 | 0.0 | 2.0 | 9.0 | 3.0 | 3.0 |  | 1.0 | 9.0 | 5.0 |  | 1.0 | 2.0 | 1.0 |
| 77 | 0.5000 | 9.0 | 9.0 | 9.0 | 9.0 | 9.0 | 9.0 |  | 9.0 | 9.0 | 9.0 |  | 8.0 | 8.0 | 8.0 |

TABLE II-continued

Preemergence Herbicidal Evaluations of Test Compounds

| Compound Number | Rate (kg/ha) | ABUTH | AMBEL | CASOB | CHEAL | GALAP | IPOHE | IPOSS | ECHCG | SETVI | GLXMAW | GLXMA | ORYSAT | TRZAWR | ZEAMX |
|---|---|---|---|---|---|---|---|---|---|---|---|---|---|---|---|
| | 0.2500 | 9.0 | 9.0 | 9.0 | 9.0 | 8.3 | 9.0 | | 6.0 | 9.0 | 7.7 | | 8.0 | 6.3 | 7.7 |
| | 0.1250 | 9.0 | 9.0 | 6.0 | 9.0 | 8.3 | 9.0 | | 4.3 | 9.0 | 6.3 | | 7.7 | 3.7 | 5.7 |
| | 0.0625 | 9.0 | 9.0 | 0.7 | 9.0 | 1.5 | 9.0 | | 0.7 | 8.3 | 3.7 | | 5.0 | 3.3 | 4.3 |
| | 0.0313 | 9.0 | 6.7 | 0.0 | 9.0 | 0.0 | 4.0 | | 0.0 | 5.3 | 1.3 | | 2.0 | 0.0 | 1.7 |
| | 0.0156 | 7.7 | 0.0 | 0.0 | 7.3 | 0.0 | 1.0 | | 0.0 | 0.0 | 0.0 | | 0.7 | 0.0 | 0.7 |
| 78 | 0.2500 | 9.0 | 9.0 | 9.0 | 9.0 | 9.0 | 9.0 | | 7.0 | 9.0 | 6.0 | | 7.0 | 5.0 | 8.0 |
| | 0.1250 | 9.0 | 9.0 | 0.0 | 9.0 | 8.0 | 9.0 | | 7.0 | 9.0 | 5.0 | | 5.0 | 2.0 | 7.0 |
| | 0.0625 | 7.0 | 9.0 | 0.0 | 9.0 | 9.0 | 3.0 | | 0.0 | 7.0 | 1.0 | | 2.0 | 0.0 | 6.0 |
| | 0.0313 | | 4.0 | 0.0 | 9.0 | 0.0 | 0.0 | | 0.0 | 0.0 | | | 0.0 | 0.0 | 0.0 |
| | 0.0156 | 5.0 | 0.0 | 0.0 | 9.0 | 0.0 | 0.0 | | 0.0 | 0.0 | | | 0.0 | 0.0 | 0.0 |
| 79 | 0.2500 | 9.0 | 9.0 | 5.0 | 9.0 | 5.0 | 9.0 | | 6.0 | 9.0 | 0.0 | | 7.0 | 3.0 | 7.0 |
| | 0.1250 | 9.0 | 9.0 | 5.0 | 9.0 | 4.0 | 9.0 | | 5.0 | 9.0 | 7.0 | | 6.0 | 1.0 | 6.0 |
| | 0.0625 | 8.0 | 7.0 | 0.0 | 9.0 | 4.0 | 2.0 | | 3.0 | 7.0 | 9.0 | | 3.0 | 0.0 | 2.0 |
| | 0.0313 | 8.0 | 9.0 | 0.0 | 9.0 | 0.0 | 0.0 | | 0.0 | 3.0 | 3.0 | | 1.0 | 0.0 | 2.0 |
| | 0.0156 | 8.0 | 9.0 | 0.0 | 9.0 | 0.0 | 2.0 | | 0.0 | 7.0 | 0.0 | | 0.0 | 0.0 | 0.0 |
| 80 | 0.2500 | 9.0 | 9.0 | 0.0 | 9.0 | 9.0 | 0.0 | | 5.0 | 9.0 | 9.0 | | 8.0 | 4.0 | 8.0 |
| | 0.1250 | 9.0 | 9.0 | 0.0 | 9.0 | 9.0 | 9.0 | | 3.0 | 9.0 | 3.0 | | 8.0 | 2.0 | 6.0 |
| | 0.0625 | 9.0 | 9.0 | 0.0 | 9.0 | 0.0 | 9.0 | | 0.0 | 9.0 | 3.0 | | 2.0 | 0.0 | 3.0 |
| | 0.0313 | 9.0 | 0.0 | 0.0 | 9.0 | 0.0 | 2.0 | | 0.0 | 6.0 | 0.0 | | 0.0 | 0.0 | 2.0 |
| | 0.0156 | 0.0 | 0.0 | 0.0 | 0.0 | 0.0 | 0.0 | | 0.0 | 0.0 | 0.0 | | 0.0 | 0.0 | 2.0 |
| 81 | 0.2500 | 9.0 | 9.0 | 5.0 | 9.0 | 9.0 | 9.0 | | 5.0 | 9.0 | 9.0 | | 6.0 | 3.0 | 8.0 |
| | 0.1250 | 9.0 | 9.0 | 9.0 | 9.0 | 9.0 | 9.0 | | 5.0 | 9.0 | 7.0 | | 5.0 | 1.0 | 7.0 |
| | 0.0625 | 9.0 | 6.0 | 9.0 | 9.0 | 3.0 | 9.0 | | 0.0 | 5.0 | 0.0 | | 3.0 | 0.0 | 4.0 |
| | 0.0313 | 9.0 | 9.0 | 3.0 | 9.0 | 3.0 | 0.0 | | 0.0 | 2.0 | 0.0 | | 1.0 | 0.0 | 3.0 |
| | 0.0156 | 9.0 | 0.0 | 0.0 | 9.0 | 0.0 | 0.0 | | 0.0 | 0.0 | 0.0 | | 1.0 | 0.0 | 0.0 |
| 82 | 0.2500 | 9.0 | 9.0 | 0.0 | 9.0 | 9.0 | 9.0 | | 5.0 | 9.0 | 1.0 | | 5.0 | 1.0 | 3.0 |
| | 0.1250 | 9.0 | 0.0 | 0.0 | 9.0 | 4.0 | 3.0 | | 4.0 | 9.0 | 0.0 | | 2.0 | 0.0 | 1.0 |
| | 0.0625 | 9.0 | 0.0 | 0.0 | 0.0 | 3.0 | 0.0 | | 0.0 | 0.0 | 0.0 | | 0.0 | 0.0 | 0.0 |
| | 0.0313 | 5.0 | 0.0 | 0.0 | 0.0 | 0.0 | 0.0 | | 0.0 | 9.0 | 0.0 | | 0.0 | 0.0 | 5.0 |
| | 0.0156 | 0.0 | 0.0 | 0.0 | 0.0 | 0.0 | 0.0 | | 0.0 | 9.0 | 0.0 | | 0.0 | 0.0 | 0.0 |
| 83 | 0.2500 | 9.0 | 9.0 | 9.0 | 9.0 | 3.0 | 9.0 | | 7.0 | 9.0 | 9.0 | | 7.0 | 3.0 | 7.0 |
| | 0.1250 | 9.0 | 9.0 | 3.0 | 9.0 | 3.0 | 9.0 | | 7.0 | 9.0 | 0.0 | | 7.0 | 3.0 | 5.0 |
| | 0.0625 | 9.0 | 9.0 | 3.0 | 9.0 | 0.0 | 9.0 | | 6.0 | 3.0 | 0.0 | | 5.0 | 1.0 | 5.0 |
| | 0.0313 | 9.0 | 9.0 | 0.0 | 9.0 | 0.0 | 9.0 | | 3.0 | 7.0 | 5.0 | | 2.0 | 0.0 | 5.0 |
| 84 | 0.2500 | 9.0 | 9.0 | 0.0 | 9.0 | 2.0 | 9.0 | | 9.0 | 9.0 | 5.0 | | 7.0 | 1.0 | 7.0 |
| | 0.1250 | 9.0 | 9.0 | 3.0 | 9.0 | 0.0 | 9.0 | | 7.0 | 3.0 | 9.0 | | 2.0 | 0.0 | 4.0 |
| | 0.0625 | 9.0 | 9.0 | 0.0 | 9.0 | 0.0 | 9.0 | | 4.0 | 9.0 | 9.0 | | 7.0 | 0.0 | 3.0 |
| | 0.0313 | 9.0 | 9.0 | 0.0 | 9.0 | 4.0 | 4.0 | | 0.0 | 0.0 | 9.0 | | 6.0 | 0.0 | 3.0 |
| | 0.0156 | 5.0 | 0.0 | 0.0 | 9.0 | 3.0 | 2.0 | | 3.0 | 0.0 | 5.0 | | 6.0 | 0.0 | 3.0 |
| 85 | 0.1250 | 9.0 | 9.0 | 0.0 | 9.0 | 0.0 | 7.0 | | 0.0 | 9.0 | 3.0 | | 3.0 | 0.0 | 6.0 |
| | 0.0625 | 9.0 | 0.0 | 0.0 | 9.0 | 0.0 | 3.0 | | 0.0 | 3.0 | 3.0 | | 5.0 | 0.0 | 3.0 |
| | 0.0313 | 0.0 | 0.0 | 0.0 | 0.0 | 0.0 | 0.0 | | 0.0 | 0.0 | 0.0 | | 1.0 | 0.0 | 3.0 |
| | 0.0156 | 0.0 | 0.0 | 0.0 | 0.0 | 0.0 | 0.0 | | 0.0 | 0.0 | 0.0 | | 0.0 | 0.0 | 0.0 |
| 86 | 0.2500 | 9.0 | 9.0 | 3.0 | 9.0 | 0.0 | 9.0 | | 9.0 | 9.0 | 0.0 | | 7.0 | 2.0 | 4.0 |
| | 0.1250 | 9.0 | 9.0 | 3.0 | 9.0 | 0.0 | 9.0 | | 7.0 | 9.0 | 5.0 | | 7.0 | 0.0 | 4.0 |

TABLE II-continued

Preemergence Herbicidal Evaluations of Test Compounds

| Compound Number | Rate (kg/ha) | ABUTH | AMBEL | CASOB | CHEAL | GALAP | IPOHE | IPOSS | ECHCG | SETVI | GLXMAW | GLXMA | ORYSAT | TRZAWR | ZEAMX |
|---|---|---|---|---|---|---|---|---|---|---|---|---|---|---|---|
|  | 0.0625 | 9.0 | 3.0 | 0.0 | 9.0 | 0.0 | 4.0 |  | 3.0 | 9.0 |  |  | 7.0 | 0.0 | 3.0 |
|  | 0.0313 | 4.0 | 0.0 | 0.0 | 9.0 | 0.0 | 0.0 |  | 0.0 | 3.0 |  |  | 3.0 | 0.0 | 3.0 |
|  | 0.0156 | 3.0 | 0.0 | 0.0 | 9.0 | 0.0 | 0.0 |  | 0.0 | 0.0 |  |  | 0.0 | 0.0 | 0.0 |
| 87 | 0.2500 | 9.0 | 9.0 | 3.0 | 9.0 | 6.0 | 9.0 |  | 8.0 | 9.0 | 0.0 |  | 6.0 | 2.0 | 8.0 |
|  | 0.1250 | 9.0 | 0.0 | 9.0 | 9.0 | 9.0 | 9.0 |  | 7.0 | 9.0 | 0.0 |  | 5.0 | 1.0 | 7.0 |
|  | 0.0625 | 9.0 | 0.0 | 3.0 | 9.0 | 9.0 | 9.0 |  | 5.0 | 7.0 | 9.0 |  | 7.0 | 0.0 | 7.0 |
|  | 0.0313 | 5.0 | 0.0 | 0.0 | 9.0 | 0.0 | 9.0 |  | 2.0 | 5.0 | 3.0 |  | 7.0 | 0.0 | 3.0 |
|  | 0.0156 | 3.0 |  | 0.0 | 9.0 | 0.0 | 0.0 |  | 0.0 | 0.0 | 3.0 |  | 2.0 | 0.0 | 3.0 |
| 88 | 0.2500 | 9.0 | 9.0 | 9.0 | 9.0 | 0.0 | 9.0 |  | 5.0 | 9.0 | 9.0 |  | 7.0 | 4.0 | 7.0 |
|  | 0.1250 | 9.0 | 9.0 | 0.0 | 9.0 | 0.0 | 9.0 |  | 4.0 | 9.0 | 3.0 |  | 3.0 | 0.0 | 7.0 |
|  | 0.0625 | 9.0 | 9.0 | 0.0 | 9.0 | 0.0 | 9.0 |  | 3.0 | 9.0 | 3.0 |  | 1.0 | 0.0 | 5.0 |
|  | 0.0313 | 9.0 | 3.0 | 0.0 | 9.0 | 0.0 | 4.0 |  | 2.0 | 0.0 | 3.0 |  | 0.0 | 0.0 | 2.0 |
|  | 0.0156 | 9.0 | 9.0 | 2.0 | 9.0 | 7.0 | 9.0 |  | 0.0 | 3.0 | 0.0 |  | 0.0 | 3.0 | 1.0 |
| 89 | 0.2500 | 9.0 | 9.0 | 0.0 | 9.0 | 6.0 | 9.0 |  | 9.0 | 9.0 | 6.0 |  | 7.0 | 1.0 | 6.0 |
|  | 0.1250 | 9.0 | 9.0 | 2.0 | 9.0 | 0.0 | 9.0 |  | 5.0 | 9.0 |  |  | 3.0 | 0.0 | 6.0 |
|  | 0.0625 | 9.0 | 9.0 | 0.0 | 9.0 | 9.0 | 9.0 |  | 2.0 | 0.0 | 3.0 |  | 3.0 | 0.0 | 2.0 |
|  | 0.0313 | 5.0 | 9.0 | 0.0 | 9.0 | 0.0 | 9.0 |  | 0.0 | 5.0 | 0.0 |  | 2.0 | 0.0 | 2.0 |
|  | 0.0156 | 5.0 | 9.0 | 0.0 | 0.0 | 0.0 | 3.0 |  | 0.0 | 0.0 | 0.0 |  | 0.0 | 0.0 | 0.0 |
| 90 | 0.2500 | 0.0 | 9.0 | 2.0 | 9.0 | 9.0 | 9.0 |  | 9.0 | 9.0 | 9.0 |  | 6.0 | 2.0 | 5.0 |
|  | 0.1250 | 2.0 | 2.0 | 0.0 | 9.0 | 0.0 | 0.0 |  | 5.0 | 0.0 | 9.0 |  | 6.0 | 1.0 | 4.0 |
|  | 0.0625 | 0.0 | 0.0 | 1.0 | 0.0 | 3.0 | 0.0 |  | 0.0 | 5.0 | 2.0 |  | 2.0 | 0.0 | 3.0 |
|  | 0.0313 | 0.0 | 0.0 | 0.0 | 0.0 | 0.0 | 0.0 |  | 0.0 | 0.0 | 1.0 |  | 1.0 | 0.0 | 1.0 |
|  | 0.0156 | 0.0 | 0.0 | 0.0 | 0.0 | 0.0 | 0.0 |  | 0.0 | 0.0 | 1.0 |  | 1.0 | 0.0 | 0.0 |
| 91 | 0.2500 | 9.0 | 9.0 | 5.0 | 9.0 | 4.0 | 9.0 |  | 5.0 | 9.0 | 0.0 |  | 0.0 | 7.0 | 7.0 |
|  | 0.1250 | 9.0 | 9.0 | 9.0 | 9.0 | 4.0 | 9.0 |  | 5.0 | 9.0 | 5.0 |  | 7.0 | 7.0 | 7.0 |
|  | 0.0625 | 6.0 | 9.0 | 5.0 | 9.0 | 2.0 | 3.0 |  | 5.0 | 6.0 | 3.0 |  | 7.0 | 3.0 | 3.0 |
|  | 0.0313 | 9.0 | 4.0 | 2.0 | 9.0 | 0.0 | 0.0 |  | 0.0 | 0.0 | 1.0 |  | 5.0 | 1.0 | 2.0 |
|  | 0.0156 | 9.0 | 4.0 | 0.0 | 0.0 | 0.0 | 0.0 |  | 0.0 | 0.0 | 0.0 |  | 6.0 | 0.0 | 0.0 |
| 92 | 0.2500 | 9.0 | 9.0 | 8.0 | 9.0 | 9.0 | 9.0 |  | 9.0 | 9.0 | 1.0 |  | 8.0 | 7.0 | 9.0 |
|  | 0.1250 | 9.0 | 9.0 | 7.0 | 9.0 | 9.0 | 9.0 |  | 3.0 | 9.0 | 6.0 |  | 8.0 | 7.0 | 9.0 |
|  | 0.0625 | 9.0 | 0.0 | 6.0 | 9.0 | 9.0 | 9.0 |  | 3.0 | 9.0 | 3.0 |  | 6.0 | 6.0 | 4.0 |
|  | 0.0313 | 9.0 | 3.0 | 2.0 | 9.0 | 0.0 | 3.0 |  | 2.0 | 0.0 | 3.0 |  | 1.0 | 0.0 | 2.0 |
|  | 0.0156 | 0.0 | 0.0 | 0.0 | 9.0 | 0.0 | 0.0 |  | 0.0 | 6.0 | 0.0 |  | 0.0 | 0.0 | 1.0 |
| 93 | 0.2500 | 0.0 | 0.0 | 0.0 | 9.0 | 0.0 | 0.0 |  | 0.0 | 0.0 | 2.0 |  | 0.0 | 7.0 | 0.0 |
|  | 0.1250 | 0.0 | 0.0 | 0.0 | 8.0 | 0.0 | 0.0 |  | 0.0 | 0.0 | 2.0 |  | 0.0 | 0.0 | 0.0 |
|  | 0.0625 | 0.0 | 0.0 | 0.0 |  | 0.0 | 0.0 |  | 0.0 | 0.0 | 0.0 |  | 0.0 | 0.0 | 0.0 |
|  | 0.0313 | 0.0 | 0.0 | 0.0 | 9.0 | 0.0 | 0.0 |  | 0.0 | 0.0 | 2.0 |  | 0.0 | 0.0 | 2.0 |
|  | 0.0156 | 0.0 | 0.0 | 0.0 | 9.0 | 0.0 | 0.0 |  | 0.0 | 0.0 | 2.0 |  | 0.0 | 0.0 | 2.0 |
| 94 | 0.2500 | 0.0 | 0.0 | 0.0 | 0.0 | 0.0 | 0.0 |  | 0.0 | 0.0 | 0.0 |  | 0.0 | 0.0 | 2.0 |
|  | 0.1250 | 0.0 | 0.0 | 0.0 | 0.0 | 0.0 | 0.0 |  | 0.0 | 0.0 | 2.0 |  | 0.0 | 0.0 | 2.0 |
|  | 0.0625 | 0.0 | 0.0 | 0.0 | 0.0 | 0.0 | 0.0 |  | 0.0 | 0.0 | 2.0 |  | 0.0 | 0.0 | 2.0 |
|  | 0.0313 | 0.0 | 0.0 | 0.0 | 0.0 | 0.0 | 0.0 |  | 0.0 | 0.0 | 0.0 |  | 0.0 | 0.0 | 0.0 |
| 95 |  |  |  |  |  |  |  |  |  |  |  |  |  |  |  |

TABLE II-continued

Preemergence Herbicidal Evaluations of Test Compounds

| Compound Number | Rate (kg/ha) | ABUTH | AMBEL | CASOB | CHEAL | GALAP | IPOHE | IPOSS | ECHCG | SETVI | GLXMAW | GLXMA | ORYSAT | TRZAWR | ZEAMX |
|---|---|---|---|---|---|---|---|---|---|---|---|---|---|---|---|
| 96 | 0.0156 | 0.0 | 0.0 | 0.0 | 0.0 | 0.0 | 0.0 | | 0.0 | 0.0 | 0.0 | | 0.0 | 0.0 | 0.0 |
| | 0.2500 | 9.0 | 9.0 | 9.0 | 9.0 | 9.0 | 9.0 | | 3.0 | 8.0 | 3.0 | | 3.0 | 9.0 | 6.0 |
| | 0.1250 | 9.0 | 0.0 | 9.0 | 9.0 | 0.0 | 3.0 | | 0.0 | 6.0 | 5.0 | | 1.0 | 4.0 | 6.0 |
| | 0.0625 | 3.0 | 0.0 | 0.0 | 0.0 | 0.0 | 0.0 | | 0.0 | 3.0 | 3.0 | | 0.0 | 0.0 | 5.0 |
| | 0.0313 | 0.0 | 0.0 | 0.0 | 0.0 | 0.0 | 0.0 | | 0.0 | 0.0 | 3.0 | | 0.0 | 0.0 | 5.0 |
| | 0.0156 | 0.0 | 0.0 | 0.0 | 0.0 | 0.0 | 0.0 | | 0.0 | 0.0 | 0.0 | | 0.0 | 0.0 | 0.0 |
| 97 | 0.2500 | 9.0 | 9.0 | 6.0 | 9.0 | 9.0 | 9.0 | | 9.0 | 9.0 | 5.0 | | 9.0 | 8.0 | 7.0 |
| | 0.1250 | 9.0 | 9.0 | 6.0 | 9.0 | 9.0 | 0.0 | | 3.0 | 9.0 | 5.0 | | 7.0 | 3.0 | 5.0 |
| | 0.0625 | 9.0 | 3.0 | 0.0 | 9.0 | 0.0 | 0.0 | | 3.0 | 9.0 | 5.0 | | 7.0 | 3.0 | 5.0 |
| | 0.0313 | 9.0 | 0.0 | 0.0 | 9.0 | 0.0 | 0.0 | | 0.0 | 7.0 | 2.0 | | 5.0 | 1.0 | 5.0 |
| | 0.0156 | 0.0 | 0.0 | 0.0 | 9.0 | 0.0 | 0.0 | | 0.0 | 0.0 | 0.0 | | 3.0 | 0.0 | 3.0 |
| 98 | 0.2500 | 9.0 | 9.0 | 9.0 | 9.0 | 9.0 | 9.0 | | 9.0 | 9.0 | 9.0 | | 8.0 | 8.0 | 8.0 |
| | 0.1250 | 9.0 | 9.0 | 9.0 | 9.0 | 8.0 | 9.0 | | 6.5 | 9.0 | 8.5 | | 7.5 | 7.5 | 6.5 |
| | 0.0625 | 9.0 | 8.0 | 7.0 | 9.0 | 4.5 | 7.0 | | 3.0 | 8.0 | 8.0 | | 5.0 | 5.0 | 4.5 |
| | 0.0313 | 9.0 | 6.5 | 6.0 | 9.0 | 4.5 | 4.0 | | 0.0 | 0.0 | 6.0 | | 2.5 | 1.0 | 0.0 |
| | 0.0156 | 9.0 | 2.5 | 0.0 | 9.0 | 4.5 | 1.5 | | 0.0 | 6.0 | 2.0 | | 0.0 | 0.0 | 0.0 |
| 99 | 0.2500 | 9.0 | 7.0 | 7.0 | 9.0 | 0.0 | 2.0 | | 4.0 | 2.0 | 9.0 | | 7.0 | 5.0 | 4.0 |
| | 0.1250 | 9.0 | 2.0 | 3.0 | 9.0 | 0.0 | 0.0 | | 0.0 | 0.0 | 3.0 | | 2.0 | 3.0 | 4.0 |
| | 0.0625 | 9.0 | 0.0 | 0.0 | 9.0 | 0.0 | 0.0 | | 0.0 | 0.0 | 0.0 | | 0.0 | 0.0 | 0.0 |
| | 0.0313 | 9.0 | 0.0 | 0.0 | 9.0 | 0.0 | 0.0 | | 0.0 | 0.0 | 0.0 | | 0.0 | 0.0 | 0.0 |
| | 0.0156 | 0.0 | 0.0 | 0.0 | 0.0 | 0.0 | 0.0 | | 0.0 | 0.0 | 0.0 | | 0.0 | 0.0 | 0.0 |
| 100 | 0.2500 | 9.0 | 9.0 | 9.0 | 9.0 | 9.0 | 9.0 | | 8.0 | 9.0 | 9.0 | | 8.0 | 9.0 | 9.0 |
| | 0.1250 | 9.0 | 9.0 | 9.0 | 9.0 | 9.0 | 9.0 | | 5.0 | 9.0 | 9.0 | | 8.0 | 9.0 | 7.5 |
| | 0.0625 | 9.0 | 7.5 | 9.0 | 9.0 | 8.0 | 9.0 | | 2.0 | 5.5 | 9.0 | | 6.0 | 6.0 | 5.5 |
| | 0.0313 | 9.0 | 0.0 | 9.0 | 9.0 | 5.0 | 9.0 | | 0.5 | 5.0 | 8.0 | | 3.0 | | 2.5 |
| | 0.0156 | 9.0 | 8.0 | 0.5 | 9.0 | 4.0 | 4.5 | | 0.0 | 0.0 | 4.5 | | 0.5 | 9.0 | 0.5 |
| 101 | 0.2500 | 9.0 | 2.0 | 0.0 | 9.0 | 9.0 | 0.0 | | 0.0 | 0.0 | 0.0 | | 8.0 | 9.0 | 1.0 |
| | 0.1250 | 3.0 | 0.0 | 0.0 | 9.0 | 5.0 | 0.0 | | 0.0 | 0.0 | 0.0 | | 0.0 | 0.0 | 0.0 |
| | 0.0625 | 0.0 | 0.0 | 0.0 | 0.0 | 0.0 | 0.0 | | 0.0 | 0.0 | 0.0 | | | 0.0 | 0.0 |
| | 0.0313 | 0.0 | 0.0 | 0.0 | 0.0 | 0.0 | 0.0 | | 0.0 | 0.0 | 0.0 | | 0.0 | 0.0 | 0.0 |
| | 0.0156 | 0.0 | 0.0 | 0.0 | 0.0 | 0.0 | 0.0 | | 0.0 | 0.0 | 0.0 | | 0.0 | 0.0 | 0.0 |
| 102 | 0.2500 | 9.0 | 9.0 | 0.0 | 9.0 | 6.0 | 9.0 | | 0.0 | 6.0 | 0.0 | | 0.0 | 0.0 | 0.0 |
| | 0.1250 | 9.0 | 7.0 | 0.0 | 9.0 | 6.0 | 3.0 | | 0.0 | 3.0 | 0.0 | | 0.0 | 0.0 | 0.0 |
| | 0.0625 | 8.0 | 2.0 | 0.0 | 9.0 | 3.0 | 0.0 | | 0.0 | 3.0 | 0.0 | | 0.0 | 0.0 | 0.0 |
| | 0.0313 | 0.0 | 0.0 | 0.0 | 0.0 | 0.0 | 0.0 | | 0.0 | 0.0 | 0.0 | | 0.0 | 0.0 | 0.0 |
| | 0.0156 | 0.0 | 0.0 | 0.0 | 0.0 | 0.0 | 0.0 | | 0.0 | 0.0 | 0.0 | | 0.0 | 0.0 | 0.0 |
| 103 | 0.5000 | 9.0 | 9.0 | 9.0 | 9.0 | | 9.0 | | 9.0 | 9.0 | 3.0 | | | | 5.0 |
| | 0.2500 | 9.0 | 9.0 | 7.3 | 9.0 | 7.5 | 9.0 | | 8.8 | 9.0 | 5.8 | | 8.5 | 6.5 | 6.3 |
| | 0.1250 | 9.0 | 8.3 | 3.5 | 9.0 | 2.5 | 9.0 | | 8.5 | 9.0 | 5.5 | | 6.0 | 5.0 | 3.8 |
| | 0.0625 | 9.0 | 2.5 | 2.3 | 9.0 | 0.5 | 7.8 | | 4.3 | 8.8 | 5.3 | | 4.0 | 3.0 | 2.8 |
| | 0.0313 | 9.0 | 3.7 | 1.3 | 9.0 | 0.5 | 6.8 | | 1.3 | 5.8 | 2.3 | | 0.5 | 0.5 | 1.8 |
| | 0.0156 | 6.3 | 0.0 | 0.0 | 9.0 | 0.0 | 4.3 | | 0.0 | 2.0 | 2.0 | | 1.5 | 0.5 | 0.7 |
| 104 | 0.2500 | 9.0 | 9.0 | 9.0 | 9.0 | 9.0 | 9.0 | | 5.5 | 9.0 | 7.5 | | 8.5 | 8.5 | 6.5 |
| | 0.1250 | 9.0 | 3.5 | 4.0 | 9.0 | 8.0 | 8.0 | | 0.5 | 6.0 | 7.0 | | 5.5 | 6.5 | 4.0 |
| | 0.0625 | 9.0 | 3.5 | 1.0 | 8.5 | 0.5 | 4.0 | | 0.5 | 1.5 | 2.0 | | 5.5 | 5.5 | 2.0 |
| | 0.0313 | 5.0 | 2.0 | 3.5 | 7.5 | 1.0 | 2.5 | | 0.0 | 0.0 | 1.5 | | 5.5 | 0.5 | 2.0 |
| | 0.0156 | 6.0 | 0.0 | 2.0 | 7.5 | 0.0 | 1.5 | | 0.0 | 0.0 | 1.5 | | 1.0 | 0.5 | 0.0 |

TABLE II-continued

Preemergence Herbicidal Evaluations of Test Compounds

| Compound Number | Rate (kg/ha) | ABUTH | AMBEL | CASOB | CHEAL | GALAP | IPOHE | IPOSS | ECHCG | SETVI | GLXMAW | GLXMA | ORYSAT | TRZAWR | ZEAMX |
|---|---|---|---|---|---|---|---|---|---|---|---|---|---|---|---|
| 105 | 0.2500 | 9.0 | 9.0 | 9.0 | 9.0 | 9.0 | 9.0 | | 9.0 | 9.0 | 9.0 | | 8.0 | 8.5 | 7.5 |
| | 0.1250 | 9.0 | 9.0 | 9.0 | 9.0 | 8.0 | 9.0 | | 9.0 | 9.0 | 9.0 | | 7.0 | 7.0 | 7.0 |
| | 0.0625 | 9.0 | 9.0 | 9.0 | 9.0 | 6.0 | 7.5 | | 9.0 | 9.0 | 7.5 | | 6.5 | 6.5 | 6.0 |
| | 0.0313 | 9.0 | 7.5 | 7.0 | 9.0 | 4.5 | 7.5 | | 8.0 | 9.0 | 7.5 | | 5.5 | 5.0 | 6.0 |
| | 0.0156 | 6.0 | 6.5 | 4.5 | 9.0 | 3.0 | 4.5 | | 5.5 | 9.0 | 3.0 | | 6.5 | 4.5 | 5.0 |
| 106 | 0.2500 | 9.0 | 2.0 | 3.0 | 9.0 | 7.0 | 2.0 | | 0.0 | 2.0 | 3.0 | | 3.0 | 0.0 | 1.0 |
| | 0.1250 | 9.0 | 1.0 | 0.0 | 9.0 | 5.0 | 1.0 | | 0.0 | 2.0 | 1.0 | | 3.0 | 0.0 | 0.0 |
| | 0.0625 | 0.0 | 0.0 | 0.0 | 5.0 | 5.0 | | 0.0 | 0.0 | 0.0 | 0.0 | | 3.0 | 0.0 | 0.0 |
| | 0.0313 | 0.0 | 0.0 | 0.0 | 5.0 | 0.0 | 0.0 | | 0.0 | 0.0 | 0.0 | | 3.0 | 0.0 | 0.0 |
| | 0.0156 | 0.0 | 0.0 | 0.0 | 9.0 | 0.0 | 0.0 | | 0.0 | 0.0 | 0.0 | | 0.0 | 0.0 | 0.0 |
| 107 | 0.2500 | 9.0 | 9.0 | 7.0 | 9.0 | 9.0 | 9.0 | | 8.0 | 9.0 | 7.0 | | 7.0 | 6.0 | 7.0 |
| | 0.1250 | 8.5 | 9.0 | 5.0 | 9.0 | 7.0 | 8.5 | | 8.0 | 9.0 | 3.0 | | 6.0 | | 5.5 |
| | 0.0625 | 4.5 | 6.0 | 4.5 | 9.0 | 6.0 | 9.0 | | 6.0 | 9.0 | 4.0 | | 5.0 | 3.0 | 5.0 |
| | 0.0313 | 1.5 | 4.0 | 1.0 | 8.0 | 0.0 | 4.5 | | 2.0 | 7.5 | 2.5 | | 3.0 | 1.0 | 2.5 |
| | 0.0156 | 1.5 | 1.0 | 3.0 | 9.0 | 3.0 | 2.0 | | 0.5 | 0.5 | 1.5 | | 1.0 | 1.0 | 0.0 |
| 108 | 0.2500 | 9.0 | 9.0 | 8.0 | 9.0 | 9.0 | 9.0 | | 7.0 | 9.0 | 5.0 | | 6.0 | 2.0 | 5.0 |
| | 0.1250 | 9.0 | 9.0 | 4.5 | 9.0 | 6.0 | 7.5 | | 5.5 | 9.0 | 2.5 | | 7.0 | 5.0 | 5.5 |
| | 0.0625 | 8.0 | 7.0 | 9.0 | 9.0 | 4.0 | 7.5 | | 3.5 | 7.5 | 1.5 | | 6.0 | 4.0 | 3.0 |
| | 0.0313 | 8.0 | 6.0 | 1.0 | 9.0 | 6.0 | 1.5 | | 0.5 | 2.5 | 1.5 | | 0.5 | 1.0 | 0.5 |
| | 0.0156 | 1.0 | 3.5 | 0.0 | 9.0 | 5.0 | 0.5 | | 0.0 | 0.5 | 0.5 | | 0.5 | 1.0 | 0.5 |
| 109 | 0.2500 | 9.0 | 9.0 | 9.0 | 9.0 | 6.0 | 8.0 | | 9.0 | 9.0 | 9.0 | | 8.0 | 7.0 | 7.0 |
| | 0.1250 | 9.0 | 9.0 | 5.0 | 9.0 | 7.0 | 9.0 | | 8.0 | 9.0 | 6.0 | | 5.0 | 4.0 | 4.0 |
| | 0.0625 | 7.0 | 9.0 | 3.0 | 9.0 | 7.0 | 4.0 | | 7.0 | 8.0 | 3.0 | | 6.0 | 2.0 | 4.0 |
| | 0.0313 | 4.0 | 6.0 | 3.0 | 9.0 | 3.0 | 9.0 | | 4.0 | 6.0 | 5.0 | | 7.0 | 1.0 | 2.0 |
| | 0.0156 | 2.0 | 1.0 | 4.0 | 9.0 | 1.0 | 4.0 | | 2.0 | 5.0 | 1.0 | | 3.0 | 1.0 | 1.0 |
| 110 | 0.2500 | 9.0 | 9.0 | 8.3 | 9.0 | 9.0 | 9.0 | | 8.7 | 9.0 | 7.7 | | 7.3 | 7.5 | 8.0 |
| | 0.1250 | 9.0 | 8.7 | 9.0 | 9.0 | 7.0 | 9.0 | | 8.3 | 9.0 | 8.0 | | 6.0 | 6.0 | 7.7 |
| | 0.0625 | 9.0 | 7.3 | 4.0 | 7.0 | 7.0 | 6.3 | | 8.0 | 8.7 | 6.7 | | 6.3 | 5.5 | 7.0 |
| | 0.0313 | 9.0 | 4.7 | 4.0 | 9.0 | 1.5 | 7.5 | | 6.7 | 5.3 | 3.0 | | 3.3 | 3.5 | 5.7 |
| | 0.0156 | 8.0 | 0.7 | 4.5 | 9.0 | 0.0 | 4.0 | | 3.7 | 7.0 | 1.3 | | 1.7 | 3.0 | 4.3 |
| 111 | 0.2500 | 9.0 | 9.0 | 7.0 | 9.0 | 9.0 | 6.0 | | 7.0 | 9.0 | 7.0 | | 7.0 | 6.0 | 7.0 |
| | 0.1250 | 9.0 | 9.0 | 9.0 | 9.0 | 7.0 | 8.0 | | 5.0 | 9.0 | 7.0 | | 7.0 | 6.0 | 7.0 |
| | 0.0625 | 9.0 | 7.0 | 7.0 | 9.0 | 6.0 | 7.0 | | 1.0 | 7.0 | 7.0 | | 2.0 | 4.0 | 6.0 |
| | 0.0313 | 6.0 | 6.0 | 1.0 | 7.0 | 2.0 | 2.0 | | 0.0 | 5.0 | 4.0 | | 2.0 | 1.0 | 1.0 |
| 112 | 0.2500 | 9.0 | 2.0 | 7.0 | 9.0 | 4.0 | 6.0 | | 0.0 | 3.0 | 1.0 | | 1.0 | 0.0 | 1.0 |
| | 0.1250 | 5.0 | 2.0 | 2.0 | 7.0 | 2.0 | 4.0 | | 1.0 | 6.0 | 5.0 | | 0.0 | 0.0 | 1.0 |
| | 0.0625 | 5.0 | 0.0 | 1.0 | 9.0 | 3.0 | 0.0 | | 0.0 | 1.0 | 2.0 | | 0.0 | 0.0 | 0.0 |
| | 0.0313 | 4.0 | 0.0 | 0.0 | 9.0 | 3.0 | 0.0 | | 0.0 | 1.0 | 1.0 | | 0.0 | 1.0 | 0.0 |
| | 0.0156 | 0.0 | 0.0 | 1.0 | 6.0 | 2.0 | 0.0 | | 0.0 | 1.0 | 0.0 | | 0.0 | 0.0 | 1.0 |
| 113 | 0.1250 | 9.0 | 9.0 | 9.0 | 9.0 | 9.0 | 9.0 | | 9.0 | 9.0 | 9.0 | | 8.5 | 8.0 | 8.5 |
| | 0.0625 | 7.5 | 6.5 | 7.5 | 9.0 | 7.0 | 9.0 | | 4.5 | 8.0 | 9.0 | | 8.5 | 7.0 | 8.0 |
| | 0.0313 | 9.0 | 4.5 | 4.0 | 9.0 | 6.0 | 7.5 | | 2.0 | 2.0 | 2.5 | | 7.0 | 6.0 | 5.0 |
| | 0.0156 | 9.0 | 5.0 | 1.0 | 9.0 | 9.0 | 9.0 | | 0.0 | 0.5 | 0.0 | | 3.0 | 2.0 | 3.0 |
| 114 | 0.5000 | 9.0 | 9.0 | 9.0 | 9.0 | 9.0 | 9.0 | | 9.0 | 9.0 | 9.0 | | 8.0 | 8.0 | 8.0 |
| | 0.2500 | 9.0 | 9.0 | 9.0 | 9.0 | 9.0 | 9.0 | | 9.0 | 9.0 | 9.0 | | 7.0 | 6.0 | 8.0 |

TABLE II-continued

Preemergence Herbicidal Evaluations of Test Compounds

| Compound Number | Rate (kg/ha) | ABUTH | AMBEL | CASOB | CHEAL | GALAP | IPOHE | IPOSS | ECHCG | SETVI | GLXMAW | GLXMA | ORYSAT | TRZAWR | ZEAMX |
|---|---|---|---|---|---|---|---|---|---|---|---|---|---|---|---|
| | 0.1250 | 9.0 | 9.0 | 6.5 | 9.0 | 9.0 | 9.0 | | 7.5 | 9.0 | 9.0 | | 6.0 | 8.0 | 7.0 |
| | 0.0640 | 9.0 | 9.0 | 6.0 | 9.0 | | 7.0 | | 8.0 | 9.0 | 7.0 | | 7.0 | | 7.0 |
| | 0.0625 | 9.0 | 9.0 | 4.5 | 9.0 | 6.5 | 8.0 | | 7.0 | 8.0 | 7.0 | | 5.5 | 7.0 | 5.5 |
| | 0.0320 | 9.0 | 9.0 | 6.0 | 9.0 | | 6.0 | | 7.0 | 9.0 | 6.0 | | 9.0 | | 7.0 |
| | 0.0313 | 8.0 | 9.0 | 8.0 | 9.0 | | 7.5 | | 6.5 | 8.0 | 5.0 | | 4.0 | 1.0 | 4.5 |
| | 0.0160 | 9.0 | 8.0 | 2.0 | 9.0 | 7.0 | 8.0 | | 7.0 | 8.0 | 3.0 | | 5.0 | | 7.0 |
| | 0.0156 | 6.0 | 4.5 | 2.0 | 9.0 | | 9.0 | | 4.5 | 5.5 | 6.5 | | 2.0 | 1.5 | 2.5 |
| 115 | 0.5000 | 9.0 | 9.0 | 5.0 | 9.0 | 6.5 | 9.0 | | 0.0 | 0.0 | 2.0 | | 0.0 | 0.0 | 3.0 |
| | 0.2500 | 9.0 | 3.0 | 0.0 | 9.0 | 0.0 | 0.0 | | 0.0 | 0.0 | 0.0 | | 0.0 | 0.0 | 0.0 |
| | 0.1250 | 0.0 | 0.0 | 0.0 | 9.0 | 0.0 | 0.0 | | 0.0 | 0.0 | 0.0 | | 0.0 | 0.0 | 0.0 |
| | 0.0625 | 0.0 | 3.0 | 0.0 | 9.0 | 0.0 | 0.0 | | 0.0 | 0.0 | 0.0 | | 0.0 | 0.0 | 0.0 |
| | 0.0313 | 0.0 | 0.0 | 0.0 | 0.0 | 0.0 | 0.0 | | 0.0 | 0.0 | 0.0 | | 0.0 | 0.0 | 0.0 |
| | 0.0156 | 0.0 | 0.0 | 0.0 | 0.0 | 0.0 | 0.0 | | 0.0 | 0.0 | 0.0 | | 0.0 | 0.0 | 0.0 |
| 116 | 0.5000 | 0.0 | 0.0 | 0.0 | 0.0 | 0.0 | 0.0 | | 0.0 | 0.0 | 0.0 | | 0.0 | 0.0 | 0.0 |
| | 0.2500 | 0.0 | 0.0 | 0.0 | 0.0 | 0.0 | 0.0 | | 0.0 | 0.0 | 0.0 | | 0.0 | 0.0 | 0.0 |
| | 0.1250 | 0.0 | 0.0 | 0.0 | 0.0 | 0.0 | 0.0 | | 0.0 | 0.0 | 0.0 | | 0.0 | 0.0 | 0.0 |
| | 0.0625 | 0.0 | 0.0 | 0.0 | 0.0 | 0.0 | 0.0 | | 0.0 | 0.0 | 0.0 | | 0.0 | 0.0 | 0.0 |
| | 0.0313 | 0.0 | 0.0 | 0.0 | 0.0 | 0.0 | 0.0 | | 0.0 | 0.0 | 0.0 | | 0.0 | 0.0 | 0.0 |
| | 0.0156 | 0.0 | 0.0 | 0.0 | 0.0 | 0.0 | 0.0 | | 0.0 | 0.0 | 0.0 | | 0.0 | 0.0 | 0.0 |
| 117 | 0.5000 | 0.0 | 0.0 | 0.0 | 0.0 | 0.0 | 0.0 | | 0.0 | 0.0 | 0.0 | | 0.0 | 0.0 | 0.0 |
| | 0.2500 | 0.0 | 0.0 | 0.0 | 0.0 | 0.0 | 0.0 | | 0.0 | 0.0 | 0.0 | | 0.0 | 0.0 | 0.0 |
| | 0.1250 | 0.0 | 0.0 | 0.0 | 0.0 | 0.0 | 0.0 | | 0.0 | 0.0 | 0.0 | | 0.0 | 0.0 | 0.0 |
| | 0.0625 | 0.0 | 0.0 | 0.0 | 0.0 | 0.0 | 0.0 | | 0.0 | 0.0 | 0.0 | | 0.0 | 0.0 | 0.0 |
| | 0.0313 | 0.0 | 0.0 | 0.0 | 0.0 | 0.0 | 0.0 | | 0.0 | 0.0 | 0.0 | | 0.0 | 0.0 | 0.0 |
| | 0.0156 | 0.0 | 0.0 | 0.0 | 0.0 | 0.0 | 0.0 | | 0.0 | 0.0 | 0.0 | | 0.0 | 0.0 | 0.0 |
| 118 | 0.2500 | 0.0 | 0.0 | 0.0 | 0.0 | 0.0 | 0.0 | | 0.0 | 0.0 | 0.0 | | 0.0 | 0.0 | 0.0 |
| | 0.1250 | 0.0 | 0.0 | 0.0 | 0.0 | 0.0 | 0.0 | | 0.0 | 0.0 | 0.0 | | 0.0 | 0.0 | 0.0 |
| | 0.0625 | 0.0 | 0.0 | 0.0 | 0.0 | 0.0 | 0.0 | | 0.0 | 0.0 | 0.0 | | 0.0 | 0.0 | 0.0 |
| | 0.0313 | 0.0 | 0.0 | 0.0 | 0.0 | 0.0 | 0.0 | | 0.0 | 0.0 | 0.0 | | 0.0 | 0.0 | 0.0 |
| | 0.0156 | 0.0 | 0.0 | 0.0 | 0.0 | 0.0 | 0.0 | | 0.0 | 0.0 | 0.0 | | 0.0 | 0.0 | 0.0 |
| 119 | 0.5000 | 9.0 | 9.0 | 9.0 | 9.0 | 9.0 | 9.0 | | 9.0 | 9.0 | 9.0 | | 9.0 | 9.0 | 9.0 |
| | 0.2500 | 9.0 | 9.0 | 9.0 | 9.0 | 9.0 | 9.0 | | 9.0 | 9.0 | 9.0 | | 9.0 | 8.5 | 8.7 |
| | 0.1250 | 9.0 | 9.0 | 9.0 | 9.0 | 9.0 | 9.0 | | 9.0 | 9.0 | 9.0 | | 8.3 | 9.0 | 8.0 |
| | 0.0625 | 9.0 | 9.0 | 2.0 | 9.0 | 9.0 | 9.0 | | 8.7 | 9.0 | 8.7 | | 7.7 | 8.5 | 8.0 |
| | 0.0313 | 9.0 | 9.0 | 1.0 | 9.0 | 8.0 | 9.0 | | 8.0 | 9.0 | 6.3 | | 6.3 | 8.0 | 7.3 |
| | 0.0156 | 9.0 | 9.0 | 0.7 | 9.0 | 8.0 | 9.0 | | 6.3 | 9.0 | 7.0 | | 7.0 | 7.0 | 7.0 |
| 120 | 0.2500 | 9.0 | 9.0 | 6.0 | 9.0 | 9.0 | 7.0 | | 8.0 | 9.0 | 9.0 | | 7.0 | 5.0 | 7.0 |
| | 0.1250 | 9.0 | 8.0 | 6.0 | 9.0 | 7.0 | 7.0 | | 8.0 | 9.0 | 9.0 | | 7.0 | 5.0 | 6.0 |
| | 0.0625 | 9.0 | 8.0 | 5.0 | 9.0 | 9.0 | 4.0 | | 7.0 | 9.0 | 7.0 | | 7.0 | 4.0 | 3.0 |
| | 0.0313 | 9.0 | 6.0 | 2.0 | 9.0 | 6.0 | 4.0 | | 3.0 | 9.0 | 5.0 | | 4.0 | 4.0 | 3.0 |
| | 0.0156 | 9.0 | 1.0 | 5.0 | 9.0 | 8.0 | 2.0 | | 1.0 | 9.0 | 6.0 | | 5.0 | 3.0 | 4.0 |
| 121 | 0.2500 | 9.0 | 9.0 | 9.0 | 9.0 | 9.0 | 9.0 | | 9.0 | 9.0 | 9.0 | | 8.0 | 7.0 | 6.0 |
| | 0.1250 | 9.0 | 9.0 | 8.0 | 9.0 | 9.0 | 9.0 | | 7.5 | 8.0 | 8.0 | | 7.0 | 7.0 | 4.5 |
| | 0.0625 | 9.0 | 9.0 | 6.5 | 9.0 | 6.0 | 9.0 | | 4.5 | 9.0 | 6.0 | | 6.5 | 2.0 | 3.5 |
| | 0.0313 | 9.0 | 8.0 | 5.0 | 9.0 | 5.0 | 9.0 | | 3.0 | 7.5 | 6.0 | | 5.5 | 2.0 | 2.5 |
| | 0.0156 | 9.0 | 8.0 | 5.5 | 9.0 | 5.0 | 7.0 | | 1.0 | 3.0 | 4.5 | | 3.0 | 6.0 | 2.5 |
| 122 | 0.2500 | 9.0 | 9.0 | 6.5 | 9.0 | 8.5 | 9.0 | | 2.5 | 9.0 | 7.0 | | 4.0 | 4.5 | 4.0 |

TABLE II-continued

Preemergence Herbicidal Evaluations of Test Compounds

| Compound Number | Rate (kg/ha) | ABUTH | AMBEL | CASOB | CHEAL | GALAP | IPOHE | IPOSS | ECHCG | SETVI | GLXMAW | GLXMA | ORYSAT | TRZAWR | ZEAMX |
|---|---|---|---|---|---|---|---|---|---|---|---|---|---|---|---|
|  | 0.1250 | 9.0 | 9.0 | 6.7 | 9.0 | 4.5 | 9.0 |  | 2.3 | 8.3 | 5.3 |  | 2.7 | 3.0 | 3.3 |
|  | 0.0625 | 9.0 | 8.7 | 3.3 | 9.0 | 3.0 | 4.3 |  | 1.0 | 6.3 | 3.3 |  | 1.0 | 0.0 | 1.7 |
|  | 0.0313 | 9.0 | 4.3 | 3.3 | 9.0 | 3.0 | 4.5 |  | 0.3 | 3.3 | 2.3 |  | 0.7 | 0.0 | 1.3 |
|  | 0.0156 | 9.0 | 3.0 | 1.5 | 9.0 | 0.0 | 3.3 |  | 0.3 | 2.3 | 2.3 |  | 0.3 |  | 1.3 |
| 123 | 0.2500 | 9.0 | 7.5 | 8.0 | 9.0 | 8.0 | 9.0 |  | 1.5 | 9.0 | 4.5 |  | 1.0 | 2.5 | 4.0 |
|  | 0.1250 | 9.0 | 4.5 | 3.0 | 9.0 | 6.0 | 6.5 |  | 0.5 | 8.0 | 2.0 |  | 2.5 | 2.5 | 4.0 |
|  | 0.0625 | 9.0 | 3.5 | 6.0 | 9.0 | 2.5 | 9.0 |  | 0.5 | 9.0 | 3.0 |  | 1.0 | 1.5 | 3.0 |
|  | 0.0313 | 9.0 | 1.5 | 1.5 | 9.0 | 2.0 | 0.5 |  | 0.0 | 2.0 | 0.0 |  | 1.5 |  | 0.5 |
|  | 0.0156 | 6.5 | 1.0 | 0.5 | 9.0 | 2.5 | 1.0 |  | 0.0 | 0.0 | 1.0 |  | 0.5 |  | 1.0 |
| 124 | 0.2500 | 9.0 | 9.0 | 6.5 | 9.0 | 9.0 | 9.0 |  | 3.5 | 9.0 | 5.0 |  | 1.5 | 0.0 | 2.5 |
|  | 0.1250 | 9.0 | 5.5 | 4.0 | 9.0 | 4.5 | 6.5 |  | 1.0 | 9.0 | 3.5 |  | 2.0 | 1.5 | 2.5 |
|  | 0.0625 | 7.5 | 6.0 | 0.0 | 9.0 | 3.0 | 1.0 |  | 0.0 | 4.5 | 1.0 |  | 1.0 | 1.0 | 1.0 |
|  | 0.0313 | 9.0 | 1.5 | 2.5 | 9.0 | 2.0 | 0.0 |  | 0.0 | 2.0 | 1.0 |  | 1.0 | 0.5 | 2.0 |
|  | 0.0156 | 5.0 | 0.0 | 2.5 | 9.0 | 0.0 | 0.0 |  | 0.0 | 2.0 | 0.0 |  | 2.0 | 0.0 | 2.0 |
| 125 | 0.5000 | 9.0 | 9.0 | 5.5 | 9.0 | 9.0 | 9.0 |  | 9.0 | 9.0 | 5.0 |  | 9.0 | 8.0 | 6.5 |
|  | 0.2500 | 9.0 | 9.0 | 5.5 | 9.0 | 9.0 | 9.0 |  | 6.8 | 9.0 | 2.7 |  | 5.0 | 7.5 | 5.3 |
|  | 0.1250 | 9.0 | 7.5 | 1.3 | 8.5 | 6.0 | 6.3 |  | 3.8 | 8.5 | 3.3 |  | 5.0 | 4.0 | 4.3 |
|  | 0.0625 | 9.0 | 5.8 | 2.7 | 9.0 | 0.0 | 5.7 |  | 1.8 | 4.5 | 2.0 |  | 4.5 | 0.0 | 3.3 |
|  | 0.0313 | 8.8 | 2.8 | 1.0 | 8.8 | 0.0 | 3.0 |  | 0.0 | 2.8 | 1.5 |  | 2.5 | 0.0 | 1.8 |
|  | 0.0156 | 5.0 | 2.7 | 0.7 | 7.0 | 0.0 | 1.3 |  | 0.0 | 2.0 | 1.3 |  | 1.0 | 0.0 | 0.7 |
| 126 | 0.2500 | 9.0 | 9.0 | 9.0 | 9.0 | 9.0 | 9.0 |  | 7.0 | 9.0 | 7.0 |  | 9.0 | 7.0 | 7.0 |
|  | 0.1250 | 9.0 | 5.0 | 7.0 | 9.0 | 9.0 | 9.0 |  | 5.0 | 9.0 | 6.0 |  | 7.0 | 9.0 | 4.0 |
|  | 0.0625 | 9.0 | 3.0 | 2.0 | 9.0 | 7.0 | 6.0 |  | 1.0 | 9.0 | 9.0 |  | 7.0 | 9.0 | 4.0 |
|  | 0.0313 | 9.0 | 3.0 | 7.0 | 9.0 | 7.0 | 3.0 |  | 0.0 | 7.0 | 7.0 |  | 8.0 | 2.0 | 1.0 |
|  | 0.0156 | 9.0 | 1.0 | 7.0 | 9.0 | 6.0 | 0.0 |  | 0.0 | 6.0 | 2.0 |  | 1.0 | 1.0 | 1.0 |
| 127 | 0.2500 | 9.0 | 9.0 | 9.0 | 9.0 | 9.0 | 9.0 |  | 7.5 | 9.0 | 7.0 |  | 9.0 | 7.5 | 7.5 |
|  | 0.1250 | 9.0 | 7.5 | 4.5 | 9.0 | 7.5 | 8.0 |  | 4.5 | 9.0 | 6.0 |  | 7.5 | 9.0 | 7.0 |
|  | 0.0625 | 9.0 | 5.5 | 4.5 | 9.0 | 7.0 | 7.0 |  | 1.5 | 9.0 | 4.0 |  | 4.5 | 2.0 | 5.5 |
|  | 0.0313 | 8.0 | 1.5 | 4.5 | 9.0 | 7.0 | 1.5 |  | 0.5 | 7.0 | 3.5 |  | 3.0 | 1.0 | 4.5 |
|  | 0.0156 | 3.5 | 1.0 | 1.0 | 9.0 | 2.0 | 0.5 |  | 0.5 | 4.5 | 1.5 |  | 3.0 | 0.5 | 0.5 |
| 128 | 0.2500 | 9.0 | 9.0 | 8.0 | 9.0 | 9.0 | 9.0 |  | 6.5 | 9.0 | 7.5 |  | 8.0 | 8.0 | 8.0 |
|  | 0.1250 | 9.0 | 8.5 | 4.5 | 9.0 | 7.5 | 9.0 |  | 2.0 | 8.0 | 4.0 |  | 8.0 | 7.5 | 6.0 |
|  | 0.0625 | 9.0 | 7.0 | 7.5 | 6.0 | 7.0 | 9.0 |  | 2.5 | 4.0 | 4.5 |  | 6.5 | 6.0 | 4.5 |
|  | 0.0313 | 7.5 | 3.5 | 2.5 | 9.0 | 7.0 | 4.5 |  | 0.0 | 1.0 | 2.5 |  | 4.0 | 3.5 | 1.5 |
|  | 0.0156 | 2.0 | 0.0 | 0.0 | 3.0 | 7.0 | 2.0 |  | 0.5 | 0.5 | 2.5 |  | 2.0 | 1.0 | 3.0 |
| 129 | 0.5000 | 9.0 | 9.0 | 9.0 | 9.0 | 9.0 | 9.0 |  | 9.0 | 9.0 | 7.0 |  |  |  | 3.0 |
|  | 0.2500 | 9.0 | 8.3 | 3.5 | 9.0 | 8.0 | 9.0 |  | 5.5 | 9.0 | 6.3 |  | 6.0 | 6.0 | 4.8 |
|  | 0.1250 | 9.0 | 5.3 | 3.8 | 9.0 | 8.0 | 9.0 |  | 3.0 | 9.0 | 5.3 |  | 5.3 | 6.0 | 3.3 |
|  | 0.0625 | 9.0 | 3.3 | 1.7 | 9.0 | 3.0 | 6.3 |  | 0.0 | 4.8 | 2.8 |  | 1.3 | 3.0 | 1.8 |
|  | 0.0313 | 9.0 | 0.5 | 0.0 | 9.0 | 0.5 | 4.8 |  | 0.0 | 2.5 | 1.5 |  | 1.3 | 2.0 | 0.8 |
|  | 0.0156 | 8.0 | 0.0 | 0.3 | 8.7 | 0.0 | 1.3 |  | 0.0 | 1.3 | 0.7 |  | 0.3 | 0.5 | 0.0 |
| 130 | 0.2500 | 9.0 | 8.0 | 9.0 | 9.0 | 5.5 | 8.0 |  | 7.3 | 8.3 | 6.7 |  | 9.0 | 7.5 | 6.3 |
|  | 0.1250 | 7.8 | 7.5 | 6.0 | 9.0 | 7.0 | 9.0 |  | 6.8 | 8.8 | 5.8 |  | 8.3 | 8.0 | 6.5 |
|  | 0.0625 | 8.3 | 4.3 | 2.3 | 8.5 | 7.0 | 7.3 |  | 4.8 | 7.3 | 4.3 |  | 6.0 | 4.5 | 5.3 |
|  | 0.0313 | 6.8 | 2.8 | 3.0 | 9.0 | 3.0 | 6.8 |  | 3.3 | 6.0 | 3.0 |  | 5.3 | 4.0 | 4.5 |
|  | 0.0156 | 6.8 | 0.3 | 0.0 | 7.3 | 0.0 | 5.3 |  | 0.5 | 1.5 | 1.0 |  | 2.7 | 2.0 | 1.0 |
| 131 | 0.2500 | 8.3 | 9.0 | 3.7 | 9.0 | 9.0 | 9.0 |  | 8.7 | 9.0 | 6.7 |  | 8.5 | 8.0 | 6.7 |

TABLE II-continued

Preemergence Herbicidal Evaluations of Test Compounds

| Compound Number | Rate (kg/ha) | ABUTH | AMBEL | CASOB | CHEAL | GALAP | IPOHE | IPOSS | ECHCG | SETVI | GLXMAW | GLXMA | ORYSAT | TRZAWR | ZEAMX |
|---|---|---|---|---|---|---|---|---|---|---|---|---|---|---|---|
| | 0.1250 | 9.0 | 8.8 | 5.0 | 9.0 | 9.0 | 9.0 | | 7.5 | 8.5 | 6.5 | | 8.7 | 7.0 | 6.8 |
| | 0.0625 | 9.0 | 6.0 | 0.0 | 9.0 | 8.0 | 7.3 | | 5.3 | 6.8 | 5.8 | | 7.0 | 6.0 | 6.3 |
| | 0.0313 | 9.0 | 4.5 | 0.0 | 9.0 | 6.0 | 6.0 | | 3.8 | 5.0 | 3.5 | | 6.0 | 1.0 | 4.5 |
| | 0.0156 | 6.8 | 2.0 | 0.7 | 7.3 | 2.0 | 4.7 | | 1.3 | 2.8 | 1.5 | | 2.7 | 2.0 | 1.3 |
| 132 | 0.2500 | 9.0 | 9.0 | 9.0 | 9.0 | 9.0 | 9.0 | | 9.0 | 9.0 | 9.0 | | 9.0 | 8.0 | 8.0 |
| | 0.1250 | 9.0 | 9.0 | 8.0 | 9.0 | 9.0 | 9.0 | | 8.5 | 9.0 | 9.0 | | 9.0 | 6.0 | 7.0 |
| | 0.0625 | 9.0 | 9.0 | 9.0 | 9.0 | 9.0 | 9.0 | | 8.0 | 9.0 | 9.0 | | 7.0 | 6.0 | 4.5 |
| | 0.0313 | 9.0 | 8.0 | 5.5 | 9.0 | 9.0 | 9.0 | | 5.5 | 8.0 | 9.0 | | 6.0 | 4.0 | 4.0 |
| | 0.0156 | 9.0 | 9.0 | 9.0 | 9.0 | 1.0 | 9.0 | | 1.5 | 9.0 | 9.0 | | 5.0 | 5.0 | 3.0 |
| 133 | 0.5000 | 9.0 | 9.0 | 9.0 | 9.0 | | 9.0 | | 9.0 | 9.0 | 9.0 | | 9.0 | | 8.0 |
| | 0.2500 | 9.0 | 9.0 | 9.0 | 9.0 | 9.0 | 9.0 | | 8.7 | 9.0 | 7.0 | | 9.0 | 7.0 | 6.7 |
| | 0.1250 | 9.0 | 8.5 | 7.5 | 9.0 | 7.0 | 9.0 | | 8.3 | 9.0 | 7.5 | | 6.5 | 7.0 | 6.0 |
| | 0.0625 | 9.0 | 6.0 | 5.5 | 9.0 | 1.0 | 9.0 | | 7.0 | 9.0 | 7.8 | | 5.0 | 9.0 | 5.0 |
| | 0.0313 | 9.0 | 2.3 | 6.8 | 9.0 | 1.0 | 9.0 | | 3.3 | 7.3 | 5.5 | | 5.0 | 9.0 | 4.3 |
| | 0.0156 | 9.0 | 2.3 | 3.3 | 9.0 | 0.0 | 9.0 | | 1.3 | 7.3 | 2.3 | | 2.5 | 6.0 | 3.7 |
| 134 | 0.2500 | 9.0 | 9.0 | 9.0 | 9.0 | 9.0 | 9.0 | | 9.0 | 9.0 | 9.0 | | 9.0 | 9.0 | 7.0 |
| | 0.1250 | 9.0 | 9.0 | 9.0 | 9.0 | 6.0 | 9.0 | | 9.0 | 9.0 | 9.0 | | 8.5 | 6.0 | 7.0 |
| | 0.0625 | 8.0 | 9.0 | 7.5 | 9.0 | 1.0 | 9.0 | | 7.5 | 9.0 | 9.0 | | 8.0 | 5.0 | 6.0 |
| | 0.0313 | 9.0 | 9.0 | 6.0 | 9.0 | 1.0 | 9.0 | | 4.0 | 9.0 | 9.0 | | 8.0 | 4.0 | 5.0 |
| | 0.0156 | 9.0 | 7.5 | 4.5 | 9.0 | 5.0 | 9.0 | | 2.0 | 5.0 | 5.0 | | 4.5 | 5.0 | 3.0 |
| 135 | 0.2500 | 9.0 | 9.0 | 9.0 | 9.0 | 5.0 | 9.0 | | 8.0 | 9.0 | 9.0 | | 8.0 | 9.0 | 7.0 |
| | 0.1250 | 9.0 | 9.0 | 1.0 | 9.0 | 5.0 | 9.0 | | 3.0 | 9.0 | 7.0 | | 3.5 | 3.0 | 6.0 |
| | 0.0625 | 9.0 | 8.5 | 0.0 | 9.0 | 5.0 | 9.0 | | 1.5 | 9.0 | 4.5 | | 4.5 | | 4.0 |
| | 0.0313 | 9.0 | 3.0 | 0.0 | 9.0 | | 6.0 | | 0.5 | 3.5 | 2.5 | | 4.5 | 4.0 | 3.5 |
| | 0.0156 | 7.0 | 0.0 | 0.0 | 9.0 | 0.0 | 5.5 | | 0.0 | 1.5 | 2.5 | | 1.0 | 3.0 | 3.5 |
| 136 | 0.2500 | 5.0 | 4.0 | 0.0 | 9.0 | 0.0 | 3.0 | | 0.0 | 4.0 | 3.0 | | 1.0 | 0.0 | 1.0 |
| | 0.1250 | 3.0 | 0.0 | 0.0 | 7.0 | 1.0 | 0.0 | | 0.0 | 0.0 | 2.0 | | 1.0 | | 0.0 |
| | 0.0625 | 0.0 | 2.0 | 0.0 | | 0.0 | 0.0 | | 0.0 | 0.0 | 1.0 | | 3.0 | 3.0 | 0.0 |
| | 0.0313 | 0.0 | 0.0 | 0.0 | 6.0 | 0.0 | 0.0 | | 0.0 | 0.0 | 2.0 | | 6.0 | | 0.0 |
| | 0.0156 | 0.0 | 1.0 | 1.0 | 9.0 | 0.0 | 0.0 | | 0.0 | 0.0 | 1.0 | | 0.0 | 0.0 | 0.0 |
| 137 | 0.2500 | 9.0 | 9.0 | 9.0 | 9.0 | 9.0 | 9.0 | | 9.0 | 9.0 | 9.0 | | 8.0 | 9.0 | 9.0 |
| | 0.1250 | 9.0 | 9.0 | 9.0 | 9.0 | 9.0 | 9.0 | | 7.0 | 9.0 | 9.0 | | 7.0 | 8.0 | 9.0 |
| | 0.0625 | 9.0 | 9.0 | 7.0 | 9.0 | 9.0 | 9.0 | | 7.0 | 9.0 | 9.0 | | 8.0 | 8.0 | 8.0 |
| | 0.0313 | 9.0 | 9.0 | 7.0 | 9.0 | 7.0 | 9.0 | | 7.0 | 9.0 | 8.0 | | 7.0 | 8.0 | 8.0 |
| | 0.0156 | 9.0 | 9.0 | 2.0 | 9.0 | 9.0 | 9.0 | | 4.0 | 9.0 | 5.0 | | 7.0 | 7.0 | 6.0 |
| 138 | 0.2500 | 9.0 | 9.0 | 7.5 | 9.0 | 9.0 | 9.0 | | 6.5 | 9.0 | 9.0 | | 7.0 | 5.0 | 6.5 |
| | 0.1250 | 9.0 | 7.5 | 7.0 | 9.0 | 5.0 | 9.0 | | 2.0 | 7.5 | 8.0 | | 4.0 | 1.5 | 3.5 |
| | 0.0625 | 9.0 | 9.0 | 5.0 | 9.0 | 4.5 | 8.0 | | 0.0 | 2.5 | 2.0 | | 0.5 | 0.5 | 2.5 |
| | 0.0313 | 2.0 | 1.5 | 0.0 | 8.5 | 4.5 | 4.5 | | 0.0 | 0.0 | 2.5 | | 0.5 | 0.5 | 1.0 |
| | 0.0156 | 0.5 | 1.0 | 0.0 | 9.0 | 0.0 | 4.0 | | 0.0 | 0.0 | 1.0 | | 1.5 | 0.5 | 0.5 |
| 139 | 0.2500 | 6.0 | 6.0 | 1.0 | 9.0 | 9.0 | 3.0 | | 5.0 | 8.0 | 4.0 | | 9.0 | 5.0 | 1.0 |
| | 0.1250 | 4.0 | 3.0 | 1.0 | 9.0 | 3.0 | 1.0 | | 3.0 | 0.0 | 6.0 | | 6.0 | 1.0 | 1.0 |
| | 0.0625 | 4.0 | 4.0 | 1.0 | 9.0 | 3.0 | 2.0 | | 1.0 | 5.0 | 5.0 | | 4.0 | 4.0 | 1.0 |
| | 0.0313 | 3.0 | 4.0 | 0.0 | 9.0 | 7.0 | 1.0 | | 2.0 | 4.0 | 1.0 | | 5.0 | 4.0 | 1.0 |
| | 0.0156 | 0.0 | 4.0 | 0.0 | 9.0 | 9.0 | 1.0 | | 2.0 | 9.0 | 1.0 | | 5.0 | 2.0 | 0.0 |
| 140 | 0.2500 | 9.0 | 9.0 | 9.0 | 9.0 | 9.0 | 9.0 | | 9.0 | 9.0 | 8.5 | | 9.0 | 9.0 | 9.0 |
| | 0.1250 | 9.0 | 9.0 | 9.0 | 9.0 | 9.0 | 9.0 | | 9.0 | 9.0 | 9.0 | | 7.5 | 7.0 | 8.0 |

TABLE II-continued

Preemergence Herbicidal Evaluations of Test Compounds

| Compound Number | Rate (kg/ha) | ABUTH | AMBEL | CASOB | CHEAL | GALAP | IPOHE | IPOSS | ECHCG | SETVI | GLXMAW | GLXMA | ORYSAT | TRZAWR | ZEAMX |
|---|---|---|---|---|---|---|---|---|---|---|---|---|---|---|---|
| | 0.0625 | 9.0 | 9.0 | 6.0 | 9.0 | 9.0 | 9.0 | | 8.7 | 9.0 | 7.7 | | 7.5 | 7.0 | 7.7 |
| | 0.0313 | 9.0 | 8.3 | 5.0 | 9.0 | 9.0 | 8.3 | | 6.7 | 9.0 | 7.0 | | 6.5 | 6.0 | 6.0 |
| | 0.0156 | 9.0 | 8.0 | 3.7 | 9.0 | 9.0 | 8.0 | | 4.0 | 9.0 | 5.0 | | 3.5 | 5.0 | 5.3 |
| 141 | 0.2500 | 9.0 | 9.0 | 9.0 | 9.0 | 9.0 | 9.0 | | 8.0 | 9.0 | 8.0 | | 8.0 | 9.0 | 8.0 |
| | 0.1250 | 9.0 | 9.0 | 7.8 | 9.0 | 9.0 | 9.0 | | 7.3 | 8.3 | 8.0 | | 8.0 | 7.0 | 6.5 |
| | 0.0625 | 9.0 | 8.3 | 5.0 | 9.0 | 8.0 | 8.5 | | 4.8 | 8.3 | 6.7 | | 7.0 | 6.0 | 4.8 |
| | 0.0313 | 7.3 | 7.8 | 3.5 | 9.0 | 8.0 | 7.3 | | 3.0 | 5.8 | 5.8 | | 6.5 | 3.0 | 3.5 |
| | 0.0156 | 9.0 | 6.8 | 1.5 | 7.3 | 6.5 | 5.5 | | 1.3 | 3.8 | 4.0 | | 4.0 | 1.5 | 1.3 |
| 142 | 0.2500 | 9.0 | 9.0 | 9.0 | 9.0 | 9.0 | 9.0 | | 9.0 | 9.0 | 9.0 | | 7.0 | 5.0 | 7.0 |
| | 0.1250 | 9.0 | 9.0 | 5.0 | 9.0 | 8.0 | 9.0 | | 8.0 | 9.0 | 9.0 | | 3.0 | 3.0 | 5.0 |
| | 0.0625 | 9.0 | 0.0 | 9.0 | 9.0 | 9.0 | 9.0 | | 7.0 | 9.0 | 9.0 | | 3.0 | | 4.0 |
| | 0.0313 | 9.0 | 0.0 | 5.0 | 9.0 | 0.0 | 9.0 | | 0.0 | 0.0 | 6.0 | | 3.0 | 0.0 | 0.0 |
| | 0.0156 | 6.0 | 9.0 | 9.0 | 9.0 | 0.0 | 9.0 | | 0.0 | 0.0 | 0.0 | | 0.0 | 0.0 | 0.0 |
| 143 | 0.2500 | 0.0 | 7.0 | 6.0 | 9.0 | 9.0 | 9.0 | | 2.0 | 8.0 | 0.0 | | 8.0 | 8.0 | 5.0 |
| | 0.1250 | 9.0 | 3.0 | 0.0 | 9.0 | 9.0 | 1.0 | | 0.0 | 5.0 | 0.0 | | 7.0 | 7.0 | 1.0 |
| | 0.0625 | 9.0 | 0.0 | 0.0 | 9.0 | 0.0 | 0.0 | | 0.0 | 0.0 | 0.0 | | 6.0 | 3.0 | 0.0 |
| | 0.0313 | 0.0 | 0.0 | 0.0 | 0.0 | 0.0 | 0.0 | | 0.0 | 0.0 | 0.0 | | 2.0 | 0.0 | 0.0 |
| | 0.0156 | 0.0 | 0.0 | 0.0 | 0.0 | 0.0 | 0.0 | | 0.0 | 0.0 | 0.0 | | 0.0 | 0.0 | 0.0 |
| 144 | 0.2500 | 9.0 | 3.0 | 8.0 | 7.0 | 0.0 | 9.0 | | 1.0 | 9.0 | 0.0 | | 4.0 | 0.0 | 0.0 |
| | 0.1250 | 9.0 | 0.0 | 0.0 | 7.0 | 0.0 | 3.0 | | 0.0 | 5.0 | 0.0 | | 0.0 | 0.0 | 0.0 |
| | 0.0625 | 0.0 | 0.0 | 0.0 | 0.0 | 0.0 | 0.0 | | 0.0 | 0.0 | 0.0 | | 0.0 | 0.0 | 0.0 |
| | 0.0313 | 0.0 | 0.0 | 0.0 | 0.0 | 0.0 | 0.0 | | 0.0 | 0.0 | 0.0 | | 0.0 | 0.0 | 0.0 |
| | 0.0156 | 0.0 | 0.0 | 0.0 | 0.0 | 0.0 | 0.0 | | 0.0 | 0.0 | 0.0 | | 0.0 | 0.0 | 0.0 |
| 145 | 0.2500 | 9.0 | 7.0 | 3.0 | 9.0 | 3.0 | 9.0 | | 3.0 | 9.0 | 7.0 | | 3.0 | 2.0 | 3.0 |
| | 0.1250 | 0.0 | 6.0 | 0.0 | 0.0 | | 0.0 | | 2.0 | 0.0 | 2.0 | | 1.0 | 1.0 | 1.0 |
| | 0.0625 | 4.0 | 2.0 | 0.0 | 9.0 | 1.0 | 2.0 | | 0.0 | 7.0 | 1.0 | | 1.0 | 0.0 | 0.0 |
| | 0.0313 | 1.0 | 0.0 | 0.0 | 9.0 | 0.0 | 0.0 | | 0.0 | 1.0 | 0.0 | | 1.0 | 0.0 | 0.0 |
| | 0.0156 | 0.0 | 0.0 | 1.0 | 9.0 | 0.0 | 0.0 | | 0.0 | 0.0 | 1.0 | | 0.0 | 0.0 | 0.0 |
| 146 | 0.2500 | 9.0 | 0.0 | 1.0 | 9.0 | 9.0 | 9.0 | | 3.0 | 9.0 | 1.0 | | 4.0 | 1.0 | 3.0 |
| | 0.1250 | 9.0 | 7.0 | 1.0 | 9.0 | 6.0 | 9.0 | | 0.0 | 4.0 | 2.0 | | 1.0 | 0.0 | 1.0 |
| | 0.0625 | 9.0 | 7.0 | 0.0 | 9.0 | 2.0 | 9.0 | | 0.0 | 2.0 | 1.0 | | 1.0 | 1.0 | 1.0 |
| | 0.0313 | 9.0 | 5.0 | 1.0 | 9.0 | | 0.0 | | 0.0 | 0.0 | 1.0 | | 1.0 | 0.0 | 1.0 |
| | 0.0156 | 0.0 | 2.0 | 0.0 | 9.0 | 0.0 | 0.0 | | 0.0 | 0.0 | 1.0 | | 1.0 | 0.0 | 1.0 |
| 147 | 0.2500 | 9.0 | 7.0 | 2.0 | 7.0 | 0.0 | 9.0 | | 0.0 | 1.0 | 1.0 | | 4.0 | 9.0 | 0.0 |
| | 0.1250 | 9.0 | 4.0 | 0.0 | 9.0 | 9.0 | 9.0 | | 0.0 | 1.0 | 1.0 | | 1.0 | 9.0 | 0.0 |
| | 0.0625 | 9.0 | 2.0 | 0.0 | 9.0 | 6.0 | 1.0 | | 0.0 | 0.0 | 0.0 | | | 4.0 | 0.0 |
| | 0.0313 | 1.0 | 2.0 | 0.0 | 9.0 | | 0.0 | | 0.0 | 1.0 | 2.0 | | 1.0 | 0.0 | 0.0 |
| | 0.0156 | 1.0 | 2.0 | 0.0 | 9.0 | | 1.0 | | 2.0 | 0.0 | 1.0 | | 0.0 | 0.0 | 1.0 |
| 148 | 0.2500 | 9.0 | 7.0 | 6.0 | 9.0 | 9.0 | 9.0 | | 0.0 | 6.0 | 9.0 | | 7.0 | 7.0 | 7.0 |
| | 0.1250 | 9.0 | 9.0 | 9.0 | 9.0 | 7.0 | 7.0 | | 2.0 | 2.0 | 5.0 | | 5.0 | 6.0 | 6.0 |
| | 0.0625 | 9.0 | 9.0 | 4.0 | 9.0 | | 9.0 | | 0.0 | 2.0 | 4.0 | | 1.0 | 4.0 | 1.0 |
| | 0.0313 | 3.0 | 3.0 | 0.0 | 9.0 | | 9.0 | | 0.0 | 1.0 | 1.0 | | 1.0 | 1.0 | 1.0 |
| | 0.0156 | | 3.0 | 0.0 | 5.0 | 4.0 | 7.0 | | 1.0 | 5.0 | 4.0 | | 1.0 | 1.0 | 1.0 |
| 149 | 0.2500 | 9.0 | 3.0 | 1.0 | 9.0 | 9.0 | 4.0 | | 0.0 | 4.0 | 1.0 | | 6.0 | 2.0 | 1.0 |
| | 0.1250 | 9.0 | 3.0 | 3.0 | 9.0 | 5.0 | 2.0 | | 0.0 | 2.0 | 2.0 | | 1.0 | | 0.0 |
| | 0.0625 | 4.0 | 1.0 | 1.0 | 7.0 | 3.0 | 1.0 | | 0.0 | 0.0 | 1.0 | | 1.0 | 0.0 | 1.0 |
| | 0.0313 | 0.0 | 0.0 | 2.0 | 7.0 | 2.0 | 0.0 | | 0.0 | 0.0 | 1.0 | | 1.0 | 0.0 | 0.0 |

TABLE II-continued

Preemergence Herbicidal Evaluations of Test Compounds

| Compound Number | Rate (kg/ha) | ABUTH | AMBEL | CASOB | CHEAL | GALAP | IPOHE | IPOSS | ECHCG | SETVI | GLXMAW | GLXMA | ORYSAT | TRZAWR | ZEAMX |
|---|---|---|---|---|---|---|---|---|---|---|---|---|---|---|---|
| 150 | 0.0156 | 0.0 | 1.0 | 1.0 | 6.0 | | 0.0 | | 0.0 | 1.0 | 0.0 | | 1.0 | 0.0 | 1.0 |
| | 0.2500 | 9.0 | 9.0 | 7.0 | 9.0 | 9.0 | 9.0 | | 7.0 | 9.0 | 9.0 | | 7.0 | 7.0 | 7.0 |
| | 0.1250 | 9.0 | 9.0 | 7.0 | 9.0 | 9.0 | 9.0 | | 3.0 | 4.0 | 9.0 | | 6.0 | 6.0 | 7.0 |
| | 0.0625 | 9.0 | 7.0 | 6.0 | 9.0 | 2.0 | 9.0 | | 1.0 | 4.0 | 6.0 | | 7.0 | 6.0 | 4.0 |
| | 0.0313 | 9.0 | 3.0 | 3.0 | 9.0 | 4.0 | 4.0 | | 1.0 | 1.0 | 3.0 | | 4.0 | 3.0 | 1.0 |
| | 0.0156 | 9.0 | 2.0 | 1.0 | 9.0 | 3.0 | 0.0 | | 0.0 | 1.0 | 1.0 | | 4.0 | 1.0 | 0.0 |
| 151 | 0.5000 | 0.0 | 0.0 | 0.0 | 2.0 | 3.0 | 0.0 | | 0.0 | 0.0 | 0.0 | | 0.0 | 0.0 | 0.0 |
| | 0.2500 | 0.0 | 0.0 | 0.0 | 0.0 | 0.0 | 0.0 | | 0.0 | 0.0 | 0.0 | | 0.0 | 0.0 | 0.0 |
| | 0.1250 | 0.0 | 0.0 | 0.0 | 0.0 | 0.0 | 0.0 | | 0.0 | 0.0 | 0.0 | | 0.0 | 0.0 | 0.0 |
| | 0.0625 | 0.0 | 0.0 | 0.0 | 0.0 | 0.0 | 0.0 | | 0.0 | 0.0 | 0.0 | | 0.0 | 0.0 | 0.0 |
| | 0.0313 | 0.0 | 0.0 | 0.0 | 0.0 | 0.0 | 0.0 | | 0.0 | 0.0 | 0.0 | | 0.0 | 0.0 | 0.0 |
| 152 | 0.2500 | 0.0 | 3.0 | 2.0 | 9.0 | 0.0 | 0.0 | | 0.0 | 0.0 | 2.0 | | 0.0 | 0.0 | 2.0 |
| | 0.1250 | 0.0 | 0.0 | 0.0 | 9.0 | 0.0 | 0.0 | | 0.0 | 0.0 | 0.0 | | 0.0 | 0.0 | 0.0 |
| | 0.0625 | 0.0 | 0.0 | 0.0 | 7.0 | 0.0 | 0.0 | | 0.0 | 0.0 | 0.0 | | 0.0 | 0.0 | 0.0 |
| | 0.0313 | 0.0 | 0.0 | 0.0 | 0.0 | 0.0 | 0.0 | | 0.0 | 0.0 | 0.0 | | 0.0 | 0.0 | 0.0 |
| | 0.0156 | 0.0 | 0.0 | 0.0 | 0.0 | 0.0 | 0.0 | | 0.0 | 0.0 | 0.0 | | 0.0 | 0.0 | 0.0 |
| 153 | 0.2500 | 9.0 | 9.0 | 9.0 | 9.0 | 7.0 | 9.0 | | 5.0 | 9.0 | 0.0 | | 3.0 | 9.0 | 6.0 |
| | 0.1250 | 9.0 | 9.0 | 4.0 | 8.0 | 3.0 | 9.0 | | 0.0 | 5.0 | 3.0 | | 0.0 | 0.0 | 4.0 |
| | 0.0625 | 9.0 | 3.0 | 0.0 | 9.0 | 3.0 | 2.0 | | 0.0 | 0.0 | 3.0 | | 0.0 | 0.0 | 0.0 |
| | 0.0313 | 9.0 | 0.0 | 0.0 | 9.0 | 3.0 | 0.0 | | 0.0 | 0.0 | 0.0 | | 0.0 | 0.0 | 0.0 |
| | 0.0156 | 9.0 | 0.0 | 0.0 | 0.0 | 0.0 | 0.0 | | 0.0 | 0.0 | 0.0 | | 0.0 | 0.0 | 0.0 |
| 154 | 0.2500 | 9.0 | 9.0 | 9.0 | 9.0 | 9.0 | 9.0 | | 5.0 | 9.0 | 9.0 | | 8.0 | 8.0 | 7.0 |
| | 0.1250 | 9.0 | 9.0 | 9.0 | 9.0 | 9.0 | 9.0 | | 0.0 | 6.0 | 7.0 | | 8.0 | 7.0 | 5.0 |
| | 0.0625 | 3.0 | 3.0 | 4.0 | 0.0 | 0.0 | 9.0 | | 0.0 | 0.0 | 0.0 | | 3.0 | 4.0 | 2.0 |
| | 0.0313 | 0.0 | 0.0 | 4.0 | 0.0 | 0.0 | 9.0 | | 0.0 | 0.0 | 0.0 | | 3.0 | 0.0 | 0.0 |
| | 0.0156 | 0.0 | 0.0 | 0.0 | 0.0 | 0.0 | 9.0 | | 0.0 | 0.0 | 0.0 | | 0.0 | 0.0 | 0.0 |
| 155 | 0.5000 | 9.0 | 9.0 | 9.0 | 9.0 | 9.0 | 9.0 | | 3.0 | 9.0 | 9.0 | | 4.0 | 8.0 | 8.0 |
| | 0.2500 | 9.0 | 9.0 | 9.0 | 9.0 | 7.0 | 9.0 | | 2.0 | 7.0 | 9.0 | | 2.0 | 6.0 | 2.0 |
| | 0.1250 | 9.0 | 9.0 | 9.0 | 9.0 | 7.0 | 9.0 | | 0.0 | 3.0 | 9.0 | | 0.0 | 4.0 | 0.0 |
| | 0.0625 | 9.0 | 3.0 | 2.0 | 9.0 | 7.0 | 9.0 | | 0.0 | 1.0 | 5.0 | | 0.0 | 3.0 | 0.0 |
| | 0.0313 | 9.0 | 0.0 | 0.0 | 0.0 | 0.0 | 9.0 | | 0.0 | 0.0 | 0.0 | | 0.0 | 2.0 | 0.0 |
| | 0.0156 | 9.0 | 0.0 | 0.0 | 0.0 | 0.0 | 6.0 | | 2.0 | 6.0 | 0.0 | | 0.0 | 1.0 | 1.0 |
| 156 | 0.2500 | 9.0 | 6.0 | 2.0 | 9.0 | 7.0 | 9.0 | | 1.0 | 3.0 | 1.0 | | 2.0 | 1.0 | 1.0 |
| | 0.1250 | 6.0 | 2.0 | 0.0 | 9.0 | 6.0 | 3.0 | | 1.0 | 3.0 | 1.0 | | 1.0 | 1.0 | 1.0 |
| | 0.0625 | 4.0 | 3.0 | 1.0 | 7.0 | 0.0 | 3.0 | | 0.0 | 1.0 | 1.0 | | 0.0 | 0.0 | 0.0 |
| | 0.0313 | 1.0 | 0.0 | 0.0 | 0.0 | 0.0 | 1.0 | | 0.0 | 1.0 | 1.0 | | 0.0 | 0.0 | 0.0 |
| | 0.0156 | 0.0 | 0.0 | 0.0 | 0.0 | 0.0 | 1.0 | | 0.0 | 0.0 | 1.0 | | 0.0 | 0.0 | 0.0 |
| 157 | 0.2500 | 9.0 | 9.0 | 9.0 | 9.0 | 9.0 | 9.0 | | 6.0 | 9.0 | 7.0 | | 7.0 | 7.0 | 8.0 |
| | 0.1250 | 9.0 | 9.0 | 4.0 | 9.0 | 7.0 | 9.0 | | 4.0 | 9.0 | 9.0 | | 6.0 | 6.0 | 7.0 |
| | 0.0625 | 9.0 | 6.0 | 2.0 | 9.0 | 6.0 | 9.0 | | 3.0 | 4.0 | 4.0 | | 6.0 | 5.0 | 3.0 |
| | 0.0313 | 9.0 | 4.0 | 0.0 | 6.0 | 0.0 | 3.0 | | 0.0 | 1.0 | 3.0 | | 3.0 | 2.0 | 1.0 |
| | 0.0156 | 6.0 | 2.0 | 0.0 | 0.0 | 0.0 | 3.0 | | 0.0 | 1.0 | 2.0 | | 1.0 | 1.0 | 0.0 |
| 158 | 0.2500 | 9.0 | 9.0 | 6.0 | 9.0 | 5.0 | 9.0 | | 7.0 | 9.0 | 5.0 | | 5.0 | 6.0 | 7.0 |
| | 0.1250 | 9.0 | 7.0 | 3.0 | 9.0 | 9.0 | 9.0 | | 5.0 | 9.0 | 5.0 | | 2.0 | 4.0 | 5.0 |
| | 0.0625 | 9.0 | 3.0 | 0.0 | 9.0 | 1.0 | 5.0 | | 2.0 | 6.0 | 3.0 | | 1.0 | 2.0 | 4.0 |
| | 0.0313 | 9.0 | 2.0 | 0.0 | 9.0 | 0.0 | 1.0 | | 1.0 | 2.0 | 1.0 | | 1.0 | 1.0 | 2.0 |
| | 0.0156 | 3.0 | 0.0 | 0.0 | 9.0 | 0.0 | 0.0 | | 0.0 | 1.0 | 1.0 | | 0.0 | 0.0 | 0.0 |

TABLE II-continued

Preemergence Herbicidal Evaluations of Test Compounds

| Compound Number | Rate (kg/ha) | ABUTH | AMBEL | CASOB | CHEAL | GALAP | IPOHE | IPOSS | ECHCG | SETVI | GLXMAW | GLXMA | ORYSAT | TRZAWR | ZEAMX |
|---|---|---|---|---|---|---|---|---|---|---|---|---|---|---|---|
| 159 | 0.2500 | 9.0 | 9.0 | 3.0 | 9.0 | 7.0 | 9.0 | | 5.0 | 6.0 | 9.0 | | 4.0 | 5.0 | 6.0 |
| | 0.1250 | 9.0 | 7.0 | 6.0 | 9.0 | 7.0 | 9.0 | | 1.0 | 4.0 | 7.0 | | 2.0 | 3.0 | 2.0 |
| | 0.0625 | 9.0 | 4.0 | 1.0 | 9.0 | 6.0 | 7.0 | | 0.0 | 1.0 | 5.0 | | | 1.0 | 0.0 |
| | 0.0313 | 9.0 | 2.0 | 1.0 | 9.0 | 3.0 | 4.0 | | 0.0 | 0.0 | 3.0 | | | 0.0 | 1.0 |
| | 0.0156 | 5.0 | 2.0 | 0.0 | 9.0 | 2.0 | 3.0 | | 1.0 | 0.0 | 1.0 | | | 0.0 | 1.0 |
| 160 | 0.2500 | 4.0 | 4.0 | 0.0 | 9.0 | 9.0 | 4.0 | | 0.0 | 0.0 | 5.0 | | 2.0 | 2.0 | 2.0 |
| | 0.1250 | 3.0 | 2.0 | 0.0 | 9.0 | 6.0 | 3.0 | | 0.0 | 1.0 | 5.0 | | 0.0 | 1.0 | 1.0 |
| | 0.0625 | 1.0 | 0.0 | 0.0 | 9.0 | 6.0 | 0.0 | | 0.0 | 1.0 | 4.0 | | 0.0 | 0.0 | 0.0 |
| | 0.0313 | 1.0 | 0.0 | 0.0 | 9.0 | 1.0 | | 0.0 | 1.0 | 1.0 | 2.0 | | 1.0 | 0.0 | 0.0 |
| | 0.0156 | 0.0 | 0.0 | 0.0 | 5.0 | 0.0 | | 0.0 | 0.0 | 0.0 | 1.0 | | 0.0 | 0.0 | 0.0 |
| 161 | 0.2500 | 9.0 | 9.0 | 4.0 | 9.0 | 9.0 | 9.0 | | 9.0 | 9.0 | 9.0 | | 7.0 | 1.0 | 9.0 |
| | 0.1250 | 9.0 | 7.0 | 4.0 | 9.0 | 9.0 | 9.0 | | 9.0 | 9.0 | 9.0 | | 6.0 | 7.0 | 8.0 |
| | 0.0625 | 9.0 | 6.0 | 1.0 | 9.0 | 6.0 | 9.0 | | 9.0 | 9.0 | 6.0 | | 5.0 | 5.0 | 7.0 |
| | 0.0313 | 9.0 | 3.0 | 1.0 | 9.0 | 6.0 | 4.0 | | 3.0 | 9.0 | 6.0 | | 2.0 | 3.0 | 5.0 |
| | 0.0156 | 6.0 | 2.0 | 1.0 | 9.0 | 3.0 | 2.0 | | 2.0 | 7.0 | 5.0 | | 1.0 | 0.0 | 1.0 |
| 170 | 0.2500 | 9.0 | 9.0 | 9.0 | 9.0 | 8.5 | 9.0 | | 8.0 | 9.0 | 8.0 | | 8.0 | 8.0 | 7.0 |
| | 0.1250 | 9.0 | 9.0 | 7.5 | 9.0 | 6.0 | 8.0 | | 6.5 | 9.0 | 9.0 | | 7.5 | 2.5 | 5.5 |
| | 0.0625 | 9.0 | 8.5 | 3.5 | 9.0 | 0.0 | 9.0 | | 6.0 | 9.0 | 6.0 | | 7.0 | 2.0 | 5.5 |
| | 0.0313 | 9.0 | 4.5 | 3.5 | 9.0 | 2.5 | 8.0 | | 4.5 | 9.0 | 4.5 | | 5.5 | 2.5 | 5.0 |
| | 0.0156 | 9.0 | 2.0 | 0.5 | 9.0 | 0.0 | 3.0 | | 2.0 | 4.0 | 2.5 | | 2.5 | 4.0 | 2.5 |
| 171 | 0.2500 | 9.0 | 6.0 | 6.0 | 9.0 | 3.0 | 9.0 | | 6.0 | 9.0 | 5.0 | | 9.0 | 5.0 | 6.0 |
| | 0.1250 | 9.0 | 7.0 | 4.0 | 9.0 | | 9.0 | | 5.0 | 8.0 | 5.0 | | 5.0 | | 6.0 |
| | 0.0625 | 9.0 | 4.0 | 4.0 | 9.0 | | 4.0 | | 4.0 | 4.0 | 5.0 | | 6.0 | | 5.0 |
| | 0.0313 | 9.0 | 4.0 | 3.0 | 9.0 | 5.0 | 6.0 | | 2.0 | 4.0 | 5.0 | | 5.0 | 3.0 | 5.0 |
| | 0.0156 | 5.0 | 0.0 | 2.0 | 9.0 | 3.0 | 3.0 | | 0.0 | 1.0 | 4.0 | | 2.0 | | 0.0 |
| 172 | 0.2500 | 9.0 | 9.0 | 9.0 | 9.0 | 9.0 | 9.0 | | 9.0 | 9.0 | 9.0 | | 9.0 | 7.0 | 7.0 |
| | 0.1250 | 9.0 | 9.0 | 5.0 | 9.0 | 9.0 | 9.0 | | 8.0 | 9.0 | 9.0 | | 8.0 | 6.0 | 5.0 |
| | 0.0625 | 9.0 | 9.0 | 4.0 | 9.0 | 7.0 | 8.0 | | 7.0 | 9.0 | 6.0 | | 7.0 | 7.0 | 4.0 |
| | 0.0313 | 9.0 | 7.0 | 4.0 | 9.0 | 3.0 | 5.0 | | 5.0 | 8.0 | 4.0 | | 7.0 | 5.0 | 5.0 |
| | 0.0156 | 9.0 | 6.0 | 4.0 | 9.0 | 5.0 | 6.0 | | 2.0 | 4.0 | 4.0 | | 4.0 | 2.0 | 2.0 |
| 173 | 0.5000 | 9.0 | 9.0 | 9.0 | 9.0 | 7.0 | 9.0 | | 8.0 | 9.0 | 9.0 | | 9.0 | 8.0 | 6.0 |
| | 0.2500 | 9.0 | 9.0 | 4.0 | 9.0 | 8.0 | 9.0 | | 7.0 | 9.0 | 5.0 | | 7.0 | 8.0 | 6.5 |
| | 0.1250 | 9.0 | 6.5 | 3.5 | 9.0 | 7.0 | 8.0 | | 4.5 | 8.0 | 6.0 | | 8.0 | 5.0 | 5.5 |
| | 0.0625 | 9.0 | 5.0 | 2.5 | 7.0 | 2.0 | 6.5 | | 3.5 | 7.0 | 3.5 | | 5.0 | 3.5 | 5.0 |
| | 0.0313 | 9.0 | 3.5 | 1.5 | 9.0 | 2.0 | 6.5 | | 2.0 | 3.5 | 2.0 | | 1.5 | 1.5 | 3.5 |
| | 0.0156 | 8.0 | 1.0 | 1.5 | 9.0 | 2.0 | 2.0 | | 1.0 | 1.0 | 2.5 | | 1.5 | 1.5 | 2.5 |
| 174 | 0.5000 | 9.0 | 9.0 | 6.0 | 9.0 | 9.0 | 9.0 | | 8.0 | 8.5 | 6.5 | | 8.0 | 9.0 | 6.5 |
| | 0.2500 | 9.0 | 9.0 | 6.3 | 9.0 | 8.0 | 9.0 | | 7.0 | 8.5 | 6.3 | | 8.5 | 5.0 | 6.0 |
| | 0.1250 | 9.0 | 7.5 | 3.0 | 9.0 | 5.5 | 9.0 | | 3.5 | 7.0 | 5.0 | | 7.0 | 4.0 | 3.8 |
| | 0.0625 | 8.8 | 6.3 | 2.0 | 8.3 | 4.5 | 5.0 | | 1.8 | 3.5 | 2.8 | | 7.0 | 3.5 | 4.5 |
| | 0.0313 | 8.3 | 4.3 | 1.3 | 8.3 | 1.5 | 2.3 | | 1.0 | 2.8 | 1.8 | | 5.0 | 3.0 | 2.8 |
| | 0.0156 | 9.0 | 2.7 | 1.0 | 9.0 | 0.5 | 2.0 | | 1.0 | 2.3 | 2.0 | | 3.5 | 2.5 | 1.7 |
| 175 | 0.2500 | 9.0 | 9.0 | 6.0 | 9.0 | 9.0 | 9.0 | | 8.0 | 9.0 | 9.0 | | 8.0 | 7.0 | 7.0 |
| | 0.1250 | 9.0 | 9.0 | 3.0 | 9.0 | 2.0 | 9.0 | | 8.0 | 9.0 | 9.0 | | 8.0 | 7.0 | 6.0 |
| | 0.0625 | 9.0 | 7.0 | 4.0 | 9.0 | 2.0 | 5.0 | | 5.0 | 5.0 | 5.0 | | 6.0 | 6.0 | 5.0 |
| | 0.0313 | 9.0 | 6.0 | 4.0 | 9.0 | 2.0 | 5.0 | | 4.0 | 5.0 | 4.0 | | 5.0 | 4.0 | 4.0 |
| | 0.0156 | 9.0 | 6.0 | 5.0 | 7.0 | 5.0 | 4.0 | | 3.0 | 2.0 | 5.0 | | 7.0 | 4.0 | 6.0 |

TABLE II-continued

Preemergence Herbicidal Evaluations of Test Compounds

| Compound Number | Rate (kg/ha) | ABUTH | AMBEL | CASOB | CHEAL | GALAP | IPOHE | IPOSS | ECHCG | SETVI | GLXMAW | GLXMA | ORYSAT | TRZAWR | ZEAMX |
|---|---|---|---|---|---|---|---|---|---|---|---|---|---|---|---|
| 176 | 0.5000 | 9.0 | 9.0 | 9.0 | 9.0 | 9.0 | 9.0 | | 9.0 | 9.0 | 5.0 | | 9.0 | 9.0 | 9.0 |
| | 0.2500 | 9.0 | 9.0 | 7.5 | 9.0 | 4.5 | 9.0 | | 7.0 | 9.0 | 9.0 | | 8.0 | 7.5 | 7.0 |
| | 0.1250 | 9.0 | 9.0 | 7.0 | 9.0 | 4.5 | 9.0 | | 7.0 | 9.0 | 6.0 | | 8.5 | 4.5 | 7.5 |
| | 0.0625 | 9.0 | 8.0 | 1.0 | 9.0 | 2.0 | 9.0 | | 3.5 | 6.0 | 4.0 | | 8.0 | 4.0 | 5.5 |
| | 0.0313 | 9.0 | 3.5 | 3.5 | 9.0 | 0.5 | 6.5 | | 1.0 | 3.5 | 2.5 | | 6.5 | 4.0 | 5.5 |
| | 0.0156 | 9.0 | 2.0 | 0.5 | 9.0 | 2.5 | 2.0 | | 0.5 | 3.0 | 3.0 | | 3.5 | 3.0 | 3.5 |
| 177 | 0.2500 | 9.0 | 9.0 | 8.0 | 9.0 | 9.0 | 9.0 | | 9.0 | 9.0 | 9.0 | | 9.0 | 6.0 | 7.0 |
| | 0.1250 | 9.0 | 9.0 | 8.0 | 9.0 | 9.0 | 9.0 | | 8.0 | 9.0 | 9.0 | | 8.0 | 5.0 | 7.0 |
| | 0.0625 | 9.0 | 9.0 | 6.0 | 9.0 | 9.0 | 8.0 | | 6.0 | 9.0 | 6.0 | | 8.0 | 4.0 | 7.0 |
| | 0.0313 | 9.0 | 7.0 | 6.0 | 9.0 | 9.0 | 9.0 | | 5.0 | 6.0 | 6.0 | | 8.0 | 4.0 | 7.0 |
| | 0.0156 | 9.0 | 6.0 | 6.0 | 9.0 | 6.0 | 9.0 | | 4.0 | 5.0 | 5.0 | | 6.0 | 1.0 | 5.0 |
| 178 | 0.2500 | 9.0 | 9.0 | 9.0 | 9.0 | 9.0 | 9.0 | | 8.0 | 9.0 | 9.0 | | 8.0 | 3.0 | 7.0 |
| | 0.1250 | 9.0 | 9.0 | 5.0 | 9.0 | 9.0 | 9.0 | | 8.0 | 9.0 | 9.0 | | 8.0 | 3.0 | 6.0 |
| | 0.0625 | 9.0 | 9.0 | 4.0 | 9.0 | 9.0 | 9.0 | | 6.0 | 8.0 | 5.0 | | 6.0 | 2.0 | 6.0 |
| | 0.0313 | 9.0 | 8.0 | 6.0 | 9.0 | 8.0 | 8.0 | | 5.0 | 6.0 | 6.0 | | 7.0 | 3.0 | 6.0 |
| | 0.0156 | 9.0 | 2.0 | 5.0 | 9.0 | 2.0 | 5.0 | | 2.0 | 6.0 | 7.0 | | 7.0 | 2.0 | 5.0 |
| 179 | 0.2500 | 9.0 | 9.0 | 9.0 | 9.0 | 9.0 | 9.0 | | 9.0 | 9.0 | 9.0 | | 9.0 | 8.5 | 8.5 |
| | 0.1250 | 9.0 | 9.0 | 7.0 | 9.0 | 9.0 | 8.0 | | 9.0 | 9.0 | 9.0 | | 8.5 | 8.5 | 8.0 |
| | 0.0640 | 9.0 | 9.0 | 7.0 | 9.0 | 9.0 | 7.0 | | 9.0 | 9.0 | 7.0 | | 8.0 | | 8.0 |
| | 0.0625 | 9.0 | 9.0 | 7.0 | 9.0 | | 8.0 | | 8.0 | 9.0 | 9.0 | | 8.5 | 8.0 | 8.0 |
| | 0.0320 | 9.0 | 8.0 | 7.0 | 9.0 | 8.0 | 7.5 | | 8.0 | 7.5 | 7.0 | | 7.5 | 7.0 | 7.0 |
| | 0.0313 | 9.0 | 9.0 | 7.0 | 9.0 | | 7.0 | | 8.0 | 9.0 | 6.0 | | 7.0 | | 7.5 |
| | 0.0160 | 9.0 | 6.0 | 7.0 | 9.0 | | 2.5 | | 8.0 | 6.0 | 7.0 | | 5.5 | 6.5 | 7.0 |
| | 0.0156 | 9.0 | 2.0 | 2.0 | 9.0 | 9.0 | 9.0 | | 6.0 | 6.0 | 5.5 | | 7.0 | 9.0 | 9.0 |
| 180 | 0.2500 | 9.0 | 9.0 | 9.0 | 9.0 | 9.0 | 9.0 | | 9.0 | 9.0 | 9.0 | | 8.0 | 8.0 | 9.0 |
| | 0.1250 | 9.0 | 9.0 | 6.0 | 9.0 | 9.0 | 9.0 | | 9.0 | 9.0 | 8.0 | | 8.0 | | 9.0 |
| | 0.0640 | 9.0 | 9.0 | 7.0 | 9.0 | | 9.0 | | 9.0 | 9.0 | 9.0 | | 9.0 | | 7.0 |
| | 0.0313 | 9.0 | 9.0 | 7.0 | 9.0 | 8.0 | 9.0 | | 9.0 | 9.0 | 9.0 | | 8.0 | 8.0 | 8.0 |
| | 0.0320 | 9.0 | 9.0 | 6.0 | 9.0 | | 9.0 | | 8.0 | 8.0 | 7.0 | | 7.0 | | 7.0 |
| | 0.0160 | 9.0 | 9.0 | 5.0 | 9.0 | 7.0 | 9.0 | | 8.0 | 9.0 | 7.0 | | 7.0 | 7.0 | 6.0 |
| | 0.0156 | 9.0 | 9.0 | 6.0 | 9.0 | | 9.0 | | 6.0 | 7.0 | 7.0 | | 7.0 | | 7.0 |
| 181 | 0.2500 | 9.0 | 9.0 | 5.0 | 9.0 | 9.0 | 9.0 | | 7.0 | 7.0 | 9.0 | | 9.0 | 9.0 | 4.0 |
| | 0.1250 | 9.0 | 9.0 | 6.0 | 9.0 | 9.0 | 9.0 | | 8.0 | 9.0 | 7.0 | | 7.0 | 7.0 | 7.0 |
| | 0.0640 | 9.0 | 9.0 | 5.0 | 9.0 | 9.0 | 7.0 | | 8.0 | 9.0 | 7.0 | | 7.0 | 9.0 | 7.0 |
| | 0.0625 | 9.0 | 7.0 | 9.0 | 9.0 | | 6.0 | | 6.0 | 9.0 | 5.0 | | 4.0 | | 6.0 |
| | 0.0320 | 9.0 | 7.0 | 5.0 | 9.0 | 9.0 | 7.0 | | 9.0 | 9.0 | 7.0 | | 7.0 | 7.0 | 7.0 |
| | 0.0313 | 9.0 | 7.0 | 0.0 | 9.0 | | 5.0 | | 7.0 | 9.0 | 3.0 | | 5.0 | | 6.0 |
| | 0.0160 | 9.0 | 6.0 | 0.0 | 9.0 | 2.0 | 5.0 | | 7.0 | 8.0 | 6.0 | | 6.0 | 6.0 | 6.0 |
| | 0.0156 | 9.0 | 4.0 | 4.0 | 9.0 | | 1.0 | | 3.0 | 5.0 | 2.0 | | 2.0 | | 3.0 |
| 182 | 0.3125 | 9.0 | 7.0 | 8.0 | 9.0 | 8.0 | 5.0 | | 5.0 | 6.0 | 9.0 | | 4.0 | 4.0 | 3.0 |
| | 0.1563 | 9.0 | 9.0 | 3.0 | 9.0 | 9.0 | 9.0 | | 9.0 | 9.0 | 7.0 | | 7.0 | 0.0 | 7.0 |
| | 0.0781 | 9.0 | 9.0 | 0.0 | 9.0 | 5.0 | 9.0 | | 6.0 | 9.0 | 3.0 | | 4.0 | 0.0 | 3.0 |
| | 0.0391 | 9.0 | 9.0 | 0.0 | 9.0 | 0.0 | 0.0 | | 0.0 | 3.0 | 3.0 | | 4.0 | 0.0 | 3.0 |
| | 0.0195 | 9.0 | 0.0 | 0.0 | 9.0 | 0.0 | 0.0 | | 0.0 | 0.0 | 0.0 | | 0.0 | 0.0 | 0.0 |
| 183 | 0.3125 | 9.0 | 9.0 | 9.0 | 9.0 | 5.0 | 9.0 | | 9.0 | 9.0 | 5.0 | | 7.0 | 5.0 | 7.0 |
| | 0.1563 | 9.0 | 9.0 | 0.0 | 9.0 | 5.0 | 9.0 | | 8.0 | 9.0 | 3.0 | | 7.0 | 3.0 | 7.0 |

TABLE II-continued

Preemergence Herbicidal Evaluations of Test Compounds

| Compound Number | Rate (kg/ha) | ABUTH | AMBEL | CASOB | CHEAL | GALAP | IPOHE | IPOSS | ECHCG | SETVI | GLXMAW | GLXMA | ORYSAT | TRZAWR | ZEAMX |
|---|---|---|---|---|---|---|---|---|---|---|---|---|---|---|---|
|  | 0.0781 | 9.0 | 9.0 | 0.0 | 9.0 | 5.0 | 9.0 |  | 6.0 | 9.0 | 3.0 |  | 7.0 | 0.0 | 7.0 |
|  | 0.0391 | 9.0 | 0.0 | 0.0 | 9.0 | 5.0 | 0.0 |  | 3.0 | 3.0 | 0.0 |  | 1.0 | 0.0 | 7.0 |
|  | 0.0195 | 0.0 | 0.0 | 0.0 | 9.0 | 0.0 | 0.0 |  | 0.0 | 3.0 | 0.0 |  | 0.0 | 0.0 | 6.0 |
| 184 | 0.3130 | 9.0 | 9.0 | 9.0 | 9.0 | 9.0 | 9.0 |  | 8.0 | 9.0 | 9.0 |  | 8.0 | 2.0 | 8.0 |
|  | 0.1565 | 9.0 | 9.0 | 0.0 | 9.0 | 5.0 | 9.0 |  | 7.0 | 9.0 | 6.0 |  | 8.0 | 0.0 | 7.0 |
|  | 0.0783 | 9.0 | 9.0 | 0.0 | 9.0 | 5.0 | 9.0 |  | 2.0 | 7.0 | 3.0 |  | 7.0 | 0.0 | 7.0 |
|  | 0.0391 | 4.0 | 4.0 | 0.0 | 9.0 | 5.0 | 2.0 |  | 0.0 | 2.0 | 3.0 |  | 2.0 | 0.0 | 7.0 |
|  | 0.0196 |  | 0.0 | 0.0 | 9.0 | 5.0 | 2.0 |  | 0.0 | 0.0 | 1.0 |  | 1.0 | 0.0 | 7.0 |
| 185 | 0.0640 | 9.0 | 9.0 | 0.0 | 9.0 | 0.0 | 8.0 |  | 0.0 | 7.0 | 5.0 |  | 4.0 | 0.0 | 3.0 |
|  | 0.0320 | 9.0 | 5.0 | 0.0 | 9.0 | 0.0 | 0.0 |  | 0.0 | 0.0 | 0.0 |  | 3.0 | 0.0 | 3.0 |
|  | 0.0160 | 4.0 | 0.0 | 0.0 | 9.0 | 0.0 | 0.0 |  | 0.0 | 6.0 | 0.0 |  | 0.0 | 0.0 | 0.0 |
| 186 | 0.5000 | 9.0 | 9.0 | 9.0 | 9.0 | 9.0 | 9.0 |  | 0.0 | 0.0 | 0.0 |  | 0.0 | 0.0 | 0.0 |
|  | 0.2500 | 9.0 | 9.0 | 3.0 | 9.0 | 9.0 | 9.0 |  | 9.0 | 9.0 | 9.0 |  | 7.0 | 3.0 | 7.0 |
|  | 0.1250 | 9.0 | 9.0 | 3.0 | 9.0 | 3.0 | 9.0 |  | 9.0 | 9.0 | 9.0 |  | 7.0 | 0.0 | 7.0 |
|  | 0.0625 | 9.0 | 9.0 | 3.0 | 9.0 | 3.0 | 9.0 |  | 8.0 | 9.0 | 7.0 |  | 5.0 | 0.0 | 6.0 |
|  | 0.0313 | 9.0 | 0.0 | 0.0 | 9.0 | 3.0 | 0.0 |  | 5.0 | 0.0 | 4.0 |  | 3.0 | 0.0 | 5.0 |
|  | 0.0156 | 6.0 | 0.0 | 0.0 | 9.0 | 0.0 | 0.0 |  | 0.0 | 0.0 | 4.0 |  | 1.0 | 0.0 | 5.0 |
| 187 | 0.2500 | 9.0 | 9.0 | 9.0 | 9.0 | 3.0 | 9.0 |  | 6.0 | 9.0 | 9.0 |  | 5.0 | 0.0 | 5.0 |
|  | 0.1250 | 9.0 | 9.0 | 3.0 | 9.0 | 3.0 | 9.0 |  | 3.0 | 9.0 | 5.0 |  | 5.0 | 0.0 | 7.0 |
|  | 0.0625 | 9.0 | 0.0 | 0.0 | 9.0 | 0.0 | 0.0 |  | 0.0 | 7.0 | 3.0 |  | 0.0 | 0.0 | 6.0 |
|  | 0.0313 | 6.0 | 0.0 | 0.0 | 9.0 | 0.0 | 0.0 |  | 0.0 | 0.0 | 3.0 |  | 0.0 | 0.0 | 5.0 |
|  | 0.0156 | 0.0 | 0.0 | 0.0 | 9.0 | 0.0 | 0.0 |  | 0.0 | 0.0 | 0.0 |  | 0.0 | 0.0 | 0.0 |
| 188 | 0.2500 | 9.0 | 7.0 | 4.0 | 9.0 | 8.0 | 7.0 |  | 6.0 | 9.0 | 5.0 |  | 4.0 | 5.0 | 5.0 |
|  | 0.1250 | 9.0 | 6.0 | 3.0 | 9.0 | 1.0 | 9.0 |  | 4.0 | 9.0 | 5.0 |  | 4.0 | 6.0 | 5.0 |
|  | 0.0625 | 9.0 | 4.0 | 3.0 | 9.0 | 1.0 | 2.0 |  | 2.0 | 5.0 | 4.0 |  | 4.0 | 5.0 | 4.0 |
|  | 0.0313 | 7.0 | 4.0 | 9.0 | 9.0 | 6.0 | 5.0 |  | 1.0 | 5.0 | 5.0 |  | 3.0 |  | 4.0 |
|  | 0.0156 | 2.0 | 2.0 | 5.0 | 9.0 | 1.0 | 7.0 |  | 1.0 | 7.0 | 4.0 |  | 5.0 |  | 3.0 |
| 189 | 0.2500 | 9.0 | 9.0 | 4.0 | 9.0 | 7.0 | 7.0 |  | 8.0 | 9.0 | 4.0 |  | 7.0 | 7.0 | 7.0 |
|  | 0.1250 | 9.0 | 4.0 | 4.0 | 9.0 | 4.0 | 4.0 |  | 5.0 | 9.0 | 4.0 |  | 7.0 | 5.0 | 3.0 |
|  | 0.0625 | 6.0 | 4.0 |  | 9.0 | 2.0 | 4.0 |  | 4.0 | 7.0 | 5.0 |  | 7.0 | 5.0 | 3.0 |
|  | 0.0313 | 9.0 | 4.0 | 2.0 | 9.0 | 1.0 | 2.0 |  | 2.0 | 6.0 | 3.0 |  | 2.0 | 4.0 | 3.0 |
|  | 0.0156 | 9.0 | 3.0 | 2.0 | 9.0 | 1.0 | 1.0 |  | 1.0 | 1.0 | 3.0 |  | 2.0 | 2.0 | 2.0 |
| 190 | 0.2500 | 9.0 | 9.0 | 8.0 | 9.0 | 9.0 | 9.0 |  | 9.0 | 9.0 | 8.0 |  | 9.0 | 7.0 | 7.0 |
|  | 0.1250 | 9.0 | 9.0 | 5.5 | 9.0 | 7.5 | 9.0 |  | 7.5 | 9.0 | 6.5 |  | 8.0 | 5.5 | 5.5 |
|  | 0.0625 | 9.0 | 8.5 | 5.5 | 9.0 | 7.5 | 9.0 |  | 5.5 | 9.0 | 6.5 |  | 6.5 | 3.5 | 4.5 |
|  | 0.0313 | 6.5 | 3.5 | 3.0 | 8.5 | 6.5 | 6.5 |  | 3.5 | 6.5 | 6.0 |  | 4.0 | 4.0 | 3.0 |
|  | 0.0156 | 9.0 | 9.0 | 2.0 | 9.0 | 3.5 | 5.0 |  | 1.5 | 3.5 | 3.5 |  | 3.0 | 2.5 | 3.0 |
| 191 | 0.2500 | 9.0 | 9.0 | 8.0 | 9.0 | 9.0 | 9.0 |  | 9.0 | 9.0 | 8.5 |  | 8.0 | 9.0 | 7.0 |
|  | 0.1250 | 9.0 | 9.0 | 6.0 | 9.0 | 4.5 | 9.0 |  | 7.0 | 9.0 | 8.0 |  | 8.0 | 7.5 | 4.0 |
|  | 0.0625 | 9.0 | 9.0 | 5.0 | 9.0 | 3.0 | 6.5 |  | 6.0 | 9.0 | 9.0 |  | 7.5 | 6.0 | 4.5 |
|  | 0.0313 | 9.0 | 4.5 | 3.0 | 9.0 | 3.0 | 6.5 |  | 5.0 | 6.5 | 5.5 |  | 3.5 | 3.0 | 2.5 |
|  | 0.0156 | 9.0 | 9.0 | 7.0 | 9.0 | 7.0 | 6.0 |  | 2.0 | 5.5 | 4.0 |  | 2.0 | 2.5 | 2.5 |
| 192 | 0.2500 | 9.0 | 9.0 | 6.0 | 9.0 | 9.0 | 9.0 |  | 9.0 | 9.0 | 9.0 |  | 9.0 | 9.0 | 7.0 |
|  | 0.1250 | 9.0 | 9.0 | 5.0 | 9.0 | 7.0 | 9.0 |  | 5.0 | 9.0 | 6.0 |  | 7.0 | 9.0 | 6.0 |
|  | 0.0625 | 9.0 | 6.0 | 6.0 | 9.0 | 3.0 | 6.0 |  | 5.0 | 9.0 | 5.0 |  | 6.0 | 4.0 | 6.0 |
|  | 0.0313 | 9.0 | 6.0 | 5.0 | 9.0 | 3.0 | 6.0 |  | 4.0 | 5.0 | 5.0 |  | 5.0 | 5.0 | 5.0 |
|  | 0.0156 | 6.0 | 7.0 | 6.0 | 9.0 | 4.0 | 5.0 |  | 4.0 | 5.0 | 5.0 |  | 5.0 | 4.0 | 4.0 |

TABLE II-continued

Preemergence Herbicidal Evaluations of Test Compounds

| Compound Number | Rate (kg/ha) | ABUTH | AMBEL | CASOB | CHEAL | GALAP | IPOHE | IPOSS | ECHCG | SETVI | GLXMAW | GLXMA | ORYSAT | TRZAWR | ZEAMX |
|---|---|---|---|---|---|---|---|---|---|---|---|---|---|---|---|
| 193 | 0.2500 | 9.0 | 4.5 | 3.0 | 9.0 | 4.0 | 5.5 | | 4.0 | 9.0 | 3.0 | | 4.5 | 8.5 | 2.5 |
| | 0.1250 | 8.0 | 2.0 | 1.5 | 9.0 | 4.5 | 3.0 | | 1.5 | 4.5 | 3.0 | | 3.5 | 7.0 | 2.0 |
| | 0.0625 | 5.0 | 3.0 | 2.5 | 9.0 | 3.0 | 4.0 | | 1.0 | 3.0 | 3.5 | | 2.5 | 3.0 | 2.5 |
| | 0.0313 | 4.5 | 0.5 | 6.0 | 9.0 | 5.0 | 1.0 | | 0.5 | 1.0 | 3.0 | | 2.0 | 2.5 | 1.5 |
| | 0.0156 | 9.0 | 0.5 | 1.0 | 6.5 | 3.0 | 4.0 | | 1.0 | 1.5 | 3.5 | | 2.0 | 2.0 | 1.5 |
| 468 | 0.2500 | 9.0 | 5.0 | 5.0 | 5.0 | 5.0 | | | | | 5.0 | | | | |
| | 0.1250 | 9.0 | 6.0 | 7.0 | 7.0 | 4.0 | | | | | 5.0 | | | | |
| | 0.0620 | 7.0 | 6.0 | 6.0 | 6.0 | 4.0 | | | | | 3.0 | | | | |
| | 0.0320 | 7.0 | 5.0 | 2.0 | 5.0 | 3.0 | | | | | 3.0 | | | | |
| 469 | 0.2500 | 9.0 | 7.0 | 6.0 | 8.0 | 3.0 | | | | | 1.5 | | | | |
| | 0.1250 | 9.0 | 6.5 | 9.0 | 5.0 | 2.5 | | | | | 0.0 | | | | |
| | 0.0620 | 9.0 | 1.5 | 4.5 | 4.5 | 1.5 | | | | | 0.0 | | | | |
| | 0.0320 | 7.0 | 0.0 | 0.0 | 2.0 | 0.0 | | | | | 0.0 | | | | |
| 470 | 0.2500 | 9.0 | 7.0 | 4.5 | 3.0 | 1.5 | | | | | 1.5 | | | | |
| | 0.1250 | 9.0 | 6.0 | 3.0 | 2.0 | 0.0 | | | | | 1.0 | | | | |
| | 0.0620 | 9.0 | 0.0 | 2.0 | 2.0 | 0.0 | | | | | 0.0 | | | | |
| | 0.0320 | 8.5 | 0.0 | 1.5 | 1.5 | 0.0 | | | | | 0.0 | | | | |
| 471 | 0.2500 | 9.0 | 9.0 | 9.0 | 9.0 | 7.0 | | | | | 5.0 | | | | |
| | 0.1250 | 6.0 | 6.0 | 9.0 | 7.0 | 5.0 | | | | | 5.0 | | | | |
| | 0.0620 | 3.0 | 6.0 | 6.0 | 6.0 | 3.0 | | | | | 3.0 | | | | |
| | 0.0320 | 0.0 | 6.0 | 7.0 | 3.0 | 0.0 | | | | | 2.0 | | | | |
| 472 | 0.2500 | 4.0 | 6.0 | 7.0 | 3.0 | 0.0 | | | | | 6.0 | | | | |
| | 0.1250 | 4.0 | 5.0 | 7.0 | 2.0 | 0.0 | | | | | 3.0 | | | | |
| | 0.0620 | 3.0 | 4.0 | 6.0 | 0.0 | 0.0 | | | | | 1.0 | | | | |
| | 0.0320 | 3.0 | 4.0 | 5.0 | 0.0 | 0.0 | | | | | 0.0 | | | | |
| 473 | 0.2500 | 4.0 | 8.0 | 7.0 | 3.0 | 0.0 | | | | | 5.0 | | | | |
| | 0.1250 | 2.0 | 6.0 | 7.0 | 2.0 | 0.0 | | | | | 4.0 | | | | |
| | 0.0620 | 2.0 | 4.0 | 6.0 | 0.0 | 0.0 | | | | | 2.0 | | | | |
| | 0.0320 | 1.0 | 2.0 | 4.0 | 0.0 | 0.0 | | | | | 0.0 | | | | |
| 474 | 0.2500 | 0.0 | 6.0 | 9.0 | 9.0 | 0.0 | | | | | 3.0 | | | | |
| | 0.1250 | 0.0 | 4.0 | 7.0 | 7.0 | 0.0 | | | | | 2.0 | | | | |
| | 0.0620 | 0.0 | 5.0 | 7.0 | 3.0 | 0.0 | | | | | 0.0 | | | | |
| | 0.0320 | 0.0 | 2.0 | 3.0 | 2.0 | 0.0 | | | | | 0.0 | | | | |
| 475 | 0.2500 | 3.0 | 9.0 | 7.0 | 9.0 | 7.0 | | | | | 9.0 | | | | |
| | 0.1250 | 2.0 | 9.0 | 5.0 | 9.0 | 6.0 | | | | | 3.0 | | | | |
| | 0.0620 | 0.0 | 6.0 | 9.0 | 9.0 | 4.0 | | | | | 0.0 | | | | |
| | 0.0320 | 0.0 | 4.0 | 9.0 | 9.0 | 0.0 | | | | | 0.0 | | | | |
| 476 | 0.2500 | 3.0 | 9.0 | 9.0 | 9.0 | 5.0 | | | | | 6.0 | | | | |
| | 0.1250 | 2.0 | 9.0 | 6.0 | 6.0 | 4.0 | | | | | 4.0 | | | | |
| | 0.0620 | 2.0 | 4.0 | 6.0 | 2.0 | 2.0 | | | | | 3.0 | | | | |
| | 0.0320 | 0.0 | 4.0 | 6.0 | 5.0 | 0.0 | | | | | 2.0 | | | | |
| 477 | 0.2500 | 3.0 | 6.0 | 9.0 | 7.0 | 2.0 | | | | | 6.0 | | | | |
| | 0.1250 | 2.0 | 5.0 | 7.0 | 6.0 | 0.0 | | | | | 4.0 | | | | |
| | 0.0620 | 0.0 | 4.0 | 6.0 | 0.0 | 0.0 | | | | | 4.0 | | | | |
| | 0.0320 | 0.0 | 4.0 | 3.0 | 0.0 | 0.0 | | | | | 3.0 | | | | |
| 478 | 0.2500 | 9.0 | 9.0 | 9.0 | 9.0 | 9.0 | | | | | 9.0 | | | | |
| | 0.1250 | 7.0 | 9.0 | 9.0 | 9.0 | 9.0 | | | | | 9.0 | | | | |

TABLE II-continued

Preemergence Herbicidal Evaluations of Test Compounds

| Compound Number | Rate (kg/ha) | ABUTH | AMBEL | CASOB | CHEAL | GALAP | IPOHE | IPOSS | ECHCG | SETVI | GLXMAW | GLXMA | ORYSAT | TRZAWR | ZEAMX |
|---|---|---|---|---|---|---|---|---|---|---|---|---|---|---|---|
| 479 | 0.0620 | 6.0 | 9.0 | 7.0 | 9.0 | 6.0 | | | | | 9.0 | | | | |
|  | 0.0320 | 4.0 | 4.0 | 6.0 | 7.0 | 6.0 | | | | | 7.0 | | | | |
|  | 0.2500 | 9.0 | 9.0 | 9.0 | 9.0 | 8.0 | | | | | 9.0 | | | | |
|  | 0.1250 | 9.0 | 5.0 | 9.0 | 9.0 | 6.0 | | | | | 9.0 | | | | |
|  | 0.0620 | 7.0 | 0.0 | 7.0 | 7.0 | 5.0 | | | | | 5.0 | | | | |
|  | 0.0320 | 7.0 | 0.0 | 0.0 | 0.0 | 3.0 | | | | | 5.0 | | | | |
| 480 | 0.2500 | 6.0 | 9.0 | 9.0 | 9.0 | 6.0 | | | | | 6.0 | | | | |
|  | 0.1250 | 5.0 | 9.0 | 3.0 | 9.0 | 5.0 | | | | | 5.0 | | | | |
|  | 0.0620 | 2.0 | 9.0 | | 9.0 | 5.0 | | | | | 5.0 | | | | |
|  | 0.0320 | 0.0 | 6.0 | 3.0 | 7.0 | 3.0 | | | | | 4.0 | | | | |
| 481 | 0.2500 | 9.0 | 9.0 | 6.0 | 9.0 | 0.0 | | | | | 7.0 | | | | |
|  | 0.1250 | 9.0 | 6.0 | | 7.0 | 0.0 | | | | | 2.0 | | | | |
|  | 0.0620 | 2.0 | 2.0 | | 7.0 | 0.0 | | | | | 0.0 | | | | |
|  | 0.0320 | 0.0 | 0.0 | | 6.0 | 0.0 | | | | | 0.0 | | | | |
| 482 | 0.2500 | 9.0 | 6.0 | | 7.0 | 7.0 | | | | | 7.0 | | | | |
|  | 0.1250 | 9.0 | 0.0 | | 6.0 | 5.0 | | | | | 6.0 | | | | |
|  | 0.0620 | 7.0 | 0.0 | | 5.0 | 4.0 | | | | | 2.0 | | | | |
|  | 0.0320 | 4.0 | 0.0 | | 4.0 | 3.0 | | | | | 0.0 | | | | |
| 483 | 0.2500 | 7.0 | 6.0 | 6.0 | 9.0 | 5.0 | | | | | 6.0 | | | | |
|  | 0.1250 | 7.0 | 5.0 | | 9.0 | 3.0 | | | | | 5.0 | | | | |
|  | 0.0620 | 7.0 | 2.0 | 4.0 | 6.0 | 0.0 | | | | | 3.0 | | | | |
|  | 0.320 | 6.0 | 0.0 | | 7.0 | 0.0 | | | | | 0.0 | | | | |
| 484 | 0.2500 | 9.0 | 9.0 | | 9.0 | | | | | | 6.0 | | | | |
|  | 0.1250 | 7.0 | 6.0 | | 9.0 | | | | | | 6.0 | | | | |
|  | 0.0620 | 4.0 | 4.0 | | 9.0 | | | | | | 5.0 | | | | |
|  | 0.0320 | 5.0 | 4.0 | 0.0 | 7.0 | 5.0 | | | | | 5.0 | | | | |
| 485 | 0.2500 | 9.0 | 6.0 | | 8.0 | 3.0 | | | | | 5.0 | | | | |
|  | 0.1250 | 6.0 | 5.0 | | 7.0 | 0.0 | | | | | 4.0 | | | | |
|  | 0.0620 | 6.0 | 4.0 | 0.0 | 7.0 | 0.0 | | | | | 2.0 | | | | |
|  | 0.0320 | 4.0 | 2.0 | 0.0 | 6.0 | 0.0 | | | | | 0.0 | | | | |
| 486 | 0.2500 | 9.0 | 6.0 | 3.0 | 9.0 | 6.0 | | | | | 6.0 | | | | |
|  | 0.1250 | 7.0 | 6.0 | | 7.0 | 3.0 | | | | | 5.0 | | | | |
|  | 0.0620 | 6.0 | 5.0 | 0.0 | 6.0 | 0.0 | | | | | 3.0 | | | | |
|  | 0.0320 | 4.0 | 4.0 | 0.0 | 5.0 | 0.0 | | | | | 0.0 | | | | |
| 487 | 0.2500 | 9.0 | 9.0 | 3.0 | 9.0 | 9.0 | | | | | 7.0 | | | | |
|  | 0.1250 | 7.0 | 6.0 | | 9.0 | 7.0 | | | | | 6.0 | | | | |
|  | 0.0620 | 7.0 | 5.0 | | 7.0 | 6.0 | | | | | 3.0 | | | | |
|  | 0.0320 | 6.0 | 4.0 | | 7.0 | 5.0 | | | | | 2.0 | | | | |
| 488 | 0.2500 | 0.0 | 5.0 | 0.0 | 9.0 | 4.0 | | | | | 4.0 | | | | |
|  | 0.1250 | 0.0 | 4.0 | 0.0 | 9.0 | 0.0 | | | | | 4.0 | | | | |
|  | 0.0620 | 0.0 | 3.0 | | 7.0 | 0.0 | | | | | 3.0 | | | | |
|  | 0.0320 | 0.0 | 3.0 | | 9.0 | 0.0 | | | | | 3.0 | | | | |
| 489 | 0.2500 | 9.0 | 9.0 | 9.0 | 9.0 | 9.0 | | | | | 6.0 | | | | |
|  | 0.1250 | 9.0 | 9.0 | 9.0 | 9.0 | 9.0 | | | | | 6.0 | | | | |
|  | 0.0620 | 7.0 | 6.0 | 7.0 | 9.0 | 9.0 | | | | | 6.0 | | | | |
|  | 0.0320 | 0.0 | 6.0 | 6.0 | 9.0 | 6.0 | | | | | 5.0 | | | | |
| 490 | 0.2500 | 9.0 | 9.0 | 9.0 | 9.0 | 9.0 | | | | | 9.0 | | | | |

TABLE II-continued

Preemergence Herbicidal Evaluations of Test Compounds

| Compound Number | Rate (kg/ha) | ABUTH | AMBEL | CASOB | CHEAL | GALAP | IPOHE | IPOSS | ECHCG | SETVI | GLXMAW | GLXMA | ORYSAT | TRZAWR | ZEAMX |
|---|---|---|---|---|---|---|---|---|---|---|---|---|---|---|---|
| | 0.1250 | 9.0 | 9.0 | 9.0 | 9.0 | 9.0 | | | | | 8.5 | | | | |
| | 0.0620 | 9.0 | 9.0 | 9.0 | 9.0 | 9.0 | | | | | 9.0 | | | | |
| | 0.0320 | 8.0 | 9.0 | 9.0 | 9.0 | 6.0 | | | | | 7.5 | | | | |
| 491 | 0.2500 | 9.0 | 9.0 | 9.0 | 9.0 | 9.0 | | | | | 7.5 | | | | |
| | 0.1250 | 9.0 | 9.0 | 9.0 | 9.0 | 9.0 | | | | | 8.0 | | | | |
| | 0.0620 | 9.0 | 7.5 | 9.0 | 9.0 | 5.5 | | | | | 6.5 | | | | |
| | 0.0320 | 9.0 | 5.0 | 7.0 | 9.0 | 5.0 | | | | | 5.0 | | | | |
| 492 | 0.2500 | 9.0 | 4.0 | 0.0 | 7.0 | 2.0 | | | | | 3.0 | | | | |
| | 0.1250 | 6.0 | 4.0 | | 7.0 | 0.0 | | | | | 2.0 | | | | |
| | 0.0620 | 6.0 | 4.0 | | 6.0 | 0.0 | | | | | 2.0 | | | | |
| | 0.0320 | 4.0 | 4.0 | | 6.0 | 0.0 | | | | | 2.0 | | | | |
| 493 | 0.2500 | 9.0 | 9.0 | 9.0 | 9.0 | 3.0 | | | | | 3.0 | | | | |
| | 0.1250 | 9.0 | 7.0 | 9.0 | 7.0 | 0.0 | | | | | 3.0 | | | | |
| | 0.0620 | 5.0 | 6.0 | | 7.0 | 0.0 | | | | | 3.0 | | | | |
| | 0.0320 | 4.0 | 4.0 | | 5.0 | 0.0 | | | | | 2.0 | | | | |
| 494 | 0.2500 | 3.0 | 5.0 | 3.0 | 6.0 | 3.0 | | | | | 2.0 | | | | |
| | 0.1250 | 3.0 | 5.0 | 0.0 | 5.0 | 0.0 | | | | | 0.0 | | | | |
| | 0.0620 | 2.0 | 4.0 | | 4.0 | 0.0 | | | | | 0.0 | | | | |
| | 0.0320 | 0.0 | 3.0 | | 4.0 | 0.0 | | | | | 0.0 | | | | |
| 495 | 0.2500 | 7.0 | 9.0 | | 9.0 | 3.0 | | | | | 0.0 | | | | |
| | 0.1250 | 5.0 | 7.0 | | 7.0 | 0.0 | | | | | 7.0 | | | | |
| | 0.0620 | 4.0 | 6.0 | | 7.0 | 0.0 | | | | | 5.0 | | | | |
| | 0.0320 | 3.0 | 6.0 | | 7.0 | 0.0 | | | | | 4.0 | | | | |
| 496 | 0.2500 | 7.0 | 9.0 | 7.0 | 8.0 | 6.0 | | | | | 2.0 | | | | |
| | 0.1250 | 6.0 | 7.0 | | 6.0 | 3.0 | | | | | 5.0 | | | | |
| | 0.0620 | 4.0 | 7.0 | | 6.0 | 0.0 | | | | | 3.0 | | | | |
| | 0.0320 | 4.0 | 0.0 | | 0.0 | 0.0 | | | | | 3.0 | | | | |
| 497 | 0.2500 | 7.0 | 9.0 | 9.0 | 9.0 | 6.0 | | | | | 0.0 | | | | |
| | 0.1250 | 4.0 | 9.0 | 6.0 | 9.0 | 2.0 | | | | | 8.0 | | | | |
| | 0.0620 | 0.0 | 6.0 | | 7.0 | 0.0 | | | | | 7.0 | | | | |
| | 0.0320 | 0.0 | 5.0 | | 6.0 | 0.0 | | | | | 3.0 | | | | |
| 498 | 0.2500 | 6.0 | 9.0 | | 8.0 | 6.0 | | | | | 0.0 | | | | |
| | 0.1250 | 5.0 | 9.0 | 0.0 | 7.0 | 3.0 | | | | | 6.0 | | | | |
| | 0.0620 | 3.0 | 5.0 | | 5.0 | 0.0 | | | | | 3.0 | | | | |
| | 0.0320 | 0.0 | 2.0 | | 4.0 | 0.0 | | | | | 2.0 | | | | |
| 499 | 0.2500 | 9.0 | 9.0 | 9.0 | 9.0 | 9.0 | | | | | 0.0 | | | | |
| | 0.1250 | 9.0 | 9.0 | 9.0 | 9.0 | 9.0 | | | | | 9.0 | | | | |
| | 0.0620 | 9.0 | 9.0 | 9.0 | 9.0 | 9.0 | | | | | 7.5 | | | | |
| | 0.0320 | 7.5 | 8.0 | 9.0 | 8.0 | 8.0 | | | | | 8.0 | | | | |
| 500 | 0.2500 | 9.0 | 9.0 | 9.0 | 9.0 | 9.0 | | | | | 6.5 | | | | |
| | 0.1250 | 7.0 | 6.0 | 9.0 | 9.0 | 7.0 | | | | | 2.0 | | | | |
| | 0.0620 | 6.0 | 6.0 | 7.0 | 7.0 | 5.0 | | | | | 2.0 | | | | |
| | 0.0320 | 4.0 | 6.0 | 9.0 | 9.0 | 6.0 | | | | | 2.0 | | | | |
| 501 | 0.2500 | 7.0 | 4.0 | 7.0 | 7.0 | 5.0 | | | | | 4.0 | | | | |
| | 0.1250 | 5.0 | 2.0 | 6.0 | 6.0 | 3.0 | | | | | 3.0 | | | | |
| | 0.0620 | 5.0 | 0.0 | 6.0 | 3.0 | 0.0 | | | | | 1.0 | | | | |
| | 0.0320 | 4.0 | 0.0 | 6.0 | 2.0 | 0.0 | | | | | 0.0 | | | | |

TABLE II-continued

Preemergence Herbicidal Evaluations of Test Compounds

| Compound Number | Rate (kg/ha) | ABUTH | AMBEL | CASOB | CHEAL | GALAP | IPOHE | IPOSS | ECHCG | SETVI | GLXMAW | GLXMA | ORYSAT | TRZAWR | ZEAMX |
|---|---|---|---|---|---|---|---|---|---|---|---|---|---|---|---|
| 502 | 0.2500 | 7.0 | 9.0 | 5.0 | 9.0 | 9.0 | | | | | 6.0 | | | | |
|  | 0.1250 | 5.0 | 9.0 | | 7.0 | 5.0 | | | | | 5.0 | | | | |
|  | 0.0620 | 3.0 | 6.0 | 2.0 | 6.0 | 2.0 | | | | | 2.0 | | | | |
|  | 0.0320 | 3.0 | 4.0 | 0.0 | 6.0 | 0.0 | | | | | 2.0 | | | | |
| 503 | 0.2500 | 6.0 | 7.0 | 6.0 | 9.0 | 8.0 | | | | | 6.0 | | | | |
|  | 0.1250 | 6.0 | 9.0 | 6.0 | 9.0 | 4.0 | | | | | 7.0 | | | | |
|  | 0.0620 | 4.0 | 6.0 | 5.0 | 9.0 | 3.0 | | | | | 3.0 | | | | |
|  | 0.0320 | 2.0 | 0.0 | | 7.0 | 0.0 | | | | | 1.0 | | | | |
| 504 | 0.2500 | 7.0 | 9.0 | | 9.0 | 0.0 | | | | | 5.0 | | | | |
|  | 0.1250 | 6.0 | 9.0 | | 9.0 | 7.0 | | | | | 3.0 | | | | |
|  | 0.0620 | 3.0 | 7.0 | 0.0 | 8.0 | | | | | | | | | | |
|  | 0.0320 | 2.0 | 4.0 | 0.0 | 6.0 | 0.0 | | | | | 3.0 | | | | |
| 505 | 0.2500 | 9.0 | 4.0 | 0.0 | 8.0 | 4.0 | | | | | 6.0 | | | | |
|  | 0.1250 | 7.0 | 3.0 | | 7.0 | 2.0 | | | | | 4.0 | | | | |
|  | 0.0620 | 6.0 | | 0.0 | 7.0 | 2.0 | | | | | 4.0 | | | | |
|  | 0.0320 | 6.0 | 0.0 | 0.0 | 7.0 | 0.0 | | | | | 4.0 | | | | |
| 506 | 0.2500 | 9.0 | 9.0 | 7.0 | 9.0 | 4.5 | | | | | 2.0 | | | | |
|  | 0.1250 | 9.0 | 9.0 | 4.5 | 9.0 | 3.0 | | | | | 1.5 | | | | |
|  | 0.0620 | 9.0 | 8.0 | 4.5 | 9.0 | 3.0 | | | | | 1.5 | | | | |
|  | 0.0320 | 7.5 | 6.5 | 4.5 | 8.0 | 2.5 | | | | | 1.5 | | | | |
| 507 | 0.2500 | 7.0 | 9.0 | | 9.0 | 9.0 | | | | | 5.0 | | | | |
|  | 0.1250 | 4.0 | 9.0 | | 9.0 | 9.0 | | | | | 7.0 | | | | |
|  | 0.0620 | 2.0 | 6.0 | | 9.0 | 9.0 | | | | | 5.0 | | | | |
|  | 0.0320 | 2.0 | 5.0 | 0.0 | 9.0 | 7.0 | | | | | 3.0 | | | | |
| 508 | 0.2500 | 9.0 | 9.0 | | 9.0 | 9.0 | | | | | 6.0 | | | | |
|  | 0.1250 | 6.0 | 7.0 | | 9.0 | 9.0 | | | | | 5.0 | | | | |
|  | 0.0620 | 5.0 | 7.0 | | 9.0 | 6.0 | | | | | 2.0 | | | | |
|  | 0.0320 | 2.0 | 6.0 | 0.0 | 9.0 | 5.0 | | | | | 0.0 | | | | |
| 509 | 0.2500 | 7.0 | 7.0 | 7.0 | 9.0 | 6.0 | | | | | 7.0 | | | | |
|  | 0.1250 | 2.0 | 4.0 | 0.0 | 4.0 | 3.0 | | | | | 3.0 | | | | |
|  | 0.0620 | 0.0 | 0.0 | 0.0 | 0.0 | 0.0 | | | | | 0.0 | | | | |
|  | 0.0320 | 0.0 | 0.0 | 0.0 | 0.0 | 0.0 | | | | | 0.0 | | | | |
| 510 | 0.2500 | 9.0 | 8.0 | 5.0 | 9.0 | 6.0 | | | | | 8.0 | | | | |
|  | 0.1250 | 9.0 | 7.0 | 3.0 | 9.0 | 5.0 | | | | | 4.0 | | | | |
|  | 0.0620 | 9.0 | 3.0 | 0.0 | 9.0 | 6.0 | | | | | 2.0 | | | | |
|  | 0.0320 | 9.0 | 0.0 | 0.0 | 7.0 | 4.0 | | | | | 0.0 | | | | |
| 511 | 0.2500 | 7.0 | 7.0 | 3.0 | 9.0 | 3.0 | | | | | 6.0 | | | | |
|  | 0.1250 | 5.0 | 2.0 | 3.0 | 7.0 | 0.0 | | | | | 5.0 | | | | |
|  | 0.0620 | 2.0 | 0.0 | 0.0 | 0.0 | 0.0 | | | | | 4.0 | | | | |
|  | 0.0320 | 0.0 | 0.0 | 0.0 | 0.0 | 0.0 | | | | | 3.0 | | | | |
| 512 | 0.2500 | 9.0 | 5.0 | 9.0 | 9.0 | 4.0 | | | | | 2.0 | | | | |
|  | 0.1250 | 9.0 | 5.0 | 9.0 | 9.0 | 2.0 | | | | | 1.0 | | | | |
|  | 0.0620 | 7.0 | 2.0 | 9.0 | 9.0 | 0.0 | | | | | 0.0 | | | | |
|  | 0.0320 | 7.0 | 0.0 | 9.0 | 9.0 | 0.0 | | | | | 0.0 | | | | |
| 513 | 0.2500 | 8.0 | 9.0 | 9.0 | 9.0 | 9.0 | | | | | 9.0 | | | | |
|  | 0.1250 | 7.0 | 6.0 | 9.0 | 9.0 | 9.0 | | | | | 9.0 | | | | |
|  | 0.0620 | 5.0 | 4.0 | 9.0 | 9.0 | 9.0 | | | | | 7.0 | | | | |
|  | 0.0320 | 0.0 | 4.0 | 9.0 | 9.0 | 9.0 | | | | | 9.0 | | | | |

TABLE II-continued

Preemergence Herbicidal Evaluations of Test Compounds

| Compound Number | Rate (kg/ha) | ABUTH | AMBEL | CASOB | CHEAL | GALAP | IPOHE | IPOSS | ECHCG | SETVI | GLXMAW | GLXMA | ORYSAT | TRZAWR | ZEAMX |
|---|---|---|---|---|---|---|---|---|---|---|---|---|---|---|---|
| 514 | 0.2500 | 8.0 | 7.0 | 0.0 | 9.0 | 0.0 | | | | | 4.0 | | | | |
| | 0.1250 | 2.0 | 2.0 | 0.0 | 9.0 | 0.0 | | | | | 1.0 | | | | |
| | 0.0620 | 1.0 | 0.0 | 0.0 | 9.0 | 0.0 | | | | | 2.0 | | | | |
| | 0.0320 | 0.0 | 0.0 | 0.0 | 9.0 | 0.0 | | | | | 2.0 | | | | |
| 515 | 0.2500 | 9.0 | 7.0 | 0.0 | 9.0 | 0.0 | | | | | 6.0 | | | | |
| | 0.1250 | 8.0 | 4.0 | 0.0 | 9.0 | 0.0 | | | | | 4.0 | | | | |
| | 0.0620 | 6.0 | 2.0 | 0.0 | 9.0 | 0.0 | | | | | 2.0 | | | | |
| | 0.0320 | 2.0 | 0.0 | 0.0 | 9.0 | 0.0 | | | | | 0.0 | | | | |
| 516 | 0.2500 | 0.0 | 0.0 | 0.0 | 9.0 | 0.0 | | | | | 3.0 | | | | |
| | 0.1250 | 0.0 | 2.0 | 0.0 | 8.0 | 0.0 | | | | | 2.0 | | | | |
| | 0.0620 | 0.0 | 0.0 | 0.0 | 6.0 | 0.0 | | | | | 1.0 | | | | |
| | 0.0320 | 0.0 | 0.0 | 0.0 | 4.0 | 0.0 | | | | | 0.0 | | | | |
| 517 | 0.2500 | 9.0 | 7.0 | 0.0 | 9.0 | 0.0 | | | | | 3.0 | | | | |
| | 0.1250 | 8.0 | 5.5 | 4.5 | 9.0 | 0.0 | | | | | 1.5 | | | | |
| | 0.0620 | 9.0 | 6.5 | 4.5 | 9.0 | 0.0 | | | | | 0.0 | | | | |
| | 0.0320 | 9.0 | 5.5 | 3.0 | 9.0 | 0.0 | | | | | 0.0 | | | | |
| 518 | 0.2500 | 7.0 | 4.0 | 0.0 | 9.0 | 0.0 | | | | | 4.0 | | | | |
| | 0.1250 | 4.0 | 2.0 | 0.0 | 9.0 | 0.0 | | | | | 4.0 | | | | |
| | 0.0620 | 2.0 | 0.0 | 0.0 | 7.0 | 0.0 | | | | | 2.0 | | | | |
| | 0.0320 | 0.0 | 0.0 | 0.0 | 4.0 | 0.0 | | | | | 1.0 | | | | |
| 519 | 0.2500 | 9.0 | 6.0 | 0.0 | 9.0 | 0.0 | | | | | 4.0 | | | | |
| | 0.1250 | 6.5 | 2.0 | 0.0 | 9.0 | 0.0 | | | | | 4.5 | | | | |
| | 0.0620 | 4.0 | 0.0 | 0.0 | 9.0 | 0.0 | | | | | 4.0 | | | | |
| | 0.0320 | 2.0 | 0.0 | 0.0 | 9.0 | 0.0 | | | | | 2.0 | | | | |
| 520 | 0.2500 | 9.0 | 4.0 | 0.0 | 9.0 | 0.0 | | | | | 3.0 | | | | |
| | 0.1250 | 8.5 | 2.0 | 0.0 | 9.0 | 0.0 | | | | | 4.5 | | | | |
| | 0.0620 | 8.0 | 0.0 | 0.0 | 9.0 | 0.0 | | | | | 3.5 | | | | |
| | 0.0320 | 6.5 | 2.0 | 0.0 | 9.0 | 0.0 | | | | | 2.0 | | | | |
| 521 | 0.2500 | 4.0 | 0.0 | 0.0 | 9.0 | 0.0 | | | | | 0.0 | | | | |
| | 0.1250 | 4.0 | 0.0 | 0.0 | 9.0 | 0.0 | | | | | 0.0 | | | | |
| | 0.0620 | 2.0 | 2.0 | 0.0 | 9.0 | 0.0 | | | | | 0.0 | | | | |
| | 0.0320 | 2.0 | 0.0 | 0.0 | 6.0 | 0.0 | | | | | 0.0 | | | | |
| 522 | 0.2500 | 9.0 | 2.0 | 0.0 | 9.0 | 0.0 | | | | | 4.5 | | | | |
| | 0.1250 | 8.0 | 0.0 | 0.0 | 9.0 | 0.0 | | | | | 4.0 | | | | |
| | 0.0620 | 6.5 | 0.0 | 0.0 | 9.0 | 0.0 | | | | | 4.0 | | | | |
| | 0.0320 | 5.5 | 0.0 | 0.0 | 9.0 | 0.0 | | | | | 2.5 | | | | |
| 523 | 0.2500 | 9.0 | 8.0 | 2.0 | 9.0 | 0.0 | | | | | 7.0 | | | | |
| | 0.1250 | 8.0 | 4.0 | 0.0 | 9.0 | 0.0 | | | | | 5.5 | | | | |
| | 0.0620 | 8.0 | 2.0 | 0.0 | 9.0 | 0.0 | | | | | 4.5 | | | | |
| | 0.0320 | 6.0 | 0.0 | 0.0 | 8.0 | 0.0 | | | | | 4.5 | | | | |
| 524 | 0.2500 | 9.0 | 7.0 | 6.0 | 9.0 | 0.0 | | | | | 9.0 | | | | |
| | 0.1250 | 9.0 | 4.0 | 2.0 | 9.0 | 0.0 | | | | | 7.0 | | | | |
| | 0.0620 | 9.0 | 2.0 | 0.0 | 9.0 | 0.0 | | | | | 4.0 | | | | |
| | 0.0320 | 7.0 | 0.0 | 0.0 | 9.0 | 0.0 | | | | | 2.0 | | | | |
| 525 | 0.2500 | 9.0 | 4.0 | 0.0 | 9.0 | 0.0 | | | | | 4.0 | | | | |
| | 0.1250 | 9.0 | 2.0 | 0.0 | 9.0 | 0.0 | | | | | 2.0 | | | | |
| | 0.0620 | 7.0 | 2.0 | 0.0 | 9.0 | 0.0 | | | | | 2.0 | | | | |

TABLE II-continued

Preemergence Herbicidal Evaluations of Test Compounds

| Compound Number | Rate (kg/ha) | ABUTH | AMBEL | CASOB | CHEAL | GALAP | IPOHE | IPOSS | ECHCG | SETVI | GLXMAW | GLXMA | ORYSAT | TRZAWR | ZEAMX |
|---|---|---|---|---|---|---|---|---|---|---|---|---|---|---|---|
| 526 | 0.0320 | 6.0 | 0.0 | 0.0 | 9.0 | 0.0 | | | | | 0.0 | | | | |
|  | 0.2500 | 6.0 | 9.0 | 0.0 | 9.0 | 0.0 | | | | | 3.0 | | | | |
|  | 0.1250 | 4.0 | 7.0 | 0.0 | 9.0 | 0.0 | | | | | 2.0 | | | | |
|  | 0.0620 | 2.0 | 4.0 | 0.0 | 9.0 | 0.0 | | | | | 2.0 | | | | |
|  | 0.0320 | 2.0 | 2.0 | 0.0 | 8.0 | 0.0 | | | | | 1.0 | | | | |
| 527 | 0.2500 | 9.0 | 4.0 | 0.0 | 9.0 | 0.0 | | | | | 4.0 | | | | |
|  | 0.1250 | 9.0 | 4.0 | 0.0 | 9.0 | 0.0 | | | | | 2.5 | | | | |
|  | 0.0620 | 8.0 | 2.0 | 0.0 | 9.0 | 0.0 | | | | | 2.5 | | | | |
|  | 0.0320 | 3.0 | 2.0 | 0.0 | 9.0 | 0.0 | | | | | 2.0 | | | | |
| 528 | 0.2500 | 9.0 | 9.0 | 0.0 | 9.0 | 3.0 | | | | | 9.0 | | | | |
|  | 0.1250 | 9.0 | 5.0 | 0.0 | 9.0 | 1.5 | | | | | 7.0 | | | | |
|  | 0.0620 | 9.0 | 5.0 | 0.0 | 9.0 | 0.0 | | | | | 3.5 | | | | |
|  | 0.0320 | 9.0 | 4.5 | 0.0 | 9.0 | 1.0 | | | | | 1.5 | | | | |
| 529 | 0.2500 | 9.0 | 0.0 | 0.0 | 0.0 | 9.0 | | | | | 9.0 | | | | |
|  | 0.1250 | 9.0 | 3.0 | 0.0 | 3.0 | 9.0 | | | | | 3.0 | | | | |
|  | 0.0620 | 9.0 | 3.0 | 0.0 | 3.0 | 9.0 | | | | | 0.0 | | | | |
|  | 0.0320 | 7.0 | 3.0 | 0.0 | 3.0 | 9.0 | | | | | 0.0 | | | | |
| 530 | 0.2500 | 9.0 | 9.0 | 0.0 | 9.0 | 3.0 | | | | | 9.0 | | | | |
|  | 0.1250 | 9.0 | 9.0 | 0.0 | 9.0 | 0.0 | | | | | 3.0 | | | | |
|  | 0.0620 | 9.0 | 0.0 | 0.0 | 9.0 | 0.0 | | | | | 0.0 | | | | |
| 531 | 0.2500 | 9.0 | 4.0 | 3.0 | 9.0 | 3.0 | | | | | 9.0 | | | | |
|  | 0.1250 | 9.0 | 4.0 | 3.0 | 9.0 | 3.0 | | | | | 3.0 | | | | |
|  | 0.0620 | 9.0 | 0.0 | 0.0 | 9.0 | 0.0 | | | | | 0.0 | | | | |
| 532 | 0.2500 | 9.0 | 9.0 | 0.0 | 9.0 | 0.0 | | | | | 2.0 | | | | |
|  | 0.1250 | 9.0 | 9.0 | 0.0 | 9.0 | 0.0 | | | | | 0.0 | | | | |
|  | 0.0620 | 9.0 | 9.0 | 0.0 | 9.0 | 0.0 | | | | | 0.0 | | | | |
|  | 0.0320 | 9.0 | 9.0 | 0.0 | 9.0 | 0.0 | | | | | 0.0 | | | | |
| 533 | 0.2500 | 9.0 | 9.0 | 9.0 | 9.0 | 4.0 | | | | | 8.0 | | | | |
|  | 0.1250 | 9.0 | 4.0 | 3.0 | 9.0 | 0.0 | | | | | 5.0 | | | | |
|  | 0.0620 | 9.0 | 3.0 | 0.0 | 9.0 | 0.0 | | | | | 4.5 | | | | |
|  | 0.0320 | 7.5 | 2.0 | 0.0 | 9.0 | 0.0 | | | | | 3.0 | | | | |
| 534 | 0.2500 | 9.0 | 9.0 | 0.0 | 9.0 | 0.0 | | | | | 4.5 | | | | |
|  | 0.1250 | 9.0 | 3.0 | 0.0 | 9.0 | 0.0 | | | | | 4.0 | | | | |
|  | 0.0620 | 4.5 | 3.0 | 5.0 | 9.0 | 0.0 | | | | | 4.0 | | | | |
|  | 0.0320 | 3.5 | 0.0 | 5.0 | 4.0 | 0.0 | | | | | 2.0 | | | | |
| 535 | 0.2500 | 4.0 | 9.0 | 3.0 | 9.0 | 3.0 | | | | | 9.0 | | | | |
|  | 0.1250 | 3.0 | 9.0 | 0.0 | 9.0 | 3.0 | | | | | 4.0 | | | | |
|  | 0.0620 | 3.0 | 6.0 | 0.0 | 6.0 | 0.0 | | | | | 3.0 | | | | |
|  | 0.0320 | 0.0 | 0.0 | 0.0 | 9.0 | 0.0 | | | | | 0.0 | | | | |
| 536 | 0.2500 | 9.0 | 4.0 | 0.0 | 9.0 | 0.0 | | | | | 4.0 | | | | |
|  | 0.1250 | 5.0 | 0.0 | 0.0 | 9.0 | 0.0 | | | | | 1.0 | | | | |
|  | 0.0620 | 4.0 | 0.0 | 0.0 | 9.0 | 0.0 | | | | | 0.0 | | | | |
|  | 0.0320 | 3.0 | 0.0 | 0.0 | 9.0 | 0.0 | | | | | 0.0 | | | | |
| 537 | 0.5000 | 9.0 | 9.0 | 0.0 | 9.0 | 0.0 | | | | | 0.0 | | | | |
|  | 0.2500 | 9.0 | 4.0 | 0.0 | 9.0 | 0.0 | | | | | 0.0 | | | | |

TABLE II-continued

Preemergence Herbicidal Evaluations of Test Compounds

| Compound Number | Rate (kg/ha) | ABUTH | AMBEL | CASOB | CHEAL | GALAP | IPOHE | IPOSS | ECHCG | SETVI | GLXMAW | GLXMA | ORYSAT | TRZAWR | ZEAMX |
|---|---|---|---|---|---|---|---|---|---|---|---|---|---|---|---|
| | 0.1250 | 5.0 | 1.0 | 0.0 | 9.0 | 0.0 | | | | | 0.0 | | | | |
| | 0.0620 | 4.4 | 0.0 | 0.0 | 9.0 | 0.0 | | | | | 0.0 | | | | |
| | 0.0320 | 3.4 | 0.0 | 0.0 | 9.0 | 0.0 | | | | | 0.0 | | | | |
| 538 | 0.5000 | 9.0 | 9.0 | 0.0 | 9.0 | 0.0 | | | | | 1.0 | | | | |
| | 0.2500 | 9.0 | 0.0 | 0.0 | 9.0 | 0.0 | | | | | 1.0 | | | | |
| | 0.1250 | 4.7 | 0.0 | 0.0 | 9.0 | 0.0 | | | | | 1.0 | | | | |
| | 0.0620 | 3.4 | 0.0 | 0.0 | 9.0 | 0.0 | | | | | 0.0 | | | | |
| | 0.0320 | 2.1 | 0.0 | 0.0 | 9.0 | 0.0 | | | | | 0.0 | | | | |
| 539 | 0.5000 | 9.0 | 9.0 | 0.0 | 9.0 | 9.0 | | | | | 5.0 | | | | |
| | 0.2500 | 7.0 | 8.0 | 2.0 | 9.0 | 4.0 | | | | | 1.0 | | | | |
| | 0.1250 | 4.7 | 6.0 | 0.0 | 9.0 | 1.0 | | | | | 1.0 | | | | |
| | 0.0620 | 3.0 | 2.0 | 0.0 | 9.0 | 0.0 | | | | | 1.0 | | | | |
| | 0.0320 | 2.1 | 0.0 | 0.0 | 8.0 | 0.0 | | | | | 0.0 | | | | |
| 540 | 0.5000 | 9.0 | 9.0 | 3.0 | 9.0 | 0.0 | | | | | 3.0 | | | | |
| | 0.2500 | 9.0 | 9.0 | 0.0 | 9.0 | 0.0 | | | | | 1.0 | | | | |
| | 0.1250 | 4.7 | 9.0 | 0.0 | 9.0 | 0.0 | | | | | 0.0 | | | | |
| | 0.0620 | 3.4 | 8.0 | 0.0 | 9.0 | 0.0 | | | | | 0.0 | | | | |
| | 0.0320 | 2.3 | 6.0 | 0.0 | 8.0 | 0.0 | | | | | 0.0 | | | | |
| 541 | 0.5000 | 6.0 | 9.0 | 0.0 | 9.0 | 0.0 | | | | | 2.0 | | | | |
| | 0.2500 | 4.0 | 6.0 | 0.0 | 9.0 | 0.0 | | | | | 0.0 | | | | |
| | 0.1250 | 0.0 | 4.0 | 0.0 | 9.0 | 0.0 | | | | | 0.0 | | | | |
| | 0.0620 | 0.0 | 3.0 | 0.0 | 9.0 | 0.0 | | | | | 0.0 | | | | |
| 542 | 0.5000 | 9.0 | 9.0 | 0.0 | 9.0 | 0.0 | | | | | 2.0 | | | | |
| | 0.2500 | 8.0 | 4.0 | 0.0 | 9.0 | 0.0 | | | | | 0.0 | | | | |
| | 0.1250 | 4.3 | 2.0 | 0.0 | 9.0 | 0.0 | | | | | 0.0 | | | | |
| | 0.0620 | 2.7 | 0.0 | | 9.0 | 0.0 | | | | | 0.0 | | | | |
| | 0.0320 | 1.7 | 0.0 | 0.0 | 7.0 | 0.0 | | | | | 0.0 | | | | |
| 543 | 0.5000 | 9.0 | 3.0 | 0.0 | 9.0 | 0.0 | | | | | 2.0 | | | | |
| | 0.2500 | 7.0 | 8.0 | 0.0 | 9.0 | 0.0 | | | | | 2.0 | | | | |
| | 0.1250 | 4.0 | 7.0 | 0.0 | 9.0 | 0.0 | | | | | 1.0 | | | | |
| | 0.0620 | 2.9 | 6.0 | 0.0 | 9.0 | 0.0 | | | | | 0.0 | | | | |
| | 0.0320 | 2.1 | 2.0 | 0.0 | 9.0 | 0.0 | | | | | 0.0 | | | | |
| 544 | 0.5000 | 9.0 | 9.0 | 4.0 | 9.0 | 9.0 | | | | | 8.0 | | | | |
| | 0.2500 | 9.0 | 9.0 | 9.0 | 9.0 | 9.0 | | | | | 9.0 | | | | |
| | 0.1250 | 6.4 | 9.0 | 7.0 | 9.0 | 8.0 | | | | | 9.0 | | | | |
| | 0.0620 | 5.6 | 9.0 | | 9.0 | 4.0 | | | | | 9.0 | | | | |
| | 0.0320 | 5.4 | 9.0 | 9.0 | 9.0 | 7.0 | | | | | 4.0 | | | | |
| 545 | 0.5000 | 9.0 | 9.0 | 6.0 | 9.0 | 9.0 | | | | | 9.0 | | | | |
| | 0.2500 | 9.0 | 7.0 | 9.0 | 9.0 | 7.0 | | | | | 9.0 | | | | |
| | 0.1250 | 7.0 | 6.0 | 0.0 | 9.0 | 4.0 | | | | | 4.0 | | | | |
| | 0.0620 | 6.6 | 5.0 | 0.0 | 7.0 | 0.0 | | | | | 2.0 | | | | |
| | 0.0320 | 5.6 | 4.0 | 0.0 | 6.0 | 0.0 | | | | | 2.0 | | | | |
| 546 | 0.5000 | 9.0 | 2.0 | 0.0 | 9.0 | 0.0 | | | | | 6.0 | | | | |
| | 0.2500 | 9.0 | 9.0 | 9.0 | 9.0 | 9.0 | | | | | 7.0 | | | | |
| | 0.1250 | 4.6 | 6.0 | 0.0 | 7.0 | 4.0 | | | | | 4.0 | | | | |
| | 0.0620 | 4.3 | 4.0 | 0.0 | 7.0 | 0.0 | | | | | 3.0 | | | | |
| | 0.0320 | 4.1 | 3.0 | 0.0 | 6.0 | 0.0 | | | | | 2.0 | | | | |

TABLE II-continued

Preemergence Herbicidal Evaluations of Test Compounds

| Compound Number | Rate (kg/ha) | ABUTH | AMBEL | CASOB | CHEAL | GALAP | IPOHE | IPOSS | ECHCG | SETVI | GLXMAW | GLXMA | ORYSAT | TRZAWR | ZEAMX |
|---|---|---|---|---|---|---|---|---|---|---|---|---|---|---|---|
| 547 | 0.5000 | 9.0 | 9.0 | 0.0 | 9.0 | 3.0 | | | | | 3.0 | | | | |
| | 0.2500 | 9.0 | 9.0 | 7.0 | 9.0 | 7.0 | | | | | 4.0 | | | | |
| | 0.1250 | 5.6 | 9.0 | 8.0 | 9.0 | 4.0 | | | | | 4.0 | | | | |
| | 0.0620 | 5.4 | 7.0 | 8.0 | 9.0 | 4.0 | | | | | 3.0 | | | | |
| | 0.0320 | 5.4 | 7.0 | 6.0 | 9.0 | 2.0 | | | | | 2.0 | | | | |
| 548 | 0.5000 | 6.0 | 0.0 | 9.0 | 9.0 | 0.0 | | | | | 4.0 | | | | |
| | 0.2500 | 9.0 | 9.0 | 9.0 | 9.0 | 4.0 | | | | | 6.0 | | | | |
| | 0.1250 | 4.9 | 8.0 | 9.0 | 9.0 | 2.0 | | | | | 4.0 | | | | |
| | 0.0620 | 3.7 | 6.0 | 9.0 | 9.0 | 0.0 | | | | | 2.0 | | | | |
| | 0.0320 | 2.9 | 2.0 | 9.0 | 8.0 | 0.0 | | | | | 3.0 | | | | |
| 549 | 0.5000 | 9.0 | 9.0 | 9.0 | 9.0 | 0.0 | | | | | 2.0 | | | | |
| | 0.2500 | 9.0 | 9.0 | 9.0 | 9.0 | 4.0 | | | | | 4.0 | | | | |
| | 0.1250 | 5.1 | 9.0 | 2.0 | 9.0 | 4.0 | | | | | 4.0 | | | | |
| | 0.0620 | 3.6 | 9.0 | 0.0 | 9.0 | 0.0 | | | | | 4.0 | | | | |
| | 0.0320 | 3.0 | 7.0 | 0.0 | 9.0 | 0.0 | | | | | 4.0 | | | | |
| 550 | 0.5000 | 9.0 | 5.0 | 0.0 | 9.0 | 0.0 | | | | | 0.0 | | | | |
| | 0.2500 | 9.0 | 7.0 | 0.0 | 9.0 | 0.0 | | | | | 0.0 | | | | |
| | 0.1250 | 5.9 | 8.0 | 0.0 | 9.0 | 0.0 | | | | | 0.0 | | | | |
| | 0.0620 | 5.9 | 8.0 | 0.0 | 9.0 | 0.0 | | | | | 3.0 | | | | |
| | 0.0320 | 4.7 | 2.0 | 0.0 | 9.0 | 0.0 | | | | | 3.0 | | | | |
| 551 | 0.5000 | 9.0 | 9.0 | 0.0 | 9.0 | 2.0 | | | | | 0.0 | | | | |
| | 0.2500 | 7.0 | 2.0 | 0.0 | 9.0 | 0.0 | | | | | 4.0 | | | | |
| | 0.1250 | 7.0 | 2.0 | 0.0 | 9.0 | 0.0 | | | | | 0.0 | | | | |
| | 0.0620 | 4.0 | 0.0 | 0.0 | 9.0 | 0.0 | | | | | 0.0 | | | | |
| 552 | 0.5000 | 9.0 | 9.0 | 9.0 | 9.0 | 5.0 | | | | | 4.0 | | | | |
| | 0.2500 | 9.0 | 9.0 | 9.0 | 9.0 | 0.0 | | | | | 7.0 | | | | |
| | 0.1250 | 4.7 | 7.0 | 4.0 | 9.0 | 0.0 | | | | | 6.0 | | | | |
| | 0.0620 | 3.7 | 8.0 | | 8.0 | 0.0 | | | | | 6.0 | | | | |
| | 0.0320 | 2.6 | 6.0 | 0.0 | 6.0 | 0.0 | | | | | 4.0 | | | | |
| 553 | 0.5000 | 7.0 | 4.0 | 9.0 | 9.0 | 0.0 | | | | | 6.0 | | | | |
| | 0.2500 | 9.0 | 9.0 | 2.0 | 9.0 | 0.0 | | | | | 4.0 | | | | |
| | 0.1250 | 6.4 | 7.0 | | 9.0 | 0.0 | | | | | 6.0 | | | | |
| | 0.0620 | 2.1 | 6.0 | 0.0 | 7.0 | 0.0 | | | | | 4.0 | | | | |
| | 0.0320 | 1.3 | 2.0 | 0.0 | 7.0 | 0.0 | | | | | 3.0 | | | | |
| 554 | 0.5000 | 7.0 | 5.0 | 9.0 | 9.0 | 0.0 | | | | | 6.0 | | | | |
| | 0.2500 | 9.0 | 9.0 | 9.0 | 9.0 | 9.0 | | | | | 7.0 | | | | |
| | 0.1250 | 5.7 | 9.0 | 4.0 | 9.0 | 9.0 | | | | | 6.0 | | | | |
| | 0.0620 | 4.1 | 7.0 | 0.0 | 9.0 | 7.0 | | | | | 4.0 | | | | |
| | 0.0320 | 3.0 | 2.0 | 0.0 | 9.0 | 2.0 | | | | | 4.0 | | | | |
| 555 | 0.5000 | 9.0 | 3.0 | 9.0 | 9.0 | 0.0 | | | | | 3.0 | | | | |
| | 0.2500 | 9.0 | 9.0 | 8.0 | 9.0 | 0.0 | | | | | 9.0 | | | | |
| | 0.1250 | 4.6 | 9.0 | 6.0 | 9.0 | 0.0 | | | | | 8.0 | | | | |
| | 0.0620 | 2.3 | 6.0 | 4.0 | 9.0 | 0.0 | | | | | 6.0 | | | | |
| | 0.0320 | 1.6 | 4.0 | 0.0 | 9.0 | 3.0 | | | | | 6.0 | | | | |
| 556 | 0.5000 | 9.0 | 3.0 | 9.0 | 9.0 | 4.0 | | | | | 5.0 | | | | |
| | 0.2500 | 9.0 | 9.0 | 9.0 | 9.0 | 4.0 | | | | | 9.0 | | | | |
| | 0.1250 | 4.4 | 7.0 | 9.0 | 9.0 | 6.0 | | | | | 8.0 | | | | |

TABLE II-continued

Preemergence Herbicidal Evaluations of Test Compounds

| Compound Number | Rate (kg/ha) | ABUTH | AMBEL | CASOB | CHEAL | GALAP | IPOHE | IPOSS | ECHCG | SETVI | GLXMAW | GLXMA | ORYSAT | TRZAWR | ZEAMX |
|---|---|---|---|---|---|---|---|---|---|---|---|---|---|---|---|
| 557 | 0.0620 | 3.6 | 2.0 | 2.0 | 9.0 | 0.0 | | | | | 7.0 | | | | |
|  | 0.0320 | 2.9 | 0.0 | 2.0 | 9.0 | 0.0 | | | | | 4.0 | | | | |
|  | 0.5000 | 9.0 | 9.0 | 5.0 | 9.0 | 4.0 | | | | | 9.0 | | | | |
|  | 0.2500 | 9.0 | 9.0 | 9.0 | 9.0 | 0.0 | | | | | 9.0 | | | | |
|  | 0.1250 | 6.3 | 9.0 | 9.0 | 9.0 | 2.0 | | | | | 8.0 | | | | |
|  | 0.0620 | 5.1 | 8.0 | 6.0 | 9.0 | 0.0 | | | | | 8.0 | | | | |
|  | 0.0320 | 4.3 | 4.0 | 0.0 | 9.0 | 0.0 | | | | | 6.0 | | | | |
| 558 | 0.5000 | 9.0 | 9.0 | 9.0 | 9.0 | 4.0 | | | | | 9.0 | | | | |
|  | 0.2500 | 9.0 | 9.0 | 9.0 | 9.0 | 8.0 | | | | | 9.0 | | | | |
|  | 0.1250 | 7.0 | 8.0 | 9.0 | 9.0 | 4.0 | | | | | 9.0 | | | | |
|  | 0.0620 | 4.7 | 6.0 | | 9.0 | 2.0 | | | | | 7.0 | | | | |
|  | 0.0320 | 4.3 | 2.0 | | 9.0 | 0.0 | | | | | 4.0 | | | | |
| 559 | 0.5000 | 9.0 | 4.0 | 9.0 | 9.0 | 0.0 | | | | | 2.0 | | | | |
|  | 0.2500 | 6.0 | 0.0 | 9.0 | 9.0 | 0.0 | | | | | 2.0 | | | | |
|  | 0.1250 | 3.0 | 0.0 | 0.0 | 9.0 | 0.0 | | | | | 2.0 | | | | |
|  | 0.0620 | 3.0 | 3.0 | 9.0 | 9.0 | 0.0 | | | | | 1.0 | | | | |
| 560 | 0.5000 | 7.0 | 9.0 | 9.0 | 9.0 | 0.0 | | | | | 1.0 | | | | |
|  | 0.2500 | 9.0 | 9.0 | 9.0 | 9.0 | 0.0 | | | | | 2.0 | | | | |
|  | 0.1250 | 4.6 | 7.0 | 7.0 | 9.0 | 0.0 | | | | | 4.0 | | | | |
|  | 0.0620 | 3.0 | 2.0 | 2.0 | 9.0 | 0.0 | | | | | 2.0 | | | | |
|  | 0.0320 | 2.0 | 0.0 | 0.0 | 8.0 | 0.0 | | | | | 3.0 | | | | |
| 561 | 0.5000 | 9.0 | 6.0 | 9.0 | 9.0 | 0.0 | | | | | 3.0 | | | | |
|  | 0.2500 | 9.0 | 9.0 | 9.0 | 9.0 | 3.0 | | | | | 2.0 | | | | |
|  | 0.1250 | 6.4 | 8.5 | 0.0 | 9.0 | 1.0 | | | | | 4.5 | | | | |
|  | 0.0620 | 4.8 | 6.0 | 0.0 | 9.0 | 0.0 | | | | | 3.5 | | | | |
|  | 0.0320 | 3.6 | 3.0 | 0.0 | 9.0 | 0.0 | | | | | 4.0 | | | | |
| 562 | 0.5000 | 9.0 | 3.0 | 0.0 | 9.0 | 0.0 | | | | | 2.5 | | | | |
|  | 0.2500 | 9.0 | 9.0 | 0.0 | 9.0 | 0.0 | | | | | 6.0 | | | | |
|  | 0.1250 | 5.1 | 9.0 | 0.0 | 9.0 | 7.0 | | | | | 9.0 | | | | |
|  | 0.0620 | 5.1 | 7.0 | 0.0 | 9.0 | 5.0 | | | | | 4.0 | | | | |
|  | 0.0320 | 2.7 | 2.0 | 4.0 | 9.0 | 0.0 | | | | | 3.0 | | | | |
| 563 | 0.5000 | 9.0 | 9.0 | 0.0 | 9.0 | 4.0 | | | | | 2.0 | | | | |
|  | 0.2500 | 9.0 | 6.0 | 4.0 | 9.0 | 2.0 | | | | | 4.0 | | | | |
|  | 0.1250 | 5.6 | 6.0 | 0.0 | 9.0 | 0.0 | | | | | 7.0 | | | | |
|  | 0.0620 | 5.1 | 2.0 | 0.0 | 8.0 | 0.0 | | | | | 7.0 | | | | |
|  | 0.0320 | 3.6 | 0.0 | 0.0 | 9.0 | 0.0 | | | | | 4.0 | | | | |
| 564 | 0.2500 | 7.0 | 9.0 | 4.0 | 9.0 | 0.0 | | | | | 0.0 | | | | |
|  | 0.1250 | 5.0 | 7.0 | 0.0 | 9.0 | 0.0 | | | | | 0.0 | | | | |
|  | 0.0620 | 4.0 | 6.0 | 0.0 | 9.0 | 0.0 | | | | | 0.0 | | | | |
|  | 0.0320 | 4.0 | 0.0 | 0.0 | 9.0 | 0.0 | | | | | 0.0 | | | | |
| 565 | 0.2500 | 0.0 | 6.0 | 0.0 | 9.0 | 0.0 | | | | | 3.0 | | | | |
|  | 0.1250 | 0.0 | 6.0 | 0.0 | 9.0 | 0.0 | | | | | 2.0 | | | | |
|  | 0.0620 | 0.0 | 3.0 | 0.0 | 9.0 | 0.0 | | | | | 0.0 | | | | |
|  | 0.0320 | 0.0 | 0.0 | 0.0 | 9.0 | 0.0 | | | | | 0.0 | | | | |
| 566 | 0.2500 | 6.0 | 0.0 | 3.0 | 9.0 | 0.0 | | | | | 6.0 | | | | |
|  | 0.1250 | 3.0 | 0.0 | 0.0 | 9.0 | 0.0 | | | | | 5.0 | | | | |
|  | 0.0620 | 3.0 | 0.0 | 0.0 | 9.0 | 0.0 | | | | | 3.0 | | | | |

TABLE II-continued

Preemergence Herbicidal Evaluations of Test Compounds

| Compound Number | Rate (kg/ha) | ABUTH | AMBEL | CASOB | CHEAL | GALAP | IPOHE | IPOSS | ECHCG | SETVI | GLXMAW | GLXMA | ORYSAT | TRZAWR | ZEAMX |
|---|---|---|---|---|---|---|---|---|---|---|---|---|---|---|---|
| 567 | 0.0320 | 3.0 | 0.0 | 0.0 | 9.0 | 0.0 | | | | | 2.0 | | | | |
| | 0.2500 | 4.0 | 9.0 | 0.0 | 9.0 | 0.0 | | | | | 2.0 | | | | |
| | 0.1250 | 2.0 | 4.0 | 0.0 | 9.0 | 0.0 | | | | | 1.0 | | | | |
| | 0.0620 | 0.0 | 9.0 | 0.0 | 3.0 | 0.0 | | | | | 0.0 | | | | |
| | 0.0320 | 0.0 | 4.0 | 0.0 | 0.0 | 0.0 | | | | | 0.0 | | | | |
| 568 | 0.2500 | 6.0 | 7.0 | 0.0 | 9.0 | 0.0 | | | | | 3.0 | | | | |
| | 0.1250 | 5.0 | 5.0 | 0.0 | 9.0 | 0.0 | | | | | 1.0 | | | | |
| | 0.0620 | 3.0 | 0.0 | 0.0 | 9.0 | 0.0 | | | | | 0.0 | | | | |
| | 0.0320 | 0.0 | 0.0 | 0.0 | 0.0 | 0.0 | | | | | 0.0 | | | | |
| 569 | 0.2500 | 5.0 | 0.0 | 0.0 | 6.0 | 9.0 | | | | | 1.0 | | | | |
| | 0.1250 | 5.0 | 0.0 | 0.0 | 6.0 | 0.0 | | | | | 0.0 | | | | |
| | 0.0620 | 4.0 | 0.0 | 0.0 | 6.0 | 0.0 | | | | | 0.0 | | | | |
| | 0.0320 | 2.0 | 0.0 | 0.0 | 4.0 | 0.0 | | | | | 0.0 | | | | |
| 570 | 0.2500 | 6.0 | 9.0 | 0.0 | 9.0 | 0.0 | | | | | 3.0 | | | | |
| | 0.1250 | 4.0 | 0.0 | 0.0 | 0.0 | 0.0 | | | | | 2.0 | | | | |
| | 0.0620 | 2.0 | 0.0 | 0.0 | 0.0 | 0.0 | | | | | 1.0 | | | | |
| | 0.0320 | 0.0 | 0.0 | 0.0 | 0.0 | 0.0 | | | | | 0.0 | | | | |
| 571 | 0.2500 | 6.0 | 9.0 | 0.0 | 9.0 | 0.0 | | | | | 2.0 | | | | |
| | 0.1250 | 3.0 | 3.0 | 0.0 | 7.0 | 0.0 | | | | | 1.0 | | | | |
| | 0.0620 | 2.0 | 3.0 | 0.0 | 6.0 | 0.0 | | | | | 0.0 | | | | |
| | 0.0320 | 0.0 | 0.0 | 0.0 | 0.0 | 0.0 | | | | | 0.0 | | | | |
| 572 | 0.2500 | 6.0 | 5.0 | 2.0 | 9.0 | 3.0 | | | | | 6.0 | | | | |
| | 0.1250 | 2.0 | 2.0 | 0.0 | 6.0 | 0.0 | | | | | 3.0 | | | | |
| | 0.0620 | 0.0 | 0.0 | 0.0 | 6.0 | 0.0 | | | | | 1.0 | | | | |
| | 0.0320 | 0.0 | 0.0 | 0.0 | 0.0 | 0.0 | | | | | 0.0 | | | | |
| 573 | 0.2500 | 7.0 | 5.0 | 4.0 | 9.0 | 2.0 | | | | | 1.0 | | | | |
| | 0.1250 | 7.0 | 5.0 | 0.0 | 9.0 | 0.0 | | | | | 0.0 | | | | |
| | 0.0620 | 7.0 | 3.0 | 0.0 | 9.0 | 0.0 | | | | | 0.0 | | | | |
| | 0.0320 | 6.0 | 0.0 | 0.0 | 0.0 | 0.0 | | | | | 0.0 | | | | |
| 574 | 0.2500 | 9.0 | 7.0 | 6.5 | 9.0 | 6.0 | | | | | 8.0 | | | | |
| | 0.1250 | 8.5 | 6.0 | 4.5 | 9.0 | 2.0 | | | | | 6.5 | | | | |
| | 0.0620 | 6.5 | 5.5 | 2.0 | 9.0 | 1.0 | | | | | 4.5 | | | | |
| | 0.0320 | 4.0 | 2.0 | 0.0 | 9.0 | 0.0 | | | | | 3.0 | | | | |
| 575 | 0.2500 | 9.0 | 6.0 | 2.0 | 9.0 | 3.0 | | | | | 2.0 | | | | |
| | 0.1250 | 6.0 | 4.0 | 0.0 | 4.0 | 0.0 | | | | | 0.0 | | | | |
| | 0.0620 | 5.0 | 0.0 | 0.0 | 4.0 | 0.0 | | | | | 0.0 | | | | |
| | 0.0320 | 2.0 | 5.0 | 4.0 | 9.0 | 4.0 | | | | | 0.0 | | | | |
| 576 | 0.2500 | 9.0 | 5.0 | 0.0 | 9.0 | 3.0 | | | | | 9.0 | | | | |
| | 0.1250 | 7.0 | 3.0 | 0.0 | 9.0 | 0.0 | | | | | 7.0 | | | | |
| | 0.0620 | 7.0 | 3.0 | 0.0 | 9.0 | 0.0 | | | | | 7.0 | | | | |
| | 0.0320 | 6.0 | 0.0 | 0.0 | 7.0 | 0.0 | | | | | 4.0 | | | | |
| 577 | 0.2500 | 9.0 | 9.0 | 3.0 | | 6.0 | | | | | 9.0 | | | | |
| | 0.1250 | 7.0 | 7.0 | 3.0 | | 6.0 | | | | | 5.0 | | | | |
| | 0.0620 | 7.0 | 4.0 | 3.0 | | 6.0 | | | | | 5.0 | | | | |
| | 0.0320 | 6.0 | 2.0 | 0.0 | | 4.0 | | | | | 4.0 | | | | |
| 578 | 0.2500 | 9.0 | 7.0 | 9.0 | | 9.0 | | | | | 7.0 | | | | |
| | 0.1250 | 7.0 | 5.0 | 6.0 | | 6.0 | | | | | 6.0 | | | | |

TABLE II-continued

Preemergence Herbicidal Evaluations of Test Compounds

| Compound Number | Rate (kg/ha) | ABUTH | AMBEL | CASOB | CHEAL | GALAP | IPOHE | IPOSS | ECHCG | SETVI | GLXMAW | GLXMA | ORYSAT | TRZAWR | ZEAMX |
|---|---|---|---|---|---|---|---|---|---|---|---|---|---|---|---|
| 579 | 0.0620 | 6.0 | 5.0 | 6.0 | | 6.0 | | | | | 5.0 | | | | |
| | 0.0320 | 5.0 | 4.0 | 3.0 | | 3.0 | | | | | 4.0 | | | | |
| | 0.2500 | 5.0 | 6.0 | 0.0 | 9.0 | 2.0 | | | | | 3.0 | | | | |
| | 0.1250 | 4.0 | 4.0 | 0.0 | 7.0 | 0.0 | | | | | 3.0 | | | | |
| | 0.0620 | 4.0 | 0.0 | 0.0 | 7.0 | 0.0 | | | | | 2.0 | | | | |
| | 0.0320 | 2.0 | 0.0 | 0.0 | 6.0 | 0.0 | | | | | 0.0 | | | | |
| 580 | 0.2500 | 9.0 | 9.0 | 8.5 | 9.0 | 8.5 | | | | | 6.5 | | | | |
| | 0.1250 | 9.0 | 9.0 | 9.0 | 9.0 | 8.0 | | | | | 4.0 | | | | |
| | 0.0620 | 9.0 | 9.0 | 9.0 | 9.0 | 8.0 | | | | | 4.0 | | | | |
| | 0.0320 | 8.5 | 3.0 | 5.5 | 4.5 | 5.5 | | | | | 1.5 | | | | |
| 581 | 0.2500 | 9.0 | 9.0 | 8.0 | 9.0 | 9.0 | | | | | 7.0 | | | | |
| | 0.1250 | 9.0 | 9.0 | 6.0 | 9.0 | 9.0 | | | | | 6.0 | | | | |
| | 0.0620 | 8.5 | 4.5 | 1.5 | 4.5 | 9.0 | | | | | 3.5 | | | | |
| | 0.0320 | 6.0 | 3.0 | 1.0 | 4.5 | 3.0 | | | | | 1.5 | | | | |
| 582 | 0.2500 | 9.0 | 6.0 | 7.0 | 7.0 | 6.0 | | | | | 3.0 | | | | |
| | 0.1250 | 7.0 | 6.0 | 0.0 | 7.0 | 6.0 | | | | | 0.0 | | | | |
| | 0.0620 | 7.0 | 4.0 | 0.0 | 7.0 | 5.0 | | | | | 0.0 | | | | |
| | 0.0320 | 6.0 | 3.0 | 0.0 | 7.0 | 5.0 | | | | | 0.0 | | | | |
| 583 | 0.2500 | 9.0 | 9.0 | 9.0 | 9.0 | 9.0 | | | | | 9.0 | | | | |
| | 0.1250 | 9.0 | 9.0 | 9.0 | 9.0 | 9.0 | | | | | 9.0 | | | | |
| | 0.0620 | 7.5 | 9.0 | 8.5 | 9.0 | 9.0 | | | | | 7.0 | | | | |
| | 0.0320 | 3.0 | 9.0 | 0.0 | 6.0 | 2.0 | | | | | 5.0 | | | | |
| 584 | 0.2500 | 9.0 | 9.0 | | 9.0 | 4.0 | | | | | 3.5 | | | | |
| | 0.1250 | 9.0 | 6.0 | 0.0 | 8.0 | 1.5 | | | | | 1.0 | | | | |
| | 0.0620 | 9.0 | 1.5 | 0.0 | 3.0 | 0.0 | | | | | 1.0 | | | | |
| | 0.0320 | 6.0 | 9.0 | 3.0 | 9.0 | 2.5 | | | | | 0.0 | | | | |
| 585 | 0.2500 | 9.0 | 9.0 | 0.0 | 4.5 | 2.0 | | | | | 1.5 | | | | |
| | 0.1250 | 8.5 | 8.5 | 0.0 | 3.5 | 1.5 | | | | | 1.5 | | | | |
| | 0.0620 | 8.5 | 2.5 | 0.0 | 3.5 | 0.0 | | | | | 1.5 | | | | |
| | 0.0320 | 5.0 | 9.0 | 4.5 | 9.0 | 0.0 | | | | | 1.0 | | | | |
| 586 | 0.2500 | 9.0 | 9.0 | 4.5 | 9.0 | 0.0 | | | | | 2.0 | | | | |
| | 0.1250 | 9.0 | 8.5 | 0.0 | 6.5 | 0.0 | | | | | 2.0 | | | | |
| | 0.0620 | 9.0 | 9.0 | 0.0 | 9.0 | 0.0 | | | | | 2.0 | | | | |
| | 0.0320 | 8.0 | 8.0 | 0.0 | 9.0 | 0.0 | | | | | 1.0 | | | | |
| 587 | 0.2500 | 9.0 | 9.0 | 0.0 | 9.0 | 5.0 | | | | | 5.0 | | | | |
| | 0.1250 | 9.0 | 9.0 | | 5.0 | 5.0 | | | | | 4.0 | | | | |
| | 0.0620 | 7.0 | 8.0 | 0.0 | 5.0 | 2.0 | | | | | 4.0 | | | | |
| | 0.0320 | 7.0 | 4.0 | 0.0 | 5.0 | 0.0 | | | | | 4.0 | | | | |
| 588 | 0.2500 | 7.0 | 6.0 | 5.0 | 8.0 | 0.0 | | | | | 3.0 | | | | |
| | 0.1250 | 9.0 | 6.0 | 5.0 | 7.0 | 0.0 | | | | | 3.0 | | | | |
| | 0.0620 | 7.0 | 2.0 | 0.0 | | 0.0 | | | | | 3.0 | | | | |
| | 0.0320 | 4.0 | 0.0 | 0.0 | | 0.0 | | | | | 0.0 | | | | |
| 589 | 0.2500 | 4.0 | 4.0 | 0.0 | 9.0 | 3.0 | | | | | 0.0 | | | | |
| | 0.1250 | 4.0 | 3.0 | 0.0 | 8.0 | 2.0 | | | | | 0.0 | | | | |
| | 0.0620 | 4.0 | 2.0 | 0.0 | 8.0 | 0.0 | | | | | 0.0 | | | | |
| | 0.0320 | 4.0 | 0.0 | 0.0 | 7.0 | 2.0 | | | | | 0.0 | | | | |
| 590 | 0.2500 | 9.0 | 9.0 | 5.0 | 9.0 | 9.0 | | | | | 6.0 | | | | |

TABLE II-continued

Preemergence Herbicidal Evaluations of Test Compounds

| Compound Number | Rate (kg/ha) | ABUTH | AMBEL | CASOB | CHEAL | GALAP | IPOHE | IPOSS | ECHCG | SETVI | GLXMAW | GLXMA | ORYSAT | TRZAWR | ZEAMX |
|---|---|---|---|---|---|---|---|---|---|---|---|---|---|---|---|
| 591 | 0.1250 | 6.0 | 7.0 |  | 7.0 | 8.0 |  |  |  |  | 5.0 |  |  |  |  |
|  | 0.0620 | 5.0 | 7.0 |  | 7.0 | 4.0 |  |  |  |  | 5.0 |  |  |  |  |
|  | 0.0320 | 3.0 | 2.0 | 0.0 |  | 3.0 |  |  |  |  | 3.0 |  |  |  |  |
| 592 | 0.2500 | 9.0 | 7.0 |  | 9.0 | 7.0 |  |  |  |  | 5.0 |  |  |  |  |
|  | 0.1250 | 7.0 | 7.0 | 0.0 | 9.0 | 7.0 |  |  |  |  | 5.0 |  |  |  |  |
|  | 0.0620 | 3.0 | 4.0 |  | 9.0 | 7.0 |  |  |  |  | 4.0 |  |  |  |  |
|  | 0.0320 | 3.0 | 3.0 | 0.0 | 7.0 | 3.0 |  |  |  |  | 4.0 |  |  |  |  |
| 593 | 0.2500 | 5.0 | 6.0 |  | 9.0 | 0.0 |  |  |  |  | 2.0 |  |  |  |  |
|  | 0.1250 | 4.0 | 4.0 | 0.0 | 9.0 | 3.0 |  |  |  |  | 4.0 |  |  |  |  |
|  | 0.0620 | 3.0 | 3.0 |  | 9.0 | 3.0 |  |  |  |  | 2.0 |  |  |  |  |
|  | 0.0320 | 0.0 | 2.0 | 0.0 | 8.0 | 0.0 |  |  |  |  | 2.0 |  |  |  |  |
| 594 | 0.2500 | 0.0 | 5.0 | 0.0 | 7.0 | 0.0 |  |  |  |  | 0.0 |  |  |  |  |
|  | 0.1250 | 0.0 | 4.0 |  | 7.0 | 0.0 |  |  |  |  | 0.0 |  |  |  |  |
|  | 0.0620 | 0.0 | 3.0 | 0.0 | 7.0 | 0.0 |  |  |  |  | 0.0 |  |  |  |  |
|  | 0.0320 | 0.0 | 3.0 |  |  |  |  |  |  |  | 0.0 |  |  |  |  |
| 595 | 0.2500 | 7.0 | 9.0 |  | 9.0 | 5.0 |  |  |  |  | 3.0 |  |  |  |  |
|  | 0.1250 | 6.0 | 5.0 |  | 9.0 | 4.0 |  |  |  |  | 2.0 |  |  |  |  |
|  | 0.0620 | 5.0 | 5.0 |  | 7.0 | 4.0 |  |  |  |  | 2.0 |  |  |  |  |
|  | 0.0320 | 3.0 | 3.0 | 0.0 | 6.0 | 2.0 |  |  |  |  | 1.0 |  |  |  |  |
| 596 | 0.2500 | 4.0 | 4.0 |  |  | 0.0 |  |  |  |  | 2.0 |  |  |  |  |
|  | 0.1250 | 3.0 | 2.0 | 0.0 |  | 0.0 |  |  |  |  | 0.0 |  |  |  |  |
|  | 0.0620 | 0.0 | 0.0 |  |  | 0.0 |  |  |  |  | 0.0 |  |  |  |  |
|  | 0.0320 | 0.0 | 0.0 |  |  | 0.0 |  |  |  |  | 0.0 |  |  |  |  |
| 597 | 0.2500 | 7.0 | 0.0 |  | 9.0 | 6.0 |  |  |  |  | 6.0 |  |  |  |  |
|  | 0.1250 | 5.0 | 0.0 | 0.0 | 7.0 | 2.0 |  |  |  |  | 4.0 |  |  |  |  |
|  | 0.0620 | 4.0 | 0.0 |  | 4.0 | 0.0 |  |  |  |  | 3.0 |  |  |  |  |
|  | 0.0320 | 0.0 | 0.0 |  | 3.0 | 0.0 |  |  |  |  | 0.0 |  |  |  |  |
| 598 | 0.2500 | 9.0 | 0.0 |  | 4.0 | 0.0 |  |  |  |  | 0.0 |  |  |  |  |
|  | 0.1250 | 7.0 | 0.0 | 0.0 |  | 0.0 |  |  |  |  | 0.0 |  |  |  |  |
|  | 0.0620 | 6.0 | 0.0 |  |  | 0.0 |  |  |  |  | 0.0 |  |  |  |  |
|  | 0.0320 | 4.0 | 0.0 |  |  | 0.0 |  |  |  |  | 3.0 |  |  |  |  |
| 599 | 0.2500 | 0.0 | 3.0 |  | 7.0 | 0.0 |  |  |  |  | 3.0 |  |  |  |  |
|  | 0.1250 | 0.0 | 2.0 | 0.0 | 7.0 | 0.0 |  |  |  |  | 3.0 |  |  |  |  |
|  | 0.0620 | 0.0 | 0.0 |  |  | 0.0 |  |  |  |  | 0.0 |  |  |  |  |
|  | 0.0320 | 4.0 | 0.0 | 0.0 | 7.0 | 0.0 |  |  |  |  | 0.0 |  |  |  |  |
| 600 | 0.2500 | 0.0 | 0.0 |  | 7.0 | 0.0 |  |  |  |  | 5.0 |  |  |  |  |
|  | 0.1250 | 2.0 | 2.0 | 0.0 | 6.0 | 0.0 |  |  |  |  | 3.0 |  |  |  |  |
|  | 0.0620 | 0.0 | 0.0 |  | 7.0 | 0.0 |  |  |  |  | 2.0 |  |  |  |  |
|  | 0.0320 | 0.0 | 0.0 |  | 7.0 | 0.0 |  |  |  |  | 4.0 |  |  |  |  |
| 601 | 0.2500 | 6.0 | 4.0 | 3.0 | 6.0 | 0.0 |  |  |  |  | 4.0 |  |  |  |  |
|  | 0.1250 | 2.0 | 4.0 | 0.0 | 9.0 | 0.0 |  |  |  |  | 3.0 |  |  |  |  |
|  | 0.0620 | 0.0 | 0.0 | 0.0 | 9.0 | 0.0 |  |  |  |  | 7.0 |  |  |  |  |
|  | 0.0320 | 0.0 | 0.0 | 0.0 | 7.0 | 0.0 |  |  |  |  | 6.0 |  |  |  |  |
| 602 | 0.2500 | 9.0 | 5.0 | 9.0 | 9.0 | 3.0 |  |  |  |  | 4.0 |  |  |  |  |

TABLE II-continued

Preemergence Herbicidal Evaluations of Test Compounds

| Compound Number | Rate (kg/ha) | ABUTH | AMBEL | CASOB | CHEAL | GALAP | IPOHE | IPOSS | ECHCG | SETVI | GLXMAW | GLXMA | ORYSAT | TRZAWR | ZEAMX |
|---|---|---|---|---|---|---|---|---|---|---|---|---|---|---|---|
| 603 | 0.1250 | 9.0 | 5.0 | 7.0 | 8.0 | 0.0 | | | | | | | | | |
|  | 0.0620 | 5.0 | 3.0 | 0.0 | 7.0 | 0.0 | | | | | | | | | |
|  | 0.0320 | 0.0 | 3.0 | | 7.0 | 0.0 | | | | | | | | | |
|  | 0.2500 | 8.0 | 7.0 | 9.0 | 9.0 | 4.0 | | | | | | | | | |
|  | 0.1250 | 6.0 | 6.0 | 8.0 | 9.0 | 2.0 | | | | | | | | | |
|  | 0.0620 | 4.0 | | | 7.0 | 0.0 | | | | | | | | | |
| 604 | 0.0320 | 0.0 | 5.0 | 0.0 | 7.0 | 0.0 | | | | | | | | | |
|  | 0.2500 | 9.0 | 6.0 | 0.0 | 8.0 | 0.0 | | | | | | | | | |
|  | 0.1250 | 7.0 | 4.0 | 0.0 | 7.0 | 0.0 | | | | | | | | | |
|  | 0.0620 | 7.0 | 3.0 | 0.0 | 6.0 | 0.0 | | | | | | | | | |
| 605 | 0.0320 | 7.0 | 0.0 | 0.0 | 5.0 | 0.0 | | | | | | | | | |
|  | 0.2500 | 7.0 | 7.0 | 0.0 | 9.0 | 7.0 | | | | | | | | | |
|  | 0.1250 | 7.0 | 7.0 | 0.0 | 7.0 | 5.0 | | | | | | | | | |
|  | 0.0620 | 4.0 | 3.0 | 0.0 | 7.0 | 4.0 | | | | | | | | | |
| 606 | 0.0320 | 4.0 | 1.0 | 0.0 | 9.0 | 4.0 | | | | | | | | | |
|  | 0.2500 | 6.0 | 9.0 | 2.0 | 9.0 | 4.0 | | | | | | | | | |
|  | 0.1250 | 5.0 | 6.0 | 2.0 | 9.0 | 4.0 | | | | | | | | | |
|  | 0.0620 | 5.0 | 6.0 | 2.0 | 7.0 | 3.0 | | | | | | | | | |
| 607 | 0.0320 | 5.0 | 4.0 | 0.0 | 7.0 | 0.0 | | | | | | 3.0 | | | |
|  | 0.2500 | 9.0 | 5.0 | 0.0 | 9.0 | 3.0 | | | | | | 2.0 | | | |
|  | 0.1250 | 9.0 | 5.0 | 0.0 | 9.0 | 0.0 | | | | | | 0.0 | | | |
|  | 0.0620 | 7.0 | 2.0 | 0.0 | 7.0 | 0.0 | | | | | | 0.0 | | | |
|  | 0.0320 | 4.0 | 0.0 | 0.0 | 6.0 | 0.0 | | | | | | | | | |
| 194 | 0.2500 | 9.0 | 9.0 | 9.0 | 9.0 | 9.0 | 9.0 | | 9.0 | 9.0 | 9.0 | | 8.0 | 7.0 | 7.0 |
|  | 0.1250 | 9.0 | 9.0 | 7.0 | 9.0 | 8.0 | 9.0 | | 8.0 | 9.0 | 9.0 | | 8.0 | 9.0 | 6.0 |
|  | 0.0625 | 9.0 | 8.0 | 6.0 | 9.0 | 9.0 | 9.0 | | 7.0 | 9.0 | 5.0 | | 7.0 | 9.0 | 5.0 |
|  | 0.0313 | 9.0 | 6.0 | 6.0 | 9.0 | 3.0 | 6.0 | | 6.0 | 8.0 | 5.0 | | 6.0 | 6.0 | 4.0 |
|  | 0.0156 | 9.0 | 7.0 | 7.0 | 9.0 | 3.0 | 9.0 | | 2.0 | 6.0 | 5.0 | | 5.0 | 5.0 | 4.0 |
| 195 | 0.2500 | 9.0 | 9.0 | 9.0 | 9.0 | 9.0 | 9.0 | | 9.0 | 9.0 | 9.0 | | 9.0 | 9.0 | 8.0 |
|  | 0.1250 | 9.0 | 9.0 | 9.0 | 9.0 | | 9.0 | | 8.0 | 9.0 | 8.0 | | 8.0 | 8.0 | 8.0 |
|  | 0.0640 | 9.0 | 9.0 | 9.0 | 9.0 | 9.0 | 7.0 | | 9.0 | 9.0 | 9.0 | | 9.0 | | 8.0 |
|  | 0.0625 | 9.0 | 9.0 | 9.0 | 9.0 | | 9.0 | | 9.0 | 9.0 | 7.0 | | 8.0 | 7.0 | 8.0 |
|  | 0.0320 | 9.0 | 9.0 | 9.0 | 9.0 | 9.0 | 9.0 | | 8.0 | 9.0 | 9.0 | | 8.0 | | 7.0 |
|  | 0.0160 | 9.0 | 9.0 | 4.0 | 9.0 | 7.0 | 6.0 | | 8.0 | 9.0 | 7.0 | | 7.0 | 7.0 | 8.0 |
|  | 0.0156 | 9.0 | 9.0 | 7.0 | 9.0 | | 9.0 | | 9.0 | 9.0 | 7.0 | | 7.0 | | 7.0 |
| 196 | 0.2500 | 9.0 | 9.0 | 9.0 | 9.0 | 9.0 | 9.0 | | 9.0 | 9.0 | 8.5 | | 9.0 | 7.0 | 8.0 |
|  | 0.1250 | 9.0 | 9.0 | 8.0 | 9.0 | 9.0 | 9.0 | | 9.0 | 9.0 | 9.0 | | 8.0 | 9.0 | 8.0 |
|  | 0.0640 | 9.0 | 9.0 | 6.0 | 9.0 | | 6.0 | | 9.0 | 9.0 | 9.0 | | 8.0 | | 8.0 |
|  | 0.0625 | 9.0 | 8.0 | 9.0 | 9.0 | 8.0 | 9.0 | | 9.0 | 9.0 | 9.0 | | 8.0 | 8.0 | 7.0 |
|  | 0.0320 | 9.0 | 8.0 | 5.0 | 9.0 | | 9.0 | | 8.0 | 8.0 | 9.0 | | 6.0 | | 7.0 |
|  | 0.0313 | 9.0 | 9.0 | 8.0 | 9.0 | 6.0 | 9.0 | | 7.5 | 8.5 | 7.5 | | 7.0 | 7.0 | 6.5 |
|  | 0.0156 | 9.0 | 7.5 | 3.5 | 9.0 | | 4.0 | | 7.0 | 9.0 | 5.0 | | 7.0 | | 6.0 |
| 197 | 0.2500 | 9.0 | 9.0 | 2.5 | 9.0 | 6.0 | 6.5 | | 1.0 | 7.0 | 4.5 | | 8.0 | 8.0 | 5.5 |
|  | 0.1250 | 5.5 | 6.5 | 2.0 | 9.0 | 4.5 | 9.0 | | 0.0 | 4.5 | 5.0 | | 3.5 | 8.5 | 2.5 |
|  | 0.0625 | 2.5 | 1.0 | 0.0 | 9.0 | 4.5 | 4.5 | | 0.0 | 1.5 | 0.0 | | 1.5 | 0.0 | 2.0 |
|  |  |  |  |  |  | 0.0 | 0.0 | | 0.0 | 1.5 | 1.0 | | 1.5 | 0.0 | 0.0 |

TABLE II-continued

Preemergence Herbicidal Evaluations of Test Compounds

| Compound Number | Rate (kg/ha) | ABUTH | AMBEL | CASOB | CHEAL | GALAP | IPOHE | IPOSS | ECHCG | SETVI | GLXMAW | GLXMA | ORYSAT | TRZAWR | ZEAMX |
|---|---|---|---|---|---|---|---|---|---|---|---|---|---|---|---|
|  | 0.0313 | 0.0 | 0.0 | 0.0 | 9.0 | 0.0 | 0.0 |  | 0.0 | 0.0 | 0.0 |  | 0.0 | 0.0 | 0.0 |
|  | 0.0156 | 0.0 | 0.0 | 0.0 | 9.0 | 0.0 | 0.0 |  | 0.0 | 0.0 | 0.0 |  | 0.0 | 0.0 | 0.0 |
| 198 | 0.2500 | 9.0 | 9.0 | 9.0 | 9.0 | 9.0 | 9.0 |  | 9.0 | 9.0 | 9.0 |  | 9.0 | 9.0 | 9.0 |
|  | 0.1250 | 9.0 | 9.0 | 8.0 | 9.0 | 7.0 | 9.0 |  | 9.0 | 9.0 | 9.0 |  | 9.0 | 9.0 | 8.5 |
|  | 0.0625 | 9.0 | 9.0 | 5.0 | 9.0 | 0.0 | 9.0 |  | 9.0 | 9.0 | 5.0 |  | 8.0 | 9.0 | 8.0 |
|  | 0.0313 | 9.0 | 9.0 | 6.0 | 9.0 | 0.0 | 8.0 |  | 7.0 | 8.5 | 4.5 |  | 7.5 | 7.0 | 8.0 |
|  | 0.0156 | 9.0 | 4.0 | 2.0 | 9.0 | 0.0 | 3.5 |  | 2.5 | 3.5 | 4.0 |  | 4.5 | 3.0 | 5.5 |
| 199 | 0.2500 | 9.0 | 6.0 | 2.0 | 9.0 | 9.0 | 4.0 |  | 9.0 | 9.0 | 9.0 |  | 6.0 | 6.0 | 8.0 |
|  | 0.1250 | 9.0 | 7.5 | 3.0 | 9.0 | 9.0 | 6.5 |  | 7.0 | 9.0 | 7.0 |  | 6.0 | 6.0 | 7.0 |
|  | 0.0625 | 7.5 | 6.0 | 2.5 | 9.0 | 7.0 | 3.5 |  | 5.0 | 6.5 | 4.5 |  | 3.5 | 1.0 | 6.5 |
|  | 0.0313 | 9.0 | 3.0 | 2.5 | 9.0 | 0.0 | 2.5 |  | 2.5 | 4.5 | 2.0 |  | 2.5 | 0.0 | 5.0 |
|  | 0.0156 | 4.5 | 2.5 | 0.0 | 9.0 | 0.0 | 1.5 |  | 0.0 | 2.0 | 1.5 |  | 1.0 | 0.0 | 2.0 |
| 200 | 0.2500 | 9.0 | 9.0 | 9.0 | 9.0 | 9.0 | 9.0 |  | 9.0 | 9.0 | 9.0 |  | 9.0 | 9.0 | 9.0 |
|  | 0.1250 | 9.0 | 9.0 | 9.0 | 9.0 | 9.0 | 9.0 |  | 8.0 | 8.5 | 9.0 |  | 8.0 | 9.0 | 8.0 |
|  | 0.0625 | 9.0 | 9.0 | 4.5 | 9.0 | 0.0 | 9.0 |  | 7.5 | 8.0 | 9.0 |  | 7.5 | 8.0 | 7.5 |
|  | 0.0313 | 9.0 | 6.0 | 1.0 | 9.0 | 0.0 | 7.0 |  | 5.0 | 3.5 | 5.0 |  | 4.5 |  | 3.5 |
| 201 | 0.2500 | 9.0 | 9.0 | 8.0 | 9.0 | 9.0 | 9.0 |  | 2.0 | 9.0 | 8.5 |  | 8.0 | 2.0 | 8.5 |
|  | 0.1250 | 9.0 | 9.0 | 7.5 | 9.0 | 9.0 | 9.0 |  | 9.0 | 9.0 | 8.5 |  | 8.0 | 8.0 | 7.5 |
|  | 0.0625 | 9.0 | 8.5 | 7.5 | 9.0 | 9.0 | 5.5 |  | 8.5 | 8.5 | 8.0 |  | 7.0 | 8.0 | 7.5 |
|  | 0.0313 | 8.0 | 6.5 | 3.0 | 9.0 | 0.0 | 3.5 |  | 4.0 | 4.5 | 4.5 |  | 6.0 | 7.0 | 7.0 |
|  | 0.0156 | 8.5 | 4.0 | 5.0 | 9.0 | 0.0 | 3.0 |  | 2.0 | 4.0 | 4.0 |  | 4.0 | 5.0 | 5.0 |
| 202 | 0.2500 | 9.0 | 9.0 | 8.0 | 9.0 | 9.0 | 9.0 |  | 8.0 | 8.5 | 9.0 |  | 8.5 | 8.0 | 8.0 |
|  | 0.1250 | 9.0 | 8.5 | 8.0 | 9.0 | 8.0 | 9.0 |  | 4.5 | 9.0 | 6.5 |  | 7.0 | 7.0 | 4.0 |
|  | 0.0625 | 9.0 | 5.0 | 3.5 | 9.0 | 6.0 | 7.0 |  | 1.5 | 3.5 | 5.0 |  | 4.5 | 2.0 | 4.0 |
|  | 0.0313 | 9.0 | 5.0 | 3.5 | 9.0 | 4.5 | 4.5 |  | 0.0 | 2.0 | 3.5 |  | 3.0 | 2.5 | 4.0 |
|  | 0.0156 | 6.5 | 2.0 | 0.5 | 9.0 | 6.0 | 4.5 |  | 0.0 | 1.0 | 3.0 |  | 0.5 | 4.0 | 1.0 |
| 203 | 0.2500 | 9.0 | 9.0 | 9.0 | 9.0 | 9.0 | 9.0 |  | 9.0 | 9.0 | 9.0 |  | 9.0 | 9.0 | 8.3 |
|  | 0.1250 | 9.0 | 9.0 | 6.8 | 9.0 | 9.0 | 9.0 |  | 9.0 | 9.0 | 7.8 |  | 8.7 | 9.0 | 8.3 |
|  | 0.0625 | 9.0 | 9.0 | 5.5 | 9.0 | 9.0 | 8.3 |  | 7.5 | 9.0 | 7.8 |  | 8.7 | 9.0 | 7.3 |
|  | 0.0313 | 8.8 | 8.3 | 5.7 | 9.0 | 4.0 | 6.0 |  | 5.0 | 8.0 | 6.3 |  | 7.0 | 8.0 | 5.5 |
|  | 0.0156 | 7.5 | 6.0 | 0.5 | 8.8 | 4.5 | 4.3 |  | 2.5 | 4.8 | 4.0 |  | 3.7 | 5.0 | 2.8 |
| 204 | 0.2500 | 9.0 | 8.5 | 7.5 | 9.0 | 9.0 | 9.0 |  | 9.0 | 9.0 | 7.5 |  | 9.0 | 9.0 | 7.5 |
|  | 0.1250 | 8.3 | 9.0 | 6.0 | 9.0 | 8.0 | 9.0 |  | 8.7 | 9.0 | 6.7 |  | 8.0 | 7.0 | 6.7 |
|  | 0.0625 | 9.0 | 6.7 | 5.0 | 9.0 | 7.0 | 6.0 |  | 6.3 | 9.0 | 6.0 |  | 7.5 | 6.0 | 5.7 |
|  | 0.0313 | 9.0 | 5.3 | 1.3 | 6.0 | 0.0 | 5.3 |  | 4.3 | 6.0 | 4.0 |  | 6.5 | 6.0 | 5.3 |
|  | 0.0156 | 6.0 | 0.7 | 0.0 | 6.0 | 7.0 | 2.0 |  | 1.7 | 1.0 | 3.3 |  | 7.0 | 6.0 | 3.0 |
| 205 | 0.2500 | 9.0 | 9.0 | 7.5 | 9.0 | 9.0 | 9.0 |  | 9.0 | 9.0 | 9.0 |  | 8.0 | 9.0 | 8.0 |
|  | 0.1250 | 9.0 | 8.0 | 7.5 | 9.0 | 9.0 | 9.0 |  | 8.5 | 9.0 | 8.0 |  | 8.0 | 8.0 | 7.5 |
|  | 0.0625 | 8.5 | 7.5 | 4.5 | 9.0 | 8.0 | 8.0 |  | 6.5 | 7.0 | 7.0 |  | 6.0 | 7.0 | 7.0 |
|  | 0.0313 | 7.0 | 3.0 | 5.5 | 8.0 | 0.0 | 5.5 |  | 7.0 | 3.0 | 6.5 |  | 6.0 | 6.0 | 6.5 |
|  | 0.0156 | 9.0 | 9.0 | 1.0 | 9.0 | 2.0 | 9.0 |  | 3.0 | 9.0 | 4.0 |  | 7.0 | 9.0 | 4.0 |
| 206 | 0.2500 | 9.0 | 9.0 | 9.0 | 9.0 | 9.0 | 9.0 |  | 9.0 | 9.0 | 9.0 |  | 9.0 | 8.0 | 7.5 |
|  | 0.1250 | 9.0 | 7.5 | 5.5 | 9.0 | 4.0 | 8.0 |  | 9.0 | 9.0 | 9.0 |  | 9.0 | 9.0 | 7.0 |
|  | 0.0625 | 9.0 | 6.5 | 5.5 | 9.0 | 5.0 | 7.5 |  | 7.0 | 9.0 | 6.5 |  | 7.0 | 9.0 | 7.0 |
|  | 0.0313 | 9.0 | 4.5 | 5.5 | 9.0 | 1.0 | 7.0 |  | 5.0 | 5.5 | 7.5 |  | 7.0 | 2.0 | 7.0 |
|  | 0.0156 | 8.0 |  |  |  |  |  |  |  |  | 4.5 |  | 0.0 |  | 4.0 |

TABLE II-continued

Preemergence Herbicidal Evaluations of Test Compounds

| Compound Number | Rate (kg/ha) | ABUTH | AMBEL | CASOB | CHEAL | GALAP | IPOHE | IPOSS | ECHCG | SETVI | GLXMAW | GLXMA | ORYSAT | TRZAWR | ZEAMX |
|---|---|---|---|---|---|---|---|---|---|---|---|---|---|---|---|
| 207 | 0.2500 | 9.0 | 9.0 | 9.0 | 9.0 | 9.0 | 9.0 | | 9.0 | 9.0 | 9.0 | | 9.0 | 9.0 | 9.0 |
| | 0.1250 | 9.0 | 9.0 | 9.0 | 9.0 | 8.0 | 9.0 | | 9.0 | 9.0 | 9.0 | | 8.5 | 9.0 | 8.5 |
| | 0.0625 | 9.0 | 9.0 | 6.0 | 9.0 | 9.0 | 9.0 | | 9.0 | 9.0 | 8.0 | | 8.0 | 9.0 | 8.0 |
| | 0.0313 | 9.0 | 8.5 | 5.0 | 9.0 | 4.0 | 9.0 | | 7.5 | 9.0 | 7.0 | | 7.0 | 9.0 | 7.0 |
| | 0.0156 | 9.0 | 8.0 | 3.5 | 9.0 | 2.0 | 9.0 | | 5.0 | 6.0 | 8.0 | | 6.0 | 5.0 | 4.5 |
| 208 | 0.1250 | 9.0 | 9.0 | 9.0 | 9.0 | 9.0 | 9.0 | | 9.0 | 9.0 | 8.0 | | 8.0 | 7.0 | 8.0 |
| | 0.0625 | 6.0 | 7.0 | 4.0 | 9.0 | 9.0 | 9.0 | | 7.0 | 9.0 | 6.0 | | 7.0 | 9.0 | 6.0 |
| | 0.0313 | 7.0 | 6.0 | 9.0 | 9.0 | 9.0 | 4.0 | | 4.0 | 9.0 | 9.0 | | 7.0 | 9.0 | 5.0 |
| | 0.0156 | 9.0 | 5.0 | 9.0 | 9.0 | 0.0 | 6.0 | | 2.0 | 7.0 | 9.0 | | 2.0 | 9.0 | 3.0 |
| 209 | 0.2500 | 9.0 | 9.0 | 5.0 | 9.0 | 9.0 | 9.0 | | 9.0 | 9.0 | 2.0 | | 8.0 | 7.0 | 8.0 |
| | 0.1250 | 9.0 | 9.0 | 3.0 | 9.0 | 0.0 | 9.0 | | 7.0 | 9.0 | 5.0 | | 7.0 | 5.0 | 7.0 |
| | 0.0625 | 9.0 | 6.0 | 1.0 | 9.0 | | 9.0 | | 6.0 | 9.0 | | | 6.0 | | 7.0 |
| | 0.0313 | 9.0 | 2.0 | 1.0 | 9.0 | 2.0 | 9.0 | | 4.0 | 4.0 | 4.0 | | 5.0 | 4.0 | 4.0 |
| | 0.0156 | 2.0 | 1.0 | 0.0 | 9.0 | 0.0 | 1.0 | | 0.0 | 4.0 | 3.0 | | 1.0 | 3.0 | 1.0 |
| 210 | 0.2500 | 9.0 | 9.0 | 3.0 | 9.0 | 9.0 | 9.0 | | 7.0 | 9.0 | 1.0 | | 9.0 | 8.0 | 8.0 |
| | 0.1250 | 9.0 | 8.0 | 9.0 | 9.0 | 7.0 | 4.0 | | 4.0 | 9.0 | 9.0 | | 6.0 | 7.0 | 7.0 |
| | 0.0625 | 9.0 | 0.0 | 9.0 | 9.0 | 2.0 | 4.0 | | 4.0 | 9.0 | 9.0 | | 6.0 | 6.0 | 5.0 |
| | 0.0313 | 9.0 | 2.0 | 7.0 | 9.0 | 0.0 | 0.0 | | 3.0 | 9.0 | 7.0 | | 4.0 | 4.0 | 4.0 |
| | 0.0156 | 0.0 | 0.0 | 5.0 | 9.0 | 0.0 | 0.0 | | 0.0 | 3.0 | 0.0 | | 0.0 | 1.0 | 0.0 |
| 211 | 0.1250 | 9.0 | 9.0 | 9.0 | 9.0 | 7.0 | 5.0 | | 3.0 | 9.0 | 6.0 | | 1.0 | 0.0 | 7.0 |
| | 0.0625 | 9.0 | 0.0 | 9.0 | 9.0 | 3.0 | 9.0 | | 3.0 | 3.0 | 1.0 | | 0.0 | 0.0 | 6.0 |
| | 0.0313 | 9.0 | 0.0 | 0.0 | 9.0 | 0.0 | 9.0 | | 0.0 | 0.0 | 0.0 | | 0.0 | 0.0 | 3.0 |
| | 0.0156 | 0.0 | 0.0 | 0.0 | 9.0 | 0.0 | 0.0 | | 0.0 | 0.0 | 0.0 | | 0.0 | 0.0 | 0.0 |
| 212 | 0.2500 | 9.0 | 9.0 | 0.0 | 9.0 | 9.0 | 9.0 | | 8.0 | 9.0 | 9.0 | | 9.0 | 6.0 | 9.0 |
| | 0.1250 | 9.0 | 9.0 | 0.0 | 9.0 | 6.0 | 9.0 | | 3.0 | 9.0 | 7.0 | | 9.0 | 6.0 | 6.0 |
| | 0.0625 | 8.0 | 5.0 | 0.0 | 9.0 | 0.0 | 9.0 | | 0.0 | 0.0 | 7.0 | | 7.0 | 3.0 | 6.0 |
| | 0.0313 | 7.0 | 4.0 | 0.0 | 7.0 | 0.0 | 9.0 | | 0.0 | 0.0 | 1.0 | | 2.0 | 1.0 | 2.0 |
| | 0.0156 | 7.0 | 0.0 | 0.0 | 9.0 | 7.0 | 3.0 | | 7.0 | 9.0 | 1.0 | | 0.0 | 0.0 | 0.0 |
| 213 | 0.5000 | 9.0 | 9.0 | 9.0 | 9.0 | 7.0 | 0.0 | | 7.0 | 9.0 | 9.0 | | 7.0 | 7.0 | 7.0 |
| | 0.2500 | 9.0 | 9.0 | 7.0 | 9.0 | 7.0 | 9.0 | | 7.0 | 9.0 | 6.0 | | 7.0 | 7.0 | 5.0 |
| | 0.1250 | 9.0 | 6.0 | 1.0 | 9.0 | 3.0 | 9.0 | | 4.0 | 6.0 | 3.0 | | 6.0 | 6.0 | 4.0 |
| | 0.0625 | 6.0 | 3.0 | 1.0 | 4.0 | 2.0 | 5.0 | | 2.0 | 4.0 | 1.0 | | 5.0 | 4.0 | 1.0 |
| | 0.0313 | 1.0 | 0.0 | 1.0 | 9.0 | 1.0 | 0.0 | | 0.0 | 4.0 | 1.0 | | 1.0 | 0.0 | 0.0 |
| 214 | 0.5000 | 9.0 | 9.0 | 6.0 | 9.0 | 9.0 | 9.0 | | 5.0 | 9.0 | 6.0 | | 7.0 | 4.0 | 6.0 |
| | 0.2500 | 7.0 | 6.0 | 4.0 | 9.0 | 7.0 | 9.0 | | 3.0 | 9.0 | 6.0 | | 4.0 | 3.0 | 6.0 |
| | 0.1250 | | 4.0 | 0.0 | 4.0 | 7.0 | 6.0 | | 0.0 | 6.0 | 4.0 | | 2.0 | 1.0 | 2.0 |
| | 0.0625 | | 2.0 | 0.0 | | 1.0 | 3.0 | | 0.0 | 0.0 | 2.0 | | 0.0 | 0.0 | 0.0 |
| | 0.0313 | 1.0 | 1.0 | 0.0 | 9.0 | 5.0 | 3.0 | | 0.0 | 1.0 | 1.0 | | 1.0 | 0.0 | 1.0 |
| 215 | 0.5000 | 1.0 | 5.0 | 1.0 | 9.0 | 4.0 | 0.0 | | 1.0 | 2.0 | 1.0 | | 1.0 | 4.0 | 1.0 |
| | 0.2500 | 0.0 | 2.0 | 0.0 | 4.0 | 2.0 | 1.0 | | 0.0 | 0.0 | 1.0 | | 0.0 | 0.0 | 1.0 |
| | 0.1250 | 2.0 | 1.0 | 1.0 | | 1.0 | 0.0 | | 0.0 | 0.0 | 1.0 | | 0.0 | 1.0 | 1.0 |
| | 0.0625 | 0.0 | 0.0 | 0.0 | | 1.0 | 0.0 | | 0.0 | 0.0 | 1.0 | | 0.0 | 1.0 | 0.0 |
| | 0.0313 | 0.0 | 0.0 | 1.0 | | 1.0 | 1.0 | | 0.0 | 0.0 | 1.0 | | 1.0 | 1.0 | 0.0 |
| 216 | 0.5000 | 9.0 | 7.0 | 5.0 | 9.0 | 6.0 | 6.0 | | 5.0 | 9.0 | 6.0 | | 7.0 | 4.0 | 7.0 |
| | 0.2500 | 9.0 | 4.0 | 2.0 | 9.0 | 2.0 | 6.0 | | 2.0 | 7.0 | 3.0 | | 4.0 | 1.0 | 4.0 |
| | 0.1250 | 9.0 | 3.0 | 1.0 | 9.0 | 1.0 | 6.0 | | 1.0 | 6.0 | 2.0 | | 3.0 | 1.0 | 4.0 |
| | 0.0625 | 6.0 | 0.0 | 0.0 | 9.0 | 1.0 | 2.0 | | 0.0 | 6.0 | 3.0 | | 1.0 | 2.0 | 1.0 |

TABLE II-continued

Preemergence Herbicidal Evaluations of Test Compounds

| Compound Number | Rate (kg/ha) | ABUTH | AMBEL | CASOB | CHEAL | GALAP | IPOHE | IPOSS | ECHCG | SETVI | GLXMAW | GLXMA | ORYSAT | TRZAWR | ZEAMX |
|---|---|---|---|---|---|---|---|---|---|---|---|---|---|---|---|
| 217 | 0.0313 | 1.0 | 1.0 | 0.0 | 5.0 | 1.0 | 1.0 | | 0.0 | 3.0 | 0.0 | | 1.0 | 1.0 | 1.0 |
| | 0.5000 | 9.0 | 7.0 | 9.0 | 9.0 | 9.0 | 9.0 | | 7.0 | 9.0 | 7.0 | | 7.0 | 7.0 | 9.0 |
| | 0.2500 | 9.0 | 6.0 | 6.0 | 9.0 | 9.0 | 9.0 | | 6.0 | 9.0 | 6.0 | | 7.0 | 4.0 | 7.0 |
| | 0.1250 | 9.0 | 4.0 | 4.0 | 9.0 | 9.0 | 5.0 | | 6.0 | 9.0 | 6.0 | | 6.0 | 1.0 | 5.0 |
| | 0.0625 | 6.0 | 1.0 | 1.0 | 9.0 | 5.0 | 2.0 | | 1.0 | 5.0 | 4.0 | | 1.0 | 1.0 | 1.0 |
| | 0.0313 | | 1.0 | | 9.0 | 5.0 | 2.0 | | 0.0 | 6.0 | 1.0 | | 0.0 | 0.0 | 0.0 |
| 218 | 0.5000 | 9.0 | 3.0 | 3.0 | 9.0 | 7.0 | 6.0 | | 3.0 | 6.0 | 3.0 | | 2.0 | | 1.0 |
| | 0.2500 | 6.0 | 3.0 | 1.0 | 9.0 | 9.0 | | | 2.0 | 4.0 | 1.0 | | 1.0 | 2.0 | 0.0 |
| | 0.1250 | 1.0 | 0.0 | 2.0 | 9.0 | 4.0 | | | 0.0 | 2.0 | | | 1.0 | 0.0 | 1.0 |
| | 0.0625 | 0.0 | 0.0 | 0.0 | 7.0 | | 0.0 | | 0.0 | 1.0 | | | 1.0 | 0.0 | 1.0 |
| | 0.0313 | 0.0 | 0.0 | 0.0 | 9.0 | | 0.0 | | 0.0 | 1.0 | 0.0 | | 0.0 | 0.0 | 0.0 |
| 219 | 0.2500 | 9.0 | 9.0 | 9.0 | 9.0 | 9.0 | 9.0 | | 9.0 | 9.0 | 9.0 | | 7.0 | 8.0 | 7.5 |
| | 0.1250 | 9.0 | 8.0 | 7.0 | 9.0 | 7.0 | 8.5 | | 8.0 | 9.0 | 5.5 | | 7.0 | 7.0 | 7.0 |
| | 0.0625 | 9.0 | 7.5 | 3.0 | 9.0 | 0.0 | 9.0 | | 6.5 | 7.5 | 3.5 | | 7.0 | 7.0 | 6.0 |
| | 0.0313 | 9.0 | 3.5 | 3.0 | 7.5 | 0.0 | 5.5 | | 5.5 | 9.0 | 1.0 | | 4.0 | 4.0 | 5.0 |
| | 0.0156 | 8.0 | 2.5 | 2.0 | 9.0 | 0.0 | 7.5 | | 1.0 | 7.0 | 1.5 | | 2.0 | 2.0 | 4.5 |
| 220 | 0.1250 | 9.0 | 9.0 | 9.0 | 9.0 | 9.0 | 9.0 | | 8.0 | 9.0 | 5.0 | | 9.0 | 8.0 | 8.0 |
| | 0.0625 | 9.0 | 4.0 | 9.0 | 9.0 | 3.0 | 9.0 | | 7.0 | 9.0 | 2.0 | | 6.0 | 7.0 | 6.0 |
| | 0.0313 | 7.0 | 2.0 | 0.0 | 9.0 | 0.0 | 9.0 | | 0.0 | 9.0 | 2.0 | | 6.0 | 3.0 | 5.0 |
| | 0.0156 | 3.0 | 0.0 | 0.0 | 9.0 | 0.0 | 3.0 | | 0.0 | 8.0 | 0.0 | | 6.0 | 1.0 | 0.0 |
| 221 | 0.2500 | 9.0 | 9.0 | 0.0 | 9.0 | 9.0 | 0.0 | | 2.0 | 9.0 | 0.0 | | 1.0 | 1.0 | 5.0 |
| | 0.1250 | 9.0 | 9.0 | 0.0 | 9.0 | 7.0 | 0.0 | | 2.0 | 9.0 | 0.0 | | 1.0 | 1.0 | 5.0 |
| | 0.0625 | 9.0 | 5.0 | 0.0 | 9.0 | 0.0 | 0.0 | | 0.0 | 9.0 | 3.0 | | 0.0 | 0.0 | 5.0 |
| | 0.0313 | 9.0 | 0.0 | 0.0 | 9.0 | 0.0 | 0.0 | | 0.0 | 9.0 | 0.0 | | 0.0 | 0.0 | 3.0 |
| | 0.0156 | 4.0 | 0.0 | 0.0 | 9.0 | 0.0 | 0.0 | | 0.0 | 9.0 | 0.0 | | 0.0 | 0.0 | 0.0 |
| 222 | 0.2500 | 9.0 | 9.0 | 4.0 | 9.0 | 0.0 | 9.0 | | 2.0 | 9.0 | 9.0 | | 1.0 | 1.0 | 6.0 |
| | 0.1250 | 9.0 | 4.0 | 0.0 | 9.0 | 0.0 | 9.0 | | 0.0 | 9.0 | 5.0 | | 1.0 | 0.0 | 1.0 |
| | 0.0625 | 3.0 | 0.0 | 0.0 | 9.0 | 0.0 | 3.0 | | 0.0 | 7.0 | 3.0 | | 0.0 | 0.0 | 1.0 |
| | 0.0313 | 2.0 | 0.0 | 0.0 | 9.0 | 0.0 | 0.0 | | 0.0 | 0.0 | 2.0 | | 0.0 | 0.0 | 1.0 |
| | 0.0156 | 0.0 | 0.0 | 0.0 | 9.0 | 0.0 | 0.0 | | 0.0 | 7.0 | 0.0 | | 0.0 | 0.0 | 0.0 |
| 223 | 0.2500 | 9.0 | 9.0 | 9.0 | 9.0 | 9.0 | 9.0 | | 9.0 | 9.0 | 9.0 | | 9.0 | 8.0 | 9.0 |
| | 0.1250 | 9.0 | 9.0 | 9.0 | 9.0 | 9.0 | 9.0 | | 9.0 | 9.0 | 9.0 | | 9.0 | 7.0 | 8.0 |
| | 0.0625 | 9.0 | 9.0 | 9.0 | 9.0 | 7.0 | 9.0 | | 7.0 | 9.0 | 4.0 | | 7.0 | 6.0 | 7.0 |
| | 0.0313 | 9.0 | 9.0 | 9.0 | 9.0 | 0.0 | 7.0 | | 6.0 | 9.0 | 9.0 | | 4.0 | 5.0 | 7.0 |
| 224 | 0.5000 | 9.0 | 9.0 | 9.0 | 9.0 | 9.0 | 9.0 | | 9.0 | 9.0 | 9.0 | | 7.0 | 7.0 | 9.0 |
| | 0.2500 | 9.0 | 9.0 | 7.0 | 9.0 | 9.0 | 9.0 | | 9.0 | 9.0 | 6.5 | | 8.0 | 6.0 | 8.0 |
| | 0.1250 | 9.0 | 9.0 | 3.0 | 9.0 | 9.0 | 9.0 | | 9.0 | 9.0 | 7.0 | | 6.0 | 5.0 | 7.0 |
| | 0.0625 | 9.0 | 7.0 | 2.0 | 9.0 | 9.0 | 9.0 | | 7.5 | 9.0 | 4.5 | | 7.0 | 5.0 | 7.0 |
| | 0.0313 | 9.0 | 5.0 | 1.5 | 9.0 | 7.0 | 6.0 | | 7.0 | 9.0 | 2.0 | | 6.0 | 3.0 | 6.5 |
| | 0.0156 | 9.0 | 2.0 | 0.0 | 9.0 | 0.0 | 0.0 | | 4.0 | 7.0 | 7.0 | | | | 4.0 |
| 225 | 0.5000 | 9.0 | 9.0 | 7.0 | 9.0 | 9.0 | 9.0 | | 9.0 | 9.0 | 7.0 | | 8.0 | 9.0 | 9.0 |
| | 0.2500 | 9.0 | 9.0 | 9.0 | 9.0 | 9.0 | 9.0 | | 7.0 | 9.0 | 9.0 | | 7.0 | 6.0 | 7.0 |
| | 0.1250 | 9.0 | 9.0 | 9.0 | 9.0 | 9.0 | 9.0 | | 5.0 | 9.0 | 6.0 | | 6.0 | 6.0 | 7.0 |
| | 0.0625 | 9.0 | 6.0 | 6.0 | 9.0 | 0.0 | 9.0 | | 4.0 | 7.0 | | | 3.0 | 6.0 | |
| | 0.0313 | 9.0 | 6.0 | 3.0 | 9.0 | 0.0 | 9.0 | | 2.0 | 4.0 | 2.0 | | 3.0 | 1.0 | 4.0 |
| 226 | 0.2500 | 9.0 | 9.0 | 0.0 | 9.0 | 0.0 | 9.0 | | 0.0 | 9.0 | 5.0 | | 0.0 | 0.0 | 5.0 |

TABLE II-continued

Preemergence Herbicidal Evaluations of Test Compounds

| Compound Number | Rate (kg/ha) | ABUTH | AMBEL | CASOB | CHEAL | GALAP | IPOHE | IPOSS | ECHCG | SETVI | GLXMAW | GLXMA | ORYSAT | TRZAWR | ZEAMX |
|---|---|---|---|---|---|---|---|---|---|---|---|---|---|---|---|
| | 0.1250 | 9.0 | 9.0 | 0.0 | 9.0 | 0.0 | 9.0 | | 0.0 | 0.0 | 3.0 | | 0.0 | 0.0 | 5.0 |
| | 0.0625 | 9.0 | 3.0 | 0.0 | 9.0 | 0.0 | 3.0 | | 0.0 | 0.0 | 0.0 | | 0.0 | 0.0 | 0.0 |
| | 0.0313 | 4.0 | 3.0 | 0.0 | 9.0 | 0.0 | | | 0.0 | 0.0 | 0.0 | | 0.0 | 0.0 | 0.0 |
| | 0.0156 | 0.0 | 3.0 | 0.0 | 9.0 | 0.0 | 0.0 | | 0.0 | 0.0 | 0.0 | | 0.0 | 0.0 | 0.0 |
| 227 | 0.2500 | 9.0 | 9.0 | 0.0 | 9.0 | 0.0 | 9.0 | | 0.0 | 0.0 | 0.0 | | 2.0 | 2.0 | 3.0 |
| | 0.1250 | 7.0 | 9.0 | 4.0 | 9.0 | 0.0 | 0.0 | | 0.0 | 0.0 | 9.0 | | 0.0 | 0.0 | 3.0 |
| | 0.0625 | 9.0 | 4.0 | 0.0 | 9.0 | 0.0 | 0.0 | | 0.0 | 0.0 | 4.0 | | 0.0 | 0.0 | 0.0 |
| | 0.0313 | 9.0 | 0.0 | 0.0 | 9.0 | 0.0 | 0.0 | | 0.0 | 0.0 | 0.0 | | 0.0 | 0.0 | 0.0 |
| | 0.0156 | 0.0 | 0.0 | 0.0 | 9.0 | 0.0 | 3.0 | | 0.0 | 0.0 | 3.0 | | 0.0 | 0.0 | 0.0 |
| 228 | 0.2500 | 3.0 | 4.0 | 4.0 | 9.0 | 0.0 | 0.0 | | 0.0 | 0.0 | 0.0 | | 0.0 | 0.0 | 4.0 |
| | 0.1250 | | 3.0 | 0.0 | 9.0 | 0.0 | 0.0 | | 0.0 | 0.0 | 3.0 | | 0.0 | 0.0 | 0.0 |
| | 0.0625 | 7.0 | 0.0 | 0.0 | 7.0 | 0.0 | 0.0 | | 0.0 | 0.0 | 0.0 | | 0.0 | 0.0 | 0.0 |
| | 0.0313 | 0.0 | 0.0 | 0.0 | 5.0 | 0.0 | 0.0 | | 0.0 | 0.0 | 0.0 | | 0.0 | 0.0 | 0.0 |
| | 0.0156 | 0.0 | 0.0 | 0.0 | | 0.0 | 0.0 | | 0.0 | 0.0 | 0.0 | | 0.0 | 0.0 | 0.0 |
| 229 | 0.2500 | 9.0 | 2.0 | 3.0 | 9.0 | 0.0 | 3.0 | | 0.0 | 0.0 | 2.0 | | 0.0 | 0.0 | 0.0 |
| | 0.1250 | 0.0 | 0.0 | 0.0 | 9.0 | 0.0 | 0.0 | | 0.0 | 0.0 | 0.0 | | 0.0 | 0.0 | 0.0 |
| | 0.0625 | 0.0 | 0.0 | 0.0 | 9.0 | 0.0 | 0.0 | | 0.0 | 0.0 | 0.0 | | 0.0 | 0.0 | 4.0 |
| | 0.0313 | 0.0 | 0.0 | 0.0 | 0.0 | 0.0 | 0.0 | | 0.0 | 0.0 | 0.0 | | 0.0 | 0.0 | 4.0 |
| | 0.0156 | 0.0 | 0.0 | 0.0 | 0.0 | 0.0 | 0.0 | | 0.0 | 0.0 | 0.0 | | 0.0 | 0.0 | 2.0 |
| 230 | 0.2500 | 9.0 | 9.0 | 9.0 | 9.0 | 0.0 | 9.0 | | 0.0 | 0.0 | 5.0 | | 0.0 | 0.0 | 0.0 |
| | 0.1250 | 9.0 | 9.0 | 0.0 | 9.0 | 5.0 | 9.0 | | 0.0 | 0.0 | 5.0 | | 0.0 | 0.0 | 0.0 |
| | 0.0625 | 9.0 | 9.0 | 0.0 | 0.0 | 5.0 | 9.0 | | 0.0 | 0.0 | 0.0 | | 0.0 | 0.0 | 0.0 |
| | 0.0313 | 9.0 | 0.0 | 0.0 | 0.0 | 0.0 | 9.0 | | 0.0 | 0.0 | 0.0 | | 0.0 | 0.0 | 0.0 |
| | 0.0156 | 9.0 | 0.0 | 0.0 | 9.0 | 5.0 | 0.0 | | 0.0 | 0.0 | 0.0 | | 0.0 | 0.0 | 4.0 |
| 231 | 0.2500 | 9.0 | 9.0 | 0.0 | 9.0 | 0.0 | 9.0 | | 2.0 | 2.0 | 3.0 | | 3.0 | 6.0 | 4.0 |
| | 0.1250 | 9.0 | 9.0 | 0.0 | 9.0 | 0.0 | 9.0 | | 0.0 | 0.0 | 3.0 | | 1.0 | 1.0 | 2.0 |
| | 0.0625 | 9.0 | 5.0 | 0.0 | 9.0 | 0.0 | 9.0 | | 0.0 | 0.0 | 0.0 | | 0.0 | 0.0 | 0.0 |
| | 0.0313 | 9.0 | 0.0 | 0.0 | 9.0 | 0.0 | 0.0 | | 0.0 | 0.0 | 0.0 | | 0.0 | 0.0 | 0.0 |
| | 0.0156 | 9.0 | 0.0 | 0.0 | 9.0 | 0.0 | 0.0 | | 0.0 | 0.0 | 0.0 | | 0.0 | 0.0 | 0.0 |
| 232 | 0.2500 | 9.0 | 9.0 | 9.0 | 9.0 | 9.0 | 9.0 | | 2.0 | 9.0 | 5.0 | | 0.0 | 0.0 | 4.0 |
| | 0.1250 | 9.0 | 9.0 | 9.0 | 9.0 | 5.0 | 9.0 | | 2.0 | 7.0 | 5.0 | | 0.0 | 0.0 | 4.0 |
| | 0.0625 | 9.0 | 4.0 | 3.0 | 9.0 | 0.0 | 9.0 | | 0.0 | 7.0 | 0.0 | | 0.0 | 0.0 | 3.0 |
| | 0.0313 | 9.0 | 0.0 | 0.0 | 9.0 | 0.0 | 0.0 | | 0.0 | 0.0 | 0.0 | | 0.0 | 0.0 | 3.0 |
| | 0.0156 | 9.0 | 0.0 | 0.0 | 9.0 | 0.0 | 0.0 | | 0.0 | 0.0 | 0.0 | | 0.0 | 0.0 | 3.0 |
| 233 | 0.2500 | 9.0 | 0.0 | 0.0 | 9.0 | 0.0 | 0.0 | | 0.0 | 9.0 | 5.0 | | 0.0 | 0.0 | 5.0 |
| | 0.1250 | 0.0 | 4.0 | 0.0 | 9.0 | 0.0 | 0.0 | | 0.0 | 0.0 | 0.0 | | 0.0 | 0.0 | 0.0 |
| | 0.0625 | 0.0 | 0.0 | 0.0 | 9.0 | 0.0 | 0.0 | | 0.0 | 0.0 | 0.0 | | 0.0 | 0.0 | 0.0 |
| | 0.0313 | 0.0 | 0.0 | 0.0 | 9.0 | 0.0 | 0.0 | | 0.0 | 0.0 | 0.0 | | 0.0 | 0.0 | 0.0 |
| | 0.0156 | 0.0 | 0.0 | 0.0 | 9.0 | 0.0 | 0.0 | | 0.0 | 0.0 | 0.0 | | 0.0 | 0.0 | 0.0 |
| 234 | 0.2500 | 9.0 | 9.0 | 2.0 | 9.0 | 9.0 | 9.0 | | 0.0 | 9.0 | 0.0 | | 0.0 | 0.0 | 6.0 |
| | 0.1250 | 9.0 | 6.0 | 2.0 | 9.0 | 0.0 | 9.0 | | 0.0 | 0.0 | 3.0 | | 4.0 | 0.0 | 4.0 |
| | 0.0625 | 9.0 | 0.0 | 2.0 | 9.0 | 0.0 | 0.0 | | 0.0 | 0.0 | | | 0.0 | 0.0 | 0.0 |
| | 0.0313 | 9.0 | 0.0 | 0.0 | 9.0 | 0.0 | 0.0 | | 0.0 | 0.0 | 0.0 | | 0.0 | 0.0 | 0.0 |
| | 0.0156 | 0.0 | 0.0 | 0.0 | 9.0 | 0.0 | 3.0 | | 0.0 | 0.0 | 0.0 | | 0.0 | 0.0 | 0.0 |
| 235 | 0.2500 | 9.0 | 7.0 | 2.0 | 9.0 | 0.0 | | | 0.0 | 0.0 | 2.0 | | 0.0 | 0.0 | 4.0 |
| | 0.1250 | 7.0 | 0.0 | 0.0 | 9.0 | 0.0 | | | 0.0 | 0.0 | 0.0 | | 0.0 | 0.0 | 4.0 |
| | 0.0625 | 9.0 | 0.0 | 0.0 | 9.0 | 0.0 | | | 0.0 | 0.0 | 0.0 | | 0.0 | 0.0 | 0.0 |

TABLE II-continued

Preemergence Herbicidal Evaluations of Test Compounds

| Compound Number | Rate (kg/ha) | ABUTH | AMBEL | CASOB | CHEAL | GALAP | IPOHE | IPOSS | ECHCG | SETVI | GLXMAW | GLXMA | ORYSAT | TRZAWR | ZEAMX |
|---|---|---|---|---|---|---|---|---|---|---|---|---|---|---|---|
| 236 | 0.0313 | 9.0 | 0.0 | 0.0 | 9.0 | 0.0 | 0.0 | | 0.0 | 0.0 | 0.0 | | 0.0 | 0.0 | 0.0 |
| | 0.0156 | 9.0 | 0.0 | 0.0 | 9.0 | 0.0 | 0.0 | | 0.0 | 0.0 | 0.0 | | 1.0 | 4.0 | 0.0 |
| | 0.2500 | 9.0 | 1.0 | 3.0 | 9.0 | 5.0 | 1.0 | | 1.0 | 3.0 | 2.0 | | 1.0 | 0.0 | 3.0 |
| | 0.1250 | 9.0 | 1.0 | 0.0 | 9.0 | 1.0 | 0.0 | | 0.0 | 1.0 | 1.0 | | 1.0 | 0.0 | 2.0 |
| | 0.0625 | 9.0 | 0.0 | 1.0 | 9.0 | 0.0 | 0.0 | | 0.0 | 0.0 | 1.0 | | 1.0 | 0.0 | 1.0 |
| | 0.0313 | 9.0 | 0.0 | 0.0 | 7.0 | 0.0 | 0.0 | | 0.0 | 2.0 | 1.0 | | 1.0 | 0.0 | 0.0 |
| | 0.0156 | 2.0 | 0.0 | 0.0 | | 0.0 | 0.0 | | 0.0 | 0.0 | 0.0 | | 0.0 | 0.0 | 0.0 |
| 237 | 0.2500 | 9.0 | 9.0 | 2.0 | 9.0 | 9.0 | 9.0 | | 5.0 | 9.0 | 5.0 | | 2.0 | 3.0 | 4.0 |
| | 0.1250 | 9.0 | 2.0 | 1.0 | 9.0 | 6.0 | 2.0 | | 1.0 | 1.0 | 2.0 | | 1.0 | 1.0 | 1.0 |
| | 0.0625 | 4.0 | 0.0 | 0.0 | 9.0 | 1.0 | 0.0 | | 0.0 | 9.0 | 2.0 | | 0.0 | 0.0 | 1.0 |
| | 0.0313 | 3.0 | 0.0 | 0.0 | 9.0 | 0.0 | 1.0 | | 0.0 | 1.0 | 0.0 | | 0.0 | 0.0 | 1.0 |
| | 0.0156 | 0.0 | 0.0 | 0.0 | 9.0 | 0.0 | 0.0 | | 0.0 | 0.0 | 1.0 | | 0.0 | 0.0 | 1.0 |
| 238 | 0.2500 | 9.0 | 9.0 | 3.0 | 9.0 | 9.0 | 9.0 | | 7.0 | 9.0 | 9.0 | | 6.0 | 6.0 | 7.0 |
| | 0.1250 | 9.0 | 9.0 | 2.0 | 9.0 | 6.0 | 9.0 | | 5.0 | 9.0 | 5.0 | | 4.0 | 3.0 | 7.0 |
| | 0.0625 | 6.0 | 7.0 | 1.0 | 9.0 | 3.0 | 0.0 | | 1.0 | 9.0 | 3.0 | | 1.0 | 1.0 | 4.0 |
| | 0.0313 | | 4.0 | 0.0 | 9.0 | 3.0 | 9.0 | | 1.0 | 1.0 | 2.0 | | 1.0 | 1.0 | 2.0 |
| | 0.0156 | 3.0 | 3.0 | 0.0 | 0.0 | 0.0 | 0.0 | | 1.0 | 1.0 | 2.0 | | 0.0 | 0.0 | 1.0 |
| 239 | 0.2500 | 9.0 | 9.0 | 9.0 | 9.0 | 9.0 | 9.0 | | 7.0 | 9.0 | 9.0 | | 7.0 | 6.0 | 7.0 |
| | 0.1250 | 9.0 | 4.0 | 6.0 | 9.0 | 3.0 | 9.0 | | 6.0 | 9.0 | 9.0 | | 7.0 | 5.0 | 7.0 |
| | 0.0625 | 9.0 | 9.0 | 3.0 | 9.0 | 3.0 | 9.0 | | 2.0 | 9.0 | 4.0 | | 4.0 | 3.0 | 5.0 |
| | 0.0313 | 9.0 | 4.0 | 0.0 | 9.0 | 9.0 | 9.0 | | 1.0 | 4.0 | 1.0 | | 0.0 | 1.0 | 0.0 |
| | 0.0156 | 2.0 | 2.0 | 0.0 | 0.0 | 7.0 | 4.0 | | 0.0 | 3.0 | 1.0 | | 0.0 | 1.0 | 0.0 |
| 245 | 0.2500 | 0.0 | 1.0 | 0.0 | 0.0 | 0.0 | 0.0 | | 0.0 | 1.0 | 2.0 | | 0.0 | 0.0 | 0.0 |
| | 0.1250 | 0.0 | 0.0 | 0.0 | 0.0 | 0.0 | 0.0 | | 0.0 | 0.0 | 2.0 | | 0.0 | 0.0 | 0.0 |
| | 0.0625 | 0.0 | 0.0 | 0.0 | 0.0 | 0.0 | 0.0 | | 0.0 | 0.0 | 0.0 | | 0.0 | 0.0 | 0.0 |
| | 0.0313 | 0.0 | 0.0 | 0.0 | 0.0 | 0.0 | 0.0 | | 0.0 | 0.0 | 0.0 | | 0.0 | 0.0 | 0.0 |
| | 0.0156 | 0.0 | 0.0 | 0.0 | 0.0 | 0.0 | 0.0 | | 0.0 | 0.0 | 0.0 | | 0.0 | 0.0 | 0.0 |
| 246 | 0.2500 | 9.0 | 0.0 | 3.0 | 9.0 | 0.0 | 9.0 | | 3.0 | 6.0 | 4.0 | | 1.0 | 7.0 | 3.0 |
| | 0.1250 | 9.0 | 0.0 | 0.0 | 9.0 | 0.0 | 0.0 | | 0.0 | 0.0 | 4.0 | | 0.0 | 0.0 | 3.0 |
| | 0.0625 | 0.0 | 0.0 | 0.0 | 0.0 | 0.0 | 0.0 | | 0.0 | 0.0 | 2.0 | | 0.0 | 0.0 | 2.0 |
| | 0.0313 | 0.0 | 0.0 | 0.0 | | 0.0 | 0.0 | | 0.0 | 0.0 | 1.0 | | 0.0 | 0.0 | 2.0 |
| | 0.0156 | 0.0 | 0.0 | 0.0 | | 0.0 | 0.0 | | 0.0 | 0.0 | 1.0 | | 0.0 | 0.0 | 0.0 |
| 256 | 0.2500 | 9.0 | 9.0 | 9.0 | 9.0 | 9.0 | 9.0 | | 9.0 | 9.0 | 9.0 | | 9.0 | 9.0 | 9.0 |
| | 0.1250 | 9.0 | 9.0 | 8.3 | 9.0 | 9.0 | 9.0 | | 9.0 | 9.0 | 9.0 | | 8.0 | 9.0 | 8.7 |
| | 0.0620 | 8.6 | 9.0 | 9.0 | 9.0 | | 9.0 | | 9.0 | 9.0 | 9.0 | | 8.0 | | 9.0 |
| | 0.0320 | 8.0 | 9.0 | 6.0 | 9.0 | | 9.0 | | 9.0 | 9.0 | 9.0 | | 8.0 | | 9.0 |
| | 0.0160 | 9.0 | 9.0 | 9.0 | 9.0 | 9.0 | 9.0 | | 9.0 | 9.0 | 9.0 | | 5.0 | | 5.0 |
| 257 | 0.2500 | 9.0 | 9.0 | 4.5 | 9.0 | 9.0 | 9.0 | | 5.0 | 9.0 | 8.0 | | 7.0 | 9.0 | 7.5 |
| | 0.1250 | 9.0 | 6.5 | 1.5 | 9.0 | 3.0 | 9.0 | | 3.0 | 8.5 | 5.5 | | 4.5 | 3.0 | 2.0 |
| | 0.0620 | 9.0 | 3.0 | 0.0 | 9.0 | 0.0 | 6.0 | | 1.0 | 1.0 | 4.5 | | 3.5 | 3.0 | 0.0 |
| | 0.0320 | 4.5 | 1.0 | 0.0 | 9.0 | 0.0 | 5.0 | | 0.0 | 0.0 | 2.0 | | 0.0 | 2.0 | 0.0 |
| | 0.0160 | 4.5 | 1.0 | 0.0 | 0.0 | 0.0 | 1.5 | | 0.0 | 0.0 | 0.0 | | 0.0 | 0.0 | 0.0 |
| 258 | 0.2500 | 9.0 | 9.0 | 8.3 | 9.0 | 7.0 | 8.0 | | 6.7 | 9.0 | 7.3 | | 6.3 | 7.5 | 7.0 |
| | 0.1250 | 9.0 | 9.0 | 4.3 | 9.0 | 3.5 | 8.0 | | 3.0 | 9.0 | 3.7 | | 3.7 | 5.5 | 3.3 |
| | 0.0620 | 9.0 | 9.0 | 1.3 | 9.0 | 0.5 | 7.3 | | 1.7 | 4.7 | 3.0 | | 2.0 | 2.5 | 1.7 |
| | 0.0320 | 4.7 | 3.70.0 | 9.0 | 0.0 | 4.7 | | 0.7 | 4.0 | 0.7 | | 1.0 | | 0.0 | 0.0 |
| | 0.0160 | 4.0 | 1.0 | 0.0 | 9.0 | 0.0 | 2.0 | | 0.0 | 0.3 | 0.0 | | 0.70.0 | 0.0 | |

TABLE II-continued

Preemergence Herbicidal Evaluations of Test Compounds

| Compound Number | Rate (kg/ha) | ABUTH | AMBEL | CASOB | CHEAL | GALAP | IPOHE | IPOSS | ECHCG | SETVI | GLXMAW | GLXMA | ORYSAT | TRZAWR | ZEAMX |
|---|---|---|---|---|---|---|---|---|---|---|---|---|---|---|---|
| 259 | 0.2500 | 9.0 | 9.0 | 7.0 | 9.0 | 0.0 | 9.0 | | 3.5 | 9.0 | 9.0 | | 7.0 | 6.0 | 6.0 |
| | 0.1250 | 9.0 | 6.5 | 3.5 | 9.0 | 0.0 | 9.0 | | 1.5 | 7.0 | 6.0 | | 6.5 | 4.0 | 1.5 |
| | 0.0620 | 4.5 | 5.5 | 0.0 | 9.0 | 0.0 | 5.5 | | 3.0 | 1.0 | 0.0 | | 1.0 | 0.0 | 0.0 |
| | 0.0320 | 1.0 | 1.0 | 0.0 | 7.0 | 0.0 | 7.5 | | 0.5 | 2.0 | 0.0 | | 0.0 | 0.0 | 0.0 |
| | 0.0160 | 0.0 | 0.0 | 0.0 | 9.0 | 0.0 | 1.5 | | 0.0 | 1.5 | 0.0 | | 0.0 | 0.0 | 0.0 |
| 260 | 0.2500 | 9.0 | 6.0 | 0.0 | 9.0 | 0.0 | 0.0 | | 0.0 | 0.0 | 0.0 | | 0.0 | 0.0 | 0.0 |
| | 0.1250 | 9.0 | 3.0 | 0.0 | 9.0 | 0.0 | 0.0 | | 0.0 | 0.0 | 0.0 | | 0.0 | 0.0 | 0.0 |
| | 0.0620 | 0.0 | 0.0 | 0.0 | 9.0 | 0.0 | 0.0 | | 0.0 | 0.0 | 0.0 | | 0.0 | 0.0 | 0.0 |
| | 0.0320 | 0.0 | 0.0 | 0.0 | 9.0 | 0.0 | 0.0 | | 0.0 | 0.0 | 0.0 | | 0.0 | 0.0 | 0.0 |
| | 0.0160 | 0.0 | 0.0 | 0.0 | 9.0 | 0.0 | 0.0 | | 0.0 | 0.0 | 0.0 | | 0.0 | 0.0 | 0.0 |
| 261 | 0.2500 | 9.0 | 9.0 | 9.0 | 9.0 | 9.0 | 9.0 | | 0.0 | 9.0 | 9.0 | | 3.0 | 2.0 | 7.0 |
| | 0.1250 | 9.0 | 5.0 | 0.0 | 9.0 | 9.0 | 7.0 | | 0.0 | 0.0 | 3.0 | | 0.0 | 0.0 | 2.0 |
| | 0.0620 | 9.0 | 0.0 | 0.0 | 9.0 | 0.0 | 9.0 | | 0.0 | 0.0 | 0.0 | | 0.0 | 0.0 | 0.0 |
| | 0.0320 | 0.0 | 0.0 | 0.0 | 9.0 | 0.0 | 0.0 | | 0.0 | 0.0 | 0.0 | | 0.0 | 0.0 | 0.0 |
| | 0.0160 | 0.0 | 0.0 | 0.0 | 9.0 | 0.0 | 0.0 | | 0.0 | 0.0 | 0.0 | | 0.0 | 0.0 | 0.0 |
| 262 | 0.2500 | 9.0 | 9.0 | 9.0 | 9.0 | | 9.0 | | 4.0 | 9.0 | 9.0 | | 4.0 | 6.0 | 6.0 |
| | 0.1250 | 9.0 | 6.5 | 7.5 | 9.0 | | 9.0 | | 4.5 | 8.5 | 8.5 | | 4.0 | 4.0 | 5.0 |
| | 0.0620 | 9.0 | 6.0 | 5.0 | 9.0 | | 9.0 | | 1.5 | 8.0 | 6.0 | | 1.5 | 3.0 | 1.0 |
| | 0.0320 | 9.0 | 5.0 | 3.5 | 9.0 | | 8.0 | | 0.0 | 2.0 | 3.0 | | 1.0 | 0.0 | 0.5 |
| | 0.0160 | 8.0 | 1.0 | 1.0 | 9.0 | | 4.5 | | 0.0 | 1.5 | 1.0 | | 0.5 | 0.0 | 0.0 |
| 263 | 0.5000 | 9.0 | 9.0 | 7.0 | 9.0 | | 9.0 | | 3.0 | 6.0 | 9.0 | | 4.0 | 3.0 | 5.0 |
| | 0.2500 | 9.0 | 5.5 | 6.5 | 9.0 | | 9.0 | | 1.0 | 3.0 | 6.0 | | 0.0 | 0.0 | 2.5 |
| | 0.1250 | 9.0 | 4.0 | 2.0 | 9.0 | | 9.0 | | 0.0 | 1.5 | 3.0 | | 0.0 | 0.0 | 0.0 |
| | 0.0620 | 9.0 | 2.0 | 1.0 | 9.0 | | 4.0 | | 0.0 | 1.0 | 1.0 | | 0.0 | 0.0 | 0.0 |
| | 0.0320 | 9.0 | 1.0 | 0.5 | 8.0 | | 0.0 | | 0.0 | 1.0 | 0.5 | | 0.0 | 0.0 | 0.0 |
| | 0.0160 | 9.0 | 0.0 | 0.0 | 4.0 | | 0.0 | | 0.0 | 1.0 | 0.0 | | 0.0 | 0.0 | 0.0 |
| 264 | 0.2500 | 9.0 | 9.0 | 8.0 | 9.0 | | 9.0 | | 8.0 | 9.0 | 8.5 | | 7.5 | 8.0 | 6.5 |
| | 0.1250 | 9.0 | 9.0 | 5.5 | 9.0 | | 9.0 | | 6.5 | 9.0 | 8.0 | | 5.5 | 7.0 | 4.5 |
| | 0.0620 | 9.0 | 9.0 | 1.0 | 9.0 | | 7.0 | | 3.5 | 9.0 | 4.5 | | 2.5 | 4.0 | 4.0 |
| | 0.0320 | 7.5 | 4.0 | 1.0 | 9.0 | | 5.5 | | 0.5 | 3.0 | 1.0 | | 1.0 | 0.0 | 1.0 |
| | 0.0160 | 7.5 | 2.0 | 1.0 | 7.5 | | 0.0 | | 0.0 | 1.5 | 0.0 | | 0.5 | 0.0 | 1.0 |
| 265 | 0.2500 | 9.0 | 0.0 | 0.0 | 9.0 | | 0.0 | | 0.0 | 0.0 | 0.0 | | 0.0 | 0.0 | 0.0 |
| | 0.1250 | 8.0 | 0.0 | 0.0 | 9.0 | | 0.0 | | 0.0 | 0.0 | 0.0 | | 0.0 | 0.0 | 0.0 |
| | 0.0620 | 0.0 | 0.0 | 0.0 | 9.0 | | 0.0 | | 0.0 | 0.0 | 0.0 | | 0.0 | 0.0 | 0.0 |
| | 0.0320 | 0.0 | 0.0 | 0.0 | 0.0 | | 0.0 | | 0.0 | 0.0 | 0.0 | | 0.0 | 0.0 | 0.0 |
| | 0.0160 | 0.0 | 0.0 | 0.0 | 0.0 | | 0.0 | | 0.0 | 0.0 | 0.0 | | 0.0 | 0.0 | 0.0 |
| 266 | 0.5000 | 9.0 | 9.0 | 7.0 | 9.0 | | 9.0 | | 9.0 | 9.0 | 7.0 | | 7.0 | 8.0 | 6.0 |
| | 0.2500 | 9.0 | 9.0 | 1.0 | 9.0 | | 9.0 | | 7.0 | 9.0 | 4.5 | | 7.0 | 3.0 | 4.5 |
| | 0.1250 | 9.0 | 6.0 | 1.0 | 9.0 | | 6.5 | | 1.0 | 5.0 | 3.0 | | 3.5 | 0.0 | 3.0 |
| | 0.0620 | 2.0 | 1.0 | 1.0 | 7.5 | | 1.0 | | 1.5 | 2.0 | 0.5 | | 1.0 | 0.0 | 1.0 |
| | 0.0320 | 2.5 | 0.5 | 1.0 | 1.0 | | 0.0 | | 0.5 | 2.5 | 0.0 | | 0.0 | 0.0 | 0.5 |
| | 0.0160 | 0.0 | 0.0 | 0.0 | 0.0 | | 0.0 | | 0.0 | 0.0 | 0.0 | | 0.0 | 0.0 | 0.0 |
| 267 | 0.2500 | 9.0 | 9.0 | 0.0 | 9.0 | | 0.0 | | 9.0 | 9.0 | 3.0 | | 0.0 | 0.0 | 6.0 |
| | 0.1250 | 9.0 | 3.0 | 0.0 | 9.0 | | 0.0 | | 9.0 | 9.0 | 3.0 | | 0.0 | 0.0 | 0.0 |
| | 0.0620 | 9.0 | 1.0 | 0.0 | 9.0 | | 0.0 | | 1.0 | 9.0 | 0.0 | | 0.0 | 0.0 | 0.0 |
| | 0.0320 | 0.0 | 0.0 | 0.0 | 9.0 | | 0.0 | | 0.0 | 0.0 | 0.0 | | 0.0 | 0.0 | 0.0 |
| | 0.0160 | 0.0 | 0.0 | 0.0 | 9.0 | | 0.0 | | 0.0 | 0.0 | 0.0 | | 0.0 | 0.0 | 0.0 |

TABLE II-continued

Preemergence Herbicidal Evaluations of Test Compounds

| Compound Number | Rate (kg/ha) | ABUTH | AMBEL | CASOB | CHEAL | GALAP | IPOHE | IPOSS | ECHCG | SETVI | GLXMAW | GLXMA | ORYSAT | TRZAWR | ZEAMX |
|---|---|---|---|---|---|---|---|---|---|---|---|---|---|---|---|
| 268 | 0.5000 | 9.0 | 9.0 | 9.0 | 9.0 | 9.0 | 9.0 | | 9.0 | 9.0 | 9.0 | | 9.0 | 8.0 | 9.0 |
| | 0.2500 | 9.0 | 9.0 | 9.0 | 9.0 | 9.0 | 9.0 | | 8.8 | 9.0 | 9.0 | | 8.8 | 5.0 | 9.0 |
| | 0.1250 | 9.0 | 9.0 | 5.3 | 9.0 | 8.0 | 9.0 | | 7.3 | 8.0 | 9.0 | | 7.5 | 3.0 | 8.3 |
| | 0.0620 | 9.0 | 9.0 | 3.8 | 9.0 | 3.0 | 9.0 | | 6.5 | 8.0 | 4.8 | | 5.5 | 1.0 | 5.3 |
| | 0.0320 | 9.0 | 7.0 | 0.8 | 8.8 | 5.0 | 7.7 | | 3.3 | 6.3 | 3.3 | | 3.3 | 1.0 | 3.0 |
| | 0.0160 | 9.0 | 8.0 | 0.3 | 9.0 | | 7.7 | | 2.3 | 6.7 | 2.0 | | 2.3 | 0.0 | 2.7 |
| 269 | 0.2500 | 0.0 | 0.0 | 0.0 | 0.0 | | 0.0 | | 0.0 | 0.0 | 0.0 | | 0.0 | 0.0 | 0.0 |
| | 0.1250 | 0.0 | 0.0 | 0.0 | 0.0 | | 0.0 | | 0.0 | 0.0 | 0.0 | | 0.0 | 0.0 | 0.0 |
| | 0.0620 | 0.0 | 0.0 | 0.0 | 0.0 | | 0.0 | | 0.0 | 0.0 | 0.0 | | 0.0 | 0.0 | 0.0 |
| | 0.0320 | 0.0 | 0.0 | 0.0 | 0.0 | | 0.0 | | 0.0 | 0.0 | 0.0 | | 0.0 | 0.0 | 0.0 |
| 270 | 0.5000 | 9.0 | 9.0 | 9.0 | 9.0 | | 9.0 | | 4.0 | 9.0 | 4.0 | | 4.0 | | 5.0 |
| | 0.2500 | 9.0 | 9.0 | 1.5 | 8.5 | | 9.0 | | 2.0 | 8.0 | 2.5 | | 1.0 | | 5.0 |
| | 0.1250 | 9.0 | 9.0 | 0.0 | 9.0 | | 8.0 | | 1.0 | 5.5 | 2.0 | | 1.0 | | 3.0 |
| | 0.0620 | 9.0 | 8.0 | 0.0 | 9.0 | | 4.5 | | 0.0 | 3.5 | 1.0 | | 1.0 | | 1.0 |
| | 0.0320 | 4.0 | 2.5 | 0.0 | 6.0 | | 0.0 | | 0.0 | 1.0 | 0.0 | | 1.0 | | 0.0 |
| | 0.0160 | 0.0 | 0.0 | 0.0 | 0.0 | | 0.0 | | 0.0 | 0.0 | 0.0 | | 0.0 | | 0.0 |
| 271 | 0.2500 | 9.0 | 9.0 | 3.0 | 9.0 | | 9.0 | | 9.0 | 9.0 | 7.0 | | 9.0 | 8.0 | 9.0 |
| | 0.1250 | 9.0 | 9.0 | 9.0 | 9.0 | 7.0 | 9.0 | | 8.0 | 9.0 | 6.0 | | 6.0 | 3.0 | 6.5 |
| | 0.0620 | 9.0 | 6.0 | 2.0 | 9.0 | 7.0 | 5.5 | | 3.0 | 6.5 | 1.5 | | 2.5 | 1.0 | 2.0 |
| | 0.0320 | 9.0 | 4.5 | 2.0 | 9.0 | 0.0 | 5.0 | | 2.5 | 2.0 | 2.0 | | 2.0 | 0.0 | 2.5 |
| | 0.0160 | 4.0 | 2.0 | 2.0 | 3.5 | 0.0 | 1.5 | | 1.0 | 0.0 | 1.0 | | 0.0 | 0.0 | 0.0 |
| 272 | 0.5000 | 9.0 | 3.0 | 0.0 | 9.0 | 9.0 | 2.0 | | 0.0 | 0.0 | 0.0 | | 0.0 | 0.0 | 0.0 |
| | 0.2500 | 3.0 | 0.0 | 0.0 | 2.0 | 2.0 | 0.0 | | 0.0 | 0.0 | 0.0 | | 0.0 | 0.0 | 0.0 |
| | 0.1250 | 2.0 | 0.0 | 0.0 | 0.0 | 0.0 | 0.0 | | 0.0 | 0.0 | 0.0 | | 0.0 | 0.0 | 0.0 |
| | 0.0620 | 0.0 | 0.0 | 0.0 | 0.0 | 0.0 | 0.0 | | 0.0 | 0.0 | 0.0 | | 0.0 | 0.0 | 0.0 |
| 273 | 0.2500 | 9.0 | 9.0 | 9.0 | 9.0 | 9.0 | 9.0 | | 0.0 | 9.0 | 3.0 | | 3.0 | 0.0 | 0.0 |
| | 0.1250 | 9.0 | 9.0 | 7.0 | 9.0 | 9.0 | 2.0 | | 0.0 | 7.0 | 0.0 | | 0.0 | 0.0 | 0.0 |
| | 0.0620 | 0.0 | 0.0 | 0.0 | 0.0 | 7.0 | 0.0 | | 0.0 | 0.0 | 0.0 | | 0.0 | 0.0 | 0.0 |
| | 0.0320 | 0.0 | 0.0 | 0.0 | 0.0 | 0.0 | 0.0 | | 0.0 | 0.0 | 0.0 | | 0.0 | 0.0 | 0.0 |
| | 0.0160 | 0.0 | 0.0 | 0.0 | 0.0 | 0.0 | 5.0 | | 7.0 | 0.0 | 0.0 | | 0.0 | 0.0 | 0.0 |
| 274 | 0.2500 | 9.0 | 0.0 | 0.0 | 9.0 | 9.0 | 0.0 | | 3.0 | 9.0 | 0.0 | | 3.0 | 0.0 | 0.0 |
| | 0.1250 | 9.0 | 3.0 | 0.0 | 9.0 | 0.0 | 0.0 | | 0.0 | 9.0 | 0.0 | | 0.0 | 0.0 | 0.0 |
| | 0.0620 | 9.0 | 0.0 | 0.0 | 0.0 | 0.0 | 0.0 | | 0.0 | 9.0 | 0.0 | | 0.0 | 0.0 | 0.0 |
| | 0.0320 | 9.0 | 0.0 | 5.0 | 0.0 | 0.0 | 3.0 | | 9.0 | 9.0 | 9.0 | | 4.0 | 3.0 | 0.0 |
| 275 | 0.2500 | 9.0 | 9.0 | 0.0 | 9.0 | 0.0 | 0.0 | | 4.0 | 7.0 | 0.0 | | 0.0 | 0.0 | 0.0 |
| | 0.1250 | 0.0 | 0.0 | 0.0 | 9.0 | 7.0 | 0.0 | | 0.0 | 0.0 | 0.0 | | 0.0 | 0.0 | 0.0 |
| | 0.0620 | 0.0 | 0.0 | 0.0 | 9.0 | 0.0 | 0.0 | | 0.0 | 0.0 | 0.0 | | 0.0 | 0.0 | 0.0 |
| | 0.0320 | 0.0 | 0.0 | 0.0 | 0.0 | 0.0 | 0.0 | | 0.0 | 0.0 | 0.0 | | 0.0 | 0.0 | 0.0 |
| 276 | 0.2500 | 9.0 | 9.0 | 7.0 | 9.0 | 9.0 | 9.0 | | 8.0 | 9.0 | 9.0 | | 8.0 | 8.0 | 7.0 |
| | 0.1250 | 9.0 | 7.0 | 3.0 | 9.0 | 7.0 | 0.0 | | 0.0 | 7.0 | 2.0 | | 4.0 | 5.0 | 6.0 |
| | 0.0620 | 9.0 | 2.0 | 0.0 | 9.0 | 0.0 | 0.0 | | 0.0 | 0.0 | 0.0 | | 0.0 | 0.0 | 0.0 |
| | 0.0320 | 9.0 | 1.0 | 0.0 | 9.0 | 0.0 | 0.0 | | 0.0 | 0.0 | 0.0 | | 0.0 | 0.0 | 0.0 |
| | 0.0160 | 0.0 | 0.0 | 0.0 | 0.0 | 0.0 | 0.0 | | 0.0 | 0.0 | 0.0 | | 0.0 | 0.0 | 0.0 |
| 277 | 0.2500 | 9.0 | 9.0 | 9.0 | 9.0 | 9.0 | 9.0 | | 9.0 | 9.0 | 9.0 | | 9.0 | 9.0 | 8.5 |
| | 0.1250 | 9.0 | 9.0 | 6.5 | 9.0 | 9.0 | 9.0 | | 9.0 | 9.0 | 8.5 | | 8.0 | 8.0 | 8.5 |
| | 0.0620 | 9.0 | 8.0 | 3.0 | 9.0 | 9.0 | 5.5 | | 9.0 | 9.0 | 6.0 | | 7.0 | 7.0 | 8.0 |

TABLE II-continued

Preemergence Herbicidal Evaluations of Test Compounds

| Compound Number | Rate (kg/ha) | ABUTH | AMBEL | CASOB | CHEAL | GALAP | IPOHE | IPOSS | ECHCG | SETVI | GLXMAW | GLXMA | ORYSAT | TRZAWR | ZEAMX |
|---|---|---|---|---|---|---|---|---|---|---|---|---|---|---|---|
| 278 | 0.0320 | 9.0 | 6.5 | 1.0 | 9.0 | 8.0 | 3.0 | | 6.0 | 9.0 | 4.5 | | 4.0 | 5.0 | 6.0 |
| | 0.0160 | 9.0 | 4.0 | 0.0 | 9.0 | 0.0 | 1.5 | | 2.5 | 9.0 | 2.5 | | 1.5 | 2.0 | 3.5 |
| | 0.2500 | 9.0 | 9.0 | 9.0 | 9.0 | 9.0 | 9.0 | | 9.0 | 9.0 | 7.0 | | 9.0 | 8.0 | 9.0 |
| | 0.1250 | 9.0 | 9.0 | 1.0 | 9.0 | 9.0 | 9.0 | | 9.0 | 9.0 | 5.0 | | 8.0 | 7.0 | 9.0 |
| | 0.0620 | 9.0 | 5.0 | 0.0 | 9.0 | 9.0 | 9.0 | | 0.0 | 9.0 | 5.0 | | 7.0 | 3.0 | 3.0 |
| | 0.0320 | 9.0 | 3.0 | 0.0 | 9.0 | 3.0 | 2.0 | | 0.0 | 9.0 | 0.0 | | 0.0 | 0.0 | 0.0 |
| | 0.0160 | 0.0 | 0.0 | 0.0 | 3.0 | 9.0 | 0.0 | | 2.0 | 0.0 | 3.0 | | 0.0 | 0.0 | 0.0 |
| 279 | 0.2500 | 9.0 | 9.0 | 0.0 | 9.0 | 9.0 | 9.0 | | 0.0 | 9.0 | 1.0 | | 7.0 | 7.0 | 7.0 |
| | 0.1250 | 9.0 | 9.0 | 0.0 | 9.0 | 4.0 | 3.0 | | 0.0 | 9.0 | 0.0 | | 1.0 | 2.0 | 5.0 |
| | 0.0620 | 9.0 | 0.0 | 0.0 | 9.0 | 0.0 | 0.0 | | 0.0 | 9.0 | 0.0 | | 0.0 | 0.0 | 0.0 |
| | 0.0320 | 0.0 | 0.0 | 0.0 | 9.0 | 0.0 | 0.0 | | 0.0 | 0.0 | 0.0 | | 0.0 | 0.0 | 0.0 |
| | 0.0160 | 0.0 | 7.0 | 7.0 | 9.0 | 1.0 | 9.0 | | 9.0 | 9.0 | 8.0 | | 7.0 | 2.0 | 8.0 |
| 280 | 0.2500 | 9.0 | 9.0 | 4.0 | 9.0 | 0.0 | 4.0 | | 9.0 | 9.0 | 2.0 | | 6.0 | 1.0 | 2.0 |
| | 0.1250 | 9.0 | 7.0 | 1.0 | 9.0 | 1.0 | 0.0 | | 9.0 | 9.0 | 1.0 | | 0.0 | 0.0 | 2.0 |
| | 0.0620 | 7.0 | 1.0 | 0.0 | 9.0 | 0.0 | 0.0 | | 0.0 | 0.0 | 0.0 | | 0.0 | 0.0 | 0.0 |
| | 0.0320 | 0.0 | 0.0 | 0.0 | 2.0 | 0.0 | 0.0 | | 0.0 | 0.0 | 0.0 | | 0.0 | 0.0 | 0.0 |
| 281 | 0.2500 | 9.0 | 9.0 | 5.0 | 9.0 | 9.0 | 9.0 | | 7.0 | 9.0 | 0.0 | | 7.0 | 7.0 | 8.0 |
| | 0.1250 | 9.0 | 9.0 | 2.0 | 9.0 | 6.0 | 9.0 | | 4.0 | 9.0 | 6.0 | | 5.0 | 2.0 | 7.0 |
| | 0.0620 | 9.0 | 6.0 | 0.0 | 9.0 | 2.0 | 9.0 | | 0.0 | 7.0 | 2.0 | | 1.0 | 1.0 | 1.0 |
| | 0.0320 | 1.0 | 4.0 | 0.0 | 9.0 | 0.0 | 0.0 | | 0.0 | 9.0 | 0.0 | | 0.0 | 1.0 | 1.0 |
| | 0.0160 | 0.0 | 0.0 | 0.0 | 0.0 | 0.0 | 0.0 | | 0.0 | 0.0 | 0.0 | | 0.0 | 0.0 | 0.0 |
| 282 | 0.5000 | 8.0 | 5.0 | 4.0 | 9.0 | 0.0 | 7.0 | | 0.0 | 2.0 | 2.0 | | 2.0 | | 0.5 |
| | 0.2500 | 2.0 | 0.0 | 0.0 | 2.5 | 0.0 | 2.0 | | 0.0 | 2.0 | 0.0 | | 0.0 | 0.0 | 0.5 |
| | 0.1250 | 0.0 | 0.0 | 0.0 | 2.5 | 0.0 | 0.0 | | 0.0 | 0.0 | 0.0 | | 0.0 | 0.0 | 0.0 |
| | 0.0620 | 0.0 | 0.0 | 0.0 | 0.0 | 0.0 | 0.0 | | 0.0 | 0.0 | 0.0 | | 0.0 | 0.0 | 0.0 |
| 283 | 0.5000 | 9.0 | 7.0 | 7.0 | 9.0 | 4.0 | 9.0 | | 9.0 | 9.0 | 6.0 | | 9.0 | 6.0 | 6.0 |
| | 0.2500 | 8.0 | 5.0 | 3.0 | 9.0 | 1.0 | 4.5 | | 1.0 | 5.5 | 2.0 | | 5.0 | 3.0 | 2.5 |
| | 0.1250 | 8.0 | 3.0 | 1.5 | 7.0 | 0.0 | 2.5 | | 0.0 | 4.5 | 1.0 | | 1.0 | 1.0 | 2.0 |
| | 0.0620 | 3.5 | 1.5 | 0.0 | 2.0 | 0.0 | 0.0 | | 0.5 | 0.0 | 0.0 | | 0.0 | 0.0 | 0.0 |
| | 0.0320 | 0.0 | 0.0 | 0.0 | 0.0 | 2.0 | 0.0 | | 0.5 | 0.0 | 0.0 | | 0.0 | 0.0 | 0.0 |
| 284 | 0.2500 | 4.0 | 2.0 | 0.0 | 9.0 | 0.0 | 1.0 | | 1.0 | 1.0 | 0.0 | | 0.0 | 1.0 | 2.0 |
| | 0.1250 | 0.0 | 0.0 | 0.0 | 1.0 | 0.0 | 0.0 | | 0.0 | 0.0 | 0.0 | | 0.0 | 0.0 | 0.0 |
| | 0.0620 | 0.0 | 0.0 | 0.0 | 0.0 | 0.0 | 0.0 | | 0.0 | 0.0 | 0.0 | | 0.0 | 0.0 | 0.0 |
| 285 | 0.5000 | 9.0 | 9.0 | 5.0 | 9.0 | 9.0 | 9.0 | | 9.0 | 9.0 | 9.0 | | 9.0 | | 9.0 |
| | 0.2500 | 9.0 | 8.0 | 2.5 | 9.0 | 9.0 | 9.0 | | 8.5 | 9.0 | 6.5 | | 8.0 | 7.0 | 8.5 |
| | 0.1250 | 9.0 | 6.0 | 1.5 | 9.0 | 9.0 | 8.0 | | 5.0 | 9.0 | 5.0 | | 6.0 | 6.0 | 6.5 |
| | 0.0620 | 9.0 | 4.0 | 1.0 | 9.0 | 7.0 | 6.0 | | 5.0 | 9.0 | 4.0 | | 5.0 | 5.0 | 7.0 |
| | 0.0320 | 5.0 | 2.0 | 0.0 | 9.0 | 2.0 | 4.0 | | 1.0 | 6.0 | 2.0 | | 1.0 | 1.0 | 3.0 |
| | 0.0160 | 5.0 | 0.0 | 1.0 | 6.0 | 2.0 | 0.0 | | 0.0 | 0.0 | 0.0 | | 1.0 | 0.0 | 1.0 |
| 286 | 0.2500 | 9.0 | 5.5 | 0.0 | 9.0 | 2.0 | 4.0 | | 1.0 | 6.5 | 0.5 | | 0.5 | 1.0 | 1.0 |
| | 0.1250 | 4.5 | 1.0 | 0.0 | 6.5 | 0.0 | 0.0 | | 0.0 | 1.5 | 0.0 | | 0.0 | 0.0 | 0.0 |
| | 0.0620 | 0.5 | 0.0 | 0.0 | 0.5 | 0.0 | 0.0 | | 0.0 | 0.0 | 0.0 | | 0.0 | 0.0 | 0.0 |
| | 0.0320 | 0.0 | 0.0 | 0.0 | 0.0 | 0.0 | 0.0 | | 0.0 | 0.0 | 0.0 | | 0.0 | 0.0 | 0.0 |
| 287 | 0.2500 | 9.0 | 7.0 | 0.0 | 9.0 | 1.0 | 5.0 | | 7.0 | 9.0 | 5.0 | | 4.0 | 4.0 | 5.0 |
| | 0.1250 | 9.0 | 4.0 | 0.0 | 9.0 | 0.0 | 1.0 | | 3.0 | 6.0 | 2.0 | | 2.0 | 4.0 | 4.0 |
| | 0.0620 | 6.0 | 3.0 | 0.0 | 9.0 | 0.0 | 0.0 | | 1.0 | 5.0 | 0.0 | | 0.0 | 0.0 | 1.0 |

TABLE II-continued

Preemergence Herbicidal Evaluations of Test Compounds

| Compound Number | Rate (kg/ha) | ABUTH | AMBEL | CASOB | CHEAL | GALAP | IPOHE | IPOSS | ECHCG | SETVI | GLXMAW | GLXMA | ORYSAT | TRZAWR | ZEAMX |
|---|---|---|---|---|---|---|---|---|---|---|---|---|---|---|---|
|  | 0.0320 | 1.0 | 0.0 | 0.0 | 0.0 | 0.0 | 0.0 |  | 0.0 | 0.0 | 0.0 |  | 0.0 | 0.0 | 0.0 |
|  | 0.0160 | 0.0 | 0.0 | 0.0 | 0.0 | 0.0 | 0.0 |  | 0.0 | 0.0 | 0.0 |  | 0.0 | 0.0 | 0.0 |
| 288 | 0.2500 | 9.0 | 9.0 | 1.0 | 9.0 | 9.0 | 9.0 |  | 5.0 | 9.0 | 5.0 |  | 4.0 | 9.0 | 9.0 |
|  | 0.1250 | 9.0 | 6.0 | 0.0 | 9.0 | 0.0 | 9.0 |  | 4.0 | 5.0 | 3.0 |  | 1.0 | 3.0 | 9.0 |
|  | 0.0620 | 9.0 | 2.0 | 0.0 | 9.0 | 0.0 | 9.0 |  | 0.0 | 0.0 | 0.0 |  | 0.0 | 0.0 | 2.0 |
|  | 0.0320 | 5.0 | 2.0 | 0.0 | 5.0 | 0.0 | 1.0 |  | 0.0 | 1.0 | 0.0 |  | 1.0 | 0.0 | 1.0 |
|  | 0.0160 |  | 0.0 | 0.0 | 9.0 | 0.0 | 9.0 |  | 0.0 | 0.0 | 0.0 |  | 0.0 | 0.0 | 0.0 |
| 289 | 0.2500 | 9.0 | 5.0 | 0.0 | 9.0 | 0.0 | 2.0 |  | 1.0 | 1.0 | 1.0 |  | 0.0 | 0.0 | 0.0 |
|  | 0.1250 | 9.0 | 1.0 | 0.0 | 9.0 | 0.0 | 9.0 |  | 0.0 | 0.0 | 0.0 |  | 0.0 | 0.0 | 0.0 |
|  | 0.0620 | 2.0 | 0.0 | 0.0 | 9.0 | 0.0 | 0.0 |  | 1.0 | 1.0 | 0.0 |  | 0.0 | 0.0 | 0.0 |
|  | 0.0320 | 0.0 | 0.0 | 0.0 | 0.0 | 0.0 | 0.0 |  | 0.0 | 0.0 | 0.0 |  | 0.0 | 0.0 | 1.0 |
|  | 0.0160 | 0.0 | 0.0 | 0.0 | 0.0 | 0.0 | 0.0 |  | 0.0 | 0.0 | 0.0 |  | 0.0 | 0.0 | 0.0 |
| 290 | 0.2500 | 5.0 | 2.0 | 0.0 | 9.0 | 0.0 | 1.0 |  | 1.0 | 3.0 | 1.0 |  | 0.0 | 0.0 | 1.0 |
|  | 0.1250 | 3.0 | 0.0 | 0.0 | 9.0 | 0.0 | 0.0 |  | 1.0 | 1.0 | 0.0 |  | 0.0 | 0.0 | 1.0 |
|  | 0.0620 | 1.0 | 0.0 | 0.0 | 1.0 | 0.0 | 0.0 |  | 1.0 | 0.0 | 0.0 |  | 0.0 | 0.0 | 1.0 |
|  | 0.0320 | 0.0 | 0.0 | 0.0 |  | 0.0 | 0.0 |  | 0.0 | 0.0 | 0.0 |  | 0.0 | 0.0 | 0.0 |
| 291 | 0.2500 | 9.0 | 9.0 | 0.0 | 9.0 | 9.0 | 9.0 |  | 0.0 | 9.0 | 2.0 |  | 7.0 | 7.0 | 4.0 |
|  | 0.1250 | 9.0 | 7.0 | 0.0 | 9.0 | 3.0 | 5.0 |  | 0.0 | 0.0 | 0.0 |  | 3.0 | 5.0 | 3.0 |
|  | 0.0620 | 9.0 | 3.0 | 0.0 | 9.0 | 3.0 | 2.0 |  | 0.0 | 0.0 | 0.0 |  | 0.0 | 3.0 | 0.0 |
|  | 0.0320 | 0.0 | 0.0 | 0.0 | 0.0 | 3.0 | 0.0 |  | 0.0 | 0.0 | 0.0 |  | 0.0 | 0.0 | 0.0 |
| 292 | 0.2500 | 9.0 | 8.0 | 6.0 | 9.0 | 5.0 | 9.0 |  | 0.0 | 3.0 | 3.0 |  | 3.0 | 8.0 | 9.0 |
|  | 0.1250 | 9.0 | 2.0 | 0.0 | 6.0 | 5.0 | 3.0 |  | 0.0 | 0.0 | 0.0 |  | 0.0 | 7.0 | 9.0 |
|  | 0.0620 | 0.0 | 0.0 | 0.0 | 0.0 | 0.0 | 0.0 |  | 0.0 | 0.0 | 0.0 |  | 0.0 | 0.0 | 0.0 |
| 293 | 0.2500 | 9.0 | 9.0 | 8.0 | 9.0 | 9.0 | 9.0 |  | 0.0 | 5.0 | 3.0 |  | 7.0 | 8.0 | 8.0 |
|  | 0.1250 | 9.0 | 5.0 | 0.0 | 9.0 | 0.0 | 3.0 |  | 0.0 | 0.0 | 0.0 |  | 4.0 | 6.0 | 4.0 |
|  | 0.0620 | 0.0 | 0.0 | 0.0 | 0.0 | 0.0 | 0.0 |  | 0.0 | 0.0 | 0.0 |  | 0.0 | 0.0 | 0.0 |
| 294 | 0.2500 | 9.0 | 3.0 | 0.0 | 9.0 | 9.0 | 3.0 |  | 0.0 | 0.0 | 2.0 |  | 3.0 | 5.0 | 6.0 |
|  | 0.1250 | 9.0 | 3.0 | 2.0 | 7.0 | 0.0 | 3.0 |  | 0.0 | 0.0 | 1.0 |  | 3.0 | 3.0 | 1.0 |
|  | 0.0620 | 9.0 | 1.0 | 0.0 | 0.0 | 0.0 | 2.0 |  | 0.0 | 0.0 | 0.0 |  | 0.0 | 0.0 | 0.0 |
|  | 0.0320 | 3.0 | 0.0 | 0.0 |  | 0.0 | 0.0 |  | 0.0 | 0.0 | 0.0 |  | 0.0 | 0.0 | 0.0 |
|  | 0.0160 | 0.0 | 0.0 | 0.0 |  | 0.0 | 0.0 |  | 0.0 | 0.0 | 0.0 |  | 0.0 | 0.0 | 0.0 |
| 295 | 0.2500 | 9.0 | 5.0 | 9.0 | 9.0 | 9.0 | 9.0 |  | 0.0 | 0.0 | 0.0 |  | 3.0 | 5.0 | 4.0 |
|  | 0.1250 | 9.0 | 1.0 | 2.0 | 9.0 | 3.0 | 9.0 |  | 0.0 | 0.0 | 0.0 |  | 0.0 | 4.0 | 2.0 |
|  | 0.0620 | 9.0 | 0.0 | 0.0 | 9.0 | 0.0 | 2.0 |  | 0.0 | 0.0 | 0.0 |  | 0.0 | 0.0 | 0.0 |
|  | 0.0320 | 9.0 | 5.0 | 0.0 | 9.0 | 0.0 | 0.0 |  | 0.0 | 0.0 | 0.0 |  | 0.0 | 0.0 | 0.0 |
| 296 | 0.2500 | 9.0 | 2.0 | 0.0 | 9.0 | 0.0 | 3.0 |  | 0.0 | 0.0 | 4.0 |  | 7.0 | 5.0 | 5.0 |
|  | 0.1250 | 9.0 | 1.0 | 0.0 | 0.0 | 0.0 | 3.0 |  | 0.0 | 0.0 | 0.0 |  | 4.0 | 5.0 | 3.0 |
|  | 0.0620 | 7.0 | 0.0 | 0.0 | 0.0 | 0.0 | 0.0 |  | 0.0 | 0.0 | 0.0 |  | 0.0 | 0.0 | 0.0 |
|  | 0.0320 | 0.0 | 0.0 | 0.0 | 0.0 | 0.0 | 5.0 |  | 0.0 | 0.0 | 0.0 |  | 0.0 | 0.0 | 0.0 |
| 297 | 0.2500 | 9.0 | 7.0 | 2.0 | 9.0 | 5.0 | 3.0 |  | 0.0 | 6.0 | 0.0 |  | 3.0 | 4.0 | 3.0 |
|  | 0.1250 | 7.0 | 6.0 | 0.0 | 9.0 | 5.0 | 0.0 |  | 0.0 | 0.0 | 0.0 |  | 1.0 | 1.0 | 0.0 |
|  | 0.0620 | 7.0 | 1.0 | 0.0 | 9.0 | 0.0 | 0.0 |  | 0.0 | 0.0 | 0.0 |  | 0.0 | 0.0 | 0.0 |
|  | 0.0320 |  | 0.0 | 0.0 | 0.0 | 0.0 | 0.0 |  | 0.0 | 0.0 | 0.0 |  | 0.0 | 0.0 | 0.0 |
| 298 | 0.2500 | 9.0 | 3.0 | 3.0 | 9.0 | 3.0 | 8.0 |  | 0.0 | 4.0 | 2.0 |  | 3.0 | 3.0 | 4.0 |
|  | 0.1250 | 9.0 | 3.0 | 0.0 | 9.0 | 0.0 | 0.0 |  | 0.0 | 0.0 | 0.0 |  | 0.0 | 0.0 | 0.0 |
|  | 0.0620 | 0.0 | 0.0 | 0.0 | 9.0 | 0.0 | 0.0 |  | 0.0 | 0.0 | 0.0 |  | 0.0 | 0.0 | 0.0 |

TABLE II-continued

Preemergence Herbicidal Evaluations of Test Compounds

| Compound Number | Rate (kg/ha) | ABUTH | AMBEL | CASOB | CHEAL | GALAP | IPOHE | IPOSS | ECHCG | SETVI | GLXMAW | GLXMA | ORYSAT | TRZAWR | ZEAMX |
|---|---|---|---|---|---|---|---|---|---|---|---|---|---|---|---|
| 299 | 0.0320 | 0.0 | 0.0 | 0.0 | 0.0 | 0.0 | 0.0 | | 0.0 | 0.0 | 0.0 | | 0.0 | 0.0 | 0.0 |
| | 0.2500 | 9.0 | 8.0 | 3.0 | 9.0 | 5.0 | 6.0 | | 0.0 | 2.0 | 2.0 | | 2.0 | 2.0 | 3.0 |
| | 0.1250 | 9.0 | 2.0 | 0.0 | 9.0 | 0.0 | 1.0 | | 0.0 | 0.0 | 0.0 | | 0.0 | 0.0 | 0.0 |
| | 0.0620 | 0.0 | 0.0 | 0.0 | 4.0 | 0.0 | 0.0 | | 0.0 | 0.0 | 0.0 | | 0.0 | 0.0 | 0.0 |
| | 0.0320 | 0.0 | 0.0 | 0.0 | 0.0 | 0.0 | 0.0 | | 0.0 | 0.0 | 0.0 | | 0.0 | 0.0 | 0.0 |
| 300 | 0.5000 | 9.0 | 9.0 | 9.0 | 9.0 | 0.0 | 9.0 | | 9.0 | 9.0 | 4.0 | | 9.0 | | 7.0 |
| | 0.2500 | 9.0 | 9.0 | 4.3 | 9.0 | 8.5 | 8.3 | | 9.0 | 9.0 | 4.3 | | 8.0 | 7.0 | 5.3 |
| | 0.1250 | 9.0 | 9.0 | 3.3 | 9.0 | 8.5 | 7.7 | | 5.3 | 9.0 | 1.7 | | 4.0 | 5.5 | 4.7 |
| | 0.0620 | 8.0 | 6.3 | 0.3 | 9.0 | 8.5 | 3.3 | | 1.3 | 8.0 | 0.0 | | 1.3 | 3.5 | 1.0 |
| | 0.0320 | 7.7 | 1.7 | 0.0 | 9.0 | 4.0 | 1.7 | | 0.0 | 0.7 | 0.0 | | 1.7 | 0.0 | 0.3 |
| | 0.0160 | 4.5 | 0.0 | 0.0 | 4.0 | 0.0 | 0.0 | | 0.0 | 0.0 | 0.0 | | 0.0 | 0.0 | 0.0 |
| 301 | 0.2500 | 9.0 | 9.0 | 0.0 | 9.0 | 9.0 | 2.0 | | 8.0 | 9.0 | 3.0 | | 0.0 | 6.0 | 4.0 |
| | 0.1250 | 9.0 | 0.0 | 0.0 | 9.0 | 9.0 | 0.0 | | 7.0 | 9.0 | 0.0 | | 0.0 | 2.0 | 4.0 |
| | 0.0620 | 9.0 | 0.0 | 0.0 | 9.0 | 9.0 | 0.0 | | 0.0 | 7.0 | 0.0 | | 0.0 | 0.0 | 0.0 |
| | 0.0320 | 4.0 | 0.0 | 0.0 | 4.0 | 0.0 | 0.0 | | 0.0 | 2.0 | 0.0 | | 0.0 | 0.0 | 0.0 |
| | 0.0160 | 0.0 | 0.0 | 0.0 | 3.0 | 0.0 | 0.0 | | 0.0 | 0.0 | 0.0 | | 0.0 | 0.0 | 0.0 |
| 302 | 0.2500 | 9.0 | 9.0 | 0.0 | 9.0 | 0.0 | 9.0 | | 9.0 | 9.0 | 5.0 | | 6.0 | 7.0 | 8.0 |
| | 0.1250 | 9.0 | 9.0 | 0.0 | 9.0 | 0.0 | 9.0 | | 9.0 | 9.0 | 4.0 | | 4.0 | 6.0 | 7.0 |
| | 0.0620 | 9.0 | 3.0 | 0.0 | 6.0 | 0.0 | 3.0 | | 6.0 | 9.0 | 3.0 | | 3.0 | 6.0 | 6.0 |
| | 0.0320 | 9.0 | 3.0 | 0.0 | 9.0 | 0.0 | 1.0 | | 3.0 | 9.0 | 3.0 | | 0.0 | 0.0 | 5.0 |
| 303 | 0.2500 | 9.0 | 9.0 | 8.0 | 9.0 | 0.0 | 9.0 | | 8.0 | 9.0 | 5.0 | | 7.0 | 7.0 | 8.0 |
| | 0.1250 | 9.0 | 9.0 | 0.0 | 9.0 | 0.0 | 3.0 | | 8.0 | 9.0 | 4.0 | | | 5.0 | 7.0 |
| | 0.0620 | 9.0 | 7.0 | 0.0 | 9.0 | 0.0 | 3.0 | | 7.0 | 9.0 | 2.0 | | 1.0 | 4.0 | 6.0 |
| | 0.0320 | 0.0 | 0.0 | 0.0 | 0.0 | 0.0 | 0.0 | | 0.0 | 4.0 | 0.0 | | 0.0 | 1.0 | 4.0 |
| 304 | 0.2500 | 9.0 | 7.0 | 4.0 | 9.0 | 9.0 | 9.0 | | 0.0 | 9.0 | 7.0 | | 4.0 | 0.0 | 3.0 |
| | 0.1250 | 7.0 | 4.0 | 1.0 | 3.0 | 7.0 | 4.0 | | 0.0 | 1.0 | 4.0 | | 0.0 | 0.0 | 1.0 |
| | 0.0620 | 3.0 | 2.0 | 0.0 | 0.0 | 0.0 | 3.0 | | 0.0 | 0.0 | 3.0 | | 0.0 | 0.0 | 0.0 |
| | 0.0320 | 0.0 | 1.0 | 0.0 | 0.0 | 0.0 | 0.0 | | 0.0 | 0.0 | 0.0 | | 0.0 | 0.0 | 0.0 |
| | 0.0160 | 0.0 | 0.0 | 0.0 | 0.0 | 0.0 | 0.0 | | 0.0 | 0.0 | 0.0 | | 0.0 | 0.0 | 0.0 |
| 305 | 0.5000 | 9.0 | 9.0 | 9.0 | 9.0 | 9.0 | 9.0 | | 5.0 | 9.0 | 8.5 | | 7.0 | 0.0 | 7.0 |
| | 0.2500 | 9.0 | 9.0 | 9.0 | 9.0 | 9.0 | 9.0 | | 2.0 | 8.3 | 7.7 | | 4.7 | 3.0 | 5.7 |
| | 0.1250 | 9.0 | 7.7 | 8.0 | 9.0 | 9.0 | 8.3 | | 0.0 | 6.3 | 7.0 | | 2.3 | 3.0 | 4.0 |
| | 0.0620 | 9.0 | 4.7 | 5.3 | 9.0 | 0.0 | 6.3 | | 0.0 | 4.0 | 5.7 | | 1.3 | 1.0 | 2.7 |
| | 0.0320 | 6.7 | 2.3 | 3.0 | 6.0 | 0.0 | 3.0 | | 0.0 | 0.0 | 3.0 | | 0.7 | 0.0 | 0.7 |
| | 0.0160 | 3.5 | 1.5 | 0.0 | 3.5 | 0.0 | 1.5 | | 0.0 | 0.0 | 1.0 | | 0.0 | 0.0 | 0.0 |
| 306 | 0.2500 | 9.0 | 0.0 | 0.0 | 9.0 | 0.0 | 1.0 | | 0.0 | 4.0 | 0.0 | | 0.0 | 0.0 | 0.0 |
| 307 | 0.2500 | 9.0 | 9.0 | 9.0 | 9.0 | 9.0 | 9.0 | | 9.0 | 9.0 | 9.0 | | 9.0 | 8.0 | 9.0 |
| | 0.1250 | 9.0 | 9.0 | 9.0 | 9.0 | 9.0 | 9.0 | | 9.0 | 9.0 | 8.3 | | 8.0 | 7.5 | 8.7 |
| | 0.0620 | 9.0 | 9.0 | 6.0 | 9.0 | 8.0 | 9.0 | | 7.7 | 9.0 | 8.3 | | 7.3 | 5.5 | 7.7 |
| | 0.0320 | 9.0 | 9.0 | 5.3 | 9.0 | 0.0 | 9.0 | | 3.7 | 8.3 | 7.7 | | 7.0 | 1.5 | 7.3 |
| | 0.0160 | 9.0 | 9.0 | 3.3 | 9.0 | 4.5 | 5.7 | | 9.0 | 9.0 | 4.7 | | 4.7 | 1.0 | 3.3 |
| 308 | 0.2500 | 9.0 | 9.0 | 9.0 | 9.0 | 9.0 | 9.0 | | 9.0 | 9.0 | 9.0 | | 9.0 | 9.0 | 9.0 |
| | 0.1250 | 9.0 | 9.0 | 9.0 | 9.0 | 9.0 | 9.0 | | 9.0 | 9.0 | 9.0 | | 8.8 | 8.7 | 8.8 |
| | 0.0620 | 9.0 | 9.0 | 9.0 | 9.0 | 9.0 | 9.0 | | 9.0 | 9.0 | 9.0 | | 8.8 | 8.0 | 8.8 |
| | 0.0320 | 9.0 | 9.0 | 8.3 | 9.0 | 9.0 | 8.8 | | 8.3 | 8.8 | 9.0 | | 7.8 | 5.7 | 8.0 |

TABLE II-continued

Preemergence Herbicidal Evaluations of Test Compounds

| Compound Number | Rate (kg/ha) | ABUTH | AMBEL | CASOB | CHEAL | GALAP | IPOHE | IPOSS | ECHCG | SETVI | GLXMAW | GLXMA | ORYSAT | TRZAWR | ZEAMX |
|---|---|---|---|---|---|---|---|---|---|---|---|---|---|---|---|
| 309 | 0.0160 | 9.0 | 8.8 | 4.4 | 9.0 | 8.5 | 7.6 | | 5.4 | 8.4 | 8.0 | | 5.8 | 4.5 | 6.0 |
| | 0.2500 | 9.0 | 9.0 | 9.0 | 9.0 | 9.0 | 9.0 | | 9.0 | 9.0 | 9.0 | | 9.0 | 9.0 | 9.0 |
| | 0.1250 | 9.0 | 9.0 | 9.0 | 9.0 | 9.0 | 9.0 | | 9.0 | 9.0 | 9.0 | | 9.0 | 8.0 | 9.0 |
| | 0.0620 | 9.0 | 9.0 | 9.0 | 9.0 | 9.0 | 9.0 | | 9.0 | 9.0 | 9.0 | | 9.0 | 6.0 | 8.5 |
| | 0.0320 | 9.0 | 9.0 | 7.5 | 9.0 | 9.0 | 9.0 | | 8.0 | 8.0 | 8.0 | | 7.0 | 4.0 | 7.0 |
| | 0.0160 | 9.0 | 9.0 | 6.5 | 9.0 | 9.0 | 9.0 | | 3.5 | 8.0 | 6.5 | | 5.5 | 2.0 | 4.5 |
| 310 | 0.2500 | 9.0 | 9.0 | 4.0 | 9.0 | 9.0 | 9.0 | | 9.0 | 9.0 | 5.0 | | 8.0 | 7.0 | 7.0 |
| | 0.1250 | 9.0 | 7.0 | 0.0 | 9.0 | 9.0 | 3.0 | | 3.0 | 9.0 | 3.0 | | 8.0 | 7.0 | 5.0 |
| | 0.0620 | 9.0 | 4.0 | 0.0 | 9.0 | 9.0 | 1.0 | | 0.0 | 8.0 | 0.0 | | 3.0 | 1.0 | 2.0 |
| | 0.0320 | 9.0 | 1.0 | 0.0 | 5.0 | 9.0 | 1.0 | | 0.0 | 0.0 | 0.0 | | 0.0 | 1.0 | 0.0 |
| | 0.0160 | 0.0 | 0.0 | 0.0 | | 0.0 | 0.0 | | 0.0 | 0.0 | 0.0 | | 0.0 | 0.0 | 0.0 |
| 311 | 0.2500 | 9.0 | 9.0 | 4.0 | 9.0 | 9.0 | 9.0 | | 7.0 | 9.0 | 4.0 | | 8.0 | 7.0 | 6.0 |
| | 0.1250 | 9.0 | 4.0 | 4.0 | 4.0 | 0.0 | 4.0 | | 0.0 | 8.0 | 4.0 | | 6.0 | 3.0 | 3.0 |
| | 0.0620 | 0.0 | 0.0 | 0.0 | | 0.0 | 0.0 | | 0.0 | 0.0 | 0.0 | | 0.0 | 0.0 | 0.0 |
| 312 | 0.2500 | 9.0 | 9.0 | 0.0 | 9.0 | 9.0 | 9.0 | | 9.0 | 9.0 | 9.0 | | 9.0 | 7.0 | 6.0 |
| | 0.1250 | 9.0 | 9.0 | 0.0 | 9.0 | 0.0 | 9.0 | | 9.0 | 9.0 | 3.0 | | 8.0 | 2.0 | 6.0 |
| | 0.0620 | 9.0 | 3.0 | | 9.0 | 0.0 | 9.0 | | 9.0 | 9.0 | 3.0 | | 5.0 | 0.0 | 4.0 |
| | 0.0320 | 9.0 | 0.0 | 0.0 | 9.0 | 0.0 | 2.0 | | 7.0 | 7.0 | 3.0 | | 5.0 | 0.0 | 3.0 |
| | 0.0160 | 4.0 | 0.0 | 0.0 | 9.0 | 0.0 | 0.0 | | 3.0 | 0.0 | 0.0 | | 0.0 | | 0.0 |
| 313 | 0.2500 | 9.0 | 9.0 | 3.0 | 9.0 | 0.0 | 9.0 | | 9.0 | 9.0 | 9.0 | | 8.0 | 3.0 | 4.0 |
| | 0.1250 | 9.0 | 4.0 | 0.0 | 9.0 | 0.0 | 4.0 | | 9.0 | 9.0 | 3.0 | | 4.0 | 0.0 | 0.0 |
| | 0.0620 | 9.0 | 0.0 | 0.0 | 9.0 | 0.0 | 0.0 | | 0.0 | 0.0 | 0.0 | | 0.0 | 0.0 | 0.0 |
| | 0.0320 | 9.0 | 0.0 | 0.0 | 9.0 | 0.0 | 0.0 | | 0.0 | 0.0 | 0.0 | | 0.0 | 0.0 | 0.0 |
| | 0.0160 | 9.0 | 0.0 | 0.0 | 9.0 | 0.0 | | | 0.0 | 0.0 | 0.0 | | 0.0 | | 0.0 |
| 314 | 0.2500 | 9.0 | 9.0 | 9.0 | 9.0 | 9.0 | 9.0 | | 9.0 | 9.0 | 9.0 | | 5.0 | 9.0 | 9.0 |
| | 0.1250 | 9.0 | 9.0 | 9.0 | 9.0 | 9.0 | 9.0 | | 9.0 | 9.0 | 9.0 | | 5.0 | 9.0 | 7.0 |
| | 0.0620 | 9.0 | 7.0 | 9.0 | 9.0 | 9.0 | 9.0 | | 9.0 | 9.0 | 2.0 | | 0.0 | 3.0 | 4.0 |
| | 0.0320 | 9.0 | 7.0 | 0.0 | 9.0 | 0.0 | 9.0 | | 2.0 | 7.0 | 0.0 | | 0.0 | 0.0 | 0.0 |
| | 0.0160 | 9.0 | 2.0 | 0.0 | 9.0 | 0.0 | 9.0 | | 0.0 | 7.0 | 0.0 | | 0.0 | 0.0 | 0.0 |
| 315 | 0.5000 | 9.0 | 9.0 | 5.0 | 9.0 | | 9.0 | | 9.0 | 9.0 | 9.0 | | 7.0 | | 5.0 |
| | 0.2500 | 9.0 | 9.0 | 2.5 | 9.0 | 9.0 | 9.0 | | 4.5 | 8.5 | 9.0 | | 7.5 | 8.0 | 3.5 |
| | 0.1250 | 9.0 | 7.0 | 0.0 | 9.0 | 9.0 | 7.5 | | 0.0 | 3.0 | 5.0 | | 5.5 | 8.0 | 2.0 |
| | 0.0620 | 7.0 | 2.5 | 0.0 | 2.0 | 0.0 | 6.5 | | 0.0 | 0.0 | 3.0 | | 2.5 | 1.0 | 0.5 |
| | 0.0320 | 6.0 | 0.0 | 0.0 | 0.0 | 0.0 | 4.0 | | 0.0 | 0.0 | 2.0 | | 0.5 | 1.0 | 0.0 |
| | 0.0160 | 0.0 | 0.0 | 0.0 | 0.0 | 0.0 | 0.0 | | 0.0 | 0.0 | 0.0 | | 0.0 | 0.0 | 0.0 |
| 316 | 0.2500 | 9.0 | 9.0 | 9.0 | 9.0 | 9.0 | 9.0 | | 9.0 | 9.0 | 6.0 | | 7.0 | 4.0 | 7.0 |
| | 0.1250 | 9.0 | 9.0 | 7.0 | 9.0 | 0.0 | 9.0 | | 7.0 | 9.0 | 6.0 | | 5.0 | 2.0 | 4.0 |
| | 0.0620 | 9.0 | 6.0 | 1.0 | 9.0 | | 3.0 | | 2.0 | 6.0 | 2.0 | | 2.0 | 1.0 | 3.0 |
| | 0.0320 | 9.0 | 4.0 | 1.0 | 9.0 | 0.0 | 3.0 | | 1.0 | 6.0 | 0.0 | | 1.0 | 1.0 | 1.0 |
| | 0.0160 | 9.0 | 0.0 | 0.0 | 9.0 | 0.0 | 0.0 | | 0.0 | 0.0 | 1.0 | | 0.0 | 0.0 | 1.0 |
| 317 | 0.2500 | 9.0 | 9.0 | 8.0 | 9.0 | 9.0 | 9.0 | | 9.0 | 9.0 | 9.0 | | 9.0 | 9.0 | 8.5 |
| | 0.1250 | 9.0 | 9.0 | 7.5 | 9.0 | 9.0 | 7.5 | | 9.0 | 9.0 | 8.0 | | 7.5 | 7.0 | 7.5 |
| | 0.0620 | 9.0 | 9.0 | 3.5 | 9.0 | 7.0 | 6.5 | | 9.0 | 9.0 | 8.0 | | 7.0 | 6.0 | 7.5 |
| | 0.0320 | 9.0 | 9.0 | 2.5 | 9.0 | 0.0 | 6.0 | | 8.0 | 9.0 | 5.5 | | 5.0 | 3.0 | 7.0 |
| | 0.0160 | 9.0 | 7.5 | 0.0 | 8.0 | 0.0 | 4.0 | | 6.5 | 9.0 | 3.0 | | 4.0 | 2.0 | 4.5 |
| 318 | 0.5000 | 9.0 | 9.0 | 9.0 | 9.0 | | 9.0 | | 9.0 | 9.0 | 9.0 | | 9.0 | | 7.0 |
| | 0.2500 | 9.0 | 9.0 | 9.0 | 9.0 | 9.0 | 9.0 | | 9.0 | 9.0 | 8.0 | | 7.5 | 7.0 | 7.5 |

TABLE II-continued

Preemergence Herbicidal Evaluations of Test Compounds

| Compound Number | Rate (kg/ha) | ABUTH | AMBEL | CASOB | CHEAL | GALAP | IPOHE | IPOSS | ECHCG | SETVI | GLXMAW | GLXMA | ORYSAT | TRZAWR | ZEAMX |
|---|---|---|---|---|---|---|---|---|---|---|---|---|---|---|---|
| | 0.1250 | 9.0 | 9.0 | 9.0 | 9.0 | 9.0 | 8.0 | | 9.0 | 9.0 | 9.0 | | 6.5 | 6.0 | 7.5 |
| | 0.0620 | 9.0 | 9.0 | 9.0 | 9.0 | 9.0 | 7.0 | | 9.0 | 9.0 | 7.0 | | 6.5 | 2.0 | 6.5 |
| | 0.0320 | 9.0 | 7.0 | 2.5 | 9.0 | 0.0 | 5.5 | | 8.0 | 9.0 | 6.5 | | 3.5 | 1.0 | 6.5 |
| | 0.0160 | 9.0 | 3.5 | 2.0 | 9.0 | 0.0 | 3.0 | | 4.0 | 9.0 | 4.0 | | 3.5 | 1.0 | 6.5 |
| 319 | 0.2500 | 9.0 | 9.0 | 1.0 | 9.0 | 9.0 | 9.0 | | 9.0 | 9.0 | 9.0 | | 6.0 | 5.0 | 2.0 |
| | 0.1250 | 9.0 | 3.0 | 0.0 | 9.0 | 7.0 | 4.0 | | 2.0 | 5.0 | 0.0 | | 4.0 | 4.0 | 2.0 |
| | 0.0620 | 1.0 | 1.0 | 0.0 | 9.0 | 0.0 | 1.0 | | 1.0 | 0.0 | 3.0 | | 1.0 | 1.0 | 1.0 |
| | 0.0320 | 0.0 | 0.0 | 0.0 | 9.0 | 0.0 | 0.0 | | 0.0 | 0.0 | 1.0 | | 0.0 | 0.0 | 0.0 |
| | 0.0160 | 0.0 | 0.0 | 0.0 | 9.0 | 0.0 | 0.0 | | 0.0 | 0.0 | 0.0 | | 0.0 | 0.0 | 0.0 |
| 320 | 0.2500 | 9.0 | 9.0 | 1.0 | 9.0 | 9.0 | 7.0 | | 9.0 | 9.0 | 4.0 | | 7.0 | 7.0 | 2.0 |
| | 0.1250 | 9.0 | 1.0 | 0.0 | 9.0 | 7.0 | 2.0 | | 2.0 | 4.0 | 2.0 | | 5.0 | 5.0 | 2.0 |
| | 0.0620 | 3.0 | 1.0 | 1.0 | 9.0 | 0.0 | 0.0 | | 0.0 | 1.0 | 2.0 | | 1.0 | 1.0 | 1.0 |
| | 0.0320 | 0.0 | 1.0 | 0.0 | 9.0 | 0.0 | 0.0 | | 0.0 | 0.0 | 0.0 | | 0.0 | 0.0 | 0.0 |
| | 0.0160 | 0.0 | 0.0 | 0.0 | 4.0 | 0.0 | 0.0 | | 0.0 | 0.0 | 0.0 | | 0.0 | 0.0 | 0.0 |
| 321 | 0.5000 | 9.0 | 9.0 | 9.0 | 9.0 | 9.0 | 9.0 | | 9.0 | 9.0 | 9.0 | | 9.0 | | 9.0 |
| | 0.2500 | 9.0 | 9.0 | 9.0 | 9.0 | 9.0 | 9.0 | | 9.0 | 9.0 | 9.0 | | 8.5 | 8.0 | 8.5 |
| | 0.1250 | 9.0 | 9.0 | 6.5 | 9.0 | 9.0 | 9.0 | | 9.0 | 9.0 | 8.0 | | 7.0 | 7.0 | 7.0 |
| | 0.0620 | 9.0 | 9.0 | 5.5 | 9.0 | 7.0 | 8.0 | | 7.0 | 9.0 | 6.0 | | 5.5 | 6.0 | 6.0 |
| | 0.0320 | 9.0 | 8.5 | 1.5 | 9.0 | 9.0 | 6.0 | | 5.0 | 7.0 | 3.5 | | 3.5 | 5.0 | 4.0 |
| | 0.0160 | 9.0 | 7.0 | 1.0 | 9.0 | 5.0 | 0.0 | | 0.0 | 2.0 | 1.0 | | 1.0 | 1.0 | 1.0 |
| 322 | 0.2500 | 9.0 | 9.0 | 6.0 | 9.0 | 9.0 | 7.0 | | 2.0 | 9.0 | 6.0 | | 6.0 | 9.0 | 7.0 |
| | 0.1250 | 9.0 | 8.0 | 3.5 | 9.0 | 9.0 | 7.5 | | 2.0 | 9.0 | 5.5 | | 3.5 | 3.0 | 5.5 |
| | 0.0620 | 7.0 | 5.0 | 2.5 | 9.0 | 1.0 | 4.0 | | 0.0 | 2.0 | 3.5 | | 1.5 | 1.0 | 2.5 |
| | 0.0320 | 6.5 | 1.5 | 0.0 | 9.0 | 1.0 | 2.0 | | 0.0 | 1.0 | 2.0 | | 1.0 | 0.0 | 1.5 |
| | 0.0160 | 3.0 | 0.5 | 0.5 | 3.0 | 1.0 | 1.5 | | 0.0 | 0.0 | 0.0 | | 1.0 | 0.0 | 0.5 |
| 323 | 0.5000 | 9.0 | 9.0 | 0.5 | 9.0 | 9.0 | 9.0 | | 9.0 | 9.0 | 7.5 | | 6.5 | 7.0 | 6.5 |
| | 0.2500 | 9.0 | 9.0 | 0.3 | 9.0 | 9.0 | 9.0 | | 6.7 | 9.0 | 4.0 | | 5.7 | 5.2 | 3.7 |
| | 0.1250 | 9.0 | 8.9 | 1.8 | 9.0 | 8.0 | 9.0 | | 4.0 | 8.6 | 2.3 | | 4.7 | 4.6 | 1.9 |
| | 0.0620 | 9.0 | 4.9 | 0.3 | 9.0 | 4.3 | 8.6 | | 1.8 | 4.3 | 1.6 | | 2.6 | 1.2 | 0.7 |
| | 0.0320 | 6.2 | 2.7 | 0.2 | 7.3 | 5.0 | 6.7 | | 0.2 | 1.0 | 0.3 | | 0.7 | 0.3 | 0.2 |
| | 0.0160 | 3.8 | 2.3 | 0.0 | 4.2 | 2.5 | 3.5 | | 0.2 | 0.0 | 0.5 | | 0.2 | 0.2 | 0.2 |
| 324 | 0.2500 | 9.0 | 9.0 | 9.0 | 9.0 | 9.0 | 9.0 | | 9.0 | 9.0 | 9.0 | | 9.0 | 9.0 | 9.0 |
| | 0.1250 | 9.0 | 9.0 | 9.0 | 9.0 | 0.0 | 9.0 | | 7.0 | 9.0 | 8.5 | | 7.0 | 9.0 | 8.5 |
| | 0.0620 | 9.0 | 8.0 | 3.0 | 9.0 | 0.0 | 9.0 | | 1.0 | 9.0 | 5.0 | | 3.5 | 3.0 | 6.0 |
| | 0.0320 | 9.0 | 7.0 | 3.0 | 9.0 | 0.0 | 4.5 | | 1.0 | 3.5 | 3.5 | | 2.0 | 1.0 | 2.5 |
| | 0.0160 | 9.0 | 9.0 | 9.0 | 9.0 | 0.0 | 9.0 | | 9.0 | 9.0 | 9.0 | | 9.0 | | 7.0 |
| 325 | 0.5000 | 9.0 | 9.0 | 9.0 | 9.0 | 9.0 | 9.0 | | 9.0 | 9.0 | 9.0 | | 6.5 | 4.0 | 7.0 |
| | 0.2500 | 9.0 | 8.0 | 6.0 | 9.0 | 8.0 | 7.5 | | 8.0 | 9.0 | 6.5 | | 5.0 | 0.0 | 5.5 |
| | 0.1250 | 9.0 | 8.5 | 3.0 | 9.0 | 0.0 | 4.0 | | 4.0 | 4.5 | 3.0 | | 2.0 | 0.0 | 2.5 |
| | 0.0620 | 6.5 | 4.0 | 0.0 | 9.0 | 0.0 | 2.0 | | 2.0 | 3.0 | 1.0 | | 2.0 | 0.0 | 1.0 |
| | 0.0320 | 0.0 | 0.0 | 0.0 | 9.0 | 0.0 | 0.0 | | 0.0 | 0.0 | 0.0 | | 0.0 | | 0.0 |
| 326 | 0.5000 | 9.0 | 9.0 | 4.0 | 9.0 | 9.0 | 9.0 | | 9.0 | 9.0 | 9.0 | | 8.0 | | 7.0 |
| | 0.2500 | 9.0 | 9.0 | 3.0 | 9.0 | 0.0 | 9.0 | | 9.0 | 9.0 | 4.5 | | 6.0 | 1.0 | 2.5 |
| | 0.1250 | 9.0 | 9.0 | 3.0 | 9.0 | 0.0 | 2.5 | | 7.0 | 4.5 | 3.0 | | 4.0 | 0.0 | 1.0 |
| | 0.0620 | 4.5 | 6.5 | 0.0 | 9.0 | 0.0 | 2.5 | | 3.0 | 4.5 | 2.0 | | 1.0 | 0.0 | 0.5 |
| | 0.0320 | 4.5 | 2.5 | 0.0 | 9.0 | 0.0 | 0.0 | | 0.0 | 2.0 | 0.0 | | 0.0 | 0.0 | 0.0 |

TABLE II-continued

Preemergence Herbicidal Evaluations of Test Compounds

| Compound Number | Rate (kg/ha) | ABUTH | AMBEL | CASOB | CHEAL | GALAP | IPOHE | IPOSS | ECHCG | SETVI | GLXMAW | GLXMA | ORYSAT | TRZAWR | ZEAMX |
|---|---|---|---|---|---|---|---|---|---|---|---|---|---|---|---|
| 327 | 0.0160 | 0.0 | 0.0 | 0.0 | 9.0 | 0.0 | 0.0 | | 0.0 | 0.0 | 0.0 | | 0.0 | 0.0 | 0.0 |
| | 0.2500 | 9.0 | 5.0 | 0.0 | 9.0 | 0.0 | 5.0 | | 7.0 | 9.0 | 3.0 | | 0.0 | 2.0 | 7.0 |
| | 0.1250 | 9.0 | 0.0 | 0.0 | 9.0 | 0.0 | 0.0 | | 3.0 | 9.0 | 1.0 | | 0.0 | 1.0 | 3.0 |
| | 0.0620 | 0.0 | 0.0 | 0.0 | 9.0 | 0.0 | 0.0 | | 0.0 | 0.0 | 0.0 | | 0.0 | 0.0 | 0.0 |
| | 0.0320 | 0.0 | 0.0 | 0.0 | 9.0 | 0.0 | 0.0 | | 0.0 | 0.0 | 0.0 | | 0.0 | 0.0 | 0.0 |
| | 0.0160 | 0.0 | 0.0 | 0.0 | 9.0 | 0.0 | 0.0 | | 0.0 | 0.0 | 0.0 | | 0.0 | 0.0 | 0.0 |
| 328 | 0.2500 | 9.0 | 5.0 | 0.0 | 9.0 | 0.0 | 9.0 | | 0.0 | 9.0 | 3.0 | | 0.0 | 0.0 | 0.0 |
| | 0.1250 | 9.0 | 3.0 | 0.0 | 9.0 | 0.0 | 9.0 | | 0.0 | 9.0 | 2.0 | | 0.0 | 0.0 | 0.0 |
| | 0.0620 | 9.0 | 0.0 | 0.0 | 9.0 | 0.0 | 0.0 | | 0.0 | 0.0 | 0.0 | | 0.0 | 0.0 | 0.0 |
| | 0.0320 | 3.0 | 0.0 | 0.0 | 9.0 | 0.0 | 0.0 | | 0.0 | 0.0 | 0.0 | | 0.0 | 0.0 | 0.0 |
| | 0.0160 | 0.0 | 0.0 | 0.0 | 9.0 | 0.0 | 0.0 | | 0.0 | 0.0 | 0.0 | | 0.0 | 0.0 | 0.0 |
| 329 | 0.2500 | 9.0 | 9.0 | 8.5 | 9.0 | 9.0 | 9.0 | | 9.0 | 9.0 | 8.0 | | 8.0 | 7.0 | 7.5 |
| | 0.1250 | 9.0 | 9.0 | 9.0 | 9.0 | 9.0 | 9.0 | | 7.0 | 9.0 | 9.0 | | 6.5 | 6.0 | 7.0 |
| | 0.0620 | 9.0 | 8.0 | 7.0 | 9.0 | 6.0 | 8.0 | | 4.5 | 9.0 | 7.5 | | 5.0 | 4.0 | 6.5 |
| | 0.0320 | 9.0 | 7.0 | 2.0 | 9.0 | 1.0 | 4.0 | | 1.0 | 2.5 | 6.0 | | 2.5 | 2.0 | 2.5 |
| | 0.0160 | 9.0 | 3.0 | 0.5 | 9.0 | 1.0 | 2.5 | | 0.0 | 1.5 | 5.0 | | 1.5 | 1.0 | 1.5 |
| 330 | 0.2500 | 9.0 | 9.0 | 2.0 | 9.0 | 9.0 | 6.0 | | 5.0 | 9.0 | 7.0 | | 6.0 | 5.0 | 7.0 |
| | 0.1250 | 9.0 | 7.0 | 0.0 | 9.0 | 9.0 | 2.0 | | 1.0 | 7.0 | 7.0 | | 3.0 | 3.0 | 5.0 |
| | 0.0620 | 9.0 | 1.0 | 1.0 | 0.0 | 0.0 | 1.0 | | 0.0 | 4.0 | 4.0 | | 0.0 | 0.0 | 1.0 |
| | 0.0320 | 3.0 | 1.0 | 0.0 | 9.0 | 0.0 | 1.0 | | 0.0 | 0.0 | 1.0 | | 0.0 | 0.0 | 0.0 |
| | 0.0160 | 1.0 | 0.0 | 0.0 | 9.0 | 0.0 | 0.0 | | 0.0 | 0.0 | 0.0 | | 0.0 | 0.0 | 0.0 |
| 331 | 0.2500 | 3.0 | 2.0 | 0.0 | 3.0 | 0.0 | 0.0 | | 0.0 | 0.0 | 0.0 | | 0.0 | 0.0 | 0.0 |
| | 0.1250 | 3.0 | 0.0 | 0.0 | 0.0 | 0.0 | 0.0 | | 0.0 | 0.0 | 0.0 | | 0.0 | 0.0 | 0.0 |
| | 0.0620 | 0.0 | 0.0 | 0.0 | 0.0 | 0.0 | 0.0 | | 0.0 | 0.0 | 0.0 | | 0.0 | 0.0 | 0.0 |
| 332 | 0.5000 | 9.0 | 9.0 | 9.0 | 9.0 | | 9.0 | | 9.0 | 9.0 | 9.0 | | 9.0 | | 5.0 |
| | 0.2500 | 9.0 | 9.0 | 6.0 | 9.0 | 9.0 | 8.5 | | 9.0 | 9.0 | 5.0 | | 6.5 | 1.0 | 4.5 |
| | 0.1250 | 9.0 | 9.0 | 4.0 | 9.0 | 9.0 | 7.0 | | 7.5 | 9.0 | 3.0 | | 5.5 | 0.0 | 1.5 |
| | 0.0620 | 8.0 | 8.0 | 0.0 | 9.0 | 8.0 | 3.0 | | 1.5 | 5.5 | 1.0 | | 3.5 | 0.0 | 0.5 |
| | 0.0320 | 4.5 | 0.0 | 0.0 | 9.0 | 0.0 | 1.5 | | 0.0 | 2.5 | 0.0 | | 1.5 | 0.0 | 0.0 |
| | 0.0160 | 0.0 | 0.0 | 0.0 | 0.0 | 0.0 | 0.0 | | 0.0 | 0.0 | 0.0 | | 0.0 | 0.0 | 0.0 |
| 333 | 0.5000 | 9.0 | 9.0 | 2.0 | 9.0 | | 9.0 | | 9.0 | 9.0 | 4.0 | | 6.0 | | 5.0 |
| | 0.2500 | 9.0 | 9.0 | 5.5 | 9.0 | 9.0 | 7.5 | | 9.0 | 9.0 | 4.0 | | 4.0 | 5.0 | 7.0 |
| | 0.1250 | 8.0 | 8.0 | 1.5 | 9.0 | 9.0 | 4.5 | | 7.5 | 7.5 | 2.0 | | 3.0 | 3.0 | 6.5 |
| | 0.0620 | 7.5 | 4.0 | 1.5 | 9.0 | 0.0 | 2.0 | | 7.5 | 7.5 | 0.5 | | 1.5 | 3.0 | 5.5 |
| | 0.0320 | 7.0 | 1.5 | 0.0 | 9.0 | 0.0 | 1.5 | | 6.5 | 7.0 | 0.5 | | 1.0 | 0.0 | 3.0 |
| | 0.0160 | 3.0 | 0.0 | 0.0 | 9.0 | 0.0 | 2.0 | | 0.0 | 7.0 | 1.0 | | 0.0 | 0.0 | 3.0 |
| 334 | 0.2500 | 9.0 | 9.0 | 1.5 | 9.0 | 9.0 | 9.0 | | 7.5 | 9.0 | 2.0 | | 4.5 | 3.0 | 4.0 |
| | 0.1250 | 9.0 | 8.5 | 1.5 | 9.0 | 5.0 | 9.0 | | 1.0 | 8.0 | 1.5 | | 1.5 | 3.0 | 1.5 |
| | 0.0620 | 9.0 | 6.5 | 0.0 | 9.0 | 1.0 | 7.5 | | 1.0 | 3.5 | 0.5 | | 0.5 | 1.0 | 1.5 |
| | 0.0320 | 8.0 | 2.0 | 0.0 | 8.0 | 0.0 | 3.5 | | 0.0 | 1.0 | 0.0 | | 0.5 | 1.0 | 0.5 |
| | 0.0160 | 7.0 | 0.5 | 0.0 | 7.5 | 0.0 | 1.5 | | 0.0 | 1.0 | 0.0 | | 0.0 | 0.0 | 0.0 |
| 335 | 0.5000 | 9.0 | 9.0 | 9.0 | 9.0 | 9.0 | 9.0 | | 9.0 | 9.0 | 9.0 | | 9.0 | | 9.0 |
| | 0.2500 | 9.0 | 9.0 | 9.0 | 9.0 | 2.7 | 9.0 | | 9.0 | 9.0 | 7.5 | | 8.5 | 8.0 | 8.3 |
| | 0.1250 | 9.0 | 9.0 | 8.3 | 9.0 | 2.3 | 9.0 | | 8.8 | 9.0 | 5.8 | | 7.3 | 5.0 | 8.0 |
| | 0.0620 | 9.0 | 6.3 | 7.8 | 9.0 | 0.0 | 5.5 | | 4.3 | 8.8 | 4.0 | | 6.3 | 3.3 | 4.3 |
| | 0.0320 | 9.0 | 2.8 | 1.8 | 9.0 | 0.3 | 4.0 | | 1.3 | 4.8 | 2.0 | | 4.3 | 1.0 | 1.5 |
| | 0.0160 | 8.5 | 2.8 | 0.0 | 7.8 | 0.3 | 4.0 | | 0.5 | 3.0 | 0.5 | | 2.3 | 0.0 | 0.5 |

TABLE II-continued

Preemergence Herbicidal Evaluations of Test Compounds

| Compound Number | Rate (kg/ha) | ABUTH | AMBEL | CASOB | CHEAL | GALAP | IPOHE | IPOSS | ECHCG | SETVI | GLXMAW | GLXMA | ORYSAT | TRZAWR | ZEAMX |
|---|---|---|---|---|---|---|---|---|---|---|---|---|---|---|---|
| 336 | 0.2500 | 9.0 | 9.0 | 7.0 | 9.0 | 8.0 | 9.0 | | 8.5 | 9.0 | 9.0 | | 7.5 | 6.0 | 6.0 |
| | 0.1250 | 9.0 | 9.0 | 6.0 | 9.0 | 2.0 | 9.0 | | 8.0 | 9.0 | 7.0 | | 6.0 | 6.0 | 6.5 |
| | 0.0620 | 9.0 | 8.0 | 4.0 | 9.0 | 4.0 | 4.5 | | 4.5 | 9.0 | 5.0 | | 5.5 | 3.0 | 5.5 |
| | 0.0320 | 9.0 | 3.5 | 2.0 | 9.0 | 0.0 | 3.0 | | 1.5 | 2.5 | 2.0 | | 3.5 | 1.0 | 3.0 |
| | 0.0160 | 6.5 | 0.0 | 0.0 | 7.5 | 0.0 | 2.5 | | 0.0 | 0.0 | 0.0 | | 1.5 | 0.0 | 1.0 |
| 337 | 0.5000 | 9.0 | 9.0 | 9.0 | 9.0 | | 9.0 | | 9.0 | 9.0 | 8.0 | | 8.0 | | 7.0 |
| | 0.2500 | 9.0 | 9.0 | 9.0 | 9.0 | 9.0 | 8.0 | | 9.0 | 9.0 | 7.5 | | 7.0 | 5.0 | 6.0 |
| | 0.1250 | 9.0 | 9.0 | 7.5 | 9.0 | 9.0 | 8.0 | | 6.0 | 3.5 | 6.0 | | 5.5 | 2.0 | 2.5 |
| | 0.0620 | 9.0 | 8.0 | 3.5 | 9.0 | 4.0 | 3.5 | | 1.5 | 2.0 | 2.5 | | 2.0 | 1.0 | 1.5 |
| | 0.0320 | 6.5 | 2.0 | 3.0 | 9.0 | 3.0 | 2.0 | | 0.0 | 0.0 | 0.5 | | 0.5 | 0.0 | 1.0 |
| | 0.0160 | 0.0 | 0.5 | 2.5 | 7.5 | 5.0 | 1.0 | | 0.0 | 0.0 | 0.5 | | 0.0 | 0.0 | 0.5 |
| 338 | 0.2500 | 9.0 | 9.0 | 7.0 | 9.0 | 9.0 | 9.0 | | 9.0 | 9.0 | 9.0 | | 8.0 | 8.0 | 7.0 |
| | 0.1250 | 9.0 | 9.0 | 5.0 | 9.0 | 6.0 | 6.0 | | 7.0 | 9.0 | 7.0 | | 6.0 | 5.0 | 5.0 |
| | 0.0620 | 9.0 | 7.0 | 2.0 | 9.0 | 6.0 | 5.0 | | 4.0 | 6.0 | 5.0 | | 4.0 | 1.0 | 3.0 |
| | 0.0320 | 9.0 | 6.0 | 0.0 | 9.0 | 1.0 | 1.0 | | 0.0 | 1.0 | 3.0 | | 1.0 | 1.0 | 1.0 |
| | 0.0160 | 9.0 | 1.0 | 0.0 | 9.0 | 1.0 | 0.0 | | 0.0 | 0.0 | 1.0 | | 0.0 | 0.0 | 0.0 |
| 339 | 0.2500 | 9.0 | 9.0 | 9.0 | 9.0 | 9.0 | 9.0 | | 9.0 | 9.0 | 9.0 | | 8.5 | 8.0 | 8.0 |
| | 0.1250 | 9.0 | 9.0 | 9.0 | 9.0 | 9.0 | 9.0 | | 7.0 | 9.0 | 7.0 | | 8.5 | 7.0 | 7.5 |
| | 0.0620 | 9.0 | 8.0 | 8.0 | 9.0 | 9.0 | 8.0 | | 6.5 | 6.5 | 4.5 | | 7.0 | 6.0 | 6.5 |
| | 0.0320 | 9.0 | 5.0 | 3.0 | 9.0 | 2.0 | 3.0 | | 3.0 | 3.5 | 2.0 | | 3.0 | 1.0 | 2.0 |
| | 0.0160 | 9.0 | 5.0 | 0.5 | 9.0 | 2.0 | 3.0 | | 1.5 | 0.0 | 0.0 | | 1.0 | 0.0 | 1.0 |
| 340 | 0.2500 | 9.0 | 9.0 | 9.0 | 9.0 | 9.0 | 9.0 | | 9.0 | 9.0 | 9.0 | | 9.0 | 8.0 | 9.0 |
| | 0.1250 | 9.0 | 9.0 | 7.0 | 9.0 | 9.0 | 9.0 | | 8.0 | 9.0 | 8.0 | | 7.5 | 7.0 | 8.0 |
| | 0.0620 | 9.0 | 9.0 | 4.5 | 9.0 | 9.0 | 7.5 | | 4.0 | 9.0 | 8.0 | | 6.0 | 5.0 | 6.0 |
| | 0.0320 | 9.0 | 9.0 | 1.0 | 9.0 | 9.0 | 6.5 | | 4.0 | 7.0 | 4.5 | | 4.5 | 2.0 | 3.5 |
| | 0.0160 | 9.0 | 7.0 | 1.0 | 9.0 | 1.0 | 5.0 | | 2.0 | 7.0 | 3.5 | | 2.0 | 1.0 | 1.5 |
| 341 | 0.5000 | 9.0 | 9.0 | 9.0 | 9.0 | | 9.0 | | 9.0 | 9.0 | 9.0 | | 7.0 | | 6.0 |
| | 0.2500 | 9.0 | 9.0 | 9.0 | 9.0 | 9.0 | 9.0 | | 9.0 | 9.0 | 8.8 | | 5.2 | 3.5 | 5.8 |
| | 0.1250 | 9.0 | 9.0 | 8.9 | 9.0 | 8.2 | 8.8 | | 8.1 | 9.0 | 8.0 | | 4.1 | 2.2 | 3.4 |
| | 0.0620 | 9.0 | 8.6 | 6.0 | 9.0 | 6.0 | 9.0 | | 6.1 | 7.9 | 5.4 | | 2.5 | 0.8 | 2.4 |
| | 0.0320 | 8.3 | 6.6 | 4.4 | 9.0 | 3.2 | 6.8 | | 3.2 | 6.1 | 3.0 | | 1.9 | 0.5 | 1.4 |
| | 0.0160 | 6.4 | 4.2 | 0.8 | 8.5 | 1.5 | 4.1 | | 0.5 | 2.6 | 1.1 | | 0.6 | 0.2 | 0.3 |
| 342 | 0.2500 | 9.0 | 5.0 | 1.0 | 9.0 | 0.0 | 2.0 | | 2.0 | 4.0 | 1.0 | | 1.0 | 2.0 | 1.0 |
| | 0.1250 | 9.0 | 2.0 | 0.0 | 9.0 | 1.0 | 0.0 | | 0.0 | 0.0 | 0.0 | | 0.0 | 0.0 | 0.0 |
| | 0.0620 | 2.0 | 1.0 | 0.0 | 5.0 | 0.0 | | | 0.0 | 0.0 | 0.0 | | 0.0 | 0.0 | 0.0 |
| | 0.0320 | 1.0 | 0.0 | 0.0 | 5.0 | 0.0 | 0.0 | | 0.0 | 0.0 | 0.0 | | 0.0 | 1.0 | 1.0 |
| | 0.0160 | 9.0 | 9.0 | 5.0 | 9.0 | 0.0 | 9.0 | | 9.0 | 9.0 | 9.0 | | 5.0 | | 5.0 |
| 343 | 0.5000 | 9.0 | 9.0 | 5.5 | 9.0 | 1.0 | 9.0 | | 7.0 | 9.0 | 3.5 | | 5.0 | 2.0 | 4.5 |
| | 0.2500 | 9.0 | 9.0 | 3.5 | 9.0 | 1.0 | 7.5 | | 6.5 | 9.0 | 2.5 | | 4.0 | 2.0 | 3.0 |
| | 0.1250 | 9.0 | 9.0 | 1.0 | 9.0 | 0.0 | 5.0 | | 1.5 | 5.5 | 1.0 | | 1.0 | 1.0 | 1.5 |
| | 0.0620 | 9.0 | 8.0 | 0.0 | 8.0 | 0.0 | 3.0 | | 0.5 | 0.5 | 0.0 | | 0.5 | 1.0 | 0.5 |
| | 0.0320 | 6.5 | 6.0 | 0.0 | 9.0 | 0.0 | | | 0.5 | 0.5 | 0.5 | | 0.0 | 0.0 | 0.5 |
| | 0.0160 | 9.0 | 3.5 | 0.5 | 9.0 | 0.0 | 0.5 | | 0.5 | 0.5 | 1.0 | | 0.0 | 0.0 | 0.5 |
| 344 | 0.5000 | 9.0 | 9.0 | 9.0 | 9.0 | 9.0 | 9.0 | | 9.0 | 9.0 | 9.0 | | 7.0 | | 7.0 |
| | 0.2500 | 9.0 | 9.0 | 9.0 | 9.0 | 8.0 | 8.0 | | 9.0 | 9.0 | 9.0 | | 6.5 | 7.0 | 6.0 |
| | 0.1250 | 9.0 | 9.0 | 7.5 | 9.0 | 0.0 | 8.0 | | 6.5 | 9.0 | 5.0 | | 6.0 | 3.0 | 5.5 |
| | 0.0620 | 9.0 | 8.0 | 5.5 | 9.0 | 0.0 | 9.0 | | 5.5 | 9.0 | 3.0 | | 3.5 | 2.0 | 3.5 |

TABLE II-continued

Preemergence Herbicidal Evaluations of Test Compounds

| Compound Number | Rate (kg/ha) | ABUTH | AMBEL | CASOB | CHEAL | GALAP | IPOHE | IPOSS | ECHCG | SETVI | GLXMAW | GLXMA | ORYSAT | TRZAWR | ZEAMX |
|---|---|---|---|---|---|---|---|---|---|---|---|---|---|---|---|
| 345 | 0.0320 | 9.0 | 7.0 | 1.5 | 9.0 | 0.0 | 5.5 |  | 2.0 | 7.5 | 1.5 |  | 3.5 | 2.0 | 2.0 |
|  | 0.0160 | 9.0 | 4.5 | 0.5 | 9.0 | 0.0 | 1.0 |  | 1.0 | 4.5 | 1.0 |  | 2.0 | 1.0 | 1.5 |
|  | 0.2500 | 9.0 | 9.0 | 4.0 | 9.0 | 9.0 | 9.0 |  | 9.0 | 9.0 | 9.0 |  | 0.0 | 6.0 | 9.0 |
|  | 0.1250 | 9.0 | 9.0 | 0.0 | 9.0 | 9.0 | 9.0 |  | 5.0 | 9.0 | 2.0 |  | 0.0 | 1.0 | 6.0 |
|  | 0.0620 | 9.0 | 9.0 |  | 9.0 | 9.0 | 0.0 |  | 7.0 | 9.0 | 1.0 |  | 0.0 | 0.0 | 1.0 |
|  | 0.0320 | 9.0 | 0.0 | 0.0 | 9.0 | 9.0 | 0.0 |  | 2.0 | 9.0 | 0.0 |  | 0.0 | 2.0 | 0.0 |
|  | 0.2500 | 0.0 | 7.0 |  |  | 0.0 |  | 4.0 | 5.0 | 6.0 | 0.0 |  | 0.0 | 0.0 | 0.0 |
|  | 0.0620 | 0.0 | 0.0 |  |  | 0.0 |  | 0.0 | 0.0 | 0.0 | 0.0 |  | 9.0 |  | 0.0 |
| 346 | 0.5000 | 9.0 | 9.0 | 9.0 | 9.0 |  | 9.0 |  | 9.0 | 9.0 | 9.0 |  | 9.0 |  | 7.0 |
| 347 | 0.2500 | 9.0 | 9.0 | 3.0 | 9.0 | 9.0 | 9.0 |  | 9.0 | 9.0 | 8.0 |  | 6.0 | 2.0 | 4.0 |
|  | 0.1250 | 9.0 | 9.0 | 3.0 | 9.0 | 0.0 | 5.5 |  | 9.0 | 9.0 | 4.5 |  | 4.5 | 0.0 | 3.0 |
|  | 0.0620 | 9.0 | 6.0 | 3.0 | 9.0 | 0.0 | 6.5 |  | 5.0 | 4.5 | 2.5 |  | 3.0 | 0.0 | 1.0 |
|  | 0.0320 | 9.0 | 4.5 | 1.5 | 4.5 | 0.0 | 4.5 |  | 3.5 | 4.0 | 2.5 |  | 1.0 | 0.0 | 0.5 |
|  | 0.0160 | 4.5 | 2.0 | 0.0 | 9.0 | 0.0 | 3.5 |  | 0.0 | 1.0 | 1.0 |  | 1.0 | 0.0 | 0.5 |
| 348 | 0.5000 | 9.0 | 9.0 | 9.0 | 9.0 | 9.0 | 9.0 |  | 9.0 | 9.0 | 5.0 |  | 7.0 |  | 9.0 |
|  | 0.2500 | 9.0 | 9.0 | 3.0 | 9.0 | 9.0 | 5.5 |  | 9.0 | 9.0 | 1.5 |  | 5.5 | 4.0 | 4.0 |
|  | 0.1250 | 9.0 | 9.0 | 6.0 | 9.0 | 9.0 | 3.0 |  | 9.0 | 9.0 | 1.5 |  | 2.5 | 1.0 | 3.0 |
|  | 0.0620 | 9.0 | 6.5 | 2.5 | 9.0 | 0.0 | 3.0 |  | 3.0 | 9.0 | 1.5 |  | 2.0 | 0.0 | 1.0 |
|  | 0.0320 | 4.5 | 3.5 | 2.0 | 9.0 | 0.0 | 2.0 |  | 2.0 | 3.5 | 1.0 |  | 0.5 | 0.0 | 0.5 |
|  | 0.0160 | 4.5 | 1.5 | 0.0 | 9.0 | 0.0 | 0.0 |  | 0.0 | 1.5 | 0.0 |  | 0.0 | 0.0 | 0.0 |
| 349 | 0.2500 | 9.0 | 9.0 | 4.0 | 9.0 | 9.0 | 9.0 |  | 9.0 | 9.0 | 7.0 |  | 8.0 | 4.0 | 7.0 |
|  | 0.1250 | 9.0 | 9.0 | 4.0 | 9.0 | 9.0 | 7.0 |  | 9.0 | 9.0 | 7.0 |  | 7.0 | 4.0 | 3.0 |
|  | 0.0620 | 9.0 | 3.0 | 0.0 | 9.0 | 9.0 | 5.0 |  | 7.0 | 9.0 | 1.0 |  | 6.0 | 1.0 | 3.0 |
|  | 0.0320 | 9.0 | 0.0 | 0.0 | 9.0 | 0.0 | 3.0 |  | 0.0 | 3.5 | 1.0 |  | 0.0 | 0.0 | 0.0 |
|  | 0.0160 | 9.0 | 0.0 | 0.0 | 9.0 | 0.0 | 0.0 |  | 0.0 | 1.5 | 0.0 |  | 0.0 | 0.0 | 0.0 |
| 350 | 0.2500 | 9.0 | 9.0 | 9.0 | 9.0 | 9.0 | 9.0 |  | 9.0 | 9.0 | 9.0 |  | 9.0 | 9.0 | 8.5 |
|  | 0.1250 | 9.0 | 9.0 | 9.0 | 9.0 | 9.0 | 9.0 |  | 9.0 | 9.0 | 9.0 |  | 8.5 | 9.0 | 8.0 |
|  | 0.0620 | 9.0 | 9.0 | 9.0 | 9.0 | 9.0 | 9.0 |  | 9.0 | 9.0 | 8.5 |  | 8.5 | 9.0 | 7.5 |
|  | 0.0320 | 9.0 | 9.0 | 7.0 | 9.0 | 9.0 | 8.0 |  | 9.0 | 9.0 | 8.5 |  | 7.5 | 9.0 | 7.5 |
|  | 0.0160 | 9.0 | 9.0 | 3.5 | 9.0 | 9.0 | 8.0 |  | 8.0 | 9.0 | 7.5 |  | 7.0 | 7.0 | 7.0 |
| 351 | 0.2500 | 9.0 | 9.0 | 6.5 | 9.0 | 9.0 | 9.0 |  | 9.0 | 9.0 | 9.0 |  | 9.0 | 9.0 | 8.5 |
|  | 0.1250 | 9.0 | 9.0 | 7.5 | 9.0 | 9.0 | 8.5 |  | 8.5 | 9.0 | 8.0 |  | 8.5 | 9.0 | 8.0 |
|  | 0.0620 | 9.0 | 9.0 | 7.5 | 9.0 | 9.0 | 5.0 |  | 7.5 | 9.0 | 9.0 |  | 7.5 | 9.0 | 7.5 |
|  | 0.0320 | 9.0 | 5.0 | 4.5 | 9.0 | 8.0 | 9.0 |  | 4.0 | 9.0 | 6.5 |  | 8.0 | 7.0 | 7.0 |
|  | 0.0160 | 9.0 | 9.0 | 0.0 | 9.0 | 8.0 | 9.0 |  | 4.5 | 3.5 | 3.0 |  | 4.0 | 2.0 | 6.0 |
| 352 | 0.2500 | 9.0 | 9.0 | 2.5 | 9.0 | 0.0 | 9.0 |  | 0.5 | 2.5 | 8.0 |  | 3.0 | 0.0 | 3.5 |
|  | 0.1250 | 9.0 | 9.0 | 3.5 | 9.0 | 0.0 | 9.0 |  | 0.0 | 0.0 | 7.0 |  | 2.5 | 0.0 | 1.0 |
|  | 0.0620 | 9.0 | 4.0 | 1.5 | 9.0 | 0.0 | 9.0 |  | 0.0 | 0.0 | 3.5 |  | 1.0 | 0.0 | 1.0 |
|  | 0.0320 | 9.0 | 0.0 | 1.5 | 7.5 | 0.0 | 7.0 |  | 0.0 | 0.0 | 1.5 |  | 0.0 | 0.0 | 1.0 |
|  | 0.0160 | 4.0 | 0.0 | 0.0 | 9.0 |  | 9.0 |  | 3.0 | 6.0 | 1.0 |  | 0.0 | 0.0 | 0.0 |
| 353 | 0.5000 | 9.0 | 9.0 | 5.0 | 9.0 |  | 9.0 |  | 1.0 | 1.0 | 3.0 |  | 4.0 | 3.0 | 3.0 |
|  | 0.2500 | 9.0 | 9.0 | 5.0 | 9.0 |  | 9.0 |  | 1.0 | 1.0 | 2.0 |  | 1.0 | 1.0 | 3.0 |
|  | 0.1250 | 9.0 | 9.0 | 1.0 | 9.0 |  | 6.0 |  | 1.0 | 1.0 | 1.0 |  | 1.0 | 1.0 | 1.0 |
|  | 0.0620 | 9.0 | 9.0 | 0.0 | 9.0 |  | 3.0 |  | 0.0 | 0.0 | 0.0 |  | 0.0 | 0.0 | 0.0 |
|  | 0.0320 | 0.0 | 1.0 | 0.0 | 9.0 |  | 1.0 |  | 0.0 | 0.0 | 0.0 |  | 0.0 | 0.0 | 0.0 |
|  | 0.0160 | 9.0 | 1.0 | 0.0 | 9.0 |  | 0.0 |  | 0.0 | 0.0 | 0.0 |  | 0.0 | 0.0 | 0.0 |
| 354 | 0.5000 | 9.0 | 9.0 | 6.0 | 9.0 |  | 9.0 |  | 9.0 | 9.0 | 7.0 |  | 8.0 | 7.0 | 9.0 |

TABLE II-continued

Preemergence Herbicidal Evaluations of Test Compounds

| Compound Number | Rate (kg/ha) | ABUTH | AMBEL | CASOB | CHEAL | GALAP | IPOHE | IPOSS | ECHCG | SETVI | GLXMAW | GLXMA | ORYSAT | TRZAWR | ZEAMX |
|---|---|---|---|---|---|---|---|---|---|---|---|---|---|---|---|
| | 0.2500 | 9.0 | 9.0 | 5.0 | 9.0 | | 7.5 | | 9.0 | 9.0 | 8.0 | | 6.5 | 7.0 | 7.0 |
| | 0.1250 | 9.0 | 9.0 | 4.5 | 9.0 | | 7.0 | | 9.0 | 9.0 | 7.0 | | 6.0 | 3.0 | 6.0 |
| | 0.0620 | 9.0 | 9.0 | 4.5 | 9.0 | | 5.5 | | 7.0 | 9.0 | 5.0 | | 5.5 | 1.0 | 5.5 |
| | 0.0320 | 9.0 | 7.0 | 4.0 | 8.5 | | 3.0 | | 3.0 | 8.0 | 3.5 | | 2.0 | 1.0 | 3.5 |
| | 0.0160 | 5.5 | 3.0 | 1.0 | 9.0 | | 2.0 | | 0.0 | 3.5 | 3.0 | | 1.0 | 0.0 | 2.0 |
| 355 | 0.5000 | 9.0 | 9.0 | 6.0 | 9.0 | | 9.0 | | 9.0 | 9.0 | 3.0 | | 6.0 | 1.0 | 6.0 |
| | 0.2500 | 9.0 | 4.0 | 1.0 | 9.0 | | 5.0 | | 8.0 | 9.0 | 3.0 | | 5.0 | 1.0 | 3.0 |
| | 0.1250 | 9.0 | 4.0 | 1.0 | 9.0 | | 2.0 | | 1.0 | 3.0 | 2.0 | | 1.0 | 1.0 | 1.0 |
| | 0.0620 | 9.0 | 4.0 | 0.0 | 9.0 | | 0.0 | | 0.0 | 0.0 | 1.0 | | 1.0 | 1.0 | 1.0 |
| | 0.0320 | 0.0 | 0.0 | 0.0 | 9.0 | | 0.0 | | 0.0 | 0.0 | 1.0 | | 0.0 | 0.0 | 1.0 |
| | 0.0160 | 0.0 | 0.0 | 0.0 | 1.0 | | 0.0 | | 0.0 | 0.0 | 0.0 | | 0.0 | 1.0 | 1.0 |
| 356 | 0.5000 | 9.0 | 9.0 | 8.0 | 9.0 | | 9.0 | | 2.5 | 6.5 | 8.0 | | 3.0 | 3.0 | 4.5 |
| | 0.2500 | 9.0 | 9.0 | 3.0 | 9.0 | | 9.0 | | 0.0 | 2.0 | 6.5 | | 1.5 | 1.0 | 3.0 |
| | 0.1250 | 9.0 | 9.0 | 3.0 | 8.0 | | 7.0 | | 0.0 | 0.5 | 3.0 | | 1.0 | 1.0 | 2.0 |
| | 0.0620 | 9.0 | 2.5 | 2.0 | 9.0 | | 5.5 | | 0.0 | 0.0 | 1.5 | | 0.0 | 0.0 | 1.0 |
| | 0.0320 | 7.5 | 2.0 | 2.0 | 9.0 | | 3.5 | | 0.0 | 0.0 | 1.0 | | 0.0 | 0.0 | 0.0 |
| | 0.0160 | 6.5 | 2.0 | 1.0 | 9.0 | | 1.0 | | 0.0 | 0.0 | 0.0 | | 0.0 | 0.0 | 0.0 |
| 357 | 0.5000 | 9.0 | 9.0 | 4.0 | 9.0 | | 9.0 | | 1.0 | 2.0 | 3.0 | | 1.0 | 1.0 | 2.0 |
| | 0.2500 | 1.0 | 9.0 | 1.0 | 9.0 | | 4.0 | | 0.0 | 0.0 | 2.0 | | 1.0 | 2.0 | 2.0 |
| | 0.1250 | 2.0 | 3.0 | 0.0 | 9.0 | | 0.0 | | 0.0 | 0.0 | 1.0 | | 1.0 | 1.0 | 2.0 |
| | 0.0620 | 1.0 | 2.0 | 0.0 | 9.0 | | 0.0 | | 0.0 | 0.0 | 0.0 | | 0.0 | 0.0 | 0.0 |
| | 0.0320 | 0.0 | 0.0 | 0.0 | 7.0 | | 1.0 | | 0.0 | 0.0 | 0.0 | | 0.0 | 0.0 | 0.0 |
| | 0.0160 | 0.0 | 0.0 | 0.0 | 9.0 | | 1.0 | | 0.0 | 0.0 | 1.0 | | 0.0 | 0.0 | 1.0 |
| 358 | 0.5000 | 9.0 | 9.0 | 3.0 | 9.0 | 8.0 | 9.0 | | 0.0 | 3.0 | 3.0 | | 1.0 | 1.0 | 2.0 |
| | 0.2500 | 9.0 | 5.0 | 0.0 | 9.0 | 7.0 | 9.0 | | 0.0 | 0.0 | 3.0 | | 0.0 | 0.0 | 0.0 |
| | 0.1250 | 3.0 | 3.0 | 0.0 | 8.0 | 0.0 | 1.0 | | 0.0 | 0.0 | 2.0 | | 0.0 | 0.0 | 0.0 |
| | 0.0620 | 1.0 | 1.0 | 0.0 | 3.0 | 0.0 | 0.0 | | 0.0 | 0.0 | 0.0 | | 0.0 | 0.0 | 0.0 |
| | 0.0320 | 0.0 | 0.0 | 0.0 | 0.0 | 0.0 | 0.0 | | 0.0 | 0.0 | 0.0 | | 0.0 | 0.0 | 0.0 |
| | 0.0160 | 0.0 | 0.0 | 0.0 | 0.0 | 0.0 | 1.0 | | 0.0 | 0.0 | 1.0 | | 0.0 | 0.0 | 1.0 |
| 359 | 0.5000 | 9.0 | 9.0 | 9.0 | 9.0 | 9.0 | 9.0 | | 9.0 | 9.0 | 5.3 | | 6.7 | 5.5 | 6.7 |
| | 0.2500 | 9.0 | 9.0 | 7.5 | 9.0 | 8.5 | 9.0 | | 7.8 | 9.0 | 3.5 | | 7.3 | 3.7 | 6.3 |
| | 0.1250 | 9.0 | 9.0 | 4.3 | 9.0 | 8.0 | 8.5 | | 5.5 | 5.5 | 2.5 | | 6.0 | 1.7 | 4.5 |
| | 0.0620 | 9.0 | 8.3 | 2.0 | 9.0 | 6.0 | 9.0 | | 2.8 | 6.8 | 1.8 | | 4.0 | 1.0 | 3.0 |
| | 0.0320 | 9.0 | 6.3 | 0.7 | 9.0 | 1.0 | 7.0 | | 1.0 | 4.8 | 1.3 | | 2.3 | 0.0 | 1.5 |
| | 0.0160 | 7.5 | 9.0 | 1.5 | 9.0 | 0.5 | 1.8 | | 7.5 | 2.0 | 0.5 | | 1.5 | 0.7 | 1.0 |
| 360 | 0.5000 | 9.0 | 9.0 | 3.0 | 9.0 | 9.0 | 7.0 | | 5.0 | 9.0 | 4.0 | | 7.5 | 6.0 | 6.5 |
| | 0.2500 | 9.0 | 7.0 | 3.0 | 9.0 | 9.0 | 3.5 | | 3.0 | 8.0 | 3.0 | | 4.0 | 3.0 | 4.0 |
| | 0.1250 | 8.0 | 4.5 | 2.5 | 9.0 | 9.0 | 3.5 | | 1.0 | 7.5 | 2.0 | | 2.0 | 1.0 | 3.0 |
| | 0.0620 | 6.5 | 0.0 | 0.0 | 4.5 | 9.0 | 1.5 | | 0.0 | 4.5 | 0.0 | | 0.5 | 1.0 | 1.5 |
| | 0.0320 | 1.5 | 0.5 | 0.0 | 0.0 | 7.0 | 1.0 | | 1.0 | 1.0 | 0.5 | | 0.0 | 1.0 | 1.5 |
| | 0.0160 | 0.0 | 0.0 | 0.0 | 9.0 | 9.0 | 0.0 | | 0.0 | 4.0 | 0.0 | | 1.0 | 0.0 | 0.5 |
| 361 | 0.5000 | 9.0 | 0.0 | 2.0 | 9.0 | 9.0 | 0.0 | | 2.0 | 0.0 | 0.0 | | 0.0 | 1.0 | 2.0 |
| | 0.2500 | 0.0 | 1.0 | 0.0 | 6.0 | 9.0 | 0.0 | | 0.0 | 0.0 | 0.0 | | 0.0 | 0.0 | 0.0 |
| | 0.1250 | 0.0 | 4.0 | 0.0 | | 4.0 | 0.0 | | 2.0 | 1.0 | 0.0 | | 1.0 | 1.0 | 1.0 |
| | 0.0620 | 0.0 | 0.0 | 0.0 | | 5.0 | 0.0 | | 0.0 | 0.0 | 0.0 | | 0.0 | 0.0 | 0.0 |
| | 0.0320 | 0.0 | 1.0 | 0.0 | 0.0 | 0.0 | 0.0 | | 0.0 | 1.0 | 1.0 | | 0.0 | 0.0 | 0.0 |
| | 0.0160 | 0.0 | 0.0 | 0.0 | 0.0 | 0.0 | 0.0 | | 0.0 | 1.0 | 0.0 | | 0.0 | 0.0 | 0.0 |

TABLE II-continued

Preemergence Herbicidal Evaluations of Test Compounds

| Compound Number | Rate (kg/ha) | ABUTH | AMBEL | CASOB | CHEAL | GALAP | IPOHE | IPOSS | ECHCG | SETVI | GLXMAW | GLXMA | ORYSAT | TRZAWR | ZEAMX |
|---|---|---|---|---|---|---|---|---|---|---|---|---|---|---|---|
| 362 | 0.5000 | 9.0 | 9.0 | 9.0 | 9.0 | 9.0 | 9.0 | | 9.0 | 9.0 | 4.5 | | 7.0 | 8.0 | 6.5 |
| | 0.2500 | 9.0 | 9.0 | 3.5 | 9.0 | 0.0 | 9.0 | | 9.0 | 9.0 | 4.0 | | 5.0 | 7.0 | 5.0 |
| | 0.1250 | 9.0 | 9.0 | 2.0 | 9.0 | 0.0 | 9.0 | | 5.5 | 9.0 | 3.5 | | 3.0 | 3.0 | 1.5 |
| | 0.0620 | 9.0 | 7.0 | 0.0 | 6.5 | 0.0 | 9.0 | | 2.5 | 8.5 | 1.0 | | 1.5 | 0.0 | 1.0 |
| | 0.0320 | 9.0 | 2.5 | 0.0 | 7.0 | 0.0 | 9.0 | | 0.0 | 4.0 | 1.0 | | 0.5 | 0.0 | 1.0 |
| | 0.0160 | 9.0 | 2.5 | 0.0 | 7.0 | 0.0 | 9.0 | | 0.0 | 2.0 | 0.0 | | 0.0 | 0.0 | 0.0 |
| 363 | 0.5000 | 9.0 | 9.0 | 8.0 | 9.0 | 9.0 | 9.0 | | 9.0 | 9.0 | 6.5 | | 9.0 | 9.0 | 8.0 |
| | 0.2500 | 9.0 | 7.7 | 6.7 | 9.0 | 9.0 | 9.0 | | 7.3 | 8.7 | 2.7 | | 7.7 | 8.0 | 6.7 |
| | 0.1250 | 9.0 | 5.7 | 5.3 | 9.0 | 9.0 | 9.0 | | 2.3 | 3.7 | 0.7 | | 4.7 | 5.0 | 5.7 |
| | 0.0620 | 8.0 | 2.7 | 3.7 | 5.7 | 0.0 | 7.3 | | 0.7 | 1.3 | 0.0 | | 3.0 | 0.0 | 2.3 |
| | 0.0320 | 4.5 | 0.0 | 0.7 | 5.0 | 0.0 | 2.3 | | 0.0 | 1.0 | 0.0 | | 1.3 | 0.0 | 0.7 |
| | 0.0160 | 9.0 | 0.0 | 0.0 | 5.0 | 0.0 | 2.0 | | 0.0 | 1.0 | 0.0 | | 0.0 | 0.0 | 0.0 |
| 364 | 0.5000 | 9.0 | 9.0 | 9.0 | 9.0 | 9.0 | 9.0 | | 9.0 | 9.0 | 7.5 | | 9.0 | 9.0 | 8.0 |
| | 0.2500 | 9.0 | 9.0 | 7.0 | 9.0 | 9.0 | 9.0 | | 8.3 | 9.0 | 5.3 | | 8.7 | 9.0 | 7.0 |
| | 0.1250 | 9.0 | 9.0 | 8.0 | 9.0 | 9.0 | 9.0 | | 3.3 | 9.0 | 4.0 | | 8.0 | 8.0 | 7.0 |
| | 0.0620 | 9.0 | 5.7 | 5.3 | 9.0 | 0.0 | 8.3 | | 0.7 | 5.0 | 1.3 | | 7.0 | 6.0 | 4.7 |
| | 0.0320 | 9.0 | 5.7 | 3.3 | 9.0 | 0.0 | 5.7 | | 0.0 | 1.0 | 0.0 | | 2.3 | 0.0 | 1.7 |
| | 0.0160 | 8.3 | 4.3 | 2.0 | 7.7 | 0.0 | 5.7 | | 0.0 | 1.0 | 0.0 | | 1.3 | 0.0 | 1.0 |
| 365 | 0.5000 | 9.0 | 9.0 | 4.0 | 9.0 | 9.0 | 9.0 | | 9.0 | 9.0 | 6.0 | | 9.0 | 9.0 | 9.0 |
| | 0.2500 | 9.0 | 9.0 | 1.0 | 9.0 | 9.0 | 9.0 | | 9.0 | 9.0 | 5.0 | | 8.0 | 8.0 | 8.0 |
| | 0.1250 | 9.0 | 9.0 | 1.0 | 9.0 | 9.0 | 9.0 | | 2.0 | 9.0 | 4.0 | | 5.0 | 4.0 | 8.0 |
| | 0.0620 | 9.0 | 7.0 | 0.0 | 9.0 | 0.0 | 3.0 | | 0.0 | 8.0 | 0.0 | | 0.0 | 0.0 | 7.0 |
| | 0.0320 | 4.0 | 2.0 | 0.0 | 4.0 | 0.0 | 1.0 | | 0.0 | 3.0 | 0.0 | | 0.0 | 0.0 | 2.0 |
| | 0.0160 | 4.0 | 0.0 | 0.0 | 4.0 | 0.0 | 1.0 | | 0.0 | 0.0 | 0.0 | | 0.0 | 0.0 | 0.0 |
| 366 | 0.5000 | 9.0 | 9.0 | 9.0 | 9.0 | 9.0 | 9.0 | | 9.0 | 9.0 | 9.0 | | 9.0 | 9.0 | 9.0 |
| | 0.2500 | 9.0 | 9.0 | 9.0 | 9.0 | 9.0 | 9.0 | | 9.0 | 9.0 | 9.0 | | 8.7 | 9.0 | 8.7 |
| | 0.1250 | 9.0 | 9.0 | 9.0 | 9.0 | 9.0 | 9.0 | | 9.0 | 9.0 | 9.0 | | 8.0 | 8.5 | 8.3 |
| | 0.0620 | 9.0 | 9.0 | 8.3 | 9.0 | 8.0 | 9.0 | | 8.0 | 9.0 | 8.3 | | 7.3 | 7.0 | 8.0 |
| | 0.0320 | 9.0 | 8.7 | 6.3 | 9.0 | 0.0 | 9.0 | | 8.0 | 9.0 | 6.7 | | 6.3 | 7.0 | 7.7 |
| 367 | 0.5000 | 9.0 | 9.0 | 5.0 | 9.0 | | 9.0 | | 8.0 | 9.0 | 9.0 | | 7.0 | | 4.0 |
| | 0.2500 | 9.0 | 8.5 | 2.5 | 9.0 | 9.0 | 6.0 | | 3.0 | 9.0 | 7.5 | | 6.0 | 7.0 | 2.5 |
| | 0.1250 | 8.0 | 6.0 | 3.0 | 9.0 | 4.0 | 3.0 | | 0.0 | 4.0 | 3.0 | | 4.5 | 4.0 | 2.0 |
| | 0.0620 | 6.0 | 1.5 | 2.0 | 9.0 | 3.0 | 1.5 | | 0.0 | 1.0 | 1.5 | | 2.0 | 1.0 | 1.0 |
| | 0.0320 | 0.0 | 0.0 | 2.0 | 2.5 | | 1.5 | | 0.0 | 0.5 | 1.5 | | 1.5 | 0.0 | 1.0 |
| | 0.0160 | 0.0 | 0.0 | 1.5 | 1.0 | 0.0 | 1.5 | | 0.0 | 0.0 | 1.0 | | 0.0 | 0.0 | 0.5 |
| 368 | 0.5000 | 9.0 | 9.0 | 9.0 | 9.0 | 9.0 | 9.0 | | 9.0 | 9.0 | 6.0 | | 8.0 | | 7.0 |
| | 0.2500 | 9.0 | 9.0 | 9.0 | 9.0 | 9.0 | 9.0 | | 8.0 | 9.0 | 5.0 | | 7.5 | 7.0 | 6.5 |
| | 0.1250 | 9.0 | 9.0 | 4.5 | 9.0 | 9.0 | 9.0 | | 5.0 | 8.0 | 3.0 | | 7.0 | 6.0 | 6.0 |

TABLE II-continued

Preemergence Herbicidal Evaluations of Test Compounds

| Compound Number | Rate (kg/ha) | ABUTH | AMBEL | CASOB | CHEAL | GALAP | IPOHE | IPOSS | ECHCG | SETVI | GLXMAW | GLXMA | ORYSAT | TRZAWR | ZEAMX |
|---|---|---|---|---|---|---|---|---|---|---|---|---|---|---|---|
| | 0.0620 | 9.0 | 8.0 | 4.0 | 9.0 | 9.0 | 7.5 | | 1.5 | 7.0 | 1.5 | | 5.5 | 4.0 | 4.0 |
| | 0.0320 | 9.0 | 4.0 | 3.0 | 9.0 | 2.0 | 9.0 | | 0.0 | 5.5 | 0.5 | | 3.0 | 1.0 | 2.5 |
| | 0.0160 | 9.0 | 2.0 | 2.0 | 7.5 | 1.0 | 5.5 | | 0.0 | 2.0 | 0.5 | | 1.5 | 0.0 | 0.0 |
| 369 | 0.5000 | 9.0 | 9.0 | 9.0 | 9.0 | | 9.0 | | 9.0 | 9.0 | 9.0 | | 9.0 | | 7.0 |
| | 0.2500 | 9.0 | 9.0 | 8.3 | 9.0 | 9.0 | 9.0 | | 9.0 | 9.0 | 5.3 | | 8.0 | | 7.7 |
| | 0.1250 | 9.0 | 9.0 | 8.0 | 9.0 | 9.0 | 9.0 | | 7.0 | 8.3 | 3.3 | | 6.7 | | 7.7 |
| | 0.0620 | 8.3 | 8.0 | 6.0 | 9.0 | 6.0 | 9.0 | | 2.3 | 7.7 | 2.3 | | 4.3 | 7.0 | 6.7 |
| | 0.0320 | 8.3 | 7.0 | 2.3 | 9.0 | 3.5 | 6.0 | | 0.0 | 2.0 | 1.7 | | 2.0 | 6.0 | 4.7 |
| | 0.0160 | 6.3 | 4.7 | 2.5 | 8.3 | 2.0 | 4.0 | | 0.0 | 0.7 | 0.7 | | 0.7 | 1.5 | 1.7 |
| 370 | 0.5000 | 9.0 | 9.0 | 7.0 | 9.0 | | 9.0 | | 0.0 | 9.0 | 9.0 | | 8.0 | 0.0 | 0.7 |
| | 0.2500 | 9.0 | 8.7 | 0.0 | 9.0 | 9.0 | 9.0 | | 9.0 | 9.0 | 5.7 | | 7.3 | 6.0 | 4.0 |
| | 0.1250 | 9.0 | 8.0 | 0.0 | 9.0 | 9.0 | 9.0 | | 3.7 | 5.7 | 1.3 | | 6.3 | 1.0 | 2.7 |
| | 0.0620 | 8.7 | 4.0 | 0.0 | 9.0 | 9.0 | 9.0 | | 2.0 | 4.7 | 2.7 | | 3.3 | 1.0 | 2.0 |
| | 0.0320 | 4.0 | 1.7 | 0.3 | 1.7 | 6.0 | 6.0 | | 0.0 | 1.7 | 1.3 | | 1.0 | 0.0 | 1.3 |
| | 0.0160 | 3.0 | 0.0 | 0.0 | 9.0 | 9.0 | 4.0 | | 0.0 | 1.0 | 0.7 | | 0.7 | 0.0 | 0.0 |
| 371 | 0.2500 | 9.0 | 9.0 | 6.0 | 9.0 | 9.0 | 9.0 | | 6.5 | 9.0 | 4.5 | | 8.0 | 7.0 | 7.0 |
| | 0.1250 | 9.0 | 8.5 | 4.0 | 9.0 | 9.0 | 7.5 | | 3.5 | 9.0 | 1.5 | | 8.0 | 7.0 | 4.5 |
| | 0.0620 | 9.0 | 6.5 | 0.0 | 9.0 | 9.0 | 5.5 | | | 8.0 | | | 5.0 | 3.0 | |

EXAMPLE 187

Rice Tolerance to Post-Transplant Applications and Preemergence Weed Control Under Flooded Paddy Conditions The tolerance of transplanted rice to post-transplanted herbicide applications is determined as follows: two ten-day-old rice seedlings (cv. Tebonnet) are transplanted into silt loam soil in 32 oz. plastic containers with a diameter of 10.5 cm and no drainage holes. After transplanting, the containers are flooded and the water level is maintained at 1.5 to 3 cm above the soil surface. Three days after transplanting, the flooded soil surface of the containers is treated with the selected aqueous/acetone 50/50 v/v mixture containing the test compounds to provide the equivalent of about 0.0313 to 0.500 kg/ha of active ingredient. The treated containers are placed on greenhouse benches, watered such that the water level is maintained as stated above, and cared for in accordance with conventional greenhouse procedures. Three to four weeks after treatment, the test is terminated and each container is examined and herbicidal effect rated according to the rating system provided in Example 185. The data obtained are reported in Table III. The compounds evaluated are reported by compound number given in Example 185.

Preemergence herbicidal activity under flooded paddy conditions is determined as follows: plant seeds or propagating organs are planted in the top 0.5 cm of silt loam soil in 32 oz. plastic containers with a diameter of 10.5 cm and no drainage holes. Water is added to these containers and maintained at 1.5 to 3 cm above the soil surface for the duration of the experiment. The test compounds are applied as aqueous/acetone mixtures 50/50 v/v pipetted directly into the flood water to give the equivalent of about 0.0313 to 0.500 kg/ha of active ingredient. The treated containers are placed on greenhouse benches and cared for in accordance with conventional greenhouse procedures. Three to four weeks after treatment, the test is terminated and each container is examined and herbicidal effect rated according to the rating system provided in Example 185. The data obtained are reported in Table III. The compounds evaluated are reported by compound number given in Example 185.

Plant species employed in this example are reported by header abbreviation, common name and scientific name.

| PLANT SPECIES EMPLOYED IN RICE TOLERANCE/PREEMERGENCE WEED CONTROL EVALUATIONS | | |
|---|---|---|
| Header Abbr. | Common Name | Scientific Name |
| ECHORC | Watergrass (Calif.) | *Echinochloa oryzoides* (Ard.) Fritsch. |
| CYPIR | Rice Flatsedge | *Cyperus iria* |
| CYPSE | Flatsedge | *Cyperus serotinus*, Rottb. |
| MOOVA | Monochoria | *Monochoria vaginalis*, Presl. |
| SAGPY | Arrowhead (Pygmaea) | *Sagittaria pygmaea*, L. |
| ORYSAT | Rice, Tebonnet | *Oryza sativa*, (L.) Tebonnet |

TABLE III

PADDY CONDITIONS - POST-TRANSPLANT RICE PREEMERGENCE WEEDS

| Compound Number | Rate (kg/ha) | ECHORC | CYPIR | CYPSE | MOOVA | SAGPY | ORYSAT |
|---|---|---|---|---|---|---|---|
| 1 | 0.5000 | 9.0 | 9.0 | 8.0 | 9.0 | 8.5 | 7.0 |
|   | 0.2500 | 9.0 | 9.0 | 9.0 | 9.0 | 8.3 | 7.7 |
|   | 0.1250 | 9.0 | 9.0 | 6.0 | 9.0 | 6.7 | 5.3 |
|   | 0.0625 | 9.0 | 9.0 | 3.0 | 9.0 | 5.0 | 4.7 |
|   | 0.0313 | 9.0 | 9.0 | 1.3 | 9.0 | 3.3 | 4.7 |
| 2 | 0.5000 | 9.0 | 9.0 | 0.0 | 9.0 | 9.0 | 9.0 |
|   | 0.2500 | 9.0 | 9.0 | 0.0 | 9.0 | 4.0 | 5.0 |
|   | 0.1250 | 9.0 | 9.0 | 0.0 | 9.0 | 2.0 | 3.0 |
|   | 0.0625 | 9.0 | 9.0 | 0.0 | 9.0 | 0.0 | 3.0 |
|   | 0.0313 | 9.0 | 8.0 | 0.0 | 7.0 | 0.0 | 2.0 |
| 3 | 0.5000 | 9.0 | 9.0 | 4.0 | 9.0 | 9.0 | 4.0 |
|   | 0.2500 | 9.0 | 9.0 | 2.0 | 9.0 | 8.0 | 4.0 |
|   | 0.1250 | 9.0 | 9.0 | 0.0 | 9.0 | 6.0 | 3.0 |
|   | 0.0625 | 9.0 | 9.0 | 0.0 | 9.0 | 2.0 | 2.0 |
|   | 0.0313 | 9.0 | 9.0 | 0.0 | 9.0 | 0.0 | 2.0 |
| 4 | 0.5000 | 9.0 | 9.0 | 9.0 | 9.0 | 9.0 | 8.0 |
|   | 0.2500 | 9.0 | 9.0 | 9.0 | 9.0 | 9.0 | 8.0 |
|   | 0.1250 | 9.0 | 9.0 | 9.0 | 9.0 | 6.0 | 7.0 |
|   | 0.0625 | 9.0 | 9.0 | 2.0 | 9.0 | 2.0 | 7.0 |
|   | 0.0313 | 9.0 | 9.0 |  | 9.0 | 2.0 | 4.0 |
| 5 | 0.5000 | 9.0 | 9.0 | 7.0 | 9.0 | 7.0 | 7.0 |
|   | 0.2500 | 9.0 | 9.0 | 8.0 | 9.0 | 7.0 | 5.0 |
|   | 0.1250 | 9.0 | 9.0 | 6.0 | 9.0 | 2.0 | 4.0 |
|   | 0.0625 | 9.0 | 9.0 | 2.0 | 9.0 | 0.0 | 3.0 |
|   | 0.0313 | 9.0 | 9.0 | 0.0 | 9.0 | 0.0 | 2.0 |
| 6 | 0.5000 | 9.0 | 9.0 | 9.0 | 9.0 | 9.0 | 8.0 |
|   | 0.2500 | 9.0 | 9.0 | 9.0 | 9.0 | 7.0 | 8.0 |
|   | 0.1250 | 8.0 | 9.0 | 7.0 | 9.0 | 7.0 | 8.0 |
|   | 0.0625 | 6.0 | 9.0 | 4.0 | 9.0 | 4.0 | 8.0 |
| 7 | 0.5000 | 9.0 | 9.0 | 9.0 | 9.0 | 9.0 | 9.0 |
|   | 0.2500 | 9.0 | 9.0 | 7.0 | 9.0 | 9.0 | 7.0 |
|   | 0.1250 | 9.0 | 9.0 | 8.0 | 9.0 | 9.0 | 7.0 |
|   | 0.0625 | 9.0 | 9.0 | 7.0 | 9.0 | 8.0 | 8.0 |
|   | 0.0313 | 9.0 | 9.0 | 7.0 | 9.0 | 6.0 | 6.0 |

TABLE III-continued

PADDY CONDITIONS - POST-TRANSPLANT RICE
PREEMERGENCE WEEDS

| Compound Number | Rate (kg/ha) | ECHORC | CYPIR | CYPSE | MOOVA | SAGPY | ORYSAT |
|---|---|---|---|---|---|---|---|
| 8 | 0.5000 | 9.0 | 9.0 | 9.0 | 9.0 | 9.0 | 9.0 |
|  | 0.2500 | 9.0 | 9.0 | 9.0 | 9.0 | 9.0 | 9.0 |
|  | 0.1250 | 9.0 | 9.0 | 9.0 | 9.0 | 9.0 | 9.0 |
|  | 0.0625 | 9.0 | 9.0 | 9.0 | 9.0 | 9.0 | 7.0 |
|  | 0.0313 | 9.0 | 9.0 | 4.0 | 9.0 | 6.0 | 7.0 |
| 9 | 0.5000 | 9.0 | 9.0 | 9.0 | 9.0 | 9.0 | 9.0 |
|  | 0.2500 | 9.0 | 9.0 | 9.0 | 9.0 | 8.0 | 8.0 |
|  | 0.1250 | 9.0 | 9.0 | 9.0 | 9.0 | 8.0 | 7.0 |
|  | 0.0625 | 9.0 | 9.0 | 4.0 | 9.0 | 2.0 | 7.0 |
|  | 0.0313 | 9.0 | 9.0 | 2.0 | 9.0 | 0.0 | 6.0 |
| 10 | 0.5000 | 9.0 | 9.0 | 7.0 | 9.0 | 9.0 | 7.0 |
|  | 0.2500 | 9.0 | 9.0 | 7.0 | 9.0 | 9.0 | 7.0 |
|  | 0.1250 | 9.0 | 9.0 | 7.0 | 9.0 | 9.0 | 6.0 |
|  | 0.0625 | 9.0 | 9.0 | 7.0 | 9.0 | 8.0 | 6.0 |
|  | 0.0313 | 9.0 | 9.0 | 4.0 | 9.0 | 2.0 | 4.0 |
| 11 | 0.5000 | 9.0 | 9.0 | 7.0 | 9.0 | 9.0 | 3.0 |
|  | 0.2500 | 8.0 | 9.0 | 2.0 | 9.0 | 2.0 | 3.0 |
|  | 0.1250 | 8.0 | 9.0 | 2.0 | 9.0 | 0.0 | 2.0 |
|  | 0.0625 | 7.0 | 9.0 | 2.0 | 9.0 | 0.0 | 2.0 |
| 12 | 0.5000 | 9.0 | 9.0 | 7.0 | 9.0 | 9.0 | 9.0 |
|  | 0.2500 | 9.0 | 9.0 | 7.0 | 9.0 | 9.0 | 8.0 |
|  | 0.1250 | 9.0 | 9.0 | 8.0 | 9.0 | 4.0 | 7.0 |
|  | 0.0625 | 9.0 | 9.0 | 7.0 | 9.0 | 2.0 | 7.0 |
|  | 0.0313 | 9.0 | 9.0 | 6.0 | 9.0 | 0.0 | 4.0 |
| 13 | 0.5000 | 9.0 | 9.0 | 7.0 | 9.0 | 9.0 | 9.0 |
|  | 0.2500 | 9.0 | 9.0 | 7.0 | 9.0 | 8.0 | 7.0 |
|  | 0.1250 | 9.0 | 9.0 | 7.0 | 9.0 | 6.0 | 7.0 |
|  | 0.0625 | 9.0 | 9.0 | 2.0 | 9.0 | 2.0 | 6.0 |
|  | 0.0313 | 9.0 | 9.0 | 0.0 | 9.0 | 0.0 | 4.0 |
| 14 | 0.2500 | 7.5 | 8.0 | 2.0 | 9.0 | 0.0 | 3.5 |
|  | 0.1250 | 6.5 | 6.0 | 1.0 | 9.0 | 0.0 | 2.5 |
|  | 0.0625 | 5.0 | 4.0 | 0.0 | 9.0 | 0.0 | 2.0 |
|  | 0.0313 | 4.0 | 2.0 | 0.0 | 9.0 | 0.0 | 2.0 |
| 16 | 0.2500 | 5.0 | 6.0 | 0.0 | 9.0 | 0.0 | 4.0 |
|  | 0.1250 | 3.5 | 4.0 | 0.0 | 9.0 | 0.0 | 2.5 |
|  | 0.0625 | 1.0 | 2.0 | 0.0 | 4.0 | 0.0 | 1.5 |
|  | 0.0313 | 1.0 | 0.0 | 0.0 | 2.0 | 0.0 | 1.0 |
| 17 | 0.2500 | 8.0 | 9.0 | 8.0 | 9.0 | 8.0 | 4.0 |
|  | 0.1250 | 7.5 | 8.0 | 2.0 | 9.0 | 2.0 | 2.5 |
|  | 0.0625 | 5.5 | 8.0 | 0.0 | 9.0 | 0.0 | 3.0 |
|  | 0.0313 | 4.0 | 4.0 | 0.0 | 8.0 | 0.0 | 2.0 |
| 18 | 0.2500 | 9.0 | 9.0 | 8.0 | 9.0 | 0.0 | 9.0 |
|  | 0.1250 | 9.0 | 9.0 | 9.0 | 9.0 | 0.0 | 4.0 |
|  | 0.0625 | 9.0 | 9.0 | 9.0 | 9.0 | 0.0 | 3.0 |
|  | 0.0313 | 9.0 | 9.0 | 6.0 | 9.0 | 0.0 | 3.0 |
| 19 | 0.2500 | 6.5 | 8.0 | 2.0 | 9.0 | 0.0 | 2.5 |
|  | 0.1250 | 5.0 | 8.0 | 0.0 | 9.0 | 0.0 | 2.0 |
|  | 0.0625 | 3.5 | 4.0 | 0.0 | 9.0 | 0.0 | 1.5 |
|  | 0.0313 | 2.0 | 2.0 | 0.0 | 8.0 | 0.0 | 1.0 |
| 20 | 0.2500 | 0.0 | 2.0 | 0.0 | 4.0 | 0.0 | 1.0 |
|  | 0.1250 | 0.0 | 1.0 | 0.0 | 2.0 | 0.0 | 0.5 |
|  | 0.0625 | 0.0 | 0.0 | 0.0 | 0.0 | 0.0 | 0.5 |
|  | 0.0313 | 0.0 | 0.0 | 0.0 | 0.0 | 0.0 | 0.5 |
| 21 | 0.2500 | 4.7 | 1.0 | 0.0 | 9.0 | 0.0 | 4.3 |
|  | 0.1250 | 2.7 | 0.5 | 0.0 | 7.5 | 0.0 | 2.3 |
|  | 0.0625 | 0.7 | 0.0 | 0.0 | 6.0 | 0.0 | 2.0 |
|  | 0.0313 | 0.0 | 0.0 | 0.0 | 4.0 | 0.0 | 1.7 |
| 22 | 0.2500 | 9.0 | 9.0 | 9.0 | 9.0 | 9.0 | 2.5 |
|  | 0.1250 | 9.0 | 9.0 | 7.0 | 9.0 | 4.0 | 2.5 |
|  | 0.0625 | 9.0 | 9.0 | 7.0 | 9.0 | 2.0 | 2.0 |
|  | 0.0313 | 9.0 | 9.0 | 2.0 | 9.0 | 0.0 | 2.0 |
| 23 | 0.2500 | 9.0 | 9.0 | 9.0 | 9.0 | 9.0 | 8.5 |
|  | 0.1250 | 8.5 | 9.0 | 8.0 | 9.0 | 9.0 | 8.0 |
|  | 0.0625 | 7.0 | 9.0 | 7.0 | 9.0 | 6.0 | 6.5 |
|  | 0.0313 | 4.5 | 7.0 | 4.0 | 9.0 | 4.0 | 5.5 |
| 24 | 0.2500 | 7.0 | 8.0 | 4.0 | 9.0 | 0.0 | 4.0 |
|  | 0.1250 | 2.0 | 6.0 | 1.0 | 9.0 | 0.0 | 3.0 |
|  | 0.0625 | 0.0 | 2.0 | 0.0 | 8.0 | 0.0 | 2.0 |
|  | 0.0313 | 0.0 | 0.0 | 0.0 | 4.0 | 0.0 | 2.0 |
| 25 | 0.2500 | 9.0 | 9.0 | 8.0 | 9.0 | 4.0 | 7.0 |
|  | 0.1250 | 9.0 | 9.0 | 7.0 | 9.0 | 1.0 | 7.0 |
|  | 0.0625 | 9.0 | 9.0 | 2.0 | 9.0 | 0.0 | 6.0 |
|  | 0.0313 | 7.0 | 9.0 | 0.0 | 9.0 | 0.0 | 4.0 |

TABLE III-continued

PADDY CONDITIONS - POST-TRANSPLANT RICE
PREEMERGENCE WEEDS

| Compound Number | Rate (kg/ha) | ECHORC | CYPIR | CYPSE | MOOVA | SAGPY | ORYSAT |
|---|---|---|---|---|---|---|---|
| 26 | 0.2500 | 9.0 | 9.0 | 9.0 | 9.0 | 9.0 | 9.0 |
|  | 0.1250 | 9.0 | 9.0 | 2.0 | 9.0 | 2.0 | 6.0 |
|  | 0.0625 | 9.0 | 8.0 | 4.0 | 9.0 | 0.0 | 4.0 |
|  | 0.0313 | 7.0 | 6.0 | 0.0 | 9.0 | 0.0 | 3.0 |
| 27 | 0.2500 | 9.0 | 9.0 | 2.0 | 9.0 | 4.0 | 6.0 |
|  | 0.1250 | 9.0 | 6.0 | 0.0 | 9.0 | 2.0 | 5.0 |
|  | 0.0625 | 7.0 | 4.0 | 0.0 | 9.0 | 0.0 | 3.0 |
|  | 0.0313 | 6.0 | 2.0 | 0.0 | 8.0 | 0.0 | 2.0 |
| 28 | 0.2500 | 9.0 | 9.0 | 4.0 | 9.0 | 8.0 | 9.0 |
|  | 0.1250 | 9.0 | 6.0 | 0.0 | 9.0 | 4.0 | 7.0 |
|  | 0.0625 | 9.0 | 4.0 | 0.0 | 9.0 | 2.0 | 4.0 |
|  | 0.0313 | 8.0 | 2.0 | 0.0 | 8.0 | 0.0 | 3.0 |
| 29 | 0.2500 | 9.0 | 9.0 | 4.0 | 9.0 | 0.0 | 4.0 |
|  | 0.1250 | 9.0 | 9.0 | 4.0 | 9.0 | 0.0 | 4.0 |
|  | 0.0625 | 9.0 | 7.0 |  | 9.0 | 0.0 | 3.0 |
|  | 0.0313 | 7.0 | 4.0 | 0.0 | 8.0 | 0.0 | 2.0 |
| 30 | 0.2500 | 9.0 | 8.0 | 2.0 | 9.0 | 7.0 | 3.5 |
|  | 0.1250 | 9.0 | 8.0 | 4.0 | 9.0 | 2.0 | 3.0 |
|  | 0.0625 | 8.5 | 6.0 | 0.0 | 9.0 | 0.0 | 3.0 |
|  | 0.0313 | 6.5 | 2.0 | 0.0 | 9.0 | 0.0 | 2.0 |
| 31 | 0.2500 | 9.0 | 9.0 | 9.0 | 9.0 | 9.0 | 8.0 |
|  | 0.1250 | 9.0 | 9.0 | 8.0 | 9.0 | 9.0 | 7.5 |
|  | 0.0625 | 8.5 | 9.0 | 7.0 | 9.0 | 7.0 | 8.0 |
|  | 0.0313 | 7.0 | 9.0 | 7.0 | 9.0 | 4.0 | 7.5 |
| 32 | 0.2500 | 7.5 | 9.0 | 7.0 | 9.0 | 9.0 | 4.5 |
|  | 0.1250 | 4.5 | 8.0 | 2.0 | 9.0 | 2.0 | 4.0 |
|  | 0.0625 | 3.5 | 6.0 | 0.0 | 9.0 | 0.0 | 2.5 |
|  | 0.0313 | 2.0 | 4.0 | 0.0 | 8.0 | 0.0 | 1.5 |
| 33 | 0.2500 | 9.0 | 4.0 | 0.0 | 9.0 | 0.0 | 3.5 |
|  | 0.1250 | 9.0 | 2.0 | 0.0 | 9.0 | 0.0 | 3.0 |
|  | 0.0625 | 8.5 | 0.0 | 0.0 | 9.0 | 0.0 | 3.0 |
|  | 0.0313 | 7.5 | 0.0 | 0.0 | 9.0 | 0.0 | 2.0 |
| 34 | 0.2500 | 4.5 | 0.0 | 0.0 | 0.0 | 0.0 | 0.0 |
|  | 0.1250 | 3.5 | 0.0 | 0.0 | 0.0 | 0.0 | 0.0 |
|  | 0.0625 | 2.5 | 0.0 | 0.0 | 0.0 | 0.0 | 0.0 |
|  | 0.0313 | 2.0 | 0.0 | 0.0 | 0.0 | 0.0 | 0.0 |
| 35 | 0.2500 | 9.0 | 9.0 | 7.0 | 9.0 | 9.0 | 5.0 |
|  | 0.1250 | 7.5 | 9.0 | 7.0 | 9.0 | 2.0 | 4.0 |
|  | 0.0625 | 6.5 | 8.0 | 2.0 | 9.0 | 0.0 | 2.5 |
|  | 0.0313 | 4.5 | 4.0 | 0.0 | 9.0 | 0.0 | 2.0 |
| 36 | 0.2500 | 0.0 |  |  |  |  | 1.0 |
|  | 0.1250 | 0.0 |  |  |  |  | 1.0 |
|  | 0.0625 | 0.0 |  |  |  |  | 1.0 |
|  | 0.0313 | 0.0 |  |  |  |  | 1.0 |
| 37 | 0.2500 | 9.0 |  |  |  |  | 1.0 |
|  | 0.1250 | 8.0 |  |  |  |  | 1.0 |
|  | 0.0625 | 7.0 |  |  |  |  | 1.0 |
|  | 0.0313 | 4.0 |  |  |  |  | 0.0 |
| 38 | 0.2500 | 2.0 | 0.0 | 0.0 | 0.0 | 0.0 | 0.0 |
|  | 0.1250 | 1.0 | 0.0 | 0.0 | 0.0 | 0.0 | 0.0 |
|  | 0.0625 | 0.0 | 0.0 | 0.0 | 0.0 | 0.0 | 0.0 |
|  | 0.0313 | 0.0 | 0.0 | 0.0 | 0.0 | 0.0 | 0.0 |
| 39 | 0.2500 | 0.0 | 0.0 | 0.0 | 0.0 | 0.0 | 0.0 |
|  | 0.1250 | 0.0 | 0.0 | 0.0 | 0.0 | 0.0 | 0.0 |
|  | 0.0625 | 0.0 | 0.0 | 0.0 | 0.0 | 0.0 | 0.0 |
|  | 0.0313 | 0.0 | 0.0 | 0.0 | 0.0 | 0.0 | 0.0 |
| 40 | 0.2500 | 9.0 | 9.0 | 9.0 | 9.0 | 6.0 | 4.0 |
|  | 0.1250 | 9.0 | 9.0 | 9.0 | 9.0 | 2.0 | 3.0 |
|  | 0.0625 | 9.0 | 4.0 | 4.0 | 9.0 | 0.0 | 3.0 |
|  | 0.0313 | 9.0 | 2.0 | 2.0 | 9.0 | 0.0 | 2.0 |
| 41 | 0.2500 | 6.0 | 2.0 | 0.0 | 9.0 | 0.0 | 0.0 |
|  | 0.1250 | 2.0 | 1.0 | 0.0 | 4.0 | 0.0 | 0.0 |
|  | 0.0625 | 0.0 | 0.0 | 0.0 | 2.0 | 0.0 | 0.0 |
|  | 0.0313 | 0.0 | 0.0 | 0.0 | 0.0 | 0.0 | 0.0 |
| 42 | 0.2500 | 0.0 | 0.0 | 0.0 | 0.0 | 0.0 | 0.0 |
|  | 0.1250 | 0.0 | 0.0 | 0.0 | 0.0 | 0.0 | 0.0 |
|  | 0.0625 | 0.0 | 0.0 | 0.0 | 0.0 | 0.0 | 0.0 |
|  | 0.0313 | 0.0 | 0.0 | 0.0 | 0.0 | 0.0 | 0.0 |
| 43 | 0.2500 | 8.0 | 0.0 | 0.0 | 9.0 | 0.0 | 3.0 |
|  | 0.1250 | 2.0 | 0.0 | 0.0 | 9.0 | 0.0 | 3.0 |
|  | 0.0625 | 0.0 | 0.0 | 0.0 | 9.0 | 0.0 | 2.0 |
|  | 0.0313 | 0.0 | 0.0 | 0.0 | 6.0 | 0.0 | 1.0 |
| 44 | 0.2500 | 0.0 | 0.0 | 0.0 | 0.0 | 0.0 | 0.0 |

TABLE III-continued

PADDY CONDITIONS - POST-TRANSPLANT RICE
PREEMERGENCE WEEDS

| Compound Number | Rate (kg/ha) | ECHORC | CYPIR | CYPSE | MOOVA | SAGPY | ORYSAT |
|---|---|---|---|---|---|---|---|
| | 0.1250 | 0.0 | 0.0 | 0.0 | 0.0 | 0.0 | 0.0 |
| | 0.0625 | 0.0 | 0.0 | 0.0 | 0.0 | 0.0 | 0.0 |
| | 0.0313 | 0.0 | 0.0 | 0.0 | 0.0 | 0.0 | 0.0 |
| 45 | 0.2500 | 9.0 | 9.0 | 9.0 | 9.0 | 6.0 | 3.0 |
| | 0.1250 | 9.0 | 9.0 | 9.0 | 9.0 | 4.0 | 3.0 |
| | 0.0625 | 9.0 | 9.0 | 2.0 | 9.0 | 0.0 | 2.0 |
| | 0.0313 | 9.0 | 6.0 | | 9.0 | 0.0 | 2.0 |
| 46 | 0.2500 | 9.0 | 9.0 | 2.0 | 9.0 | 7.0 | 3.0 |
| | 0.1250 | 9.0 | 9.0 | | 9.0 | 2.0 | 2.0 |
| | 0.0625 | 9.0 | 6.0 | 0.0 | 9.0 | 0.0 | 1.0 |
| | 0.0313 | 9.0 | 2.0 | 0.0 | 9.0 | 0.0 | 1.0 |
| 47 | 0.2500 | 5.0 | 1.0 | 2.0 | 9.0 | 0.0 | 6.0 |
| | 0.1250 | 3.5 | 0.0 | 1.0 | 5.5 | 0.0 | 4.0 |
| | 0.0625 | 1.5 | 0.0 | 0.0 | 4.5 | 0.0 | 2.5 |
| | 0.0313 | 0.0 | 0.0 | 0.0 | 4.5 | 0.0 | 1.5 |
| 48 | 0.2500 | 6.0 | 0.0 | | 9.0 | 0.0 | 6.0 |
| | 0.1250 | 2.0 | 0.0 | 0.0 | 9.0 | 0.0 | 4.0 |
| | 0.0625 | 0.0 | 0.0 | 0.0 | 9.0 | 0.0 | 2.0 |
| | 0.0313 | 0.0 | 0.0 | 0.0 | 6.0 | 0.0 | 2.0 |
| 49 | 0.2500 | 8.0 | 8.0 | 0.0 | 9.0 | 0.0 | 2.0 |
| | 0.1250 | 6.0 | 2.0 | 0.0 | 9.0 | 0.0 | 1.0 |
| | 0.0625 | 4.0 | 0.0 | 0.0 | 9.0 | 0.0 | 1.0 |
| | 0.0313 | 0.0 | 0.0 | 0.0 | 4.0 | 0.0 | 1.0 |
| 50 | 0.2500 | 9.0 | 6.0 | 0.0 | 9.0 | 0.0 | 3.0 |
| | 0.1250 | 9.0 | 2.0 | 0.0 | 9.0 | 0.0 | 2.0 |
| | 0.0625 | 9.0 | 2.0 | 0.0 | 9.0 | 0.0 | 2.0 |
| | 0.0313 | 9.0 | 0.0 | 0.0 | 9.0 | 0.0 | 2.0 |
| 51 | 0.2500 | 9.0 | 9.0 | 9.0 | 9.0 | 9.0 | 9.0 |
| | 0.1250 | 9.0 | 9.0 | 7.0 | 9.0 | 4.0 | 9.0 |
| | 0.0625 | 7.0 | 8.0 | 2.0 | 9.0 | 2.0 | 9.0 |
| | 0.0313 | 4.0 | 7.0 | 0.0 | 9.0 | 2.0 | 7.0 |
| 52 | 0.2500 | 7.0 | 0.0 | | 9.0 | 0.0 | 0.0 |
| | 0.1250 | 4.0 | | | 9.0 | 0.0 | 0.0 |
| | 0.0625 | 2.0 | 0.0 | 0.0 | 9.0 | 0.0 | 0.0 |
| | 0.0313 | 0.0 | 0.0 | 0.0 | 8.0 | 0.0 | 0.0 |
| 53 | 0.2500 | 9.0 | 9.0 | 0.0 | 9.0 | 0.0 | 7.0 |
| | 0.1250 | 6.0 | 9.0 | 0.0 | 9.0 | 0.0 | 5.0 |
| | 0.0625 | 2.0 | 6.0 | 0.0 | 9.0 | 0.0 | 4.0 |
| | 0.0313 | 0.0 | 2.0 | 0.0 | 8.0 | 0.0 | 2.0 |
| 54 | 0.2500 | 9.0 | 9.0 | 2.0 | 9.0 | 0.0 | 6.0 |
| | 0.1250 | 7.0 | 7.0 | 1.0 | 9.0 | 0.0 | 3.0 |
| | 0.0625 | 6.0 | 4.0 | 0.0 | 9.0 | 0.0 | 2.0 |
| | 0.0313 | 2.0 | 2.0 | 0.0 | 8.0 | 0.0 | 2.0 |
| 55 | 0.2500 | 9.0 | 9.0 | 0.0 | 9.0 | 0.0 | 6.0 |
| | 0.1250 | 9.0 | 6.0 | 0.0 | 9.0 | 0.0 | 3.0 |
| | 0.0625 | 7.0 | 2.0 | 0.0 | 9.0 | 0.0 | 1.0 |
| | 0.0313 | 5.0 | 0.0 | 0.0 | 7.0 | 0.0 | 2.0 |
| 56 | 0.2500 | 9.0 | 9.0 | 2.0 | 9.0 | 0.0 | 6.0 |
| | 0.1250 | 9.0 | 9.0 | 2.0 | 9.0 | 0.0 | 3.0 |
| | 0.0625 | 9.0 | 9.0 | 0.0 | 9.0 | 0.0 | 2.0 |
| | 0.0313 | 9.0 | 6.0 | 0.0 | 9.0 | 0.0 | 1.0 |
| 57 | 0.2500 | 9.0 | 9.0 | 0.0 | 9.0 | 0.0 | 6.0 |
| | 0.1250 | 9.0 | 9.0 | 0.0 | 9.0 | 0.0 | 5.0 |
| | 0.0625 | 9.0 | 9.0 | 0.0 | 9.0 | 0.0 | 4.0 |
| | 0.0313 | 9.0 | 9.0 | 0.0 | 9.0 | 0.0 | 3.0 |
| 58 | 0.2500 | 9.0 | 9.0 | 0.0 | 9.0 | 0.0 | 5.0 |
| | 0.1250 | 9.0 | 9.0 | 0.0 | 9.0 | 0.0 | 3.0 |
| | 0.0625 | 9.0 | 9.0 | 0.0 | 9.0 | 0.0 | 2.0 |
| | 0.0313 | 9.0 | 9.0 | 0.0 | 9.0 | 0.0 | 2.0 |
| 59 | 0.2500 | 9.0 | 9.0 | 0.0 | 9.0 | 0.0 | 4.0 |
| | 0.1250 | 9.0 | 8.0 | 0.0 | 9.0 | 0.0 | 4.0 |
| | 0.0625 | 9.0 | 7.0 | 0.0 | 9.0 | 0.0 | 3.0 |
| | 0.0313 | 9.0 | 7.0 | 0.0 | 9.0 | 0.0 | 2.0 |
| 60 | 0.2500 | 9.0 | 0.0 | 0.0 | 9.0 | 0.0 | 0.0 |
| | 0.1250 | 8.0 | 0.0 | 0.0 | 9.0 | 0.0 | 0.0 |
| | 0.0625 | 4.0 | 0.0 | 0.0 | 9.0 | 0.0 | 0.0 |
| | 0.0313 | 2.0 | 0.0 | 0.0 | 9.0 | 0.0 | 0.0 |
| 61 | 0.2500 | 8.0 | 2.0 | 0.0 | 9.0 | 0.0 | 0.0 |
| | 0.1250 | 8.0 | 2.0 | 0.0 | 9.0 | 0.0 | 0.0 |
| | 0.0625 | 7.0 | 0.0 | 0.0 | 8.0 | 0.0 | 0.0 |
| | 0.0313 | 4.0 | 0.0 | 0.0 | 8.0 | 0.0 | 0.0 |
| 62 | 0.2500 | 9.0 | 9.0 | 9.0 | 9.0 | 7.0 | 9.0 |
| | 0.1250 | 9.0 | 9.0 | 2.0 | 9.0 | 4.0 | 9.0 |

TABLE III-continued

PADDY CONDITIONS - POST-TRANSPLANT RICE
PREEMERGENCE WEEDS

| Compound Number | Rate (kg/ha) | ECHORC | CYPIR | CYPSE | MOOVA | SAGPY | ORYSAT |
|---|---|---|---|---|---|---|---|
| | 0.0625 | 9.0 | 6.0 | 1.0 | 9.0 | 1.0 | 9.0 |
| | 0.0313 | 6.0 | 4.0 | 0.0 | 9.0 | 0.0 | 4.0 |
| 63 | 0.2500 | 9.0 | 9.0 | 0.0 | 9.0 | 0.0 | 3.0 |
| | 0.1250 | 9.0 | 9.0 | 0.0 | 9.0 | 0.0 | 2.0 |
| | 0.0625 | 9.0 | 8.0 | 0.0 | 9.0 | 0.0 | 2.0 |
| | 0.0313 | 9.0 | 7.0 | 0.0 | 9.0 | 0.0 | 1.0 |
| 64 | 0.2500 | 9.0 | 7.0 | 0.0 | 9.0 | 0.0 | 7.0 |
| | 0.1250 | 8.0 | 7.0 | 0.0 | 9.0 | 0.0 | 4.0 |
| | 0.0625 | 8.0 | 4.0 | 0.0 | 9.0 | 0.0 | 3.0 |
| | 0.0313 | 6.0 | 2.0 | 0.0 | 9.0 | 0.0 | 3.0 |
| 65 | 0.2500 | 0.0 | 0.0 | 0.0 | 0.0 | 0.0 | 0.0 |
| | 0.1250 | 0.0 | 0.0 | 0.0 | 0.0 | 0.0 | 0.0 |
| | 0.0625 | 0.0 | 0.0 | 0.0 | 0.0 | 0.0 | 0.0 |
| | 0.0313 | 0.0 | 0.0 | 0.0 | 0.0 | 0.0 | 0.0 |
| 66 | 0.2500 | 9.0 | 9.0 | 9.0 | 9.0 | 2.0 | 2.0 |
| | 0.1250 | 9.0 | 9.0 | 9.0 | 9.0 | 0.0 | 2.0 |
| | 0.0625 | 9.0 | 9.0 | 2.0 | 9.0 | 0.0 | 1.0 |
| | 0.0313 | 9.0 | 8.0 | 0.0 | 9.0 | 0.0 | 1.0 |
| 67 | 0.2500 | 9.0 | 0.0 | 6.0 | 9.0 | 0.0 | 1.0 |
| | 0.1250 | 9.0 | 0.0 | 1.0 | 9.0 | 0.0 | 1.0 |
| | 0.0625 | 8.0 | 0.0 | 0.0 | 9.0 | 0.0 | 0.5 |
| | 0.0313 | 5.5 | 0.0 | 0.0 | 8.0 | 0.0 | 0.5 |
| 68 | 0.2500 | 9.0 | 9.0 | 7.0 | 9.0 | 2.0 | 1.0 |
| | 0.1250 | 9.0 | 9.0 | | 9.0 | 2.0 | 1.5 |
| | 0.0625 | 9.0 | 9.0 | 7.0 | 9.0 | 0.0 | 1.0 |
| | 0.0313 | 7.5 | 7.0 | 6.0 | 9.0 | 0.0 | 0.5 |
| 69 | 0.2500 | 9.0 | 7.0 | 9.0 | 9.0 | 9.0 | 8.0 |
| | 0.1250 | 9.0 | 4.0 | 2.0 | 9.0 | 2.0 | 6.5 |
| | 0.0625 | 9.0 | 2.0 | 0.0 | 9.0 | 0.0 | 5.0 |
| | 0.0313 | 9.0 | 0.0 | 0.0 | 9.0 | 0.0 | 3.5 |
| 70 | 0.2500 | 9.0 | 9.0 | 0.0 | 9.0 | 2.0 | 6.5 |
| | 0.1250 | 9.0 | 9.0 | 0.0 | 9.0 | 1.0 | 6.0 |
| | 0.0625 | 8.0 | 7.0 | 0.0 | 9.0 | 0.0 | 4.5 |
| | 0.0313 | 4.0 | 2.0 | 0.0 | 9.0 | 0.0 | 3.0 |
| 71 | 0.2500 | 9.0 | 2.0 | 9.0 | 9.0 | 4.0 | 7.0 |
| | 0.1250 | 8.5 | 0.0 | 2.0 | 9.0 | 0.0 | 5.5 |
| | 0.0625 | 7.5 | 0.0 | 0.0 | 9.0 | 0.0 | 3.5 |
| | 0.0313 | 5.5 | 0.0 | 0.0 | 8.0 | 0.0 | 2.0 |
| 72 | 0.2500 | 9.0 | 7.0 | 9.0 | 9.0 | 4.0 | 7.0 |
| | 0.1250 | 8.5 | 4.0 | 2.0 | 9.0 | 0.0 | 6.0 |
| | 0.0625 | 8.0 | 0.0 | 2.0 | 9.0 | 0.0 | 5.0 |
| | 0.0313 | 7.5 | 0.0 | 0.0 | 9.0 | 0.0 | 4.0 |
| 73 | 0.2500 | 9.0 | 8.0 | 9.0 | 9.0 | 2.0 | 6.0 |
| | 0.1250 | 9.0 | 8.0 | 2.0 | 9.0 | 0.0 | 4.0 |
| | 0.0625 | 6.5 | 6.0 | 0.0 | 9.0 | 0.0 | 3.0 |
| | 0.0313 | 8.0 | 2.0 | 0.0 | 9.0 | 0.0 | 2.5 |
| 74 | 0.2500 | 9.0 | 8.0 | 6.0 | 9.0 | 0.0 | 7.0 |
| | 0.1250 | 9.0 | 7.0 | 2.0 | 9.0 | 0.0 | 5.0 |
| | 0.0625 | 7.5 | 2.0 | 0.0 | 9.0 | 0.0 | 4.0 |
| | 0.0313 | 6.5 | 0.0 | 0.0 | 8.0 | 0.0 | 2.5 |
| 75 | 0.2500 | 9.0 | 7.0 | 0.0 | 9.0 | 4.0 | 8.0 |
| | 0.1250 | 8.5 | 4.0 | 0.0 | 9.0 | 0.0 | 5.0 |
| | 0.0625 | 9.0 | 2.0 | 0.0 | 9.0 | 0.0 | 3.0 |
| | 0.0313 | 6.5 | 0.0 | 0.0 | 9.0 | 0.0 | 2.0 |
| 76 | 0.2500 | 9.0 | 9.0 | 2.0 | 9.0 | 9.0 | 5.5 |
| | 0.1250 | 9.0 | 9.0 | 1.0 | 9.0 | 2.0 | 3.5 |
| | 0.0625 | 8.5 | 6.0 | 0.0 | 9.0 | 0.0 | 2.5 |
| | 0.0313 | 8.0 | 4.0 | 0.0 | 8.0 | 0.0 | 2.5 |
| 77 | 0.2500 | 9.0 | | | | | 7.0 |
| | 0.1250 | 9.0 | | | | | 7.0 |
| | 0.0625 | 9.0 | | | | | 4.0 |
| | 0.0313 | 9.0 | | | | | 3.0 |
| 78 | 0.2500 | 9.0 | | | | | 4.0 |
| | 0.1250 | 9.0 | | | | | 4.0 |
| | 0.0625 | 9.0 | | | | | 4.0 |
| | 0.0313 | 9.0 | | | | | 3.0 |
| 79 | 0.2500 | 9.0 | | | | | 4.0 |
| | 0.1250 | 9.0 | | | | | 4.0 |
| | 0.0625 | 9.0 | | | | | 4.0 |
| | 0.0313 | 9.0 | | | | | 3.0 |
| 80 | 0.2500 | 9.0 | | | | | 4.0 |
| | 0.1250 | 9.0 | | | | | 3.0 |
| | 0.0625 | 9.0 | | | | | 3.0 |

TABLE III-continued

PADDY CONDITIONS - POST-TRANSPLANT RICE
PREEMERGENCE WEEDS

| Compound Number | Rate (kg/ha) | ECHORC | CYPIR | CYPSE | MOOVA | SAGPY | ORYSAT |
|---|---|---|---|---|---|---|---|
| | 0.0313 | 9.0 | | | | | 4.0 |
| 81 | 0.2500 | 9.0 | | | | | 4.0 |
| | 0.1250 | 9.0 | | | | | 4.0 |
| | 0.0625 | 9.0 | | | | | 4.0 |
| | 0.0313 | 9.0 | | | | | 4.0 |
| 82 | 0.2500 | 9.0 | | | | | 3.0 |
| | 0.1250 | 9.0 | | | | | 3.0 |
| | 0.0625 | 9.0 | | | | | 2.0 |
| | 0.0313 | 9.0 | | | | | 1.0 |
| 83 | 0.2500 | 9.0 | | | | | 5.0 |
| | 0.1250 | 9.0 | | | | | 6.0 |
| | 0.0625 | 9.0 | | | | | 5.0 |
| | 0.0313 | 9.0 | | | | | 3.0 |
| 84 | 0.2500 | 9.0 | | | | | 7.0 |
| | 0.1250 | 9.0 | | | | | 4.0 |
| | 0.0625 | 9.0 | | | | | 3.0 |
| | 0.0313 | 9.0 | | | | | 3.0 |
| 85 | 0.2500 | 9.0 | | | | | 1.0 |
| | 0.1250 | 9.0 | | | | | 0.0 |
| | 0.0625 | 9.0 | | | | | 0.0 |
| | 0.0313 | 8.0 | | | | | 0.0 |
| 86 | 0.2500 | 9.0 | | | | | 3.0 |
| | 0.1250 | 9.0 | | | | | 2.0 |
| | 0.0625 | 9.0 | | | | | 3.0 |
| | 0.0313 | 9.0 | | | | | 2.0 |
| 87 | 0.2500 | 9.0 | | | | | 4.0 |
| | 0.1250 | 9.0 | | | | | 4.0 |
| | 0.0625 | 9.0 | | | | | 3.0 |
| | 0.0313 | 9.0 | | | | | 3.0 |
| 88 | 0.2500 | 9.0 | | | | | 7.0 |
| | 0.1250 | 9.0 | | | | | 6.0 |
| | 0.0625 | 9.0 | | | | | 4.0 |
| | 0.0313 | 9.0 | | | | | 3.0 |
| 89 | 0.2500 | 9.0 | | | | | 5.0 |
| | 0.1250 | 9.0 | | | | | 4.0 |
| | 0.0625 | 9.0 | | | | | 3.0 |
| | 0.0313 | 9.0 | | | | | 4.0 |
| 90 | 0.2500 | 9.0 | | | | | 7.0 |
| | 0.1250 | 9.0 | | | | | 6.0 |
| | 0.0625 | 9.0 | | | | | 6.0 |
| | 0.0313 | 9.0 | | | | | 4.0 |
| 91 | 0.2500 | 9.0 | | | | | 1.0 |
| | 0.1250 | 9.0 | | | | | 0.0 |
| | 0.0625 | 9.0 | | | | | 0.0 |
| | 0.0313 | 9.0 | | | | | 0.0 |
| 92 | 0.2500 | 9.0 | | | | | 6.0 |
| | 0.1250 | 9.0 | | | | | 6.0 |
| | 0.0625 | 6.0 | | | | | 5.0 |
| | 0.0313 | 4.0 | | | | | 3.0 |
| 93 | 0.2500 | 9.0 | 7.0 | 9.0 | 9.0 | | 7.0 |
| | 0.1250 | 8.0 | 4.0 | 9.0 | 9.0 | 7.0 | 6.0 |
| | 0.0625 | 8.0 | 2.0 | 2.0 | 9.0 | 0.0 | 4.0 |
| | 0.0313 | 7.0 | 0.0 | | 9.0 | 0.0 | 4.0 |
| 94 | 0.2500 | 7.0 | 7.0 | 0.0 | 9.0 | 0.0 | 0.0 |
| | 0.1250 | 4.0 | 4.0 | 0.0 | 9.0 | 0.0 | 1.0 |
| | 0.0625 | 2.0 | 2.0 | 0.0 | 9.0 | 0.0 | 0.0 |
| | 0.0313 | 0.0 | 0.0 | 0.0 | 6.0 | 0.0 | 0.0 |
| 95 | 0.2500 | 0.0 | 8.0 | 0.0 | 9.0 | 0.0 | 4.0 |
| | 0.1250 | 0.0 | 2.0 | 0.0 | 6.0 | 0.0 | 2.0 |
| | 0.0625 | 0.0 | 0.0 | 0.0 | 2.0 | 0.0 | 2.0 |
| | 0.0313 | 0.0 | 0.0 | 0.0 | 0.0 | 0.0 | 0.0 |
| 96 | 0.2500 | 7.0 | 0.0 | 2.0 | 9.0 | 0.0 | 2.0 |
| | 0.1250 | 4.0 | 0.0 | 0.0 | 9.0 | 0.0 | 3.0 |
| | 0.0625 | 4.0 | 0.0 | 0.0 | 9.0 | 0.0 | 2.0 |
| | 0.0313 | 2.0 | 0.0 | 0.0 | 8.0 | 0.0 | 2.0 |
| 97 | 0.2500 | 8.5 | 0.0 | 0.0 | 9.0 | 0.0 | 5.5 |
| | 0.1250 | 7.5 | 0.0 | 0.0 | 4.0 | 0.0 | 4.0 |
| | 0.0625 | 5.5 | 0.0 | 0.0 | 2.0 | 0.0 | 2.5 |
| | 0.0313 | 5.5 | 0.0 | 0.0 | 0.0 | 0.0 | 1.5 |
| 98 | 0.2500 | 6.5 | 6.0 | 0.0 | 9.0 | 0.0 | 7.0 |
| | 0.1250 | 6.5 | 6.0 | 0.0 | 9.0 | 0.0 | 7.0 |
| | 0.0625 | 5.0 | 4.0 | 0.0 | 4.0 | 0.0 | 6.0 |
| | 0.0313 | 3.0 | 0.0 | 0.0 | 2.0 | 0.0 | 4.0 |

TABLE III-continued

PADDY CONDITIONS - POST-TRANSPLANT RICE
PREEMERGENCE WEEDS

| Compound Number | Rate (kg/ha) | ECHORC | CYPIR | CYPSE | MOOVA | SAGPY | ORYSAT |
|---|---|---|---|---|---|---|---|
| 99 | 0.2500 | 4.5 | 2.0 | 0.0 | 9.0 | 0.0 | 3.5 |
| | 0.1250 | 4.5 | 0.0 | 0.0 | 8.0 | 0.0 | 2.5 |
| | 0.0625 | 3.0 | 0.0 | 0.0 | | 0.0 | 1.5 |
| | 0.0313 | 1.0 | 0.0 | 0.0 | 2.0 | 0.0 | 0.5 |
| 100 | 0.2500 | 0.0 | 0.0 | 0.0 | 9.0 | 0.0 | 3.0 |
| | 0.1250 | 0.0 | 0.0 | 0.0 | 8.0 | 0.0 | 3.0 |
| | 0.0625 | 0.0 | 0.0 | 0.0 | 8.0 | 0.0 | 2.0 |
| | 0.0313 | 0.0 | 0.0 | 0.0 | 6.0 | 0.0 | 2.0 |
| 101 | 0.2500 | 0.0 | 0.0 | 0.0 | 9.0 | 0.0 | 1.0 |
| | 0.1250 | 0.0 | 0.0 | 0.0 | 4.0 | 0.0 | 0.0 |
| | 0.0625 | 0.0 | 0.0 | 0.0 | 0.0 | 0.0 | 0.0 |
| | 0.0313 | 0.0 | 0.0 | 0.0 | 0.0 | 0.0 | 0.0 |
| 102 | 0.2500 | 0.0 | 0.0 | 0.0 | 4.0 | 0.0 | 2.0 |
| | 0.1250 | 0.0 | 0.0 | 0.0 | 2.0 | 0.0 | 1.0 |
| | 0.0625 | 0.0 | 0.0 | 0.0 | 0.0 | 0.0 | 0.0 |
| | 0.0313 | 0.0 | 0.0 | 0.0 | 0.0 | 0.0 | 0.0 |
| 103 | 0.2500 | 6.0 | 0.0 | 0.0 | 9.0 | 0.0 | 4.0 |
| | 0.1250 | 4.0 | 0.0 | 0.0 | 9.0 | 0.0 | 4.0 |
| | 0.0625 | 2.0 | 0.0 | 0.0 | 9.0 | 0.0 | 3.0 |
| | 0.0313 | 0.0 | 0.0 | 0.0 | 8.0 | 0.0 | 2.0 |
| 104 | 0.2500 | 0.0 | 0.0 | 0.0 | 9.0 | 0.0 | 4.0 |
| | 0.1250 | 0.0 | 0.0 | 0.0 | 8.0 | 0.0 | 3.0 |
| | 0.0625 | 0.0 | 0.0 | 0.0 | 7.0 | 0.0 | 2.0 |
| | 0.0313 | 0.0 | 0.0 | 0.0 | 7.0 | 0.0 | 2.0 |
| 105 | 0.2500 | 9.0 | 9.0 | 9.0 | 9.0 | 9.0 | 8.0 |
| | 0.1250 | 9.0 | 9.0 | 9.0 | 9.0 | 9.0 | 8.0 |
| | 0.0625 | 9.0 | 8.0 | 7.0 | 9.0 | 4.0 | 6.0 |
| | 0.0313 | 9.0 | 8.0 | 7.0 | 9.0 | 2.0 | 6.0 |
| 106 | 0.2500 | 0.0 | 4.0 | 0.0 | 8.0 | 0.0 | 0.0 |
| | 0.1250 | 0.0 | 2.0 | 0.0 | 8.0 | 0.0 | 0.0 |
| | 0.0625 | 0.0 | 0.0 | 0.0 | 4.0 | 0.0 | 0.0 |
| | 0.0313 | 0.0 | 0.0 | 0.0 | 2.0 | 0.0 | 0.0 |
| 107 | 0.2500 | 4.0 | 6.0 | 0.0 | 9.0 | 0.0 | 6.0 |
| | 0.1250 | 1.0 | 2.0 | 0.0 | 9.0 | 0.0 | 5.0 |
| | 0.0625 | 0.0 | 0.0 | 0.0 | 9.0 | 0.0 | 3.0 |
| | 0.0313 | 0.0 | 0.0 | 0.0 | 9.0 | 0.0 | 2.0 |
| 108 | 0.2500 | 0.0 | 0.0 | 0.0 | 8.0 | 0.0 | 0.0 |
| | 0.1250 | 0.0 | 0.0 | 0.0 | 4.0 | 0.0 | 0.0 |
| | 0.0625 | 0.0 | 0.0 | 0.0 | 0.0 | 0.0 | 0.0 |
| | 0.0313 | 0.0 | 0.0 | 0.0 | 0.0 | 0.0 | 0.0 |
| 109 | 0.2500 | 7.0 | 8.0 | 0.0 | 9.0 | 0.0 | 4.0 |
| | 0.1250 | 4.0 | 4.0 | 0.0 | 9.0 | 0.0 | 4.0 |
| | 0.0625 | 2.0 | 0.0 | 0.0 | 9.0 | 0.0 | 2.0 |
| | 0.0313 | 0.0 | 0.0 | 0.0 | 9.0 | 0.0 | 2.0 |
| 110 | 0.2500 | 7.0 | 7.0 | 0.0 | 9.0 | 0.0 | 6.0 |
| | 0.1250 | 4.0 | 2.0 | 0.0 | 9.0 | 0.0 | 5.0 |
| | 0.0625 | 1.0 | 0.0 | 0.0 | 9.0 | 0.0 | 4.0 |
| | 0.0313 | 0.0 | 0.0 | 0.0 | 9.0 | 0.0 | 3.0 |
| 112 | 0.2500 | 0.0 | 0.0 | 0.0 | 0.0 | 0.0 | 0.0 |
| | 0.1250 | 0.0 | 0.0 | 0.0 | 0.0 | 0.0 | 0.0 |
| | 0.0625 | 0.0 | 0.0 | 0.0 | 0.0 | 0.0 | 0.0 |
| | 0.0313 | 0.0 | 0.0 | 0.0 | 0.0 | 0.0 | 0.0 |
| 114 | 0.2500 | 6.0 | 9.0 | 6.0 | 8.0 | 6.0 | 7.0 |
| | 0.1250 | 4.0 | 9.0 | 2.0 | 9.0 | 6.0 | 7.0 |
| | 0.0625 | 0.0 | 9.0 | 0.0 | 9.0 | 2.0 | 6.0 |
| | 0.0313 | 0.0 | 9.0 | 0.0 | 9.0 | 0.0 | 4.0 |
| 116 | 0.2500 | 0.0 | 0.0 | 0.0 | 8.0 | 0.0 | 0.0 |
| | 0.1250 | 0.0 | 0.0 | 0.0 | 8.0 | 0.0 | 0.0 |
| | 0.0625 | 0.0 | 0.0 | 0.0 | 2.0 | 0.0 | 0.0 |
| | 0.0313 | 0.0 | 0.0 | 0.0 | 0.0 | 0.0 | 0.0 |
| 117 | 0.2500 | 0.0 | 0.0 | 0.0 | 4.0 | 0.0 | 0.0 |
| | 0.1250 | 0.0 | 0.0 | 0.0 | 2.0 | 0.0 | 0.0 |
| | 0.0625 | 0.0 | 0.0 | 0.0 | 0.0 | 0.0 | 0.0 |
| | 0.0313 | 0.0 | 0.0 | 0.0 | 0.0 | 0.0 | 0.0 |
| 118 | 0.2500 | 0.0 | 0.0 | 0.0 | 0.0 | 0.0 | 0.0 |
| | 0.1250 | 0.0 | 0.0 | 0.0 | 0.0 | 0.0 | 0.0 |
| | 0.0625 | 0.0 | 0.0 | 0.0 | 0.0 | 0.0 | 0.0 |
| | 0.0313 | 0.0 | 0.0 | 0.0 | 0.0 | 0.0 | 0.0 |
| 119 | 0.2500 | 9.0 | 9.0 | 9.0 | 9.0 | 9.0 | 9.0 |
| | 0.1250 | 9.0 | 9.0 | 8.0 | 9.0 | 8.0 | 9.0 |
| | 0.0625 | 9.0 | 9.0 | 4.0 | 9.0 | 8.0 | 8.0 |
| | 0.0313 | 4.0 | 9.0 | 2.0 | 9.0 | 6.0 | 7.0 |
| 121 | 0.2500 | 9.0 | 4.0 | 4.0 | 9.0 | 0.0 | 9.0 |

TABLE III-continued

PADDY CONDITIONS - POST-TRANSPLANT RICE PREEMERGENCE WEEDS

| Compound Number | Rate (kg/ha) | ECHORC | CYPIR | CYPSE | MOOVA | SAGPY | ORYSAT |
|---|---|---|---|---|---|---|---|
| | 0.1250 | 8.0 | 2.0 | 2.0 | 9.0 | 0.0 | 6.0 |
| | 0.0625 | 7.0 | 0.0 | 0.0 | 9.0 | 0.0 | 4.0 |
| | 0.0313 | 6.0 | 0.0 | 0.0 | 9.0 | 0.0 | 3.0 |
| 122 | 0.2500 | 9.0 | 0.0 | 0.0 | 9.0 | 0.0 | 4.0 |
| | 0.1250 | 8.0 | 0.0 | 0.0 | 9.0 | 0.0 | 4.0 |
| | 0.0625 | 7.0 | 0.0 | 0.0 | 8.0 | 0.0 | 3.0 |
| | 0.0313 | 4.0 | 0.0 | 0.0 | 6.0 | 0.0 | 2.0 |
| 128 | 0.2500 | 0.0 | 0.0 | 0.0 | 9.0 | 0.0 | 0.0 |
| | 0.1250 | 0.0 | 0.0 | 0.0 | 7.0 | 0.0 | 0.0 |
| | 0.0625 | 0.0 | 0.0 | 0.0 | 4.0 | 0.0 | 0.0 |
| | 0.0313 | 0.0 | 0.0 | 0.0 | 2.0 | 0.0 | 0.0 |
| 129 | 0.2500 | 2.0 | 7.0 | 0.0 | 9.0 | 0.0 | 3.0 |
| | 0.1250 | 1.0 | 7.0 | 0.0 | 9.0 | 0.0 | 3.0 |
| | 0.0625 | 0.0 | 4.0 | 0.0 | 9.0 | 0.0 | 2.0 |
| | 0.0313 | 0.0 | 0.0 | 0.0 | 8.0 | 0.0 | 1.0 |
| 130 | 0.2500 | 2.0 | 6.0 | 0.0 | 9.0 | 0.0 | 7.0 |
| | 0.1250 | 0.0 | 2.0 | 0.0 | 9.0 | 0.0 | 7.0 |
| | 0.0625 | 0.0 | 0.0 | 0.0 | 9.0 | 0.0 | 4.0 |
| | 0.0313 | 0.0 | 0.0 | 0.0 | 9.0 | 0.0 | 3.0 |
| 131 | 0.2500 | 4.0 | 8.0 | 0.0 | 9.0 | 0.0 | 7.0 |
| | 0.1250 | 0.0 | 2.0 | 0.0 | 9.0 | 0.0 | 6.0 |
| | 0.0625 | 0.0 | 0.0 | 0.0 | 9.0 | 0.0 | 3.0 |
| | 0.0313 | 0.0 | 0.0 | 0.0 | 8.0 | 0.0 | 2.0 |
| 132 | 0.2500 | 9.0 | 9.0 | 2.0 | | 4.0 | 9.0 |
| | 0.1250 | 9.0 | 9.0 | 2.0 | 0.0 | 2.0 | 6.0 |
| | 0.0625 | 6.0 | 9.0 | 0.0 | 0.0 | 0.0 | 3.0 |
| | 0.0313 | 4.0 | 9.0 | 0.0 | 0.0 | 0.0 | 3.0 |
| 133 | 0.2500 | 9.0 | 9.0 | 0.0 | 2.0 | 0.0 | 5.0 |
| | 0.1250 | 6.0 | 9.0 | 0.0 | 1.0 | 0.0 | 4.0 |
| | 0.0625 | 2.0 | 9.0 | 0.0 | 0.0 | 0.0 | 3.0 |
| | 0.0313 | 1.0 | 9.0 | 0.0 | 0.0 | 0.0 | 2.0 |
| 134 | 0.2500 | 8.0 | 9.0 | 9.0 | 7.0 | 4.0 | 9.0 |
| | 0.1250 | 9.0 | 9.0 | 4.0 | 4.0 | 2.0 | 7.0 |
| | 0.0625 | 9.0 | 9.0 | 4.0 | 4.0 | 2.0 | 4.0 |
| | 0.0313 | 6.0 | 9.0 | 2.0 | 2.0 | 2.0 | 3.0 |
| 135 | 0.2500 | 6.0 | 9.0 | 0.0 | 0.0 | 0.0 | 4.0 |
| | 0.1250 | 2.0 | 9.0 | 0.0 | 0.0 | 0.0 | 3.0 |
| | 0.0625 | 0.0 | 8.0 | 0.0 | 0.0 | 0.0 | 3.0 |
| | 0.0313 | 0.0 | 6.0 | 0.0 | 0.0 | 0.0 | 2.0 |
| 136 | 0.2500 | 0.0 | 0.0 | 0.0 | 0.0 | 0.0 | 0.0 |
| | 0.1250 | 0.0 | 0.0 | 0.0 | 0.0 | 0.0 | 0.0 |
| | 0.0625 | 0.0 | 0.0 | 0.0 | 0.0 | 0.0 | 0.0 |
| | 0.0313 | 0.0 | 0.0 | 0.0 | 0.0 | 0.0 | 0.0 |
| 137 | 0.2500 | 7.0 | 9.0 | 6.0 | 4.0 | 4.0 | 8.0 |
| | 0.1250 | 2.0 | 9.0 | 0.0 | 2.0 | 0.0 | 8.0 |
| | 0.0625 | 0.0 | 9.0 | 0.0 | 0.0 | 0.0 | 7.0 |
| | 0.0313 | 0.0 | 9.0 | 0.0 | 0.0 | 0.0 | 4.0 |
| 138 | 0.1250 | 0.0 | 8.0 | 0.0 | 0.0 | 0.0 | 3.0 |
| | 0.0625 | 0.0 | 6.0 | 0.0 | 0.0 | 0.0 | 3.0 |
| | 0.0313 | 0.0 | 2.0 | 0.0 | 0.0 | 0.0 | 2.0 |
| 139 | 0.1250 | 9.0 | 9.0 | 4.0 | 8.0 | 0.0 | 4.0 |
| | 0.0625 | 6.0 | 9.0 | 0.0 | 6.0 | 0.0 | 4.0 |
| | 0.0313 | 4.0 | 9.0 | 0.0 | 2.0 | 0.0 | 3.0 |
| 140 | 0.1250 | 6.0 | 9.0 | 0.0 | 2.0 | 0.0 | 8.0 |
| | 0.0625 | 4.0 | 9.0 | 0.0 | 2.0 | 0.0 | 7.0 |
| | 0.0313 | 2.0 | 9.0 | 0.0 | 2.0 | 0.0 | 6.0 |
| 141 | 0.1250 | 2.0 | 9.0 | 0.0 | 0.0 | 0.0 | 3.0 |
| | 0.0625 | 1.0 | 4.0 | 0.0 | 0.0 | 0.0 | 3.0 |
| | 0.0313 | 0.0 | 2.0 | 0.0 | 0.0 | 0.0 | 2.0 |
| 142 | 0.2500 | 9.0 | 8.0 | 9.0 | 9.0 | 0.0 | 9.0 |
| | 0.1250 | 9.0 | 6.0 | 2.0 | 9.0 | 0.0 | 7.0 |
| | 0.0625 | 9.0 | 6.0 | 0.0 | 9.0 | 0.0 | 6.0 |
| | 0.0313 | 9.0 | 4.0 | 0.0 | 9.0 | 0.0 | 3.0 |
| 143 | 0.2500 | 6.0 | 0.0 | 0.0 | 9.0 | 0.0 | 4.0 |
| | 0.1250 | 2.0 | 0.0 | 0.0 | 9.0 | 0.0 | 3.0 |
| | 0.0625 | 0.0 | 0.0 | 0.0 | 9.0 | 0.0 | 3.0 |
| | 0.0313 | 0.0 | 0.0 | 0.0 | 9.0 | 0.0 | 3.0 |
| 144 | 0.2500 | 9.0 | 8.0 | 0.0 | 9.0 | 0.0 | 2.0 |
| | 0.1250 | 9.0 | 4.0 | 0.0 | 9.0 | 0.0 | 2.0 |
| | 0.0625 | 6.0 | 2.0 | 0.0 | 4.0 | 0.0 | 2.0 |
| | 0.0313 | 2.0 | 0.0 | 0.0 | 2.0 | 0.0 | 1.0 |
| 170 | 0.2500 | 9.0 | 6.0 | 0.0 | 9.0 | 0.0 | 8.0 |
| | 0.1250 | 9.0 | 4.0 | 0.0 | 9.0 | 0.0 | 6.0 |

TABLE III-continued

PADDY CONDITIONS - POST-TRANSPLANT RICE
PREEMERGENCE WEEDS

| Compound Number | Rate (kg/ha) | ECHORC | CYPIR | CYPSE | MOOVA | SAGPY | ORYSAT |
|---|---|---|---|---|---|---|---|
| | 0.0625 | 9.0 | 0.0 | 0.0 | 2.0 | 0.0 | 5.0 |
| | 0.0313 | 9.0 | 0.0 | 0.0 | 0.0 | 0.0 | 3.0 |
| 171 | 0.2500 | 9.0 | 2.0 | 0.0 | 9.0 | 0.0 | 2.0 |
| | 0.1250 | 9.0 | 2.0 | 0.0 | 9.0 | 0.0 | 1.0 |
| | 0.0625 | 9.0 | 0.0 | 0.0 | 9.0 | 0.0 | 0.0 |
| | 0.0313 | 8.5 | 0.0 | 0.0 | 9.0 | 0.0 | 0.0 |
| 172 | 0.2500 | 9.0 | 4.0 | 2.0 | 9.0 | 0.0 | 8.0 |
| | 0.1250 | 9.0 | 4.0 | 1.0 | 9.0 | 0.0 | 6.0 |
| | 0.0625 | 9.0 | 2.0 | 0.0 | 9.0 | 0.0 | 3.5 |
| | 0.0313 | 6.5 | 2.0 | 0.0 | 9.0 | 0.0 | 2.5 |
| 173 | 0.2500 | 9.0 | 2.0 | | 9.0 | 0.0 | 3.5 |
| | 0.1250 | 6.5 | 1.0 | 0.0 | 9.0 | 0.0 | 3.0 |
| | 0.0625 | 4.5 | 0.0 | 0.0 | 9.0 | 0.0 | 2.5 |
| | 0.0313 | 2.0 | 0.0 | 0.0 | 8.0 | 0.0 | 2.0 |
| 174 | 0.2500 | 8.5 | 2.0 | 0.0 | 9.0 | 0.0 | 4.0 |
| | 0.1250 | 6.5 | 2.0 | 0.0 | 9.0 | 0.0 | 2.5 |
| | 0.0625 | 5.5 | 2.0 | 0.0 | 9.0 | 0.0 | 2.5 |
| | 0.0313 | 4.5 | 1.0 | 0.0 | 9.0 | 0.0 | 1.5 |
| 175 | 0.2500 | 8.0 | 2.0 | 0.0 | 9.0 | 0.0 | 6.0 |
| | 0.1250 | 8.0 | 1.0 | 0.0 | 9.0 | 0.0 | 5.0 |
| | 0.0625 | 7.5 | 6.0 | 0.0 | 9.0 | 0.0 | 3.5 |
| | 0.0313 | 6.5 | 0.0 | 0.0 | 8.0 | 0.0 | 2.5 |
| 176 | 0.2500 | 8.0 | 8.0 | 0.0 | 9.0 | 0.0 | 6.5 |
| | 0.1250 | 8.0 | 4.0 | 0.0 | 9.0 | 0.0 | 5.0 |
| | 0.0625 | 5.5 | 2.0 | 0.0 | 9.0 | 0.0 | 3.5 |
| | 0.0313 | 4.5 | 2.0 | 0.0 | 9.0 | 0.0 | 2.5 |
| 177 | 0.2500 | 9.0 | 4.0 | 8.0 | 9.0 | 0.0 | 6.5 |
| | 0.1250 | 9.0 | 4.0 | 7.0 | 9.0 | 0.0 | 4.5 |
| | 0.0625 | 6.5 | 2.0 | 0.0 | 9.0 | 0.0 | 3.5 |
| | 0.0313 | 3.0 | 0.0 | 0.0 | 9.0 | 0.0 | 2.5 |
| 178 | 0.2500 | 8.5 | 2.0 | 0.0 | 9.0 | 0.0 | 6.0 |
| | 0.1250 | 7.5 | 1.0 | 0.0 | 9.0 | 0.0 | 5.0 |
| | 0.0625 | 7.5 | 0.0 | 0.0 | 9.0 | 0.0 | 3.5 |
| | 0.0313 | 4.0 | 0.0 | 0.0 | 9.0 | 0.0 | 2.5 |
| 179 | 0.2500 | 9.0 | 6.0 | 6.0 | 9.0 | 4.0 | 9.0 |
| | 0.1250 | 9.0 | 6.0 | 6.0 | 9.0 | 0.0 | 8.5 |
| | 0.0625 | 8.0 | 4.0 | 2.0 | 9.0 | 0.0 | 8.0 |
| | 0.0313 | 4.5 | 2.0 | 0.0 | 9.0 | 0.0 | 6.5 |
| 180 | 0.2500 | 8.5 | 8.0 | 6.0 | 9.0 | 0.0 | 8.5 |
| | 0.1250 | 8.0 | 7.0 | 4.0 | 9.0 | 0.0 | 8.0 |
| | 0.0625 | 5.0 | 4.0 | 0.0 | 9.0 | 0.0 | 7.5 |
| | 0.0313 | 3.5 | 2.0 | 0.0 | 9.0 | 0.0 | 6.0 |
| 181 | 0.2500 | 9.0 | 9.0 | 8.0 | 9.0 | 0.0 | 7.0 |
| | 0.1250 | 9.0 | 9.0 | 7.0 | 9.0 | 0.0 | 6.0 |
| | 0.0625 | 8.5 | 9.0 | 7.0 | 9.0 | 0.0 | 5.0 |
| | 0.0313 | 8.5 | 7.0 | 4.0 | 9.0 | 0.0 | 3.5 |
| 182 | 0.0630 | 9.0 | 9.0 | 4.0 | 9.0 | 4.0 | 9.0 |
| | 0.0315 | 9.0 | 9.0 | 2.0 | 9.0 | 4.0 | 7.0 |
| 183 | 0.0630 | 9.0 | 9.0 | 0.0 | 9.0 | 0.0 | 9.0 |
| | 0.0315 | 9.0 | 9.0 | 0.0 | 9.0 | 0.0 | 8.0 |
| 184 | 0.0630 | 9.0 | 4.0 | 6.0 | 9.0 | 4.0 | 9.0 |
| | 0.0315 | 9.0 | 1.0 | 2.0 | 9.0 | 2.0 | 7.0 |
| 185 | 0.0630 | 0.0 | 0.0 | 0.0 | 9.0 | 0.0 | 0.0 |
| | 0.0315 | 0.0 | 0.0 | 0.0 | 9.0 | 0.0 | 0.0 |
| 186 | 0.0630 | 9.0 | 9.0 | 9.0 | 9.0 | 9.0 | 9.0 |
| | 0.0315 | 9.0 | 9.0 | 9.0 | 9.0 | 9.0 | 9.0 |
| 187 | 0.2500 | 9.0 | 4.0 | 0.0 | 9.0 | 0.0 | 6.0 |
| | 0.1250 | 6.0 | 2.0 | 0.0 | 9.0 | 0.0 | 3.0 |
| | 0.0625 | 2.0 | 0.0 | 0.0 | 9.0 | 0.0 | 3.0 |
| | 0.0313 | 0.0 | 0.0 | 0.0 | 8.0 | 0.0 | 2.0 |
| 188 | 0.2500 | 8.0 | 0.0 | | 9.0 | 0.0 | 2.0 |
| | 0.1250 | 2.0 | 0.0 | | 9.0 | 0.0 | 2.0 |
| | 0.0625 | 0.0 | 0.0 | | 9.0 | 0.0 | 1.0 |
| | 0.0313 | 0.0 | 0.0 | 0.0 | 9.0 | 0.0 | 1.0 |
| 189 | 0.2500 | 0.0 | 0.0 | 0.0 | 8.0 | 0.0 | 0.0 |
| | 0.1250 | 0.0 | 0.0 | 0.0 | 2.0 | 0.0 | 0.0 |
| | 0.0625 | 0.0 | 0.0 | 0.0 | 0.0 | 0.0 | 0.0 |
| | 0.0313 | 0.0 | 0.0 | 0.0 | 0.0 | 0.0 | 0.0 |
| 190 | 0.2500 | 8.0 | 4.0 | 0.0 | 9.0 | 0.0 | 7.0 |
| | 0.1250 | 7.0 | 2.0 | 0.0 | 9.0 | 0.0 | 4.0 |
| | 0.0625 | 4.0 | 0.0 | 0.0 | 9.0 | 0.0 | 3.0 |
| | 0.0313 | 2.0 | 0.0 | 0.0 | 9.0 | 0.0 | 2.0 |
| 191 | 0.2500 | 7.0 | 4.0 | | 9.0 | 0.0 | 6.0 |

TABLE III-continued

PADDY CONDITIONS - POST-TRANSPLANT RICE
PREEMERGENCE WEEDS

| Compound Number | Rate (kg/ha) | ECHORC | CYPIR | CYPSE | MOOVA | SAGPY | ORYSAT |
|---|---|---|---|---|---|---|---|
| | 0.1250 | 4.0 | 2.0 | 0.0 | 9.0 | 0.0 | 3.0 |
| | 0.0625 | 2.0 | 0.0 | 0.0 | 9.0 | 0.0 | 2.0 |
| | 0.0313 | 0.0 | 0.0 | 0.0 | 9.0 | 0.0 | 1.0 |
| 192 | 0.2500 | 9.0 | 7.0 | | 9.0 | 9.0 | 4.0 |
| | 0.1250 | 9.0 | 2.0 | 0.0 | 9.0 | 2.0 | 3.0 |
| | 0.0625 | 4.0 | 0.0 | 0.0 | 9.0 | 0.0 | 2.0 |
| | 0.0313 | 1.0 | 0.0 | 0.0 | 9.0 | 0.0 | 1.0 |
| 193 | 0.2500 | 0.0 | 0.0 | 0.0 | 9.0 | 0.0 | 1.0 |
| | 0.1250 | 0.0 | 0.0 | 0.0 | 9.0 | 0.0 | 0.0 |
| | 0.0625 | 0.0 | 0.0 | 0.0 | 4.0 | 0.0 | 0.0 |
| | 0.0313 | 0.0 | 0.0 | 0.0 | 2.0 | 0.0 | 0.0 |
| 194 | 0.2500 | 9.0 | 0.0 | 0.0 | 9.0 | 0.0 | 4.0 |
| | 0.1250 | 6.0 | 0.0 | 0.0 | 9.0 | 0.0 | 3.0 |
| | 0.0625 | 2.0 | 0.0 | 0.0 | 9.0 | 0.0 | 3.0 |
| | 0.0313 | 0.0 | 0.0 | 0.0 | 9.0 | 0.0 | 2.0 |
| 195 | 0.2500 | 9.0 | 9.0 | 7.0 | 9.0 | 2.0 | 9.0 |
| | 0.1250 | 6.0 | 4.0 | 2.0 | 9.0 | 1.0 | 9.0 |
| | 0.0625 | 3.0 | 2.0 | 0.0 | 9.0 | 0.0 | 7.0 |
| | 0.0313 | 2.0 | 0.0 | 0.0 | 9.0 | 0.0 | 6.0 |
| 196 | 0.2500 | 4.0 | 4.0 | 9.0 | 9.0 | 0.0 | 8.0 |
| | 0.1250 | 4.0 | 1.0 | 6.0 | 9.0 | 0.0 | 8.0 |
| | 0.0625 | 2.0 | 0.0 | 4.0 | 9.0 | 0.0 | 6.0 |
| | 0.0313 | 0.0 | 0.0 | 2.0 | 9.0 | 0.0 | 4.0 |
| 198 | 0.2500 | 9.0 | 7.0 | 8.0 | 9.0 | 4.0 | 9.0 |
| | 0.1250 | 9.0 | 4.0 | 4.0 | 9.0 | 2.0 | 8.0 |
| | 0.0625 | 6.0 | 2.0 | 2.0 | 9.0 | 0.0 | 7.0 |
| | 0.0313 | 4.0 | 0.0 | 0.0 | 9.0 | 0.0 | 4.0 |
| 199 | 0.2500 | 7.0 | 8.0 | 0.0 | 9.0 | 0.0 | 8.0 |
| | 0.1250 | 7.0 | 4.0 | 0.0 | 9.0 | 0.0 | 6.0 |
| | 0.0625 | 4.0 | 2.0 | 0.0 | 9.0 | 0.0 | 4.0 |
| | 0.0313 | 2.0 | 0.0 | 0.0 | 8.0 | 0.0 | 3.0 |
| 200 | 0.2500 | 9.0 | 8.0 | 7.0 | 9.0 | 4.0 | 9.0 |
| | 0.1250 | 6.0 | 7.0 | 2.0 | 9.0 | 0.0 | 9.0 |
| | 0.0625 | 2.0 | 6.0 | 0.0 | 9.0 | 0.0 | 7.0 |
| | 0.0313 | 0.0 | 4.0 | 0.0 | 9.0 | 0.0 | 7.0 |
| 202 | 0.2500 | 2.0 | 9.0 | 0.0 | 0.0 | 0.0 | 6.0 |
| | 0.1250 | 2.0 | 9.0 | 0.0 | 0.0 | 0.0 | 5.0 |
| | 0.0625 | 1.0 | 9.0 | 0.0 | 0.0 | 0.0 | 4.0 |
| | 0.0313 | 1.0 | 9.0 | 0.0 | 0.0 | 0.0 | 3.0 |
| 203 | 0.2500 | 4.0 | 9.0 | 6.0 | 8.0 | 4.0 | 7.0 |
| | 0.1250 | 2.0 | 9.0 | 2.0 | 2.0 | 2.0 | 6.0 |
| | 0.0625 | 0.0 | 9.0 | 0.0 | 0.0 | 0.0 | 6.0 |
| | 0.0313 | 0.0 | 9.0 | 0.0 | 0.0 | 0.0 | 4.0 |
| 204 | 0.2500 | 9.0 | 9.0 | 7.0 | 7.0 | 0.0 | 7.0 |
| | 0.1250 | 4.0 | 9.0 | 2.0 | 4.0 | 0.0 | 7.0 |
| | 0.0625 | 2.0 | 9.0 | 0.0 | 2.0 | 0.0 | 4.0 |
| | 0.0313 | 0.0 | 9.0 | 0.0 | 0.0 | 0.0 | 3.0 |
| 206 | 0.2500 | 9.0 | 9.0 | 7.0 | 4.0 | 4.0 | 9.0 |
| | 0.1250 | 2.0 | 9.0 | 7.0 | 1.0 | 1.0 | 7.0 |
| | 0.0625 | 2.0 | 9.0 | 2.0 | 0.0 | 0.0 | 6.0 |
| | 0.0313 | 0.0 | 9.0 | 0.0 | 0.0 | 0.0 | 5.0 |
| 207 | 0.2560 | 5.5 | 8.5 | 6.0 | 7.5 | 1.0 | 7.5 |
| | 0.1250 | 2.0 | 8.5 | 1.0 | 5.5 | 0.0 | 7.0 |
| | 0.0625 | 1.5 | 6.5 | 0.0 | 4.5 | 0.0 | 6.0 |
| | 0.0313 | 1.0 | 5.5 | 0.0 | 4.0 | 0.0 | 5.0 |
| 208 | 0.2500 | 0.0 | 9.0 | 0.0 | 4.0 | 0.0 | 5.0 |
| | 0.1250 | 0.0 | 9.0 | 0.0 | 2.0 | 0.0 | 3.0 |
| | 0.0625 | 0.0 | 9.0 | 0.0 | 2.0 | 0.0 | 3.0 |
| | 0.0313 | 0.0 | 9.0 | 0.0 | 0.0 | 0.0 | 2.0 |
| 209 | 0.1250 | 2.0 | 8.0 | 0.0 | 0.0 | 0.0 | 4.0 |
| | 0.0625 | 2.0 | 4.0 | 0.0 | 0.0 | 0.0 | 3.0 |
| | 0.0313 | 1.0 | 2.0 | 0.0 | 0.0 | 0.0 | 3.0 |
| 210 | 0.2500 | 9.0 | 7.0 | 0.0 | 9.0 | 0.0 | 7.0 |
| | 0.1250 | 9.0 | | 0.0 | 9.0 | 0.0 | 6.0 |
| | 0.0625 | 9.0 | 7.0 | 0.0 | 9.0 | 0.0 | 4.0 |
| | 0.0313 | 9.0 | 2.0 | 0.0 | 9.0 | 0.0 | 3.0 |
| 211 | 0.2500 | 9.0 | 4.0 | 0.0 | 9.0 | 0.0 | 3.0 |
| | 0.1250 | 7.0 | 4.0 | 0.0 | 9.0 | 0.0 | 2.0 |
| | 0.0625 | 4.0 | 0.0 | 0.0 | 9.0 | 0.0 | 2.0 |
| | 0.0313 | 2.0 | 0.0 | 0.0 | 9.0 | 0.0 | 2.0 |
| 212 | 0.2500 | 4.0 | 2.0 | 0.0 | 9.0 | 0.0 | 7.0 |
| | 0.1250 | 2.0 | 0.0 | 0.0 | 9.0 | 0.0 | 6.0 |
| | 0.0625 | 0.0 | 0.0 | 0.0 | 8.0 | 0.0 | 4.0 |

TABLE III-continued

PADDY CONDITIONS - POST-TRANSPLANT RICE
PREEMERGENCE WEEDS

| Compound Number | Rate (kg/ha) | ECHORC | CYPIR | CYPSE | MOOVA | SAGPY | ORYSAT |
|---|---|---|---|---|---|---|---|
|  | 0.0313 | 0.0 | 0.0 | 0.0 | 4.0 | 0.0 | 3.0 |
| 213 | 0.2500 | 0.0 |  | 0.0 | 2.0 | 0.0 | 7.0 |
|  | 0.1250 | 0.0 | 0.0 | 0.0 | 0.0 | 0.0 | 6.0 |
|  | 0.0625 | 0.0 | 0.0 | 0.0 | 0.0 | 0.0 | 4.0 |
|  | 0.0313 | 0.0 | 0.0 | 0.0 | 0.0 | 0.0 | 3.0 |
| 214 | 0.2500 | 0.0 | 7.0 | 0.0 | 9.0 | 0.0 | 5.0 |
|  | 0.1250 | 0.0 | 7.0 | 0.0 | 9.0 | 0.0 | 3.0 |
|  | 0.0625 | 0.0 | 4.0 | 0.0 | 9.0 | 0.0 | 2.0 |
|  | 0.0313 | 0.0 | 2.0 | 0.0 | 8.0 | 0.0 | 2.0 |
| 217 | 0.2500 | 0.0 | 0.0 | 0.0 | 7.0 | 0.0 | 4.0 |
|  | 0.1250 | 0.0 | 0.0 | 0.0 | 7.0 | 0.0 | 3.0 |
|  | 0.0625 | 0.0 | 0.0 | 0.0 | 4.0 | 0.0 | 2.0 |
|  | 0.0313 | 0.0 | 0.0 | 0.0 | 2.0 | 0.0 | 2.0 |
| 218 | 0.2500 | 4.0 | 0.0 | 0.0 | 9.0 | 0.0 | 3.0 |
|  | 0.1250 | 2.0 | 0.0 | 0.0 | 9.0 | 0.0 | 3.0 |
|  | 0.0625 | 0.0 | 0.0 | 0.0 | 9.0 | 0.0 | 2.0 |
|  | 0.0313 | 0.0 | 0.0 | 0.0 | 8.0 | 0.0 | 1.0 |
| 223 | 0.2500 | 9.0 | 9.0 | 8.0 | 9.0 | 9.0 | 9.0 |
|  | 0.1250 | 8.0 | 7.0 | 6.0 | 9.0 | 6.0 | 8.0 |
|  | 0.0625 | 6.0 | 7.0 | 4.0 | 9.0 | 2.0 | 8.0 |
|  | 0.0313 | 6.0 | 4.0 | 0.0 | 9.0 | 0.0 | 7.0 |
| 224 | 0.2500 | 9.0 | 8.0 | 7.0 | 9.0 | 8.0 | 9.0 |
|  | 0.1250 | 9.0 | 8.0 | 2.0 | 9.0 | 4.0 | 8.0 |
|  | 0.0625 | 9.0 | 7.0 | 0.0 | 9.0 | 2.0 | 7.0 |
|  | 0.0313 | 6.0 | 4.0 | 0.0 | 9.0 | 0.0 | 6.0 |
| 225 | 0.2500 | 7.0 | 7.0 | 0.0 | 9.0 | 0.0 | 7.0 |
|  | 0.1250 | 4.0 | 2.0 | 0.0 | 9.0 | 0.0 | 6.0 |
|  | 0.0625 | 2.0 | 0.0 | 0.0 | 8.0 | 0.0 | 4.0 |
|  | 0.0313 | 0.0 | 0.0 | 0.0 | 8.0 | 0.0 | 3.0 |
| 245 | 0.2500 | 0.0 | 0.0 | 0.0 | 0.0 | 0.0 | 0.0 |
|  | 0.1250 | 0.0 | 0.0 | 0.0 | 0.0 | 0.0 | 0.0 |
|  | 0.0625 | 0.0 | 0.0 | 0.0 | 0.0 | 0.0 | 0.0 |
|  | 0.0313 | 0.0 | 0.0 | 0.0 | 0.0 | 0.0 | 0.0 |
| 246 | 0.2500 | 9.0 | 4.0 |  | 9.0 | 2.0 | 2.0 |
|  | 0.1250 | 9.0 | 4.0 | 0.0 | 9.0 | 2.0 | 2.0 |
|  | 0.0625 | 7.0 | 2.0 | 0.0 | 9.0 | 0.0 | 1.0 |
|  | 0.0313 | 6.0 | 0.0 | 0.0 | 9.0 | 0.0 | 0.0 |
| 256 | 0.2500 | 9.0 | 9.0 | 9.0 | 9.0 | 8.0 | 9.0 |
|  | 0.1250 | 7.0 | 9.0 | 6.0 | 9.0 | 4.0 | 8.0 |
|  | 0.0620 | 3.0 | 9.0 | 2.0 | 9.0 | 0.0 | 8.0 |
|  | 0.0320 | 1.0 | 8.0 | 0.0 | 8.0 | 0.0 | 6.0 |
| 257 | 0.2500 | 0.0 | 6.0 |  | 9.0 | 0.0 | 2.0 |
|  | 0.1250 | 0.0 | 4.0 |  | 9.0 | 0.0 | 1.0 |
|  | 0.0620 | 0.0 | 2.0 | 0.0 | 9.0 | 0.0 | 0.0 |
|  | 0.0320 | 0.0 | 0.0 | 0.0 | 8.0 | 0.0 | 0.0 |
| 258 | 0.2500 | 0.0 | 8.0 |  | 9.0 | 0.0 | 4.0 |
|  | 0.1250 | 0.0 | 7.0 | 0.0 | 9.0 | 0.0 | 3.0 |
|  | 0.0620 | 0.0 | 2.0 | 0.0 | 9.0 | 0.0 | 2.0 |
|  | 0.0320 | 0.0 | 0.0 | 0.0 | 9.0 | 0.0 | 2.0 |
| 259 | 0.2500 | 2.0 | 4.0 |  | 9.0 | 0.0 | 3.0 |
|  | 0.1250 | 0.0 | 4.0 |  | 9.0 | 0.0 | 2.0 |
|  | 0.0620 | 0.0 | 2.0 | 0.0 | 9.0 | 0.0 | 1.0 |
|  | 0.0320 | 0.0 | 0.0 | 0.0 | 6.0 | 0.0 | 1.0 |
| 260 | 0.2500 | 0.0 | 0.0 | 0.0 | 0.0 | 0.0 | 0.0 |
| 261 | 0.2500 | 0.0 | 2.0 | 0.0 | 3.0 | 0.0 | 0.0 |
|  | 0.1250 | 2.0 | 5.5 | 4.5 | 6.0 | 0.0 | 0.0 |
|  | 0.0620 | 2.0 | 4.5 | 4.5 | 4.5 | 0.0 | 0.0 |
|  | 0.0320 | 2.5 | 4.0 | 4.5 | 4.5 | 0.0 | 0.0 |
| 262 | 0.2500 | 3.0 | 9.0 | 0.0 | 9.0 | 0.0 | 3.0 |
|  | 0.1250 | 0.0 | 6.0 | 0.0 | 9.0 | 0.0 | 0.0 |
|  | 0.0620 | 0.0 | 0.0 | 0.0 | 0.0 | 0.0 | 0.0 |
| 263 | 0.2500 | 2.0 | 9.0 | 9.0 | 9.0 | 0.0 | 4.0 |
|  | 0.1250 | 0.0 | 9.0 | 9.0 | 6.0 | 0.0 | 0.0 |
|  | 0.0620 | 0.0 | 7.0 | 9.0 | 0.0 | 0.0 | 0.0 |
|  | 0.0320 | 0.0 | 4.0 | 9.0 | 0.0 | 0.0 | 0.0 |
| 264 | 0.2500 | 2.0 | 5.0 | 9.0 | 9.0 | 0.0 | 5.0 |
|  | 0.1250 | 0.0 | 5.0 | 9.0 | 9.0 | 0.0 | 0.0 |
|  | 0.0620 | 0.0 | 5.0 | 4.0 | 9.0 | 0.0 | 0.0 |
|  | 0.0320 | 0.0 | 5.0 | 4.0 | 9.0 | 0.0 | 0.0 |
| 265 | 0.2500 | 0.0 | 3.0 | 0.0 | 9.0 | 0.0 | 0.0 |
|  | 0.1250 | 0.0 | 0.0 | 0.0 | 9.0 | 0.0 | 0.0 |
|  | 0.0620 | 0.0 | 0.0 | 0.0 | 9.0 | 0.0 | 0.0 |
|  | 0.0320 | 0.0 | 0.0 | 0.0 | 9.0 | 0.0 | 0.0 |

TABLE III-continued

PADDY CONDITIONS - POST-TRANSPLANT RICE
PREEMERGENCE WEEDS

| Compound Number | Rate (kg/ha) | ECHORC | CYPIR | CYPSE | MOOVA | SAGPY | ORYSAT |
|---|---|---|---|---|---|---|---|
| 266 | 0.2500 | 0.0 | 9.0 | 3.0 | 9.0 | 0.0 | 0.0 |
|  | 0.1250 | 0.0 | 5.0 | 0.0 | 9.0 | 0.0 | 0.0 |
|  | 0.0620 | 0.0 | 5.0 | 0.0 | 9.0 | 0.0 | 0.0 |
|  | 0.0320 | 0.0 | 5.0 | 0.0 | 9.0 | 0.0 | 0.0 |
| 267 | 0.2500 | 9.0 | 9.0 | 9.0 | 9.0 | 5.0 | 6.0 |
|  | 0.1250 | 9.0 | 9.0 | 5.5 | 9.0 | 3.0 | 4.5 |
|  | 0.0620 | 9.0 | 8.0 | 0.0 | 9.0 | 1.0 | 3.0 |
|  | 0.0320 | 9.0 | 8.0 | 0.0 | 7.5 | 0.0 | 2.0 |
| 268 | 0.2500 | 4.5 | 7.5 | 9.0 | 9.0 | 4.0 | 7.5 |
|  | 0.1250 | 4.5 | 6.0 | 9.0 | 9.0 | 1.0 | 5.0 |
|  | 0.0620 | 3.0 | 3.0 | 5.5 | 9.0 | 1.0 | 4.0 |
|  | 0.0320 | 1.0 | 1.0 | 1.0 | 7.5 | 0.0 | 3.5 |
| 269 | 0.5000 | 4.0 | 0.0 | 0.0 | 9.0 | 0.0 | 0.0 |
|  | 0.2500 | 0.0 | 0.0 | 0.0 | 0.0 | 0.0 | 0.0 |
| 270 | 0.5000 | 9.0 | 9.0 | 3.0 | 9.0 | 5.0 | 2.0 |
|  | 0.2500 | 9.0 | 9.0 | 9.0 | 9.0 | 0.0 | 8.0 |
|  | 0.1250 | 4.3 | 9.0 | 7.0 | 9.0 | 0.0 | 7.0 |
|  | 0.0620 | 2.7 | 9.0 | 0.0 | 9.0 | 0.0 | 4.0 |
|  | 0.0320 | 1.3 | 8.0 | 0.0 | 9.0 | 0.0 | 4.0 |
| 271 | 0.5000 | 0.0 | 0.0 | 0.0 | 9.0 | 0.0 | 0.0 |
|  | 0.2500 | 0.0 | 0.0 | 0.0 | 9.0 | 0.0 | 3.0 |
|  | 0.1250 | 0.0 | 0.0 | 0.0 | 4.0 | 0.0 | 2.0 |
|  | 0.0620 | 0.0 | 0.0 | 0.0 | 0.0 | 0.0 | 1.0 |
| 272 | 0.5000 | 0.0 | 0.0 | 0.0 | 0.0 | 0.0 | 0.0 |
| 273 | 0.5000 | 9.0 | 4.0 | 9.0 | 9.0 | 0.0 | 3.0 |
|  | 0.2500 | 9.0 | 9.0 | 7.0 | 9.0 | 6.0 | 4.0 |
|  | 0.1250 | 6.0 | 9.0 |  | 9.0 | 0.0 | 3.0 |
|  | 0.0620 | 5.1 | 9.0 | 0.0 | 9.0 | 0.0 | 2.0 |
|  | 0.0320 | 3.9 | 6.0 | 0.0 | 9.0 | 0.0 | 0.0 |
| 274 | 0.5000 | 9.0 | 2.0 | 9.0 | 9.0 | 4.0 | 7.0 |
|  | 0.2500 | 9.0 | 9.0 | 9.0 | 9.0 | 9.0 | 8.0 |
|  | 0.1250 | 5.9 | 9.0 | 8.0 | 9.0 | 4.0 | 4.0 |
|  | 0.0620 | 4.1 | 8.0 | 2.0 | 9.0 | 0.0 | 4.0 |
|  | 0.0320 | 3.3 | 7.0 | 0.0 | 9.0 | 0.0 | 2.0 |
| 275 | 0.5000 | 7.0 | 0.0 | 0.0 | 9.0 | 0.0 | 5.0 |
|  | 0.2500 | 9.0 | 7.0 | 9.0 | 9.0 | 9.0 | 4.0 |
|  | 0.1250 | 4.1 | 6.0 | 9.0 | 9.0 | 3.0 | 3.0 |
|  | 0.0620 | 3.9 | 4.0 | 9.0 | 9.0 | 0.0 | 0.0 |
|  | 0.0320 | 3.7 | 0.0 | 9.0 | 6.0 | 0.0 | 0.0 |
| 276 | 0.5000 | 9.0 | 9.0 | 7.0 | 9.0 | 9.0 | 9.0 |
|  | 0.2500 | 9.0 | 9.0 | 7.0 | 9.0 | 9.0 | 7.0 |
|  | 0.1250 | 7.9 | 9.0 | 8.0 | 9.0 | 9.0 | 6.0 |
|  | 0.0620 | 7.7 | 9.0 | 2.0 | 9.0 | 9.0 | 5.0 |
|  | 0.0320 | 4.0 | 8.0 | 2.0 | 9.0 | 8.0 | 4.0 |
| 277 | 0.5000 | 9.0 | 9.0 | 9.0 | 9.0 | 9.0 | 9.0 |
|  | 0.2500 | 9.0 | 9.0 | 9.0 | 9.0 | 9.0 | 8.0 |
|  | 0.1250 | 9.0 | 9.0 | 9.0 | 9.0 | 9.0 | 7.0 |
|  | 0.0620 | 8.6 | 9.0 | 9.0 | 9.0 | 8.0 | 7.0 |
|  | 0.0320 | 7.0 | 9.0 | 2.0 | 9.0 | 6.0 | 5.0 |
| 278 | 0.5000 | 9.0 | 9.0 | 9.0 | 9.0 | 9.0 | 8.0 |
|  | 0.2500 | 8.0 | 9.0 | 4.0 | 9.0 | 2.0 | 7.0 |
|  | 0.1250 | 7.4 | 7.0 | 2.0 | 9.0 | 0.0 | 4.0 |
|  | 0.0620 | 6.1 | 2.0 | 0.0 | 8.0 | 0.0 | 3.0 |
|  | 0.0320 | 0.0 | 0.0 | 0.0 | 6.0 | 0.0 | 2.0 |
| 279 | 0.5000 | 7.0 | 9.0 | 5.0 | 9.0 | 9.0 | 6.0 |
|  | 0.2500 | 6.0 | 6.0 |  | 9.0 | 4.0 | 4.0 |
|  | 0.1250 | 6.1 | 2.0 | 0.0 | 8.0 | 0.0 | 4.0 |
|  | 0.0620 | 5.7 | 0.0 | 0.0 |  | 0.0 | 3.0 |
|  | 0.0320 | 0.0 | 0.0 | 0.0 |  | 0.0 | 2.0 |
| 280 | 0.5000 | 9.0 | 9.0 | 3.0 | 9.0 | 9.0 | 9.0 |
|  | 0.2500 | 9.0 | 9.0 | 2.0 | 9.0 | 9.0 | 8.0 |
|  | 0.1250 | 7.6 | 8.0 | 0.0 | 9.0 | 2.0 | 7.0 |
|  | 0.0620 | 5.7 | 6.0 | 0.0 | 9.0 | 0.0 | 3.0 |
|  | 0.0320 | 0.0 | 2.0 | 0.0 | 9.0 | 0.0 | 3.0 |
| 281 | 0.5000 | 7.0 | 9.0 | 9.0 | 9.0 | 9.0 | 4.0 |
|  | 0.2500 | 9.0 | 9.0 | 9.0 | 9.0 | 8.0 | 6.0 |
|  | 0.1250 | 7.1 | 9.0 | 9.0 | 9.0 | 2.0 | 4.0 |
|  | 0.0620 | 5.9 | 8.0 | 9.0 | 9.0 | 0.0 | 2.0 |
|  | 0.0320 | 0.0 | 4.0 | 9.0 | 9.0 | 0.0 | 0.0 |
| 282 | 0.5000 | 0.0 | 9.0 | 0.0 | 9.0 | 0.0 | 0.0 |
|  | 0.2500 | 0.0 | 8.0 | 0.0 | 9.0 | 0.0 | 4.0 |
|  | 0.1250 | 1.9 | 8.0 | 0.0 | 9.0 | 0.0 | 4.0 |
|  | 0.0620 | 0.0 | 8.0 | 0.0 | 9.0 | 0.0 | 3.0 |

TABLE III-continued

PADDY CONDITIONS - POST-TRANSPLANT RICE PREEMERGENCE WEEDS

| Compound Number | Rate (kg/ha) | ECHORC | CYPIR | CYPSE | MOOVA | SAGPY | ORYSAT |
|---|---|---|---|---|---|---|---|
|  | 0.0320 | 0.0 | 4.0 | 0.0 | 6.0 | 0.0 | 2.0 |
| 283 | 0.5000 | 6.0 | 9.0 | 0.0 | 9.0 | 9.0 | 4.0 |
|  | 0.2500 | 6.0 | 9.0 |  | 9.0 |  | 5.0 |
|  | 0.1250 | 3.4 | 8.0 |  | 9.0 | 0.0 | 4.0 |
|  | 0.0620 | 3.4 | 4.0 |  | 8.0 | 0.0 | 2.0 |
|  | 0.0320 | 0.0 | 0.0 |  | 2.0 | 0.0 | 2.0 |
| 284 | 0.2500 | 0.0 | 9.0 | 9.0 | 9.0 | 0.0 | 0.0 |
|  | 0.1250 | 0.0 | 9.0 | 2.0 | 9.0 | 0.0 | 0.0 |
|  | 0.0620 | 0.0 | 9.0 | 0.0 | 9.0 | 0.0 | 0.0 |
|  | 0.0320 | 0.0 | 4.0 | 0.0 | 4.0 | 0.0 | 0.0 |
| 285 | 0.2500 | 7.0 | 9.0 | 0.0 | 9.0 | 3.0 | 7.0 |
|  | 0.1250 | 7.0 | 9.0 | 0.0 | 9.0 | 0.0 | 7.0 |
|  | 0.0620 | 7.0 | 9.0 | 0.0 | 9.0 | 0.0 | 7.0 |
|  | 0.0320 | 3.0 | 5.0 | 0.0 | 4.0 | 0.0 | 3.0 |
| 286 | 0.2500 | 8.0 | 9.0 | 0.0 | 9.0 | 0.0 | 2.0 |
|  | 0.1250 | 3.0 | 7.0 | 0.0 | 9.0 | 0.0 | 1.0 |
|  | 0.0620 | 0.0 | 7.0 | 0.0 | 9.0 | 0.0 | 0.0 |
|  | 0.0320 | 0.0 | 3.0 | 0.0 | 9.0 | 0.0 | 0.0 |
| 287 | 0.2500 | 7.0 | 9.0 | 4.0 | 9.0 | 0.0 | 5.0 |
|  | 0.1250 | 5.0 | 9.0 | 0.0 | 9.0 | 0.0 | 3.0 |
|  | 0.0620 | 2.0 | 9.0 | 0.0 | 9.0 | 0.0 | 3.0 |
|  | 0.0320 | 0.0 | 0.0 | 0.0 | 9.0 | 0.0 | 0.0 |
| 288 | 0.2500 | 5.0 | 6.0 | 0.0 | 6.0 | 0.0 | 2.0 |
|  | 0.1250 | 4.0 | 4.0 | 0.0 | 3.0 | 0.0 | 1.0 |
|  | 0.0620 | 0.0 | 0.0 | 0.0 | 0.0 | 0.0 | 0.0 |
|  | 0.0320 | 0.0 | 0.0 | 0.0 | 0.0 | 0.0 | 0.0 |
| 289 | 0.2500 | 4.0 | 9.0 | 0.0 | 9.0 | 0.0 | 0.0 |
|  | 0.1250 | 3.0 | 9.0 | 0.0 | 9.0 | 0.0 | 0.0 |
|  | 0.0620 | 2.0 | 0.0 | 0.0 | 0.0 | 0.0 | 0.0 |
|  | 0.0320 | 0.0 | 0.0 | 0.0 | 0.0 | 0.0 | 0.0 |
| 290 | 0.2500 | 7.0 | 6.0 | 0.0 | 7.0 | 0.0 | 0.0 |
|  | 0.1250 | 3.0 | 6.0 | 0.0 | 7.0 | 0.0 | 0.0 |
|  | 0.0620 | 0.0 | 6.0 | 0.0 | 7.0 | 0.0 | 0.0 |
|  | 0.0320 | 0.0 | 6.0 | 0.0 | 0.0 | 0.0 | 0.0 |
| 291 | 0.2500 | 0.0 | 9.0 |  | 9.0 | 0.0 | 0.0 |
|  | 0.1250 | 0.0 | 9.0 |  | 9.0 | 0.0 | 0.0 |
|  | 0.0620 | 0.0 | 0.0 |  | 9.0 | 0.0 | 0.0 |
|  | 0.0320 | 0.0 | 0.0 |  | 0.0 | 0.0 | 0.0 |
| 292 | 0.2500 | 0.0 | 9.0 |  | 9.0 | 5.0 | 0.0 |
|  | 0.1250 | 0.0 | 9.0 |  | 9.0 | 0.0 | 0.0 |
|  | 0.0620 | 0.0 | 9.0 |  | 9.0 | 0.0 | 0.0 |
|  | 0.0320 | 0.0 | 9.0 |  | 9.0 | 0.0 | 0.0 |
| 293 | 0.2500 | 0.0 | 9.0 |  | 9.0 | 6.0 | 0.0 |
|  | 0.1250 | 0.0 | 9.0 |  | 9.0 | 0.0 | 0.0 |
|  | 0.0620 | 0.0 | 9.0 |  | 9.0 | 0.0 | 0.0 |
|  | 0.0320 | 0.0 | 9.0 |  | 9.0 | 0.0 | 0.0 |
| 294 | 0.2500 | 0.0 | 9.0 |  | 9.0 | 0.0 | 0.0 |
|  | 0.1250 | 0.0 | 3.0 |  | 9.0 | 0.0 | 0.0 |
|  | 0.0620 | 0.0 | 0.0 |  | 9.0 | 0.0 | 0.0 |
|  | 0.0320 | 0.0 | 0.0 |  | 9.0 | 0.0 | 0.0 |
| 295 | 0.2500 | 0.0 | 9.0 |  | 9.0 | 6.0 | 0.0 |
|  | 0.1250 | 0.0 | 9.0 |  | 9.0 | 0.0 | 0.0 |
|  | 0.0620 | 0.0 | 0.0 |  | 0.0 | 0.0 | 0.0 |
| 296 | 0.2500 | 4.0 | 7.0 |  | 9.0 | 7.0 | 2.0 |
|  | 0.1250 | 2.0 | 7.0 |  | 9.0 | 5.0 | 0.0 |
|  | 0.0620 | 0.0 | 7.0 |  | 9.0 | 0.0 | 0.0 |
|  | 0.0320 | 0.0 | 6.0 |  | 9.0 | 0.0 | 0.0 |
| 297 | 0.2500 | 4.0 | 9.0 |  | 9.0 | 9.0 | 2.0 |
|  | 0.1250 | 3.0 | 7.0 |  | 9.0 | 3.0 | 0.0 |
|  | 0.0620 | 0.0 | 5.0 |  | 9.0 | 0.0 | 0.0 |
|  | 0.0320 | 0.0 | 4.0 |  | 9.0 | 0.0 | 0.0 |
| 298 | 0.2500 | 3.0 | 9.0 |  | 9.0 | 9.0 | 0.0 |
|  | 0.1250 | 0.0 | 9.0 |  | 9.0 | 3.0 | 0.0 |
|  | 0.0620 | 0.0 | 9.0 |  | 9.0 | 0.0 | 0.0 |
|  | 0.0320 | 0.0 | 3.0 |  | 9.0 | 0.0 | 0.0 |
| 299 | 0.2500 | 5.0 | 9.0 |  | 9.0 | 7.0 | 5.0 |
|  | 0.1250 | 2.0 | 9.0 |  | 9.0 | 3.0 | 3.0 |
|  | 0.0620 | 0.0 | 7.0 |  | 9.0 | 0.0 | 0.0 |
|  | 0.0320 | 0.0 | 3.0 |  | 7.0 | 0.0 | 0.0 |
| 300 | 0.2500 | 9.0 | 9.0 |  | 9.0 | 7.0 | 5.0 |
|  | 0.1250 | 7.0 | 9.0 |  | 9.0 | 6.0 | 4.0 |
|  | 0.0620 | 6.0 | 6.0 |  | 9.0 | 5.0 | 4.0 |
|  | 0.0320 | 3.0 | 3.0 |  | 9.0 | 2.0 | 2.0 |

TABLE III-continued

PADDY CONDITIONS - POST-TRANSPLANT RICE
PREEMERGENCE WEEDS

| Compound Number | Rate (kg/ha) | ECHORC | CYPIR | CYPSE | MOOVA | SAGPY | ORYSAT |
|---|---|---|---|---|---|---|---|
| 301 | 0.2500 | 9.0 | 9.0 | 9.0 | 9.0 | 8.5 | 3.5 |
|  | 0.1250 | 9.0 | 9.0 | 9.0 | 9.0 | 7.0 | 2.5 |
|  | 0.0620 | 9.0 | 9.0 | 9.0 | 9.0 | 4.5 | 1.0 |
|  | 0.0320 | 9.0 | 9.0 | 9.0 | 9.0 | 2.0 | 1.0 |
| 302 | 0.2500 | 8.5 | 8.5 | 6.0 | 9.0 | 9.0 | 8.0 |
|  | 0.1250 | 8.0 | 8.5 | 4.5 | 9.0 | 9.0 | 7.0 |
|  | 0.0620 | 5.0 | 8.0 | 4.5 | 7.0 | 0.0 | 4.5 |
|  | 0.0320 | 4.0 | 8.0 | 4.5 | 7.0 | 0.0 | 1.0 |
| 303 | 0.2500 | 9.0 | 8.5 | 6.0 | 9.0 | 9.0 | 7.5 |
|  | 0.1250 | 9.0 | 8.5 | 5.0 | 9.0 | 8.5 | 5.0 |
|  | 0.0620 | 7.5 | 8.0 | 4.0 | 9.0 | 2.0 | 4.5 |
|  | 0.0320 | 2.5 | 8.0 | 0.0 | 7.0 | 2.0 | 2.0 |
| 304 | 0.2500 | 0.0 | 9.0 | 0.0 | 9.0 | 0.0 | 4.0 |
|  | 0.1250 | 0.0 | 9.0 | 0.0 | 7.0 | 0.0 | 4.0 |
|  | 0.0620 | 0.0 | 4.0 | 0.0 | 7.0 | 0.0 | 2.0 |
|  | 0.0320 | 0.0 | 0.0 | 0.0 | 0.0 | 0.0 | 0.0 |
| 305 | 0.2500 | 0.0 | 0.0 | 0.0 | 0.0 | 0.0 | 0.0 |
| 306 | 0.2500 | 0.0 | 0.0 | 0.0 | 0.0 | 0.0 | 0.0 |
| 307 | 0.2500 | 9.0 | 7.5 | 9.0 | 9.0 | 9.0 | 9.0 |
|  | 0.1250 | 8.5 | 6.5 | 7.0 | 9.0 | 6.5 | 8.5 |
|  | 0.0620 | 5.0 | 6.5 | 3.5 | 8.0 | 1.0 | 6.0 |
|  | 0.0320 | 6.0 | 6.5 | 0.0 | 6.0 | 0.0 | 5.0 |
| 308 | 0.2500 | 9.0 | 0.0 | 9.0 | 0.0 | 9.0 | 7.0 |
|  | 0.1250 | 6.0 | 0.0 | 3.0 | 0.0 | 3.0 | 6.0 |
|  | 0.0620 | 5.0 | 0.0 | 0.0 | 0.0 | 0.0 | 5.0 |
|  | 0.0320 | 5.0 | 0.0 | 0.0 | 0.0 | 0.0 | 5.0 |
| 309 | 0.2500 | 7.0 | 9.0 | 7.0 | 9.0 | 8.0 | 7.0 |
|  | 0.1250 | 4.0 | 9.0 | 0.0 | 9.0 | 4.0 | 5.0 |
|  | 0.0620 | 2.0 | 9.0 | 0.0 | 6.0 | 3.0 | 4.0 |
|  | 0.0320 | 1.0 | 9.0 | 0.0 | 6.0 | 2.0 | 3.0 |
| 310 | 0.2500 | 3.0 | 9.0 | 0.0 | 9.0 | 0.0 | 3.0 |
|  | 0.1250 | 2.0 | 9.0 | 0.0 | 9.0 | 0.0 | 2.0 |
|  | 0.0620 | 0.0 | 9.0 | 0.0 | 9.0 | 0.0 | 0.0 |
|  | 0.0320 | 0.0 | 9.0 | 0.0 | 9.0 | 0.0 | 0.0 |
| 311 | 0.2500 | 0.0 | 9.0 | 0.0 | 9.0 | 0.0 | 2.0 |
|  | 0.1250 | 0.0 | 9.0 | 0.0 | 9.0 | 0.0 | 2.0 |
|  | 0.0620 | 0.0 | 9.0 | 0.0 | 9.0 | 0.0 | 0.0 |
|  | 0.0320 | 0.0 | 0.0 | 0.0 | 0.0 | 0.0 | 0.0 |
| 312 | 0.2500 | 9.0 | 9.0 | 6.0 | 9.0 | 6.5 | 7.5 |
|  | 0.1250 | 9.0 | 9.0 | 4.5 | 9.0 | 5.5 | 7.0 |
|  | 0.0620 | 6.5 | 6.5 | 3.5 | 6.0 | 2.0 | 6.5 |
|  | 0.0320 | 6.0 | 4.5 | 0.0 | 4.5 | 0.0 | 5.0 |
| 313 | 0.2500 | 9.0 | 9.0 | 2.0 | 9.0 | 3.0 | 4.0 |
|  | 0.1250 | 6.0 | 9.0 | 0.0 | 9.0 | 0.0 | 3.0 |
|  | 0.0620 | 5.0 | 0.0 | 0.0 | 9.0 | 0.0 | 1.0 |
|  | 0.0320 | 4.0 | 0.0 | 0.0 | 0.0 | 0.0 | 0.0 |
| 314 | 0.2500 | 9.0 | 9.0 | 0.0 | 9.0 | 0.0 | 5.0 |
|  | 0.1250 | 9.0 | 9.0 | 0.0 | 9.0 | 0.0 | 4.0 |
|  | 0.0620 | 5.0 | 9.0 | 0.0 | 9.0 | 0.0 | 3.0 |
|  | 0.0320 | 5.0 | 9.0 | 0.0 | 9.0 | 0.0 | 3.0 |
| 315 | 0.2500 | 3.0 | 9.0 | 3.0 | 9.0 | 4.0 | 2.0 |
|  | 0.1250 | 0.0 | 5.0 | 3.0 | 9.0 | 3.0 | 0.0 |
|  | 0.0620 | 0.0 | 0.0 | 0.0 | 9.0 | 0.0 | 0.0 |
|  | 0.0320 | 0.0 | 0.0 | 0.0 | 9.0 | 0.0 | 0.0 |
| 316 | 0.2500 | 9.0 | 6.0 | 0.0 | 9.0 | 3.0 | 4.0 |
|  | 0.1250 | 9.0 | 7.5 | 4.5 | 9.0 | 1.0 | 4.5 |
|  | 0.0620 | 9.0 | 7.5 | 4.5 | 9.0 | 3.0 | 4.0 |
|  | 0.0320 | 5.5 | 8.5 | 1.0 | 8.0 | 0.0 | 4.5 |
| 318 | 0.2500 | 5.0 | 6.0 | 9.0 | 9.0 | 4.0 | 9.0 |
|  | 0.1250 | 5.0 | 5.0 | 0.0 | 9.0 | 0.0 | 5.0 |
|  | 0.0620 | 3.0 | 2.0 | 0.0 | 6.0 | 0.0 | 5.0 |
|  | 0.0320 | 0.0 | 0.0 | 0.0 | 4.0 | 0.0 | 5.0 |
| 319 | 0.2500 | 9.0 | 9.0 | 6.0 | 9.0 | 9.0 | 7.0 |
|  | 0.1250 | 9.0 | 9.0 | 6.0 | 9.0 | 9.0 | 6.0 |
|  | 0.0620 | 7.0 | 9.0 | 6.0 | 9.0 | 6.0 | 6.0 |
|  | 0.0320 | 3.0 | 3.0 | 4.0 | 9.0 | 6.0 | 5.0 |
| 320 | 0.2500 | 2.5 | 8.0 |  | 9.0 | 5.0 | 2.5 |
|  | 0.1250 | 0.0 | 5.5 |  | 3.0 | 2.5 | 2.0 |
|  | 0.0620 | 0.0 | 2.0 |  | 0.0 | 2.5 | 2.0 |
|  | 0.0320 | 0.0 | 0.0 |  | 0.0 | 1.0 | 1.5 |
| 321 | 0.2500 | 8.0 | 9.0 | 9.0 | 9.0 | 8.5 | 9.0 |
|  | 0.1250 | 6.5 | 8.5 | 9.0 | 9.0 | 8.5 | 9.0 |
|  | 0.0620 | 5.0 | 7.5 | 1.0 | 9.0 | 6.5 | 8.0 |

TABLE III-continued

PADDY CONDITIONS - POST-TRANSPLANT RICE
PREEMERGENCE WEEDS

| Compound Number | Rate (kg/ha) | ECHORC | CYPIR | CYPSE | MOOVA | SAGPY | ORYSAT |
|---|---|---|---|---|---|---|---|
| | 0.0320 | 4.0 | 4.0 | 0.0 | 8.0 | 5.5 | 8.0 |
| 322 | 0.2500 | 9.0 | 9.0 | 9.0 | 9.0 | 9.0 | 7.0 |
| | 0.1250 | 9.0 | 7.0 | 6.0 | 9.0 | 3.0 | 5.0 |
| | 0.0620 | 9.0 | 6.0 | 5.0 | 9.0 | 3.0 | 5.0 |
| | 0.0320 | 9.0 | 4.0 | 5.0 | 5.0 | 3.0 | 5.0 |
| 323 | 0.2500 | 8.0 | 8.0 | 7.5 | 9.0 | 9.0 | 7.5 |
| | 0.1250 | 8.0 | 8.0 | 6.5 | 9.0 | 3.5 | 6.0 |
| | 0.0620 | 6.5 | 4.5 | 6.0 | 9.0 | 3.5 | 5.0 |
| | 0.0320 | 4.5 | 3.5 | 5.0 | 8.0 | 0.0 | 3.5 |
| 324 | 0.2500 | 6.0 | 9.0 | 7.0 | 9.0 | 9.0 | 9.0 |
| | 0.1250 | 5.0 | 9.0 | 3.0 | 9.0 | 9.0 | 7.0 |
| | 0.0620 | 4.0 | 9.0 | 0.0 | 9.0 | 3.0 | 4.0 |
| | 0.0320 | 0.0 | 9.0 | 0.0 | 9.0 | 0.0 | 3.0 |
| 325 | 0.2500 | 9.0 | 9.0 | 9.0 | 9.0 | 9.0 | 4.0 |
| | 0.1250 | 9.0 | 9.0 | 7.3 | 9.0 | 6.3 | 3.7 |
| | 0.0620 | 9.0 | 8.7 | 9.0 | 9.0 | 4.3 | 3.0 |
| | 0.0320 | 7.7 | 8.0 | 4.7 | 8.0 | 4.0 | 2.7 |
| 326 | 0.2500 | 9.0 | 9.0 | 7.5 | 9.0 | 9.0 | 5.5 |
| | 0.1250 | 9.0 | 7.0 | 4.5 | 9.0 | 5.5 | 5.5 |
| | 0.0620 | 8.5 | 7.0 | 4.5 | 9.0 | 1.0 | 5.5 |
| | 0.0320 | 5.5 | 6.0 | 4.0 | 9.0 | 0.0 | 5.5 |
| 327 | 0.2500 | 9.0 | 9.0 | 9.0 | 9.0 | 7.5 | 4.0 |
| | 0.1250 | 9.0 | 9.0 | 5.5 | 9.0 | 5.5 | 3.5 |
| | 0.0620 | 9.0 | 9.0 | 5.5 | 9.0 | 5.5 | 2.5 |
| | 0.0320 | 9.0 | 9.0 | 1.0 | 9.0 | 3.0 | 3.0 |
| 328 | 0.2500 | 9.0 | 9.0 | 9.0 | 9.0 | 4.5 | 4.5 |
| | 0.1250 | 9.0 | 9.0 | 7.5 | 9.0 | 4.5 | 4.0 |
| | 0.0620 | 9.0 | 9.0 | 6.0 | 9.0 | 3.0 | 3.0 |
| | 0.0320 | 9.0 | 9.0 | 6.0 | 9.0 | 2.5 | 2.0 |
| 329 | 0.2500 | 3.0 | 0.0 | 0.0 | 9.0 | 4.0 | 3.0 |
| | 0.1250 | 3.0 | 0.0 | 0.0 | 9.0 | 4.0 | 3.0 |
| | 0.0620 | 3.0 | 0.0 | 0.0 | 9.0 | 4.0 | 3.0 |
| | 0.0320 | 2.0 | 0.0 | 0.0 | 9.0 | 3.0 | 3.0 |
| 330 | 0.2500 | 9.0 | 6.0 | 5.0 | 9.0 | 0.0 | 7.0 |
| | 0.1250 | 9.0 | 6.0 | 5.0 | 9.0 | 0.0 | 7.0 |
| | 0.0620 | 7.0 | 0.0 | 5.0 | 9.0 | 0.0 | 7.0 |
| | 0.0320 | 7.0 | 0.0 | 5.0 | 9.0 | 0.0 | 7.0 |
| 331 | 0.2500 | 8.0 | 9.0 | 0.0 | 9.0 | 0.0 | 1.0 |
| | 0.1250 | 4.0 | 5.0 | 0.0 | 9.0 | 0.0 | 0.0 |
| | 0.0620 | 2.0 | 0.0 | 0.0 | 9.0 | 0.0 | 0.0 |
| | 0.0320 | 0.0 | 0.0 | 0.0 | 9.0 | 0.0 | 0.0 |
| 332 | 0.2500 | 9.0 | 9.0 | 7.5 | 9.0 | 9.0 | 7.5 |
| | 0.1250 | 9.0 | 9.0 | 4.5 | 9.0 | 6.5 | 5.5 |
| | 0.0620 | 8.5 | 9.0 | 4.5 | 9.0 | 3.5 | 5.5 |
| | 0.0320 | 6.5 | 9.0 | 4.0 | 9.0 | 3.0 | 5.5 |
| 333 | 0.2500 | 9.0 | 9.0 | 7.5 | 9.0 | 9.0 | 7.0 |
| | 0.1250 | 9.0 | 9.0 | 7.5 | 9.0 | 8.5 | 7.0 |
| | 0.0620 | 9.0 | 9.0 | 7.0 | 9.0 | 8.0 | 6.0 |
| | 0.0320 | 9.0 | 9.0 | 7.0 | 9.0 | 5.5 | 4.0 |
| 334 | 0.2500 | 3.0 | 6.0 | 2.0 | | 4.0 | 3.0 |
| | 0.1250 | 0.0 | 6.0 | 2.0 | | 4.0 | 3.0 |
| | 0.0620 | 0.0 | 5.0 | 0.0 | | 0.0 | 0.0 |
| | 0.0320 | 0.0 | 3.0 | 0.0 | | 0.0 | 0.0 |
| 335 | 0.2500 | 9.0 | 2.0 | 6.0 | | 4.0 | 7.0 |
| | 0.1250 | 7.0 | 2.0 | 6.0 | | 4.0 | 5.0 |
| | 0.0620 | 7.0 | 0.0 | 0.0 | | 0.0 | 4.0 |
| | 0.0320 | 6.0 | 0.0 | 0.0 | | 0.0 | 3.0 |
| 336 | 0.2500 | 9.0 | 9.0 | 3.0 | 9.0 | 9.0 | 9.0 |
| | 0.1250 | 9.0 | 4.0 | 2.0 | 9.0 | 1.0 | 4.5 |
| | 0.0620 | 9.0 | 1.0 | 0.0 | 9.0 | 0.0 | 4.5 |
| | 0.0320 | 6.5 | 0.0 | 0.0 | 9.0 | 0.0 | 2.0 |
| 337 | 0.2500 | 6.0 | 9.0 | 9.0 | | 3.0 | 3.0 |
| | 0.1250 | 6.0 | 6.0 | 0.0 | | 0.0 | 3.0 |
| | 0.0620 | 2.0 | 0.0 | 0.0 | | 0.0 | 3.0 |
| | 0.0320 | 2.0 | 0.0 | 0.0 | | 0.0 | 3.0 |
| 338 | 0.2500 | 9.0 | 8.0 | 5.0 | | 5.0 | 6.0 |
| | 0.1250 | 4.0 | 3.0 | 0.0 | | 2.0 | 3.0 |
| | 0.0620 | 2.0 | 3.0 | 0.0 | | 2.0 | 0.0 |
| | 0.0320 | 2.0 | 3.0 | 0.0 | | 0.0 | 0.0 |
| 339 | 0.2500 | 6.0 | 7.0 | 9.0 | | 9.0 | 9.0 |
| | 0.1250 | 4.0 | 7.0 | 6.0 | | 5.0 | 9.0 |
| | 0.0620 | 0.0 | 4.0 | 0.0 | | 5.0 | 7.0 |
| | 0.0320 | 0.0 | 4.0 | 0.0 | | 5.0 | 5.0 |

TABLE III-continued

PADDY CONDITIONS - POST-TRANSPLANT RICE PREEMERGENCE WEEDS

| Compound Number | Rate (kg/ha) | ECHORC | CYPIR | CYPSE | MOOVA | SAGPY | ORYSAT |
|---|---|---|---|---|---|---|---|
| 340 | 0.2500 | 9.0 | 9.0 | 7.0 | | 7.0 | 9.0 |
| | 0.1250 | 9.0 | 7.0 | 6.0 | | 5.0 | 7.0 |
| | 0.0620 | 6.0 | 5.0 | 3.0 | | 4.0 | 6.0 |
| | 0.0320 | 5.0 | 2.0 | 3.0 | | 4.0 | 5.0 |
| 341 | 0.2500 | 8.5 | 4.0 | 3.5 | 9.0 | 4.5 | 3.5 |
| | 0.1250 | 8.0 | 3.5 | 2.5 | 9.0 | 4.5 | 3.0 |
| | 0.0620 | 5.5 | 2.0 | 0.0 | 9.0 | 4.5 | 2.5 |
| | 0.0320 | 3.0 | 1.0 | 0.0 | 7.0 | 1.0 | 1.5 |
| 342 | 0.2500 | 7.0 | 8.0 | 9.0 | | 2.0 | 3.0 |
| | 0.1250 | 7.0 | 4.0 | 0.0 | | 0.0 | 2.0 |
| | 0.0620 | 4.0 | 0.0 | 0.0 | | 0.0 | 0.0 |
| | 0.0320 | 4.0 | 0.0 | 0.0 | | 0.0 | 0.0 |
| 343 | 0.2500 | 9.0 | 6.0 | 6.0 | | 3.0 | 4.0 |
| | 0.1250 | 7.0 | 0.0 | 4.0 | | 0.0 | 3.0 |
| | 0.0620 | 6.0 | 0.0 | 3.0 | | 0.0 | 2.0 |
| | 0.0320 | 3.0 | 0.0 | 0.0 | | 0.0 | 0.0 |
| 344 | 0.2500 | 9.0 | 9.0 | 6.0 | | 6.0 | 9.0 |
| | 0.1250 | 7.0 | 7.0 | 6.0 | | 3.0 | 5.0 |
| | 0.0620 | 7.0 | 6.0 | 6.0 | | 0.0 | 5.0 |
| | 0.0320 | 4.0 | 6.0 | 6.0 | | 0.0 | 2.0 |
| 345 | 0.2500 | 9.0 | 9.0 | 9.0 | 9.0 | 9.0 | 6.0 |
| | 0.1250 | 9.0 | 9.0 | 4.5 | 9.0 | 9.0 | 5.5 |
| | 0.0620 | 9.0 | 9.0 | 9.0 | 9.0 | 9.0 | 5.5 |
| | 0.0320 | 9.0 | 9.0 | 5.0 | 9.0 | 4.5 | 5.5 |
| 347 | 0.2500 | 9.0 | 9.0 | 7.0 | | 5.0 | 9.0 |
| | 0.1250 | 9.0 | 9.0 | 4.0 | | 4.0 | 7.0 |
| | 0.0620 | 9.0 | 9.0 | 0.0 | | 3.0 | 6.0 |
| | 0.0320 | 7.0 | 7.0 | 0.0 | | 2.0 | 3.0 |
| 348 | 0.2500 | 9.0 | 9.0 | 0.0 | | 9.0 | 5.0 |
| | 0.1250 | 7.0 | 6.0 | 0.0 | | 7.0 | 4.0 |
| | 0.0620 | 6.0 | 0.0 | 0.0 | | 6.0 | 3.0 |
| | 0.0320 | 6.0 | 0.0 | 0.0 | | 4.0 | 2.0 |
| 349 | 0.2500 | 7.0 | 7.0 | 4.0 | | 6.0 | 7.0 |
| | 0.1250 | 6.0 | 7.0 | 4.0 | | 5.0 | 7.0 |
| | 0.0620 | 5.0 | 4.0 | 4.0 | | 5.0 | 5.0 |
| | 0.0320 | 5.0 | 0.0 | 4.0 | | 4.0 | 4.0 |
| 350 | 0.2500 | 9.0 | 9.0 | 9.0 | 9.0 | 9.0 | 9.0 |
| | 0.1250 | 8.0 | 9.0 | 8.5 | 9.0 | 7.5 | 9.0 |
| | 0.0620 | 7.5 | 5.0 | 8.5 | 9.0 | 7.0 | 9.0 |
| | 0.0320 | 6.0 | 4.0 | 7.5 | 9.0 | 5.5 | 9.0 |
| 351 | 0.2500 | 7.0 | 9.0 | 8.0 | | 7.0 | 9.0 |
| | 0.1250 | 6.0 | 7.0 | 6.0 | | 7.0 | 7.0 |
| | 0.0620 | 6.0 | 7.0 | 6.0 | | 6.0 | 7.0 |
| | 0.0320 | 5.0 | 6.0 | 0.0 | | 5.0 | 7.0 |
| 352 | 0.2500 | 9.0 | 9.0 | 0.0 | 9.0 | 9.0 | 3.0 |
| | 0.1250 | 6.5 | 7.5 | 1.0 | 9.0 | 9.0 | 2.5 |
| | 0.0620 | 4.0 | 6.5 | 0.0 | 9.0 | 5.0 | 1.0 |
| | 0.0320 | 2.5 | 2.0 | 0.0 | 6.0 | 2.5 | 0.5 |
| 353 | 0.2500 | 3.0 | 3.0 | 2.5 | 8.0 | 0.0 | 4.0 |
| | 0.1250 | 2.5 | 1.0 | 1.5 | 8.0 | 0.0 | 3.5 |
| | 0.0620 | 2.0 | 0.0 | 0.0 | 6.5 | 0.0 | 3.0 |
| | 0.0320 | 0.0 | 0.0 | 0.0 | 3.5 | 0.0 | 2.5 |
| 354 | 0.2500 | 9.0 | 9.0 | 9.0 | 9.0 | 9.0 | 9.0 |
| | 0.1250 | 9.0 | 9.0 | 9.0 | 9.0 | 9.0 | 9.0 |
| | 0.0620 | 9.0 | 9.0 | 9.0 | 9.0 | 9.0 | 8.0 |
| | 0.0320 | 9.0 | 8.3 | 8.0 | 9.0 | 6.3 | 7.3 |
| 355 | 0.2500 | 9.0 | 5.0 | 5.0 | 9.0 | 9.0 | 5.0 |
| | 0.1250 | 9.0 | 6.5 | 3.5 | 9.0 | 4.5 | 5.5 |
| | 0.0620 | 9.0 | 4.5 | 1.0 | 9.0 | 4.5 | 3.0 |
| | 0.0320 | 7.0 | 4.5 | 0.0 | 9.0 | 2.0 | 2.5 |
| 356 | 0.2500 | 9.0 | 9.0 | 6.5 | 9.0 | 8.0 | 2.0 |
| | 0.1250 | 6.5 | 9.0 | 5.0 | 9.0 | 5.5 | 4.5 |
| | 0.0620 | 5.0 | 9.0 | 0.0 | 9.0 | 4.5 | 2.5 |
| | 0.0320 | 3.5 | 6.5 | 0.0 | 7.5 | 4.5 | 0.5 |
| 357 | 0.2500 | 7.0 | 6.0 | 0.0 | 9.0 | 4.0 | 3.0 |
| | 0.1250 | 5.0 | 2.0 | 0.0 | 9.0 | 0.0 | 2.0 |
| | 0.0620 | 5.0 | 0.0 | 0.0 | 9.0 | 0.0 | 2.0 |
| | 0.0320 | 4.0 | 0.0 | 0.0 | 9.0 | 0.0 | 2.0 |
| 358 | 0.2500 | 5.0 | 7.0 | 0.0 | 9.0 | 6.0 | 3.0 |
| | 0.1250 | 5.0 | 0.0 | 0.0 | 9.0 | 6.0 | 3.0 |
| | 0.0620 | 5.0 | 0.0 | 0.0 | 9.0 | 5.0 | 3.0 |
| | 0.0320 | 4.0 | 0.0 | 0.0 | 9.0 | 5.0 | 2.0 |
| 359 | 0.5000 | 9.0 | 9.0 | | 9.0 | 5.0 | 9.0 |

TABLE III-continued

PADDY CONDITIONS - POST-TRANSPLANT RICE PREEMERGENCE WEEDS

| Compound Number | Rate (kg/ha) | ECHORC | CYPIR | CYPSE | MOOVA | SAGPY | ORYSAT |
|---|---|---|---|---|---|---|---|
| | 0.2500 | 9.0 | 9.0 | 9.0 | 9.0 | 4.5 | 9.0 |
| | 0.1250 | 9.0 | 8.5 | 9.0 | 9.0 | 1.8 | 8.8 |
| | 0.0620 | 9.0 | 7.5 | 6.0 | 9.0 | 0.5 | 7.3 |
| | 0.0320 | 8.5 | 6.3 | 9.0 | 8.8 | 0.0 | 6.5 |
| 360 | 0.5000 | 9.0 | 9.0 | | 9.0 | 9.0 | 9.0 |
| | 0.2500 | 7.5 | 9.0 | 9.0 | 9.0 | 9.0 | 9.0 |
| | 0.1250 | 5.0 | 9.0 | 0.0 | 4.5 | 4.5 | 3.5 |
| | 0.0620 | 2.0 | 2.5 | 0.0 | 4.5 | 4.5 | 2.0 |
| | 0.0320 | 0.0 | 0.0 | 0.0 | 4.5 | 1.5 | 1.0 |
| 361 | 0.5000 | 4.0 | 6.0 | | 9.0 | 5.0 | 3.0 |
| | 0.2500 | 4.0 | 6.0 | | 9.0 | 5.0 | 5.0 |
| | 0.1250 | 0.0 | 0.0 | | 9.0 | 5.0 | 4.0 |
| | 0.0620 | 0.0 | 0.0 | | 9.0 | 4.0 | 0.0 |
| | 0.0320 | 0.0 | 0.0 | | 9.0 | 4.0 | 0.0 |
| 362 | 0.5000 | 9.0 | 9.0 | 9.0 | 9.0 | 9.0 | 8.0 |
| | 0.2500 | 9.0 | 7.0 | 9.0 | 9.0 | 9.0 | 6.0 |
| | 0.1250 | 7.0 | 5.0 | 9.0 | 9.0 | 9.0 | 4.0 |
| | 0.0620 | 7.0 | 5.0 | 9.0 | 9.0 | 9.0 | 4.0 |
| | 0.0320 | 4.0 | 3.0 | 6.0 | 9.0 | 9.0 | 4.0 |
| 363 | 0.5000 | 7.0 | 8.0 | 7.0 | 9.0 | 9.0 | 9.0 |
| | 0.2500 | 6.0 | 7.0 | 7.0 | 9.0 | 9.0 | 7.0 |
| | 0.1250 | 5.0 | 7.0 | 5.0 | 9.0 | 7.0 | 6.0 |
| | 0.0620 | 4.0 | 7.0 | 0.0 | 9.0 | 5.0 | 5.0 |
| | 0.0320 | 3.0 | 6.0 | 0.0 | 9.0 | 3.0 | 4.0 |
| 364 | 0.5000 | 7.0 | 9.0 | 7.0 | 9.0 | 9.0 | 9.0 |
| | 0.2500 | 6.0 | 9.0 | 9.0 | 9.0 | 9.0 | 9.0 |
| | 0.1250 | 6.0 | 9.0 | 5.0 | 9.0 | 5.0 | 6.0 |
| | 0.0620 | 5.0 | 7.0 | 3.0 | 9.0 | 4.0 | 5.0 |
| | 0.0320 | 3.0 | 7.0 | 3.0 | 9.0 | 4.0 | 4.0 |
| 365 | 0.5000 | 9.0 | 9.0 | 9.0 | 9.0 | 6.0 | 6.0 |
| | 0.2500 | 9.0 | 9.0 | 9.0 | 9.0 | 5.0 | 5.0 |
| | 0.1250 | 9.0 | 6.0 | 4.0 | 9.0 | 5.0 | 5.0 |
| | 0.0620 | 6.0 | 6.0 | 4.0 | 9.0 | 5.0 | 5.0 |
| | 0.0320 | 4.0 | 4.0 | 4.0 | 9.0 | 3.0 | 3.0 |
| 366 | 0.5000 | 9.0 | 9.0 | 9.0 | 9.0 | 9.0 | 9.0 |
| | 0.2500 | 9.0 | 9.0 | 9.0 | 9.0 | 9.0 | 9.0 |
| | 0.1250 | 9.0 | 9.0 | 9.0 | 9.0 | 9.0 | 9.0 |
| | 0.0620 | 8.5 | 9.0 | 8.0 | 9.0 | 8.0 | 9.0 |
| | 0.0320 | 8.0 | 8.5 | 8.0 | 9.0 | 7.0 | 7.5 |
| 367 | 0.2500 | 6.0 | 9.0 | 9.0 | 9.0 | 9.0 | 6.0 |
| | 0.1250 | 3.0 | 7.0 | 9.0 | 9.0 | 5.0 | 5.0 |
| | 0.0620 | 0.0 | 5.0 | 9.0 | 9.0 | 2.0 | 0.0 |
| | 0.0320 | 0.0 | 0.0 | 0.0 | 9.0 | 0.0 | 0.0 |
| 368 | 0.2500 | 8.0 | 9.0 | 8.0 | 9.0 | 9.0 | 7.0 |
| | 0.1250 | 7.0 | 9.0 | 7.0 | 9.0 | 9.0 | 6.0 |
| | 0.0620 | 7.0 | 9.0 | 4.0 | 9.0 | 6.0 | 5.0 |
| | 0.0320 | 3.0 | 7.0 | 0.0 | 9.0 | 5.0 | 5.0 |
| 369 | 0.2500 | 8.0 | 9.0 | 9.0 | 9.0 | 9.0 | 7.0 |
| | 0.1250 | 6.0 | 9.0 | 4.0 | 9.0 | 9.0 | 7.0 |
| | 0.0620 | 3.0 | 7.0 | 3.0 | 9.0 | 6.0 | 6.0 |
| | 0.0320 | 3.0 | 7.0 | 0.0 | 9.0 | 0.0 | 6.0 |
| 370 | 0.2500 | 7.0 | 9.0 | 9.0 | 9.0 | 9.0 | 5.0 |
| | 0.1250 | 6.0 | 9.0 | 7.0 | 9.0 | 7.0 | 4.0 |
| | 0.0620 | 4.0 | 7.0 | 4.0 | 9.0 | 3.0 | 4.0 |
| | 0.0320 | 3.0 | 4.0 | 0.0 | 7.0 | 0.0 | 3.0 |
| 371 | 0.2500 | 7.0 | 9.0 | 9.0 | 9.0 | 9.0 | 9.0 |
| | 0.1250 | 6.0 | 9.0 | 6.0 | 9.0 | 9.0 | 6.0 |
| | 0.0620 | 4.0 | 6.0 | 0.0 | 9.0 | 4.0 | 6.0 |
| | 0.0320 | 3.0 | 4.0 | 0.0 | 9.0 | 3.0 | 5.0 |
| 372 | 0.2500 | 9.0 | 9.0 | 9.0 | 9.0 | 9.0 | 9.0 |
| | 0.1250 | 9.0 | 9.0 | 8.5 | 9.0 | 9.0 | 8.0 |
| | 0.0620 | 9.0 | 9.0 | 5.0 | 9.0 | 9.0 | 8.0 |
| | 0.0320 | 9.0 | 8.5 | 1.0 | 9.0 | 8.5 | 6.0 |
| 373 | 0.2500 | 9.0 | 9.0 | 8.0 | 9.0 | 9.0 | 8.0 |
| | 0.1250 | 9.0 | 9.0 | 7.5 | 9.0 | 9.0 | 6.0 |
| | 0.0620 | 9.0 | 9.0 | 5.0 | 9.0 | 8.5 | 6.5 |
| | 0.0320 | 6.5 | 6.5 | 2.0 | 9.0 | 5.5 | 5.5 |
| 374 | 0.2500 | 6.0 | 9.0 | 5.0 | 9.0 | 9.0 | 7.0 |
| | 0.1250 | 4.0 | 9.0 | 0.0 | 9.0 | 6.0 | 6.0 |
| | 0.0620 | 3.0 | 9.0 | 0.0 | 9.0 | 3.0 | 4.0 |
| | 0.0320 | 3.0 | 6.0 | 0.0 | 9.0 | 2.0 | 4.0 |
| 375 | 0.2500 | 9.0 | 9.0 | 7.0 | 9.0 | 9.0 | 6.0 |
| | 0.1250 | 9.0 | 6.0 | 4.0 | 9.0 | 9.0 | 4.0 |

TABLE III-continued

PADDY CONDITIONS - POST-TRANSPLANT RICE PREEMERGENCE WEEDS

| Compound Number | Rate (kg/ha) | ECHORC | CYPIR | CYPSE | MOOVA | SAGPY | ORYSAT |
|---|---|---|---|---|---|---|---|
| | 0.0620 | 6.0 | 4.0 | 0.0 | 9.0 | 9.0 | 4.0 |
| | 0.0320 | 6.0 | 3.0 | 0.0 | 9.0 | 7.0 | 2.0 |
| 376 | 0.2500 | 9.0 | 9.0 | 8.0 | 9.0 | 9.0 | 8.5 |
| | 0.1250 | 6.5 | 9.0 | 5.5 | 9.0 | 9.0 | 6.0 |
| | 0.0620 | 5.5 | 8.0 | 4.0 | 9.0 | 8.5 | 6.0 |
| | 0.0320 | 3.0 | 3.0 | 3.0 | 9.0 | 8.0 | 4.0 |
| 377 | 0.2500 | 9.0 | 8.0 | 8.5 | 9.0 | 9.0 | 9.0 |
| | 0.1250 | 7.0 | 4.5 | 5.0 | 9.0 | 8.5 | 8.0 |
| | 0.0620 | 5.0 | 3.0 | 3.0 | 9.0 | 4.0 | 6.5 |
| | 0.0320 | 2.0 | 2.0 | 1.0 | 9.0 | 0.0 | 5.5 |
| 378 | 0.2500 | 9.0 | 9.0 | 9.0 | 9.0 | 9.0 | 9.0 |
| | 0.1250 | 9.0 | 9.0 | 9.0 | 9.0 | 9.0 | 9.0 |
| | 0.0620 | 9.0 | 9.0 | 9.0 | 9.0 | 9.0 | 9.0 |
| | 0.0320 | 9.0 | 9.0 | 9.0 | 9.0 | 9.0 | 9.0 |
| 379 | 0.2500 | 8.0 | 9.0 | 8.5 | 9.0 | 9.0 | 9.0 |
| | 0.1250 | 7.5 | 9.0 | 8.5 | 9.0 | 9.0 | 9.0 |
| | 0.0620 | 5.0 | 7.5 | 6.5 | 9.0 | 6.5 | 8.5 |
| | 0.0320 | 2.0 | 5.5 | 2.5 | 9.0 | 3.5 | 7.0 |
| 380 | 0.2500 | 9.0 | 9.0 | 8.0 | 9.0 | 9.0 | 6.5 |
| | 0.1250 | 9.0 | 9.0 | 8.0 | 9.0 | 4.0 | 5.0 |
| | 0.0620 | 9.0 | 9.0 | 3.5 | 9.0 | 0.0 | 4.0 |
| | 0.0320 | 9.0 | 9.0 | 3.5 | 9.0 | 0.0 | 2.5 |
| 381 | 0.2500 | 6.0 | 8.0 | 7.0 | 8.0 | 7.0 | 7.0 |
| | 0.1250 | 4.0 | 8.0 | 7.0 | 8.0 | 6.0 | 6.0 |
| | 0.0620 | 3.0 | 7.0 | 4.0 | 7.0 | 5.0 | 3.0 |
| | 0.0320 | 0.0 | 6.0 | 0.0 | 6.0 | 3.0 | 3.0 |
| 382 | 0.2500 | 7.0 | 9.0 | 7.0 | 9.0 | 9.0 | 5.0 |
| | 0.1250 | 4.0 | 7.0 | 7.0 | 9.0 | 7.0 | 6.0 |
| | 0.0620 | 3.0 | 6.0 | 0.0 | 9.0 | 4.0 | 6.0 |
| | 0.0320 | 0.0 | 5.0 | 0.0 | 9.0 | 3.0 | 5.0 |
| 383 | 0.2500 | 8.0 | 8.0 | 9.0 | 9.0 | 9.0 | 6.5 |
| | 0.1250 | 7.5 | 7.0 | 7.5 | 9.0 | 9.0 | 6.0 |
| | 0.0620 | 6.5 | 7.0 | 5.5 | 9.0 | 7.5 | 4.5 |
| | 0.0320 | 4.0 | 2.5 | 4.5 | 9.0 | 3.0 | 3.5 |
| 384 | 0.2500 | 6.0 | 8.0 | 7.0 | 9.0 | 6.0 | 6.0 |
| | 0.1250 | 4.0 | 8.0 | 7.0 | 9.0 | 6.0 | 7.0 |
| | 0.0620 | 4.0 | 7.0 | 7.0 | 9.0 | 6.0 | 4.0 |
| | 0.0320 | 2.0 | 4.0 | 7.0 | 9.0 | 5.0 | 4.0 |
| 385 | 0.2500 | 6.0 | 9.0 | 7.0 | 9.0 | 9.0 | 7.0 |
| | 0.1250 | 3.0 | 6.0 | 7.0 | 9.0 | 9.0 | 7.0 |
| | 0.0620 | 3.0 | 6.0 | 6.0 | 9.0 | 0.0 | 5.0 |
| | 0.0320 | 0.0 | 4.0 | 6.0 | 9.0 | 0.0 | 3.0 |
| 386 | 0.2500 | 5.0 | 9.0 | 7.0 | 9.0 | 9.0 | 5.0 |
| | 0.1250 | 4.0 | 9.0 | 7.0 | 9.0 | 9.0 | 5.0 |
| | 0.0620 | 3.0 | 9.0 | 7.0 | 9.0 | 7.0 | 5.0 |
| | 0.0320 | 0.0 | 7.0 | 3.0 | 9.0 | 4.0 | 5.0 |
| 387 | 0.2500 | 3.0 | 7.0 | 5.0 | 9.0 | 6.0 | 2.0 |
| | 0.1250 | 0.0 | 6.0 | 5.0 | 9.0 | 5.0 | 2.0 |
| | 0.0620 | 0.0 | 5.0 | 5.0 | 9.0 | 4.0 | 0.0 |
| | 0.0320 | 0.0 | 0.0 | 2.0 | 4.0 | 3.0 | 0.0 |
| 388 | 0.2500 | 6.0 | 9.0 | 6.0 | 9.0 | 7.0 | 6.0 |
| | 0.1250 | 5.0 | 7.0 | | 9.0 | 4.0 | 4.0 |
| | 0.0620 | 2.0 | 7.0 | | 9.0 | 4.0 | 4.0 |
| | 0.0320 | 0.0 | 4.0 | 6.0 | 9.0 | 3.0 | 3.0 |
| 389 | 0.2500 | 7.0 | 9.0 | 8.0 | 9.0 | 9.0 | 5.0 |
| | 0.1250 | 4.0 | 7.0 | 7.0 | 9.0 | 7.0 | 4.0 |
| | 0.0620 | 4.0 | 5.0 | | 9.0 | 4.0 | 4.0 |
| | 0.0320 | 3.0 | 5.0 | 0.0 | 7.0 | 3.0 | 3.0 |
| 390 | 0.5000 | 9.0 | 9.0 | 6.0 | 9.0 | 9.0 | 5.0 |
| | 0.2500 | 9.0 | 9.0 | 9.0 | 9.0 | 8.0 | 6.5 |
| | 0.1250 | 8.0 | 7.0 | 4.0 | 9.0 | 8.0 | 6.0 |
| | 0.0620 | 7.0 | 4.0 | | 9.0 | 5.5 | 5.5 |
| | 0.0320 | 5.5 | 1.0 | 2.5 | 9.0 | 2.5 | 4.0 |
| 391 | 0.5000 | 6.0 | 9.0 | 3.0 | 9.0 | 9.0 | 3.0 |
| | 0.2500 | 4.0 | 6.0 | 0.0 | 9.0 | 7.0 | 3.0 |
| | 0.1250 | 2.0 | 4.0 | 0.0 | 9.0 | 7.0 | 3.0 |
| | 0.0620 | 0.0 | 3.0 | 0.0 | 9.0 | 6.0 | 2.0 |
| | 0.0320 | 0.0 | 3.0 | 0.0 | 6.0 | 6.0 | 2.0 |
| 392 | 0.2500 | 9.0 | 7.0 | 0.0 | 9.0 | 0.0 | |
| | 0.1250 | 9.0 | 3.0 | 0.0 | 7.0 | 0.0 | |
| | 0.0620 | 7.0 | 0.0 | 0.0 | 7.0 | 0.0 | |
| | 0.0320 | 5.0 | 0.0 | 0.0 | 6.0 | 0.0 | |
| 393 | 0.2500 | 9.0 | 6.0 | 6.0 | 9.0 | 4.0 | |

TABLE III-continued

PADDY CONDITIONS - POST-TRANSPLANT RICE
PREEMERGENCE WEEDS

| Compound Number | Rate (kg/ha) | ECHORC | CYPIR | CYPSE | MOOVA | SAGPY | ORYSAT |
|---|---|---|---|---|---|---|---|
| | 0.1250 | 4.0 | 3.0 | 3.0 | 8.0 | 3.0 | |
| | 0.0620 | 4.0 | 3.0 | 0.0 | 8.0 | | |
| | 0.0320 | 2.0 | 0.0 | 0.0 | 7.0 | 0.0 | |
| 394 | 0.2500 | 6.0 | 7.0 | 2.0 | 9.0 | 0.0 | |
| | 0.1250 | 4.0 | 5.0 | 0.0 | 9.0 | 0.0 | |
| | 0.0620 | 0.0 | 3.0 | 0.0 | 8.0 | 0.0 | |
| | 0.0320 | 0.0 | 0.0 | 0.0 | 8.0 | | |
| 395 | 0.2500 | 3.0 | 3.0 | 0.0 | 9.0 | 5.0 | |
| | 0.1250 | 2.0 | 0.0 | 0.0 | 9.0 | 4.0 | |
| | 0.0620 | 0.0 | 0.0 | 0.0 | 9.0 | 2.0 | |
| | 0.0320 | 0.0 | 0.0 | 0.0 | 9.0 | 0.0 | |
| 396 | 0.2500 | 9.0 | 9.0 | 6.0 | 9.0 | 8.0 | |
| | 0.1250 | 9.0 | 9.0 | 0.0 | 9.0 | 8.0 | |
| | 0.0620 | 9.0 | 8.0 | 0.0 | 9.0 | 7.0 | |
| | 0.0320 | 9.0 | 7.0 | 0.0 | 9.0 | 7.0 | |
| 397 | 0.2500 | 9.0 | 9.0 | 0.0 | 9.0 | 5.0 | |
| | 0.1250 | 9.0 | 9.0 | 0.0 | 9.0 | 5.0 | |
| | 0.0620 | 9.0 | 7.0 | | 9.0 | 5.0 | |
| | 0.0320 | 9.0 | 6.0 | 0.0 | 9.0 | 4.0 | |
| 398 | 0.2500 | 8.0 | 8.0 | 3.0 | 9.0 | 3.0 | |
| | 0.1250 | 3.0 | 6.0 | 3.0 | 9.0 | 0.0 | |
| | 0.0620 | 2.0 | 3.0 | 0.0 | 9.0 | 0.0 | |
| | 0.0320 | 0.0 | 0.0 | 0.0 | 6.0 | 0.0 | |
| 399 | 0.2500 | 3.0 | 8.0 | 0.0 | 9.0 | 0.0 | |
| | 0.1250 | 2.0 | 7.0 | 0.0 | 8.0 | 0.0 | |
| | 0.0620 | 0.0 | 2.0 | 0.0 | 7.0 | 0.0 | |
| | 0.0320 | 0.0 | 0.0 | 0.0 | 6.0 | 0.0 | |
| 400 | 0.2500 | 0.0 | 9.0 | 0.0 | 9.0 | 0.0 | |
| | 0.1250 | 0.0 | 9.0 | 0.0 | 7.0 | 0.0 | |
| | 0.0620 | 0.0 | 3.0 | 0.0 | 7.0 | 0.0 | |
| | 0.0320 | 0.0 | 3.0 | 0.0 | 6.0 | 0.0 | |
| 401 | 0.2500 | 6.0 | 6.0 | 3.0 | 9.0 | 3.0 | 5.0 |
| | 0.1250 | 2.0 | 5.0 | 0.0 | 7.0 | 2.0 | 4.0 |
| | 0.0620 | 0.0 | 4.0 | 0.0 | 7.0 | 0.0 | 4.0 |
| | 0.0320 | 0.0 | 3.0 | | 6.0 | 0.0 | 3.0 |
| 402 | 0.2500 | 4.0 | 7.0 | 5.0 | 9.0 | 3.0 | 4.0 |
| | 0.1250 | 3.0 | 3.0 | 0.0 | 9.0 | 0.0 | 2.0 |
| | 0.0620 | 0.0 | 2.0 | 0.0 | 7.0 | 0.0 | 0.0 |
| | 0.0320 | 0.0 | 0.0 | | 7.0 | 0.0 | 0.0 |
| 403 | 0.2500 | 4.0 | 9.0 | 4.0 | 9.0 | 9.0 | |
| | 0.1250 | 4.0 | 7.0 | 2.0 | 9.0 | 9.0 | |
| | 0.0620 | 2.0 | 6.0 | 0.0 | 6.0 | 9.0 | |
| | 0.0320 | 0.0 | 5.0 | 0.0 | 7.0 | 3.0 | |
| 404 | 0.2500 | 7.0 | 6.0 | 0.0 | 6.0 | 0.0 | 2.0 |
| | 0.1250 | 6.0 | 2.0 | 0.0 | 5.0 | 0.0 | 0.0 |
| | 0.0620 | 3.0 | 0.0 | 0.0 | 5.0 | 0.0 | 0.0 |
| | 0.0320 | 0.0 | 0.0 | 0.0 | 4.0 | 0.0 | 0.0 |
| 405 | 0.2500 | 9.0 | 8.0 | 0.0 | 7.0 | 6.0 | 2.0 |
| | 0.1250 | 9.0 | 7.0 | 0.0 | 7.0 | 5.0 | 2.0 |
| | 0.0620 | 7.0 | 4.0 | 0.0 | 6.0 | 0.0 | 0.0 |
| | 0.0320 | 7.0 | 4.0 | 0.0 | 6.0 | 0.0 | 0.0 |
| 406 | 0.2500 | 7.0 | 7.0 | 6.0 | 9.0 | 4.0 | 4.0 |
| | 0.1250 | 7.0 | 4.0 | 3.0 | 9.0 | 4.0 | 2.0 |
| | 0.0620 | 6.0 | 4.0 | 0.0 | 7.0 | 4.0 | 0.0 |
| | 0.0320 | 6.0 | 0.0 | 0.0 | 4.0 | 3.0 | 0.0 |
| 407 | 0.2500 | 7.0 | 9.0 | 7.0 | 9.0 | 7.0 | 5.0 |
| | 0.1250 | 7.0 | 9.0 | 5.0 | 9.0 | 6.0 | 3.0 |
| | 0.0620 | 3.0 | 4.0 | 0.0 | 7.0 | 2.0 | 2.0 |
| | 0.0320 | 0.0 | 3.0 | 0.0 | 6.0 | 0.0 | 0.0 |
| 408 | 0.2500 | 7.0 | 9.0 | 6.0 | 9.0 | 6.0 | 3.0 |
| | 0.1250 | 6.0 | 9.0 | 5.0 | 9.0 | 4.0 | 2.0 |
| | 0.0620 | 3.0 | 9.0 | 0.0 | 9.0 | 0.0 | 2.0 |
| | 0.0320 | 2.0 | 6.0 | 0.0 | 7.0 | 0.0 | 0.0 |
| 409 | 0.2500 | 9.0 | 9.0 | 9.0 | 9.0 | 9.0 | 9.0 |
| | 0.1250 | 9.0 | 9.0 | 9.0 | 9.0 | 7.0 | 7.0 |
| | 0.0620 | 4.0 | 9.0 | 5.0 | 9.0 | 4.0 | 5.0 |
| | 0.0320 | 3.0 | 7.0 | 2.0 | 9.0 | 2.0 | 3.0 |
| 410 | 0.2500 | 9.0 | 9.0 | 9.0 | 9.0 | 9.0 | 7.0 |
| | 0.1250 | 9.0 | 9.0 | 9.0 | 9.0 | 9.0 | 5.0 |
| | 0.0620 | 0.0 | 9.0 | 5.0 | 9.0 | 7.0 | 3.0 |
| | 0.0320 | 0.0 | 9.0 | 2.0 | 9.0 | 3.0 | 0.0 |
| 411 | 0.2500 | 6.0 | 9.0 | 9.0 | 9.0 | | 5.0 |
| | 0.1250 | 0.0 | 3.0 | 7.0 | 9.0 | | 2.0 |

TABLE III-continued

PADDY CONDITIONS - POST-TRANSPLANT RICE PREEMERGENCE WEEDS

| Compound Number | Rate (kg/ha) | ECHORC | CYPIR | CYPSE | MOOVA | SAGPY | ORYSAT |
|---|---|---|---|---|---|---|---|
| | 0.0620 | 0.0 | 2.0 | 2.0 | 9.0 | | 0.0 |
| | 0.0320 | 0.0 | 0.0 | 0.0 | 9.0 | | 0.0 |
| 412 | 0.2500 | | 8.0 | 6.0 | 9.0 | | 4.0 |
| | 0.1250 | 0.0 | 4.0 | 4.0 | 9.0 | | 2.0 |
| | 0.0620 | 0.0 | 0.0 | 0.0 | 9.0 | | 0.0 |
| | 0.0320 | 0.0 | 0.0 | 0.0 | 7.0 | | 0.0 |
| 413 | 0.2500 | 6.0 | 7.0 | 9.0 | 9.0 | | 9.0 |
| | 0.1250 | 0.0 | 5.0 | 5.0 | 9.0 | | 7.0 |
| | 0.0620 | 0.0 | 2.0 | 3.0 | 9.0 | | 5.0 |
| | 0.0320 | 0.0 | 0.0 | 0.0 | 7.0 | | 3.0 |
| 414 | 0.2500 | 7.0 | 9.0 | 9.0 | 7.0 | | 9.0 |
| | 0.1250 | 2.0 | 6.0 | | 7.0 | | 5.0 |
| | 0.0620 | 0.0 | 2.0 | | 7.0 | | 5.0 |
| | 0.0320 | 0.0 | 0.0 | 0.0 | | | 5.0 |
| 415 | 0.2500 | 9.0 | 6.0 | | 8.0 | | 9.0 |
| | 0.1250 | 3.0 | 2.0 | | 5.0 | | 5.0 |
| | 0.0620 | 0.0 | 0.0 | 0.0 | 5.0 | | 4.0 |
| | 0.0320 | 0.0 | 0.0 | 0.0 | 5.0 | | 3.0 |
| 416 | 0.2500 | 9.0 | 8.0 | 3.0 | 9.0 | | 9.0 |
| | 0.1250 | 3.0 | 4.0 | 0.0 | 7.0 | | 9.0 |
| | 0.0620 | 3.0 | 4.0 | 0.0 | 7.0 | | 7.0 |
| | 0.0320 | 0.0 | 4.0 | 0.0 | 7.0 | | 6.0 |
| 417 | 0.2500 | 3.0 | 6.0 | | 9.0 | | 3.0 |
| | 0.1250 | 3.0 | 5.0 | 3.0 | 9.0 | | 0.0 |
| | 0.0620 | 0.0 | 4.0 | | 6.0 | | 0.0 |
| | 0.0320 | 0.0 | 4.0 | | 6.0 | | 0.0 |
| 418 | 0.2500 | 3.0 | 0.0 | 0.0 | 0.0 | | 3.0 |
| | 0.1250 | 1.0 | 0.0 | | 0.0 | | 2.0 |
| | 0.0620 | 0.0 | 0.0 | 0.0 | 0.0 | | 0.0 |
| 419 | 0.2500 | 7.0 | 6.0 | 0.0 | 5.0 | | 3.0 |
| | 0.1250 | 2.0 | 3.0 | 0.0 | 4.0 | | 1.0 |
| | 0.0620 | 0.0 | 0.0 | 0.0 | 0.0 | | 0.0 |
| 420 | 0.2500 | 7.0 | 6.0 | 0.0 | 9.0 | 3.0 | 5.0 |
| | 0.1250 | 7.0 | 6.0 | | 9.0 | 2.0 | 3.0 |
| | 0.0620 | 7.0 | 4.0 | | 9.0 | 0.0 | 2.0 |
| | 0.0320 | 7.0 | 2.0 | | 9.0 | 0.0 | 0.0 |
| 421 | 0.2500 | 9.0 | 9.0 | 4.0 | 9.0 | 2.0 | 2.0 |
| | 0.1250 | 7.0 | 8.0 | | 7.0 | 0.0 | 0.0 |
| | 0.0620 | 5.0 | 6.0 | | 6.0 | 0.0 | 0.0 |
| | 0.0320 | 5.0 | 2.0 | | 5.0 | 0.0 | 0.0 |
| 422 | 0.2500 | 9.0 | 9.0 | | 9.0 | 6.0 | 3.0 |
| | 0.1250 | 9.0 | 9.0 | | 9.0 | 3.0 | 2.0 |
| | 0.0620 | 6.0 | 6.0 | 5.0 | 9.0 | 0.0 | 0.0 |
| | 0.0320 | 5.0 | 5.0 | 0.0 | 7.0 | 0.0 | 0.0 |
| 423 | 0.2500 | 9.0 | 9.0 | 9.0 | 9.0 | 9.0 | 7.0 |
| | 0.1250 | 9.0 | 9.0 | 9.0 | 9.0 | 9.0 | 7.0 |
| | 0.0620 | 9.0 | 7.0 | 9.0 | 9.0 | 9.0 | 6.0 |
| | 0.0320 | 6.0 | 6.0 | 9.0 | 9.0 | 9.0 | 5.0 |
| 424 | 0.2500 | 3.0 | 7.0 | 3.0 | 9.0 | 0.0 | 2.0 |
| | 0.1250 | 3.0 | 6.0 | 3.0 | 9.0 | 0.0 | 0.0 |
| | 0.0620 | 0.0 | 5.0 | | 9.0 | 0.0 | 0.0 |
| | 0.0320 | 0.0 | 4.0 | | 7.0 | 0.0 | 0.0 |
| 425 | 0.2500 | 9.0 | 9.0 | 3.0 | 9.0 | 4.0 | 8.0 |
| | 0.1250 | 9.0 | 6.0 | 3.0 | 9.0 | 3.0 | 7.0 |
| | 0.0620 | 9.0 | 0.0 | 3.0 | 7.0 | 0.0 | 6.0 |
| | 0.0320 | 6.0 | 0.0 | 0.0 | 6.0 | 0.0 | 4.0 |
| 426 | 0.2500 | 9.0 | 9.0 | 2.0 | | 4.0 | 6.0 |
| | 0.1250 | 5.0 | 7.0 | 0.0 | | 4.0 | 4.0 |
| | 0.0620 | 5.0 | 7.0 | 0.0 | | 2.0 | 2.0 |
| | 0.0320 | 5.0 | 5.0 | 0.0 | | 0.0 | 2.0 |
| 427 | 0.2500 | 9.0 | 9.0 | 4.0 | | 9.0 | 3.0 |
| | 0.1250 | 9.0 | 7.0 | | | 6.0 | 1.0 |
| | 0.0620 | 7.0 | 7.0 | 0.0 | | 5.0 | 0.0 |
| | 0.0320 | 7.0 | 7.0 | 0.0 | | 4.0 | 0.0 |
| 428 | 0.2500 | 9.0 | 7.0 | | 9.0 | 6.0 | 6.0 |
| | 0.1250 | 6.0 | 4.0 | | 9.0 | 2.0 | 6.0 |
| | 0.0620 | 3.0 | 2.0 | 0.0 | 9.0 | 0.0 | 2.0 |
| | 0.0320 | 2.0 | 0.0 | 0.0 | 9.0 | 0.0 | 0.0 |
| 429 | 0.2500 | 9.0 | 9.0 | 1.0 | 9.0 | 3.0 | 3.0 |
| | 0.1250 | 9.0 | 8.3 | 1.0 | 9.0 | 2.3 | 2.3 |
| | 0.0620 | 9.0 | 7.7 | 1.0 | 9.0 | 2.3 | 2.0 |
| | 0.0320 | 9.0 | 7.3 | 0.0 | 9.0 | 2.0 | 1.3 |
| 430 | 0.2500 | 9.0 | 6.0 | 7.0 | 9.0 | 7.0 | 3.0 |

TABLE III-continued

PADDY CONDITIONS - POST-TRANSPLANT RICE
PREEMERGENCE WEEDS

| Compound Number | Rate (kg/ha) | ECHORC | CYPIR | CYPSE | MOOVA | SAGPY | ORYSAT |
|---|---|---|---|---|---|---|---|
| | 0.1250 | 7.0 | 7.0 | 2.0 | 9.0 | 6.0 | 4.0 |
| | 0.0620 | 5.0 | 6.0 | 0.0 | 9.0 | | 2.0 |
| | 0.0320 | 5.0 | 2.0 | 0.0 | 9.0 | | 3.0 |
| 431 | 0.2500 | 9.0 | 9.0 | 9.0 | 9.0 | 9.0 | 6.5 |
| | 0.1250 | 8.5 | 9.0 | 7.5 | 9.0 | 7.5 | 5.0 |
| | 0.0620 | 9.0 | 9.0 | 4.0 | 9.0 | 5.5 | 5.5 |
| | 0.0320 | 8.0 | 8.0 | 0.0 | 9.0 | 3.5 | 3.5 |
| 432 | 0.2500 | 9.0 | 9.0 | 9.0 | 9.0 | 8.5 | 7.5 |
| | 0.1250 | 9.0 | 9.0 | 6.5 | 9.0 | 7.5 | 6.5 |
| | 0.0620 | 9.0 | 9.0 | 3.5 | 9.0 | 3.5 | 6.0 |
| | 0.0320 | 9.0 | 8.0 | 0.0 | 9.0 | 0.0 | 6.0 |
| 433 | 0.2500 | 9.0 | 9.0 | 7.5 | 9.0 | 7.0 | 7.5 |
| | 0.1250 | 9.0 | 9.0 | 7.5 | 9.0 | 6.0 | 5.0 |
| | 0.0620 | 9.0 | 8.5 | 6.0 | 9.0 | 4.5 | 4.0 |
| | 0.0320 | 8.0 | 5.5 | 0.0 | 8.5 | 2.0 | 2.0 |
| 434 | 0.2500 | 9.0 | 8.0 | 7.0 | 9.0 | 6.0 | 7.0 |
| | 0.1250 | 7.0 | 7.0 | 4.0 | 9.0 | 5.0 | 6.0 |
| | 0.0620 | 7.0 | 3.0 | | 9.0 | 4.0 | 6.0 |
| | 0.0320 | 6.0 | 3.0 | 4.0 | 9.0 | 4.0 | 4.0 |
| 435 | 0.2500 | 9.0 | 3.0 | 2.0 | 9.0 | 6.0 | 2.0 |
| | 0.1250 | 7.0 | 2.0 | 3.0 | 9.0 | 0.0 | 2.0 |
| | 0.0620 | 7.0 | 0.0 | 0.0 | 9.0 | 0.0 | 1.0 |
| | 0.0320 | 5.0 | 0.0 | | 9.0 | 0.0 | 2.0 |
| 436 | 0.2500 | 9.0 | 7.0 | 6.0 | 9.0 | 3.0 | 6.0 |
| | 0.1250 | 9.0 | 7.0 | | 9.0 | 2.0 | 7.0 |
| | 0.0620 | 9.0 | 2.0 | 6.0 | 9.0 | 0.0 | 5.0 |
| | 0.0320 | 6.0 | 0.0 | 4.0 | 9.0 | 0.0 | 3.0 |
| 437 | 0.2500 | 8.0 | 6.0 | 7.0 | 9.0 | 7.0 | 7.0 |
| | 0.1250 | 7.0 | 4.0 | 3.0 | 9.0 | 4.0 | 6.0 |
| | 0.0620 | 7.0 | 0.0 | 2.0 | 9.0 | 3.0 | 5.0 |
| | 0.0320 | 5.0 | 0.0 | 0.0 | 9.0 | 0.0 | 4.0 |
| 438 | 0.2500 | 9.0 | 9.0 | 9.0 | 9.0 | 9.0 | 8.0 |
| | 0.1250 | 9.0 | 8.5 | 7.0 | 9.0 | 8.5 | 7.0 |
| | 0.0620 | 8.0 | 6.5 | 9.0 | 8.5 | 3.5 | 5.0 |
| | 0.0320 | 7.0 | 4.5 | 4.5 | 8.0 | 2.0 | 4.0 |
| 439 | 0.2500 | 6.0 | 5.0 | 0.0 | 7.0 | 3.0 | 0.0 |
| | 0.1250 | 6.0 | 4.0 | 0.0 | 7.0 | 0.0 | 0.0 |
| | 0.0620 | 3.0 | 3.0 | 0.0 | 6.0 | 0.0 | 0.0 |
| | 0.0320 | 2.0 | 1.0 | 0.0 | 5.0 | 0.0 | 0.0 |
| 440 | 0.2500 | 9.0 | 9.0 | 9.0 | 9.0 | 9.0 | 4.0 |
| | 0.1250 | 9.0 | 9.0 | 9.0 | 9.0 | 7.0 | 4.0 |
| | 0.0620 | 7.0 | 9.0 | 9.0 | 9.0 | 6.0 | 4.0 |
| | 0.0320 | 5.0 | 5.0 | 6.0 | 7.0 | 4.0 | 3.0 |
| 441 | 0.2500 | 3.0 | 9.0 | 7.0 | 9.0 | 6.0 | 3.0 |
| | 0.1250 | 0.0 | 9.0 | 4.0 | 9.0 | 3.0 | 2.0 |
| | 0.0620 | 0.0 | 6.0 | 0.0 | 9.0 | 2.0 | 0.0 |
| | 0.0320 | 0.0 | 4.0 | | 9.0 | 0.0 | 0.0 |
| 442 | 0.2500 | 9.0 | 9.0 | 4.5 | 9.0 | 4.0 | 3.3 |
| | 0.1250 | 9.0 | 8.7 | 0.0 | 9.0 | 2.0 | 1.7 |
| | 0.0620 | 9.0 | 6.3 | 0.0 | 8.3 | 1.7 | 1.3 |
| | 0.0320 | 8.3 | 4.3 | 0.0 | 6.0 | 1.3 | 0.3 |
| 443 | 0.2500 | 9.0 | 7.0 | | 7.0 | 5.0 | 8.0 |
| | 0.1250 | 7.0 | 7.0 | 0.0 | 7.0 | 4.0 | 5.0 |
| | 0.0620 | 5.0 | 6.0 | 0.0 | 6.0 | 3.0 | 4.0 |
| | 0.0320 | 6.0 | 4.0 | 0.0 | 5.0 | 3.0 | 3.0 |
| 444 | 0.2500 | 9.0 | 9.0 | 9.0 | 9.0 | 9.0 | 8.5 |
| | 0.1250 | 8.5 | 9.0 | 9.0 | 9.0 | 7.0 | 9.0 |
| | 0.0620 | 6.0 | 8.0 | 9.0 | 9.0 | 6.0 | 6.5 |
| | 0.0320 | 3.5 | 7.5 | 3.5 | 8.0 | 4.5 | 4.5 |
| 445 | 0.2500 | 9.0 | 9.0 | 8.5 | 9.0 | 9.0 | 8.0 |
| | 0.1250 | 9.0 | 9.0 | 8.0 | 9.0 | 8.5 | 7.0 |
| | 0.0620 | 8.5 | 8.0 | 8.5 | 9.0 | 8.0 | 6.5 |
| | 0.0320 | 8.5 | 6.5 | 7.5 | 9.0 | 4.5 | 5.0 |
| 446 | 0.2500 | 9.0 | 9.0 | 9.0 | 9.0 | 9.0 | 9.0 |
| | 0.1250 | 7.0 | 9.0 | 9.0 | 9.0 | 9.0 | 9.0 |
| | 0.0620 | 6.0 | 9.0 | 9.0 | 9.0 | 9.0 | 7.0 |
| | 0.0320 | 6.0 | 9.0 | 9.0 | 9.0 | 9.0 | 6.0 |
| 447 | 0.2500 | 9.0 | 9.0 | 4.0 | 9.0 | 9.0 | 7.0 |
| | 0.1250 | 7.0 | 7.0 | | 9.0 | 5.0 | 5.0 |
| | 0.0620 | 6.0 | 6.0 | 0.0 | 9.0 | 4.0 | 4.0 |
| | 0.0320 | 4.0 | 4.0 | 0.0 | 7.0 | 4.0 | 4.0 |
| 448 | 0.2500 | 9.0 | 9.0 | 6.5 | 9.0 | 3.5 | 4.0 |
| | 0.1250 | 9.0 | 9.0 | 4.5 | 9.0 | 2.5 | 4.0 |

TABLE III-continued

PADDY CONDITIONS - POST-TRANSPLANT RICE
PREEMERGENCE WEEDS

| Compound Number | Rate (kg/ha) | ECHORC | CYPIR | CYPSE | MOOVA | SAGPY | ORYSAT |
|---|---|---|---|---|---|---|---|
| | 0.0620 | 9.0 | 9.0 | 4.5 | 9.0 | 1.5 | 4.0 |
| | 0.0320 | 9.0 | 8.5 | 4.5 | 9.0 | 0.0 | 3.5 |
| 449 | 0.2500 | 9.0 | 9.0 | 4.0 | 9.0 | 6.0 | 9.0 |
| | 0.1250 | 9.0 | 8.0 | | 9.0 | 4.0 | 3.0 |
| | 0.0620 | 7.0 | 5.0 | | 7.0 | 4.0 | 3.0 |
| | 0.0320 | 5.0 | 4.0 | 2.0 | 7.0 | 2.0 | 2.0 |
| 450 | 0.2500 | 9.0 | 9.0 | | 9.0 | 9.0 | 9.0 |
| | 0.1250 | 6.0 | 9.0 | | 9.0 | 6.0 | 5.0 |
| | 0.0620 | 2.0 | 7.0 | | 7.0 | 5.0 | 4.0 |
| | 0.0320 | 0.0 | 6.0 | 0.0 | 7.0 | 5.0 | 3.0 |
| 451 | 0.2500 | 7.0 | 9.0 | 0.0 | 9.0 | 9.0 | 6.0 |
| | 0.1250 | 6.0 | 7.0 | | 9.0 | 6.0 | 6.0 |
| | 0.0620 | 0.0 | 5.0 | 0.0 | 9.0 | 5.0 | 4.0 |
| | 0.0320 | 0.0 | 5.0 | | 9.0 | 4.0 | 4.0 |
| 452 | 0.2500 | 7.0 | 9.0 | 7.0 | 9.0 | 2.0 | 7.0 |
| | 0.1250 | 3.0 | 9.0 | | 9.0 | 0.0 | 6.0 |
| | 0.0620 | 3.0 | 6.0 | | 9.0 | 0.0 | 5.0 |
| | 0.0320 | 0.0 | 4.0 | 0.0 | 9.0 | 0.0 | 3.0 |
| 453 | 0.2500 | 9.0 | 9.0 | 9.0 | 9.0 | 9.0 | 9.0 |
| | 0.1250 | 9.0 | 9.0 | 9.0 | 9.0 | 9.0 | 9.0 |
| | 0.0620 | 9.0 | 9.0 | 9.0 | 9.0 | 9.0 | 9.0 |
| | 0.0320 | 9.0 | 9.0 | 9.0 | 9.0 | 9.0 | 9.0 |
| 454 | 0.2500 | 7.0 | 9.0 | 8.0 | 9.0 | 6.0 | 5.0 |
| | 0.1250 | 6.0 | 6.0 | 4.0 | 9.0 | 3.0 | 5.0 |
| | 0.0620 | 3.0 | 1.0 | 0.0 | 7.0 | 2.0 | 2.0 |
| | 0.0320 | 3.0 | 0.0 | | 2.0 | 0.0 | 2.0 |
| 455 | 0.2500 | 9.0 | 9.0 | 9.0 | 9.0 | 9.0 | 9.0 |
| | 0.1250 | 9.0 | 9.0 | 8.0 | 9.0 | 7.0 | 9.0 |
| | 0.0620 | 9.0 | 7.0 | 6.0 | 7.0 | 6.0 | 8.0 |
| | 0.0320 | 9.0 | 6.0 | 2.0 | 6.0 | 4.0 | 6.0 |
| 456 | 0.2500 | 9.0 | 6.0 | 4.0 | 9.0 | 4.0 | 9.0 |
| | 0.1250 | 7.0 | 6.0 | 2.0 | 9.0 | 2.0 | 8.0 |
| | 0.0620 | 6.0 | 4.0 | 0.0 | 9.0 | 0.0 | 8.0 |
| | 0.0320 | 4.0 | 0.0 | 0.0 | 7.0 | 0.0 | 7.0 |
| 457 | 0.2500 | 9.0 | 7.0 | 0.0 | 7.0 | 3.0 | 3.0 |
| | 0.1250 | 9.0 | 5.0 | 0.0 | 7.0 | 3.0 | 0.0 |
| | 0.0620 | 7.0 | 3.0 | 0.0 | 4.0 | 0.0 | 0.0 |
| | 0.0320 | 5.0 | 0.0 | 0.0 | 2.0 | 0.0 | 0.0 |
| 458 | 0.2500 | 8.0 | 7.0 | 6.0 | 9.0 | 8.0 | 5.0 |
| | 0.1250 | 7.0 | 7.0 | 9.0 | 9.0 | 6.0 | 5.0 |
| | 0.0620 | 6.0 | 4.0 | | 6.0 | 2.0 | 3.0 |
| | 0.0320 | 5.0 | 0.0 | 2.0 | 4.0 | 2.0 | 3.0 |
| 459 | 0.2500 | 9.0 | 4.0 | 3.0 | 7.0 | 0.0 | 5.0 |
| | 0.1250 | 9.0 | 4.0 | 0.0 | 7.0 | 0.0 | 5.0 |
| | 0.0620 | 7.0 | 2.0 | 0.0 | 5.0 | 0.0 | 4.0 |
| | 0.0320 | 7.0 | 0.0 | 0.0 | 3.0 | 0.0 | 2.0 |
| 460 | 0.2500 | 9.0 | 3.0 | 0.0 | 4.0 | 3.0 | 5.0 |
| | 0.1250 | 9.0 | 3.0 | 0.0 | 4.0 | 3.0 | 4.0 |
| | 0.0620 | 7.0 | 2.0 | | 4.0 | 0.0 | 4.0 |
| | 0.0320 | 6.0 | 0.0 | | 3.0 | 0.0 | 4.0 |
| 461 | 0.2500 | 9.0 | 9.0 | 7.0 | 9.0 | 6.0 | 6.0 |
| | 0.1250 | 9.0 | 9.0 | | 9.0 | 4.0 | 5.0 |
| | 0.0620 | 9.0 | 9.0 | | 7.0 | 3.0 | 5.0 |
| | 0.0320 | 9.0 | 6.0 | 0.0 | 7.0 | 2.0 | 5.0 |
| 462 | 0.2500 | 9.0 | 9.0 | | 9.0 | 6.0 | 6.0 |
| | 0.1250 | 9.0 | 9.0 | | 9.0 | 5.0 | 9.0 |
| | 0.0620 | 9.0 | 9.0 | 3.0 | 9.0 | 4.0 | 5.0 |
| | 0.0320 | 9.0 | 9.0 | | 9.0 | 1.0 | 5.0 |
| 463 | 0.2500 | 9.0 | 9.0 | 7.0 | 9.0 | 7.0 | 6.0 |
| | 0.1250 | 9.0 | 9.0 | 6.0 | 9.0 | 5.0 | 5.0 |
| | 0.0620 | 6.0 | 6.0 | | 9.0 | 3.0 | 2.0 |
| | 0.0320 | 2.0 | 5.0 | 2.0 | 7.0 | 0.0 | 0.0 |
| 464 | 0.2500 | 9.0 | 5.0 | 7.0 | 6.0 | 4.0 | 4.0 |
| | 0.1250 | 6.0 | 3.0 | 0.0 | 9.0 | 6.0 | 2.0 |
| | 0.0620 | | 3.0 | 0.0 | 9.0 | 0.0 | 2.0 |
| | 0.0320 | 6.0 | 0.0 | 0.0 | 7.0 | 0.0 | 0.0 |
| 465 | 0.2500 | 9.0 | 8.0 | 9.0 | 9.0 | 6.0 | 5.0 |
| | 0.1250 | 7.0 | 3.0 | 7.0 | 6.0 | 5.0 | 4.0 |
| | 0.0620 | 6.0 | 0.0 | 4.0 | 3.0 | 5.0 | 3.0 |
| | 0.0320 | 6.0 | 0.0 | 0.0 | 2.0 | 2.0 | 2.0 |
| 466 | 0.2500 | 7.0 | 9.0 | 1.0 | 9.0 | 7.0 | 9.0 |
| | 0.1250 | 5.0 | 7.0 | | 9.0 | 3.0 | 7.0 |
| | 0.0620 | 4.0 | 3.0 | | 7.0 | 0.0 | 5.0 |

TABLE III-continued

PADDY CONDITIONS - POST-TRANSPLANT RICE
PREEMERGENCE WEEDS

| Compound Number | Rate (kg/ha) | ECHORC | CYPIR | CYPSE | MOOVA | SAGPY | ORYSAT |
|---|---|---|---|---|---|---|---|
| | 0.0320 | 2.0 | 3.0 | | 7.0 | 0.0 | 4.0 |
| 467 | 0.2500 | 9.0 | 9.0 | 9.0 | 9.0 | 7.0 | 5.0 |
| | 0.1250 | 9.0 | 6.0 | 9.0 | 9.0 | 3.0 | 4.0 |
| | 0.0620 | 7.0 | 5.0 | 7.0 | 9.0 | 0.0 | 2.0 |
| | 0.0320 | 6.0 | 2.0 | 6.0 | 7.0 | 0.0 | 2.0 |
| 468 | 0.2500 | 9.0 | 5.0 | 5.0 | 5.0 | 5.0 | 5.0 |
| | 0.1250 | 9.0 | 6.0 | 7.0 | 7.0 | 4.0 | 5.0 |
| | 0.0620 | 7.0 | 6.0 | 6.0 | 6.0 | 4.0 | 3.0 |
| | 0.0320 | 7.0 | 5.0 | 2.0 | 5.0 | 3.0 | 3.0 |
| 469 | 0.2500 | 9.0 | 7.0 | 6.0 | 8.0 | 3.0 | 1.5 |
| | 0.1250 | 9.0 | 6.5 | 9.0 | 5.0 | 2.5 | 0.0 |
| | 0.0620 | 9.0 | 1.5 | 4.5 | 4.5 | 1.5 | 0.0 |
| | 0.0320 | 7.0 | 0.0 | 0.0 | 2.0 | 0.0 | 0.0 |
| 470 | 0.2500 | 9.0 | 7.0 | 4.5 | 3.0 | 1.5 | 1.5 |
| | 0.1250 | 9.0 | 6.0 | 0.0 | 2.0 | 0.0 | 1.0 |
| | 0.0620 | 9.0 | 0.0 | 0.0 | 2.0 | 0.0 | 0.0 |
| | 0.0320 | 8.5 | 0.0 | 0.0 | 1.5 | 0.0 | 0.0 |
| 471 | 0.2500 | 9.0 | 9.0 | 7.0 | 9.0 | 7.0 | 5.0 |
| | 0.1250 | 6.0 | 9.0 | | 9.0 | 5.0 | 5.0 |
| | 0.0620 | 3.0 | 6.0 | | 7.0 | 3.0 | 3.0 |
| | 0.0320 | 0.0 | 6.0 | 3.0 | 6.0 | 0.0 | 2.0 |
| 472 | 0.2500 | 4.0 | 6.0 | 9.0 | 7.0 | 3.0 | 6.0 |
| | 0.1250 | 4.0 | 5.0 | 6.0 | 7.0 | 2.0 | 3.0 |
| | 0.0620 | 3.0 | 4.0 | | 6.0 | 0.0 | 1.0 |
| | 0.0320 | 3.0 | 4.0 | 0.0 | 5.0 | 0.0 | 0.0 |
| 473 | 0.2500 | 4.0 | 8.0 | 5.0 | 7.0 | 3.0 | 5.0 |
| | 0.1250 | 2.0 | 6.0 | | 7.0 | 2.0 | 4.0 |
| | 0.0620 | 2.0 | 4.0 | 0.0 | 6.0 | 0.0 | 2.0 |
| | 0.0320 | 1.0 | 2.0 | 0.0 | 4.0 | 0.0 | 0.0 |
| 474 | 0.2500 | 0.0 | 6.0 | 0.0 | 9.0 | 0.0 | 3.0 |
| | 0.1250 | 0.0 | 4.0 | 0.0 | 7.0 | 0.0 | 2.0 |
| | 0.0620 | 0.0 | 5.0 | 0.0 | 3.0 | 0.0 | 0.0 |
| | 0.0320 | 0.0 | 2.0 | 0.0 | 2.0 | 0.0 | 0.0 |
| 475 | 0.2500 | 3.0 | 9.0 | 7.0 | 9.0 | 7.0 | 9.0 |
| | 0.1250 | 2.0 | 9.0 | 5.0 | 9.0 | 6.0 | 3.0 |
| | 0.0620 | 0.0 | 6.0 | | 9.0 | 4.0 | 0.0 |
| | 0.0320 | 0.0 | 4.0 | 0.0 | 9.0 | 0.0 | 0.0 |
| 476 | 0.2500 | 3.0 | 9.0 | 6.0 | 9.0 | 5.0 | 6.0 |
| | 0.1250 | 2.0 | 9.0 | 3.0 | 6.0 | 4.0 | 4.0 |
| | 0.0620 | 2.0 | 4.0 | | 6.0 | 2.0 | 3.0 |
| | 0.0320 | 0.0 | 4.0 | 0.0 | 5.0 | 0.0 | 2.0 |
| 477 | 0.2500 | 3.0 | 6.0 | 3.0 | 7.0 | 2.0 | 6.0 |
| | 0.1250 | 2.0 | 5.0 | | 6.0 | 0.0 | 4.0 |
| | 0.0620 | 0.0 | 4.0 | 3.0 | 3.0 | 0.0 | 4.0 |
| | 0.0320 | 0.0 | 4.0 | 3.0 | 3.0 | 0.0 | 3.0 |
| 478 | 0.2500 | 9.0 | 9.0 | 9.0 | 9.0 | 9.0 | 9.0 |
| | 0.1250 | 7.0 | 9.0 | 9.0 | 9.0 | 9.0 | 9.0 |
| | 0.0620 | 6.0 | 9.0 | 7.0 | 9.0 | 6.0 | 9.0 |
| | 0.0320 | 4.0 | 4.0 | 6.0 | 7.0 | 6.0 | 7.0 |
| 479 | 0.2500 | 9.0 | 9.0 | 9.0 | 9.0 | 8.0 | 9.0 |
| | 0.1250 | 9.0 | 5.0 | 9.0 | 9.0 | 6.0 | 9.0 |
| | 0.0620 | 7.0 | 0.0 | 7.0 | 7.0 | 5.0 | 5.0 |
| | 0.0320 | 7.0 | 0.0 | 0.0 | 0.0 | 3.0 | 5.0 |
| 480 | 0.2500 | 6.0 | 9.0 | | 9.0 | 6.0 | 6.0 |
| | 0.1250 | 5.0 | 9.0 | 3.0 | 9.0 | 5.0 | 5.0 |
| | 0.0620 | 2.0 | 9.0 | | 9.0 | 3.0 | 5.0 |
| | 0.0320 | 0.0 | 6.0 | 3.0 | 7.0 | 0.0 | 4.0 |
| 481 | 0.2500 | 9.0 | 9.0 | 6.0 | 9.0 | | 7.0 |
| | 0.1250 | 9.0 | 6.0 | | 7.0 | 0.0 | 2.0 |
| | 0.0620 | 2.0 | 2.0 | | 7.0 | 0.0 | 0.0 |
| | 0.0320 | 0.0 | 0.0 | | 6.0 | 0.0 | 0.0 |
| 482 | 0.2500 | 9.0 | 6.0 | | 7.0 | 7.0 | 7.0 |
| | 0.1250 | 9.0 | 0.0 | | 6.0 | 5.0 | 6.0 |
| | 0.0620 | 7.0 | 0.0 | | 5.0 | 4.0 | 2.0 |
| | 0.0320 | 4.0 | 0.0 | | 4.0 | 3.0 | 0.0 |
| 483 | 0.2500 | 7.0 | 6.0 | 6.0 | 9.0 | 5.0 | 6.0 |
| | 0.1250 | 7.0 | 5.0 | | 9.0 | 3.0 | 5.0 |
| | 0.0620 | 7.0 | 2.0 | 4.0 | 9.0 | 0.0 | 3.0 |
| | 0.320 | 6.0 | 0.0 | | 7.0 | 0.0 | 3.0 |
| 484 | 0.2500 | 9.0 | 9.0 | | 9.0 | | 6.0 |
| | 0.1250 | 7.0 | 6.0 | | 9.0 | | 6.0 |
| | 0.0620 | 4.0 | 4.0 | | 9.0 | | 5.0 |
| | 0.0320 | 5.0 | 4.0 | 0.0 | 7.0 | 5.0 | 5.0 |

TABLE III-continued

PADDY CONDITIONS - POST-TRANSPLANT RICE
PREEMERGENCE WEEDS

| Compound Number | Rate (kg/ha) | ECHORC | CYPIR | CYPSE | MOOVA | SAGPY | ORYSAT |
|---|---|---|---|---|---|---|---|
| 485 | 0.2500 | 9.0 | 6.0 | | 8.0 | 3.0 | 5.0 |
| | 0.1250 | 6.0 | 5.0 | | 7.0 | 0.0 | 4.0 |
| | 0.0620 | 6.0 | 4.0 | 0.0 | 6.0 | 0.0 | 2.0 |
| | 0.0320 | 4.0 | 2.0 | 0.0 | 4.0 | 0.0 | 0.0 |
| 486 | 0.2500 | 9.0 | 6.0 | 3.0 | 9.0 | 6.0 | 6.0 |
| | 0.1250 | 7.0 | 6.0 | | 7.0 | 3.0 | 5.0 |
| | 0.0620 | 6.0 | 5.0 | 0.0 | 6.0 | 0.0 | 3.0 |
| | 0.0320 | 4.0 | 4.0 | 0.0 | 5.0 | 0.0 | 0.0 |
| 487 | 0.2500 | 9.0 | 9.0 | 3.0 | 9.0 | 7.0 | 7.0 |
| | 0.1250 | 7.0 | 6.0 | | 9.0 | 6.0 | 6.0 |
| | 0.0620 | 7.0 | 5.0 | | 9.0 | 5.0 | 3.0 |
| | 0.0320 | 6.0 | 4.0 | | 7.0 | 4.0 | 2.0 |
| 488 | 0.2500 | 0.0 | 5.0 | | 9.0 | 0.0 | 4.0 |
| | 0.1250 | 0.0 | 4.0 | 0.0 | 9.0 | 0.0 | 4.0 |
| | 0.0620 | 0.0 | 3.0 | 0.0 | 9.0 | 0.0 | 3.0 |
| | 0.0320 | 0.0 | 3.0 | | 7.0 | 0.0 | 3.0 |
| 489 | 0.2500 | 9.0 | 9.0 | 9.0 | 9.0 | 9.0 | 6.0 |
| | 0.1250 | 9.0 | 9.0 | 9.0 | 9.0 | 9.0 | 6.0 |
| | 0.0620 | 7.0 | 9.0 | 7.0 | 9.0 | 9.0 | 6.0 |
| | 0.0320 | 7.0 | 6.0 | 6.0 | 9.0 | 6.0 | 5.0 |
| 490 | 0.2500 | 9.0 | 9.0 | 9.0 | 9.0 | 9.0 | 9.0 |
| | 0.1250 | 9.0 | 9.0 | 9.0 | 9.0 | 9.0 | 8.5 |
| | 0.0620 | 9.0 | 9.0 | 9.0 | 9.0 | 9.0 | 9.0 |
| | 0.0320 | 8.0 | 9.0 | 9.0 | 9.0 | 6.0 | 7.5 |
| 491 | 0.2500 | 9.0 | 9.0 | 9.0 | 9.0 | 9.0 | 7.5 |
| | 0.1250 | 9.0 | 9.0 | 9.0 | 9.0 | 9.0 | 8.0 |
| | 0.0620 | 9.0 | 9.0 | 9.0 | 9.0 | 5.5 | 6.5 |
| | 0.0320 | 9.0 | 7.5 | 7.0 | 9.0 | 5.0 | 5.0 |
| 492 | 0.2500 | 9.0 | 5.0 | 0.0 | 7.0 | 2.0 | 3.0 |
| | 0.1250 | 6.0 | 4.0 | | 7.0 | 0.0 | 2.0 |
| | 0.0620 | 6.0 | 4.0 | | 6.0 | 0.0 | 2.0 |
| | 0.0320 | 4.0 | 4.0 | | 6.0 | 0.0 | 2.0 |
| 493 | 0.2500 | 9.0 | 9.0 | 9.0 | 9.0 | 3.0 | 3.0 |
| | 0.1250 | 9.0 | 7.0 | 9.0 | 7.0 | 0.0 | 3.0 |
| | 0.0620 | 5.0 | 6.0 | | 7.0 | 0.0 | 2.0 |
| | 0.0320 | 4.0 | 4.0 | | 5.0 | 0.0 | 2.0 |
| 494 | 0.2500 | 3.0 | 5.0 | 3.0 | 6.0 | 3.0 | 0.0 |
| | 0.1250 | 3.0 | 5.0 | 0.0 | 5.0 | 0.0 | 0.0 |
| | 0.0620 | 2.0 | 4.0 | | 4.0 | 0.0 | 0.0 |
| | 0.0320 | 0.0 | 3.0 | | 4.0 | 0.0 | 0.0 |
| 495 | 0.2500 | 7.0 | 9.0 | | 9.0 | | 7.0 |
| | 0.1250 | 5.0 | 7.0 | | 9.0 | 3.0 | 5.0 |
| | 0.0620 | 4.0 | 6.0 | | 7.0 | 0.0 | 4.0 |
| | 0.0320 | 3.0 | 6.0 | | 7.0 | 0.0 | 2.0 |
| 496 | 0.2500 | 7.0 | 9.0 | 7.0 | 8.0 | 6.0 | 5.0 |
| | 0.1250 | 6.0 | 7.0 | | 6.0 | 3.0 | 3.0 |
| | 0.0620 | 4.0 | 7.0 | | 6.0 | 0.0 | 3.0 |
| | 0.0320 | 4.0 | 0.0 | | 0.0 | 0.0 | 0.0 |
| 497 | 0.2500 | 7.0 | 9.0 | 9.0 | 9.0 | 6.0 | 8.0 |
| | 0.1250 | 4.0 | 9.0 | 6.0 | 9.0 | 2.0 | 7.0 |
| | 0.0620 | 0.0 | 6.0 | | 7.0 | 0.0 | 3.0 |
| | 0.0320 | 0.0 | 5.0 | | 6.0 | 0.0 | 0.0 |
| 498 | 0.2500 | 6.0 | 9.0 | | 8.0 | 6.0 | 6.0 |
| | 0.1250 | 5.0 | 9.0 | 0.0 | 7.0 | 3.0 | 3.0 |
| | 0.0620 | 3.0 | 5.0 | | 5.0 | 0.0 | 2.0 |
| | 0.0320 | 0.0 | 2.0 | | 4.0 | 0.0 | 0.0 |
| 499 | 0.2500 | 9.0 | 9.0 | 9.0 | 9.0 | 9.0 | 9.0 |
| | 0.1250 | 9.0 | 9.0 | 9.0 | 9.0 | 9.0 | 7.5 |
| | 0.0620 | 9.0 | 9.0 | 9.0 | 9.0 | 9.0 | 8.0 |
| | 0.0320 | 7.5 | 8.0 | 9.0 | 8.0 | 8.0 | 6.5 |
| 500 | 0.2500 | 9.0 | 9.0 | 0.0 | 9.0 | 9.0 | 2.0 |
| | 0.1250 | 7.0 | 6.0 | 0.0 | 9.0 | 7.0 | 2.0 |
| | 0.0620 | 6.0 | 6.0 | 0.0 | 9.0 | 7.0 | 2.0 |
| | 0.0320 | 4.0 | 6.0 | 0.0 | 7.0 | 5.0 | 2.0 |
| 501 | 0.2500 | 7.0 | 6.0 | 5.0 | 9.0 | 6.0 | 4.0 |
| | 0.1250 | 5.0 | 4.0 | 3.0 | 7.0 | 5.0 | 3.0 |
| | 0.0620 | 5.0 | 2.0 | 0.0 | 6.0 | 3.0 | 1.0 |
| | 0.0320 | 4.0 | 0.0 | 0.0 | 6.0 | 2.0 | 0.0 |
| 502 | 0.2500 | 7.0 | 9.0 | 5.0 | 9.0 | 9.0 | 6.0 |
| | 0.1250 | 5.0 | 9.0 | | 7.0 | 5.0 | 5.0 |
| | 0.0620 | 3.0 | 6.0 | 2.0 | 6.0 | 2.0 | 2.0 |
| | 0.0320 | 3.0 | 4.0 | 0.0 | 6.0 | 0.0 | 2.0 |
| 503 | 0.2500 | 6.0 | 7.0 | 6.0 | 9.0 | 8.0 | 6.0 |

TABLE III-continued

PADDY CONDITIONS - POST-TRANSPLANT RICE
PREEMERGENCE WEEDS

| Compound Number | Rate (kg/ha) | ECHORC | CYPIR | CYPSE | MOOVA | SAGPY | ORYSAT |
|---|---|---|---|---|---|---|---|
| | 0.1250 | 6.0 | 9.0 | 5.0 | 9.0 | 4.0 | 7.0 |
| | 0.0620 | 4.0 | 6.0 | | 9.0 | 3.0 | 3.0 |
| | 0.0320 | 2.0 | 0.0 | | 7.0 | 0.0 | 1.0 |
| 504 | 0.2500 | 7.0 | 9.0 | | 9.0 | 7.0 | 5.0 |
| | 0.1250 | 6.0 | 9.0 | 0.0 | 9.0 | | 3.0 |
| | 0.0620 | 3.0 | 7.0 | 0.0 | 8.0 | | |
| | 0.0320 | 2.0 | 4.0 | 0.0 | 6.0 | 0.0 | 3.0 |
| 505 | 0.2500 | 9.0 | 4.0 | | 8.0 | 4.0 | 6.0 |
| | 0.1250 | 7.0 | 3.0 | 0.0 | 7.0 | 2.0 | 4.0 |
| | 0.0620 | 6.0 | | 0.0 | 7.0 | 2.0 | 4.0 |
| | 0.0320 | 6.0 | 0.0 | | 7.0 | 0.0 | 4.0 |
| 506 | 0.2500 | 9.0 | 9.0 | 7.0 | 9.0 | 4.5 | 2.0 |
| | 0.1250 | 9.0 | 9.0 | 4.5 | 9.0 | 3.0 | 1.5 |
| | 0.0620 | 9.0 | 8.0 | 4.5 | 9.0 | 3.0 | 1.5 |
| | 0.0320 | 7.5 | 6.5 | 4.5 | 8.0 | 2.5 | 1.5 |
| 507 | 0.2500 | 7.0 | 9.0 | | 9.0 | 9.0 | 5.0 |
| | 0.1250 | 4.0 | 9.0 | | 9.0 | 9.0 | 7.0 |
| | 0.0620 | 2.0 | 6.0 | | 9.0 | 9.0 | 5.0 |
| | 0.0320 | 2.0 | 5.0 | 0.0 | 9.0 | 7.0 | 3.0 |
| 508 | 0.2500 | 9.0 | 9.0 | | 9.0 | 9.0 | 6.0 |
| | 0.1250 | 6.0 | 7.0 | | 9.0 | 9.0 | 5.0 |
| | 0.0620 | 5.0 | 7.0 | | 9.0 | 6.0 | 2.0 |
| | 0.0320 | 2.0 | 6.0 | 0.0 | 9.0 | 5.0 | 0.0 |
| 509 | 0.2500 | 7.0 | 7.0 | 7.0 | 9.0 | 6.0 | 7.0 |
| | 0.1250 | 2.0 | 4.0 | 0.0 | 4.0 | 3.0 | 3.0 |
| | 0.0620 | 0.0 | 0.0 | 0.0 | 0.0 | 0.0 | 0.0 |
| 510 | 0.2500 | 9.0 | 8.0 | 5.0 | 9.0 | 6.0 | 8.0 |
| | 0.1250 | 9.0 | 7.0 | 3.0 | 9.0 | 5.0 | 4.0 |
| | 0.0620 | 9.0 | 3.0 | 0.0 | 7.0 | 4.0 | 2.0 |
| | 0.0320 | 9.0 | 0.0 | 0.0 | 6.0 | 3.0 | 0.0 |
| 511 | 0.2500 | 7.0 | 7.0 | 3.0 | | 7.0 | 6.0 |
| | 0.1250 | 5.0 | 2.0 | 3.0 | | 0.0 | 5.0 |
| | 0.0620 | 2.0 | 0.0 | 0.0 | | 0.0 | 4.0 |
| | 0.0320 | 0.0 | 0.0 | 0.0 | | 0.0 | 3.0 |
| 512 | 0.2500 | 9.0 | 5.0 | 0.0 | 9.0 | 4.0 | 2.0 |
| | 0.1250 | 9.0 | 5.0 | 0.0 | 9.0 | 2.0 | 1.0 |
| | 0.0620 | 7.0 | 2.0 | 0.0 | 9.0 | 0.0 | 0.0 |
| | 0.0320 | 7.0 | 0.0 | 0.0 | 9.0 | 0.0 | 0.0 |
| 513 | 0.2500 | 8.0 | 9.0 | 9.0 | 9.0 | 9.0 | 9.0 |
| | 0.1250 | 7.0 | 6.0 | 9.0 | 9.0 | 9.0 | 9.0 |
| | 0.0620 | 5.0 | 4.0 | 9.0 | 9.0 | 9.0 | 7.0 |
| | 0.0320 | 0.0 | 4.0 | 9.0 | 9.0 | 9.0 | 9.0 |
| 514 | 0.2500 | 8.0 | 7.0 | 0.0 | 9.0 | 0.0 | 4.0 |
| | 0.1250 | 2.0 | 2.0 | 0.0 | 9.0 | 0.0 | 1.0 |
| | 0.0620 | 1.0 | 0.0 | 0.0 | 9.0 | 0.0 | 2.0 |
| | 0.0320 | 0.0 | 0.0 | 0.0 | 9.0 | 0.0 | 2.0 |
| 515 | 0.2500 | 9.0 | 7.0 | 0.0 | 9.0 | 0.0 | 6.0 |
| | 0.1250 | 8.0 | 4.0 | 0.0 | 9.0 | 0.0 | 4.0 |
| | 0.0620 | 6.0 | 2.0 | 0.0 | 9.0 | 0.0 | 2.0 |
| | 0.0320 | 2.0 | 0.0 | 0.0 | 9.0 | 0.0 | 0.0 |
| 516 | 0.2500 | 0.0 | 2.0 | 0.0 | 9.0 | 0.0 | 3.0 |
| | 0.1250 | 0.0 | 0.0 | 0.0 | 8.0 | 0.0 | 2.0 |
| | 0.0620 | 0.0 | 0.0 | 0.0 | 6.0 | 0.0 | 1.0 |
| | 0.0320 | 0.0 | 0.0 | 0.0 | 4.0 | 0.0 | 0.0 |
| 517 | 0.2500 | 9.0 | 7.0 | 0.0 | 9.0 | 0.0 | 3.0 |
| | 0.1250 | 8.0 | 5.5 | 4.5 | 9.0 | 0.0 | 1.5 |
| | 0.0620 | 9.0 | 6.5 | 4.5 | 9.0 | 0.0 | 0.0 |
| | 0.0320 | 9.0 | 5.5 | 3.0 | 9.0 | 0.0 | 0.0 |
| 518 | 0.2500 | 7.0 | 4.0 | 0.0 | 9.0 | 0.0 | 4.0 |
| | 0.1250 | 4.0 | 2.0 | 0.0 | 9.0 | 0.0 | 4.0 |
| | 0.0620 | 2.0 | 2.0 | 0.0 | 7.0 | 0.0 | 2.0 |
| | 0.0320 | 0.0 | 0.0 | 0.0 | 4.0 | 0.0 | 1.0 |
| 519 | 0.2500 | 9.0 | 6.0 | 0.0 | 9.0 | 0.0 | 4.0 |
| | 0.1250 | 6.5 | 2.0 | 0.0 | 9.0 | 0.0 | 4.5 |
| | 0.0620 | 4.0 | 0.0 | 0.0 | 9.0 | 0.0 | 4.0 |
| | 0.0320 | 2.0 | 0.0 | 0.0 | 9.0 | 0.0 | 2.0 |
| 520 | 0.2500 | 9.0 | 4.0 | 0.0 | 9.0 | 0.0 | 3.0 |
| | 0.1250 | 8.5 | 2.0 | 0.0 | 9.0 | 0.0 | 4.5 |
| | 0.0620 | 8.0 | 0.0 | 0.0 | 9.0 | 0.0 | 3.5 |
| | 0.0320 | 6.5 | 0.0 | 0.0 | 9.0 | 0.0 | 2.0 |
| 521 | 0.2500 | 4.0 | 2.0 | 0.0 | 9.0 | 0.0 | 0.0 |
| | 0.1250 | 4.0 | 0.0 | 0.0 | 9.0 | 0.0 | 0.0 |
| | 0.0620 | 2.0 | 0.0 | 0.0 | 9.0 | 0.0 | 0.0 |

TABLE III-continued

PADDY CONDITIONS - POST-TRANSPLANT RICE PREEMERGENCE WEEDS

| Compound Number | Rate (kg/ha) | ECHORC | CYPIR | CYPSE | MOOVA | SAGPY | ORYSAT |
|---|---|---|---|---|---|---|---|
|  | 0.0320 | 2.0 | 0.0 | 0.0 | 6.0 | 0.0 | 0.0 |
| 522 | 0.2500 | 9.0 | 2.0 | 0.0 | 9.0 | 0.0 | 4.5 |
|  | 0.1250 | 8.0 | 0.0 | 0.0 | 9.0 | 0.0 | 4.0 |
|  | 0.0620 | 6.5 | 0.0 | 0.0 | 9.0 | 0.0 | 4.0 |
|  | 0.0320 | 5.5 | 0.0 | 0.0 | 9.0 | 0.0 | 2.5 |
| 523 | 0.2500 | 9.0 | 8.0 | 9.0 | 9.0 | 0.0 | 7.0 |
|  | 0.1250 | 8.0 | 4.0 | 2.0 | 9.0 | 0.0 | 5.5 |
|  | 0.0620 | 8.0 | 2.0 | 0.0 | 9.0 | 0.0 | 4.5 |
|  | 0.0320 | 6.0 | 0.0 | 0.0 | 8.0 | 0.0 | 4.5 |
| 524 | 0.2500 | 9.0 | 7.0 | 6.0 | 9.0 | 0.0 | 9.0 |
|  | 0.1250 | 9.0 | 4.0 | 2.0 | 9.0 | 0.0 | 7.0 |
|  | 0.0620 | 9.0 | 2.0 | 0.0 | 9.0 | 0.0 | 4.0 |
|  | 0.0320 | 7.0 | 2.0 | 0.0 | 9.0 | 0.0 | 2.0 |
| 525 | 0.2500 | 9.0 | 4.0 | 0.0 | 9.0 | 0.0 | 4.0 |
|  | 0.1250 | 9.0 | 2.0 | 0.0 | 9.0 | 0.0 | 2.0 |
|  | 0.0620 | 7.0 | 2.0 | 0.0 | 9.0 | 0.0 | 2.0 |
|  | 0.0320 | 6.0 | 0.0 | 0.0 | 9.0 | 0.0 | 0.0 |
| 526 | 0.2500 | 6.0 | 9.0 | 0.0 | 9.0 | 0.0 | 3.0 |
|  | 0.1250 | 4.0 | 7.0 | 0.0 | 9.0 | 0.0 | 2.0 |
|  | 0.0620 | 2.0 | 4.0 | 0.0 | 9.0 | 0.0 | 2.0 |
|  | 0.0320 | 2.0 | 2.0 | 0.0 | 8.0 | 0.0 | 1.0 |
| 527 | 0.2500 | 9.0 | 4.0 | 0.0 | 9.0 | 0.0 | 4.0 |
|  | 0.1250 | 9.0 | 4.0 | 0.0 | 9.0 | 0.0 | 2.5 |
|  | 0.0620 | 8.0 | 2.0 | 0.0 | 9.0 | 0.0 | 2.5 |
|  | 0.0320 | 3.0 | 2.0 | 0.0 | 9.0 | 0.0 | 2.0 |
| 528 | 0.2500 | 9.0 | 9.0 | 0.0 | 9.0 | 3.0 | 9.0 |
|  | 0.1250 | 9.0 | 5.0 | 0.0 | 9.0 | 1.5 | 7.0 |
|  | 0.0620 | 9.0 | 5.0 | 0.0 | 9.0 | 0.0 | 3.5 |
|  | 0.0320 | 9.0 | 4.5 | 0.0 | 9.0 | 1.0 | 1.5 |
| 529 | 0.2500 | 9.0 | 0.0 | 0.0 | 0.0 | 9.0 | 9.0 |
|  | 0.1250 | 9.0 | 3.0 | 0.0 | 3.0 | 9.0 | 3.0 |
|  | 0.0620 | 9.0 | 3.0 | 0.0 | 3.0 | 9.0 | 0.0 |
|  | 0.0320 | 7.0 | 3.0 | 0.0 | 3.0 | 9.0 | 0.0 |
| 530 | 0.2500 | 9.0 | 9.0 | 0.0 | 9.0 | 9.0 | 9.0 |
|  | 0.1250 | 9.0 | 9.0 | 0.0 | 9.0 | 3.0 | 3.0 |
|  | 0.0620 | 9.0 | 9.0 | 0.0 | 9.0 | 0.0 | 0.0 |
|  | 0.0320 | 9.0 | 0.0 | 0.0 | 9.0 | 0.0 | 0.0 |
| 531 | 0.2500 | 9.0 | 4.0 | 3.0 | 9.0 | 3.0 | 9.0 |
|  | 0.1250 | 9.0 | 4.0 | 3.0 | 9.0 | 3.0 | 3.0 |
|  | 0.0620 | 9.0 | 0.0 | 0.0 | 9.0 | 0.0 | 0.0 |
|  | 0.0320 | 9.0 | 0.0 | 0.0 | 9.0 | 0.0 | 0.0 |
| 532 | 0.2500 | 9.0 | 9.0 | 0.0 | 9.0 | 9.0 | 2.0 |
|  | 0.1250 | 9.0 | 9.0 | 0.0 | 9.0 | 0.0 | 0.0 |
|  | 0.0620 | 9.0 | 9.0 | 0.0 | 9.0 | 0.0 | 0.0 |
|  | 0.0320 | 9.0 | 9.0 | 0.0 | 9.0 | 0.0 | 0.0 |
| 533 | 0.2500 | 9.0 | 9.0 | 9.0 | 9.0 | 4.0 | 8.0 |
|  | 0.1250 | 9.0 | 4.0 | 3.0 | 9.0 | 0.0 | 5.0 |
|  | 0.0620 | 9.0 | 3.0 | 0.0 | 9.0 | 0.0 | 4.5 |
|  | 0.0320 | 7.5 | 2.0 | 0.0 | 9.0 | 0.0 | 3.0 |
| 534 | 0.2500 | 9.0 | 9.0 | 0.0 | 9.0 | 0.0 | 4.5 |
|  | 0.1250 | 9.0 | 3.0 | 0.0 | 9.0 | 0.0 | 4.0 |
|  | 0.0620 | 4.5 | 3.0 | 0.0 | 9.0 | 0.0 | 4.0 |
|  | 0.0320 | 3.5 | 0.0 | 0.0 | 4.0 | 0.0 | 2.0 |
| 535 | 0.2500 | 4.0 | 9.0 | 5.0 | 9.0 | 3.0 | 9.0 |
|  | 0.1250 | 3.0 | 9.0 | 5.0 | 9.0 | 3.0 | 4.0 |
|  | 0.0620 | 3.0 | 6.0 | 3.0 | 9.0 | 0.0 | 3.0 |
|  | 0.0320 | 0.0 | 0.0 | 0.0 | 6.0 | 0.0 | 0.0 |
| 536 | 0.2500 | 9.0 | 4.0 | 0.0 | 9.0 | 0.0 | 4.0 |
|  | 0.1250 | 5.0 | 0.0 | 0.0 | 9.0 | 0.0 | 1.0 |
|  | 0.0620 | 4.0 | 0.0 | 0.0 | 9.0 | 0.0 | 0.0 |
|  | 0.0320 | 3.0 | 0.0 | 0.0 | 9.0 | 0.0 | 0.0 |
| 537 | 0.5000 | 9.0 | 9.0 | 0.0 | 9.0 | 0.0 | 0.0 |
|  | 0.2500 | 9.0 | 4.0 | 0.0 | 9.0 | 0.0 | 0.0 |
|  | 0.1250 | 5.0 | 1.0 | 0.0 | 9.0 | 0.0 | 0.0 |
|  | 0.0620 | 4.4 | 0.0 | 0.0 | 9.0 | 0.0 | 0.0 |
|  | 0.0320 | 3.4 | 0.0 | 0.0 | 9.0 | 0.0 | 0.0 |
| 538 | 0.5000 | 9.0 | 9.0 | 0.0 | 9.0 | 0.0 | 1.0 |
|  | 0.2500 | 9.0 | 0.0 | 0.0 | 9.0 | 0.0 | 1.0 |
|  | 0.1250 | 4.7 | 0.0 | 0.0 | 9.0 | 0.0 | 1.0 |
|  | 0.0620 | 3.4 | 0.0 | 0.0 | 9.0 | 0.0 | 0.0 |
|  | 0.0320 | 2.1 | 0.0 | 0.0 | 9.0 | 0.0 | 0.0 |
| 539 | 0.5000 | 9.0 | 9.0 | 2.0 | 9.0 | 9.0 | 5.0 |
|  | 0.2500 | 7.0 | 8.0 | 0.0 | 9.0 | 4.0 | 1.0 |

TABLE III-continued

PADDY CONDITIONS - POST-TRANSPLANT RICE PREEMERGENCE WEEDS

| Compound Number | Rate (kg/ha) | ECHORC | CYPIR | CYPSE | MOOVA | SAGPY | ORYSAT |
|---|---|---|---|---|---|---|---|
| | 0.1250 | 4.7 | 6.0 | 0.0 | 9.0 | 1.0 | 1.0 |
| | 0.0620 | 3.0 | 2.0 | 0.0 | 9.0 | 0.0 | 1.0 |
| | 0.0320 | 2.1 | 0.0 | 0.0 | 8.0 | 0.0 | 0.0 |
| 540 | 0.5000 | 9.0 | 9.0 | 3.0 | 9.0 | 0.0 | 3.0 |
| | 0.2500 | 9.0 | 9.0 | 0.0 | 9.0 | 0.0 | 1.0 |
| | 0.1250 | 4.7 | 9.0 | 0.0 | 9.0 | 0.0 | 0.0 |
| | 0.0620 | 3.4 | 8.0 | 0.0 | 9.0 | 0.0 | 0.0 |
| | 0.0320 | 2.3 | 6.0 | 0.0 | 8.0 | 0.0 | 0.0 |
| 541 | 0.5000 | 6.0 | 9.0 | 0.0 | 9.0 | 0.0 | 2.0 |
| | 0.2500 | 4.0 | 6.0 | 0.0 | 9.0 | 0.0 | 0.0 |
| | 0.1250 | 0.0 | 4.0 | 0.0 | 9.0 | 0.0 | 0.0 |
| | 0.0620 | 0.0 | 3.0 | 0.0 | 9.0 | 0.0 | 0.0 |
| 542 | 0.5000 | 9.0 | 9.0 | 0.0 | 9.0 | 9.0 | 2.0 |
| | 0.2500 | 8.0 | 4.0 | | 9.0 | 0.0 | 0.0 |
| | 0.1250 | 4.3 | 2.0 | 0.0 | 9.0 | 0.0 | 0.0 |
| | 0.0620 | 2.7 | 0.0 | 0.0 | 9.0 | 0.0 | 0.0 |
| | 0.0320 | 1.7 | 0.0 | 0.0 | 7.0 | 0.0 | 0.0 |
| 543 | 0.5000 | 9.0 | 3.0 | 0.0 | 9.0 | 0.0 | 2.0 |
| | 0.2500 | 7.0 | 8.0 | 0.0 | 9.0 | 0.0 | 2.0 |
| | 0.1250 | 4.0 | 7.0 | 0.0 | 9.0 | 0.0 | 1.0 |
| | 0.0620 | 2.9 | 6.0 | 0.0 | 9.0 | 0.0 | 0.0 |
| | 0.0320 | 2.1 | 2.0 | 0.0 | 9.0 | 0.0 | 0.0 |
| 544 | 0.5000 | 9.0 | 9.0 | 4.0 | 9.0 | 9.0 | 8.0 |
| | 0.2500 | 9.0 | 9.0 | 9.0 | 9.0 | 9.0 | 9.0 |
| | 0.1250 | 6.4 | 9.0 | 7.0 | 9.0 | 8.0 | 9.0 |
| | 0.0620 | 5.6 | 9.0 | | 9.0 | 4.0 | 9.0 |
| | 0.0320 | 5.4 | 9.0 | 9.0 | 9.0 | 7.0 | 4.0 |
| 545 | 0.5000 | 9.0 | 9.0 | 6.0 | 9.0 | 9.0 | 9.0 |
| | 0.2500 | 9.0 | 7.0 | 9.0 | 9.0 | 7.0 | 9.0 |
| | 0.1250 | 7.0 | 6.0 | 9.0 | 9.0 | 4.0 | 4.0 |
| | 0.0620 | 6.6 | 5.0 | 0.0 | 7.0 | 0.0 | 2.0 |
| | 0.0320 | 5.6 | 4.0 | 0.0 | 6.0 | 0.0 | 2.0 |
| 546 | 0.5000 | 9.0 | 2.0 | 0.0 | 9.0 | 9.0 | 6.0 |
| | 0.2500 | 9.0 | 9.0 | 9.0 | 9.0 | 9.0 | 7.0 |
| | 0.1250 | 4.6 | 6.0 | 9.0 | 7.0 | 4.0 | 4.0 |
| | 0.0620 | 4.3 | 4.0 | 0.0 | 7.0 | 0.0 | 3.0 |
| | 0.0320 | 4.1 | 3.0 | 0.0 | 6.0 | 0.0 | 2.0 |
| 547 | 0.5000 | 9.0 | 9.0 | 0.0 | 9.0 | 3.0 | 3.0 |
| | 0.2500 | 9.0 | 9.0 | 7.0 | 9.0 | 7.0 | 4.0 |
| | 0.1250 | 5.6 | 9.0 | 8.0 | 9.0 | 4.0 | 4.0 |
| | 0.0620 | 5.4 | 7.0 | 8.0 | 9.0 | 4.0 | 3.0 |
| | 0.0320 | 5.4 | 7.0 | 6.0 | 9.0 | 2.0 | 2.0 |
| 548 | 0.5000 | 6.0 | 0.0 | 9.0 | 9.0 | 0.0 | 4.0 |
| | 0.2500 | 9.0 | 9.0 | 9.0 | 9.0 | 4.0 | 6.0 |
| | 0.1250 | 4.9 | 8.0 | 9.0 | 9.0 | 2.0 | 4.0 |
| | 0.0620 | 3.7 | 6.0 | 9.0 | 9.0 | 0.0 | 2.0 |
| | 0.0320 | 2.9 | 2.0 | | 8.0 | 0.0 | 3.0 |
| 549 | 0.5000 | 9.0 | 9.0 | 9.0 | 9.0 | 0.0 | 2.0 |
| | 0.2500 | 9.0 | 9.0 | 9.0 | 9.0 | 4.0 | 4.0 |
| | 0.1250 | 5.1 | 9.0 | 2.0 | 9.0 | 4.0 | 4.0 |
| | 0.0620 | 3.6 | 9.0 | 0.0 | 9.0 | 0.0 | 4.0 |
| | 0.0320 | 3.0 | 7.0 | 0.0 | 9.0 | 0.0 | 4.0 |
| 550 | 0.5000 | 9.0 | 5.0 | 9.0 | 9.0 | 0.0 | 0.0 |
| | 0.2500 | 9.0 | 7.0 | 0.0 | 9.0 | 0.0 | 0.0 |
| | 0.1250 | 5.9 | 8.0 | 0.0 | 9.0 | 0.0 | 0.0 |
| | 0.0620 | 5.9 | 8.0 | 0.0 | 9.0 | 0.0 | 0.0 |
| | 0.0320 | 4.7 | 2.0 | 0.0 | 9.0 | 0.0 | 0.0 |
| 551 | 0.5000 | 9.0 | 9.0 | 0.0 | 9.0 | 2.0 | 4.0 |
| | 0.2500 | 7.0 | 2.0 | 0.0 | 9.0 | 0.0 | 3.0 |
| | 0.1250 | 7.0 | 0.0 | 0.0 | 9.0 | 0.0 | 3.0 |
| | 0.0620 | 4.0 | 0.0 | 0.0 | 0.0 | 0.0 | 0.0 |
| 552 | 0.5000 | 9.0 | 9.0 | 9.0 | 9.0 | 5.0 | 4.0 |
| | 0.2500 | 9.0 | 9.0 | 9.0 | 9.0 | 0.0 | 7.0 |
| | 0.1250 | 4.7 | 7.0 | 4.0 | 9.0 | 0.0 | 6.0 |
| | 0.0620 | 3.7 | 8.0 | | 8.0 | 0.0 | 6.0 |
| | 0.0320 | 2.6 | 6.0 | 0.0 | 6.0 | 0.0 | 4.0 |
| 553 | 0.5000 | 7.0 | 4.0 | 9.0 | 9.0 | 0.0 | 4.0 |
| | 0.2500 | 9.0 | 9.0 | 2.0 | 9.0 | 0.0 | 6.0 |
| | 0.1250 | 6.4 | 7.0 | | 9.0 | 0.0 | 4.0 |
| | 0.0620 | 2.1 | 6.0 | 0.0 | 9.0 | 0.0 | 4.0 |
| | 0.0320 | 1.3 | 2.0 | 0.0 | 7.0 | 0.0 | 3.0 |
| 554 | 0.5000 | 7.0 | 5.0 | 9.0 | 9.0 | 0.0 | 6.0 |
| | 0.2500 | 9.0 | 9.0 | 9.0 | 9.0 | 9.0 | 7.0 |

TABLE III-continued

PADDY CONDITIONS - POST-TRANSPLANT RICE PREEMERGENCE WEEDS

| Compound Number | Rate (kg/ha) | ECHORC | CYPIR | CYPSE | MOOVA | SAGPY | ORYSAT |
|---|---|---|---|---|---|---|---|
|  | 0.1250 | 5.7 | 9.0 | 4.0 | 9.0 | 0.0 | 6.0 |
|  | 0.0620 | 4.1 | 7.0 | 0.0 | 9.0 | 0.0 | 4.0 |
|  | 0.0320 | 3.0 | 2.0 | 0.0 | 9.0 | 0.0 | 4.0 |
| 555 | 0.5000 | 9.0 | 3.0 | 9.0 | 9.0 | 0.0 | 3.0 |
|  | 0.2500 | 9.0 | 9.0 | 8.0 | 9.0 | 7.0 | 9.0 |
|  | 0.1250 | 4.6 | 9.0 | 8.0 | 9.0 | 2.0 | 8.0 |
|  | 0.0620 | 2.3 | 6.0 | 6.0 | 9.0 | 0.0 | 6.0 |
|  | 0.0320 | 1.6 | 4.0 | 4.0 | 9.0 | 0.0 | 6.0 |
| 556 | 0.5000 | 9.0 | 3.0 | 0.0 | 9.0 | 3.0 | 5.0 |
|  | 0.2500 | 9.0 | 9.0 | 9.0 | 9.0 | 4.0 | 9.0 |
|  | 0.1250 | 4.4 | 7.0 | 9.0 | 9.0 | 6.0 | 8.0 |
|  | 0.0620 | 3.6 | 2.0 | 2.0 | 9.0 | 0.0 | 7.0 |
|  | 0.0320 | 2.9 | 0.0 | 2.0 | 9.0 | 0.0 | 4.0 |
| 557 | 0.5000 | 9.0 | 9.0 | 5.0 | 9.0 | 4.0 | 9.0 |
|  | 0.2500 | 9.0 | 9.0 | 9.0 | 9.0 | 4.0 | 9.0 |
|  | 0.1250 | 6.3 | 9.0 | 6.0 | 9.0 | 2.0 | 8.0 |
|  | 0.0620 | 5.1 | 8.0 |  | 9.0 | 0.0 | 8.0 |
|  | 0.0320 | 4.3 | 4.0 | 0.0 | 9.0 | 0.0 | 6.0 |
| 558 | 0.5000 | 9.0 | 9.0 | 9.0 | 9.0 | 4.0 | 9.0 |
|  | 0.2500 | 9.0 | 9.0 | 9.0 | 9.0 | 8.0 | 9.0 |
|  | 0.1250 | 7.0 | 8.0 | 9.0 | 9.0 | 4.0 | 9.0 |
|  | 0.0620 | 4.7 | 6.0 |  | 9.0 | 2.0 | 7.0 |
|  | 0.0320 | 4.3 | 2.0 |  | 9.0 | 2.0 | 4.0 |
| 559 | 0.5000 | 9.0 | 4.0 | 9.0 | 9.0 | 0.0 | 2.0 |
|  | 0.2500 | 6.0 | 0.0 | 9.0 | 9.0 | 0.0 | 2.0 |
|  | 0.1250 | 3.0 | 0.0 | 0.0 | 9.0 | 0.0 | 1.0 |
|  | 0.0620 | 3.0 | 0.0 | 0.0 | 9.0 | 0.0 | 1.0 |
| 560 | 0.5000 | 7.0 | 3.0 | 9.0 | 9.0 | 0.0 | 2.0 |
|  | 0.2500 | 9.0 | 9.0 | 9.0 | 9.0 | 0.0 | 4.0 |
|  | 0.1250 | 4.6 | 7.0 | 7.0 | 9.0 | 0.0 | 2.0 |
|  | 0.0620 | 3.0 | 2.0 | 2.0 | 9.0 | 0.0 | 3.0 |
|  | 0.0320 | 2.0 | 0.0 | 0.0 | 8.0 | 0.0 | 3.0 |
| 561 | 0.5000 | 9.0 | 6.0 | 9.0 | 9.0 | 0.0 | 2.0 |
|  | 0.2500 | 9.0 | 9.0 | 0.0 | 9.0 | 3.0 | 4.5 |
|  | 0.1250 | 6.4 | 8.5 | 0.0 | 9.0 | 1.0 | 3.5 |
|  | 0.0620 | 4.8 | 6.0 | 0.0 | 9.0 | 0.0 | 4.0 |
|  | 0.0320 | 3.6 | 3.0 | 0.0 | 9.0 | 0.0 | 2.5 |
| 562 | 0.5000 | 9.0 | 3.0 | 9.0 | 9.0 | 0.0 | 6.0 |
|  | 0.2500 | 9.0 | 9.0 | 9.0 | 9.0 | 7.0 | 9.0 |
|  | 0.1250 | 5.1 | 9.0 | 9.0 | 9.0 | 5.0 | 4.0 |
|  | 0.0620 | 5.1 | 7.0 | 4.0 | 9.0 | 0.0 | 3.0 |
|  | 0.0320 | 2.7 | 2.0 |  | 9.0 | 0.0 | 2.0 |
| 563 | 0.5000 | 9.0 | 9.0 | 0.0 | 9.0 | 4.0 | 4.0 |
|  | 0.2500 | 9.0 | 6.0 | 4.0 | 9.0 | 2.0 | 7.0 |
|  | 0.1250 | 5.6 | 6.0 | 0.0 | 9.0 | 0.0 | 7.0 |
|  | 0.0620 | 5.1 | 2.0 | 0.0 | 9.0 | 0.0 | 7.0 |
|  | 0.0320 | 3.6 | 0.0 | 0.0 | 8.0 | 0.0 | 4.0 |
| 564 | 0.2500 | 7.0 | 9.0 | 4.0 | 9.0 | 0.0 | 0.0 |
|  | 0.1250 | 5.0 | 7.0 | 0.0 | 9.0 | 0.0 | 0.0 |
|  | 0.0620 | 4.0 | 6.0 | 0.0 | 9.0 | 0.0 | 0.0 |
|  | 0.0320 | 4.0 | 6.0 | 0.0 | 9.0 | 0.0 | 0.0 |
| 565 | 0.2500 | 0.0 | 6.0 | 0.0 | 9.0 | 0.0 | 3.0 |
|  | 0.1250 | 0.0 | 6.0 | 0.0 | 9.0 | 0.0 | 2.0 |
|  | 0.0620 | 0.0 | 3.0 | 0.0 | 9.0 | 0.0 | 0.0 |
|  | 0.0320 | 0.0 | 0.0 | 0.0 | 9.0 | 0.0 | 0.0 |
| 566 | 0.2500 | 6.0 | 9.0 | 3.0 | 9.0 | 9.0 | 6.0 |
|  | 0.1250 | 3.0 | 0.0 | 0.0 | 9.0 | 0.0 | 5.0 |
|  | 0.0620 | 3.0 | 0.0 | 0.0 | 9.0 | 0.0 | 3.0 |
|  | 0.0320 | 3.0 | 0.0 | 0.0 | 9.0 | 0.0 | 2.0 |
| 567 | 0.2500 | 4.0 | 9.0 | 0.0 | 9.0 | 0.0 | 2.0 |
|  | 0.1250 | 2.0 | 4.0 | 0.0 | 9.0 | 0.0 | 1.0 |
|  | 0.0620 | 0.0 | 9.0 | 0.0 | 3.0 | 0.0 | 0.0 |
|  | 0.0320 | 0.0 | 4.0 | 0.0 | 0.0 | 0.0 | 0.0 |
| 568 | 0.2500 | 6.0 | 7.0 | 0.0 | 9.0 | 0.0 | 3.0 |
|  | 0.1250 | 5.0 | 5.0 | 0.0 | 9.0 | 0.0 | 1.0 |
|  | 0.0620 | 3.0 | 0.0 | 0.0 | 9.0 | 0.0 | 0.0 |
|  | 0.0320 | 0.0 | 0.0 | 0.0 | 0.0 | 0.0 | 0.0 |
| 569 | 0.2500 | 5.0 | 0.0 | 0.0 | 6.0 | 9.0 | 1.0 |
|  | 0.1250 | 5.0 | 0.0 | 0.0 | 6.0 | 0.0 | 0.0 |
|  | 0.0620 | 4.0 | 0.0 | 0.0 | 6.0 | 0.0 | 0.0 |
|  | 0.0320 | 2.0 | 0.0 | 0.0 | 4.0 | 0.0 | 0.0 |
| 570 | 0.2500 | 6.0 | 9.0 | 0.0 | 9.0 | 0.0 | 3.0 |
|  | 0.1250 | 4.0 | 0.0 | 0.0 | 0.0 | 0.0 | 2.0 |

TABLE III-continued

PADDY CONDITIONS - POST-TRANSPLANT RICE PREEMERGENCE WEEDS

| Compound Number | Rate (kg/ha) | ECHORC | CYPIR | CYPSE | MOOVA | SAGPY | ORYSAT |
|---|---|---|---|---|---|---|---|
|  | 0.0620 | 2.0 | 0.0 | 0.0 | 0.0 | 0.0 | 1.0 |
|  | 0.0320 | 0.0 | 0.0 | 0.0 | 0.0 | 0.0 | 0.0 |
| 571 | 0.2500 | 6.0 | 9.0 | 0.0 | 9.0 | 0.0 | 2.0 |
|  | 0.1250 | 3.0 | 3.0 | 0.0 | 7.0 | 0.0 | 1.0 |
|  | 0.0620 | 2.0 | 3.0 | 0.0 | 6.0 | 0.0 | 0.0 |
|  | 0.0320 | 0.0 | 0.0 | 0.0 | 0.0 | 0.0 | 0.0 |
| 572 | 0.2500 | 6.0 | 5.0 | 2.0 | 9.0 | 3.0 | 6.0 |
|  | 0.1250 | 2.0 | 2.0 | 0.0 | 6.0 | 0.0 | 3.0 |
|  | 0.0620 | 0.0 | 0.0 | 0.0 | 6.0 | 0.0 | 1.0 |
|  | 0.0320 | 0.0 | 0.0 | 0.0 | 0.0 | 0.0 | 0.0 |
| 573 | 0.2500 | 7.0 | 5.0 | 4.0 | 9.0 | 2.0 | 1.0 |
|  | 0.1250 | 7.0 | 5.0 | 0.0 | 9.0 | 0.0 | 0.0 |
|  | 0.0620 | 7.0 | 3.0 | 0.0 | 9.0 | 0.0 | 0.0 |
|  | 0.0320 | 6.0 | 0.0 | 0.0 | 9.0 | 0.0 | 0.0 |
| 574 | 0.2500 | 9.0 | 7.0 | 6.5 | 9.0 | 6.0 | 8.0 |
|  | 0.1250 | 8.5 | 6.0 | 4.5 | 9.0 | 2.0 | 6.5 |
|  | 0.0620 | 6.5 | 5.5 | 2.0 | 9.0 | 1.0 | 4.5 |
|  | 0.0320 | 4.0 | 2.0 | 0.0 | 9.0 | 0.0 | 3.0 |
| 575 | 0.2500 | 9.0 | 6.0 | 2.0 | 9.0 | 3.0 | 2.0 |
|  | 0.1250 | 6.0 | 4.0 | 0.0 | 9.0 | 0.0 | 0.0 |
|  | 0.0620 | 5.0 | 0.0 | 0.0 | 4.0 | 0.0 | 0.0 |
|  | 0.0320 | 2.0 | 0.0 | 0.0 | 4.0 | 0.0 | 0.0 |
| 576 | 0.2500 | 9.0 | 5.0 | 4.0 | 9.0 | 4.0 | 9.0 |
|  | 0.1250 | 7.0 | 3.0 | 0.0 | 9.0 | 3.0 | 7.0 |
|  | 0.0620 | 7.0 | 3.0 | 0.0 | 9.0 | 0.0 | 7.0 |
|  | 0.0320 | 6.0 | 0.0 | 0.0 | 7.0 | 0.0 | 4.0 |
| 577 | 0.2500 | 9.0 | 9.0 | 3.0 |  | 6.0 | 9.0 |
|  | 0.1250 | 7.0 | 7.0 | 3.0 |  | 6.0 | 5.0 |
|  | 0.0620 | 7.0 | 4.0 | 3.0 |  | 6.0 | 5.0 |
|  | 0.0320 | 6.0 | 2.0 | 0.0 |  | 4.0 | 4.0 |
| 578 | 0.2500 | 9.0 | 7.0 | 9.0 |  | 9.0 | 7.0 |
|  | 0.1250 | 7.0 | 5.0 | 6.0 |  | 6.0 | 6.0 |
|  | 0.0620 | 6.0 | 5.0 | 6.0 |  | 6.0 | 5.0 |
|  | 0.0320 | 5.0 | 4.0 | 3.0 |  | 3.0 | 4.0 |
| 579 | 0.2500 | 5.0 | 6.0 | 0.0 | 9.0 | 2.0 | 3.0 |
|  | 0.1250 | 4.0 | 4.0 | 0.0 | 7.0 | 0.0 | 3.0 |
|  | 0.0620 | 4.0 | 0.0 | 0.0 | 7.0 | 0.0 | 2.0 |
|  | 0.0320 | 2.0 | 0.0 | 0.0 | 6.0 | 0.0 | 0.0 |
| 580 | 0.2500 | 9.0 | 9.0 | 8.5 | 9.0 | 8.5 | 6.5 |
|  | 0.1250 | 9.0 | 9.0 | 9.0 | 9.0 | 8.0 | 4.0 |
|  | 0.0620 | 9.0 | 9.0 | 9.0 | 9.0 | 8.0 | 4.0 |
|  | 0.0320 | 8.5 | 3.0 | 5.5 | 4.5 | 5.5 | 1.5 |
| 581 | 0.2500 | 9.0 | 9.0 | 8.0 | 9.0 | 9.0 | 7.0 |
|  | 0.1250 | 9.0 | 9.0 | 6.0 | 9.0 | 9.0 | 6.0 |
|  | 0.0620 | 8.5 | 4.5 | 1.5 | 4.5 | 9.0 | 3.5 |
|  | 0.0320 | 6.0 | 3.0 | 1.0 | 4.5 | 3.0 | 1.5 |
| 582 | 0.2500 | 9.0 | 6.0 | 7.0 | 7.0 | 6.0 | 3.0 |
|  | 0.1250 | 7.0 | 6.0 | 0.0 | 7.0 | 6.0 | 0.0 |
|  | 0.0620 | 7.0 | 4.0 | 0.0 | 7.0 | 5.0 | 0.0 |
|  | 0.0320 | 6.0 | 3.0 | 0.0 | 7.0 | 5.0 | 0.0 |
| 583 | 0.2500 | 9.0 | 9.0 | 9.0 | 9.0 | 9.0 | 9.0 |
|  | 0.1250 | 9.0 | 9.0 | 9.0 | 9.0 | 9.0 | 9.0 |
|  | 0.0620 | 7.5 | 9.0 | 9.0 | 9.0 | 9.0 | 7.0 |
|  | 0.0320 | 3.0 | 9.0 | 8.5 | 6.0 | 9.0 | 5.0 |
| 584 | 0.2500 | 9.0 | 9.0 | 0.0 | 9.0 | 2.0 | 3.5 |
|  | 0.1250 | 9.0 | 9.0 |  | 9.0 | 4.0 | 1.0 |
|  | 0.0620 | 9.0 | 6.0 | 0.0 | 8.0 | 1.5 | 1.0 |
|  | 0.0320 | 6.0 | 1.5 | 0.0 | 3.0 | 0.0 | 0.0 |
| 585 | 0.2500 | 9.0 | 9.0 | 3.0 | 9.0 | 2.5 | 1.5 |
|  | 0.1250 | 8.5 | 9.0 | 0.0 | 4.5 | 2.0 | 1.5 |
|  | 0.0620 | 8.5 | 8.5 | 0.0 | 3.5 | 1.5 | 1.5 |
|  | 0.0320 | 5.0 | 2.5 | 0.0 | 3.5 | 0.0 | 1.0 |
| 586 | 0.2500 | 9.0 | 9.0 | 4.5 | 9.0 | 0.0 | 2.0 |
|  | 0.1250 | 9.0 | 9.0 | 4.5 | 9.0 | 0.0 | 2.0 |
|  | 0.0620 | 9.0 | 8.5 | 0.0 | 6.5 | 0.0 | 2.0 |
|  | 0.0320 | 8.0 | 8.0 | 0.0 | 9.0 | 0.0 | 1.0 |
| 587 | 0.2500 | 9.0 | 9.0 |  | 9.0 | 5.0 | 5.0 |
|  | 0.1250 | 9.0 | 9.0 | 0.0 | 9.0 | 5.0 | 4.0 |
|  | 0.0620 | 7.0 | 8.0 |  | 5.0 | 2.0 | 4.0 |
|  | 0.0320 | 7.0 | 4.0 | 0.0 | 5.0 | 0.0 | 4.0 |
| 588 | 0.2500 | 7.0 | 6.0 | 5.0 | 8.0 | 0.0 | 3.0 |
|  | 0.1250 | 9.0 | 6.0 | 5.0 | 7.0 | 0.0 | 3.0 |
|  | 0.0620 | 7.0 | 2.0 | 0.0 |  | 0.0 | 3.0 |

TABLE III-continued

PADDY CONDITIONS - POST-TRANSPLANT RICE PREEMERGENCE WEEDS

| Compound Number | Rate (kg/ha) | ECHORC | CYPIR | CYPSE | MOOVA | SAGPY | ORYSAT |
|---|---|---|---|---|---|---|---|
| | 0.0320 | 4.0 | 0.0 | 0.0 | | 0.0 | 0.0 |
| 589 | 0.2500 | 4.0 | 4.0 | | 9.0 | 3.0 | 0.0 |
| | 0.1250 | 4.0 | 3.0 | 0.0 | 8.0 | 2.0 | 0.0 |
| | 0.0620 | 4.0 | 2.0 | 0.0 | 8.0 | 2.0 | 0.0 |
| | 0.0320 | 4.0 | 0.0 | 0.0 | 7.0 | 0.0 | 0.0 |
| 590 | 0.2500 | 9.0 | 9.0 | 5.0 | 9.0 | 9.0 | 6.0 |
| | 0.1250 | 6.0 | 7.0 | | 7.0 | 8.0 | 5.0 |
| | 0.0620 | 5.0 | 7.0 | | 7.0 | 4.0 | 5.0 |
| | 0.0320 | 3.0 | 2.0 | 0.0 | | 3.0 | 3.0 |
| 591 | 0.2500 | 9.0 | 7.0 | | 9.0 | 7.0 | 5.0 |
| | 0.1250 | 7.0 | 7.0 | 0.0 | 9.0 | 7.0 | 4.0 |
| | 0.0620 | 3.0 | 4.0 | | 9.0 | 3.0 | 4.0 |
| | 0.0320 | 3.0 | 3.0 | 0.0 | 7.0 | 0.0 | 2.0 |
| 592 | 0.2500 | 5.0 | 6.0 | | 9.0 | | 4.0 |
| | 0.1250 | 4.0 | 4.0 | 0.0 | 9.0 | 3.0 | 4.0 |
| | 0.0620 | 3.0 | 3.0 | | 9.0 | 3.0 | 2.0 |
| | 0.0320 | 0.0 | 2.0 | 0.0 | 8.0 | 0.0 | 2.0 |
| 593 | 0.2500 | 0.0 | 5.0 | 0.0 | 7.0 | 0.0 | 0.0 |
| | 0.1250 | 0.0 | 4.0 | 0.0 | 7.0 | 0.0 | 0.0 |
| | 0.0620 | 0.0 | 3.0 | | 7.0 | 0.0 | 0.0 |
| | 0.0320 | 0.0 | 3.0 | | | 0.0 | 0.0 |
| 594 | 0.2500 | 7.0 | 9.0 | | 9.0 | | 3.0 |
| | 0.1250 | 6.0 | 5.0 | | 9.0 | 5.0 | 2.0 |
| | 0.0620 | 5.0 | 5.0 | | 7.0 | 4.0 | 2.0 |
| | 0.0320 | 3.0 | 3.0 | 0.0 | 6.0 | 2.0 | 1.0 |
| 595 | 0.2500 | 4.0 | 4.0 | | | 0.0 | 2.0 |
| | 0.1250 | 3.0 | 2.0 | 0.0 | | 0.0 | 0.0 |
| | 0.0620 | 0.0 | 0.0 | | | 0.0 | 0.0 |
| 596 | 0.2500 | 7.0 | 0.0 | 0.0 | 9.0 | 6.0 | 6.0 |
| | 0.1250 | 5.0 | 0.0 | 0.0 | 7.0 | 2.0 | 4.0 |
| | 0.0620 | 4.0 | 0.0 | 0.0 | 4.0 | 0.0 | 3.0 |
| | 0.0320 | 0.0 | 0.0 | 0.0 | 3.0 | 0.0 | 0.0 |
| 597 | 0.2500 | 9.0 | 0.0 | 0.0 | 4.0 | 0.0 | 0.0 |
| | 0.1250 | 7.0 | 0.0 | 0.0 | | 0.0 | 0.0 |
| | 0.0620 | 6.0 | 0.0 | 0.0 | 4.0 | 0.0 | 0.0 |
| | 0.0320 | 4.0 | 0.0 | 0.0 | | 0.0 | 0.0 |
| 598 | 0.2500 | 0.0 | 3.0 | 0.0 | 7.0 | 0.0 | 3.0 |
| | 0.1250 | 0.0 | 2.0 | | 7.0 | 0.0 | 3.0 |
| | 0.0620 | 0.0 | 0.0 | | | 0.0 | 0.0 |
| | 0.0320 | 0.0 | 0.0 | 0.0 | | 0.0 | 0.0 |
| 599 | 0.2500 | 4.0 | 3.0 | 0.0 | 7.0 | 0.0 | 5.0 |
| | 0.1250 | 0.0 | | | | 0.0 | 3.0 |
| | 0.0620 | 0.0 | 0.0 | 0.0 | 7.0 | 0.0 | 3.0 |
| | 0.0320 | 0.0 | 0.0 | | 6.0 | 0.0 | 2.0 |
| 600 | 0.2500 | 2.0 | 2.0 | 0.0 | 7.0 | 0.0 | 4.0 |
| | 0.1250 | 0.0 | 0.0 | | 7.0 | 0.0 | 4.0 |
| | 0.0620 | 0.0 | 0.0 | 0.0 | 6.0 | 0.0 | 3.0 |
| | 0.0320 | 0.0 | 0.0 | 0.0 | 6.0 | 0.0 | 3.0 |
| 601 | 0.2500 | 6.0 | 4.0 | 3.0 | 9.0 | 0.0 | 7.0 |
| | 0.1250 | 2.0 | 4.0 | 0.0 | 9.0 | 0.0 | 6.0 |
| | 0.0620 | 0.0 | 0.0 | 0.0 | 7.0 | 0.0 | 5.0 |
| | 0.0320 | 0.0 | 0.0 | 0.0 | 6.0 | 0.0 | 4.0 |
| 602 | 0.2500 | 9.0 | 5.0 | 9.0 | 9.0 | 3.0 | |
| | 0.1250 | 9.0 | 5.0 | 7.0 | 8.0 | 0.0 | |
| | 0.0620 | 5.0 | 3.0 | 0.0 | 7.0 | 0.0 | |
| | 0.0320 | 0.0 | 3.0 | | 7.0 | 0.0 | |
| 603 | 0.2500 | 8.0 | 7.0 | 9.0 | 9.0 | 4.0 | |
| | 0.1250 | 6.0 | 6.0 | 8.0 | 9.0 | 2.0 | |
| | 0.0620 | 4.0 | | | 7.0 | 0.0 | |
| | 0.0320 | 0.0 | 5.0 | 0.0 | 7.0 | 0.0 | |
| 604 | 0.2500 | 9.0 | 6.0 | 0.0 | 8.0 | 0.0 | |
| | 0.1250 | 7.0 | 4.0 | 0.0 | 7.0 | 0.0 | |
| | 0.0620 | 7.0 | 3.0 | 0.0 | 6.0 | 0.0 | |
| | 0.0320 | 7.0 | 0.0 | 0.0 | 5.0 | 0.0 | |
| 605 | 0.2500 | 7.0 | 7.0 | 0.0 | 9.0 | 7.0 | |
| | 0.1250 | 7.0 | 7.0 | 0.0 | 9.0 | 5.0 | |
| | 0.0620 | 4.0 | 3.0 | 0.0 | 9.0 | 4.0 | |
| | 0.0320 | 4.0 | 1.0 | 0.0 | 9.0 | 4.0 | |
| 606 | 0.2500 | 6.0 | 9.0 | 2.0 | 9.0 | 4.0 | |
| | 0.1250 | 5.0 | 6.0 | 2.0 | 7.0 | 3.0 | |
| | 0.0620 | 5.0 | 6.0 | 2.0 | 7.0 | | |
| | 0.0320 | 5.0 | 4.0 | 0.0 | 6.0 | 0.0 | |
| 607 | 0.2500 | 9.0 | 5.0 | 0.0 | 9.0 | 3.0 | 3.0 |

TABLE III-continued

PADDY CONDITIONS - POST-TRANSPLANT RICE PREEMERGENCE WEEDS

| Compound Number | Rate (kg/ha) | ECHORC | CYPIR | CYPSE | MOOVA | SAGPY | ORYSAT |
|---|---|---|---|---|---|---|---|
| | 0.1250 | 9.0 | 5.0 | 0.0 | 9.0 | 0.0 | 2.0 |
| | 0.0620 | 7.0 | 2.0 | 0.0 | 7.0 | 0.0 | 0.0 |
| | 0.0320 | 4.0 | 0.0 | | 6.0 | 0.0 | 0.0 |

EXAMPLE 188

Rice Tolerance to Post-Transplant Applications and Postemergence Weed Control Under Flooded Paddy Conditions Plastic containers containing weeds which are 3 to 5 cm tall and rice seedlings at the 1.5 to 2.5 leaf stage are flooded with water. The water is maintained at 1.5 to 3 cm above the soil surface for the duration of the experiment. Test compounds are applied as aqueous/acetone mixtures 50/50 v/v directly into the flood water to provide the equivalent of about 0.0313 to 0.500 kg/ha of active ingredient. The treated containers are placed on greenhouse benches and cared for in accordance with conventional greenhouse procedures. Three to four weeks after treatment, the test is terminated and each container is examined and herbicidal effect rated according to the rating system provided in Example 185. The results are summarized in Table IV. The compounds evaluated are reported by compound number given in Example 185.

TABLE IV

| Compound Number | Rate (kg/ha) | ECHORC | CYPIR | CYPSE | MOOVA | SAGPY | ORYSAT |
|---|---|---|---|---|---|---|---|
| 1 | 0.5000 | 9.0 | 9.0 | 6.5 | 6.5 | 3.0 | 7.0 |
| | 0.2500 | 8.0 | 9.0 | 5.5 | 5.5 | 1.0 | 6.0 |
| | 0.1250 | 6.5 | 9.0 | 3.0 | 4.5 | 0.0 | 4.0 |
| | 0.0625 | 2.5 | 4.0 | 1.0 | 1.0 | 0.0 | 3.0 |
| | 0.0313 | 1.0 | 0.0 | 1.0 | 0.0 | 0.0 | 3.0 |
| 2 | 0.5000 | 9.0 | 9.0 | 0.0 | 9.0 | 4.0 | 8.0 |
| | 0.2500 | 9.0 | 9.0 | 0.0 | 9.0 | 2.0 | 7.0 |
| | 0.1250 | 7.0 | 9.0 | 0.0 | 9.0 | 0.0 | 3.0 |
| | 0.0625 | 4.0 | 9.0 | 0.0 | 9.0 | 0.0 | 2.0 |
| | 0.0313 | 4.0 | 9.0 | 0.0 | 9.0 | 0.0 | 2.0 |
| 3 | 0.5000 | 4.0 | 9.0 | 0.0 | 9.0 | 0.0 | 3.0 |
| | 0.2500 | 2.0 | 9.0 | 0.0 | 9.0 | 0.0 | 3.0 |
| | 0.1250 | 0.0 | 9.0 | 0.0 | 9.0 | 0.0 | 3.0 |
| | 0.0625 | 0.0 | 9.0 | 0.0 | 9.0 | 0.0 | 2.0 |
| | 0.0313 | 0.0 | 9.0 | 0.0 | 9.0 | 0.0 | 2.0 |
| 4 | 0.5000 | 9.0 | 9.0 | 9.0 | 9.0 | 9.0 | 8.0 |
| | 0.2500 | 9.0 | 9.0 | 7.0 | 9.0 | 9.0 | 8.0 |
| | 0.1250 | 9.0 | 9.0 | 7.0 | 9.0 | 6.0 | 7.0 |
| | 0.0625 | 9.0 | 9.0 | 4.0 | 9.0 | 2.0 | 4.0 |
| | 0.0313 | 7.0 | 8.0 | 2.0 | 8.0 | 3.0 | 3.0 |
| 5 | 0.5000 | 9.0 | 9.0 | 0.0 | 9.0 | 8.0 | 8.0 |
| | 0.2500 | 9.0 | 9.0 | 0.0 | 9.0 | 6.0 | 6.0 |
| | 0.1250 | 6.0 | 9.0 | 0.0 | 9.0 | 4.0 | 4.0 |
| | 0.0625 | 7.0 | 9.0 | 0.0 | 9.0 | 2.0 | 2.0 |
| | 0.0313 | 2.0 | 9.0 | 0.0 | 9.0 | 2.0 | 2.0 |
| 6 | 0.5000 | 9.0 | 9.0 | 9.0 | 9.0 | 9.0 | 9.0 |
| | 0.2500 | 9.0 | 9.0 | 7.0 | 9.0 | 8.0 | 9.0 |
| | 0.1250 | 9.0 | 9.0 | 7.0 | 9.0 | 6.0 | 9.0 |
| | 0.0625 | 7.0 | 9.0 | 2.0 | 9.0 | 4.0 | 4.0 |
| | 0.0313 | 4.0 | 9.0 | 0.0 | 9.0 | 2.0 | 4.0 |
| 7 | 0.5000 | 9.0 | 9.0 | 8.0 | 9.0 | 9.0 | 8.0 |
| | 0.2500 | 9.0 | 9.0 | 9.0 | 9.0 | 9.0 | 7.0 |
| | 0.1250 | 9.0 | 9.0 | 9.0 | 9.0 | 4.0 | 7.0 |
| | 0.0625 | 9.0 | 9.0 | 6.0 | 9.0 | 2.0 | 7.0 |
| | 0.0313 | 9.0 | 9.0 | 2.0 | 9.0 | 0.0 | 7.0 |
| 8 | 0.5000 | 9.0 | 9.0 | 9.0 | 9.0 | 9.0 | 9.0 |
| | 0.2500 | 9.0 | 9.0 | 7.0 | 9.0 | 9.0 | 8.0 |
| | 0.1250 | 9.0 | 9.0 | 7.0 | 9.0 | 4.0 | 6.0 |
| | 0.0625 | 9.0 | 9.0 | 2.0 | 9.0 | 4.0 | 6.0 |
| | 0.0313 | 6.0 | 9.0 | 0.0 | 9.0 | 2.0 | 4.0 |
| 9 | 0.5000 | 9.0 | 9.0 | 9.0 | 9.0 | 9.0 | 9.0 |
| | 0.2500 | 9.0 | 9.0 | 7.0 | 9.0 | 9.0 | 9.0 |
| | 0.1250 | 9.0 | 9.0 | 2.0 | 9.0 | 2.0 | 7.0 |
| | 0.0625 | 4.0 | 9.0 | 0.0 | 9.0 | 0.0 | 6.0 |
| | 0.0313 | 0.0 | 9.0 | 0.0 | 9.0 | 0.0 | 4.0 |
| 10 | 0.5000 | 9.0 | 9.0 | 7.0 | 9.0 | 4.0 | 4.0 |

TABLE IV-continued

| Compound Number | Rate (kg/ha) | ECHORC | CYPIR | CYPSE | MOOVA | SAGPY | ORYSAT |
|---|---|---|---|---|---|---|---|
| | 0.2500 | 9.0 | 9.0 | 6.0 | 9.0 | 4.0 | 3.0 |
| | 0.1250 | 9.0 | 9.0 | 2.0 | 9.0 | 4.0 | 4.0 |
| | 0.0625 | 9.0 | 9.0 | 0.0 | 9.0 | 2.0 | 2.0 |
| | 0.0313 | 7.0 | 9.0 | 0.0 | 9.0 | 2.0 | 2.0 |
| 11 | 0.5000 | 7.0 | 9.0 | 0.0 | 9.0 | 7.0 | 1.0 |
| | 0.2500 | 4.0 | 9.0 | 0.0 | 9.0 | 4.0 | 1.0 |
| | 0.1250 | 2.0 | 9.0 | 0.0 | 9.0 | 0.0 | 0.0 |
| | 0.0625 | 0.0 | 9.0 | 0.0 | 9.0 | 0.0 | 0.0 |
| | 0.0313 | 0.0 | 8.0 | 0.0 | 9.0 | 0.0 | 0.0 |
| 12 | 0.5000 | 9.0 | 9.0 | 2.0 | 9.0 | 9.0 | 7.0 |
| | 0.2500 | 9.0 | 9.0 | | 9.0 | 4.0 | 7.0 |
| | 0.1250 | 6.0 | 9.0 | | 9.0 | 0.0 | 7.0 |
| | 0.0625 | 2.0 | 9.0 | 0.0 | 9.0 | 0.0 | 4.0 |
| | 0.0313 | 0.0 | 9.0 | 0.0 | 9.0 | 0.0 | 4.0 |
| 13 | 0.5000 | 9.0 | 9.0 | 2.0 | 9.0 | 9.0 | 7.0 |
| | 0.2500 | 8.0 | 9.0 | 4.0 | 9.0 | 2.0 | 4.0 |
| | 0.1250 | 6.0 | 9.0 | 2.0 | 9.0 | 2.0 | 4.0 |
| | 0.0625 | 2.0 | 9.0 | 0.0 | 9.0 | 0.0 | 2.0 |
| | 0.0313 | 0.0 | 9.0 | 0.0 | 9.0 | 0.0 | 2.0 |
| 49 | 0.2500 | 9.0 | 6.0 | 0.0 | 9.0 | 0.0 | 0.0 |
| | 0.1250 | 9.0 | 4.0 | 0.0 | 9.0 | 0.0 | 0.0 |
| 50 | 0.2500 | 9.0 | 9.0 | 0.0 | 9.0 | 0.0 | 0.0 |
| | 0.1250 | 9.0 | 9.0 | 0.0 | 9.0 | 0.0 | 0.0 |
| 63 | 0.5000 | 4.0 | | 0.0 | 9.0 | 0.0 | 0.0 |
| | 0.2500 | 2.0 | | 0.0 | 9.0 | 0.0 | 0.0 |
| | 0.1250 | 0.0 | | 0.0 | 2.0 | 0.0 | 0.0 |
| 261 | 0.2500 | 0.0 | 6.0 | 0.0 | 9.0 | 0.0 | 0.0 |
| | 0.1250 | 0.0 | 6.0 | 0.0 | 9.0 | 0.0 | 0.0 |
| | 0.0620 | 0.0 | 6.0 | 0.0 | 9.0 | 0.0 | 0.0 |
| | 0.0320 | 0.0 | 5.0 | 0.0 | 9.0 | 0.0 | 0.0 |
| 267 | 0.2500 | 9.0 | 9.0 | 0.0 | 9.0 | 0.0 | 7.0 |
| | 0.1250 | 9.0 | 9.0 | 0.0 | 9.0 | 0.0 | 6.0 |
| | 0.0620 | 8.0 | 9.0 | 0.0 | 9.0 | 0.0 | 5.0 |
| | 0.0320 | 4.0 | 9.0 | 0.0 | 9.0 | 0.0 | 2.0 |
| 327 | 0.2500 | 9.0 | 9.0 | 2.0 | 9.0 | 4.0 | 4.0 |
| | 0.1250 | 9.0 | 9.0 | 0.0 | 9.0 | 4.0 | 5.0 |
| | 0.0620 | 7.0 | 9.0 | 0.0 | 9.0 | 0.0 | 3.0 |
| | 0.0320 | 9.0 | 9.0 | 0.0 | 9.0 | 0.0 | 2.0 |
| 328 | 0.2500 | 9.0 | 9.0 | 6.0 | 9.0 | 6.0 | 4.0 |
| | 0.1250 | 9.0 | 9.0 | 6.0 | 9.0 | 2.0 | 4.0 |
| | 0.0620 | 9.0 | 9.0 | 2.0 | 9.0 | 0.0 | 4.0 |
| | 0.0320 | 7.0 | 9.0 | 0.0 | 9.0 | 0.0 | 2.0 |
| 333 | 0.2500 | 9.0 | 9.0 | 8.0 | 9.0 | 4.0 | 6.0 |
| | 0.1250 | 9.0 | 9.0 | 4.0 | 9.0 | 4.0 | 6.0 |
| | 0.0620 | 9.0 | 9.0 | 2.0 | 9.0 | 2.0 | 5.0 |
| | 0.0320 | 9.0 | 9.0 | 0.0 | 9.0 | 0.0 | 4.0 |
| 354 | 0.1250 | 9.0 | 9.0 | 9.0 | 9.0 | 9.0 | 6.0 |
| | 0.0620 | 7.0 | 9.0 | 2.0 | 9.0 | 2.0 | 6.0 |
| | 0.0320 | 4.0 | | 1.0 | 6.0 | 0.0 | |
| 359 | 0.1250 | 6.0 | 9.0 | 0.0 | 9.0 | 0.0 | 4.0 |
| | 0.0620 | 6.0 | 7.0 | 0.0 | 7.0 | 0.0 | 3.0 |
| | 0.0320 | 2.0 | 4.0 | 0.0 | 7.0 | 0.0 | 2.0 |
| 362 | 0.2500 | 9.0 | 4.0 | 9.0 | 9.0 | 8.0 | 6.0 |
| | 0.1250 | 7.0 | 8.0 | 9.0 | 9.0 | 4.0 | 3.0 |
| | 0.0620 | 2.0 | 7.0 | 9.0 | 9.0 | 0.0 | 3.0 |
| | 0.0320 | 0.0 | 4.0 | 0.0 | 9.0 | 0.0 | 3.0 |
| 378 | 0.1250 | 9.0 | 9.0 | 9.0 | 9.0 | 9.0 | 9.0 |
| | 0.0620 | 9.0 | 9.0 | 9.0 | 9.0 | 9.0 | 8.0 |
| | 0.0320 | 9.0 | 9.0 | 9.0 | 9.0 | 9.0 | 8.0 |

TABLE IV-continued

| Compound Number | Rate (kg/ha) | ECHORC | CYPIR | CYPSE | MOOVA | SAGPY | ORYSAT |
|---|---|---|---|---|---|---|---|
| 380 | 0.2500 | 9.0 | 9.0 | 8.0 | 9.0 | 8.0 | 7.0 |
|  | 0.1250 | 9.0 | 9.0 | 2.0 | 9.0 | 2.0 | 7.0 |
|  | 0.0620 | 8.0 | 9.0 | 2.0 | 9.0 | 0.0 | 7.0 |
|  | 0.0320 | 7.0 | 9.0 | 0.0 | 9.0 | 0.0 | 3.0 |
| 429 | 0.2500 | 9.0 | 9.0 | 0.0 | 7.0 | 0.0 | 2.0 |
|  | 0.1250 | 6.0 | 7.0 | 0.0 | 7.0 | 0.0 | 2.0 |
|  | 0.0620 | 6.0 | 6.0 | 0.0 | 4.0 | 0.0 | 1.0 |
|  | 0.0320 | 4.0 | 4.0 | 0.0 | 2.0 | 0.0 | 1.0 |
| 432 | 0.2500 | 9.0 | 9.0 | 9.0 | 9.0 | 4.0 | 7.0 |
|  | 0.1250 | 9.0 | 9.0 | 7.0 | 9.0 | 2.0 | 7.0 |
|  | 0.0620 | 9.0 | 8.0 | 4.0 | 9.0 | 0.0 | 4.0 |
|  | 0.0320 | 9.0 | 8.0 | 0.0 | 9.0 | 0.0 | 4.0 |
| 431 | 0.2500 | 9.0 | 9.0 | 4.0 | 9.0 | 4.0 | 7.0 |
|  | 0.1250 | 9.0 | 9.0 | 0.0 | 9.0 | 0.0 | 3.0 |
|  | 0.0620 | 9.0 | 7.0 | 0.0 | 9.0 | 0.0 | 3.0 |
|  | 0.0320 | 7.0 | 4.0 | 0.0 | 6.0 | 0.0 | 3.0 |
| 445 | 0.2500 | 9.0 | 9.0 | 4.0 | 9.0 | 9.0 | 7.0 |
|  | 0.1250 | 9.0 | 9.0 | 4.0 | 2.0 | 4.0 | 7.0 |
|  | 0.0620 | 7.0 | 7.0 | 2.0 | 0.0 | 0.0 | 6.0 |
|  | 0.0320 | 4.0 | 4.0 | 0.0 | 0.0 | 0.0 | 3.0 |
| 448 | 0.2500 | 2.0 | 9.0 | 0.0 | 4.0 | 0.0 | 2.0 |
|  | 0.1250 | 1.0 | 7.0 | 0.0 | 1.0 | 0.0 | 1.0 |
|  | 0.0620 | 0.0 |  | 0.0 | 0.0 | 0.0 | 0.0 |
| 517 | 0.2500 | 0.0 | 9.0 | 0.0 | 9.0 | 0.0 | 0.0 |
|  | 0.1250 | 0.0 | 9.0 | 0.0 | 9.0 | 0.0 | 0.0 |
|  | 0.0620 | 0.0 | 5.0 | 0.0 | 9.0 | 0.0 | 0.0 |
|  | 0.0320 | 0.0 | 3.0 | 0.0 | 9.0 | 0.0 | 0.0 |
| 528 | 0.2500 | 9.0 | 6.0 | 9.0 | 9.0 | 3.0 | 3.0 |
|  | 0.1250 | 9.0 | 6.0 | 0.0 | 9.0 | 0.0 | 2.0 |
|  | 0.0620 | 7.0 | 6.0 | 0.0 | 0.0 | 0.0 | 0.0 |
|  | 0.0320 | 0.0 | 6.0 | 0.0 | 0.0 | 0.0 | 0.0 |

EXAMPLE 189

Comparative Herbicidal Evaluations

The preemergence and postemergence herbicidal properties of certain compounds of the present invention are compared with certain compounds disclosed in U.S. Pat. Nos. 5,484,763 and 5,523,278. The evaluations are performed as described in Examples 185 and 186. The results are reported in Tables V and VI. Data in Tables V and VI are reported by the compound number given in Example 185 for the compounds of this invention or by comparative compound letter for the compounds disclosed in U.S. Pat. Nos. 5,484,763 and 5,523,278.

As can be seen from the data in Tables V and VI, the compounds of this invention are more effective herbicidal agents than the compounds disclosed in U.S. Pat. Nos. 5,484,763 and 5,523,278.

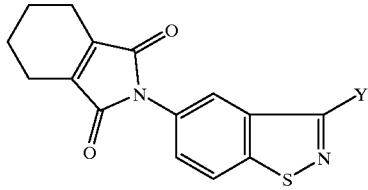

Comparative Compound Letter

| Comparative Compound Letter | Y |
|---|---|
| A | 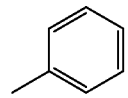 |
| B | CH$_3$ |
| C | H |

TABLE V

Preemergence Comparative Evaluations

| Compound Number | Rate (kg/ha) | ABUTH | AMBEL | CASOB | CHEAL | GALAP | IPOHE | IPOSS | ECHCG | SETVI | GLXMAW | GLXMA | ORYSAT | TRZAWR | ZEAMX |
|---|---|---|---|---|---|---|---|---|---|---|---|---|---|---|---|
| 4 | 0.5000 | 9.0 | 9.0 | 9.0 | 9.0 | 9.0 | | 9.0 | 9.0 | 9.0 | | 9.0 | 7.0 | 7.0 | 7.0 |
| | 0.2500 | 9.0 | 9.0 | 9.0 | 9.0 | 9.0 | | 9.0 | 9.0 | 9.0 | | 7.0 | 7.0 | 7.0 | 7.0 |
| | 0.1250 | 9.0 | 9.0 | 6.0 | 9.0 | 6.0 | | 7.0 | 9.0 | 9.0 | | 9.0 | 7.0 | 7.0 | 7.0 |
| | 0.0625 | 9.0 | 7.0 | 7.0 | 9.0 | 9.0 | | 4.0 | 9.0 | 9.0 | | 9.0 | 7.0 | 5.0 | 7.0 |
| | 0.0313 | 9.0 | 7.0 | 7.0 | 9.0 | 9.0 | | 2.0 | 9.0 | 3.0 | | 3.0 | 3.0 | 2.0 | 3.0 |
| A | 0.5000 | 7.0 | 5.0 | 2.0 | 9.0 | 9.0 | | 2.0 | 0.0 | 2.0 | | | 3.0 | | 0.0 |
| | 0.2500 | 6.0 | 6.0 | 2.0 | 7.0 | 9.0 | | 0.0 | 0.0 | 2.5 | | | 3.0 | | 0.0 |
| | 0.1250 | 5.0 | 3.5 | 1.5 | 5.0 | 9.0 | | 0.0 | 0.0 | 0.0 | 0.0 | | 0.5 | | 0.0 |
| | 0.0625 | 0.0 | 2.0 | 0.0 | 2.5 | 7.0 | | 0.0 | 0.0 | 0.0 | 0.0 | | 0.5 | | 0.0 |
| | 0.0320 | 0.0 | 0.0 | 0.0 | 5.5 | 4.5 | | 0.0 | 0.0 | 0.0 | 0.0 | | 0.0 | | 0.0 |
| | 0.0313 | 0.0 | 1.5 | 0.0 | 2.5 | | | 0.0 | 0.0 | 0.0 | 0.0 | 0.0 | 0.5 | 0.0 | 0.0 |
| | 0.0160 | 0.0 | 0.0 | 0.0 | 2.0 | 5.5 | | 0.0 | 0.0 | 0.0 | | | 0.0 | | 0.0 |
| 6 | 0.5000 | 9.0 | 9.0 | 9.0 | 9.0 | 9.0 | | 9.0 | 9.0 | 9.0 | 0.0 | 0.0 | 9.0 | 9.0 | 9.0 |
| | 0.2500 | 9.0 | 9.0 | 9.0 | 9.0 | 9.0 | 3.0 | 9.0 | 9.0 | 9.0 | 7.0 | 9.0 | 8.0 | 8.0 | 9.0 |
| | 0.1250 | 9.0 | 7.0 | 6.5 | 9.0 | 9.0 | 9.0 | 9.0 | 6.0 | 9.0 | 0.0 | 9.0 | 8.0 | 8.7 | 6.5 |
| | 0.0630 | 9.0 | 9.0 | 7.0 | 9.0 | 9.0 | 3.0 | | 9.0 | 6.0 | 0.0 | 7.0 | 7.0 | 7.0 | 8.0 |
| | 0.0625 | 9.0 | 6.0 | 5.5 | 9.0 | 5.3 | 3.0 | 7.0 | 5.5 | 8.4 | 2.3 | 4.0 | 7.0 | 8.3 | 6.0 |
| | 0.0320 | 9.0 | 7.4 | 6.0 | 9.0 | 8.5 | 4.0 | 7.5 | 5.6 | 9.0 | 7.0 | 2.0 | 4.4 | 5.6 | 4.2 |
| | 0.0315 | 9.0 | 9.0 | 9.0 | 9.0 | 9.0 | 7.5 | | 8.0 | 5.5 | 0.0 | | 7.0 | 6.5 | 7.5 |
| | 0.0313 | 4.5 | 4.5 | 4.5 | 8.0 | 4.8 | 0.0 | 7.0 | 4.5 | 7.0 | 1.3 | 2.0 | 7.0 | 6.3 | 5.3 |
| | 0.0160 | 8.0 | 6.4 | 4.4 | 8.8 | 8.5 | 1.0 | 7.5 | 2.2 | 9.0 | 1.5 | 2.0 | 2.8 | 3.0 | 3.6 |
| | 0.0158 | 9.0 | 8.0 | 6.5 | 9.0 | | 5.5 | | 6.0 | 7.0 | 0.0 | | 4.0 | 3.5 | 6.0 |
| | 0.0157 | 3.0 | 0.0 | 0.0 | 5.0 | | 0.0 | | 0.0 | 0.0 | 0.0 | | | 3.5 | 2.3 |
| B | 0.5000 | 5.0 | 8.0 | 0.0 | 9.0 | 7.0 | | 5.0 | 5.0 | 4.0 | 1.0 | | 4.0 | | 1.0 |
| | 0.2500 | 2.0 | 3.0 | 0.0 | 9.0 | 9.0 | | 2.0 | 5.0 | 6.0 | 1.0 | | 2.0 | | 0.0 |
| | 0.1250 | | 2.0 | 0.0 | 9.0 | 5.0 | | 0.0 | 3.0 | 2.0 | 0.0 | | 2.0 | | 0.0 |
| | 0.0625 | | 0.0 | 0.0 | 6.0 | 0.0 | | 0.0 | 0.0 | 0.0 | 0.0 | | 0.0 | | 0.0 |
| | 0.0313 | 0.0 | 0.0 | 0.0 | 9.0 | 0.0 | | 0.0 | 0.0 | 0.0 | 0.0 | | 0.0 | | 0.0 |
| 35 | 0.2500 | 9.0 | 9.0 | 9.0 | 9.0 | 9.0 | 9.0 | | 9.0 | 9.0 | 9.0 | | 8.0 | 8.0 | 8.0 |
| | 0.1250 | 9.0 | 9.0 | 9.0 | 9.0 | 9.0 | 9.0 | | 9.0 | 9.0 | 9.0 | | 8.0 | 9.0 | 8.0 |
| | 0.0625 | 9.0 | 9.0 | 9.0 | 9.0 | 8.0 | 7.0 | | 9.0 | 9.0 | 7.0 | | 8.0 | 7.0 | 8.0 |
| | 0.0313 | 9.0 | 8.0 | 7.0 | 9.0 | 7.0 | 6.0 | | 7.0 | 9.0 | 5.0 | | 7.0 | 6.0 | 7.0 |
| | 0.0156 | 9.0 | 8.0 | 6.0 | 9.0 | 7.0 | 4.0 | | 6.0 | 7.0 | 1.0 | | 6.0 | 3.0 | 5.0 |
| C | 0.5000 | 9.0 | 6.0 | 5.5 | 7.0 | 7.5 | | 2.0 | 6.0 | 5.0 | 0.0 | | 3.0 | | 0.0 |
| | 0.2500 | 9.0 | 2.0 | 0.0 | 3.0 | 6.0 | | 0.0 | 6.0 | 4.0 | 0.0 | 2.0 | 4.0 | | 0.0 |
| | 0.1250 | 4.0 | 2.0 | 0.0 | 5.0 | 2.0 | | 0.0 | 4.0 | 2.0 | 0.0 | 2.0 | 4.0 | | 0.0 |
| | 0.0625 | 2.0 | 3.0 | 0.0 | 4.0 | 2.0 | | 0.0 | 2.0 | 0.0 | 0.0 | | 2.0 | | 0.0 |
| | 0.0313 | 0.0 | 3.0 | 1.0 | 3.0 | | | 0.0 | 0.0 | 0.0 | 0.0 | | 1.0 | | 0.0 |

TABLE VI

Postemergence Comparative Evaluations

| Compound Number | Rate (kg/ha) | ABUTH | AMBEL | CASOB | CHEAL | GALAP | IPOHE | IPOSS | ECHCG | SETVI | GLXMAW | GLXMA | ORYSAT | TRZAWR | ZEAMX |
|---|---|---|---|---|---|---|---|---|---|---|---|---|---|---|---|
| 4 | 0.5000 | 9.0 | 9.0 | 9.0 | 9.0 | 9.0 | | 9.0 | 9.0 | 9.0 | | 9.0 | 4.0 | 4.0 | 3.0 |
|   | 0.2500 | 9.0 | 9.0 | 9.0 | 9.0 | 9.0 | | 9.0 | 8.0 | 9.0 | | 9.0 | 3.0 | 3.0 | 3.0 |
|   | 0.1250 | 9.0 | 9.0 | 9.0 | 9.0 | 9.0 | | 9.0 | 8.0 | 9.0 | | 7.0 | 3.0 | 3.0 | 3.0 |
|   | 0.0625 | 9.0 | 9.0 | 9.0 | 9.0 | 9.0 | | 9.0 | 7.0 | 9.0 | | 4.0 | 2.0 | 3.0 | 3.0 |
|   | 0.0313 | 9.0 | 7.0 | 7.0 | 9.0 | 9.0 | | 9.0 | 5.0 | 9.0 | | 5.0 | 2.0 | 2.0 | 2.0 |
|   | 0.0157 | 9.0 | 9.0 | 7.0 | 9.0 | 4.0 | | 7.0 | 2.0 | 8.0 | | 6.0 | 2.0 | 2.0 | 2.0 |
| A | 0.5000 | 9.0 | 9.0 | 9.0 | 9.0 | 9.0 | | | 2.0 | 2.0 | 4.5 | 4.5 | | 4.0 | |
|   | 0.2500 | 9.0 | 9.0 | 9.0 | 9.0 | 8.3 | 7.5 | 9.0 | 2.7 | 2.7 | 4.6 | 3.6 | 4.3 | 3.8 | |
|   | 0.1250 | 9.0 | 7.0 | 8.9 | 7.9 | 6.4 | 6.0 | 8.4 | 1.8 | 3.0 | 4.6 | 2.9 | 4.0 | 4.2 | |
|   | 0.0625 | 8.6 | 6.9 | 7.9 | 7.1 | 5.4 | | 7.5 | 1.0 | 2.1 | 4.6 | 2.6 | 2.3 | 3.7 | |
|   | 0.0320 | 9.0 | 9.0 | 0.0 | 9.0 | 8.5 | | 9.0 | 1.0 | 1.0 | | 4.3 | 3.8 | 3.8 | 4.0 |
|   | 0.0313 | 7.8 | 5.6 | 6.9 | 6.3 | 4.2 | 5.7 | 6.8 | 0.6 | 1.6 | 4.0 | 2.1 | 2.0 | 3.4 | |
|   | 0.0160 | 3.0 | 7.0 | 0.0 | 9.0 | 5.5 | | 5.5 | 1.0 | 1.0 | | 3.5 | 2.0 | 2 | |
|   | 0.0157 | 7.0 | 6.0 | 7.6 | 5.8 | 3.8 | 5.0 | 5.0 | 0.5 | 1.2 | 4.0 | | 2.0 | | |
| 6 | 0.5000 | 9.0 | 9.0 | 7.0 | 9.0 | 9.0 | | 9.0 | 7.0 | 9.0 | 7.0 | 7.0 | 5.0 | 6.0 | 3.0 |
|   | 0.2500 | 9.0 | 9.0 | 8.0 | 9.0 | 9.0 | 9.0 | 9.0 | 6.0 | 9.0 | 7.0 | 6.0 | 5.0 | 5.0 | 3.5 |
|   | 0.1250 | 9.0 | 9.0 | 7.0 | 9.0 | 9.0 | 5.0 | 9.0 | 7.0 | 9.0 | 6.0 | 6.0 | 4.5 | 2.5 | 3.5 |
|   | 0.0640 | 9.0 | 9.0 | | 9.0 | 5.0 | | | 3.0 | 7.0 | 4.8 | | 1.0 | 3.0 | 5.0 |
|   | 0.0630 | 6.5 | 9.0 | 2.5 | 7.0 | 9.0 | | | 1.5 | 2.0 | 7.0 | | 1.8 | 1.5 | 4.5 |
|   | 0.0625 | 9.0 | 9.0 | 4.0 | 9.0 | 5.0 | 9.0 | 9.0 | 2.0 | 9.0 | 5.5 | 4.0 | 1.5 | 2.0 | 3.5 |
|   | 0.0320 | 9.0 | 9.0 | 2.3 | 6.5 | 3.0 | | 9.0 | 1.0 | 6.0 | 3.8 | 5.0 | 1.5 | 2.5 | 3.8 |
|   | 0.0315 | 9.0 | 6.0 | 1.5 | 5.0 | 3.0 | 4.0 | | 1.0 | 2.5 | 7.0 | | 1.0 | 0.8 | 4.3 |
|   | 0.0313 | 9.0 | 8.0 | 0.0 | 9.0 | 9.0 | | 8.0 | 2.0 | 7.0 | 5.5 | 4.0 | 1.5 | 1.5 | 3.5 |
|   | 0.0160 | 5.7 | 7.7 | 0.0 | 3.0 | 2.7 | 6.0 | 7.5 | 0.7 | 3.7 | 7.0 | 2.5 | 1.5 | 2.0 | 3.5 |
|   | 0.0158 | 5.0 | 3.0 | 0.0 | 0.0 | 0.0 | 2.5 | | 0.0 | 0.0 | 5.5 | | 0.5 | 0.0 | 4.0 |
|   | 0.0157 | 8.0 | 7.0 | 0.0 | 9.0 | 4.0 | | 7.0 | 2.0 | 7.0 | 3.0 | 4.0 | 2.0 | 2.0 | 2.0 |
| B | 0.5000 | 9.0 | 9.0 | 9.0 | 9.0 | 8.0 | | 9.0 | 6.0 | 5.0 | 7.5 | | 6.0 | | 5.5 |
|   | 0.2500 | 9.0 | 9.0 | 9.0 | 8.0 | 8.0 | | 8.0 | 5.0 | 5.0 | 7.0 | | 5.5 | | 6.0 |
|   | 0.1250 | 9.0 | 8.0 | 8.0 | 9.0 | 7.0 | | 8.0 | 4.0 | 4.0 | 6.0 | | 4.5 | | 5.5 |
|   | 0.0625 | 9.0 | 8.0 | 8.0 | 7.0 | 7.0 | | 8.0 | 2.0 | 2.0 | 5.5 | | 4.5 | | 5.0 |
|   | 0.0313 | 8.0 | 6.0 | 7.0 | 7.0 | 7.0 | 4.0 | 7.0 | 2.0 | 0.0 | 5.5 | | 4.0 | | 5.5 |
|   | 0.0157 | 2.0 | 2.0 | 6.0 | 3.0 | 5.0 | 3.0 | 6.0 | 0.0 | 0.0 | 5.5 | | 3.5 | | 5.0 |
| 35 | 0.0315 | 9.0 | 9.0 | 5.0 | 9.0 | 2.0 | | | 1.0 | 2.0 | 4.0 | | 1.0 | 1.5 | 5.0 |
|   | 0.0158 | 9.0 | 5.0 | 2.0 | 5.0 | 9.0 | | | 0.0 | 2.0 | 3.5 | | 0.5 | 1.0 | 4.5 |
| C | 0.5000 | 9.0 | 9.0 | 9.0 | 4.0 | 6.0 | | 7.0 | 0.0 | 0.0 | 4.5 | | 4.5 | | 3.0 |
|   | 0.2500 | 9.0 | 7.0 | 7.0 | 3.0 | 6.0 | | 6.0 | 0.0 | 0.0 | 2.5 | | 3.0 | | 2.5 |
|   | 0.1250 | 9.0 | 8.0 | 7.0 | 3.0 | 5.0 | | 7.0 | 0.0 | 0.0 | 2.0 | | 2.5 | | 1.5 |
|   | 0.0625 | 9.0 | 7.0 | 7.0 | 3.0 | 3.0 | | 5.0 | 0.0 | 0.0 | 3.0 | | 2.5 | | 1.5 |
|   | 0.0313 | 9.0 | 6.0 | 8.0 | 3.0 | 3.0 | | 6.0 | 0.0 | 0.0 | 1.5 | | 2.0 | | 2.0 |
|   | 0.0157 | 8.0 | 6.0 | 3.0 | 0.0 | 2.0 | | 2.0 | 0.0 | 0.0 | 1.0 | | 2.0 | | 1.5 |

What is claimed is:
1. A compound having the structural formula

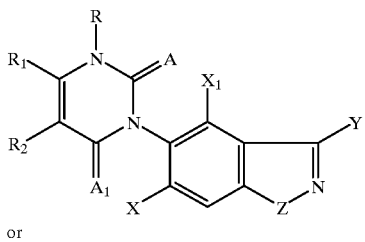

(I)

or

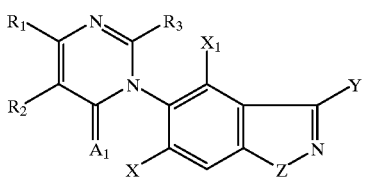

(II)

wherein

R is $C_1$–$C_6$alkyl, $C_1$–$C_6$haloalkyl, $C_3$–$C_7$cycloalkyl, $C_3$–$C_6$alkenyl, $C_3$–$C_6$alkynyl, benzyl, $OR_4$ or $NR_5R_6$;

$R_1$ and $R_2$ are each independently hydrogen, halogen, $C_1$–$C_6$alkyl, $C_3$–$C_7$cycloalkyl, $C_1$–$C_6$haloalkyl, $C_3$–$C_6$alkenyl, $C_3$–$C_6$haloalkenyl, $C_3$–$C_6$alkynyl, $OR_7$, $S(O)_nR_8$ or $NR_9R_{10}$;

$R_3$ is halogen or $A_2R_{11}$;

X is hydrogen, halogen or $C_1$–$C_4$alkyl;

$X_1$ is hydrogen, halogen, $C_1$–$C_4$alkyl, $C_1$–$C_4$haloalkyl, $C_1$–$C_4$alkoxy or $C_1$–$C_4$haloalkoxy;

Z is O or $S(O)_m$;

Y is halogen, cyano, $R_{12}$, $X_2R_{12}$, $X_3R_{12}$, $X_2X_3R_{12}$ or $X_3X_2R_{12}$;

$X_2$ is O, $S(O)_p$ or $NR_{13}$;

$X_3$ is —C(=$A_3$)—, —C(=$NOR_{14}$)— or —C(=N—$NR_{13}R_{50}$);

$R_4$, $R_5$, $R_6$, $R_7$, $R_8$, $R_9$, $R_{10}$, $R_{11}$ and $R_{14}$ are each independently hydrogen, $C_1$–$C_6$alkyl, $C_3$–$C_7$cycloalkyl, $C_2$–$C_8$alkoxyalkyl, $C_2$–$C_6$alkenyl, $C_2$–$C_6$alkynyl or benzyl;

$R_{12}$ is hydrogen,
a $C_1$–$C_8$alkyl, $C_3$–$C_7$cycloalkyl, $C_2$–$C_6$alkenyl, $C_5$–$C_6$cycloalkenyl or $C_2$–$C_8$alkynyl group, wherein each group is optionally substituted with any combination of one to six halogen atoms, one to three $C_1$–$C_{20}$alkoxy groups optionally substituted with one $C_1$–$C_8$alkoxy, benzyloxy or $C_1$–$C_6$alkylthio group, one or two $C_1$–$C_{10}$haloalkoxy groups, one or two $NR_{15}R_{16}$ groups, one to three $S(O)_qR_{17}$ groups, one or two cyano groups, one or two $C_3$–$C_7$cycloalkyl groups, one thiocyano group, one $O(SO_2)R_{17}$ group, one $O(NO_2)$ group, one or two $C(O)R_{18}$ groups, one or two $CO_2R_{19}$ groups, one or two $C(O)SR_{19}$ groups, one or two $C(O)NR_{20}R_{21}$ groups, one to three $X_4R_{22}$ groups, one or two $P(O)(OR_{23})_2$ groups, one or two $Si(R_{24})_3$ groups, one 4- to 10-membered monocyclic or fused bicyclic heterocyclic ring optionally substituted with any combination of one or two oxo groups, one or two thioxo groups, one to three halogen atoms, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups or one or two $X_4R_{22}$ groups,
one quaternary organic ammonium group, or
one or two phenyl groups wherein each phenyl group is independently optionally substituted with any combination of one to three halogen atoms, one to three $C_1$–$C_6$alkyl groups, one to three $C_1$–$C_6$alkoxy groups, one $C_3$–$C_7$cycloalkyl group, one $C_1$–$C_4$haloalkyl group, one $C_1$–$C_4$alkylthio group, one cyano group, one nitro group, one $C(O)R_{25}$ group, one $CO_2R_{26}$ group or one $X_5R_{27}$ group,
phenyl optionally substituted with any combination of one to three halogen atoms, one to three $C_1$–$C_4$alkyl groups, one to three $C_1$–$C_4$alkoxy groups, one $C_3$–$C_6$cycloalkyl group, one $C_1$–$C_4$haloalkyl group, one $C_1$–$C_4$alkylthio group, one cyano group, one nitro group, one $C(O)R_{25}$ group, one $CO_2R_{26}$ group, one $X_4R_{22}$ group, one CH=$CHR_{22}$ group, one $CH_2CH(R_{28})R_{22}$ group or one $N(R_{29})SO_2R_{30}$ group, or
indan optionally substituted with any combination of one or two halogen atoms, one or two $C_1$–$C_4$alkyl groups, one $C_1$–$C_4$alkoxy group, one $C_1$–$C_4$haloalkyl group, one $C_1$–$C_4$alkylthio group, one cyano group, one nitro group, one $C(O)R_{25}$ group, one $CO_2R_{26}$ group, one $X_4R_{22}$ group, one CH=$CHR_{22}$ group, one $CH_2CH(R_{28})R_{22}$ group or one $N(R_{29})SO_2R_{30}$ group,
and when $R_{12}$ and $R_{13}$ are taken together with the nitrogen atom to which they are attached, they form a 5- to 12-membered monocyclic or fused bicyclic, heterocyclic ring optionally substituted with one or more groups independently selected from halogen, cyano, nitro, amino, hydroxyl, $C_1$–$C_4$alkyl, $C_1$–$C_4$haloalkyl, $C_1$–$C_4$alkoxy, $C_1$–$C_4$haloalkoxy, $C_1$–$C_4$haloalkylsulfonyl or $X_4R_{22}$ groups;

$R_{13}$ is hydrogen, $C_1$–$C_8$alkoxyalkyl, $C_1$–$C_6$alkyl, $C_3$–$C_7$cycloalkyl, $C_3$–$C_6$alkenyl, $C_3$–$C_6$alkynyl, benzyl, $OR_{23}$, cyano, $SO_2R_{51}$ or one 5- to 12-membered monocyclic or fused bicyclic heterocyclic ring optionally substituted with one or more groups independently selected from halogen, cyano, nitro, amino, hydroxyl, $C_1$–$C_4$alkyl, $C_1$–$C_4$haloalkyl, $C_1$–$C_4$alkoxy or $C_1$–$C_4$haloalkoxy, and when $R_{13}$ and $R_{12}$ are taken together with the nitrogen atom to which they are attached, they form a 5- to 12-membered monocyclic or fused bicyclic, heterocyclic ring optionally substituted with one or more groups independently selected from halogen, cyano, nitro, amino, hydroxyl, $C_1$–$C_4$alkyl, $C_1$–$C_4$haloalkyl, $C_1$–$C_4$alkoxy, $C_1$–$C_4$haloalkoxy, $C_1$–$C_4$haloalkylsulfonyl or $X_4R_{22}$ groups;

$R_{28}$ is halogen;

$R_{22}$ and $R_{27}$ are each independently hydrogen, $Si(R_{31})_3$, $C(O)NR_{35}R_{36}$, $C(O)R_{33}$, $SO_2R_{47}$,
$C_1$–$C_{20}$alkyl substituted with one hydroxyl, benzyloxy, nitro, $OC(O)R_{33}$, $C_1$–$C_6$alkoxy, $CO_2R_{32}$, $C(O)R_{33}$, $C(A_4R_{34})_2$, $C(O)NR_{35}R_{36}$, $C(O)ON$=$CR_{37}R_{38}$, $P(O)(OH)NH_2$, $P(O)(OH)(OR_{23})$, $C(O)NR_{35}OR_{23}$, cyano or 2-dioxolanyl group,
one phenyl, dihydrofuranone or furanone ring wherein each ring is optionally substituted with any combination of one to three halogen atoms, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups, or one 5- to 12-membered monocyclic or fused bicyclic, heterocyclic ring optionally substituted with one or more groups independently selected from halogen, cyano, nitro, amino, hydroxyl, $C_1$–$C_4$alkyl, $C_1$–$C_4$haloalkyl, $C_1$–$C_4$alkoxy, $C_1$–$C_4$haloalkoxy or $C_1$–$C_4$haloalkylsulfonyl groups, $C_3$–$C_{20}$alkenyl optionally substituted with one to three halogen atoms, one hydroxyl group, one $C_1$–$C_6$alkoxy, $CO_2R_{32}$, $C(O)R_{33}$, $C(A_4R_{34})_2$, $C(O)NR_{35}R_{36}$, $C(O)ON=CR_{37}R_{38}$, $C(O)NR_{35}OR_{23}$, cyano or 2-dioxolanyl group, or one phenyl, dihydrofuranone or furanone ring wherein each ring is optionally substituted with any combination of one to three halogen atoms, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups, $C_5$–$C_8$cycloalkenyl optionally substituted with one hydroxyl, $C_1$–$C_6$alkoxy, $C_1$–$C_4$alkyl, $C_2$–$C_4$alkenyl, $CO_2R_{32}$, $C(O)R_{33}$, $C(A_4R_{34})_2$, $C(O)NR_{35}R_{36}$, $C(O)ON=CR_{37}R_{38}$, $C(O)NR_{35}OR_{23}$, cyano or 2-dioxolanyl group, or one phenyl, dihydrofuranone or furanone ring wherein each ring is optionally substituted with any combination of one to three halogen atoms, one to three $C_1$–$C_4$alkyl groups, one to three $C_1$–$C_4$alkoxy groups or one to three $C_1$–$C_4$haloalkoxy groups, $C_3$–$C_{10}$alkynyl optionally substituted with one hydroxyl, $C_1$–$C_6$alkoxy, $CO_2R_{32}$, $C(O)R_{33}$, $C(A_4R_{34})_2$, $C(O)NR_{35}R_{36}$, $C(O)ON=CR_{37}R_{38}$, $C(O)NR_{35}OR_{23}$, cyano or 2-dioxolanyl group, or one phenyl, dihydrofuranone or furanone ring wherein each ring is optionally substituted with any combination of one to three halogen atoms, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups, phenyl optionally substituted with any combination of one to three halogen atoms, one to three $C_1$–$C_6$alkyl groups, one to three $C_1$–$C_6$alkoxy groups, one $C_1$–$C_4$haloalkyl group, one $C_1$–$C_4$haloalkoxy group, one cyano group, one nitro group, one $NR_{39}R_{40}$ group or one $C(O)R_{33}$ group, benzyl optionally substituted on the phenyl ring with any combination of one to three halogen atoms, one to three $C_1$–$C_6$alkyl groups, one to three $C_1$–$C_6$alkoxy groups, one $C_1$–$C_4$haloalkyl group, one $C_1$–$C_4$haloalkoxy group, one cyano group, one nitro group, one $NR_{39}R_{40}$ group or one $C(O)R_{33}$ group, or a 4- to 10-membered heterocyclic ring optionally substituted with any combination of one or two oxo groups, one or two thioxo groups, one to three halogen atoms, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups;

$R_{15}$ and $R_{20}$ are each independently hydrogen, a $C_1$–$C_6$alkyl, $C_3$–$C_7$cycloalkyl, $C_2$–$C_6$alkenyl or $C_2$–$C_6$alkynyl group wherein each group is optionally substituted with one $CO_2R_{42}$ group, benzyl optionally substituted with any combination of one to three halogen atoms, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups, phenyl optionally substituted with any combination of one to three halogen atoms, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups, one $CO_2R_{26}$ group, $C(O)R_{43}$, or $CO_2R_{42}$;

$R_{16}$ and $R_{21}$ are each independently hydrogen, $C_1$–$C_6$alkyl, $C_1$–$C_4$alkoxy, $C_3$–$C_7$cycloalkyl, $C_2$–$C_6$alkenyl, $C_3$–$C_7$cycloalkenyl, $C_2$–$C_6$alkynyl, $P(O)(OR_{44})_2$, $SO_2R_{45}$, $C(O)R_{46}$, benzyl optionally substituted with any combination of one to three halogen atoms, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups or one $X_4R_{22}$ group, or phenyl optionally substituted with any combination of one to three halogen atoms, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups or one $X_4R_{22}$ group;

$R_{17}$, $R_{18}$, $R_{25}$, $R_{30}$, $R_{33}$, $R_{45}$ and $R_{51}$ are each independently $NR_{46}R_{48}$, $-N=CR_{46}R_{48}$, $C_1$–$C_8$alkyl optionally substituted with one $C_1$–$C_6$alkoxy, thiophene or furan group, $C_1$–$C_6$haloalkyl, $C_3$–$C_8$cycloalkyl, $CO_2R_{23}$, $C_2$–$C_6$alkenyl optionally substituted with phenyl, benzyl optionally substituted with any combination of one to three halogen atoms, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups, one nitro group, one cyano group or one $X_4R_{22}$ group, phenyl optionally substituted with any combination of one to three halogen atoms, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups, one nitro group, one cyano group or one $X_4R_{22}$ group, or a 5- to 12-membered monocyclic or fused bicyclic, heterocyclic ring optionally substituted with one or more groups independently selected from halogen, cyano, nitro, amino, hydroxyl, $C_1$–$C_4$alkyl, $C_1$–$C_4$haloalkyl, $C_1$–$C_4$alkoxy, $C_1$–$C_4$haloalkoxy, $C_1$–$C_4$haloalkylsulfonyl or $X_4R_{22}$ groups;

$R_{19}$ and $R_{26}$ are each independently hydrogen, $C_1$–$C_{20}$alkyl, $C_1$–$C_8$haloalkyl, $C_3$–$C_7$cycloalkyl, $C_3$–$C_7$halocycloalkyl, $C_3$–$C_{20}$alkenyl, $C_3$–$C_8$haloalkenyl, $C_5$–$C_8$cycloalkenyl, $C_5$–$C_8$halocycloalkenyl, $C_3$–$C_8$alkynyl, $C_3$–$C_8$haloalkynyl, $Si(R_{41})_3$, benzyl, phenyl, furfuryl, pyridyl, thienyl, oximino or an alkali metal, alkaline earth metal, manganese, copper, zinc, cobalt, silver, nickel, ammonium or organic ammonium cation;

$R_{32}$ is hydrogen, $Si(R_{47})_3$, $di(C_1$–$C_4$alkyl)imino, $C_1$–$C_{20}$alkyl optionally substituted with one $CO_2R_{48}$, $C_1$–$C_6$alkoxy, $C_1$–$C_6$thioalkyl, $C_2$–$C_{20}$alkoxyalkoxy, phenyl, $OSi(R_{47})_3$, $OC(O)R_{33}$, $C_3$–$C_7$cycloalkyl or $di(C_1$–$C_4$alkyl)imino group, $C_1$–$C_{15}$haloalkyl, $C_3$–$C_8$cycloalkyl optionally substituted with one $CO_2R_{48}$ group, $C_3$–$C_8$halocycloalkyl, $C_3$–$C_{20}$ alkenyl optionally substituted with one phenyl group, $C_3$–$C_{15}$haloalkenyl,
$C_5$–$C_8$cycloalkenyl,
$C_5$–$C_8$halocycloalkenyl,
$C_3$–$C_{20}$alkynyl optionally substituted with one phenyl group,
$C_3$–$C_{20}$haloalkynyl,
benzyl optionally substituted with one or more groups independently selected from halogen, cyano, nitro, $C_1$–$C_4$alkyl, $C_1$–$C_4$haloalkyl, $C_1$–$C_4$alkoxy and $C_1$–$C_4$haloalkoxy groups,
phenyl optionally substituted with one or more groups independently selected from halogen, cyano, nitro, $C_1$–$C_4$alkyl, $C_1$–$C_4$haloalkyl, $C_1$–$C_4$alkoxy and $C_1$–$C_4$haloalkoxy groups,
2-, 3- or 4-pyridyl,
2- or 3-furyl,
2- or 3-thienyl,
2-tetrahydrofuranyl,
$C_1$–$C_4$alkyl substituted with one pyridyl, furyl, thienyl, tetrahydrofuryl, $C_3$–$C_8$cycloalkyl, dioxane or $NR_{49}R_{50}$ group, or
an alkali metal, alkaline earth metal, manganese, copper, zinc, cobalt, silver, nickel, ammonium or organic ammonium cation;
$R_{34}$, $R_{37}$ and $R_{38}$ are each independently $C_1$–$C_6$alkyl;
$R_{35}$ and $R_{49}$ are each independently hydrogen or $C_1$–$C_6$alkyl and $R_{36}$ and $R_{50}$ are each independently hydrogen, cyano, $C_1$–$C_6$alkyl, $SO_2R_{51}$ or phenyl optionally substituted with one or more groups independently selected from halogen, cyano, nitro, $C_1$–$C_4$alkyl, $C_1$–$C_4$haloalkyl, $C_1$–$C_4$alkoxy and $C_1$–$C_4$haloalkoxy groups, or when $R_{35}$ and $R_{36}$ or $R_{49}$ and $R_{50}$ are taken together with the nitrogen atom to which they are attached, they form a 5- to 12-membered monocyclic or fused bicyclic, heterocyclic ring optionally substituted with one or more groups independently selected from halogen, cyano, nitro, amino, hydroxyl, $C_1$–$C_4$alkyl, $C_1$–$C_4$haloalkyl, $C_1$–$C_4$alkoxy, $C_1$–$C_4$haloalkoxy or $C_1$–$C_4$haloalkylsulfonyl groups;
m, n, p and q are each independently an integer of 0, 1 or 2;
$R_{29}$ is hydrogen, $C_1$–$C_4$alkyl or $C_1$–$C_4$haloalkyl;
$R_{24}$, $R_{31}$, $R_{41}$ and $R_{47}$ are each independently $C_1$–$C_4$alkyl,
benzyl optionally substituted with one or more groups independently selected from halogen, cyano, nitro, $C_1$–$C_4$alkyl, $C_1$–$C_4$haloalkyl, $C_1$–$C_4$alkoxy and $C_1$–$C_4$haloalkoxy groups, or
phenyl optionally substituted with one or more groups independently selected from halogen, cyano, nitro, $C_1$–$C_4$alkyl, $C_1$–$C_4$haloalkyl, $C_1$–$C_4$alkoxy and $C_1$–$C_4$haloalkoxy groups;
$R_{23}$, $R_{39}$, $R_{40}$, $R_{42}$, $R_{43}$, $R_{44}$, $R_{46}$ and $R_{48}$ are each independently hydrogen, $C_2$–$C_6$alkenyl, $C_3$–$C_8$cycloalkyl,
$C_1$–$C_8$alkyl optionally substituted with one or two $C_1$–$C_4$alkoxy groups,
benzyl optionally substituted with one or more groups independently selected from halogen, cyano, nitro, $C_1$–$C_4$alkyl, $C_1$–$C_4$haloalkyl, $C_1$–$C_4$alkoxy and $C_1$–$C_4$haloalkoxy groups, or
phenyl optionally substituted with one or more groups independently selected from halogen, cyano, nitro, $C_1$–$C_4$alkyl, $C_1$–$C_4$haloalkyl, $C_1$–$C_4$alkoxy and $C_1$–$C_4$haloalkoxy groups, and
when $R_{46}$ and $R_{48}$ are taken together with the atom to which they are attached, they form a 5- to 12-membered monocyclic or fused bicyclic, heterocyclic or cycloalkyl ring optionally substituted with one or more groups independently selected from halogen, cyano, nitro, amino, hydroxyl, $C_1$–$C_4$alkyl, $C_1$–$C_4$haloalkyl, $C_1$–$C_4$alkoxy, $C_1$–$C_4$haloalkoxy or $C_1$–$C_4$haloalkylsulfonyl groups; and
A, $A_1$, $A_2$, $A_3$, $A_4$, $X_4$ and $X_5$ are each independently O or S; and
the optical isomers, diastereomers and/or tautomers thereof.

2. The compound according to claim 1 wherein
R is $C_1$–$C_6$alkyl, $C_1$–$C_6$haloalkyl, $C_3$–$C_7$cycloalkyl, $C_3$–$C_6$alkenyl, $C_3$–$C_6$alkynyl, benzyl, $OR_4$ or $NR_5R_6$;
$R_1$ and $R_2$ are each independently hydrogen, halogen, $C_1$–$C_6$alkyl, $C_3$–$C_7$cycloalkyl, $C_1$–$C_6$haloalkyl, $C_3$–$C_6$alkenyl, $C_3$–$C_6$haloalkenyl, $C_3$–$C_6$alkynyl, $OR_7$, $S(O)_nR_8$ or $NR_9R_{10}$;
$R_3$ is halogen or $A_2R_{11}$;
X is hydrogen, halogen or $C_1$–$C_4$alkyl;
$X_1$ is hydrogen, halogen, $C_1$–$C_4$alkyl, $C_1$–$C_4$haloalkyl, $C_1$–$C_4$alkoxy or $C_1$–$C_4$haloalkoxy;
Z is O or $S(O)_m$;
Y is halogen, cyano, $R_{12}$, $X_2R_{12}$, $X_3R_{12}$, $X_2X_3R_{12}$ or $X_3X_2R_{12}$;
$X_2$ is O, $S(O)_p$ or $NR_{13}$;
$X_3$ is —C(=$A_3$)— or —C(=$NOR_{14}$)—;
$R_4$, $R_5$, $R_6$, $R_7$, $R_8$, $R_9$, $R_{10}$, $R_{11}$ and $R_{14}$ are each independently hydrogen, $C_1$–$C_6$alkyl, $C_3$–$C_7$cycloalkyl, $C_2$–$C_6$alkenyl, $C_2$–$C_6$ alkynyl or benzyl;
$R_{12}$ is hydrogen,
a $C_1$–$C_6$alkyl, $C_3$–$C_7$cycloalkyl, $C_2$–$C_6$alkenyl, $C_5$–$C_6$cycloalkenyl or $C_2$–$C_6$alkynyl group, wherein each group is optionally substituted with any combination of one to six halogen atoms, one to three $C_1$–$C_{20}$alkoxy groups, one or two $C_1$–$C_{10}$haloalkoxy groups, one or two $NR_{15}R_{16}$ groups, one to three $S(O)_qR_{17}$ groups, one or two cyano groups, one or two $C(O)R_{18}$ groups, one or two $CO_2R_{19}$ groups, one or two $C(O)NR_{20}R_{21}$ groups, one to three $X_4R_2$ groups, one or two $P(O)(OR_{23})_2$ groups, one or two $Si(R_{24})_3$ groups,
one 4- to 10-membered heterocyclic ring optionally substituted with any combination of one or two oxo groups, one or two thioxo groups, one to three halogen atoms, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups or one or two $X_4R_{22}$ groups,
one quaternary organic ammonium group, or
one phenyl group optionally substituted with any combination of one to three halogen atoms, one to three $C_1$–$C_6$alkyl groups, one to three $C_1$–$C_6$alkoxy groups, one $C_3$–$C_7$cycloalkyl group, one $C_1$–$C_4$haloalkyl group, one $C_1$–$C_4$alkylthio group, one cyano group, one nitro group, one $C(O)R_{25}$ group, one $CO_2R_{26}$ group or one $X_5R_{27}$ group, or
phenyl optionally substituted with any combination of one to three halogen atoms, one to three $C_1$–$C_4$alkyl groups, one to three $C_1$–$C_4$alkoxy groups, one $C_3$–$C_6$cycloalkyl group, one $C_1$–$C_4$haloalkyl group, one $C_1$–$C_4$alkylthio group, one cyano group, one nitro group, one $C(O)R_{25}$ group, one $CO_2R_{26}$ group, one $X_4R_{22}$ group, one CH=$CHR_{22}$ group, one $CH_2CH(R_{28})R_{22}$ group or one $N(R_{29})SO_2R_{30}$ group, and when $R_{12}$ and $R_{13}$ are taken together with the nitrogen atom to which they are attached, they form a 5- to 12-membered monocyclic or fused bicyclic, heterocyclic ring optionally substituted with one or more groups independently selected from halogen, cyano, nitro, amino, hydroxyl, $C_1$–$C_4$alkyl, $C_1$–$C_4$haloalkyl, $C_1$–$C_4$alkoxy, $C_1$–$C_4$haloalkoxy, $C_1$–$C_4$haloalkylsulfonyl or $X_4R_{22}$ groups;

$R_{13}$ is hydrogen, $C_1$–$C_6$alkyl, $C_3$–$C_7$cycloalkyl, $C_3$–$C_6$alkenyl, $C_3$–$C_6$alkynyl, benzyl, $OR_{23}$, cyano or $SO_2R_{51}$, and when $R_{13}$ and $R_{12}$ are taken together with the nitrogen atom to which they are attached, they form a 5- to 12-membered monocyclic or fused bicyclic, heterocyclic ring optionally substituted with one or more groups independently selected from halogen, cyano, nitro, amino, hydroxyl, $C_1$–$C_4$alkyl, $C_1$–$C_4$haloalkyl, $C_1$–$C_4$alkoxy, $C_1$–$C_4$haloalkoxy, $C_1$–$C_4$haloalkylsulfonyl or $X_4R_{22}$ groups;

$R_{28}$ is halogen;

$R_{22}$ and $R_{27}$ are each independently hydrogen, $Si(R_{31})_3$, $C_1$–$C_{20}$alkyl substituted with one $C_1$–$C_6$alkoxy, $CO_2R_{32}$, $C(O)R_{33}$, $C(A_4R_{34})_2$, $C(O)NR_{35}R_{36}$, $C(O)ON=CR_{37}R_{38}$, $P(O)(OH)NH_2$, $P(O)(OH)(OR_{23})$, $C(O)NHOR_{23}$, cyano or 2-dioxolanyl group, one phenyl, dihydrofuranone or furanone ring wherein each ring is optionally substituted with any combination of one to three halogen atoms, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups, or one 5- to 12-membered monocyclic or fused bicyclic, heterocyclic ring optionally substituted with one or more groups independently selected from halogen, cyano, nitro, amino, hydroxyl, $C_1$–$C_4$alkyl, $C_1$–$C_4$haloalkyl, $C_1$–$C_4$alkoxy, $C_1$–$C_4$haloalkoxy or $C_1$–$C_4$haloalkylsulfonyl groups, $C_3$–$C_{20}$alkenyl optionally substituted with one to three halogen atoms, one $C_1$–$C_6$alkoxy, $CO_2R_{32}$, $C(O)R_{33}$, $C(A_4R_{34})_2$, $C(O)NR_{35}R_{36}$, $C(O)ON=CR_{37}R_{38}$, $C(O)NHOR_{23}$, cyano or 2-dioxolanyl group, or one phenyl, dihydrofuranone or furanone ring wherein each ring is optionally substituted with any combination of one to three halogen atoms, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups, $C_5$–$C_8$cycloalkenyl optionally substituted with one $C_1$–$C_6$alkoxy, $C_1$–$C_4$alkyl, $C_2$–$C_4$alkenyl, $CO_2R_{32}$, $C(O)R_{33}$, $C(A_4R_{34})_2$, $C(O)NR_{35}R_{36}$, $C(O)ON=CR_{37}R_{38}$, $C(O)NHOR_{23}$, cyano or 2-dioxolanyl group, or one phenyl, dihydrofuranone or furanone ring wherein each ring is optionally substituted with any combination of one to three halogen atoms, one to three $C_1$–$C_4$alkyl groups, one to three $C_1$–$C_4$alkoxy groups or one to three $C_1$–$C_4$haloalkoxy groups, $C_3$–$C_{10}$alkynyl optionally substituted with one $C_1$–$C_6$alkoxy, $CO_2R_{32}$, $C(O)R_{33}$, $C(A_4R_{34})_2$, $C(O)NR_{35}R_{36}$, $C(O)ON=CR_{37}R_{38}$, $C(O)NHOR_{23}$, cyano or 2-dioxolanyl group, or one phenyl, dihydrofuranone or furanone ring wherein each ring is optionally substituted with any combination of one to three halogen atoms, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups, phenyl optionally substituted with any combination of one to three halogen atoms, one to three $C_1$–$C_6$alkyl groups, one to three $C_1$–$C_6$alkoxy groups, one $C_1$–$C_4$haloalkyl group, one $C_1$–$C_4$haloalkoxy group, one cyano group, one nitro group, one $NR_{39}R_{40}$ group or one $C(O)R_{33}$ group, benzyl optionally substituted on the phenyl ring with any combination of one to three halogen atoms, one to three $C_1$–$C_6$alkyl groups, one to three $C_1$–$C_6$alkoxy groups, one $C_1$–$C_4$haloalkyl group, one $C_1$–$C_4$haloalkoxy group, one cyano group, one nitro group, one $NR_{39}R_{40}$ group or one $C(O)R_{33}$ group, or a 4- to 10-membered heterocyclic ring optionally substituted with any combination of one or two oxo groups, one or two thioxo-groups, one to three halogen atoms, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups;

$R_{15}$ and $R_{20}$ are each independently hydrogen, a $C_1$–$C_6$alkyl, $C_3$–$C_7$cycloalkyl, $C_2$–$C_6$alkenyl or $C_2$–$C_6$alkynyl group wherein each group is optionally substituted with one $CO_2R_{42}$ group, benzyl optionally substituted with any combination of one to three halogen atoms, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups, phenyl optionally substituted with any combination of one to three halogen atoms, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups, or $C(O)R_{43}$;

$R_{16}$ and $R_{21}$ are each independently hydrogen, $C_1$–$C_6$alkyl, $C_3$–$C_7$cycloalkyl, $C_2$–$C_6$alkenyl, $C_3$–$C_7$cycloalkenyl, $C_2$–$C_6$alkynyl, $P(O)(OR_{44})_2$, $SO_2R_{45}$, $C(O)R_{46}$, benzyl optionally substituted with any combination of one to three halogen atoms, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups or one $X_4R_{22}$ group, or phenyl optionally substituted with any combination of one to three halogen atoms, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups or one $X_4R_{22}$ group;

$R_{17}$, $R_{18}$, $R_{25}$, $R_{30}$, $R_{33}$, $R_{45}$ and $R_{51}$ are each independently $C_1$–$C_4$alkyl, $C_1$–$C_4$haloalkyl, $CO_2R_{23}$, $C_2$–$C_6$alkenyl optionally substituted with phenyl, benzyl optionally substituted with any combination of one to three halogen atoms, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups, one nitro group, one cyano group or one $X_4R_{22}$ group, phenyl optionally substituted with any combination of one to three halogen atoms, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups, one nitro group, one cyano group or one $X_4R_{22}$ group, or a 5- to 12-membered monocyclic or fused bicyclic, heterocyclic ring optionally substituted with one or more groups independently selected from halogen, cyano, nitro, amino, hydroxyl, $C_1$–$C_4$alkyl, $C_1$–$C_4$haloalkyl, $C_1$–$C_4$alkoxy, $C_1$–$C_4$haloalkoxy, $C_1$–$C_4$haloalkylsulfonyl or $X_4R_{22}$ groups;

$R_{19}$ and $R_{26}$ are each independently hydrogen, $C_1$–$C_{20}$alkyl, $C_1$–$C_8$haloalkyl, $C_3$–$C_7$cycloalkyl, $C_3$–$C_7$halocycloalkyl, $C_3$–$C_{20}$alkenyl, $C_3$–$C_8$haloalkenyl, $C_5$–$C_8$cycloalkenyl, $C_5$–$C_8$halocycloalkenyl, $C_3$–$C_8$alkynyl, $C_3$–$C_8$haloalkynyl, $Si(R_{41})_3$, benzyl, phenyl, furfuryl, pyridyl, thienyl, oximino or an alkali metal, alkaline earth metal, manganese, copper, zinc, cobalt, silver, nickel, ammonium or organic ammonium cation;

$R_{32}$ is hydrogen,
  $Si(R_{47})_3$,
  di($C_1$–$C_4$alkyl)imino,
  $C_1$–$C_{20}$alkyl optionally substituted with one $CO_2R_{48}$, $C_1$–$C_6$alkoxy or di($C_1$–$C_4$alkyl)imino group,
  $C_1$–$C_{15}$haloalkyl,
  $C_3$–$C_8$cycloalkyl,
  $C_3$–$C_8$halocycloalkyl,
  $C_3$–$C_{20}$alkenyl optionally substituted with one phenyl group,
  $C_3$–$C_{15}$haloalkenyl,
  $C_5$–$C_8$cycloalkenyl,
  $C_5$–$C_8$halocycloalkenyl,
  $C_3$–$C_{20}$alkynyl optionally substituted with one phenyl group,
  $C_3$–$C_{20}$haloalkynyl,
  benzyl optionally substituted with one or more groups independently selected from halogen, cyano, nitro, $C_1$–$C_4$alkyl, $C_1$–$C_4$haloalkyl, $C_1$–$C_4$alkoxy and $C_1$–$C_4$haloalkoxy groups,
  phenyl optionally substituted with one or more groups independently selected from halogen, cyano, nitro, $C_1$–$C_4$alkyl, $C_1$–$C_4$haloalkyl, $C_1$–$C_4$alkoxy and $C_1$–$C_4$haloalkoxy groups,
  2-, 3- or 4-pyridyl,
  2- or 3-furyl,
  2- or 3-thienyl,
  2-tetrahydrofuranyl,
  $C_1$–$C_4$alkyl substituted with one pyridyl, furyl, thienyl, tetrahydrofuryl or $NR_{49}R_{50}$ group, or
  an alkali metal, alkaline earth metal, manganese, copper, zinc, cobalt, silver, nickel, ammonium or organic ammonium cation;

$R_{34}$, $R_{37}$ and $R_{38}$ are each independently $C_1$–$C_6$alkyl;

$R_{35}$ and $R_{49}$ are each independently hydrogen or $C_1$–$C_6$alkyl and $R_{36}$ and $R_{50}$ are each independently hydrogen, cyano, $C_1$–$C_6$alkyl, $SO_2R_{51}$ or phenyl optionally substituted with one or more groups independently selected from halogen, cyano, nitro, $C_1$–$C_4$alkyl, $C_1$–$C_4$haloalkyl, $C_1$–$C_4$alkoxy and $C_1$–$C_4$haloalkoxy groups, or when $R_{35}$ and $R_{36}$ or $R_{49}$ and $R_{50}$ are taken together with the nitrogen atom to which they are attached, they form a 5- to 12-membered monocyclic or fused bicyclic, heterocyclic ring optionally substituted with one or more groups independently selected from halogen, cyano, nitro, amino, hydroxyl, $C_1$–$C_4$alkyl, $C_1$–$C_4$haloalkyl, $C_1$–$C_4$alkoxy, $C_1$–$C_4$haloalkoxy or $C_1$–$C_4$haloalkylsulfonyl groups;

m, n, p and q are each independently an integer of 0, 1 or 2;

$R_{29}$ is hydrogen, $C_1$–$C_4$alkyl or $C_1$–$C_4$haloalkyl;

$R_{24}$, $R_{31}$, $R_{41}$ and $R_{47}$ are each independently $C_1$–$C_4$alkyl, benzyl optionally substituted with one or more groups independently selected from halogen, cyano, nitro, $C_1$–$C_4$alkyl, $C_1$–$C_4$haloalkyl, $C_1$–$C_4$alkoxy and $C_1$–$C_4$haloalkoxy groups, or phenyl optionally substituted with one or more groups independently selected from halogen, cyano, nitro, $C_1$–$C_4$alkyl, $C_1$–$C_4$haloalkyl, $C_1$–$C_4$alkoxy and $C_1$–$C_4$haloalkoxy groups;

$R_{23}$, $R_{39}$, $R_{40}$, $R_{42}$, $R_{43}$, $R_{44}$, $R_{46}$ and $R_{48}$ are each independently hydrogen, $C_1$–$C_4$alkyl,
  benzyl optionally substituted with one or more groups independently selected from halogen, cyano, nitro, $C_1$–$C_4$alkyl, $C_1$–$C_4$haloalkyl, $C_1$–$C_4$alkoxy and $C_1$–$C_4$haloalkoxy groups, or
  phenyl optionally substituted with one or more groups independently selected from halogen, cyano, nitro, $C_1$–$C_4$alkyl, $C_1$–$C_4$haloalkyl, $C_1$–$C_4$alkoxy and $C_1$–$C_4$haloalkoxy groups; and A, $A_1$, $A_2$, $A_3$, $A_4$, $X_4$ and $X_5$ are each independently O or S; and the optical isomers, diastereomers and/or tautomers thereof.

3. The compound according to claim 1 having the structural formula (I)

4. The compound according to claim 3 wherein

R is $C_1$–$C_4$alkyl, $C_1$–$C_4$haloalkyl, $C_3$–$C_4$alkenyl, $C_3$–$C_4$alkynyl or benzyl;

$R_1$ is halogen or $C_1$–$C_4$haloalkyl;

$R_2$ is hydrogen, halogen or $C_1$–$C_4$haloalkyl;

X and $X_1$ are each independently hydrogen or halogen;

Z is O or S;

Y is cyano, $R_{12}$, $X_2R_{12}$ or $X_3X_2R_{12}$;

$X_2$ is O, S or $NR_{13}$;

$R_{12}$ is hydrogen,
  a $C_1$–$C_6$alkyl, $C_3$–$C_7$cycloalkyl, $C_2$–$C_6$alkenyl, $C_5$–$C_6$cycloalkenyl or $C_2$–$C_6$alkynyl group, wherein each group is optionally substituted with any combination of one to three halogen atoms, one or two $C_1$–$C_{20}$alkoxy groups, one or two $C_1$–$C_{10}$haloalkoxy groups, one $NR_{15}R_{16}$ group, one $S(O)_qR_{17}$ group, one or two cyano groups, one or two $C(O)R_{18}$ groups, one or two $CO_2R_{19}$ groups, one or two $C(O)SR_{19}$ groups, one or two $C(O)NR_{20}R_{21}$ groups, one or two $X_4R_{22}$ groups, one $P(O)(OR_{23})_2$ group, one $Si(R_{24})_3$ group,
  one 4- to 10-membered monocyclic or fused bicyclic heterocyclic ring optionally substituted with any combination of one or two oxo groups, one or two thioxo groups, one to three halogen atoms, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups or one or two $X_4R_{22}$ groups,
  one quaternary organic ammonium group, or
  one phenyl group optionally substituted with any combination of one to three halogen atoms, one $C_1$–$C_6$alkyl group, one $C_1$–$C_6$alkoxy group, one $C_3$–$C_7$cycloalkyl group, one cyano group, one nitro group, one C(O)$R_{25}$ group, one $CO_2R_{26}$ group or one $X_5R_{27}$ group, or phenyl optionally substituted with any combination of one or two halogen atoms, one to three $C_1$–$C_4$alkyl groups, one or two $C_1$–$C_4$alkoxy groups, one $C_3$–$C_6$cycloalkyl group, one $C_1$–$C_4$haloalkyl group, one $C_1$–$C_4$alkylthio group, one cyano group, one nitro group, one C(O)$R_{25}$ group, one $CO_2R_{26}$ group, one $X_4R_{22}$ group, one CH=CH$R_{22}$ group, one $CH_2CH(R_{28})R_{22}$ group or one N($R_{29}$)$SO_2R_{30}$ group;

$R_{13}$ is hydrogen, $C_2$–$C_6$alkoxyalkyl, $C_1$–$C_4$alkyl, $C_3$–$C_7$cycloalkyl, $C_3$–$C_6$alkenyl, $C_3$–$C_6$alkynyl, benzyl, $OR_{23}$, cyano or $SO_2R_{51}$;

$R_{14}$ is hydrogen, $C_1$–$C_6$alkyl, $C_3$–$C_7$cycloalkyl, $C_2$–$C_8$alkoxyalkyl, $C_2$–$C_6$alkenyl, $C_2$–$C_6$alkynyl or benzyl;

$R_{16}$ and $R_{21}$ are each independently hydrogen, $C_1$–$C_6$alkyl, $C_1$–$C_4$alkoxy, $C_3$–$C_7$cycloalkyl, $C_2$–$C_6$alkenyl, $C_3$–$C_7$cycloalkenyl, $C_2$–$C_6$alkynyl, P(O)(O$R_{44}$)$_2$, $SO_2R_{45}$, C(O)$R_{46}$, benzyl optionally substituted with any combination of one to three halogen atoms, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups, or phenyl optionally substituted with any combination of one to three halogen atoms, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups; and $R_{32}$ is hydrogen,
Si($R_{47}$)$_3$,
$C_1$–$C_{20}$alkyl optionally substituted with one $CO_2R_{48}$, $C_1$–$C_6$alkoxy, $C_1$–$C_6$thioalkyl, $C_2$–$C_{20}$alkoxyalkyl, phenyl, OSi($R_{47}$)$_3$, OC(O)$R_{33}$, $C_3$–$C_7$cycloalkyl or di($C_1$–$C_4$alkyl)imino group,
$C_1$–$C_{15}$haloalkyl,
$C_3$–$C_8$cycloalkyl optionally substituted with one $CO_2R_{48}$ group,
$C_3$–$C_8$halocycloalkyl,
$C_3$–$C_{20}$alkenyl optionally substituted with one phenyl group,
$C_3$–$C_{15}$haloalkenyl,
$C_5$–$C_8$cycloalkenyl,
$C_5$–$C_8$halocycloalkenyl,
$C_3$–$C_{20}$alkynyl optionally substituted with one phenyl group,
$C_3$–$C_{20}$haloalkynyl, benzyl optionally substituted with one or more groups independently selected from halogen, cyano, nitro, $C_1$–$C_4$alkyl, $C_1$–$C_4$haloalkyl, $C_1$–$C_4$alkoxy and $C_1$–$C_4$haloalkoxy groups, phenyl optionally substituted with one or more groups independently selected from halogen, cyano, nitro, $C_1$–$C_4$alkyl, $C_1$–$C_4$haloalkyl, $C_1$–$C_4$alkoxy and $C_1$–$C_4$haloalkoxy groups, $C_1$–$C_4$alkyl substituted with one pyridyl, furyl, thienyl, tetrahydrofuryl, $C_3$–$C_8$cycloalkyl, dioxane or $NR_{49}R_{50}$ group, or an alkali metal, alkaline earth metal, manganese, copper, zinc, cobalt, silver, nickel, ammonium or organic ammonium cation.

5. The compound according to claim 4 wherein
R is $C_1$–$C_4$alkyl;
$R_1$ is $C_1$–$C_4$haloalkyl;
$R_2$ is hydrogen,
Y is $R_{12}$, $OR_{12}$, C(O)N$R_{13}R_{12}$, C(O)$R_{12}$, $CO_2R_{12}$, C(O)S$R_{12}$ or C(=NO$R_{14}$);
$R_{12}$ is hydrogen, a $C_1$–$C_6$alkyl or $C_2$–$C_6$alkenyl group, wherein each group is optionally substituted with any combination of one to three halogen atoms, one or two $C_1$–$C_4$alkoxy groups, one $C_1$–$C_{10}$haloalkoxy group, one N$R_{15}R_{16}$ group, one S(O)$_q$$R_{17}$ group, one or two cyano groups, one or two C(O)$R_{18}$ groups, one or two $CO_2R_{19}$ groups, one or two C(O)N$R_{20}R_{21}$ groups, one $X_4R_{22}$ group, one P(O)(O$R_{23}$)$_2$ group, one OC(O)$R_{33}$ group, one imidazole ring optionally substituted with any combination of one to three halogen atoms, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups, one phthalimide ring optionally substituted with any combination of one to three halogen atoms, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups, one quaternary organic ammonium group, or one phenyl group optionally substituted with any combination of one to three halogen atoms, one $C_1$–$C_4$alkyl group, one $C_1$–$C_4$alkoxy group or one $X_5R_{27}$ group, or phenyl optionally substituted with any combination of one or two halogen atoms, one to three $C_1$–$C_4$alkyl groups, one $C_1$–$C_4$alkoxy group, one C(O)$R_{25}$ group, one $CO_2R_{26}$ group, one $X_4R_{22}$ group, one CH=CH$R_{22}$ group, one $CH_2CH(R_{28})R_{22}$ group or one N($R_{29}$)$SO_2R_{30}$ group;

$R_{13}$ is hydrogen, $C_1$–$C_6$alkoxyalkyl, $C_1$–$C_4$alkyl, $OR_{23}$, cyano or $SO_2R_{51}$;

$R_{22}$ and $R_{27}$ are each independently hydrogen, C(O)$R_{33}$, $SO_2R_{47}$, $C_1$–$C_4$alkyl substituted with one $C_1$–$C_6$alkoxy, $CO_2R_{32}$, C(O)$R_{33}$, C(O)$N_{35}R_{36}$, C(O)ON=CR$_{37}R_{38}$, C(O)NHO$R_{23}$, cyano or 2-dioxolanyl group, or one phenyl, dihydrofuranone or furanone ring wherein each ring is optionally substituted with any combination of one to three halogen atoms, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups, $C_3$–$C_6$alkenyl optionally substituted with one $C_1$–$C_6$alkoxy, $CO_2R_{32}$, C(O)$R_{33}$ or C(O$R_{34}$)$_2$ group,
$C_3$–$C_6$alkynyl, phenyl optionally substituted with any combination of one to three halogen atoms, one or two $C_1$–$C_4$alkyl groups, one or two $C_1$–$C_4$alkoxy groups, one $C_1$–$C_4$haloalkyl group, one $C_1$–$C_4$haloalkoxy group, one cyano group, one nitro group, one N$R_{39}R_{40}$ group or one C(O)$R_{33}$ group, or benzyl optionally substituted on the phenyl ring with any combination of one to three halogen atoms, one or two $C_1$–$C_4$alkyl groups, one or two $C_1$–$C_4$alkoxy groups, one $C_1$–$C_4$haloalkyl group, one $C_1$–$C_4$haloalkoxy group, one cyano group, one nitro group, one N$R_{39}R_{40}$ group or one C(O)$R_{33}$ group;

$R_{15}$ is hydrogen,
$C_1$–$C_4$alkyl optionally substituted with one $CO_2R_{42}$ group, benzyl optionally substituted with any combination of one to three halogen atoms, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups, or $C(O)R_{43}$;

$R_{16}$ is hydrogen, $C_1$–$C_4$alkyl, $P(O)(OR_{44})_2$, $SO_2R_{45}$, $C(O)R_{46}$, or benzyl optionally substituted with any combination of one to three halogen atoms, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups;

$R_{17}$, $R_{18}$, $R_{25}$, $R_{30}$, $R_{33}$, $R_{45}$ and $R_{51}$ are each independently $NR_{46}R_{48}$, $C_1$–$C_4$alkyl, $C_1$–$C_4$haloalkyl, $C_2$–$C_6$alkenyl optionally substituted with phenyl, benzyl optionally substituted with any combination of one to three halogen atoms, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups, one nitro group, one cyano group or one $X_4R_{22}$ group, or phenyl optionally substituted with any combination of one to three halogen atoms, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups, one nitro group, one cyano group or one $X_4R_{22}$ group;

$R_{19}$ and $R_{26}$ are each independently hydrogen, $C_1$–$C_4$alkyl, $C_3$–$C_6$alkenyl, $C_3$–$C_6$alkynyl, $Si(R_{41})_3$, benzyl, phenyl, furfuryl, pyridyl, thienyl, oximino or an alkali metal, alkaline earth metal, manganese, copper, zinc, cobalt, silver, nickel, ammonium or organic ammonium cation;

$R_{32}$ is hydrogen, $Si(R_{47})_3$, $C_1$–$C_4$alkyl optionally substituted with one $CO_2R_{48}$, $OC(O)R_{33}$ or $C_1$–$C_4$alkoxy group, $C_1$–$C_4$haloalkyl, $C_3$–$C_8$cycloalkyl, $C_3$–$C_8$halocycloalkyl, $C_3$–$C_6$alkenyl optionally substituted with one phenyl group, $C_3$–$C_6$haloalkenyl, $C_5$–$C_8$cycloalkenyl, $C_5$–$C_8$halocycloalkenyl, $C_3$–$C_6$alkynyl optionally substituted with one phenyl group, $C_3$–$C_6$haloalkynyl, benzyl optionally substituted with one or more groups independently selected from halogen, cyano, nitro, $C_1$–$C_4$alkyl, $C_1$–$C_4$haloalkyl, $C_1$–$C_4$alkoxy and $C_1$–$C_4$haloalkoxy groups, phenyl optionally substituted with one or more groups independently selected from halogen, cyano, nitro, $C_1$–$C_4$alkyl, $C_1$–$C_4$haloalkyl, $C_1$–$C_4$alkoxy and $C_1$–$C_4$haloalkoxy groups, $C_1$–$C_4$alkyl substituted with one pyridyl, furyl, thienyl, tetrahydrofuryl or $NR_{49}R_{50}$ group, or an alkali metal, alkaline earth metal, manganese, copper, zinc, cobalt, silver, nickel, ammonium or organic ammonium cation;

$R_{35}$ and $R_{49}$ are each independently hydrogen or $C_1$–$C_4$alkyl and $R_{36}$ and $R_{50}$ are each independently hydrogen, cyano, $C_1$–$C_4$alkyl, $SO_2R_{51}$ or phenyl optionally substituted with one or more groups independently selected from halogen, cyano, nitro, $C_1$–$C_4$alkyl, $C_1$–$C_4$haloalkyl, $C_1$–$C_4$alkoxy and $C_1$–$C_4$haloalkoxy groups, or when $R_{35}$ and $R_{36}$ or $R_{49}$ and $R_{50}$ are taken together with the nitrogen atom to which they are attached, they form a 5- to 12-membered monocyclic or fused bicyclic, heterocyclic ring optionally substituted with one or more groups independently selected from halogen, cyano, nitro, amino, hydroxyl, $C_1$–$C_4$alkyl, $C_1$–$C_4$haloalkyl, $C_1$–$C_4$alkoxy, $C_1$–$C_4$haloalkoxy or $C_1$–$C_4$haloalkylsulfonyl groups;

$R_{23}$ is hydrogen or $C_1$–$C_4$ alkyl; and

A is O.

6. The compound according to claim 5 wherein

R is methyl;

$R_1$ is trifluoromethyl;

$X_1$ is hydrogen;

X is hydrogen or fluorine;

Y is $R_{12}$, $CO_2R_{12}$, $C(O)R_{12}$ or $C(O)NR_{13}R_{12}$;

$R_{12}$ is hydrogen, $C_1$–$C_6$alkyl optionally substituted with any combination of one to three halogen atoms, one hydroxyl group, one or two $C_1$–$C_4$alkoxy groups, one $C_1$–$C_4$haloalkoxy group, one $SO_2R_{17}$ group, one or two cyano groups, one $C(O)R_{18}$ group, one or two $CO_2R_{19}$ groups, one or two $C(O)NR_{20}R_{21}$ groups, one $P(O)(OR_{23})_2$ group or one $OC(O)R_{33}$ group, $C_2$–$C_6$alkenyl optionally substituted with any combination of one $C(O)R_{18}$ group or one $CO_2R_{19}$ group,

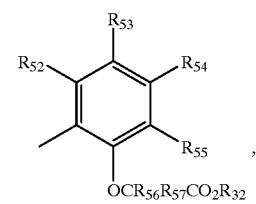

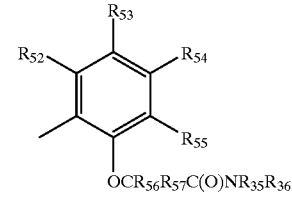

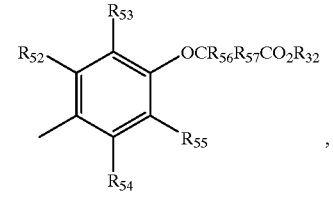

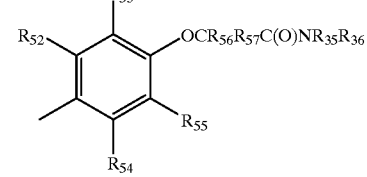

or

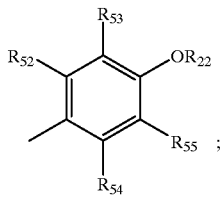

$R_{13}$ is hydrogen, $C_1$–$C_4$ alkyl or $SO_2R_{51}$;

$R_{14}$ is hydrogen, $C_1$–$C_4$alkyl or benzyl;

$R_{18}$, $R_{23}$, $R_{56}$ and $R_{57}$ are each independently hydrogen or $C_1$–$C_3$alkyl;

$R_{52}$, $R_{53}$, $R_{54}$ and $R_{55}$ are each independently hydrogen, $C_1$–$C_3$alkyl, $C_2$–$C_3$alkenyl, $C_1$–$C_3$alkoxy or halogen, provided that at least one of $R_{52}$, $R_{53}$, $R_{54}$ and $R_{55}$ is hydrogen;

$R_{19}$ is hydrogen, $C_1$–$C_4$alkyl, $C_3$–$C_6$alkenyl, $C_3$–$C_6$alkynyl, benzyl, pyridyl or an alkali metal, alkaline earth metal, ammonium or organic ammonium cation;

$R_{22}$ is hydrogen, $C(O)R_{33}$, $SO_2R_{47}$, $C_1$–$C_4$alkyl optionally substituted with one cyano group, $C_3$–$C_6$alkenyl, or $C_3$–$C_6$alkynyl;

$R_{32}$ is hydrogen,
$C_1$–$C_4$alkyl optionally substituted with one $CO_2R_{48}$ or $C_1$–$C_4$alkoxy group,
$C_1$–$C_4$haloalkyl,
$C_3$–$C_6$alkenyl optionally substituted with one phenyl group,
$C_3$–$C_6$alkynyl optionally substituted with one phenyl group,
$C_1$–$C_4$alkyl substituted with one pyridyl, furyl, thienyl, tetrahydrofuryl or $NR_{49}R_{50}$ group, or
an alkali metal, alkaline earth metal, ammonium or organic ammonium cation;

$R_{35}$ and $R_{49}$ are each independently hydrogen or $C_1$–$C_4$alkyl;

$R_{36}$ is $SO_2R_{51}$ or $C_1$–$C_3$alkoxy;

$R_{17}$, $R_{33}$ and $R_{51}$ are each independently $C_1$–$C_4$alkyl, $C_1$–$C_4$haloalkyl, $NR_{46}R_{48}$, $C_3$–$C_6$cycloalkyl or an isoxazole ring;

$R_{46}$ and $R_{48}$ are each independently hydrogen, $C_1$–$C_4$alkyl or benzyl;

$R_{47}$ is $C_1$–$C_4$alkyl;

$R_{50}$ is $C_1$–$C_4$alkyl or
phenyl optionally substituted with one or more groups independently selected from halogen, cyano, $C_1$–$C_4$alkyl, $C_1$–$C_4$haloalkyl, $C_1$–$C_4$alkoxy and $C_1$–$C_4$haloalkoxy groups; and $A_1$ is O.

7. The compound according to claim 6 wherein

Y is $C_1$–$C_3$alkyl, $CO_2R_{32}$, halomethyl, cyanomethyl, $C(CH_3)_2CO_2R_{32}$, $C_1$–$C_3$alkoxyethyl, $C_1$–$C_3$alkoxymethyl, hydroxymethyl, CHO, $C(O)CH_3$, $CH(CH_3)(C_1$–$C_4$alkoxy), $C(CH_3)_2CN$, $CH[O(C_1$–$C_3$alkyl)]_2$, $CH_2SO_2R_{17}$, $C(O)NHSO_2R_{51}$,

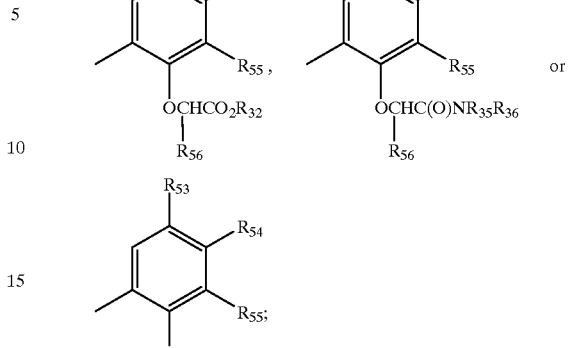

$R_{53}$, $R_{54}$, $R_{55}$ and $R_{56}$ are each independently hydrogen or methyl, provided that at least one of $R_{53}$, $R_{54}$ and $R_{55}$ is hydrogen;

$R_{22}$ is cyanomethyl, methyl, ethyl, allyl or propargyl;

$R_{32}$ is hydrogen,
$C_1$–$C_4$alkyl optionally substituted with one $CO_2R_{48}$ group,
$C_1$–$C_4$haloalkyl,
$C_3$–$C_6$alkenyl, or
$C_3$–$C_6$alkynyl; and $R_{35}$ is hydrogen.

8. The compound according to claim 1 selected from the group consisting of
isopropyl{{2-{5-[3,6-dihydro-3-methyl-2,6-dioxo-4-(trifluoromethyl)-1(2H)-pyrimidinyl]-1,2-benzisothiazol-3-yl}-p-tolyl}oxy}acetate;
methyl{{2-{5-[3,6-dihydro-3-methyl-4-(trifluoromethyl)-2,6-dioxo-1(2H)-pyrimidinyl]-1,2-benzisothiazol-3-yl}-p-tolyl}oxy}acetate;
2-(dimethylamino)ethyl{{2-{5-[3,6-dihydro-3-methyl-2,6-dioxo-4-(trifluoromethyl)-1(2H)-pyrimidinyl]-1,2-benzisothiazol-3-yl}-p-tolyl}oxy}acetate;
methyl 2-{{2-{5-[3,6-dihydro-3-methyl-4-(trifluoromethyl)-2,6-dioxo-1(2H)-pyrimidinyl]-1,2-benzisothiazol-3-yl}-p-tolyl}oxy}propionate;
methyl 2-{{6-{5-[3,6-dihydro-3-methyl-4-(trifluoromethyl)-2,6-dioxo-1(2H)-pyrimidinyl]-1,2-benzisothiazol-3-yl}-3,4-xylyl}oxy}propionate;
2-propynyl{{2-{5-[3,6-dihydro-3-methyl-2,6-dioxo-4-(trifluoromethyl)-1(2H)-pyrimidinyl]-1,2-benzisothiazol-3-yl}-p-tolyl}oxy}acetate;
3-[3-(6-methoxy-m-tolyl)-1,2-benzisothiazol-5-yl]-1-methyl-6-(trifluoromethyl)-2,4(1H,3H)-pyrimidinedione;
3-[3-(p-ethylphenyl)-1,2-benzisothiazol-5-yl]-1-methyl-6-(trifluoromethyl)-2,4(1H,3H)-pyrimidinedione;
1-methyl-3-(3-methyl-1,2-benzisothiazol-5-yl)-6-(trifluoromethyl)-2,4(1H,3H)-pyrimidinedione;
methyl 2-{{6-{5-[3,6-dihydro-3-methyl-4-(trifluoromethyl)-2,6-dioxo-1(2H)-pyrimidinyl]-1,2-benzisothiazol-3-yl}-m-tolyl}oxy}propionate;
methyl{{6-{5-[3,6-dihydro-3-methyl-4-(trifluoromethyl)-2,6-dioxo-1(2H)-pyrimidinyl]-1,2-benzisothiazol-3-yl}-3,4-xylyl}oxy}acetate;
3-[3-(dibromomethyl)-1,2-benzisothiazol-5-yl]-1-methyl-6-(trifluoromethyl)-2,4(1H,3H)-pyrimidinedione;
3-(6-fluoro-3-methyl-1,2-benzisoxazol-5-yl)-1-methyl-6-(trifluoromethyl)-2,4(1H,3H)-pyrimidinedione;

ethyl{{2-{5-[3,6-dihydro-3-methyl-2,6-dioxo-4-(trifluoromethyl)-1(2H)-pyrimidinyl]-1,2-benzisothiazol-3-yl}-p-tolyl}oxy}acetate;

1-methyl-3-{3-[6-(2-propynyloxy)-m-tolyl]-1,2-benzisothiazol-5-yl}-6-(trifluoromethyl)-2,4(1H,3H)-pyrimidinedione;

3-{3-{6-[(1-benzimidazolylcarbonyl)methoxy]-m-tolyl}-1,2-benzisothiazol-5-yl}-1-methyl-6-trifluoromethyl)-2,4(1H,3H)-pyrimidinedione;

3-{3-{6-{[(m-cyanophenyl)carbamoyl]methoxy}-m-tolyl}-1,2-benzisothiazol-5-yl}-1-methyl-6-(trifluoromethyl)-2,4(1H,3H)pyrimidinedione;

allyl{{2-{5-[3,6-dihydro-3-methyl-2,6-dioxo-4-(trifluoromethyl)-1(2H)-pyrimidinyl]-1,2-benzisothiazol-3-yl}-p-tolyl}oxy}acetate;

3-phenyl-2-propynyl{{2-{5-[3,6-dihydro-3-methyl-2,6-dioxo-4-(trifluoromethyl)-1(2H)-pyrimidinyl]-1,2-benzisothiazol-3-yl}-p-tolyl}oxy}acetate;

1-methyl-2-propynyl{{2-{5-[3,6-dihydro-3-methyl-2,6-dioxo-4-(trifluoromethyl)-1(2H)-pyrimidinyl]-1,2-benzisothiazol-3-yl}-p-tolyl}oxy}acetate;

2-chloroethyl 2-{{2-{5-[3,6-dihydro-3-methyl-2,6-dioxo-4-(trifluoromethyl)-1(2H)-pyrimidinyl]-1,2-benzisothiazol-3-yl}-p-tolyl}oxy}propionate;

2,2,2-trifluoroethyl{{2-{5-[3,6-dihydro-3-methyl-2,6-dioxo-4-(trifluoromethyl)-1(2H)-pyrimidinyl]-1,2-benzisothiazol-3-yl}-p-tolyl}oxy}acetate;

3-[3-(2-methoxy-p-tolyl)-1,2-benzisothiazol-5-yl]-1-methyl-6-(trifluoromethyl)-2,4(1H,3H)-pyrimidinedione;

2-[3-(6-methoxy-3,4-xylyl)-1,2-benzisothiazol-5-yl]-1-methyl-6-(trifluoromethyl)-2,4(1H,3H)-pyrimidinedione;

methyl 2-{{6-{5-[3,6-dihydro-3-methyl-4-(trifluoromethyl)-2,6-dioxo-1(2H)-pyrimidinyl]-1,2-benzisothiazol-3-yl}-3,4-xylyl}oxy}propionate;

methyl{{6-{5-[3,6-dihydro-3-methyl-2,6-dioxo-4-(trifluoromethyl)-1(2H)-pyrimidinyl]-1,2-benzisothiazol-3-yl}-2,4-xylyl}oxy}acetate;

3-{3-{6-{[(m-cyanophenyl)carbamoyl]methoxy}-m-tolyl}-1,2-benzisothiazol-5-yl}-1-methyl-6-(trifluoromethyl)-2,4(1H,3H)-pyrimidinedione;

methyl{{2-{5-[3,6-dihydro-3-methyl-2,6-dioxo-4-(trifluoromethyl)-1(2H)-pyrimidinyl]-1,2-benzisoxazol-3-yl}-p-tolyl}oxy}acetate;

1-methyl-3-{3-[(methylsulfonyl)methyl]-1,2-benzisothiazol-5-yl}-6-(trifluoromethyl)-2,4(1H,3H)-pyrimidinedione;

2-propynyl{{2-{5-[3,6-dihydro-3-methyl-2,6-dioxo-4-(trifluoromethyl)-1(2H)-pyrimidinyl]-1,2-benzisoxazol-3-yl}-p-tolyl}oxy}acetate;

3-[3-(o-methoxyphenyl)-1,2-benzisothiazol-5-yl]-1-methyl-6-(trifluoromethyl)-2,4(1H,3H)-pyrimidinedione;

N-{{{2-{5-[3,6-dihydro-3-methyl-2,6-dioxo-4-(trifluoromethyl)-1(2H)-pyrimidinyl]-1,2-benzisothiazol-3-yl}-p-tolyl}oxy}acetyl}methanesulfonamide;

2-propynyl 2-{{2-{5-[3,6-dihydro-3-methyl-2,6-dioxo-4-(trifluoromethyl)-1(2H)-pyrimidinyl]-1,2-benzisoxazol-3-yl}-p-tolyl}oxy}propionate;

2-propynyl{o-{5-[3,6-dihydro-3-methyl-2,6-dioxo-4-(trifluoromethyl)-1(2H)-pyrimidinyl]-1,2-benzisothiazol-3-yl}phenoxy}acetate;

5-[3,6-dihydro-3-methyl-2,6-dioxo-4-(trifluoromethyl)-1(2H)-pyrimidinyl]-1,2-benzisothiazole-3-acetonitrile;

3-{3-[(allyloxy)methyl]-1,2-benzisothiazol-5-yl}-1-methyl-6-(trifluoromethyl)-2,4(1H,3H)-pyrimidinedione;

5-[3,6-dihydro-3-methyl-2,6-dioxo-4-(trifluoromethyl)-1(2H)-pyrimidinyl]-N-(methylsulfonyl)-1,2-benzisothiazole-carboxamide;

methyl{{2-{5-[3,6-dihydro-3-methyl-2,6-dioxo-4-(trifluoromethyl)-1(2H)-pyrimidinyl]-6-fluoro-1,2-benzisoxazol-3-yl}-p-tolyl}oxy}acetate;

methyl{{6-{5-[3,6-dihydro-3-methyl-2,6-dioxo-4-(trifluoromethyl)-1(2H)-pyrimidinyl]-6-fluoro-1,2-benzisothiazol-3-yl}-m-tolyl}oxy}acetate;

{o-{5-[3,6-dihydro-3-methyl-2,6-dioxo-4-(trifluoromethyl)-1(2H)-pyrimidinyl]-1,2-benzisothiazol-3-yl}phenoxy}acetic acid;

2-{o-{5-[3,6-dihydro-3-methyl-2,6-dioxo-4-(trifluoromethyl)-1(2H)-pyrimidinyl]-1,2-benzisothiazol-3-yl}phenoxy}propionic acid;

2-{{2-{5-[3,6-dihydro-3-methyl-2,6-dioxo-4-(trifluoromethyl)-1(2H)-pyrimidinyl]-1,2-benzisothiazol-3-yl}-p-tolyl}oxy}-N-methoxyacetamide;

methyl 2-{2-{5-[3,6-dihydro-3-methyl-2,6-dioxo-4-(trifluoromethyl)-1(2H)-pyrimidinyl]-1,2-benzisothiazol-3-yl}-4-methoxyphenoxy}propionate;

2-{o-{5-[3,6-dihydro-3-methyl-2,6-dioxo-4-(trifluoromethyl)-1(2H)-pyrimidinyl]-1,2-benzisothiazol-3-yl}phenoxy}-N-(methylsulfonyl)acetamide;

2-{o-{5-[3,6-dihydro-3-methyl-2,6-dioxo-4-(trifluoromethyl)-1(2H)-pyrimidinyl]-1,2-benzisothiazol-3-yl}phenoxy}-N-(methylsulfonyl)propionamide;

2-{{2-{5-[3,6-dihydro-3-methyl-2,6-dioxo-4-(trifluoromethyl)-1(2H)-pyrimidinyl]-1,2-benzisothiazol-3-yl}-p-tolyl}oxy}-N-methyl-N-(methylsulfonyl)acetamide;

2-{o-{5-[3,6-dihydro-3-methyl-2,6-dioxo-4-(trifluoromethyl)-1(2H)-pyrimidinyl]-1,2-benzisothiazol-3-yl}phenoxy}-N-methyl-N-(methylsulfonyl)acetamide;

2-{o-{5-[3,6-dihydro-3-methyl-2,6-dioxo-4-(trifluoromethyl)-1(2H)-pyrimidinyl]-1,2-benzisothiazol-3-yl}phenoxy}-N-(ethylsulfonyl)acetamide;

3-[3-(hydroxymethyl)-1,2-benzisothiazol-5-yl]-1-methyl-6-(trifluoromethyl)-2,4(1H,3H)-pyrimidinedione, 2-thiophenecarboxylate (ester);

3-[3-(hydroxymethyl)-1,2-benzisothiazol-5-yl]-1-methyl-6-(trifluoromethyl)-2,4(1H,3H)-pyrimidinedione, benzoate (ester);

3-[3-(hydroxymethyl)-1,2-benzisothiazol-5-yl]-1-methyl-6-(trifluoromethyl)-2,4(1H,3H)-pyrimidinedione, methoxyacetate (ester);

5-[3,6-dihydro-3-methyl-2,6-dioxo-4-(trifluoromethyl)-1(2H)-pyrimidinyl]-N-(ethylsulfonyl)-1,2-benzisothiazole-3-carboxamide;

5-[3,6-dihydro-3-methyl-2,6-dioxo-4-(trifluoromethyl)-1(2H)-pyrimidinyl]-α,α-dimethyl-1,2-benzisothiazole-3-acetonitrile;

5-[3,6-dihydro-3-methyl-2,6-dioxo-4-(trifluoromethyl)-1(2H)-pyrimidinyl]-6-fluoro-1,2-benzisothiazole-3-acetonitrile;

5-[3,6-dihydro-3-methyl-2,6-dioxo-4-(trifluoromethyl)-1(2H)-pyrimidinyl]-α-ethyl-1,2-benzisothiazole-3-acetonitrile;

5-[3,6-dihydro-3-methyl-2,6-dioxo-4-(trifluoromethyl)-1(2H)-pyrimidinyl]-α,α-diethyl-1,2-benzisothiazole-3-acetonitrile;

3-[6-fluoro-3-(methoxymethyl)-1,2-benzisothiazol-5-yl]-1-methyl-6-(trifluoromethyl)-2,4(1H,3H)-pyrimidinedione;

3-[3-(hydroxymethyl)-1,2-benzisothiazol-5-yl]-1-methyl-6-(trifluoromethyl)-2,4(1H,3H)-pyrimidinedione, 5-isoxazolecarboxylate (ester);

3-[3-(hydroxymethyl)-1,2-benzisothiazol-5-yl]-1-methyl-6-(trifluoromethyl)-2,4(1H,3H)-pyrimidinedione, cyclopropanecarboxylate (ester);

3-(3-acetyl-1,2-benzisothiazol-5-yl)-1-methyl-6-(trifluoromethyl)-2,4(1H,3H)-pyrimidinedione;

3-[3-(1-methoxyethyl)-1,2-benzisothiazol-5-yl]-1-methyl-6-(trifluoromethyl)-2,4(1H,3H)-pyrimidinedione;
N-(benzylsulfonyl)-5-[3,6-dihydro-3-methyl-2,6-dioxo-4-(trifluoromethyl)-1(2H)-pyrimidinyl]-1,2-benzisothiazole-3-carboxamide;
methyl 5-[3,6-dihydro-3-methyl-2,6-dioxo-4-(trifluoromethyl)-1(2H)-pyrimidinyl]-1,2-benzisothiazole-3-carboxylate;
benzyl 5-[3,6-dihydro-3-methyl-2,6-dioxo-4-(trifluoromethyl)-1(2H)-pyrimidinyl]-α,α-dimethyl-1,2-benzisothiazole-3-acetate;
N-(benzylsulfonyl)-5-[3,6-dihydro-3-methyl-2,6-dioxo-4-(trifluoromethyl)-1(2H)-pyrimidinyl]-6-fluoro-1,2-benzisothiazole-3-carboxamide;
5-[3,6-dihydro-3-methyl-2,6-dioxo-4-(trifluoromethyl)-1(2H)-pyrimidinyl]-N-(methylsulfonyl)-1,2-benzisothiazole-3-carboxamide;
5-[3,6-dihydro-3-methyl-2,6-dioxo-4-(trifluoromethyl)-1(2H)-pyrimidinyl]-N-(isopropylsulfonyl)-1,2-benzisothiazole-3-carboxamide;
5-[3,6-dihydro-3-methyl-2,6-dioxo-4-(trifluoromethyl)-1(2H)-pyrimidinyl]-N-(ethylsulfonyl)-1,2-benzisothiazole-3-carboxamide;
5-[3,6-dihydro-3-methyl-2,6-dioxo-4-(trifluoromethyl)-1(2H)-pyrimidinyl]-N-[(p-methylbenzyl)sulfonyl]-1,2-benzisothiazole-3-carboxamide;
N-(benzylsulfonyl)-5-[3,6-dihydro-3-methyl-2,6-dioxo-4-(trifluoromethyl)-1(2H)-pyrimidinyl]-6-fluoro-1,2-benzisothiazole-3-carboxamide;
3-[3-(1-hydroxyethyl)-1,2-benzisothiazol-5-yl]-1-methyl-6-(trifluoromethyl)-2,4(1H,3H)-pyrimidinedione;
5-[3,6-dihydro-3-methyl-2,6-dioxo-4-(trifluoromethyl)-1(2H)-pyrimidinyl]-1,2-benzisothiazole-3-carboxaldehyde, 3-(dimethyl acetal);
3-(6-fluoro-3-methyl-1,2-benzisothiazol-5-yl)-1-methyl-6-(trifluoromethyl)-2,4(1H,3H)-pyrimidinedione;
5-[3,6-dihydro-3-methyl-2,6-dioxo-4-(trifluoromethyl)-1(2H)-pyrimidinyl]-6-fluoro-1,2-benzisothiazole-3-carboxaldehyde, 3-(dimethyl acetal);
5-[3,6-dihydro-3-methyl-2,6-dioxo-4-(trifluoromethyl)-1(2H)-pyrimidinyl]-6-fluoro-1,2-benzisothiazole-3-carboxylic acid;
5-[3,6-dihydro-3-methyl-2,6-dioxo-4-(trifluoromethyl)-1(2H)-pyrimidinyl]-α-methyl-1,2-benzisothiazole-3-acetonitrile;
N-(benzylsulfonyl)-5-[3,6-dihydro-3-methyl-2,6-dioxo-4-(trifluoromethyl)-1(2H)-pyrimidinyl]-N-(ethoxymethyl)-1,2-benzisothiazole-3-carboxamide;
5-[3,6-dihydro-3-methyl-2,6-dioxo-4-(trifluoromethyl)-1(2H)-pyrimidinyl]-N-(dimethylsulfamoyl)-1,2-benzisothiazole-3-carboxamide;
5-[3,6-dihydro-3-methyl-2,6-dioxo-4-(trifluoromethyl)-1(2H)-pyrimidinyl]-N-(isopropylsulfamoyl)-1,2-benzisothiazole-3-carboxamide;
methyl 5-[3,6-dihydro-3-methyl-2,6-dioxo-4-(trifluoromethyl)-1(2H)-pyrimidinyl]-α,α-dimethyl-1,2-benzisothiazole-3-acetate;
3-[3-(hydroxymethyl)-1,2-benzisothiazol-5-yl]-1-methyl-6-(trifluoromethyl)-2,4(1H,3H)-pyrimidinedione, 2-furoate (ester);
N-[(m-chlorobenzyl)sulfonyl]-5-[3,6-dihydro-3-methyl-2,6-dioxo-4-(trifluoromethyl)-1(2H)-pyrimidinyl]-1,2-benzisothiazole-3-carboxamide;
5-[3,6-dihydro-3-methyl-2,6-dioxo-4-(trifluoromethyl)-1(2H)-pyrimidinyl]-N-(diisopropylsulfamoyl)-1,2-benzisothiazole-3-carboxamide; and
3-[3-(hydroxymethyl)-1,2-benzisothiazol-5-yl]-1-methyl-6-(trifluoromethyl)-2,4(1H,3H)-pyrimidinedione, methylcarbamate (ester).

9. A method for the control of undesirable plant species which comprises applying to the foliage of said plants or to the soil or water containing seeds or other propagating organs thereof, a herbicidally effective amount of a compound according to claim 1.

10. A method for the control of undesirable plant species which comprises applying to the foliage of said plants or to the soil or water containing seeds or other propagating organs thereof, a herbicidally effective amount of a compound according to claim 2.

11. The method according to claim 9 wherein the compound has the structural formula (I)

12. A method for the control of undesirable plant species which comprises applying to the foliage of said plants or to the soil or water containing seeds or other propagating organs thereof, a herbicidally effective amount of a compound according to claim 4.

13. A method for the control of undesirable plant species which comprises applying to the foliage of said plants or to the soil or water containing seeds or other propagating organs thereof, a herbicidally effective amount of a compound according to claim 8.

14. The method according to claim 9 wherein the compound is applied to the foliage of the undesirable plant species or to the soil or water containing seeds or other propagating organs thereof in the presence of crop plants, crop seeds or other crop propagating organs.

15. The method according to claim 14 wherein the crop is a cereal crop.

16. The method according to claim 15 wherein the cereal crop is selected from the group consisting of corn, wheat and rice.

17. The method according to claim 16 wherein the cereal crop is corn and the compound is selected from the group consisting of
isopropyl{{2-{5-[3,6-dihydro-3-methyl-2,6-dioxo-4-(trifluoromethyl)-1(2H)-pyrimidinyl]-1,2-benzisothiazol-3-yl}-p-tolyl}oxy}acetate;
methyl{{2-{5-[3,6-dihydro-3-methyl-4-(trifluoromethyl)-2,6-dioxo-1(2H)-pyrimidinyl]-1,2-benzisothiazol-3-yl}-p-tolyl}oxy}acetate;
2-(dimethylamino)ethyl{{2-{5-[3,6-dihydro-3-methyl-2,6-dioxo-4-(trifluoromethyl)-1(2H)-pyrimidinyl]-1,2-benzisothiazol-3-yl}-p-tolyl}oxy}acetate;
2-propynyl{{2-{5-[3,6-dihydro-3-methyl-2,6-dioxo-4-(trifluoromethyl)-1(2H)-pyrimidinyl]-1,2-benzisothiazol-3-yl}-p-tolyl}oxy}acetate;
3-[3-(p-ethylphenyl)-1,2-benzisothiazol-5-yl]-1-methyl-6-(trifluoromethyl)-2,4(1H,3H)-pyrimidinedione;
methyl{{6-{5-[3,6-dihydro-3-methyl-4-(trifluoromethyl)-2,6-dioxo-1(2H)-pyrimidinyl]-1,2-benzisothiazol-3-yl}-3,4-xylyl}oxy}acetate;
3-[3-(dibromomethyl)-1,2-benzisothiazol-5-yl]-1-methyl-6-(trifluoromethyl)-2,4(1H,3H)-pyrimidinedione;
1-methyl-2-propynyl{{2-{5-[3,6-dihydro-3-methyl-2,6-dioxo-4-(trifluoromethyl)-1(2H)-pyrimidinyl]-1,2-benzisothiazol-3-yl}-p-tolyl}oxy}acetate;

methyl{{2-{5-[3,6-dihydro-3-methyl-2,6-dioxo-4-(trifluoromethyl)-1(2H)-pyrimidinyl]-1,2-benzisoxazol-3-yl}-p-tolyl}oxy}acetate;

1-methyl-3-{3-[(methylsulfonyl)methyl]-1,2-benzisothiazol-5-yl}-6-(trifluoromethyl)-2,4(1H,3H)-pyrimidinedione;

2-propynyl{{2-{5-[3,6-dihydro-3-methyl-2,6-dioxo-4-(trifluoromethyl)-1(2H)-pyrimidinyl]-1,2-benzisoxazol-3-yl}-p-tolyl}oxy}acetate;

3-[3-(o-methoxyphenyl)-1,2-benzisothiazol-5-yl]-1-methyl-6-(trifluoromethyl)-2,4(1H,3H)-pyrimidinedione;

N-{{{2-{5-[3,6-dihydro-3-methyl-2,6-dioxo-4-(trifluoromethyl)-1(2H)-pyrimidinyl]-1,2-benzisothiazol-3-yl}-p-tolyl}oxy}acetyl}methanesulfonamide;

2-propynyl{o-{5-[3,6-dihydro-3-methyl-2,6-dioxo-4-(trifluoromethyl)-1(2H)-pyrimidinyl]-1,2-benzisothiazol-3-yl}phenoxy}acetate;

5-[3,6-dihydro-3-methyl-2,6-dioxo-4-(trifluoromethyl)-1(2H)-pyrimidinyl]-1,2-benzisothiazole-3-acetonitrile;

3-{3-[(allyloxy)methyl]-1,2-benzisothiazol-5-yl}-1-methyl-6-(trifluoromethyl)-2,4(1H,3H)-pyrimidinedione;

5-[3,6-dihydro-3-methyl-2,6-dioxo-4-(trifluoromethyl)-1(2H)-pyrimidinyl]-N-(methylsulfonyl)-1,2-benzisothiazole-3-carboxamide;

2-{{2-{5-[3,6-dihydro-3-methyl-2,6-dioxo-4-(trifluoromethyl)-1(2H)-pyrimidinyl]-1,2-benzisothiazol-3-yl}-p-tolyl}oxy}-N-methyl-N-(methylsulfonyl)acetamide;

3-[3-(hydroxymethyl)-1,2-benzisothiazol-5-yl]-1-methyl-6-(trifluoromethyl)-2,4(1H,3H)-pyrimidinedione, methylcarbamate (ester);

N-(benzylsulfonyl)-5-[3,6-dihydro-3-methyl-2,6-dioxo-4-(trifluoromethyl)-1(2H)-pyrimidinyl]-1,2-benzisothiazole-3-carboxamide;

5-[3,6-dihydro-3-methyl-2,6-dioxo-4-(trifluoromethyl)-1(2H)-pyrimidinyl]-N-(isopropylsulfonyl)-1,2-benzisothiazole-3-carboxamide;

5-[3,6-dihydro-3-methyl-2,6-dioxo-4-(trifluoromethyl)-1(2H)-pyrimidinyl]-N-(ethylsulfonyl)-1,2-benzisothiazole-3-carboxamide;

5-[3,6-dihydro-3-methyl-2,6-dioxo-4-(trifluoromethyl)-1(2H)-pyrimidinyl]-N-(diisopropylsulfamoyl)-1,2-benzisothiazole-3-carboxamide;

5-[3,6-dihydro-3-methyl-2,6-dioxo-4-(trifluoromethyl)-1(2H)-pyrimidinyl]-N-(isopropylsulfamoyl)-1,2-benzisothiazole-3-carboxamide;

5-[3,6-dihydro-3-methyl-2,6-dioxo-4-(trifluoromethyl)-1(2H)-pyrimidinyl]-N-(dimethylsulfamoyl)-1,2-benzisothiazole-3-carboxamide;

5-[3,6-dihydro-3-methyl-2,6-dioxo-4-(trifluoromethyl)-1(2H)-pyrimidinyl]-6-fluoro-1,2-benzisothiazole-3-carboxylic acid; and N-(benzylsulfonyl)-5-[3,6-dihydro-3-methyl-2,6-dioxo-4-(trifluoromethyl)-1(2H)-pyrimidinyl]-6-fluoro-1,2-benzisothiazole-3-carboxamide.

18. The method according to claim 16 wherein the cereal crop is wheat and the compound is selected from the group consisting of isopropyl{{2-{5-[3,6-dihydro-3-methyl-2,6-dioxo-4-(trifluoromethyl)-1(2H)-pyrimidinyl]-1,2-benzisothiazol-3-yl}-p-tolyl}oxy}acetate;

methyl{{2-{5-[3,6-dihydro-3-methyl-4-(trifluoromethyl)-2,6-dioxo-1(2H)-pyrimidinyl]-1,2-benzisothiazol-3-yl}-p-tolyl}oxy}acetate;

2-(dimethylamino)ethyl{{2-{5-[3,6-dihydro-3-methyl-2,6-dioxo-4-(trifluoromethyl)-1(2H)-pyrimidinyl]-1,2-benzisothiazol-3-yl}-p-tolyl}oxy}acetate;

2-propynyl{{2-{5-[3,6-dihydro-3-methyl-2,6-dioxo-4-(trifluoromethyl)-1(2H)-pyrimidinyl]-1,2-benzisothiazol-3-yl}-p-tolyl}oxy}acetate;

methyl 2-{{6-{5-[3,6-dihydro-3-methyl-4-(trifluoromethyl)-2,6-dioxo-1(2H)-pyrimidinyl]-1,2-benzisothiazol-3-yl}-m-tolyl}oxy}propionate;

3-(6-fluoro-3-methyl-1,2-benzisoxazol-5-yl)-1-methyl-6-(trifluoromethyl)-2,4(1H,3H)-pyrimidinedione;

3-{3-{6-[(1-benzimidazolylcarbonyl)methoxy]-m-tolyl}-1,2-benzisothiazol-5-yl}-1-methyl-6-trifluoromethyl)-2,4(1H,3H)-pyrimidinedione;

allyl{{2-{5-[3,6-dihydro-3-methyl-2,6-dioxo-4-(trifluoromethyl)-1(2H)-pyrimidinyl]-1,2-benzisothiazol-3-yl}-p-tolyl}oxy}acetate;

3-phenyl-2-propynyl{{2-{5-[3,6-dihydro-3-methyl-2,6-dioxo-4-(trifluoromethyl)-1(2H)-pyrimidinyl]-1,2-benzisothiazol-3-yl}-p-tolyl}oxy}acetate;

2-chloroethyl 2-{{2-{5-[3,6-dihydro-3-methyl-2,6-dioxo-4-(trifluoromethyl)-1(2H)-pyrimidinyl]-1,2-benzisothiazol-3-yl}-p-tolyl}oxy}propionate;

2,2,2-trifluoroethyl{{2-{5-[3,6-dihydro-3-methyl-2,6-dioxo-4-(trifluoromethyl)-1(2H)-pyrimidinyl]-1,2-benzisothiazol-3-yl}-p-tolyl}oxy}acetate;

methyl{{6-{5-[3,6-dihydro-3-methyl-2,6-dioxo-4-(trifluoromethyl)-1(2H)-pyrimidinyl]-1,2-benzisothiazol-3-yl}-2,4-xylyl}oxy}acetate;

{o-{5-[3,6-dihydro-3-methyl-2,6-dioxo-4-(trifluoromethyl)-1(2H)-pyrimidinyl]-1,2-benzisothiazol-3-yl}phenoxy}acetic acid;

2-{{2-{5-[3,6-dihydro-3-methyl-2,6-dioxo-4-(trifluoromethyl)-1(2H)-pyrimidinyl]-1,2-benzisothiazol-3-yl}-p-tolyl}oxy}-N-methoxyacetamide;

2-{{2-{5-[3,6-dihydro-3-methyl-2,6-dioxo-4-(trifluoromethyl)-1(2H)-pyrimidinyl]-1,2-benzisothiazol-3-yl}-p-tolyl}oxy}-N-methyl-N-(methylsulfonyl)acetamide;

methyl{{6-{5-[3,6-dihydro-3-methyl-2,6-dioxo-4-(trifluoromethyl)-1(2H)-pyrimidinyl]-6-fluoro-1,2-benzisothiazol-3-yl}-m-tolyl}oxy}acetate;

3-(3-acetyl-1,2-benzisothiazol-5-yl)-1-methyl-6-(trifluoromethyl)-2,4(1H,3H)-pyrimidinedione;

methyl 5-[3,6-dihydro-3-methyl-2,6-dioxo-4-(trifluoromethyl)-1(2H)-pyrimidinyl]-1,2-benzisothiazole-3-carboxylate;

5-[3,6-dihydro-3-methyl-2,6-dioxo-4-(trifluoromethyl)-1(2H)-pyrimidinyl]-N-(isopropylsulfonyl)-1,2-benzisothiazole-3-carboxamide;

5-[3,6-dihydro-3-methyl-2,6-dioxo-4-(trifluoromethyl)-1(2H)-pyrimidinyl]-N-(ethylsulfonyl)-1,2-benzisothiazole-3-carboxamide;

N-[(m-chlorobenzyl)sulfonyl]-5-[3,6-dihydro-3-methyl-2,6-dioxo-4-(trifluoromethyl)-1(2H)-pyrimidinyl]-1,2-benzisothiazole-3-carboxamide;

5-[3,6-dihydro-3-methyl-2,6-dioxo-4-(trifluoromethyl)-1(2H)-pyrimidinyl]-N-(diisopropylsulfamoyl)-1,2-benzisothiazole-3-carboxamide;

5-[3,6-dihydro-3-methyl-2,6-dioxo-4-(trifluoromethyl)-1(2H)-pyrimidinyl]-N-((isopropylsulfamoyl)-1,2-benzisothiazole-3-carboxamide; and 5-[3,6-dihydro-3-methyl-2,6-dioxo-4-(trifluoromethyl)-1(2H)-pyrimidinyl]-N-(dimethylsulfamoyl)-1,2-benzisothiazole-3-carboxamide.

19. The method according to claim 16 wherein the cereal crop is rice and the compound is selected from the group consisting of isopropyl{{2-{5-[3,6-dihydro-3-methyl-2,6-dioxo-4-(trifluoromethyl)-1(2H)-pyrimidinyl]-1,2-benzisothiazol-3-yl}-p-tolyl}oxy}acetate;

methyl{{2-{5-[3,6-dihydro-3-methyl-4-(trifluoromethyl)-2,
6-dioxo-1(2H)-pyrimidinyl]-1,2-benzisothiazol-3-yl}-p-
tolyl}oxy}acetate;
3-[3-(6-methoxy-m-tolyl)-1,2-benzisothiazol-5-yl-1-
methyl-6-(trifluoromethyl)-2,4(1H,3H)-pyrimidinedione;
ethyl{{2-{5-[3,6-dihydro-3-methyl-2,6-dioxo-4-
(trifluoromethyl)-1(2H)-pyrimidinyl]-1,2-benzisothiazol-
3-yl}-p-tolyl}oxy}acetate;
1-methyl-3-{3-[6-(2-propynyloxy)-m-tolyl]-1,2-
benzisothiazol-5-yl}-6-(trifluoromethyl)-2,4(1H,3H)-
pyrimidinedione;
3-{3-{6-{[(m-cyanophenyl)carbamoyl]methoxy}-m-tolyl}-
1,2-benzisothiazol-5-yl}-1-methyl-6-(trifluoromethyl)-2,
4(1H,3H)pyrimidinedione;
3-[3-(2-methoxy-p-tolyl)-1,2-benzisothiazol-5-yl]-1-
methyl-6-(trifluoromethyl)-2,4(1H,3H)-pyrimidinedione;
2-[3-(6-methoxy-3,4-xylyl)-1,2-benzisothiazol-5-yl]-1-
methyl-6-(trifluoromethyl)-2,4(1H,3H)-pyrimidinedione;
3-{3-{6-{[(m-cyanophenyl)carbamoyl]methoxy}-m-tolyl}-
1,2-benzisothiazol-5-yl}-1-methyl-6-(trifluoromethyl)-2,
4(1H,3H)-pyrimidinedione;
2-propynyl{o-{5-[3,6-dihydro-3-methyl-2,6-dioxo-4-
(trifluoromethyl)-1(2H)-pyrimidinyl]-1,2-benzisothiazol-
3-yl}phenoxy}acetate;
3-{3-[(allyloxy)methyl]-1,2-benzisothiazol-5-yl}-1-methyl-
6-(trifluoromethyl)-2,4(1H,3H)-pyrimidinedione;
5-[3,6-dihydro-3-methyl-2,6-dioxo-4-(trifluoromethyl)-1
(2H)-pyrimidinyl]-α-ethyl-1,2-benzisothiazole-3-
acetonitrile;
5-[3,6-dihydro-3-methyl-2,6-dioxo-4-(trifluoromethyl)-1
(2H)-pyrimidinyl]-α,α-diethyl-1,2-benzisothiazole-3-
acetonitrile;
3-[3-(hydroxymethyl)-1,2-benzisothiazol-5-yl]-1-methyl-6-
(trifluoromethyl)-2,4(1H,3H)-pyrimidinedione,
5-isoxazolecarboxylate (ester);
3-[3-(hydroxymethyl)-1,2-benzisothiazol-5-yl]-1-methyl-6-
(trifluoromethyl)-2,4(1H,3H)-pyrimidinedione,
cyclopropanecarboxylate (ester);
methyl 5-[3,6-dihydro-3-methyl-2,6-dioxo-4-
(trifluoromethyl)-1(2H)-pyrimidinyl]-1,2-
benzisothiazole-3-carboxylate;
5-[3,6-dihydro-3-methyl-2,6-dioxo-4-(trifluoromethyl)-1
(2H)-pyrimidinyl]-N-(isopropylsulfonyl)-1,2-
benzisothiazole-3-carboxamide;
5-[3,6-dihydro-3-methyl-2,6-dioxo-4-(trifluoromethyl)-1
(2H)-pyrimidinyl]-N-(ethylsulfonyl)-1,2-
benzisothiazole-3-carboxamide;
benzyl 5-[3,6-dihydro-3-methyl-2,6-dioxo-4-
(trifluoromethyl)-1(2H)-pyrimidinyl]-α,α-dimethyl-1,2-
benzisothiazole-3-acetate;
5-[3,6-dihydro-3-methyl-2,6-dioxo-4-(trifluoromethyl)-1
(2H)-pyrimidinyl]-N-(diisopropylsulfamoyl)-1,2-
benzisothiazole-3-carboxamide;
5-[3,6-dihydro-3-methyl-2,6-dioxo-4-(trifluoromethyl)-1
(2H)-pyrimidinyl]-N-(isopropylsulfamoyl)-1,2-
benzisothiazole-3-carboxamide; and
5-[3,6-dihydro-3-methyl-2,6-dioxo-4-(trifluoromethyl)-1
(2H)-pyrimidinyl]-N-(dimethylsulfamoyl)-1,2-
benzisothiazole-3-carboxamide.

20. The method according to claim 14 wherein the crop is soybean.

21. The method according to claim 20 wherein the compound is selected from the group consisting of
methyl 2-{{2-{5-[3,6-dihydro-3-methyl-4-
(trifluoromethyl)-2,6-dioxo-1(2H)-pyrimidinyl]-1,2-
benzisothiazol-3-yl}-p-tolyl}oxy}propionate;
methyl 2-{{6-{5-[3,6-dihydro-3-methyl-4-
(trifluoromethyl)-2,6-dioxo-1(2H)-pyrimidinyl]-1,2-
benzisothiazol-3-yl}-3,4-xylyl}oxy}propionate;
1-methyl-3-(3-methyl-1,2-benzisothiazol-5-yl)-6-
(trifluoromethyl)-2,4(1H,3H)-pyrimidinedione;
methyl 2-{{6-{5-[3,6-dihydro-3-methyl-4-
(trifluoromethyl)-2,6-dioxo-1(2H)-pyrimidinyl]-1,2-
benzisothiazol-3-yl}-3,4-xylyl}oxy}propionate;
2-propynyl{{2-{5-[3,6-dihydro-3-methyl-2,6-dioxo-4-
(trifluoromethyl)-1(2H)-pyrimidinyl]-1,2-benzisoxazol-
3-yl}-p-tolyl}oxy}acetate;
3-[3-(o-methoxyphenyl)-1,2-benzisothiazol-5-yl]-1-methyl-
6-(trifluoromethyl)-2,4(1H,3H)-pyrimidinedione;
2-propynyl 2-{{2-{5-[3,6-dihydro-3-methyl-2,6-dioxo-4-
(trifluoromethyl)-1(2H)-pyrimidinyl]-1,2-benzisoxazol-
3-yl}-p-tolyl}oxy}propionate;
2-propynyl{o-{5-[3,6-dihydro-3-methyl-2,6-dioxo-4-
(trifluoromethyl)-1(2H)-pyrimidinyl]-1,2-benzisothiazol-
3-yl}phenoxy}acetate;
3-{3-[(allyloxy)methyl]-1,2-benzisothiazol-5-yl}-1-methyl-
6-(trifluoromethyl)-2,4(1H,3H)-pyrimidinedione;
5-[3,6-dihydro-3-methyl-2,6-dioxo-4-(trifluoromethyl)-1
(2H)-pyrimidinyl]-N-(methylsulfonyl)-1,2-
benzisothiazole-3-carboxamide;
methyl{{2-{5-[3,6-dihydro-3-methyl-2,6-dioxo-4-
(trifluoromethyl)-1(2H)-pyrimidinyl]-6-fluoro-1,2-
benzisoxazol-3-yl}-p-tolyl}oxy}acetate;
methyl{{6-{5-[3,6-dihydro-3-methyl-2,6-dioxo-4-
(trifluoromethyl)-1(2H)-pyrimidinyl]-6-fluoro-1,2-
benzisothiazol-3-yl}-m-tolyl}oxy}acetate;
3-(3-(hydroxymethyl)-1,2-benzisothiazol-5-yl]-1-methyl-6-
(trifluoromethyl)-2,4(1H,3H)-pyrimidinedione, benzoate
(ester);
3-[3-(hydroxymethyl)-1,2-benzisothiazol-5-yl]-1-methyl-6-
(trifluoromethyl)-2,4(1H,3H)-pyrimidinedione,
2-thiophenecarboxylate (ester);
3-[3-(hydroxymethyl)-1,2-benzisothiazol-5-yl]-1-methyl-6-
(trifluoromethyl)-2,4(1H,3H)-pyrimidinedione, methoxy-
acetate (ester);
3-[3-(hydroxymethyl)-1,2-benzisothiazol-5-yl]-1-methyl-6-
(trifluoromethyl)-2,4(1H,3H)-pyrimidinedione,
cyclopropanecarboxylate (ester);
3-[3-(hydroxymethyl)-1,2-benzisothiazol-5-yl]-1-methyl-6-
(trifluoromethyl)-2,4(1H,3H)-pyrimidinedione, 2-furoate
(ester);
5-[3,6-dihydro-3-methyl-2,6-dioxo-4-(trifluoromethyl)-1
(2H)-pyrimidinyl]-N-(methylsulfonyl)-1,2-
benzisothiazole-3-carboxamide;
5-[3,6-dihydro-3-methyl-2,6-dioxo-4-(trifluoromethyl)-1
(2H)-pyrimidinyl]-N-(isopropylsulfonyl)-1,2-
benzisothiazole-3-carboxamide;
5-[3,6-dihydro-3-methyl-2,6-dioxo-4-(trifluoromethyl)-1
(2H)-pyrimidinyl]-N-(ethylsulfonyl)-1,2-
benzisothiazole-3-carboxamide;
5-[3,6-dihydro-3-methyl-2,6-dioxo-4-(trifluoromethyl)-1
(2H)-pyrimidinyl]-N-(isopropylsulfamoyl)-1,2-
benzisothiazole-3-carboxamide; and
5-[3,6-dihydro-3-methyl-2,6-dioxo-4-(trifluoromethyl)-1
(2H)-pyrimidinyl]-N-(dimethylsulfamoyl)-1,2-
benzisothiazole-3-carboxamide.

22. The method according to claim 9 wherein the compound is applied to the foliage of the undesirable plant species or to the soil or water containing seeds or other propagating organs thereof at a rate of about 0.001 kg/ha to 1 kg/ha.

23. A herbicidal composition which comprises an inert solid or liquid carrier and a herbicidally effective amount of a compound according to claim 1.

24. The composition according to claim 23 wherein the compound is a compound set forth in claim 2.

25. The composition according to claim 23 wherein the compound has the structural formula

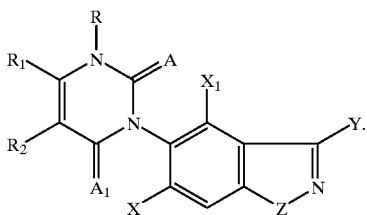

(I)

26. The composition according to claim 25 wherein the compound is a compound set forth in claim 4.

27. The composition according to claim 23 wherein the compound is a compound set forth in claim 8.

28. An intermediate compound having the structural formula

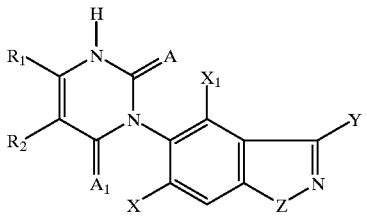

wherein
- $R_1$ and $R_2$ are each independently hydrogen, halogen, $C_1$–$C_6$alkyl, $C_3$–$C_7$cycloalkyl, $C_1$–$C_6$haloalkyl, $C_3$–$C_6$alkenyl, $C_3$–$C_6$haloalkenyl, $C_3$–$C_6$alkynyl, $OR_7$, $S(O)_nR_8$ or $NR_9R_{10}$;
- X is hydrogen, halogen or $C_1$–$C_4$alkyl;
- $X_1$ is hydrogen, halogen, $C_1$–$C_4$alkyl, $C_1$–$C_4$haloalkyl, $C_1$–$C_4$alkoxy or $C_1$–$C_4$haloalkoxy;
- Z is O or $S(O)_m$;
- Y is halogen, cyano, $R_{12}$, $X_2R_{12}$, $X_3R_{12}$, $X_2X_3R_{12}$ or $X_3X_2R_{12}$;
- $X_2$ is O, $S(O)_p$ or $NR_{13}$;
- $X_3$ is —C(=$A_3$)—, —C(=$NOR_{14}$)— or —C(=N—$NR_{13}R_{50}$);
- $R_4$, $R_5$, $R_6$, $R_7$, $R_8$, $R_9$, $R_{10}$ and $R_{14}$ are each independently hydrogen, $C_1$–$C_6$alkyl, $C_3$–$C_7$cycloalkyl, $C_2$–$C_8$-alkoxyalkyl, $C_2$–$C_6$alkenyl, $C_2$–$C_6$alkynyl or benzyl;
- $R_{12}$ is hydrogen,
  a $C_1$–$C_8$alkyl, $C_3$–$C_7$cycloalkyl, $C_2$–$C_8$alkenyl, $C_5$–$C_6$cycloalkenyl or $C_2$–$C_8$alkynyl group, wherein each group is optionally substituted with any combination of one to six halogen atoms, one to three $C_1$–$C_{20}$alkoxy groups optionally substituted with one $C_1$–$C_5$alkoxy, benzyloxy or $C_1$–$C_6$alkylthio group, one or two $C_1$–$C_{10}$haloalkoxy groups, one or two $NR_{15}R_{16}$ groups, one to three $S(O)_qR_{17}$ groups, one or two cyano groups, one or two $C_3$–$C_7$cycloalkyl groups, one thiocyano group, one $O(SO_2)R_{17}$ group, one $O(NO_2)$ group, one or two $C(O)R_{18}$ groups, one or two $CO_2R_{19}$ groups, one or two $C(O)SR_{19}$ groups, one or two $C(O)NR_{20}R_{21}$ groups, one to three $X_4R_{22}$ groups, one or two $P(O)(OR_{23})_2$ groups, one or two $Si(R_{24})_3$ groups, one 4- to 10-membered monocyclic or fused bicyclic heterocyclic ring optionally substituted with any combination of one or two oxo groups, one or two thioxo groups, one to three halogen atoms, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups or one or two $X_4R_{22}$ groups,
  one quaternary organic ammonium group, or
  one or two phenyl groups wherein each phenyl group is independently optionally substituted with any combination of one to three halogen atoms, one to three $C_1$–$C_6$alkyl groups, one to three $C_1$–$C_6$alkoxy groups, one $C_3$–$C_7$cycloalkyl group, one $C_1$–$C_4$haloalkyl group, one $C_1$–$C_4$alkylthio group, one cyano group, one nitro group, one $C(O)R_{25}$ group, one $CO_2R_{26}$ group or one $X_5R_{27}$ group,
  phenyl optionally substituted with any combination of one to three halogen atoms, one to three $C_1$–$C_4$alkyl groups, one to three $C_1$–$C_4$alkoxy groups, one $C_3$–$C_6$cycloalkyl group, one $C_1$–$C_4$haloalkyl group, one $C_1$–$C_4$alkylthio group, one cyano group, one nitro group, one $C(O)R_{25}$ group, one $CO_2R_{26}$ group, one $X_4R_{22}$ group, one CH=$CHR_{22}$ group, one $CH_2CH(R_{28})R_{22}$ group or one $N(R_{29})SO_2R_{30}$ group, or
  indan optionally substituted with any combination of one or two halogen atoms, one or two $C_1$–$C_4$alkyl groups, one $C_1$–$C_4$alkoxy group, one $C_1$–$C_4$haloalkyl group, one $C_1$–$C_4$alkylthio group, one cyano group, one nitro group, one $C(O)R_{25}$ group, one $CO_2R_{26}$ group, one $X_4R_{22}$ group, one CH=$CHR_{22}$ group, one $CH_2CH(R_{28})R_{22}$ group or one $N(R_{29})SO_2R_{30}$ group,
  and when $R_{12}$ and $R_{13}$ are taken together with the nitrogen atom to which they are attached, they form a 5- to 12-membered monocyclic or fused bicyclic, heterocyclic ring optionally substituted with one or more groups independently selected from halogen, cyano, nitro, amino, hydroxyl, $C_1$–$C_4$alkyl, $C_1$–$C_4$haloalkyl, $C_1$–$C_4$alkoxy, $C_1$–$C_4$haloalkoxy, $C_1$–$C_4$haloalkylsulfonyl or $X_4R_{22}$ groups;
- $R_{13}$ is hydrogen, $C_1$–$C_8$alkoxyalkyl, $C_1$–$C_6$alkyl, $C_3$–$C_7$cycloalkyl, $C_3$–$C_6$alkenyl, $C_3$–$C_6$alkynyl, benzyl, $OR_{23}$, cyano, $SO_2R_{51}$ or one 5- to 12-membered monocyclic or fused bicyclic heterocyclic ring optionally substituted with one or more groups independently selected from halogen, cyano, nitro, amino, hydroxyl, $C_1$–$C_4$alkyl, $C_1$–$C_4$haloalkyl, $C_1$–$C_4$alkoxy or $C_1$–$C_4$haloalkoxy, and when $R_{13}$ and $R_{12}$ are taken together with the nitrogen atom to which they are attached, they form a 5- to 12-membered monocyclic or fused bicyclic, heterocyclic ring optionally substituted with one or more groups independently selected from halogen, cyano, nitro, amino, hydroxyl, $C_1$–$C_4$alkyl, $C_1$–$C_4$haloalkyl, $C_1$–$C_4$alkoxy, $C_1$–$C_4$haloalkoxy, $C_1$–$C_4$haloalkylsulfonyl or $X_4R_{22}$ groups;
- $R_{28}$ is halogen;
- $R_{22}$ and $R_{27}$ are each independently hydrogen, $Si(R_{31})_3$, $C(O)NR_{35}R_{36}$, $C(O)R_{33}$, $SO_2R_{47}$, $C_1$–$C_{20}$alkyl substituted with one hydroxyl, benzyloxy, nitro, $OC(O)R_{33}$, $C_1$–$C_6$alkoxy, $CO_2R_{32}$, $C(O)R_{33}$, $C(A_4R_{34})_2$, $C(O)NR_{35}R_{36}$, $C(O)ON=CR_{37}R_{38}$, $P(O)(OH)NH_2$, $P(O)(OH)(OR_{23})$, $C(O)NR_{35}OR_{23}$, cyano or 2-dioxolanyl group,
  one phenyl, dihydrofuranone or furanone ring wherein each ring is optionally substituted with any combination of one to three halogen atoms, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups, or one 5- to 12-membered monocyclic or fused bicyclic, heterocyclic ring optionally substituted with one or more groups independently selected from halogen, cyano, nitro, amino, hydroxyl, $C_1$–$C_4$alkyl, $C_1$–$C_4$haloalkyl, $C_1$–$C_4$alkoxy, $C_1$–$C_4$haloalkoxy or $C_1$–$C_4$haloalkylsulfonyl groups, $C_3$–$C_{20}$alkenyl optionally substituted with one to three halogen atoms, one hydroxyl group, one $C_1$–$C_6$alkoxy, $CO_2R_{32}$, $C(O)R_{33}$, $C(A_4R_{34})_2$, $C(O)NR_{35}R_{36}$, $C(O)ON=CR_{37}R_{38}$, $C(O)NR_{35}R_{23}$, cyano or 2-dioxolanyl group, or one phenyl, dihydrofuranone or furanone ring wherein each ring is optionally substituted with any combination of one to three halogen atoms, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups, $C_5$–$C_8$cycloalkenyl optionally substituted with one hydroxyl, $C_1$–$C_6$alkoxy, $C_1$–$C_4$alkyl, $C_2$–$C_4$alkenyl, $CO_2R_{32}$, $C(O)R_{33}$, $C(A_4R_{34})_2$, $C(O)NR_{35}R_{36}$, $C(O)ON=CR_{37}R_{38}$, $C(O)NR_{35}OR_{23}$, cyano or 2-dioxolanyl group, or one phenyl, dihydrofuranone or furanone ring wherein each ring is optionally substituted with any combination of one to three halogen atoms, one to three $C_1$–$C_4$alkyl groups, one to three $C_1$–$C_4$alkoxy groups or one to three $C_1$–$C_4$haloalkoxy groups, $C_3$–$C_{10}$alkynyl optionally substituted with one hydroxyl, $C_1$–$C_6$alkoxy, $CO_2R_{32}$, $C(O)R_{33}$, $C(A_4R_{34})_2$, $C(O)NR_{35}R_{36}$, $C(O)ON=CR_{37}R_{38}$, $C(O)NR_{35}OR_{23}$, cyano or 2-dioxolanyl group, or one phenyl, dihydrofuranone or furanone ring wherein each ring is optionally substituted with any combination of one to three halogen atoms, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups, phenyl optionally substituted with any combination of one to three halogen atoms, one to three $C_1$–$C_6$alkyl groups, one to three $C_1$–$C_6$alkoxy groups, one $C_1$–$C_4$haloalkyl group, one $C_1$–$C_4$haloalkoxy group, one cyano group, one nitro group, one $NR_{39}R_{40}$ group or one $C(O)R_{23}$ group, benzyl optionally substituted on the phenyl ring with any combination of one to three halogen atoms, one to three $C_1$–$C_6$alkyl groups, one to three $C_1$–$C_6$alkoxy groups, one $C_1$–$C_4$haloalkyl group, one $C_1$–$C_4$haloalkoxy group, one cyano group, one nitro group, one $NR_{39}R_{40}$ group or one $C(O)R_{33}$ group, or a 4- to 10-membered heterocyclic ring optionally substituted with any combination of one or two oxo groups, one or two thioxo groups, one to three halogen atoms, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups;

$R_{15}$ and $R_{20}$ are each independently hydrogen, a $C_1$–$C_6$alkyl, $C_3$–$C_7$cycloalkyl, $C_2$–$C_6$alkenyl or $C_2$–$C_6$alkynyl group wherein each group is optionally substituted with one $CO_2R_{42}$ group, benzyl optionally substituted with any combination of one to three halogen atoms, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups, phenyl optionally substituted with any combination of one to three halogen atoms, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups, one $CO_2R_{26}$ group, $C(O)R_{43}$, or $CO_2R_{42}$;

$R_{16}$ and $R_{21}$ are each independently hydrogen, $C_1$–$C_6$alkyl, $C_1$–$C_4$alkoxy, $C_3$–$C_7$cycloalkyl, $C_2$–$C_6$alkenyl, $C_3$–$C_7$cycloalkenyl, $C_2$–$C_6$alkynyl, $P(O)(OR_{44})_2$, $SO_2R_{45}$, $C(O)R_{46}$, benzyl optionally substituted with any combination of one to three halogen atoms, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups or one $X_4R_{22}$ group, or phenyl optionally substituted with any combination of one to three halogen atoms, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups or one $X_4R_{22}$ group;

$R_{17}$, $R_{18}$, $R_{25}$, $R_{30}$, $R_{33}$, $R_{45}$ and $R_{51}$ are each independently $NR_{46}R_{48}$, —$N=CR_{46}R_{48}$, $C_1$–$C_8$alkyl optionally substituted with one $C_1$–$C_6$alkoxy, thiophene or furan group, $C_1$–$C_6$haloalkyl, $C_3$–$C_8$cycloalkyl, $CO_2R_{23}$, $C_2$–$C_6$alkenyl optionally substituted with phenyl, benzyl optionally substituted with any combination of one to three halogen atoms, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups, one nitro group, one cyano group or one $X_4R_{22}$ group, phenyl optionally substituted with any combination of one to three halogen atoms, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups, one nitro group, one cyano group or one $X_4R_{22}$ group, or a 5- to 12-membered monocyclic or fused bicyclic, heterocyclic ring optionally substituted with one or more groups independently selected from halogen, cyano, nitro, amino, hydroxyl, $C_1$–$C_4$alkyl, $C_1$–$C_4$haloalkyl, $C_1$–$C_4$alkoxy, $C_1$–$C_4$haloalkoxy, $C_1$–$C_4$haloalkylsulfonyl or $X_4R_{22}$ groups;

$R_{19}$ and $R_{26}$ are each independently hydrogen, $C_1$–$C_{20}$alkyl, $C_1$–$C_8$haloalkyl, $C_3$–$C_7$cycloalkyl, $C_3$–$C_7$halocycloalkyl, $C_3$–$C_{20}$alkenyl, $C_3$–$C_8$haloalkenyl, $C_5$–$C_8$cycloalkenyl, $C_5$–$C_8$halocycloalkenyl, $C_3$–$C_8$alkynyl, $C_3$–$C_8$haloalkynyl, $Si(R_{41})_3$, benzyl, phenyl, furfuryl, pyridyl, thienyl, oximino or an alkali metal, alkaline earth metal, manganese, copper, zinc, cobalt, silver, nickel, ammonium or organic ammonium cation;

$R_{32}$ is hydrogen, $Si(R_{47})_3$, di($C_1$–$C_4$alkyl)imino, $C_1$–$C_{20}$alkyl optionally substituted with one $CO_2R_{48}$, $C_1$–$C_6$alkoxy, $C_1$–$C_6$thioalkyl, $C_2$–$C_{20}$alkoxyalkoxy, phenyl, $OSi(R_{47})_3$, $OC(O)R_{33}$, $C_3$–$C_7$cycloalkyl or di($C_1$–$C_4$alkyl)imino group, $C_1$–$C_{15}$haloalkyl, $C_3$–$C_8$cycloalkyl optionally substituted with one $CO_2R_{48}$ group, $C_3$–$C_8$halocycloalkyl, $C_3$–$C_{20}$alkenyl optionally substituted with one phenyl group, $C_3$–$C_{15}$haloalkenyl, $C_5$–$C_8$cycloalkenyl, $C_5$–$C_8$halocycloalkenyl, $C_3$–$C_{20}$alkynyl optionally substituted with one phenyl group, $C_3$–$C_{20}$haloalkynyl, benzyl optionally substituted with one or more groups independently selected from halogen, cyano, nitro, $C_1$–$C_4$alkyl, $C_1$–$C_4$haloalkyl, $C_1$–$C_4$alkoxy and $C_1$–$C_4$haloalkoxy groups, phenyl optionally substituted with one or more groups independently selected from halogen, cyano, nitro, $C_1$–$C_4$alkyl, $C_1$–$C_4$haloalkyl, $C_1$–$C_4$alkoxy and $C_1$–$C_4$haloalkoxy groups, 2-, 3- or 4-pyridyl, 2- or 3-furyl, 2- or 3-thienyl, 2-tetrahydrofuranyl, $C_1$–$C_4$alkyl substituted with one pyridyl, furyl, thienyl, tetrahydrofuryl, $C_3$–$C_8$cycloalkyl, dioxane or $NR_{49}R_{50}$ group, or an alkali metal, alkaline earth metal, manganese, copper, zinc, cobalt, silver, nickel, ammonium or organic ammonium cation;

$R_{34}$, $R_{37}$ and $R_{38}$ are each independently $C_1$–$C_6$alkyl;

$R_{35}$ and $R_{49}$ are each independently hydrogen or $C_1$–$C_6$alkyl and $R_{36}$ and $R_{50}$ are each independently hydrogen, cyano, $C_1$–$C_6$alkyl, $SO_2R_{51}$ or phenyl optionally substituted with one or more groups independently selected from halogen, cyano, nitro, $C_1$–$C_4$alkyl, $C_1$–$C_4$haloalkyl, $C_1$–$C_4$alkoxy and $C_1$–$C_4$haloalkoxy groups, or when $R_{35}$ and $R_{36}$ or $R_{49}$ and $R_{50}$ are taken together with the nitrogen atom to which they are attached, they form a 5- to 12-membered monocyclic or fused bicyclic, heterocyclic ring optionally substituted with one or more groups independently selected from halogen, cyano, nitro, amino, hydroxyl, $C_1$–$C_4$alkyl, $C_1$–$C_4$haloalkyl, $C_1$–$C_4$alkoxy, $C_1$–$C_4$haloalkoxy or $C_1$–$C_4$haloalkylsulfonyl groups;

m, n, p and q are each independently an integer of 0, 1 or 2;

$R_{29}$ is hydrogen, $C_1$–$C_4$alkyl or $C_1$–$C_4$haloalkyl;

$R_{24}$, $R_{31}$, $R_{41}$ and $R_{47}$ are each independently $C_1$–$C_4$alkyl, benzyl optionally substituted with one or more groups independently selected from halogen, cyano, nitro, $C_1$–$C_4$alkyl, $C_1$–$C_4$haloalkyl, $C_1$–$C_4$alkoxy and $C_1$–$C_4$haloalkoxy groups, or phenyl optionally substituted with one or more groups independently selected from halogen, cyano, nitro, $C_1$–$C_4$alkyl, $C_1$–$C_4$haloalkyl, $C_1$–$C_4$alkoxy and $C_1$–$C_4$haloalkoxy groups;

$R_{23}$, $R_{39}$, $R_{40}$, $R_{42}$, $R_{43}$, $R_{44}$, $R_{46}$ and $R_{48}$ are each independently hydrogen, $C_2$–$C_6$alkenyl, $C_3$–$C_8$cycloalkyl, $C_1$–$C_8$alkyl optionally substituted with one or two $C_1$–$C_4$alkoxy groups, benzyl optionally substituted with one or more groups independently selected from halogen, cyano, nitro, $C_1$–$C_4$alkyl, $C_1$–$C_4$haloalkyl, $C_1$–$C_4$alkoxy and $C_1$–$C_4$haloalkoxy groups, or phenyl optionally substituted with one or more groups independently selected from halogen, cyano, nitro, $C_1$–$C_4$alkyl, $C_1$–$C_4$haloalkyl, $C_1$–$C_4$alkoxy and $C_1$–$C_4$haloalkoxy groups, and when $R_{46}$ and $R_{48}$ are taken together with the atom to which they are attached, they form a 5- to 12-membered monocyclic or fused bicyclic, heterocyclic or cycloalkyl ring optionally substituted with one or more groups independently selected from halogen, cyano, nitro, amino, hydroxyl, $C_1$–$C_4$alkyl, $C_1$–$C_4$haloalkyl, $C_1$–$C_4$alkoxy, $C_1$–$C_4$haloalkoxy or $C_1$–$C_4$haloalkylsulfonyl groups; and A, $A_1$, $A_3$, $A_4$, $X_4$ and $X_5$ are each independently O or S; and the optical isomers, diastereomers and/or tautomers thereof.

29. The compound according to claim 28 wherein $R_1$ and $R_2$ are each independently hydrogen, halogen, $C_1$–$C_6$alkyl, $C_3$–$C_7$cycloalkyl, $C_1$–$C_6$haloalkyl, $C_3$–$C_6$alkenyl, $C_3$–$C_6$haloalkenyl, $C_3$–$C_6$alkynyl, $OR_7$, $S(O)_nR_8$ or $NR_9R_{10}$;

X is hydrogen, halogen or $C_1$–$C_4$alkyl;

$X_1$ is hydrogen, halogen, $C_1$–$C_4$alkyl, $C_1$–$C_4$haloalkyl, $C_1$–$C_4$alkoxy or $C_1$–$C_4$haloalkoxy;

Z is O or $S(O)_m$;

Y is halogen, cyano, $R_{12}$, $X_2R_{12}$, $X_3R_{12}$, $X_2X_3R_{12}$ or $X_3X_2R_{12}$;

$X_2$ is O, $S(O)_p$ or $NR_{13}$;

$X_3$ is —C(=$A_3$)— or —C(=$NOR_{14}$)—;

$R_4$, $R_5$, $R_6$, $R_7$, $R_8$, $R_9$, $R_{10}$ and $R_{14}$ are each independently hydrogen, $C_1$–$C_6$alkyl, $C_3$–$C_7$Cycloalkyl, $C_2$–$C_6$alkenyl, $C_2$–$C_6$alkynyl or benzyl;

$R_{12}$ is hydrogen, a $C_1$–$C_6$alkyl, $C_3$–$C_7$cycloalkyl, $C_2$–$C_6$alkenyl, $C_5$–$C_6$cycloalkenyl or $C_2$–$C_6$alkynyl group, wherein each group is optionally substituted with any combination of one to six halogen atoms, one to three $C_1$–$C_{20}$alkoxy groups, one or two $C_1$–$C_{10}$haloalkoxy groups, one or two $NR_{15}R_{16}$ groups, one to three $S(O)_qR_{17}$ groups, one or two cyano groups, one or two $C(O)R_{18}$ groups, one or two $CO_2R_{19}$ groups, one or two $C(O)NR_{20}R_{21}$ groups, one to three $X_4R_{22}$ groups, one or two $P(O)(OR_{23})_2$ groups, one or two $Si(R_{24})_3$ groups, one 4- to 10-membered heterocyclic ring optionally substituted with any combination of one or two oxo groups, one or two thioxo groups, one to three halogen atoms, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups or one or two $X_4R_{22}$ groups, one quaternary organic ammonium group, or one phenyl group optionally substituted with any combination of one to three halogen atoms, one to three $C_1$–$C_6$alkyl groups, one to three $C_1$–$C_6$alkoxy groups, one $C_3$–$C_7$cycloalkyl group, one $C_1$–$C_4$haloalkyl group, one $C_1$–$C_4$alkylthio group, one cyano group, one nitro group, one $C(O)R_{25}$ group, one $CO_2R_{26}$ group or one $X_5R_{27}$ group, or phenyl optionally substituted with any combination of one to three halogen atoms, one to three $C_1$–$C_4$alkyl groups, one to three $C_1$–$C_4$alkoxy groups, one $C_3$–$C_6$cycloalkyl group, one $C_1$–$C_4$haloalkyl group, one $C_1$–$C_4$alkylthio group, one cyano group, one nitro group, one $C(O)R_{25}$ group, one $CO_2R_{26}$ group, one $X_4R_{22}$ group, one $CH=CHR_{22}$ group, one $CH_2CH(R_{28})R_{22}$ group or one $N(R_{29})SO_2R_{30}$ group, and when $R_{12}$ and $R_{13}$ are taken together with the nitrogen atom to which they are attached, they form a 5- to 12-membered monocyclic or fused bicyclic, heterocyclic ring optionally substituted with one or more groups independently selected from halogen, cyano, nitro, amino, hydroxyl, $C_1$–$C_4$alkyl, $C_1$–$C_4$haloalkyl, $C_1$–$C_4$alkoxy, $C_1$–$C_4$haloalkoxy, $C_1$–$C_4$haloalkylsulfonyl or $X_4R_{22}$ groups;

$R_{13}$ is hydrogen, $C_1$–$C_6$alkyl, $C_3$–$C_7$cycloalkyl, $C_3$–$C_6$alkenyl, $C_3$–$C_6$alkynyl, benzyl, $OR_{23}$, cyano or $SO_2R_{51}$, and when $R_{13}$ and $R_{12}$ are taken together with the nitrogen atom to which they are attached, they form a 5- to 12-membered monocyclic or fused bicyclic, heterocyclic ring optionally substituted with one or more groups independently selected from halogen, cyano, nitro, amino, hydroxyl, $C_1$–$C_4$alkyl, $C_1$–$C_4$haloalkyl, $C_1$–$C_4$alkoxy, $C_1$–$C_4$haloalkoxy, $C_1$–$C_4$haloalkylsulfonyl or $X_4R_{22}$ groups;

$R_{28}$ is halogen;

$R_{22}$ and $R_{27}$ are each independently hydrogen, $Si(R_{31})_3$, $C_1$–$C_{20}$alkyl substituted with one $C_1$–$C_6$alkoxy, $CO_2R_{32}$, $C(O)R_{33}$, $C(A_4R_{34})_2$, $C(O)NR_{35}R_{36}$, $C(O)ON=CR_{37}R_{38}$, $P(O)(OH)NH_2$, $P(O)(OH)(OR_{23})$, $C(O)NHOR_{23}$, cyano or 2-dioxolanyl group, one phenyl, dihydrofuranone or furanone ring wherein each ring is optionally substituted with any combination of one to three halogen atoms, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups, or one 5- to 12-membered monocyclic or fused bicyclic, heterocyclic ring optionally substituted with one or more groups independently selected from halogen, cyano, nitro, amino, hydroxyl, $C_1$–$C_4$alkyl, $C_1$–$C_4$haloalkyl, $C_1$–$C_4$alkoxy, $C_1$–$C_4$haloalkoxy or $C_1$–$C_4$haloalkylsulfonyl groups, $C_3$–$C_{20}$alkenyl optionally substituted with one to three halogen atoms, one $C_1$–$C_6$alkoxy, $CO_2R_{32}$, $C(O)R_{33}$, $C(A_4R_{34})_2$, $C(O)NR_{35}R_{36}$, $C(O)ON=CR_{37}R_{38}$, $C(O)NHOR_{23}$, cyano or 2-dioxolanyl group, or one phenyl, dihydrofuranone or furanone ring wherein each ring is optionally substituted with any combination of one to three halogen atoms, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups, $C_5$–$C_8$cycloalkenyl optionally substituted with one $C_1$–$C_6$alkoxy, $C_1$–$C_4$alkyl, $C_2$–$C_4$alkenyl, $CO_2R_{32}$, $C(O)R_{33}$, $C(A_4R_{34})_2$, $C(O)NR_{35}R_{36}$, $C(O)ON=CR_{37}R_{38}$, $C(O)NHOR_{23}$, cyano or 2-dioxolanyl group, or one phenyl, dihydrofuranone or furanone ring wherein each ring is optionally substituted with any combination of one to three halogen atoms, one to three $C_1$–$C_4$alkyl groups, one to three $C_1$–$C_4$alkoxy groups or one to three $C_1$–$C_4$haloalkoxy groups, $C_3$–$C_{10}$alkynyl optionally substituted with one $C_1$–$C_6$alkoxy, $CO_2R_{32}$, $C(O)R_{33}$, $C(A_4R_{34})_2$, $C(O)NR_{35}R_{36}$, $C(O)ON=CR_{37}R_{38}$, $C(O)NHOR_{23}$, cyano or 2-dioxolanyl group, or one phenyl, dihydrofuranone or furanone ring wherein each ring is optionally substituted with any combination of one to three halogen atoms, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups, phenyl optionally substituted with any combination of one to three halogen atoms, one to three $C_1$–$C_6$alkyl groups, one to three $C_1$–$C_6$alkoxy groups, one $C_1$–$C_4$haloalkyl group, one $C_1$–$C_4$haloalkoxy group, one cyano group, one nitro group, one $NR_{39}R_{40}$ group or one $C(O)R_{33}$ group, benzyl optionally substituted on the phenyl ring with any combination of one to three halogen atoms, one to three $C_1$–$C_6$alkyl groups, one to three $C_1$–$C_6$alkoxy groups, one $C_1$–$C_4$haloalkyl group, one $C_1$–$C_4$haloalkoxy group, one cyano group, one nitro group, one $NR_{39}R_{40}$ group or one $C(O)R_{33}$ group, or a 4- to 10-membered heterocyclic ring optionally substituted with any combination of one or two oxo groups, one or two thioxo groups, one to three halogen atoms, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups;

$R_{15}$ and $R_{20}$ are each independently hydrogen, a $C_1$–$C_6$alkyl, $C_3$–$C_7$cycloalkyl, $C_2$–$C_6$alkenyl or $C_2$–$C_6$alkynyl group wherein each group is optionally substituted with one $CO_2R_{42}$ group, benzyl optionally substituted with any combination of one to three halogen atoms, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups, phenyl optionally substituted with any combination of one to three halogen atoms, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups, or $C(O)R_{43}$;

$R_{16}$ and $R_{21}$ are each independently hydrogen, $C_1$–$C_6$alkyl, $C_3$–$C_7$cycloalkyl, $C_2$–$C_6$alkenyl, $C_3$–$C_7$cycloalkenyl, $C_2$–$C_6$alkynyl, $P(O)(OR_{44})_2$, $SO_2R_{45}$, $C(O)R_{46}$, benzyl optionally substituted with any combination of one to three halogen atoms, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups or one $X_4R_{22}$ group, or phenyl optionally substituted with any combination of one to three halogen atoms, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups or one $X_4R_{22}$ group;

$R_{17}$, $R_{18}$, $R_{25}$, $R_{30}$, $R_{33}$, $R_{45}$ and $R_{51}$ are each independently $C_1$–$C_4$alkyl, $C_1$–$C_4$haloalkyl, $CO_2R_{23}$, $C_2$–$C_6$alkenyl optionally substituted with phenyl, benzyl optionally substituted with any combination of one to three halogen atoms, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups, one nitro group, one cyano group or one $X_4R_{22}$ group, phenyl optionally substituted with any combination of one to three halogen atoms, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups, one nitro group, one cyano group or one $X_4R_{22}$ group, or a 5- to 12-membered monocyclic or fused bicyclic, heterocyclic ring optionally substituted with one or more groups independently selected from halogen, cyano, nitro, amino, hydroxyl, $C_1$–$C_4$alkyl, $C_1$–$C_4$haloalkyl, $C_1$–$C_4$alkoxy, $C_1$–$C_4$haloalkoxy, $C_1$–$C_4$haloalkylsulfonyl or $X_4R_{22}$ groups;

$R_{19}$ and $R_{26}$ are each independently hydrogen, $C_1$–$C_{20}$alkyl, $C_1$–$C_8$haloalkyl, $C_3$–$C_7$cycloalkyl, $C_3$–$C_7$halocycloalkyl, $C_3$–$C_{20}$alkenyl, $C_3$–$C_8$haloalkenyl, $C_5$–$C_8$cycloalkenyl, $C_5$–$C_8$halocycloalkenyl, $C_3$–$C_8$alkynyl, $C_3$–$C_8$haloalkynyl, $Si(R_{41})_3$, benzyl, phenyl, furfuryl, pyridyl, thienyl, oximino or an alkali metal, alkaline earth metal, manganese, copper, zinc, cobalt, silver, nickel, ammonium or organic ammonium cation;

$R_{32}$ is hydrogen,
$Si(R_{47})_3$,
di($C_1$–$C_4$alkyl)imino,
$C_1$–$C_{20}$alkyl optionally substituted with one $CO_2R_{48}$, $C_1$–$C_6$alkoxy or di($C_1$–$C_4$alkyl)imino group,
$C_1$–$C_{15}$haloalkyl,
$C_3$–$C_8$cycloalkyl,
$C_3$–$C_8$halocycloalkyl,
$C_3$–$C_{20}$alkenyl optionally substituted with one phenyl group,
$C_3$–$C_{15}$haloalkenyl,
$C_5$–$C_8$cycloalkenyl,
$C_5$–$C_8$halocycloalkenyl,
$C_3$–$C_{20}$alkynyl optionally substituted with one phenyl group,
$C_3$–$C_{20}$haloalkynyl,
benzyl optionally substituted with one or more groups independently selected from halogen, cyano, nitro, $C_1$–$C_4$alkyl, $C_1$–$C_4$haloalkyl, $C_1$–$C_4$alkoxy and $C_1$–$C_4$haloalkoxy groups,
phenyl optionally substituted with one or more groups independently selected from halogen, cyano, nitro, $C_1$–$C_4$alkyl, $C_1$–$C_4$haloalkyl, $C_1$–$C_4$alkoxy and $C_1$–$C_4$haloalkoxy groups,
2-, 3- or 4-pyridyl,
2- or 3-furyl,
2- or 3-thienyl,
2-tetrahydrofuranyl,
$C_1$–$C_4$alkyl substituted with one pyridyl, furyl, thienyl, tetrahydrofuryl or $NR_{49}R_{50}$ group, or
an alkali metal, alkaline earth metal, manganese, copper, zinc, cobalt, silver, nickel, ammonium or organic ammonium cation;

$R_{34}$, $R_{37}$ and $R_{38}$ are each independently $C_1$–$C_6$alkyl;

$R_{35}$ and $R_{49}$ are each independently hydrogen or $C_1$–$C_6$alkyl and $R_{36}$ and $R_{50}$ are each independently hydrogen, cyano, $C_1$–$C_6$alkyl, $SO_2R_{51}$ or phenyl optionally substituted with one or more groups independently selected from halogen, cyano, nitro, $C_1$–$C_4$alkyl, $C_1$–$C_4$haloalkyl, $C_1$–$C_4$alkoxy and $C_1$–$C_4$haloalkoxy groups, or when $R_{35}$ and $R_{36}$ or $R_{49}$ and $R_{50}$ are taken together with the nitrogen atom to which they are attached, they form a 5- to 12-membered monocyclic or fused bicyclic, heterocyclic ring optionally substituted with one or more groups independently selected from halogen, cyano, nitro, amino, hydroxyl, $C_1$–$C_4$alkyl, $C_1$–$C_4$haloalkyl, $C_1$–$C_4$alkoxy, $C_1$–$C_4$haloalkoxy or $C_1$–$C_4$haloalkylsulfonyl groups;

m, n, p and q are each independently an integer of 0, 1 or 2;

$R_{29}$ is hydrogen, $C_1$–$C_4$alkyl or $C_1$–$C_4$haloalkyl;

$R_{24}$, $R_{31}$, $R_{41}$ and $R_{47}$ are each independently $C_1$–$C_4$alkyl, benzyl optionally substituted with one or more groups independently selected from halogen, cyano, nitro, $C_1$–$C_4$alkyl, $C_1$–$C_4$haloalkyl, $C_1$–$C_4$alkoxy and $C_1$–$C_4$haloalkoxy groups, or
phenyl optionally substituted with one or more groups independently selected from halogen, cyano, nitro, $C_1$–$C_4$alkyl, $C_1$–$C_4$haloalkyl, $C_1$–$C_4$alkoxy and $C_1$–$C_4$haloalkoxy groups;

$R_{23}$, $R_{39}$, $R_{40}$, $R_{42}$, $R_{43}$, $R_{44}$, $R_{46}$ and $R_{48}$ are each independently hydrogen, $C_1$–$C_4$alkyl,
benzyl optionally substituted with one or more groups independently selected from halogen, cyano, nitro, $C_1$–$C_4$alkyl, $C_1$–$C_4$haloalkyl, $C_1$–$C_4$alkoxy and $C_1$–$C_4$haloalkoxy groups, or
phenyl optionally substituted with one or more groups independently selected from halogen, cyano, nitro, $C_1$–$C_4$alkyl, $C_1$–$C_4$haloalkyl, $C_1$–$C_4$alkoxy and $C_1$–$C_4$haloalkoxy groups; and A, $A_1$, $A_3$, $A_4$, $X_4$ and $X_5$ are each independently O or S; and
the optical isomers, diastereomers and/or tautomers thereof.

30. The compound according to claim 28 wherein
$R_1$ and $R_2$ are each independently hydrogen, halogen, $C_1$–$C_6$alkyl, $C_3$–$C_7$cycloalkyl, $C_1$–$C_6$haloalkyl, $C_3$–$C_6$alkenyl, $C_3$–$C_6$haloalkenyl, $C_3$–$C_6$alkynyl, $OR_7$, $S(O)_nR_8$ or $NR_9R_{10}$;

X is hydrogen, halogen or $C_1$–$C_4$alkyl;

$X_1$ is hydrogen, halogen, $C_1$–$C_4$alkyl, $C_1$–$C_4$haloalkyl, $C_1$–$C_4$alkoxy or $C_1$–$C_4$haloalkoxy;

Z is O or $S(O)_m$;

Y is halogen, cyano, $R_{12}$, $X_2R_{12}$, $X_3R_{12}$, $X_2X_3R_{12}$ or $X_3X_2R_{12}$;

$X_2$ is O, $S(O)_p$ or $NR_{13}$;

$X_3$ is —C(=$A_3$)—, —C(=$NOR_{14}$)— or —C(=N—$NR_{13}R_{50}$);

$R_4$, $R_5$, $R_6$, $R_7$, $R_8$, $R_9$, $R_{10}$ and $R_{14}$ are each independently hydrogen, $C_1$–$C_6$alkyl, $C_3$–$C_7$cycloalkyl, $C_2$–$C_8$alkoxyalkyl, $C_2$–$C_6$alkenyl, $C_2$–$C_6$alkynyl or benzyl;

$R_{12}$ is hydrogen,
a $C_1$–$C_4$alkyl, $C_3$–$C_7$cycloalkyl, $C_2$–$C_8$alkenyl, $C_5$–$C_6$cycloalkenyl or $C_2$–$C_8$alkynyl group, wherein each group is optionally substituted with any combination of one to six halogen atoms, one to three $C_1$–$C_{20}$alkoxy groups optionally substituted with one $C_1$–$C_6$alkoxy, benzyloxy or $C_1$–$C_6$alkylthio group, one or two $C_1$–$C_{10}$haloalkoxy groups, one or two $NR_{15}R_{16}$ groups, one to three $S(O)_qR_{17}$ groups, one or two cyano groups, one or two $C_3$–$C_7$cycloalkyl groups, one thiocyano group, one $O(SO_2)R_{17}$ group, one $O(NO_2)$ group, one or two $C(O)R_{18}$ groups, one or two $CO_2R_{19}$ groups, one or two $C(O)SR_{19}$ groups, one or two $C(O)NR_{20}R_{21}$ groups, one to three $X_4R_{22}$ groups, one or two $P(O)(OR_{23})_2$ groups, one or two $Si(R_{24})_3$ groups, one 4- to 10-membered monocyclic or fused bicyclic heterocyclic ring optionally substituted with any combination of one or two oxo groups, one or two thioxo groups, one to three halogen atoms, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups or one or two $X_4R_{22}$ groups, one quaternary organic ammonium group, or
one or two phenyl groups wherein each phenyl group is independently optionally substituted with any combination of one to three halogen atoms, one to three $C_1$–$C_6$alkyl groups, one to three $C_1$–$C_6$alkoxy groups, one $C_3$–$C_7$cycloalkyl group, one $C_1$–$C_4$haloalkyl group, one $C_1$–$C_4$alkylthio group, one cyano group, one nitro group, one $C(O)R_{25}$ group, one $CO_2R_{26}$ group or one $X_5R_{27}$ group,
phenyl optionally substituted with any combination of one to three halogen atoms, one to three $C_1$–$C_4$alkyl groups, one to three $C_1$–$C_4$alkoxy groups, one $C_3$–$C_6$cycloalkyl group, one $C_1$–$C_4$haloalkyl group, one $C_1$–$C_4$alkylthio group, one cyano group, one nitro group, one $C(O)R_{25}$ group, one $CO_2R_{26}$ group, one $X_4R_{22}$ group, one $CH=CHR_{22}$ group, one $CH_2CH(R_{28})R_{22}$ group or one $N(R_{29})SO_2R_{30}$ group, or
indan optionally substituted with any combination of one or two halogen atoms, one or two $C_1$–$C_4$alkyl groups, one $C_1$–$C_4$alkoxy group, one $C_1$–$C_4$haloalkyl group, one $C_1$–$C_4$alkylthio group, one cyano group, one nitro group, one $C(O)R_{25}$ group, one $CO_2R_{26}$ group, one $X_4R_{22}$ group, one $CH=CHR_{22}$ group, one $CH_2CH(R_{28})R_{22}$ group or one $N(R_{29})SO_2R_{30}$ group,
and when $R_{12}$ and $R_{13}$ are taken together with the nitrogen atom to which they are attached, they form a 5- to 12-membered monocyclic or fused bicyclic, heterocyclic ring optionally substituted with one or more groups independently selected from halogen, cyano, nitro, amino, hydroxyl, $C_1$–$C_4$alkyl, $C_1$–$C_4$haloalkyl, $C_1$–$C_4$alkoxy, $C_1$–$C_4$haloalkoxy, $C_1$–$C_4$haloalkylsulfonyl or $X_4R_{22}$ groups;
$R_{13}$ is hydrogen, $C_1$–$C_8$alkoxyalkyl, $C_1$–$C_6$alkyl, $C_3$–$C_7$cycloalkyl, $C_3$–$C_6$alkenyl, $C_3$–$C_6$alkynyl, benzyl, $OR_{23}$, cyano, $SO_2R_{51}$ or one 5- to 12-membered monocyclic or fused bicyclic heterocyclic ring optionally substituted with one or more groups independently selected from halogen, cyano, nitro, amino, hydroxyl, $C_1$–$C_4$alkyl, $C_1$–$C_4$haloalkyl, $C_1$–$C_4$alkoxy or $C_1$–$C_4$haloalkoxy, and when $R_{13}$ and $R_{12}$ are taken together with the nitrogen atom to which they are attached, they form a 5- to 12-membered monocyclic or fused bicyclic, heterocyclic ring optionally substituted with one or more groups independently selected from halogen, cyano, nitro, amino, hydroxyl, $C_1$–$C_4$alkyl, $C_1$–$C_4$haloalkyl, $C_1$–$C_4$alkoxy, $C_1$–$C_4$haloalkoxy, $C_1$–$C_4$haloalkylsulfonyl or $X_4R_{22}$ groups;
$R_{28}$ is halogen;
$R_{22}$ and $R_{27}$ are each independently hydrogen, $Si(R_{31})_3$, $C(O)NR_{35}R_{36}$, $C(O)R_{33}$, $SO_2R_{47}$,
$C_1$–$C_{20}$alkyl substituted with one hydroxyl, benzyloxy, nitro, $OC(O)R_{33}$, $C_1$–$C_6$alkoxy, $CO_2R_{32}$, $C(O)R_{33}$, $C(A_4R_{34})_2$, $C(O)NR_{35}R_{36}$, $C(O)ON=CR_{37}R_{38}$, $P(O)(OH)NH_2$, $P(O)(OH)(OR_{23})$, $C(O)NR_{35}OR_{23}$, cyano or 2-dioxolanyl group,
one phenyl, dihydrofuranone or furanone ring wherein each ring is optionally substituted with any combination of one to three halogen atoms, one to three $C_1$–$C_4$alkyl groups, one to three $C_1$–$C_4$haloalkyl groups, one to three $C_1$–$C_4$alkoxy groups ox one to three $C_1$–$C_4$haloalkoxy groups, or
one 5- to 12-membered monocyclic or fused bicyclic, heterocyclic ring optionally substituted with one or more groups independently selected from halogen, cyano, nitro, amino, hydroxyl, $C_1$–$C_4$alkyl, $C_1$–$C_4$haloalkyl, $C_1$–$C_4$alkoxy, $C_1$–$C_4$haloalkoxy or $C_1$–$C_4$haloalkylsulfonyl groups,
$C_3$–$C_{20}$alkenyl optionally substituted with one to three halogen atoms, one hydroxyl group, one $C_1$–$C_6$alkoxy, $CO_2R_{32}$, $C(O)R_{33}$, $C(A_4R_{34})_2$, $C(O)NR_{35}R_{36}$, $C(O)ON=CR_{37}R_{38}$, $C(O)NR_{35}R_{23}$, cyano or 2-dioxolanyl group, or one phenyl, dihydrofuranone or furanone ring wherein each ring is optionally substituted with any combination of one to three halogen atoms, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups,
$C_5$–$C_8$cycloalkenyl optionally substituted with one hydroxyl, $C_1$–$C_6$alkoxy, $C_1$–$C_4$alkyl, $C_2$–$C_4$alkenyl, $CO_2R_{32}$, $C(O)R_{33}$, $C(A_4R_{34})_2$, $C(O))NR_{35}R_{36}$, $C(O)ON=CR_{37}R_{38}$, $C(O)NR_{35}OR_{23}$, cyano or 2-dioxolanyl group, or one phenyl, dihydrofuranone or furanone ring wherein each ring is optionally substituted with any combination of one to three halogen atoms, one to three $C_1$–$C_4$alkyl groups, one to three $C_1$–$C_4$alkoxy groups or one to three $C_1$–$C_4$haloalkoxy groups,
$C_3$–$C_{10}$alkynyl optionally substituted with one hydroxyl, $C_1$–$C_6$alkoxy, $CO_2R_{32}$, $C(O)R_{33}$, $C(A_4R_{34})_2$, $C(O)NR_{35}R_{36}$, $C(O)ON=CR_{37}R_{38}$, $C(O)NR_{35}OR_{23}$, cyano or 2-dioxolanyl group, or one phenyl, dihydrofuranone or furanone ring wherein each ring is optionally substituted with any combination of one to three halogen atoms, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups,
phenyl optionally substituted with any combination of one to three halogen atoms, one to three $C_1$–$C_6$alkyl groups, one to three $C_1$–$C_6$alkoxy groups, one $C_1$–$C_4$haloalkyl group, one $C_1$–$C_4$haloalkoxy group, one cyano group, one nitro group, one $NR_{39}R_{40}$ group or one $C(O)R_{23}$ group,
benzyl optionally substituted on the phenyl ring with any combination of one to three halogen atoms, one to three $C_1$–$C_6$alkyl groups, one to three $C_1$–$C_6$alkoxy groups, one $C_1$–$C_4$haloalkyl group, one $C_1$–$C_4$haloalkoxy group, one cyano group, one nitro group, one $NR_{39}R_{40}$ group or one $C(O)R_{33}$ group, or
a 4- to 10-membered heterocyclic ring optionally substituted with any combination of one or two oxo groups, one or two thioxo groups, one to three halogen atoms, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups;
$R_{15}$ and $R_{20}$ are each independently hydrogen,
a $C_1$–$C_6$alkyl, $C_3$–$C_7$cycloalkyl, $C_2$–$C_6$alkenyl or $C_2$–$C_6$alkynyl group wherein each group is optionally substituted with one $CO_2R_{42}$ group,
benzyl optionally substituted with any combination of one to three halogen atoms, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups,
phenyl optionally substituted with any combination of one to three halogen atoms, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups, one $CO_2R_{26}$ group, $C(O)R_{43}$, or $CO_2R_{42}$;

$R_{16}$ and $R_{21}$ are each independently hydrogen, $C_1$–$C_6$alkyl, $C_1$–$C_4$alkoxy, $C_3$–$C_7$cycloalkyl, $C_2$–$C_6$alkenyl, $C_3$–$C_7$cycloalkenyl, $C_2$–$C_6$alkynyl, $P(O)(OR_{44})_2$, $SO_2R_{45}$, $C(O)R_{46}$,
  benzyl optionally substituted with any combination of one to three halogen atoms, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups or one $X_4R_{22}$ group, or
  phenyl optionally substituted with any combination of one to three halogen atoms, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups or one $X_4R_{22}$ group;

$R_{17}$, $R_{18}$, $R_{25}$, $R_{30}$, $R_{33}$, $R_{45}$ and $R_{51}$ are each independently $NR_{46}R_{48}$, —N=$CR_{46}R_{48}$, $C_1$–$C_8$alkyl optionally substituted with one $C_1$–$C_6$alkoxy, thiophene or furan group, $C_1$–$C_6$haloalkyl, $C_3$–$C_8$cycloalkyl, $CO_2R_{23}$, $C_2$–$C_6$alkenyl optionally substituted with phenyl,
  benzyl optionally substituted with any combination of one to three halogen atoms, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups, one nitro group, one cyano group or one $X_4R_{22}$ group,
  phenyl optionally substituted with any combination of one to three halogen atoms, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups, one nitro group, one cyano group or one $X_4R_{22}$ group, or
  a 5- to 12-membered monocyclic or fused bicyclic, heterocyclic ring optionally substituted with one or more groups independently selected from halogen, cyano, nitro, amino, hydroxyl, $C_1$–$C_4$alkyl, $C_1$–$C_4$haloalkyl, $C_1$–$C_4$alkoxy, $C_1$–$C_4$haloalkoxy, $C_1$–$C_4$haloalkylsulfonyl or $X_4R_{22}$ groups;

$R_{19}$ and $R_{26}$ are each independently hydrogen, $C_1$–$C_{20}$alkyl, $C_1$–$C_8$haloalkyl, $C_3$–$C_7$cycloalkyl, $C_3$–$C_7$halocycloalkyl, $C_3$–$C_{20}$alkenyl, $C_3$–$C_8$haloalkenyl, $C_5$–$C_8$cycloalkenyl, $C_5$–$C_8$halocycloalkenyl, $C_3$–$C_8$alkynyl, $C_3$–$C_8$haloalkynyl, $Si(R_{41})_3$, benzyl, phenyl, furfuryl, pyridyl, thienyl, oximino or an alkali metal, alkaline earth metal, manganese, copper, zinc, cobalt, silver, nickel, ammonium or organic ammonium cation;

$R_{32}$ is hydrogen,
  $Si(R_{47})_3$,
  $di(C_1$–$C_4$alkyl)imino,
  $C_1$–$C_{20}$alkyl optionally substituted with one $CO_2R_{48}$, $C_1$–$C_6$alkoxy, $C_1$–$C_6$thioalkyl, $C_2$–$C_{20}$alkoxyalkoxy, phenyl, $OSi(R_{47})_3$, $OC(O)R_{33}$, $C_3$–$C_7$cycloalkyl or $di(C_1$–$C_4$alkyl)imino group,
  $C_1$–$C_{15}$haloalkyl,
  $C_3$–$C_8$cycloalkyl optionally substituted with one $CO_2R_{48}$ group,
  $C_3$–$C_8$halocycloalkyl,
  $C_3$–$C_{20}$alkenyl optionally substituted with one phenyl group,
  $C_3$–$C_{15}$haloalkenyl,
  $C_5$–$C_8$cycloalkenyl,
  $C_5$–$C_8$halocycloalkenyl,
  $C_3$–$C_{20}$alkynyl optionally substituted with one phenyl group,
  $C_3$–$C_{20}$haloalkynyl,
  benzyl optionally substituted with one or more groups independently selected from halogen, cyano, nitro, $C_1$–$C_4$alkyl, $C_1$–$C_4$haloalkyl, $C_1$–$C_4$alkoxy and $C_1$–$C_4$haloalkoxy groups,
  phenyl optionally substituted with one or more groups independently selected from halogen, cyano, nitro, $C_1$–$C_4$alkyl, $C_1$–$C_4$haloalkyl, $C_1$–$C_4$alkoxy and $C_1$–$C_4$haloalkoxy groups,
  2-, 3- or 4-pyridyl,
  2- or 3-furyl,
  2- or 3-thienyl,
  2-tetrahydrofuranyl,
  $C_1$–$C_4$alkyl substituted with one pyridyl, furyl, thienyl, tetrahydrofuryl, $C_3$–$C_8$cycloalkyl, dioxane or $NR_{49}R_{50}$ group, or
  an alkali metal, alkaline earth metal, manganese, copper, zinc, cobalt, silver, nickel, ammonium or organic ammonium cation;

$R_{34}$, $R_{37}$ and $R_{38}$ are each independently $C_1$–$C_6$alkyl;

$R_{35}$ and $R_{49}$ are each independently hydrogen or $C_1$–$C_6$alkyl and $R_{36}$ and $R_{50}$ are each independently hydrogen, cyano, $C_1$–$C_6$alkyl, $SO_2R_{51}$ or phenyl optionally substituted with one or more groups independently selected from halogen, cyano, nitro, $C_1$–$C_4$alkyl, $C_1$–$C_4$haloalkyl, $C_1$–$C_4$alkoxy and $C_1$–$C_4$haloalkoxy groups, or when $R_{35}$ and $R_{36}$ or $R_{49}$ and $R_{50}$ are taken together with the nitrogen atom to which they are attached, they form a 5- to 12-membered monocyclic or fused bicyclic, heterocyclic ring optionally substituted with one or more groups independently selected from halogen, cyano, nitro, amino, hydroxyl, $C_1$–$C_4$alkyl, $C_1$–$C_4$haloalkyl, $C_1$–$C_4$alkoxy, $C_1$–$C_4$haloalkoxy or $C_1$–$C_4$haloalkylsulfonyl groups;

m, n, p and q are each independently an integer of 0, 1 or 2;

$R_{29}$ is hydrogen, $C_1$–$C_4$alkyl or $C_1$–$C_4$haloalkyl;

$R_{24}$, $R_{31}$, $R_{41}$ and $R_{47}$ are each independently $C_1$–$C_4$alkyl, benzyl optionally substituted with one or more groups independently selected from halogen, cyano, nitro, $C_1$–$C_4$alkyl, $C_1$–$C_4$haloalkyl, $C_1$–$C_4$alkoxy and $C_1$–$C_4$haloalkoxy groups, or
  phenyl optionally substituted with one or more groups independently selected from halogen, cyano, nitro, $C_1$–$C_4$alkyl, $C_1$–$C_4$haloalkyl, $C_1$–$C_4$alkoxy and $C_1$–$C_4$haloalkoxy groups;

$R_{23}$, $R_{39}$, $R_{40}$, $R_{42}$, $R_{43}$, $R_{44}$, $R_{46}$ and $R_{48}$ are each independently hydrogen, $C_2$–$C_6$alkenyl, $C_3$–$C_8$cycloalkyl,
  $C_1$–$C_8$alkyl optionally substituted with one or two $C_1$–$C_4$alkoxy groups,
  benzyl optionally substituted with one or more groups independently selected from halogen, cyano, nitro, $C_1$–$C_4$alkyl, $C_1$–$C_4$haloalkyl, $C_1$–$C_4$alkoxy and $C_1$–$C_4$haloalkoxy groups, or
  phenyl optionally substituted with one or more groups independently selected from halogen, cyano, nitro, $C_1$–$C_4$alkyl, $C_1$–$C_4$haloalkyl, $C_1$–$C_4$alkoxy and $C_1$–$C_4$haloalkoxy groups, and
  when $R_{46}$ and $R_{48}$ are taken together with the atom to which they are attached, they form a 5- to 12-membered monocyclic or fused bicyclic, heterocyclic or cycloalkyl ring optionally substituted with one or more groups independently selected from halogen, cyano, nitro, amino, hydroxyl, $C_1$–$C_4$alkyl, $C_1$–$C_4$haloalkyl, $C_1$–$C_4$alkoxy, $C_1$–$C_4$haloalkoxy or $C_1$–$C_4$haloalkylsulfonyl groups; and A, $A_1$, $A_3$, $A_4$, $X_4$ and $X_5$ are each independently O or S; and the optical isomers, diastereomers and/or tautomers thereof.

31. The compound according to claim 30 wherein $R_1$ is halogen or $C_1$–$C_4$haloalkyl;

$R_2$ is hydrogen, halogen or $C_1$–$C_4$haloalkyl;

X and $X_1$ are each independently hydrogen or halogen;

Z is O or S;

Y is cyano, $R_{12}$, $X_2R_{12}$ or $X_3X_2R_{12}$;

$X_2$ is O, S or $NR_{13}$;

$X_3$ is —C(=$A_3$)—, —C(=$NOR_{14}$)— or —C(=N—$NR_{13}R_{50}$);

$R_{12}$ is hydrogen, a $C_1$–$C_6$alkyl, $C_3$–$C_7$cycloalkyl, $C_2$–$C_6$alkenyl, $C_5$–$C_6$cycloalkenyl or $C_2$–$C_6$alkynyl group, wherein each group is optionally substituted with any combination of one to three halogen atoms, one or two $C_1$–$C_{20}$alkoxy groups, one or two $C_1$–$C_{10}$haloalkoxy groups, one $NR_{15}R_{16}$ group, one $S(O)_qR_{17}$ group, one or two cyano groups, one or two $C(O)R_{18}$ groups, one or two $CO_2R_{19}$ groups, one or two $C(O)SR_{19}$ groups, one or two $C(O)NR_{20}R_{21}$ groups, one or two $X_4R_{22}$ groups, one $P(O)(OR_{23})_2$ group, one $Si(R_{24})_3$ group, one 4- to 10-membered monocyclic or fused bicyclic heterocyclic ring optionally substituted with any combination of one or two oxo groups, one or two thioxo groups, one to three halogen atoms, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups or one or two $X_4R_{22}$ groups, one quaternary organic ammonium group, or one phenyl group optionally substituted with any combination of one to three halogen atoms, one $C_1$–$C_6$alkyl group, one $C_1$–$C_6$alkoxy group, one $C_3$–$C_7$cycloalkyl group, one cyano group, one nitro group, one $C(O)R_{25}$ group, one $CO_2R_{26}$ group or one $X_5R_{27}$ group, or phenyl optionally substituted with any combination of one or two halogen atoms, one to three $C_1$–$C_4$alkyl groups, one or two $C_1$–$C_4$alkoxy groups, one $C_3$–$C_6$cycloalkyl group, one $C_1$–$C_4$haloalkyl group, one $C_1$–$C_4$alkylthio group, one cyano group, one nitro group, one $C(O)R_{25}$ group, one $CO_2R_{26}$ group, one $X_4R_{22}$ group, one CH=$CHR_{22}$ group, one $CH_2CH(R_{28})R_{22}$ group or one $N(R_{29})SO_2R_{30}$ group;

$R_{13}$ is hydrogen, $C_2$–$C_6$alkoxyalkyl, $C_1$–$C_4$alkyl, $C_3$–$C_7$cycloalkyl, $C_3$–$C_6$alkenyl, $C_3$–$C_6$alkynyl, benzyl, $OR_{23}$, cyano or $SO_2R_{51}$;

$R_{28}$ is halogen;

$R_{22}$ and $R_{27}$ are each independently hydrogen, $Si(R_{31})_3$, $C(O)NR_{35}R_{36}$, $C(O)R_{33}$, $SO_2R_{47}$, $C_1$–$C_{20}$ alkyl substituted with one hydroxyl, benzyloxy, nitro, $OC(O)R_{33}$, $C_1$–$C_6$alkoxy, $CO_2R_{32}$, $C(O)R_{33}$, $C(A_4R_{34})_2$, $C(O)NR_{35}R_{36}$, $C(O)ON$=$CR_{37}R_{38}$, $P(O)(OH)NR_2$, $P(O)(OH)(OR_{23})$, $C(O)NR_{35}OR_{23}$, cyano or 2-dioxolanyl group, one phenyl, dihydrofuranone or furanone ring wherein each ring is optionally substituted with any combination of one to three halogen atoms, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups, or one 5- to 12-membered monocyclic or fused bicyclic, heterocyclic ring optionally substituted with one or more groups independently selected from halogen, cyano, nitro, amino, hydroxyl, $C_1$–$C_4$alkyl, $C_1$–$C_4$haloalkyl, $C_1$–$C_4$alkoxy, $C_1$–$C_4$haloalkoxy or $C_1$–$C_4$haloalkylsulfonyl groups, $C_3$–$C_{20}$alkenyl optionally substituted with one to three halogen atoms, one hydroxyl group, one $C_1$–$C_6$alkoxy, $CO_2R_{32}$, $C(O)R_{33}$, $C(A_4R_{34})_2$, $C(O)NR_{35}R_{36}$, $C(O)ON$=$CR_{37}R_{38}$, $C(O)NR_{35}OR_{23}$, cyano or 2-dioxolanyl group, or one phenyl, dihydrofuranone or furanone ring wherein each ring is optionally substituted with any combination of one to three halogen atoms, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups, $C_5$–$C_8$cycloalkenyl optionally substituted with one hydroxyl, $C_1$–$C_6$alkoxy, $C_1$–$C_4$alkyl, $C_2$–$C_4$alkenyl, $CO_2R_{32}$, $C(O)R_{33}$, $C(A_4R_{34})_2$, $C(O)NR_{35}R_{36}$, $C(O)ON$=$CR_{37}R_{38}$, $C(O)NR_{35}OR_{23}$, cyano or 2-dioxolanyl group, or one phenyl, dihydrofuranone or furanone ring wherein each ring is optionally substituted with any combination of one to three halogen atoms, one to three $C_1$–$C_4$alkyl groups, one to three $C_1$–$C_4$alkoxy groups or one to three $C_1$–$C_4$haloalkoxy groups, $C_3$–$C_{10}$alkynyl optionally substituted with one hydroxyl, $C_1$–$C_6$alkoxy, $CO_2R_{32}$, $C(O)R_{33}$, $C(A_4R_{34})_2$, $C(O)NR_{35}R_{36}$, $C(O)ON$=$CR_{37}R_{38}$, $C(O)NR_{35}OR_{23}$, cyano or 2-dioxolanyl group, or one phenyl, dihydrofuranone or furanone ring wherein each ring is optionally substituted with any combination of one to three halogen atoms, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups, phenyl optionally substituted with any combination of one to three halogen atoms, one to three $C_1$–$C_6$alkyl groups, one to three $C_1$–$C_6$alkoxy groups, one $C_1$–$C_4$haloalkyl group, one $C_1$–$C_4$haloalkoxy group, one cyano group, one nitro group, one $NR_{39}R_{40}$ group or one $C(O)R_{33}$ group, benzyl optionally substituted on the phenyl ring with any combination of one to three halogen atoms, one to three $C_1$–$C_6$alkyl groups, one to three $C_1$–$C_6$alkoxy groups, one $C_1$–$C_4$haloalkyl group, one $C_1$–$C_4$haloalkoxy group, one cyano group, one nitro group, one $NR_{39}R_{40}$ group or one $C(O)R_{33}$ group, or a 4- to 10-membered heterocyclic ring optionally substituted with any combination of one or two oxo groups, one or two thioxo groups, one to three halogen atoms, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups;

$R_{15}$ and $R_{20}$ are each independently hydrogen, a $C_1$–$C_6$alkyl, $C_3$–$C_7$cycloalkyl, $C_2$–$C_6$alkenyl or $C_2$–$C_6$alkynyl group wherein each group is optionally substituted with one $CO_2R_{42}$ group, benzyl optionally substituted with any combination of one to three halogen atoms, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups, phenyl optionally substituted with any combination of one to three halogen atoms, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups, one $CO_2R_{26}$ group, $C(O)R_{43}$, or $CO_2R_{42}$;

$R_{14}$ is hydrogen, $C_1$–$C_6$alkyl, $C_3$–$C_7$cycloalkyl, $C_2$–$C_6$alkoxyalkyl, $C_2$–$C_6$alkenyl, $C_2$–$C_6$alkynyl or benzyl;

$R_{16}$ and $R_{21}$ are each independently hydrogen, $C_1$–$C_4$alkyl, $C_1$–$C_4$alkoxy, $C_3$–$C_7$cycloalkyl, $C_2$–$C_6$alkenyl, $C_3$–$C_7$cycloalkenyl, $C_2$–$C_6$alkynyl, $P(O)(OR_{44})_2$, $SO_2R_{45}$, $C(O)R_{46}$, benzyl optionally substituted with any combination of one to three halogen atoms, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups, or phenyl optionally substituted with any combination of one to three halogen atoms, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups;

$R_{17}$, $R_{18}$, $R_{25}$, $R_{30}$, $R_{33}$, $R_{45}$ and $R_{51}$ are each independently $NR_{46}R_{48}$, —N=$CR_{46}R_{48}$, $C_1$–$C_8$alkyl optionally substituted with one $C_1$–$C_6$alkoxy, thiophene or furan group, $C_1$–$C_6$haloalkyl, $C_3$–$C_8$cycloalkyl, $CO_2R_{23}$, $C_2$–$C_6$alkenyl optionally substituted with phenyl, benzyl optionally substituted with any combination of one to three halogen atoms, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups, one nitro group, one cyano group or one $X_4R_{22}$ group, phenyl optionally substituted with any combination of one to three halogen atoms, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups, one nitro group, one cyano group or one $X_4R_{22}$ group, or a 5- to 12-membered monocyclic or fused bicyclic, heterocyclic ring optionally substituted with one or more groups independently selected from halogen, cyano, nitro, amino, hydroxyl, $C_1$–$C_4$alkyl, $C_1$–$C_4$haloalkyl, $C_1$–$C_4$alkoxy, $C_1$–$C_4$haloalkoxy, $C_1$–$C_4$haloalkylsulfonyl or $X_4R_{22}$ groups;

$R_{19}$ and $R_{26}$ are each independently hydrogen, $C_1$–$C_{20}$alkyl, $C_1$–$C_8$haloalkyl, $C_3$–$C_7$cycloalkyl, $C_3$–$C_7$halocycloalkyl, $C_3$–$C_{20}$alkenyl, $C_3$–$C_8$haloalkenyl, $C_5$–$C_8$cycloalkenyl, $C_5$–$C_8$halocycloalkenyl, $C_3$–$C_8$alkynyl, $C_3$–$C_8$haloalkynyl, $Si(R_{41})_3$, benzyl, phenyl, furfuryl, pyridyl, thienyl, oximino or an alkali metal, alkaline earth metal, manganese, copper, zinc, cobalt, silver, nickel, ammonium or organic ammonium cation;

$R_{32}$ is hydrogen,
$Si(R_{47})_3$,
$C_1$–$C_{20}$alkyl optionally substituted with one $CO_2R_{48}$, $C_1$–$C_6$alkoxy, $C_1$–$C_6$thioalkyl, $C_2$–$C_{20}$alkoxyalkoxy, phenyl, $OSi(R_{47})_3$, $OC(O)R_{33}$, $C_3$–$C_7$cycloalkyl or di($C_1$–$C_4$alkyl)imino group, $C_1$–$C_{15}$haloalkyl, $C_3$–$C_8$cycloalkyl optionally substituted with one $CO_2R_{48}$ group, $C_3$–$C_8$halocycloalkyl, $C_3$–$C_{20}$alkenyl optionally substituted with one phenyl group, $C_3$–$C_{15}$haloalkenyl, $C_5$–$C_8$cycloalkenyl, $C_5$–$C_8$halocycloalkenyl, $C_3$–$C_{20}$alkynyl optionally substituted with one phenyl group, $C_3$–$C_{20}$haloalkynyl, benzyl optionally substituted with one or more groups independently selected from halogen, cyano, nitro, $C_1$–$C_4$alkyl, $C_1$–$C_4$haloalkyl, $C_1$–$C_4$alkoxy and $C_1$–$C_4$haloalkoxy groups, phenyl optionally substituted with one or more groups independently selected from halogen, cyano, nitro, $C_1$–$C_4$alkyl, $C_1$–$C_4$haloalkyl, $C_1$–$C_4$alkoxy and $C_1$–$C_4$haloalkoxy groups, $C_1$–$C_4$alkyl substituted with one pyridyl, furyl, thienyl, tetrahydrofuryl, $C_3$–$C_8$cycloalkyl, dioxane or $NR_{49}R_{50}$ group, or an alkali metal, alkaline earth metal, manganese, copper, zinc, cobalt, silver, nickel, ammonium or organic ammonium cation;

$R_{34}$, $R_{37}$ and $R_{38}$ are each independently $C_1$–$C_6$alkyl;

$R_{35}$ and $R_{49}$ are each independently hydrogen or $C_1$–$C_6$alkyl and $R_{36}$ and $R_{50}$ are each independently hydrogen, cyano, $C_1$–$C_6$alkyl, $SO_2R_{51}$ or phenyl optionally substituted with one or more groups independently selected from halogen, cyano, nitro, $C_1$–$C_4$alkyl, $C_1$–$C_4$haloalkyl, $C_1$–$C_4$alkoxy and $C_1$–$C_4$haloalkoxy groups, or when $R_{35}$ and $R_{36}$ or $R_{49}$ and $R_{50}$ are taken together with the nitrogen atom to which they are attached, they form a 5- to 12-membered monocyclic or fused bicyclic, heterocyclic ring optionally substituted with one or more groups independently selected from halogen, cyano, nitro, amino, hydroxyl, $C_1$–$C_4$alkyl, $C_1$–$C_4$haloalkyl, $C_1$–$C_4$alkoxy, $C_1$–$C_4$haloalkoxy or $C_1$–$C_4$haloalkylsulfonyl groups;

q is an integer of 0, 1 or 2;

$R_{29}$ is hydrogen, $C_1$–$C_4$alkyl or $C_1$–$C_4$haloalkyl;

$R_{24}$, $R_{31}$, $R_{41}$ and $R_{47}$ are each independently $C_1$–$C_4$alkyl, benzyl optionally substituted with one or more groups independently selected from halogen, cyano, nitro, $C_1$–$C_4$alkyl, $C_1$–$C_4$haloalkyl, $C_1$–$C_4$alkoxy and $C_1$–$C_4$haloalkoxy groups, or phenyl optionally substituted with one or more groups independently selected from halogen, cyano, nitro, $C_1$–$C_4$alkyl, $C_1$–$C_4$haloalkyl, $C_1$–$C_4$alkoxy and $C_1$–$C_4$haloalkoxy groups;

$R_{23}$, $R_{39}$, $R_{40}$, $R_{42}$, $R_{43}$, $R_{44}$, $R_{46}$ and $R_{48}$ are each independently hydrogen, $C_2$–$C_6$alkenyl, $C_3$–$C_8$cycloalkyl, $C_1$–$C_8$alkyl optionally substituted with one or two $C_1$–$C_4$alkoxy groups, benzyl optionally substituted with one or more groups independently selected from halogen, cyano, nitro, $C_1$–$C_4$alkyl, $C_1$–$C_4$haloalkyl, $C_1$–$C_4$alkoxy and $C_1$–$C_4$haloalkoxy groups, or phenyl optionally substituted with one or more groups independently selected from halogen, cyano, nitro, $C_1$–$C_4$alkyl, $C_1$–$C_4$haloalkyl, $C_1$–$C_4$alkoxy and $C_1$–$C_4$haloalkoxy groups; and A, $A_1$, $A_3$, $A_4$, $X_4$ and $X_5$ are each independently O or S; and the optical isomers, diastereomers and/or tautomers thereof.

32. A process for the preparation of a compound having the structural formula

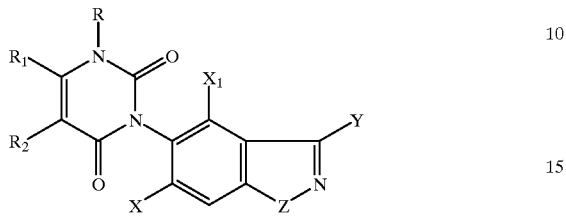

wherein

R is $C_1$–$C_6$alkyl, $C_1$–$C_6$haloalkyl, $C_3$–$C_7$cycloalkyl, $C_3$–$C_6$alkenyl, $C_3$–$C_6$alkynyl, benzyl, $OR_4$ or $NR_5R_6$;

$R_1$ and $R_2$ are each independently hydrogen, halogen, $C_1$–$C_6$alkyl, $C_3$–$C_7$cycloalkyl, $C_1$–$C_6$haloalkyl, $C_3$–$C_6$alkenyl, $C_3$–$C_6$haloalkenyl, $C_3$–$C_6$alkynyl, $OR_7$, $S(O)_nR_8$ or $NR_9R_{10}$;

X is hydrogen, halogen or $C_1$–$C_4$alkyl;

$X_1$ is hydrogen, halogen, $C_1$–$C_4$alkyl, $C_1$–$C_4$haloalkyl, $C_1$–$C_4$alkoxy or $C_1$–$C_4$haloalkoxy;

Z is O or $S(O)_m$;

Y is halogen, cyano, $R_{12}$, $X_2R_{12}$, $X_3R_{12}$, $X_2X_3R_{12}$ or $X_3X_2R_{12}$;

$X_2$ is O, S(O)$_p$ or $NR_{13}$;

$X_3$ is —C(=$A_3$)—, —C(=$NOR_{14}$)— or —C(=N—$NR_{13}R_{50}$);

$R_4$, $R_5$, $R_6$, $R_7$, $R_8$, $R_9$, $R_{10}$ and $R_{14}$ are each independently hydrogen, $C_1$–$C_6$alkyl, $C_3$–$C_7$cycloalkyl, $C_2$–$C_8$alkoxyalkyl, $C_2$–$C_6$alkenyl, $C_2$–$C_6$alkynyl or benzyl;

$R_{12}$ is hydrogen, a $C_1$–$C_8$alkyl, $C_3$–$C_7$cycloalkyl, $C_2$–$C_8$alkenyl, $C_5$–$C_6$cycloalkenyl or $C_2$–$C_8$alkynyl group, wherein each group is optionally substituted with any combination of one to six halogen atoms, one to three $C_1$–$C_{20}$alkoxy groups optionally substituted with one $C_1$–$C_6$alkoxy, benzyloxy or $C_1$–$C_6$alkylthio group, one or two $C_1$–$C_{10}$haloalkoxy groups, one or two $NR_{15}R_{16}$ groups, one to three $S(O)_qR_{17}$ groups, one or two cyano groups, one or two $C_3$–$C_7$cycloalkyl groups, one thiocyano group, one $O(SO_2)R_{17}$ group, one $O(NO_2)$ group, one or two $C(O)R_{18}$ groups, one or two $CO_2R_{19}$ groups, one or two $C(O)SR_{19}$ groups, one or two $C(O)NR_{20}R_{21}$ groups, one to three $X_4R_{22}$ groups, one or two $P(O)(OR_{23})_2$ groups, one or two $Si(R_{24})_3$ groups, one 4- to 10-membered monocyclic or fused bicyclic heterocyclic ring optionally substituted with any combination of one or two oxo groups, one or two thioxo groups, one to three halogen atoms, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups or one or two $X_4R_{22}$ groups, one quaternary organic ammonium group, or one or two phenyl groups wherein each phenyl group is independently optionally substituted with any combination of one to three halogen atoms, one to three $C_1$–$C_6$alkyl groups, one to three $C_1$–$C_6$alkoxy groups, one $C_3$–$C_7$cycloalkyl group, one $C_1$–$C_4$haloalkyl group, one $C_1$–$C_4$alkylthio group, one cyano group, one nitro group, one $C(O)R_{25}$ group, one $CO_2R_{26}$ group or one $X_5R_{27}$ group, phenyl optionally substituted with any combination of one to three halogen atoms, one to three $C_1$–$C_4$alkyl groups, one to three $C_1$–$C_4$alkoxy groups, one $C_3$–$C_6$cycloalkyl group, one $C_1$–$C_4$haloalkyl group, one $C_1$–$C_4$alkylthio group, one cyano group, one nitro group, one $C(O)R_{25}$ group, one $CO_2R_{26}$ group, one $X_4R_{22}$ group, one $CH=CHR_{22}$ group, one $CH_2CH(R_{28})R_{22}$ group or one $N(R_{29})SO_2R_{30}$ group, or indan optionally substituted with any combination of one or two halogen atoms, one or two $C_1$–$C_4$alkyl groups, one $C_1$–$C_4$alkoxy group, one $C_1$–$C_4$haloalkyl group, one $C_1$–$C_4$alkylthio group, one cyano group, one nitro group, one $C(O)R_{25}$ group, one $CO_2R_{26}$ group, one $X_4R_{22}$ group, one $CH=CHR_{22}$ group, one $CH_2CH(R_{28})R_{22}$ group or one $N(R_{29})SO_2R_{30}$ group, and when $R_{12}$ and $R_{13}$ are taken together with the nitrogen atom to which they are attached, they form a 5- to 12-membered monocyclic or fused bicyclic, heterocyclic ring optionally substituted with one or more groups independently selected from halogen, cyano, nitro, amino, hydroxyl, $C_1$–$C_4$alkyl, $C_1$–$C_4$haloalkyl, $C_1$–$C_4$alkoxy, $C_1$–$C_4$haloalkoxy, $C_1$–$C_4$haloalkylsulfonyl or $X_4R_{22}$ groups;

$R_{13}$ is hydrogen, $C_1$–$C_8$alkoxyalkyl, $C_1$–$C_6$alkyl, $C_3$–$C_7$cycloalkyl, $C_3$–$C_6$alkenyl, $C_3$–$C_6$alkynyl, benzyl, $OR_{23}$, cyano, $SO_2R_{51}$ or one 5- to 12-membered monocyclic or fused bicyclic heterocyclic ring optionally substituted with one or more groups independently selected from halogen, cyano, nitro, amino, hydroxyl, $C_1$–$C_4$alkyl, $C_1$–$C_4$haloalkyl, $C_1$–$C_4$alkoxy or $C_1$–$C_4$haloalkoxy, and when $R_{13}$ and $R_{12}$ are taken together with the nitrogen atom to which they are attached, they form a 5- to 12-membered monocyclic or fused bicyclic, heterocyclic ring optionally substituted with one or more groups independently selected from halogen, cyano, nitro, amino, hydroxyl, $C_1$–$C_4$alkyl, $C_1$–$C_4$haloalkyl, $C_1$–$C_4$alkoxy, $C_1$–$C_4$haloalkoxy, $C_1$–$C_4$haloalkylsulfonyl or $X_4R_{22}$ groups;

$R_{28}$ is halogen;

$R_{22}$ and $R_{27}$ are each independently hydrogen, $Si(R_{31})_3$, $C(O)NR_{35}R_{36}$, $C(O)R_{33}$, $SO_2R_{47}$, $C_1$–$C_{20}$alkyl substituted with one hydroxyl, benzyloxy, nitro, $OC(O)R_{33}$, $C_1$–$C_6$alkoxy, $CO_2R_{32}$, $C(O)R_{33}$, $C(A_4R_{34})_2$, $C(O)NR_{35}R_{36}$, $C(O)ON=CR_{37}R_{38}$, $P(O)(OH)NH_2$, $P(O)(OH)(OR_{23})$, $C(O)NR_{35}OR_{23}$, cyano or 2-dioxolanyl group, one phenyl, dihydrofuranone or furanone ring wherein each ring is optionally substituted with any combination of one to three halogen atoms, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups, or one 5- to 12-membered monocyclic or fused bicyclic, heterocyclic ring optionally substituted with one or more groups independently selected from halogen, cyano, nitro, amino, hydroxyl, $C_1$–$C_4$alkyl, $C_1$–$C_4$haloalkyl, $C_1$–$C_4$alkoxy, $C_1$–$C_4$haloalkoxy or $C_1$–$C_4$haloalkylsulfonyl groups, $C_3$–$C_{20}$alkenyl optionally substituted with one to three halogen atoms, one hydroxyl group, one $C_1$–$C_6$alkoxy, $CO_2R_{32}$, $C(O\ R_{33})$, $C(A_4R_{34})_2$, $C(O)NR_{35}R_{36}$, $C(O)ON=CR_{37}R_{38}$, $C(O)NR_{35}R_{23}$, cyano or 2-dioxolanyl group, or one phenyl, dihydrofuranone or furanone ring wherein each ring is optionally substituted with any combination of one to three halogen atoms, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups, $C_5$–$C_8$cycloalkenyl optionally substituted with one hydroxyl, $C_1$–$C_6$alkoxy, $C_1$–$C_4$alkyl, $C_2$–$C_4$alkenyl, $CO_2R_{32}$, $C(O)R_{33}$, $C(A_4R_{34})_2$, $C(O)NR_{35}R_{36}$, $C(O)ON=CR_{37}R_{38}$, $C(O)NR_{35}OR_{23}$, cyano or 2-dioxolanyl group, or one phenyl, dihydrofuranone or furanone ring wherein each ring is optionally substituted with any combination of one to three halogen atoms, one to three $C_1$–$C_4$alkyl groups, one to three $C_1$–$C_4$alkoxy groups or one to three $C_1$–$C_4$haloalkoxy groups, $C_3$–$C_{10}$alkynyl optionally substituted with one hydroxyl, $C_1$–$C_6$alkoxy, $CO_2R_{32}$, $C(O)R_{33}$, $C(A_4R_{34})_2$, $C(O)NR_{35}R_{36}$, $C(O)ON=CR_{37}R_{38}$, $C(O)NR_{35}OR_{23}$, cyano or 2-dioxolanyl group, or one phenyl, dihydrofuranone or furanone ring wherein each ring is optionally substituted with any combination of one to three halogen atoms, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups, phenyl optionally substituted with any combination of one to three halogen atoms, one to three $C_1$–$C_6$alkyl groups, one to three $C_1$–$C_6$alkoxy groups, one $C_1$–$C_4$haloalkyl group, one $C_1$–$C_4$haloalkoxy group, one cyano group, one nitro group, one $NR_{39}R_{40}$ group or one $C(O)R_{33}$ group, benzyl optionally substituted on the phenyl ring with any combination of one to three halogen atoms, one to three $C_1$–$C_6$alkyl groups, one to three $C_1$–$C_6$alkoxy groups, one $C_1$–$C_4$haloalkyl group, one $C_1$–$C_4$haloalkoxy group, one cyano group, one nitro group, one $NR_{39}R_{40}$ group or one $C(O)R_{33}$ group, or a 4- to 10-membered heterocyclic ring optionally substituted with any combination of one or two oxo groups, one or two thioxo groups, one to three halogen atoms, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups;

$R_{15}$ and $R_{20}$ are each independently hydrogen,
a $C_1$–$C_6$alkyl, $C_3$–$C_7$cycloalkyl, $C_2$–$C_6$alkenyl or $C_2$–$C_6$alkynyl group wherein each group is optionally substituted with one $CO_2R_{42}$ group, benzyl optionally substituted with any combination of one to three halogen atoms, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups, phenyl optionally substituted with any combination of one to three halogen atoms, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups, one $CO_2R_{26}$ group, $C(O)R_{43}$, or $CO_2R_{42}$;

$R_{16}$ and $R_{21}$ are each independently hydrogen, $C_1$–$C_6$alkyl, $C_1$–$C_4$alkoxy, $C_3$–$C_7$cycloalkyl, $C_2$–$C_6$alkenyl, $C_3$–$C_7$cycloalkenyl, $C_2$–$C_6$alkynyl, $P(O)(OR_{44})_2$, $SO_2R_{45}$, $C(O)R_{46}$, benzyl optionally substituted with any combination of one to three halogen atoms, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups or one $X_4R_{22}$ group, or phenyl optionally substituted with any combination of one to three halogen atoms, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups or one $X_4R_{22}$ group;

$R_{17}$, $R_{18}$, $R_{25}$, $R_{30}$, $R_{33}$, $R_{45}$ and $R_{51}$ are each independently $NR_{46}R_{48}$, —$N=CR_{46}R_{48}$, $C_1$–$C_8$alkyl optionally substituted with one $C_1$–$C_6$alkoxy, thiophene or furan group, $C_1$–$C_6$haloalkyl, $C_3$–$C_8$cycloalkyl, $CO_2R_{23}$, $C_2$–$C_6$alkenyl optionally substituted with phenyl, benzyl optionally substituted with any combination of one to three halogen atoms, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups, one nitro group, one cyano group or one $X_4R_{22}$ group, phenyl optionally substituted with any combination of one to three halogen atoms, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups, one nitro group, one cyano group or one $X_4R_{22}$ group, or a 5- to 12-membered monocyclic or fused bicyclic, heterocyclic ring optionally substituted with one or more groups independently selected from halogen, cyano, nitro, amino, hydroxyl, $C_1$–$C_4$alkyl, $C_1$–$C_4$haloalkyl, $C_1$–$C_4$alkoxy, $C_1$–$C_4$haloalkoxy, $C_1$–$C_4$haloalkylsulfonyl or $X_4R_{22}$ groups;

$R_{19}$ and $R_{26}$ are each independently hydrogen, $C_1$–$C_{20}$alkyl, $C_1$–$C_8$haloalkyl, $C_3$–$C_7$cycloalkyl, $C_3$–$C_7$halocycloalkyl, $C_3$–$C_{20}$alkenyl, $C_3$–$C_8$haloalkenyl, $C_5$–$C_8$cycloalkenyl, $C_5$–$C_8$halocycloalkenyl, $C_3$–$C_8$alkynyl, $C_3$–$C_8$haloalkynyl, $Si(R_{41})_3$, benzyl, phenyl, furfuryl, pyridyl, thienyl, oximino or an alkali metal, alkaline earth metal, manganese, copper, zinc, cobalt, silver, nickel, ammonium or organic ammonium cation;

$R_{32}$ is hydrogen,
$Si(R_{47})_3$,
di($C_1$–$C_4$alkyl)imino,
$C_1$–$C_{20}$alkyl optionally substituted with one $CO_2R_{48}$, $C_1$–$C_6$alkoxy, $C_1$–$C_6$thioalkyl, $C_2$–$C_{20}$alkoxyalkoxy, phenyl, $OSi(R_{47})_3$, $OC(O)R_{33}$, $C_3$–$C_7$cycloalkyl or di($C_1$–$C_4$alkyl)imino group,
$C_1$–$C_{15}$haloalkyl,
$C_3$–$C_8$cycloalkyl optionally substituted with one $CO_2R_{48}$ group,
$C_3$–$C_8$halocycloalkyl,
$C_3$–$C_{20}$alkenyl optionally substituted with one phenyl group,
$C_3$–$C_{15}$haloalkenyl,
$C_5$–$C_8$cycloalkenyl,
$C_5$–$C_8$halocycloalkenyl,
$C_3$–$C_{20}$alkynyl optionally substituted with one phenyl group, $C_3$–$C_{20}$haloalkynyl, benzyl optionally substituted with one or more groups independently selected from halogen, cyano, nitro, $C_1$–$C_4$alkyl, $C_1$–$C_4$haloalkyl, $C_1$–$C_4$alkoxy and $C_1$–$C_4$haloalkoxy groups, phenyl optionally substituted with one or more groups independently selected from halogen, cyano, nitro, $C_1$–$C_4$alkyl, $C_1$–$C_4$haloalkyl, $C_1$–$C_4$alkoxy and $C_1$–$C_4$haloalkoxy groups, 2-, 3- or 4-pyridyl, 2- or 3-furyl, 2- or 3-thienyl, 2-tetrahydrofuranyl, $C_1$–$C_4$alkyl substituted with one pyridyl, furyl, thienyl, tetrahydrofuryl, $C_3$–$C_8$cycloalkyl, dioxane or $NR_{49}R_{50}$ group, or an alkali metal, alkaline earth metal, manganese, copper, zinc, cobalt, silver, nickel, ammonium or organic ammonium cation;

$R_{34}$, $R_{37}$ and $R_{38}$ are each independently $C_1$–$C_6$alkyl;

$R_{35}$ and $R_{49}$ are each independently hydrogen or $C_1$–$C_6$alkyl and $R_{36}$ and $R_{50}$ are each independently hydrogen, cyano, $C_1$–$C_6$alkyl, $SO_2R_{51}$ or phenyl optionally substituted with one or more groups independently selected from halogen, cyano, nitro, $C_1$–$C_4$alkyl, $C_1$–$C_4$haloalkyl, $C_1$–$C_4$alkoxy and $C_1$–$C_4$haloalkoxy groups, or when $R_{35}$ and $R_{36}$ or $R_{49}$ and $R_{50}$ are taken together with the nitrogen atom to which they are attached, they form a 5- to 12-membered monocyclic or fused bicyclic, heterocyclic ring optionally substituted with one or more groups independently selected from halogen, cyano, nitro, amino, hydroxyl, $C_1$–$C_4$alkyl, $C_1$–$C_4$haloalkyl, $C_1$–$C_4$alkoxy, $C_1$–$C_4$haloalkoxy or $C_1$–$C_4$haloalkylsulfonyl groups;

m, n, p and q are each independently an integer of 0, 1 or 2;

$R_{29}$ is hydrogen, $C_1$–$C_4$alkyl or $C_1$–$C_4$haloalkyl;

$R_{24}$, $R_{31}$, $R_{41}$ and $R_{47}$ are each independently $C_1$–$C_4$alkyl, benzyl optionally substituted with one or more groups independently selected from halogen, cyano, nitro, $C_1$–$C_4$alkyl, $C_1$–$C_4$haloalkyl, $C_1$–$C_4$alkoxy and $C_1$–$C_4$haloalkoxy groups, or phenyl optionally substituted with one or more groups independently selected from halogen, cyano, nitro, $C_1$–$C_4$alkyl, $C_1$–$C_4$haloalkyl, $C_1$–$C_4$alkoxy and $C_1$–$C_4$haloalkoxy groups;

$R_{23}$, $R_{39}$, $R_{40}$, $R_{42}$, $R_{43}$, $R_{44}$, $R_{46}$ and $R_{48}$ are each independently hydrogen, $C_2$–$C_6$alkenyl, $C_3$–$C_8$cycloalkyl, $C_1$–$C_8$alkyl optionally substituted with one or two $C_1$–$C_4$alkoxy groups, benzyl optionally substituted with one or more groups independently selected from halogen, cyano, nitro, $C_1$–$C_4$alkyl, $C_1$–$C_4$haloalkyl, $C_1$–$C_4$alkoxy and $C_1$–$C_4$haloalkoxy groups, or phenyl optionally substituted with one or more groups independently selected from halogen, cyano, nitro, $C_1$–$C_4$alkyl, $C_1$–$C_4$haloalkyl, $C_1$–$C_4$alkoxy and $C_1$–$C_4$haloalkoxy groups, and when $R_{46}$ and $R_{48}$ are taken together with the atom to which they are attached, they form a 5- to 12-membered monocyclic or fused bicyclic, heterocyclic or cycloalkyl ring optionally substituted with one or more groups independently selected from halogen, cyano, nitro, amino, hydroxyl, $C_1$–$C_4$alkyl, $C_1$–$C_4$haloalkyl, $C_1$–$C_4$alkoxy, $C_1$–$C_4$haloalkoxy or $C_1$–$C_4$haloalkylsulfonyl groups; and A, $A_1$, $A_3$, $A_4$, $X_4$ and $X_5$ are each independently O or S, which process comprises reacting an amine having the structural formula

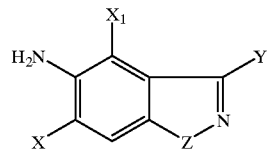

wherein X, $X_1$, Y and Z are as described above with a 2-dialkylamino-6H-1,3-oxazin-6-one having the structural formula

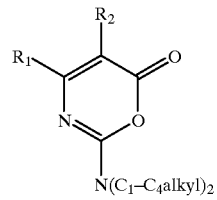

wherein $R_1$ and $R_2$ are as described above in the presence of an organic acid to form an intermediate compound having the structural formula

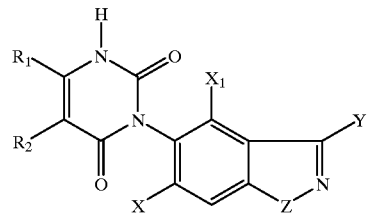

wherein $R_1$, $R_2$, X, $X_1$, Y and Z are as described above, and reacting the intermediate compound with an electrophile having the structural formula $Z_1R$ wherein R is as described above and $Z_1$ is chlorine, bromine or iodine in the presence of a base.

* * * * *